US008507235B2

(12) United States Patent
Chotani et al.

(10) Patent No.: US 8,507,235 B2

(45) Date of Patent: Aug. 13, 2013

(54) ISOPRENE PRODUCTION USING THE DXP AND MVA PATHWAY

(75) Inventors: Gopal K. Chotani, Cupertino, CA (US); Joseph C. McAuliffe, Sunnyvale, CA (US); Michael C. Miller, San Francisco, CA (US); Rachel E. Muir, Redwood City, CA (US); Dmitrii V. Vaviline, Palo Alto, CA (US); Walter Weyler, San Francisco, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 44 days.

(21) Appl. No.: 12/817,134

(22) Filed: Jun. 16, 2010

(65) Prior Publication Data

US 2011/0014672 A1 Jan. 20, 2011

Related U.S. Application Data

(60) Provisional application No. 61/187,941, filed on Jun. 17, 2009, provisional application No. 61/187,930, filed on Jun. 17, 2009, provisional application No. 61/314,985, filed on Mar. 17, 2010, provisional application No. 61/314,979, filed on Mar. 17, 2010.

(51) Int. Cl.

| | |
|---|---|
| ***C12P 5/02*** | (2006.01) |
| ***C12N 1/00*** | (2006.01) |
| ***C12N 1/20*** | (2006.01) |

(52) U.S. Cl.

USPC .... 435/167; 435/243; 435/252.3; 435/254.11

(58) Field of Classification Search

USPC .......................... 435/167, 243, 252.3, 254.11

See application file for complete search history.

(56) References Cited

U.S. PATENT DOCUMENTS

| | | | |
|---|---|---|---|
| 4,570,029 | A | 2/1986 | Kulprathipanja et al. |
| 4,683,202 | A | 7/1987 | Mullis |
| 4,703,007 | A | 10/1987 | Mulholland et al. |
| 5,849,970 | A | 12/1998 | Fall et al. |
| 5,874,276 | A | 2/1999 | Fowler et al. |
| 6,022,725 | A | 2/2000 | Fowler et al. |
| 6,106,888 | A | 8/2000 | Dale et al. |
| 6,176,176 | B1 | 1/2001 | Dale et al. |
| 6,268,328 | B1 | 7/2001 | Mitchinson et al. |
| 6,316,695 | B1 | 11/2001 | Han et al. |
| 6,998,471 | B2 | 2/2006 | Hallahan et al. |
| 7,129,392 | B2 | 10/2006 | Hahn et al. |
| 7,132,527 | B2 | 11/2006 | Payne et al. |
| 7,241,587 | B2 | 7/2007 | Dodge et al. |
| 7,262,041 | B2 | 8/2007 | Baldwin et al. |
| 7,659,097 | B2 | 2/2010 | Renninger et al. |
| 8,173,410 | B2 | 5/2012 | Bott et al. |
| 2005/0079617 | A1 | 4/2005 | Cervin et al. |
| 2005/0287625 | A1 | 12/2005 | Miller et al. |
| 2008/0038805 | A1 | 2/2008 | Melis |
| 2008/0274523 | A1 | 11/2008 | Renninger et al. |
| 2009/0137014 | A1 | 5/2009 | Tsuruta et al. |
| 2009/0203102 | A1 | 8/2009 | Cervin et al. |
| 2009/0282545 | A1 | 11/2009 | Eichelberger et al. |
| 2010/0048964 | A1 | 2/2010 | Calabria et al. |
| 2010/0086978 | A1 | 4/2010 | Beck et al. |
| 2010/0113846 | A1 | 5/2010 | McAuliffe et al. |
| 2010/0167370 | A1 | 7/2010 | Chotani et al. |
| 2010/0167371 | A1 | 7/2010 | Chotani et al. |
| 2010/0178679 | A1 | 7/2010 | Anthony et al. |
| 2010/0184178 | A1 | 7/2010 | Beck et al. |
| 2010/0297749 | A1 | 11/2010 | Aravanis et al. |
| 2011/0045563 | A1 | 2/2011 | Melis |
| 2011/0178261 | A1 | 7/2011 | Feher et al. |
| 2012/0164711 | A1 | 6/2012 | Muir et al. |
| 2012/0329102 | A1 | 12/2012 | McAuliffe et al. |

FOREIGN PATENT DOCUMENTS

| | | | |
|---|---|---|---|
| EP | 0 215 594 | A2 | 3/1987 |
| EP | 0 215 594 | A3 | 3/1987 |
| EP | 0 215 594 | B1 | 3/1987 |
| EP | 0 215 594 | B2 | 3/1987 |
| EP | 0 238 023 | A2 | 9/1987 |
| EP | 0 238 023 | A3 | 9/1987 |
| EP | 0 238 023 | B1 | 9/1987 |
| EP | 0 238 023 | B2 | 9/1987 |
| EP | 0 244 234 | A2 | 11/1987 |
| EP | 0 244 234 | A3 | 11/1987 |
| EP | 0 244 234 | B1 | 11/1987 |
| EP | 0 244 234 | B2 | 11/1987 |
| WO | WO-95/04134 | A1 | 2/1995 |
| WO | WO-96/35796 | A1 | 11/1996 |
| WO | WO-98/02550 | A2 | 1/1998 |
| WO | WO-98/02550 | A3 | 1/1998 |
| WO | WO-2004/033646 | A2 | 4/2004 |

(Continued)

OTHER PUBLICATIONS

Broun et al., Catalytic plasticity of fatty acid modification enzymes underlying chemical diversity of plant lipids. Science, 1998, vol. 282: 1315-1317.*

Chica et al., Semi-rational approaches to engineering enzyme activity: combining the benefits of directed evolution and rational design. Curr. Opi. Biotechnol., 2005, vol. 16: 378-384.*

Devos et al., Practical limits of function prediction. Proteins: Structure, Function, and Genetics. 2000, vol. 41: 98-107.*

Grawert et al., IspH protein of *Escherichia coli*: Studies on iron-sulfur cluster implemntation and catalysis. JACS., 2004, vol. 126: 12847-12855.*

Kimchi-Sarfaty et al., A “Silent” polymorphism in the MDR1 gene changes substrate specificty. Science, 2007, vol. 315: 525-528.*

Kisselev L., Polypeptide release factors in prokaryotes and eukaryotes: same function, different structure. Structure, 2002, vol. 10: 8-9.*

Nackley et al., Human Caechol-O-Methytransferase haplotypes modulate protein expression by altering mRNA secondary structure. Science, 2006, vol. 314: 1930-1933.*

(Continued)

*Primary Examiner* — Ganapathirama Raghu

(74) *Attorney, Agent, or Firm* — Morrison & Foerster LLP

(57) ABSTRACT

The invention provides for methods for producing isoprene from cultured cells using various components of the DXP pathway and MVA pathway, or components associated with the DXP pathway and MVA pathway, iron-sulfur cluster-interacting redox polypeptides, and isoprene synthase. The invention also provides compositions that include these cultured cells.

16 Claims, 205 Drawing Sheets

(56) References Cited

FOREIGN PATENT DOCUMENTS

| | | | |
|---|---|---|---|
| WO | WO-2004/033646 A3 | | 4/2004 |
| WO | WO-2005/001036 A2 | | 1/2005 |
| WO | WO-2005/001036 C1 | | 1/2005 |
| WO | WO-2008/003078 A2 | | 1/2008 |
| WO | WO-2008/003078 A3 | | 1/2008 |
| WO | WO-2008/003078 A8 | | 1/2008 |
| WO | WO-2008/128159 A1 | | 10/2008 |
| WO | WO-2009/041581 A1 | | 4/2009 |
| WO | WO-2009/076676 A2 | | 6/2009 |
| WO | WO2009/076676 A2 | * | 6/2009 |
| WO | WO-2009/076676 A3 | | 6/2009 |
| WO | WO-2009/079448 | | 6/2009 |
| WO | WO-2009/132220 A2 | | 10/2009 |
| WO | WO-2009/132220 A3 | | 10/2009 |
| WO | WO-2010/003007 A2 | | 1/2010 |
| WO | WO-2010/003007 A3 | | 1/2010 |
| WO | WO-2010/031062 A1 | | 3/2010 |
| WO | WO-2010/031068 A1 | | 3/2010 |
| WO | WO-2010/031076 A2 | | 3/2010 |
| WO | WO-2010/031076 A3 | | 3/2010 |
| WO | WO-2010/031077 A1 | | 3/2010 |
| WO | WO-2010/031079 A1 | | 3/2010 |
| WO | WO-2010/078457 A2 | | 7/2010 |
| WO | WO-2010/078457 A3 | | 7/2010 |
| WO | WO-2010/124146 A2 | | 10/2010 |
| WO | WO-2010/124146 A3 | | 10/2010 |
| WO | WO-2010/148150 A1 | | 12/2010 |
| WO | WO-2010/148256 A1 | | 12/2010 |
| WO | WO-2011/034863 A1 | | 3/2011 |
| WO | WO-2012/058494 A2 | | 5/2012 |
| WO | WO-2012/058494 A3 | | 5/2012 |
| WO | WO-2012/088450 A1 | | 6/2012 |
| WO | WO-2012/088462 A1 | | 6/2012 |

OTHER PUBLICATIONS

Puan et al., fldA is an essential gene required in the 2-C-methyl-D-erythritol 4-phospahte pathway for isoprenoid synthesis. FEBS Lett., 2005, vol. 579: 3802-3806.*

Sauna et al., Silent polymorhisms speak: How they affect pharmacogenomics and the treatment of cancer. Cancer Res., 2007, vol. 67(20): 9609-9612.*

Sen et al., Developments in directed evolution for improving enzyme functions. Appl. Biochem. Biotechnol., 2007, vol. 143: 212-223.*

Whisstock et al., Prediction of protein function from protein sequence. Q. Rev. Biophysics., 2003, vol. 36 (3): 307-340.*

Wishart et al., A single mutation converts a novel phosphotyrosine binding domain into a dual-specificity phosphatase. J. Biol. Chem., 1995, vol. 270(45): 26782-26785.*

Witkowski et al., Conversion of b-ketoacyl synthase to a Malonyl Decarboxylase by replacement of the active cysteine with glutamine. Biochemistry, 1999, vol. 38: 11643-11650.*

Zepeck et al., Biosynthesis of isoprenoids. Purification and properties of ispG protein from *Escherichia coli*. J. Org. Chem., 2005, vol. 70: 9168-9174.*

Kajiwara, S. et al. (1997). "Expression of an exogenous isopentenyl diphosphate isomerase gene enhances isoprenoid biosynthesis in *Escherichia coli," Biochem. J.* 324:421-426.

Akhtar, M.K. et al. (2008). "Deletion of iscR Stimulates Recombinant Clostridial Fe—Fe Hydrogenase Activity and $H_2$-Accumulation in *Escherichia coli* BL21(DE3)," *Applied Microbiol Biotechnol*, 78(5):853-865.

Alexopoulos, C.J. (1962). *Introductory Mycology*, Wiley, New York.

Anderson, M.S. et al. (Nov. 15, 1989). "Isopentenyl Diphosphate: Dimethylallyl Diphosphate Isomerare. An Improved Purification of the Enzyme and Isolation of the Gene From *Saccharomyces cerevisia," J. Biol. Chem.* 264(32):19169-19175.

Ausubel, F.M. et al. eds. (1987). Current Protocols in Molecular Biology, Supplement 30, section 7.7.18.

Baba, T. et al. (2006). "Construction of *Escherichia coli* K-12 In-Frame, Single-Gene Knockout Mutants: The Keio Collection," *Mol. Syst. Biol.*, 2006.008:1-11.

Bellion, E. et al. (1993). "Methylamine Utilization in Yeast and Bacteria: Studies Using in vivo NMR," Chapter 32 in *Microbial Growth* $C_1$ *Compounds*, Muerrell, J.C. et al. eds, Intercept Ltd: Andover, UK, pp. 415-432.

Bennett, J.W. et al. eds. (1991). "Gene Cloning and Analysis," Chapter 3 in *More Gene Manipulations in Fungi*, Academic Press, San Diego, CA pp. 70-76.

Boel, E. et al. (1984). "Two Different Types of Intervening Sequences in the Glucoamylase Gene from *Aspergillus niger," The EMBO Journal* 3(7):1581-1585.

Bouvier, F. et al. (2005). "Biogenesis, Molecular Regulation and Function of Plant Isoprenoids," *Progress in Lipid Res.* 44:357-429.

Brown, L. et al. (1996). "Enyzymatic Saccharification of Lignocellulosic Biomass," *NREL standard assay method Lap-009.*

Campbell, E.I. et al. (1989). "Improved Transformation Efficiency of *Aspergillus niger* Using the Homologus *nia*D Gene for Nitrate Reductase," *Curr. Genet.* 16:53-56.

Cao, Q-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.

Chao, Y-P et al. (2002). "Stringent Regulation and High-Level Expression of Heterologous Genes in *Escherichia coli* Using T7 System Controllable by the araBAD Promoter," *Biotechnol. Prog.*, 18(2):394-400.

Chen, J-S et al. (1979). "A Simple Hydrogenase-Linked Assay for Ferredoxin and Flavordoxin," *Analytical Biochem*, 93:216-222.

Cirino, P. et al. (2006). "Engineering *Escherichia coli* for Xylitol Production From Glucose-Xylose Mixture," *Biotech. Bioeng.*, 95:1167-1176.

Dhe-Paganon, S. et al. (1994). "Mechanism of Mevalonate Pyrophosphate Decarboxylase: Evidence for a Carbocationic Transition State," *Biochemistry* 33(45):13355-13362.

Djaman, O. et al. (2004). "Repair of Oxidized Iron-Sulfur Clusters in *Escherichia coli," J. of Biol. Chem.*, 279(43):44590-44599.

Ecocyc. (2005) "ribF-ileS-IspA-fkpB-ispH 5-gene operon," located at <http://ecocyc.org/ECOLI/substring-search?type=NIL?object-+ribF-ileS-IspA-fkpB-ispH+,> last visited on May 29, 2012, three pages.

Eppler, T. et al. (1999). "Glycerol-3-Phosphate-Mediated Repression of malt in *Escherichia coli* Does Not Require Metabolism, Depends on Enzyme $IIA^{Glc}$ And Is Mediated by cAMP Levels," *Mol.l Microbiol.*, 33:1221-1231.

Finkelstein, D.B. (1992). "Transformation," Chapter 6 in *Biotechnology of Filamentous Fungi*, Butterworth-Heinemann: Boston, MA, pp. 113-156.

Fraenkel, D.G. (1968). "Selection of *Escherichia coli* Mutants Lacking Glucose-6-Phosphate Dehydrogenase or Gluconate-6-Phosphate Dehydrogenase," *J. Bacteriol.*, 95(4):1267-1271.

GenBank Accession No. AAQ84170, last updated on Feb. 15, 2005, located at <http://www.ncbi.nlm.nih.gov/protein/AAQ84170>, last visited on Dec. 22, 2011, 2 pages.

GenBank Accession No. AJ457070, last updated on Apr. 15, 2005, located at <http://www.ncbi.nlm.nih.gov/nuccore/38092202>, last visited on Jun. 2, 2010, 2 pages.

GenBank Accession No. AY182241, last updated on May 4, 2004, located at <http://www.ncbi.nlm.nih.gov/nuccore/32265057>, last visited on Jun. 2, 2010, 2 pages.

GenBank Accession No. AY279379, last updated on Mar. 11, 2005, located at <http://www.ncbi.nlm.nih.gov/nuccore/30984014>, last visited on Jun. 2, 2010, 2 pages.

GenBank Accession No. AY316691, last updated on Feb. 15, 2005, located at <http://www.ncbi.nlm.nih.gov/nuccore/35187003>, last visited on Jun. 2, 2010, 2 pages.

GenBank Accession No. AY341431, last updated on Feb. 15, 2005, located at <http://www.ncbi.nlm.nih.gov/nuccore/33358228>, last visited on Jun. 2, 2010, 3 pages.

GenBank Accession No. CAC35696, last updated Apr. 15, 2005, located at <http://www.ncbi.nlm.nih.gov/protein/CAC35696>, last visited on Nov. 1, 2011, 2 pages.

GenBank Accession No. CP001164, last updated Dec. 14, 2011, located at <http://www.ncbi.nim.nih.gov/protein/CP001164> last visted on May 29, 2012, seventy-six pages.

GenBank Accession No. D86235, last updated Oct. 29, 1997, located at <http://www.ncbi.nlm.nih.gov/nuccore/D86235> last visited on Feb. 27, 2012, two pages.
GenBank Accession No. E02927, last updated Nov. 4, 2005, located at <http://www.ncbi.nlm.nih.gov/nuccore/E02927> last visited on May 29, 2012, one page.
Gerhardt, P. et al. eds. (1994). Methods for General and Molecular Bacteriology, American Society for Microbiology: Washington, D.C., p. v, (Table of Contents Only).
Goedegebuur, F. et al. (2002). "Cloning and Relational Analysis of 15 Novel Fungal Endoglucanases form Family 12 Glycosyl Hydrolase," *Curr Genet.* 41:89-98.
Gottschalk, G. (1986). Bacterial Metabolism, Second Edition, Springer Verlag: New York, NY, pp. xi-xiii, (Table of Contents Only).
Grawert, T. et al. (2004, e-pub. Sep. 21, 2004). "IspH Protein of *Escherichia coli*: Studies on Iron-Sulfur Cluster Implementation and Catalysis," *Journal American Chemistry Society* 126:12847-12855.
Greenberg, J.P. et al. (1993). "Sub-Parts Per Billion Detection of Isoprene Using a Reduction Gas Detector with a Portable Gas Chormatograph," *Atmos. Environ.* 27A(16):2689-2692.
Guzman, L.M. et al. (Jul. 1995). "Tight Regulation, Modulation, and High-Level Expression by Vectors Containing the Arabinsoe $P_{BAD}$ Promoter," *Journal of Bacteriology* 177(14):4121-4130.
Hale, W.G. et al. (1991). The Harper Collins Dictionary of Biology, Ehrlich, E. ed., Harper Perennial: New York, NY, 2 pages.
Harkki, A. et al. (Jun. 1989). "A Novel Fungal Expression System: Secretion of Active Calf Chymosin From the Filamentous Fungus *Trichoderma ressei,*" *Bio. Technol.* 7:596-603.
Harkki, A. et al. (Mar. 1991). "Genetic Engineering of *Trichoderma* to Produce Strains with Novel Cellulase Profiles," *Enzyme Microb. Technol.* 13:277-233.
Hedl, M. et al. (Apr. 2002). "*Enterococcus faecalis* Acetoacetyl-Coenzyme A Thiolase/3-Hydroxy-3-Methyglutaryl-Coenzyme A Reductase, A Dual-Function Protein of Isopentenyl Diphosphate Biosynthesis," *J. Bacteriol.* 184(8):2116-2122.
Hoeffler, J-F. et al. (2002). "Isoprenoid Biosynthesis via the Methylerythritol Phosphate Pathway. Mechanistic Investigations of the 1-Deoxy-$_D$-Xylulose 5-Phosphate Reductiosimerase," *Eur. J. Biochem.* 269:4446-4457.
Hunter, B.K. (1985). "Formaldehyde Metabolism by *Escherichia coli.* Carbon and Solvent Deuterium Incoproration into Glycerol, 1,2-Propanediol, and 1,3-Propanediol," *Biochemistry* 24(15):4148-4155.
Ilmen, M. et al. (Apr. 1997). "Regulation of Cellulase Gene Expression in the Filamentous Fungus *Trichoderma reesei,*" *Appl. Environ. Microbiol.* 63(4):1298-1306.
Innis, M.A. et al. (1985). "Expression, Glycosylation, and Secretion of an *Aspergillus* Glucoamylase by *Saccharomyces cerevisiae,*" *Science* 228:21-26.
International Search Report mailed on Sep. 9, 2010, for PCT Patent Application No. PCT/US2010/038904, filed Jun. 16, 2010, 2 pgs.
Jawaid, S. et al. (2009). "Kinetic Charaterization and Phosphoregulation of the *Francisella tularensis* 1-Deoxy-D0Xylulose 5-Phosphate Reductoisomerase (MEP Synthase)," *PLoS One*, 4(12):e8288.
Jobling, M. et al. (1990). "Construction of Vectors With the p15a Replicon, Kanamycin Resistance, Inducible lasZα and pUC18 or pUC19 Multiple Cloning Sites," *Nucleic Acids Research*, 18(17):5315-5316.
Julsing, M.K. et al. (2007). "Functional Analysis of Genes Involved in the Biosynthesis of Isoprene in *Bacillus subtilis,*" *Applied Microbiol. Biotechnol.*75:1377-1384.
Kajiwara, Y. et al. (1997). "Production of Acid-Stable α-Amylase by *Aspergillus kawachii* During Barley Shochu-Koji Production," *Journal of Fermentation and Bioengineering,* 84(3):224-227.
Kelley, J.M. et al. (1985). "Transformation of *Aspergillus niger* by the *amd*S Gene of *Asperfillus nidulans,*" *The EMBO Journal* 4(2):475-479.
Kinghorn, J.R. et al. (1992). Applied Molecular Genetics of Filamentous Fungi, Blackie Academic Professional and Chapman and Hall: London, 3 pages, (Table of Contents Only).
Koppisch, A.T. et al. (2002). "*E. coli* MEP Synthase: Steady-State Kinetic Analysis and Substrate Binding," *Biochemistry* 41:236-243.
Kovach, M.E. et al. (1995). "Four New Derivatives of the Broad-Host-Range Cloning Vector pBBR1MCS, Carrying Different Antibiotic-Resistance Cassettes," *Gene* 166:175-176.
Kreigler, M. (1990). Gene Transfer and Expression: A Laboratory Manual, W.H. Freeman and Company: New York, NY, pp. vii-x, (Table of Contents Only.).
Leonardi, R. et al. (2003). "Thiamine Biosynthesis in *Escherichia coli*: Isolation and Initial Characterisation of the ThiGH Complex,"*FEBS Lett.*, 539(1-3):95-99.
Leonardi, R. et al. (2004). "Thiamine Biosynthesis in *Escherichia coli,*" *J. Biol. Chem.*, 279(17):17054-17062.
Lerner, C.G. et al. (1990). "Low Copy Number Plasmids for Regulated Low-Level Expression of Cloned Genes in *Escherichia coli* With Blue/White Insert Screening Capability," *Nucleic Acids Research*, 18(15):4631.
Lüttgen, H. et al. (Feb. 1, 2000). "Biosynthesis of Terpenoids: YchB Protein *Escherichia coli* Phosphorylates the 2-Hydroxy Group of 4-Diphosphocytidyl-2C-Methyl-$_D$-Erythritol," *PNAS* 97(3):1062-1067.
Lynch, et al. (2007). *Nat. Methods*, 4(1):87-93.
Martin, V. et al. (2003). "Engineering a Mevalonate Pathway in *Escherichia coli* for Production of Terpenoids," *Nature Biotechnology*,21(7):796-802.
Miller, B. et al. (2001, e-pub. May 10, 2001). "First Isolation of an Isoprene Synthase Gene from Poplar and Successful Expression of the Gene in *Escherichia coli,*" *Planta* 213:483-487.
NCBI. (2012). Located at <http://www.ncbi.nlm.nih.gov/> last visited on May 29, 2012, two pages.
Nemeria, N. et al. (2005). "Glutamate 636 of the *Escherichia coli* Pyruvate Dehydrogenase-E1 Participates in Active Center Communication and Behaves as an Engineered Acetolactate Synthase With Unusual Stereoselectivity," *J. Biol. Chem..*, 280(22):21473-21482.
Nevalainen, K.M.H. et al. (1992). "The Molecular Biology of *Trichoderma* and Its Application to the Expression of Both Homologous and Heterologous Genes," Chapter 6 in *Molecular Industrial Mycology, Systems and Applications for Filamentous Fungi,* Leong, S.A. et al. eds., Marcel Dekker Inc.: New York, NY, pp. 129-148.
Nunberg, J.H. et al. (Nov. 1984). "Molecular Cloning and Characterization of the Glucoamylase Gene of *Aspergillus awamori,*" *Mol. Cell. Biol.* 4(11):2306-2315.
Okada, et al. (2005). *J. Biol. Chem.*, 280(21):20627-20629.
Oulmouden, A. et al. (1991). "Nucleotide Sequence of the *ERG12* Gene of *Saccharomyces cerevisiae* Encoding Mevalonate Kinase," *Curr. Genet.* 19:9-14.
Palmeros, B. et al. (2000). "A Family of Removable Cassettes Designed to Obtain Antibiotic-Resistance-Free Genomic Modifications of *Escherichia coli* and Other Bacteria," *Gene,* 18:247(1-2):255-264.
Paun, K-J. et al. (2005). "fldA is an Essential Gene Required in the 2-C-Methyl-D-Erythritol 4-Phosphate Pathway for Isoprenoid Biosynthesis," *FEBS Letters* 579:3802-3806.
Penttila, M. et al. (1987). "A Versatile Transformation System for the Cellulolytic Filamentous Fungus *Trichoderma reesei,*" *Gene* 61:155-164.
Perrenoud, A. et al. (2005). "Impact of Global Transcriptional Regulation by ArcA, ArcB, Cra, Crp, Cya, Fnr, and Mlc on gloucose Catabolism in *Escherichia coli,*" *Journal of Bacteriology*, 187(9):3171-3179.
Pourquie, J. et al. (1988). "Scale Up of Cellulase Production and Utilization," in *Biochemistry and Genetics of Cellulose Degradation*, Aubert, J.-P. et al. eds., Academic Press: San Diego, CA, pp. 71-86.
Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-C-Methylerythritol," *PNAS* 96(21):11758-11763.
Rohdich, F. et al. (Jun. 6, 2000). "Biosynthesis of Terpenoids: 4-Diphosphocytidyl-2C-Methyl-$_D$-Erythritol Synthase of *Arabidopsis thaliana,*" *PNAS* 97(12):6451-6456.
Sambrook, J. et al. (1989). Molecular Cloning: A Laboratory Manual, 2nd edition, Cold Spring Harbor Laboratory Press: New York, NY, pp. xi-xxxviii (Table of Contents Only).

Sasaki, K. et al. (2005). "Gene Expression and Characterization of Isoprene Synthase from *Populus alba*," *FEBS Letters*, 579:2514-2518.
Sauret-Gueto, S. et al. (2006). "A Mutant Pyruvate Dehydrogenase E1 Subunit Allows Survival of *Escherichia coli* Strains Defective in 1-Deoxy-d-Xylulose 5-Phosphate Synthase," *FEBS Letters*, 580:736-740.
Schnitzler, J.-P. et al. (2005, e-pub. Jul. 29, 2005). "Biochemical Properties of Isoprene Synthase in Poplar (*Populus x canescens*)," *Planta* 222(5):777-786.
Schwartz, et al. (2001). *PNAS*, 98(26):14751-14753.
Seemann, M. et al. (2002). *Agnew. Chem, Int. Ed.*, 41:4337-4339.
Seemann, M. et al. (2006). "Isoprenoid Bioisynthesis in Plant Chloroplasts Via the MEP Pathway: Direct Thylakoid/Ferrdoxin-Dependent Potoreduction of GcpE/IspG," *FEBS Letters*, 580(6):1547-1552.
Seta, F.D., et al. (1997). "Characterization of *Escherichia Coli* Strains With gapA and gapB Genes Deleted," *Journal of Bacteriology*, 179(16):5218-5221.
Sharkey, T.D. et al. (Feb. 2005). "Evolution of the Isoprene Biosynthetic Pathway in Kudzu," *Plant Physiology* 137:700-712.
Sheir-Neiss, G. et al. (Jul. 1984). "Characterization of the Secreted Ceullulases of *Trichoderma ressei* Wild Type and Mutants During Controlled Fermentations," *Appl. Microbiol. Biotechnol.* 20(1):46-53.
Silver, G.M. et al. (1991). "Enzymatic Synthesis of Isoprene from Dimethylallyl Diphosphate in Aspen Leaf Extracts," *Plant Physiol.* 97:1588-1591.
Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.
Sivy, et al. (2002). *Biochem Biophys Res Commun.*, 294:71-75.
Sprenger, G.A. et al. (Nov. 1997). "Identification of a Thiamin-Dependent Synthase in *Escherichia coli* Required for the Formation of the 1-Deoxy-$_D$-Xylulose 5-Phosphate Precursor to Isoprenoids, Thiamin, and Pyridoxol," *PNAS* 94:12857-12862.
Sulter, G.J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.
Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *J. Bacteriol.* 184(15):4065-4070.
Tchieu, et al. (2001), *J. Mol. Microbiol. Biotechnol.*, 3(3):329-346.
Teymouri, F. et al. (2005, e-pub. Feb. 24, 2005). "Optimization of the Ammonia Fiber Explosion (AFEX) Treatment Parameters for Enzymeatic Hydrolysis of Corn Stover," *Bioresource Technology* 96:2014-2018.
Thomason, L. et al. (2004). "Identification of the *Escherichia coli* K-12 ybhE Gene as pgl, Encoding 6-Phosphogluconolactonase," *Journal of Bacteriology,* 186(24):8248-8253.
Tokumoto, et al. (2001). *J Biochem.*, 130:63-71.
Tsay, Y.H. et al. (Feb. 1991). "Cloning and Characterization of *ERG8*, an Essential Gene of *Saccharomyces cerevisiae* That Encodes Phosphomevalonate Kinase," *Mol. Cell Biol.* 11(2):620-631.
Van Den Hondel, C.A.M.J.J. et al. (1991). "Heterologous Gene Expression in Filamentous Fungi," Chapter 18 in *More Gene Manipulations in Fungi,* Bennet J.W. et al. eds., Academic Press, Inc.: San Diego, CA, pp. 396-428.
Vander Horn, et al. (1993). *J. Bacteriol.*, 175(4):982-992.
Wagner, W.P. et al. (2000). "Isoprene Biosynthesis in *Bacillus subtilis* Via the Methylerythritol Phosphate Pathway," *J. Nat. Prod.*, 63:37-40.
Ward, M. et al. (1993). "Use of *Aspergillus* Overproducing Mutants, Cured for Integrated Plasmid, to Overproduce Heterologous Proteins," *Appl. Microbiol. Biotechnol.*, 39(6):738-743.
Withers, S.T. et al. (Oct. 2007, e-pub. Aug. 10, 2007). "Identification of Isopentenol Biosynthetic from *Bacillus subtilis* by a Screening Method Based on Isorpenoid Precursor Toxicity," *Appl. Environ Microbiol.* 73(19):6277-6283.
Wolff,M. et al. (2003). "Isoprenoid Biosynthesis Via the Methylerthritol Phosphate Pathway: The (E)-4-Hydroxy-3-Methylbut-2-Enyl Diphosphate Reductase (LytB/IspH) from *Escherichia cili* is a [4Fe-4S] Protein," *FEBS Letters,* 54:115-120.
World-wide web at "expasy.org", Swiss Institute of Bioinformatics Swiss-Prot group CMU—1 rue Michel Servet CH-1211 Geneva 4, Switzerland, May 21, 2012.
World-wide web at genome.jp/kegg/pathway/map/map00100.html, last visited on May 29, 2012, one page.
Yamada, K. et al. (1989). "Production of Glycerol from Methanol by a Mutant Strain of *Candida boidinii* No. 2201," *Agric. Biol. Chem.* 53(2):541-543.
Yelton, M.M. et al. (Mar. 1984). "Transformation of *Aspergillus nidulans* by Using a *trpC* Plasmid," *PNAS* 81:1470-1474.
Zepeck, F. et al. (2005, e-pub. Oct. 14, 2005). "Biosynthesis of Isoprenoids. Purification and Properties of IspG Protein from *Escherichia coli," J. Org. Chem.* 70:9168-9174.
Berka, R.M. et al. (1989). "The Development of Gene Expression Systems for Filamentous Fungi," *Biotechnology Advances* 7(2):127-154.
Bhayana, V. et al. (Jun. 1984). "Amino Acid Sequence of *Escherichia coli* Citrate Synthase," *Biochemistry* 23(13):2900-2905.
Bitoun, J.P. et al. (Dec. 2008). "*Escherichia coli* FtnA Acts as an Iron Buffer for Reassembly of Iron-Sulfur Clusters in Response to Hydrogen Peroxide Stress," *Biometals* 21(6):693-703.
Bologna, F.P. et al. (Aug. 2007). "*Escherichia coli* Malic Enzymes: Two Isoforms with Substantial Differences in Kinetic Properties, Metabolic Regulation, and Structure," *Journal of Bacteriology* 189(16):5937-5946.
Bukau, B. et al. (Feb. 6, 1998). "The Hsp70 and Hsp60 Chaperone Machines," *Cell* 92:351-366.
Bunch, P.K. et al. (1997). "The *IdhA* Gene Encoding the Fermentative Lactate Dehydrogenase of *Escherichia coli," Microbiology* 143:187-195.
Duckworth, H.W. et al. (1987). "Structural Basis for Regulation in Gram-Negative Bacterial Citrate Synthases," *Biochem. Soc. Symp.* 54:83-92.
GenBank Accession No. NC_001416, last updated Mar. 11, 2011, located at <http://www.ncbi.nlm.nih.gov/nuccore/NC_001416> last visited on Feb. 8, 2013, forty-two pages.
International Search Report mailed on Mar. 2, 2012, for PCT Patent Application No. PCT/US2011/066924, filed on Dec. 22, 2011, published on Jun. 28, 2012 as WO 2012/088450, 3 pages.
International Search Report mailed on May 18, 2012, for PCT Patent Application No. PCT/US2011/066949, filed on Dec. 22, 2011, published on Jun. 28, 2012, as WO 2012/088462, 3 pages.
Iwakura, M. et al. (1979). "Studies on Regulatory Functions of Malic Enzymes," *J. Biochem.* 85:1355-1365.
Justino, M.C. et al. (Apr. 6, 2007). "*Escherichia coli* Di-iron YtfE Protein Is Necessary for the Repair of Stress-damaged Iron-Sulfur Clusters," *The Journal of Biological Chemistry* 282(14):10352-10359.
Justino, M.C. et al. (2009) "Di-iron Proteins of the Ric Family are Involved in Iron-sulfur Cluster Repair," *Biometals* 22:99-108.
Kakuda, H. et al. (Jun. 13, 1994). "Identification and Characterization of the *ackA* (Acetate Kinase A)-*pta* (Phosphotransacetylase) Operon and Complementation Analysis of Acetate Utilization by an *ackA-pta* Deletion Mutant of *Escherichia coli*," J. Biochem. 116:916-922.
Lindberg, P. et al. (Jan. 2010). "Engineering a Platform for Photosynthetic Isoprene Production in Cyanobacteria, Using *Synechocystis* as the Model Organism," Metabolic Engineering 12(1):70-79.
Loiseau, L. et al. (Aug. 21, 2007). "ErpA, an Iron-Sulfur (Fe—S) Protein of the A-type Essential for Respiratory Metabolism in *Escherichia coli," PNAS* 104(34):13626-13631.
Maurus, R. et al. (2003). "Insights into the Evolution of Allosteric Properties. The NADH Binding Site of Hexameric Type II Citrate Synthases," *Biochemistry* 42:5555-5565.
Ner, S.S. et al. (Nov. 8, 1983). "Complete Sequence of the *glt* A Gene Encoding Citrate Synthase in *Escherichia coli," Biochemistry* 22(23):5243-5249.

Ogasawara, H. et al. (Aug. 2007). "PdhR (Pyruvate Dehydrogenase Complex Regulator) Controls the Respiratory Electron Transport System in *Escherichia coli," Journal of Bacteriology* 189(15):5534-5541.
Oh, M-K. et al. (Apr. 12, 2002). "Global Expression Profiling of Acetate-grown *Escherichia coli," J. Biol. Chem.* 277(15):13175-13183.
Romanos, M.A. et al. (Jun. 1992). "Foreign Gene Expression in Yeast: a Review," *Yeast* 8(6):423-488.
Sakamoto, I, et al. (2000), "Synthesis of 2-*C*-Methyl-D-erythritol and 2-*C*-Methyl-L-threitol; Determination of the Absolute Configuration of 2-*C*-Methyl-1,2,3,4-butanetetrol Isolated from *Phlox sublata* L," *Biosci. Biotechnol. Biochem.* 64(9):1915-1922.
Sánchez, A.M. et al. (May 2005). "Novel Pathway Engineering Design of the Anaerobic Central Metabolic Pathway in *Escherichia coli* to Increase Succinate Yield and Productivity," Metabolic Engineering 7(3):229-239.
Sangari, F.J. et al. (Aug. 10, 2010). "A New Family of Enzymes Catalyzing the First Committed Step of the Methylerythritol 4-phosphate (MEP) Pathway for Isoprenoid Biosynthesis in Bacteria," *PNAS* 107(32):14081-14086.
Seffernick, J.L. et al. (Apr. 2001). "Melamine Deaminase and Atrazine Chlorohydrolase: 98 Percent Identical but Functionally Different," *J. Bacteriol.* 183(8):2405-2410.
Shimizu, M. et al. (1969) "Phosphotransacetylase of *Escherichia coli* B, Purification and Properties," *Biochim. Biophys. Acta.* 191(3):550-558.
Stokell, D.J. et al. (Sep. 12, 2003). "Probing the Roles of Key Residues in the Unique Regulatory NADH Binding Site of Type II Citrate Synthase of *Escherichia coli," J. Biol. Chem.* 278(37):35435-35443.
U.S. Appl. No. 13/283,564, filed Oct. 27, 2011 by Beck et al.
Underwood, S.A. et al. (Mar. 2002). "Flux through Citrate Synthase Limits the Growth of Ethanologenic *Escherichia coli* KO11 during Xylose Fermentation," *Applied and Environmental Microbiology* 68(3):1071-1081.
Vinella, D. et al. (May 29, 2009). "Iron-Sulfur (Fe/S) Protein Biogenesis: Phylogenomic and Genetic Studies of A-Type Carriers," *PLOS Genetics* 5(5):1-16 of e1000497.
Wiegand, G. et al. (1986). "Citrate Synthase: Structure, Control, and Mechanism," *Ann. Rev. Biophys. Biophys. Chem.* 15:97-117.
Wolfe, A. (Mar. 2005). "The Acetate Switch," *Microbiology and Molecular Biology Reviews* 69(1):12-50.
Miller, B. (2001). "Erstmalige Isolierung eines Isoprensynthase-Gens and heterologe Expression des aus der Pappel stammenden Gens sowie Charakterisierung der Eingangsgene des Mevalonat-unabhängigen Isoprenoidbiosyntheseweges aus dem Cyanobakterium Synechococcus leopoliensis," located at <http://kups.ub.uni-koeln.de/volltexte/2003/883/pdf/millerbarbara.pdf>, last visited on Feb. 25, 2013, two pages (with English Translation).
Singh, N. et al. (2007). "Targeting the Methyl Erythritol Phosphate (MEP) Pathway for Novel Antimalarial, Antibacterial and Herbicidal Drug Discovery: Inhibition of 1-Deoxy-D-Xylulose-5-Phosphate Reductoisomerase (DXR) Enzyme," *Current Pharmaceutical Design* 13(11):1161-1177.

* cited by examiner

Figure 1

1-
*atg*tgtgcgacctcttctcaatttactcagattaccgagcataattcccgtcgttccgcaaact
atcagccaaacctgtggaatttcgaattcctgcaatccctggagaacgacctgaaagtggaaaa
gctggaggagaaagcgaccaaactggaggaagaagttcgctgcatgatcaaccgtgtagacacc
cagccgctgtccctgctggagctgatcgacgatgtgcagcgcctgggtctgacctacaaatttg
aaaaagacatcattaaagccctggaaaacatcgtactgctggacgaaaacaaaaagaacaaatc
tgacctgcacgcaaccgctctgtctttccgtctgctgcgtcagcacggtttcgaggtttctcag
gatgtttttgagcgtttcaaggataaagaaggtggtttcagcggtgaactgaaaggtgacgtcc
aaggcctgctgagcctgtatgaagcgtcttacctgggtttcgagggtgagaacctgctggagga
ggcgcgtaccttttccatcacccacctgaagaacaacctgaaagaaggcattaataccaaggtt
gcagaacaagtgagccacgccctggaactgccatatcaccagcgtctgcaccgtctggaggcac
gttggttcctggataaatacgaaccgaaagaaccgcatcaccagctgctgctggagctggcgaa
gctggattttaacatggtacagaccctgcaccagaaagagctgcaagatctgtcccgctggtgg
accgagatgggcctggctagcaaactggattttgtacgcgaccgcctgatggaagtttatttct
gggcactgggtatggcgccagacccgcagtttggtgaatgtcgcaaagctgttactaaaatgtt
tggtctggtgacgatcatcgatgacgtgtatgacgtttatggcactctggacgaactgcaactg
ttcaccgatgctgtagagcgctgggacgttaacgctattaacaccctgccggactatatgaaac
tgtgtttcctggcactgtacaacaccgttaacgacacgtcctattctattctgaaagagaaagg
tcataacaacctgtcctatctgacgaaaagctggcgtgaactgtgcaaagcctttctgcaagag
gcgaaatggtccaacaacaaaattatcccggctttctccaagtacctggaaaacgccagcgttt
cctcctccggtgtagcgctgctggcgccgtcttacttttccgtatgccagcagcaggaagacat
ctccgaccacgcgctgcgttccctgaccgacttccatggtctggtgcgttctagctgcgttatc
ttccgcctgtgcaacgatctggccacctctgcggcggagctggaacgtggcgagactaccaatt
ctatcattagctacatgcacgaaaacgatggtaccagcgaggaacaggcccgcgaagaactgcg
taaactgatcgacgccgaatggaaaaagatgaatcgtgaacgcgttagcgactccaccctgctg
cctaaagcgttcatggaaatcgcagttaacatggcacgtgtttcccactgcacctaccagtatg
gcgatggtctgggtcgcccagactacgcgactgaaaaccgcatcaaactgctgctgattgaccc
tttcccgattaaccagctgatgtatgtc
taactgcag
(SEQ ID NO:1)

Figure 3A 1-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaata<u>aggagg</u>aataaaccATGtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtc*TAA*ctgca
gctggtaccatatgggaattcgaagctttctagaacaaaaactcatctcagaagaggatctgaa
tagcgccgtcgaccatcatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgaccccatgccgaactcagaagtg
aaacgccgtagcgccgatggtagtgtggggtctccccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg

Figure 3B agggtggcgggcaggacgcccgccataaactgccaggcatcaaattaagcagaaggccatcctg
acggatggcctttttgcgtttctacaaactctttttgtttatttttctaaatacattcaaatat
gtatccgctcatgagacaataaccctgataaatgcttcaataatattgaaaaaggaagagtatg
agtattcaacatttccgtgtcgcccttattcccttttttgcggcattttgccttcctgtttttg
ctcacccagaaacgctggtgaaagtaaaagatgctgaagatcagttgggtgcacgagtgggtta
catcgaactggatctcaacagcggtaagatccttgagagttttcgccccgaagaacgttttcca
atgatgagcacttttaaagttctgctatgtggcgcggtattatcccgtgttgacgccgggcaag
agcaactcggtcgccgcatacactattctcagaatgacttggttgagtactcaccagtcacaga
aaagcatcttacggatggcatgacagtaagagaattatgcagtgctgccataaccatgagtgat
aacactgcggccaacttacttctgacaacgatcggaggaccgaaggagctaaccgcttttttgc
acaacatgggggatcatgtaactcgccttgatcgttgggaaccggagctgaatgaagccatacc
aaacgacgagcgtgacaccacgatgcctgtagcaatggcaacaacgttgcgcaaactattaact
ggcgaactacttactctagcttcccggcaacaattaatagactggatggaggcggataaagttg
caggaccacttctgcgctcggcccttccggctggctggtttattgctgataaatctggagccgg
tgagcgtgggtctcgcggtatcattgcagcactggggccagatggtaagccctcccgtatcgta
gttatctacacgacggggagtcaggcaactatggatgaacgaaatagacagatcgctgagatag
gtgcctcactgattaagcattggtaactgtcagaccaagtttactcatatatactttagattga
tttaaaacttcatttttaatttaaaaggatctaggtgaagatcctttttgataatctcatgacc
aaaatcccttaacgtgagttttcgttccactgagcgtcagaccccgtagaaaagatcaaaggat
cttcttgagatcctttttttctgcgcgtaatctgctgcttgcaaacaaaaaaaccaccgctacc
agcggtggtttgtttgccggatcaagagctaccaactctttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccagggggaaacgcctggtatctt
tatagtcctgtcgggtttcgccacctctgacttgagcgtcgatttttgtgatgctcgtcagggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct

Figure 3C

Gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
(SEQ ID NO:2)

Figure 5A 1-
ttctcatgtttgacagcttatcatcgataagctttaatgcggtagtttatcacagttaaattgc
taacgcagtcaggcaccgtgtatgaaatctaacaatgcgctcatcgtcatcctcggcaccgtca
ccctggatgctgtaggcataggcttggttatgccggtactgccgggcctcttgcgggatatccg
gatatagttcctcctttcagcaaaaaacccctcaagacccgtttagaggccccaaggggttatg
ctagttattgctcagcggtggcagcagccaactcagcttcctttcgggctttgttagcagccgg
atccctgcagttagacatacatcagctggttaatcgggaaagggtcaatcagcagcagtttgat
gcggttttcagtcgcgtagtctgggcgacccagaccatcgccatactggtaggtgcagtgggaa
acacgtgccatgttaactgcgatttccatgaacgctttaggcagcagggtggagtcgctaacgc
gttcacgattcatctttttccattcggcgtcgatcagtttacgcagttcttcgcgggcctgttc
ctcgctggtaccatcgttttcgtgcatgtagctaatgatagaattggtagtctcgccacgttcc
agctccgccgcagaggtggccagatcgttgcacaggcggaagataacgcagctagaacgcacca
gaccatggaagtcggtcagggaacgcagcgcgtggtcggagatgtcttcctgctgctggcatac
ggaaaagtaagacggcgccagcagcgctacaccggaggaggaaacgctggcgttttccaggtac
ttggagaaagccgggataatttgttgttggaccatttcgcctcttgcagaaaggctttgcaca
gttcacgccagcttttcgtcagataggacaggttgttatgacctttctctttcagaatagaata
ggacgtgtcgttaacggtgttgtacagtgccaggaaacacagtttcatatagtccggcagggtg
ttaatagcgttaacgtcccagcgctctacagcatcggtgaacagttgcagttcgtccagagtgc
cataaacgtcatacacgtcatcgatgatcgtcaccagaccaaacattttagtaacagctttgcg
acattcaccaaactgcgggtctggcgccatacccagtgcccagaaataaacttccatcaggcgg
tcgcgtacaaaatccagtttgctagccaggcccatctcggtccaccagcgggacagatcttgca
gctctttctggtgcagggtctgtaccatgttaaaatccagcttcgccagctccagcagcagctg
gtgatgcggttctttcggttcgtatttatccaggaaccaacgtgcctccagacggtgcagacgc
tggtgatatggcagttccagggcgtggctcacttgttctgcaaccttggtattaatgccttctt
tcaggttgttcttcaggtgggtgatggaaaaggtacgcgcctcctccagcaggttctcaccctc
gaaacccaggtaagacgcttcatacaggctcagcaggccttggacgtcacctttcagttcaccg
ctgaaaccaccttctttatccttgaaacgctcaaaaacatcctgagaaacctcgaaaccgtgct
gacgcagcagacggaaagacagagcggttgcgtgcaggtcagatttgttctttttgttttcgtc
cagcagtacgatgttttccagggctttaatgatgtctttttcaaatttgtaggtcagacccagg
cgctgcacatcgtcgatcagctccagcagggacagcggctgggtgtctacacggttgatcatgc
agcgaacttcttcctccagtttggtcgctttctcctccagcttttccactttcaggtcgttctc
cagggattgcaggaattcgaaattccacaggtttggctgatagtttgcggaacgacggaatta
tgctcggtaatctgagtaaattgagaagaggtcgcacacatatgacgaccttcgatatggccgc
tgctgtgatgatgatgatgatgatgatgatgatggcccatggtatatctccttcttaaagttaa
acaaaattatttctagaggggaattgttatccgctcacaattcccctatagtgagtcgtattaa
tttcgcgggatcgagatctcgatcctctacgccggacgcatcgtggccggcatcaccggcgcca
caggtgcggttgctggcgcctatatcgccgacatcaccgatggggaagatcgggctcgccactt
cgggctcatgagcgcttgtttcggcgtgggtatggtggcaggccccgtggccgggggactgttg
ggcgccatctccttgcatgcaccattccttgcggcggcggtgctcaacggcctcaacctactac
tgggctgcttcctaatgcaggagtcgcataagggagagcgtcgagatcccggacaccatcgaat
ggcgcaaaacctttcgcggtatggcatgatagcgcccggaagagagtcaattcagggtggtgaa
tgtgaaaccagtaacgttatacgatgtcgcagagtatgccggtgtctcttatcagaccgtttcc
cgcgtggtgaaccaggccagccacgtttctgcgaaaacgcgggaaaaagtggaagcggcgatgg
cggagctgaattacattcccaaccgcgtggcacaacaactggcgggcaaacagtcgttgctgat
tggcgttgccacctccagtctggccctgcacgcgccgtcgcaaattgtcgcggcgattaaatct

Figure 5B cgcgccgatcaactgggtgccagcgtggtggtgtcgatggtagaacgaagcggcgtcgaagcct
gtaaagcggcggtgcacaatcttctcgcgcaacgcgtcagtgggctgatcattaactatccgct
ggatgaccaggatgccattgctgtggaagctgcctgcactaatgttccggcgttatttcttgat
gtctctgaccagacacccatcaacagtattattttctcccatgaagacggtacgcgactgggcg
tggagcatctggtcgcattgggtcaccagcaaatcgcgctgttagcgggcccattaagttctgt
ctcggcgcgtctgcgtctggctggctggcataaatatctcactcgcaatcaaattcagccgata
gcggaacgggaaggcgactggagtgccatgtccggttttcaacaaaccatgcaaatgctgaatg
agggcatcgttcccactgcgatgctggttgccaacgatcagatggcgctgggcgcaatgcgcgc
cattaccgagtccgggctgcgcgttggtgcggatatctcggtagtgggatacgacgataccgaa
gacagctcatgttatatcccgccgttaaccaccatcaaacaggattttcgcctgctggggcaaa
ccagcgtggaccgcttgctgcaactctctcagggccaggcggtgaagggcaatcagctgttgcc
cgtctcactggtgaaaagaaaaaccaccctggcgcccaatacgcaaaccgcctctccccgcgcg
ttggccgattcattaatgcagctggcacgacaggtttcccgactggaaagcgggcagtgagcgc
aacgcaattaatgtaagttagctcactcattaggcaccgggatctcgaccgatgcccttgagag
ccttcaacccagtcagctccttccggtgggcgcggggcatgactatcgtcgccgcacttatgac
tgtcttctttatcatgcaactcgtaggacaggtgccggcagcgctctgggtcattttcggcgag
gaccgctttcgctggagcgcgacgatgatcggcctgtcgcttgcggtattcggaatcttgcacg
ccctcgctcaagccttcgtcactggtcccgccaccaaacgtttcggcgagaagcaggccattat
cgccggcatggcggccgacgcgctgggctacgtcttgctggcgttcgcgacgcgaggctggatg
gccttccccattatgattcttctcgcttccggcggcatcgggatgcccgcgttgcaggccatgc
tgtccaggcaggtagatgacgaccatcagggacagcttcaaggatcgctcgcggctcttaccag
cctaacttcgatcactggaccgctgatcgtcacggcgatttatgccgcctcggcgagcacatgg
aacgggttggcatggattgtaggcgccgccctataccttgtctgcctccccgcgttgcgtcgcg
gtgcatggagccgggccacctcgacctgaatggaagccggcggcacctcgctaacggattcacc
actccaagaattggagccaatcaattcttgcggagaactgtgaatgcgcaaaccaacccttggc
agaacatatccatcgcgtccgccatctccagcagccgcacgcggcgcatctcgggcagcgttgg
gtcctggccacgggtgcgcatgatcgtgctcctgtcgttgaggacccggctaggctggcggggt
tgccttactggttagcagaatgaatcaccgatacgcgagcgaacgtgaagcgactgctgctgca
aaacgtctgcgacctgagcaacaacatgaatggtcttcggtttccgtgtttcgtaaagtctgga
aacgcggaagtcagcgccctgcaccattatgttccggatctgcatcgcaggatgctgctggcta
ccctgtggaacacctacatctgtattaacgaagcgctggcattgaccctgagtgatttttctct
ggtcccgccgcatccataccgccagttgtttaccctcacaacgttccagtaaccgggcatgttc
atcatcagtaacccgtatcgtgagcatcctctctcgtttcatcggtatcattacccccatgaac
agaaatcccccttacacggaggcatcagtgaccaaacaggaaaaaaccgcccttaacatggccc
gctttatcagaagccagacattaacgcttctggagaaactcaacgagctggacgcggatgaaca
ggcagacatctgtgaatcgcttcacgaccacgctgatgagctttaccgcagctgcctcgcgcgt
ttcggtgatgacggtgaaaacctctgacacatgcagctcccggagacggtcacagcttgtctgt
aagcggatgccgggagcagacaagcccgtcagggcgcgtcagcgggtgttggcgggtgtcgggg
cgcagccatgacccagtcacgtagcgatagcggagtgtatactggcttaactatgcggcatcag
agcagattgtactgagagtgcaccatatatgcggtgtgaaataccgcacagatgcgtaaggaga
aaataccgcatcaggcgctcttccgcttcctcgctcactgactcgctgcgctcggtcgttcggc
tgcggcgagcggtatcagctcactcaaaggcggtaatacggttatccacagaatcaggggataa
cgcaggaaagaacatgtgagcaaaaggccagcaaaaggccaggaaccgtaaaaaggccgcgttg
ctggcgtttttccataggctccgcccccctgacgagcatcacaaaaatcgacgctcaagtcaga

Figure 5C ggtggcgaaacccgacaggactataaagataccaggcgtttccccctggaagctccctcgtgcg
ctctcctgttccgaccctgccgcttaccggatacctgtccgcctttctcccttcgggaagcgtg
gcgctttctcatagctcacgctgtaggtatctcagttcggtgtaggtcgttcgctccaagctgg
gctgtgtgcacgaaccccccgttcagcccgaccgctgcgccttatccggtaactatcgtcttga
gtccaacccggtaagacacgacttatcgccactggcagcagccactggtaacaggattagcaga
gcgaggtatgtaggcggtgctacagagttcttgaagtggtggcctaactacggctacactagaa
ggacagtatttggtatctgcgctctgctgaagccagttaccttcggaaaaagagttggtagctc
ttgatccggcaaacaaaccaccgctggtagcggtggtttttttgtttgcaagcagcagattacg
cgcagaaaaaaaggatctcaagaagatcctttgatcttttctacggggtctgacgctcagtgga
acgaaaactcacgttaagggattttggtcatgagattatcaaaaaggatcttcacctagatcct
tttaaattaaaaatgaagttttaaatcaatctaaagtatatatgagtaaacttggtctgacagt
taccaatgcttaatcagtgaggcacctatctcagcgatctgtctatttcgttcatccatagttg
cctgactccccgtcgtgtagataactacgatacgggagggcttaccatctggccccagtgctgc
aatgataccgcgagacccacgctcaccggctccagatttatcagcaataaaccagccagccgga
agggccgagcgcagaagtggtcctgcaactttatccgcctccatccagtctattaattgttgcc
gggaagctagagtaagtagttcgccagttaatagtttgcgcaacgttgttgccattgctgcagg
catcgtggtgtcacgctcgtcgtttggtatggcttcattcagctccggttcccaacgatcaagg
cgagttacatgatcccccatgttgtgcaaaaaagcggttagctccttcggtcctccgatcgttg
tcagaagtaagttggccgcagtgttatcactcatggttatggcagcactgcataattctcttac
tgtcatgccatccgtaagatgcttttctgtgactggtgagtactcaaccaagtcattctgagaa
tagtgtatgcggcgaccgagttgctcttgcccggcgtcaacacgggataataccgcgccacata
gcagaactttaaaagtgctcatcattggaaaacgttcttcggggcgaaaactctcaaggatctt
accgctgttgagatccagttcgatgtaacccactcgtgcacccaactgatcttcagcatctttt
actttcaccagcgtttctgggtgagcaaaaacaggaaggcaaaatgccgcaaaaaagggaataa
gggcgacacggaaatgttgaatactcatactcttcctttttcaatattattgaagcatttatca
gggttattgtctcatgagcggatacatatttgaatgtatttagaaaaataaacaaataggggtt
ccgcgcacatttccccgaaaagtgccacctgacgtctaagaaaccattattatcatgacattaa
cctataaaaataggcgtatcacgaggccctttcgtcttcaagaa
(SEQ ID NO:5)

Figure 7A 1-
cccgtcttactgtcgggaattcgcgttggccgattcattaatgcagctggcacgacaggtttcc
cgactggaaagcgggcagtgagcgcaacgcaattaatgtgagttagctcactcattaggcaccc
caggctttacactttatgcttccggctcgtatgttgtgtggaattgtgagcggataacaatttc
acacaggaaacagctatgaccatgattacgccaagcttgtatcgattaaataaggaggaataaa
ccatgtgtgcgacctcttctcaatttactcagattaccgagcataattcccgtcgttccgcaaa
ctatcagccaaacctgtggaatttcgaattcctgcaatccctggagaacgacctgaaagtggaa
aagctggaggagaaagcgaccaaactggaggaagaagttcgctgcatgatcaaccgtgtagaca
cccagccgctgtccctgctggagctgatcgacgatgtgcagcgcctgggtctgacctacaaatt
tgaaaaagacatcattaaagccctggaaaacatcgtactgctggacgaaaacaaaaagaacaaa
tctgacctgcacgcaaccgctctgtctttccgtctgctgcgtcagcacggtttcgaggtttctc
aggatgtttttgagcgtttcaaggataaagaaggtggtttcagcggtgaactgaaaggtgacgt
ccaaggcctgctgagcctgtatgaagcgtcttacctgggtttcgagggtgagaacctgctggag
gaggcgcgtacctttttccatcacccacctgaagaacaacctgaaagaaggcattaataccaagg
ttgcagaacaagtgagccacgccctggaactgccatatcaccagcgtctgcaccgtctggaggc
acgttggttcctggataaatacgaaccgaaagaaccgcatcaccagctgctgctggagctggcg
aagctggattttaacatggtacagaccctgcaccagaaagagctgcaagatctgtcccgctggt
ggaccgagatgggcctggctagcaaactggattttgtacgcgaccgcctgatggaagtttattt
ctgggcactgggtatggcgccagacccgcagtttggtgaatgtcgcaaagctgttactaaaatg
tttggtctggtgacgatcatcgatgacgtgtatgacgtttatggcactctggacgaactgcaac
tgttcaccgatgctgtagagcgctgggacgttaacgctattaacaccctgccggactatatgaa
actgtgtttcctggcactgtacaacaccgttaacgacacgtcctattctattctgaaagagaaa
ggtcataacaacctgtcctatctgacgaaaagctggcgtgaactgtgcaaagcctttctgcaag
aggcgaaatggtccaacaacaaaattatcccggctttctccaagtacctggaaaacgccagcgt
ttcctcctccggtgtagcgctgctggcgccgtcttacttttccgtatgccagcagcaggaagac
atctccgaccacgcgctgcgttccctgaccgacttccatggtctggtgcgttctagctgcgtta
tcttccgcctgtgcaacgatctggccacctctgcggcggagctggaacgtggcgagactaccaa
ttctatcattagctacatgcacgaaaacgatggtaccagcgaggaacaggcccgcgaagaactg
cgtaaactgatcgacgccgaatggaaaaagatgaatcgtgaacgcgttagcgactccaccctgc
tgcctaaagcgttcatggaaatcgcagttaacatggcacgtgtttcccactgcacctaccagta
tggcgatggtctgggtcgcccagactacgcgactgaaaaccgcatcaaactgctgctgattgac
cctttcccgattaaccagctgatgtatgtctaactgcaggtcgactctagaggatccccgggta
ccgagctcgaattcactggccgtcgttttacaacgtcgtgactgggaaaaccctggcgttaccc
aacttaatcgccttgcagcacatccccctttcgccagctggcgtaatagcgaagaggcccgcac
cgatcgcccttcccaacagttgcgcagcctgaatggcgaatggcgcctgatgcggtattttctc
cttacgcatctgtgcggtatttcacaccgcatatggtgcactctcagtacaatctgctctgatg
ccgcatagttaagccagccccgacacccgccaacacccgctgacgagcttagtaaagccctcgc
tagattttaatgcggatgttgcgattacttcgccaactattgcgataacaagaaaaagccagcc
tttcatgatatatctcccaatttgtgtagggcttattatgcacgcttaaaaataataaaagcag
acttgacctgatagtttggctgtgagcaattatgtgcttagtgcatctaacgcttgagttaagc
cgcgccgcgaagcggcgtcggcttgaacgaattgttagacattatttgccgactaccttggtga
tctcgcctttcacgtagtggacaaattcttccaactgatctgcgcgcgaggccaagcgatcttc
ttcttgtccaagataagcctgtctagcttcaagtatgacgggctgatactgggccggcaggcgc
tccattgcccagtcggcagcgacatccttcggcgcgatttgccggttactgcgctgtaccaaa
tgcgggacaacgtaagcactacatttcgctcatcgccagcccagtcgggcggcgagttccatag

Figure 7B cgttaaggtttcatttagcgcctcaaatagatcctgttcaggaaccggatcaaagagttcctcc
gccgctggacctaccaaggcaacgctatgttctcttgcttttgtcagcaagatagccagatcaa
tgtcgatcgtggctggctcgaagatacctgcaagaatgtcattgcgctgccattctccaaattg
cagttcgcgcttagctggataacgccacggaatgatgtcgtcgtgcacaacaatggtgacttct
acagcgcggagaatctcgctctctccaggggaagccgaagtttccaaaaggtcgttgatcaaag
ctcgccgcgttgtttcatcaagccttacggtcaccgtaaccagcaaatcaatatcactgtgtgg
cttcaggccgccatccactgcggagccgtacaaatgtacggccagcaacgtcggttcgagatgg
cgctcgatgacgccaactacctctgatagttgagtcgatacttcggcgatcaccgcttccctca
tgatgtttaactttgttttagggcgactgccctgctgcgtaacatcgttgctgctccataacat
caaacatcgacccacggcgtaacgcgcttgctgcttggatgcccgaggcatagactgtacccca
aaaaaacagtcataacaagccatgaaaaccgccactgcgccgttaccaccgctgcgttcggtca
aggttctggaccagttgcgtgagcgcatacgctacttgcattacagcttacgaaccgaacaggc
ttatgtccactgggttcgtgccttcatccgtttccacggtgtgcgtcacccggcaaccttgggc
agcagcgaagtcgaggcatttctgtcctggctggcgaacgagcgcaaggtttcggtctccacgc
atcgtcaggcattggcggccttgctgttcttctacggcaaggtgctgtgcacggatctgccctg
gcttcaggagatcggaagacctcggccgtcgcggcgcttgccggtggtgctgaccccggatgaa
gtggttcgcatcctcggttttctggaaggcgagcatcgtttgttcgcccagcttctgtatggaa
cgggcatgcggatcagtgagggtttgcaactgcgggtcaaggatctggatttcgatcacggcac
gatcatcgtgcgggagggcaagggctccaaggatcgggccttgatgttacccgagagcttggca
cccagcctgcgcgagcaggggaattaattcccacgggttttgctgcccgcaaacgggctgttct
ggtgttgctagtttgttatcagaatcgcagatccggcttcagccggtttgccggctgaaagcgc
tatttcttccagaattgccatgattttttccccacgggaggcgtcactggctcccgtgttgtcg
gcagctttgattcgataagcagcatcgcctgtttcaggctgtctatgtgtgactgttgagctgt
aacaagttgtctcaggtgttcaatttcatgttctagttgctttgttttactggtttcacctgtt
ctattaggtgttacatgctgttcatctgttacattgtcgatctgttcatggtgaacagctttga
atgcaccaaaaactcgtaaaagctctgatgtatctatcttttttacaccgttttcatctgtgca
tatggacagttttccctttgatatgtaacggtgaacagttgttctactttgtttgttagtctt
gatgcttcactgatagatacaagagccataagaacctcagatccttccgtatttagccagtatg
ttctctagtgtggttcgttgtttttgcgtgagccatgagaacgaaccattgagatcatacttac
tttgcatgtcactcaaaaattttgcctcaaaactggtgagctgaattttttgcagttaaagcatc
gtgtagtgtttttcttagtccgttatgtaggtaggaatctgatgtaatggttgttggtattttg
tcaccattcatttttatctggttgttctcaagttcggttacgagatccatttgtctatctagtt
caacttggaaaatcaacgtatcagtcgggcggcctcgcttatcaaccaccaatttcatattgct
gtaagtgtttaaatctttacttattggtttcaaaacccattggttaagccttttaaactcatgg
tagttattttcaagcattaacatgaacttaaattcatcaaggctaatctctatatttgccttgt
gagttttcttttgtgttagttcttttaataaccactcataaatcctcatagagtatttgttttc
aaaagacttaacatgttccagattatattttatgaattttttaactggaaaagataaggcaat
atctcttcactaaaaactaattctaatttttcgcttgagaacttggcatagtttgtccactgga
aaatctcaaagcctttaaccaaaggattcctgatttccacagttctcgtcatcagctctctggt
tgctttagctaatacaccataagcattttccctactgatgttcatcatctgagcgtattggtta
taagtgaacgataccgtccgttctttccttgtagggttttcaatcgtggggttgagtagtgcca
cacagcataaaattagcttggtttcatgctccgttaagtcatagcgactaatcgctagttcatt
tgctttgaaaacaactaattcagacatacatctcaattggtctaggtgattttaatcactatac
caattgagatgggctagtcaatgataattactagtcctttttcctttgagttgtgggtatctgta

Figure 7C

Aattctgctagacctttgctggaaaacttgtaaattctgctagaccctctgtaaattccgctag
acctttgtgtgttttttttgtttatattcaagtggttataatttatagaataaagaaagaataa
aaaaagataaaaagaatagatcccagccctgtgtataactcactactttagtcagttccgcagt
attacaaaaggatgtcgcaaacgctgtttgctcctctacaaaacagaccttaaaaccctaaagg
cttaagtagcaccctcgcaagctcgggcaaatcgctgaatattccttttgtctccgaccatcag
gcacctgagtcgctgtctttttcgtgacattcagttcgctgcgctcacggctctggcagtgaat
gggggtaaatggcactacaggcgccttttatggattcatgcaaggaaactacccataatacaag
aaaagcccgtcacgggcttctcagggcgttttatggcgggtctgctatgtggtgctatctgact
ttttgctgttcagcagttcctgccctctgattttccagtctgaccacttcggattatcccgtga
caggtcattcagactggctaatgcacccagtaaggcagcggtatcatcaacaggctta
(SEQ ID NO:7)

Figure 9
A.
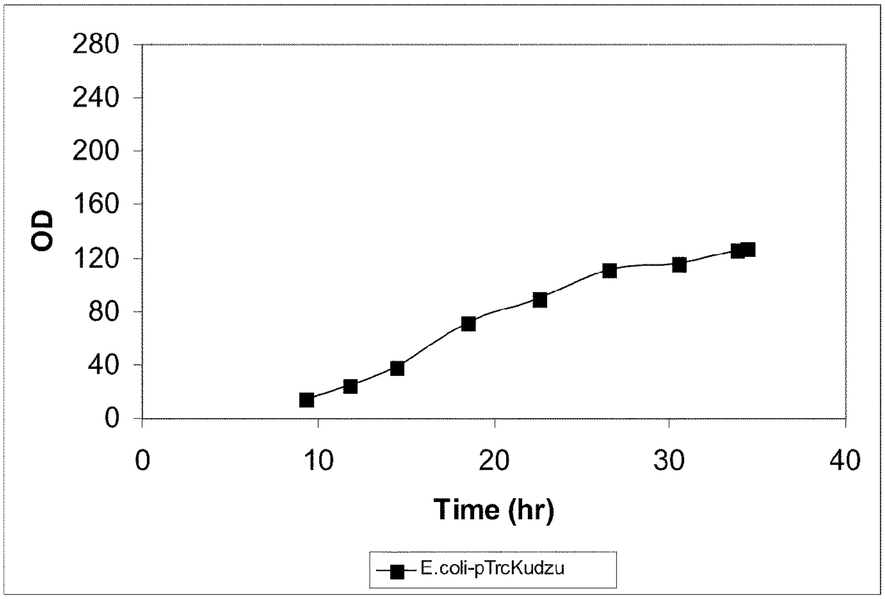
B.
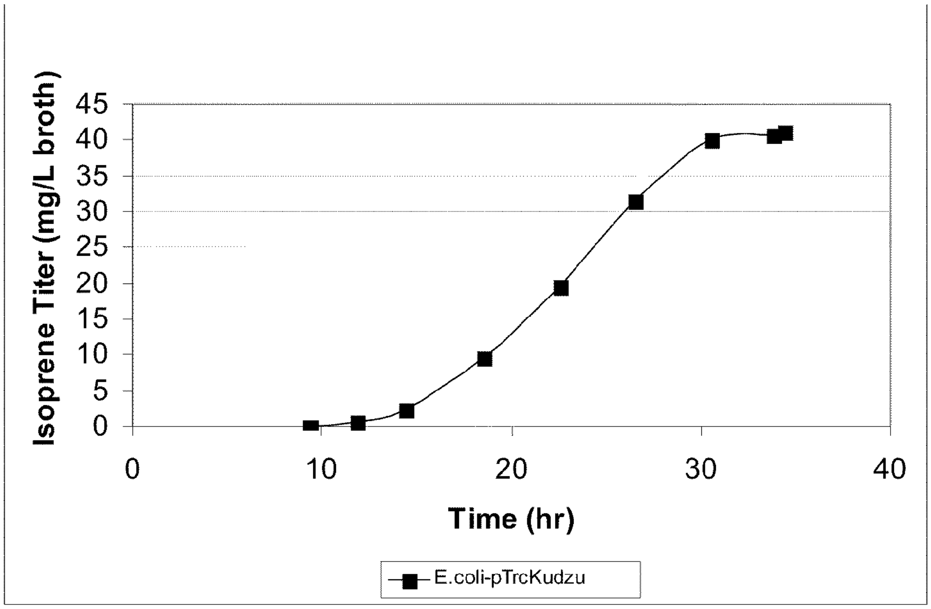

Figure 12A 1-
gaattgctccatttcttctgctatcaaaataacagactcgtgattttccaaacgagctttcaa
aaaagcctctgccccttgcaaatcggatgcctgtctataaaattcccgatattggttaaacagc
ggcgcaatggcggccgcatctgatgtctttgcttggcgaatgttcatcttatttcttcctccct
ctcaataatttttcattctatccctttctgtaaagtttatttttcagaatacttttatcatc
atgctttgaaaaaatatcacgataatatccattgttctcacggaagcacacgcaggtcatttga
acgaatttttcgacaggaatttgccgggactcaggagcatttaacctaaaaaagcatgacatt
tcagcataatgaacatttactcatgtctattttcgttcttttctgtatgaaaatagttatttcg
agtctctacggaaatagcgagagatgatatacctaaatagagataaaatcatctcaaaaaatg
ggtctactaaaatattattccatctattacaataaattcacagaatagtcttttaagtaagtct
actctgaatttttttaaaaggagagggtaaagagtgtgtgcgacctcttctcaatttactcaga
ttaccgagcataattcccgtcgttccgcaaactatcagccaaacctgtggaatttcgaattcct
gcaatccctggagaacgacctgaaagtggaaaagctggaggagaaagcgaccaaactggaggaa
gaagttcgctgcatgatcaaccgtgtagacacccagccgctgtccctgctggagctgatcgacg
atgtgcagcgcctgggtctgacctacaaatttgaaaaagacatcattaaagccctggaaaacat
cgtactgctggacgaaaacaaaaagaacaaatctgacctgcacgcaaccgctctgtctttccgt
ctgctgcgtcagcacggtttcgaggtttctcaggatgtttttgagcgtttcaaggataaagaag
gtggtttcagcggtgaactgaaaggtgacgtccaaggcctgctgagcctgtatgaagcgtctta
cctgggtttcgagggtgagaacctgctggaggaggcgcgtaccttttccatcacccacctgaag
aacaacctgaaagaaggcattaataccaaggttgcagaacaagtgagccacgccctggaactgc
catatcaccagcgtctgcaccgtctggaggcacgttggttcctggataaatacgaaccgaaaga
accgcatcaccagctgctgctggagctggcgaagctggattttaacatggtacagaccctgcac
cagaaagagctgcaagatctgtcccgctggtggaccgagatgggcctggctagcaaactggatt
ttgtacgcgaccgcctgatggaagtttatttctgggcactgggtatggcgccagacccgcagtt
tggtgaatgtcgcaaagctgttactaaaatgtttggtctggtgacgatcatcgatgacgtgtat
gacgtttatggcactctggacgaactgcaactgttcaccgatgctgtagagcgctgggacgtta
acgctattaacaccctgccggactatatgaaactgtgtttcctggcactgtacaacaccgttaa
cgacacgtcctattctattctgaaagagaaaggtcataacaacctgtcctatctgacgaaaagc
tggcgtgaactgtgcaaagcctttctgcaagaggcgaaatggtccaacaacaaaattatcccgg
ctttctccaagtacctggaaaacgccagcgtttcctcctccggtgtagcgctgctggcgccgtc
ttacttttccgtatgccagcagcaggaagacatctccgaccacgcgctgcgttccctgaccgac
ttccatggtctggtgcgttctagctgcgttatcttccgcctgtgcaacgatctggccacctctg
cggcggagctggaacgtggcgagactaccaattctatcattagctacatgcacgaaaacgatgg
taccagcgaggaacaggcccgcgaagaactgcgtaaactgatcgacgccgaatggaaaaagatg
aatcgtgaacgcgttagcgactccaccctgctgcctaaagcgttcatggaaatcgcagttaaca
tggcacgtgtttcccactgcacctaccagtatggcgatggtctgggtcgcccagactacgcgac
tgaaaaccgcatcaaactgctgctgattgaccctttcccgattaaccagctgatgtatgtctaa
aaaaaaccggccttggccccgccggtttttattatttttcttcctccgcatgttcaatccgct
ccataatcgacggatggctccctctgaaaatttaacgagaaacggcgggttgacccggctcag
tcccgtaacggccaagtcctgaaacgtctcaatcgccgcttcccggtttccggtcagctcaatg
ccgtaacggtcggcggcgttttcctgataccgggagacggcattcgtaatcggatcctctagag
tcgacctgcaggcatgcaagctttgcctcgcgcgtttcggtgatgacggtgaaaacctctgaca
catgcagctcccggagacggtcacagcttgtctgtaagcggatgccgggagcagacaagcccgt
cagggcgcgtcagcgggtgttggcgggtgtcggggcgcagccatgacccagtcacgtagcgata

Figure 12B gcggagtgtatactggcttaactatgcggcatcagagcagattgtactgagagtgcaccatatg
cggtgtgaaataccgcacagatgcgtaaggagaaaataccgcatcaggcgctcttccgcttcct
cgctcactgactcgctgcgctcggtcgttcggctgcggcgagcggtatcagctcactcaaaggc
ggtaatacggttatccacagaatcaggggataacgcaggaaagaacatgtgagcaaaaggccag
caaaaggccaggaaccgtaaaaaggccgcgttgctggcgtttttccataggctccgcccccctg
acgagcatcacaaaaatcgacgctcaagtcagaggtggcgaaacccgacaggactataaagata
ccaggcgtttccccctggaagctccctcgtgcgctctcctgttccgaccctgccgcttaccgga
tacctgtccgcctttctcccttcgggaagcgtggcgctttctcaatgctcacgctgtaggtatc
tcagttcggtgtaggtcgttcgctccaagctgggctgtgtgcacgaaccccccgttcagcccga
ccgctgcgccttatccggtaactatcgtcttgagtccaacccggtaagacacgacttatcgcca
ctggcagcagccactggtaacaggattagcagagcgaggtatgtaggcggtgctacagagttct
tgaagtggtggcctaactacggctacactagaaggacagtatttggtatctgcgctctgctgaa
gccagttaccttcggaaaaagagttggtagctcttgatccggcaaacaaaccaccgctggtagc
ggtggtttttttgtttgcaagcagcagattacgcgcagaaaaaaaggatctcaagaagatcctt
tgatcttttctacggggtctgacgctcagtggaacgaaaactcacgttaagggattttggtcat
gagattatcaaaaaggatcgaagtcggttcagaaaaagaaggatatggatctggagctgtaata
taaaaaccttcttcaactaacggggcaggttagtgacattagaaaaccgactgtaaaaagtaca
gtcggcattatctcatattataaaagccagtcattaggcctatctgacaattcctgaatagagt
tcataaacaatcctgcatgataaccatcacaaacagaatgatgtacctgtaaagatagcggtaa
atatattgaattacctttattaatgaattttcctgctgtaataatgggtagaaggtaattacta
ttattattgatatttaagttaaacccagtaaatgaagtccatggaataatagaaagagaaaaag
cattttcaggtataggtgttttgggaaacaatttaaaagaaccattatatttctctacatcaga
aaggtataaatcataaaactctttgaagtcattctttacaggagtccaaataccagagaatgtt
ttagatacaccatcaaaaattgtataaagtggctctaacttatcccaataacctaactctccgt
cgctattgtaaccagttctaaaagctgtatttgagtttatcacccttgtcactaagaaaataaa
tgcagggtaaaatttatatccttcttgttttatgtttcggtataaaacactaatatcaatttct
gtggttatactaaaagtcgtttgttggttcaaataatgattaaatatctcttttctcttccaat
tgtctaaatcaattttattaaagttcatttgatatgcctcctaaatttttatctaaagtgaatt
taggaggcttacttgtctgctttcttcattagaatcaatcctttttaaagtcaatattactgt
aacataaatatatattttaaaaatatcccactttatccaattttcgtttgttgaactaatgggt
gctttagttgaagaataaagaccacattaaaaaatgtggtcttttgtgtttttttaaaggattt
gagcgtacgcgaaaaatcctttttctttctttcttatcttgataataagggtaactattgccggt
tgtccattcatggctgaactctgcttcctctgttgacatgacacacatcatctcaatatccgaa
tagggcccatcagtctgacgaccaagagagccataaacaccaatagccttaacatcatccccat
atttatccaatattcgttccttaatttcatgaacaatcttcattctttcttctctagtcattat
tattggtccattcactattctcattcccttttcagataattttagatttgcttttctaaataag
aatatttggagagcaccgttcttattcagctattaataactcgtcttcctaagcatccttcaat
ccttttaataacaattatagcatctaatcttcaacaaactggcccgtttgttgaactactcttt
aataaaataatttttccgttcccaattccacattgcaataatagaaaatccatcttcatcggct
ttttcgtcatcatctgtatgaatcaaatcgccttcttctgtgtcatcaaggtttaatttttat
gtatttcttttaacaaaccaccataggagattaaccttttacggtgtaaaccttcctccaaatc
agacaaacgtttcaaattcttttcttcatcatcggtcataaaatccgtatcctttacaggatat
tttgcagtttcgtcaattgccgattgtatatccgatttatatttatttttcggtcgaatcattt
gaacttttacatttggatcatagtctaatttcattgcctttttccaaaattgaatccattgttt

Figure 12C ttgattcacgtagttttctgttattctaaaataagttggttccacacataccattacatgcatg
tgctgattataagaattatctttattatttattgtcacatccgttgcacgcataaaaccaacaa
gattttattaattttttttatattgcatcattcggcgaaatccttgagccatatctgtcaaact
cttatttaattcttcgccatcataaacattttaactgttaatgtgagaaacaaccaacgaact
gttggcttttgtttaataacttcagcaacaaccttttgtgactgaatgccatgtttcattgctc
tcctccagttgcacattggacaaagcctggatttgcaaaaccacactcgataccactttctttc
gcctgtttcacgattttgtttatactctaatatttcagcacaatctttactctttcagccttt
ttaaattcaagaatatgcagaagttcaaagtaatcaacattagcgatttcttttctctccatg
gtctcacttttccactttttgtcttgtccactaaaacccttgatttttcatctgaataaatgct
actattaggacacataatattaaaagaaaccccatctatttagttatttgtttagtcacttat
aactttaacagatggggtttttctgtgcaaccaattttaagggttttcaatactttaaaacaca
tacataccaacacttcaacgcacctttcagcaactaaaataaaaatgacgttatttctatatgt
atcaagataagaaagaacaagttcaaaaccatcaaaaaaagacaccttttcaggtgcttttttt
attttataaactcattccctgatctcgacttcgttctttttttacctctcggttatgagttagt
tcaaattcgttctttttaggttctaaatcgtgtttttcttggaattgtgctgttttatccttta
ccttgtctacaaaccccttaaaaacgtttttaaaggcttttaagccgtctgtacgttccttaag (SEQ ID NO:56)

Figure 13

ATGTGTGCAACCTCCTCCCAGTTTACTCAGATTACCGAGCATAATTCTCGACGATCTGCTAACT
ACCAGCCGAACCTTTGGAACTTTGAGTTTCTCCAGTCTCTCGAAAATGACCTGAAGGTGGAAAA
GCTCGAGGAGAAGGCGACCAAACTCGAGGAGGAGGTGCGATGTATGATCAACAGAGTTGACACC
CAACCCCTGTCTTTGCTGGAGCTGATCGACGATGTGCAGCGGTTGGGTTTGACTTATAAATTCG
AGAAGGACATTATCAAGGCACTGGAGAACATTGTGCTCCTCGACGAGAACAAGAAGAACAAGTC
TGATCTTCACGCTACCGCTCTCTCTTTCCGACTTCTTCGACAACACGGCTTCGAGGTGTCGCAG
GACGTCTTCGAGAGATTTAAGGACAAGGAGGGAGGATTTAGCGGCGAGCTGAAGGGAGACGTTC
AGGGTCTTCTCTCCTTGTACGAGGCGTCCTACCTGGGATTCGAGGGAGAGAACCTCCTGGAGGA
AGCTCGTACATTTTCCATCACTCACCTTAAGAATAACCTTAAGGAGGGAATTAACACCAAGGTG
GCCGAGCAGGTTTCTCACGCCCTGGAGCTCCCCTACCACCAACGGCTCCATAGACTGGAGGCTC
GTTGGTTCCTGGACAAATATGAGCCAAAGGAGCCTCATCATCAGTTGCTGTTGGAGTTGGCCAA
GCTGGACTTCAATATGGTTCAGACGCTGCACCAAAAGGAGTTGCAGGACCTGTCTCGATGGTGG
ACCGAGATGGGATTGGCCTCGAAGCTGGATTTTGTCCGTGACCGACTTATGGAGGTCTATTTTT
GGGCCCTTGGAATGGCGCCTGACCCCCAGTTCGGAGAGTGCCGGAAGGCGGTGACGAAGATGTT
CGGTCTTGTGACTATCATCGACGACGTCTACGATGTCTACGGCACACTCGACGAGTTGCAGCTG
TTCACTGACGCCGTCGAGCGATGGGATGTGAACGCCATTAATACTCTCCCTGACTATATGAAGC
TGTGCTTCCTGGCTCTGTACAACACTGTCAACGATACCTCGTACTCTATCCTCAAGGAGAAGGG
ACACAACAATCTCTCCTACTTGACCAAATCCTGGCGAGAACTGTGCAAGGCTTTTCTGCAGGAG
GCTAAATGGTCCAATAACAAGATCATTCCTGCTTTTTCTAAATACCTGGAAAATGCCTCGGTGT
CGAGCTCTGGCGTCGCCCTTCTGGCCCCTTCCTACTTCTCCGTCTGCCAGCAGCAGGAGGATAT
TTCCGATCATGCTCTTAGATCGCTGACCGATTTTCACGGCCTCGTGCGATCTTCCTGCGTGATT
TTTCGGTTGTGTAATGACCTTGCGACCTCTGCTGCTGAGCTGGAACGAGGCGAGACTACAAATT
CCATTATTTCTTACATGCACGAAAACGATGGAACATCTGAAGAACAGGCTAGAGAGGAACTGCG
AAAGTTGATCGACGCCGAGTGGAAGAAGATGAACAGAGAGCGGGTGTCCGACTCTACCCTGCTT
CCCAAGGCCTTCATGGAGATCGCCGTGAACATGGCTCGAGTTTCCCATTGTACTTACCAGTACG
GTGACGGCCTGGGTCGTCCGGACTACGCTACAGAGAACCGAATCAAGCTGCTGCTCATCGACCC
CTTCCCTATCAACCAATTGATGTACGTGTAA
(SEQ ID NO:8)

Figure 15A

```
   1 TCGACCGGTG AGAAGAACAG CATCGGGACA AGGGAAGGAA GAACAAAGAC AAAGAAAACA
  61 AAAGAAAGCA ATTGAAAACA AAACAAAACA ATTTTCATTC CTTCTCTTAT CATTCCTTTT
 121 CTTTTCTTTT CTCTCATTCA ACGCACTCCA TCGTATCCGT ATTCCTCTTA TTTTTTCTCT
 181 TTCTCTATAT CCATTTCTTT CTCTCTAGGT GTGTCCTCTC TCTCTCTTCA ATTTCTCTAC
 241 TCCGCATTCC AACGCATCCT TCCCCCAACC TCCCATTTCC TCCTTACGGC CCGATAGCGA
 301 TCGTCTTTCC CTCGCTATCA CTCGCTACCG GCCCCTCCTC TGCACCGTAA CCTCCTACGT
 361 ATTTACCATA TCATAAAGTT TTTTCCGACG CTTATCGCTG ACCCCCTGTC GCCCTCCTAT
 421 TGGCTTCCGG ATTATCTTCT TGTCCATAAG GTGATCCATG CTTCCTGAAG ATTCCCGAAA
 481 TGTGTCCACT TTGGCGGGGA ATCATTCCAT CCACTTCTTT CTCTCTCGCT TTCCTCATTC
 541 GGCGCTCCCC TTCCGCGTCT CATTGGTCTT CCGCTCCGTT TTTGCTTTGC CGATGTTACT
 601 TGGGGAGAGG TGCGATAATC CTTTCGCAAA AACTCGGTTT GACGCCTCCC ATGGTATAAA
 661 TAGTGGGTGG TGGACAGGTG CCTTCGCTTT TCTTTAAGCA AGAGAATCCC ATTGTCTTGA
 721 CTATCACGAA TTCACATACA TTATGAAGAT CACCGCTGTC ATTGCCCTTT TATTCTCACT
 781 TGCTGCTGCC TCACCTATTC CAGTTGCCGA TCCTGGTGTG GTTTCAGTTA GCAAGTCATA
 841 TGCTGATTTC CTTCGTGTTT ACCAAAGTTG GAACACTTTT GCTAATCCTG ATAGACCCAA
 901 CCTTAAGAAG AGAAATGATA CACCTGCAAG TGGATATCAA GTTGAAAAAG TCGTAATTTT
 961 GTCACGTCAC GGTGTTAGGG CCCCTACAAA AATGACTCAA ACCATGCGTG ATGTCACTCC
1021 TAATACATGG CCAGAATGGC CCGTTAAATT AGGATATATT ACACCAAGAG GTGAACACTT
1081 GATATCACTT ATGGGCGGTT TTTACCGTCA AAAATTCCAG CAACAAGGAA TCCTTTCTCA
1141 GGGCTCCTGT CCTACTCCTA ACTCCATATA TGTCTGGGCT GACGTCGATC AGCGTACTTT
1201 AAAAACTGGT GAAGCATTCC TTGCTGGTTT GGCACCACAA TGTGGCTTGA CAATTCATCA
1261 CCAACAAAAT CTTGAGAAAG CTGATCCTCT TTTTCATCCC GTTAAAGCTG GAACCTGCTC
1321 TATGGATAAA ACTCAAGTTC AACAAGCTGT TGAGAAGGAG GCACAAACTC CTATAGATAA
1381 TTTGAATCAA CATTACATCC CCTTTTTAGC TTTAATGAAT ACAACATTAA ATTTTAGTAC
1441 TTCTGCCTGG TGCCAAAAAC ACTCTGCTGA TAAATCCTGT GACCTAGGTT TATCCATGCC
1501 TTCTAAATTG TCCATAAAAG ATAATGGTAA CAAGGTCGCA TTGGATGGAG CTATTGGTCT
1561 ATCCTCTACT TTGGCCGAGA TTTTTCTTCT TGAATATGCT CAAGGCATGC CTCAAGCTGC
1621 TTGGGGTAAC ATCCACTCAG AGCAAGAGTG GGCTTCCTTG CTAAAGTTGC ATAATGTTCA
1681 ATTCGATTTG ATGGCCCGAA CACCTTATAT TGCTCGACAT AACGGTACTC CTTTATTGCA
1741 AGCTATATCA AATGCCCTTA ATCCCAACGC CACTGAATCA AAACTTCCAG ATATTTCACC
1801 TGATAACAAA ATATTGTTCA TTGCAGGTCA TGACACAAAT ATTGCTAATA TAGCCGGCAT
1861 GTTAAATATG CGTTGGACAT TACCAGGTCA ACCAGATAAT ACTCCTCCAG GTGGTGCCCT
1921 AGTATTTGAA CGTCTTGCTG ATAAAAGTGG AAAACAATAT GTTTCTGTAT CTATGGTTTA
1981 TCAAACACTA GAACAACTTC GATCACAGAC TCCCCTTTCT CTAAATCAGC CTGCCGGATC
2041 TGTTCAACTT AAAATTCCAG GTTGCAATGA TCAAACAGCC GAGGGTTACT GTCCTCTTTC
2101 CACTTTTACA AGAGTTGTTT CCCAATCTGT TGAACCTGGA TGCCAACTTC AATAATGAGG
2161 ATCCAAGTAA GGGAATGAGA ATGTGATCCA CTTTTAATTC CTAATGAATA CATGCCTATA
2221 GTTCTTTTCT TTTGTTCTTT ATGTCGTTTT TCGATGGTAC GGCCGTTGTC AATCTCAGTT
2281 TGTGTGCTTG GTTGCAGCTT GGTTTCAAAT CTGTTCATCT CATGAATCTT TTACCATTTC
2341 ACCACACGTT TATACCATTC TCTCATAGAA TCTTCATCAA ACCATCTCGG GGTTAGAGTG
2401 GAAAGAAAGT CTTGTTCTTT TATTTCCTTT TTTCCATCTT CAAGGCTTTT CTTTTCTTCC
2461 TCCTCCTCGT TCATCTTGAG GTTTGACGTG TCTGTTTAGA ATTTTGAGCT GTTGCAGCAT
2521 CTTATTTTTT GTTTTGCGAA AACGAAGCGC TTTACTCTCT TCATCAGTTG GACGATTGTA
2581 CCTTTGAAAA CCAACTACTT TTGCATGTTT TGTATAGAAA TCAATGATAT TAGAATCCCA
2641 TCCTTTAATT TCTTTCAAAG TAGTTGAGCT ATAGTTAAGT GTAAGGGCCC TACTGCGAAA
2701 GCATTTGCCA AGGATGTTTT CATTAATCAA GAACGAAAGT TAGGGGATCG AAGACGATCA
2761 GATACCGTCG TAGTCTTAAC CATAAACTAT GCCGACTAGG GATCGGGCAA TGTTTCATTT
2821 ATCGACTTGC TCGGCACCTT ACGAGAAATC AAAGTCTTTG GGTTCCGGGG GGAGTATGGT
2881 CGCAAGGCTG AAACTTAAAG GAATTGACGG AAGGGCACCA CAATGGAGTG GAGCCTGCGG
2941 CTTAATTTGA CTCAACACGG GGAAACTCAC CAGGTCCAGA CATAGTAAGG ATTGACAGAT
3001 TGAGAGCTCT TTCTTGATTC TATGGGTGGT GGTGCATGGC CGTTCTTAGT TGGTGGAGTG
3061 ATTTGTCTGC TTAATTGCGA TAACGAACGA GACCTTAACC TGCTAAATAG CTGGATCAGC
3121 CATTTTGGCT GATCATTAGC TTCTTAGAGG GACTATTGGC ATAAAGCCAA TGGAAGTTTG
3181 AGGCAATAAC AGGTCTGTGA TGCCCTTAGA TGTTCTGGGC CGCACGCGCG CTACACTGAC
3241 GGAGCCAACG AGTTGAAAAA AATCTTTTGA TTTTTTATCC TTGGCCGGAA GGTCTGGGTA
3301 ATCTTGTTAA ACTCCGTCGT GCTGGGGATA GAGCATTGCA ATTATTGCGG CCGCTCCTCA
3361 ATTCGATGTT GCAGATTTTA CAAGTTTTTA AAATGTATTT CATTATTACT TTTTATATGC
3421 CTAATAAAAA AGCCATAGTT TAATCTATAG ATAACTTTTT TTCCAGTGCA CTAACGGACG
```

Figure 15B

```
3481 TTACATTCCC ATACAAAACT GCGTAGTTAA AGCTAAGGAA AAGTTAATAT CATGTTAATT
3541 AAATACGCTA TTTACAATAA GACATTGAAC TCATTTATAT CGTTGAATAT GAATAACCAA
3601 TTTCAGCGAA TTTTTAACAA ACATCGTTCA CCTCGTTTAA GGATATCTTG TGTATGGGGT
3661 GTTGACTTGC TTTATCGAAT AATTACCGTA CCTGTAATTG GCTTGCTGGA TATAGCGGTA
3721 GTCTAATATC TAGCAAAAAT CTTTTGGGTG AAAAGGCTTG CAATTTCACG ACACCGAACT
3781 ATTTGTCATT TTTTAATAAG GAAGTTTTCC ATAAATTCCT GTAATTCTCG GTTGATCTAA
3841 TTGAAAAGAG TAGTTTTGCA TCACGATGAG GAGGGCTTTT GTAGAAAGAA ATACGAACGA
3901 AACGAAAATC AGCGTTGCCA TCGCTTTGGA CAAAGCTCCC TTACCTGAAG AGTCGAATTT
3961 TATTGATGAA CTTATAACTT CCAAGCATGC AAACCAAAAG GGAGAACAAG TAATCCAAGT
4021 AGACACGGGA ATTGGATTCT TGGATCACAT GTATCATGCA CTGGCTAAAC ATGCAGGCTG
4081 GAGCTTACGA CTTTACTCAA GAGGTGATTT AATCATCGAT GATCATCACA CTGCAGAAGA
4141 TACTGCTATT GCACTTGGTA TTGCATTCAA GCAGGCTATG GGTAACTTTG CCGGCGTTAA
4201 AAGATTTGGA CATGCTTATT GTCCACTTGA CGAAGCTCTT TCTAGAAGCG TAGTTGACTT
4261 GTCGGGACGG CCCTATGCTG TTATCGATTT GGGATTAAAG CGTGAAAAGG TTGGGGAATT
4321 GTCCTGTGAA ATGATCCCTC ACTTACTATA TTCCTTTTCG GTAGCAGCTG GAATTACTTT
4381 GCATGTTACC TGCTTATATG GTAGTAATGA CCATCATCGT GCTGAAAGCG CTTTTAAATC
4441 TCTGGCTGTT GCCATGCGCG CGGCTACTAG TCTTACTGGA AGTTCTGAAG TCCCAAGCAC
4501 GAAGGGAGTG TTGTAAAGAT GAATTGGATT ATGTCAGGAA AAGAACGACA ATTTTGCATC
4561 CAAATTGTCT AAATTTTAGA GTTGCTTGAA AACAATAGAA CCTTACTTGC TTTATAATTA
4621 CGTTAATTAG AAGCGTTATC TCGTGAAGGA ATATAGTACG TAGCCGTATA AATTGAATTG
4681 AATGTTCAGC TTATAGAATA GAGACACTTT GCTGTTCAAT GCGTCGTCAC TTACCATACT
4741 CACTTTATTA TACGACTTTA AGTATAAACT CCGCGGTTAT GGTAAAATTA ATGATGCACA
4801 AACGTCCGAT TCCATATGGG TACACTACAA TTAAATACTT TTAAGCTGAT CCCCCACACA
4861 CCATAGCTTC AAAATGTTTC TACTCCTTTT TTACTCTTCC AGATTTTCTC GGACTCCGCG
4921 CATCGCCGTA CCACTTCAAA ACACCCAAGC ACAGCATACT AAATTTTCCC TCTTTCTTCC
4981 TCTAGGGTGT CGTTAATTAC CCGTACTAAA GGTTTGGAAA AGAAAAAAGA GACCGCCTCG
5041 TTTCTTTTTC TTCGTCGAAA AAGGCAATAA AAATTTTTAT CACGTTTCTT TTTCTTGAAA
5101 TTTTTTTTTT TAGTTTTTTT CTCTTTCAGT GACCTCCATT GATATTTAAG TTAATAAACG
5161 GTCTTCAATT TCTCAAGTTT CAGTTTCATT TTTCTTGTTC TATTACAACT TTTTTTACTT
5221 CTTGTTCATT AGAAAGAAAG CATAGCAATC TAATCTAAGG GCGGTGTTGA CAATTAATCA
5281 TCGGCATAGT ATATCGGCAT AGTATAATAC GACAAGGTGA GGAACTAAAC CATGGCCAAG
5341 TTGACCAGTG CCGTTCCGGT GCTCACCGCG CGCGACGTCG CCGGAGCGGT CGAGTTCTGG
5401 ACCGACCGGC TCGGGTTCTC CCGGGACTTC GTGGAGGACG ACTTCGCCGG TGTGGTCCGG
5461 GACGACGTGA CCCTGTTCAT CAGCGCGGTC CAGGACCAGG TGGTGCCGGA CAACACCCTG
5521 GCCTGGGTGT GGGTGCGCGG CCTGGACGAG CTGTACGCCG AGTGGTCGGA GGTCGTGTCC
5581 ACGAACTTCC GGGACGCCTC CGGGCCGGCC ATGACCGAGA TCGGCGAGCA GCCGTGGGGG
5641 CGGGAGTTCG CCCTGCGCGA CCCGGCCGGC AACTGCGTGC ACTTCGTGGC CGAGGAGCAG
5701 GACTGACACG TCCGACGGCG GCCCACGGGT CCCAGGCCTC GGAGATCCGT CCCCCTTTTC
5761 CTTTGTCGAT ATCATGTAAT TAGTTATGTC ACGCTTACAT TCACGCCCTC CCCCCACATC
5821 CGCTCTAACC GAAAAGGAAG GAGTTAGACA ACCTGAAGTC TAGGTCCCTA TTTATTTTTT
5881 TATAGTTATG TTAGTATTAA GAACGTTATT TATATTTCAA ATTTTTCTTT TTTTTCTGTA
5941 CAGACGCGAG CTTCCCAGTA AATGTGCCAT CTCGTAGGCA GAAAACGGTT CCCCCGTAGG
6001 GTCTCTCTCT TGGCCTCCTT TCTAGGTCGG GCTGATTGCT CTTGAAGCTC TCTAGGGGGG
6061 CTCACACCAT AGGCAGATAA CGTTCCCCAC CGGCTCGCCT CGTAAGCGCA CAAGGACTGC
6121 TCCCAAAGAT CCTAGGCGGG ATTTTGCCGA TTTCGGCCTA AAGGAACCGG AACACGTAGA
6181 AAGCCAGTCC GCAGAAACGG TGCTGACCCC GGATGAATGT CAGCTACTGG GCTATCTGGA
6241 CAAGGGAAAA CGCAAGCGCA AAGAGAAAGC AGGTAGCTTG CAGTGGGCTT ACATGGCGAT
6301 AGCTAGACTG GGCGGTTTTA TGGACAGCAA GCGAACCGGA ATTGCCAGCT GGGGCGCCCT
6361 CTGGTAAGGT TGGGAAGCCC TGCAAAGTAA ACTGGATGGC TTTCTTGCCG CCAAGGATCT
6421 GATGGCGCAG GGGATCAAGA TCTGATCAAG AGACAGGATG AGGATCGTTT CGCATGATTG
6481 AACAAGATGG ATTGCACGCA GGTTCTCCGG CCGCTTGGGT GGAGAGGCTA TTCGGCTATG
6541 ACTGGGCACA ACAGACAATC GGCTGCTCTG ATGCCGCCGT GTTCCGGCTG TCAGCGCAGG
6601 GGCGCCCGGT TCTTTTTGTC AAGACCGACC TGTCCGGTGC CCTGAATGAA CTGCAGGACG
6661 AGGCAGCGCG GCTATCGTGG CTGGCCACGA CGGGCGTTCC TTGCGCAGCT GTGCTCGACG
6721 TTGTCACTGA AGCGGGAAGG GACTGGCTGC TATTGGGCGA AGTGCCGGGG CAGGATCTCC
6781 TGTCATCTCG CCTTGCTCCT GCCGAGAAAG TATCCATCAT GGCTGATGCA ATGCGGCGGC
6841 TGCATACGCT TGATCCGGCT ACCTGCCCAT TCGACCACCA AGCGAAACAT CGCATCGAGC
6901 GAGCACGTAC TCGGATGGAA GCCGGTCTTG TCGATCAGGA TGATCTGGAC GAAGAGCATC
6961 AGGGGCTCGC GCCAGCCGAA CTGTTCGCCA GGCTCAAGGC GCGCATGCCC GACGGCGAGG
```

Figure 15C

```
7021 ATCTCGTCGT GATCCATGGC GATGCCTGCT TGCCGAATAT CATGGTGGAA AATGGCCGCT
7081 TTTCTGGATT CAACGACTGT GGCCGGCTGG GTGTGGCGGA CCGCTATCAG GACATAGCGT
7141 TGGATACCCG TGATATTGCT GAAGAGCTTG GCGGCGAATG GGCTGACCGC TTCCTCGTGC
7201 TTTACGGTAT CGCCGCTCCC GATTCGCAGC GCATCGCCTT CTATCGCCTT CTTGACGAGT
7261 TCTTCTGAAT TGAAAAAGGT ACCAAGTTTA CTCATATATA CTTTAGATTG ATTTAAAACT
7321 TCATTTTTAA TTTAAAAGGA TCTAGGTGAA GATCCTTTTT GATAATCTCA TGACCAAAAT
7381 CCCTTAACGT GAGTTTTCGT TCCACTGAGC GTCAGACCCC GTAGAAAAGA TCAAAGGATC
7441 TTCTTGAGAT CCTTTTTTTC TGCGCGTAAT CTGCTGCTTG CAAACAAAAA AACCACCGCT
7501 ACCAGCGGTG GTTTGTTTGC CGGATCAAGA GCTACCAACT CTTTTTCCGA AGGTAACTGG
7561 CTTCAGCAGA GCGCAGATAC CAAATACTGT CCTTCTAGTG TAGCCGTAGT TAGGCCACCA
7621 CTTCAAGAAC TCTGTAGCAC CGCCTACATA CCTCGCTCTG CTAATCCTGT TACCAGTGGC
7681 TGCTGCCAGT GGCGATAAGT CGTGTCTTAC CGGGTTGGAC TCAAGACGAT AGTTACCGGA
7741 TAAGGCGCAG CGGTCGGGCT GAACGGGGGG TTCGTGCACA CAGCCCAGCT TGGAGCGAAC
7801 GACCTACACC GAACTGAGAT ACCTACAGCG TGAGCATTGA GAAAGCGCCA CGCTTCCCGA
7861 AGGGAGAAAG GCGGACAGGT ATCCGGTAAG CGGCAGGGTC GGAACAGGAG AGCGCACGAG
7921 GGAGCTTCCA GGGGGAAACG CCTGGTATCT TTATAGTCCT GTCGGGTTTC GCCACCTCTG
7981 ACTTGAGCGT CGATTTTTGT GATGCTCGTC AGGGGGGCGG AGCCTATGGA AAAACGCCAG
8041 CAACGCGGCC TTTTTACGGT TCCTGGCCTT TTGCTGGCCT TTTGCTCACA TGTTCTTTCC
8101 TGCGTTATCC CCTGATTCTG TGGATAACCG TATTACCGCC TTTGAGTGAG CTGATACCGC
8161 TCGCCGCAGC CGAACGACCG AGCGCAGCGA G
```

(SEQ ID NO:11)

Figure 16

```
   1 GAATTCAAAA CAAAATGTGT GCAACCTCCT CCCAGTTTAC TCAGATTACC GAGCATAATT
  61 CTCGACGATC TGCTAACTAC CAGCCGAACC TTTGGAACTT TGAGTTTCTC CAGTCTCTCG
 121 AAAATGACCT GAAGGTGGAA AAGCTCGAGG AGAAGGCGAC CAAACTCGAG GAGGAGGTGC
 181 GATGTATGAT CAACAGAGTT GACACCCAAC CCCTGTCTTT GCTGGAGCTG ATCGACGATG
 241 TGCAGCGGTT GGGTTTGACT TATAAATTCG AGAAGGACAT TATCAAGGCA CTGGAGAACA
 301 TTGTGCTCCT CGACGAGAAC AAGAAGAACA AGTCTGATCT TCACGCTACC GCTCTCTCTT
 361 TCCGACTTCT TCGACAACAC GGCTTCGAGG TGTCGCAGGA CGTCTTCGAG AGATTTAAGG
 421 ACAAGGAGGG AGGATTTAGC GGCGAGCTGA AGGGAGACGT TCAGGGTCTT CTCTCCTTGT
 481 ACGAGGCGTC CTACCTGGGA TTCGAGGGAG AGAACCTCCT GGAGGAAGCT CGTACATTTT
 541 CCATCACTCA CCTTAAGAAT AACCTTAAGG AGGGAATTAA CACCAAGGTG GCCGAGCAGG
 601 TTTCTCACGC CCTGGAGCTC CCCTACCACC AACGGCTCCA TAGACTGGAG GCTCGTTGGT
 661 TCCTGGACAA ATATGAGCCA AAGGAGCCTC ATCATCAGTT GCTGTTGGAG TTGGCCAAGC
 721 TGGACTTCAA TATGGTTCAG ACGCTGCACC AAAAGGAGTT GCAGGACCTG TCTCGATGGT
 781 GGACCGAGAT GGGATTGGCC TCGAAGCTGG ATTTTGTCCG TGACCGACTT ATGGAGGTCT
 841 ATTTTTGGGC CCTTGGAATG GCGCCTGACC CCCAGTTCGG AGAGTGCCGG AAGGCGGTGA
 901 CGAAGATGTT CGGTCTTGTG ACTATCATCG ACGACGTCTA CGATGTCTAC GGCACACTCG
 961 ACGAGTTGCA GCTGTTCACT GACGCCGTCG AGCGATGGGA TGTGAACGCC ATTAATACTC
1021 TCCCTGACTA TATGAAGCTG TGCTTCCTGG CTCTGTACAA CACTGTCAAC GATACCTCGT
1081 ACTCTATCCT CAAGGAGAAG GGACACAACA ATCTCTCCTA CTTGACCAAA TCCTGGCGAG
1141 AACTGTGCAA GGCTTTTCTG CAGGAGGCTA AATGGTCCAA TAACAAGATC ATTCCTGCTT
1201 TTTCTAAATA CCTGGAAAAT GCCTCGGTGT CGAGCTCTGG CGTCGCCCTT CTGGCCCCTT
1261 CCTACTTCTC CGTCTGCCAG CAGCAGGAGG ATATTTCCGA TCATGCTCTT AGATCGCTGA
1321 CCGATTTTCA CGGCCTCGTG CGATCTTCCT GCGTGATTTT TCGGTTGTGT AATGACCTTG
1381 CGACCTCTGC TGCTGAGCTG GAACGAGGCG AGACTACAAA TTCCATTATT TCTTACATGC
1441 ACGAAAACGA TGGAACATCT GAAGAACAGG CTAGAGAGGA ACTGCGAAAG TTGATCGACG
1501 CCGAGTGGAA GAAGATGAAC AGAGAGCGGG TGTCCGACTC TACCCTGCTT CCCAAGGCCT
1561 TCATGGAGAT CGCCGTGAAC ATGGCTCGAG TTTCCCATTG TACTTACCAG TACGGTGACG
1621 GCCTGGGTCG TCCGGACTAC GCTACAGAGA ACCGAATCAA GCTGCTGCTC ATCGACCCCT
1681 TCCCTATCAA CCAATTGATG TACGTGTAAT AGTCTAGAGG ATCC
```

(SEQ ID NO:12)

Figure 17

```
   1 GAATTCAACA AAAATGTGCT CTGTTTCCAC TGAGAACGTG TCCTTTACTG AGACTGAGAC
  61 TGAAGCACGT AGAAGCGCCA ACTACGAACC CAACTCCTGG GATTATGACT TTCTGCTGTC
 121 TTCTGACACC GACGAGTCGA TCGAGGTTTA TAAGGATAAG GCCAAGAAAC TTGAGGCCGA
 181 GGTCAGACGA GAGATTAACA ACGAGAAGGC CGAGTTCCTG ACCCTTCTTG AGCTGATCGA
 241 CAACGTTCAA CGACTTGGTC TTGGTTACCG TTTCGAATCC GATATCCGAC GTGCATTGGA
 301 TCGATTTGTC TCGTCCGGAG GTTTCGATGG TGTGACTAAG ACGTCGCTGC ACGCCACAGC
 361 TCTTTCCTTC AGACTGTTGC GGCAGCATGG ATTTGAGGTT TCCCAGGAAG CCTTTTCTGG
 421 TTTCAAGGAT CAGAACGGAA ACTTTTTGGA GAATCTCAAG GAGGACACCA AGGCCATCCT
 481 GTCGTTGTAT GAGGCCTCGT TCCTGGCTCT TGAGGGCGAG AATATTCTGG ATGAGGCTCG
 541 GGTTTTCGCT ATTTCGCACC TGAAGGAGTT GTCGGAGGAA AAGATCGGAA AGGAACTGGC
 601 CGAGCAGGTC AACCATGCAC TTGAACTTCC CCTGCATCGA CGTACCCAGC GACTGGAGGC
 661 CGTGTGGAGC ATCGAGGCGT ACAGAAAAAA GGAGGATGCT AATCAGGTTC TGCTCGAACT
 721 CGCTATCCTC GACTATAACA TGATTCAGAG CGTGTACCAG CGTGACTTGC GAGAGACAAG
 781 CCGGTGGTGG CGACGGGTGG GACTGGCCAC GAAGCTCCAC TTTGCTAAAG ATCGATTGAT
 841 TGAGTCGTTC TACTGGGCAG TGGGTGTGGC CTTTGAGCCT CAGTACTCCG ACTGCCGAAA
 901 CTCCGTTGCA AAGATGTTTT CTTTTGTCAC TATCATCGAC GACATCTACG ATGTTTACGG
 961 CACTCTCGAT GAACTCGAAC TCTTCACGGA CGCTGTCGAG CGATGGGATG TGAATGCCAT
1021 TAATGATCTG CCAGATTATA TGAAGTTGTG TTTCTTGGCG CTCTACAACA CAATTAATGA
1081 AATTGCCTAC GACAACCTCA AGGACAAGGG AGAGAACATT CTGCCCTACC TTACTAAAGC
1141 CTGGGCCGAC CTGTGTAACG CCTTTTTGCA GGAAGCCAAG TGGCTCTATA ACAAATCTAC
1201 TCCTACATTT GATGACTACT TCGGCAACGC TTGGAAGTCT TCCAGCGGCC CTCTCCAGTT
1261 GATCTTCGCT TACTTTGCAG TGGTCCAGAA CATCAAGAAA GAGGAGATTG AGAACCTCCA
1321 GAAGTATCAC GACATCATCT CCCGACCTTC GCACATCTTT CGACTGTGCA ATGACCTTGC
1381 CTCCGCATCC GCTGAGATTG CCCGAGGAGA AACAGCCAAT TCTGTGTCGT GTTACATGCG
1441 TACAAAGGGC ATCTCCGAGG AGCTGGCTAC CGAGTCTGTG ATGAACCTGA TCGATGAAAC
1501 CTGTAAGAAG ATGAACAAAG AGAAACTGGG CGGTTCTCTG TTCGCCAAAC CATTTGTTGA
1561 AACCGCGATC AATCTGGCTC GTCAGTCTCA TTGTACTTAC CATAACGGTG ACGCGCACAC
1621 TTCGCCGGAC GAATTGACCC GTAAGCGTGT GCTTTCGGTG ATTACCGAGC CGATCCTGCC
1681 GTTCGAAAGA TAATAGGATC C
```

(SEQ ID NO:13)

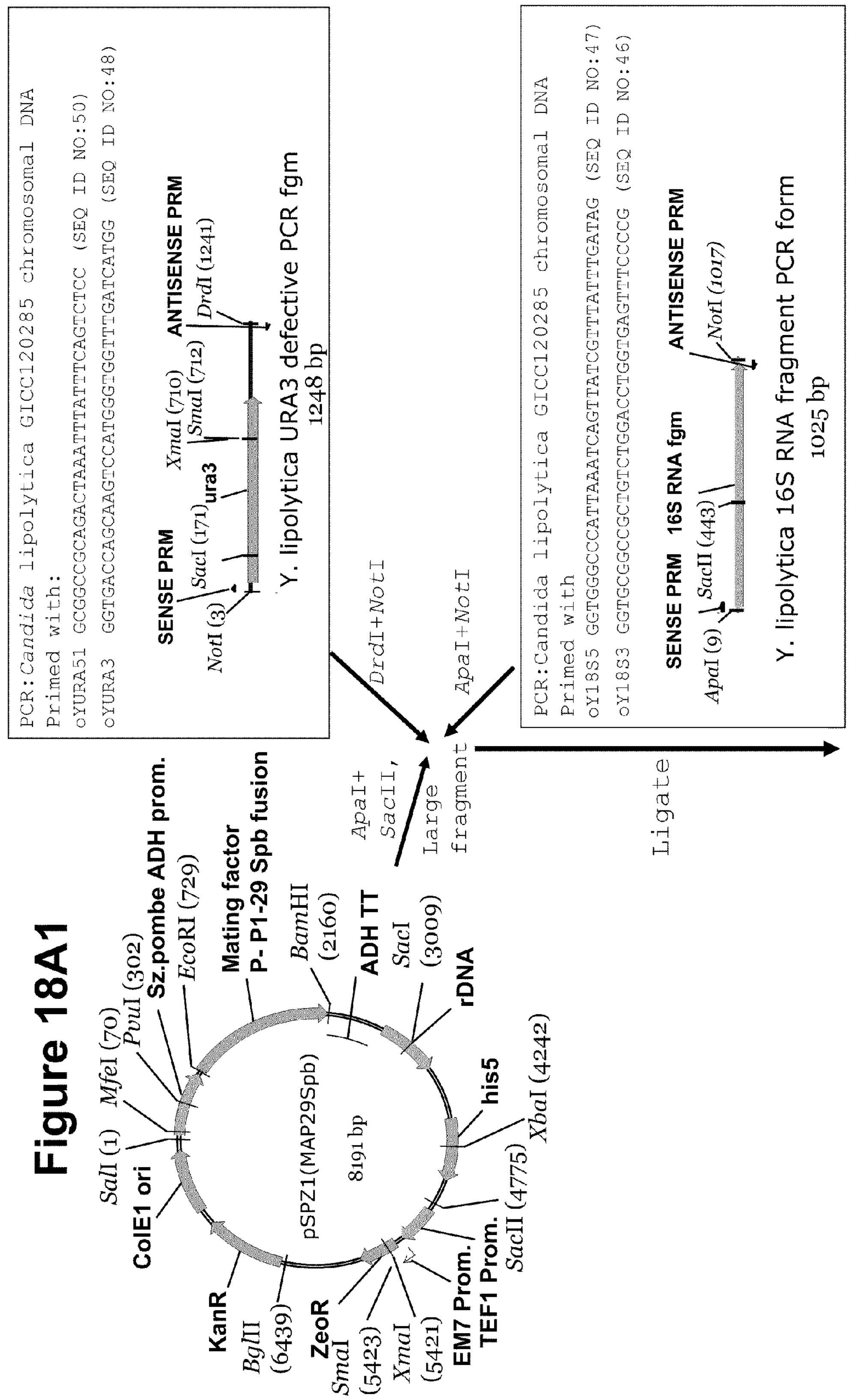
Figure 18A1
SalI (1)
MfeI (70)
PvuI (302)
Sz.pombe ADH prom.
EcoRI (729)
Mating factor
P- P1-29 Spb fusion
BamHI (2160)
ADH TT
SacI (3009)
rDNA
his5
XbaI (4242)
SacII (4775)
TEF1 Prom.
EM7 Prom.
XmaI (5421)
SmaI (5423)
ZeoR
BglII (6439)
KanR
ColE1 ori
pSPZ1(MAP29Spb)
8191 bp
ApaI+ SacII,
Large fragment
Ligate
DrdI+NotI
ApaI+NotI
PCR:Candida lipolytica GICC120285 chromosomal DNA
Primed with:
oYURA51 GCGGCCGCAGACTAAATTTATTTCAGTCTCC (SEQ ID NO:50)
oYURA3 GGTGACCAGCAAGTCCATGGGTGGTTTGATCATGG (SEQ ID NO:48)
SENSE PRM
NotI (3)
SacI (171)
ura3
XmaI (710)
SmaI (712)
ANTISENSE PRM
DrdI (1241)
Y. lipolytica URA3 defective PCR fgm
1248 bp
PCR:Candida lipolytica GICC120285 chromosomal DNA
Primed with
oY18S5 GGTGGGCCCATTAAATCAGTTATCGTTTATTTGATAG (SEQ ID NO:47)
oY18S3 GGTGCGGCCGCTGTCTGGACCTGGTGAGTTTCCCCG (SEQ ID NO:46)
SENSE PRM
16S RNA fgm
ApaI (9)
SacII (443)
ANTISENSE PRM
NotI (1017)
Y. lipolytica 16S RNA fragment PCR form
1025 bp Figure 18A2
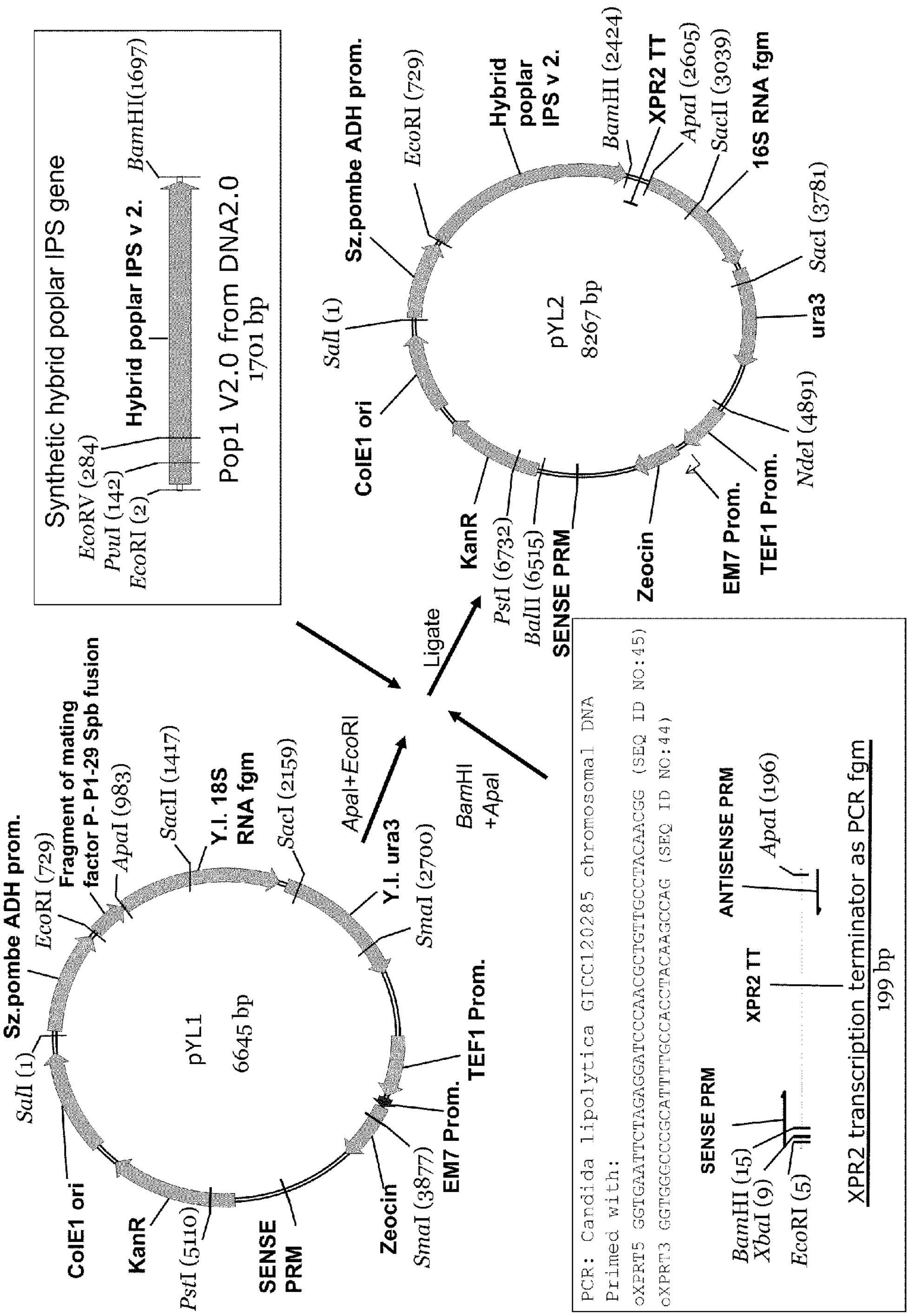

Figure 20
*Y. lipolytica* CLIB122:: pYLA(MAP29)
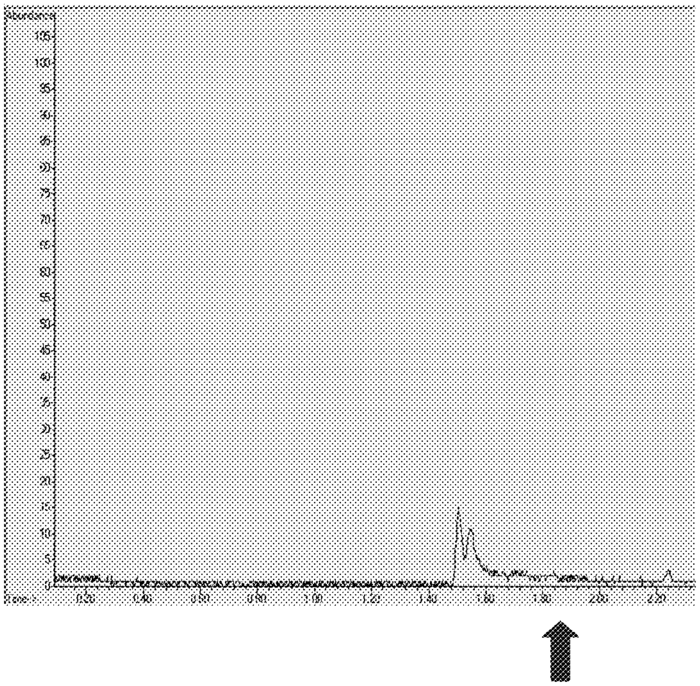
*Y. lipolytica* CLIB122:: pYLA(KZ1)
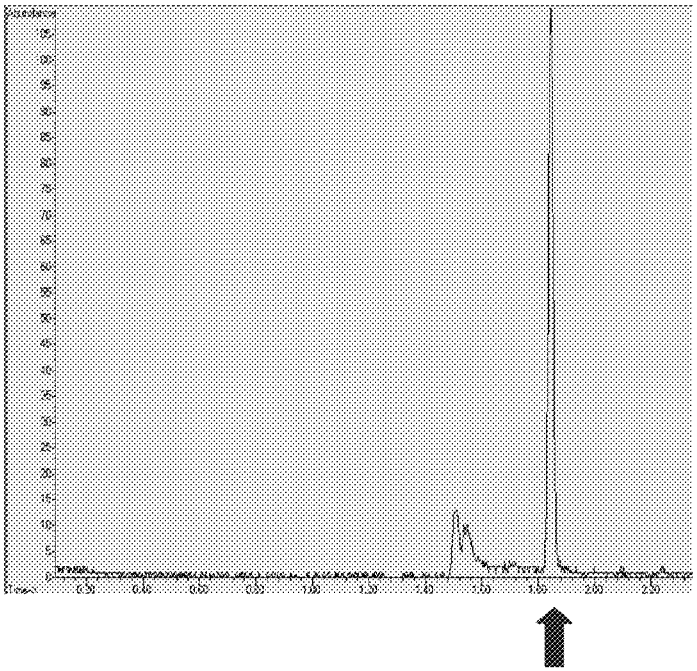

Figure 22A 1-
gctggtaccatatgggaattcgaagctttctagaacaaaaactcatctcagaagaggatctgaa
tagcgccgtcgaccatcatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgaccccatgccgaactcagaagtg
aaacgccgtagcgccgatggtagtgtggggtctccccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg
agggtggcgggcaggacgcccgccataaactgccaggcatcaaattaagcagaaggccatcctg
acggatggcctttttgcgtttctacaaactctttttgtttatttttctaaatacattcaaatat
gtatccgcttaaccggaattgccagctggggcgccctctggtaaggttgggaagccctgcaaag
taaactggatggctttctcgccgccaaggatctgatggcgcaggggatcaagctctgatcaaga
gacaggatgaggatcgtttcgcatgattgaacaagatggattgcacgcaggttctccggccgct
tgggtggagaggctattcggctatgactgggcacaacagacaatcggctgctctgatgccgccg
tgttccggctgtcagcgcaggggcgcccggttctttttgtcaagaccgacctgtccggtgccct
gaatgaactgcaagacgaggcagcgcggctatcgtggctggccacgacgggcgttccttgcgca
gctgtgctcgacgttgtcactgaagcgggaagggactggctgctattgggcgaagtgccggggc
aggatctcctgtcatctcaccttgctcctgccgagaaagtatccatcatggctgatgcaatgcg
gcggctgcatacgcttgatccggctacctgcccattcgaccaccaagcgaaacatcgcatcgag
cgagcacgtactcggatggaagccggtcttgtcgatcaggatgatctggacgaagagcatcagg
ggctcgcgccagccgaactgttcgccaggctcaaggcgagcatgcccgacggcgaggatctcgt
cgtgacccatggcgatgcctgcttgccgaatatcatggtggaaaatggccgcttttctggattc
atcgactgtggccggctgggtgtggcggaccgctatcaggacatagcgttggctacccgtgata
ttgctgaagagcttggcggcgaatgggctgaccgcttcctcgtgctttacggtatcgccgctcc
cgattcgcagcgcatcgccttctatcgccttcttgacgagttcttctgacatgaccaaaatccc
ttaacgtgagttttcgttccactgagcgtcagaccccgtagaaaagatcaaaggatcttcttga
gatcctttttttctgcgcgtaatctgctgcttgcaaacaaaaaaaccaccgctaccagcggtgg
tttgtttgccggatcaagagctaccaactctttttccgaaggtaactggcttcagcagagcgca
gataccaaatactgtccttctagtgtagccgtagttaggccaccacttcaagaactctgtagca
ccgcctacatacctcgctctgctaatcctgttaccagtggctgctgccagtggcgataagtcgt
gtcttaccgggttggactcaagacgatagttaccggataaggcgcagcggtcgggctgaacggg
gggttcgtgcacacagcccagcttggagcgaacgacctacaccgaactgagatacctacagcgt
gagctatgagaaagcgccacgcttcccgaagggagaaaggcggacaggtatccggtaagcggca
gggtcggaacaggagagcgcacgagggagcttccagggggaaacgcctggtatctttatagtcc
tgtcgggtttcgccacctctgacttgagcgtcgatttttgtgatgctcgtcaggggggcggagc
ctatggaaaaacgccagcaacgcggcctttttacggttcctggccttttgctggccttttgctc
acatgttctttcctgcgttatcccctgattctgtggataaccgtattaccgcctttgagtgagc
tgataccgctcgccgcagccgaacgaccgagcgcagcgagtcagtgagcgaggaagcggaagag
cgcctgatgcggtattttctccttacgcatctgtgcggtatttcacaccgcatatggtgcactc
tcagtacaatctgctctgatgccgcatagttaagccagtatacactccgctatcgctacgtgac
tgggtcatggctgcgccccgacacccgccaacacccgctgacgcgccctgacgggcttgtctgc
tcccggcatccgcttacagacaagctgtgaccgtctccgggagctgcatgtgtcagaggttttc
accgtcatcaccgaaacgcgcgaggcagcagatcaattcgcgcgcgaaggcgaagcggcatgca
tttacgttgacaccatcgaatggtgcaaaacctttcgcggtatggcatgatagcgcccggaaga

Figure 22B gagtcaattcagggtggtgaatgtgaaaccagtaacgttatacgatgtcgcagagtatgccggt
gtctcttatcagaccgtttcccgcgtggtgaaccaggccagccacgtttctgcgaaaacgcggg
aaaaagtggaagcggcgatggcggagctgaattacattcccaaccgcgtggcacaacaactggc
gggcaaacagtcgttgctgattggcgttgccacctccagtctggccctgcacgcgccgtcgcaa
attgtcgcggcgattaaatctcgcgccgatcaactgggtgccagcgtggtggtgtcgatggtag
aacgaagcggcgtcgaagcctgtaaagcggcggtgcacaatcttctcgcgcaacgcgtcagtgg
gctgatcattaactatccgctggatgaccaggatgccattgctgtggaagctgcctgcactaat
gttccggcgttatttcttgatgtctctgaccagacacccatcaacagtattattttctcccatg
aagacggtacgcgactgggcgtggagcatctggtcgcattgggtcaccagcaaatcgcgctgtt
agcgggcccattaagttctgtctcggcgcgtctgcgtctggctggctggcataaatatctcact
cgcaatcaaattcagccgatagcggaacgggaaggcgactggagtgccatgtccggttttcaac
aaaccatgcaaatgctgaatgagggcatcgttcccactgcgatgctggttgccaacgatcagat
ggcgctgggcgcaatgcgcgccattaccgagtccgggctgcgcgttggtgcggatatctcggta
gtgggatacgacgataccgaagacagctcatgttatatcccgccgtcaaccaccatcaaacagg
attttcgcctgctggggcaaaccagcgtggaccgcttgctgcaactctctcagggccaggcggt
gaagggcaatcagctgttgcccgtctcactggtgaaaagaaaaaccaccctggcgcccaatacg
caaaccgcctctccccgcgcgttggccgattcattaatgcagctggcacgacaggtttcccgac
tggaaagcgggcagtgagcgcaacgcaattaatgtgagttagcgcgaattgatctggtttgaca
gcttatcatcgactgcacggtgcaccaatgcttctggcgtcaggcagccatcggaagctgtggt
atggctgtgcaggtcgtaaatcactgcataattcgtgtcgctcaaggcgcactcccgttctgga
taatgtttttgcgccgacatcataacggttctggcaaatattctgaaatgagctgttgacaat
taatcatccggctcgtataatgtgtggaattgtgagcggataacaatttcacacaggaaacagc
gccgctgagaaaaagcgaagcggcactgctctttaacaatttatcagacaatctgtgtgggcac
tcgaccggaattatcgattaactttattattaaaaattaaagaggtatatattaatgtatcgat
taaataaggaggaataaaccatgtgtgcgacctcttctcaatttactcagattaccgagcataa
ttcccgtcgttccgcaaactatcagccaaacctgtggaatttcgaattcctgcaatccctggag
aacgacctgaaagtggaaaagctggaggagaaagcgaccaaactggaggaagaagttcgctgca
tgatcaaccgtgtagacacccagccgctgtccctgctggagctgatcgacgatgtgcagcgcct
gggtctgacctacaaatttgaaaaagacatcattaaagccctggaaaacatcgtactgctggac
gaaaacaaaaagaacaaatctgacctgcacgcaaccgctctgtctttccgtctgctgcgtcagc
acggtttcgaggtttctcaggatgtttttgagcgtttcaaggataaagaaggtggtttcagcgg
tgaactgaaaggtgacgtccaaggcctgctgagcctgtatgaagcgtcttacctgggtttcgag
ggtgagaacctgctggaggaggcgcgtaccttttccatcacccacctgaagaacaacctgaaag
aaggcattaataccaaggttgcagaacaagtgagccacgccctggaactgccatatcaccagcg
tctgcaccgtctggaggcacgttggttcctggataaatacgaaccgaaagaaccgcatcaccag
ctgctgctggagctggcgaagctggattttaacatggtacagaccctgcaccagaaagagctgc
aagatctgtcccgctggtggaccgagatgggcctggctagcaaactggattttgtacgcgaccg
cctgatggaagtttatttctgggcactgggtatggcgccagacccgcagtttggtgaatgtcgc
aaagctgttactaaaatgtttggtctggtgacgatcatcgatgacgtgtatgacgtttatggca
ctctggacgaactgcaactgttcaccgatgctgtagagcgctgggacgttaacgctattaacac
cctgccggactatatgaaactgtgtttcctggcactgtacaacaccgttaacgacacgtcctat
tctattctgaaagagaaaggtcataacaacctgtcctatctgacgaaaagctggcgtgaactgt
gcaaagcctttctgcaagaggcgaaatggtccaacaacaaaattatcccggctttctccaagta
cctggaaaacgccagcgtttcctcctccggtgtagcgctgctggcgccgtcttacttttccgta

Figure 22C tgccagcagcaggaagacatctccgaccacgcgctgcgttccctgaccgacttccatggtctgg
tgcgttctagctgcgttatcttccgcctgtgcaacgatctggccacctctgcggcggagctgga
acgtggcgagactaccaattctatcattagctacatgcacgaaaacgatggtaccagcgaggaa
caggcccgcgaagaactgcgtaaactgatcgacgccgaatggaaaaagatgaatcgtgaacgcg
ttagcgactccaccctgctgcctaaagcgttcatggaaatcgcagttaacatggcacgtgtttc
ccactgcacctaccagtatggcgatggtctgggtcgcccagactacgcgactgaaaaccgcatc
aaactgctgctgattgaccctttcccgattaaccagctgatgtatgtctaactgcatcgcccctt
aggaggtaaaaaaaaatgactgccgacaacaatagtatgccccatggtgcagtatctagttacg
ccaaattagtgcaaaaccaaacacctgaagacattttggaagagtttcctgaaattattccatt
acaacaaagacctaatacccgatctagtgagacgtcaaatgacgaaagcggagaaacatgtttt
tctggtcatgatgaggagcaaattaagttaatgaatgaaaattgtattgttttggattgggacg
ataatgctattggtgccggtaccaagaaagtttgtcatttaatggaaaatattgaaaagggttt
actacatcgtgcattctccgtctttattttcaatgaacaaggtgaattacttttacaacaaaga
gccactgaaaaaataactttccctgatctttggactaacacatgctgctctcatccactatgta
ttgatgacgaattaggtttgaagggtaagctagacgataagattaagggcgctattactgcggc
ggtgagaaaactagatcatgaattaggtattccagaagatgaaactaagacaaggggtaagttt
cactttttaaacagaatccattacatggcaccaagcaatgaaccatggggtgaacatgaaattg
attacatcctattttataagatcaacgctaaagaaaacttgactgtcaacccaaacgtcaatga
agttagagacttcaaatgggtttcaccaaatgatttgaaaactatgtttgctgacccaagttac
aagtttacgccttggtttaagattatttgcgagaattacttattcaactggtgggagcaattag
atgacctttctgaagtggaaaatgacaggcaaattcatagaatgctataacaacgcgtcctgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacaccccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagttttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaaagacccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgaccttt
gctgcgggtctggcgattggtgggtacaaacccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg

Figure 22D cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgca
(SEQ ID NO:20)

Figure 25A

5'-
tagaaaaactcatcgagcatcaaatgaaactgcaatttattcatatcaggattatcaataccat
atttttgaaaaagccgtttctgtaatgaaggagaaaactcaccgaggcagttccataggatggc
aagatcctggtatcggtctgcgattccgactcgtccaacatcaatacaacctattaatttcccc
tcgtcaaaaataaggttatcaagtgagaaatcaccatgagtgacgactgaatccggtgagaatg
gcaaaagtttatgcatttctttccagacttgttcaacaggccagccattacgctcgtcatcaaa
atcactcgcatcaaccaaaccgttattcattcgtgattgcgcctgagcgaggcgaaatacgcga
tcgctgttaaaaggacaattacaaacaggaatcgagtgcaaccggcgcaggaacactgccagcg
catcaacaatattttcacctgaatcaggatattcttctaatacctggaacgctgtttttccggg
gatcgcagtggtgagtaaccatgcatcatcaggagtacggataaaatgcttgatggtcggaagt
ggcataaattccgtcagccagtttagtctgaccatctcatctgtaacatcattggcaacgctac
ctttgccatgtttcagaaacaactctggcgcatcgggcttcccatacaagcgatagattgtcgc
acctgattgcccgacattatcgcgagcccatttatacccatataaatcagcatccatgttggaa
tttaatcgcggcctcgacgtttcccgttgaatatggctcatattcttcctttttcaatattatt
gaagcatttatcagggttattgtctcatgagcggatacatatttgaatgtatttagaaaaataa
acaaataggggtcagtgttacaaccaattaaccaattctgaacattatcgcgagcccatttata
cctgaatatggctcataacaccccttgtttgcctggcggcagtagcgcggtggtcccacctgac
cccatgccgaactcagaagtgaaacgccgtagcgccgatggtagtgtggggactccccatgcga
gagtagggaactgccaggcatcaaataaaacgaaaggctcagtcgaaagactgggcctttcgcc
cgggctaattagggggtgtcgccctttagtcgctgaacatgtgctctgtttctaccgagaacgt
ttccttcactgagacggaaaccgaggcacgtcgtagcgcgaactacgagccgaatagctgggac
tacgatttcctgctgtcttccgatactgacgaatctattgaggtgtacaaagacaaagcaaaga
aactggaggctgaagtgcgccgcgaaattaacaacgagaaagctgaattcctgactctgctgga
gctgatcgataacgtacagcgcctgggtctgggttaccgcttcgaatctgatatccgtcgcgca
ctggatcgtttcgtaagcagcggcggtttcgatggcgtgaccaaaacgagcctgcacgctaccg
cgctgtccttccgtctgctgcgtcagcacggcttcgaagtttctcaggaagcattctccggttt
caaagatcaaaacggtaacttcctggaaaacctgaaagaagacactaaggcgatcctgagcctg
tatgaggcaagctttctggccctggagggtgagaacatcctggatgaggcgcgcgtattcgcca
tctcccatctgaaagagctgtctgaagagaaaatcggtaaggaactggcagagcaggttaatca
cgcactggaactgccgctgcatcgtcgtacccagcgtctggaggcggtttggtccatcgaagcg
taccgcaaaaaggaggatgctaaccaggttctgctggaactggccatcctggactacaacatga
tccagtccgtttaccagcgtgatctgcgtgaaacctcccgttggtggcgccgtgtgggcctggc
gaccaaactgcacttcgctaaggaccgcctgattgagtctttttactgggcagtcggcgttgcg
ttcgaacctcagtattctgactgccgtaacagcgttgcgaaaatgttcagcttcgttactatta
tcgacgacatctacgacgtttacggtactctggacgagctggaactgtttaccgacgctgtcga
acgttgggatgttaacgccatcaacgatctgcctgactacatgaaactgtgcttcctggcactg
tataacacgatcaacgaaattgcatacgacaacctgaaagacaaaggtgaaaacatcctgccgt
acctgactaaagcgtgggcggatctgtgtaacgcttttctgcaagaagcgaaatggctgtataa
caaatccactccgacctttgacgattatttcggcaatgcctggaaatccagctctggcccgctg
caactgatcttcgcttattttgcggttgtccaaaacatcaaaaaggaggaaattgaaaacctgc
aaaaataccacgatatcattagccgtccttctcatatctttcgcctgtgcaacgacctggcaag
cgcgtccgcagagatcgcacgtggcgaaaccgctaactctgtttcctgctacatgcgcaccaag
ggcatttccgaagagctggcaaccgagagcgtaatgaatctgatcgacgaaacctgtaagaaaa
tgaacaaagaaaaactgggtggctccctgttcgctaaaccgttcgtagagactgctattaacct

Figure 25B ggcacgtcagagccactgcacctaccacaatggtgacgcacatactagcccggatgaactgact
cgtaaacgtgtactgtctgttatcaccgaaccgattctgccgttcgaacgttaactgcagcgtc
aatcgaaagggcgacacaaaatttattctaaatgcataataaatactgataacatcttatagtt
tgtattatattttgtattatcgttgacatgtataattttgatatcaaaaactgattttcccttt
attattttcgagatttattttcttaattctctttaacaaactagaaatattgtatatacaaaaa
atcataaataatagatgaatagtttaattataggtgttcatcaatcgaaaaagcaacgtatctt
atttaaagtgcgttgctttttttctcatttataaggttaaataattctcatatatcaagcaaagt
gacaggcgcccttaaatattctgacaaatgctctttccctaaactccccccataaaaaaacccg
ccgaagcgggtttttacgttatttgcggattaacgattactcgttatcagaaccgcccaggggg
cccgagcttaagactggccgtcgttttacaacacagaaagagtttgtagaaacgcaaaaaggcc
atccgtcaggggccttctgcttagtttgatgcctggcagttccctactctcgccttccgcttcc
tcgctcactgactcgctgcgctcggtcgttcggctgcggcgagcggtatcagctcactcaaagg
cggtaatacggttatccacagaatcaggggataacgcaggaaagaacatgtgagcaaaaggcca
gcaaaaggccaggaaccgtaaaaaggccgcgttgctggcgtttttccataggctccgcccccct
gacgagcatcacaaaaatcgacgctcaagtcagaggtggcgaaacccgacaggactataaagat
accaggcgtttccccctggaagctccctcgtgcgctctcctgttccgaccctgccgcttaccgg
atacctgtccgcctttctcccttcgggaagcgtggcgctttctcatagctcacgctgtaggtat
ctcagttcggtgtaggtcgttcgctccaagctgggctgtgtgcacgaaccccccgttcagcccg
accgctgcgccttatccggtaactatcgtcttgagtccaacccggtaagacacgacttatcgcc
actggcagcagccactggtaacaggattagcagagcgaggtatgtaggcggtgctacagagttc
ttgaagtggtggcctaactacggctacactagaagaacagtatttggtatctgcgctctgctga
agccagttaccttcggaaaaagagttggtagctcttgatccggcaaacaaaccaccgctggtag
cggtggtttttttgtttgcaagcagcagattacgcgcagaaaaaaaggatctcaagaagatcct
ttgatcttttctacggggtctgacgctcagtggaacgacgcgcgcgtaactcacgttaaggat
tttggtcatgagcttgcgccgtcccgtcaagtcagcgtaatgctctgcttt
(SEQ ID NO:21)

Figure 27A

5'-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgtttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgctctgtttctaccgagaacgtttccttcact
gagacggaaaccgaggcacgtcgtagcgcgaactacgagccgaatagctgggactacgatttcc
tgctgtcttccgatactgacgaatctattgaggtgtacaaagacaaagcaaagaaactggaggc
tgaagtgcgccgcgaaattaacaacgagaaagctgaattcctgactctgctggagctgatcgat
aacgtacagcgcctgggtctgggttaccgcttcgaatctgatatccgtcgcgcactggatcgtt
tcgtaagcagcggcggtttcgatggcgtgaccaaaacgagcctgcacgctaccgcgctgtcctt
ccgtctgctgcgtcagcacggcttcgaagtttctcaggaagcattctccggtttcaaagatcaa
aacggtaacttcctggaaaacctgaaagaagacactaaggcgatcctgagcctgtatgaggcaa
gctttctggccctggagggtgagaacatcctggatgaggcgcgcgtattcgccatctcccatct
gaaagagctgtctgaagagaaaatcggtaaggaactggcagagcaggttaatcacgcactggaa
ctgccgctgcatcgtcgtacccagcgtctggaggcggtttggtccatcgaagcgtaccgcaaaa
aggaggatgctaaccaggttctgctggaactggccatcctggactacaacatgatccagtccgt
ttaccagcgtgatctgcgtgaaacctcccgttggtggcgccgtgtgggcctggcgaccaaactg
cacttcgctaaggaccgcctgattgagtctttttactgggcagtcggcgttgcgttcgaacctc
agtattctgactgccgtaacagcgttgcgaaaatgttcagcttcgttactattatcgacgacat
ctacgacgtttacggtactctggacgagctggaactgtttaccgacgctgtcgaacgttgggat
gttaacgccatcaacgatctgcctgactacatgaaactgtgcttcctggcactgtataacacga
tcaacgaaattgcatacgacaacctgaaagacaaaggtgaaaacatcctgccgtacctgactaa
agcgtgggcggatctgtgtaacgcttttctgcaagaagcgaaatggctgtataacaaatccact
ccgacctttgacgattatttcggcaatgcctggaaatccagctctggcccgctgcaactgatct
tcgcttattttgcggttgtccaaaacatcaaaaaggaggaaattgaaaacctgcaaaaatacca
cgatatcattagccgtccttctcatatctttcgcctgtgcaacgacctggcaagcgcgtccgca
gagatcgcacgtggcgaaaccgctaactctgtttcctgctacatgcgcaccaagggcatttccg
aagagctggcaaccgagagcgtaatgaatctgatcgacgaaacctgtaagaaaatgaacaaaga
aaaactgggtggctccctgttcgctaaaccgttcgtagagactgctattaacctggcacgtcag
agccactgcacctaccacaatggtgacgcacatactagcccggatgaactgactcgtaaacgtg
tactgtctgttatcaccgaaccgattctgccgttcgaacgttaactgcagctggtaccatatgg
gaattcgaagctttctagaacaaaaactcatctcagaagaggatctgaatagcgccgtcgacca
tcatcatcatcatcattgagtttaaacggtctccagcttggctgttttggcggatgagagaaga
ttttcagcctgatacagattaaatcagaacgcagaagcggtctgataaaacagaatttgcctgg
cggcagtagcgcggtggtcccacctgaccccatgccgaactcagaagtgaaacgccgtagcgcc
gatggtagtgtggggtctccccatgcgagagtagggaactgccaggcatcaaataaaacgaaag
gctcagtcgaaagactgggcctttcgttttatctgttgtttgtcggtgaacgctctcctgagta
ggacaaatccgccgggagcggatttgaacgttgcgaagcaacggcccggagggtggcgggcagg
acgcccgccataaactgccaggcatcaaattaagcagaaggccatcctgacggatggcctttt
gcgtttctacaaactctttttgtttatttttctaaatacattcaaatatgtatccgctcatgag
acaataaccctgataaatgcttcaataatattgaaaaaggaagagtatgagtattcaacatttc

Figure 27B cgtgtcgcccttattcccttttttgcggcattttgccttcctgtttttgctcacccagaaacgc
tggtgaaagtaaaagatgctgaagatcagttgggtgcacgagtgggttacatcgaactggatct
caacagcggtaagatccttgagagttttcgccccgaagaacgttttccaatgatgagcactttt
aaagttctgctatgtggcgcggtattatcccgtgttgacgccgggcaagagcaactcggtcgcc
gcatacactattctcagaatgacttggttgagtactcaccagtcacagaaaagcatcttacgga
tggcatgacagtaagagaattatgcagtgctgccataaccatgagtgataacactgcggccaac
ttacttctgacaacgatcggaggaccgaaggagctaaccgcttttttgcacaacatgggggatc
atgtaactcgccttgatcgttgggaaccggagctgaatgaagccataccaaacgacgagcgtga
caccacgatgcctgtagcaatggcaacaacgttgcgcaaactattaactggcgaactacttact
ctagcttcccggcaacaattaatagactggatggaggcggataaagttgcaggaccacttctgc
gctcggcccttccggctggctggtttattgctgataaatctggagccggtgagcgtgggtctcg
cggtatcattgcagcactggggccagatggtaagccctcccgtatcgtagttatctacacgacg
gggagtcaggcaactatggatgaacgaaatagacagatcgctgagataggtgcctcactgatta
agcattggtaactgtcagaccaagtttactcatatatactttagattgatttaaaacttcattt
ttaatttaaaaggatctaggtgaagatcctttttgataatctcatgaccaaaatcccttaacgt
gagttttcgttccactgagcgtcagaccccgtagaaaagatcaaaggatcttcttgagatcctt
tttttctgcgcgtaatctgctgcttgcaaacaaaaaaaccaccgctaccagcggtggtttgttt
gccggatcaagagctaccaactctttttccgaaggtaactggcttcagcagagcgcagatacca
aatactgtccttctagtgtagccgtagttaggccaccacttcaagaactctgtagcaccgccta
catacctcgctctgctaatcctgttaccagtggctgctgccagtggcgataagtcgtgtcttac
cgggttggactcaagacgatagttaccggataaggcgcagcggtcgggctgaacggggggttcg
tgcacacagcccagcttggagcgaacgacctacaccgaactgagatacctacagcgtgagctat
gagaaagcgccacgcttcccgaagggagaaaggcggacaggtatccggtaagcggcagggtcgg
aacaggagagcgcacgagggagcttccagggggaaacgcctggtatctttatagtcctgtcggg
tttcgccacctctgacttgagcgtcgatttttgtgatgctcgtcaggggggcggagcctatgga
aaaacgccagcaacgcggcctttttacggttcctggccttttgctggccttttgctcacatgtt
ctttcctgcgttatcccctgattctgtggataaccgtattaccgcctttgagtgagctgatacc
gctcgccgcagccgaacgaccgagcgcagcgagtcagtgagcgaggaagcggaagagcgcctga
tgcggtattttctccttacgcatctgtgcggtatttcacaccgcatatggtgcactctcagtac
aatctgctctgatgccgcatagttaagccagtatacactccgctatcgctacgtgactgggtca
tggctgcgccccgacacccgccaacacccgctgacgcgccctgacgggcttgtctgctcccggc
atccgcttacagacaagctgtgaccgtctccgggagctgcatgtgtcagaggttttcaccgtca
tcaccgaaacgcgcgaggcagcagatcaattcgcgcgcgaaggcgaagcggcatgcatttacgt
tgacaccatcgaatggtgcaaaacctttcgcggtatggcatgatagcgcccggaagagagtcaa
ttcagggtggtgaatgtgaaaccagtaacgttatacgatgtcgcagagtatgccggtgtctctt
atcagaccgtttcccgcgtggtgaaccaggccagccacgtttctgcgaaaacgcgggaaaaagt
ggaagcggcgatggcggagctgaattacattcccaaccgcgtggcacaacaactggcgggcaaa
cagtcgttgctgattggcgttgccacctccagtctggccctgcacgcgccgtcgcaaattgtcg
cggcgattaaatctcgcgccgatcaactgggtgccagcgtggtggtgtcgatggtagaacgaag
cggcgtcgaagcctgtaaagcggcggtgcacaatcttctcgcgcaacgcgtcagtgggctgatc
attaactatccgctggatgaccaggatgccattgctgtggaagctgcctgcactaatgttccgg
cgttatttcttgatgtctctgaccagacacccatcaacagtattattttctcccatgaagacgg
tacgcgactgggcgtggagcatctggtcgcattgggtcaccagcaaatcgcgctgttagcgggc
ccattaagttctgtctcggcgcgtctgcgtctggctggctggcataaatatctcactcgcaatc

Figure 27C aaattcagccgatagcggaacgggaaggcgactggagtgccatgtccggttttcaacaaaccat
gcaaatgctgaatgagggcatcgttcccactgcgatgctggttgccaacgatcagatggcgctg
ggcgcaatgcgcgccattaccgagtccgggctgcgcgttggtgcggatatctcggtagtgggat
acgacgataccgaagacagctcatgttatatcccgccgtcaaccaccatcaaacaggattttcg
cctgctggggcaaaccagcgtggaccgcttgctgcaactctctcagggccaggcggtgaagggc
aatcagctgttgcccgtctcactggtgaaaagaaaaaccaccctggcgcccaatacgcaaaccg
cctctccccgcgcgttggccgattcattaatgcagctggcacgacaggtttcccgactggaaag
cgggcagtgagcgcaacgcaattaatgtgagttagcgcgaattgatctg
(SEQ ID NO:22)

Figure 29A

5′-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt

Figure 29B ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtctaactgca
tcgcccttaggaggtaaaaaaaaatgactgccgacaacaatagtatgccccatggtgcagtatc
tagttacgccaaattagtgcaaaaccaaacacctgaagacattttggaagagtttcctgaaatt
attccattacaacaaagacctaatacccgatctagtgagacgtcaaatgacgaaagcggagaaa
catgtttttctggtcatgatgaggagcaaattaagttaatgaatgaaaattgtattgttttgga
ttgggacgataatgctattggtgccggtaccaagaaagtttgtcatttaatggaaaatattgaa
aagggtttactacatcgtgcattctccgtctttattttcaatgaacaaggtgaattacttttac
aacaaagagccactgaaaaaataactttccctgatctttggactaacacatgctgctctcatcc
actatgtattgatgacgaattaggtttgaagggtaagctagacgataagattaagggcgctatt
actgcggcggtgagaaaactagatcatgaattaggtattccagaagatgaaactaagacaaggg
gtaagtttcactttttaaacagaatccattacatggcaccaagcaatgaaccatggggtgaaca
tgaaattgattacatcctattttataagatcaacgctaaagaaaacttgactgtcaacccaaac
gtcaatgaagttagagacttcaaatgggtttcaccaaatgatttgaaaactatgtttgctgacc
caagttacaagtttacgccttggtttaagattatttgcgagaattacttattcaactggtggga
gcaattagatgacctttctgaagtggaaaatgacaggcaaattcatagaatgctataacaacgc
gtcctgcagctggtaccatatgggaattcgaagctttctagaacaaaaactcatctcagaagag
gatctgaatagcgccgtcgaccatcatcatcatcatcattgagtttaaacggtctccagcttgg
ctgttttggcggatgagagaagattttcagcctgatacagattaaatcagaacgcagaagcggt
ctgataaaacagaatttgcctggcggcagtagcgcggtggtcccacctgaccccatgccgaact
cagaagtgaaacgccgtagcgccgatggtagtgtggggtctccccatgcgagagtagggaactg
ccaggcatcaaataaaacgaaaggctcagtcgaaagactgggcctttcgttttatctgttgttt
gtcggtgaacgctctcctgagtaggacaaatccgccgggagcggatttgaacgttgcgaagcaa
cggcccggagggtggcgggcaggacgcccgccataaactgccaggcatcaaattaagcagaagg
ccatcctgacggatggcctttttgcgtttctacaaactctttttgtttatttttctaaatacat
tcaaatatgtatccgcttaaccggaattgccagctggggcgccctctggtaaggttgggaagcc
ctgcaaagtaaactggatggctttctcgccgccaaggatctgatggcgcaggggatcaagctct
gatcaagagacaggatgaggatcgtttcgcatgattgaacaagatggattgcacgcaggttctc
cggccgcttgggtggagaggctattcggctatgactgggcacaacagacaatcggctgctctga
tgccgccgtgttccggctgtcagcgcaggggcgcccggttctttttgtcaagaccgacctgtcc
ggtgccctgaatgaactgcaagacgaggcagcgcggctatcgtggctggccacgacgggcgttc
cttgcgcagctgtgctcgacgttgtcactgaagcgggaagggactggctgctattgggcgaagt
gccggggcaggatctcctgtcatctcaccttgctcctgccgagaaagtatccatcatggctgat

Figure 29C gcaatgcggcggctgcatacgcttgatccggctacctgcccattcgaccaccaagcgaaacatc
gcatcgagcgagcacgtactcggatggaagccggtcttgtcgatcaggatgatctggacgaaga
gcatcaggggctcgcgccagccgaactgttcgccaggctcaaggcgagcatgcccgacggcgag
gatctcgtcgtgacccatggcgatgcctgcttgccgaatatcatggtggaaaatggccgctttt
ctggattcatcgactgtggccggctgggtgtggcggaccgctatcaggacatagcgttggctac
ccgtgatattgctgaagagcttggcggcgaatgggctgaccgcttcctcgtgctttacggtatc
gccgctcccgattcgcagcgcatcgccttctatcgccttcttgacgagttcttctgacatgacc
aaaatcccttaacgtgagttttcgttccactgagcgtcagaccccgtagaaaagatcaaaggat
cttcttgagatcctttttttctgcgcgtaatctgctgcttgcaaacaaaaaaaccaccgctacc
agcggtggtttgtttgccggatcaagagctaccaactctttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccagggggaaacgcctggtatctt
tatagtcctgtcgggtttcgccacctctgacttgagcgtcgatttttgtgatgctcgtcagggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
(SEQ ID NO:23)

Figure 31A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct

Figure 31B attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtctaactgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacaccccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagttttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaaagacccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgaccttt
gctgcgggtctggcgattggtgggtacaaacccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg
cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgcagctggtaccatatgggaattcgaagctt
tctagaacaaaaactcatctcagaagaggatctgaatagcgccgtcgaccatcatcatcatcat
cattgagtttaaacggtctccagcttggctgttttggcggatgagagaagattttcagcctgat
acagattaaatcagaacgcagaagcggtctgataaaacagaatttgcctggcggcagtagcgcg

Figure 31C gtggtcccacctgaccccatgccgaactcagaagtgaaacgccgtagcgccgatggtagtgtgg
ggtctccccatgcgagagtagggaactgccaggcatcaaataaaacgaaaggctcagtcgaaag
actgggcctttcgttttatctgttgtttgtcggtgaacgctctcctgagtaggacaaatccgcc
gggagcggatttgaacgttgcgaagcaacggcccggagggtggcgggcaggacgcccgccataa
actgccaggcatcaaattaagcagaaggccatcctgacggatggcctttttgcgtttctacaaa
ctctttttgtttatttttctaaatacattcaaatatgtatccgcttaaccggaattgccagctg
gggcgccctctggtaaggttgggaagccctgcaaagtaaactggatggctttctcgccgccaag
gatctgatggcgcaggggatcaagctctgatcaagagacaggatgaggatcgtttcgcatgatt
gaacaagatggattgcacgcaggttctccggccgcttgggtggagaggctattcggctatgact
gggcacaacagacaatcggctgctctgatgccgccgtgttccggctgtcagcgcaggggcgccc
ggttctttttgtcaagaccgacctgtccggtgccctgaatgaactgcaagacgaggcagcgcgg
ctatcgtggctggccacgacgggcgttccttgcgcagctgtgctcgacgttgtcactgaagcgg
gaagggactggctgctattgggcgaagtgccggggcaggatctcctgtcatctcaccttgctcc
tgccgagaaagtatccatcatggctgatgcaatgcggcggctgcatacgcttgatccggctacc
tgcccattcgaccaccaagcgaaacatcgcatcgagcgagcacgtactcggatggaagccggtc
ttgtcgatcaggatgatctggacgaagagcatcaggggctcgcgccagccgaactgttcgccag
gctcaaggcgagcatgcccgacggcgaggatctcgtcgtgacccatggcgatgcctgcttgccg
aatatcatggtggaaaatggccgcttttctggattcatcgactgtggccggctgggtgtggcgg
accgctatcaggacatagcgttggctacccgtgatattgctgaagagcttggcggcgaatgggc
tgaccgcttcctcgtgctttacggtatcgccgctcccgattcgcagcgcatcgccttctatcgc
cttcttgacgagttcttctgacgcatgaccaaaatcccttaacgtgagttttcgttccactgag
cgtcagaccccgtagaaaagatcaaaggatcttcttgagatcctttttttctgcgcgtaatctg
ctgcttgcaaacaaaaaaaccaccgctaccagcggtggtttgtttgccggatcaagagctacca
actctttttccgaaggtaactggcttcagcagagcgcagataccaaatactgtccttctagtgt
agccgtagttaggccaccacttcaagaactctgtagcaccgcctacatacctcgctctgctaat
cctgttaccagtggctgctgccagtggcgataagtcgtgtcttaccgggttggactcaagacga
tagttaccggataaggcgcagcggtcgggctgaacggggggttcgtgcacacagcccagcttgg
agcgaacgacctacaccgaactgagatacctacagcgtgagctatgagaaagcgccacgcttcc
cgaagggagaaaggcggacaggtatccggtaagcggcagggtcggaacaggagagcgcacgagg
gagcttccagggggaaacgcctggtatctttatagtcctgtcgggtttcgccacctctgacttg
agcgtcgatttttgtgatgctcgtcaggggggcggagcctatggaaaaacgccagcaacgcggc
ctttttacggttcctggccttttgctggccttttgctcacatgttctttcctgcgttatcccct
gattctgtggataaccgtattaccgcctttgagtgagctgataccgctcgccgcagccgaacga
ccgagcgcagcgagtcagtgagcgaggaagcggaagagcgcctgatgcggtattttctccttac
gcatctgtgcggtatttcacaccgcatatggtgcactctcagtacaatctgctctgatgccgca
tagttaagccagtatacactccgctatcgctacgtgactgggtcatggctgcgccccgacaccc
gccaacacccgctgacgcgccctgacgggc
(SEQ ID NO:24)

Figure 33A

5’-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctccaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcacccagcctgcgcgagcaggggaattaattcccacggg
ttttgctgcccgcaaacgggctgttctggtgttgctagtttgttatcagaatcgcagatccggc
ttcagccggtttgccggctgaaagcgctatttcttccagaattgccatgatttttccccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttccctttgatatgtaacggtgaaca
gttgttctacttttgtttgttagtcttgatgcttcactgatagatacaagagccataagaacct
cagatccttccgtatttagccagtatgttctctagtgtggttcgttgttttgcgtgagccatg
agaacgaaccattgagatcatacttactttgcatgtcactcaaaaattttgcctcaaaactggt
gagctgaattttgcagttaaagcatcgtgtagtgtttttcttagtccgttatgtaggtaggaa
tctgatgtaatggttgttggtattttgtcaccattcatttttatctggttgttctcaagttcgg

Figure 33B ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
ttttttaactggaaaagataaggcaatatctcttcactaaaaactaattctaattttttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaaacttgtaaattc
tgctagaccctctgtaaattccgctagacctttgtgtgttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtctttttcgtgacattcagttc
gctgcgctcacggctctggcagtgaatgggggtaaatggcactacaggcgccttttatggattc
atgcaaggaaactacccataatacaagaaaagcccgtcacgggcttctcagggcgttttatggc
gggtctgctatgtggtgctatctgactttttgctgttcagcagttcctgccctctgattttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaaagacatcattaaa
gccctggaaaacatcgtactgctggacgaaaacaaaaagaacaaatctgacctgcacgcaaccg
ctctgtctttccgtctgctgcgtcagcacggtttcgaggtttctcaggatgtttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtaccttttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggattttaacatgg
tacagaccctgcaccagaaagagctgcaagatctgtcccgctggtggaccgagatgggcctggc
tagcaaactggattttgtacgcgaccgcctgatggaagtttatttctggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct

Figure 33C atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgaccctttcccgattaaccagc
tgatgtatgtctaactgcagctggtaccatatgggaattcgaagctttctagaacaaaaactca
tctcagaagaggatctgaatagcgccgtcgaccatcatcatcatcatcattgagtttaaacggt
ctccagcttggctgttttggcggatgagagaagattttcagcctgatacagattaaatcagaac
gcagaagcggtctgataaaacagaatttgcctggcggcagtagcgcggtggtcccacctgaccc
catgccgaactcagaagtgaaacgccgtagcgccgatggtagtgtggggtctccccatgcgaga
gtagggaactgccaggcatcaaataaaacgaaaggctcagtcgaaagactgggcctttcgtttt
atctgttgtttgtcggtgaacgctctcctgagtaggacaaatccgccgggagcggatttgaacg
ttgcgaagcaacggcccggagggtggcgggcaggacgcccgccataaactgccaggcatcaaat
taagcagaaggccatcctgacggatggcctttttgcgtttctacaaactctttttgtttatttt
tctaaatacattcaaatatgtatccgctcatgagacaataaccctgataaatgcttcaataat
(SEQ ID NO:25)

Figure 35A

5'-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggccgttgcttcgcaacgttcaaatccgctcccgg
cggatttgtcctactcaggagagcgttcaccgacaaacaacagataaaacgaaaggcccagtct
ttcgactgagcctttcgttttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaaatcttctctcatccgccaaaacagccaagctggagaccgtttaaactcaatgat
gatgatgatgatggtcgacggcgctattcagatcctcttctgagatgagtttttgttctagaaa
gcttcgaattcccatatggtaccagctgcagttagacatacatcagctggttaatcgggaaagg
gtcaatcagcagcagtttgatgcggttttcagtcgcgtagtctgggcgacccagaccatcgcca
tactggtaggtgcagtgggaaacacgtgccatgttaactgcgatttccatgaacgctttaggca
gcagggtggagtcgctaacgcgttcacgattcatctttttccattcggcgtcgatcagtttacg
cagttcttcgcgggcctgttcctcgctggtaccatcgttttcgtgcatgtagctaatgatagaa
ttggtagtctcgccacgttccagctccgccgcagaggtggccagatcgttgcacaggcggaaga
taacgcagctagaacgcaccagaccatggaagtcggtcagggaacgcagcgcgtggtcggagat
gtcttcctgctgctggcatacggaaaagtaagacggcgccagcagcgctacaccggaggaggaa
acgctggcgttttccaggtacttggagaaagccgggataattttgttgttggaccatttcgcct
cttgcagaaaggctttgcacagttcacgccagcttttcgtcagataggacaggttgttatgacc
tttctctttcagaatagaataggacgtgtcgttaacggtgttgtacagtgccaggaaacacagt
ttcatatagtccggcagggtgttaatagcgttaacgtcccagcgctctacagcatcggtgaaca
gttgcagttcgtccagagtgccataaacgtcatacacgtcatcgatgatcgtcaccagaccaaa
cattttagtaacagctttgcgacattcaccaaactgcgggtctggcgccatacccagtgcccag
aaataaacttccatcaggcggtcgcgtacaaaatccagtttgctagccaggcccatctcggtcc
accagcgggacagatcttgcagctctttctggtgcagggtctgtaccatgttaaaatccagctt
cgccagctccagcagcagctggtgatgcggttctttcggttcgtatttatccaggaaccaacgt
gcctccagacggtgcagacgctggtgatatggcagttccagggcgtggctcacttgttctgcaa
ccttggtattaatgccttctttcaggttgttcttcaggtgggtgatggaaaaggtacgcgcctc
ctccagcaggttctcaccctcgaaacccaggtaagacgcttcatacaggctcagcaggccttgg
acgtcacctttcagttcaccgctgaaaccaccttctttatccttgaaacgctcaaaaacatcct
gagaaacctcgaaaccgtgctgacgcagcagacggaaagacagagcggttgcgtgcaggtcaga
tttgttctttttgttttcgtccagcagtacgatgttttccagggctttaatgatgtctttttca
aatttgtaggtcagacccaggcgctgcacatcgtcgatcagctccagcagggacagcggctggg
tgtctacacggttgatcatgcagcgaacttcttcctccagtttggtcgctttctcctccagctt
ttccactttcaggtcgttctccagggattgcaggaattcgaaattccacaggtttggctgatag
tttgcggaacgacgggaattatgctcggtaatctgagtaaattgagaagaggtcgcacacatgg
tttattcctccttatttaatcgatacattaatatatacctctttaatttttaataataaagtta
atcgataattccggtcgagtgcccacacagattgtctgataaattgttaaagagcagtgccgct
tcgcttttctcagcggcgctgtttcctgtgtgaaattgttatccgctcacaattccacacatt
atacgagccggatgattaattgtcaacagctcatttcagaatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc

Figure 35B tgatgccgcatagttaagccagccccgacacccgccaacacccgctgacgagcttagtaaagcc
ctcgctagattttaatgcggatgttgcgattacttcgccaactattgcgataacaagaaaaagc
cagcctttcatgatatatctcccaatttgtgtagggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactacctt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagcccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat
caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgcggcgcttgccggtggtgctgaccccgg
atgaagtggttcgcatcctcggttttctggaaggcgagcatcgtttgttcgcccagcttctgta
tggaacgggcatgcggatcagtgagggtttgcaactgcgggtcaaggatctggatttcgatcac
ggcacgatcatcgtgcgggagggcaagggctccaaggatcgggccttgatgttacccgagagct
tggcacccagcctgcgcgagcaggggaattaattcccacgggttttgctgcccgcaaacgggct
gttctggtgttgctagtttgttatcagaatcgcagatccggcttcagccggtttgccggctgaa
agcgctatttcttccagaattgccatgatttttccccacgggaggcgtcactggctcccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatcttttttacaccgttttcatct
gtgcatatggacagttttccctttgatatgtaacggtgaacagttgttctacttttgtttgtta
gtcttgatgcttcactgatagatacaagagccataagaacctcagatccttccgtatttagcca
gtatgttctctagtgtggttcgttgtttttgcgtgagccatgagaacgaaccattgagatcata
cttactttgcatgtcactcaaaaattttgcctcaaaactggtgagctgaatttttgcagttaaa
gcatcgtgtagtgtttttcttagtccgttatgtaggtaggaatctgatgtaatggttgttggta
ttttgtcaccattcattttttatctggttgttctcaagttcggttacgagatccatttgtctatc
tagttcaacttggaaaatcaacgtatcagtcgggcggcctcgcttatcaaccaccaatttcata
ttgctgtaagtgtttaaatctttacttattggtttcaaaacccattggttaagccttttaaact
catggtagttattttcaagcattaacatgaacttaaattcatcaaggctaatctctatatttgc

Figure 35C cttgtgagttttcttttgtgttagttcttttaataaccactcataaatcctcatagagtatttg
ttttcaaaagacttaacatgttccagattatattttatgaatttttttaactggaaaagataag
gcaatatctcttcactaaaaactaattctaattttcgcttgagaacttggcatagtttgtcca
ctggaaaatctcaaagcctttaaccaaaggattcctgatttccacagttctcgtcatcagctct
ctggttgctttagctaatacaccataagcattttccctactgatgttcatcatctgagcgtatt
ggttataagtgaacgataccgtccgttctttccttgtagggttttcaatcgtggggttgagtag
tgccacacagcataaaattagcttggtttcatgctccgttaagtcatagcgactaatcgctagt
tcatttgctttgaaaacaactaattcagacatacatctcaattggtctaggtgattttaatcac
tataccaattgagatgggctagtcaatgataattactagtcctttttcctttgagttgtgggtat
ctgtaaattctgctagacctttgctggaaaacttgtaaattctgctagaccctctgtaaattcc
gctagacctttgtgtgtttttttttgtttatattcaagtggttataatttatagaataaagaaag
aataaaaaaagataaaaagaatagatcccagccctgtgtataactcactactttagtcagttcc
gcagtattacaaaaggatgtcgcaaacgctgtttgctcctctacaaaacagaccttaaaccct
aaaggcttaagtagcaccctcgcaagctcgggcaaatcgctgaatattccttttgtctccgacc
atcaggcacctgagtcgctgtctttttcgtgacattcagttcgctgcgctcacggctctggcag
tgaatgggggtaaatggcactacaggcgccttttatggattcatgcaaggaaactacccataat
acaagaaaagcccgtcacgggcttctcagggcgttttatggcgggtctgctatgtggtgctatc
tgacttttgctgttcagcagttcctgccctctgattttccagtctgaccacttcggattatcc
cgtgacaggtcattcagactggctaatgcacccagtaaggcagcggtatcatcaacaggctta
(SEQ ID NO:26)

Figure 37A

5′-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctccaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcacccagcctgcgcgagcaggggaattaattcccacggg
ttttgctgcccgcaaacgggctgttctggtgttgctagtttgttatcagaatcgcagatccggc
ttcagccggtttgccggctgaaagcgctatttcttccagaattgccatgatttttccccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttccctttgatatgtaacggtgaaca
gttgttctactttgtttgttagtcttgatgcttcactgatagatacaagagccataagaacct
cagatccttccgtatttagccagtatgttctctagtgtggttcgttgtttttgcgtgagccatg
agaacgaaccattgagatcatacttactttgcatgtcactcaaaaattttgcctcaaaactggt
gagctgaattttgcagttaaagcatcgtgtagtgtttttcttagtccgttatgtaggtaggaa
tctgatgtaatggttgttggtattttgtcaccattcattttatctggttgttctcaagttcgg

Figure 37B ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
ttttttaactggaaaagataaggcaatatctcttcactaaaaactaattctaatttttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaaacttgtaaattc
tgctagaccctctgtaaattccgctagacctttgtgtgttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtctttttcgtgacattcagttc
gctgcgctcacggctctggcagtgaatgggggtaaatggcactacaggcgccttttatggattc
atgcaaggaaactacccataatacaagaaaagcccgtcacgggcttctcagggcgttttatggc
gggtctgctatgtggtgctatctgactttttgctgttcagcagttcctgccctctgattttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaaagacatcattaaa
gccctggaaaacatcgtactgctggacgaaaacaaaaagaacaaatctgacctgcacgcaaccg
ctctgtctttccgtctgctgcgtcagcacggtttcgaggtttctcaggatgtttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtacctttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggattttaacatgg
tacagaccctgcaccagaaagagctgcaagatctgtcccgctggtggaccgagatgggcctggc
tagcaaactggattttgtacgcgaccgcctgatggaagtttatttctgggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct

Figure 37C atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgaccctttcccgattaaccagc
tgatgtatgtctaactgcatcgcccttaggaggtaaaaaaaaatgactgccgacaacaatagta
tgccccatggtgcagtatctagttacgccaaattagtgcaaaaccaaacacctgaagacatttt
ggaagagtttcctgaaattattccattacaacaaagacctaatacccgatctagtgagacgtca
aatgacgaaagcggagaaacatgtttttctggtcatgatgaggagcaaattaagttaatgaatg
aaaattgtattgttttggattgggacgataatgctattggtgccggtaccaagaaagtttgtca
tttaatggaaaatattgaaaagggtttactacatcgtgcattctccgtctttattttcaatgaa
caaggtgaattacttttacaacaaagagccactgaaaaaataactttccctgatctttggacta
acacatgctgctctcatccactatgtattgatgacgaattaggtttgaagggtaagctagacga
taagattaagggcgctattactgcggcggtgagaaaactagatcatgaattaggtattccagaa
gatgaaactaagacaaggggtaagtttcacttttaaacagaatccattacatggcaccaagca
atgaaccatggggtgaacatgaaattgattacatcctattttataagatcaacgctaaagaaaa
cttgactgtcaacccaaacgtcaatgaagttagagacttcaaatgggtttcaccaaatgatttg
aaaactatgtttgctgacccaagttacaagtttacgccttggtttaagattatttgcgagaatt
acttattcaactggtgggagcaattagatgacctttctgaagtggaaaatgacaggcaaattca
tagaatgctataacgacgcgtcctgcagctggtaccatatgggaattcgaagctttctagaacg
aaaactcatctcagaagaggatctgaatagcgccgtcgaccatcatcatcatcatcattgagtt
taaacggtctccagcttggctgttttggcggatgagagaagattttcagcctgatacagattaa
atcagaacgcagaagcggtctgataaaacagaatttgcctggcggcagtagcgcggtggtccca
cctgaccccatgccgaactcagaagtgaaacgccgtagcgccgatggtagtgtggggtctcccc
atgcgagagtagggaactgccaggcatcaaataaaacgaaaggctcagtcgaaagactgggcct
ttcgttttatctgttgtttgtcggtgaacgctctcctgagtaggacaaatccgccgggagcgga
tttgaacgttgcgaagcaacggcccggagggtggcgggcaggacgcccgccataaactgccagg
catcaaattaagcagaaggccatcctgacggatggcctttttgcgtttctacaaactctttttg
tttatttttctaaatacattcaaatatgtatccgctcatgagacaataaccctgataaatgctt
caataat
(SEQ ID NO:27)

Figure 39A

5'-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggccgttgcttcgcaacgttcaaatccgctcccgg
cggatttgtcctactcaggagagcgttcaccgacaaacaacagataaaacgaaaggcccagtct
ttcgactgagcctttcgttttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaaatcttctctcatccgccaaaacagccaagctggagaccgtttaaactcaatgat
gatgatgatgatggtcgacggcgctattcagatcctcttctgagatgagtttttgttctagaaa
gcttcgaattcccatatggtaccagctgcagttatgccagccaggccttgattttggcttccat
accagcggcatcgaggccgagttcggcgcgcatttcttcctgagttccttgcggaataaagaag
tccggcaggccaatgttcagcacgggtactggtttacgatgggccatcagcacttcgttcacgc
cgctgcctgcgccgcccataatggcgttttcttctacggtgaccagcgcttcatggctggcggc
catttccagaattaacgcttcatcaagcggtttcacaaaacgcatatcgaccagcgtggcgttc
agcgattcggcgactttcgccgcttctggcatcagcgtaccaaagttaaggatcgccagtttct
cgccacgacgcttcacaatgcctttgccaattggtagtttttccagcggcgtcagttccacgcc
gaccgcgttgccacgcgggtagcgcaccgctgacgggccatcgttatagtgatagccggtatag
agcatctggcgacattcgttttcatcgctcggggtcataatgaccatttccggtatgcagcgca
ggtaagagagatcaaaagcaccctgatgggtttgaccgtcagcaccaacaatgcccgcgcggtc
gatggcgaacaggaccggaagcttttgaatcgccacgtcatgcagcacctgatcataggcgcgt
tgcaggaaagtggagtaaatcgcgacaatgggtttgtacccaccaatcgccagacccgcagcaa
aggtcaccgcgtgttgctcggcaattgccacgtcgaagtagcgatccgggaatttacgtgaaaa
ctcgaccatgccggaaccttcacgcatcgccggagtaatcgccatcagcttgttgtctttcgct
gccgtttcgcacaaccagtcgccaaagatttttgaatagctcggcaaaccgccgctacttttcg
gcaaacaaccgctggagggatcaaatttaggcacggcgtggaaagtgatcgggtctttttctgc
cggttcataaccacgacctttttttggtcatgatatgcaggaactgcgggcctttcaggtcgcgc
atgttctttagcgtggtgataagccccagcacatcgtgaccgtccaccgggccgatgtagttaa
agcccagctcttcaaacaacgtgccaggcactaccatgcctttaatatgttcttcggtgcgttt
gagcagctctttaattggcggcacgccagagaaactttttcccgccttcgcgcagtgaagag
taaagcttaccggaaagcagctgtgccagatggttgttgagcgcgccgacattttcggaaatcg
acatttcattgtcgttgagaatcaccagcatatcaggacggatatcgcccgcgtgattcatcgc
ttcaaacgccatgcctgcggtaatcgcgccatcgccaatgacacagacggtgcggcgattttg
ccttctttttcggcagcaaccgcaataccaattccggcactgatggaggttgatgaatgcccga
cgcttaatacgtcatattcgctttcgccgcgccacgggaacgggtgcagaccgcctttctgacg
gatggtgccgattttgtcgcggcgtccggtcaaaattttatgcggataagcctgatgccccaca
tcccaaatcaattggtcaaacggggtgttgtagacatagtgcagcgccacggtcagttcgaccg
tgcccagcccggaggcgaagtgcccgctggaacggctcacgctgtcgagtaaatagcggcgcag
ttcgtcgcagagtttcggtaaactctctttcggcaacagtcgtaactcctgggtggagtcgacc
agtgccagggtcgggtatttggcaatatcaaaactcatgtttttttacctcctaagggcgaatg
cagttagacatacatcagctggttaatcgggaaagggtcaatcagcagcagtttgatgcggttt
tcagtcgcgtagtctgggcgacccagaccatcgccatactggtaggtgcagtgggaaacacgtg
ccatgttaactgcgatttccatgaacgctttaggcagcagggtggagtcgctaacgcgttcacg

Figure 39B attcatctttttccattcggcgtcgatcagtttacgcagttcttcgcgggcctgttcctcgctg
gtaccatcgttttcgtgcatgtagctaatgatagaattggtagtctcgccacgttccagctccg
ccgcagaggtggccagatcgttgcacaggcggaagataacgcagctagaacgcaccagaccatg
gaagtcggtcagggaacgcagcgcgtggtcggagatgtcttcctgctgctggcatacggaaaag
taagacggcgccagcagcgctacaccggaggaggaaacgctggcgttttccaggtacttggaga
aagccgggataatttgttgttggaccatttcgcctcttgcagaaaggctttgcacagttcacg
ccagcttttcgtcagataggacaggttgttatgacctttctctttcagaatagaataggacgtg
tcgttaacggtgttgtacagtgccaggaaacacagtttcatatagtccggcagggtgttaatag
cgttaacgtcccagcgctctacagcatcggtgaacagttgcagttcgtccagagtgccataaac
gtcatacacgtcatcgatgatcgtcaccagaccaaacatttagtaacagctttgcgacattca
ccaaactgcgggtctggcgccatacccagtgcccagaaataaacttccatcaggcggtcgcgta
caaaatccagtttgctagccaggcccatctcggtccaccagcgggacagatcttgcagctcttt
ctggtgcagggtctgtaccatgttaaaatccagcttcgccagctccagcagcagctggtgatgc
ggttctttcggttcgtatttatccaggaaccaacgtgcctccagacggtgcagacgctggtgat
atggcagttccagggcgtggctcacttgttctgcaaccttggtattaatgccttctttcaggtt
gttcttcaggtgggtgatggaaaaggtacgcgcctcctccagcaggttctcaccctcgaaaccc
aggtaagacgcttcatacaggctcagcaggccttggacgtcacctttcagttcaccgctgaaac
caccttctttatccttgaaacgctcaaaaacatcctgagaaacctcgaaaccgtgctgacgcag
cagacggaaagacagagcggttgcgtgcaggtcagatttgttctttttgttttcgtccagcagt
acgatgttttccagggctttaatgatgtctttttcaaatttgtaggtcagacccaggcgctgca
catcgtcgatcagctccagcagggacagcggctgggtgtctacacggttgatcatgcagcgaac
ttcttcctccagtttggtcgctttctcctccagcttttccactttcaggtcgttctccagggat
tgcaggaattcgaaattccacaggtttggctgatagtttgcggaacgacgggaattatgctcgg
taatctgagtaaattgagaagaggtcgcacacatggtttattcctccttatttaatcgatacat
taatatatacctctttaatttttaataataaagttaatcgataattccggtcgagtgcccacac
agattgtctgataaattgttaaagagcagtgccgcttcgctttttctcagcggcgctgtttcct
gtgtgaaattgttatccgctcacaattccacacattatacgagccggatgattaattgtcaaca
gctcatttcagaatctggcgtaatagcgaagaggcccgcaccgatcgcccttcccaacagttgc
gcagcctgaatggcgaatggcgcctgatgcggtattttctccttacgcatctgtgcggtatttc
acaccgcatatggtgcactctcagtacaatctgctctgatgccgcatagttaagccagccccga
cacccgccaacacccgctgacgagcttagtaaagccctcgctagattttaatgcggatgttgcg
attacttcgccaactattgcgataacaagaaaaagccagcctttcatgatatatctcccaattt
gtgtagggcttattatgcacgcttaaaaataataaaagcagacttgacctgatagtttggctgt
gagcaattatgtgcttagtgcatctaacgcttgagttaagccgcgccgcgaagcggcgtcggct
tgaacgaattgttagacattatttgccgactaccttggtgatctcgcctttcacgtagtggaca
aattcttccaactgatctgcgcgcgaggccaagcgatcttcttcttgtccaagataagcctgtc
tagcttcaagtatgacgggctgatactgggccggcaggcgctccattgcccagtcggcagcgac
atccttcggcgcgattttgccggttactgcgctgtaccaaatgcgggacaacgtaagcactaca
tttcgctcatcgccagcccagtcgggcggcgagttccatagcgttaaggtttcatttagcgcct
caaatagatcctgttcaggaaccggatcaaagagttcctccgccgctggacctaccaaggcaac
gctatgttctcttgcttttgtcagcaagatagccagatcaatgtcgatcgtggctggctcgaag
atacctgcaagaatgtcattgcgctgccattctccaaattgcagttcgcgcttagctggataac
gccacggaatgatgtcgtcgtgcacaacaatggtgacttctacagcgcggagaatctcgctctc
tccaggggaagccgaagtttccaaaaggtcgttgatcaaagctcgccgcgttgtttcatcaagc

Figure 39C cttacggtcaccgtaaccagcaaatcaatatcactgtgtggcttcaggccgccatccactgcgg
agccgtacaaatgtacggccagcaacgtcggttcgagatggcgctcgatgacgccaactacctc
tgatagttgagtcgatacttcggcgatcaccgcttccctcatgatgtttaactttgttttaggg
cgactgccctgctgcgtaacatcgttgctgctccataacatcaaacatcgacccacggcgtaac
gcgcttgctgcttggatgcccgaggcatagactgtaccccaaaaaaacagtcataacaagccat
gaaaaccgccactgcgccgttaccaccgctgcgttcggtcaaggttctggaccagttgcgtgag
cgcatacgctacttgcattacagcttacgaaccgaacaggcttatgtccactgggttcgtgcct
tcatccgtttccacggtgtgcgtcacccggcaaccttgggcagcagcgaagtcgaggcatttct
gtcctggctggcgaacgagcgcaaggtttcggtctccacgcatcgtcaggcattggcggccttg
ctgttcttctacggcaaggtgctgtgcacggatctgccctggcttcaggagatcggaagacctc
ggccgtcgcggcgcttgccggtggtgctgaccccggatgaagtggttcgcatcctcggttttct
ggaaggcgagcatcgtttgttcgcccagcttctgtatggaacgggcatgcggatcagtgagggt
ttgcaactgcgggtcaaggatctggatttcgatcacggcacgatcatcgtgcgggagggcaagg
gctccaaggatcgggccttgatgttacccgagagcttggcacccagcctgcgcgagcaggggaa
ttaattcccacgggttttgctgcccgcaaacgggctgttctggtgttgctagtttgttatcaga
atcgcagatccggcttcagccggtttgccggctgaaagcgctatttcttccagaattgccatga
tttttccccacgggaggcgtcactggctcccgtgttgtcggcagctttgattcgataagcagc
atcgcctgtttcaggctgtctatgtgtgactgttgagctgtaacaagttgtctcaggtgttcaa
tttcatgttctagttgctttgttttactggtttcacctgttctattaggtgttacatgctgttc
atctgttacattgtcgatctgttcatggtgaacagctttgaatgcaccaaaaactcgtaaaagc
tctgatgtatctatcttttttacaccgttttcatctgtgcatatggacagttttccctttgata
tgtaacggtgaacagttgttctacttttgtttgttagtcttgatgcttcactgatagatacaag
agccataagaacctcagatccttccgtatttagccagtatgttctctagtgtggttcgttgttt
ttgcgtgagccatgagaacgaaccattgagatcatacttactttgcatgtcactcaaaaatttt
gcctcaaaactggtgagctgaattttttgcagttaaagcatcgtgtagtgtttttcttagtccgt
tatgtaggtaggaatctgatgtaatggttgttggtattttgtcaccattcatttttatctggtt
gttctcaagttcggttacgagatccatttgtctatctagttcaacttggaaaatcaacgtatca
gtcgggcggcctcgcttatcaaccaccaatttcatattgctgtaagtgtttaaatctttactta
ttggtttcaaaacccattggttaagccttttaaactcatggtagttattttcaagcattaacat
gaacttaaattcatcaaggctaatctctatatttgccttgtgagttttcttttgtgttagttct
tttaataaccactcataaatcctcatagagtatttgttttcaaaagacttaacatgttccagat
tatattttatgaatttttttaactggaaaagataaggcaatatctcttcactaaaaactaattc
taatttttcgcttgagaacttggcatagtttgtccactggaaaatctcaaagcctttaaccaaa
ggattcctgatttccacagttctcgtcatcagctctctggttgctttagctaatacaccataag
cattttccctactgatgttcatcatctgagcgtattggttataagtgaacgataccgtccgttc
tttccttgtagggttttcaatcgtggggttgagtagtgccacacagcataaaattagcttggtt
tcatgctccgttaagtcatagcgactaatcgctagttcatttgctttgaaaacaactaattcag
acatacatctcaattggtctaggtgattttaatcactataccaattgagatgggctagtcaatg
ataattactagtccttttcctttgagttgtgggtatctgtaaattctgctagacctttgctgga
aaacttgtaaattctgctagaccctctgtaaattccgctagacctttgtgtgttttttttgttt
atattcaagtggttataatttatagaataaagaaagaataaaaaaagataaaaagaatagatcc
cagccctgtgtataactcactactttagtcagttccgcagtattacaaaaggatgtcgcaaacg
ctgtttgctcctctacaaaacagaccttaaaaccctaaaggcttaagtagcaccctcgcaagct
cgggcaaatcgctgaatattccttttgtctccgaccatcaggcacctgagtcgctgtcttttc

Figure 39D

Gtgacattcagttcgctgcgctcacggctctggcagtgaatgggggtaaatggcactacaggcg
ccttttatggattcatgcaaggaaactacccataatacaagaaaagcccgtcacgggcttctca
gggcgttttatggcgggtctgctatgtggtgctatctgactttttgctgttcagcagttcctgc
cctctgattttccagtctgaccacttcggattatcccgtgacaggtcattcagactggctaatg
cacccagtaaggcagcggtatcatcaacaggctta
(SEQ ID NO:28)

A.

B.

C.

D.

E.

A

B

C

D

Figure 46F 1-
tctataatcacggcagaaaagtccacattgattatttgcacggcgtcacactttgctatgccatagcatttttatccataagattagcggatcctac
ctgacgctttttatcgcaactctctactgtttctccatacccgtttttttgggctagcgaattcgagctcggtacccggggatcctctagagtcgac
ctgcaggcatgcaagcttggctgttttggcggatgagagaagattttcagcctgatacagattaaatcagaacgcagaagcggtctgataaa
acagaatttgcctggcggcagtagcgcggtggtcccacctgaccccatgccgaactcagaagtgaaacgccgtagcgccgatggtagtgt
ggggtctccccatgcgagagtagggaactgccaggcatcaaataaaacgaaaggctcagtcgaaagactgggcctttcgttttatctgttgt
tgtcggtgaacgctctcctgagtaggacaaatccgccgggagcggatttgaacgttgcgaagcaacggcccggagggtggcgggcagg
acgcccgccataaactgccaggcatcaaattaagcagaaggccatcctgacggatggcctttttgcgtttctacaaactcttttgtttatttttcta
aatacattcaaatatgtatccgctcatgagacaataaccctgataaatgcttcaataatattgaaaaaggaagagtatgagtattcaacatttccg
tgtcgcccttattcccttttttgcggcattttgccttcctgtttttgctcacccagaaacgctggtgaaagtaaaagatgctgaagatcagttgggt
gcagcaaactattaactggcgaactacttactctagcttcccggcaacaattaatagactggatggaggcggataaagttgcaggaccacttc
tgcgctcggcccttccggctggctggtttattgctgataaatctggagccggtgagcgtgggtctcgcggtatcattgcagcactggggcca
gatggtaagccctcccgtatcgtagttatctacacgacggggagtcaggcaactatggatgaacgaaatagacagatcgctgagataggtg
cctcactgattaagcattggtaactgtcagaccaagtttactcatatatactttagattgatttacgcgccctgtagcggcgcattaagcgcggc
gggtgtggtggttacgcgcagcgtgaccgctacacttgccagcgccctagcgcccgctcctttcgctttcttcccttcctttctcgccacgttc
gccggctttccccgtcaagctctaaatcgggggctccctttagggttccgatttagtgctttacggcacctcgaccccaaaaaacttgatttgg
gtgatggttcacgtagtgggccatcgccctgatagacggtttttcgccctttgacgttggagtccacgttctttaatagtggactcttgttccaaa
cttgaacaacactcaaccctatctcgggctattcttttgatttataagggattttgccgatttcggcctattggttaaaaaatgagctgatttaacaa
aaatttaacgcgaattttaacaaaatattaacgtttacaatttaaaaggatctaggtgaagatcctttttgataatctcatgaccaaaatcccttaac
gtgagttttcgttccactgagcgtcagaccccgtagaaaagatcaaaggatcttcttgagatcctttttttctgcgcgtaatctgctgcttgcaaa
caaaaaaaccaccgctaccagcggtggtttgtttgccggatcaagagctaccaactctttttccgaaggtaactggcttcagcagagcgcag
ataccaaatactgtccttctagtgtagccgtagttaggccaccacttcaagaactctgtagcaccgcctacatacctcgctctgctaatcctgtta
ccagtcaggcatttgagaagcacacggtcacactgcttccggtagtcaataaaccggtaaaccagcaatagacataagcggctatttaacga
ccctgccctgaaccgacgaccgggtcgaatttgctttcgaatttctgccattcatccgcttattatcacttattcaggcgtagcaccaggcgttta
agggcaccaataactgccttaaaaaaattacgccccgccctgccactcatcgcagtactgttgtaattcattaagcattctgccgacatggaa
gccatcacagacggcatgatgaacctgaatcgccagcggcatcagcaccttgtcgccttgcgtataatatttgcccatggtgaaaacgggg
gcgaagaagttgtccatattggccacgtttaaatcaaaactggtgaaactcacccagggattggctgagacgaaaaacatattctcaataaac
cctttagggaaataggccaggttttcaccgtaacacgccacatcttgcgaatatatgtgtagaaactgccggaaatcgtcgtggtattcactcc
agagcgatgaaaacgtttcagtttgctcatggaaaacggtgtaacaagggtgaacactatcccatatcaccagctcaccgtctttcattgccat
acggaattccggatgagcattcatcaggcgggcaagaatgtgaataaaggccggataaaacttgtgcttatttttctttacggtctttaaaaag
gccgtaatatccagctgaacggtctggttataggtacattgagcaactgactgaaatgcctcaaaatgttctttacgatgccattgggatatatc
aacggtggtatatccagtgatttttttctccattttagcttccttagctcctgaaaatctcgataactcaaaaaatacgcccggtagtgatcttatttc
attatggtgaaagttggaacctcttacgtgccgatcaacgtctcattttcgccaaaagttggcccagggcttcccggtatcaacagggacacc
aggatttatttattctgcgaagtgatcttccgtcacaggtatttattcggcgcaaagtgcgtcgggtgatgctgccaacttactgatttagtgtatg
atggtgtttttgaggtgctccagtggcttctgtttctatcagctgtccctcctgttcagctactgacggggtggtgcgtaacggcaaaagcaccg
ccggacatcagcgctagcggagtgtatactggcttactatgttggcactgatgagggtgtcagtgaagtgcttcatgtggcaggagaaaaaa
ggctgcaccggtgcgtcagcagaatatgtgatacaggatatattccgcttcctcgctcactgactcgctacgctcggtcgttcgactgcggcg
agcggaaatggcttacgaacggggcggagatttcctggaagatgccaggaagatacttaacagggaagtgagagggccgcggcaaagc
cgtttttccataggctccgcccccctgacaagcatcacgaaatctgacgctcaaatcagtggtggcgaaacccgacaggactataaagatac
caggcgtttccccctggcggctccctcgtgcgctctcctgttcctgcctttcggtttaccggtgtcattccgctgttatggccgcgtttgtctcatt
ccacgcctgacactcagttccgggtaggcagttcgctccaagctggactgtatgcacgaaccccccgttcagtccgaccgctgcgccttatc
cggtaactatcgtcttgagtccaacccggaaagacatgcaaaagcaccactggcagcagccactggtaattgatttagaggagttagtcttg
aagtcatgcgccggttaaggctaaactgaaaggacaagttttggtgactgcgctcctccaagccagttacctcggttcaaagagttggtagct
cagagaaccttcgaaaaaccgccctgcaaggcggttttttcgttttcagagcaagagattacgcgcagaccaaaacgatctcaagaagatca

Figure 46G tcttattaatcagataaaatatttgctcatgagcccgaagtggcgagcccgatcttccccatcggtgatgtcggcgatataggcgccagcaac
cgcacctgtggcgccggtgatgccggccacgatgcgtccggcgtagaggatctgctcatgtttgacagcttatcatcgatgcataatgtgcc
tgtcaaatggacgaagcagggattctgcaaaccctatgctactccgtcaagccgtcaattgtctgattcgttaccaattatgacaacttgacgg
ctacatcattcactttttcttcacaaccggcacggaactcgctcgggctggccccggtgcattttttaaatacccgcgagaaatagagttgatcg
tcaaaaccaacattgcgaccgacggtggcgataggcatccgggtggtgctcaaaagcagcttcgcctggctgatacgttggtcctcgcgcc
agcttaagacgctaatccctaactgctggcggaaaagatgtgacagacgcgacggcgacaagcaaacatgctgtgcgacgctggcgatat
caaaattgctgtctgccaggtgatcgctgatgtactgacaagcctcgcgtacccgattatccatcggtggatggagcgactcgttaatcgcttc
catgcgccgcagtaacaattgctcaagcagatttatcgccagcagctccgaatagcgcccttccccttgcccggcgttaatgatttgcccaaa
caggtcgctgaaatgcggctggtgcgcttcatccgggcgaaagaaccccgtattggcaaatattgacggccagttaagccattcatgccagt
aggcgcgcggacgaaagtaaacccactggtgataccattcgcgagcctccggatgacgaccgtagtgatgaatctctcctggcgggaaca
gcaaaatatcacccggtcggcaaacaaattctcgtccctgatttttcaccaccccctgaccgcgaatggtgagattgagaatataacctttcatt
cccagcggtcggtcgataaaaaaatcgagataaccgttggcctcaatcggcgttaaacccgccaccagatgggcattaaacgagtatcccg
gcagcaggggatcattttgcgcttcagccatacttttcatactcccgccattcagagaagaaaccaattgtccatattgcatcagacattgccgt
cactgcgtcttttactggctcttctcgctaaccaaaccggtaaccccgcttattaaaagcattctgtaacaaagcgggaccaaagccatgacaa
aaacgcgtaacaaaagtg (SEQ ID NO:51)

Figure 46I 1-
gcaaactattaactggcgaactacttactctagcttcccggcaacaattaatagactggatggaggcggataaagttgcaggaccacttctgc
gctcggcccttccggctggctggtttattgctgataaatctggagccggtgagcgtgggtctcgcggtatcattgcagcactggggccagat
ggtaagccctcccgtatcgtagttatctacacgacggggagtcaggcaactatggatgaacgaaatagacagatcgctgagataggtgcct
cactgattaagcattggtaactgtcagaccaagtttactcatatatactttagattgatttacgcgccctgtagcggcgcattaagcgcggcggg
tgtggtggttacgcgcagcgtgaccgctacacttgccagcgccctagcgcccgctcctttcgctttcttcccttcctttctcgccacgttcgccg
gctttccccgtcaagctctaaatcgggggctccctttagggttccgatttagtgctttacggcacctcgaccccaaaaaacttgatttgggtgat
ggttcacgtagtgggccatcgccctgatagacggtttttcgccctttgacgttggagtccacgttctttaatagtggactcttgttccaaacttga
acaacactcaaccctatctcgggctattcttttgatttataagggattttgccgatttcggcctattggttaaaaaatgagctgatttaacaaaaatt
taacgcgaattttaacaaaatattaacgtttacaatttaaaaggatctaggtgaagatcctttttgataatctcatgaccaaaatcccttaacgtga
gttttcgttccactgagcgtcagaccccgtagaaaagatcaaaggatcttcttgagatcctttttttctgcgcgtaatctgctgcttgcaaacaaa
aaaaccaccgctaccagcggtggtttgtttgccggatcaagagctaccaactctttttccgaaggtaactggcttcagcagagcgcagatac
caaatactgtccttctagtgtagccgtagttaggccaccacttcaagaactctgtagcaccgcctacatacctcgctctgctaatcctgttacca
gtcaggcatttgagaagcacacggtcacactgcttccggtagtcaataaaccggtaaaccagcaatagacataagcggctatttaacgaccc
tgccctgaaccgacgaccgggtcgaatttgctttcgaatttctgccattcatccgcttattatcacttattcaggcgtagcaccaggcgtttaagg
gcaccaataactgccttaaaaaaattacgccccgccctgccactcatcgcagtactgttgtaattcattaagcattctgccgacatggaagcca
tcacagacggcatgatgaacctgaatcgccagcggcatcagcaccttgtcgccttgcgtataatatttgcccatggtgaaaacgggggcga
agaagttgtccatattggccacgtttaaatcaaaactggtgaaactcacccagggattggctgagacgaaaaacatattctcaataaacccttt
agggaaataggccaggttttcaccgtaacacgccacatcttgcgaatatatgtgtagaaactgccggaaatcgtcgtggtattcactccagag
cgatgaaaacgtttcagtttgctcatggaaaacggtgtaacaagggtgaacactatcccatatcaccagctcaccgtctttcattgccatacgg
aattccggatgagcattcatcaggcgggcaagaatgtgaataaaggccggataaaacttgtgcttatttttctttacggtctttaaaaaggccgt
aatatccagctgaacggtctggttataggtacattgagcaactgactgaaatgcctcaaaatgttctttacgatgccattgggatatatcaacgg
tggtatatccagtgatttttttctccattttagcttccttagctcctgaaaatctcgataactcaaaaaatacgcccggtagtgatcttatttcattatg
gtgaaagttggaacctcttacgtgccgatcaacgtctcattttcgccaaaagttggcccagggcttcccggtatcaacagggacaccaggatt
tatttattctgcgaagtgatcttccgtcacaggtatttattcggcgcaaagtgcgtcgggtgatgctgccaacttactgatttagtgtatgatggtg
tttttgaggtgctccagtggcttctgtttctatcagctgtccctcctgttcagctactgacggggtggtgcgtaacggcaaaagcaccgccgga
catcagcgctagcggagtgtatactggcttactatgttggcactgatgagggtgtcagtgaagtgcttcatgtggcaggagaaaaaaggctg
caccggtgcgtcagcagaatatgtgatacaggatatattccgcttcctcgctcactgactcgctacgctcggtcgttcgactgcggcgagcg
gaaatggcttacgaacggggcggagatttcctggaagatgccaggaagatacttaacagggaagtgagagggccgcggcaaagccgttt
ttccataggctccgcccccctgacaagcatcacgaaatctgacgctcaaatcagtggtggcgaaacccgacaggactataaagataccag
gcgtttccccctggcggctccctcgtgcgctctcctgttcctgcctttcggtttaccggtgtcattccgctgttatggccgcgtttgtctcattcca
cgcctgacactcagttccgggtaggcagttcgctccaagctggactgtatgcacgaaccccccgttcagtccgaccgctgcgccttatccg
gtaactatcgtcttgagtccaacccggaaagacatgcaaaagcaccactggcagcagccactggtaattgatttagaggagttagtcttgaa
gtcatgcgccggttaaggctaaactgaaaggacaagttttggtgactgcgctcctccaagccagttacctcggttcaaagagttggtagctca
gagaaccttcgaaaaaccgccctgcaaggcggttttttcgttttcagagcaagagattacgcgcagaccaaaacgatctcaagaagatcatc
ttattaatcagataaaatatttgctcatgagcccgaagtggcgagcccgatcttccccatcggtgatgtcggcgatataggcgccagcaaccg
cacctgtggcgccggtgatgccggccacgatgcgtccggcgtagaggatctgctcatgtttgacagcttatcatcgatgcataatgtgcctgt
caaatggacgaagcagggattctgcaaaccctatgctactccgtcaagccgtcaattgtctgattcgttaccaattatgacaacttgacggcta
catcattcactttttcttcacaaccggcacggaactcgctcgggctggccccggtgcattttttaaatacccgcgagaaatagagttgatcgtca
aaaccaacattgcgaccgacggtggcgataggcatccgggtggtgctcaaaagcagcttcgcctggctgatacgttggtcctcgcgccag
cttaagacgctaatccctaactgctggcggaaaagatgtgacagacgcgacggcgacaagcaaacatgctgtgcgacgctggcgatatca
aaattgctgtctgccaggtgatcgctgatgtactgacaagcctcgcgtacccgattatccatcggtggatggagcgactcgttaatcgcttcca
tgcgccgcagtaacaattgctcaagcagatttatcgccagcagctccgaatagcgcccttccccttgcccggcgttaatgatttgcccaaaca
ggtcgctgaaatgcggctggtgcgcttcatccgggcgaaagaaccccgtattggcaaatattgacggccagttaagccattcatgccagta

Figure 46J ggcgcgcggacgaaagtaaacccactggtgataccattcgcgagcctccggatgacgaccgtagtgatgaatctctcctggcgggaaca
gcaaaatatcacccggtcggcaaacaaattctcgtccctgatttttcaccaccccctgaccgcgaatggtgagattgagaatataacctttcatt
cccagcggtcggtcgataaaaaaatcgagataaccgttggcctcaatcggcgttaaacccgccaccagatgggcattaaacgagtatcccg
gcagcaggggatcattttgcgcttcagccatacttttcatactcccgccattcagagaagaaaccaattgtccatattgcatcagacattgccgt
cactgcgtcttttactggctcttctcgctaaccaaaccggtaaccccgcttattaaaagcattctgtaacaaagcgggaccaaagccatgacaa
aaacgcgtaacaaaagtgtctataatcacggcagaaaagtccacattgattatttgcacggcgtcacactttgctatgccatagcatttttatcc
ataagattagcggatcctacctgacgctttttatcgcaactctctactgtttctccatacccgtttttttgggctagcgaattcgagctcggtaccc
cccattctgaaatgagctgttgacaattaatcatccggctcgtataatgtgtggaattgtgagcggataacaatttcacacaggaaacagcgcc
gctgagaaaaagcgaagcggcactgctctttaacaatttatcagacaatctgtgtgggcactcgaccggaattatcgattaactttattattaaa
aattaaagaggtatatattaatgtatcgattaaataaggaggaataaaccatgtgtgcgacctcttctcaatttactcagattaccgagcataattc
ccgtcgttccgcaaactatcagccaaacctgtggaatttcgaattcctgcaatccctggagaacgacctgaaagtggaaaagctggaggag
aaagcgaccaaactggaggaagaagttcgctgcatgatcaaccgtgtagacacccagccgctgtccctgctggagctgatcgacgatgtg
cagcgcctgggtctgacctacaaatttgaaaaagacatcattaaagccctggaaaacatcgtactgctggacgaaaacaaaaagaacaaat
ctgacctgcacgcaaccgctctgtctttccgtctgctgcgtcagcacggtttcgaggtttctcaggatgtttttgagcgtttcaaggataaagaa
ggtggtttcagcggtgaactgaaaggtgacgtccaaggcctgctgagcctgtatgaagcgtcttacctgggtttcgagggtgagaacctgct
ggaggaggcgcgtaccttttccatcacccacctgaagaacaacctgaaagaaggcattaataccaaggttgcagaacaagtgagccacgc
cctggaactgccatatcaccagcgtctgcaccgtctggaggcacgttggttcctggataaatacgaaccgaaagaaccgcatcaccagctg
ctgctggagctggcgaagctggattttaacatggtacagaccctgcaccagaaagagctgcaagatctgtcccgctggtggaccgagatg
ggcctggctagcaaactggattttgtacgcgaccgcctgatggaagtttatttctgggcactgggtatggcgccagacccgcagtttggtgaa
tgtcgcaaagctgttactaaaatgtttggtctggtgacgatcatcgatgacgtgtatgacgtttatggcactctggacgaactgcaactgttcac
cgatgctgtagagcgctgggacgttaacgctattaacaccctgccggactatatgaaactgtgtttcctggcactgtacaacaccgttaacga
cacgtcctattctattctgaaagagaaaggtcataacaacctgtcctatctgacgaaaagctggcgtgaactgtgcaaagcctttctgcaaga
ggcgaaatggtccaacaacaaaattatcccggctttctccaagtacctggaaaacgccagcgtttcctcctccggtgtagcgctgctggcgc
cgtcttacttttccgtatgccagcagcaggaagacatctccgaccacgcgctgcgttccctgaccgacttccatggtctggtgcgttctagctg
cgttatcttccgcctgtgcaacgatctggccacctctgcggcggagctggaacgtggcgagactaccaattctatcattagctacatgcacga
aaacgatggtaccagcgaggaacaggcccgcgaagaactgcgtaaactgatcgacgccgaatggaaaaagatgaatcgtgaacgcgtta
gcgactccaccctgctgcctaaagcgttcatggaaatcgcagttaacatggcacgtgtttcccactgcacctaccagtatggcgatggtctgg
gtcgcccagactacgcgactgaaaaccgcatcaaactgctgctgattgaccctttcccgattaaccagctgatgtatgtctaactgcagggca
tgcaagcttggctgttttggcggatgagagaagattttcagcctgatacagattaaatcagaacgcagaagcggtctgataaaacagaatttg
cctggcggcagtagcgcggtggtcccacctgaccccatgccgaactcagaagtgaaacgccgtagcgccgatggtagtgtggggtctcc
ccatgcgagagtagggaactgccaggcatcaaataaaacgaaaggctcagtcgaaagactgggcctttcgttttatctgttgtttgtcggtga
acgctctcctgagtaggacaaatccgccgggagcggatttgaacgttgcgaagcaacggcccggagggtggcgggcaggacgcccgc
cataaactgccaggcatcaaattaagcagaaggccatcctgacggatggcctttttgcgtttctacaaactcttttgtttatttttctaaatacattc
aaatatgtatccgctcatgagacaataaccctgataaatgcttcaataatattgaaaaaggaagagtatgagtattcaacatttccgtgtcgccc
ttattcccttttttgcggcattttgccttcctgtttttgctcacccagaaacgctggtgaaagtaaaagatgctgaagatcagttgggtgca
(SEQ ID NO: 52)

Figure 46L 1-
gcaaactattaactggcgaactacttactctagcttcccggcaacaattaatagactggatggaggcggataaagttgcaggaccacttctgc
gctcggcccttccggctggctggtttattgctgataaatctggagccggtgagcgtgggtctcgcggtatcattgcagcactggggccagat
ggtaagccctcccgtatcgtagttatctacacgacggggagtcaggcaactatggatgaacgaaatagacagatcgctgagataggtgcct
cactgattaagcattggtaactgtcagaccaagtttactcatatatactttagattgatttacgcgccctgtagcggcgcattaagcgcggcggg
tgtggtggttacgcgcagcgtgaccgctacacttgccagcgccctagcgcccgctcctttcgctttcttcccttcctttctcgccacgttcgccg
gctttccccgtcaagctctaaatcgggggctccctttagggttccgatttagtgctttacggcacctcgaccccaaaaaacttgatttgggtgat
ggttcacgtagtgggccatcgccctgatagacggtttttcgccctttgacgttggagtccacgttctttaatagtggactcttgttccaaacttga
acaacactcaaccctatctcgggctattcttttgatttataagggattttgccgatttcggcctattggttaaaaaatgagctgatttaacaaaaatt
taacgcgaattttaacaaaatattaacgtttacaatttaaaaggatctaggtgaagatcctttttgataatctcatgaccaaaatcccttaacgtga
gttttcgttccactgagcgtcagaccccgtagaaaagatcaaaggatcttcttgagatcctttttttctgcgcgtaatctgctgcttgcaaacaaa
aaaaccaccgctaccagcggtggtttgtttgccggatcaagagctaccaactctttttccgaaggtaactggcttcagcagagcgcagatac
caaatactgtccttctagtgtagccgtagttaggccaccacttcaagaactctgtagcaccgcctacatacctcgctctgctaatcctgttacca
gtcaggcatttgagaagcacacggtcacactgcttccggtagtcaataaaccggtaaaccagcaatagacataagcggctatttaacgaccc
tgccctgaaccgacgaccgggtcgaatttgctttcgaatttctgccattcatccgcttattatcacttattcaggcgtagcaccaggcgtttaagg
gcaccaataactgccttaaaaaaattacgccccgccctgccactcatcgcagtactgttgtaattcattaagcattctgccgacatggaagcca
tcacagacggcatgatgaacctgaatcgccagcggcatcagcaccttgtcgccttgcgtataatatttgcccatggtgaaaacgggggcga
agaagttgtccatattggccacgtttaaatcaaaactggtgaaactcacccagggattggctgagacgaaaaacatattctcaataaaccctt
agggaaataggccaggttttcaccgtaacacgccacatcttgcgaatatatgtgtagaaactgccggaaatcgtcgtggtattcactccagag
cgatgaaaacgtttcagtttgctcatggaaaacggtgtaacaagggtgaacactatcccatatcaccagctcaccgtctttcattgccatacgg
aattccggatgagcattcatcaggcgggcaagaatgtgaataaaggccggataaaacttgtgcttatttttctttacggtctttaaaaaggccgt
aatatccagctgaacggtctggttataggtacattgagcaactgactgaaatgcctcaaaatgttctttacgatgccattgggatatatcaacgg
tggtatatccagtgatttttttctccattttagcttccttagctcctgaaaatctcgataactcaaaaaatacgcccggtagtgatcttatttcattatg
gtgaaagttggaacctcttacgtgccgatcaacgtctcattttcgccaaaagttggcccagggcttcccggtatcaacagggacaccaggatt
tatttattctgcgaagtgatcttccgtcacaggtatttattcggcgcaaagtgcgtcgggtgatgctgccaacttactgatttagtgtatgatggtg
tttttgaggtgctccagtggcttctgtttctatcagctgtccctcctgttcagctactgacggggtggtgcgtaacggcaaaagcaccgccgga
catcagcgctagcggagtgtatactggcttactatgttggcactgatgagggtgtcagtgaagtgcttcatgtggcaggagaaaaaaggctg
caccggtgcgtcagcagaatatgtgatacaggatatattccgcttcctcgctcactgactcgctacgctcggtcgttcgactgcggcgagcg
gaaatggcttacgaacggggcggagatttcctggaagatgccaggaagatacttaacagggaagtgagagggccgcggcaaagccgttt
ttccataggctccgcccccctgacaagcatcacgaaatctgacgctcaaatcagtggtggcgaaacccgacaggactataaagataccag
gcgtttccccctggcggctccctcgtgcgctctcctgttcctgcctttcggtttaccggtgtcattccgctgttatggccgcgtttgtctcattcca
cgcctgacactcagttccgggtaggcagttcgctccaagctggactgtatgcacgaaccccccgttcagtccgaccgctgcgccttatccg
gtaactatcgtcttgagtccaacccggaaagacatgcaaaagcaccactggcagcagccactggtaattgatttagaggagttagtcttgaa
gtcatgcgccggttaaggctaaactgaaaggacaagttttggtgactgcgctcctccaagccagttacctcggttcaaagagttggtagctca
gagaaccttcgaaaaaccgccctgcaaggcggttttttcgttttcagagcaagagattacgcgcagaccaaaacgatctcaagaagatcatc
ttattaatcagataaaatatttgctcatgagcccgaagtggcgagcccgatcttccccatcggtgatgtcggcgatataggcgccagcaaccg
cacctgtggcgccggtgatgccggccacgatgcgtccggcgtagaggatctgctcatgtttgacagcttatcatcgatgcataatgtgcctgt
caaatggacgaagcagggattctgcaaaccctatgctactccgtcaagccgtcaattgtctgattcgttaccaattatgacaacttgacggcta
catcattcactttttcttcacaaccggcacggaactcgctcgggctggccccggtgcattttttaaatacccgcgagaaatagagttgatcgtca
aaaccaacattgcgaccgacggtggcgataggcatccgggtggtgctcaaaagcagcttcgcctggctgatacgttggtcctcgcgccag
cttaagacgctaatccctaactgctggcggaaaagatgtgacagacgcgacggcgacaagcaaacatgctgtgcgacgctggcgatatca
aaattgctgtctgccaggtgatcgctgatgtactgacaagcctcgcgtacccgattatccatcggtggatggagcgactcgttaatcgcttcca
tgcgccgcagtaacaattgctcaagcagatttatcgccagcagctccgaatagcgcccttccccttgcccggcgttaatgatttgcccaaaca
ggtcgctgaaatgcggctggtgcgcttcatccgggcgaaagaaccccgtattggcaaatattgacggccagttaagccattcatgccagta

Figure 46M ggcgcgcggacgaaagtaaacccactggtgataccattcgcgagcctccggatgacgaccgtagtgatgaatctctcctggcgggaaca
gcaaaatatcacccggtcggcaaacaaattctcgtccctgatttttcaccaccccctgaccgcgaatggtgagattgagaatataacctttcatt
cccagcggtcggtcgataaaaaaatcgagataaccgttggcctcaatcggcgttaaacccgccaccagatgggcattaaacgagtatcccg
gcagcaggggatcattttgcgcttcagccatacttttcatactcccgccattcagagaagaaaccaattgtccatattgcatcagacattgccgt
cactgcgtcttttactggctcttctcgctaaccaaaccggtaaccccgcttattaaaagcattctgtaacaaagcgggaccaaagccatgacaa
aaacgcgtaacaaaagtgtctataatcacggcagaaaagtccacattgattatttgcacggcgtcacactttgctatgccatagcatttttatcc
ataagattagcggatcctacctgacgctttttatcgcaactctctactgtttctccatacccgtttttttgggctagcgaattcgagctcggtaccc
cccattctgaaatgagctgttgacaattaatcatccggctcgtataatgtgtggaattgtgagcggataacaatttcacacaggaaacagcgcc
gctgagaaaaagcgaagcggcactgctctttaacaatttatcagacaatctgtgtgggcactcgaccggaattatcgattaactttattattaaa
aattaaagaggtatatattaatgtatcgattaaataaggaggaataaaccatgtgtgcgacctcttctcaatttactcagattaccgagcataattc
ccgtcgttccgcaaactatcagccaaacctgtggaatttcgaattcctgcaatccctggagaacgacctgaaagtggaaaagctggaggag
aaagcgaccaaactggaggaagaagttcgctgcatgatcaaccgtgtagacacccagccgctgtccctgctggagctgatcgacgatgtg
cagcgcctgggtctgacctacaaatttgaaaaagacatcattaaagccctggaaaacatcgtactgctggacgaaaacaaaaagaacaaat
ctgacctgcacgcaaccgctctgtctttccgtctgctgcgtcagcacggtttcgaggtttctcaggatgtttttgagcgtttcaaggataaagaa
ggtggtttcagcggtgaactgaaaggtgacgtccaaggcctgctgagcctgtatgaagcgtcttacctgggtttcgagggtgagaacctgct
ggaggaggcgcgtaccttttccatcacccacctgaagaacaacctgaaagaaggcattaataccaaggttgcagaacaagtgagccacgc
cctggaactgccatatcaccagcgtctgcaccgtctggaggcacgttggttcctggataaatacgaaccgaaagaaccgcatcaccagctg
ctgctggagctggcgaagctggattttaacatggtacagaccctgcaccagaaagagctgcaagatctgtcccgctggtggaccgagatg
ggcctggctagcaaactggattttgtacgcgaccgcctgatggaagtttatttctgggcactgggtatggcgccagacccgcagtttggtgaa
tgtcgcaaagctgttactaaaatgtttggtctggtgacgatcatcgatgacgtgtatgacgtttatggcactctggacgaactgcaactgttcac
cgatgctgtagagcgctgggacgttaacgctattaacaccctgccggactatatgaaactgtgtttcctggcactgtacaacaccgttaacga
cacgtcctattctattctgaaagagaaaggtcataacaacctgtcctatctgacgaaaagctggcgtgaactgtgcaaagcctttctgcaaga
ggcgaaatggtccaacaacaaaattatcccggctttctccaagtacctggaaaacgccagcgtttcctcctccggtgtagcgctgctggcgc
cgtcttacttttccgtatgccagcagcaggaagacatctccgaccacgcgctgcgttccctgaccgacttccatggtctggtgcgttctagctg
cgttatcttccgcctgtgcaacgatctggccacctctgcggcggagctggaacgtggcgagactaccaattctatcattagctacatgcacga
aaacgatggtaccagcgaggaacaggcccgcgaagaactgcgtaaactgatcgacgccgaatggaaaaagatgaatcgtgaacgcgtta
gcgactccaccctgctgcctaaagcgttcatggaaatcgcagttaacatggcacgtgtttcccactgcacctaccagtatggcgatggtctgg
gtcgcccagactacgcgactgaaaaccgcatcaaactgctgctgattgaccctttcccgattaaccagctgatgtatgtctaactgcatactag
tttcaagaggtatttcactcatggctatcactggcatctttttcggcagcgacaccggtaataccgaaaatatcgcaaaaatgattcaaaaacag
cttggtaaagacgttgccgatgtccatgacattgcaaaaagcagcaaagaagatctggaagcttatgacattctgctgctgggcatcccaac
ctggtattacggcgaagcgcagtgtgactgggatgacttcttcccgactctcgaagagattgatttcaacggcaaactggttgcgctgtttggt
tgtggtgaccaggaagattacgccgaatatttctgcgacgcattgggcaccatccgcgacatcattgaaccgcgcggtgcaaccatcgttgg
tcactggccaactgcgggctatcatttcgaagcatcaaaaggtctggcagatgacgaccactttgtcggtctggctatcgacgaagaccgtc
agccggaactgaccgctgaacgtgtagaaaaatgggttaaacagatttctgaagagttgcatctcgacgaaattctcaatgcctgactgcag
ggcatgcaagcttggctgttttggcggatgagagaagattttcagcctgatacagattaaatcagaacgcagaagcggtctgataaaacaga
atttgcctggcggcagtagcgcggtggtcccacctgaccccatgccgaactcagaagtgaaacgccgtagcgccgatggtagtgtggggt
ctccccatgcgagagtagggaactgccaggcatcaaataaaacgaaaggctcagtcgaaagactgggcctttcgttttatctgttgtttgtcg
gtgaacgctctcctgagtaggacaaatccgccgggagcggatttgaacgttgcgaagcaacggcccggagggtggcgggcaggacgcc
cgccataaactgccaggcatcaaattaagcagaaggccatcctgacggatggcctttttgcgtttctacaaactcttttgtttatttttctaaatac
attcaaatatgtatccgctcatgagacaataaccctgataaatgcttcaataatattgaaaaaggaagagtatgagtattcaacatttccgtgtcg
cccttattcccttttttgcggcattttgccttcctgtttttgctcacccagaaacgctggtgaaagtaaaagatgctgaagatcagttgggtgca
(SEQ ID NO:53)

MCM617-625 - gi1.x integrated at dxs
9013bp

Figure 55A accttcgggagcgcctgaagcccgttctggacgccctggggccgttgaatcgggatatgcaggccaaggccgccgcgatcatcaaggcc
gtgggcgaaaagctgctgacggaacagcgggaagtccagcgccagaaacaggcccagcgccagcaggaacgcgggcgcgcacattt
ccccgaaaagtgccacctggcggcgttgtgacaatttaccgaacaactccgcggccgggaagccgatctcggcttgaacgaattgttaggt
ggcggtacttgggtcgatatcaaagtgcatcacttcttcccgtatgcccaactttgtatagagagccactgcgggatcgtcaccgtaatctgctt
gcacgtagatcacataagcaccaagcgcgttggcctcatgcttgaggagattgatgagcgcggtggcaatgccctgcctccggtgctcgcc
ggagactgcgagatcatagatatagatctcactacgcggctgctcaaacctgggcagaacgtaagccgcgagagcgccaacaaccgcttc
ttggtcgaaggcagcaagcgcgatgaatgtcttactacggagcaagttcccgaggtaatcggagtccggctgatgttgggagtaggtggct
acgtctccgaactcacgaccgaaaagatcaagagcagcccgcatggatttgacttggtcagggccgagcctacatgtgcgaatgatgccc
atacttgagccacctaactttgttttagggcgactgccctgctgcgtaacatcgttgctgctgcgtaacatcgttgctgctccataacatcaaac
atcgacccacggcgtaacgcgcttgctgcttggatgcccgaggcatagactgtacaaaaaaacagtcataacaagccatgaaaaccgcca
ctgcgccgttaccaccgctgcgttcggtcaaggttctggaccagttgcgtgagcgcatacgctacttgcattacagtttacgaaccgaacag
gcttatgtcaactgggttcgtgccttcatccgtttccacggtgtgcgtccatgggcaaatattatacgcaaggcgacaaggtgctgatgccgct
ggcgattcaggttcatcatgccgtttgtgatggcttccatgtcggcagaatgcttaatgaattacaacagtttttatgcatgcgcccaatacgca
aaccgcctctccccgcgcgttggccgattcattaatgcagctggcacgacaggtttcccgactggaaagcgggcagtgagcgcaacgcaa
ttaatgtgagttagctcactcattaggcaccccaggctttacactttatgcttccggctcgtatgttgtgtggaattgtgagcggataacaatttca
cacaggaaacagctatgaccatgattacgccaagcgcgcaattaaccctcactaaagggaacaaaagctgggtaccctgcccgctttccag
tcgggaaacctgtcgtgccagctgcattaatgaatcggccaacgcgcggggagaggcggtttgcgtattgggcgccagggtggtttttctttt
caccagtgagacgggcaacagctgattgcccttcaccgcctggccctgagagagttgcagcaagcggtccacgctggtttgccccagcag
gcgaaaatcctgtttgatggtggttaacggcgggatataacatgagctgtcttcggtatcgtcgtatcccactaccgagatatccgcaccaac
gcgcagcccggactcggtaatggcgcgcattgcgcccagcgccatctgatcgttggcaaccagcatcgcagtgggaacgatgccctcatt
cagcatttgcatggtttgttgaaaaccggacatggcactccagtcgccttcccgttccgctatcggctgaatttgattgcgagtgagatatttatg
ccagccagccagacgcagacgcgccgagacagaacttaatgggcccgctaacagcgcgatttgctggtgacccaatgcgaccagatgct
ccacgcccagtcgcgtaccgtcttcatgggagaaaataatactgttgatgggtgtctggtcagagacatcaagaaataacgccggaacatta
gtgcaggcagcttccacagcaatggcatcctggtcatccagcggatagttaatgatcagcccactgacgcgttgcgcgagaagattgtgca
ccgccgctttacaggcttcgacgccgcttcgttctaccatcgacaccaccacgctggcacccagttgatcggcgcgagatttaatcgccgcg
acaatttgcgacggcgcgtgcagggccagactggaggtggcaacgccaatcagcaacgactgtttgcccgccagttgttgtgccacgcgg
ttgggaatgtaattcagctccgccatcgccgcttccactttttcccgcgttttcgcagaaacgtggctggcctggttcaccacgcgggaaacg
gtctgataagagacaccggcatactctgcgacatcgtataacgttactggtttcacattcaccaccctgaattgactctcttccgggcgctatca
tgccataccgcgaaaggttttgcgccattcgatggtgtccgggatctcgacgctctcccttatgcgactcctgcattaggaagcagcccagta
gtaggttgaggccgttgagcaccgccgccgcaaggaatggtgcatgcaaggagatggcgcccaacagtcccccggccacggggcctg
ccaccatacccacgccgaaacaagcgctcatgagcccgaagtggcgagcccgatcttccccatcggtgatgtcggcgatataggcgcca
gcaaccgcacctgtggcgccggtgatgccggccacgatgcgtccggcgtagaggatcgagatctcgatcccgcgaaattaatacgactca
ctataggggaattgtgagcggataacaattcccctctagaaataattttgtttaactttaagaaggagatatacatatggaagctcgtcgttctgc
gaactacgaacctaacagctgggactatgattacctgctgtcctccgacacggacgagtccatcgaagtatacaaagacaaagcgaaaaa
gctggaagccgaagttcgtcgcgagattaataacgaaaaagcagaatttctgaccctgctggaactgattgacaacgtccagcgcctgggc
ctgggttaccgtttcgagtctgatatccgtggtgcgctggatcgcttcgtttcctccggcggcttcgatgcggtaaccaagacttccctgcacg
gtacggcactgtctttccgtctgctgcgtcaacacggttttgaggtttctcaggaagcgttcagcggcttcaaagaccaaaacggcaacttcct
ggagaacctgaaggaagatatcaaagctatcctgagcctgtacgaggccagcttcctggctctggaaggcgaaaacatcctggacgaggc
gaaggttttcgcaatctctcatctgaaagaactgtctgaagaaaagatcggtaaagagctggcagaacaggtgaaccatgcactggaactg
ccactgcatcgccgtactcagcgtctggaagcagtatggtctatcgaggcctaccgtaaaaaggaggacgcgaatcaggttctgctggagc
tggcaattctggattacaacatgatccagtctgtataccagcgtgatctgcgtgaaacgtcccgttggtggcgtcgtgtgggtctggcgacca
aactgcactttgctcgtgaccgcctgattgagagcttctactgggccgtgggtgtagcattcgaaccgcaatactccgactgccgtaactccg
tcgcaaaaatgttttctttcgtaaccattatcgacgatatctacgatgtatacggcaccctggacgaactggagctgtttactgatgcagttgagc
gttgggacgtaaacgccatcaacgacctgccggattacatgaaactgtgctttctggctctgtataacactattaacgaaatcgcctacgacaa

Figure 55B cctgaaagataaaggtgagaacatcctgccgtatctgaccaaagcctgggctgacctgtgcaacgctttcctgcaagaagccaagtggctg
tacaacaaatctactccgacctttgacgactacttcggcaacgcatggaaatcctcttctggcccgctgcaactggtgttcgcttacttcgctgt
cgtgcagaacattaaaaaggaagagatcgaaaacctgcaaaaataccatgacaccatctctcgtccttcccatatcttccgtctgtgcaatga
cctggctagcgcgtctgcggaaattgcgcgtggtgaaaccgcaaatagcgtttcttgttacatgcgcactaaaggtatctccgaagaactgg
ctaccgaaagcgtgatgaatctgatcgatgaaacctggaaaaagatgaacaaggaaaaactgggtggtagcctgttcgcgaaaccgttcgt
ggaaaccgcgatcaacctggcacgtcaatctcactgcacttatcataacggcgacgcgcatacctctccggatgagctgacccgcaaacg
cgttctgtctgtaatcactgaaccgattctgccgtttgaacgctaaggatccgaattcgagctccgtcgacaagcttgcggccgcactcgagc
accaccaccaccaccactgagatccggctgctaacaaagcccgaaaggaagctgagttggctgctgccaccgctgagcaataactagcat
aaccccttggggcctctaaacgggtcttgaggggttttttgactagttctagagcggccgccaccgcggtggagctccaattcgccctatagt
gagtcgtattacgcgcgctcactggccgtcgttttacaacgtcgtgactgggaaaaccctggcgttacccaacttaatcgccttgcagcacat
ccccctttcgccagctggcgtaatagcgaagaggcccgcaccgatcgcccttcccaacagttgcgcagcctgaatggcgaatggaaattgt
aagcgttaatattttgttaaaattcgcgttaaatttttgttaaatcagctcattttttaaccaataggccgactgcgatgagtggcagggcggggc
gtaatttttttaaggcagttattggtgcccttaaacgcctggtgctacgcctgaataagtgataataagcggatgaatggcagaaattcgaaag
caaattcgacccggtcgtcggttcagggcagggtcgttaaatagccgcttatgtctattgctggtttaccggtttattgactaccggaagcagt
gtgaccgtgtgcttctcaaatgcctgaggccagtttgctcaggctctccccgtggaggtaataattgacgatatgatcatttattctgcctccca
gagcctgataaaaacggtgaatccgttagcgaggtgccgccggcttccattcaggtcgaggtggcccggctccatgcaccgcgacgcaa
cgcggggaggcagacaaggtatagggcggcgaggcggctacagccgatagtctggaacagcgcacttacgggttgctgcgcaaccca
agtgctaccggcgcggcagcgtgacccgtgtcggcggctccaacggctcgccatcgtccagaaaacacggctcatcgggcatcggcag
gcgctgctgcccgcgccgttcccattcctccgtttcggtcaaggctggcaggtctggttccatgcccggaatgccgggctggctgggcggc
tcctcgccggggccggtcggtagttgctgctcgcccggatacagggtcgggatgcggcgcaggtcgccatgccccaacagcgattcgtc
ctggtcgtcgtgatcaaccaccacggcggcactgaacaccgacaggcgcaactggtcgcggggctggccccacgccacgcggtcattg
accacgtaggccgacacggtgccggggccgttgagcttcacgacggagatccagcgctcggccaccaagtccttgactgcgtattggac
cgtccgcaaagaacgtccgatgagcttggaaagtgtcttctggctgaccaccacggcgttctggtggcccatctgcgccacgaggtgatgc
agcagcattgccgccgtgggtttcctcgcaataagcccggcccacgcctcatgcgctttgcgttccgtttgcacccagtgaccgggcttgttc
ttggcttgaatgccgatttctctggactgcgtggccatgcttatctccatgcggtagggtgccgcacggttgcggcaccatgcgcaatcagct
gcaacttttcggcagcgcgacaacaattatgcgttgcgtaaaagtggcagtcaattacagattttctttaacctacgcaatgagctattgcggg
gggtgccgcaatgagctgttgcgtacccccttttttaagttgttgatttttaagtctttcgcatttcgccctatatctagttctttggtgcccaaaga
agggcacccctgcggggttcccccacgccttcggcgcggctcccccctccggcaaaaagtggcccctccggggcttgttgatcgactgcg
cggccttcggccttgcccaaggtggcgctgccccccttggaacccccgcactcgccgccgtgaggctcgggggggcaggcgggcgggctt
cgccttcgactgcccccactcgcataggcttgggtcgttccaggcgcgtcaaggccaagccgctgcgcggtcgctgcgcgagccttgacc
cgccttccacttggtgtccaaccggcaagcgaagcgcgcaggccgcaggccggaggcttttccccagagaaaattaaaaaaattgatggg
gcaaggccgcaggccgcgcagttggagccggtgggtatgtggtcgaaggctgggtagccggtgggcaatccctgtggtcaagctcgtg
ggcaggcgcagcctgtccatcagcttgtccagcagggttgtccacgggccgagcgaagcgagccagccggtggccgctcgcggccatc
gtccacatatccacgggctggcaagggagcgcagcgaccgcgcagggcgaagcccggagagcaagcccgtagggcgccgcagccg
ccgtaggcggtcacgactttgcgaagcaaagtctagtgagtatactcaagcattgagtggcccgccggaggcaccgccttgcgctgcccc
cgtcgagccggttggacaccaaaagggaggggcaggcatggcggcatacgcgatcatgcgatgcaagaagctggcgaaaatgggcaa
cgtggcggccagtctcaagcacgcctaccgcgagcgcgagacgcccaacgctgacgccagcaggacgccagagaacgagcactggg
cggccagcagcaccgatgaagcgatgggccgactgcgcgagttgctgccagagaagcggcgcaaggacgctgtgttggcggtcgagt
acgtcatgacggccagcccggaatggtggaagtcggccagccaagaacagcaggcggcgttcttcgagaaggcgcacaagtggctgg
cggacaagtacggggcggatcgcatcgtgacggccagcatccaccgtgacgaaaccagcccgcacatgaccgcgttcgtggtgccgct
gacgcaggacggcaggctgtcggccaaggagttcatcggcaacaaagcgcagatgacccgcgaccagaccacgtttgcggccgctgtg
gccgatctagggctgcaacggggcatcgagggcagcaaggcacgtcacacgcgcattcaggcgttctacgaggccctggagcggccac
cagtgggccacgtcaccatcagcccgcaagcggtcgagccacgcgcctatgcaccgcagggattggccgaaaagctgggaatctcaaa

Figure 55C gcgcgttgagacgccggaagccgtggccgaccggctgacaaaagcggttcggcaggggtatgagcctgccctacaggccgccgcagg
agcgcgtgagatgcgcaagaaggccgatcaagcccaagagacggcccgag (SEQ ID NO:73)

Figure 56A cgataagctagcttcacgctgccgcaagcactcagggcgcaagggctgctaaaggaagcggaacacgtagaaagccagtccgcagaaa
cggtgctgaccccggatgaatgtcagctactgggctatctggacaagggaaaacgcaagcgcaaagagaaagcaggtagcttgcagtgg
gcttacatggcgatagctagactgggcggttttatggacagcaagcgaaccggaattgccagctggggcgccctctggtaaggttgggaa
gccctgcaaagtaaactggatggctttcttgccgccaaggatctgatggcgcaggggatcaagatctgatcaagagacaggatgaggatc
gtttcgcatgattgaacaagatggattgcacgcaggttctccggccgcttgggtggagaggctattcggctatgactgggcacaacagacaa
tcggctgctctgatgccgccgtgttccggctgtcagcgcaggggcgcccggttctttttgtcaagaccgacctgtccggtgccctgaatgaa
ctccaagacgaggcagcgcggctatcgtggctggccacgacgggcgttccttgcgcagctgtgctcgacgttgtcactgaagcgggaag
ggactggctgctattgggcgaagtgccggggcaggatctcctgtcatctcaccttgctcctgccgagaaagtatccatcatggctgatgcaat
gcggcggctgcatacgcttgatccggctacctgcccattcgaccaccaagcgaaacatcgcatcgagcgagcacgtactcggatggaag
ccggtcttgtcgatcaggatgatctggacgaagagcatcaggggctcgcgccagccgaactgttcgccaggctcaaggcgcggatgccc
gacggcgaggatctcgtcgtgacccatggcgatgcctgcttgccgaatatcatggtggaaaatggccgcttttctggattcatcgactgtggc
cggctgggtgtggcggaccgctatcaggacatagcgttggctacccgtgatattgctgaagagcttggcggcgaatgggctgaccgcttcc
tcgtgctttacggtatcgccgctcccgattcgcagcgcatcgccttctatcgccttcttgacgagttcttctgagcgggactctggggttcgcga
tgataagctgtcaaacatgagaattacaacttatatcgtatggggctgacttcaggtgctacatttgaagagataaattgcactgaaatctagaa
atattttatctgattaataagatgatcttcttgagatcgttttggtctgcgcgtaatctcttgctctgaaaacgaaaaaaccgccttgcagggcggt
ttttcgaaggttctctgagctaccaactctttgaaccgaggtaactggcttggaggagcgcagtcaccaaaacttgtcctttcagtttagccttaa
ccggcgcatgacttcaagactaactcctctaaatcaattaccagtggctgctgccagtggtgcttttgcatgtctttccgggttggactcaagac
gatagttaccggataaggcgcagcggtcggactgaacggggggttcgtgcatacagtccagcttggagcgaactgcctacccggaactg
agtgtcaggcgtggaatgagacaaacgcggccataacagcggaatgacaccggtaaaccgaaaggcaggaacaggagagcgcacga
gggagccgccagggggaaacgcctggtatctttatagtcctgtcgggtttcgccaccactgatttgagcgtcagatttcgtgatgcttgtcagg
ggggcggagcctatggaaaaacggctttgccttctttcctgcgttatcccctgattctgtggataaccgtattaccgcctttgagtgagctgata
ccgctcgccgcagccgaacgaccgagcgcagcgagtcagtgagcgaggaagcggaagagcgcccaatacgcaaaccgcctctcccc
gcgcgttggccgattcattaatgcagctggcacgacaggtttcccgactggaaagcgggcagtgagcgcaacgcaattaatgtgagttagc
tcactcattaggcaccccaggctttacactttatgcttccggctcgtatgttgtgtggaattgtgagcggataacaatttcacacaggaaacagc
tatgaccatgattacgaattctgttgacaattaatcatcggctcgtataatgtgtggaattgtgagcggataacaatttcacacaggaaacagatt
acggatccatttgaggagtaagccatgcaaacgttgccaagcccagttcaagctacaccaacggaaacagctattgttagacgcaaaccc
gcccggttccgataggctccgttgttattggtggcggccatcccgtggctgttcagtcaatgattaacgaagacactctggatatcgaaggttc
tgttgctgcaattcggcgcttacacgagatcggttgcgagatcgtacgtgtgactgtaccttcattagcacacgcgaaagcaatggaagagat
tcgggatcggctttataaaacgtacaaaccggtccccttagttgccgacgtgcatcataacggaatgaaaatcgcgttagaggttgccaagta
cgtggacaatgtgcgcattaatcctggattatacgtgtttgagaagccaaaaccaaatcgcacggagtacactcaagctgaatttgacgagat
tggcgcgaaaatccgtgaaacgttggaaccactggtaatttcactgcgggatcagggaaagtcgatgcgcattggcgttaatcatggcagtc
tggcggaacggatgctgtttacctatggcgataccccagagggtatggtagagagtgcacttgagtttatacgcatctgtgaaagtctcaactt
ctataacttagaaatttcccttaaagctagccgcgtcccggttatgatagccgccaatcggcttatggttaagcgcatggacgagctgggtatg
gattatccgttgcatctcggagtgactgaggcaggtgatggtgaatatggccgtattaaaagcacagcaggcattgcaacactgctggcgga
aggaattggagacacaatccgtgtttcattgactgaagctccggaaaaggaaatccccgtgtgctatggcatccttcaagccctcggtctccg
ccgcaccatggtagaatatgtagcttgcccgtcgtgtggtcggacattgtttaacctggaagaggttctgcacaaggtgagagaagcgacta
aacacctgacgggactgaatattgcggttatgggatgtattgtaaatggacctggcgaaatggccgatgcagactacggctatgtaggtaaa
cagccgggatatataagtctttaccgcggccgggaagaagtcaagaaagtgcccgaggccgagggcgttgcagctctggtcgaactgata
aaagcggatggtagatgggtagatccataagtggagctccccggtaccgtggacgaggtttaatatggcgacgtataaagtcacactggtc
cgtccggatggcagcgaaacgaccatcgatgttccggaggacgaatacatactggatgtcgccgaagaacaaggtctggatctcccgtttt
cttgtcgcgccggtgcctgctctacctgtgctggcaaattgttggagggagaagtcgatcaaagcgaccagagcttcttggatgacgatcag
atcgaaaaaggattcgtgcttacttgtgtggcctacccccgttcggactgcaagatcttgacgaaccaagaggaggagctgtactaagaggt
cgacgacgcatgcattaacagaggttagtatgtataatgccactaactctcgctcacgtatgttccggtacgaagttgtggggctgcgccaaa
cggcggagacggagaaaacaaattacgcgatcagaaactctggctcgcagttctttaatgtgccttatgaccgcatgaaccagtttatgcag

Figure 56B cagatcactcggtggggcggtaaaattgtcagtattcagccccttaacggaaccgtggccccacttgctgcaaccacggagccagctgcca
ataacggagctgcacctgtgaaagaaaagaaagtcgatataccggtcaacatctaccgtcccaataatccctgcataggtaaggttattagc
aacgaggaactggtccgggaaggcggtgagggtacggtgaaacatattatctttgatatatcggggaccgaattacgttacttggaagggc
agtcaatcggtatcattcccgcgggcacggacgcgaacggtaaaccacataagctgcgtctgtattccattgcttccacaagacatggtgac
tttcaggatgacaagacggtgtccttatgcgtacggagattagaatacaaagataaagagaccggggagaccatttatggcgtgtgcagttc
gtatcttaatcagttacagcctggagatgaagtcaaaatcacaggtcctgttgggaaagaaatgcttctctctgacgacccagaagcgactatt
attatgctggctaccggcactggaatagcgccatttcgggcatttttatggcggatgttcaaagagaacaacccggattaccagttcaaaggc
cttgcgtggctgttctttggcgtcgcttatactgccaatatcctgtataaggacgagcttgaagctatccaagcccagtatcccgatcattttcgg
ttaacctacgcgatttcccgtgaacaaaaaaccccggacggagggaaaatgtacatccagggtcggatcgcagagcacgctgatgaaatc
tggcaactgctgcaaaagaaaaacacccacgtgtacatgtgtggcctgcgtgggatggaacctggaatagacgaggccatgaccgcagc
ggccgcgaaaaacggagctgactggcaggagtttctgaaaggtacgctgaaaaaggaaggcagatggcatgtcgaaacttattaactgca
gtacaaataaaaaaggcacgtcagatgacgtgcctttttcttgaagcttggcactggccgtcgttttacaacgtcgtgactgggaaaaccctg
gcgttacccaacttaatcgccttgcagcacatccccctttcgccagctggcgtaatagcgaagaggcccgcaccgatcgcccttcccaaca
gttgcgcagcctgaatggcgaatggcg (SEQ ID NO:74)

Figure 57A acttcgggagcgcctgaagcccgttctggacgccctggggccgttgaatcgggatatgcaggccaaggccgccgcgatcatcaaggcc
gtgggcgaaaagctgctgacggaacagcgggaagtccagcgccagaaacaggcccagcgccagcaggaacgcgggcgcgcacattt
ccccgaaaagtgccacctggcggcgttgtgacaatttaccgaacaactccgcggccgggaagccgatctcggcttgaacgaattgttaggt
ggcggtacttgggtcgatatcaaagtgcatcacttcttcccgtatgcccaactttgtatagagagccactgcgggatcgtcaccgtaatctgctt
gcacgtagatcacataagcaccaagcgcgttggcctcatgcttgaggagattgatgagcgcggtggcaatgccctgcctccggtgctcgcc
ggagactgcgagatcatagatatagatctcactacgcggctgctcaaacctgggcagaacgtaagccgcgagagcgccaacaaccgcttc
ttggtcgaaggcagcaagcgcgatgaatgtcttactacggagcaagttcccgaggtaatcggagtccggctgatgttgggagtaggtggct
acgtctccgaactcacgaccgaaaagatcaagagcagcccgcatggatttgacttggtcagggccgagcctacatgtgcgaatgatgccc
atacttgagccacctaactttgttttagggcgactgccctgctgcgtaacatcgttgctgctgcgtaacatcgttgctgctccataacatcaaac
atcgacccacggcgtaacgcgcttgctgcttggatgcccgaggcatagactgtacaaaaaaacagtcataacaagccatgaaaaccgcca
ctgcgccgttaccaccgctgcgttcggtcaaggttctggaccagttgcgtgagcgcatacgctacttgcattacagtttacgaaccgaacag
gcttatgtcaactgggttcgtgccttcatccgtttccacggtgtgcgtccatgggcaaatattatacgcaaggcgacaaggtgctgatgccgct
ggcgattcaggttcatcatgccgtttgtgatggcttccatgtcggcagaatgcttaatgaattacaacagtttttatgcatgcgcccaatacgca
aaccgcctctccccgcgcgttggccgattcattaatgcagctggcacgacaggtttcccgactggaaagcgggcagtgagcgcaacgcaa
ttaatgtgagttagctcactcattaggcaccccaggctttacactttatgcttccggctcgtatgttgtgtggaattgtgagcggataacaatttca
cacaggaaacagctatgaccatgattacgccaagcgcgcaattaaccctcactaaagggaacaaaagctgggtaccctgcccgctttccag
tcgggaaacctgtcgtgccagctgcattaatgaatcggccaacgcgcggggagaggcggtttgcgtattgggcgccagggtggtttttctttt
caccagtgagacgggcaacagctgattgcccttcaccgcctggccctgagagagttgcagcaagcggtccacgctggtttgccccagcag
gcgaaaatcctgtttgatggtggttaacggcgggatataacatgagctgtcttcggtatcgtcgtatcccactaccgagatatccgcaccaac
gcgcagcccggactcggtaatggcgcgcattgcgcccagcgccatctgatcgttggcaaccagcatcgcagtgggaacgatgccctcatt
cagcatttgcatggtttgttgaaaaccggacatggcactccagtcgccttcccgttccgctatcggctgaatttgattgcgagtgagatatttatg
ccagccagccagacgcagacgcgccgagacagaacttaatgggcccgctaacagcgcgatttgctggtgacccaatgcgaccagatgct
ccacgcccagtcgcgtaccgtcttcatgggagaaaataatactgttgatgggtgtctggtcagagacatcaagaaataacgccggaacatta
gtgcaggcagcttccacagcaatggcatcctggtcatccagcggatagttaatgatcagcccactgacgcgttgcgcgagaagattgtgca
ccgccgctttacaggcttcgacgccgcttcgttctaccatcgacaccaccacgctggcacccagttgatcggcgcgagatttaatcgccgcg
acaatttgcgacggcgcgtgcagggccagactggaggtggcaacgccaatcagcaacgactgtttgcccgccagttgttgtgccacgcgg
ttgggaatgtaattcagctccgccatcgccgcttccactttttcccgcgttttcgcagaaacgtggctggcctggttcaccacgcgggaaacg
gtctgataagagacaccggcatactctgcgacatcgtataacgttactggtttcacattcaccaccctgaattgactctcttccgggcgctatca
tgccataccgcgaaaggttttgcgccattcgatggtgtccgggatctcgacgctctcccttatgcgactcctgcattaggaagcagcccagta
gtaggttgaggccgttgagcaccgccgccgcaaggaatggtgcatgcaaggagatggcgcccaacagtcccccggccacggggcctg
ccaccatacccacgccgaaacaagcgctcatgagcccgaagtggcgagcccgatcttccccatcggtgatgtcggcgatataggcgcca
gcaaccgcacctgtggcgccggtgatgccggccacgatgcgtccggcgtagaggatcgagatctcgatcccgcgaaattaatacgactca
ctataggggaattgtgagcggataacaattcccctctagaaataattttgtttaactttaagaaggagatatacatatgaccgaagctcgtcgttc
tgcgaactacgaacctaacagctgggactatgattacctgctgtcctccgacacggacgagtccatcgaagtatacaaagacaaagcgaaa
aagctggaagccgaagttcgtcgcgagattaataacgaaaaagcagaatttctgaccctgctggaactgattgacaacgtccagcgcctgg
gcctgggttaccgtttcgagtctgatatccgtggtgcgctggatcgcttcgtttcctccggcggcttcgatgcggtaaccaagacttccctgca
cggtacggcactgtctttccgtctgctgcgtcaacacggttttgaggtttctcaggaagcgttcagcggcttcaaagaccaaaacggcaactt
cctggagaacctgaaggaagatatcaaagctatcctgagcctgtacgaggccagcttcctggctctggaaggcgaaaacatcctggacga
ggcgaaggttttcgcaatctctcatctgaaagaactgtctgaagaaaagatcggtaaagagctggcagaacaggtgaaccatgcactggaa
ctgccactgcatcgccgtactcagcgtctggaagcagtatggtctatcgaggcctaccgtaaaaaggaggacgcgaatcaggttctgctgg
agctggcaattctggattacaacatgatccagtctgtataccagcgtgatctgcgtgaaacgtcccgttggtggcgtcgtgtgggtctggcga
ccaaactgcactttgctcgtgaccgcctgattgagagcttctactgggccgtgggtgtagcattcgaaccgcaatactccgactgccgtaact
ccgtcgcaaaaatgttttctttcgtaaccattatcgacgatatctacgatgtatacggcaccctggacgaactggagctgtttactgatgcagttg
agcgttgggacgtaaacgccatcaacgacctgccggattacatgaaactgtgctttctggctctgtataacactattaacgaaatcgcctacg

Figure 57B acaacctgaaagataaaggtgagaacatcctgccgtatctgaccaaagcctgggctgacctgtgcaacgctttcctgcaagaagccaagtg
gctgtacaacaaatctactccgacctttgacgactacttcggcaacgcatggaaatcctcttctggcccgctgcaactggtgttcgcttacttcg
ctgtcgtgcagaacattaaaaggaagagatcgaaaacctgcaaaaataccatgacaccatctctcgtccttcccatatcttccgtctgtgcaa
tgacctggctagcgcgtctgcggaaattgcgcgtggtgaaaccgcaaatagcgtttcttgttacatgcgcactaaaggtatctccgaagaact
ggctaccgaaagcgtgatgaatctgatcgatgaaacctggaaaaagatgaacaaggaaaaactgggtggtagcctgttcgcgaaaccgtt
cgtggaaaccgcgatcaacctggcacgtcaatctcactgcacttatcataacggcgacgcgcatacctctccggatgagctgacccgcaaa
cgcgttctgtctgtaatcactgaaccgattctgccgtttgaacgctaaggatccgaattcgagctccgtcgacaagcttgcggccgcactcga
gcaccaccaccaccaccactgagatccggctgctaacaaagcccgaaaggaagctgagttggctgctgccaccgctgagcaataactag
cataaccccttggggcctctaaacgggtcttgaggggttttttgactagttctagagcggccgccaccgcggtggagctccaattcgccctat
agtgagtcgtattacgcgcgctcactggccgtcgttttacaacgtcgtgactgggaaaaccctggcgttacccaacttaatcgccttgcagca
catccccctttcgccagctggcgtaatagcgaagaggcccgcaccgatcgcccttcccaacagttgcgcagcctgaatggcgaatggaaa
ttgtaagcgttaatattttgttaaaattcgcgttaaatttttgttaaatcagctcattttttaaccaataggccgactgcgatgagtggcagggcggg
gcgtaatttttttaaggcagttattggtgcccttaaacgcctggtgctacgcctgaataagtgataataagcggatgaatggcagaaattcgaa
agcaaattcgacccggtcgtcggttcagggcagggtcgttaaatagccgcttatgtctattgctggtttaccggtttattgactaccggaagca
gtgtgaccgtgtgcttctcaaatgcctgaggccagtttgctcaggctctccccgtggaggtaataattgacgatatgatcatttattctgcctccc
agagcctgataaaaacggtgaatccgttagcgaggtgccgccggcttccattcaggtcgaggtggcccggctccatgcaccgcgacgca
acgcggggaggcagacaaggtatagggcggcgaggcggctacagccgatagtctggaacagcgcacttacgggttgctgcgcaaccc
aagtgctaccggcgcggcagcgtgacccgtgtcggcggctccaacggctcgccatcgtccagaaaacacggctcatcgggcatcggca
ggcgctgctgcccgcgccgttcccattcctccgtttcggtcaaggctggcaggtctggttccatgcccggaatgccgggctggctgggcgg
ctcctcgccggggccggtcggtagttgctgctcgcccggatacagggtcgggatgcggcgcaggtcgccatgccccaacagcgattcgt
cctggtcgtcgtgatcaaccaccacggcggcactgaacaccgacaggcgcaactggtcgcggggctggccccacgccacgcggtcatt
gaccacgtaggccgacacggtgccggggccgttgagcttcacgacggagatccagcgctcggccaccaagtccttgactgcgtattgga
ccgtccgcaaagaacgtccgatgagcttggaaagtgtcttctggctgaccaccacggcgttctggtggcccatctgcgccacgaggtgatg
cagcagcattgccgccgtgggtttcctcgcaataagcccggcccacgcctcatgcgctttgcgttccgtttgcacccagtgaccgggcttgtt
cttggcttgaatgccgatttctctggactgcgtggccatgcttatctccatgcggtagggtgccgcacggttgcggcaccatgcgcaatcagc
tgcaacttttcggcagcgcgacaacaattatgcgttgcgtaaaagtggcagtcaattacagattttctttaacctacgcaatgagctattgcggg
gggtgccgcaatgagctgttgcgtacccccctttttttaagttgttgatttttaagtctttcgcatttcgccctatatctagttctttggtgcccaaaga
agggcacccctgcggggttcccccacgccttcggcgcggctcccctccggcaaaaagtggcccctccggggcttgttgatcgactgcg
cggccttcggccttgcccaaggtggcgctgcccccttggaacccccgcactcgccgccgtgaggctcgggggcaggcgggcgggctt
cgccttcgactgcccccactcgcataggcttgggtcgttccaggcgcgtcaaggccaagccgctgcgcggtcgctgcgcgagccttgacc
cgccttccacttggtgtccaaccggcaagcgaagcgcgcaggccgcaggccggaggcttttccccagagaaaattaaaaaaattgatggg
gcaaggccgcaggccgcgcagttggagccggtgggtatgtggtcgaaggctgggtagccggtgggcaatccctgtggtcaagctcgtg
ggcaggcgcagcctgtccatcagcttgtccagcagggttgtccacgggccgagcgaagcgagccagccggtggccgctcgcggccatc
gtccacatatccacgggctggcaagggagcgcagcgaccgcgcagggcgaagcccggagagcaagcccgtagggcgccgcagccg
ccgtaggcggtcacgactttgcgaagcaaagtctagtgagtatactcaagcattgagtggcccgccggaggcaccgccttgcgctgcccc
cgtcgagccggttggacaccaaaagggaggggcaggcatggcggcatacgcgatcatgcgatgcaagaagctggcgaaaatgggcaa
cgtggcggccagtctcaagcacgcctaccgcgagcgcgagacgcccaacgctgacgccagcaggacgccagagaacgagcactggg
cggccagcagcaccgatgaagcgatgggccgactgcgcgagttgctgccagagaagcggcgcaaggacgctgtgttggcggtcgagt
acgtcatgacggccagcccggaatggtggaagtcggccagccaagaacagcaggcggcgttcttcgagaaggcgcacaagtggctgg
cggacaagtacggggcggatcgcatcgtgacggccagcatccaccgtgacgaaaccagcccgcacatgaccgcgttcgtggtgccgct
gacgcaggacggcaggctgtcggccaaggagttcatcggcaacaaagcgcagatgacccgcgaccagaccacgtttgcggccgctgtg
gccgatctagggctgcaacggggcatcgagggcagcaaggcacgtcacacgcgcattcaggcgttctacgaggccctggagcggccac
cagtgggccacgtcaccatcagcccgcaagcggtcgagccacgcgcctatgcaccgcagggattggccgaaaagctgggaatctcaaa

Figure 57C gcgcgttgagacgccggaagccgtggccgaccggctgacaaaagcggttcggcaggggtatgagcctgccctacaggccgccgcagg
agcgcgtgagatgcgcaagaaggccgatcaagcccaagagacggcccgag (SEQ ID NO:75)

Figure 58A accttcgggagcgcctgaagcccgttctggacgccctggggccgttgaatcgggatatgcaggccaaggccgccgcgatcatcaaggcc
gtgggcgaaaagctgctgacggaacagcgggaagtccagcgccagaaacaggcccagcgccagcaggaacgcgggcgcgcacattt
ccccgaaaagtgccacctggcggcgttgtgacaatttaccgaacaactccgcggccgggaagccgatctcggcttgaacgaattgttaggt
ggcggtacttgggtcgatatcaaagtgcatcacttcttcccgtatgcccaactttgtatagagagccactgcgggatcgtcaccgtaatctgctt
gcacgtagatcacataagcaccaagcgcgttggcctcatgcttgaggagattgatgagcgcggtggcaatgccctgcctccggtgctcgcc
ggagactgcgagatcatagatatagatctcactacgcggctgctcaaacctgggcagaacgtaagccgcgagagcgccaacaaccgcttc
ttggtcgaaggcagcaagcgcgatgaatgtcttactacggagcaagttcccgaggtaatcggagtccggctgatgttgggagtaggtggct
acgtctccgaactcacgaccgaaaagatcaagagcagcccgcatggatttgacttggtcagggccgagcctacatgtgcgaatgatgccc
atacttgagccacctaactttgttttagggcgactgccctgctgcgtaacatcgttgctgctgcgtaacatcgttgctgctccataacatcaaac
atcgacccacggcgtaacgcgcttgctgcttggatgcccgaggcatagactgtacaaaaaaacagtcataacaagccatgaaaaccgcca
ctgcgccgttaccaccgctgcgttcggtcaaggttctggaccagttgcgtgagcgcatacgctacttgcattacagtttacgaaccgaacag
gcttatgtcaactgggttcgtgccttcatccgtttccacggtgtgcgtccatgggcaaatattatacgcaaggcgacaaggtgctgatgccgct
ggcgattcaggttcatcatgccgtttgtgatggcttccatgtcggcagaatgcttaatgaattacaacagtttttatgcatgcgcccaatacgca
aaccgcctctccccgcgcgttggccgattcattaatgcagctggcacgacaggtttcccgactggaaagcgggcagtgagcgcaacgcaa
ttaatgtgagttagctcactcattaggcaccccaggctttacactttatgcttccggctcgtatgttgtgtggaattgtgagcggataacaatttca
cacaggaaacagctatgaccatgattacgccaagcgcgcaattaaccctcactaaagggaacaaaagctgggtaccctgcccgctttccag
tcgggaaacctgtcgtgccagctgcattaatgaatcggccaacgcgcggggagaggcggtttgcgtattgggcgccagggtggtttttctttt
caccagtgagacgggcaacagctgattgcccttcaccgcctggccctgagagagttgcagcaagcggtccacgctggtttgccccagcag
gcgaaaatcctgtttgatggtggttaacggcgggatataacatgagctgtcttcggtatcgtcgtatcccactaccgagatatccgcaccaac
gcgcagcccggactcggtaatggcgcgcattgcgcccagcgccatctgatcgttggcaaccagcatcgcagtgggaacgatgccctcatt
cagcatttgcatggtttgttgaaaaccggacatggcactccagtcgccttcccgttccgctatcggctgaatttgattgcgagtgagatatttatg
ccagccagccagacgcagacgcgccgagacagaacttaatgggcccgctaacagcgcgatttgctggtgacccaatgcgaccagatgct
ccacgcccagtcgcgtaccgtcttcatgggagaaaataatactgttgatgggtgtctggtcagagacatcaagaaataacgccggaacatta
gtgcaggcagcttccacagcaatggcatcctggtcatccagcggatagttaatgatcagcccactgacgcgttgcgcgagaagattgtgca
ccgccgctttacaggcttcgacgccgcttcgttctaccatcgacaccaccacgctggcacccagttgatcggcgcgagatttaatcgccgcg
acaatttgcgacggcgcgtgcagggccagactggaggtggcaacgccaatcagcaacgactgtttgcccgccagttgttgtgccacgcgg
ttgggaatgtaattcagctccgccatcgccgcttccactttttcccgcgttttcgcagaaacgtggctggcctggttcaccacgcgggaaacg
gtctgataagagacaccggcatactctgcgacatcgtataacgttactggtttcacattcaccaccctgaattgactctcttccgggcgctatca
tgccataccgcgaaaggttttgcgccattcgatggtgtccgggatctcgacgctctcccttatgcgactcctgcattaggaagcagcccagta
gtaggttgaggccgttgagcaccgccgccgcaaggaatggtgcatgcaaggagatggcgcccaacagtcccccggccacggggcctg
ccaccatacccacgccgaaacaagcgctcatgagcccgaagtggcgagcccgatcttccccatcggtgatgtcggcgatataggcgcca
gcaaccgcacctgtggcgccggtgatgccggccacgatgcgtccggcgtagaggatcgagatctcgatcccgcgaaattaatacgactca
ctataggggaattgtgagcggataacaattcccctctagaaataattttgtttaactttaagaaggagatatacatatgaccgaaaatgtgtctttc
accgaaactgaaaccgaagctcgtcgttctgcgaactacgaacctaacagctgggactatgattacctgctgtcctccgacacggacgagt
ccatcgaagtatacaaagacaaagcgaaaaagctggaagccgaagttcgtcgcgagattaataacgaaaaagcagaatttctgaccctgct
ggaactgattgacaacgtccagcgcctgggcctgggttaccgtttcgagtctgatatccgtggtgcgctggatcgcttcgtttcctccggcgg
cttcgatgcggtaaccaagacttccctgcacggtacggcactgtctttccgtctgctgcgtcaacacggttttgaggtttctcaggaagcgttc
agcggcttcaaagaccaaaacggcaacttcctggagaacctgaaggaagatatcaaagctatcctgagcctgtacgaggccagcttcctg
gctctggaaggcgaaaacatcctggacgaggcgaaggttttcgcaatctctcatctgaaagaactgtctgaagaaaagatcggtaaagagc
tggcagaacaggtgaaccatgcactggaactgccactgcatcgccgtactcagcgtctggaagcagtatggtctatcgaggcctaccgtaa
aaaggaggacgcgaatcaggttctgctggagctggcaattctggattacaacatgatccagtctgtataccagcgtgatctgcgtgaaacgt
cccgttggtggcgtcgtgtgggtctggcgaccaaactgcactttgctcgtgaccgcctgattgagagcttctactgggccgtgggtgtagcat
tcgaaccgcaatactccgactgccgtaactccgtcgcaaaaatgttttctttcgtaaccattatcgacgatatctacgatgtatacggcaccctg
gacgaactggagctgtttactgatgcagttgagcgttgggacgtaaacgccatcaacgacctgccggattacatgaaactgtgctttctggct

Figure 58B ctgtataacactattaacgaaatcgcctacgacaacctgaaagataaaggtgagaacatcctgccgtatctgaccaaagcctgggctgacct
gtgcaacgctttcctgcaagaagccaagtggctgtacaacaaatctactccgacctttgacgactacttcggcaacgcatggaaatcctcttct
ggcccgctgcaactggtgttcgcttacttcgctgtcgtgcagaacattaaaaaggaagagatcgaaaacctgcaaaaataccatgacaccat
ctctcgtccttcccatatcttccgtctgtgcaatgacctggctagcgcgtctgcggaaattgcgcgtggtgaaaccgcaaatagcgtttcttgtt
acatgcgcactaaaggtatctccgaagaactggctaccgaaagcgtgatgaatctgatcgatgaaacctggaaaaagatgaacaaggaaa
aactgggtggtagcctgttcgcgaaaccgttcgtggaaaccgcgatcaacctggcacgtcaatctcactgcacttatcataacggcgacgc
gcatacctctccggatgagctgacccgcaaacgcgttctgtctgtaatcactgaaccgattctgccgtttgaacgctaaggatccgaattcga
gctccgtcgacaagcttgcggccgcactcgagcaccaccaccaccaccactgagatccggctgctaacaaagcccgaaaggaagctga
gttggctgctgccaccgctgagcaataactagcataaccccttggggcctctaaacgggtcttgaggggttttttgactagttctagagcggc
cgccaccgcggtggagctccaattcgccctatagtgagtcgtattacgcgcgctcactggccgtcgttttacaacgtcgtgactgggaaaac
cctggcgttacccaacttaatcgccttgcagcacatccccctttcgccagctggcgtaatagcgaagaggcccgcaccgatcgcccttccca
acagttgcgcagcctgaatggcgaatggaaattgtaagcgttaatattttgttaaaattcgcgttaaatttttgttaaatcagctcattttttaaccaa
taggccgactgcgatgagtggcagggcggggcgtaatttttttaaggcagttattggtgcccttaaacgcctggtgctacgcctgaataagtg
ataataagcggatgaatggcagaaattcgaaagcaaattcgacccggtcgtcggttcagggcagggtcgttaaatagccgcttatgtctattg
ctggtttaccggtttattgactaccggaagcagtgtgaccgtgtgcttctcaaatgcctgaggccagtttgctcaggctctccccgtggaggta
ataattgacgatatgatcatttattctgcctcccagagcctgataaaaacggtgaatccgttagcgaggtgccgccggcttccattcaggtcga
ggtggcccggctccatgcaccgcgacgcaacgcggggaggcagacaaggtatagggcggcgaggcggctacagccgatagtctgga
acagcgcacttacgggttgctgcgcaacccaagtgctaccggcgcggcagcgtgacccgtgtcggcggctccaacggctcgccatcgtc
cagaaaacacggctcatcgggcatcggcaggcgctgctgcccgcgccgttcccattcctccgtttcggtcaaggctggcaggtctggttcc
atgcccggaatgccgggctggctgggcggctcctcgccggggccggtcggtagttgctgctcgcccggatacagggtcgggatgcggc
gcaggtcgccatgccccaacagcgattcgtcctggtcgtcgtgatcaaccaccacggcggcactgaacaccgacaggcgcaactggtcg
cggggctggccccacgccacgcggtcattgaccacgtaggccgacacggtgccggggccgttgagcttcacgacggagatccagcgct
cggccaccaagtccttgactgcgtattggaccgtccgcaaagaacgtccgatgagcttggaaagtgtcttctggctgaccaccacggcgttc
tggtggcccatctgcgccacgaggtgatgcagcagcattgccgccgtgggtttcctcgcaataagcccggcccacgcctcatgcgctttgc
gttccgtttgcacccagtgaccgggcttgttcttggcttgaatgccgatttctctggactgcgtggccatgcttatctccatgcggtagggtgcc
gcacggttgcggcaccatgcgcaatcagctgcaacttttcggcagcgcgacaacaattatgcgttgcgtaaaagtggcagtcaattacagat
tttctttaacctacgcaatgagctattgcgggggggtgccgcaatgagctgttgcgtaccccccttttttaagttgttgatttttaagtctttcgcattt
cgccctatatctagttctttggtgcccaaagaagggcacccctgcggggttcccccacgccttcggcgcggctcccccctccggcaaaagt
ggcccctccggggcttgttgatcgactgcgcggccttcggccttgcccaaggtggcgctgcccccttggaacccccgcactcgccgccgt
gaggctcgggggggcaggcgggcgggcttcgccttcgactgcccccactcgcataggcttgggtcgttccaggcgcgtcaaggccaagc
cgctgcgcggtcgctgcgcgagccttgacccgccttccacttggtgtccaaccggcaagcgaagcgcgcaggccgcaggccggaggct
tttccccagagaaaattaaaaaaattgatggggcaaggccgcaggccgcgcagttggagccggtgggtatgtggtcgaaggctgggtagc
cggtgggcaatccctgtggtcaagctcgtgggcaggcgcagcctgtccatcagcttgtccagcagggttgtccacgggccgagcgaagc
gagccagccggtggccgctcgcggccatcgtccacatatccacgggctggcaagggagcgcagcgaccgcgcagggcgaagcccgg
agagcaagcccgtagggcgccgcagccgccgtaggcggtcacgactttgcgaagcaaagtctagtgagtatactcaagcattgagtggc
ccgccggaggcaccgccttgcgctgcccccgtcgagccggttggacaccaaaagggagggggcaggcatggcggcatacgcgatcatg
cgatgcaagaagctggcgaaaatgggcaacgtggcggccagtctcaagcacgcctaccgcgagcgcgagacgcccaacgctgacgcc
agcaggacgccagagaacgagcactgggcggccagcagcaccgatgaagcgatgggccgactgcgcgagttgctgccagagaagcg
gcgcaaggacgctgtgttggcggtcgagtacgtcatgacggccagcccggaatggtggaagtcggccagccaagaacagcaggcggc
gttcttcgagaaggcgcacaagtggctggcggacaagtacggggcggatcgcatcgtgacggccagcatccaccgtgacgaaaccagc
ccgcacatgaccgcgttcgtggtgccgctgacgcaggacggcaggctgtcggccaaggagttcatcggcaacaaagcgcagatgaccc
gcgaccagaccacgtttgcggccgctgtggccgatctagggctgcaacggggcatcgagggcagcaaggcacgtcacacgcgcattca
ggcgttctacgaggccctggagcggccaccagtgggccacgtcaccatcagcccgcaagcggtcgagccacgcgcctatgcaccgcag

Figure 58C

Ggattggccgaaaagctgggaatctcaaagcgcgttgagacgccggaagccgtggccgaccggctgacaaaagcggttcggcagggg tatgagcctgccctacaggccgccgcaggagcgcgtgagatgcgcaagaaggccgatcaagcccaagagacggcccgag (SEQ ID NO:76)

Figure 59A cgataagctagcttcacgctgccgcaagcactcagggcgcaagggctgctaaaggaagcggaacacgtagaaagccagtccgcagaaa
cggtgctgaccccggatgaatgtcagctactgggctatctggacaagggaaaacgcaagcgcaaagagaaagcaggtagcttgcagtgg
gcttacatggcgatagctagactgggcggttttatggacagcaagcgaaccggaattgccagctggggcgccctctggtaaggttgggaa
gccctgcaaagtaaactggatggctttcttgccgccaaggatctgatggcgcaggggatcaagatctgatcaagagacaggatgaggatc
gtttcgcatgattgaacaagatggattgcacgcaggttctccggccgcttgggtggagaggctattcggctatgactgggcacaacagacaa
tcggctgctctgatgccgccgtgttccggctgtcagcgcaggggcgcccggttctttttgtcaagaccgacctgtccggtgccctgaatgaa
ctccaagacgaggcagcgcggctatcgtggctggccacgacgggcgttccttgcgcagctgtgctcgacgttgtcactgaagcgggaag
ggactggctgctattgggcgaagtgccggggcaggatctcctgtcatctcaccttgctcctgccgagaaagtatccatcatggctgatgcaat
gcggcggctgcatacgcttgatccggctacctgcccattcgaccaccaagcgaaacatcgcatcgagcgagcacgtactcggatggaag
ccggtcttgtcgatcaggatgatctggacgaagagcatcaggggctcgcgccagccgaactgttcgccaggctcaaggcgcggatgccc
gacggcgaggatctcgtcgtgacccatggcgatgcctgcttgccgaatatcatggtggaaaatggccgcttttctggattcatcgactgtggc
cggctgggtgtggcggaccgctatcaggacatagcgttggctacccgtgatattgctgaagagcttggcggcgaatgggctgaccgcttcc
tcgtgctttacggtatcgccgctcccgattcgcagcgcatcgccttctatcgccttcttgacgagttcttctgagcgggactctggggttcgcga
tgataagctgtcaaacatgagaattacaacttatatcgtatggggctgacttcaggtgctacatttgaagagataaattgcactgaaatctagaa
atattttatctgattaataagatgatcttcttgagatcgttttggtctgcgcgtaatctcttgctctgaaaacgaaaaaaccgccttgcagggcggt
ttttcgaaggttctctgagctaccaactctttgaaccgaggtaactggcttggaggagcgcagtcaccaaaacttgtcctttcagtttagccttaa
ccggcgcatgacttcaagactaactcctctaaatcaattaccagtggctgctgccagtggtgcttttgcatgtctttccgggttggactcaagac
gatagttaccggataaggcgcagcggtcggactgaacggggggttcgtgcatacagtccagcttggagcgaactgcctacccggaactg
agtgtcaggcgtggaatgagacaaacgcggccataacagcggaatgacaccggtaaaccgaaaggcaggaacaggagagcgcacga
gggagccgccagggggaaacgcctggtatctttatagtcctgtcgggtttcgccaccactgatttgagcgtcagatttcgtgatgcttgtcagg
ggggcggagcctatggaaaaacggctttgccttctttcctgcgttatcccctgattctgtggataaccgtattaccgcctttgagtgagctgata
ccgctcgccgcagccgaacgaccgagcgcagcgagtcagtgagcgaggaagcggaagagcgcccaatacgcaaaccgcctctcccc
gcgcgttggccgattcattaatgcagctggcacgacaggtttcccgactggaaagcgggcagtgagcgcaacgcaattaatgtgagttagc
tcactcattaggcaccccaggctttacactttatgcttccggctcgtatgttgtgtggaattgtgagcggataacaatttcacacaggaaacagc
tatgaccatgattacgaattctgttgacaattaatcatcggctcgtataatgtgtggaattgtgagcggataacaatttcacacaggaaacagatt
acggatccatttgaggagtaagccatgcaaacgttgccaagcccagttcaagctacaccaacggaaacagctattgttagacgcaaaaccc
gcccggttccgataggctccgttgttattggtggcggccatcccgtggctgttcagtcaatgattaacgaagacactctggatatcgaaggttc
tgttgctgcaattcggcgcttacacgagatcggttgcgagatcgtacgtgtgactgtaccttcattagcacacgcgaaagcaatggaagagat
tcgggatcggctttataaaacgtacaaaccggtccccttagttgccgacgtgcatcataacggaatgaaaatcgcgttagaggttgccaagta
cgtggacaatgtgcgcattaatcctggattatacgtgtttgagaagccaaaaccaaatcgcacggagtacactcaagctgaatttgacgagat
tggcgcgaaaatccgtgaaacgttggaaccactggtaatttcactgcgggatcagggaaagtcgatgcgcattggcgttaatcatggcagtc
tggcggaacggatgctgtttacctatggcgataccccagagggtatggtagagagtgcacttgagtttatacgcatctgtgaaagtctcaactt
ctataacttagaaatttcccttaaagctagccgcgtcccggttatgatagccgccaatcggcttatggttaagcgcatggacgagctgggtatg
gattatccgttgcatctcggagtgactgaggcaggtgatggtgaatatggccgtattaaaagcacagcaggcattgcaacactgctggcgga
aggaattggagacacaatccgtgtttcattgactgaagctccggaaaaggaaatccccgtgtgctatggcatccttcaagccctcggtctccg
ccgcaccatggtagaatatgtagcttgcccgtcgtgtggtcggacattgtttaacctggaagaggttctgcacaaggtgagagaagcgacta
aacacctgacgggactgaatattgcggttatgggatgtattgtaaatggacctggcgaaatggccgatgcagactacggctatgtaggtaaa
cagccgggatatataagtctttaccgcggccgggaagaagtcaagaaagtgcccgaggccgagggcgttgcagctctggtcgaactgata
aaagcggatggtagatgggtagatccataagtggagctccagcccggggcactggaggcgtaaatggatacacgtgcgttcaaacgttca
cttcattcgtcggaaaattaccatcgcaaaggctttggacatggcgaggaagttaaccagcaattgcagggcgaatatcagtctagcctcata
cagcagattagagccaatggttatcgctggcagcagggcgatgttacaattcgtctggcagaagcgtttggcttctgctggggtgtggaaag
agccgtcgctcttgcttacgaaaccagaacccatttcccgaccgagcgcatatggataaccaacgaaattattcacaacccctcagttaatga
acgtctgcgccaaatggccgtcgagttcattcctgtagtgaacggcgtcaaagatttttcgggagtacggcccggcgatgtcgtcatactgcc
agcatttggggcgtcagttcaggagatgcagttattaaacgaacgcggttgtactatcgtagatacgacgtgtccgtgggtgagcaaagtatg

Figure 59B cattcggtggaaaaacataagaaagtttccttcacgagcattatacacggtaaatacaaccacgaggagactattgcaacatcctcatttgcg
ggaacttacttgatcgtactgaacctcgaagaggcccgttacgtttgtgactacattttacatggcggcgatcgcgctgcatttatggcgaaatt
tgccaaggcttgctcacctggttttgacccggaccgggatctggtccgggtagggatagctaaccaaacaacaatgttaaaaggcgagacc
gaacagattggcaaattgtttgagcgcaccatgattcaaaagtatggtccggatcgccttaacgagcacttcatgtcgtttaatactatttgcgat
gcgacacaggaacggcaagacgcaatgttgagtttagtaaaagagccgttagatctgatggtagtcattggcggttataattcttccaatacta
cgcatttgcaggagattgcaatcgaacacggcattccatcctatcatatcgactcagcggatcgtatcggaccaggtaatcggattgaacata
agccattgcaccaaaatccgacagttgccgaaaattggttaccggatcgcccgatcactatcggcattacttcaggtgcatcaactcccgata
aagttgttgaagaggtgctgaataagatctttgctttacgcagcgttgcaacggttagttgatccactagtcccggtaccgtggacgaggttta
atatggcgacgtataaagtcacactggtccgtccggatggcagcgaaacgaccatcgatgttccggaggacgaatacatactggatgtcgc
cgaagaacaaggtctggatctcccgttttcttgtcgcgccggtgcctgctctacctgtgctggcaaattgttggagggagaagtcgatcaaag
cgaccagagcttcttggatgacgatcagatcgaaaaaggattcgtgcttacttgtgtggcctacccccgttcggactgcaagatcttgacgaa
ccaagaggaggagctgtactaagaggtcgacgacgcatgcattaacagaggttagtatgtataatgccactaactctcgctcacgtatgttcc
ggtacgaagttgtggggctgcgccaaacggcggagacggagaaaacaaattacgcgatcagaaactctggctcgcagttctttaatgtgcc
ttatgaccgcatgaaccagtttatgcagcagatcactcggtggggcggtaaaattgtcagtattcagccccttaacggaaccgtggccccact
tgctgcaaccacggagccagctgccaataacggagctgcacctgtgaaagaaaagaaagtcgatataccggtcaacatctaccgtcccaa
taatccctgcataggtaaggttattagcaacgaggaactggtccgggaaggcggtgagggtacggtgaaacatattatctttgatatatcggg
gaccgaattacgttacttggaagggcagtcaatcggtatcattcccgcgggcacggacgcgaacggtaaaccacataagctgcgtctgtatt
ccattgcttccacaagacatggtgactttcaggatgacaagacggtgtccttatgcgtacggagattagaatacaaagataaagagaccggg
gagaccatttatggcgtgtgcagttcgtatcttaatcagttacagcctggagatgaagtcaaaatcacaggtcctgttgggaaagaaatgcttc
tctctgacgacccagaagcgactattattatgctggctaccggcactggaatagcgccatttcgggcatttttatggcggatgttcaaagagaa
caacccggattaccagttcaaaggccttgcgtggctgttctttggcgtcgcttatactgccaatatcctgtataaggacgagcttgaagctatcc
aagcccagtatcccgatcattttcggttaacctacgcgatttcccgtgaacaaaaaaccccggacggagggaaaatgtacatccagggtcg
gatcgcagagcacgctgatgaaatctggcaactgctgcaaaagaaaaacacccacgtgtacatgtgtggcctgcgtgggatggaacctgg
aatagacgaggccatgaccgcagcggccgcgaaaaacggagctgactggcaggagtttctgaaaggtacgctgaaaaaggaaggcag
atggcatgtcgaaacttattaactgcagtacaaataaaaaaggcacgtcagatgacgtgcctttttttcttgaagcttggcactggccgtcgtttta
caacgtcgtgactgggaaaaccctggcgttacccaacttaatcgccttgcagcacatccccctttcgccagctggcgtaatagcgaagagg
cccgcaccgatcgcccttcccaacagttgcgcagcctgaatggcgaatggcg (SEQ ID NO:77)

Diagnostic primers used to verify the removal of *iscR* from the BL21(DE3) genome

Figure 64A accttcgggagcgcctgaagcccgttctggacgccctggggccgttgaatcgggatatgcaggccaaggccgccgcgatcatcaaggcc
gtgggcgaaaagctgctgacggaacagcgggaagtccagcgccagaaacaggcccagcgccagcaggaacgcgggcgcgcacattt
ccccgaaaagtgccacctggcggcgttgtgacaatttaccgaacaactccgcggccgggaagccgatctcggcttgaacgaattgttaggt
ggcggtacttgggtcgatatcaaagtgcatcacttcttcccgtatgcccaactttgtatagagagccactgcgggatcgtcaccgtaatctgctt
gcacgtagatcacataagcaccaagcgcgttggcctcatgcttgaggagattgatgagcgcggtggcaatgccctgcctccggtgctcgcc
ggagactgcgagatcatagatatagatctcactacgcggctgctcaaacctgggcagaacgtaagccgcgagagcgccaacaaccgcttc
ttggtcgaaggcagcaagcgcgatgaatgtcttactacggagcaagttcccgaggtaatcggagtccggctgatgttgggagtaggtggct
acgtctccgaactcacgaccgaaaagatcaagagcagcccgcatggatttgacttggtcagggccgagcctacatgtgcgaatgatgccc
atacttgagccacctaactttgttttagggcgactgccctgctgcgtaacatcgttgctgctgcgtaacatcgttgctgctccataacatcaaac
atcgacccacggcgtaacgcgcttgctgcttggatgcccgaggcatagactgtacaaaaaaacagtcataacaagccatgaaaaccgcca
ctgcgccgttaccaccgctgcgttcggtcaaggttctggaccagttgcgtgagcgcatacgctacttgcattacagtttacgaaccgaacag
gcttatgtcaactgggttcgtgccttcatccgtttccacggtgtgcgtccatgggcaaatattatacgcaaggcgacaaggtgctgatgccgct
ggcgattcaggttcatcatgccgtttgtgatggcttccatgtcggcagaatgcttaatgaattacaacagtttttatgcatgcgcccaatacgca
aaccgcctctccccgcgcgttggccgattcattaatgcagctggcacgacaggtttcccgactggaaagcgggcagtgagcgcaacgcaa
ttaatgtgagttagctcactcattaggcaccccaggctttacactttatgcttccggctcgtatgttgtgtggaattgtgagcggataacaatttca
cacaggaaacagctatgaccatgattacgccaagcgcgcaattaaccctcactaaagggaacaaaagctgggtaccctgcccgctttccag
tcgggaaacctgtcgtgccagctgcattaatgaatcggccaacgcgcggggagaggcggtttgcgtattgggcgccagggtggtttttctttt
caccagtgagacgggcaacagctgattgcccttcaccgcctggccctgagagagttgcagcaagcggtccacgctggtttgccccagcag
gcgaaaatcctgtttgatggtggttaacggcgggatataacatgagctgtcttcggtatcgtcgtatcccactaccgagatatccgcaccaac
gcgcagcccggactcggtaatggcgcgcattgcgcccagcgccatctgatcgttggcaaccagcatcgcagtgggaacgatgccctcatt
cagcatttgcatggtttgttgaaaaccggacatggcactccagtcgccttcccgttccgctatcggctgaatttgattgcgagtgagatatttatg
ccagccagccagacgcagacgcgccgagacagaacttaatgggcccgctaacagcgcgatttgctggtgacccaatgcgaccagatgct
ccacgcccagtcgcgtaccgtcttcatgggagaaaataatactgttgatgggtgtctggtcagagacatcaagaaataacgccggaacatta
gtgcaggcagcttccacagcaatggcatcctggtcatccagcggatagttaatgatcagcccactgacgcgttgcgcgagaagattgtgca
ccgccgctttacaggcttcgacgccgcttcgttctaccatcgacaccaccacgctggcacccagttgatcggcgcgagatttaatcgccgcg
acaatttgcgacggcgcgtgcagggccagactggaggtggcaacgccaatcagcaacgactgtttgcccgccagttgttgtgccacgcgg
ttgggaatgtaattcagctccgccatcgccgcttccactttttcccgcgttttcgcagaaacgtggctggcctggttcaccacgcgggaaacg
gtctgataagagacaccggcatactctgcgacatcgtataacgttactggtttcacattcaccaccctgaattgactctcttccgggcgctatca
tgccataccgcgaaaggttttgcgccattcgatggtgtccgggatctcgacgctctcccttatgcgactcctgcattaggaagcagcccagta
gtaggttgaggccgttgagcaccgccgccgcaaggaatggtgcatgcaaggagatggcgcccaacagtcccccggccacggggcctg
ccaccatacccacgccgaaacaagcgctcatgagcccgaagtggcgagcccgatcttccccatcggtgatgtcggcgatataggcgcca
gcaaccgcacctgtggcgccggtgatgccggccacgatgcgtccggcgtagaggatcgagatctcgatcccgcgaaattaatacgactca
ctataggggaattgtgagcggataacaattcccctctagaaataattttgtttaactttaagaaggagatatacatatggaagctcgtcgttctgc
gaactacgaacctaacagctgggactatgattacctgctgtcctccgacacggacgagtccatcgaagtatacaaagacaaagcgaaaaa
gctggaagccgaagttcgtcgcgagattaataacgaaaaagcagaatttctgaccctgctggaactgattgacaacgtccagcgcctgggc
ctgggttaccgtttcgagtctgatatccgtggtgcgctggatcgcttcgtttcctccggcggcttcgatgcggtaaccaagacttccctgcacg
gtacggcactgtctttccgtctgctgcgtcaacacggttttgaggtttctcaggaagcgttcagcggcttcaaagaccaaaacggcaacttcct
ggagaacctgaaggaagatatcaaagctatcctgagcctgtacgaggccagcttcctggctctggaaggcgaaaacatcctggacgaggc
gaaggttttcgcaatctctcatctgaaagaactgtctgaagaaaagatcggtaaagagctggcagaacaggtgaaccatgcactggaactg
ccactgcatcgccgtactcagcgtctggaagcagtatggtctatcgaggcctaccgtaaaaaggaggacgcgaatcaggttctgctggagc
tggcaattctggattacaacatgatccagtctgtataccagcgtgatctgcgtgaaacgtcccgttggtggcgtcgtgtgggtctggcgacca
aactgcactttgctcgtgaccgcctgattgagagcttctactgggccgtgggtgtagcattcgaaccgcaatactccgactgccgtaactccg
tcgcaaaaatgttttctttcgtaaccattatcgacgatatctacgatgtatacggcaccctggacgaactggagctgtttactgatgcagttgagc
gttgggacgtaaacgccatcaacgacctgccggattacatgaaactgtgctttctggctctgtataacactattaacgaaatcgcctacgacaa

Figure 64B cctgaaagataaaggtgagaacatcctgccgtatctgaccaaagcctgggctgacctgtgcaacgctttcctgcaagaagccaagtggctg
tacaacaaatctactccgacctttgacgactacttcggcaacgcatggaaatcctcttctggcccgctgcaactggtgttcgcttacttcgctgt
cgtgcagaacattaaaaaggaagagatcgaaaacctgcaaaaataccatgacaccatctctcgtccttcccatatcttccgtctgtgcaatga
cctggctagcgcgtctgcggaaattgcgcgtggtgaaaccgcaaatagcgtttcttgttacatgcgcactaaaggtatctccgaagaactgg
ctaccgaaagcgtgatgaatctgatcgatgaaacctggaaaaagatgaacaaggaaaaactgggtggtagcctgttcgcgaaaccgttcgt
ggaaaccgcgatcaacctggcacgtcaatctcactgcacttatcataacggcgacgcgcatacctctccggatgagctgacccgcaaacg
cgttctgtctgtaatcactgaaccgattctgccgtttgaacgctaaggatccgaattcgagctccgtcgacaagcttgcggccgcactcgagc
accaccaccaccaccactgagatccggctgctaacaaagcccgaaaggaagctgagttggctgctgccaccgctgagcaataactagcat
aaccccttggggcctctaaacgggtcttgaggggttttttgactagttctagagcggccgccaccgcggtggagctccaattcgccctatagt
gagtcgtattacgcgcgctcactggccgtcgttttacaacgtcgtgactgggaaaaccctggcgttacccaacttaatcgccttgcagcacat
ccccctttcgccagctggcgtaatagcgaagaggcccgcaccgatcgcccttcccaacagttgcgcagcctgaatggcgaatggaaattgt
aagcgttaatattttgttaaaattcgcgttaaatttttgttaaatcagctcattttttaaccaataggccgactgcgatgagtggcagggcggggc
gtaatttttttaaggcagttattggtgcccttaaacgcctggtgctacgcctgaataagtgataataagcggatgaatggcagaaattcgaaag
caaattcgacccggtcgtcggttcagggcagggtcgttaaatagccgcttatgtctattgctggtttaccggtttattgactaccggaagcagt
gtgaccgtgtgcttctcaaatgcctgaggccagtttgctcaggctctccccgtggaggtaataattgacgatatgatcatttattctgcctccca
gagcctgataaaaacggtgaatccgttagcgaggtgccgccggcttccattcaggtcgaggtggcccggctccatgcaccgcgacgcaa
cgcggggaggcagacaaggtatagggcggcgaggcggctacagccgatagtctggaacagcgcacttacgggttgctgcgcaaccca
agtgctaccggcgcggcagcgtgacccgtgtcggcggctccaacggctcgccatcgtccagaaaacacggctcatcgggcatcggcag
gcgctgctgcccgcgccgttcccattcctccgtttcggtcaaggctggcaggtctggttccatgcccggaatgccgggctggctgggcggc
tcctcgccggggccggtcggtagttgctgctcgcccggatacagggtcgggatgcggcgcaggtcgccatgccccaacagcgattcgtc
ctggtcgtcgtgatcaaccaccacggcggcactgaacaccgacaggcgcaactggtcgcggggctggccccacgccacgcggtcattg
accacgtaggccgacacggtgccggggccgttgagcttcacgacggagatccagcgctcggccaccaagtccttgactgcgtattggac
cgtccgcaaagaacgtccgatgagcttggaaagtgtcttctggctgaccaccacggcgttctggtggcccatctgcgccacgaggtgatgc
agcagcattgccgccgtgggtttcctcgcaataagcccggcccacgcctcatgcgctttgcgttccgtttgcacccagtgaccgggcttgttc
ttggcttgaatgccgatttctctggactgcgtggccatgcttatctccatgcggtagggtgccgcacggttgcggcaccatgcgcaatcagct
gcaacttttcggcagcgcgacaacaattatgcgttgcgtaaaagtggcagtcaattacagattttctttaacctacgcaatgagctattgcggg
gggtgccgcaatgagctgttgcgtaccccccttttttaagttgttgatttttaagtctttcgcatttcgccctatatctagttctttggtgcccaaaga
agggcacccctgcggggttcccccacgccttcggcgcggctcccccctccggcaaaaagtggcccctccggggcttgttgatcgactgcg
cggccttcggccttgcccaaggtggcgctgccccttggaacccccgcactcgccgccgtgaggctcgggggggcaggcgggcgggctt
cgccttcgactgcccccactcgcataggcttgggtcgttccaggcgcgtcaaggccaagccgctgcgcggtcgctgcgcgagccttgacc
cgccttccacttggtgtccaaccggcaagcgaagcgcgcaggccgcaggccggaggcttttccccagagaaaattaaaaaaattgatggg
gcaaggccgcaggccgcgcagttggagccggtgggtatgtggtcgaaggctgggtagccggtgggcaatccctgtggtcaagctcgtg
ggcaggcgcagcctgtccatcagcttgtccagcagggttgtccacgggccgagcgaagcgagccagccggtggccgctcgcggccatc
gtccacatatccacgggctggcaagggagcgcagcgaccgcgcagggcgaagcccggagagcaagcccgtagggcgccgcagccg
ccgtaggcggtcacgactttgcgaagcaaagtctagtgagtatactcaagcattgagtggcccgccggaggcaccgccttgcgctgcccc
cgtcgagccggttggacaccaaaagggaggggcaggcatggcggcatacgcgatcatgcgatgcaagaagctggcgaaaatgggcaa
cgtggcggccagtctcaagcacgcctaccgcgagcgcgagacgcccaacgctgacgccagcaggacgccagagaacgagcactggg
cggccagcagcaccgatgaagcgatgggccgactgcgcgagttgctgccagagaagcggcgcaaggacgctgtgttggcggtcgagt
acgtcatgacggccagcccggaatggtggaagtcggccagccaagaacagcaggcggcgttcttcgagaaggcgcacaagtggctgg
cggacaagtacggggcggatcgcatcgtgacggccagcatccaccgtgacgaaaccagcccgcacatgaccgcgttcgtggtgccgct
gacgcaggacggcaggctgtcggccaaggagttcatcggcaacaaagcgcagatgacccgcgaccagaccacgtttgcggccgctgtg
gccgatctagggctgcaacggggcatcgagggcagcaaggcacgtcacacgcgcattcaggcgttctacgaggccctggagcggccac
cagtgggccacgtcaccatcagcccgcaagcggtcgagccacgcgcctatgcaccgcagggattggccgaaaagctgggaatctcaaa

Figure 64C

Gcgcgttgagacgccggaagccgtggccgaccggctgacaaaagcggttcggcaggggtatgagcctgccctacaggccgccgcag
gagcgcgtgagatgcgcaagaaggccgatcaagcccaagagacggcccgag (SEQ ID NO:78)

Figure 65A tggcgaatgggacgcgccctgtagcggcgcattaagcgcggcgggtgtggtggttacgcgcagcgtgaccgctacacttgccagcgccc
tagcgcccgctcctttcgctttcttcccttcctttctcgccacgttcgccggctttccccgtcaagctctaaatcgggggctccctttagggttcc
gatttagtgctttacggcacctcgaccccaaaaaacttgattagggtgatggttcacgtagtgggccatcgccctgatagacggtttttcgccc
tttgacgttggagtccacgttctttaatagtggactcttgttccaaactggaacaacactcaaccctatctcggtctattcttttgatttataagggat
tttgccgatttcggcctattggttaaaaaatgagctgatttaacaaaaatttaacgcgaattttaacaaaatattaacgtttacaatttcaggtggca
cttttcggggaaatgtgcgcggaacccctatttgtttatttttctaaatacattcaaatatgtatccgctcatgaattaattcttagaaaaactcatcg
agcatcaaatgaaactgcaatttattcatatcaggattatcaataccatatttttgaaaaagccgtttctgtaatgaaggagaaaactcaccgag
gcagttccataggatggcaagatcctggtatcggtctgcgattccgactcgtccaacatcaatacaacctattaatttcccctcgtcaaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatattttcacctgaatcaggatattcttc
taatacctggaatgctgttttcccggggatcgcagtggtgagtaaccatgcatcatcaggagtacggataaaatgcttgatggtcggaagag
gcataaattccgtcagccagtttagtctgaccatctcatctgtaacatcattggcaacgctacctttgccatgtttcagaaacaactctggcgcat
cgggcttcccatacaatcgatagattgtcgcacctgattgcccgacattatcgcgagcccatttatacccatataaatcagcatccatgttggaa
tttaatcgcggcctagagcaagacgtttcccgttgaatatggctcataacaccccttgtattactgtttatgtaagcagacagttttattgttcatga
ccaaaatcccttaacgtgagttttcgttccactgagcgtcagaccccgtagaaaagatcaaaggatcttcttgagatcctttttttctgcgcgtaa
tctgctgcttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacgaggga
gcttccagggggaaacgcctggtatctttatagtcctgtcgggtttcgccacctctgacttgagcgtcgatttttgtgatgctcgtcaggggggc
ggagcctatggaaaaacgccagcaacgcggcctttttacggttcctggccttttgctggccttttgctcacatgttctttcctgcgttatcccct
gattctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcatatatggtgcactctcagtacaatctgctct
gatgccgcatagttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttcaccgtcatc
accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
ggggatttctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttcgttaataca
gatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcacccgtggggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcggcgacgatagtcatgccccgcgcccaccggaaggagctgactgggttgaag
gctctcaagggcatcggtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgccagggtggtttttcttttcacca
gtgagacgggcaacagctgattgcccttcaccgcctggccctgagagagttgcagcaagcggtccacgctggtttgccccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttggcaaccagcatcgcagtgggaacgatgccctcattcagc
atttgcatggtttgttgaaaaccggacatggcactccagtcgccttcccgttccgctatcggctgaatttgattgcgagtgagatatttatgccag
ccagccagacgcagacgcgccgagacagaacttaatgggcccgctaacagcgcgatttgctggtgacccaatgcgaccagatgctccac

Figure 65B gcccagtcgcgtaccgtcttcatgggagaaaataatactgttgatgggtgtctggtcagagacatcaagaaataacgccggaacattagtgc
aggcagcttccacagcaatggcatcctggtcatccagcggatagttaatgatcagcccactgacgcgttgcgcgagaagattgtgcaccgc
cgctttacaggcttcgacgccgcttcgttctaccatcgacaccaccacgctggcacccagttgatcggcgcgagatttaatcgccgcgacaa
tttgcgacggcgcgtgcagggccagactggaggtggcaacgccaatcagcaacgactgtttgcccgccagttgttgtgccacgcggttgg
gaatgtaattcagctccgccatcgccgcttccactttttcccgcgttttcgcagaaacgtggctggcctggttcaccacgcgggaaacggtct
gataagagacaccggcatactctgcgacatcgtataacgttactggtttcacattcaccaccctgaattgactctcttccgggcgctatcatgc
cataccgcgaaaggttttgcgccattcgatggtgtccgggatctcgacgctctcccttatgcgactcctgcattaggaagcagcccagtagta
ggttgaggccgttgagcaccgccgccgcaaggaatggtgcatgcaaggagatggcgcccaacagtcccccggccacggggcctgcca
ccatacccacgccgaaacaagcgctcatgagcccgaagtggcgagcccgatcttccccatcggtgatgtcggcgatataggcgccagca
accgcacctgtggcgccggtgatgccggccacgatgcgtccggcgtagaggatcgagatctcgatcccgcgaaattaatacgactcacta
taggggaattgtgagcggataacaattcccctctagaaataattttgtttaactttaagaaggagatatacatatgagttttgatattgccaaatac
ccgaccctggcactggttgactccacccaggagttacgactgttgccgaaagagagtttaccgaaactctgcgacgaactgcgccgctattt
actcgacagcgtgagccgttccagcgggcacttcgcctccgggctgggcacggtcgaactgaccgtggcgctgcactatgtctacaacac
cccgtttgaccaattgatttgggatgtggggcatcaggcttatccgcataaaattttgaccggacgccgcgacaaaatcggcaccatccgtca
gaaaggcggtctgcacccgttcccgtggcgcggcgaaagcgaatatgacgtattaagcgtcgggcattcatcaacctccatcagtgccgg
aattggtattgcggttgctgccgaaaaagaaggcaaaaatcgccgcaccgtctgtgtcattggcgatggcgcgattaccgcaggcatggcg
tttgaagcgatgaatcacgcgggcgatatccgtcctgatatgctggtgattctcaacgacaatgaaatgtcgatttccgaaaatgtcggcgcg
ctcaacaaccatctggcacagctgctttccggtaagctgtactcttcactgcgcgaaggcgggaaaaaagttttctctggcgtgccgccaatt
aaagagctgctcaaacgcaccgaagaacatattaaaggcatggtagtgcctggcacgttgtttgaagagctgggctttaactacatcggccc
ggtggacggtcacgatgtgctggggcttatcaccacgctaaagaacatgcgcgacctgaaaggcccgcagttcctgcatatcatgaccaaa
aaaggtcgtggttatgaaccggcagaaaaagacccgatcactttccacgccgtgcctaaatttgatccctccagcggttgtttgccgaaaagt
agcggcggtttgccgagctattcaaaaatctttggcgactggttgtgcgaaacggcagcgaaagacaacaagctgatggcgattactccgg
cgatgcgtgaaggttccggcatggtcgagttttcacgtaaattcccggatcgctacttcgacgtggcaattgccgagcaacacgcggtgacc
tttgctgcgggtctggcgattggtgggtacaaacccattgtcgcgatttactccactttcctgcaacgcgcctatgatcaggtgctgcatgacgt
ggcgattcaaaaacttccggtcctgttcgccatcgaccgcgcgggcattgttggtgctgacggtcaaacccatcagggtgcttttgatctctct
tacctgcgctgcataccggaaatggtcattatgaccccgagcgatgaaaacgaatgtcgccagatgctctataccggctatcactataacgat
ggcccgtcagcggtgcgctacccgcgtggcaacgcggtcggcgtggaactgacgccgctggaaaaactaccaattggcaaaggcattgt
gaagcgtcgtggcgagaaactggcgatccttaactttggtacgctgatgccagaagcggcgaaagtcgccgaatcgctgaacgccacgct
ggtcgatatgcgttttgtgaaaccgcttgatgaagcgttaattctggaaatggccgccagccatgaagcgctggtcaccgtagaagaaaacg
ccattatgggcggcgcaggcagcggcgtgaacgaagtgctgatggcccatcgtaaaccagtacccgtgctgaacattggcctgccggact
tctttattccgcaaggaactcaggaagaaatgcgcgccgaactcggcctcgatgccgctggtatggaagccaaaatcaaggcctggctgg
cataagccttcttaaggtagctgctgacagatatttcgcccttaaagctttacaaggaggaaaaaaacatgaagcaactcaccattctgggctc
gaccggctcgattggttgcagcacgctggacgtggtgcgccataatcccgaacacttccgcgtagttgcgctggtggcaggcaaaaatgtc
actcgcatggtagaacagtgcctggaattttctccccgctatgccgtaatggacgatgaagcgagtgcgaaacttcttaaaacgatgctacag
caacagggtagccgcaccgaagtcttaagtgggcaacaagccgcttgcgatatggcagcgcttgaggatgttgatcaggtgatggcagcc
attgttggcgctgctgggctgttacctacgcttgctgcgatccgcgcgggtaaaaccattttgctggccaataaagaatcactggttacctgcg
gacgtctgtttatggacgccgtaaagcagagcaaagcgcaattgttaccggtcgatagcgaacataacgccatttttcagagtttaccgcaac
ctatccagcataatctgggatacgctgaccttgagcaaaatggcgtggtgtccattttacttaccgggtctggtggccctttccgtgagacgcc
attgcgcgatttggcaacaatgacgccggatcaagcctgccgtcatccgaactggtcgatggggcgtaaaatttctgtcgattcggctaccat
gatgaacaaaggtctggaatacattgaagcgcgttggctgtttaacgccagcgccagccagatggaagtgctgattcacccgcagtcagtg
attcactcaatggtgcgctatcaggacggcagtgttctggcgcagctgggggaaccggatatgcgtacgccaattgcccacacgatggcat
ggccgaatcgcgtgaactctggcgtgaagccgctcgatttttgcaaactaagtgcgttgacatttgccgcaccggattatgatcgttatccatg
cctgaaactggcgatggaggcgttcgaacaaggccaggcagcgacgacagcattgaatgccgcaaacgaaatcaccgttgctgcttttctt
gcgcaacaaatccgctttacggatatcgctgcgttgaatttatccgtactggaaaaaatggatatgcgcgaaccacaatgtgtggacgatgtg

Figure 65C ttatctgttgatgcgaacgcgcgtgaagtcgccagaaaagaggtgatgcgtctcgcaagctgagtccgactttgcgataggcctgcaccctt
aacgtcgacacgtaaggaggaaaaaaacatggcaaccactcatttggatgtttgcgccgtggttccggcggccggatttggccgtcgaatg
caaacggaatgtcctaagcaatatctctcaatcggtaatcaaaccattcttgaacactcggtgcatgcgctgctggcgcatccccgtgtgaaa
cgtgtcgtcattgccataagtcctggcgatagccgttttgcacaacttcctctggcgaatcatccgcaaatcaccgttgtagatggcggtgatg
agcgtgccgattccgtgctggcaggtctgaaagccgctggcgacgcgcagtgggtattggtgcatgacgccgctcgtccttgtttgcatcag
gatgacctcgcgcgattgttggcgttgagcgaaaccagccgcacgggggggcatcctcgccgcaccagtgcgcgatactatgaaacgtgc
cgaaccgggcaaaaatgccattgctcataccgttgatcgcaacggcttatggcacgcgctgacgccgcaatttttccctcgtgagctgttaca
tgactgtctgacgcgcgctctaaatgaaggcgcgactattaccgacgaagcctcggcgctggaatattgcggattccatcctcagttggtcg
aaggccgtgcggataacattaaagtcacgcgcccggaagatttggcactggccgagttttacctcacccgaaccatccatcaggagaatac
ataatttcggatgcttatacacgccagatatttcattacggagctcatacaaggaggaaaaaaacatgcggacacagtggccctctccggca
aaacttaatctgtttttatacattaccggtcagcgtgcggatggttaccacacgctgcaaacgctgtttcagtttcttgattacggcgacaccatc
agcattgagcttcgtgacgatggggatattcgtctgttaacgcccgttgaaggcgtggaacatgaagataacctgatcgttcgcgcagcgcg
attgttgatgaaaactgcggcagacagcgggcgtcttccgacgggaagcggtgcgaatatcagcattgacaagcgtttgccgatgggcgg
cggtctcggcggtggttcatccaatgccgcgacggtcctggtggcattaaatcatctctggcaatgcgggctaagcatggatgagctggcg
gaaatggggctgacgctgggcgcagatgttcctgtctttgttcgggggcatgccgcgtttgccgaaggcgttggtgaaatactaacgccggt
ggacccgccagagaagtggtatctggtggcgcaccctggtgtaagtattccgactccggtgatttttaaagatcctgaactcccgcgcaata
cgccaaaaaggtcaatagaaacgttgctaaaatgtgaatttagcaatgattgcgaggttatcgcaagaaaacgttttcgcgaggttgatgcgg
tgctttcctggctgttagaatacgccccgtcgcgcctgactgggacaggggcctgtgtctttgctgaatttgatacagagtctgaagcccgcc
aggtgctagagcaagccccggaatggctcaatggctttgtggcgaaaggcgctaatctttccccattgcacagagccatgctttaatttgcga
ttgagatccggcctgcacccttaaccggatccgattcaaggaggaaaaaaacatgcgaattggacacggttttgacgtacatgcctttggcg
gtgaaggcccaattatcattggtggcgtacgcattccttacgaaaaaggattgctggcgcattctgatggcgacgtggcgctccatgcgttga
ccgatgcattgcttggcgcggcggcgctgggggatatcggcaagctgttcccggataccgatccggcatttaaaggtgccgatagccgcg
agctgctacgcgaagcctggcgtcgtattcaggcgaagggttatacccttggcaacgtcgatgtcactatcatcgctcaggcaccgaagatg
ttgccgcacattccacaaatgcgcgtgtttattgccgaagatttgggctgccacatggatgatgttaacgtgaaagccactactacggaaaaa
ctgggatttaccggacgtggggaagggattgcctgtgaagcggtggcgctactcattaaggcaacaaaatgatttaccgtattattctttagac
aacggattaagctagcacataaggaggaaaaaaacatgcataaccaggctccaattcaacgtagaaaatcaacacgtatttacgttgggaat
gtgccgattggcgatggtgctcccatcgccgtacagtccatgaccaatacgcgtacgacagacgtcgaagcaacggtcaatcaaatcaag
gcgctggaacgcgttggcgctgatatcgtccgtgtatccgtaccgacgatggacgcggcagaagcgttcaaactcatcaaacagcaggtta
acgtgccgctggtggctgacatccacttcgactatcgcattgcgctgaaagtagcggaatacggcgtcgattgtctgcgtattaaccctggca
atatcggtaatgaagagcgtattcgcatggtggttgactgtgcgcgcgataaaaacattccgatccgtattggcgttaacgccggatcgctgg
aaaaagatttgcaagaaaagtatggcgaaccgacgccgcaggcgttgctggaatctgccatgcgtcatgttgatcatctcgatcgcctgaac
ttcgatcagttcaaagtcagcgtgaaagcgtctgacgtcttcctcgctgttgagtcttatcgtttgctggcaaaacagatcgatcagccgttgca
tctggggatcaccgaagccggtggtgcgcgcagcggggcagtaaaatccgccattggtttaggtctgctgctgtctgaaggcatcggcga
cacgctgcgcgtatcgctggcggccgatccggtcgaagagatcaaagtcggtttcgatattttgaaatcgctgcgtatccgttcgcgaggga
tcaacttcatcgcctgcccgacctgttcgcgtcaggaatttgatgttatcggtacggttaacgcgctggagcaacgcctggaagatatcatca
ctccgatggacgtttcgattatcggctgcgtggtgaatggcccaggtgaggcgctggtttctacactcggcgtcaccggcggcaacaagaa
aagcggcctctatgaagatggcgtgcgcaaagaccgtctggacaacaacgatatgatcgaccagctggaagcacgcattcgtgcgaaag
ccagtcagctggacgaagcgcgtcgaattgacgttcagcaggttgaaaaataattacaagtaaatgattcaggttataactacgttgcggccg
caaggaggaaaaaaacatgcagatcctgttggccaacccgcgtggtttttgtgccggggtagaccgcgctatcagcattgttgaaaacgcg
ctggccatttacggcgcaccgatatatgtccgtcacgaagtggtacataaccgctatgtggtcgatagcttgcgtgagcgtggggctatcttta
ttgagcagattagcgaagtaccggacggcgcgatcctgattttctccgcacacggtgtttctcaggcggtacgtaacgaagcaaaaagtcgc
gatttgacggtgtttgatgccacctgtccgctggtgaccaaagtgcacatggaagtcgcccgcgccagtcgccgtggcgaagaatctattct
catcggtcacgccgggcacccggaagtggaagggacaatgggccagtacagtaacccggaaggggggaatgtatctggtcgaatcgccg
gacgatgtgtggaaactgacggtcaaaaacgaagagaagctctcctttatgacccagaccacgctgtcggtggatgacacgtctgatgtgat

Figure 65D cgacgcgctgcgtaaacgcttcccgaaaattgtcggtccgcgcaaagatgacatctgctacgccacgactaaccgtcaggaagcggtacg
cgccctggcagaacaggcggaagttgtgttggtggtcggttcgaaaaactcctccaactccaaccgtctggcggagctggcccagcgtat
gggcaaacgcgcgtttttgattgacgatgcgaaagacatccaggaagagtgggtgaaagaggttaaatgcgtcggcgtgactgcgggcg
catcggctccggatattctggtgcagaatgtggtggcacgtttgcagcagctgggcggtggtgaagccattccgctggaaggccgtgaaga
aaacattgttttcgaagtgccgaaagagctgcgtgtcgatattcgtgaagtcgattaatttgcattagctattacgtaattcgtatagtcggtacca
ctaaggaggaaaaaaacatgactgccgacaacaatagtatgccgcatggtgcagtatctagttacgccaaattagtgcaaaaccaaacacc
tgaagacattttggaagagtttcctgaaattattccattacaacaaagacctaatacccgatctagtgagacgtcaaatgacgaaagcggaga
aacatgtttttctggtcatgatgaggagcaaattaagttaatgaatgaaaattgtattgttttggattgggacgataatgctattggtgccggcacc
aagaaagtttgtcatttaatggaaaatattgaaaagggtttactacatcgtgcattctccgtctttattttcaatgaacaaggtgaattacttttacaa
caaagagccactgaaaaaataactttccctgatctttggactaacacatgctgctctcatccactatgtattgatgacgaattaggtttgaagggt
aagctagacgataagattaagggcgctattactgcggcggtgagaaaactagatcatgaattaggtattccagaagatgaaactaagacaa
ggggtaagtttcactttttaaacagaatccattacatggcaccaagcaatgaaccgtggggtgaacatgaaattgattacatcctattttataag
atcaacgctaaagaaaacttgactgtcaacccaaacgtcaatgaagttagagacttcaaatgggtttcaccaaatgatttgaaaactatgtttgc
tgacccaagttacaagtttacgccttggtttaagattatttgcgagaattacttattcaactggtgggagcaattagatgacctttctgaagtggaa
aatgacaggcaaattcatagaatgctataagaattcctcgagcaccaccaccaccaccactgagatccggctgctaacaaagcccgaaag
gaagctgagttggctgctgccaccgctgagcaataactagcataaccccttggggcctctaaacgggtcttgaggggtttt (SEQ ID NO:79)

Figure 71A tggcgaatgggacgcgccctgtagcggcgcattaagcgcggcgggtgtggtggttacgcgcagcgtgaccgctacacttgccagcgccc
tagcgcccgctcctttcgctttcttcccttcctttctcgccacgttcgccggctttccccgtcaagctctaaatcgggggctccctttagggttcc
gatttagtgctttacggcacctcgaccccaaaaaacttgattagggtgatggttcacgtagtgggccatcgccctgatagacggtttttcgccc
tttgacgttggagtccacgttctttaatagtggactcttgttccaaactggaacaacactcaaccctatctcggtctattcttttgatttataagggat
tttgccgatttcggcctattggttaaaaaatgagctgatttaacaaaaatttaacgcgaattttaacaaaatattaacgtttacaatttcaggtggca
cttttcggggaaatgtgcgcggaacccctatttgtttatttttctaaatacattcaaatatgtatccgctcatgaattaattcttagaaaaactcatcg
agcatcaaatgaaactgcaatttattcatatcaggattatcaataccatatttttgaaaaagccgtttctgtaatgaaggagaaaactcaccgag
gcagttccataggatggcaagatcctggtatcggtctgcgattccgactcgtccaacatcaatacaacctattaatttcccctcgtcaaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatattttcacctgaatcaggatattcttc
taatacctggaatgctgttttcccggggatcgcagtggtgagtaaccatgcatcatcaggagtacggataaaatgcttgatggtcggaagag
gcataaattccgtcagccagtttagtctgaccatctcatctgtaacatcattggcaacgctacctttgccatgtttcagaaacaactctggcgcat
cgggcttcccatacaatcgatagattgtcgcacctgattgcccgacattatcgcgagcccatttatacccatataaatcagcatccatgttggaa
tttaatcgcggcctagagcaagacgtttcccgttgaatatggctcataacaccccttgtattactgtttatgtaagcagacagttttattgttcatga
ccaaaatcccttaacgtgagttttcgttccactgagcgtcagaccccgtagaaaagatcaaaggatcttcttgagatcctttttttctgcgcgtaa
tctgctgcttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacgaggga
gcttccagggggaaacgcctggtatctttatagtcctgtcgggtttcgccacctctgacttgagcgtcgatttttgtgatgctcgtcaggggggg
cggagcctatggaaaaacgccagcaacgcggcctttttacggttcctggccttttgctggccttttgctcacatgttctttcctgcgttatcccct
gattctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcatatatggtgcactctcagtacaatctgctct
gatgccgcatagttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttcaccgtcatc
accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
ggggatttctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttcgttaataca
gatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcacccgtggggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcggcgacgatagtcatgccccgcgcccaccggaaggagctgactgggttgaag
gctctcaagggcatcggtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgccagggtggtttttcttttcacca
gtgagacgggcaacagctgattgcccttcaccgcctggccctgagagagttgcagcaagcggtccacgctggtttgccccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttggcaaccagcatcgcagtgggaacgatgccctcattcagc
atttgcatggtttgttgaaaaccggacatggcactccagtcgccttcccgttccgctatcggctgaatttgattgcgagtgagatatttatgccag
ccagccagacgcagacgcgccgagacagaacttaatgggcccgctaacagcgcgatttgctggtgacccaatgcgaccagatgctccac

Figure 71B gcccagtcgcgtaccgtcttcatgggagaaaataatactgttgatgggtgtctggtcagagacatcaagaaataacgccggaacattagtgc
aggcagcttccacagcaatggcatcctggtcatccagcggatagttaatgatcagcccactgacgcgttgcgcgagaagattgtgcaccgc
cgctttacaggcttcgacgccgcttcgttctaccatcgacaccaccacgctggcacccagttgatcggcgcgagatttaatcgccgcgacaa
tttgcgacggcgcgtgcagggccagactggaggtggcaacgccaatcagcaacgactgtttgcccgccagttgttgtgccacgcggttgg
gaatgtaattcagctccgccatcgccgcttccactttttcccgcgttttcgcagaaacgtggctggcctggttcaccacgcgggaaacggtct
gataagagacaccggcatactctgcgacatcgtataacgttactggtttcacattcaccaccctgaattgactctcttccgggcgctatcatgc
cataccgcgaaaggttttgcgccattcgatggtgtccgggatctcgacgctctcccttatgcgactcctgcattaggaagcagcccagtagta
ggttgaggccgttgagcaccgccgccgcaaggaatggtgcatgcaaggagatggcgcccaacagtcccccggccacggggcctgcca
ccatacccacgccgaaacaagcgctcatgagcccgaagtggcgagcccgatcttccccatcggtgatgtcggcgatataggcgccagca
accgcacctgtggcgccggtgatgccggccacgatgcgtccggcgtagaggatcgagatctcgatcccgcgaaattaatacgactcacta
taggggaattgtgagcggataacaattcccctctagaaataattttgtttaactttaagaaggagatatacatatggaagctcgtcgttctgcga
actacgaacctaacagctgggactatgattacctgctgtcctccgacacggacgagtccatcgaagtatacaaagacaaagcgaaaaagct
ggaagccgaagttcgtcgcgagattaataacgaaaaagcagaatttctgaccctgctggaactgattgacaacgtccagcgcctgggcctg
ggttaccgtttcgagtctgatatccgtggtgcgctggatcgcttcgtttcctccggcggcttcgatgcggtaaccaagacttccctgcacggta
cggcactgtctttccgtctgctgcgtcaacacggttttgaggtttctcaggaagcgttcagcggcttcaaagaccaaaacggcaacttcctgg
agaacctgaaggaagatatcaaagctatcctgagcctgtacgaggccagcttcctggctctggaaggcgaaaacatcctggacgaggcga
aggttttcgcaatctctcatctgaaagaactgtctgaagaaaagatcggtaaagagctggcagaacaggtgaaccatgcactggaactgcca
ctgcatcgccgtactcagcgtctggaagcagtatggtctatcgaggcctaccgtaaaaaggaggacgcgaatcaggttctgctggagctgg
caattctggattacaacatgatccagtctgtataccagcgtgatctgcgtgaaacgtcccgttggtggcgtcgtgtgggtctggcgaccaaac
tgcactttgctcgtgaccgcctgattgagagcttctactgggccgtgggtgtagcattcgaaccgcaatactccgactgccgtaactccgtcg
caaaaatgttttctttcgtaaccattatcgacgatatctacgatgtatacggcaccctggacgaactggagctgtttactgatgcagttgagcgtt
gggacgtaaacgccatcaacgacctgccggattacatgaaactgtgctttctggctctgtataacactattaacgaaatcgcctacgacaacc
tgaaagataaaggtgagaacatcctgccgtatctgaccaaagcctgggctgacctgtgcaacgctttcctgcaagaagccaagtggctgta
caacaaatctactccgacctttgacgactacttcggcaacgcatggaaatcctcttctggcccgctgcaactggtgttcgcttacttcgctgtcg
tgcagaacattaaaaaggaagagatcgaaaacctgcaaaaataccatgacaccatctctcgtccttcccatatcttccgtctgtgcaatgacct
ggctagcgcgtctgcggaaattgcgcgtggtgaaaccgcaaatagcgtttcttgttacatgcgcactaaaggtatctccgaagaactggcta
ccgaaagcgtgatgaatctgatcgatgaaacctggaaaaagatgaacaaggaaaaactgggtggtagcctgttcgcgaaaccgttcgtgg
aaaccgcgatcaacctggcacgtcaatctcactgcacttatcataacggcgacgcgcatacctctccggatgagctgacccgcaaacgcgt
tctgtctgtaatcactgaaccgattctgccgtttgaacgctaaggatccgaattcgagctccgtcgacaagcttgcggccgcactcgagcacc
accaccaccaccactgagatccggctgctaacaaagcccgaaaggaagctgagttggctgctgccaccgctgagcaataactagcataac
cccttggggcctctaaacgggtcttgaggggttttttgctgaaaggaggaactatatccggat (SEQ ID NO:108)

Figure 72A tggcgaatgggacgcgccctgtagcggcgcattaagcgcggcgggtgtggtggttacgcgcagcgtgaccgctacacttgccagcgccc
tagcgcccgctcctttcgctttcttcccttcctttctcgccacgttcgccggctttccccgtcaagctctaaatcgggggctccctttagggttcc
gatttagtgctttacggcacctcgaccccaaaaaacttgattagggtgatggttcacgtagtgggccatcgccctgatagacggtttttcgccc
tttgacgttggagtccacgttctttaatagtggactcttgttccaaactggaacaacactcaaccctatctcggtctattcttttgatttataagggat
tttgccgatttcggcctattggttaaaaaatgagctgatttaacaaaaatttaacgcgaattttaacaaaatattaacgtttacaatttcaggtggca
cttttcggggaaatgtgcgcggaacccctatttgtttatttttctaaatacattcaaatatgtatccgctcatgaattaattcttagaaaaactcatcg
agcatcaaatgaaactgcaatttattcatatcaggattatcaataccatatttttgaaaaagccgtttctgtaatgaaggagaaaactcaccgag
gcagttccataggatggcaagatcctggtatcggtctgcgattccgactcgtccaacatcaatacaacctattaatttcccctcgtcaaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatattttcacctgaatcaggatattcttc
taatacctggaatgctgttttcccggggatcgcagtggtgagtaaccatgcatcatcaggagtacggataaaatgcttgatggtcggaagag
gcataaattccgtcagccagtttagtctgaccatctcatctgtaacatcattggcaacgctacctttgccatgtttcagaaacaactctggcgcat
cgggcttcccatacaatcgatagattgtcgcacctgattgcccgacattatcgcgagcccatttatacccatataaatcagcatccatgttggaa
tttaatcgcggcctagagcaagacgtttcccgttgaatatggctcataacaccccttgtattactgtttatgtaagcagacagttttattgttcatga
ccaaaatcccttaacgtgagttttcgttccactgagcgtcagaccccgtagaaaagatcaaaggatcttcttgagatcctttttttctgcgcgtaa
tctgctgcttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacgaggga
gcttccagggggaaacgcctggtatctttatagtcctgtcgggtttcgccacctctgacttgagcgtcgatttttgtgatgctcgtcagggggg
cggagcctatggaaaaacgccagcaacgcggcctttttacggttcctggccttttgctggccttttgctcacatgttctttcctgcgttatcccct
gattctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcatatatggtgcactctcagtacaatctgctct
gatgccgcatagttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttcaccgtcatc
accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
ggggatttctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttcgttaataca
gatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcacccgtggggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcggcgacgatagtcatgccccgcgcccaccggaaggagctgactgggttgaag
gctctcaagggcatcggtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgccagggtggtttttcttttcacca
gtgagacgggcaacagctgattgcccttcaccgcctggccctgagagagttgcagcaagcggtccacgctggtttgccccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttggcaaccagcatcgcagtgggaacgatgccctcattcagc
atttgcatggtttgttgaaaaccggacatggcactccagtcgccttcccgttccgctatcggctgaatttgattgcgagtgagatatttatgccag
ccagccagacgcagacgcgccgagacagaacttaatgggcccgctaacagcgcgatttgctggtgacccaatgcgaccagatgctccac

Figure 72B gcccagtcgcgtaccgtcttcatgggagaaaataatactgttgatgggtgtctggtcagagacatcaagaaataacgccggaacattagtgc
aggcagcttccacagcaatggcatcctggtcatccagcggatagttaatgatcagcccactgacgcgttgcgcgagaagattgtgcaccgc
cgctttacaggcttcgacgccgcttcgttctaccatcgacaccaccacgctggcacccagttgatcggcgcgagatttaatcgccgcgacaa
tttgcgacggcgcgtgcagggccagactggaggtggcaacgccaatcagcaacgactgtttgcccgccagttgttgtgccacgcggttgg
gaatgtaattcagctccgccatcgccgcttccactttttcccgcgttttcgcagaaacgtggctggcctggttcaccacgcgggaaacggtct
gataagagacaccggcatactctgcgacatcgtataacgttactggtttcacattcaccaccctgaattgactctcttccgggcgctatcatgc
cataccgcgaaaggttttgcgccattcgatggtgtccgggatctcgacgctctcccttatgcgactcctgcattaggaagcagcccagtagta
ggttgaggccgttgagcaccgccgccgcaaggaatggtgcatgcaaggagatggcgcccaacagtcccccggccacggggcctgcca
ccatacccacgccgaaacaagcgctcatgagcccgaagtggcgagcccgatcttccccatcggtgatgtcggcgatataggcgccagca
accgcacctgtggcgccggtgatgccggccacgatgcgtccggcgtagaggatcgagatctcgatcccgcgaaattaatacgactcacta
taggggaattgtgagcggataacaattcccctctagaaataattttgtttaactttaagaaggagatatacatatggaagctcgtcgttctgcga
actacgaacctaacagctgggactatgattacctgctgtcctccgacacggacgagtccatcgaagtatacaaagacaaagcgaaaaagct
ggaagccgaagttcgtcgcgagattaataacgaaaaagcagaatttctgaccctgctggaactgattgacaacgtccagcgcctgggcctg
ggttaccgtttcgagtctgatatccgtggtgcgctggatcgcttcgtttcctccggcggcttcgatgcggtaaccaagacttccctgcacggta
cggcactgtctttccgtctgctgcgtcaacacggttttgaggtttctcaggaagcgttcagcggcttcaaagaccaaaacggcaacttcctgg
agaacctgaaggaagatatcaaagctatcctgagcctgtacgaggccagcttcctggctctggaaggcgaaaacatcctggacgaggcga
aggttttcgcaatctctcatctgaaagaactgtctgaagaaaagatcggtaaagagctggcagaacaggtgaaccatgcactggaactgcca
ctgcatcgccgtactcagcgtctggaagcagtatggtctatcgaggcctaccgtaaaaaggaggacgcgaatcaggttctgctggagctgg
caattctggattacaacatgatccagtctgtataccagcgtgatctgcgtgaaacgtcccgttggtggcgtcgtgtgggtctggcgaccaaac
tgcactttgctcgtgaccgcctgattgagagcttctactgggccgtgggtgtagcattcgaaccgcaatactccgactgccgtaactccgtcg
caaaaatgttttctttcgtaaccattatcgacgatatctacgatgtatacggcaccctggacgaactggagctgtttactgatgcagttgagcgtt
gggacgtaaacgccatcaacgacctgccggattacatgaaactgtgctttctggctctgtataacactattaacgaaatcgcctacgacaacc
tgaaagataaaggtgagaacatcctgccgtatctgaccaaagcctgggctgacctgtgcaacgctttcctgcaagaagccaagtggctgta
caacaaatctactccgacctttgacgactacttcggcaacgcatggaaatcctcttctggcccgctgcaactggtgttcgcttacttcgctgtcg
tgcagaacattaaaaaggaagagatcgaaaacctgcaaaaataccatgacaccatctctcgtccttcccatatcttccgtctgtgcaatgacct
ggctagcgcgtctgcggaaattgcgcgtggtgaaaccgcaaatagcgtttcttgttacatgcgcactaaaggtatctccgaagaactggcta
ccgaaagcgtgatgaatctgatcgatgaaacctggaaaaagatgaacaaggaaaaactgggtggtagcctgttcgcgaaaccgttcgtgg
aaaccgcgatcaacctggcacgtcaatctcactgcacttatcataacggcgacgcgcatacctctccggatgagctgacccgcaaacgcgt
tctgtctgtaatcactgaaccgattctgccgtttgaacgctaaggatccattcgcccttaggaggtaaaaaaacatgagttttgatattgccaaat
acccgaccctggcactggtcgactccacccaggagttacgactgttgccgaaagagagtttaccgaaactctgcgacgaactgcgccgct
atttactcgacagcgtgagccgttccagcgggcacttcgcctccgggctgggcacggtcgaactgaccgtggcgctgcactatgtctacaa
caccccgtttgaccaattgatttgggatgtggggcatcaggcttatccgcataaaattttgaccggacgccgcgacaaaatcggcaccatcc
gtcagaaaggcggtctgcacccgttcccgtggcgcggcgaaagcgaatatgacgtattaagcgtcgggcattcatcaacctccatcagtgc
cggaattggtattgcggttgctgccgaaaaagaaggcaaaaatcgccgcaccgtctgtgtcattggcgatggcgcgattaccgcaggcatg
gcgtttgaagcgatgaatcacgcgggcgatatccgtcctgatatgctggtgattctcaacgacaatgaaatgtcgatttccgaaaatgtcggc
gcgctcaacaaccatctggcacagctgctttccggtaagctttactcttcactgcgcgaaggcgggaaaaaagttttctctggcgtgccgcca
attaaagagctgctcaaacgcaccgaagaacatattaaaggcatggtagtgcctggcacgttgtttgaagagctgggctttaactacatcggc
ccggtggacggtcacgatgtgctggggcttatcaccacgctaaagaacatgcgcgacctgaaaggcccgcagttcctgcatatcatgacca
aaaaaggtcgtggttatgaaccggcagaaaaagacccgatcactttccacgccgtgcctaaatttgatccctccagcggttgtttgccgaaaa
gtagcggcggtttgccgagctattcaaaaatctttggcgactggttgtgcgaaacggcagcgaaagacaacaagctgatggcgattactcc
ggcgatgcgtgaaggttccggcatggtcgagttttcacgtaaattcccggatcgctacttcgacgtggcaattgccgagcaacacgcggtga
cctttgctgcgggtctggcgattggtgggtacaaacccattgtcgcgatttactccactttcctgcaacgcgcctatgatcaggtgctgcatga
cgtggcgattcaaaagcttccggtcctgttcgccatcgaccgcgcgggcattgttggtgctgacggtcaaacccatcagggtgcttttgatct
ctcttacctgcgctgcataccggaaatggtcattatgaccccgagcgatgaaaacgaatgtcgccagatgctctataccggctatcactataa

Figure 72C cgatggcccgtcagcggtgcgctacccgcgtggcaacgcggtcggcgtggaactgacgccgctggaaaaactaccaattggcaaaggc
attgtgaagcgtcgtggcgagaaactggcgatccttaactttggtacgctgatgccagaagcggcgaaagtcgccgaatcgctgaacgcca
cgctggtcgatatgcgttttgtgaaaccgcttgatgaagcgttaattctggaaatggccgccagccatgaagcgctggtcaccgtagaagaa
aacgccattatgggcggcgcaggcagcggcgtgaacgaagtgctgatggcccatcgtaaaccagtacccgtgctgaacattggcctgcc
ggacttctttattccgcaaggaactcaggaagaaatgcgcgccgaactcggcctcgatgccgctggtatggaagccaaaatcaaggcctg
gctggcataactgcatcgcccttaggaggtaaaaaaaaatgactgccgacaacaatagtatgccccatggtgcagtatctagttacgccaaa
ttagtgcaaaaccaaacacctgaagacattttggaagagtttcctgaaattattccattacaacaaagacctaatacccgatctagtgagacgt
caaatgacgaaagcggagaaacatgtttttctggtcatgatgaggagcaaattaagttaatgaatgaaaattgtattgttttggattgggacgat
aatgctattggtgccggtaccaagaaagtttgtcatttaatggaaaatattgaaaagggtttactacatcgtgcattctccgtctttattttcaatga
acaaggtgaattacttttacaacaaagagccactgaaaaaataactttccctgatctttggactaacacatgctgctctcatccactatgtattgat
gacgaattaggtttgaagggtaagctagacgataagattaagggcgctattactgcggcggtgagaaaactagatcatgaattaggtattcca
gaagatgaaactaagacaaggggtaagtttcactttttaaacagaatccattacatggcaccaagcaatgaaccatggggtgaacatgaaatt
gattacatcctattttataagatcaacgctaaagaaaacttgactgtcaacccaaacgtcaatgaagttagagacttcaaatgggtttcaccaaa
tgatttgaaaactatgtttgctgacccaagttacaagtttacgccttggtttaagattatttgcgagaattacttattcaactggtgggagcaattag
atgacctttctgaagtggaaaatgacaggcaaattcatagaatgctataacaacgcgtcctgcagctggcggccgcactcgagcaccacca
ccaccaccactgagatccggctgctaacaaagcccgaaaggaagctgagttggctgctgccaccgctgagcaataactagcataacccct
tggggcctctaaacgggtcttgaggggttttttgctgaaaggaggaactatatccggat (SEQ ID NO:109)

Figure 73A tggcgaatgggacgcgccctgtagcggcgcattaagcgcggcgggtgtggtggttacgcgcagcgtgaccgctacacttgccagcgccc
tagcgcccgctcctttcgctttcttcccttcctttctcgccacgttcgccggctttccccgtcaagctctaaatcgggggctccctttagggttcc
gatttagtgctttacggcacctcgaccccaaaaaacttgattagggtgatggttcacgtagtgggccatcgccctgatagacggtttttcgccc
tttgacgttggagtccacgttctttaatagtggactcttgttccaaactggaacaacactcaaccctatctcggtctattcttttgatttataagggat
tttgccgatttcggcctattggttaaaaaatgagctgatttaacaaaaatttaacgcgaattttaacaaaatattaacgtttacaatttcaggtggca
cttttcggggaaatgtgcgcggaacccctatttgtttatttttctaaatacattcaaatatgtatccgctcatgaattaattcttagaaaaactcatcg
agcatcaaatgaaactgcaatttattcatatcaggattatcaataccatatttttgaaaaagccgtttctgtaatgaaggagaaaactcaccgag
gcagttccataggatggcaagatcctggtatcggtctgcgattccgactcgtccaacatcaatacaacctattaatttcccctcgtcaaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatattttcacctgaatcaggatattcttc
taatacctggaatgctgttttcccggggatcgcagtggtgagtaaccatgcatcatcaggagtacggataaaatgcttgatggtcggaagag
gcataaattccgtcagccagtttagtctgaccatctcatctgtaacatcattggcaacgctacctttgccatgtttcagaaacaactctggcgcat
cgggcttcccatacaatcgatagattgtcgcacctgattgcccgacattatcgcgagcccatttatacccatataaatcagcatccatgttggaa
tttaatcgcggcctagagcaagacgtttcccgttgaatatggctcataacaccccttgtattactgtttatgtaagcagacagttttattgttcatga
ccaaaatcccttaacgtgagttttcgttccactgagcgtcagaccccgtagaaaagatcaaaggatcttcttgagatcctttttttctgcgcgtaa
tctgctgcttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacgaggga
gcttccagggggaaacgcctggtatctttatagtcctgtcgggtttcgccacctctgacttgagcgtcgatttttgtgatgctcgtcagggggg
cggagcctatggaaaaacgccagcaacgcggcctttttacggttcctggccttttgctggccttttgctcacatgttctttcctgcgttatcccct
gattctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcatatatggtgcactctcagtacaatctgctct
gatgccgcatagttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttcaccgtcatc
accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
ggggatttctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttcgttaataca
gatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcacccgtggggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcggcgacgatagtcatgccccgcgcccaccggaaggagctgactgggttgaag
gctctcaagggcatcggtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgccagggtggtttttcttttcacca
gtgagacgggcaacagctgattgcccttcaccgcctggccctgagagagttgcagcaagcggtccacgctggtttgccccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttggcaaccagcatcgcagtgggaacgatgccctcattcagc
atttgcatggtttgttgaaaaccggacatggcactccagtcgccttcccgttccgctatcggctgaatttgattgcgagtgagatatttatgccag
ccagccagacgcagacgcgccgagacagaacttaatgggcccgctaacagcgcgatttgctggtgacccaatgcgaccagatgctccac

Figure 73B gcccagtcgcgtaccgtcttcatgggagaaaataatactgttgatgggtgtctggtcagagacatcaagaaataacgccggaacattagtgc
aggcagcttccacagcaatggcatcctggtcatccagcggatagttaatgatcagcccactgacgcgttgcgcgagaagattgtgcaccgc
cgctttacaggcttcgacgccgcttcgttctaccatcgacaccaccacgctggcacccagttgatcggcgcgagatttaatcgccgcgacaa
tttgcgacggcgcgtgcagggccagactggaggtggcaacgccaatcagcaacgactgtttgcccgccagttgttgtgccacgcggttgg
gaatgtaattcagctccgccatcgccgcttccactttttcccgcgttttcgcagaaacgtggctggcctggttcaccacgcgggaaacggtct
gataagagacaccggcatactctgcgacatcgtataacgttactggtttcacattcaccaccctgaattgactctcttccgggcgctatcatgc
cataccgcgaaaggttttgcgccattcgatggtgtccgggatctcgacgctctcccttatgcgactcctgcattaggaagcagcccagtagta
ggttgaggccgttgagcaccgccgccgcaaggaatggtgcatgcaaggagatggcgcccaacagtcccccggccacggggcctgcca
ccatacccacgccgaaacaagcgctcatgagcccgaagtggcgagcccgatcttccccatcggtgatgtcggcgatataggcgccagca
accgcacctgtggcgccggtgatgccggccacgatgcgtccggcgtagaggatcgagatctcgatcccgcgaaattaatacgactcacta
taggggaattgtgagcggataacaattcccctctagaaataattttgtttaactttaagaaggagatatacatatggaagctcgtcgttctgcga
actacgaacctaacagctgggactatgattacctgctgtcctccgacacggacgagtccatcgaagtatacaaagacaaagcgaaaaagct
ggaagccgaagttcgtcgcgagattaataacgaaaaagcagaatttctgaccctgctggaactgattgacaacgtccagcgcctgggcctg
ggttaccgtttcgagtctgatatccgtggtgcgctggatcgcttcgtttcctccggcggcttcgatgcggtaaccaagacttccctgcacggta
cggcactgtctttccgtctgctgcgtcaacacggttttgaggtttctcaggaagcgttcagcggcttcaaagaccaaaacggcaacttcctgg
agaacctgaaggaagatatcaaagctatcctgagcctgtacgaggccagcttcctggctctggaaggcgaaaacatcctggacgaggcga
aggttttcgcaatctctcatctgaaagaactgtctgaagaaaagatcggtaaagagctggcagaacaggtgaaccatgcactggaactgcca
ctgcatcgccgtactcagcgtctggaagcagtatggtctatcgaggcctaccgtaaaaaggaggacgcgaatcaggttctgctggagctgg
caattctggattacaacatgatccagtctgtataccagcgtgatctgcgtgaaacgtcccgttggtggcgtcgtgtgggtctggcgaccaaac
tgcactttgctcgtgaccgcctgattgagagcttctactgggccgtgggtgtagcattcgaaccgcaatactccgactgccgtaactccgtcg
caaaaatgttttctttcgtaaccattatcgacgatatctacgatgtatacggcaccctggacgaactggagctgtttactgatgcagttgagcgtt
gggacgtaaacgccatcaacgacctgccggattacatgaaactgtgctttctggctctgtataacactattaacgaaatcgcctacgacaacc
tgaaagataaaggtgagaacatcctgccgtatctgaccaaagcctgggctgacctgtgcaacgctttcctgcaagaagccaagtggctgta
caacaaatctactccgacctttgacgactacttcggcaacgcatggaaatcctcttctggcccgctgcaactggtgttcgcttacttcgctgtcg
tgcagaacattaaaaaggaagagatcgaaaacctgcaaaaataccatgacaccatctctcgtccttcccatatcttccgtctgtgcaatgacct
ggctagcgcgtctgcggaaattgcgcgtggtgaaaccgcaaatagcgtttcttgttacatgcgcactaaaggtatctccgaagaactggcta
ccgaaagcgtgatgaatctgatcgatgaaacctggaaaaagatgaacaaggaaaaactgggtggtagcctgttcgcgaaaccgttcgtgg
aaaccgcgatcaacctggcacgtcaatctcactgcacttatcataacggcgacgcgcatacctctccggatgagctgacccgcaaacgcgt
tctgtctgtaatcactgaaccgattctgccgtttgaacgctaaggatccattcgcccttaggaggtaaaaaaacatgagttttgatattgccaaat
acccgaccctggcactggtcgactccacccaggagttacgactgttgccgaaagagagtttaccgaaactctgcgacgaactgcgccgct
atttactcgacagcgtgagccgttccagcgggcacttcgcctccgggctgggcacggtcgaactgaccgtggcgctgcactatgtctacaa
caccccgtttgaccaattgatttgggatgtggggcatcaggcttatccgcataaaattttgaccggacgccgcgacaaaatcggcaccatcc
gtcagaaaggcggtctgcacccgttcccgtggcgcggcgaaagcgaatatgacgtattaagcgtcgggcattcatcaacctccatcagtgc
cggaattggtattgcggttgctgccgaaaaagaaggcaaaaatcgccgcaccgtctgtgtcattggcgatggcgcgattaccgcaggcatg
gcgtttgaagcgatgaatcacgcgggcgatatccgtcctgatatgctggtgattctcaacgacaatgaaatgtcgatttccgaaaatgtcggc
gcgctcaacaaccatctggcacagctgctttccggtaagctttactcttcactgcgcgaaggcgggaaaaaagttttctctggcgtgccgcca
attaaagagctgctcaaacgcaccgaagaacatattaaaggcatggtagtgcctggcacgttgtttgaagagctgggctttaactacatcggc
ccggtggacggtcacgatgtgctggggcttatcaccacgctaaagaacatgcgcgacctgaaaggcccgcagttcctgcatatcatgacca
aaaaaggtcgtggttatgaaccggcagaaaaagacccgatcactttccacgccgtgcctaaatttgatccctccagcggttgtttgccgaaaa
gtagcggcggtttgccgagctattcaaaaatctttggcgactggttgtgcgaaacggcagcgaaagacaacaagctgatggcgattactcc
ggcgatgcgtgaaggttccggcatggtcgagttttcacgtaaattcccggatcgctacttcgacgtggcaattgccgagcaacacgcggtga
cctttgctgcgggtctggcgattggtgggtacaaacccattgtcgcgatttactccactttcctgcaacgcgcctatgatcaggtgctgcatga
cgtggcgattcaaaagcttccggtcctgttcgccatcgaccgcgcgggcattgttggtgctgacggtcaaacccatcagggtgcttttgatct
ctcttacctgcgctgcataccggaaatggtcattatgaccccgagcgatgaaacgaatgtcgccagatgctctataccggctatcactataa

Figure 73C cgatggcccgtcagcggtgcgctacccgcgtggcaacgcggtcggcgtggaactgacgccgctggaaaaactaccaattggcaaaggc
attgtgaagcgtcgtggcgagaaactggcgatccttaactttggtacgctgatgccagaagcggcgaaagtcgccgaatcgctgaacgcca
cgctggtcgatatgcgttttgtgaaaccgcttgatgaagcgttaattctggaaatggccgccagccatgaagcgctggtcaccgtagaagaa
aacgccattatgggcggcgcaggcagcggcgtgaacgaagtgctgatggcccatcgtaaaccagtacccgtgctgaacattggcctgcc
ggacttctttattccgcaaggaactcaggaagaaatgcgcgccgaactcggcctcgatgccgctggtatggaagccaaaatcaaggcctg
gctggcataactgcatcgcccttaggaggtaaaaaaaaatgactgccgacaacaatagtatgccccatggtgcagtatctagttacgccaaa
ttagtgcaaaaccaaacacctgaagacattttggaagagtttcctgaaattattccattacaacaaagacctaatacccgatctagtgagacgt
caaatgacgaaagcggagaaacatgtttttctggtcatgatgaggagcaaattaagttaatgaatgaaaattgtattgttttggattgggacgat
aatgctattggtgccggtaccaagaaagtttgtcatttaatggaaaatattgaaaagggtttactacatcgtgcattctccgtctttattttcaatga
acaaggtgaattacttttacaacaaagagccactgaaaaaataactttccctgatctttggactaacacatgctgctctcatccactatgtattgat
gacgaattaggtttgaagggtaagctagacgataagattaagggcgctattactgcggcggtgagaaaactagatcatgaattaggtattcca
gaagatgaaactaagacaaggggtaagtttcactttttaaacagaatccattacatggcaccaagcaatgaaccatggggtgaacatgaaatt
gattacatcctattttataagatcaacgctaaagaaaacttgactgtcaacccaaacgtcaatgaagttagagacttcaaatgggtttcaccaaa
tgatttgaaaactatgtttgctgacccaagttacaagtttacgccttggtttaagattatttgcgagaattacttattcaactggtgggagcaattag
atgacctttctgaagtggaaaatgacaggcaaattcatagaatgctataacaacgcgtcctgcagctggcggccgcactcgagcaccacca
ccaccaccactgagatccggctgctaacaaagcccgaaaggaagctgagttggctgctgccaccgctgagcaataactagcataacccct
tggggcctctaaacgggtcttgaggggttttttgctgaaaggaggaactatatccggat (SEQ ID NO:110)

Figure 74

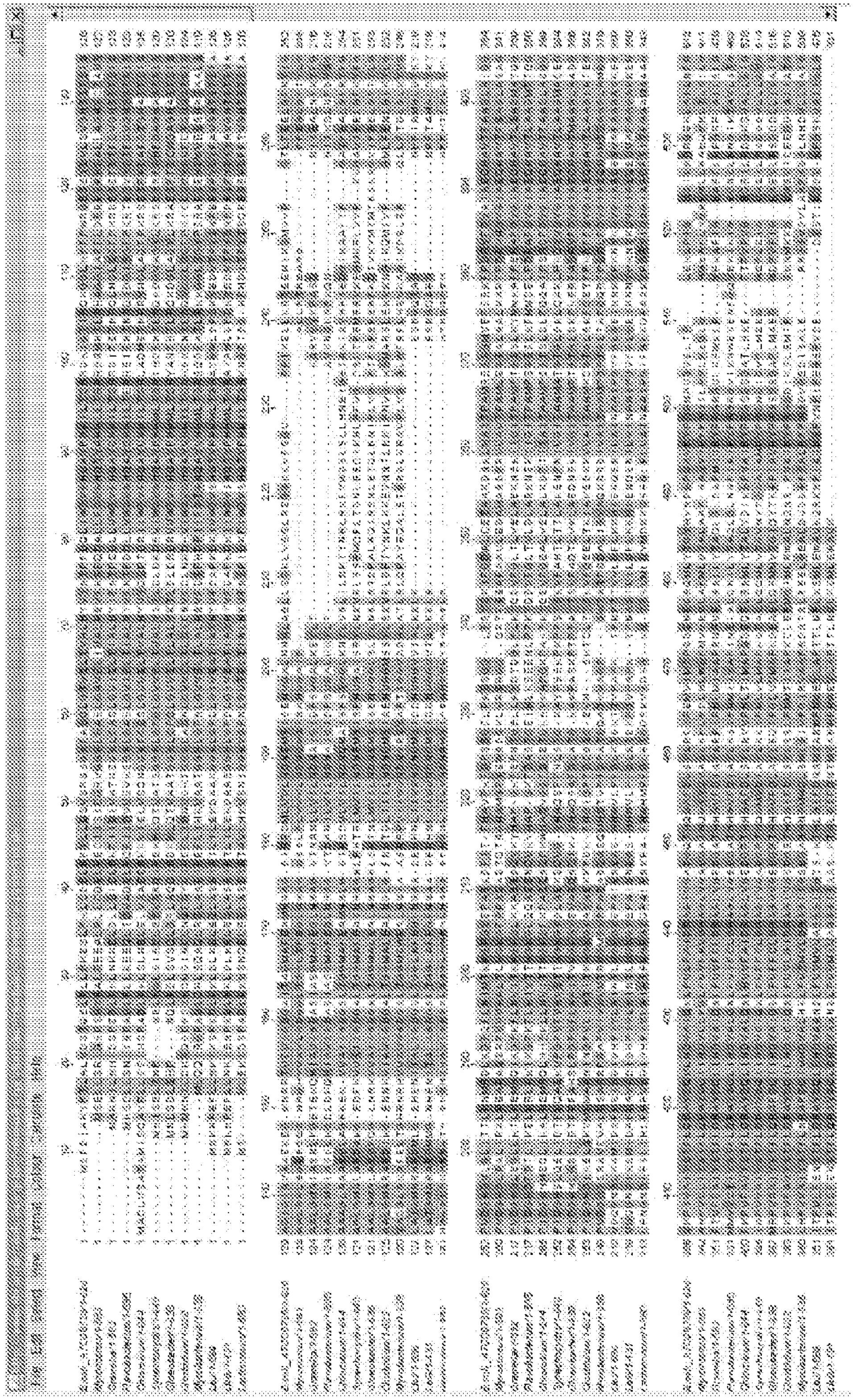

SEQ ID NO:194
SEQ ID NO:195
SEQ ID NO:196
SEQ ID NO:197
SEQ ID NO:198
SEQ ID NO:199
SEQ ID NO:200
SEQ ID NO:201
SEQ ID NO:202
SEQ ID NO:203
SEQ ID NO:204
SEQ ID NO:205

SEQ ID NO:194
SEQ ID NO:195
SEQ ID NO:196
SEQ ID NO:197
SEQ ID NO:198
SEQ ID NO:199
SEQ ID NO:200
SEQ ID NO:201
SEQ ID NO:202
SEQ ID NO:203
SEQ ID NO:204
SEQ ID NO:205

SEQ ID NO:194
SEQ ID NO:195
SEQ ID NO:196
SEQ ID NO:197
SEQ ID NO:198
SEQ ID NO:199
SEQ ID NO:200
SEQ ID NO:201
SEQ ID NO:202
SEQ ID NO:203
SEQ ID NO:204
SEQ ID NO:205

SEQ ID NO:194
SEQ ID NO:195
SEQ ID NO:196
SEQ ID NO:197
SEQ ID NO:198
SEQ ID NO:199
SEQ ID NO:200
SEQ ID NO:201
SEQ ID NO:202
SEQ ID NO:203
SEQ ID NO:204

Figure 75A 1-
ttcttgaagacgaaagggcctcgtgatacgcctatttttataggttaatgtcatgataataatggtttcttagacgtcaggtggcacttttcgggga
aatgtgcgcggaacccctatttgtttatttttctaaatacattcaaatatgtatccgctcatgagacaataaccctgataaatgcttcaataatattg
aaaaaggaagagtatgagtattcaacatttccgtgtcgcccttattcccttttttgcggcattttgccttcctgtttttgctcacccagaaacgctgg
tgaaagtaaaagatgctgaagatcagttgggtgcacgagtgggttacatcgaactggatctcaacagcggtaagatccttgagagttttcgcc
ccgaagaacgttttccaatgatgagcacttttaaagttctgctatgtggcgcggtattatcccgtgttgacgccgggcaagagcaactcggtc
gccgcatacactattctcagaatgacttggttgagtactcaccagtcacagaaaagcatcttacggatggcatgacagtaagagaattatgca
gtgctgccataaccatgagtgataacactgcggccaacttacttctgacaacgatcggaggaccgaaggagctaaccgcttttttgcacaac
atgggggatcatgtaactcgccttgatcgttgggaaccggagctgaatgaagccataccaaacgacgagcgtgacaccacgatgcctgca
gcaatggcaacaacgttgcgcaaactattaactggcgaactacttactctagcttcccggcaacaattaatagactggatggaggcggataa
agttgcaggaccacttctgcgctcggcccttccggctggctggtttattgctgataaatctggagccggtgagcgtgggtctcgcggtatcatt
gcagcactggggccagatggtaagccctcccgtatcgtagttatctacacgacggggagtcaggcaactatggatgaacgaaatagacag
atcgctgagataggtgcctcactgattaagcattggtaactgtcagaccaagtttactcatatatactttagattgatttaaaacttcatttttaattta
aaaggatctaggtgaagatcctttttgataatctcatgaccaaaatcccttaacgtgagttttcgttccactgagcgtcagaccccgtagaaaag
atcaaaggatcttcttgagatcctttttttctgcgcgtaatctgctgcttgcaaacaaaaaaaccaccgctaccagcggtggtttgtttgccggat
caagagctaccaactctttttccgaaggtaactggcttcagcagagcgcagataccaaatactgtccttctagtgtagccgtagttaggccac
cacttcaagaactctgtagcaccgcctacatacctcgctctgctaatcctgttaccagtggctgctgccagtggcgataagtcgtgtcttaccg
ggttggactcaagacgatagttaccggataaggcgcagcggtcgggctgaacggggggttcgtgcacacagcccagcttggagcgaac
gacctacaccgaactgagatacctacagcgtgagctatgagaaagcgccacgcttcccgaagggagaaaggcggacaggtatccggtaa
gcggcagggtcggaacaggagagcgcacgagggagcttccagggggaaacgcctggtatctttatagtcctgtcgggtttcgccacctct
gacttgagcgtcgatttttgtgatgctcgtcaggggggcggagcctatggaaaaacgccagcaacgcggcctttttacggttcctggcctttt
gctggccttttgctcacatgttctttcctgcgttatcccctgattctgtggataaccgtattaccgcctttgagtgagctgataccgctcgccgcag
ccgaacgaccgagcgcagcgagtcagtgagcgaggaagcggaagagcgcctgatgcggtattttctccttacgcatctgtgcggtatttca
caccgcatatatggtgcactctcagtacaatctgctctgatgccgcatagttaagccagtatacactccgctatcgctacgtgactgggtcatg
gctgcgccccgacacccgccaacacccgctgacgcgccctgacgggcttgtctgctcccggcatccgcttacagacaagctgtgaccgtc
tccgggagctgcatgtgtcagaggttttcaccgtcatcaccgaaacgcgcgaggcagctgcggtaaagctcatcagcgtggtcgtgaagc
gattcacagatgtctgcctgttcatccgcgtccagctcgttgagtttctccagaagcgttaatgtctggcttctgataaagcgggccatgttaag
ggcggtttttttcctgtttggtcactgatgcctccgtgtaagggggatttctgttcatgggggtaatgataccgatgaaacgagagaggatgctc
acgatacgggttactgatgatgaacatgcccggttactggaacgttgtgagggtaaacaactggcggtatggatgcggcgggaccagaga
aaaatcactcagggtcaatgccagcgcttcgttaatacagatgtaggtgttccacagggtagccagcagcatcctgcgatgcagatccgga
acataatggtgcagggcgctgacttccgcgtttccagactttacgaaacacggaaaccgaagaccattcatgttgttgctcaggtcgcagac
gttttgcagcagcagtcgcttcacgttcgctcgcgtatcggtgattcattctgctaaccagtaaggcaaccccgccagcctagccgggtcctc
aacgacaggagcacgatcatgcgcacccgtggccaggacccaacgctgcccgagatgcgccgcgtgcggctgctggagatggcggac
gcgatggatatgttctgccaagggttggtttgcgcattcacagttctccgcaagaattgattggctccaattcttggagtggtgaatccgttagc
gaggtgccgccggcttccattcaggtcgaggtggcccggctccatgcaccgcgacgcaacgcggggaggcagacaaggtatagggcg
gcgcctacaatccatgccaacccgttccatgtgctcgccgaggcggcataaatcgccgtgacgatcagcggtccagtgatcgaagttaggc
tggtaagagccgcgagcgatccttgaagctgtccctgatggtcgtcatctacctgcctggacagcatggcctgcaacgcgggcatcccgat
gccgccggaagcgagaagaatcataatggggaaggccatccagcctcgcgtcgcgaacgccagcaagacgtagcccagcgcgtcggc
cgccatgccggcgataatggcctgcttctcgccgaaacgtttggtggcgggaccagtgacgaaggcttgagcgagggcgtgcaagattcc
gaataccgcaagcgacaggccgatcatcgtcgcgctccagcgaaagcggtcctcgccgaaaatgacccagagcgctgccggcacctgt
cctacgagttgcatgataaagaagacagtcataagtgcggcgacgatagtcatgccccgcgcccaccggaaggagctgactgggttgaa
ggctctcaagggcatcggtcgagatcccggtgcctaatgagtgagctaacttacattaattgcgttgcgctcactgcccgctttccagtcggg
aaacctgtcgtgccagctgcattaatgaatcggccaacgcgcggggagaggcggtttgcgtattgggcgccagggtggtttttcttttcacca
gtgagacgggcaacagctgattgcccttcaccgcctggccctgagagagttgcagcaagcggtccacgctggtttgccccagcaggcga

Figure 75B aaatcctgtttgatggtggttaacggcgggatataacatgagctgtcttcggtatcgtcgtatccca
ctaccgagatatccgcaccaacgcgcagcccggactcggtaatggcgcgcattgcgcccagc
gccatctgatcgttggcaaccagcatcgcagtgggaacgatgccctcattcagcatttgcatggtt
tgttgaaaaccggacatggcactccagtcgccttcccgttccgctatcggctgaatttgattgcga
gtgagatatttatgccagccagccagacgcagacgcgccgagacagaacttaatgggcccgc
taacagcgcgatttgctggtgacccaatgcgaccagatgctccacgcccagtcgcgtaccgtctt
catgggagaaaataatactgttgatgggtgtctggtcagagacatcaagaaataacgccggaa
cattagtgcaggcagcttccacagcaatggcatcctggtcatccagcggatagttaatgatcagc
ccactgacgcgttgcgcgagaagattgtgcaccgccgctttacaggcttcgacgccgcttcgttct
accatcgacaccaccacgctggcacccagttgatcggcgcgagatttaatcgccgcgacaattt
gcgacggcgcgtgcagggccagactggaggtggcaacgccaatcagcaacgactgtttgcc
cgccagttgttgtgccacgcggttgggaatgtaattcagctccgccatcgccgcttccactttttccc
gcgttttcgcagaaacgtggctggcctggttcaccacgcgggaaacggtctgataagagacac
cggcatactctgcgacatcgtataacgttactggtttcacattcaccaccctgaattgactctcttcc
gggcgctatcatgccataccgcgaaaggttttgcgccattcgatggtgtccgggatctcgacgct
ctcccttatgcgactcctgcattaggaagcagcccagtagtaggttgaggccgttgagcaccgc
cgccgcaaggaatggtgcatgcaaggagatggcgcccaacagtcccccggccacggggcct
gccaccatacccacgccgaaacaagcgctcatgagcccgaagtggcgagcccgatcttccc
catcggtgatgtcggcgatataggcgccagcaaccgcacctgtggcgccggtgatgccggcc
acgatgcgtccggcgtagaggatcgagatctcgatcccgcgaaattaatacgactcactatag
gggaattgtgagcggataacaattcccctctagaaataattttgtttaactttaagaaggagatata
ccatgggccatcatcatcatcatcatcatcatcatcacagcagcggccatatcgaaggtcgtcat
atgactgccgacaacaatagtatgccccatggtgcagtatctagttacgccaaattagtgcaaa
accaaacacctgaagacattttggaagagtttcctgaaattattccattacaacaaagacctaat
acccgatctagtgagacgtcaaatgacgaaagcggagaaacatgtttttctggtcatgatgagg
agcaaattaagttaatgaatgaaaattgtattgttttggattgggacgataatgctattggtgccggt
accaagaaagtttgtcatttaatggaaaatattgaaaagggtttactacatcgtgcattctccgtctt
tattttcaatgaacaaggtgaattacttttacaacaaagagccactgaaaaaataactttccctgat
ctttggactaacacatgctgctctcatccactatgtattgatgacgaattaggtttgaagggtaagct
agacgataagattaagggcgctattactgcggcggtgagaaaactagatcatgaattaggtatt
ccagaagatgaaactaagacaaggggtaagtttcactttttaaacagaatccattacatggcac
caagcaatgaaccatggggtgaacatgaaattgattacatcctattttataagatcaacgctaaa
gaaaacttgactgtcaacccaaacgtcaatgaagttagagacttcaaatgggtttcaccaaatg
atttgaaaactatgtttgctgacccaagttacaagtttacgccttggtttaagattatttgcgagaatt
acttattcaactggtgggagcaattagatgacctttctgaagtggaaaatgacaggcaaattcat
agaatgctataacaacgcgtcggatccggctgctaacaaagcccgaaaggaagctgagttgg
ctgctgccaccgctgagcaataactagcataaccccttggggcctctaaacgggtcttgagggg
ttttttgctgaaaggaggaactatatccggatatcccgcaagaggcccggcagtaccggcataa
ccaagcctatgcctacagcatccagggtgacggtgccgaggatgacgatgagcgcattgttag
atttcatacacggtgcctgactgcgttagcaatttaactgtgataaactaccgcattaaagcttatc
gatgataagctgtcaaacatgagaa (SEQ ID NO:192)

GB-CMP-GI1.X-yidi construct design

Frag A fused to Frag B via overlap PCR to yield GB-CMP-GI1.X-yidi

B

Figure 101 panel A
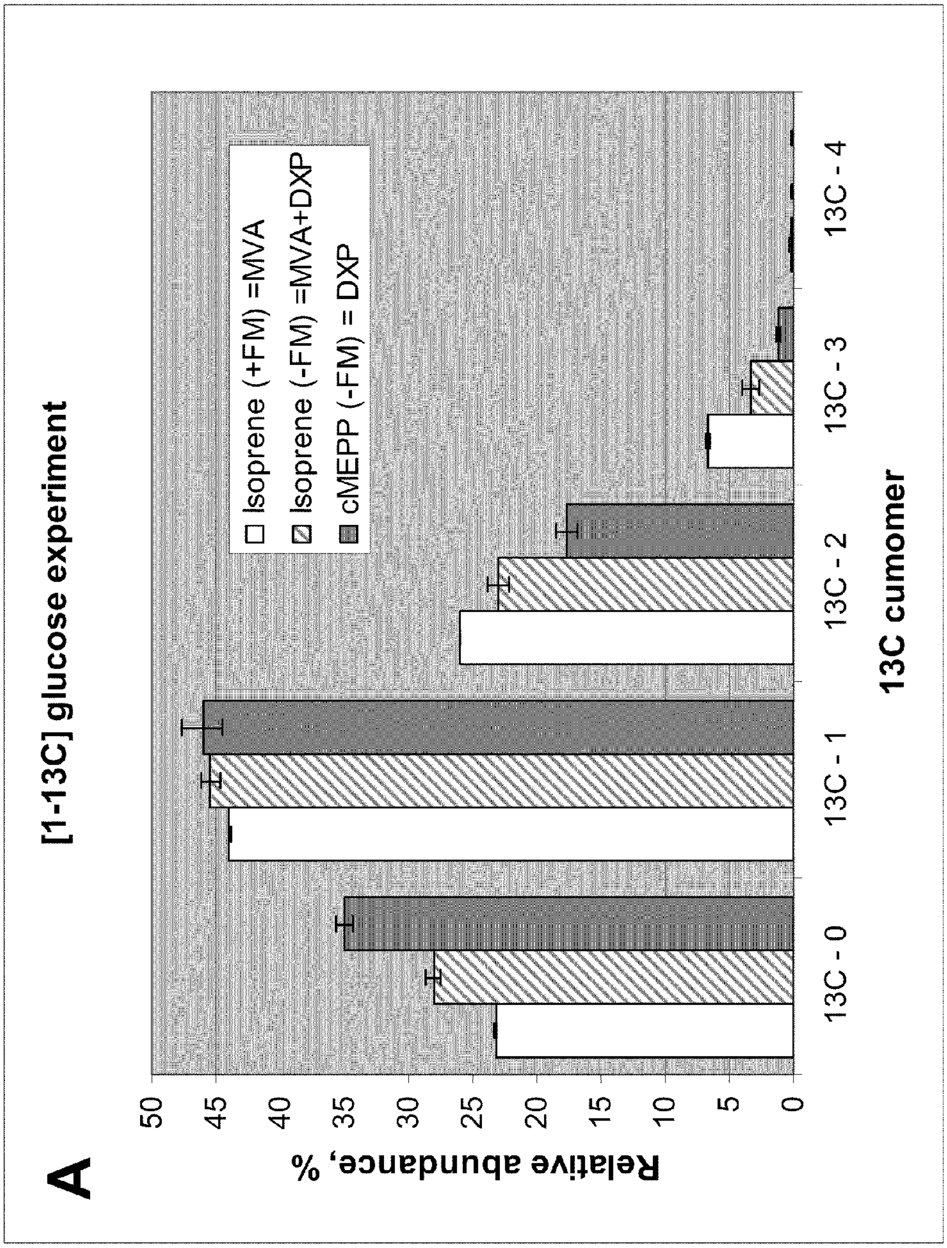

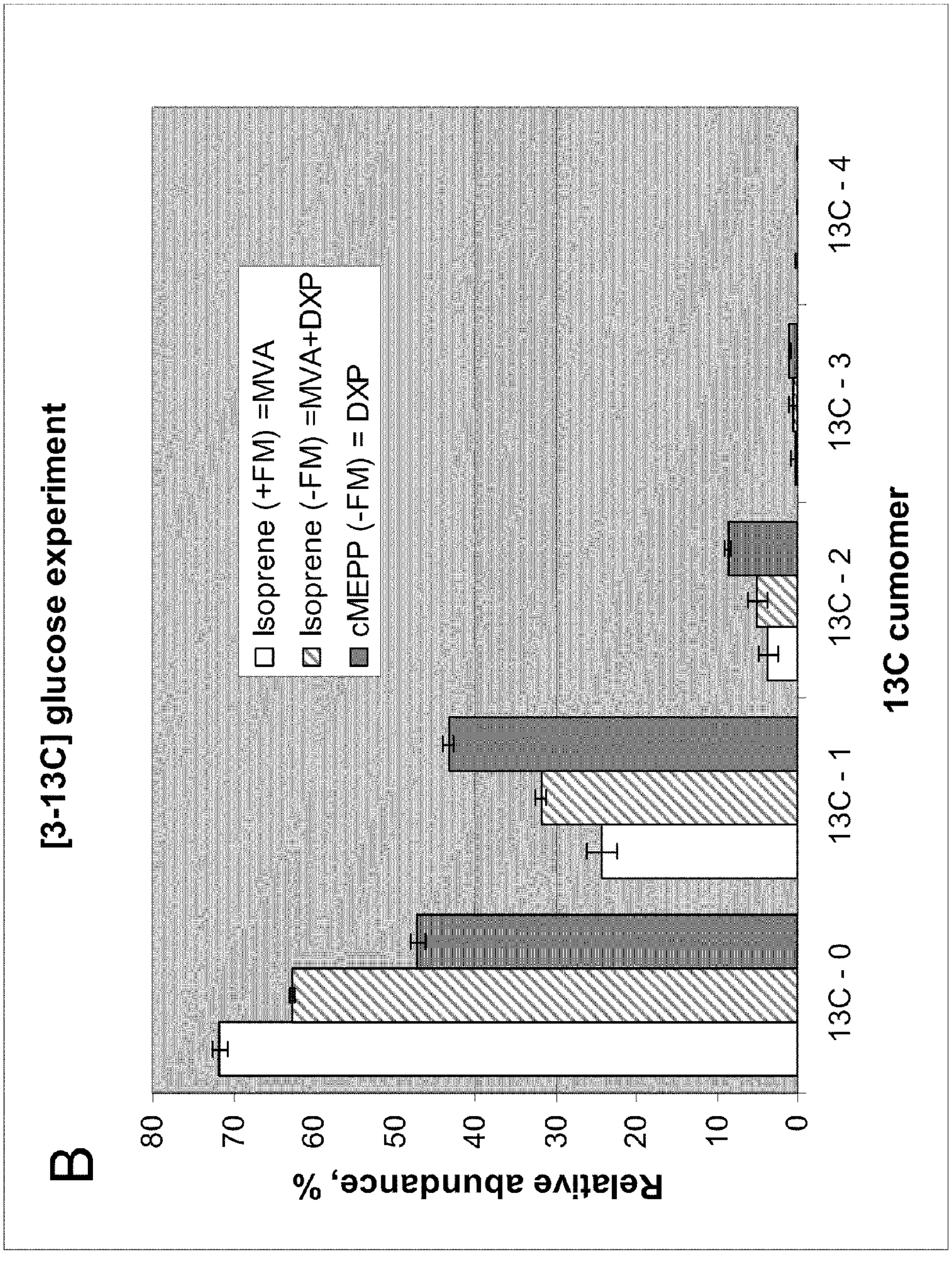
Figure 101 panel B

Step 1: Grow strain on 1-$^{13}$C-glucose and collect BioIsoprene on small carbon filter.

Step 2: Desorb BioIsoprene with CDCl$_3$ into an NMR tube and record $^{13}$C NMR spectrum

Figure 107

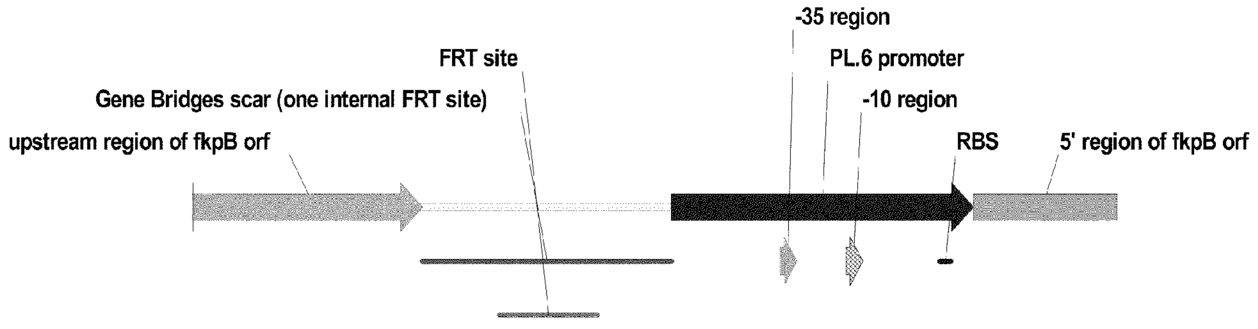

PL.6 fkpB locus
323 bp agattgctgcgaaatcgtaggccggataaggcgtttacgccgcatccggcaaaaatccttaaatataa
gagcaaacctgcaattaaccctcactaaagggcggccgcgaagttcctattctctagaaagtat
aggaacttcctcgagccctatagtgagtcgtattaagataaccatctgcggtgataaattatctctgg
cggtgttgacataaataccactggcggtgatactgagcacatcagcaggacgcactgcaaaggagg
taaaaacatgtctgaatctgtacagagcaatagcgccgtcctggtgcacttcacgct

SEQ ID NO:193

Figure 108 (con't)
D
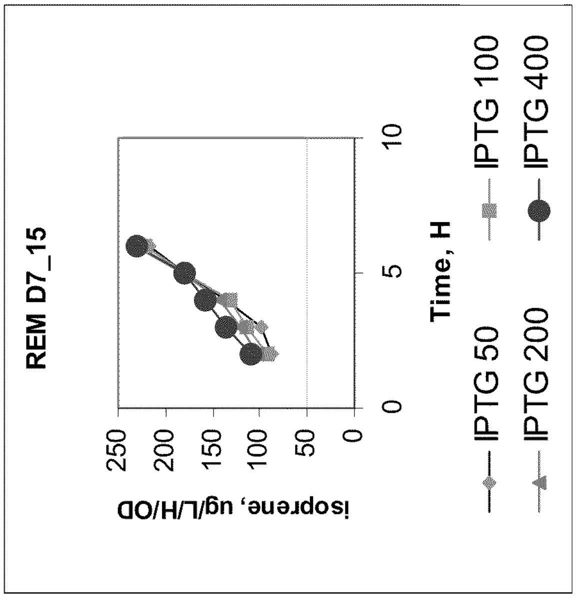

SEQUENCE LISTING

```
<160> NUMBER OF SEQ ID NOS: 205

<210> SEQ ID NO 1
<211> LENGTH: 1692
<212> TYPE: DNA
<213> ORGANISM: Artificial Sequence
<220> FEATURE:
<223> OTHER INFORMATION: Synthetic Construct

<400> SEQUENCE: 1
```

atgtgtgcga cctcttctca atttactcag attaccgagc ataattcccg tcgttccgca 60
aactatcagc caaacctgtg gaatttcgaa ttcctgcaat ccctggagaa cgacctgaaa 120
gtggaaaagc tggaggagaa agcgaccaaa ctggaggaag aagttcgctg catgatcaac 180
cgtgtagaca cccagccgct gtccctgctg gagctgatcg acgatgtgca gcgcctgggt 240
ctgacctaca aatttgaaaa agacatcatt aaagccctgg aaaacatcgt actgctggac 300
gaaaacaaaa agaacaaatc tgacctgcac gcaaccgctc tgtctttccg tctgctgcgt 360
cagcacggtt tcgaggtttc tcaggatgtt tttgagcgtt tcaaggataa agaaggtggt 420
ttcagcggtg aactgaaagg tgacgtccaa ggcctgctga gcctgtatga agcgtcttac 480
ctgggtttcg agggtgagaa cctgctggag gaggcgcgta ccttttccat cacccacctg 540
aagaacaacc tgaaagaagg cattaatacc aaggttgcag aacaagtgag ccacgccctg 600
gaactgccat atcaccagcg tctgcaccgt ctggaggcac gttggttcct ggataaatac 660
gaaccgaaag aaccgcatca ccagctgctg ctggagctgg cgaagctgga ttttaacatg 720
gtacagaccc tgcaccagaa agagctgcaa gatctgtccc gctggtggac cgagatgggc 780
ctggctagca aactggattt tgtacgcgac cgcctgatgg aagtttattt ctgggcactg 840
ggtatggcgc cagacccgca gtttggtgaa tgtcgcaaag ctgttactaa aatgtttggt 900
ctggtgacga tcatcgatga cgtgtatgac gtttatggca ctctggacga actgcaactg 960
ttcaccgatg ctgtagagcg ctgggacgtt aacgctatta acaccctgcc ggactatatg 1020
aaactgtgtt tcctggcact gtacaacacc gttaacgaca cgtcctattc tattctgaaa 1080
gagaaaggtc ataacaacct gtcctatctg acgaaaagct ggcgtgaact gtgcaaagcc 1140
tttctgcaag aggcgaaatg gtccaacaac aaaattatcc cggctttctc caagtacctg 1200
gaaaacgcca gcgtttcctc ctccggtgta gcgctgctgg cgccgtctta cttttccgta 1260
tgccagcagc aggaagacat ctccgaccac gcgctgcgtt ccctgaccga cttccatggt 1320
ctggtgcgtt ctagctgcgt tatcttccgc ctgtgcaacg atctggccac ctctgcggcg 1380
gagctggaac gtggcgagac taccaattct atcattagct acatgcacga aaacgatggt 1440
accagcgagg aacaggcccg cgaagaactg cgtaaactga tcgacgccga atggaaaaag 1500
atgaatcgtg aacgcgttag cgactccacc ctgctgccta aagcgttcat ggaaatcgca 1560
gttaacatgg cacgtgtttc ccactgcacc taccagtatg gcgatggtct gggtcgccca 1620
gactacgcga ctgaaaaccg catcaaactg ctgctgattg accctttccc gattaaccag 1680
ctgatgtatg tc 1692

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 2
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gtttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagcgccgct gagaaaaagc gaagcggcac tgctctttaa 300
caatttatca gacaatctgt gtgggcactc gaccggaatt atcgattaac tttattatta 360

```
aaaattaaag aggtatatat taatgtatcg attaaataag gaggaataaa ccatgtgtgc    420
gacctcttct caatttactc agattaccga gcataattcc cgtcgttccg caaactatca    480
gccaaacctg tggaatttcg aattcctgca atccctggag aacgacctga aagtggaaaa    540
gctggaggag aaagcgacca aactggagga agaagttcgc tgcatgatca accgtgtaga    600
cacccagccg ctgtccctgc tggagctgat cgacgatgtg cagcgcctgg gtctgaccta    660
caaatttgaa aaagacatca ttaaagccct ggaaaacatc gtactgctgg acgaaaacaa    720
aaagaacaaa tctgacctgc acgcaaccgc tctgtctttc cgtctgctgc gtcagcacgg    780
tttcgaggtt tctcaggatg tttttgagcg tttcaaggat aaagaaggtg gtttcagcgg    840
tgaactgaaa ggtgacgtcc aaggcctgct gagcctgtat gaagcgtctt acctgggttt    900
cgagggtgag aacctgctgg aggaggcgcg taccttttcc atcacccacc tgaagaacaa    960
cctgaaagaa ggcattaata ccaaggttgc agaacaagtg agccacgccc tggaactgcc   1020
atatcaccag cgtctgcacc gtctggaggc acgttggttc ctggataaat acgaaccgaa   1080
agaaccgcat caccagctgc tgctggagct ggcgaagctg gattttaaca tggtacagac   1140
cctgcaccag aaagagctgc aagatctgtc ccgctggtgg accgagatgg gcctggctag   1200
caaactggat tttgtacgcg accgcctgat ggaagtttat ttctgggcac tgggtatggc   1260
gccagacccg cagtttggtg aatgtcgcaa agctgttact aaaatgtttg gtctggtgac   1320
gatcatcgat gacgtgtatg acgtttatgg cactctggac gaactgcaac tgttcaccga   1380
tgctgtagag cgctgggacg ttaacgctat taacaccctg ccggactata tgaaactgtg   1440
tttcctggca ctgtacaaca ccgttaacga cacgtcctat tctattctga aagagaaagg   1500
tcataacaac ctgtcctatc tgacgaaaag ctggcgtgaa ctgtgcaaag cctttctgca   1560
agaggcgaaa tggtccaaca acaaaattat cccggctttc tccaagtacc tggaaaacgc   1620
cagcgtttcc tcctccggtg tagcgctgct ggcgccgtct tacttttccg tatgccagca   1680
gcaggaagac atctccgacc acgcgctgcg ttccctgacc gacttccatg gtctggtgcg   1740
ttctagctgc gttatcttcc gcctgtgcaa cgatctggcc acctctgcgg cggagctgga   1800
acgtggcgag actaccaatt ctatcattag ctacatgcac gaaaacgatg gtaccagcga   1860
ggaacaggcc cgcgaagaac tgcgtaaact gatcgacgcc gaatggaaaa agatgaatcg   1920
tgaacgcgtt agcgactcca ccctgctgcc taaagcgttc atggaaatcg cagttaacat   1980
ggcacgtgtt tcccactgca cctaccagta tggcgatggt ctgggtcgcc cagactacgc   2040
gactgaaaac cgcatcaaac tgctgctgat tgaccctttc ccgattaacc agctgatgta   2100
tgtctaactg cagctggtac catatgggaa ttcgaagctt tctagaacaa aaactcatct   2160
cagaagagga tctgaatagc gccgtcgacc atcatcatca tcatcattga gtttaaacgg   2220
tctccagctt ggctgttttg gcggatgaga gaagattttc agcctgatac agattaaatc   2280
agaacgcaga agcggtctga taaaacagaa tttgcctggc ggcagtagcg cggtggtccc   2340
acctgacccc atgccgaact cagaagtgaa acgccgtagc gccgatggta gtgtggggtc   2400
tccccatgcg agagtaggga actgccaggc atcaaataaa acgaaaggct cagtcgaaag   2460
actgggcctt tcgttttatc tgttgtttgt cggtgaacgc tctcctgagt aggacaaatc   2520
cgccgggagc ggatttgaac gttgcgaagc aacggcccgg agggtggcgg gcaggacgcc   2580
cgccataaac tgccaggcat caaattaagc agaaggccat cctgacggat ggcctttttg   2640
cgtttctaca aactcttttt gtttattttt ctaaatacat tcaaatatgt atccgctcat   2700
gagacaataa ccctgataaa tgcttcaata atattgaaaa aggaagagta tgagtattca   2760
```

acatttccgt gtcgccctta ttcccttttt tgcggcattt tgccttcctg tttttgctca 2820
cccagaaacg ctggtgaaag taaaagatgc tgaagatcag ttgggtgcac gagtgggtta 2880
catcgaactg gatctcaaca gcggtaagat ccttgagagt tttcgccccg aagaacgttt 2940
tccaatgatg agcactttta aagttctgct atgtggcgcg gtattatccc gtgttgacgc 3000
cgggcaagag caactcggtc gccgcataca ctattctcag aatgacttgg ttgagtactc 3060
accagtcaca gaaaagcatc ttacggatgg catgacagta agagaattat gcagtgctgc 3120
cataaccatg agtgataaca ctgcggccaa cttacttctg acaacgatcg gaggaccgaa 3180
ggagctaacc gcttttttgc acaacatggg ggatcatgta actcgccttg atcgttggga 3240
accggagctg aatgaagcca taccaaacga cgagcgtgac accacgatgc ctgtagcaat 3300
ggcaacaacg ttgcgcaaac tattaactgg cgaactactt actctagctt cccggcaaca 3360
attaatagac tggatggagg cggataaagt tgcaggacca cttctgcgct cggcccttcc 3420
ggctggctgg tttattgctg ataaatctgg agccggtgag cgtgggtctc gcggtatcat 3480
tgcagcactg gggccagatg gtaagccctc ccgtatcgta gttatctaca cgacggggag 3540
tcaggcaact atggatgaac gaaatagaca gatcgctgag ataggtgcct cactgattaa 3600
gcattggtaa ctgtcagacc aagtttactc atatatactt tagattgatt taaaacttca 3660
tttttaattt aaaaggatct aggtgaagat cctttttgat aatctcatga ccaaaatccc 3720
ttaacgtgag ttttcgttcc actgagcgtc agaccccgta gaaaagatca aaggatcttc 3780
ttgagatcct ttttttctgc gcgtaatctg ctgcttgcaa acaaaaaaac caccgctacc 3840
agcggtggtt tgtttgccgg atcaagagct accaactctt tttccgaagg taactggctt 3900
cagcagagcg cagataccaa atactgtcct tctagtgtag ccgtagttag gccaccactt 3960
caagaactct gtagcaccgc ctacatacct cgctctgcta atcctgttac cagtggctgc 4020
tgccagtggc gataagtcgt gtcttaccgg gttggactca agacgatagt taccggataa 4080
ggcgcagcgg tcgggctgaa cggggggttc gtgcacacag cccagcttgg agcgaacgac 4140
ctacaccgaa ctgagatacc tacagcgtga gctatgagaa agcgccacgc ttcccgaagg 4200
gagaaaggcg gacaggtatc cggtaagcgg cagggtcgga acaggagagc gcacgaggga 4260
gcttccaggg ggaaacgcct ggtatcttta tagtcctgtc gggtttcgcc acctctgact 4320
tgagcgtcga tttttgtgat gctcgtcagg ggggcggagc ctatggaaaa acgccagcaa 4380
cgcggccttt ttacggttcc tggccttttg ctggcctttt gctcacatgt tctttcctgc 4440
gttatcccct gattctgtgg ataaccgtat taccgccttt gagtgagctg ataccgctcg 4500
ccgcagccga acgaccgagc gcagcgagtc agtgagcgag gaagcggaag agcgcctgat 4560
gcggtatttt ctccttacgc atctgtgcgg tatttcacac cgcatatggt gcactctcag 4620
tacaatctgc tctgatgccg catagttaag ccagtataca ctccgctatc gctacgtgac 4680
tgggtcatgg ctgcgccccg acacccgcca acacccgctg acgcgccctg acgggcttgt 4740
ctgctcccgg catccgctta cagacaagct gtgaccgtct ccgggagctg catgtgtcag 4800
aggttttcac cgtcatcacc gaaacgcgcg aggcagcaga tcaattcgcg cgcgaaggcg 4860
aagcggcatg catttacgtt gacaccatcg aatggtgcaa aacctttcgc ggtatggcat 4920
gatagcgccc ggaagagagt caattcaggg tggtgaatgt gaaaccagta acgttatacg 4980
atgtcgcaga gtatgccggt gtctcttatc agaccgtttc ccgcgtggtg aaccaggcca 5040
gccacgtttc tgcgaaaacg cgggaaaaag tggaagcggc gatggcggag ctgaattaca 5100
ttcccaaccg cgtggcacaa caactggcgg gcaaacagtc gttgctgatt ggcgttgcca 5160
cctccagtct ggccctgcac gcgccgtcgc aaattgtcgc ggcgattaaa tctcgcgccg 5220
atcaactggg tgccagcgtg gtggtgtcga tggtagaacg aagcggcgtc gaagcctgta 5280
aagcggcggt gcacaatctt ctcgcgcaac gcgtcagtgg gctgatcatt aactatccgc 5340
tggatgacca ggatgccatt gctgtggaag ctgcctgcac taatgttccg gcgttatttc 5400
ttgatgtctc tgaccagaca cccatcaaca gtattatttt ctcccatgaa gacggtacgc 5460
gactgggcgt ggagcatctg gtcgcattgg gtcaccagca aatcgcgctg ttagcgggcc 5520
cattaagttc tgtctcggcg cgtctgcgtc tggctggctg gcataaatat ctcactcgca 5580
atcaaattca gccgatagcg gaacgggaag gcgactggag tgccatgtcc ggttttcaac 5640
aaaccatgca aatgctgaat gagggcatcg ttcccactgc gatgctggtt gccaacgatc 5700
agatggcgct gggcgcaatg cgcgccatta ccgagtccgg gctgcgcgtt ggtgcggata 5760
tctcggtagt gggatacgac gataccgaag acagctcatg ttatatcccg ccgtcaacca 5820
ccatcaaaca ggattttcgc ctgctggggc aaaccagcgt ggaccgcttg ctgcaactct 5880
ctcagggcca ggcggtgaag ggcaatcagc tgttgcccgt ctcactggtg aaaagaaaaa 5940
ccaccctggc gcccaatacg caaaccgcct ctccccgcgc gttggccgat tcattaatgc 6000
agctggcacg acaggtttcc cgactggaaa gcgggcagtg agcgcaacgc aattaatgtg 6060
agttagcgcg aattgatctg 6080

<210> SEQ ID NO 3
<211> LENGTH: 37
<212> TYPE: DNA
<213> ORGANISM: Artificial Sequence
<220> FEATURE:
<223> OTHER INFORMATION: Synthetic Construct

<400> SEQUENCE: 3
cgtgagatca tatgtgtgcg acctcttctc aatttac 37

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4
cggtcgacgg atccctgcag ttagacatac atcagctg 38

<210> SEQ ID NO 5
<211> LENGTH: 7404
<212> TYPE: DNA
<213> ORGANISM: Artificial Sequence
<220> FEATURE:
<223> OTHER INFORMATION: Synthetic Construct

<400> SEQUENCE: 5
ttctcatgtt tgacagctta tcatcgataa gctttaatgc ggtagtttat cacagttaaa 60
ttgctaacgc agtcaggcac cgtgtatgaa atctaacaat gcgctcatcg tcatcctcgg 120
caccgtcacc ctggatgctg taggcatagg cttggttatg ccggtactgc cgggcctctt 180
gcgggatatc cggatatagt tcctcctttc agcaaaaaac ccctcaagac ccgtttagag 240
gccccaaggg gttatgctag ttattgctca gcggtggcag cagccaactc agcttccttt 300
cgggctttgt tagcagccgg atccctgcag ttagacatac atcagctggt taatcgggaa 360
agggtcaatc agcagcagtt tgatgcggtt ttcagtcgcg tagtctgggc gacccagacc 420

```
atcgccatac tggtaggtgc agtgggaaac acgtgccatg ttaactgcga tttccatgaa    480
cgctttaggc agcagggtgg agtcgctaac gcgttcacga ttcatctttt tccattcggc    540
gtcgatcagt ttacgcagtt cttcgcgggc ctgttcctcg ctggtaccat cgttttcgtg    600
catgtagcta atgatagaat tggtagtctc gccacgttcc agctccgccg cagaggtggc    660
cagatcgttg cacaggcgga agataacgca gctagaacgc accagaccat ggaagtcggt    720
cagggaacgc agcgcgtggt cggagatgtc ttcctgctgc tggcatacgg aaaagtaaga    780
cggcgccagc agcgctacac cggaggagga aacgctggcg ttttccaggt acttggagaa    840
agccgggata attttgttgt tggaccattt cgcctcttgc agaaaggctt tgcacagttc    900
acgccagctt ttcgtcagat aggacaggtt gttatgacct ttctctttca gaatagaata    960
ggacgtgtcg ttaacggtgt tgtacagtgc caggaaacac agtttcatat agtccggcag   1020
ggtgttaata gcgttaacgt cccagcgctc tacagcatcg gtgaacagtt gcagttcgtc   1080
cagagtgcca taaacgtcat acacgtcatc gatgatcgtc accagaccaa acattttagt   1140
aacagctttg cgacattcac caaactgcgg gtctggcgcc atacccagtg cccagaaata   1200
aacttccatc aggcggtcgc gtacaaaatc cagtttgcta gccaggccca tctcggtcca   1260
ccagcgggac agatcttgca gctctttctg gtgcagggtc tgtaccatgt taaaatccag   1320
cttcgccagc tccagcagca gctggtgatg cggttctttc ggttcgtatt tatccaggaa   1380
ccaacgtgcc tccagacggt gcagacgctg gtgatatggc agttccaggg cgtggctcac   1440
ttgttctgca accttggtat taatgccttc tttcaggttg ttcttcaggt gggtgatgga   1500
aaaggtacgc gcctcctcca gcaggttctc accctcgaaa cccaggtaag acgcttcata   1560
caggctcagc aggccttgga cgtcaccttt cagttcaccg ctgaaaccac cttctttatc   1620
cttgaaacgc tcaaaaacat cctgagaaac ctcgaaaccg tgctgacgca gcagacggaa   1680
agacagagcg gttgcgtgca ggtcagattt gttctttttg ttttcgtcca gcagtacgat   1740
gttttccagg gctttaatga tgtctttttc aaatttgtag gtcagaccca ggcgctgcac   1800
atcgtcgatc agctccagca gggacagcgg ctgggtgtct acacggttga tcatgcagcg   1860
aacttcttcc tccagtttgg tcgctttctc ctccagcttt tccactttca ggtcgttctc   1920
cagggattgc aggaattcga aattccacag gtttggctga tagtttgcgg aacgacggga   1980
attatgctcg gtaatctgag taaattgaga agaggtcgca cacatatgac gaccttcgat   2040
atggccgctg ctgtgatgat gatgatgatg atgatgatga tggcccatgg tatatctcct   2100
tcttaaagtt aaacaaaatt atttctagag gggaattgtt atccgctcac aattccccta   2160
tagtgagtcg tattaatttc gcgggatcga gatctcgatc ctctacgccg gacgcatcgt   2220
ggccggcatc accggcgcca caggtgcggt tgctggcgcc tatatcgccg acatcaccga   2280
tggggaagat cgggctcgcc acttcgggct catgagcgct tgtttcggcg tgggtatggt   2340
ggcaggcccc gtggccgggg gactgttggg cgccatctcc ttgcatgcac cattccttgc   2400
ggcggcggtg ctcaacggcc tcaacctact actgggctgc ttcctaatgc aggagtcgca   2460
taagggagag cgtcgagatc ccggacacca tcgaatggcg caaaaccttt cgcggtatgg   2520
catgatagcg cccggaagag agtcaattca gggtggtgaa tgtgaaacca gtaacgttat   2580
acgatgtcgc agagtatgcc ggtgtctctt atcagaccgt ttcccgcgtg gtgaaccagg   2640
ccagccacgt ttctgcgaaa acgcgggaaa aagtggaagc ggcgatggcg gagctgaatt   2700
acattcccaa ccgcgtggca caacaactgg cgggcaaaca gtcgttgctg attggcgttg   2760
ccacctccag tctggccctg cacgcgccgt cgcaaattgt cgcggcgatt aaatctcgcg   2820
```

ccgatcaact gggtgccagc gtggtggtgt cgatggtaga acgaagcggc gtcgaagcct 2880
gtaaagcggc ggtgcacaat cttctcgcgc aacgcgtcag tgggctgatc attaactatc 2940
cgctggatga ccaggatgcc attgctgtgg aagctgcctg cactaatgtt ccggcgttat 3000
ttcttgatgt ctctgaccag acacccatca acagtattat tttctcccat gaagacggta 3060
cgcgactggg cgtggagcat ctggtcgcat tgggtcacca gcaaatcgcg ctgttagcgg 3120
gcccattaag ttctgtctcg gcgcgtctgc gtctggctgg ctggcataaa tatctcactc 3180
gcaatcaaat tcagccgata gcggaacggg aaggcgactg gagtgccatg tccggttttc 3240
aacaaaccat gcaaatgctg aatgagggca tcgttcccac tgcgatgctg gttgccaacg 3300
atcagatggc gctgggcgca atgcgcgcca ttaccgagtc cgggctgcgc gttggtgcgg 3360
atatctcggt agtgggatac gacgataccg aagacagctc atgttatatc ccgccgttaa 3420
ccaccatcaa acaggatttt cgcctgctgg ggcaaaccag cgtggaccgc ttgctgcaac 3480
tctctcaggg ccaggcggtg aagggcaatc agctgttgcc cgtctcactg gtgaaaagaa 3540
aaaccaccct ggcgcccaat acgcaaaccg cctctccccg cgcgttggcc gattcattaa 3600
tgcagctggc acgacaggtt tcccgactgg aaagcgggca gtgagcgcaa cgcaattaat 3660
gtaagttagc tcactcatta ggcaccggga tctcgaccga tgcccttgag agccttcaac 3720
ccagtcagct ccttccggtg ggcgcggggc atgactatcg tcgccgcact tatgactgtc 3780
ttctttatca tgcaactcgt aggacaggtg ccggcagcgc tctgggtcat tttcggcgag 3840
gaccgctttc gctggagcgc gacgatgatc ggcctgtcgc ttgcggtatt cggaatcttg 3900
cacgccctcg ctcaagcctt cgtcactggt cccgccacca aacgtttcgg cgagaagcag 3960
gccattatcg ccggcatggc ggccgacgcg ctgggctacg tcttgctggc gttcgcgacg 4020
cgaggctgga tggccttccc cattatgatt cttctcgctt ccggcggcat cgggatgccc 4080
gcgttgcagg ccatgctgtc caggcaggta gatgacgacc atcagggaca gcttcaagga 4140
tcgctcgcgg ctcttaccag cctaacttcg atcactggac cgctgatcgt cacggcgatt 4200
tatgccgcct cggcgagcac atggaacggg ttggcatgga ttgtaggcgc cgccctatac 4260
cttgtctgcc tccccgcgtt gcgtcgcggt gcatggagcc gggccacctc gacctgaatg 4320
gaagccggcg gcacctcgct aacggattca ccactccaag aattggagcc aatcaattct 4380
tgcggagaac tgtgaatgcg caaaccaacc cttggcagaa catatccatc gcgtccgcca 4440
tctccagcag ccgcacgcgg cgcatctcgg gcagcgttgg gtcctggcca cgggtgcgca 4500
tgatcgtgct cctgtcgttg aggacccggc taggctggcg gggttgcctt actggttagc 4560
agaatgaatc accgatacgc gagcgaacgt gaagcgactg ctgctgcaaa acgtctgcga 4620
cctgagcaac aacatgaatg gtcttcggtt tccgtgtttc gtaaagtctg gaaacgcgga 4680
agtcagcgcc ctgcaccatt atgttccgga tctgcatcgc aggatgctgc tggctaccct 4740
gtggaacacc tacatctgta ttaacgaagc gctggcattg accctgagtg atttttctct 4800
ggtcccgccg catccatacc gccagttgtt taccctcaca acgttccagt aaccgggcat 4860
gttcatcatc agtaacccgt atcgtgagca tcctctctcg tttcatcggt atcattaccc 4920
ccatgaacag aaatccccct tacacggagg catcagtgac caaacaggaa aaaaccgccc 4980
ttaacatggc ccgctttatc agaagccaga cattaacgct tctggagaaa ctcaacgagc 5040
tggacgcgga tgaacaggca gacatctgtg aatcgcttca cgaccacgct gatgagcttt 5100
accgcagctg cctcgcgcgt ttcggtgatg acggtgaaaa cctctgacac atgcagctcc 5160
cggagacggt cacagcttgt ctgtaagcgg atgccgggag cagacaagcc cgtcagggcg 5220

```
cgtcagcggg tgttggcggg tgtcggggcg cagccatgac ccagtcacgt agcgatagcg   5280
gagtgtatac tggcttaact atgcggcatc agagcagatt gtactgagag tgcaccatat   5340
atgcggtgtg aaataccgca cagatgcgta aggagaaaat accgcatcag gcgctcttcc   5400
gcttcctcgc tcactgactc gctgcgctcg gtcgttcggc tgcggcgagc ggtatcagct   5460
cactcaaagg cggtaatacg gttatccaca gaatcagggg ataacgcagg aaagaacatg   5520
tgagcaaaag gccagcaaaa ggccaggaac cgtaaaaagg ccgcgttgct ggcgtttttc   5580
cataggctcc gcccccctga cgagcatcac aaaaatcgac gctcaagtca gaggtggcga   5640
aacccgacag gactataaag ataccaggcg tttccccctg gaagctccct cgtgcgctct   5700
cctgttccga ccctgccgct taccggatac ctgtccgcct ttctcccttc gggaagcgtg   5760
gcgctttctc atagctcacg ctgtaggtat ctcagttcgg tgtaggtcgt tcgctccaag   5820
ctgggctgtg tgcacgaacc ccccgttcag cccgaccgct gcgccttatc cggtaactat   5880
cgtcttgagt ccaacccggt aagacacgac ttatcgccac tggcagcagc cactggtaac   5940
aggattagca gagcgaggta tgtaggcggt gctacagagt tcttgaagtg gtggcctaac   6000
tacggctaca ctagaaggac agtatttggt atctgcgctc tgctgaagcc agttaccttc   6060
ggaaaaagag ttggtagctc ttgatccggc aaacaaacca ccgctggtag cggtggtttt   6120
tttgtttgca agcagcagat tacgcgcaga aaaaaaggat ctcaagaaga tcctttgatc   6180
ttttctacgg ggtctgacgc tcagtggaac gaaaactcac gttaagggat tttggtcatg   6240
agattatcaa aaaggatctt cacctagatc cttttaaatt aaaaatgaag ttttaaatca   6300
atctaaagta tatatgagta aacttggtct gacagttacc aatgcttaat cagtgaggca   6360
cctatctcag cgatctgtct atttcgttca tccatagttg cctgactccc cgtcgtgtag   6420
ataactacga tacgggaggg cttaccatct ggccccagtg ctgcaatgat accgcgagac   6480
ccacgctcac cggctccaga tttatcagca ataaaccagc cagccggaag ggccgagcgc   6540
agaagtggtc ctgcaacttt atccgcctcc atccagtcta ttaattgttg ccgggaagct   6600
agagtaagta gttcgccagt taatagtttg cgcaacgttg ttgccattgc tgcaggcatc   6660
gtggtgtcac gctcgtcgtt tggtatggct tcattcagct ccggttccca acgatcaagg   6720
cgagttacat gatcccccat gttgtgcaaa aaagcggtta gctccttcgg tcctccgatc   6780
gttgtcagaa gtaagttggc cgcagtgtta tcactcatgg ttatggcagc actgcataat   6840
tctcttactg tcatgccatc cgtaagatgc ttttctgtga ctggtgagta ctcaaccaag   6900
tcattctgag aatagtgtat gcggcgaccg agttgctctt gcccggcgtc aacacgggat   6960
aataccgcgc cacatagcag aactttaaaa gtgctcatca ttggaaaacg ttcttcgggg   7020
cgaaaactct caaggatctt accgctgttg agatccagtt cgatgtaacc cactcgtgca   7080
cccaactgat cttcagcatc ttttactttc accagcgttt ctgggtgagc aaaaacagga   7140
aggcaaaatg ccgcaaaaaa gggaataagg gcgacacgga aatgttgaat actcatactc   7200
ttcctttttc aatattattg aagcatttat cagggttatt gtctcatgag cggatacata   7260
tttgaatgta tttagaaaaa taaacaaata ggggttccgc gcacatttcc ccgaaaagtg   7320
ccacctgacg tctaagaaac cattattatc atgacattaa cctataaaaa taggcgtatc   7380
acgaggccct ttcgtcttca agaa                                          7404
```

```
<210> SEQ ID NO 6
<211> LENGTH: 41
<212> TYPE: DNA
<213> ORGANISM: Artificial Sequence
```

<220> FEATURE:
<223> OTHER INFORMATION: Synthetic Construct

<400> SEQUENCE: 6
catatgaaag cttgtatcga ttaaataagg aggaataaac c 41

<210> SEQ ID NO 7
<211> LENGTH: 6266
<212> TYPE: DNA
<213> ORGANISM: Artificial Sequence
<220> FEATURE:
<223> OTHER INFORMATION: Synthetic Construct

<400> SEQUENCE: 7
cccgtcttac tgtcgggaat tcgcgttggc cgattcatta atgcagctgg cacgacaggt 60
ttcccgactg gaaagcgggc agtgagcgca acgcaattaa tgtgagttag ctcactcatt 120
aggcacccca ggctttacac tttatgcttc cggctcgtat gttgtgtgga attgtgagcg 180
gataacaatt tcacacagga aacagctatg accatgatta cgccaagctt gtatcgatta 240
aataaggagg aataaaccat gtgtgcgacc tcttctcaat ttactcagat taccgagcat 300
aattcccgtc gttccgcaaa ctatcagcca aacctgtgga atttcgaatt cctgcaatcc 360
ctggagaacg acctgaaagt ggaaaagctg gaggagaaag cgaccaaact ggaggaagaa 420
gttcgctgca tgatcaaccg tgtagacacc cagccgctgt ccctgctgga gctgatcgac 480
gatgtgcagc gcctgggtct gacctacaaa tttgaaaaag acatcattaa agccctggaa 540
aacatcgtac tgctggacga aaacaaaaag aacaaatctg acctgcacgc aaccgctctg 600
tctttccgtc tgctgcgtca gcacggtttc gaggtttctc aggatgtttt tgagcgtttc 660
aaggataaag aaggtggttt cagcggtgaa ctgaaaggtg acgtccaagg cctgctgagc 720
ctgtatgaag cgtcttacct gggtttcgag ggtgagaacc tgctggagga ggcgcgtacc 780
ttttccatca cccacctgaa gaacaacctg aaagaaggca ttaataccaa ggttgcagaa 840
caagtgagcc acgccctgga actgccatat caccagcgtc tgcaccgtct ggaggcacgt 900
tggttcctgg ataaatacga accgaaagaa ccgcatcacc agctgctgct ggagctggcg 960
aagctggatt ttaacatggt acagaccctg caccagaaag agctgcaaga tctgtcccgc 1020
tggtggaccg agatgggcct ggctagcaaa ctggattttg tacgcgaccg cctgatggaa 1080
gtttatttct gggcactggg tatggcgcca gacccgcagt ttggtgaatg tcgcaaagct 1140
gttactaaaa tgtttggtct ggtgacgatc atcgatgacg tgtatgacgt ttatggcact 1200
ctggacgaac tgcaactgtt caccgatgct gtagagcgct gggacgttaa cgctattaac 1260
accctgccgg actatatgaa actgtgtttc ctggcactgt acaacaccgt taacgacacg 1320
tcctattcta ttctgaaaga gaaaggtcat aacaacctgt cctatctgac gaaaagctgg 1380
cgtgaactgt gcaaagcctt tctgcaagag gcgaaatggt ccaacaacaa aattatcccg 1440
gctttctcca agtacctgga aaacgccagc gtttcctcct ccggtgtagc gctgctggcg 1500
ccgtcttact tttccgtatg ccagcagcag gaagacatct ccgaccacgc gctgcgttcc 1560
ctgaccgact tccatggtct ggtgcgttct agctgcgtta tcttccgcct gtgcaacgat 1620
ctggccacct ctgcggcgga gctggaacgt ggcgagacta ccaattctat cattagctac 1680
atgcacgaaa acgatggtac cagcgaggaa caggcccgcg aagaactgcg taaactgatc 1740
gacgccgaat ggaaaaagat gaatcgtgaa cgcgttagcg actccaccct gctgcctaaa 1800
gcgttcatgg aaatcgcagt taacatggca cgtgtttccc actgcaccta ccagtatggc 1860
gatggtctgg gtcgcccaga ctacgcgact gaaaaccgca tcaaactgct gctgattgac 1920

-continued

```
cctttcccga ttaaccagct gatgtatgtc taactgcagg tcgactctag aggatccccg   1980
ggtaccgagc tcgaattcac tggccgtcgt tttacaacgt cgtgactggg aaaaccctgg   2040
cgttacccaa cttaatcgcc ttgcagcaca tccccctttc gccagctggc gtaatagcga   2100
agaggcccgc accgatcgcc cttcccaaca gttgcgcagc ctgaatggcg aatggcgcct   2160
gatgcggtat tttctcctta cgcatctgtg cggtatttca caccgcatat ggtgcactct   2220
cagtacaatc tgctctgatg ccgcatagtt aagccagccc cgacacccgc caacacccgc   2280
tgacgagctt agtaaagccc tcgctagatt ttaatgcgga tgttgcgatt acttcgccaa   2340
ctattgcgat aacaagaaaa agccagcctt tcatgatata tctcccaatt tgtgtagggc   2400
ttattatgca cgcttaaaaa taataaaagc agacttgacc tgatagtttg gctgtgagca   2460
attatgtgct tagtgcatct aacgcttgag ttaagccgcg ccgcgaagcg gcgtcggctt   2520
gaacgaattg ttagacatta tttgccgact accttggtga tctcgccttt cacgtagtgg   2580
acaaattctt ccaactgatc tgcgcgcgag gccaagcgat cttcttcttg tccaagataa   2640
gcctgtctag cttcaagtat gacgggctga tactgggccg gcaggcgctc cattgcccag   2700
tcggcagcga catccttcgg cgcgattttg ccggttactg cgctgtacca aatgcgggac   2760
aacgtaagca ctacatttcg ctcatcgcca gcccagtcgg gcggcgagtt ccatagcgtt   2820
aaggtttcat ttagcgcctc aaatagatcc tgttcaggaa ccggatcaaa gagttcctcc   2880
gccgctggac ctaccaaggc aacgctatgt tctcttgctt ttgtcagcaa gatagccaga   2940
tcaatgtcga tcgtggctgg ctcgaagata cctgcaagaa tgtcattgcg ctgccattct   3000
ccaaattgca gttcgcgctt agctggataa cgccacggaa tgatgtcgtc gtgcacaaca   3060
atggtgactt ctacagcgcg gagaatctcg ctctctccag gggaagccga agtttccaaa   3120
aggtcgttga tcaaagctcg ccgcgttgtt tcatcaagcc ttacggtcac cgtaaccagc   3180
aaatcaatat cactgtgtgg cttcaggccg ccatccactg cggagccgta caaatgtacg   3240
gccagcaacg tcggttcgag atggcgctcg atgacgccaa ctacctctga tagttgagtc   3300
gatacttcgg cgatcaccgc ttccctcatg atgtttaact ttgttttagg gcgactgccc   3360
tgctgcgtaa catcgttgct gctccataac atcaaacatc gacccacggc gtaacgcgct   3420
tgctgcttgg atgcccgagg catagactgt accccaaaaa aacagtcata acaagccatg   3480
aaaaccgcca ctgcgccgtt accaccgctg cgttcggtca aggttctgga ccagttgcgt   3540
gagcgcatac gctacttgca ttacagctta cgaaccgaac aggcttatgt ccactgggtt   3600
cgtgccttca tccgtttcca cggtgtgcgt cacccggcaa ccttgggcag cagcgaagtc   3660
gaggcatttc tgtcctggct ggcgaacgag cgcaaggttt cggtctccac gcatcgtcag   3720
gcattggcgg ccttgctgtt cttctacggc aaggtgctgt gcacggatct gccctggctt   3780
caggagatcg gaagacctcg gccgtcgcgg cgcttgccgg tggtgctgac cccggatgaa   3840
gtggttcgca tcctcggttt tctggaaggc gagcatcgtt tgttcgccca gcttctgtat   3900
ggaacgggca tgcggatcag tgagggtttg caactgcggg tcaaggatct ggatttcgat   3960
cacggcacga tcatcgtgcg ggagggcaag ggctccaagg atcgggcctt gatgttaccc   4020
gagagcttgg cacccagcct gcgcgagcag gggaattaat tcccacgggt tttgctgccc   4080
gcaaacgggc tgttctggtg ttgctagttt gttatcagaa tcgcagatcc ggcttcagcc   4140
ggtttgccgg ctgaaagcgc tatttcttcc agaattgcca tgattttttc cccacgggag   4200
gcgtcactgg ctcccgtgtt gtcggcagct ttgattcgat aagcagcatc gcctgtttca   4260
ggctgtctat gtgtgactgt tgagctgtaa caagttgtct caggtgttca atttcatgtt   4320
```

-continued

```
ctagttgctt tgttttactg gtttcacctg ttctattagg tgttacatgc tgttcatctg   4380
ttacattgtc gatctgttca tggtgaacag ctttgaatgc accaaaaact cgtaaaagct   4440
ctgatgtatc tatctttttt acaccgtttt catctgtgca tatggacagt tttccctttg   4500
atatgtaacg gtgaacagtt gttctacttt tgtttgttag tcttgatgct tcactgatag   4560
atacaagagc cataagaacc tcagatcctt ccgtatttag ccagtatgtt ctctagtgtg   4620
gttcgttgtt tttgcgtgag ccatgagaac gaaccattga gatcatactt actttgcatg   4680
tcactcaaaa attttgcctc aaaactggtg agctgaattt ttgcagttaa agcatcgtgt   4740
agtgtttttc ttagtccgtt atgtaggtag gaatctgatg taatggttgt tggtattttg   4800
tcaccattca tttttatctg gttgttctca agttcggtta cgagatccat ttgtctatct   4860
agttcaactt ggaaaatcaa cgtatcagtc gggcggcctc gcttatcaac caccaatttc   4920
atattgctgt aagtgtttaa atctttactt attggtttca aaacccattg gttaagcctt   4980
ttaaactcat ggtagttatt ttcaagcatt aacatgaact taaattcatc aaggctaatc   5040
tctatatttg ccttgtgagt tttcttttgt gttagttctt ttaataacca ctcataaatc   5100
ctcatagagt atttgttttc aaaagactta acatgttcca gattatattt tatgaatttt   5160
tttaactgga aaagataagg caatatctct tcactaaaaa ctaattctaa tttttcgctt   5220
gagaacttgg catagtttgt ccactggaaa atctcaaagc ctttaaccaa aggattcctg   5280
atttccacag ttctcgtcat cagctctctg gttgctttag ctaatacacc ataagcattt   5340
tccctactga tgttcatcat ctgagcgtat tggttataag tgaacgatac cgtccgttct   5400
ttccttgtag ggttttcaat cgtggggttg agtagtgcca cacagcataa aattagcttg   5460
gtttcatgct ccgttaagtc atagcgacta atcgctagtt catttgcttt gaaaacaact   5520
aattcagaca tacatctcaa ttggtctagg tgattttaat cactatacca attgagatgg   5580
gctagtcaat gataattact agtccttttc ctttgagttg tgggtatctg taaattctgc   5640
tagaccttttg ctggaaaact tgtaaattct gctagaccct ctgtaaattc cgctagacct   5700
ttgtgtgttt tttttgttta tattcaagtg gttataattt atagaataaa gaaagaataa   5760
aaaaagataa aaagaataga tcccagccct gtgtataact cactacttta gtcagttccg   5820
cagtattaca aaaggatgtc gcaaacgctg tttgctcctc tacaaaacag accttaaaac   5880
cctaaaggct taagtagcac cctcgcaagc tcgggcaaat cgctgaatat tccttttgtc   5940
tccgaccatc aggcacctga gtcgctgtct ttttcgtgac attcagttcg ctgcgctcac   6000
ggctctggca gtgaatgggg gtaaatggca ctacaggcgc cttttatgga ttcatgcaag   6060
gaaactaccc ataatacaag aaaagcccgt cacgggcttc tcagggcgtt ttatggcggg   6120
tctgctatgt ggtgctatct gactttttgc tgttcagcag ttcctgccct ctgattttcc   6180
agtctgacca cttcggatta tcccgtgaca ggtcattcag actggctaat gcacccagta   6240
aggcagcggt atcatcaaca ggctta                                       6266
```

<210> SEQ ID NO 8
<211> LENGTH: 1695
<212> TYPE: DNA
<213> ORGANISM: Artificial Sequence
<220> FEATURE:
<223> OTHER INFORMATION: Synthetic Construct

<400> SEQUENCE: 8

```
atgtgtgcaa cctcctccca gtttactcag attaccgagc ataattctcg acgatctgct     60
aactaccagc cgaacctttg gaactttgag tttctccagt ctctcgaaaa tgacctgaag    120
```

gtggaaaagc tcgaggagaa ggcgaccaaa ctcgaggagg aggtgcgatg tatgatcaac 180
agagttgaca cccaacccct gtctttgctg gagctgatcg acgatgtgca gcggttgggt 240
ttgacttata aattcgagaa ggacattatc aaggcactgg agaacattgt gctcctcgac 300
gagaacaaga agaacaagtc tgatcttcac gctaccgctc tctctttccg acttcttcga 360
caacacggct tcgaggtgtc gcaggacgtc ttcgagagat ttaaggacaa ggagggagga 420
tttagcggcg agctgaaggg agacgttcag ggtcttctct ccttgtacga ggcgtcctac 480
ctgggattcg agggagagaa cctcctggag gaagctcgta cattttccat cactcacctt 540
aagaataacc ttaaggaggg aattaacacc aaggtggccg agcaggtttc tcacgccctg 600
gagctcccct accaccaacg gctccataga ctggaggctc gttggttcct ggacaaatat 660
gagccaaagg agcctcatca tcagttgctg ttggagttgg ccaagctgga cttcaatatg 720
gttcagacgc tgcaccaaaa ggagttgcag gacctgtctc gatggtggac cgagatggga 780
ttggcctcga agctggattt tgtccgtgac cgacttatgg aggtctattt ttgggccctt 840
ggaatggcgc ctgaccccca gttcggagag tgccggaagg cggtgacgaa gatgttcggt 900
cttgtgacta tcatcgacga cgtctacgat gtctacggca cactcgacga gttgcagctg 960
ttcactgacg ccgtcgagcg atgggatgtg aacgccatta atactctccc tgactatatg 1020
aagctgtgct tcctggctct gtacaacact gtcaacgata cctcgtactc tatcctcaag 1080
gagaagggac acaacaatct ctcctacttg accaaatcct ggcgagaact gtgcaaggct 1140
tttctgcagg aggctaaatg gtccaataac aagatcattc ctgctttttc taaatacctg 1200
gaaaatgcct cggtgtcgag ctctggcgtc gcccttctgg ccccttccta cttctccgtc 1260
tgccagcagc aggaggatat ttccgatcat gctcttagat cgctgaccga ttttcacggc 1320
ctcgtgcgat cttcctgcgt gatttttcgg ttgtgtaatg accttgcgac ctctgctgct 1380
gagctggaac gaggcgagac tacaaattcc attatttctt acatgcacga aaacgatgga 1440
acatctgaag aacaggctag agaggaactg cgaaagttga tcgacgccga gtggaagaag 1500
atgaacagag agcgggtgtc cgactctacc ctgcttccca aggccttcat ggagatcgcc 1560
gtgaacatgg ctcgagtttc ccattgtact taccagtacg gtgacggcct gggtcgtccg 1620
gactacgcta cagagaaccg aatcaagctg ctgctcatcg accccttccc tatcaaccaa 1680
ttgatgtacg tgtaa 1695

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9
gcttatggat cctctagact attacacgta catcaattgg 40

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10
caccatgtgt gcaacctcct cccagtttac 30

<210> SEQ ID NO 11
<211> LENGTH: 8191
<212> TYPE: DNA
<213> ORGANISM: Artificial Sequence
<220> FEATURE:
<223> OTHER INFORMATION: Synthetic Construct

<400> SEQUENCE: 11
tcgaccggtg agaagaacag catcgggaca agggaaggaa gaacaaagac aaagaaaaca 60
aaagaaagca attgaaaaca aaacaaaaca attttcattc cttctcttat cattcctttt 120
cttttctttt ctctcattca acgcactcca tcgtatccgt attcctctta ttttttctct 180
ttctctatat ccatttcttt ctctctaggt gtgtcctctc tctctcttca atttctctac 240
tccgcattcc aacgcatcct tcccccaacc tcccatttcc tccttacggc ccgatagcga 300
tcgtctttcc ctcgctatca ctcgctaccg gcccctcctc tgcaccgtaa cctcctacgt 360
atttaccata tcataaagtt ttttccgacg cttatcgctg accccctgtc gccctcctat 420
tggcttccgg attatcttct tgtccataag gtgatccatg cttcctgaag attcccgaaa 480
tgtgtccact ttggcgggga atcattccat ccacttcttt ctctctcgct ttcctcattc 540
ggcgctcccc ttccgcgtct cattggtctt ccgctccgtt tttgctttgc cgatgttact 600
tggggagagg tgcgataatc ctttcgcaaa aactcggttt gacgcctccc atggtataaa 660
tagtgggtgg tggacaggtg ccttcgcttt tctttaagca agagaatccc attgtcttga 720
ctatcacgaa ttcacataca ttatgaagat caccgctgtc attgcccttt tattctcact 780
tgctgctgcc tcacctattc cagttgccga tcctggtgtg gtttcagtta gcaagtcata 840
tgctgatttc cttcgtgttt accaaagttg gaacactttt gctaatcctg atagacccaa 900
ccttaagaag agaaatgata cacctgcaag tggatatcaa gttgaaaaag tcgtaatttt 960
gtcacgtcac ggtgttaggg cccctacaaa aatgactcaa accatgcgtg atgtcactcc 1020
taatacatgg ccagaatggc ccgttaaatt aggatatatt acaccaagag gtgaacactt 1080
gatatcactt atgggcggtt tttaccgtca aaaattccag caacaaggaa tcctttctca 1140
gggctcctgt cctactccta actccatata tgtctgggct gacgtcgatc agcgtacttt 1200
aaaaactggt gaagcattcc ttgctggttt ggcaccacaa tgtggcttga caattcatca 1260
ccaacaaaat cttgagaaag ctgatcctct ttttcatccc gttaaagctg gaacctgctc 1320
tatggataaa actcaagttc aacaagctgt tgagaaggag gcacaaactc ctatagataa 1380
tttgaatcaa cattacatcc cctttttagc tttaatgaat acaacattaa attttagtac 1440
ttctgcctgg tgccaaaaac actctgctga taaatcctgt gacctaggtt tatccatgcc 1500
ttctaaattg tccataaaag ataatggtaa caaggtcgca ttggatggag ctattggtct 1560
atcctctact ttggccgaga tttttcttct tgaatatgct caaggcatgc ctcaagctgc 1620
ttggggtaac atccactcag agcaagagtg ggcttccttg ctaaagttgc ataatgttca 1680
attcgatttg atggcccgaa caccttatat tgctcgacat aacggtactc ctttattgca 1740
agctatatca aatgccctta atcccaacgc cactgaatca aaacttccag atatttcacc 1800
tgataacaaa atattgttca ttgcaggtca tgacacaaat attgctaata tagccggcat 1860
gttaaatatg cgttggacat taccaggtca accagataat actcctccag gtggtgccct 1920
agtatttgaa cgtcttgctg ataaaagtgg aaaacaatat gtttctgtat ctatggttta 1980
tcaaacacta gaacaacttc gatcacagac tccccctttct ctaaatcagc ctgccggatc 2040
tgttcaactt aaaattccag gttgcaatga tcaaacagcc gagggttact gtcctctttc 2100
cacttttaca agagttgttt cccaatctgt tgaacctgga tgccaacttc aataatgagg 2160
atccaagtaa gggaatgaga atgtgatcca cttttaattc ctaatgaata catgcctata 2220
gttcttttct tttgttcttt atgtcgtttt tcgatggtac ggccgttgtc aatctcagtt 2280
tgtgtgcttg gttgcagctt ggtttcaaat ctgttcatct catgaatctt ttaccatttc 2340
accacacgtt tataccattc tctcatagaa tcttcatcaa accatctcgg ggttagagtg 2400
gaaagaaagt cttgttcttt tatttccttt tttccatctt caaggctttt cttttcttcc 2460
tcctcctcgt tcatcttgag gtttgacgtg tctgtttaga attttgagct gttgcagcat 2520
cttatttttt gttttgcgaa aacgaagcgc tttactctct tcatcagttg gacgattgta 2580
cctttgaaaa ccaactactt ttgcatgttt tgtatagaaa tcaatgatat tagaatccca 2640
tcctttaatt tctttcaaag tagttgagct atagttaagt gtaagggccc tactgcgaaa 2700
gcatttgcca aggatgtttt cattaatcaa gaacgaaagt taggggatcg aagacgatca 2760
gataccgtcg tagtcttaac cataaactat gccgactagg gatcgggcaa tgtttcattt 2820
atcgacttgc tcggcacctt acgagaaatc aaagtctttg ggttccgggg ggagtatggt 2880
cgcaaggctg aaacttaaag gaattgacgg aagggcacca caatggagtg gagcctgcgg 2940
cttaatttga ctcaacacgg ggaaactcac caggtccaga catagtaagg attgacagat 3000
tgagagctct ttcttgattc tatgggtggt ggtgcatggc cgttcttagt tggtggagtg 3060
atttgtctgc ttaattgcga taacgaacga gaccttaacc tgctaaatag ctggatcagc 3120
cattttggct gatcattagc ttcttagagg gactattggc ataaagccaa tggaagtttg 3180
aggcaataac aggtctgtga tgcccttaga tgttctgggc cgcacgcgcg ctacactgac 3240
ggagccaacg agttgaaaaa aatcttttga ttttttatcc ttggccggaa ggtctgggta 3300
atcttgttaa actccgtcgt gctggggata gagcattgca attattgcgg ccgctcctca 3360
attcgatgtt gcagatttta caagttttta aaatgtattt cattattact ttttatatgc 3420
ctaataaaaa agccatagtt taatctatag ataacttttt ttccagtgca ctaacggacg 3480
ttacattccc atacaaaact gcgtagttaa agctaaggaa aagttaatat catgttaatt 3540
aaatacgcta tttacaataa gacattgaac tcatttatat cgttgaatat gaataaccaa 3600
tttcagcgaa tttttaacaa acatcgttca cctcgtttaa ggatatcttg tgtatggggt 3660
gttgacttgc tttatcgaat aattaccgta cctgtaattg gcttgctgga tatagcggta 3720
gtctaatatc tagcaaaaat cttttgggtg aaaaggcttg caatttcacg acaccgaact 3780
atttgtcatt ttttaataag gaagttttcc ataaattcct gtaattctcg gttgatctaa 3840
ttgaaaagag tagttttgca tcacgatgag gagggctttt gtagaaagaa atacgaacga 3900
aacgaaaatc agcgttgcca tcgctttgga caaagctccc ttacctgaag agtcgaattt 3960
tattgatgaa cttataactt ccaagcatgc aaaccaaaag ggagaacaag taatccaagt 4020
agacacggga attggattct tggatcacat gtatcatgca ctggctaaac atgcaggctg 4080
gagcttacga ctttactcaa gaggtgattt aatcatcgat gatcatcaca ctgcagaaga 4140
tactgctatt gcacttggta ttgcattcaa gcaggctatg ggtaactttg ccggcgttaa 4200
aagatttgga catgcttatt gtccacttga cgaagctctt tctagaagcg tagttgactt 4260
gtcgggacgg ccctatgctg ttatcgattt gggattaaag cgtgaaaagg ttggggaatt 4320
gtcctgtgaa atgatccctc acttactata ttccttttcg gtagcagctg gaattacttt 4380
gcatgttacc tgcttatatg gtagtaatga ccatcatcgt gctgaaagcg cttttaaatc 4440
tctggctgtt gccatgcgcg cggctactag tcttactgga agttctgaag tcccaagcac 4500
gaagggagtg ttgtaaagat gaattggatt atgtcaggaa aagaacgaca attttgcatc 4560
caaattgtct aaattttaga gttgcttgaa aacaatagaa ccttacttgc tttataatta 4620
cgttaattag aagcgttatc tcgtgaagga atatagtacg tagccgtata aattgaattg 4680
aatgttcagc ttatagaata gagacacttt gctgttcaat gcgtcgtcac ttaccatact 4740
cactttatta tacgacttta agtataaact ccgcggttat ggtaaaatta atgatgcaca 4800
aacgtccgat tccatatggg tacactacaa ttaaatactt ttaagctgat cccccacaca 4860
ccatagcttc aaaatgtttc tactcctttt ttactcttcc agattttctc ggactccgcg 4920
catcgccgta ccacttcaaa acacccaagc acagcatact aaatttcccc tctttcttcc 4980
tctagggtgt cgttaattac ccgtactaaa ggtttggaaa agaaaaaaga gaccgcctcg 5040
tttctttttc ttcgtcgaaa aaggcaataa aaatttttat cacgtttctt tttcttgaaa 5100
tttttttttt tagttttttt ctctttcagt gacctccatt gatatttaag ttaataaacg 5160
gtcttcaatt tctcaagttt cagtttcatt tttcttgttc tattacaact ttttttactt 5220
cttgttcatt agaaagaaag catagcaatc taatctaagg gcggtgttga caattaatca 5280
tcggcatagt atatcggcat agtataatac gacaaggtga ggaactaaac catggccaag 5340
ttgaccagtg ccgttccggt gctcaccgcg cgcgacgtcg ccggagcggt cgagttctgg 5400
accgaccggc tcgggttctc ccgggacttc gtggaggacg acttcgccgg tgtggtccgg 5460
gacgacgtga ccctgttcat cagcgcggtc caggaccagg tggtgccgga caacaccctg 5520
gcctgggtgt gggtgcgcgg cctggacgag ctgtacgccg agtggtcgga ggtcgtgtcc 5580
acgaacttcc gggacgcctc cgggccggcc atgaccgaga tcggcgagca gccgtggggg 5640
cgggagttcg ccctgcgcga cccggccggc aactgcgtgc acttcgtggc cgaggagcag 5700
gactgacacg tccgacggcg gcccacgggt cccaggcctc ggagatccgt cccccttttc 5760
ctttgtcgat atcatgtaat tagttatgtc acgcttacat tcacgccctc cccccacatc 5820
cgctctaacc gaaaaggaag gagttagaca acctgaagtc taggtcccta tttatttttt 5880
tatagttatg ttagtattaa gaacgttatt tatatttcaa atttttcttt tttttctgta 5940
cagacgcgag cttcccagta aatgtgccat ctcgtaggca gaaaacggtt cccccgtagg 6000
gtctctctct tggcctcctt tctaggtcgg gctgattgct cttgaagctc tctagggggg 6060
ctcacaccat aggcagataa cgttccccac cggctcgcct cgtaagcgca caaggactgc 6120
tcccaaagat cctaggcggg attttgccga tttcggccta aaggaaccgg aacacgtaga 6180
aagccagtcc gcagaaacgg tgctgacccc ggatgaatgt cagctactgg gctatctgga 6240
caagggaaaa cgcaagcgca aagagaaagc aggtagcttg cagtgggctt acatggcgat 6300
agctagactg ggcggtttta tggacagcaa gcgaaccgga attgccagct ggggcgccct 6360
ctggtaaggt tgggaagccc tgcaaagtaa actggatggc tttcttgccg ccaaggatct 6420
gatggcgcag gggatcaaga tctgatcaag agacaggatg aggatcgttt cgcatgattg 6480
aacaagatgg attgcacgca ggttctccgg ccgcttgggt ggagaggcta ttcggctatg 6540
actgggcaca acagacaatc ggctgctctg atgccgccgt gttccggctg tcagcgcagg 6600
ggcgcccggt tctttttgtc aagaccgacc tgtccggtgc cctgaatgaa ctgcaggacg 6660
aggcagcgcg gctatcgtgg ctggccacga cgggcgttcc ttgcgcagct gtgctcgacg 6720
ttgtcactga agcgggaagg gactggctgc tattgggcga agtgccgggg caggatctcc 6780
tgtcatctcg ccttgctcct gccgagaaag tatccatcat ggctgatgca atgcggcggc 6840
tgcatacgct tgatccggct acctgcccat tcgaccacca agcgaaacat cgcatcgagc 6900
gagcacgtac tcggatggaa gccggtcttg tcgatcagga tgatctggac gaagagcatc 6960

```
aggggctcgc gccagccgaa ctgttcgcca ggctcaaggc gcgcatgccc gacggcgagg   7020

atctcgtcgt gatccatggc gatgcctgct tgccgaatat catggtggaa aatggccgct   7080

tttctggatt caacgactgt ggccggctgg gtgtggcgga ccgctatcag gacatagcgt   7140

tggatacccg tgatattgct gaagagcttg gcggcgaatg ggctgaccgc ttcctcgtgc   7200

tttacggtat cgccgctccc gattcgcagc gcatcgcctt ctatcgcctt cttgacgagt   7260

tcttctgaat tgaaaaaggt accaagttta ctcatatata ctttagattg atttaaaact   7320

tcatttttaa tttaaaagga tctaggtgaa gatccttttt gataatctca tgaccaaaat   7380

cccttaacgt gagttttcgt tccactgagc gtcagacccc gtagaaaaga tcaaaggatc   7440

ttcttgagat cctttttttc tgcgcgtaat ctgctgcttg caaacaaaaa aaccaccgct   7500

accagcggtg gtttgtttgc cggatcaaga gctaccaact ctttttccga aggtaactgg   7560

cttcagcaga gcgcagatac caaatactgt ccttctagtg tagccgtagt taggccacca   7620

cttcaagaac tctgtagcac cgcctacata cctcgctctg ctaatcctgt taccagtggc   7680

tgctgccagt ggcgataagt cgtgtcttac cgggttggac tcaagacgat agttaccgga   7740

taaggcgcag cggtcgggct gaacgggggg ttcgtgcaca cagcccagct tggagcgaac   7800

gacctacacc gaactgagat acctacagcg tgagcattga gaaagcgcca cgcttcccga   7860

agggagaaag gcggacaggt atccggtaag cggcagggtc ggaacaggag agcgcacgag   7920

ggagcttcca gggggaaacg cctggtatct ttatagtcct gtcgggtttc gccacctctg   7980

acttgagcgt cgatttttgt gatgctcgtc aggggggcgg agcctatgga aaaacgccag   8040

caacgcggcc tttttacggt tcctggcctt ttgctggcct tttgctcaca tgttctttcc   8100

tgcgttatcc cctgattctg tggataaccg tattaccgcc tttgagtgag ctgataccgc   8160

tcgccgcagc cgaacgaccg agcgcagcga g                                  8191
```

<210> SEQ ID NO 12
<211> LENGTH: 1724
<212> TYPE: DNA
<213> ORGANISM: Artificial Sequence
<220> FEATURE:
<223> OTHER INFORMATION: Synthetic Construct

<400> SEQUENCE: 12

```
gaattcaaaa caaaatgtgt gcaacctcct cccagtttac tcagattacc gagcataatt     60

ctcgacgatc tgctaactac cagccgaacc tttggaactt tgagtttctc cagtctctcg    120

aaaatgacct gaaggtggaa aagctcgagg agaaggcgac caaactcgag gaggaggtgc    180

gatgtatgat caacagagtt gacacccaac ccctgtcttt gctggagctg atcgacgatg    240

tgcagcggtt gggtttgact tataaattcg agaaggacat tatcaaggca ctggagaaca    300

ttgtgctcct cgacgagaac aagaagaaca agtctgatct tcacgctacc gctctctctt    360

tccgacttct tcgacaacac ggcttcgagg tgtcgcagga cgtcttcgag agatttaagg    420

acaaggaggg aggatttagc ggcgagctga agggagacgt tcagggtctt ctctccttgt    480

acgaggcgtc ctacctggga ttcgagggag agaacctcct ggaggaagct cgtacatttt    540

ccatcactca ccttaagaat aaccttaagg agggaattaa caccaaggtg gccgagcagg    600

tttctcacgc cctggagctc ccctaccacc aacggctcca tagactggag gctcgttggt    660

tcctggacaa atatgagcca aaggagcctc atcatcagtt gctgttggag ttggccaagc    720

tggacttcaa tatggttcag acgctgcacc aaaaggagtt gcaggacctg tctcgatggt    780

ggaccgagat gggattggcc tcgaagctgg attttgtccg tgaccgactt atggaggtct    840
```

```
atttttgggc ccttggaatg gcgcctgacc cccagttcgg agagtgccgg aaggcggtga    900
cgaagatgtt cggtcttgtg actatcatcg acgacgtcta cgatgtctac ggcacactcg    960
acgagttgca gctgttcact gacgccgtcg agcgatggga tgtgaacgcc attaatactc   1020
tccctgacta tatgaagctg tgcttcctgg ctctgtacaa cactgtcaac gatacctcgt   1080
actctatcct caaggagaag ggacacaaca atctctccta cttgaccaaa tcctggcgag   1140
aactgtgcaa ggcttttctg caggaggcta aatggtccaa taacaagatc attcctgctt   1200
tttctaaata cctggaaaat gcctcggtgt cgagctctgg cgtcgccctt ctggcccctt   1260
cctacttctc cgtctgccag cagcaggagg atatttccga tcatgctctt agatcgctga   1320
ccgattttca cggcctcgtg cgatcttcct gcgtgatttt tcggttgtgt aatgaccttg   1380
cgacctctgc tgctgagctg gaacgaggcg agactacaaa ttccattatt tcttacatgc   1440
acgaaaacga tggaacatct gaagaacagg ctagagagga actgcgaaag ttgatcgacg   1500
ccgagtggaa gaagatgaac agagagcggg tgtccgactc taccctgctt cccaaggcct   1560
tcatggagat cgccgtgaac atggctcgag tttcccattg tacttaccag tacggtgacg   1620
gcctgggtcg tccggactac gctacagaga accgaatcaa gctgctgctc atcgacccct   1680
tccctatcaa ccaattgatg tacgtgtaat agtctagagg atcc                    1724
```

<210> SEQ ID NO 13
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 13

```
gaattcaaca aaaatgtgct ctgtttccac tgagaacgtg tcctttactg agactgagac     60
tgaagcacgt agaagcgcca actacgaacc caactcctgg gattatgact ttctgctgtc    120
ttctgacacc gacgagtcga tcgaggttta taaggataag gccaagaaac ttgaggccga    180
ggtcagacga gagattaaca acgagaaggc cgagttcctg acccttcttg agctgatcga    240
caacgttcaa cgacttggtc ttggttaccg tttcgaatcc gatatccgac gtgcattgga    300
tcgatttgtc tcgtccggag gtttcgatgg tgtgactaag acgtcgctgc acgccacagc    360
tctttccttc agactgttgc ggcagcatgg atttgaggtt tcccaggaag ccttttctgg    420
tttcaaggat cagaacggaa actttttgga gaatctcaag gaggacacca aggccatcct    480
gtcgttgtat gaggcctcgt tcctggctct tgagggcgag aatattctgg atgaggctcg    540
ggttttcgct atttcgcacc tgaaggagtt gtcggaggaa aagatcggaa aggaactggc    600
cgagcaggtc aaccatgcac ttgaacttcc cctgcatcga cgtacccagc gactggaggc    660
cgtgtggagc atcgaggcgt acagaaaaaa ggaggatgct aatcaggttc tgctcgaact    720
cgctatcctc gactataaca tgattcagag cgtgtaccag cgtgacttgc gagagacaag    780
ccggtggtgg cgacgggtgg gactggccac gaagctccac tttgctaaag atcgattgat    840
tgagtcgttc tactgggcag tgggtgtggc ctttgagcct cagtactccg actgccgaaa    900
ctccgttgca aagatgtttt cttttgtcac tatcatcgac gacatctacg atgtttacgg    960
cactctcgat gaactcgaac tcttcacgga cgctgtcgag cgatgggatg tgaatgccat   1020
taatgatctg ccagattata tgaagttgtg tttcttggcg ctctacaaca caattaatga   1080
aattgcctac gacaacctca aggacaaggg agagaacatt ctgccctacc ttactaaagc   1140
ctgggccgac ctgtgtaacg cctttttgca ggaagccaag tggctctata acaaatctac   1200
```

tcctacattt gatgactact tcggcaacgc ttggaagtct tccagcggcc ctctccagtt 1260
gatcttcgct tactttgcag tggtccagaa catcaagaaa gaggagattg agaacctcca 1320
gaagtatcac gacatcatct cccgaccttc gcacatcttt cgactgtgca atgaccttgc 1380
ctccgcatcc gctgagattg cccgaggaga aacagccaat tctgtgtcgt gttacatgcg 1440
tacaaagggc atctccgagg agctggctac cgagtctgtg atgaacctga tcgatgaaac 1500
ctgtaagaag atgaacaaag agaaactggg cggttctctg ttcgccaaac catttgttga 1560
aaccgcgatc aatctggctc gtcagtctca ttgtacttac cataacggtg acgcgcacac 1620
ttcgccggac gaattgaccc gtaagcgtgt gctttcggtg attaccgagc cgatcctgcc 1680
gttcgaaaga taataggatc c 1701

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct

<400> SEQUENCE: 14
gatcaagctt aaccggaatt gccagctg 28

<210> SEQ ID NO 15
<211> LENGTH: 33
<212> TYPE: DNA
<213> ORGANISM: Artificial Sequence
<220> FEATURE:
<223> OTHER INFORMATION: Synthetic Construct

<400> SEQUENCE: 15
gatccgatcg tcagaagaac tcgtcaagaa ggc 33

<210> SEQ ID NO 16
<211> LENGTH: 38
<212> TYPE: DNA
<213> ORGANISM: Artificial Sequence
<220> FEATURE:
<223> OTHER INFORMATION: Synthetic Construct

<400> SEQUENCE: 16
catcaatgca tcgcccttag gaggtaaaaa aaaatgac 38

<210> SEQ ID NO 17
<211> LENGTH: 26
<212> TYPE: DNA
<213> ORGANISM: Artificial Sequence
<220> FEATURE:
<223> OTHER INFORMATION: Synthetic Construct

<400> SEQUENCE: 17
ccttctgcag gacgcgttgt tatagc 26

<210> SEQ ID NO 18
<211> LENGTH: 60
<212> TYPE: DNA
<213> ORGANISM: Artificial Sequence
<220> FEATURE:
<223> OTHER INFORMATION: Synthetic Construct

<400> SEQUENCE: 18
gatcatgcat tcgcccttag gaggtaaaaa aacatgagtt ttgatattgc caaatacccg 60

<210> SEQ ID NO 19
<211> LENGTH: 31
<212> TYPE: DNA
<213> ORGANISM: Artificial Sequence
<220> FEATURE:
<223> OTHER INFORMATION: Synthetic Construct

<400> SEQUENCE: 19
catgctgcag ttatgccagc caggccttga t 31

<210> SEQ ID NO 20
<211> LENGTH: 8804
<212> TYPE: DNA
<213> ORGANISM: Artificial Sequence
<220> FEATURE:
<223> OTHER INFORMATION: Synthetic Construct

<400> SEQUENCE: 20
gctggtacca tatgggaatt cgaagctttc tagaacaaaa actcatctca gaagaggatc 60
tgaatagcgc cgtcgaccat catcatcatc atcattgagt ttaaacggtc tccagcttgg 120
ctgttttggc ggatgagaga agattttcag cctgatacag attaaatcag aacgcagaag 180
cggtctgata aaacagaatt tgcctggcgg cagtagcgcg gtggtcccac ctgaccccat 240
gccgaactca gaagtgaaac gccgtagcgc cgatggtagt gtggggtctc cccatgcgag 300
agtagggaac tgccaggcat caaataaaac gaaaggctca gtcgaaagac tgggcctttc 360
gttttatctg ttgtttgtcg gtgaacgctc tcctgagtag gacaaatccg ccgggagcgg 420
atttgaacgt tgcgaagcaa cggcccggag ggtggcgggc aggacgcccg ccataaactg 480
ccaggcatca aattaagcag aaggccatcc tgacggatgg cctttttgcg tttctacaaa 540
ctctttttgt ttatttttct aaatacattc aaatatgtat ccgcttaacc ggaattgcca 600
gctggggcgc cctctggtaa ggttgggaag ccctgcaaag taaactggat ggctttctcg 660
ccgccaagga tctgatggcg caggggatca agctctgatc aagagacagg atgaggatcg 720
tttcgcatga ttgaacaaga tggattgcac gcaggttctc cggccgcttg ggtggagagg 780
ctattcggct atgactgggc acaacagaca atcggctgct ctgatgccgc cgtgttccgg 840
ctgtcagcgc aggggcgccc ggttcttttt gtcaagaccg acctgtccgg tgccctgaat 900
gaactgcaag acgaggcagc gcggctatcg tggctggcca cgacgggcgt tccttgcgca 960
gctgtgctcg acgttgtcac tgaagcggga agggactggc tgctattggg cgaagtgccg 1020
gggcaggatc tcctgtcatc tcaccttgct cctgccgaga aagtatccat catggctgat 1080
gcaatgcggc ggctgcatac gcttgatccg gctacctgcc cattcgacca ccaagcgaaa 1140
catcgcatcg agcgagcacg tactcggatg gaagccggtc ttgtcgatca ggatgatctg 1200
gacgaagagc atcaggggct cgcgccagcc gaactgttcg ccaggctcaa ggcgagcatg 1260
cccgacggcg aggatctcgt cgtgacccat ggcgatgcct gcttgccgaa tatcatggtg 1320
gaaaatggcc gcttttctgg attcatcgac tgtggccggc tgggtgtggc ggaccgctat 1380
caggacatag cgttggctac ccgtgatatt gctgaagagc ttggcggcga atgggctgac 1440
cgcttcctcg tgctttacgg tatcgccgct cccgattcgc agcgcatcgc cttctatcgc 1500
cttcttgacg agttcttctg acatgaccaa aatcccttaa cgtgagtttt cgttccactg 1560
agcgtcagac cccgtagaaa agatcaaagg atcttcttga gatccttttt ttctgcgcgt 1620
aatctgctgc ttgcaaacaa aaaaaccacc gctaccagcg gtggtttgtt tgccggatca 1680
agagctacca actctttttc cgaaggtaac tggcttcagc agagcgcaga taccaaatac 1740
tgtccttcta gtgtagccgt agttaggcca ccacttcaag aactctgtag caccgcctac 1800

-continued

```
atacctcgct ctgctaatcc tgttaccagt ggctgctgcc agtggcgata agtcgtgtct   1860
taccgggttg gactcaagac gatagttacc ggataaggcg cagcggtcgg gctgaacggg   1920
gggttcgtgc acacagccca gcttggagcg aacgacctac accgaactga gatacctaca   1980
gcgtgagcta tgagaaagcg ccacgcttcc cgaagggaga aaggcggaca ggtatccggt   2040
aagcggcagg gtcggaacag gagagcgcac gagggagctt ccagggggaa acgcctggta   2100
tctttatagt cctgtcgggt ttcgccacct ctgacttgag cgtcgatttt tgtgatgctc   2160
gtcagggggg cggagcctat ggaaaaacgc cagcaacgcg gcctttttac ggttcctggc   2220
cttttgctgg ccttttgctc acatgttctt tcctgcgtta tcccctgatt ctgtggataa   2280
ccgtattacc gcctttgagt gagctgatac cgctcgccgc agccgaacga ccgagcgcag   2340
cgagtcagtg agcgaggaag cggaagagcg cctgatgcgg tattttctcc ttacgcatct   2400
gtgcggtatt tcacaccgca tatggtgcac tctcagtaca atctgctctg atgccgcata   2460
gttaagccag tatacactcc gctatcgcta cgtgactggg tcatggctgc gccccgacac   2520
ccgccaacac ccgctgacgc gccctgacgg gcttgtctgc tcccggcatc cgcttacaga   2580
caagctgtga ccgtctccgg gagctgcatg tgtcagaggt tttcaccgtc atcaccgaaa   2640
cgcgcgaggc agcagatcaa ttcgcgcgcg aaggcgaagc ggcatgcatt tacgttgaca   2700
ccatcgaatg gtgcaaaacc tttcgcggta tggcatgata gcgcccggaa gagagtcaat   2760
tcagggtggt gaatgtgaaa ccagtaacgt tatacgatgt cgcagagtat gccggtgtct   2820
cttatcagac cgtttcccgc gtggtgaacc aggccagcca cgtttctgcg aaaacgcggg   2880
aaaaagtgga agcggcgatg gcggagctga attacattcc caaccgcgtg gcacaacaac   2940
tggcgggcaa acagtcgttg ctgattggcg ttgccacctc cagtctggcc ctgcacgcgc   3000
cgtcgcaaat tgtcgcggcg attaaatctc gcgccgatca actgggtgcc agcgtggtgg   3060
tgtcgatggt agaacgaagc ggcgtcgaag cctgtaaagc ggcggtgcac aatcttctcg   3120
cgcaacgcgt cagtgggctg atcattaact atccgctgga tgaccaggat gccattgctg   3180
tggaagctgc ctgcactaat gttccggcgt tatttcttga tgtctctgac cagacaccca   3240
tcaacagtat tattttctcc catgaagacg gtacgcgact gggcgtggag catctggtcg   3300
cattgggtca ccagcaaatc gcgctgttag cgggcccatt aagttctgtc tcggcgcgtc   3360
tgcgtctggc tggctggcat aaatatctca ctcgcaatca aattcagccg atagcggaac   3420
gggaaggcga ctggagtgcc atgtccggtt ttcaacaaac catgcaaatg ctgaatgagg   3480
gcatcgttcc cactgcgatg ctggttgcca acgatcagat ggcgctgggc gcaatgcgcg   3540
ccattaccga gtccgggctg cgcgttggtg cggatatctc ggtagtggga tacgacgata   3600
ccgaagacag ctcatgttat atcccgccgt caaccaccat caaacaggat tttcgcctgc   3660
tggggcaaac cagcgtggac cgcttgctgc aactctctca gggccaggcg gtgaagggca   3720
atcagctgtt gcccgtctca ctggtgaaaa gaaaaaccac cctggcgccc aatacgcaaa   3780
ccgcctctcc ccgcgcgttg gccgattcat taatgcagct ggcacgacag gtttcccgac   3840
tggaaagcgg gcagtgagcg caacgcaatt aatgtgagtt agcgcgaatt gatctggttt   3900
gacagcttat catcgactgc acggtgcacc aatgcttctg gcgtcaggca gccatcggaa   3960
gctgtggtat ggctgtgcag gtcgtaaatc actgcataat tcgtgtcgct caaggcgcac   4020
tcccgttctg gataatgttt tttgcgccga catcataacg gttctggcaa atattctgaa   4080
atgagctgtt gacaattaat catccggctc gtataatgtg tggaattgtg agcggataac   4140
aatttcacac aggaaacagc gccgctgaga aaaagcgaag cggcactgct ctttaacaat   4200
```

ttatcagaca atctgtgtgg gcactcgacc ggaattatcg attaacttta ttattaaaaa 4260
ttaaagaggt atatattaat gtatcgatta aataaggagg aataaaccat gtgtgcgacc 4320
tcttctcaat ttactcagat taccgagcat aattcccgtc gttccgcaaa ctatcagcca 4380
aacctgtgga atttcgaatt cctgcaatcc ctggagaacg acctgaaagt ggaaaagctg 4440
gaggagaaag cgaccaaact ggaggaagaa gttcgctgca tgatcaaccg tgtagacacc 4500
cagccgctgt ccctgctgga gctgatcgac gatgtgcagc gcctgggtct gacctacaaa 4560
tttgaaaaag acatcattaa agccctggaa aacatcgtac tgctggacga aaacaaaaag 4620
aacaaatctg acctgcacgc aaccgctctg tctttccgtc tgctgcgtca gcacggtttc 4680
gaggtttctc aggatgtttt tgagcgtttc aaggataaag aaggtggttt cagcggtgaa 4740
ctgaaaggtg acgtccaagg cctgctgagc ctgtatgaag cgtcttacct gggtttcgag 4800
ggtgagaacc tgctggagga ggcgcgtacc ttttccatca cccacctgaa gaacaacctg 4860
aaagaaggca ttaataccaa ggttgcagaa caagtgagcc acgccctgga actgccatat 4920
caccagcgtc tgcaccgtct ggaggcacgt tggttcctgg ataaatacga accgaaagaa 4980
ccgcatcacc agctgctgct ggagctggcg aagctggatt ttaacatggt acagaccctg 5040
caccagaaag agctgcaaga tctgtcccgc tggtggaccg agatgggcct ggctagcaaa 5100
ctggattttg tacgcgaccg cctgatggaa gtttatttct gggcactggg tatggcgcca 5160
gacccgcagt ttggtgaatg tcgcaaagct gttactaaaa tgtttggtct ggtgacgatc 5220
atcgatgacg tgtatgacgt ttatggcact ctggacgaac tgcaactgtt caccgatgct 5280
gtagagcgct gggacgttaa cgctattaac accctgccgg actatatgaa actgtgtttc 5340
ctggcactgt acaacaccgt taacgacacg tcctattcta ttctgaaaga gaaaggtcat 5400
aacaacctgt cctatctgac gaaaagctgg cgtgaactgt gcaaagcctt tctgcaagag 5460
gcgaaatggt ccaacaacaa aattatcccg gctttctcca agtacctgga aaacgccagc 5520
gtttcctcct ccggtgtagc gctgctggcg ccgtcttact tttccgtatg ccagcagcag 5580
gaagacatct ccgaccacgc gctgcgttcc ctgaccgact tccatggtct ggtgcgttct 5640
agctgcgtta tcttccgcct gtgcaacgat ctggccacct ctgcggcgga gctggaacgt 5700
ggcgagacta ccaattctat cattagctac atgcacgaaa acgatggtac cagcgaggaa 5760
caggcccgcg aagaactgcg taaactgatc gacgccgaat ggaaaaagat gaatcgtgaa 5820
cgcgttagcg actccaccct gctgcctaaa gcgttcatgg aaatcgcagt taacatggca 5880
cgtgtttccc actgcaccta ccagtatggc gatggtctgg gtcgcccaga ctacgcgact 5940
gaaaaccgca tcaaactgct gctgattgac cctttcccga ttaaccagct gatgtatgtc 6000
taactgcatc gcccttagga ggtaaaaaaa aatgactgcc gacaacaata gtatgcccca 6060
tggtgcagta tctagttacg ccaaattagt gcaaaaccaa acacctgaag acattttgga 6120
agagtttcct gaaattattc cattacaaca aagacctaat acccgatcta gtgagacgtc 6180
aaatgacgaa agcggagaaa catgtttttc tggtcatgat gaggagcaaa ttaagttaat 6240
gaatgaaaat tgtattgttt tggattggga cgataatgct attggtgccg gtaccaagaa 6300
agtttgtcat ttaatggaaa atattgaaaa gggtttacta catcgtgcat tctccgtctt 6360
tattttcaat gaacaaggtg aattactttt acaacaaaga gccactgaaa aaataacttt 6420
ccctgatctt tggactaaca catgctgctc tcatccacta tgtattgatg acgaattagg 6480
tttgaagggt aagctagacg ataagattaa gggcgctatt actgcggcgg tgagaaaact 6540
agatcatgaa ttaggtattc cagaagatga aactaagaca aggggtaagt ttcacttttt 6600
aaacagaatc cattacatgg caccaagcaa tgaaccatgg ggtgaacatg aaattgatta 6660
catcctattt tataagatca acgctaaaga aaacttgact gtcaacccaa acgtcaatga 6720
agttagagac ttcaaatggg tttcaccaaa tgatttgaaa actatgtttg ctgacccaag 6780
ttacaagttt acgccttggt ttaagattat ttgcgagaat tacttattca actggtggga 6840
gcaattagat gacctttctg aagtggaaaa tgacaggcaa attcatagaa tgctataaca 6900
acgcgtcctg cattcgccct taggaggtaa aaaaacatga gttttgatat tgccaaatac 6960
ccgaccctgg cactggtcga ctccacccag gagttacgac tgttgccgaa agagagttta 7020
ccgaaactct gcgacgaact gcgccgctat ttactcgaca gcgtgagccg ttccagcggg 7080
cacttcgcct ccgggctggg cacggtcgaa ctgaccgtgg cgctgcacta tgtctacaac 7140
accccgtttg accaattgat ttgggatgtg gggcatcagg cttatccgca taaaattttg 7200
accggacgcc gcgacaaaat cggcaccatc cgtcagaaag gcggtctgca cccgttcccg 7260
tggcgcggcg aaagcgaata tgacgtatta agcgtcgggc attcatcaac ctccatcagt 7320
gccggaattg gtattgcggt tgctgccgaa aaagaaggca aaaatcgccg caccgtctgt 7380
gtcattggcg atggcgcgat taccgcaggc atggcgtttg aagcgatgaa tcacgcgggc 7440
gatatccgtc ctgatatgct ggtgattctc aacgacaatg aaatgtcgat ttccgaaaat 7500
gtcggcgcgc tcaacaacca tctggcacag ctgctttccg gtaagcttta ctcttcactg 7560
cgcgaaggcg ggaaaaaagt ttctctggc gtgccgccaa ttaaagagct gctcaaacgc 7620
accgaagaac atattaaagg catggtagtg cctggcacgt tgtttgaaga gctgggcttt 7680
aactacatcg gcccggtgga cggtcacgat gtgctggggc ttatcaccac gctaaagaac 7740
atgcgcgacc tgaaaggccc gcagttcctg catatcatga ccaaaaaagg tcgtggttat 7800
gaaccggcag aaaaagaccc gatcactttc cacgccgtgc ctaaatttga tccctccagc 7860
ggttgtttgc cgaaaagtag cggcggtttg ccgagctatt caaaaatctt tggcgactgg 7920
ttgtgcgaaa cggcagcgaa agacaacaag ctgatggcga ttactccggc gatgcgtgaa 7980
ggttccggca tggtcgagtt ttcacgtaaa ttcccggatc gctacttcga cgtggcaatt 8040
gccgagcaac acgcggtgac ctttgctgcg ggtctggcga ttggtgggta caaacccatt 8100
gtcgcgattt actccacttt cctgcaacgc gcctatgatc aggtgctgca tgacgtggcg 8160
attcaaaagc ttccggtcct gttcgccatc gaccgcgcgg gcattgttgg tgctgacggt 8220
caaacccatc agggtgcttt tgatctctct tacctgcgct gcataccgga aatggtcatt 8280
atgaccccga gcgatgaaaa cgaatgtcgc cagatgctct ataccggcta tcactataac 8340
gatggcccgt cagcggtgcg ctacccgcgt ggcaacgcgg tcggcgtgga actgacgccg 8400
ctggaaaaac taccaattgg caaaggcatt gtgaagcgtc gtggcgagaa actggcgatc 8460
cttaactttg gtacgctgat gccagaagcg gcgaaagtcg ccgaatcgct gaacgccacg 8520
ctggtcgata tgcgttttgt gaaaccgctt gatgaagcgt taattctgga aatggccgcc 8580
agccatgaag cgctggtcac cgtagaagaa aacgccatta tgggcggcgc aggcagcggc 8640
gtgaacgaag tgctgatggc ccatcgtaaa ccagtacccg tgctgaacat tggcctgccg 8700
gacttcttta ttccgcaagg aactcaggaa gaaatgcgcg ccgaactcgg cctcgatgcc 8760
gctggtatgg aagccaaaat caaggcctgg ctggcataac tgca 8804

<210> SEQ ID NO 21
<211> LENGTH: 4339
<212> TYPE: DNA
<213> ORGANISM: Artificial Sequence
<220> FEATURE:
<223> OTHER INFORMATION: Synthetic Construct

<400> SEQUENCE: 21

```
tagaaaaact catcgagcat caaatgaaac tgcaatttat tcatatcagg attatcaata     60

ccatattttt gaaaaagccg tttctgtaat gaaggagaaa actcaccgag gcagttccat    120

aggatggcaa gatcctggta tcggtctgcg attccgactc gtccaacatc aatacaacct    180

attaatttcc cctcgtcaaa aataaggtta tcaagtgaga aatcaccatg agtgacgact    240

gaatccggtg agaatggcaa aagtttatgc atttctttcc agacttgttc aacaggccag    300

ccattacgct cgtcatcaaa atcactcgca tcaaccaaac cgttattcat tcgtgattgc    360

gcctgagcga ggcgaaatac gcgatcgctg ttaaaaggac aattacaaac aggaatcgag    420

tgcaaccggc gcaggaacac tgccagcgca tcaacaatat tttcacctga atcaggatat    480

tcttctaata cctggaacgc tgtttttccg gggatcgcag tggtgagtaa ccatgcatca    540

tcaggagtac ggataaaatg cttgatggtc ggaagtggca taaattccgt cagccagttt    600

agtctgacca tctcatctgt aacatcattg gcaacgctac ctttgccatg tttcagaaac    660

aactctggcg catcgggctt cccatacaag cgatagattg tcgcacctga ttgcccgaca    720

ttatcgcgag cccatttata cccatataaa tcagcatcca tgttggaatt taatcgcggc    780

ctcgacgttt cccgttgaat atggctcata ttcttccttt ttcaatatta ttgaagcatt    840

tatcagggtt attgtctcat gagcggatac atatttgaat gtatttagaa aaataaacaa    900

ataggggtca gtgttacaac caattaacca attctgaaca ttatcgcgag cccatttata    960

cctgaatatg gctcataaca ccccttgttt gcctggcggc agtagcgcgg tggtcccacc   1020

tgaccccatg ccgaactcag aagtgaaacg ccgtagcgcc gatggtagtg tggggactcc   1080

ccatgcgaga gtagggaact gccaggcatc aaataaaacg aaaggctcag tcgaaagact   1140

gggcctttcg cccgggctaa ttagggggtg tcgcccttta gtcgctgaac atgtgctctg   1200

tttctaccga gaacgtttcc ttcactgaga cggaaaccga ggcacgtcgt agcgcgaact   1260

acgagccgaa tagctgggac tacgatttcc tgctgtcttc cgatactgac gaatctattg   1320

aggtgtacaa agacaaagca aagaaactgg aggctgaagt gcgccgcgaa attaacaacg   1380

agaaagctga attcctgact ctgctggagc tgatcgataa cgtacagcgc ctgggtctgg   1440

gttaccgctt cgaatctgat atccgtcgcg cactggatcg tttcgtaagc agcggcggtt   1500

tcgatggcgt gaccaaaacg agcctgcacg ctaccgcgct gtccttccgt ctgctgcgtc   1560

agcacggctt cgaagtttct caggaagcat tctccggttt caaagatcaa aacggtaact   1620

tcctggaaaa cctgaaagaa gacactaagg cgatcctgag cctgtatgag gcaagctttc   1680

tggccctgga gggtgagaac atcctggatg aggcgcgcgt attcgccatc tcccatctga   1740

aagagctgtc tgaagagaaa atcggtaagg aactggcaga gcaggttaat cacgcactgg   1800

aactgccgct gcatcgtcgt acccagcgtc tggaggcggt ttggtccatc gaagcgtacc   1860

gcaaaaagga ggatgctaac caggttctgc tggaactggc catcctggac tacaacatga   1920

tccagtccgt ttaccagcgt gatctgcgtg aaacctcccg ttggtggcgc cgtgtgggcc   1980

tggcgaccaa actgcacttc gctaaggacc gcctgattga gtctttttac tgggcagtcg   2040

gcgttgcgtt cgaacctcag tattctgact gccgtaacag cgttgcgaaa atgttcagct   2100

tcgttactat tatcgacgac atctacgacg tttacggtac tctggacgag ctggaactgt   2160

ttaccgacgc tgtcgaacgt tgggatgtta acgccatcaa cgatctgcct gactacatga   2220

aactgtgctt cctggcactg tataacacga tcaacgaaat tgcatacgac aacctgaaag   2280
```

acaaaggtga aaacatcctg ccgtacctga ctaaagcgtg ggcggatctg tgtaacgctt 2340
ttctgcaaga agcgaaatgg ctgtataaca aatccactcc gacctttgac gattatttcg 2400
gcaatgcctg gaaatccagc tctggcccgc tgcaactgat cttcgcttat tttgcggttg 2460
tccaaaacat caaaaaggag gaaattgaaa acctgcaaaa ataccacgat atcattagcc 2520
gtccttctca tatctttcgc ctgtgcaacg acctggcaag cgcgtccgca gagatcgcac 2580
gtggcgaaac cgctaactct gtttcctgct acatgcgcac caagggcatt tccgaagagc 2640
tggcaaccga gagcgtaatg aatctgatcg acgaaacctg taagaaaatg aacaaagaaa 2700
aactgggtgg ctccctgttc gctaaaccgt tcgtagagac tgctattaac ctggcacgtc 2760
agagccactg cacctaccac aatggtgacg cacatactag cccggatgaa ctgactcgta 2820
aacgtgtact gtctgttatc accgaaccga ttctgccgtt cgaacgttaa ctgcagcgtc 2880
aatcgaaagg gcgacacaaa atttattcta aatgcataat aaatactgat aacatcttat 2940
agtttgtatt atattttgta ttatcgttga catgtataat tttgatatca aaaactgatt 3000
ttccctttat tattttcgag atttattttc ttaattctct ttaacaaact agaaatattg 3060
tatatacaaa aaatcataaa taatagatga atagtttaat tataggtgtt catcaatcga 3120
aaaagcaacg tatcttattt aaagtgcgtt gcttttttct catttataag gttaaataat 3180
tctcatatat caagcaaagt gacaggcgcc cttaaatatt ctgacaaatg ctctttccct 3240
aaactccccc cataaaaaaa cccgccgaag cgggttttta cgttatttgc ggattaacga 3300
ttactcgtta tcagaaccgc ccagggggcc cgagcttaag actggccgtc gttttacaac 3360
acagaaagag tttgtagaaa cgcaaaaagg ccatccgtca ggggccttct gcttagtttg 3420
atgcctggca gttccctact ctcgccttcc gcttcctcgc tcactgactc gctgcgctcg 3480
gtcgttcggc tgcggcgagc ggtatcagct cactcaaagg cggtaatacg gttatccaca 3540
gaatcagggg ataacgcagg aaagaacatg tgagcaaaag gccagcaaaa ggccaggaac 3600
cgtaaaaagg ccgcgttgct ggcgtttttc cataggctcc gcccccctga cgagcatcac 3660
aaaaatcgac gctcaagtca gaggtggcga aacccgacag gactataaag ataccaggcg 3720
tttccccctg gaagctccct cgtgcgctct cctgttccga ccctgccgct taccggatac 3780
ctgtccgcct ttctcccttc gggaagcgtg gcgctttctc atagctcacg ctgtaggtat 3840
ctcagttcgg tgtaggtcgt tcgctccaag ctgggctgtg tgcacgaacc ccccgttcag 3900
cccgaccgct gcgccttatc cggtaactat cgtcttgagt ccaacccggt aagacacgac 3960
ttatcgccac tggcagcagc cactggtaac aggattagca gagcgaggta tgtaggcggt 4020
gctacagagt tcttgaagtg gtggcctaac tacggctaca ctagaagaac agtatttggt 4080
atctgcgctc tgctgaagcc agttaccttc ggaaaaagag ttggtagctc ttgatccggc 4140
aaacaaacca ccgctggtag cggtggtttt tttgtttgca agcagcagat tacgcgcaga 4200
aaaaaaggat ctcaagaaga tcctttgatc ttttctacgg ggtctgacgc tcagtggaac 4260
gacgcgcgcg taactcacgt taagggattt tggtcatgag cttgcgccgt cccgtcaagt 4320
cagcgtaatg ctctgcttt 4339

<210> SEQ ID NO 22
<211> LENGTH: 6065
<212> TYPE: DNA
<213> ORGANISM: Artificial Sequence
<220> FEATURE:
<223> OTHER INFORMATION: Synthetic Construct

<400> SEQUENCE: 22

```
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gtttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgtgctc    420
tgtttctacc gagaacgttt ccttcactga gacggaaacc gaggcacgtc gtagcgcgaa    480
ctacgagccg aatagctggg actacgattt cctgctgtct tccgatactg acgaatctat    540
tgaggtgtac aaagacaaag caaagaaact ggaggctgaa gtgcgccgcg aaattaacaa    600
cgagaaagct gaattcctga ctctgctgga gctgatcgat aacgtacagc gcctgggtct    660
gggttaccgc ttcgaatctg atatccgtcg cgcactggat cgtttcgtaa gcagcggcgg    720
tttcgatggc gtgaccaaaa cgagcctgca cgctaccgcg ctgtccttcc gtctgctgcg    780
tcagcacggc ttcgaagttt ctcaggaagc attctccggt ttcaaagatc aaaacggtaa    840
cttcctggaa aacctgaaag aagacactaa ggcgatcctg agcctgtatg aggcaagctt    900
tctggccctg gagggtgaga acatcctgga tgaggcgcgc gtattcgcca tctcccatct    960
gaaagagctg tctgaagaga aaatcggtaa ggaactggca gagcaggtta atcacgcact   1020
ggaactgccg ctgcatcgtc gtacccagcg tctggaggcg gtttggtcca tcgaagcgta   1080
ccgcaaaaag gaggatgcta accaggttct gctggaactg gccatcctgg actacaacat   1140
gatccagtcc gtttaccagc gtgatctgcg tgaaacctcc cgttggtggc gccgtgtggg   1200
cctggcgacc aaactgcact tcgctaagga ccgcctgatt gagtcttttt actgggcagt   1260
cggcgttgcg ttcgaacctc agtattctga ctgccgtaac agcgttgcga aaatgttcag   1320
cttcgttact attatcgacg acatctacga cgtttacggt actctggacg agctggaact   1380
gtttaccgac gctgtcgaac gttgggatgt taacgccatc aacgatctgc ctgactacat   1440
gaaactgtgc ttcctggcac tgtataacac gatcaacgaa attgcatacg acaacctgaa   1500
agacaaaggt gaaaacatcc tgccgtacct gactaaagcg tgggcggatc tgtgtaacgc   1560
ttttctgcaa gaagcgaaat ggctgtataa caaatccact ccgacctttg acgattattt   1620
cggcaatgcc tggaaatcca gctctggccc gctgcaactg atcttcgctt attttgcggt   1680
tgtccaaaac atcaaaaagg aggaaattga aaacctgcaa aaataccacg atatcattag   1740
ccgtccttct catatctttc gcctgtgcaa cgacctggca agcgcgtccg cagagatcgc   1800
acgtggcgaa accgctaact ctgtttcctg ctacatgcgc accaagggca tttccgaaga   1860
gctggcaacc gagagcgtaa tgaatctgat cgacgaaacc tgtaagaaaa tgaacaaaga   1920
aaaactgggt ggctccctgt tcgctaaacc gttcgtagag actgctatta acctggcacg   1980
tcagagccac tgcacctacc acaatggtga cgcacatact agcccggatg aactgactcg   2040
taaacgtgta ctgtctgtta tcaccgaacc gattctgccg ttcgaacgtt aactgcagct   2100
ggtaccatat gggaattcga agctttctag aacaaaaact catctcagaa gaggatctga   2160
atagcgccgt cgaccatcat catcatcatc attgagttta aacggtctcc agcttggctg   2220
ttttggcgga tgagagaaga ttttcagcct gatacagatt aaatcagaac gcagaagcgg   2280
tctgataaaa cagaatttgc ctggcggcag tagcgcggtg gtcccacctg accccatgcc   2340
gaactcagaa gtgaaacgcc gtagcgccga tggtagtgtg gggtctcccc atgcgagagt   2400
```

-continued

```
agggaactgc caggcatcaa ataaaacgaa aggctcagtc gaaagactgg gcctttcgtt   2460
ttatctgttg tttgtcggtg aacgctctcc tgagtaggac aaatccgccg ggagcggatt   2520
tgaacgttgc gaagcaacgg cccggagggt ggcgggcagg acgcccgcca taaactgcca   2580
ggcatcaaat taagcagaag gccatcctga cggatggcct ttttgcgttt ctacaaactc   2640
tttttgttta tttttctaaa tacattcaaa tatgtatccg ctcatgagac aataaccctg   2700
ataaatgctt caataatatt gaaaaaggaa gagtatgagt attcaacatt tccgtgtcgc   2760
ccttattccc ttttttgcgg cattttgcct tcctgttttt gctcacccag aaacgctggt   2820
gaaagtaaaa gatgctgaag atcagttggg tgcacgagtg ggttacatcg aactggatct   2880
caacagcggt aagatccttg agagttttcg ccccgaagaa cgttttccaa tgatgagcac   2940
ttttaaagtt ctgctatgtg gcgcggtatt atcccgtgtt gacgccgggc aagagcaact   3000
cggtcgccgc atacactatt ctcagaatga cttggttgag tactcaccag tcacagaaaa   3060
gcatcttacg gatggcatga cagtaagaga attatgcagt gctgccataa ccatgagtga   3120
taacactgcg gccaacttac ttctgacaac gatcggagga ccgaaggagc taaccgcttt   3180
tttgcacaac atgggggatc atgtaactcg ccttgatcgt tgggaaccgg agctgaatga   3240
agccatacca aacgacgagc gtgacaccac gatgcctgta gcaatggcaa caacgttgcg   3300
caaactatta actggcgaac tacttactct agcttcccgg caacaattaa tagactggat   3360
ggaggcggat aaagttgcag gaccacttct gcgctcggcc cttccggctg gctggtttat   3420
tgctgataaa tctggagccg gtgagcgtgg gtctcgcggt atcattgcag cactggggcc   3480
agatggtaag ccctcccgta tcgtagttat ctacacgacg gggagtcagg caactatgga   3540
tgaacgaaat agacagatcg ctgagatagg tgcctcactg attaagcatt ggtaactgtc   3600
agaccaagtt tactcatata tactttagat tgatttaaaa cttcattttt aatttaaaag   3660
gatctaggtg aagatccttt ttgataatct catgaccaaa atcccttaac gtgagttttc   3720
gttccactga gcgtcagacc ccgtagaaaa gatcaaagga tcttcttgag atcctttttt   3780
tctgcgcgta atctgctgct tgcaaacaaa aaaaccaccg ctaccagcgg tggtttgttt   3840
gccggatcaa gagctaccaa ctctttttcc gaaggtaact ggcttcagca gagcgcagat   3900
accaaatact gtccttctag tgtagccgta gttaggccac cacttcaaga actctgtagc   3960
accgcctaca tacctcgctc tgctaatcct gttaccagtg gctgctgcca gtggcgataa   4020
gtcgtgtctt accgggttgg actcaagacg atagttaccg gataaggcgc agcggtcggg   4080
ctgaacgggg ggttcgtgca cacagcccag cttggagcga acgacctaca ccgaactgag   4140
atacctacag cgtgagctat gagaaagcgc cacgcttccc gaagggagaa aggcggacag   4200
gtatccggta agcggcaggg tcggaacagg agagcgcacg agggagcttc caggggggaaa   4260
cgcctggtat ctttatagtc ctgtcgggtt tcgccacctc tgacttgagc gtcgattttt   4320
gtgatgctcg tcaggggggc ggagcctatg gaaaaacgcc agcaacgcgg cctttttacg   4380
gttcctggcc ttttgctggc cttttgctca catgttcttt cctgcgttat cccctgattc   4440
tgtggataac cgtattaccg cctttgagtg agctgatacc gctcgccgca gccgaacgac   4500
cgagcgcagc gagtcagtga gcgaggaagc ggaagagcgc ctgatgcggt attttctcct   4560
tacgcatctg tgcggtattt cacaccgcat atggtgcact ctcagtacaa tctgctctga   4620
tgccgcatag ttaagccagt atacactccg ctatcgctac gtgactgggt catggctgcg   4680
ccccgacacc cgccaacacc cgctgacgcg ccctgacggg cttgtctgct cccggcatcc   4740
gcttacagac aagctgtgac cgtctccggg agctgcatgt gtcagaggtt ttcaccgtca   4800
```

tcaccgaaac gcgcgaggca gcagatcaat tcgcgcgcga aggcgaagcg gcatgcattt 4860
acgttgacac catcgaatgg tgcaaaacct ttcgcggtat ggcatgatag cgcccggaag 4920
agagtcaatt cagggtggtg aatgtgaaac cagtaacgtt atacgatgtc gcagagtatg 4980
ccggtgtctc ttatcagacc gtttcccgcg tggtgaacca ggccagccac gtttctgcga 5040
aaacgcggga aaaagtggaa gcggcgatgg cggagctgaa ttacattccc aaccgcgtgg 5100
cacaacaact ggcgggcaaa cagtcgttgc tgattggcgt tgccacctcc agtctggccc 5160
tgcacgcgcc gtcgcaaatt gtcgcggcga ttaaatctcg cgccgatcaa ctgggtgcca 5220
gcgtggtggt gtcgatggta gaacgaagcg gcgtcgaagc ctgtaaagcg gcggtgcaca 5280
atcttctcgc gcaacgcgtc agtgggctga tcattaacta tccgctggat gaccaggatg 5340
ccattgctgt ggaagctgcc tgcactaatg ttccggcgtt atttcttgat gtctctgacc 5400
agacacccat caacagtatt attttctccc atgaagacgg tacgcgactg ggcgtggagc 5460
atctggtcgc attgggtcac cagcaaatcg cgctgttagc gggcccatta agttctgtct 5520
cggcgcgtct gcgtctggct ggctggcata aatatctcac tcgcaatcaa attcagccga 5580
tagcggaacg ggaaggcgac tggagtgcca tgtccggttt tcaacaaacc atgcaaatgc 5640
tgaatgaggg catcgttccc actgcgatgc tggttgccaa cgatcagatg gcgctgggcg 5700
caatgcgcgc cattaccgag tccgggctgc gcgttggtgc ggatatctcg gtagtgggat 5760
acgacgatac cgaagacagc tcatgttata tcccgccgtc aaccaccatc aaacaggatt 5820
ttcgcctgct ggggcaaacc agcgtggacc gcttgctgca actctctcag ggccaggcgg 5880
tgaagggcaa tcagctgttg cccgtctcac tggtgaaaag aaaaaccacc ctggcgccca 5940
atacgcaaac cgcctctccc cgcgcgttgg ccgattcatt aatgcagctg gcacgacagg 6000
tttcccgact ggaaagcggg cagtgagcgc aacgcaatta atgtgagtta gcgcgaattg 6060
atctg 6065

<210> SEQ ID NO 23
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 23
ttgtctgctc ccggcatccg cttacagaca agctgtgacc gtctccggga gctgcatgtg 60
tcagaggttt tcaccgtcat caccgaaacg cgcgaggcag cagatcaatt cgcgcgcgaa 120
ggcgaagcgg catgcattta cgttgacacc atcgaatggt gcaaaacctt tcgcggtatg 180
gcatgatagc gcccggaaga gagtcaattc agggtggtga atgtgaaacc agtaacgtta 240
tacgatgtcg cagagtatgc cggtgtctct tatcagaccg tttcccgcgt ggtgaaccag 300
gccagccacg tttctgcgaa aacgcgggaa aaagtggaag cggcgatggc ggagctgaat 360
tacattccca accgcgtggc acaacaactg gcgggcaaac agtcgttgct gattggcgtt 420
gccacctcca gtctggccct gcacgcgccg tcgcaaattg tcgcggcgat taaatctcgc 480
gccgatcaac tgggtgccag cgtggtggtg tcgatggtag aacgaagcgg cgtcgaagcc 540
tgtaaagcgg cggtgcacaa tcttctcgcg caacgcgtca gtgggctgat cattaactat 600
ccgctggatg accaggatgc cattgctgtg gaagctgcct gcactaatgt tccggcgtta 660
tttcttgatg tctctgacca gacacccatc aacagtatta ttttctccca tgaagacggt 720
acgcgactgg gcgtggagca tctggtcgca ttgggtcacc agcaaatcgc gctgttagcg 780

```
ggcccattaa gttctgtctc ggcgcgtctg cgtctggctg gctggcataa atatctcact    840
cgcaatcaaa ttcagccgat agcggaacgg gaaggcgact ggagtgccat gtccggtttt    900
caacaaacca tgcaaatgct gaatgagggc atcgttccca ctgcgatgct ggttgccaac    960
gatcagatgg cgctgggcgc aatgcgcgcc attaccgagt ccgggctgcg cgttggtgcg   1020
gatatctcgg tagtgggata cgacgatacc gaagacagct catgttatat cccgccgtca   1080
accaccatca aacaggattt tcgcctgctg gggcaaacca gcgtggaccg cttgctgcaa   1140
ctctctcagg gccaggcggt gaagggcaat cagctgttgc ccgtctcact ggtgaaaaga   1200
aaaaccaccc tggcgcccaa tacgcaaacc gcctctcccc gcgcgttggc cgattcatta   1260
atgcagctgg cacgacaggt ttcccgactg gaaagcgggc agtgagcgca acgcaattaa   1320
tgtgagttag cgcgaattga tctggtttga cagcttatca tcgactgcac ggtgcaccaa   1380
tgcttctggc gtcaggcagc catcggaagc tgtggtatgg ctgtgcaggt cgtaaatcac   1440
tgcataattc gtgtcgctca aggcgcactc ccgttctgga taatgttttt tgcgccgaca   1500
tcataacggt tctggcaaat attctgaaat gagctgttga caattaatca tccggctcgt   1560
ataatgtgtg gaattgtgag cggataacaa tttcacacag gaaacagcgc cgctgagaaa   1620
aagcgaagcg gcactgctct ttaacaattt atcagacaat ctgtgtgggc actcgaccgg   1680
aattatcgat taactttatt attaaaaatt aaagaggtat atattaatgt atcgattaaa   1740
taaggaggaa taaaccatgt gtgcgacctc ttctcaattt actcagatta ccgagcataa   1800
ttcccgtcgt tccgcaaact atcagccaaa cctgtggaat ttcgaattcc tgcaatccct   1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgtttttg agcgtttcaa   2160
ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga acaacctgaa agaaggcatt aataccaagg ttgcagaaca   2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta acgacacgtc   2820
ctattctatt ctgaaagaga aaggtcataa caacctgtcc tatctgacga aaagctggcg   2880
tgaactgtgc aaagcctttc tgcaagaggc gaaatggtcc aacaacaaaa ttatcccggc   2940
tttctccaag tacctggaaa acgccagcgt ttcctcctcc ggtgtagcgc tgctggcgcc   3000
gtcttacttt tccgtatgcc agcagcagga agacatctcc gaccacgcgc tgcgttccct   3060
gaccgacttc catggtctgg tgcgttctag ctgcgttatc ttccgcctgt gcaacgatct   3120
ggccacctct gcggcggagc tggaacgtgg cgagactacc aattctatca ttagctacat   3180
```

gcacgaaaac gatggtacca gcgaggaaca ggcccgcgaa gaactgcgta aactgatcga 3240
cgccgaatgg aaaaagatga atcgtgaacg cgttagcgac tccaccctgc tgcctaaagc 3300
gttcatggaa atcgcagtta acatggcacg tgtttcccac tgcacctacc agtatggcga 3360
tggtctgggt cgcccagact acgcgactga aaaccgcatc aaactgctgc tgattgaccc 3420
tttcccgatt aaccagctga tgtatgtcta actgcatcgc ccttaggagg taaaaaaaaa 3480
tgactgccga caacaatagt atgccccatg gtgcagtatc tagttacgcc aaattagtgc 3540
aaaaccaaac acctgaagac attttggaag agtttcctga aattattcca ttacaacaaa 3600
gacctaatac ccgatctagt gagacgtcaa atgacgaaag cggagaaaca tgtttttctg 3660
gtcatgatga ggagcaaatt aagttaatga atgaaaattg tattgttttg gattgggacg 3720
ataatgctat tggtgccggt accaagaaag tttgtcattt aatggaaaat attgaaaagg 3780
gtttactaca tcgtgcattc tccgtcttta ttttcaatga acaaggtgaa ttacttttac 3840
aacaaagagc cactgaaaaa ataactttcc ctgatctttg gactaacaca tgctgctctc 3900
atccactatg tattgatgac gaattaggtt tgaagggtaa gctagacgat aagattaagg 3960
gcgctattac tgcggcggtg agaaaactag atcatgaatt aggtattcca gaagatgaaa 4020
ctaagacaag ggtaagttt cactttttaa acagaatcca ttacatggca ccaagcaatg 4080
aaccatgggg tgaacatgaa attgattaca tcctatttta taagatcaac gctaaagaaa 4140
acttgactgt caacccaaac gtcaatgaag ttagagactt caaatgggtt tcaccaaatg 4200
atttgaaaac tatgtttgct gacccaagtt acaagtttac gccttggttt aagattattt 4260
gcgagaatta cttattcaac tggtgggagc aattagatga cctttctgaa gtggaaaatg 4320
acaggcaaat tcatagaatg ctataacaac gcgtcctgca gctggtacca tatgggaatt 4380
cgaagctttc tagaacaaaa actcatctca gaagaggatc tgaatagcgc cgtcgaccat 4440
catcatcatc atcattgagt ttaaacggtc tccagcttgg ctgttttggc ggatgagaga 4500
agattttcag cctgatacag attaaatcag aacgcagaag cggtctgata aaacagaatt 4560
tgcctggcgg cagtagcgcg gtggtcccac ctgaccccat gccgaactca gaagtgaaac 4620
gccgtagcgc cgatggtagt gtggggtctc cccatgcgag agtagggaac tgccaggcat 4680
caaataaaac gaaaggctca gtcgaaagac tgggcctttc gttttatctg ttgtttgtcg 4740
gtgaacgctc tcctgagtag gacaaatccg ccgggagcgg atttgaacgt tgcgaagcaa 4800
cggcccggag ggtggcgggc aggacgcccg ccataaactg ccaggcatca aattaagcag 4860
aaggccatcc tgacggatgg cctttttgcg tttctacaaa ctctttttgt ttatttttct 4920
aaatacattc aaatatgtat ccgcttaacc ggaattgcca gctggggcgc cctctggtaa 4980
ggttgggaag ccctgcaaag taaactggat ggctttctcg ccgccaagga tctgatggcg 5040
caggggatca agctctgatc aagagacagg atgaggatcg tttcgcatga ttgaacaaga 5100
tggattgcac gcaggttctc cggccgcttg ggtggagagg ctattcggct atgactgggc 5160
acaacagaca atcggctgct ctgatgccgc cgtgttccgg ctgtcagcgc aggggcgccc 5220
ggttcttttt gtcaagaccg acctgtccgg tgccctgaat gaactgcaag acgaggcagc 5280
gcggctatcg tggctggcca cgacgggcgt tccttgcgca gctgtgctcg acgttgtcac 5340
tgaagcggga agggactggc tgctattggg cgaagtgccg gggcaggatc tcctgtcatc 5400
tcaccttgct cctgccgaga aagtatccat catggctgat gcaatgcggc ggctgcatac 5460
gcttgatccg gctacctgcc cattcgacca ccaagcgaaa catcgcatcg agcgagcacg 5520
tactcggatg gaagccggtc ttgtcgatca ggatgatctg gacgaagagc atcaggggct 5580
cgcgccagcc gaactgttcg ccaggctcaa ggcgagcatg cccgacggcg aggatctcgt 5640
cgtgacccat ggcgatgcct gcttgccgaa tatcatggtg gaaaatggcc gcttttctgg 5700
attcatcgac tgtggccggc tgggtgtggc ggaccgctat caggacatag cgttggctac 5760
ccgtgatatt gctgaagagc ttggcggcga atgggctgac cgcttcctcg tgctttacgg 5820
tatcgccgct cccgattcgc agcgcatcgc cttctatcgc cttcttgacg agttcttctg 5880
acatgaccaa aatcccttaa cgtgagtttt cgttccactg agcgtcagac cccgtagaaa 5940
agatcaaagg atcttcttga gatccttttt ttctgcgcgt aatctgctgc ttgcaaacaa 6000
aaaaaccacc gctaccagcg gtggtttgtt tgccggatca agagctacca actctttttc 6060
cgaaggtaac tggcttcagc agagcgcaga taccaaatac tgtccttcta gtgtagccgt 6120
agttaggcca ccacttcaag aactctgtag caccgcctac atacctcgct ctgctaatcc 6180
tgttaccagt ggctgctgcc agtggcgata agtcgtgtct taccgggttg gactcaagac 6240
gatagttacc ggataaggcg cagcggtcgg gctgaacggg gggttcgtgc acacagccca 6300
gcttggagcg aacgacctac accgaactga gatacctaca gcgtgagcta tgagaaagcg 6360
ccacgcttcc cgaagggaga aaggcggaca ggtatccggt aagcggcagg gtcggaacag 6420
gagagcgcac gagggagctt ccagggggaa acgcctggta tctttatagt cctgtcgggt 6480
ttcgccacct ctgacttgag cgtcgatttt tgtgatgctc gtcagggggg cggagcctat 6540
ggaaaaacgc cagcaacgcg gcctttttac ggttcctggc cttttgctgg ccttttgctc 6600
acatgttctt tcctgcgtta tcccctgatt ctgtggataa ccgtattacc gcctttgagt 6660
gagctgatac cgctcgccgc agccgaacga ccgagcgcag cgagtcagtg agcgaggaag 6720
cggaagagcg cctgatgcgg tattttctcc ttacgcatct gtgcggtatt tcacaccgca 6780
tatggtgcac tctcagtaca atctgctctg atgccgcata gttaagccag tatacactcc 6840
gctatcgcta cgtgactggg tcatggctgc gccccgacac ccgccaacac ccgctgacgc 6900
gccctgacgg gc 6912

<210> SEQ ID NO 24
<211> LENGTH: 7902
<212> TYPE: DNA
<213> ORGANISM: Artificial Sequence
<220> FEATURE:
<223> OTHER INFORMATION: Synthetic Construct

<400> SEQUENCE: 24
ttgtctgctc ccggcatccg cttacagaca agctgtgacc gtctccggga gctgcatgtg 60
tcagaggttt tcaccgtcat caccgaaacg cgcgaggcag cagatcaatt cgcgcgcgaa 120
ggcgaagcgg catgcattta cgttgacacc atcgaatggt gcaaaacctt tcgcggtatg 180
gcatgatagc gcccggaaga gagtcaattc agggtggtga atgtgaaacc agtaacgtta 240
tacgatgtcg cagagtatgc cggtgtctct tatcagaccg tttcccgcgt ggtgaaccag 300
gccagccacg tttctgcgaa aacgcgggaa aaagtggaag cggcgatggc ggagctgaat 360
tacattccca accgcgtggc acaacaactg gcgggcaaac agtcgttgct gattggcgtt 420
gccacctcca gtctggccct gcacgcgccg tcgcaaattg tcgcggcgat taaatctcgc 480
gccgatcaac tgggtgccag cgtggtggtg tcgatggtag aacgaagcgg cgtcgaagcc 540
tgtaaagcgg cggtgcacaa tcttctcgcg caacgcgtca gtgggctgat cattaactat 600
ccgctggatg accaggatgc cattgctgtg gaagctgcct gcactaatgt tccggcgtta 660
tttcttgatg tctctgacca gacacccatc aacagtatta ttttctccca tgaagacggt 720

```
acgcgactgg gcgtggagca tctggtcgca ttgggtcacc agcaaatcgc gctgttagcg    780
ggcccattaa gttctgtctc ggcgcgtctg cgtctggctg gctggcataa atatctcact    840
cgcaatcaaa ttcagccgat agcggaacgg gaaggcgact ggagtgccat gtccggtttt    900
caacaaacca tgcaaatgct gaatgagggc atcgttccca ctgcgatgct ggttgccaac    960
gatcagatgg cgctgggcgc aatgcgcgcc attaccgagt ccgggctgcg cgttggtgcg   1020
gatatctcgg tagtgggata cgacgatacc gaagacagct catgttatat cccgccgtca   1080
accaccatca aacaggattt tcgcctgctg gggcaaacca gcgtggaccg cttgctgcaa   1140
ctctctcagg gccaggcggt gaagggcaat cagctgttgc ccgtctcact ggtgaaaaga   1200
aaaaccaccc tggcgcccaa tacgcaaacc gcctctcccc gcgcgttggc cgattcatta   1260
atgcagctgg cacgacaggt ttcccgactg gaaagcgggc agtgagcgca acgcaattaa   1320
tgtgagttag cgcgaattga tctggtttga cagcttatca tcgactgcac ggtgcaccaa   1380
tgcttctggc gtcaggcagc catcggaagc tgtggtatgg ctgtgcaggt cgtaaatcac   1440
tgcataattc gtgtcgctca aggcgcactc ccgttctgga taatgttttt tgcgccgaca   1500
tcataacggt tctggcaaat attctgaaat gagctgttga caattaatca tccggctcgt   1560
ataatgtgtg gaattgtgag cggataacaa tttcacacag gaaacagcgc cgctgagaaa   1620
aagcgaagcg gcactgctct ttaacaattt atcagacaat ctgtgtgggc actcgaccgg   1680
aattatcgat taactttatt attaaaaatt aaagaggtat atattaatgt atcgattaaa   1740
taaggaggaa taaaccatgt gtgcgacctc ttctcaattt actcagatta ccgagcataa   1800
ttcccgtcgt tccgcaaact atcagccaaa cctgtggaat ttcgaattcc tgcaatccct   1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgtttttg agcgtttcaa   2160
ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga acaacctgaa agaaggcatt aataccaagg ttgcagaaca   2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta acgacacgtc   2820
ctattctatt ctgaaagaga aaggtcataa caacctgtcc tatctgacga aaagctggcg   2880
tgaactgtgc aaagcctttc tgcaagaggc gaaatggtcc aacaacaaaa ttatcccggc   2940
tttctccaag tacctggaaa acgccagcgt ttcctcctcc ggtgtagcgc tgctggcgcc   3000
gtcttacttt tccgtatgcc agcagcagga agacatctcc gaccacgcgc tgcgttccct   3060
gaccgacttc catggtctgg tgcgttctag ctgcgttatc ttccgcctgt gcaacgatct   3120
```

-continued

```
ggccacctct gcggcggagc tggaacgtgg cgagactacc aattctatca ttagctacat   3180
gcacgaaaac gatggtacca gcgaggaaca ggcccgcgaa gaactgcgta aactgatcga   3240
cgccgaatgg aaaaagatga atcgtgaacg cgttagcgac tccaccctgc tgcctaaagc   3300
gttcatggaa atcgcagtta acatggcacg tgtttcccac tgcacctacc agtatggcga   3360
tggtctgggt cgcccagact acgcgactga aaaccgcatc aaactgctgc tgattgaccc   3420
tttcccgatt aaccagctga tgtatgtcta actgcattcg cccttaggag gtaaaaaaac   3480
atgagttttg atattgccaa atacccgacc ctggcactgg tcgactccac ccaggagtta   3540
cgactgttgc cgaaagagag tttaccgaaa ctctgcgacg aactgcgccg ctatttactc   3600
gacagcgtga gccgttccag cgggcacttc gcctccgggc tgggcacggt cgaactgacc   3660
gtggcgctgc actatgtcta caacaccccg tttgaccaat tgatttggga tgtggggcat   3720
caggcttatc cgcataaaat tttgaccgga cgccgcgaca aaatcggcac catccgtcag   3780
aaaggcggtc tgcacccgtt cccgtggcgc ggcgaaagcg aatatgacgt attaagcgtc   3840
gggcattcat caacctccat cagtgccgga attggtattg cggttgctgc cgaaaaagaa   3900
ggcaaaaatc gccgcaccgt ctgtgtcatt ggcgatggcg cgattaccgc aggcatggcg   3960
tttgaagcga tgaatcacgc gggcgatatc cgtcctgata tgctggtgat tctcaacgac   4020
aatgaaatgt cgatttccga aaatgtcggc gcgctcaaca accatctggc acagctgctt   4080
tccggtaagc tttactcttc actgcgcgaa ggcgggaaaa aagttttctc tggcgtgccg   4140
ccaattaaag agctgctcaa acgcaccgaa gaacatatta aaggcatggt agtgcctggc   4200
acgttgtttg aagagctggg ctttaactac atcggcccgg tggacggtca cgatgtgctg   4260
gggcttatca ccacgctaaa gaacatgcgc gacctgaaag gcccgcagtt cctgcatatc   4320
atgaccaaaa aaggtcgtgg ttatgaaccg gcagaaaaag acccgatcac tttccacgcc   4380
gtgcctaaat ttgatccctc cagcggttgt ttgccgaaaa gtagcggcgg tttgccgagc   4440
tattcaaaaa tctttggcga ctggttgtgc gaaacggcag cgaaagacaa caagctgatg   4500
gcgattactc cggcgatgcg tgaaggttcc ggcatggtcg agttttcacg taaattcccg   4560
gatcgctact tcgacgtggc aattgccgag caacacgcgg tgacctttgc tgcgggtctg   4620
gcgattggtg ggtacaaacc cattgtcgcg atttactcca ctttcctgca acgcgcctat   4680
gatcaggtgc tgcatgacgt ggcgattcaa aagcttccgg tcctgttcgc catcgaccgc   4740
gcgggcattg ttggtgctga cggtcaaacc catcagggtg cttttgatct ctcttacctg   4800
cgctgcatac cggaaatggt cattatgacc ccgagcgatg aaaacgaatg tcgccagatg   4860
ctctataccg gctatcacta taacgatggc ccgtcagcgg tgcgctaccc gcgtggcaac   4920
gcggtcggcg tggaactgac gccgctggaa aaactaccaa ttggcaaagg cattgtgaag   4980
cgtcgtggcg agaaactggc gatccttaac tttggtacgc tgatgccaga agcggcgaaa   5040
gtcgccgaat cgctgaacgc cacgctggtc gatatgcgtt ttgtgaaacc gcttgatgaa   5100
gcgttaattc tggaaatggc cgccagccat gaagcgctgg tcaccgtaga agaaaacgcc   5160
attatgggcg gcgcaggcag cggcgtgaac gaagtgctga tggcccatcg taaaccagta   5220
cccgtgctga acattggcct gccggacttc tttattccgc aaggaactca ggaagaaatg   5280
cgcgccgaac tcggcctcga tgccgctggt atggaagcca aaatcaaggc ctggctggca   5340
taactgcagc tggtaccata tgggaattcg aagctttcta gaacaaaaac tcatctcaga   5400
agaggatctg aatagcgccg tcgaccatca tcatcatcat cattgagttt aaacggtctc   5460
cagcttggct gttttggcgg atgagagaag attttcagcc tgatacagat taaatcagaa   5520
```

-continued cgcagaagcg gtctgataaa acagaatttg cctggcggca gtagcgcggt ggtcccacct 5580
gaccccatgc cgaactcaga agtgaaacgc cgtagcgccg atggtagtgt ggggtctccc 5640
catgcgagag tagggaactg ccaggcatca aataaaacga aaggctcagt cgaaagactg 5700
ggcctttcgt tttatctgtt gtttgtcggt gaacgctctc ctgagtagga caaatccgcc 5760
gggagcggat ttgaacgttg cgaagcaacg gcccggaggg tggcgggcag gacgcccgcc 5820
ataaactgcc aggcatcaaa ttaagcagaa ggccatcctg acggatggcc tttttgcgtt 5880
tctacaaact ctttttgttt atttttctaa atacattcaa atatgtatcc gcttaaccgg 5940
aattgccagc tggggcgccc tctggtaagg ttgggaagcc ctgcaaagta aactggatgg 6000
ctttctcgcc gccaaggatc tgatggcgca ggggatcaag ctctgatcaa gagacaggat 6060
gaggatcgtt tcgcatgatt gaacaagatg gattgcacgc aggttctccg gccgcttggg 6120
tggagaggct attcggctat gactgggcac aacagacaat cggctgctct gatgccgccg 6180
tgttccggct gtcagcgcag gggcgcccgg ttctttttgt caagaccgac ctgtccggtg 6240
ccctgaatga actgcaagac gaggcagcgc ggctatcgtg gctggccacg acgggcgttc 6300
cttgcgcagc tgtgctcgac gttgtcactg aagcgggaag ggactggctg ctattgggcg 6360
aagtgccggg gcaggatctc ctgtcatctc accttgctcc tgccgagaaa gtatccatca 6420
tggctgatgc aatgcggcgg ctgcatacgc ttgatccggc tacctgccca ttcgaccacc 6480
aagcgaaaca tcgcatcgag cgagcacgta ctcggatgga agccggtctt gtcgatcagg 6540
atgatctgga cgaagagcat caggggctcg cgccagccga actgttcgcc aggctcaagg 6600
cgagcatgcc cgacggcgag gatctcgtcg tgacccatgg cgatgcctgc ttgccgaata 6660
tcatggtgga aaatggccgc ttttctggat tcatcgactg tggccggctg ggtgtggcgg 6720
accgctatca ggacatagcg ttggctaccc gtgatattgc tgaagagctt ggcggcgaat 6780
gggctgaccg cttcctcgtg ctttacggta tcgccgctcc cgattcgcag cgcatcgcct 6840
tctatcgcct tcttgacgag ttcttctgac gcatgaccaa aatcccttaa cgtgagtttt 6900
cgttccactg agcgtcagac cccgtagaaa agatcaaagg atcttcttga gatccttttt 6960
ttctgcgcgt aatctgctgc ttgcaaacaa aaaaaccacc gctaccagcg gtggtttgtt 7020
tgccggatca agagctacca actctttttc cgaaggtaac tggcttcagc agagcgcaga 7080
taccaaatac tgtccttcta gtgtagccgt agttaggcca ccacttcaag aactctgtag 7140
caccgcctac atacctcgct ctgctaatcc tgttaccagt ggctgctgcc agtggcgata 7200
agtcgtgtct taccgggttg gactcaagac gatagttacc ggataaggcg cagcggtcgg 7260
gctgaacggg gggttcgtgc acacagccca gcttggagcg aacgacctac accgaactga 7320
gatacctaca gcgtgagcta tgagaaagcg ccacgcttcc cgaagggaga aaggcggaca 7380
ggtatccggt aagcggcagg gtcggaacag gagagcgcac gagggagctt ccagggggaa 7440
acgcctggta tctttatagt cctgtcgggt ttcgccacct ctgacttgag cgtcgatttt 7500
tgtgatgctc gtcagggggg cggagcctat ggaaaaacgc cagcaacgcg gcctttttac 7560
ggttcctggc cttttgctgg ccttttgctc acatgttctt tcctgcgtta tcccctgatt 7620
ctgtggataa ccgtattacc gcctttgagt gagctgatac cgctcgccgc agccgaacga 7680
ccgagcgcag cgagtcagtg agcgaggaag cggaagagcg cctgatgcgg tattttctcc 7740
ttacgcatct gtgcggtatt tcacaccgca tatggtgcac tctcagtaca atctgctctg 7800
atgccgcata gttaagccag tatacactcc gctatcgcta cgtgactggg tcatggctgc 7860
gccccgacac ccgccaacac ccgctgacgc gccctgacgg gc 7902

<210> SEQ ID NO 25
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 25
ctggcgtaat agcgaagagg cccgcaccga tcgcccttcc caacagttgc gcagcctgaa 60
tggcgaatgg cgcctgatgc ggtattttct ccttacgcat ctgtgcggta tttcacaccg 120
catatggtgc actctcagta caatctgctc tgatgccgca tagttaagcc agccccgaca 180
cccgccaaca cccgctgacg agcttagtaa agccctcgct agattttaat gcggatgttg 240
cgattacttc gccaactatt gcgataacaa gaaaaagcca gcctttcatg atatatctcc 300
caatttgtgt agggcttatt atgcacgctt aaaaataata aaagcagact tgacctgata 360
gtttggctgt gagcaattat gtgcttagtg catctaacgc ttgagttaag ccgcgccgcg 420
aagcggcgtc ggcttgaacg aattgttaga cattatttgc cgactacctt ggtgatctcg 480
cctttcacgt agtggacaaa ttcttccaac tgatctgcgc gcgaggccaa gcgatcttct 540
tcttgtccaa gataagcctg tctagcttca agtatgacgg gctgatactg ggccggcagg 600
cgctccattg cccagtcggc agcgacatcc ttcggcgcga ttttgccggt tactgcgctg 660
taccaaatgc gggacaacgt aagcactaca tttcgctcat cgccagccca gtcgggcggc 720
gagttccata gcgttaaggt ttcatttagc gcctcaaata gatcctgttc aggaaccgga 780
tcaaagagtt cctccgccgc tggacctacc aaggcaacgc tatgttctct tgcttttgtc 840
agcaagatag ccagatcaat gtcgatcgtg gctggctcga agatacctgc aagaatgtca 900
ttgcgctgcc attctccaaa ttgcagttcg cgcttagctg gataacgcca cggaatgatg 960
tcgtcgtgca caacaatggt gacttctaca gcgcggagaa tctcgctctc tccaggggaa 1020
gccgaagttt ccaaaaggtc gttgatcaaa gctcgccgcg ttgtttcatc aagccttacg 1080
gtcaccgtaa ccagcaaatc aatatcactg tgtggcttca ggccgccatc cactgcggag 1140
ccgtacaaat gtacggccag caacgtcggt tcgagatggc gctcgatgac gccaactacc 1200
tctgatagtt gagtcgatac ttcggcgatc accgcttccc tcatgatgtt taactttgtt 1260
ttagggcgac tgccctgctg cgtaacatcg ttgctgctcc ataacatcaa acatcgaccc 1320
acggcgtaac gcgcttgctg cttggatgcc cgaggcatag actgtacccc aaaaaaacag 1380
tcataacaag ccatgaaaac cgccactgcg ccgttaccac cgctgcgttc ggtcaaggtt 1440
ctggaccagt tgcgtgagcg catacgctac ttgcattaca gcttacgaac cgaacaggct 1500
tatgtccact gggttcgtgc cttcatccgt ttccacggtg tgcgtcaccc ggcaaccttg 1560
ggcagcagcg aagtcgaggc atttctgtcc tggctggcga acgagcgcaa ggtttcggtc 1620
tccacgcatc gtcaggcatt ggcggccttg ctgttcttct acggcaaggt gctgtgcacg 1680
gatctgccct ggcttcagga gatcggaaga cctcggccgt cgcggcgctt gccggtggtg 1740
ctgaccccgg atgaagtggt tcgcatcctc ggttttctgg aaggcgagca tcgtttgttc 1800
gcccagcttc tgtatggaac gggcatgcgg atcagtgagg gtttgcaact gcgggtcaag 1860
gatctggatt tcgatcacgg cacgatcatc gtgcgggagg gcaagggctc caaggatcgg 1920
gccttgatgt tacccgagag cttggcaccc agcctgcgcg agcaggggaa ttaattccca 1980
cgggttttgc tgcccgcaaa cgggctgttc tggtgttgct agtttgttat cagaatcgca 2040
gatccggctt cagccggttt gccggctgaa agcgctattt cttccagaat tgccatgatt 2100

-continued

```
ttttccccac gggaggcgtc actggctccc gtgttgtcgg cagctttgat tcgataagca   2160
gcatcgcctg tttcaggctg tctatgtgtg actgttgagc tgtaacaagt tgtctcaggt   2220
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct tttttacacc gttttcatct gtgcatatgg   2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgtttttgc gtgagccatg agaacgaacc attgagatca   2580
tacttacttt gcatgtcact caaaaatttt gcctcaaaac tggtgagctg aatttttgca   2640
gttaaagcat cgtgtagtgt ttttcttagt ccgttatgta ggtaggaatc tgatgtaatg   2700
gttgttggta ttttgtcacc attcattttt atctggttgt tctcaagttc ggttacgaga   2760
tccatttgtc tatctagttc aacttggaaa atcaacgtat cagtcgggcg gcctcgctta   2820
tcaaccacca atttcatatt gctgtaagtg tttaaatctt tacttattgg tttcaaaacc   2880
cattggttaa gccttttaaa ctcatggtag ttattttcaa gcattaacat gaacttaaat   2940
tcatcaaggc taatctctat atttgccttg tgagttttct tttgtgttag ttcttttaat   3000
aaccactcat aaatcctcat agagtatttg ttttcaaaag acttaacatg ttccagatta   3060
tattttatga attttttaa ctggaaaaga taaggcaata tctcttcact aaaaactaat   3120
tctaattttt cgcttgagaa cttggcatag tttgtccact ggaaaatctc aaagccttta   3180
accaaaggat tcctgatttc cacagttctc gtcatcagct ctctggttgc tttagctaat   3240
acaccataag cattttccct actgatgttc atcatctgag cgtattggtt ataagtgaac   3300
gataccgtcc gttctttcct tgtagggttt tcaatcgtgg ggttgagtag tgccacacag   3360
cataaaatta gcttggtttc atgctccgtt aagtcatagc gactaatcgc tagttcattt   3420
gctttgaaaa caactaattc agacatacat ctcaattggt ctaggtgatt ttaatcacta   3480
taccaattga gatgggctag tcaatgataa ttactagtcc ttttcctttg agttgtgggt   3540
atctgtaaat tctgctagac ctttgctgga aaacttgtaa attctgctag accctctgta   3600
aattccgcta gacctttgtg tgtttttttt gtttatattc aagtggttat aatttataga   3660
ataaagaaag aataaaaaaa gataaaaaga atagatccca gccctgtgta taactcacta   3720
ctttagtcag ttccgcagta ttacaaaagg atgtcgcaaa cgctgtttgc tcctctacaa   3780
aacagacctt aaaaccctaa aggcttaagt agcaccctcg caagctcggg caaatcgctg   3840
aatattcctt ttgtctccga ccatcaggca cctgagtcgc tgtctttttc gtgacattca   3900
gttcgctgcg ctcacggctc tggcagtgaa tgggggtaaa tggcactaca ggcgcctttt   3960
atggattcat gcaaggaaac tacccataat acaagaaaag cccgtcacgg gcttctcagg   4020
gcgttttatg gcgggtctgc tatgtggtgc tatctgactt tttgctgttc agcagttcct   4080
gccctctgat tttccagtct gaccacttcg gattatcccg tgacaggtca ttcagactgg   4140
ctaatgcacc cagtaaggca gcggtatcat caacaggctt acccgtctta ctgtcgggaa   4200
ttcgcgttgg ccgattcatt aatgcagatt ctgaaatgag ctgttgacaa ttaatcatcc   4260
ggctcgtata atgtgtggaa ttgtgagcgg ataacaattt cacacaggaa acagcgccgc   4320
tgagaaaaag cgaagcggca ctgctcttta acaatttatc agacaatctg tgtgggcact   4380
cgaccggaat tatcgattaa ctttattatt aaaaattaaa gaggtatata ttaatgtatc   4440
gattaaataa ggaggaataa accatgtgtg cgacctcttc tcaatttact cagattaccg   4500
```

```
agcataattc ccgtcgttcc gcaaactatc agccaaacct gtggaatttc gaattcctgc   4560
aatccctgga gaacgacctg aaagtggaaa agctggagga gaaagcgacc aaactggagg   4620
aagaagttcg ctgcatgatc aaccgtgtag acacccagcc gctgtccctg ctggagctga   4680
tcgacgatgt gcagcgcctg ggtctgacct acaaatttga aaaagacatc attaaagccc   4740
tggaaaacat cgtactgctg gacgaaaaca aaaagaacaa atctgacctg cacgcaaccg   4800
ctctgtcttt ccgtctgctg cgtcagcacg gtttcgaggt ttctcaggat gtttttgagc   4860
gtttcaagga taaagaaggt ggtttcagcg gtgaactgaa aggtgacgtc caaggcctgc   4920
tgagcctgta tgaagcgtct tacctgggtt tcgagggtga gaacctgctg gaggaggcgc   4980
gtaccttttc catcacccac ctgaagaaca acctgaaaga aggcattaat accaaggttg   5040
cagaacaagt gagccacgcc ctggaactgc catatcacca gcgtctgcac cgtctggagg   5100
cacgttggtt cctggataaa tacgaaccga aagaaccgca tcaccagctg ctgctggagc   5160
tggcgaagct ggattttaac atggtacaga ccctgcacca gaaagagctg caagatctgt   5220
cccgctggtg gaccgagatg ggcctggcta gcaaactgga ttttgtacgc gaccgcctga   5280
tggaagttta tttctgggca ctgggtatgg cgccagaccc gcagtttggt gaatgtcgca   5340
aagctgttac taaaatgttt ggtctggtga cgatcatcga tgacgtgtat gacgtttatg   5400
gcactctgga cgaactgcaa ctgttcaccg atgctgtaga gcgctgggac gttaacgcta   5460
ttaacaccct gccggactat atgaaactgt gtttcctggc actgtacaac accgttaacg   5520
acacgtccta ttctattctg aaagagaaag gtcataacaa cctgtcctat ctgacgaaaa   5580
gctggcgtga actgtgcaaa gcctttctgc aagaggcgaa atggtccaac aacaaaatta   5640
tcccggcttt ctccaagtac ctggaaaacg ccagcgtttc ctcctccggt gtagcgctgc   5700
tggcgccgtc ttacttttcc gtatgccagc agcaggaaga catctccgac cacgcgctgc   5760
gttccctgac cgacttccat ggtctggtgc gttctagctg cgttatcttc cgcctgtgca   5820
acgatctggc cacctctgcg gcggagctgg aacgtggcga gactaccaat tctatcatta   5880
gctacatgca cgaaaacgat ggtaccagcg aggaacaggc ccgcgaagaa ctgcgtaaac   5940
tgatcgacgc cgaatggaaa aagatgaatc gtgaacgcgt tagcgactcc accctgctgc   6000
ctaaagcgtt catggaaatc gcagttaaca tggcacgtgt ttcccactgc acctaccagt   6060
atggcgatgg tctgggtcgc ccagactacg cgactgaaaa ccgcatcaaa ctgctgctga   6120
ttgacccttt cccgattaac cagctgatgt atgtctaact gcagctggta ccatatggga   6180
attcgaagct ttctagaaca aaaactcatc tcagaagagg atctgaatag cgccgtcgac   6240
catcatcatc atcatcattg agtttaaacg gtctccagct tggctgtttt ggcggatgag   6300
agaagatttt cagcctgata cagattaaat cagaacgcag aagcggtctg ataaaacaga   6360
atttgcctgg cggcagtagc gcggtggtcc cacctgaccc catgccgaac tcagaagtga   6420
aacgccgtag cgccgatggt agtgtggggt ctccccatgc gagagtaggg aactgccagg   6480
catcaaataa aacgaaaggc tcagtcgaaa gactgggcct ttcgttttat ctgttgtttg   6540
tcggtgaacg ctctcctgag taggacaaat ccgccgggag cggatttgaa cgttgcgaag   6600
caacggcccg gagggtggcg ggcaggacgc ccgccataaa ctgccaggca tcaaattaag   6660
cagaaggcca tcctgacgga tggccttttt gcgtttctac aaactctttt tgtttatttt   6720
tctaaataca ttcaaatatg tatccgctca tgagacaata accctgataa atgcttcaat   6780
aat                                                                 6783
```

<210> SEQ ID NO 26
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 26

```
cccgtcttac tgtcgggaat tcgcgttggc cgattcatta atgcagatta ttgaagcatt     60
tatcagggtt attgtctcat gagcggatac atatttgaat gtatttagaa aaataaacaa    120
aaagagtttg tagaaacgca aaaaggccat ccgtcaggat ggccttctgc ttaatttgat    180
gcctggcagt ttatggcggg cgtcctgccc gccaccctcc gggccgttgc ttcgcaacgt    240
tcaaatccgc tcccggcgga tttgtcctac tcaggagagc gttcaccgac aaacaacaga    300
taaaacgaaa ggcccagtct ttcgactgag cctttcgttt tatttgatgc ctggcagttc    360
cctactctcg catggggaga ccccacacta ccatcggcgc tacggcgttt cacttctgag    420
ttcggcatgg ggtcaggtgg gaccaccgcg ctactgccgc caggcaaatt ctgttttatc    480
agaccgcttc tgcgttctga tttaatctgt atcaggctga aaatcttctc tcatccgcca    540
aaacagccaa gctggagacc gtttaaactc aatgatgatg atgatgatgg tcgacggcgc    600
tattcagatc ctcttctgag atgagttttt gttctagaaa gcttcgaatt cccatatggt    660
accagctgca gttagacata catcagctgg ttaatcggga aagggtcaat cagcagcagt    720
ttgatgcggt tttcagtcgc gtagtctggg cgacccagac catcgccata ctggtaggtg    780
cagtgggaaa cacgtgccat gttaactgcg atttccatga acgctttagg cagcagggtg    840
gagtcgctaa cgcgttcacg attcatcttt ttccattcgg cgtcgatcag tttacgcagt    900
tcttcgcggg cctgttcctc gctggtacca tcgttttcgt gcatgtagct aatgatagaa    960
ttggtagtct cgccacgttc cagctccgcc gcagaggtgg ccagatcgtt gcacaggcgg   1020
aagataacgc agctagaacg caccagacca tggaagtcgg tcagggaacg cagcgcgtgg   1080
tcggagatgt cttcctgctg ctggcatacg gaaaagtaag acggcgccag cagcgctaca   1140
ccggaggagg aaacgctggc gttttccagg tacttggaga aagccgggat aattttgttg   1200
ttggaccatt tcgcctcttg cagaaaggct ttgcacagtt cacgccagct tttcgtcaga   1260
taggacaggt tgttatgacc tttctctttc agaatagaat aggacgtgtc gttaacggtg   1320
ttgtacagtg ccaggaaaca cagtttcata tagtccggca gggtgttaat agcgttaacg   1380
tcccagcgct ctacagcatc ggtgaacagt tgcagttcgt ccagagtgcc ataaacgtca   1440
tacacgtcat cgatgatcgt caccagacca aacattttag taacagcttt gcgacattca   1500
ccaaactgcg ggtctggcgc catacccagt gcccagaaat aaacttccat caggcggtcg   1560
cgtacaaaat ccagtttgct agccaggccc atctcggtcc accagcggga cagatcttgc   1620
agctctttct ggtgcagggt ctgtaccatg ttaaaatcca gcttcgccag ctccagcagc   1680
agctggtgat gcggttcttt cggttcgtat ttatccagga accaacgtgc ctccagacgg   1740
tgcagacgct ggtgatatgg cagttccagg gcgtggctca cttgttctgc aaccttggta   1800
ttaatgcctt ctttcaggtt gttcttcagg tgggtgatgg aaaaggtacg cgcctcctcc   1860
agcaggttct caccctcgaa acccaggtaa gacgcttcat acaggctcag caggccttgg   1920
acgtcacctt tcagttcacc gctgaaacca ccttctttat ccttgaaacg ctcaaaaaca   1980
tcctgagaaa cctcgaaacc gtgctgacgc agcagacgga aagacagagc ggttgcgtgc   2040
aggtcagatt tgttcttttt gttttcgtcc agcagtacga tgttttccag ggctttaatg   2100
atgtcttttt caaatttgta ggtcagaccc aggcgctgca catcgtcgat cagctccagc   2160
```

agggacagcg gctgggtgtc tacacggttg atcatgcagc gaacttcttc ctccagtttg 2220
gtcgctttct cctccagctt ttccactttc aggtcgttct ccagggattg caggaattcg 2280
aaattccaca ggtttggctg atagtttgcg gaacgacggg aattatgctc ggtaatctga 2340
gtaaattgag aagaggtcgc acacatggtt tattcctcct tatttaatcg atacattaat 2400
atatacctct ttaattttta ataataaagt taatcgataa ttccggtcga gtgcccacac 2460
agattgtctg ataaattgtt aaagagcagt gccgcttcgc tttttctcag cggcgctgtt 2520
tcctgtgtga aattgttatc cgctcacaat tccacacatt atacgagccg gatgattaat 2580
tgtcaacagc tcatttcaga atctggcgta atagcgaaga ggcccgcacc gatcgccctt 2640
cccaacagtt gcgcagcctg aatggcgaat ggcgcctgat gcggtatttt ctccttacgc 2700
atctgtgcgg tatttcacac cgcatatggt gcactctcag tacaatctgc tctgatgccg 2760
catagttaag ccagccccga cacccgccaa cacccgctga cgagcttagt aaagccctcg 2820
ctagatttta atgcggatgt tgcgattact tcgccaacta ttgcgataac aagaaaaagc 2880
cagcctttca tgatatatct cccaatttgt gtagggctta ttatgcacgc ttaaaaataa 2940
taaaagcaga cttgacctga tagtttggct gtgagcaatt atgtgcttag tgcatctaac 3000
gcttgagtta agccgcgccg cgaagcggcg tcggcttgaa cgaattgtta gacattattt 3060
gccgactacc ttggtgatct cgcctttcac gtagtggaca aattcttcca actgatctgc 3120
gcgcgaggcc aagcgatctt cttcttgtcc aagataagcc tgtctagctt caagtatgac 3180
gggctgatac tgggccggca ggcgctccat tgcccagtcg gcagcgacat ccttcggcgc 3240
gattttgccg gttactgcgc tgtaccaaat gcgggacaac gtaagcacta catttcgctc 3300
atcgccagcc cagtcgggcg gcgagttcca tagcgttaag gtttcattta gcgcctcaaa 3360
tagatcctgt tcaggaaccg gatcaaagag ttcctccgcc gctggaccta ccaaggcaac 3420
gctatgttct cttgcttttg tcagcaagat agccagatca atgtcgatcg tggctggctc 3480
gaagatacct gcaagaatgt cattgcgctg ccattctcca aattgcagtt cgcgcttagc 3540
tggataacgc cacggaatga tgtcgtcgtg cacaacaatg gtgacttcta cagcgcggag 3600
aatctcgctc tctccagggg aagccgaagt ttccaaaagg tcgttgatca aagctcgccg 3660
cgttgtttca tcaagcctta cggtcaccgt aaccagcaaa tcaatatcac tgtgtggctt 3720
caggccgcca tccactgcgg agccgtacaa atgtacggcc agcaacgtcg gttcgagatg 3780
gcgctcgatg acgccaacta cctctgatag ttgagtcgat acttcggcga tcaccgcttc 3840
cctcatgatg tttaactttg ttttagggcg actgccctgc tgcgtaacat cgttgctgct 3900
ccataacatc aaacatcgac ccacggcgta acgcgcttgc tgcttggatg cccgaggcat 3960
agactgtacc ccaaaaaaac agtcataaca agccatgaaa accgccactg cgccgttacc 4020
accgctgcgt tcggtcaagg ttctggacca gttgcgtgag cgcatacgct acttgcatta 4080
cagcttacga accgaacagg cttatgtcca ctgggttcgt gccttcatcc gtttccacgg 4140
tgtgcgtcac ccggcaacct tgggcagcag cgaagtcgag gcatttctgt cctggctggc 4200
gaacgagcgc aaggtttcgg tctccacgca tcgtcaggca ttggcggcct tgctgttctt 4260
ctacggcaag gtgctgtgca cggatctgcc ctggcttcag gagatcggaa gacctcggcc 4320
gtcgcggcgc ttgccggtgg tgctgacccc ggatgaagtg gttcgcatcc tcggttttct 4380
ggaaggcgag catcgtttgt tcgcccagct tctgtatgga acgggcatgc ggatcagtga 4440
gggtttgcaa ctgcgggtca aggatctgga tttcgatcac ggcacgatca tcgtgcggga 4500
gggcaagggc tccaaggatc gggccttgat gttacccgag agcttggcac ccagcctgcg 4560

```
cgagcagggg aattaattcc cacgggtttt gctgcccgca aacgggctgt tctggtgttg   4620
ctagtttgtt atcagaatcg cagatccggc ttcagccggt ttgccggctg aaagcgctat   4680
ttcttccaga attgccatga tttttttcccc acgggaggcg tcactggctc ccgtgttgtc   4740
ggcagctttg attcgataag cagcatcgcc tgtttcaggc tgtctatgtg tgactgttga   4800
gctgtaacaa gttgtctcag gtgttcaatt tcatgttcta gttgctttgt tttactggtt   4860
tcacctgttc tattaggtgt tacatgctgt tcatctgtta cattgtcgat ctgttcatgg   4920
tgaacagctt tgaatgcacc aaaaactcgt aaaagctctg atgtatctat cttttttaca   4980
ccgttttcat ctgtgcatat ggacagtttt ccctttgata tgtaacggtg aacagttgtt   5040
ctacttttgt ttgttagtct tgatgcttca ctgatagata caagagccat aagaacctca   5100
gatccttccg tatttagcca gtatgttctc tagtgtggtt cgttgttttt gcgtgagcca   5160
tgagaacgaa ccattgagat catacttact ttgcatgtca ctcaaaaatt ttgcctcaaa   5220
actggtgagc tgaatttttg cagttaaagc atcgtgtagt gtttttctta gtccgttatg   5280
taggtaggaa tctgatgtaa tggttgttgg tattttgtca ccattcattt ttatctggtt   5340
gttctcaagt tcggttacga gatccatttg tctatctagt tcaacttgga aaatcaacgt   5400
atcagtcggg cggcctcgct tatcaaccac caatttcata ttgctgtaag tgtttaaatc   5460
tttacttatt ggtttcaaaa cccattggtt aagcctttta aactcatggt agttattttc   5520
aagcattaac atgaacttaa attcatcaag gctaatctct atatttgcct tgtgagtttt   5580
cttttgtgtt agttctttta ataaccactc ataaatcctc atagagtatt tgttttcaaa   5640
agacttaaca tgttccagat tatattttat gaattttttt aactggaaaa gataaggcaa   5700
tatctcttca ctaaaaacta attctaattt ttcgcttgag aacttggcat agtttgtcca   5760
ctggaaaatc tcaaagcctt taaccaaagg attcctgatt tccacagttc tcgtcatcag   5820
ctctctggtt gctttagcta atacaccata agcattttcc ctactgatgt tcatcatctg   5880
agcgtattgg ttataagtga acgataccgt ccgttctttc cttgtagggt tttcaatcgt   5940
ggggttgagt agtgccacac agcataaaat tagcttggtt tcatgctccg ttaagtcata   6000
gcgactaatc gctagttcat ttgctttgaa aacaactaat tcagacatac atctcaattg   6060
gtctaggtga ttttaatcac tataccaatt gagatgggct agtcaatgat aattactagt   6120
ccttttcctt tgagttgtgg gtatctgtaa attctgctag acctttgctg gaaaacttgt   6180
aaattctgct agaccctctg taaattccgc tagacctttg tgtgtttttt ttgtttatat   6240
tcaagtggtt ataatttata gaataaagaa agaataaaaa aagataaaaa gaatagatcc   6300
cagccctgtg tataactcac tactttagtc agttccgcag tattacaaaa ggatgtcgca   6360
aacgctgttt gctcctctac aaaacagacc ttaaaaccct aaaggcttaa gtagcaccct   6420
cgcaagctcg ggcaaatcgc tgaatattcc ttttgtctcc gaccatcagg cacctgagtc   6480
gctgtctttt tcgtgacatt cagttcgctg cgctcacggc tctggcagtg aatgggggta   6540
aatggcacta caggcgcctt ttatggattc atgcaaggaa actacccata atacaagaaa   6600
agcccgtcac gggcttctca gggcgtttta tggcgggtct gctatgtggt gctatctgac   6660
tttttgctgt tcagcagttc ctgccctctg attttccagt ctgaccactt cggattatcc   6720
cgtgacaggt cattcagact ggctaatgca cccagtaagg cagcggtatc atcaacaggc   6780
tta                                                                 6783
```

<210> SEQ ID NO 27
<211> LENGTH: 7687

<212> TYPE: DNA
<213> ORGANISM: Artificial Sequence
<220> FEATURE:
<223> OTHER INFORMATION: Synthetic Construct

<400> SEQUENCE: 27

```
ctggcgtaat agcgaagagg cccgcaccga tcgcccttcc caacagttgc gcagcctgaa     60
tggcgaatgg cgcctgatgc ggtattttct ccttacgcat ctgtgcggta tttcacaccg    120
catatggtgc actctcagta caatctgctc tgatgccgca tagttaagcc agccccgaca    180
cccgccaaca cccgctgacg agcttagtaa agccctcgct agattttaat gcggatgttg    240
cgattacttc gccaactatt gcgataacaa gaaaaagcca gcctttcatg atatatctcc    300
caatttgtgt agggcttatt atgcacgctt aaaaataata aaagcagact tgacctgata    360
gtttggctgt gagcaattat gtgcttagtg catctaacgc ttgagttaag ccgcgccgcg    420
aagcggcgtc ggcttgaacg aattgttaga cattatttgc cgactacctt ggtgatctcg    480
cctttcacgt agtggacaaa ttcttccaac tgatctgcgc gcgaggccaa gcgatcttct    540
tcttgtccaa gataagcctg tctagcttca agtatgacgg gctgatactg ggccggcagg    600
cgctccattg cccagtcggc agcgacatcc ttcggcgcga ttttgccggt tactgcgctg    660
taccaaatgc gggacaacgt aagcactaca tttcgctcat cgccagccca gtcgggcggc    720
gagttccata gcgttaaggt ttcatttagc gcctcaaata gatcctgttc aggaaccgga    780
tcaaagagtt cctccgccgc tggacctacc aaggcaacgc tatgttctct tgcttttgtc    840
agcaagatag ccagatcaat gtcgatcgtg gctggctcga agatacctgc aagaatgtca    900
ttgcgctgcc attctccaaa ttgcagttcg cgcttagctg gataacgcca cggaatgatg    960
tcgtcgtgca caacaatggt gacttctaca gcgcggagaa tctcgctctc tccaggggaa   1020
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt taactttgtt   1260
ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgg atcagtgagg gtttgcaact gcgggtcaag   1860
gatctggatt tcgatcacgg cacgatcatc gtgcgggagg gcaagggctc caaggatcgg   1920
gccttgatgt tacccgagag cttggcaccc agcctgcgcg agcaggggaa ttaattccca   1980
cgggttttgc tgcccgcaaa cgggctgttc tggtgttgct agtttgttat cagaatcgca   2040
gatccggctt cagccggttt gccggctgaa agcgctattt cttccagaat tgccatgatt   2100
ttttccccac gggaggcgtc actggctccc gtgttgtcgg cagctttgat tcgataagca   2160
gcatcgcctg tttcaggctg tctatgtgtg actgttgagc tgtaacaagt tgtctcaggt   2220
```

-continued

```
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct tttttacacc gttttcatct gtgcatatgg   2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgtttttgc gtgagccatg agaacgaacc attgagatca   2580
tacttacttt gcatgtcact caaaaatttt gcctcaaaac tggtgagctg aatttttgca   2640
gttaaagcat cgtgtagtgt tttcttagt ccgttatgta ggtaggaatc tgatgtaatg   2700
gttgttggta ttttgtcacc attcattttt atctggttgt tctcaagttc ggttacgaga   2760
tccatttgtc tatctagttc aacttggaaa atcaacgtat cagtcgggcg gcctcgctta   2820
tcaaccacca atttcatatt gctgtaagtg tttaaatctt tacttattgg tttcaaaacc   2880
cattggttaa gccttttaaa ctcatggtag ttattttcaa gcattaacat gaacttaaat   2940
tcatcaaggc taatctctat atttgccttg tgagttttct tttgtgttag ttcttttaat   3000
aaccactcat aaatcctcat agagtatttg ttttcaaaag acttaacatg ttccagatta   3060
tattttatga attttttaa ctggaaaaga taaggcaata tctcttcact aaaaactaat   3120
tctaattttt cgcttgagaa cttggcatag tttgtccact ggaaaatctc aaagccttta   3180
accaaaggat tcctgatttc cacagttctc gtcatcagct ctctggttgc tttagctaat   3240
acaccataag cattttccct actgatgttc atcatctgag cgtattggtt ataagtgaac   3300
gataccgtcc gttctttcct tgtagggttt tcaatcgtgg ggttgagtag tgccacacag   3360
cataaaatta gcttggtttc atgctccgtt aagtcatagc gactaatcgc tagttcattt   3420
gctttgaaaa caactaattc agacatacat ctcaattggt ctaggtgatt ttaatcacta   3480
taccaattga gatgggctag tcaatgataa ttactagtcc ttttcctttg agttgtgggt   3540
atctgtaaat tctgctagac ctttgctgga aaacttgtaa attctgctag accctctgta   3600
aattccgcta gacctttgtg tgtttttttt gtttatattc aagtggttat aatttataga   3660
ataaagaaag aataaaaaaa gataaaaaga atagatccca gccctgtgta taactcacta   3720
ctttagtcag ttccgcagta ttacaaaagg atgtcgcaaa cgctgtttgc tcctctacaa   3780
aacagacctt aaaaccctaa aggcttaagt agcaccctcg caagctcggg caaatcgctg   3840
aatattcctt ttgtctccga ccatcaggca cctgagtcgc tgtctttttc gtgacattca   3900
gttcgctgcg ctcacggctc tggcagtgaa tgggggtaaa tggcactaca ggcgcctttt   3960
atggattcat gcaaggaaac tacccataat acaagaaaag cccgtcacgg gcttctcagg   4020
gcgttttatg gcgggtctgc tatgtggtgc tatctgactt tttgctgttc agcagttcct   4080
gccctctgat tttccagtct gaccacttcg gattatcccg tgacaggtca ttcagactgg   4140
ctaatgcacc cagtaaggca gcggtatcat caacaggctt acccgtctta ctgtcgggaa   4200
ttcgcgttgg ccgattcatt aatgcagatt ctgaaatgag ctgttgacaa ttaatcatcc   4260
ggctcgtata atgtgtggaa ttgtgagcgg ataacaattt cacacaggaa acagcgccgc   4320
tgagaaaaag cgaagcggca ctgctcttta acaatttatc agacaatctg tgtgggcact   4380
cgaccggaat tatcgattaa ctttattatt aaaaattaaa gaggtatata ttaatgtatc   4440
gattaaataa ggaggaataa accatgtgtg cgacctcttc tcaatttact cagattaccg   4500
agcataattc ccgtcgttcc gcaaactatc agccaaacct gtggaatttc gaattcctgc   4560
aatccctgga gaacgacctg aaagtggaaa agctggagga gaaagcgacc aaactggagg   4620
```

-continued

```
aagaagttcg ctgcatgatc aaccgtgtag acacccagcc gctgtccctg ctggagctga   4680
tcgacgatgt gcagcgcctg ggtctgacct acaaatttga aaaagacatc attaaagccc   4740
tggaaaacat cgtactgctg gacgaaaaca aaaagaacaa atctgacctg cacgcaaccg   4800
ctctgtcttt ccgtctgctg cgtcagcacg gtttcgaggt ttctcaggat gtttttgagc   4860
gtttcaagga taaagaaggt ggtttcagcg gtgaactgaa aggtgacgtc caaggcctgc   4920
tgagcctgta tgaagcgtct tacctgggtt tcgagggtga gaacctgctg gaggaggcgc   4980
gtacctttc catcacccac ctgaagaaca acctgaaaga aggcattaat accaaggttg    5040
cagaacaagt gagccacgcc ctggaactgc catatcacca gcgtctgcac cgtctggagg   5100
cacgttggtt cctggataaa tacgaaccga aagaaccgca tcaccagctg ctgctggagc   5160
tggcgaagct ggattttaac atggtacaga ccctgcacca gaaagagctg caagatctgt   5220
cccgctggtg gaccgagatg ggcctggcta gcaaactgga ttttgtacgc gaccgcctga   5280
tggaagttta tttctgggca ctgggtatgg cgccagaccc gcagtttggt gaatgtcgca   5340
aagctgttac taaaatgttt ggtctggtga cgatcatcga tgacgtgtat gacgtttatg   5400
gcactctgga cgaactgcaa ctgttcaccg atgctgtaga gcgctgggac gttaacgcta   5460
ttaacaccct gccggactat atgaaactgt gtttcctggc actgtacaac accgttaacg   5520
acacgtccta ttctattctg aaagagaaag gtcataacaa cctgtcctat ctgacgaaaa   5580
gctggcgtga actgtgcaaa gcctttctgc aagaggcgaa atggtccaac aacaaaatta   5640
tcccggcttt ctccaagtac ctggaaaacg ccagcgtttc ctcctccggt gtagcgctgc   5700
tggcgccgtc ttacttttcc gtatgccagc agcaggaaga catctccgac cacgcgctgc   5760
gttccctgac cgacttccat ggtctggtgc gttctagctg cgttatcttc cgcctgtgca   5820
acgatctggc cacctctgcg gcggagctgg aacgtggcga gactaccaat tctatcatta   5880
gctacatgca cgaaaacgat ggtaccagcg aggaacaggc ccgcgaagaa ctgcgtaaac   5940
tgatcgacgc cgaatggaaa aagatgaatc gtgaacgcgt tagcgactcc accctgctgc   6000
ctaaagcgtt catggaaatc gcagttaaca tggcacgtgt ttcccactgc acctaccagt   6060
atggcgatgg tctgggtcgc ccagactacg cgactgaaaa ccgcatcaaa ctgctgctga   6120
ttgacccttt cccgattaac cagctgatgt atgtctaact gcatcgccct taggaggtaa   6180
aaaaaaatga ctgccgacaa caatagtatg ccccatggtg cagtatctag ttacgccaaa   6240
ttagtgcaaa accaaacacc tgaagacatt ttggaagagt ttcctgaaat tattccatta   6300
caacaaagac ctaatacccg atctagtgag acgtcaaatg acgaaagcgg agaaacatgt   6360
ttttctggtc atgatgagga gcaaattaag ttaatgaatg aaaattgtat tgttttggat   6420
tgggacgata atgctattgg tgccggtacc aagaaagttt gtcatttaat ggaaaatatt   6480
gaaaagggtt tactacatcg tgcattctcc gtctttattt tcaatgaaca aggtgaatta   6540
cttttacaac aaagagccac tgaaaaaata actttccctg atctttggac taacacatgc   6600
tgctctcatc cactatgtat tgatgacgaa ttaggtttga agggtaagct agacgataag   6660
attaagggcg ctattactgc ggcggtgaga aaactagatc atgaattagg tattccagaa   6720
gatgaaacta agacaagggg taagtttcac tttttaaaca gaatccatta catggcacca   6780
agcaatgaac catggggtga acatgaaatt gattacatcc tattttataa gatcaacgct   6840
aaagaaaact tgactgtcaa cccaaacgtc aatgaagtta gagacttcaa atgggtttca   6900
ccaaatgatt tgaaaactat gtttgctgac ccaagttaca agtttacgcc ttggtttaag   6960
attatttgcg agaattactt attcaactgg tgggagcaat tagatgacct ttctgaagtg   7020
```

gaaaatgaca ggcaaattca tagaatgcta taacgacgcg tcctgcagct ggtaccatat 7080
gggaattcga agctttctag aacgaaaact catctcagaa gaggatctga atagcgccgt 7140
cgaccatcat catcatcatc attgagttta aacggtctcc agcttggctg ttttggcgga 7200
tgagagaaga ttttcagcct gatacagatt aaatcagaac gcagaagcgg tctgataaaa 7260
cagaatttgc ctggcggcag tagcgcggtg gtcccacctg accccatgcc gaactcagaa 7320
gtgaaacgcc gtagcgccga tggtagtgtg gggtctcccc atgcgagagt agggaactgc 7380
caggcatcaa ataaaacgaa aggctcagtc gaaagactgg gcctttcgtt ttatctgttg 7440
tttgtcggtg aacgctctcc tgagtaggac aaatccgccg ggagcggatt tgaacgttgc 7500
gaagcaacgg cccggagggt ggcgggcagg acgcccgcca taaactgcca ggcatcaaat 7560
taagcagaag gccatcctga cggatggcct ttttgcgttt ctacaaactc tttttgttta 7620
tttttctaaa tacattcaaa tatgtatccg ctcatgagac aataaccctg ataaatgctt 7680
caataat 7687

<210> SEQ ID NO 28
<211> LENGTH: 8675
<212> TYPE: DNA
<213> ORGANISM: Artificial Sequence
<220> FEATURE:
<223> OTHER INFORMATION: Synthetic Construct

<400> SEQUENCE: 28
cccgtcttac tgtcgggaat tcgcgttggc cgattcatta atgcagatta ttgaagcatt 60
tatcagggtt attgtctcat gagcggatac atatttgaat gtatttagaa aaataaacaa 120
aaagagtttg tagaaacgca aaaaggccat ccgtcaggat ggccttctgc ttaatttgat 180
gcctggcagt ttatggcggg cgtcctgccc gccaccctcc gggccgttgc ttcgcaacgt 240
tcaaatccgc tcccggcgga tttgtcctac tcaggagagc gttcaccgac aaacaacaga 300
taaaacgaaa ggcccagtct ttcgactgag cctttcgttt tatttgatgc ctggcagttc 360
cctactctcg catggggaga ccccacacta ccatcggcgc tacggcgttt cacttctgag 420
ttcggcatgg ggtcaggtgg gaccaccgcg ctactgccgc caggcaaatt ctgttttatc 480
agaccgcttc tgcgttctga tttaatctgt atcaggctga aaatcttctc tcatccgcca 540
aaacagccaa gctggagacc gtttaaactc aatgatgatg atgatgatgg tcgacggcgc 600
tattcagatc ctcttctgag atgagttttt gttctagaaa gcttcgaatt cccatatggt 660
accagctgca gttatgccag ccaggccttg attttggctt ccataccagc ggcatcgagg 720
ccgagttcgg cgcgcatttc ttcctgagtt ccttgcggaa taaagaagtc cggcaggcca 780
atgttcagca cgggtactgg tttacgatgg gccatcagca cttcgttcac gccgctgcct 840
gcgccgccca taatggcgtt ttcttctacg gtgaccagcg cttcatggct ggcggccatt 900
tccagaatta acgcttcatc aagcggtttc acaaaacgca tatcgaccag cgtggcgttc 960
agcgattcgg cgactttcgc cgcttctggc atcagcgtac caaagttaag gatcgccagt 1020
ttctcgccac gacgcttcac aatgcctttg ccaattggta gtttttccag cggcgtcagt 1080
tccacgccga ccgcgttgcc acgcgggtag cgcaccgctg acgggccatc gttatagtga 1140
tagccggtat agagcatctg gcgacattcg ttttcatcgc tcggggtcat aatgaccatt 1200
tccggtatgc agcgcaggta agagagatca aaagcaccct gatgggtttg accgtcagca 1260
ccaacaatgc ccgcgcggtc gatggcgaac aggaccggaa gcttttgaat cgccacgtca 1320
tgcagcacct gatcataggc gcgttgcagg aaagtggagt aaatcgcgac aatgggtttg 1380

-continued

```
tacccaccaa tcgccagacc cgcagcaaag gtcaccgcgt gttgctcggc aattgccacg   1440
tcgaagtagc gatccgggaa tttacgtgaa aactcgacca tgccggaacc ttcacgcatc   1500
gccggagtaa tcgccatcag cttgttgtct ttcgctgccg tttcgcacaa ccagtcgcca   1560
aagattttg aatagctcgg caaaccgccg ctacttttcg gcaaacaacc gctggaggga   1620
tcaaatttag gcacggcgtg gaaagtgatc gggtcttttt ctgccggttc ataaccacga   1680
cctttttgg tcatgatatg caggaactgc gggcctttca ggtcgcgcat gttctttagc   1740
gtggtgataa gccccagcac atcgtgaccg tccaccgggc cgatgtagtt aaagcccagc   1800
tcttcaaaca acgtgccagg cactaccatg cctttaatat gttcttcggt gcgtttgagc   1860
agctctttaa ttggcggcac gccagagaaa actttttcc cgccttcgcg cagtgaagag   1920
taaagcttac cggaaagcag ctgtgccaga tggttgttga gcgcgccgac attttcggaa   1980
atcgacattt cattgtcgtt gagaatcacc agcatatcag gacggatatc gcccgcgtga   2040
ttcatcgctt caaacgccat gcctgcggta atcgcgccat cgccaatgac acagacggtg   2100
cggcgatttt tgccttcttt ttcggcagca accgcaatac caattccggc actgatggag   2160
gttgatgaat gcccgacgct taatacgtca tattcgcttt cgccgcgcca cgggaacggg   2220
tgcagaccgc ctttctgacg gatggtgccg attttgtcgc ggcgtccggt caaaatttta   2280
tgcggataag cctgatgccc cacatcccaa atcaattggt caaacggggt gttgtagaca   2340
tagtgcagcg ccacggtcag ttcgaccgtg cccagcccgg aggcgaagtg cccgctggaa   2400
cggctcacgc tgtcgagtaa atagcggcgc agttcgtcgc agagtttcgg taaactctct   2460
ttcggcaaca gtcgtaactc ctgggtggag tcgaccagtg ccagggtcgg gtatttggca   2520
atatcaaaac tcatgttttt ttacctccta agggcgaatg cagttagaca tacatcagct   2580
ggttaatcgg gaaagggtca atcagcagca gtttgatgcg gttttcagtc gcgtagtctg   2640
ggcgacccag accatcgcca tactggtagg tgcagtggga aacacgtgcc atgttaactg   2700
cgatttccat gaacgcttta ggcagcaggg tggagtcgct aacgcgttca cgattcatct   2760
ttttccattc ggcgtcgatc agtttacgca gttcttcgcg ggcctgttcc tcgctggtac   2820
catcgttttc gtgcatgtag ctaatgatag aattggtagt ctcgccacgt tccagctccg   2880
ccgcagaggt ggccagatcg ttgcacaggc ggaagataac gcagctagaa cgcaccagac   2940
catggaagtc ggtcagggaa cgcagcgcgt ggtcggagat gtcttcctgc tgctggcata   3000
cggaaaagta agacggcgcc agcagcgcta caccggagga ggaaacgctg gcgttttcca   3060
ggtacttgga gaaagccggg ataattttgt tgttggacca tttcgcctct tgcagaaagg   3120
ctttgcacag ttcacgccag cttttcgtca gataggacag gttgttatga cctttctctt   3180
tcagaataga ataggacgtg tcgttaacgg tgttgtacag tgccaggaaa cacagtttca   3240
tatagtccgg cagggtgtta atagcgttaa cgtcccagcg ctctacagca tcggtgaaca   3300
gttgcagttc gtccagagtg ccataaacgt catacacgtc atcgatgatc gtcaccagac   3360
caaacatttt agtaacagct ttgcgacatt caccaaactg cgggtctggc gccataccca   3420
gtgcccagaa ataaacttcc atcaggcggt cgcgtacaaa atccagtttg ctagccaggc   3480
ccatctcggt ccaccagcgg gacagatctt gcagctcttt ctggtgcagg gtctgtacca   3540
tgttaaaatc cagcttcgcc agctccagca gcagctggtg atgcggttct ttcggttcgt   3600
atttatccag gaaccaacgt gcctccagac ggtgcagacg ctggtgatat ggcagttcca   3660
gggcgtggct cacttgttct gcaaccttgg tattaatgcc ttctttcagg ttgttcttca   3720
ggtgggtgat ggaaaaggta cgcgcctcct ccagcaggtt ctcaccctcg aaacccaggt   3780
```

-continued

```
aagacgcttc atacaggctc agcaggcctt ggacgtcacc tttcagttca ccgctgaaac   3840
caccttcttt atccttgaaa cgctcaaaaa catcctgaga aacctcgaaa ccgtgctgac   3900
gcagcagacg gaaagacaga gcggttgcgt gcaggtcaga tttgttcttt ttgttttcgt   3960
ccagcagtac gatgttttcc agggctttaa tgatgtcttt ttcaaatttg taggtcagac   4020
ccaggcgctg cacatcgtcg atcagctcca gcagggacag cggctgggtg tctacacggt   4080
tgatcatgca gcgaacttct tcctccagtt tggtcgcttt ctcctccagc ttttccactt   4140
tcaggtcgtt ctccagggat tgcaggaatt cgaaattcca caggtttggc tgatagtttg   4200
cggaacgacg ggaattatgc tcggtaatct gagtaaattg agaagaggtc gcacacatgg   4260
tttattcctc cttatttaat cgatacatta atatatacct ctttaatttt taataataaa   4320
gttaatcgat aattccggtc gagtgcccac acagattgtc tgataaattg ttaaagagca   4380
gtgccgcttc gctttttctc agcggcgctg tttcctgtgt gaaattgtta tccgctcaca   4440
attccacaca ttatacgagc cggatgatta attgtcaaca gctcatttca gaatctggcg   4500
taatagcgaa gaggcccgca ccgatcgccc ttcccaacag ttgcgcagcc tgaatggcga   4560
atggcgcctg atgcggtatt ttctccttac gcatctgtgc ggtatttcac accgcatatg   4620
gtgcactctc agtacaatct gctctgatgc cgcatagtta agccagcccc gacacccgcc   4680
aacacccgct gacgagctta gtaaagccct cgctagattt taatgcggat gttgcgatta   4740
cttcgccaac tattgcgata acaagaaaaa gccagccttt catgatatat ctcccaattt   4800
gtgtagggct tattatgcac gcttaaaaat aataaaagca gacttgacct gatagtttgg   4860
ctgtgagcaa ttatgtgctt agtgcatcta acgcttgagt taagccgcgc cgcgaagcgg   4920
cgtcggcttg aacgaattgt tagacattat ttgccgacta ccttggtgat ctcgcctttc   4980
acgtagtgga caaattcttc caactgatct gcgcgcgagg ccaagcgatc ttcttcttgt   5040
ccaagataag cctgtctagc ttcaagtatg acgggctgat actgggccgg caggcgctcc   5100
attgcccagt cggcagcgac atccttcggc gcgattttgc cggttactgc gctgtaccaa   5160
atgcgggaca acgtaagcac tacatttcgc tcatcgccag cccagtcggg cggcgagttc   5220
catagcgtta aggtttcatt tagcgcctca aatagatcct gttcaggaac cggatcaaag   5280
agttcctccg ccgctggacc taccaaggca acgctatgtt ctcttgcttt tgtcagcaag   5340
atagccagat caatgtcgat cgtggctggc tcgaagatac ctgcaagaat gtcattgcgc   5400
tgccattctc caaattgcag ttcgcgctta gctggataac gccacggaat gatgtcgtcg   5460
tgcacaacaa tggtgacttc tacagcgcgg agaatctcgc tctctccagg ggaagccgaa   5520
gtttccaaaa ggtcgttgat caaagctcgc cgcgttgttt catcaagcct tacggtcacc   5580
gtaaccagca aatcaatatc actgtgtggc ttcaggccgc catccactgc ggagccgtac   5640
aaatgtacgg ccagcaacgt cggttcgaga tggcgctcga tgacgccaac tacctctgat   5700
agttgagtcg atacttcggc gatcaccgct tccctcatga tgtttaactt tgttttaggg   5760
cgactgccct gctgcgtaac atcgttgctg ctccataaca tcaaacatcg acccacggcg   5820
taacgcgctt gctgcttgga tgcccgaggc atagactgta ccccaaaaaa acagtcataa   5880
caagccatga aaaccgccac tgcgccgtta ccaccgctgc gttcggtcaa ggttctggac   5940
cagttgcgtg agcgcatacg ctacttgcat tacagcttac gaaccgaaca ggcttatgtc   6000
cactgggttc gtgccttcat ccgtttccac ggtgtgcgtc acccggcaac cttgggcagc   6060
agcgaagtcg aggcatttct gtcctggctg gcgaacgagc gcaaggtttc ggtctccacg   6120
catcgtcagg cattggcggc cttgctgttc ttctacggca aggtgctgtg cacggatctg   6180
```

```
ccctggcttc aggagatcgg aagacctcgg ccgtcgcggc gcttgccggt ggtgctgacc   6240
ccggatgaag tggttcgcat cctcggtttt ctggaaggcg agcatcgttt gttcgcccag   6300
cttctgtatg gaacgggcat gcggatcagt gagggtttgc aactgcgggt caaggatctg   6360
gatttcgatc acggcacgat catcgtgcgg gagggcaagg gctccaagga tcgggccttg   6420
atgttacccg agagcttggc acccagcctg cgcgagcagg ggaattaatt cccacgggtt   6480
ttgctgcccg caaacgggct gttctggtgt tgctagtttg ttatcagaat cgcagatccg   6540
gcttcagccg gtttgccggc tgaaagcgct atttcttcca gaattgccat gatttttcc   6600
ccacgggagg cgtcactggc tcccgtgttg tcggcagctt tgattcgata agcagcatcg   6660
cctgtttcag gctgtctatg tgtgactgtt gagctgtaac aagttgtctc aggtgttcaa   6720
tttcatgttc tagttgcttt gttttactgg tttcacctgt tctattaggt gttacatgct   6780
gttcatctgt tacattgtcg atctgttcat ggtgaacagc tttgaatgca ccaaaaactc   6840
gtaaaagctc tgatgtatct atcttttta caccgttttc atctgtgcat atggacagtt   6900
ttccctttga tatgtaacgg tgaacagttg ttctactttt gtttgttagt cttgatgctt   6960
cactgataga tacaagagcc ataagaacct cagatccttc cgtatttagc cagtatgttc   7020
tctagtgtgg ttcgttgttt ttgcgtgagc catgagaacg aaccattgag atcatactta   7080
ctttgcatgt cactcaaaaa ttttgcctca aaactggtga gctgaatttt tgcagttaaa   7140
gcatcgtgta gtgtttttct tagtccgtta tgtaggtagg aatctgatgt aatggttgtt   7200
ggtattttgt caccattcat ttttatctgg ttgttctcaa gttcggttac gagatccatt   7260
tgtctatcta gttcaacttg gaaaatcaac gtatcagtcg ggcggcctcg cttatcaacc   7320
accaatttca tattgctgta agtgtttaaa tctttactta ttggtttcaa aacccattgg   7380
ttaagccttt taaactcatg gtagttattt tcaagcatta acatgaactt aaattcatca   7440
aggctaatct ctatatttgc cttgtgagtt ttcttttgtg ttagttcttt taataaccac   7500
tcataaatcc tcatagagta tttgttttca aaagacttaa catgttccag attatatttt   7560
atgaattttt ttaactggaa aagataaggc aatatctctt cactaaaaac taattctaat   7620
ttttcgcttg agaacttggc atagtttgtc cactggaaaa tctcaaagcc tttaaccaaa   7680
ggattcctga tttccacagt tctcgtcatc agctctctgg ttgctttagc taatacacca   7740
taagcatttt ccctactgat gttcatcatc tgagcgtatt ggttataagt gaacgatacc   7800
gtccgttctt tccttgtagg gttttcaatc gtggggttga gtagtgccac acagcataaa   7860
attagcttgg tttcatgctc cgttaagtca tagcgactaa tcgctagttc atttgctttg   7920
aaaacaacta attcagacat acatctcaat tggtctaggt gattttaatc actataccaa   7980
ttgagatggg ctagtcaatg ataattacta gtccttttcc tttgagttgt gggtatctgt   8040
aaattctgct agacctttgc tggaaaactt gtaaattctg ctagaccctc tgtaaattcc   8100
gctagacctt tgtgtgtttt ttttgtttat attcaagtgg ttataattta tagaataaag   8160
aaagaataaa aaaagataaa aagaatagat cccagccctg tgtataactc actactttag   8220
tcagttccgc agtattacaa aaggatgtcg caaacgctgt ttgctcctct acaaaacaga   8280
ccttaaaacc ctaaaggctt aagtagcacc ctcgcaagct cgggcaaatc gctgaatatt   8340
ccttttgtct ccgaccatca ggcacctgag tcgctgtctt tttcgtgaca ttcagttcgc   8400
tgcgctcacg gctctggcag tgaatggggg taaatggcac tacaggcgcc ttttatggat   8460
tcatgcaagg aaactaccca taatacaaga aaagcccgtc acgggcttct cagggcgttt   8520
tatggcgggt ctgctatgtg gtgctatctg actttttgct gttcagcagt tcctgccctc   8580
```

tgattttcca gtctgaccac ttcggattat cccgtgacag gtcattcaga ctggctaatg    8640
cacccagtaa ggcagcggta tcatcaacag gctta    8675

<210> SEQ ID NO 29
<211> LENGTH: 31
<212> TYPE: DNA
<213> ORGANISM: Artificial Sequence
<220> FEATURE:
<223> OTHER INFORMATION: Synthetic Construct

<400> SEQUENCE: 29
gacatcaatt gctccatttt cttctgctat c    31

<210> SEQ ID NO 30
<211> LENGTH: 41
<212> TYPE: DNA
<213> ORGANISM: Artificial Sequence
<220> FEATURE:
<223> OTHER INFORMATION: Synthetic Construct

<400> SEQUENCE: 30
attgagaaga ggtcgcacac actctttacc ctctcctttt a    41

<210> SEQ ID NO 31
<211> LENGTH: 41
<212> TYPE: DNA
<213> ORGANISM: Artificial Sequence
<220> FEATURE:
<223> OTHER INFORMATION: Synthetic Construct

<400> SEQUENCE: 31
taaaaggaga gggtaaagag tgtgtgcgac ctcttctcaa t    41

<210> SEQ ID NO 32
<211> LENGTH: 41
<212> TYPE: DNA
<213> ORGANISM: Artificial Sequence
<220> FEATURE:
<223> OTHER INFORMATION: Synthetic Construct

<400> SEQUENCE: 32
ccaaggccgg ttttttttag acatacatca gctggttaat c    41

<210> SEQ ID NO 33
<211> LENGTH: 41
<212> TYPE: DNA
<213> ORGANISM: Artificial Sequence
<220> FEATURE:
<223> OTHER INFORMATION: Synthetic Construct

<400> SEQUENCE: 33
gattaaccag ctgatgtatg tctaaaaaaa accggccttg g    41

<210> SEQ ID NO 34
<211> LENGTH: 32
<212> TYPE: DNA
<213> ORGANISM: Artificial Sequence
<220> FEATURE:
<223> OTHER INFORMATION: Synthetic Construct

<400> SEQUENCE: 34
gacatgacgg atccgattac gaatgccgtc tc    32

<210> SEQ ID NO 35
<211> LENGTH: 31

<212> TYPE: DNA
<213> ORGANISM: Artificial Sequence
<220> FEATURE:
<223> OTHER INFORMATION: Synthetic Construct

<400> SEQUENCE: 35
gacatcaatt gctccatttt cttctgctat c 31

<210> SEQ ID NO 36
<211> LENGTH: 27
<212> TYPE: DNA
<213> ORGANISM: Artificial Sequence
<220> FEATURE:
<223> OTHER INFORMATION: Synthetic Construct

<400> SEQUENCE: 36
gacatgaatt cctccatttt cttctgc 27

<210> SEQ ID NO 37
<211> LENGTH: 20
<212> TYPE: DNA
<213> ORGANISM: Artificial Sequence
<220> FEATURE:
<223> OTHER INFORMATION: Synthetic Construct

<400> SEQUENCE: 37
aggagagggt aaagagtgag 20

<210> SEQ ID NO 38
<211> LENGTH: 22
<212> TYPE: DNA
<213> ORGANISM: Artificial Sequence
<220> FEATURE:
<223> OTHER INFORMATION: Synthetic Construct

<400> SEQUENCE: 38
cttttccatc acccacctga ag 22

<210> SEQ ID NO 39
<211> LENGTH: 28
<212> TYPE: DNA
<213> ORGANISM: Artificial Sequence
<220> FEATURE:
<223> OTHER INFORMATION: Synthetic Construct

<400> SEQUENCE: 39
ggcgaaatgg tccaacaaca aaattatc 28

<210> SEQ ID NO 40
<211> LENGTH: 51
<212> TYPE: DNA
<213> ORGANISM: Artificial Sequence
<220> FEATURE:
<223> OTHER INFORMATION: Synthetic Construct

<400> SEQUENCE: 40
ggtgaattca gtctactggg gattcccaaa tctatatata ctgcaggtga c 51

<210> SEQ ID NO 41
<211> LENGTH: 23
<212> TYPE: DNA
<213> ORGANISM: Artificial Sequence
<220> FEATURE:
<223> OTHER INFORMATION: Synthetic Construct

<400> SEQUENCE: 41
gcaggtggga aactatgcac tcc 23

<210> SEQ ID NO 42
<211> LENGTH: 36
<212> TYPE: DNA
<213> ORGANISM: Artificial Sequence
<220> FEATURE:
<223> OTHER INFORMATION: Synthetic Construct

<400> SEQUENCE: 42
cctgaattct gttggattgg aggattggat agtggg 36

<210> SEQ ID NO 43
<211> LENGTH: 30
<212> TYPE: DNA
<213> ORGANISM: Artificial Sequence
<220> FEATURE:
<223> OTHER INFORMATION: Synthetic Construct

<400> SEQUENCE: 43
ggtgtcgacg tacggtcgag cttattgacc 30

<210> SEQ ID NO 44
<211> LENGTH: 32
<212> TYPE: DNA
<213> ORGANISM: Artificial Sequence
<220> FEATURE:
<223> OTHER INFORMATION: Synthetic Construct

<400> SEQUENCE: 44
ggtgggcccg cattttgcca cctacaagcc ag 32

<210> SEQ ID NO 45
<211> LENGTH: 40
<212> TYPE: DNA
<213> ORGANISM: Artificial Sequence
<220> FEATURE:
<223> OTHER INFORMATION: Synthetic Construct

<400> SEQUENCE: 45
ggtgaattct agaggatccc aacgctgttg cctacaacgg 40

<210> SEQ ID NO 46
<211> LENGTH: 36
<212> TYPE: DNA
<213> ORGANISM: Artificial Sequence
<220> FEATURE:
<223> OTHER INFORMATION: Synthetic Construct

<400> SEQUENCE: 46
ggtgcggccg ctgtctggac ctggtgagtt tccccg 36

<210> SEQ ID NO 47
<211> LENGTH: 37
<212> TYPE: DNA
<213> ORGANISM: Artificial Sequence
<220> FEATURE:
<223> OTHER INFORMATION: Synthetic Construct

<400> SEQUENCE: 47
ggtgggccca ttaaatcagt tatcgtttat ttgatag 37

<210> SEQ ID NO 48
<211> LENGTH: 35
<212> TYPE: DNA
<213> ORGANISM: Artificial Sequence
<220> FEATURE:
<223> OTHER INFORMATION: Synthetic Construct

<400> SEQUENCE: 48
ggtgaccagc aagtccatgg gtggtttgat catgg 35

<210> SEQ ID NO 49
<211> LENGTH: 35
<212> TYPE: DNA
<213> ORGANISM: Artificial Sequence
<220> FEATURE:
<223> OTHER INFORMATION: Synthetic Construct

<400> SEQUENCE: 49
ggtgcggccg cctttggagt acgactccaa ctatg 35

<210> SEQ ID NO 50
<211> LENGTH: 31
<212> TYPE: DNA
<213> ORGANISM: Artificial Sequence
<220> FEATURE:
<223> OTHER INFORMATION: Synthetic Construct

<400> SEQUENCE: 50
gcggccgcag actaaattta tttcagtctc c 31

<210> SEQ ID NO 51
<211> LENGTH: 5356
<212> TYPE: DNA
<213> ORGANISM: Artificial Sequence
<220> FEATURE:
<223> OTHER INFORMATION: Synthetic Construct

<400> SEQUENCE: 51
tctataatca cggcagaaaa gtccacattg attatttgca cggcgtcaca ctttgctatg 60
ccatagcatt tttatccata agattagcgg atcctacctg acgcttttta tcgcaactct 120
ctactgtttc tccatacccg tttttttggg ctagcgaatt cgagctcggt acccggggat 180
cctctagagt cgacctgcag gcatgcaagc ttggctgttt tggcggatga gagaagattt 240
tcagcctgat acagattaaa tcagaacgca gaagcggtct gataaaacag aatttgcctg 300
gcggcagtag cgcggtggtc ccacctgacc ccatgccgaa ctcagaagtg aaacgccgta 360
gcgccgatgg tagtgtgggg tctccccatg cgagagtagg gaactgccag gcatcaaata 420
aaacgaaagg ctcagtcgaa agactgggcc tttcgtttta tctgttgttt gtcggtgaac 480
gctctcctga gtaggacaaa tccgccggga gcggatttga acgttgcgaa gcaacggccc 540
ggagggtggc gggcaggacg cccgccataa actgccaggc atcaaattaa gcagaaggcc 600
atcctgacgg atggcctttt tgcgtttcta caaactcttt tgtttatttt tctaaataca 660
ttcaaatatg tatccgctca tgagacaata accctgataa atgcttcaat aatattgaaa 720
aaggaagagt atgagtattc aacatttccg tgtcgccctt attccctttt ttgcggcatt 780
ttgccttcct gtttttgctc acccagaaac gctggtgaaa gtaaaagatg ctgaagatca 840
gttgggtgca gcaaactatt aactggcgaa ctacttactc tagcttcccg gcaacaatta 900
atagactgga tggaggcgga taaagttgca ggaccacttc tgcgctcggc ccttccggct 960
ggctggttta ttgctgataa atctggagcc ggtgagcgtg ggtctcgcgg tatcattgca 1020
gcactggggc cagatggtaa gccctcccgt atcgtagtta tctacacgac ggggagtcag 1080
gcaactatgg atgaacgaaa tagacagatc gctgagatag gtgcctcact gattaagcat 1140
tggtaactgt cagaccaagt ttactcatat atactttaga ttgatttacg cgccctgtag 1200
cggcgcatta agcgcggcgg gtgtggtggt tacgcgcagc gtgaccgcta cacttgccag 1260
cgccctagcg cccgctcctt tcgctttctt cccttccttt ctcgccacgt tcgccggctt 1320
tccccgtcaa gctctaaatc gggggctccc tttagggttc cgatttagtg ctttacggca 1380
cctcgacccc aaaaaacttg atttgggtga tggttcacgt agtgggccat cgccctgata 1440
gacggttttt cgccctttga cgttggagtc cacgttcttt aatagtggac tcttgttcca 1500
aacttgaaca acactcaacc ctatctcggg ctattctttt gatttataag ggattttgcc 1560
gatttcggcc tattggttaa aaaatgagct gatttaacaa aaatttaacg cgaattttaa 1620
caaaatatta acgtttacaa tttaaaagga tctaggtgaa gatccttttt gataatctca 1680
tgaccaaaat cccttaacgt gagttttcgt tccactgagc gtcagacccc gtagaaaaga 1740
tcaaaggatc ttcttgagat cctttttttc tgcgcgtaat ctgctgcttg caaacaaaaa 1800
aaccaccgct accagcggtg gtttgtttgc cggatcaaga gctaccaact ctttttccga 1860
aggtaactgg cttcagcaga gcgcagatac caaatactgt ccttctagtg tagccgtagt 1920
taggccacca cttcaagaac tctgtagcac cgcctacata cctcgctctg ctaatcctgt 1980
taccagtcag gcatttgaga agcacacggt cacactgctt ccggtagtca ataaaccggt 2040
aaaccagcaa tagacataag cggctattta acgaccctgc cctgaaccga cgaccgggtc 2100
gaatttgctt tcgaatttct gccattcatc cgcttattat cacttattca ggcgtagcac 2160
caggcgttta agggcaccaa taactgcctt aaaaaaatta cgccccgccc tgccactcat 2220
cgcagtactg ttgtaattca ttaagcattc tgccgacatg gaagccatca cagacggcat 2280
gatgaacctg aatcgccagc ggcatcagca ccttgtcgcc ttgcgtataa tatttgccca 2340
tggtgaaaac gggggcgaag aagttgtcca tattggccac gtttaaatca aaactggtga 2400
aactcaccca gggattggct gagacgaaaa acatattctc aataaaccct ttagggaaat 2460
aggccaggtt ttcaccgtaa cacgccacat cttgcgaata tatgtgtaga aactgccgga 2520
aatcgtcgtg gtattcactc cagagcgatg aaaacgtttc agtttgctca tggaaaacgg 2580
tgtaacaagg gtgaacacta tcccatatca ccagctcacc gtctttcatt gccatacgga 2640
attccggatg agcattcatc aggcgggcaa gaatgtgaat aaaggccgga taaaacttgt 2700
gcttattttt ctttacggtc tttaaaaagg ccgtaatatc cagctgaacg gtctggttat 2760
aggtacattg agcaactgac tgaaatgcct caaaatgttc tttacgatgc cattgggata 2820
tatcaacggt ggtatatcca gtgatttttt tctccatttt agcttcctta gctcctgaaa 2880
atctcgataa ctcaaaaaat acgcccggta gtgatcttat ttcattatgg tgaaagttgg 2940
aacctcttac gtgccgatca acgtctcatt ttcgccaaaa gttggcccag ggcttcccgg 3000
tatcaacagg gacaccagga tttatttatt ctgcgaagtg atcttccgtc acaggtattt 3060
attcggcgca aagtgcgtcg ggtgatgctg ccaacttact gatttagtgt atgatggtgt 3120
ttttgaggtg ctccagtggc ttctgtttct atcagctgtc cctcctgttc agctactgac 3180
ggggtggtgc gtaacggcaa aagcaccgcc ggacatcagc gctagcggag tgtatactgg 3240
cttactatgt tggcactgat gagggtgtca gtgaagtgct tcatgtggca ggagaaaaaa 3300
ggctgcaccg gtgcgtcagc agaatatgtg atacaggata tattccgctt cctcgctcac 3360
tgactcgcta cgctcggtcg ttcgactgcg gcgagcggaa atggcttacg aacggggcgg 3420
agatttcctg gaagatgcca ggaagatact taacagggaa gtgagagggc cgcggcaaag 3480
ccgtttttcc ataggctccg cccccctgac aagcatcacg aaatctgacg ctcaaatcag 3540
tggtggcgaa acccgacagg actataaaga taccaggcgt ttccccctgg cggctccctc 3600
gtgcgctctc ctgttcctgc ctttcggttt accggtgtca ttccgctgtt atggccgcgt 3660
ttgtctcatt ccacgcctga cactcagttc cgggtaggca gttcgctcca agctggactg 3720
tatgcacgaa ccccccgttc agtccgaccg ctgcgcctta tccggtaact atcgtcttga 3780
gtccaacccg gaaagacatg caaaagcacc actggcagca gccactggta attgatttag 3840
aggagttagt cttgaagtca tgcgccggtt aaggctaaac tgaaaggaca agttttggtg 3900
actgcgctcc tccaagccag ttacctcggt tcaaagagtt ggtagctcag agaaccttcg 3960
aaaaaccgcc ctgcaaggcg gttttttcgt tttcagagca agagattacg cgcagaccaa 4020
aacgatctca agaagatcat cttattaatc agataaaata tttgctcatg agcccgaagt 4080
ggcgagcccg atcttcccca tcggtgatgt cggcgatata ggcgccagca accgcacctg 4140
tggcgccggt gatgccggcc acgatgcgtc cggcgtagag gatctgctca tgtttgacag 4200
cttatcatcg atgcataatg tgcctgtcaa atggacgaag cagggattct gcaaacccta 4260
tgctactccg tcaagccgtc aattgtctga ttcgttacca attatgacaa cttgacggct 4320
acatcattca ctttttcttc acaaccggca cggaactcgc tcgggctggc cccggtgcat 4380
tttttaaata cccgcgagaa atagagttga tcgtcaaaac caacattgcg accgacggtg 4440
gcgataggca tccgggtggt gctcaaaagc agcttcgcct ggctgatacg ttggtcctcg 4500
cgccagctta agacgctaat ccctaactgc tggcggaaaa gatgtgacag acgcgacggc 4560
gacaagcaaa catgctgtgc gacgctggcg atatcaaaat tgctgtctgc caggtgatcg 4620
ctgatgtact gacaagcctc gcgtacccga ttatccatcg gtggatggag cgactcgtta 4680
atcgcttcca tgcgccgcag taacaattgc tcaagcagat ttatcgccag cagctccgaa 4740
tagcgccctt ccccttgccc ggcgttaatg atttgcccaa acaggtcgct gaaatgcggc 4800
tggtgcgctt catccgggcg aaagaacccc gtattggcaa atattgacgg ccagttaagc 4860
cattcatgcc agtaggcgcg cggacgaaag taaacccact ggtgatacca ttcgcgagcc 4920
tccggatgac gaccgtagtg atgaatctct cctggcggga acagcaaaat atcacccggt 4980
cggcaaacaa attctcgtcc ctgatttttc accaccccct gaccgcgaat ggtgagattg 5040
agaatataac ctttcattcc cagcggtcgg tcgataaaaa aatcgagata accgttggcc 5100
tcaatcggcg ttaaacccgc caccagatgg gcattaaacg agtatcccgg cagcagggga 5160
tcattttgcg cttcagccat acttttcata ctcccgccat tcagagaaga aaccaattgt 5220
ccatattgca tcagacattg ccgtcactgc gtcttttact ggctcttctc gctaaccaaa 5280
ccggtaaccc cgcttattaa aagcattctg taacaaagcg ggaccaaagc catgacaaaa 5340
acgcgtaaca aaagtg 5356

<210> SEQ ID NO 52
<211> LENGTH: 7271
<212> TYPE: DNA
<213> ORGANISM: Artificial Sequence
<220> FEATURE:
<223> OTHER INFORMATION: Synthetic Construct

<400> SEQUENCE: 52
gcaaactatt aactggcgaa ctacttactc tagcttcccg gcaacaatta atagactgga 60
tggaggcgga taaagttgca ggaccacttc tgcgctcggc ccttccggct ggctggttta 120
ttgctgataa atctggagcc ggtgagcgtg ggtctcgcgg tatcattgca gcactggggc 180
cagatggtaa gccctcccgt atcgtagtta tctacacgac ggggagtcag gcaactatgg 240
atgaacgaaa tagacagatc gctgagatag gtgcctcact gattaagcat tggtaactgt 300
cagaccaagt ttactcatat atactttaga ttgatttacg cgccctgtag cggcgcatta 360

-continued

```
agcgcggcgg gtgtggtggt tacgcgcagc gtgaccgcta cacttgccag cgccctagcg    420
cccgctcctt tcgctttctt cccttccttt ctcgccacgt tcgccggctt tccccgtcaa    480
gctctaaatc gggggctccc tttagggttc cgatttagtg ctttacggca cctcgacccc    540
aaaaaacttg atttgggtga tggttcacgt agtgggccat cgccctgata gacggttttt    600
cgccctttga cgttggagtc cacgttcttt aatagtggac tcttgttcca aacttgaaca    660
acactcaacc ctatctcggg ctattctttt gatttataag ggattttgcc gatttcggcc    720
tattggttaa aaaatgagct gatttaacaa aaatttaacg cgaattttaa caaaatatta    780
acgtttacaa tttaaaagga tctaggtgaa gatccttttt gataatctca tgaccaaaat    840
cccttaacgt gagttttcgt tccactgagc gtcagacccc gtagaaaaga tcaaaggatc    900
ttcttgagat cctttttttc tgcgcgtaat ctgctgcttg caaacaaaaa aaccaccgct    960
accagcggtg gtttgtttgc cggatcaaga gctaccaact ctttttccga aggtaactgg   1020
cttcagcaga gcgcagatac caaatactgt ccttctagtg tagccgtagt taggccacca   1080
cttcaagaac tctgtagcac cgcctacata cctcgctctg ctaatcctgt taccagtcag   1140
gcatttgaga agcacacggt cacactgctt ccggtagtca ataaaccggt aaaccagcaa   1200
tagacataag cggctattta acgaccctgc cctgaaccga cgaccgggtc gaatttgctt   1260
tcgaatttct gccattcatc cgcttattat cacttattca ggcgtagcac caggcgttta   1320
agggcaccaa taactgcctt aaaaaaatta cgccccgccc tgccactcat cgcagtactg   1380
ttgtaattca ttaagcattc tgccgacatg gaagccatca cagacggcat gatgaacctg   1440
aatcgccagc ggcatcagca ccttgtcgcc ttgcgtataa tatttgccca tggtgaaaac   1500
gggggcgaag aagttgtcca tattggccac gtttaaatca aaactggtga aactcaccca   1560
gggattggct gagacgaaaa acatattctc aataaaccct ttagggaaat aggccaggtt   1620
ttcaccgtaa cacgccacat cttgcgaata tatgtgtaga aactgccgga aatcgtcgtg   1680
gtattcactc cagagcgatg aaaacgtttc agtttgctca tggaaaacgg tgtaacaagg   1740
gtgaacacta tcccatatca ccagctcacc gtctttcatt gccatacgga attccggatg   1800
agcattcatc aggcgggcaa gaatgtgaat aaaggccgga taaaacttgt gcttattttt   1860
ctttacggtc tttaaaaagg ccgtaatatc cagctgaacg gtctggttat aggtacattg   1920
agcaactgac tgaaatgcct caaaatgttc tttacgatgc cattgggata tatcaacggt   1980
ggtatatcca gtgatttttt tctccatttt agcttcctta gctcctgaaa atctcgataa   2040
ctcaaaaaat acgcccggta gtgatcttat ttcattatgg tgaaagttgg aacctcttac   2100
gtgccgatca acgtctcatt ttcgccaaaa gttggcccag ggcttcccgg tatcaacagg   2160
gacaccagga tttatttatt ctgcgaagtg atcttccgtc acaggtattt attcggcgca   2220
aagtgcgtcg ggtgatgctg ccaacttact gatttagtgt atgatggtgt ttttgaggtg   2280
ctccagtggc ttctgtttct atcagctgtc cctcctgttc agctactgac ggggtggtgc   2340
gtaacggcaa aagcaccgcc ggacatcagc gctagcggag tgtatactgg cttactatgt   2400
tggcactgat gagggtgtca gtgaagtgct tcatgtggca ggagaaaaaa ggctgcaccg   2460
gtgcgtcagc agaatatgtg atacaggata tattccgctt cctcgctcac tgactcgcta   2520
cgctcggtcg ttcgactgcg gcgagcggaa atggcttacg aacggggcgg agatttcctg   2580
gaagatgcca ggaagatact taacagggaa gtgagagggc cgcggcaaag ccgtttttcc   2640
ataggctccg cccccctgac aagcatcacg aaatctgacg ctcaaatcag tggtggcgaa   2700
acccgacagg actataaaga taccaggcgt ttccccctgg cggctccctc gtgcgctctc   2760
```

-continued ctgttcctgc ctttcggttt accggtgtca ttccgctgtt atggccgcgt ttgtctcatt 2820
ccacgcctga cactcagttc cgggtaggca gttcgctcca agctggactg tatgcacgaa 2880
ccccccgttc agtccgaccg ctgcgcctta tccggtaact atcgtcttga gtccaacccg 2940
gaaagacatg caaaagcacc actggcagca gccactggta attgatttag aggagttagt 3000
cttgaagtca tgcgccggtt aaggctaaac tgaaaggaca agttttggtg actgcgctcc 3060
tccaagccag ttacctcggt tcaaagagtt ggtagctcag agaaccttcg aaaaaccgcc 3120
ctgcaaggcg gttttttcgt tttcagagca agagattacg cgcagaccaa aacgatctca 3180
agaagatcat cttattaatc agataaaata tttgctcatg agcccgaagt ggcgagcccg 3240
atcttcccca tcggtgatgt cggcgatata ggcgccagca accgcacctg tggcgccggt 3300
gatgccggcc acgatgcgtc cggcgtagag gatctgctca tgtttgacag cttatcatcg 3360
atgcataatg tgcctgtcaa atggacgaag cagggattct gcaaacccta tgctactccg 3420
tcaagccgtc aattgtctga ttcgttacca attatgacaa cttgacggct acatcattca 3480
ctttttcttc acaaccggca cggaactcgc tcgggctggc cccggtgcat tttttaaata 3540
cccgcgagaa atagagttga tcgtcaaaac caacattgcg accgacggtg gcgataggca 3600
tccgggtggt gctcaaaagc agcttcgcct ggctgatacg ttggtcctcg cgccagctta 3660
agacgctaat ccctaactgc tggcggaaaa gatgtgacag acgcgacggc gacaagcaaa 3720
catgctgtgc gacgctggcg atatcaaaat tgctgtctgc caggtgatcg ctgatgtact 3780
gacaagcctc gcgtacccga ttatccatcg gtggatggag cgactcgtta atcgcttcca 3840
tgcgccgcag taacaattgc tcaagcagat ttatcgccag cagctccgaa tagcgccctt 3900
ccccttgccc ggcgttaatg atttgcccaa acaggtcgct gaaatgcggc tggtgcgctt 3960
catccgggcg aaagaacccc gtattggcaa atattgacgg ccagttaagc cattcatgcc 4020
agtaggcgcg cggacgaaag taaacccact ggtgatacca ttcgcgagcc tccggatgac 4080
gaccgtagtg atgaatctct cctggcggga acagcaaaat atcacccggt cggcaaacaa 4140
attctcgtcc ctgatttttc accaccccct gaccgcgaat ggtgagattg agaatataac 4200
ctttcattcc cagcggtcgg tcgataaaaa aatcgagata accgttggcc tcaatcggcg 4260
ttaaacccgc caccagatgg gcattaaacg agtatcccgg cagcagggga tcattttgcg 4320
cttcagccat acttttcata ctcccgccat tcagagaaga aaccaattgt ccatattgca 4380
tcagacattg ccgtcactgc gtcttttact ggctcttctc gctaaccaaa ccggtaaccc 4440
cgcttattaa aagcattctg taacaaagcg ggaccaaagc catgacaaaa acgcgtaaca 4500
aaagtgtcta taatcacggc agaaaagtcc acattgatta tttgcacggc gtcacacttt 4560
gctatgccat agcattttta tccataagat tagcggatcc tacctgacgc tttttatcgc 4620
aactctctac tgtttctcca tacccgtttt tttgggctag cgaattcgag ctcggtaccc 4680
cccattctga aatgagctgt tgacaattaa tcatccggct cgtataatgt gtggaattgt 4740
gagcggataa caatttcaca caggaaacag cgccgctgag aaaaagcgaa gcggcactgc 4800
tctttaacaa tttatcagac aatctgtgtg ggcactcgac cggaattatc gattaacttt 4860
attattaaaa attaaagagg tatatattaa tgtatcgatt aaataaggag gaataaacca 4920
tgtgtgcgac ctcttctcaa tttactcaga ttaccgagca taattcccgt cgttccgcaa 4980
actatcagcc aaacctgtgg aatttcgaat tcctgcaatc cctggagaac gacctgaaag 5040
tggaaaagct ggaggagaaa gcgaccaaac tggaggaaga agttcgctgc atgatcaacc 5100
gtgtagacac ccagccgctg tccctgctgg agctgatcga cgatgtgcag cgcctgggtc 5160
tgacctacaa atttgaaaaa gacatcatta aagccctgga aaacatcgta ctgctggacg 5220
aaaacaaaaa gaacaaatct gacctgcacg caaccgctct gtctttccgt ctgctgcgtc 5280
agcacggttt cgaggtttct caggatgttt ttgagcgttt caaggataaa gaaggtggtt 5340
tcagcggtga actgaaaggt gacgtccaag gcctgctgag cctgtatgaa gcgtcttacc 5400
tgggtttcga gggtgagaac ctgctggagg aggcgcgtac cttttccatc acccacctga 5460
agaacaacct gaaagaaggc attaatacca aggttgcaga acaagtgagc cacgccctgg 5520
aactgccata tcaccagcgt ctgcaccgtc tggaggcacg ttggttcctg gataaatacg 5580
aaccgaaaga accgcatcac cagctgctgc tggagctggc gaagctggat tttaacatgg 5640
tacagaccct gcaccagaaa gagctgcaag atctgtcccg ctggtggacc gagatgggcc 5700
tggctagcaa actggatttt gtacgcgacc gcctgatgga agtttatttc tgggcactgg 5760
gtatggcgcc agacccgcag tttggtgaat gtcgcaaagc tgttactaaa atgtttggtc 5820
tggtgacgat catcgatgac gtgtatgacg tttatggcac tctggacgaa ctgcaactgt 5880
tcaccgatgc tgtagagcgc tgggacgtta acgctattaa caccctgccg gactatatga 5940
aactgtgttt cctggcactg tacaacaccg ttaacgacac gtcctattct attctgaaag 6000
agaaaggtca taacaacctg tcctatctga cgaaaagctg gcgtgaactg tgcaaagcct 6060
ttctgcaaga ggcgaaatgg tccaacaaca aaattatccc ggctttctcc aagtacctgg 6120
aaaacgccag cgtttcctcc tccggtgtag cgctgctggc gccgtcttac ttttccgtat 6180
gccagcagca ggaagacatc tccgaccacg cgctgcgttc cctgaccgac ttccatggtc 6240
tggtgcgttc tagctgcgtt atcttccgcc tgtgcaacga tctggccacc tctgcggcgg 6300
agctggaacg tggcgagact accaattcta tcattagcta catgcacgaa aacgatggta 6360
ccagcgagga acaggcccgc gaagaactgc gtaaactgat cgacgccgaa tggaaaaaga 6420
tgaatcgtga acgcgttagc gactccaccc tgctgcctaa agcgttcatg gaaatcgcag 6480
ttaacatggc acgtgtttcc cactgcacct accagtatgg cgatggtctg ggtcgcccag 6540
actacgcgac tgaaaaccgc atcaaactgc tgctgattga ccctttcccg attaaccagc 6600
tgatgtatgt ctaactgcag ggcatgcaag cttggctgtt ttggcggatg agagaagatt 6660
ttcagcctga tacagattaa atcagaacgc agaagcggtc tgataaaaca gaatttgcct 6720
ggcggcagta gcgcggtggt cccacctgac cccatgccga actcagaagt gaaacgccgt 6780
agcgccgatg gtagtgtggg gtctccccat gcgagagtag ggaactgcca ggcatcaaat 6840
aaaacgaaag gctcagtcga aagactgggc ctttcgtttt atctgttgtt tgtcggtgaa 6900
cgctctcctg agtaggacaa atccgccggg agcggatttg aacgttgcga agcaacggcc 6960
cggagggtgg cgggcaggac gcccgccata aactgccagg catcaaatta agcagaaggc 7020
catcctgacg gatggccttt ttgcgtttct acaaactctt ttgtttattt ttctaaatac 7080
attcaaatat gtatccgctc atgagacaat aaccctgata aatgcttcaa taatattgaa 7140
aaaggaagag tatgagtatt caacatttcc gtgtcgccct tattcccttt tttgcggcat 7200
tttgccttcc tgtttttgct cacccagaaa cgctggtgaa agtaaaagat gctgaagatc 7260
agttgggtgc a 7271

<210> SEQ ID NO 53
<211> LENGTH: 7833
<212> TYPE: DNA
<213> ORGANISM: Artificial Sequence
<220> FEATURE:
<223> OTHER INFORMATION: Synthetic Construct

<400> SEQUENCE: 53

```
gcaaactatt aactggcgaa ctacttactc tagcttcccg gcaacaatta atagactgga     60
tggaggcgga taaagttgca ggaccacttc tgcgctcggc ccttccggct ggctggttta    120
ttgctgataa atctggagcc ggtgagcgtg ggtctcgcgg tatcattgca gcactggggc    180
cagatggtaa gccctcccgt atcgtagtta tctacacgac ggggagtcag gcaactatgg    240
atgaacgaaa tagacagatc gctgagatag gtgcctcact gattaagcat tggtaactgt    300
cagaccaagt ttactcatat atactttaga ttgatttacg cgccctgtag cggcgcatta    360
agcgcggcgg gtgtggtggt tacgcgcagc gtgaccgcta cacttgccag cgccctagcg    420
cccgctcctt tcgctttctt cccttccttt ctcgccacgt tcgccggctt tccccgtcaa    480
gctctaaatc gggggctccc tttagggttc cgatttagtg ctttacggca cctcgacccc    540
aaaaaacttg atttgggtga tggttcacgt agtgggccat cgccctgata gacggttttt    600
cgccctttga cgttggagtc cacgttcttt aatagtggac tcttgttcca aacttgaaca    660
acactcaacc ctatctcggg ctattctttt gatttataag ggattttgcc gatttcggcc    720
tattggttaa aaaatgagct gatttaacaa aaatttaacg cgaattttaa caaaatatta    780
acgtttacaa tttaaaagga tctaggtgaa gatccttttt gataatctca tgaccaaaat    840
cccttaacgt gagttttcgt tccactgagc gtcagacccc gtagaaaaga tcaaaggatc    900
ttcttgagat cctttttttc tgcgcgtaat ctgctgcttg caaacaaaaa aaccaccgct    960
accagcggtg gtttgtttgc cggatcaaga gctaccaact ctttttccga aggtaactgg   1020
cttcagcaga gcgcagatac caaatactgt ccttctagtg tagccgtagt taggccacca   1080
cttcaagaac tctgtagcac cgcctacata cctcgctctg ctaatcctgt taccagtcag   1140
gcatttgaga agcacacggt cacactgctt ccggtagtca ataaaccggt aaaccagcaa   1200
tagacataag cggctattta acgaccctgc cctgaaccga cgaccgggtc gaatttgctt   1260
tcgaatttct gccattcatc cgcttattat cacttattca ggcgtagcac caggcgttta   1320
agggcaccaa taactgcctt aaaaaaatta cgccccgccc tgccactcat cgcagtactg   1380
ttgtaattca ttaagcattc tgccgacatg gaagccatca cagacggcat gatgaacctg   1440
aatcgccagc ggcatcagca ccttgtcgcc ttgcgtataa tatttgccca tggtgaaaac   1500
gggggcgaag aagttgtcca tattggccac gtttaaatca aaactggtga aactcaccca   1560
gggattggct gagacgaaaa acatattctc aataaaccct ttagggaaat aggccaggtt   1620
ttcaccgtaa cacgccacat cttgcgaata tatgtgtaga aactgccgga aatcgtcgtg   1680
gtattcactc cagagcgatg aaaacgtttc agtttgctca tggaaaacgg tgtaacaagg   1740
gtgaacacta tcccatatca ccagctcacc gtctttcatt gccatacgga attccggatg   1800
agcattcatc aggcgggcaa gaatgtgaat aaaggccgga taaaacttgt gcttattttt   1860
ctttacggtc tttaaaaagg ccgtaatatc cagctgaacg gtctggttat aggtacattg   1920
agcaactgac tgaaatgcct caaaatgttc tttacgatgc cattgggata tatcaacggt   1980
ggtatatcca gtgatttttt tctccatttt agcttcctta gctcctgaaa atctcgataa   2040
ctcaaaaaat acgcccggta gtgatcttat ttcattatgg tgaaagttgg aacctcttac   2100
gtgccgatca acgtctcatt ttcgccaaaa gttggcccag ggcttcccgg tatcaacagg   2160
gacaccagga tttatttatt ctgcgaagtg atcttccgtc acaggtattt attcggcgca   2220
aagtgcgtcg ggtgatgctg ccaacttact gatttagtgt atgatggtgt ttttgaggtg   2280
ctccagtggc ttctgtttct atcagctgtc cctcctgttc agctactgac ggggtggtgc   2340
```

```
gtaacggcaa aagcaccgcc ggacatcagc gctagcggag tgtatactgg cttactatgt   2400
tggcactgat gagggtgtca gtgaagtgct tcatgtggca ggagaaaaaa ggctgcaccg   2460
gtgcgtcagc agaatatgtg atacaggata tattccgctt cctcgctcac tgactcgcta   2520
cgctcggtcg ttcgactgcg gcgagcggaa atggcttacg aacggggcgg agatttcctg   2580
gaagatgcca ggaagatact taacagggaa gtgagagggc cgcggcaaag ccgtttttcc   2640
ataggctccg cccccctgac aagcatcacg aaatctgacg ctcaaatcag tggtggcgaa   2700
acccgacagg actataaaga taccaggcgt ttccccctgg cggctccctc gtgcgctctc   2760
ctgttcctgc ctttcggttt accggtgtca ttccgctgtt atggccgcgt ttgtctcatt   2820
ccacgcctga cactcagttc cgggtaggca gttcgctcca agctggactg tatgcacgaa   2880
ccccccgttc agtccgaccg ctgcgcctta tccggtaact atcgtcttga gtccaacccg   2940
gaaagacatg caaaagcacc actggcagca gccactggta attgatttag aggagttagt   3000
cttgaagtca tgcgccggtt aaggctaaac tgaaaggaca agttttggtg actgcgctcc   3060
tccaagccag ttacctcggt tcaaagagtt ggtagctcag agaaccttcg aaaaaccgcc   3120
ctgcaaggcg gttttttcgt tttcagagca agagattacg cgcagaccaa aacgatctca   3180
agaagatcat cttattaatc agataaaata tttgctcatg agcccgaagt ggcgagcccg   3240
atcttcccca tcggtgatgt cggcgatata ggcgccagca accgcacctg tggcgccggt   3300
gatgccggcc acgatgcgtc cggcgtagag gatctgctca tgtttgacag cttatcatcg   3360
atgcataatg tgcctgtcaa atggacgaag cagggattct gcaaacccta tgctactccg   3420
tcaagccgtc aattgtctga ttcgttacca attatgacaa cttgacggct acatcattca   3480
ctttttcttc acaaccggca cggaactcgc tcgggctggc cccggtgcat ttttaaata   3540
cccgcgagaa atagagttga tcgtcaaaac caacattgcg accgacggtg gcgataggca   3600
tccgggtggt gctcaaaagc agcttcgcct ggctgatacg ttggtcctcg cgccagctta   3660
agacgctaat ccctaactgc tggcggaaaa gatgtgacag acgcgacggc gacaagcaaa   3720
catgctgtgc gacgctggcg atatcaaaat tgctgtctgc caggtgatcg ctgatgtact   3780
gacaagcctc gcgtacccga ttatccatcg gtggatggag cgactcgtta atcgcttcca   3840
tgcgccgcag taacaattgc tcaagcagat ttatcgccag cagctccgaa tagcgccctt   3900
ccccttgccc ggcgttaatg atttgcccaa acaggtcgct gaaatgcggc tggtgcgctt   3960
catccgggcg aaagaacccc gtattggcaa atattgacgg ccagttaagc cattcatgcc   4020
agtaggcgcg cggacgaaag taaacccact ggtgatacca ttcgcgagcc tccggatgac   4080
gaccgtagtg atgaatctct cctggcggga acagcaaaat atcacccggt cggcaaacaa   4140
attctcgtcc ctgatttttc accacccccct gaccgcgaat ggtgagattg agaatataac   4200
ctttcattcc cagcggtcgg tcgataaaaa aatcgagata accgttggcc tcaatcggcg   4260
ttaaacccgc caccagatgg gcattaaacg agtatcccgg cagcagggga tcattttgcg   4320
cttcagccat acttttcata ctcccgccat tcagagaaga aaccaattgt ccatattgca   4380
tcagacattg ccgtcactgc gtcttttact ggctcttctc gctaaccaaa ccggtaaccc   4440
cgcttattaa aagcattctg taacaaagcg ggaccaaagc catgacaaaa acgcgtaaca   4500
aaagtgtcta taatcacggc agaaaagtcc acattgatta tttgcacggc gtcacacttt   4560
gctatgccat agcattttta tccataagat tagcggatcc tacctgacgc tttttatcgc   4620
aactctctac tgtttctcca tacccgtttt tttgggctag cgaattcgag ctcggtaccc   4680
cccattctga aatgagctgt tgacaattaa tcatccggct cgtataatgt gtggaattgt   4740
```

gagcggataa caatttcaca caggaaacag cgccgctgag aaaaagcgaa gcggcactgc 4800
tctttaacaa tttatcagac aatctgtgtg ggcactcgac cggaattatc gattaacttt 4860
attattaaaa attaaagagg tatatattaa tgtatcgatt aaataaggag gaataaacca 4920
tgtgtgcgac ctcttctcaa tttactcaga ttaccgagca taattcccgt cgttccgcaa 4980
actatcagcc aaacctgtgg aatttcgaat tcctgcaatc cctggagaac gacctgaaag 5040
tggaaaagct ggaggagaaa gcgaccaaac tggaggaaga agttcgctgc atgatcaacc 5100
gtgtagacac ccagccgctg tccctgctgg agctgatcga cgatgtgcag cgcctgggtc 5160
tgacctacaa atttgaaaaa gacatcatta aagccctgga aaacatcgta ctgctggacg 5220
aaaacaaaaa gaacaaatct gacctgcacg caaccgctct gtctttccgt ctgctgcgtc 5280
agcacggttt cgaggtttct caggatgttt ttgagcgttt caaggataaa gaaggtggtt 5340
tcagcggtga actgaaaggt gacgtccaag gcctgctgag cctgtatgaa gcgtcttacc 5400
tgggtttcga gggtgagaac ctgctggagg aggcgcgtac cttttccatc acccacctga 5460
agaacaacct gaaagaaggc attaatacca aggttgcaga acaagtgagc cacgccctgg 5520
aactgccata tcaccagcgt ctgcaccgtc tggaggcacg ttggttcctg gataaatacg 5580
aaccgaaaga accgcatcac cagctgctgc tggagctggc gaagctggat tttaacatgg 5640
tacagaccct gcaccagaaa gagctgcaag atctgtcccg ctggtggacc gagatgggcc 5700
tggctagcaa actggatttt gtacgcgacc gcctgatgga agtttatttc tgggcactgg 5760
gtatggcgcc agacccgcag tttggtgaat gtcgcaaagc tgttactaaa atgtttggtc 5820
tggtgacgat catcgatgac gtgtatgacg tttatggcac tctggacgaa ctgcaactgt 5880
tcaccgatgc tgtagagcgc tgggacgtta acgctattaa caccctgccg gactatatga 5940
aactgtgttt cctggcactg tacaacaccg ttaacgacac gtcctattct attctgaaag 6000
agaaaggtca taacaacctg tcctatctga cgaaaagctg gcgtgaactg tgcaaagcct 6060
ttctgcaaga ggcgaaatgg tccaacaaca aaattatccc ggctttctcc aagtacctgg 6120
aaaacgccag cgtttcctcc tccggtgtag cgctgctggc gccgtcttac ttttccgtat 6180
gccagcagca ggaagacatc tccgaccacg cgctgcgttc cctgaccgac ttccatggtc 6240
tggtgcgttc tagctgcgtt atcttccgcc tgtgcaacga tctggccacc tctgcggcgg 6300
agctggaacg tggcgagact accaattcta tcattagcta catgcacgaa aacgatggta 6360
ccagcgagga acaggcccgc gaagaactgc gtaaactgat cgacgccgaa tggaaaaaga 6420
tgaatcgtga acgcgttagc gactccaccc tgctgcctaa agcgttcatg gaaatcgcag 6480
ttaacatggc acgtgtttcc cactgcacct accagtatgg cgatggtctg ggtcgcccag 6540
actacgcgac tgaaaaccgc atcaaactgc tgctgattga ccctttcccg attaaccagc 6600
tgatgtatgt ctaactgcat actagtttca agaggtattt cactcatggc tatcactggc 6660
atctttttcg gcagcgacac cggtaatacc gaaaatatcg caaaaatgat tcaaaaacag 6720
cttggtaaag acgttgccga tgtccatgac attgcaaaaa gcagcaaaga agatctggaa 6780
gcttatgaca ttctgctgct gggcatccca acctggtatt acggcgaagc gcagtgtgac 6840
tgggatgact tcttcccgac tctcgaagag attgatttca acggcaaact ggttgcgctg 6900
tttggttgtg gtgaccagga agattacgcc gaatatttct gcgacgcatt gggcaccatc 6960
cgcgacatca ttgaaccgcg cggtgcaacc atcgttggtc actggccaac tgcgggctat 7020
catttcgaag catcaaaagg tctggcagat gacgaccact ttgtcggtct ggctatcgac 7080
gaagaccgtc agccggaact gaccgctgaa cgtgtagaaa aatgggttaa acagatttct 7140
gaagagttgc atctcgacga aattctcaat gcctgactgc agggcatgca agcttggctg 7200
ttttggcgga tgagagaaga ttttcagcct gatacagatt aaatcagaac gcagaagcgg 7260
tctgataaaa cagaatttgc ctggcggcag tagcgcggtg gtcccacctg accccatgcc 7320
gaactcagaa gtgaaacgcc gtagcgccga tggtagtgtg gggtctcccc atgcgagagt 7380
agggaactgc caggcatcaa ataaaacgaa aggctcagtc gaaagactgg gcctttcgtt 7440
ttatctgttg tttgtcggtg aacgctctcc tgagtaggac aaatccgccg ggagcggatt 7500
tgaacgttgc gaagcaacgg cccggagggt ggcgggcagg acgcccgcca taaactgcca 7560
ggcatcaaat taagcagaag gccatcctga cggatggcct ttttgcgttt ctacaaactc 7620
ttttgtttat ttttctaaat acattcaaat atgtatccgc tcatgagaca ataaccctga 7680
taaatgcttc aataatattg aaaaaggaag agtatgagta ttcaacattt ccgtgtcgcc 7740
cttattccct tttttgcggc attttgcctt cctgtttttg ctcacccaga aacgctggtg 7800
aaagtaaaag atgctgaaga tcagttgggt gca 7833

<210> SEQ ID NO 54
<211> LENGTH: 36
<212> TYPE: DNA
<213> ORGANISM: Artificial Sequence
<220> FEATURE:
<223> OTHER INFORMATION: Synthetic Construct

<400> SEQUENCE: 54
ggatgcatac tagtttcaag aggtatttca ctcatg 36

<210> SEQ ID NO 55
<211> LENGTH: 30
<212> TYPE: DNA
<213> ORGANISM: Artificial Sequence
<220> FEATURE:
<223> OTHER INFORMATION: Synthetic Construct

<400> SEQUENCE: 55
atcctgcagt caggcattga gaatttcgtc 30

<210> SEQ ID NO 56
<211> LENGTH: 6592
<212> TYPE: DNA
<213> ORGANISM: Artificial Sequence
<220> FEATURE:
<223> OTHER INFORMATION: Synthetic Construct

<400> SEQUENCE: 56
gaattgctcc attttcttct gctatcaaaa taacagactc gtgattttcc aaacgagctt 60
tcaaaaaagc ctctgcccct tgcaaatcgg atgcctgtct ataaaattcc cgatattggt 120
taaacagcgg cgcaatggcg gccgcatctg atgtctttgc ttggcgaatg ttcatcttat 180
ttcttcctcc ctctcaataa ttttttcatt ctatcccttt tctgtaaagt ttatttttca 240
gaatactttt atcatcatgc tttgaaaaaa tatcacgata atatccattg ttctcacgga 300
agcacacgca ggtcatttga acgaattttt tcgacaggaa tttgccggga ctcaggagca 360
tttaacctaa aaaagcatga catttcagca taatgaacat ttactcatgt ctattttcgt 420
tcttttctgt atgaaaatag ttatttcgag tctctacgga aatagcgaga gatgatatac 480
ctaaatagag ataaaatcat ctcaaaaaaa tgggtctact aaaatattat tccatctatt 540
acaataaatt cacagaatag tcttttaagt aagtctactc tgaatttttt taaaaggaga 600
gggtaaagag tgtgtgcgac ctcttctcaa tttactcaga ttaccgagca taattcccgt 660

```
cgttccgcaa actatcagcc aaacctgtgg aatttcgaat tcctgcaatc cctggagaac    720
gacctgaaag tggaaaagct ggaggagaaa gcgaccaaac tggaggaaga agttcgctgc    780
atgatcaacc gtgtagacac ccagccgctg tccctgctgg agctgatcga cgatgtgcag    840
cgcctgggtc tgacctacaa atttgaaaaa gacatcatta aagccctgga aaacatcgta    900
ctgctggacg aaaacaaaaa gaacaaatct gacctgcacg caaccgctct gtctttccgt    960
ctgctgcgtc agcacggttt cgaggtttct caggatgttt ttgagcgttt caaggataaa   1020
gaaggtggtt tcagcggtga actgaaaggt gacgtccaag gcctgctgag cctgtatgaa   1080
gcgtcttacc tgggtttcga gggtgagaac ctgctggagg aggcgcgtac cttttccatc   1140
acccacctga agaacaacct gaaagaaggc attaatacca aggttgcaga acaagtgagc   1200
cacgccctgg aactgccata tcaccagcgt ctgcaccgtc tggaggcacg ttggttcctg   1260
gataaatacg aaccgaaaga accgcatcac cagctgctgc tggagctggc gaagctggat   1320
tttaacatgg tacagaccct gcaccagaaa gagctgcaag atctgtcccg ctggtggacc   1380
gagatgggcc tggctagcaa actggatttt gtacgcgacc gcctgatgga agtttatttc   1440
tgggcactgg gtatggcgcc agacccgcag tttggtgaat gtcgcaaagc tgttactaaa   1500
atgtttggtc tggtgacgat catcgatgac gtgtatgacg tttatggcac tctggacgaa   1560
ctgcaactgt tcaccgatgc tgtagagcgc tgggacgtta acgctattaa caccctgccg   1620
gactatatga aactgtgttt cctggcactg tacaacaccg ttaacgacac gtcctattct   1680
attctgaaag agaaaggtca taacaacctg tcctatctga cgaaaagctg gcgtgaactg   1740
tgcaaagcct ttctgcaaga ggcgaaatgg tccaacaaca aaattatccc ggctttctcc   1800
aagtacctgg aaaacgccag cgtttcctcc tccggtgtag cgctgctggc gccgtcttac   1860
ttttccgtat gccagcagca ggaagacatc tccgaccacg cgctgcgttc cctgaccgac   1920
ttccatggtc tggtgcgttc tagctgcgtt atcttccgcc tgtgcaacga tctggccacc   1980
tctgcggcgg agctggaacg tggcgagact accaattcta tcattagcta catgcacgaa   2040
aacgatggta ccagcgagga acaggcccgc gaagaactgc gtaaactgat cgacgccgaa   2100
tggaaaaaga tgaatcgtga acgcgttagc gactccaccc tgctgcctaa agcgttcatg   2160
gaaatcgcag ttaacatggc acgtgtttcc cactgcacct accagtatgg cgatggtctg   2220
ggtcgcccag actacgcgac tgaaaaccgc atcaaactgc tgctgattga ccctttcccg   2280
attaaccagc tgatgtatgt ctaaaaaaaa ccggccttgg ccccgccggt tttttattat   2340
ttttcttcct ccgcatgttc aatccgctcc ataatcgacg gatggctccc tctgaaaatt   2400
ttaacgagaa acggcgggtt gacccggctc agtcccgtaa cggccaagtc ctgaaacgtc   2460
tcaatcgccg cttcccggtt tccggtcagc tcaatgccgt aacggtcggc ggcgttttcc   2520
tgataccggg agacggcatt cgtaatcgga tcctctagag tcgacctgca ggcatgcaag   2580
ctttgcctcg cgcgtttcgg tgatgacggt gaaaacctct gacacatgca gctcccggag   2640
acggtcacag cttgtctgta agcggatgcc gggagcagac aagcccgtca gggcgcgtca   2700
gcgggtgttg gcgggtgtcg gggcgcagcc atgacccagt cacgtagcga tagcggagtg   2760
tatactggct taactatgcg gcatcagagc agattgtact gagagtgcac catatgcggt   2820
gtgaaatacc gcacagatgc gtaaggagaa aataccgcat caggcgctct tccgcttcct   2880
cgctcactga ctcgctgcgc tcggtcgttc ggctgcggcg agcggtatca gctcactcaa   2940
aggcggtaat acggttatcc acagaatcag gggataacgc aggaaagaac atgtgagcaa   3000
aaggccagca aaaggccagg aaccgtaaaa aggccgcgtt gctggcgttt ttccataggc   3060
```

```
tccgcccccc tgacgagcat cacaaaaatc gacgctcaag tcagaggtgg cgaaacccga   3120
caggactata aagataccag gcgtttcccc ctggaagctc cctcgtgcgc tctcctgttc   3180
cgaccctgcc gcttaccgga tacctgtccg cctttctccc ttcgggaagc gtggcgcttt   3240
ctcaatgctc acgctgtagg tatctcagtt cggtgtaggt cgttcgctcc aagctgggct   3300
gtgtgcacga accccccgtt cagcccgacc gctgcgcctt atccggtaac tatcgtcttg   3360
agtccaaccc ggtaagacac gacttatcgc cactggcagc agccactggt aacaggatta   3420
gcagagcgag gtatgtaggc ggtgctacag agttcttgaa gtggtggcct aactacggct   3480
acactagaag gacagtattt ggtatctgcg ctctgctgaa gccagttacc ttcggaaaaa   3540
gagttggtag ctcttgatcc ggcaaacaaa ccaccgctgg tagcggtggt ttttttgttt   3600
gcaagcagca gattacgcgc agaaaaaaag gatctcaaga agatcctttg atcttttcta   3660
cggggtctga cgctcagtgg aacgaaaact cacgttaagg gattttggtc atgagattat   3720
caaaaaggat cgaagtcggt tcagaaaaag aaggatatgg atctggagct gtaatataaa   3780
aaccttcttc aactaacggg gcaggttagt gacattagaa aaccgactgt aaaaagtaca   3840
gtcggcatta tctcatatta taaaagccag tcattaggcc tatctgacaa ttcctgaata   3900
gagttcataa acaatcctgc atgataacca tcacaaacag aatgatgtac ctgtaaagat   3960
agcggtaaat atattgaatt acctttatta atgaattttc ctgctgtaat aatgggtaga   4020
aggtaattac tattattatt gatatttaag ttaaacccag taaatgaagt ccatggaata   4080
atagaaagag aaaaagcatt ttcaggtata ggtgttttgg gaaacaattt aaaagaacca   4140
ttatatttct ctacatcaga aaggtataaa tcataaaact ctttgaagtc attctttaca   4200
ggagtccaaa taccagagaa tgttttagat acaccatcaa aaattgtata aagtggctct   4260
aacttatccc aataacctaa ctctccgtcg ctattgtaac cagttctaaa agctgtattt   4320
gagtttatca cccttgtcac taagaaaata aatgcagggt aaaatttata tccttcttgt   4380
tttatgtttc ggtataaaac actaatatca atttctgtgg ttatactaaa agtcgtttgt   4440
tggttcaaat aatgattaaa tatctctttt ctcttccaat tgtctaaatc aattttatta   4500
aagttcattt gatatgcctc ctaaattttt atctaaagtg aatttaggag gcttacttgt   4560
ctgctttctt cattagaatc aatccttttt taaagtcaat attactgtaa cataaatata   4620
tattttaaaa atatcccact ttatccaatt ttcgtttgtt gaactaatgg gtgctttagt   4680
tgaagaataa agaccacatt aaaaaatgtg gtcttttgtg tttttttaaa ggatttgagc   4740
gtacgcgaaa aatccttttc tttctttctt atcttgataa taagggtaac tattgccggt   4800
tgtccattca tggctgaact ctgcttcctc tgttgacatg acacacatca tctcaatatc   4860
cgaatagggc ccatcagtct gacgaccaag agagccataa acaccaatag ccttaacatc   4920
atccccatat ttatccaata ttcgttcctt aatttcatga acaatcttca ttctttcttc   4980
tctagtcatt attattggtc cattcactat tctcattccc ttttcagata attttagatt   5040
tgcttttcta aataagaata tttggagagc accgttctta ttcagctatt aataactcgt   5100
cttcctaagc atccttcaat ccttttaata acaattatag catctaatct tcaacaaact   5160
ggcccgtttg ttgaactact ctttaataaa ataatttttc cgttcccaat tccacattgc   5220
aataatagaa aatccatctt catcggcttt ttcgtcatca tctgtatgaa tcaaatcgcc   5280
ttcttctgtg tcatcaaggt ttaatttttt atgtatttct tttaacaaac caccatagga   5340
gattaacctt ttacggtgta aaccttcctc caaatcagac aaacgtttca aattcttttc   5400
ttcatcatcg gtcataaaat ccgtatcctt tacaggatat tttgcagttt cgtcaattgc   5460
```

cgattgtata tccgatttat atttattttt cggtcgaatc atttgaactt ttacatttgg 5520
atcatagtct aatttcattg cctttttcca aaattgaatc cattgttttt gattcacgta 5580
gttttctgtt attctaaaat aagttggttc cacacatacc attacatgca tgtgctgatt 5640
ataagaatta tctttattat ttattgtcac atccgttgca cgcataaaac caacaagatt 5700
tttattaatt tttttatatt gcatcattcg gcgaaatcct tgagccatat ctgtcaaact 5760
cttatttaat tcttcgccat cataaacatt tttaactgtt aatgtgagaa acaaccaacg 5820
aactgttggc ttttgtttaa taacttcagc aacaaccttt tgtgactgaa tgccatgttt 5880
cattgctctc ctccagttgc acattggaca aagcctggat ttgcaaaacc acactcgata 5940
ccactttctt tcgcctgttt cacgattttg tttatactct aatatttcag cacaatcttt 6000
tactctttca gcctttttaa attcaagaat atgcagaagt tcaaagtaat caacattagc 6060
gattttcttt tctctccatg gtctcacttt tccacttttt gtcttgtcca ctaaaaccct 6120
tgatttttca tctgaataaa tgctactatt aggacacata atattaaaag aaaccccccat 6180 ctatttagtt atttgtttag tcacttataa ctttaacaga tggggttttt ctgtgcaacc 6240
aattttaagg gttttcaata ctttaaaaca catacatacc aacacttcaa cgcacctttc 6300
agcaactaaa ataaaaatga cgttatttct atatgtatca agataagaaa gaacaagttc 6360
aaaaccatca aaaaaagaca ccttttcagg tgcttttttt attttataaa ctcattccct 6420
gatctcgact tcgttctttt tttacctctc ggttatgagt tagttcaaat tcgttctttt 6480
taggttctaa atcgtgtttt tcttggaatt gtgctgtttt atcctttacc ttgtctacaa 6540
accccttaaa aacgttttta aaggctttta agccgtctgt acgttcctta ag 6592

<210> SEQ ID NO 57
<211> LENGTH: 176
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 144
<223> OTHER INFORMATION: n = A,T,C or G

<400> SEQUENCE: 57
ctctctttcg gcaacagtcg taactcctgg gtggagtcga ccagtgccag ggtcgggtat 60
ttggcaatat caaaactcat atattccacc agctatttgt tagtgaataa aagtggttga 120
attatttgct caggatgtgg catngtcaag ggctaatacg actcactata gggctc 176

<210> SEQ ID NO 58
<211> LENGTH: 103
<212> TYPE: DNA
<213> ORGANISM: Artificial Sequence
<220> FEATURE:
<223> OTHER INFORMATION: Synthetic Construct

<400> SEQUENCE: 58
tcgatacctc ggcactggaa gcgctagcgg actacatcat ccagcgtaat aaataaacaa 60
taagtattaa taggcccctg aattaaccct cactaaaggg cgg 103

<210> SEQ ID NO 59
<211> LENGTH: 22
<212> TYPE: DNA
<213> ORGANISM: Artificial Sequence
<220> FEATURE:
<223> OTHER INFORMATION: Synthetic Construct

<400> SEQUENCE: 59
ttgtagacat agtgcagcgc ca 22

<210> SEQ ID NO 60
<211> LENGTH: 24
<212> TYPE: DNA
<213> ORGANISM: Artificial Sequence
<220> FEATURE:
<223> OTHER INFORMATION: Synthetic Construct

<400> SEQUENCE: 60
aaagaccgac caagcgacgt ctga 24

<210> SEQ ID NO 61
<211> LENGTH: 36
<212> TYPE: DNA
<213> ORGANISM: Artificial Sequence
<220> FEATURE:
<223> OTHER INFORMATION: Synthetic Construct

<400> SEQUENCE: 61
gctgggtacc ctgcccgctt tccagtcggg aaacct 36

<210> SEQ ID NO 62
<211> LENGTH: 36
<212> TYPE: DNA
<213> ORGANISM: Artificial Sequence
<220> FEATURE:
<223> OTHER INFORMATION: Synthetic Construct

<400> SEQUENCE: 62
tagaactagt caaaaaaccc ctcaagaccc gtttag 36

<210> SEQ ID NO 63
<211> LENGTH: 17
<212> TYPE: DNA
<213> ORGANISM: Artificial Sequence
<220> FEATURE:
<223> OTHER INFORMATION: Synthetic Construct

<400> SEQUENCE: 63
gtaaaacgac ggccagt 17

<210> SEQ ID NO 64
<211> LENGTH: 22
<212> TYPE: DNA
<213> ORGANISM: Artificial Sequence
<220> FEATURE:
<223> OTHER INFORMATION: Synthetic Construct

<400> SEQUENCE: 64
gcactgtctt tccgtctgct gc 22

<210> SEQ ID NO 65
<211> LENGTH: 20
<212> TYPE: DNA
<213> ORGANISM: Artificial Sequence
<220> FEATURE:
<223> OTHER INFORMATION: Synthetic Construct

<400> SEQUENCE: 65
ctcgtacagg ctcaggatag 20

<210> SEQ ID NO 66
<211> LENGTH: 20

<212> TYPE: DNA
<213> ORGANISM: Artificial Sequence
<220> FEATURE:
<223> OTHER INFORMATION: Synthetic Construct

<400> SEQUENCE: 66
ttacgtccca acgctcaact 20

<210> SEQ ID NO 67
<211> LENGTH: 36
<212> TYPE: DNA
<213> ORGANISM: Artificial Sequence
<220> FEATURE:
<223> OTHER INFORMATION: Synthetic Construct

<400> SEQUENCE: 67
gctgggtacc ctgcccgctt tccagtcggg aaacct 36

<210> SEQ ID NO 68
<211> LENGTH: 36
<212> TYPE: DNA
<213> ORGANISM: Artificial Sequence
<220> FEATURE:
<223> OTHER INFORMATION: Synthetic Construct

<400> SEQUENCE: 68
tagaactagt caaaaaaccc ctcaagaccc gtttag 36

<210> SEQ ID NO 69
<211> LENGTH: 17
<212> TYPE: DNA
<213> ORGANISM: Artificial Sequence
<220> FEATURE:
<223> OTHER INFORMATION: Synthetic Construct

<400> SEQUENCE: 69
gtaaaacgac ggccagt 17

<210> SEQ ID NO 70
<211> LENGTH: 22
<212> TYPE: DNA
<213> ORGANISM: Artificial Sequence
<220> FEATURE:
<223> OTHER INFORMATION: Synthetic Construct

<400> SEQUENCE: 70
gcactgtctt tccgtctgct gc 22

<210> SEQ ID NO 71
<211> LENGTH: 20
<212> TYPE: DNA
<213> ORGANISM: Artificial Sequence
<220> FEATURE:
<223> OTHER INFORMATION: Synthetic Construct

<400> SEQUENCE: 71
ctcgtacagg ctcaggatag 20

<210> SEQ ID NO 72
<211> LENGTH: 20
<212> TYPE: DNA
<213> ORGANISM: Artificial Sequence
<220> FEATURE:
<223> OTHER INFORMATION: Synthetic Construct

<400> SEQUENCE: 72
ttacgtccca acgctcaact 20

<210> SEQ ID NO 73
<211> LENGTH: 8069
<212> TYPE: DNA
<213> ORGANISM: Artificial Sequence
<220> FEATURE:
<223> OTHER INFORMATION: Synthetic Construct

<400> SEQUENCE: 73
accttcggga gcgcctgaag cccgttctgg acgccctggg gccgttgaat cgggatatgc 60
aggccaaggc cgccgcgatc atcaaggccg tgggcgaaaa gctgctgacg gaacagcggg 120
aagtccagcg ccagaaacag gcccagcgcc agcaggaacg cgggcgcgca catttccccg 180
aaaagtgcca cctggcggcg ttgtgacaat ttaccgaaca actccgcggc cgggaagccg 240
atctcggctt gaacgaattg ttaggtggcg gtacttgggt cgatatcaaa gtgcatcact 300
tcttcccgta tgcccaactt tgtatagaga gccactgcgg gatcgtcacc gtaatctgct 360
tgcacgtaga tcacataagc accaagcgcg ttggcctcat gcttgaggag attgatgagc 420
gcggtggcaa tgccctgcct ccggtgctcg ccggagactg cgagatcata gatatagatc 480
tcactacgcg gctgctcaaa cctgggcaga acgtaagccg cgagagcgcc aacaaccgct 540
tcttggtcga aggcagcaag cgcgatgaat gtcttactac ggagcaagtt cccgaggtaa 600
tcggagtccg gctgatgttg ggagtaggtg gctacgtctc cgaactcacg accgaaaaga 660
tcaagagcag cccgcatgga tttgacttgg tcagggccga gcctacatgt gcgaatgatg 720
cccatacttg agccacctaa ctttgtttta gggcgactgc cctgctgcgt aacatcgttg 780
ctgctgcgta acatcgttgc tgctccataa catcaaacat cgacccacgg cgtaacgcgc 840
ttgctgcttg gatgcccgag gcatagactg tacaaaaaaa cagtcataac aagccatgaa 900
aaccgccact gcgccgttac caccgctgcg ttcggtcaag gttctggacc agttgcgtga 960
gcgcatacgc tacttgcatt acagtttacg aaccgaacag gcttatgtca actgggttcg 1020
tgccttcatc cgtttccacg gtgtgcgtcc atgggcaaat attatacgca aggcgacaag 1080
gtgctgatgc cgctggcgat tcaggttcat catgccgttt gtgatggctt ccatgtcggc 1140
agaatgctta atgaattaca acagttttta tgcatgcgcc caatacgcaa accgcctctc 1200
cccgcgcgtt ggccgattca ttaatgcagc tggcacgaca ggtttcccga ctggaaagcg 1260
ggcagtgagc gcaacgcaat taatgtgagt tagctcactc attaggcacc ccaggcttta 1320
cactttatgc ttccggctcg tatgttgtgt ggaattgtga gcggataaca atttcacaca 1380
ggaaacagct atgaccatga ttacgccaag cgcgcaatta accctcacta aagggaacaa 1440
aagctgggta ccctgcccgc tttccagtcg ggaaacctgt cgtgccagct gcattaatga 1500
atcggccaac gcgcggggag aggcggtttg cgtattgggc gccagggtgg tttttctttt 1560
caccagtgag acgggcaaca gctgattgcc cttcaccgcc tggccctgag agagttgcag 1620
caagcggtcc acgctggttt gccccagcag gcgaaaatcc tgtttgatgg tggttaacgg 1680
cgggatataa catgagctgt cttcggtatc gtcgtatccc actaccgaga tatccgcacc 1740
aacgcgcagc ccggactcgg taatggcgcg cattgcgccc agcgccatct gatcgttggc 1800
aaccagcatc gcagtgggaa cgatgccctc attcagcatt tgcatggttt gttgaaaacc 1860
ggacatggca ctccagtcgc cttcccgttc cgctatcggc tgaatttgat tgcgagtgag 1920
atatttatgc cagccagcca gacgcagacg cgccgagaca gaacttaatg ggcccgctaa 1980
cagcgcgatt tgctggtgac ccaatgcgac cagatgctcc acgcccagtc gcgtaccgtc 2040
ttcatgggag aaaataatac tgttgatggg tgtctggtca gagacatcaa gaaataacgc 2100

-continued cggaacatta gtgcaggcag cttccacagc aatggcatcc tggtcatcca gcggatagtt 2160
aatgatcagc ccactgacgc gttgcgcgag aagattgtgc accgccgctt tacaggcttc 2220
gacgccgctt cgttctacca tcgacaccac cacgctggca cccagttgat cggcgcgaga 2280
tttaatcgcc gcgacaattt gcgacggcgc gtgcagggcc agactggagg tggcaacgcc 2340
aatcagcaac gactgtttgc ccgccagttg ttgtgccacg cggttgggaa tgtaattcag 2400
ctccgccatc gccgcttcca ctttttcccg cgttttcgca gaaacgtggc tggcctggtt 2460
caccacgcgg gaaacggtct gataagagac accggcatac tctgcgacat cgtataacgt 2520
tactggtttc acattcacca ccctgaattg actctcttcc gggcgctatc atgccatacc 2580
gcgaaaggtt ttgcgccatt cgatggtgtc cgggatctcg acgctctccc ttatgcgact 2640
cctgcattag gaagcagccc agtagtaggt tgaggccgtt gagcaccgcc gccgcaagga 2700
atggtgcatg caaggagatg gcgcccaaca gtcccccggc cacggggcct gccaccatac 2760
ccacgccgaa acaagcgctc atgagcccga agtggcgagc ccgatcttcc ccatcggtga 2820
tgtcggcgat ataggcgcca gcaaccgcac ctgtggcgcc ggtgatgccg gccacgatgc 2880
gtccggcgta gaggatcgag atctcgatcc cgcgaaatta atacgactca ctatagggga 2940
attgtgagcg gataacaatt cccctctaga aataattttg tttaacttta agaaggagat 3000
atacatatgg aagctcgtcg ttctgcgaac tacgaaccta acagctggga ctatgattac 3060
ctgctgtcct ccgacacgga cgagtccatc gaagtataca aagacaaagc gaaaaagctg 3120
gaagccgaag ttcgtcgcga gattaataac gaaaaagcag aatttctgac cctgctggaa 3180
ctgattgaca acgtccagcg cctgggcctg ggttaccgtt tcgagtctga tatccgtggt 3240
gcgctggatc gcttcgtttc ctccggcggc ttcgatgcgg taaccaagac ttccctgcac 3300
ggtacggcac tgtctttccg tctgctgcgt caacacggtt ttgaggtttc tcaggaagcg 3360
ttcagcggct tcaaagacca aaacggcaac ttcctggaga acctgaagga agatatcaaa 3420
gctatcctga gcctgtacga ggccagcttc ctggctctgg aaggcgaaaa catcctggac 3480
gaggcgaagg ttttcgcaat ctctcatctg aaagaactgt ctgaagaaaa gatcggtaaa 3540
gagctggcag aacaggtgaa ccatgcactg gaactgccac tgcatcgccg tactcagcgt 3600
ctggaagcag tatggtctat cgaggcctac cgtaaaaagg aggacgcgaa tcaggttctg 3660
ctggagctgg caattctgga ttacaacatg atccagtctg tataccagcg tgatctgcgt 3720
gaaacgtccc gttggtggcg tcgtgtgggt ctggcgacca aactgcactt tgctcgtgac 3780
cgcctgattg agagcttcta ctgggccgtg ggtgtagcat tcgaaccgca atactccgac 3840
tgccgtaact ccgtcgcaaa aatgttttct ttcgtaacca ttatcgacga tatctacgat 3900
gtatacggca ccctggacga actggagctg tttactgatg cagttgagcg ttgggacgta 3960
aacgccatca acgacctgcc ggattacatg aaactgtgct ttctggctct gtataacact 4020
attaacgaaa tcgcctacga caacctgaaa gataaaggtg agaacatcct gccgtatctg 4080
accaaagcct gggctgacct gtgcaacgct ttcctgcaag aagccaagtg gctgtacaac 4140
aaatctactc cgacctttga cgactacttc ggcaacgcat ggaaatcctc ttctggcccg 4200
ctgcaactgg tgttcgctta cttcgctgtc gtgcagaaca ttaaaaagga agagatcgaa 4260
aacctgcaaa aataccatga caccatctct cgtccttccc atatcttccg tctgtgcaat 4320
gacctggcta gcgcgtctgc ggaaattgcg cgtggtgaaa ccgcaaatag cgtttcttgt 4380
tacatgcgca ctaaaggtat ctccgaagaa ctggctaccg aaagcgtgat gaatctgatc 4440
gatgaaacct ggaaaaagat gaacaaggaa aaactgggtg gtagcctgtt cgcgaaaccg 4500

```
ttcgtggaaa ccgcgatcaa cctggcacgt caatctcact gcacttatca taacggcgac   4560
gcgcatacct ctccggatga gctgacccgc aaacgcgttc tgtctgtaat cactgaaccg   4620
attctgccgt ttgaacgcta aggatccgaa ttcgagctcc gtcgacaagc ttgcggccgc   4680
actcgagcac caccaccacc accactgaga tccggctgct aacaaagccc gaaaggaagc   4740
tgagttggct gctgccaccg ctgagcaata actagcataa ccccttgggg cctctaaacg   4800
ggtcttgagg ggttttttga ctagttctag agcggccgcc accgcggtgg agctccaatt   4860
cgccctatag tgagtcgtat tacgcgcgct cactggccgt cgttttacaa cgtcgtgact   4920
gggaaaaccc tggcgttacc caacttaatc gccttgcagc acatccccct ttcgccagct   4980
ggcgtaatag cgaagaggcc cgcaccgatc gcccttccca acagttgcgc agcctgaatg   5040
gcgaatggaa attgtaagcg ttaatatttt gttaaaattc gcgttaaatt tttgttaaat   5100
cagctcattt tttaaccaat aggccgactg cgatgagtgg cagggcgggg cgtaattttt   5160
ttaaggcagt tattggtgcc cttaaacgcc tggtgctacg cctgaataag tgataataag   5220
cggatgaatg gcagaaattc gaaagcaaat tcgacccggt cgtcggttca gggcagggtc   5280
gttaaatagc cgcttatgtc tattgctggt ttaccggttt attgactacc ggaagcagtg   5340
tgaccgtgtg cttctcaaat gcctgaggcc agtttgctca ggctctcccc gtggaggtaa   5400
taattgacga tatgatcatt tattctgcct cccagagcct gataaaaacg gtgaatccgt   5460
tagcgaggtg ccgccggctt ccattcaggt cgaggtggcc cggctccatg caccgcgacg   5520
caacgcgggg aggcagacaa ggtatagggc ggcgaggcgg ctacagccga tagtctggaa   5580
cagcgcactt acgggttgct gcgcaaccca agtgctaccg gcgcggcagc gtgacccgtg   5640
tcggcggctc caacggctcg ccatcgtcca gaaaacacgg ctcatcgggc atcggcaggc   5700
gctgctgccc gcgccgttcc cattcctccg tttcggtcaa ggctggcagg tctggttcca   5760
tgcccggaat gccgggctgg ctgggcggct cctcgccggg gccggtcggt agttgctgct   5820
cgcccggata cagggtcggg atgcggcgca ggtcgccatg ccccaacagc gattcgtcct   5880
ggtcgtcgtg atcaaccacc acggcggcac tgaacaccga caggcgcaac tggtcgcggg   5940
gctggcccca cgccacgcgg tcattgacca cgtaggccga cacggtgccg gggccgttga   6000
gcttcacgac ggagatccag cgctcggcca ccaagtcctt gactgcgtat tggaccgtcc   6060
gcaaagaacg tccgatgagc ttggaaagtg tcttctggct gaccaccacg gcgttctggt   6120
ggcccatctg cgccacgagg tgatgcagca gcattgccgc cgtgggtttc ctcgcaataa   6180
gcccggccca cgcctcatgc gctttgcgtt ccgtttgcac ccagtgaccg ggcttgttct   6240
tggcttgaat gccgatttct ctggactgcg tggccatgct tatctccatg cggtagggtg   6300
ccgcacggtt gcggcaccat gcgcaatcag ctgcaacttt tcggcagcgc gacaacaatt   6360
atgcgttgcg taaaagtggc agtcaattac agattttctt taacctacgc aatgagctat   6420
tgcgggggggt gccgcaatga gctgttgcgt acccccccttt tttaagttgt tgatttttaa   6480
gtctttcgca tttcgcccta tatctagttc tttggtgccc aaagaagggc acccctgcgg   6540
ggttccccca cgccttcggc gcggctcccc ctccggcaaa aagtggcccc tccggggctt   6600
gttgatcgac tgcgcggcct tcggccttgc ccaaggtggc gctgcccccct tggaaccccc   6660
gcactcgccg ccgtgaggct cggggggcag gcgggcgggc ttcgccttcg actgccccca   6720
ctcgcatagg cttgggtcgt tccaggcgcg tcaaggccaa gccgctgcgc ggtcgctgcg   6780
cgagccttga cccgccttcc acttggtgtc caaccggcaa gcgaagcgcg caggccgcag   6840
gccggaggct tttccccaga gaaaattaaa aaaattgatg ggcaaggcc gcaggccgcg   6900
```

-continued cagttggagc cggtgggtat gtggtcgaag gctgggtagc cggtgggcaa tccctgtggt 6960
caagctcgtg ggcaggcgca gcctgtccat cagcttgtcc agcagggttg tccacgggcc 7020
gagcgaagcg agccagccgg tggccgctcg cggccatcgt ccacatatcc acgggctggc 7080
aagggagcgc agcgaccgcg cagggcgaag cccggagagc aagcccgtag ggcgccgcag 7140
ccgccgtagg cggtcacgac tttgcgaagc aaagtctagt gagtatactc aagcattgag 7200
tggcccgccg gaggcaccgc cttgcgctgc ccccgtcgag ccggttggac accaaaaggg 7260
aggggcaggc atggcggcat acgcgatcat gcgatgcaag aagctggcga aaatgggcaa 7320
cgtggcggcc agtctcaagc acgcctaccg cgagcgcgag acgcccaacg ctgacgccag 7380
caggacgcca gagaacgagc actgggcggc cagcagcacc gatgaagcga tgggccgact 7440
gcgcgagttg ctgccagaga agcggcgcaa ggacgctgtg ttggcggtcg agtacgtcat 7500
gacggccagc ccggaatggt ggaagtcggc cagccaagaa cagcaggcgg cgttcttcga 7560
gaaggcgcac aagtggctgg cggacaagta cggggcggat cgcatcgtga cggccagcat 7620
ccaccgtgac gaaaccagcc cgcacatgac cgcgttcgtg gtgccgctga cgcaggacgg 7680
caggctgtcg gccaaggagt tcatcggcaa caaagcgcag atgacccgcg accagaccac 7740
gtttgcggcc gctgtggccg atctagggct gcaacggggc atcgagggca gcaaggcacg 7800
tcacacgcgc attcaggcgt tctacgaggc cctggagcgg ccaccagtgg gccacgtcac 7860
catcagcccg caagcggtcg agccacgcgc ctatgcaccg cagggattgg ccgaaaagct 7920
gggaatctca aagcgcgttg agacgccgga agccgtggcc gaccggctga caaaagcggt 7980
tcggcagggg tatgagcctg ccctacaggc cgccgcagga gcgcgtgaga tgcgcaagaa 8040
ggccgatcaa gcccaagaga cggcccgag 8069

<210> SEQ ID NO 74
<211> LENGTH: 5270
<212> TYPE: DNA
<213> ORGANISM: Artificial Sequence
<220> FEATURE:
<223> OTHER INFORMATION: Synthetic Construct

<400> SEQUENCE: 74
cgataagcta gcttcacgct gccgcaagca ctcagggcgc aagggctgct aaaggaagcg 60
gaacacgtag aaagccagtc cgcagaaacg gtgctgaccc cggatgaatg tcagctactg 120
ggctatctgg acaagggaaa acgcaagcgc aaagagaaag caggtagctt gcagtgggct 180
tacatggcga tagctagact gggcggtttt atggacagca agcgaaccgg aattgccagc 240
tggggcgccc tctggtaagg ttgggaagcc ctgcaaagta aactggatgg ctttcttgcc 300
gccaaggatc tgatggcgca ggggatcaag atctgatcaa gagacaggat gaggatcgtt 360
tcgcatgatt gaacaagatg gattgcacgc aggttctccg gccgcttggg tggagaggct 420
attcggctat gactgggcac aacagacaat cggctgctct gatgccgccg tgttccggct 480
gtcagcgcag gggcgcccgg ttctttttgt caagaccgac ctgtccggtg ccctgaatga 540
actccaagac gaggcagcgc ggctatcgtg gctggccacg acgggcgttc cttgcgcagc 600
tgtgctcgac gttgtcactg aagcgggaag ggactggctg ctattgggcg aagtgccggg 660
gcaggatctc ctgtcatctc accttgctcc tgccgagaaa gtatccatca tggctgatgc 720
aatgcggcgg ctgcatacgc ttgatccggc tacctgccca ttcgaccacc aagcgaaaca 780
tcgcatcgag cgagcacgta ctcggatgga agccggtctt gtcgatcagg atgatctgga 840
cgaagagcat caggggctcg cgccagccga actgttcgcc aggctcaagg cgcggatgcc 900
cgacggcgag gatctcgtcg tgacccatgg cgatgcctgc ttgccgaata tcatggtgga 960
aaatggccgc ttttctggat tcatcgactg tggccggctg ggtgtggcgg accgctatca 1020
ggacatagcg ttggctaccc gtgatattgc tgaagagctt ggcggcgaat gggctgaccg 1080
cttcctcgtg ctttacggta tcgccgctcc cgattcgcag cgcatcgcct tctatcgcct 1140
tcttgacgag ttcttctgag cgggactctg gggttcgcga tgataagctg tcaaacatga 1200
gaattacaac ttatatcgta tggggctgac ttcaggtgct acatttgaag agataaattg 1260
cactgaaatc tagaaatatt ttatctgatt aataagatga tcttcttgag atcgttttgg 1320
tctgcgcgta atctcttgct ctgaaaacga aaaaaccgcc ttgcagggcg gtttttcgaa 1380
ggttctctga gctaccaact ctttgaaccg aggtaactgg cttggaggag cgcagtcacc 1440
aaaacttgtc ctttcagttt agccttaacc ggcgcatgac ttcaagacta actcctctaa 1500
atcaattacc agtggctgct gccagtggtg cttttgcatg tctttccggg ttggactcaa 1560
gacgatagtt accggataag gcgcagcggt cggactgaac ggggggttcg tgcatacagt 1620
ccagcttgga gcgaactgcc tacccggaac tgagtgtcag gcgtggaatg agacaaacgc 1680
ggccataaca gcggaatgac accggtaaac cgaaaggcag gaacaggaga gcgcacgagg 1740
gagccgccag ggaaacgcc tggtatcttt atagtcctgt cgggtttcgc caccactgat 1800
ttgagcgtca gatttcgtga tgcttgtcag gggggcggag cctatggaaa aacggctttg 1860
ccttctttcc tgcgttatcc cctgattctg tggataaccg tattaccgcc tttgagtgag 1920
ctgataccgc tcgccgcagc cgaacgaccg agcgcagcga gtcagtgagc gaggaagcgg 1980
aagagcgccc aatacgcaaa ccgcctctcc ccgcgcgttg gccgattcat taatgcagct 2040
ggcacgacag gtttcccgac tggaaagcgg gcagtgagcg caacgcaatt aatgtgagtt 2100
agctcactca ttaggcaccc caggctttac actttatgct tccggctcgt atgttgtgtg 2160
gaattgtgag cggataacaa tttcacacag gaaacagcta tgaccatgat tacgaattct 2220
gttgacaatt aatcatcggc tcgtataatg tgtggaattg tgagcggata acaatttcac 2280
acaggaaaca gattacggat ccatttgagg agtaagccat gcaaacgttg ccaagcccag 2340
ttcaagctac accaacggaa acagctattg ttagacgcaa aacccgcccg gttccgatag 2400
gctccgttgt tattggtggc ggccatcccg tggctgttca gtcaatgatt aacgaagaca 2460
ctctggatat cgaaggttct gttgctgcaa ttcggcgctt acacgagatc ggttgcgaga 2520
tcgtacgtgt gactgtacct tcattagcac acgcgaaagc aatggaagag attcgggatc 2580
ggctttataa aacgtacaaa ccggtcccct tagttgccga cgtgcatcat aacggaatga 2640
aaatcgcgtt agaggttgcc aagtacgtgg acaatgtgcg cattaatcct ggattatacg 2700
tgtttgagaa gccaaaacca aatcgcacgg agtacactca agctgaattt gacgagattg 2760
gcgcgaaaat ccgtgaaacg ttggaaccac tggtaatttc actgcgggat cagggaaagt 2820
cgatgcgcat tggcgttaat catggcagtc tggcggaacg gatgctgttt acctatggcg 2880
ataccccaga gggtatggta gagagtgcac ttgagtttat acgcatctgt gaaagtctca 2940
acttctataa cttagaaatt tcccttaaag ctagccgcgt cccggttatg atagccgcca 3000
atcggcttat ggttaagcgc atggacgagc tgggtatgga ttatccgttg catctcggag 3060
tgactgaggc aggtgatggt gaatatggcc gtattaaaag cacagcaggc attgcaacac 3120
tgctggcgga aggaattgga gacacaatcc gtgtttcatt gactgaagct ccggaaaagg 3180
aaatccccgt gtgctatggc atccttcaag ccctcggtct ccgccgcacc atggtagaat 3240
atgtagcttg cccgtcgtgt ggtcggacat tgtttaacct ggaagaggtt ctgcacaagg 3300
tgagagaagc gactaaacac ctgacgggac tgaatattgc ggttatggga tgtattgtaa 3360
atggacctgg cgaaatggcc gatgcagact acggctatgt aggtaaacag ccgggatata 3420
taagtcttta ccgcggccgg gaagaagtca agaaagtgcc cgaggccgag ggcgttgcag 3480
ctctggtcga actgataaaa gcggatggta gatgggtaga tccataagtg gagctccccg 3540
gtaccgtgga cgaggtttaa tatggcgacg tataaagtca cactggtccg tccggatggc 3600
agcgaaacga ccatcgatgt tccggaggac gaatacatac tggatgtcgc cgaagaacaa 3660
ggtctggatc tcccgttttc ttgtcgcgcc ggtgcctgct ctacctgtgc tggcaaattg 3720
ttggagggag aagtcgatca aagcgaccag agcttcttgg atgacgatca gatcgaaaaa 3780
ggattcgtgc ttacttgtgt ggcctacccc cgttcggact gcaagatctt gacgaaccaa 3840
gaggaggagc tgtactaaga ggtcgacgac gcatgcatta acagaggtta gtatgtataa 3900
tgccactaac tctcgctcac gtatgttccg gtacgaagtt gtggggctgc gccaaacggc 3960
ggagacggag aaaacaaatt acgcgatcag aaactctggc tcgcagttct ttaatgtgcc 4020
ttatgaccgc atgaaccagt ttatgcagca gatcactcgg tggggcggta aaattgtcag 4080
tattcagccc cttaacggaa ccgtggcccc acttgctgca accacggagc cagctgccaa 4140
taacggagct gcacctgtga aagaaaagaa agtcgatata ccggtcaaca tctaccgtcc 4200
caataatccc tgcataggta aggttattag caacgaggaa ctggtccggg aaggcggtga 4260
gggtacggtg aaacatatta tctttgatat atcggggacc gaattacgtt acttggaagg 4320
gcagtcaatc ggtatcattc ccgcgggcac ggacgcgaac ggtaaaccac ataagctgcg 4380
tctgtattcc attgcttcca caagacatgg tgactttcag gatgacaaga cggtgtcctt 4440
atgcgtacgg agattagaat acaaagataa agagaccggg gagaccattt atggcgtgtg 4500
cagttcgtat cttaatcagt tacagcctgg agatgaagtc aaaatcacag gtcctgttgg 4560
gaaagaaatg cttctctctg acgacccaga agcgactatt attatgctgg ctaccggcac 4620
tggaatagcg ccatttcggg catttttatg gcggatgttc aaagagaaca acccggatta 4680
ccagttcaaa ggccttgcgt ggctgttctt tggcgtcgct tatactgcca atatcctgta 4740
taaggacgag cttgaagcta tccaagccca gtatcccgat cattttcggt taacctacgc 4800
gatttcccgt gaacaaaaaa ccccggacgg agggaaaatg tacatccagg gtcggatcgc 4860
agagcacgct gatgaaatct ggcaactgct gcaaaagaaa aacacccacg tgtacatgtg 4920
tggcctgcgt gggatggaac ctggaataga cgaggccatg accgcagcgg ccgcgaaaaa 4980
cggagctgac tggcaggagt ttctgaaagg tacgctgaaa aaggaaggca gatggcatgt 5040
cgaaacttat taactgcagt acaaataaaa aaggcacgtc agatgacgtg cctttttttct 5100 tgaagcttgg cactggccgt cgttttacaa cgtcgtgact gggaaaaccc tggcgttacc 5160
caacttaatc gccttgcagc acatccccct ttcgccagct ggcgtaatag cgaagaggcc 5220
cgcaccgatc gcccttccca acagttgcgc agcctgaatg gcgaatggcg 5270

<210> SEQ ID NO 75
<211> LENGTH: 8072
<212> TYPE: DNA
<213> ORGANISM: Artificial Sequence
<220> FEATURE:
<223> OTHER INFORMATION: Synthetic Construct

<400> SEQUENCE: 75
accttcggga gcgcctgaag cccgttctgg acgccctggg gccgttgaat cgggatatgc 60
aggccaaggc cgccgcgatc atcaaggccg tgggcgaaaa gctgctgacg gaacagcggg 120

```
aagtccagcg ccagaaacag gcccagcgcc agcaggaacg cgggcgcgca catttccccg    180
aaaagtgcca cctggcggcg ttgtgacaat ttaccgaaca actccgcggc cgggaagccg    240
atctcggctt gaacgaattg ttaggtggcg gtacttgggt cgatatcaaa gtgcatcact    300
tcttcccgta tgcccaactt tgtatagaga gccactgcgg gatcgtcacc gtaatctgct    360
tgcacgtaga tcacataagc accaagcgcg ttggcctcat gcttgaggag attgatgagc    420
gcggtggcaa tgccctgcct ccggtgctcg ccggagactg cgagatcata gatatagatc    480
tcactacgcg gctgctcaaa cctgggcaga acgtaagccg cgagagcgcc aacaaccgct    540
tcttggtcga aggcagcaag cgcgatgaat gtcttactac ggagcaagtt cccgaggtaa    600
tcggagtccg gctgatgttg ggagtaggtg gctacgtctc cgaactcacg accgaaaaga    660
tcaagagcag cccgcatgga tttgacttgg tcagggccga gcctacatgt gcgaatgatg    720
cccatacttg agccacctaa ctttgtttta gggcgactgc cctgctgcgt aacatcgttg    780
ctgctgcgta acatcgttgc tgctccataa catcaaacat cgacccacgg cgtaacgcgc    840
ttgctgcttg gatgcccgag gcatagactg tacaaaaaaa cagtcataac aagccatgaa    900
aaccgccact gcgccgttac caccgctgcg ttcggtcaag gttctggacc agttgcgtga    960
gcgcatacgc tacttgcatt acagtttacg aaccgaacag gcttatgtca actgggttcg   1020
tgccttcatc cgtttccacg gtgtgcgtcc atgggcaaat attatacgca aggcgacaag   1080
gtgctgatgc cgctggcgat tcaggttcat catgccgttt gtgatggctt ccatgtcggc   1140
agaatgctta atgaattaca acagttttta tgcatgcgcc caatacgcaa accgcctctc   1200
cccgcgcgtt ggccgattca ttaatgcagc tggcacgaca ggtttcccga ctggaaagcg   1260
ggcagtgagc gcaacgcaat taatgtgagt tagctcactc attaggcacc ccaggcttta   1320
cactttatgc ttccggctcg tatgttgtgt ggaattgtga gcggataaca atttcacaca   1380
ggaaacagct atgaccatga ttacgccaag cgcgcaatta accctcacta aagggaacaa   1440
aagctgggta ccctgcccgc tttccagtcg ggaaacctgt cgtgccagct gcattaatga   1500
atcggccaac gcgcggggag aggcggtttg cgtattgggc gccagggtgg tttttctttt   1560
caccagtgag acgggcaaca gctgattgcc cttcaccgcc tggccctgag agagttgcag   1620
caagcggtcc acgctggttt gccccagcag gcgaaaatcc tgtttgatgg tggttaacgg   1680
cgggatataa catgagctgt cttcggtatc gtcgtatccc actaccgaga tatccgcacc   1740
aacgcgcagc ccggactcgg taatggcgcg cattgcgccc agcgccatct gatcgttggc   1800
aaccagcatc gcagtgggaa cgatgccctc attcagcatt tgcatggttt gttgaaaacc   1860
ggacatggca ctccagtcgc cttcccgttc cgctatcggc tgaatttgat tgcgagtgag   1920
atatttatgc cagccagcca gacgcagacg cgccgagaca gaacttaatg ggcccgctaa   1980
cagcgcgatt tgctggtgac ccaatgcgac cagatgctcc acgcccagtc gcgtaccgtc   2040
ttcatgggag aaaataatac tgttgatggg tgtctggtca gagacatcaa gaaataacgc   2100
cggaacatta gtgcaggcag cttccacagc aatggcatcc tggtcatcca gcggatagtt   2160
aatgatcagc ccactgacgc gttgcgcgag aagattgtgc accgccgctt tacaggcttc   2220
gacgccgctt cgttctacca tcgacaccac cacgctggca cccagttgat cggcgcgaga   2280
tttaatcgcc gcgacaattt gcgacggcgc gtgcagggcc agactggagg tggcaacgcc   2340
aatcagcaac gactgtttgc ccgccagttg ttgtgccacg cggttgggaa tgtaattcag   2400
ctccgccatc gccgcttcca ctttttcccg cgttttcgca gaaacgtggc tggcctggtt   2460
caccacgcgg gaaacggtct gataagagac accggcatac tctgcgacat cgtataacgt   2520
```

-continued

```
tactggtttc acattcacca ccctgaattg actctcttcc gggcgctatc atgccatacc   2580
gcgaaaggtt ttgcgccatt cgatggtgtc cgggatctcg acgctctccc ttatgcgact   2640
cctgcattag gaagcagccc agtagtaggt tgaggccgtt gagcaccgcc gccgcaagga   2700
atggtgcatg caaggagatg gcgcccaaca gtcccccggc cacggggcct gccaccatac   2760
ccacgccgaa acaagcgctc atgagcccga agtggcgagc ccgatcttcc ccatcggtga   2820
tgtcggcgat ataggcgcca gcaaccgcac ctgtggcgcc ggtgatgccg gccacgatgc   2880
gtccggcgta gaggatcgag atctcgatcc cgcgaaatta atacgactca ctatagggga   2940
attgtgagcg gataacaatt cccctctaga aataattttg tttaacttta agaaggagat   3000
atacatatga ccgaagctcg tcgttctgcg aactacgaac ctaacagctg ggactatgat   3060
tacctgctgt cctccgacac ggacgagtcc atcgaagtat acaaagacaa agcgaaaaag   3120
ctggaagccg aagttcgtcg cgagattaat aacgaaaaag cagaatttct gaccctgctg   3180
gaactgattg acaacgtcca gcgcctgggc ctgggttacc gtttcgagtc tgatatccgt   3240
ggtgcgctgg atcgcttcgt ttcctccggc ggcttcgatg cggtaaccaa gacttccctg   3300
cacggtacgg cactgtcttt ccgtctgctg cgtcaacacg gttttgaggt ttctcaggaa   3360
gcgttcagcg gcttcaaaga ccaaaacggc aacttcctgg agaacctgaa ggaagatatc   3420
aaagctatcc tgagcctgta cgaggccagc ttcctggctc tggaaggcga aaacatcctg   3480
gacgaggcga aggttttcgc aatctctcat ctgaaagaac tgtctgaaga aaagatcggt   3540
aaagagctgg cagaacaggt gaaccatgca ctggaactgc cactgcatcg ccgtactcag   3600
cgtctggaag cagtatggtc tatcgaggcc taccgtaaaa aggaggacgc gaatcaggtt   3660
ctgctggagc tggcaattct ggattacaac atgatccagt ctgtatacca gcgtgatctg   3720
cgtgaaacgt cccgttggtg gcgtcgtgtg ggtctggcga ccaaactgca ctttgctcgt   3780
gaccgcctga ttgagagctt ctactgggcc gtgggtgtag cattcgaacc gcaatactcc   3840
gactgccgta actccgtcgc aaaaatgttt tctttcgtaa ccattatcga cgatatctac   3900
gatgtatacg gcaccctgga cgaactggag ctgtttactg atgcagttga gcgttgggac   3960
gtaaacgcca tcaacgacct gccggattac atgaaactgt gctttctggc tctgtataac   4020
actattaacg aaatcgccta cgacaacctg aaagataaag gtgagaacat cctgccgtat   4080
ctgaccaaag cctgggctga cctgtgcaac gctttcctgc aagaagccaa gtggctgtac   4140
aacaaatcta ctccgacctt tgacgactac ttcggcaacg catggaaatc ctcttctggc   4200
ccgctgcaac tggtgttcgc ttacttcgct gtcgtgcaga acattaaaaa ggaagagatc   4260
gaaaacctgc aaaaatacca tgacaccatc tctcgtcctt cccatatctt ccgtctgtgc   4320
aatgacctgg ctagcgcgtc tgcggaaatt gcgcgtggtg aaaccgcaaa tagcgtttct   4380
tgttacatgc gcactaaagg tatctccgaa gaactggcta ccgaaagcgt gatgaatctg   4440
atcgatgaaa cctggaaaaa gatgaacaag gaaaaactgg gtggtagcct gttcgcgaaa   4500
ccgttcgtgg aaaccgcgat caacctggca cgtcaatctc actgcactta tcataacggc   4560
gacgcgcata cctctccgga tgagctgacc cgcaaacgcg ttctgtctgt aatcactgaa   4620
ccgattctgc cgtttgaacg ctaaggatcc gaattcgagc tccgtcgaca agcttgcggc   4680
cgcactcgag caccaccacc accaccactg agatccggct gctaacaaag cccgaaagga   4740
agctgagttg gctgctgcca ccgctgagca ataactagca taaccccttg gggcctctaa   4800
acgggtcttg aggggttttt tgactagttc tagagcggcc gccaccgcgg tggagctcca   4860
attcgcccta tagtgagtcg tattacgcgc gctcactggc cgtcgtttta caacgtcgtg   4920
```

```
actgggaaaa ccctggcgtt acccaactta atcgccttgc agcacatccc cctttcgcca   4980
gctggcgtaa tagcgaagag gcccgcaccg atcgcccttc ccaacagttg cgcagcctga   5040
atggcgaatg gaaattgtaa gcgttaatat tttgttaaaa ttcgcgttaa atttttgtta   5100
aatcagctca ttttttaacc aataggccga ctgcgatgag tggcagggcg gggcgtaatt   5160
tttttaaggc agttattggt gcccttaaac gcctggtgct acgcctgaat aagtgataat   5220
aagcggatga atggcagaaa ttcgaaagca aattcgaccc ggtcgtcggt tcagggcagg   5280
gtcgttaaat agccgcttat gtctattgct ggtttaccgg tttattgact accggaagca   5340
gtgtgaccgt gtgcttctca aatgcctgag gccagtttgc tcaggctctc cccgtggagg   5400
taataattga cgatatgatc atttattctg cctcccagag cctgataaaa acggtgaatc   5460
cgttagcgag gtgccgccgg cttccattca ggtcgaggtg gcccggctcc atgcaccgcg   5520
acgcaacgcg gggaggcaga caaggtatag ggcggcgagg cggctacagc cgatagtctg   5580
gaacagcgca cttacgggtt gctgcgcaac ccaagtgcta ccggcgcggc agcgtgaccc   5640
gtgtcggcgg ctccaacggc tcgccatcgt ccagaaaaca cggctcatcg ggcatcggca   5700
ggcgctgctg cccgcgccgt tcccattcct ccgtttcggt caaggctggc aggtctggtt   5760
ccatgcccgg aatgccgggc tggctgggcg gctcctcgcc ggggccggtc ggtagttgct   5820
gctcgcccgg atacagggtc gggatgcggc gcaggtcgcc atgccccaac agcgattcgt   5880
cctggtcgtc gtgatcaacc accacggcgg cactgaacac cgacaggcgc aactggtcgc   5940
ggggctggcc ccacgccacg cggtcattga ccacgtaggc cgacacggtg ccggggccgt   6000
tgagcttcac gacggagatc cagcgctcgg ccaccaagtc cttgactgcg tattggaccg   6060
tccgcaaaga acgtccgatg agcttggaaa gtgtcttctg gctgaccacc acggcgttct   6120
ggtggcccat ctgcgccacg aggtgatgca gcagcattgc cgccgtgggt ttcctcgcaa   6180
taagcccggc ccacgcctca tgcgctttgc gttccgtttg cacccagtga ccgggcttgt   6240
tcttggcttg aatgccgatt tctctggact gcgtggccat gcttatctcc atgcggtagg   6300
gtgccgcacg gttgcggcac catgcgcaat cagctgcaac ttttcggcag cgcgacaaca   6360
attatgcgtt gcgtaaaagt ggcagtcaat tacagatttt ctttaaccta cgcaatgagc   6420
tattgcgggg ggtgccgcaa tgagctgttg cgtacccccc ttttttaagt tgttgatttt   6480
taagtctttc gcatttcgcc ctatatctag ttctttggtg cccaaagaag ggcacccctg   6540
cggggttccc ccacgccttc ggcgcggctc cccctccggc aaaaagtggc ccctccgggg   6600
cttgttgatc gactgcgcgg ccttcggcct tgcccaaggt ggcgctgccc ccttggaacc   6660
cccgcactcg ccgccgtgag gctcgggggg caggcgggcg ggcttcgcct tcgactgccc   6720
ccactcgcat aggcttgggt cgttccaggc gcgtcaaggc caagccgctg cgcggtcgct   6780
gcgcgagcct tgacccgcct tccacttggt gtccaaccgg caagcgaagc gcgcaggccg   6840
caggccggag gcttttcccc agagaaaatt aaaaaaattg atggggcaag gccgcaggcc   6900
gcgcagttgg agccggtggg tatgtggtcg aaggctgggt agccggtggg caatccctgt   6960
ggtcaagctc gtgggcaggc gcagcctgtc catcagcttg tccagcaggg ttgtccacgg   7020
gccgagcgaa gcgagccagc cggtggccgc tcgcggccat cgtccacata tccacgggct   7080
ggcaagggag cgcagcgacc gcgcagggcg aagcccggag agcaagcccg tagggcgccg   7140
cagccgccgt aggcggtcac gactttgcga agcaaagtct agtgagtata ctcaagcatt   7200
gagtggcccg ccggaggcac cgccttgcgc tgcccccgtc gagccggttg gacaccaaaa   7260
gggaggggca ggcatggcgg catacgcgat catgcgatgc aagaagctgg cgaaaatggg   7320
```

caacgtggcg gccagtctca agcacgccta ccgcgagcgc gagacgccca acgctgacgc 7380
cagcaggacg ccagagaacg agcactgggc ggccagcagc accgatgaag cgatgggccg 7440
actgcgcgag ttgctgccag agaagcggcg caaggacgct gtgttggcgg tcgagtacgt 7500
catgacggcc agcccggaat ggtggaagtc ggccagccaa gaacagcagg cggcgttctt 7560
cgagaaggcg cacaagtggc tggcggacaa gtacggggcg gatcgcatcg tgacggccag 7620
catccaccgt gacgaaacca gcccgcacat gaccgcgttc gtggtgccgc tgacgcagga 7680
cggcaggctg tcggccaagg agttcatcgg caacaaagcg cagatgaccc gcgaccagac 7740
cacgtttgcg gccgctgtgg ccgatctagg gctgcaacgg ggcatcgagg gcagcaaggc 7800
acgtcacacg cgcattcagg cgttctacga ggccctggag cggccaccag tgggccacgt 7860
caccatcagc ccgcaagcgg tcgagccacg cgcctatgca ccgcagggat tggccgaaaa 7920
gctgggaatc tcaaagcgcg ttgagacgcc ggaagccgtg gccgaccggc tgacaaaagc 7980
ggttcggcag ggtatgagc ctgccctaca ggccgccgca ggagcgcgtg agatgcgcaa 8040
gaaggccgat caagcccaag agacggcccg ag 8072

<210> SEQ ID NO 76
<211> LENGTH: 8102
<212> TYPE: DNA
<213> ORGANISM: Artificial Sequence
<220> FEATURE:
<223> OTHER INFORMATION: Synthetic Construct

<400> SEQUENCE: 76
accttcggga gcgcctgaag cccgttctgg acgccctggg gccgttgaat cgggatatgc 60
aggccaaggc cgccgcgatc atcaaggccg tgggcgaaaa gctgctgacg gaacagcggg 120
aagtccagcg ccagaaacag gcccagcgcc agcaggaacg cgggcgcgca catttccccg 180
aaaagtgcca cctggcggcg ttgtgacaat ttaccgaaca actccgcggc cgggaagccg 240
atctcggctt gaacgaattg ttaggtggcg gtacttgggt cgatatcaaa gtgcatcact 300
tcttcccgta tgcccaactt tgtatagaga gccactgcgg gatcgtcacc gtaatctgct 360
tgcacgtaga tcacataagc accaagcgcg ttggcctcat gcttgaggag attgatgagc 420
gcggtggcaa tgccctgcct ccggtgctcg ccggagactg cgagatcata gatatagatc 480
tcactacgcg gctgctcaaa cctgggcaga acgtaagccg cgagagcgcc aacaaccgct 540
tcttggtcga aggcagcaag cgcgatgaat gtcttactac ggagcaagtt cccgaggtaa 600
tcggagtccg gctgatgttg ggagtaggtg gctacgtctc cgaactcacg accgaaaaga 660
tcaagagcag cccgcatgga tttgacttgg tcagggccga gcctacatgt gcgaatgatg 720
cccatacttg agccacctaa ctttgtttta gggcgactgc cctgctgcgt aacatcgttg 780
ctgctgcgta acatcgttgc tgctccataa catcaaacat cgacccacgg cgtaacgcgc 840
ttgctgcttg gatgcccgag gcatagactg tacaaaaaaa cagtcataac aagccatgaa 900
aaccgccact gcgccgttac caccgctgcg ttcggtcaag gttctggacc agttgcgtga 960
gcgcatacgc tacttgcatt acagtttacg aaccgaacag gcttatgtca actgggttcg 1020
tgccttcatc cgtttccacg gtgtgcgtcc atgggcaaat attatacgca aggcgacaag 1080
gtgctgatgc cgctggcgat tcaggttcat catgccgttt gtgatggctt ccatgtcggc 1140
agaatgctta atgaattaca acagttttta tgcatgcgcc caatacgcaa accgcctctc 1200
cccgcgcgtt ggccgattca ttaatgcagc tggcacgaca ggtttcccga ctggaaagcg 1260
ggcagtgagc gcaacgcaat taatgtgagt tagctcactc attaggcacc ccaggcttta 1320
cactttatgc ttccggctcg tatgttgtgt ggaattgtga gcggataaca atttcacaca 1380
ggaaacagct atgaccatga ttacgccaag cgcgcaatta accctcacta aagggaacaa 1440
aagctgggta ccctgcccgc tttccagtcg ggaaacctgt cgtgccagct gcattaatga 1500
atcggccaac gcgcggggag aggcggtttg cgtattgggc gccagggtgg tttttctttt 1560
caccagtgag acgggcaaca gctgattgcc cttcaccgcc tggccctgag agagttgcag 1620
caagcggtcc acgctggttt gccccagcag gcgaaaatcc tgtttgatgg tggttaacgg 1680
cgggatataa catgagctgt cttcggtatc gtcgtatccc actaccgaga tatccgcacc 1740
aacgcgcagc ccggactcgg taatggcgcg cattgcgccc agcgccatct gatcgttggc 1800
aaccagcatc gcagtgggaa cgatgccctc attcagcatt tgcatggttt gttgaaaacc 1860
ggacatggca ctccagtcgc cttcccgttc cgctatcggc tgaatttgat tgcgagtgag 1920
atatttatgc cagccagcca gacgcagacg cgccgagaca gaacttaatg ggcccgctaa 1980
cagcgcgatt tgctggtgac ccaatgcgac cagatgctcc acgcccagtc gcgtaccgtc 2040
ttcatgggag aaaataatac tgttgatggg tgtctggtca gagacatcaa gaaataacgc 2100
cggaacatta gtgcaggcag cttccacagc aatggcatcc tggtcatcca gcggatagtt 2160
aatgatcagc ccactgacgc gttgcgcgag aagattgtgc accgccgctt tacaggcttc 2220
gacgccgctt cgttctacca tcgacaccac cacgctggca cccagttgat cggcgcgaga 2280
tttaatcgcc gcgacaattt gcgacggcgc gtgcagggcc agactggagg tggcaacgcc 2340
aatcagcaac gactgtttgc ccgccagttg ttgtgccacg cggttgggaa tgtaattcag 2400
ctccgccatc gccgcttcca ctttttcccg cgttttcgca gaaacgtggc tggcctggtt 2460
caccacgcgg gaaacggtct gataagagac accggcatac tctgcgacat cgtataacgt 2520
tactggtttc acattcacca ccctgaattg actctcttcc gggcgctatc atgccatacc 2580
gcgaaaggtt ttgcgccatt cgatggtgtc cgggatctcg acgctctccc ttatgcgact 2640
cctgcattag gaagcagccc agtagtaggt tgaggccgtt gagcaccgcc gccgcaagga 2700
atggtgcatg caaggagatg gcgcccaaca gtcccccggc cacggggcct gccaccatac 2760
ccacgccgaa acaagcgctc atgagcccga agtggcgagc ccgatcttcc ccatcggtga 2820
tgtcggcgat ataggcgcca gcaaccgcac ctgtggcgcc ggtgatgccg gccacgatgc 2880
gtccggcgta gaggatcgag atctcgatcc cgcgaaatta atacgactca ctatagggga 2940
attgtgagcg gataacaatt cccctctaga aataattttg tttaacttta agaaggagat 3000
atacatatga ccgaaaatgt gtctttcacc gaaactgaaa ccgaagctcg tcgttctgcg 3060
aactacgaac ctaacagctg ggactatgat tacctgctgt cctccgacac ggacgagtcc 3120
atcgaagtat acaaagacaa agcgaaaaag ctggaagccg aagttcgtcg cgagattaat 3180
aacgaaaaag cagaatttct gaccctgctg gaactgattg acaacgtcca gcgcctgggc 3240
ctgggttacc gtttcgagtc tgatatccgt ggtgcgctgg atcgcttcgt ttcctccggc 3300
ggcttcgatg cggtaaccaa gacttccctg cacggtacgg cactgtcttt ccgtctgctg 3360
cgtcaacacg gttttgaggt ttctcaggaa gcgttcagcg gcttcaaaga ccaaaacggc 3420
aacttcctgg agaacctgaa ggaagatatc aaagctatcc tgagcctgta cgaggccagc 3480
ttcctggctc tggaaggcga aaacatcctg gacgaggcga aggttttcgc aatctctcat 3540
ctgaaagaac tgtctgaaga aaagatcggt aaagagctgg cagaacaggt gaaccatgca 3600
ctggaactgc cactgcatcg ccgtactcag cgtctggaag cagtatggtc tatcgaggcc 3660
taccgtaaaa aggaggacgc gaatcaggtt ctgctggagc tggcaattct ggattacaac 3720

```
atgatccagt ctgtatacca gcgtgatctg cgtgaaacgt cccgttggtg gcgtcgtgtg   3780
ggtctggcga ccaaactgca ctttgctcgt gaccgcctga ttgagagctt ctactgggcc   3840
gtgggtgtag cattcgaacc gcaatactcc gactgccgta actccgtcgc aaaaatgttt   3900
tctttcgtaa ccattatcga cgatatctac gatgtatacg gcaccctgga cgaactggag   3960
ctgtttactg atgcagttga gcgttgggac gtaaacgcca tcaacgacct gccggattac   4020
atgaaactgt gctttctggc tctgtataac actattaacg aaatcgccta cgacaacctg   4080
aaagataaag gtgagaacat cctgccgtat ctgaccaaag cctgggctga cctgtgcaac   4140
gctttcctgc aagaagccaa gtggctgtac aacaaatcta ctccgacctt tgacgactac   4200
ttcggcaacg catggaaatc ctcttctggc ccgctgcaac tggtgttcgc ttacttcgct   4260
gtcgtgcaga acattaaaaa ggaagagatc gaaaacctgc aaaaatacca tgacaccatc   4320
tctcgtcctt cccatatctt ccgtctgtgc aatgacctgg ctagcgcgtc tgcggaaatt   4380
gcgcgtggtg aaaccgcaaa tagcgtttct tgttacatgc gcactaaagg tatctccgaa   4440
gaactggcta ccgaaagcgt gatgaatctg atcgatgaaa cctggaaaaa gatgaacaag   4500
gaaaaactgg gtggtagcct gttcgcgaaa ccgttcgtgg aaaccgcgat caacctggca   4560
cgtcaatctc actgcactta tcataacggc gacgcgcata cctctccgga tgagctgacc   4620
cgcaaacgcg ttctgtctgt aatcactgaa ccgattctgc cgtttgaacg ctaaggatcc   4680
gaattcgagc tccgtcgaca agcttgcggc cgcactcgag caccaccacc accaccactg   4740
agatccggct gctaacaaag cccgaaagga agctgagttg gctgctgcca ccgctgagca   4800
ataactagca taaccccttg gggcctctaa acgggtcttg aggggttttt tgactagttc   4860
tagagcggcc gccaccgcgg tggagctcca attcgcccta tagtgagtcg tattacgcgc   4920
gctcactggc cgtcgtttta caacgtcgtg actgggaaaa ccctggcgtt acccaactta   4980
atcgccttgc agcacatccc cctttcgcca gctggcgtaa tagcgaagag gcccgcaccg   5040
atcgcccttc ccaacagttg cgcagcctga atggcgaatg gaaattgtaa gcgttaatat   5100
tttgttaaaa ttcgcgttaa atttttgtta aatcagctca ttttttaacc aataggccga   5160
ctgcgatgag tggcagggcg gggcgtaatt tttttaaggc agttattggt gcccttaaac   5220
gcctggtgct acgcctgaat aagtgataat aagcggatga atggcagaaa ttcgaaagca   5280
aattcgaccc ggtcgtcggt tcagggcagg gtcgttaaat agccgcttat gtctattgct   5340
ggtttaccgg tttattgact accggaagca gtgtgaccgt gtgcttctca aatgcctgag   5400
gccagtttgc tcaggctctc cccgtggagg taataattga cgatatgatc atttattctg   5460
cctcccagag cctgataaaa acggtgaatc cgttagcgag gtgccgccgg cttccattca   5520
ggtcgaggtg gcccggctcc atgcaccgcg acgcaacgcg gggaggcaga caaggtatag   5580
ggcggcgagg cggctacagc cgatagtctg gaacagcgca cttacgggtt gctgcgcaac   5640
ccaagtgcta ccggcgcggc agcgtgaccc gtgtcggcgg ctccaacggc tcgccatcgt   5700
ccagaaaaca cggctcatcg ggcatcggca ggcgctgctg cccgcgccgt tcccattcct   5760
ccgtttcggt caaggctggc aggtctggtt ccatgcccgg aatgccgggc tggctgggcg   5820
gctcctcgcc ggggccggtc ggtagttgct gctcgcccgg atacagggtc gggatgcggc   5880
gcaggtcgcc atgccccaac agcgattcgt cctggtcgtc gtgatcaacc accacggcgg   5940
cactgaacac cgacaggcgc aactggtcgc ggggctggcc ccacgccacg cggtcattga   6000
ccacgtaggc cgacacggtg ccggggccgt tgagcttcac gacggagatc cagcgctcgg   6060
ccaccaagtc cttgactgcg tattggaccg tccgcaaaga acgtccgatg agcttggaaa   6120
```

-continued

```
gtgtcttctg gctgaccacc acggcgttct ggtggcccat ctgcgccacg aggtgatgca   6180

gcagcattgc cgccgtgggt ttcctcgcaa taagcccggc ccacgcctca tgcgctttgc   6240

gttccgtttg cacccagtga ccgggcttgt tcttggcttg aatgccgatt tctctggact   6300

gcgtggccat gcttatctcc atgcggtagg gtgccgcacg gttgcggcac catgcgcaat   6360

cagctgcaac ttttcggcag cgcgacaaca attatgcgtt gcgtaaaagt ggcagtcaat   6420

tacagatttt ctttaaccta cgcaatgagc tattgcgggg ggtgccgcaa tgagctgttg   6480

cgtacccccc ttttttaagt tgttgatttt taagtctttc gcatttcgcc ctatatctag   6540

ttctttggtg cccaaagaag ggcacccctg cggggttccc ccacgccttc ggcgcggctc   6600

cccctccggc aaaaagtggc ccctccgggg cttgttgatc gactgcgcgg ccttcggcct   6660

tgcccaaggt ggcgctgccc ccttggaacc cccgcactcg ccgccgtgag gctcgggggg   6720

caggcgggcg ggcttcgcct tcgactgccc ccactcgcat aggcttgggt cgttccaggc   6780

gcgtcaaggc caagccgctg cgcggtcgct gcgcgagcct tgacccgcct tccacttggt   6840

gtccaaccgg caagcgaagc gcgcaggccg caggccggag gcttttcccc agagaaaatt   6900

aaaaaaattg atggggcaag gccgcaggcc gcgcagttgg agccggtggg tatgtggtcg   6960

aaggctgggt agccggtggg caatccctgt ggtcaagctc gtgggcaggc gcagcctgtc   7020

catcagcttg tccagcaggg ttgtccacgg gccgagcgaa gcgagccagc cggtggccgc   7080

tcgcggccat cgtccacata tccacgggct ggcaagggag cgcagcgacc gcgcagggcg   7140

aagcccggag agcaagcccg tagggcgccg cagccgccgt aggcggtcac gactttgcga   7200

agcaaagtct agtgagtata ctcaagcatt gagtggcccg ccggaggcac cgccttgcgc   7260

tgcccccgtc gagccggttg gacaccaaaa gggaggggca ggcatggcgg catacgcgat   7320

catgcgatgc aagaagctgg cgaaaatggg caacgtggcg gccagtctca agcacgccta   7380

ccgcgagcgc gagacgccca acgctgacgc cagcaggacg ccagagaacg agcactgggc   7440

ggccagcagc accgatgaag cgatgggccg actgcgcgag ttgctgccag agaagcggcg   7500

caaggacgct gtgttggcgg tcgagtacgt catgacggcc agcccggaat ggtggaagtc   7560

ggccagccaa gaacagcagg cggcgttctt cgagaaggcg cacaagtggc tggcggacaa   7620

gtacggggcg gatcgcatcg tgacggccag catccaccgt gacgaaacca gcccgcacat   7680

gaccgcgttc gtggtgccgc tgacgcagga cggcaggctg tcggccaagg agttcatcgg   7740

caacaaagcg cagatgaccc gcgaccagac cacgtttgcg gccgctgtgg ccgatctagg   7800

gctgcaacgg ggcatcgagg gcagcaaggc acgtcacacg cgcattcagg cgttctacga   7860

ggccctggag cggccaccag tggccacgt caccatcagc ccgcaagcgg tcgagccacg   7920

cgcctatgca ccgcagggat tggccgaaaa gctgggaatc tcaaagcgcg ttgagacgcc   7980

ggaagccgtg gccgaccggc tgacaaaagc ggttcggcag ggtatgagc ctgccctaca   8040

ggccgccgca ggagcgcgtg agatgcgcaa gaaggccgat caagcccaag agacggcccg   8100

ag                                                                  8102
```

<210> SEQ ID NO 77
<211> LENGTH: 6511
<212> TYPE: DNA
<213> ORGANISM: Artificial Sequence
<220> FEATURE:
<223> OTHER INFORMATION: Synthetic Construct

<400> SEQUENCE: 77

```
cgataagcta gcttcacgct gccgcaagca ctcagggcgc aagggctgct aaaggaagcg     60
```

```
gaacacgtag aaagccagtc cgcagaaacg gtgctgaccc cggatgaatg tcagctactg    120
ggctatctgg acaagggaaa acgcaagcgc aaagagaaag caggtagctt gcagtgggct    180
tacatggcga tagctagact gggcggtttt atggacagca agcgaaccgg aattgccagc    240
tggggcgccc tctggtaagg ttgggaagcc ctgcaaagta aactggatgg ctttcttgcc    300
gccaaggatc tgatggcgca ggggatcaag atctgatcaa gagacaggat gaggatcgtt    360
tcgcatgatt gaacaagatg gattgcacgc aggttctccg gccgcttggg tggagaggct    420
attcggctat gactgggcac aacagacaat cggctgctct gatgccgccg tgttccggct    480
gtcagcgcag gggcgcccgg ttctttttgt caagaccgac ctgtccggtg ccctgaatga    540
actccaagac gaggcagcgc ggctatcgtg gctggccacg acgggcgttc cttgcgcagc    600
tgtgctcgac gttgtcactg aagcgggaag ggactggctg ctattgggcg aagtgccggg    660
gcaggatctc ctgtcatctc accttgctcc tgccgagaaa gtatccatca tggctgatgc    720
aatgcggcgg ctgcatacgc ttgatccggc tacctgccca ttcgaccacc aagcgaaaca    780
tcgcatcgag cgagcacgta ctcggatgga agccggtctt gtcgatcagg atgatctgga    840
cgaagagcat caggggctcg cgccagccga actgttcgcc aggctcaagg cgcggatgcc    900
cgacggcgag gatctcgtcg tgacccatgg cgatgcctgc ttgccgaata tcatggtgga    960
aaatggccgc ttttctggat tcatcgactg tggccggctg ggtgtggcgg accgctatca   1020
ggacatagcg ttggctaccc gtgatattgc tgaagagctt ggcggcgaat gggctgaccg   1080
cttcctcgtg ctttacggta tcgccgctcc cgattcgcag cgcatcgcct tctatcgcct   1140
tcttgacgag ttcttctgag cgggactctg gggttcgcga tgataagctg tcaaacatga   1200
gaattacaac ttatatcgta tggggctgac ttcaggtgct acatttgaag agataaattg   1260
cactgaaatc tagaaatatt ttatctgatt aataagatga tcttcttgag atcgttttgg   1320
tctgcgcgta atctcttgct ctgaaaacga aaaaaccgcc ttgcagggcg gtttttcgaa   1380
ggttctctga gctaccaact ctttgaaccg aggtaactgg cttggaggag cgcagtcacc   1440
aaaacttgtc ctttcagttt agccttaacc ggcgcatgac ttcaagacta actcctctaa   1500
atcaattacc agtggctgct gccagtggtg cttttgcatg tctttccggg ttggactcaa   1560
gacgatagtt accggataag gcgcagcggt cggactgaac ggggggttcg tgcatacagt   1620
ccagcttgga gcgaactgcc tacccggaac tgagtgtcag gcgtggaatg agacaaacgc   1680
ggccataaca gcggaatgac accggtaaac cgaaaggcag gaacaggaga gcgcacgagg   1740
gagccgccag ggaaacgcc tggtatcttt atagtcctgt cgggtttcgc caccactgat    1800
ttgagcgtca gatttcgtga tgcttgtcag gggggcggag cctatggaaa aacggctttg   1860
ccttctttcc tgcgttatcc cctgattctg tggataaccg tattaccgcc tttgagtgag   1920
ctgataccgc tcgccgcagc cgaacgaccg agcgcagcga gtcagtgagc gaggaagcgg   1980
aagagcgccc aatacgcaaa ccgcctctcc ccgcgcgttg gccgattcat taatgcagct   2040
ggcacgacag gtttcccgac tggaaagcgg gcagtgagcg caacgcaatt aatgtgagtt   2100
agctcactca ttaggcaccc caggctttac actttatgct tccggctcgt atgttgtgtg   2160
gaattgtgag cggataacaa tttcacacag gaaacagcta tgaccatgat tacgaattct   2220
gttgacaatt aatcatcggc tcgtataatg tgtggaattg tgagcggata acaatttcac   2280
acaggaaaca gattacggat ccatttgagg agtaagccat gcaaacgttg ccaagcccag   2340
ttcaagctac accaacggaa acagctattg ttagacgcaa aacccgcccg gttccgatag   2400
gctccgttgt tattggtggc ggccatcccg tggctgttca gtcaatgatt aacgaagaca   2460
```

-continued

```
ctctggatat cgaaggttct gttgctgcaa ttcggcgctt acacgagatc ggttgcgaga   2520
tcgtacgtgt gactgtacct tcattagcac acgcgaaagc aatggaagag attcgggatc   2580
ggctttataa aacgtacaaa ccggtcccct tagttgccga cgtgcatcat aacggaatga   2640
aaatcgcgtt agaggttgcc aagtacgtgg acaatgtgcg cattaatcct ggattatacg   2700
tgtttgagaa gccaaaacca aatcgcacgg agtacactca agctgaattt gacgagattg   2760
gcgcgaaaat ccgtgaaacg ttggaaccac tggtaatttc actgcgggat cagggaaagt   2820
cgatgcgcat tggcgttaat catggcagtc tggcggaacg gatgctgttt acctatggcg   2880
ataccccaga gggtatggta gagagtgcac ttgagtttat acgcatctgt gaaagtctca   2940
acttctataa cttagaaatt tcccttaaag ctagccgcgt cccggttatg atagccgcca   3000
atcggcttat ggttaagcgc atggacgagc tgggtatgga ttatccgttg catctcggag   3060
tgactgaggc aggtgatggt gaatatggcc gtattaaaag cacagcaggc attgcaacac   3120
tgctggcgga aggaattgga gacacaatcc gtgtttcatt gactgaagct ccggaaaagg   3180
aaatccccgt gtgctatggc atccttcaag ccctcggtct ccgccgcacc atggtagaat   3240
atgtagcttg cccgtcgtgt ggtcggacat tgtttaacct ggaagaggtt ctgcacaagg   3300
tgagagaagc gactaaacac ctgacgggac tgaatattgc ggttatggga tgtattgtaa   3360
atggacctgg cgaaatggcc gatgcagact acggctatgt aggtaaacag ccgggatata   3420
taagtcttta ccgcggccgg gaagaagtca agaaagtgcc cgaggccgag ggcgttgcag   3480
ctctggtcga actgataaaa gcggatggta gatgggtaga tccataagtg gagctccagc   3540
ccggggcact ggaggcgtaa atggatacac gtgcgttcaa acgttcactt cattcgtcgg   3600
aaaattacca tcgcaaaggc tttggacatg gcgaggaagt taaccagcaa ttgcagggcg   3660
aatatcagtc tagcctcata cagcagatta gagccaatgg ttatcgctgg cagcagggcg   3720
atgttacaat tcgtctggca gaagcgtttg gcttctgctg gggtgtggaa agagccgtcg   3780
ctcttgctta cgaaaccaga acccatttcc cgaccgagcg catatggata accaacgaaa   3840
ttattcacaa cccctcagtt aatgaacgtc tgcgccaaat ggccgtcgag ttcattcctg   3900
tagtgaacgg cgtcaaagat ttttcgggag tacggcccgg cgatgtcgtc atactgccag   3960
catttggggc gtcagttcag gagatgcagt tattaaacga acgcggttgt actatcgtag   4020
atacgacgtg tccgtgggtg agcaaagtat gcattcggtg gaaaaacata agaaagtttc   4080
cttcacgagc attatacacg gtaaatacaa ccacgaggag actattgcaa catcctcatt   4140
tgcgggaact tacttgatcg tactgaacct cgaagaggcc cgttacgttt gtgactacat   4200
tttacatggc ggcgatcgcg ctgcatttat ggcgaaattt gccaaggctt gctcacctgg   4260
ttttgacccg gaccgggatc tggtccgggt agggatagct aaccaaacaa caatgttaaa   4320
aggcgagacc gaacagattg gcaaattgtt tgagcgcacc atgattcaaa agtatggtcc   4380
ggatcgcctt aacgagcact tcatgtcgtt taatactatt tgcgatgcga cacaggaacg   4440
gcaagacgca atgttgagtt tagtaaaaga gccgttagat ctgatggtag tcattggcgg   4500
ttataattct tccaatacta cgcatttgca ggagattgca atcgaacacg gcattccatc   4560
ctatcatatc gactcagcgg atcgtatcgg accaggtaat cggattgaac ataagccatt   4620
gcaccaaaat ccgacagttg ccgaaaattg gttaccggat cgcccgatca ctatcggcat   4680
tacttcaggt gcatcaactc ccgataaagt tgttgaagag gtgctgaata agatctttgc   4740
tttacgcagc gttgcaacgg ttagttgatc cactagtccc ggtaccgtgg acgaggttta   4800
atatggcgac gtataaagtc acactggtcc gtccggatgg cagcgaaacg accatcgatg   4860
```

ttccggagga cgaatacata ctggatgtcg ccgaagaaca aggtctggat ctcccgtttt 4920
cttgtcgcgc cggtgcctgc tctacctgtg ctggcaaatt gttggaggga gaagtcgatc 4980
aaagcgacca gagcttcttg gatgacgatc agatcgaaaa aggattcgtg cttacttgtg 5040
tggcctaccc ccgttcggac tgcaagatct tgacgaacca agaggaggag ctgtactaag 5100
aggtcgacga cgcatgcatt aacagaggtt agtatgtata atgccactaa ctctcgctca 5160
cgtatgttcc ggtacgaagt tgtggggctg cgccaaacgg cggagacgga gaaaacaaat 5220
tacgcgatca gaaactctgg ctcgcagttc tttaatgtgc cttatgaccg catgaaccag 5280
tttatgcagc agatcactcg gtggggcggt aaaattgtca gtattcagcc ccttaacgga 5340
accgtggccc cacttgctgc aaccacggag ccagctgcca ataacggagc tgcacctgtg 5400
aaagaaaaga aagtcgatat accggtcaac atctaccgtc ccaataatcc ctgcataggt 5460
aaggttatta gcaacgagga actggtccgg gaaggcggtg agggtacggt gaaacatatt 5520
atctttgata tatcggggac cgaattacgt tacttggaag ggcagtcaat cggtatcatt 5580
cccgcgggca cggacgcgaa cggtaaacca cataagctgc gtctgtattc cattgcttcc 5640
acaagacatg gtgactttca ggatgacaag acggtgtcct tatgcgtacg gagattagaa 5700
tacaaagata aagagaccgg ggagaccatt tatggcgtgt gcagttcgta tcttaatcag 5760
ttacagcctg gagatgaagt caaaatcaca ggtcctgttg ggaaagaaat gcttctctct 5820
gacgacccag aagcgactat tattatgctg gctaccggca ctggaatagc gccatttcgg 5880
gcatttttat ggcggatgtt caaagagaac aacccggatt accagttcaa aggccttgcg 5940
tggctgttct ttggcgtcgc ttatactgcc aatatcctgt ataaggacga gcttgaagct 6000
atccaagccc agtatcccga tcattttcgg ttaacctacg cgatttcccg tgaacaaaaa 6060
accccggacg gagggaaaat gtacatccag ggtcggatcg cagagcacgc tgatgaaatc 6120
tggcaactgc tgcaaaagaa aaacacccac gtgtacatgt gtggcctgcg tgggatggaa 6180
cctggaatag acgaggccat gaccgcagcg gccgcgaaaa acggagctga ctggcaggag 6240
tttctgaaag gtacgctgaa aaaggaaggc agatggcatg tcgaaactta ttaactgcag 6300
tacaaataaa aaaggcacgt cagatgacgt gcctttttc ttgaagcttg gcactggccg 6360
tcgttttaca acgtcgtgac tgggaaaacc ctggcgttac ccaacttaat cgccttgcag 6420
cacatccccc tttcgccagc tggcgtaata gcgaagaggc ccgcaccgat cgcccttccc 6480
aacagttgcg cagcctgaat ggcgaatggc g 6511

<210> SEQ ID NO 78
<211> LENGTH: 8069
<212> TYPE: DNA
<213> ORGANISM: Artificial Sequence
<220> FEATURE:
<223> OTHER INFORMATION: Synthetic Construct

<400> SEQUENCE: 78
accttcggga gcgcctgaag cccgttctgg acgccctggg gccgttgaat cgggatatgc 60
aggccaaggc cgccgcgatc atcaaggccg tgggcgaaaa gctgctgacg gaacagcggg 120
aagtccagcg ccagaaacag gcccagcgcc agcaggaacg cgggcgcgca catttccccg 180
aaaagtgcca cctggcggcg ttgtgacaat ttaccgaaca actccgcggc cgggaagccg 240
atctcggctt gaacgaattg ttaggtggcg gtacttgggt cgatatcaaa gtgcatcact 300
tcttcccgta tgcccaactt tgtatagaga gccactgcgg gatcgtcacc gtaatctgct 360
tgcacgtaga tcacataagc accaagcgcg ttggcctcat gcttgaggag attgatgagc 420

```
gcggtggcaa tgccctgcct ccggtgctcg ccggagactg cgagatcata gatatagatc    480
tcactacgcg gctgctcaaa cctgggcaga acgtaagccg cgagagcgcc aacaaccgct    540
tcttggtcga aggcagcaag cgcgatgaat gtcttactac ggagcaagtt cccgaggtaa    600
tcggagtccg gctgatgttg ggagtaggtg gctacgtctc cgaactcacg accgaaaaga    660
tcaagagcag cccgcatgga tttgacttgg tcagggccga gcctacatgt gcgaatgatg    720
cccatacttg agccacctaa ctttgtttta gggcgactgc cctgctgcgt aacatcgttg    780
ctgctgcgta acatcgttgc tgctccataa catcaaacat cgacccacgg cgtaacgcgc    840
ttgctgcttg gatgcccgag gcatagactg tacaaaaaaa cagtcataac aagccatgaa    900
aaccgccact gcgccgttac caccgctgcg ttcggtcaag gttctggacc agttgcgtga    960
gcgcatacgc tacttgcatt acagtttacg aaccgaacag gcttatgtca actgggttcg   1020
tgccttcatc cgtttccacg gtgtgcgtcc atgggcaaat attatacgca aggcgacaag   1080
gtgctgatgc cgctggcgat tcaggttcat catgccgttt gtgatggctt ccatgtcggc   1140
agaatgctta atgaattaca acagttttta tgcatgcgcc caatacgcaa accgcctctc   1200
cccgcgcgtt ggccgattca ttaatgcagc tggcacgaca ggtttcccga ctggaaagcg   1260
ggcagtgagc gcaacgcaat taatgtgagt tagctcactc attaggcacc ccaggcttta   1320
cactttatgc ttccggctcg tatgttgtgt ggaattgtga gcggataaca atttcacaca   1380
ggaaacagct atgaccatga ttacgccaag cgcgcaatta accctcacta aagggaacaa   1440
aagctgggta ccctgcccgc tttccagtcg ggaaacctgt cgtgccagct gcattaatga   1500
atcggccaac gcgcggggag aggcggtttg cgtattgggc gccagggtgg tttttctttt   1560
caccagtgag acgggcaaca gctgattgcc cttcaccgcc tggccctgag agagttgcag   1620
caagcggtcc acgctggttt gccccagcag gcgaaaatcc tgtttgatgg tggttaacgg   1680
cgggatataa catgagctgt cttcggtatc gtcgtatccc actaccgaga tatccgcacc   1740
aacgcgcagc ccggactcgg taatggcgcg cattgcgccc agcgccatct gatcgttggc   1800
aaccagcatc gcagtgggaa cgatgccctc attcagcatt tgcatggttt gttgaaaacc   1860
ggacatggca ctccagtcgc cttcccgttc cgctatcggc tgaatttgat tgcgagtgag   1920
atatttatgc cagccagcca gacgcagacg cgccgagaca gaacttaatg ggcccgctaa   1980
cagcgcgatt tgctggtgac ccaatgcgac cagatgctcc acgcccagtc gcgtaccgtc   2040
ttcatgggag aaaataatac tgttgatggg tgtctggtca gagacatcaa gaaataacgc   2100
cggaacatta gtgcaggcag cttccacagc aatggcatcc tggtcatcca gcggatagtt   2160
aatgatcagc ccactgacgc gttgcgcgag aagattgtgc accgccgctt tacaggcttc   2220
gacgccgctt cgttctacca tcgacaccac cacgctggca cccagttgat cggcgcgaga   2280
tttaatcgcc gcgacaattt gcgacggcgc gtgcagggcc agactggagg tggcaacgcc   2340
aatcagcaac gactgtttgc ccgccagttg ttgtgccacg cggttgggaa tgtaattcag   2400
ctccgccatc gccgcttcca ctttttcccg cgttttcgca gaaacgtggc tggcctggtt   2460
caccacgcgg gaaacggtct gataagagac accggcatac tctgcgacat cgtataacgt   2520
tactggtttc acattcacca ccctgaattg actctcttcc gggcgctatc atgccatacc   2580
gcgaaaggtt ttgcgccatt cgatggtgtc cgggatctcg acgctctccc ttatgcgact   2640
cctgcattag gaagcagccc agtagtaggt tgaggccgtt gagcaccgcc gccgcaagga   2700
atggtgcatg caaggagatg gcgcccaaca gtcccccggc cacggggcct gccaccatac   2760
ccacgccgaa acaagcgctc atgagcccga agtggcgagc ccgatcttcc ccatcggtga   2820
```

-continued

```
tgtcggcgat ataggcgcca gcaaccgcac ctgtggcgcc ggtgatgccg gccacgatgc   2880

gtccggcgta gaggatcgag atctcgatcc cgcgaaatta atacgactca ctatagggga   2940

attgtgagcg gataacaatt cccctctaga aataattttg tttaacttta agaaggagat   3000

atacatatgg aagctcgtcg ttctgcgaac tacgaaccta acagctggga ctatgattac   3060

ctgctgtcct ccgacacgga cgagtccatc gaagtataca aagacaaagc gaaaaagctg   3120

gaagccgaag ttcgtcgcga gattaataac gaaaaagcag aatttctgac cctgctggaa   3180

ctgattgaca acgtccagcg cctgggcctg ggttaccgtt tcgagtctga tatccgtggt   3240

gcgctggatc gcttcgtttc ctccggcggc ttcgatgcgg taaccaagac ttccctgcac   3300

ggtacggcac tgtctttccg tctgctgcgt caacacggtt ttgaggtttc tcaggaagcg   3360

ttcagcggct tcaaagacca aaacggcaac ttcctggaga acctgaagga agatatcaaa   3420

gctatcctga gcctgtacga ggccagcttc ctggctctgg aaggcgaaaa catcctggac   3480

gaggcgaagg ttttcgcaat ctctcatctg aaagaactgt ctgaagaaaa gatcggtaaa   3540

gagctggcag aacaggtgaa ccatgcactg gaactgccac tgcatcgccg tactcagcgt   3600

ctggaagcag tatggtctat cgaggcctac cgtaaaaagg aggacgcgaa tcaggttctg   3660

ctggagctgg caattctgga ttacaacatg atccagtctg tataccagcg tgatctgcgt   3720

gaaacgtccc gttggtggcg tcgtgtgggt ctggcgacca aactgcactt tgctcgtgac   3780

cgcctgattg agagcttcta ctgggccgtg ggtgtagcat tcgaaccgca atactccgac   3840

tgccgtaact ccgtcgcaaa aatgttttct ttcgtaacca ttatcgacga tatctacgat   3900

gtatacggca ccctggacga actggagctg tttactgatg cagttgagcg ttgggacgta   3960

aacgccatca acgacctgcc ggattacatg aaactgtgct ttctggctct gtataacact   4020

attaacgaaa tcgcctacga caacctgaaa gataaaggtg agaacatcct gccgtatctg   4080

accaaagcct gggctgacct gtgcaacgct ttcctgcaag aagccaagtg gctgtacaac   4140

aaatctactc cgacctttga cgactacttc ggcaacgcat ggaaatcctc ttctggcccg   4200

ctgcaactgg tgttcgctta cttcgctgtc gtgcagaaca ttaaaaagga agagatcgaa   4260

aacctgcaaa aataccatga caccatctct cgtccttccc atatcttccg tctgtgcaat   4320

gacctggcta gcgcgtctgc ggaaattgcg cgtggtgaaa ccgcaaatag cgtttcttgt   4380

tacatgcgca ctaaaggtat ctccgaagaa ctggctaccg aaagcgtgat gaatctgatc   4440

gatgaaacct ggaaaaagat gaacaaggaa aaactgggtg gtagcctgtt cgcgaaaccg   4500

ttcgtggaaa ccgcgatcaa cctggcacgt caatctcact gcacttatca taacggcgac   4560

gcgcatacct ctccggatga gctgacccgc aaacgcgttc tgtctgtaat cactgaaccg   4620

attctgccgt ttgaacgcta aggatccgaa ttcgagctcc gtcgacaagc ttgcggccgc   4680

actcgagcac caccaccacc accactgaga tccggctgct aacaaagccc gaaaggaagc   4740

tgagttggct gctgccaccg ctgagcaata actagcataa ccccttgggg cctctaaacg   4800

ggtcttgagg ggttttttga ctagttctag agcggccgcc accgcggtgg agctccaatt   4860

cgccctatag tgagtcgtat tacgcgcgct cactggccgt cgttttacaa cgtcgtgact   4920

gggaaaaccc tggcgttacc caacttaatc gccttgcagc acatccccct ttcgccagct   4980

ggcgtaatag cgaagaggcc cgcaccgatc gcccttccca acagttgcgc agcctgaatg   5040

gcgaatggaa attgtaagcg ttaatatttt gttaaaattc gcgttaaatt tttgttaaat   5100

cagctcattt tttaaccaat aggccgactg cgatgagtgg cagggcgggg cgtaattttt   5160

ttaaggcagt tattggtgcc cttaaacgcc tggtgctacg cctgaataag tgataataag   5220
```

```
cggatgaatg gcagaaattc gaaagcaaat tcgacccggt cgtcggttca gggcagggtc   5280
gttaaatagc cgcttatgtc tattgctggt ttaccggttt attgactacc ggaagcagtg   5340
tgaccgtgtg cttctcaaat gcctgaggcc agtttgctca ggctctcccc gtggaggtaa   5400
taattgacga tatgatcatt tattctgcct cccagagcct gataaaaacg gtgaatccgt   5460
tagcgaggtg ccgccggctt ccattcaggt cgaggtggcc cggctccatg caccgcgacg   5520
caacgcgggg aggcagacaa ggtatagggc ggcgaggcgg ctacagccga tagtctggaa   5580
cagcgcactt acgggttgct gcgcaaccca agtgctaccg gcgcggcagc gtgacccgtg   5640
tcggcggctc caacggctcg ccatcgtcca gaaaacacgg ctcatcgggc atcggcaggc   5700
gctgctgccc gcgccgttcc cattcctccg tttcggtcaa ggctggcagg tctggttcca   5760
tgcccggaat gccgggctgg ctgggcggct cctcgccggg gccggtcggt agttgctgct   5820
cgcccggata cagggtcggg atgcggcgca ggtcgccatg ccccaacagc gattcgtcct   5880
ggtcgtcgtg atcaaccacc acggcggcac tgaacaccga caggcgcaac tggtcgcggg   5940
gctggcccca cgccacgcgg tcattgacca cgtaggccga cacggtgccg gggccgttga   6000
gcttcacgac ggagatccag cgctcggcca ccaagtcctt gactgcgtat tggaccgtcc   6060
gcaaagaacg tccgatgagc ttggaaagtg tcttctggct gaccaccacg gcgttctggt   6120
ggcccatctg cgccacgagg tgatgcagca gcattgccgc cgtgggtttc ctcgcaataa   6180
gcccggccca cgcctcatgc gctttgcgtt ccgtttgcac ccagtgaccg ggcttgttct   6240
tggcttgaat gccgatttct ctggactgcg tggccatgct tatctccatg cggtagggtg   6300
ccgcacggtt gcggcaccat gcgcaatcag ctgcaacttt tcggcagcgc gacaacaatt   6360
atgcgttgcg taaaagtggc agtcaattac agattttctt taacctacgc aatgagctat   6420
tgcggggggt gccgcaatga gctgttgcgt accccccttt tttaagttgt tgatttttaa   6480
gtctttcgca tttcgcccta tatctagttc tttggtgccc aaagaagggc acccctgcgg   6540
ggttccccca cgccttcggc gcggctcccc ctccggcaaa aagtggcccc tccggggctt   6600
gttgatcgac tgcgcggcct tcggccttgc ccaaggtggc gctgccccct tggaaccccc   6660
gcactcgccg ccgtgaggct cggggggcag gcgggcgggc ttcgccttcg actgccccca   6720
ctcgcatagg cttgggtcgt tccaggcgcg tcaaggccaa gccgctgcgc ggtcgctgcg   6780
cgagccttga cccgccttcc acttggtgtc caaccggcaa gcgaagcgcg caggccgcag   6840
gccggaggct tttccccaga gaaaattaaa aaaattgatg gggcaaggcc gcaggccgcg   6900
cagttggagc cggtgggtat gtggtcgaag gctgggtagc cggtgggcaa tccctgtggt   6960
caagctcgtg ggcaggcgca gcctgtccat cagcttgtcc agcagggttg tccacgggcc   7020
gagcgaagcg agccagccgg tggccgctcg cggccatcgt ccacatatcc acgggctggc   7080
aagggagcgc agcgaccgcg cagggcgaag cccggagagc aagcccgtag ggcgccgcag   7140
ccgccgtagg cggtcacgac tttgcgaagc aaagtctagt gagtatactc aagcattgag   7200
tggcccgccg gaggcaccgc cttgcgctgc ccccgtcgag ccggttggac accaaaaggg   7260
aggggcaggc atggcggcat acgcgatcat gcgatgcaag aagctggcga aaatgggcaa   7320
cgtggcggcc agtctcaagc acgcctaccg cgagcgcgag acgcccaacg ctgacgccag   7380
caggacgcca gagaacgagc actgggcggc cagcagcacc gatgaagcga tgggccgact   7440
gcgcgagttg ctgccagaga agcggcgcaa ggacgctgtg ttggcggtcg agtacgtcat   7500
gacggccagc ccggaatggt ggaagtcggc cagccaagaa cagcaggcgg cgttcttcga   7560
gaaggcgcac aagtggctgg cggacaagta cggggcggat cgcatcgtga cggccagcat   7620
```

ccaccgtgac gaaaccagcc cgcacatgac cgcgttcgtg gtgccgctga cgcaggacgg 7680
caggctgtcg gccaaggagt tcatcggcaa caaagcgcag atgacccgcg accagaccac 7740
gtttgcggcc gctgtggccg atctagggct gcaacggggc atcgagggca gcaaggcacg 7800
tcacacgcgc attcaggcgt tctacgaggc cctggagcgg ccaccagtgg gccacgtcac 7860
catcagcccg caagcggtcg agccacgcgc ctatgcaccg cagggattgg ccgaaaagct 7920
gggaatctca aagcgcgttg agacgccgga agccgtggcc gaccggctga caaaagcggt 7980
tcggcagggg tatgagcctg ccctacaggc cgccgcagga gcgcgtgaga tgcgcaagaa 8040
ggccgatcaa gcccaagaga cggcccgag 8069

<210> SEQ ID NO 79
<211> LENGTH: 13661
<212> TYPE: DNA
<213> ORGANISM: Artificial Sequence
<220> FEATURE:
<223> OTHER INFORMATION: Synthetic Construct

<400> SEQUENCE: 79
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500
gatccttttt ttctgcgcgt aatctgctgc ttgcaaacaa aaaaaccacc gctaccagcg 1560
gtggtttgtt tgccggatca agagctacca actctttttc cgaaggtaac tggcttcagc 1620

-continued agagcgcaga taccaaatac tgtccttcta gtgtagccgt agttaggcca ccacttcaag 1680
aactctgtag caccgcctac atacctcgct ctgctaatcc tgttaccagt ggctgctgcc 1740
agtggcgata agtcgtgtct taccgggttg gactcaagac gatagttacc ggataaggcg 1800
cagcggtcgg gctgaacggg gggttcgtgc acacagccca gcttggagcg aacgacctac 1860
accgaactga gatacctaca gcgtgagcta tgagaaagcg ccacgcttcc cgaagggaga 1920
aaggcggaca ggtatccggt aagcggcagg gtcggaacag gagagcgcac gagggagctt 1980
ccagggggaa acgcctggta tctttatagt cctgtcgggt ttcgccacct ctgacttgag 2040
cgtcgatttt tgtgatgctc gtcagggggg cggagcctat ggaaaaacgc cagcaacgcg 2100
gcctttttac ggttcctggc cttttgctgg ccttttgctc acatgttctt tcctgcgtta 2160
tcccctgatt ctgtggataa ccgtattacc gcctttgagt gagctgatac cgctcgccgc 2220
agccgaacga ccgagcgcag cgagtcagtg agcgaggaag cggaagagcg cctgatgcgg 2280
tattttctcc ttacgcatct gtgcggtatt tcacaccgca tatatggtgc actctcagta 2340
caatctgctc tgatgccgca tagttaagcc agtatacact ccgctatcgc tacgtgactg 2400
ggtcatggct gcgccccgac acccgccaac acccgctgac gcgccctgac gggcttgtct 2460
gctcccggca tccgcttaca gacaagctgt gaccgtctcc gggagctgca tgtgtcagag 2520
gttttcaccg tcatcaccga aacgcgcgag gcagctgcgg taaagctcat cagcgtggtc 2580
gtgaagcgat tcacagatgt ctgcctgttc atccgcgtcc agctcgttga gtttctccag 2640
aagcgttaat gtctggcttc tgataaagcg ggccatgtta agggcggttt tttcctgttt 2700
ggtcactgat gcctccgtgt aagggggatt tctgttcatg gggtaatga taccgatgaa 2760
acgagagagg atgctcacga tacgggttac tgatgatgaa catgcccggt tactggaacg 2820
ttgtgagggt aaacaactgg cggtatggat gcggcgggac cagagaaaaa tcactcaggg 2880
tcaatgccag cgcttcgtta atacagatgt aggtgttcca cagggtagcc agcagcatcc 2940
tgcgatgcag atccggaaca taatggtgca gggcgctgac ttccgcgttt ccagacttta 3000
cgaaacacgg aaaccgaaga ccattcatgt tgttgctcag gtcgcagacg ttttgcagca 3060
gcagtcgctt cacgttcgct cgcgtatcgg tgattcattc tgctaaccag taaggcaacc 3120
ccgccagcct agccgggtcc tcaacgacag gagcacgatc atgcgcaccc gtggggccgc 3180
catgccggcg ataatggcct gcttctcgcc gaaacgtttg gtggcgggac cagtgacgaa 3240
ggcttgagcg agggcgtgca agattccgaa taccgcaagc gacaggccga tcatcgtcgc 3300
gctccagcga aagcggtcct cgccgaaaat gacccagagc gctgccggca cctgtcctac 3360
gagttgcatg ataaagaaga cagtcataag tgcggcgacg atagtcatgc cccgcgccca 3420
ccggaaggag ctgactgggt tgaaggctct caagggcatc ggtcgagatc ccggtgccta 3480
atgagtgagc taacttacat taattgcgtt gcgctcactg cccgctttcc agtcgggaaa 3540
cctgtcgtgc cagctgcatt aatgaatcgg ccaacgcgcg gggagaggcg gtttgcgtat 3600
tgggcgccag ggtggttttt cttttcacca gtgagacggg caacagctga ttgcccttca 3660
ccgcctggcc ctgagagagt tgcagcaagc ggtccacgct ggtttgcccc agcaggcgaa 3720
aatcctgttt gatggtggtt aacggcggga tataacatga gctgtcttcg gtatcgtcgt 3780
atcccactac cgagatatcc gcaccaacgc gcagcccgga ctcggtaatg gcgcgcattg 3840
cgcccagcgc catctgatcg ttggcaacca gcatcgcagt gggaacgatg ccctcattca 3900
gcatttgcat ggtttgttga aaaccggaca tggcactcca gtcgccttcc cgttccgcta 3960
tcggctgaat ttgattgcga gtgagatatt tatgccagcc agccagacgc agacgcgccg 4020
agacagaact taatgggccc gctaacagcg cgatttgctg gtgacccaat gcgaccagat 4080
gctccacgcc cagtcgcgta ccgtcttcat gggagaaaat aatactgttg atgggtgtct 4140
ggtcagagac atcaagaaat aacgccggaa cattagtgca ggcagcttcc acagcaatgg 4200
catcctggtc atccagcgga tagttaatga tcagcccact gacgcgttgc gcgagaagat 4260
tgtgcaccgc cgctttacag gcttcgacgc cgcttcgttc taccatcgac accaccacgc 4320
tggcacccag ttgatcggcg cgagatttaa tcgccgcgac aatttgcgac ggcgcgtgca 4380
gggccagact ggaggtggca acgccaatca gcaacgactg tttgcccgcc agttgttgtg 4440
ccacgcggtt gggaatgtaa ttcagctccg ccatcgccgc ttccactttt tcccgcgttt 4500
tcgcagaaac gtggctggcc tggttcacca cgcgggaaac ggtctgataa gagacaccgg 4560
catactctgc gacatcgtat aacgttactg gtttcacatt caccaccctg aattgactct 4620
cttccgggcg ctatcatgcc ataccgcgaa aggttttgcg ccattcgatg gtgtccggga 4680
tctcgacgct ctcccttatg cgactcctgc attaggaagc agcccagtag taggttgagg 4740
ccgttgagca ccgccgccgc aaggaatggt gcatgcaagg agatggcgcc caacagtccc 4800
ccggccacgg ggcctgccac catacccacg ccgaaacaag cgctcatgag cccgaagtgg 4860
cgagcccgat cttccccatc ggtgatgtcg gcgatatagg cgccagcaac cgcacctgtg 4920
gcgccggtga tgccggccac gatgcgtccg gcgtagagga tcgagatctc gatcccgcga 4980
aattaatacg actcactata ggggaattgt gagcggataa caattcccct ctagaaataa 5040
ttttgtttaa ctttaagaag gagatataca tatgagtttt gatattgcca aatacccgac 5100
cctggcactg gttgactcca cccaggagtt acgactgttg ccgaaagaga gtttaccgaa 5160
actctgcgac gaactgcgcc gctatttact cgacagcgtg agccgttcca gcgggcactt 5220
cgcctccggg ctgggcacgg tcgaactgac cgtggcgctg cactatgtct acaacacccc 5280
gtttgaccaa ttgatttggg atgtggggca tcaggcttat ccgcataaaa ttttgaccgg 5340
acgccgcgac aaaatcggca ccatccgtca gaaaggcggt ctgcacccgt tcccgtggcg 5400
cggcgaaagc gaatatgacg tattaagcgt cgggcattca tcaacctcca tcagtgccgg 5460
aattggtatt gcggttgctg ccgaaaaaga aggcaaaaat cgccgcaccg tctgtgtcat 5520
tggcgatggc gcgattaccg caggcatggc gtttgaagcg atgaatcacg cgggcgatat 5580
ccgtcctgat atgctggtga ttctcaacga caatgaaatg tcgatttccg aaaatgtcgg 5640
cgcgctcaac aaccatctgg cacagctgct ttccggtaag ctgtactctt cactgcgcga 5700
aggcgggaaa aaagttttct ctggcgtgcc gccaattaaa gagctgctca aacgcaccga 5760
agaacatatt aaaggcatgg tagtgcctgg cacgttgttt gaagagctgg gctttaacta 5820
catcggcccg gtggacggtc acgatgtgct ggggcttatc accacgctaa agaacatgcg 5880
cgacctgaaa ggcccgcagt tcctgcatat catgaccaaa aaaggtcgtg gttatgaacc 5940
ggcagaaaaa gacccgatca ctttccacgc cgtgcctaaa tttgatccct ccagcggttg 6000
tttgccgaaa agtagcggcg gtttgccgag ctattcaaaa atctttggcg actggttgtg 6060
cgaaacggca gcgaaagaca acaagctgat ggcgattact ccggcgatgc gtgaaggttc 6120
cggcatggtc gagttttcac gtaaattccc ggatcgctac ttcgacgtgg caattgccga 6180
gcaacacgcg gtgacctttg ctgcgggtct ggcgattggt gggtacaaac ccattgtcgc 6240
gatttactcc actttcctgc aacgcgccta tgatcaggtg ctgcatgacg tggcgattca 6300
aaaacttccg gtcctgttcg ccatcgaccg cgcgggcatt gttggtgctg acggtcaaac 6360
ccatcagggt gcttttgatc tctcttacct gcgctgcata ccggaaatgg tcattatgac 6420
cccgagcgat gaaaacgaat gtcgccagat gctctatacc ggctatcact ataacgatgg 6480
cccgtcagcg gtgcgctacc cgcgtggcaa cgcggtcggc gtggaactga cgccgctgga 6540
aaaactacca attggcaaag gcattgtgaa gcgtcgtggc gagaaactgg cgatccttaa 6600
ctttggtacg ctgatgccag aagcggcgaa agtcgccgaa tcgctgaacg ccacgctggt 6660
cgatatgcgt tttgtgaaac cgcttgatga agcgttaatt ctggaaatgg ccgccagcca 6720
tgaagcgctg gtcaccgtag aagaaaacgc cattatgggc ggcgcaggca gcggcgtgaa 6780
cgaagtgctg atggcccatc gtaaaccagt acccgtgctg aacattggcc tgccggactt 6840
ctttattccg caaggaactc aggaagaaat gcgcgccgaa ctcggcctcg atgccgctgg 6900
tatggaagcc aaaatcaagg cctggctggc ataagccttc ttaaggtagc tgctgacaga 6960
tatttcgccc ttaaagcttt acaaggagga aaaaaacatg aagcaactca ccattctggg 7020
ctcgaccggc tcgattggtt gcagcacgct ggacgtggtg cgccataatc ccgaacactt 7080
ccgcgtagtt gcgctggtgg caggcaaaaa tgtcactcgc atggtagaac agtgcctgga 7140
attttctccc cgctatgccg taatggacga tgaagcgagt gcgaaacttc ttaaaacgat 7200
gctacagcaa cagggtagcc gcaccgaagt cttaagtggg caacaagccg cttgcgatat 7260
ggcagcgctt gaggatgttg atcaggtgat ggcagccatt gttggcgctg ctgggctgtt 7320
acctacgctt gctgcgatcc gcgcgggtaa aaccattttg ctggccaata aagaatcact 7380
ggttacctgc ggacgtctgt ttatggacgc cgtaaagcag agcaaagcgc aattgttacc 7440
ggtcgatagc gaacataacg ccatttttca gagtttaccg caacctatcc agcataatct 7500
gggatacgct gaccttgagc aaaatggcgt ggtgtccatt ttacttaccg ggtctggtgg 7560
ccctttccgt gagacgccat tgcgcgattt ggcaacaatg acgccggatc aagcctgccg 7620
tcatccgaac tggtcgatgg ggcgtaaaat ttctgtcgat tcggctacca tgatgaacaa 7680
aggtctggaa tacattgaag cgcgttggct gtttaacgcc agcgccagcc agatggaagt 7740
gctgattcac ccgcagtcag tgattcactc aatggtgcgc tatcaggacg gcagtgttct 7800
ggcgcagctg gggaaccgg atatgcgtac gccaattgcc cacacgatgg catggccgaa 7860
tcgcgtgaac tctggcgtga agccgctcga tttttgcaaa ctaagtgcgt tgacatttgc 7920
cgcaccggat tatgatcgtt atccatgcct gaaactggcg atggaggcgt tcgaacaagg 7980
ccaggcagcg acgacagcat tgaatgccgc aaacgaaatc accgttgctg cttttcttgc 8040
gcaacaaatc cgctttacgg atatcgctgc gttgaattta tccgtactgg aaaaaatgga 8100
tatgcgcgaa ccacaatgtg tggacgatgt gttatctgtt gatgcgaacg cgcgtgaagt 8160
cgccagaaaa gaggtgatgc gtctcgcaag ctgagtccga ctttgcgata ggcctgcacc 8220
cttaacgtcg acacgtaagg aggaaaaaaa catggcaacc actcatttgg atgtttgcgc 8280
cgtggttccg gcggccggat ttggccgtcg aatgcaaacg gaatgtccta agcaatatct 8340
ctcaatcggt aatcaaacca ttcttgaaca ctcggtgcat gcgctgctgg cgcatccccg 8400
tgtgaaacgt gtcgtcattg ccataagtcc tggcgatagc cgttttgcac aacttcctct 8460
ggcgaatcat ccgcaaatca ccgttgtaga tggcggtgat gagcgtgccg attccgtgct 8520
ggcaggtctg aaagccgctg gcgacgcgca gtgggtattg gtgcatgacg ccgctcgtcc 8580
ttgtttgcat caggatgacc tcgcgcgatt gttggcgttg agcgaaacca gccgcacggg 8640
gggcatcctc gccgcaccag tgcgcgatac tatgaaacgt gccgaaccgg gcaaaaatgc 8700
cattgctcat accgttgatc gcaacggctt atggcacgcg ctgacgccgc aattttcccc 8760
tcgtgagctg ttacatgact gtctgacgcg cgctctaaat gaaggcgcga ctattaccga 8820
cgaagcctcg gcgctggaat attgcggatt ccatcctcag ttggtcgaag gccgtgcgga 8880
taacattaaa gtcacgcgcc cggaagattt ggcactggcc gagttttacc tcacccgaac 8940
catccatcag gagaatacat aatttcggat gcttatacac gccagatatt tcattacgga 9000
gctcatacaa ggaggaaaaa aacatgcgga cacagtggcc ctctccggca aaacttaatc 9060
tgtttttata cattaccggt cagcgtgcgg atggttacca cacgctgcaa acgctgtttc 9120
agtttcttga ttacggcgac accatcagca ttgagcttcg tgacgatggg gatattcgtc 9180
tgttaacgcc cgttgaaggc gtggaacatg aagataacct gatcgttcgc gcagcgcgat 9240
tgttgatgaa aactgcggca gacagcgggc gtcttccgac gggaagcggt gcgaatatca 9300
gcattgacaa gcgtttgccg atgggcggcg gtctcggcgg tggttcatcc aatgccgcga 9360
cggtcctggt ggcattaaat catctctggc aatgcgggct aagcatggat gagctggcgg 9420
aaatggggct gacgctgggc gcagatgttc ctgtctttgt tcgggggcat gccgcgtttg 9480
ccgaaggcgt tggtgaaata ctaacgccgg tggacccgcc agagaagtgg tatctggtgg 9540
cgcaccctgg tgtaagtatt ccgactccgg tgatttttaa agatcctgaa ctcccgcgca 9600
atacgccaaa aaggtcaata gaaacgttgc taaaatgtga atttagcaat gattgcgagg 9660
ttatcgcaag aaaacgtttt cgcgaggttg atgcggtgct ttcctggctg ttagaatacg 9720
ccccgtcgcg cctgactggg acaggggcct gtgtctttgc tgaatttgat acagagtctg 9780
aagcccgcca ggtgctagag caagccccgg aatggctcaa tggctttgtg gcgaaaggcg 9840
ctaatctttc cccattgcac agagccatgc tttaatttgc gattgagatc cggcctgcac 9900
ccttaaccgg atccgattca aggaggaaaa aaacatgcga attggacacg gttttgacgt 9960
acatgccttt ggcggtgaag gcccaattat cattggtggc gtacgcattc cttacgaaaa 10020
aggattgctg gcgcattctg atggcgacgt ggcgctccat gcgttgaccg atgcattgct 10080
tggcgcggcg gcgctggggg atatcggcaa gctgttcccg gataccgatc cggcatttaa 10140
aggtgccgat agccgcgagc tgctacgcga agcctggcgt cgtattcagg cgaagggtta 10200
tacccttggc aacgtcgatg tcactatcat cgctcaggca ccgaagatgt tgccgcacat 10260
tccacaaatg cgcgtgttta ttgccgaaga tttgggctgc cacatggatg atgttaacgt 10320
gaaagccact actacggaaa aactgggatt taccggacgt ggggaaggga ttgcctgtga 10380
agcggtggcg ctactcatta aggcaacaaa atgatttacc gtattattct ttagacaacg 10440
gattaagcta gcacataagg aggaaaaaaa catgcataac caggctccaa ttcaacgtag 10500
aaaatcaaca cgtatttacg ttgggaatgt gccgattggc gatggtgctc ccatcgccgt 10560
acagtccatg accaatacgc gtacgacaga cgtcgaagca acggtcaatc aaatcaaggc 10620
gctggaacgc gttggcgctg atatcgtccg tgtatccgta ccgacgatgg acgcggcaga 10680
agcgttcaaa ctcatcaaac agcaggttaa cgtgccgctg gtggctgaca tccacttcga 10740
ctatcgcatt gcgctgaaag tagcggaata cggcgtcgat tgtctgcgta ttaaccctgg 10800
caatatcggt aatgaagagc gtattcgcat ggtggttgac tgtgcgcgcg ataaaaacat 10860
tccgatccgt attggcgtta acgccggatc gctggaaaaa gatttgcaag aaaagtatgg 10920
cgaaccgacg ccgcaggcgt tgctggaatc tgccatgcgt catgttgatc atctcgatcg 10980
cctgaacttc gatcagttca aagtcagcgt gaaagcgtct gacgtcttcc tcgctgttga 11040
gtcttatcgt ttgctggcaa aacagatcga tcagccgttg catctgggga tcaccgaagc 11100
cggtggtgcg cgcagcgggg cagtaaaatc cgccattggt ttaggtctgc tgctgtctga 11160
aggcatcggc gacacgctgc gcgtatcgct ggcggccgat ccggtcgaag agatcaaagt 11220
cggtttcgat attttgaaat cgctgcgtat ccgttcgcga gggatcaact tcatcgcctg 11280
cccgacctgt tcgcgtcagg aatttgatgt tatcggtacg gttaacgcgc tggagcaacg 11340
cctggaagat atcatcactc cgatggacgt ttcgattatc ggctgcgtgg tgaatggccc 11400
aggtgaggcg ctggtttcta cactcggcgt caccggcggc aacaagaaaa gcggcctcta 11460
tgaagatggc gtgcgcaaag accgtctgga caacaacgat atgatcgacc agctggaagc 11520
acgcattcgt gcgaaagcca gtcagctgga cgaagcgcgt cgaattgacg ttcagcaggt 11580
tgaaaaataa ttacaagtaa atgattcagg ttataactac gttgcggccg caaggaggaa 11640
aaaaacatgc agatcctgtt ggccaacccg cgtggttttt gtgccggggt agaccgcgct 11700
atcagcattg ttgaaaacgc gctggccatt tacggcgcac cgatatatgt ccgtcacgaa 11760
gtggtacata accgctatgt ggtcgatagc ttgcgtgagc gtggggctat ctttattgag 11820
cagattagcg aagtaccgga cggcgcgatc ctgattttct ccgcacacgg tgtttctcag 11880
gcggtacgta acgaagcaaa aagtcgcgat ttgacggtgt ttgatgccac ctgtccgctg 11940
gtgaccaaag tgcacatgga agtcgcccgc gccagtcgcc gtggcgaaga atctattctc 12000
atcggtcacg ccgggcaccc ggaagtggaa gggacaatgg gccagtacag taacccggaa 12060
gggggaatgt atctggtcga atcgccggac gatgtgtgga aactgacggt caaaaacgaa 12120
gagaagctct cctttatgac ccagaccacg ctgtcggtgg atgacacgtc tgatgtgatc 12180
gacgcgctgc gtaaacgctt cccgaaaatt gtcggtccgc gcaaagatga catctgctac 12240
gccacgacta accgtcagga agcggtacgc gccctggcag aacaggcgga agttgtgttg 12300
gtggtcggtt cgaaaaactc ctccaactcc aaccgtctgg cggagctggc ccagcgtatg 12360
ggcaaacgcg cgtttttgat tgacgatgcg aaagacatcc aggaagagtg ggtgaaagag 12420
gttaaatgcg tcggcgtgac tgcgggcgca tcggctccgg atattctggt gcagaatgtg 12480
gtggcacgtt tgcagcagct gggcggtggt gaagccattc cgctggaagg ccgtgaagaa 12540
aacattgttt tcgaagtgcc gaaagagctg cgtgtcgata ttcgtgaagt cgattaattt 12600
gcattagcta ttacgtaatt cgtatagtcg gtaccactaa ggaggaaaaa aacatgactg 12660
ccgacaacaa tagtatgccg catggtgcag tatctagtta cgccaaatta gtgcaaaacc 12720
aaacacctga agacattttg gaagagtttc ctgaaattat tccattacaa caaagaccta 12780
atacccgatc tagtgagacg tcaaatgacg aaagcggaga aacatgtttt tctggtcatg 12840
atgaggagca aattaagtta atgaatgaaa attgtattgt tttggattgg gacgataatg 12900
ctattggtgc cggcaccaag aaagtttgtc atttaatgga aaatattgaa aagggtttac 12960
tacatcgtgc attctccgtc tttattttca atgaacaagg tgaattactt ttacaacaaa 13020
gagccactga aaaaataact ttccctgatc tttggactaa cacatgctgc tctcatccac 13080
tatgtattga tgacgaatta ggtttgaagg gtaagctaga cgataagatt aagggcgcta 13140
ttactgcggc ggtgagaaaa ctagatcatg aattaggtat tccagaagat gaaactaaga 13200
caaggggtaa gtttcacttt ttaaacagaa tccattacat ggcaccaagc aatgaaccgt 13260
ggggtgaaca tgaaattgat tacatcctat tttataagat caacgctaaa gaaaacttga 13320
ctgtcaaccc aaacgtcaat gaagttagag acttcaaatg ggtttcacca aatgatttga 13380
aaactatgtt tgctgaccca agttacaagt ttacgccttg gtttaagatt atttgcgaga 13440
attacttatt caactggtgg gagcaattag atgacctttc tgaagtggaa aatgacaggc 13500
aaattcatag aatgctataa gaattcctcg agcaccacca ccaccaccac tgagatccgg 13560
ctgctaacaa agcccgaaag gaagctgagt tggctgctgc caccgctgag caataactag 13620
cataacccct tggggcctct aaacgggtct tgaggggttt t 13661

<210> SEQ ID NO 80
<211> LENGTH: 64
<212> TYPE: DNA
<213> ORGANISM: Artificial Sequence
<220> FEATURE:
<223> OTHER INFORMATION: Synthetic Construct

<400> SEQUENCE: 80
gggcgagttt gaggtgaagt aagacatgag actgacatct gaaccctcac taaagggcgg 60
ccgc 64

<210> SEQ ID NO 81
<211> LENGTH: 102
<212> TYPE: DNA
<213> ORGANISM: Artificial Sequence
<220> FEATURE:
<223> OTHER INFORMATION: Synthetic Construct

<400> SEQUENCE: 81
ttctttttat taagcgcgta acttaacgtc gatcgcgtct tgaagttcct atactttcta 60
gagaatagga acttcttacg ccccgccctg ccactcatcg ca 102

<210> SEQ ID NO 82
<211> LENGTH: 21
<212> TYPE: DNA
<213> ORGANISM: Artificial Sequence
<220> FEATURE:
<223> OTHER INFORMATION: Synthetic Construct

<400> SEQUENCE: 82
agccaggagt tgaatatcct g 21

<210> SEQ ID NO 83
<211> LENGTH: 21
<212> TYPE: DNA
<213> ORGANISM: Artificial Sequence
<220> FEATURE:
<223> OTHER INFORMATION: Synthetic Construct

<400> SEQUENCE: 83
tgatggacac gaggatggtg t 21

<210> SEQ ID NO 84
<211> LENGTH: 22
<212> TYPE: DNA
<213> ORGANISM: Artificial Sequence
<220> FEATURE:
<223> OTHER INFORMATION: Synthetic Construct

<400> SEQUENCE: 84
caccatggta tcctgttctg cg 22

<210> SEQ ID NO 85
<211> LENGTH: 22
<212> TYPE: DNA
<213> ORGANISM: Artificial Sequence
<220> FEATURE:
<223> OTHER INFORMATION: Synthetic Construct

<400> SEQUENCE: 85
ttaatctact ttcagacctt gc 22

<210> SEQ ID NO 86
<211> LENGTH: 37
<212> TYPE: DNA
<213> ORGANISM: Artificial Sequence
<220> FEATURE:
<223> OTHER INFORMATION: Synthetic Construct

<400> SEQUENCE: 86
aggaggtggt ctcaaatgac tgccgacaac aatagta 37

<210> SEQ ID NO 87
<211> LENGTH: 50
<212> TYPE: DNA
<213> ORGANISM: Artificial Sequence
<220> FEATURE:
<223> OTHER INFORMATION: Synthetic Construct

<400> SEQUENCE: 87
aggaggtggt ctcagcgctc tgcagttata gcattctatg aatttgcctg 50

<210> SEQ ID NO 88
<211> LENGTH: 73
<212> TYPE: DNA
<213> ORGANISM: Artificial Sequence
<220> FEATURE:
<223> OTHER INFORMATION: Synthetic Construct

<400> SEQUENCE: 88
gaacaatcac cggcgcagta acagacgggt aacgcgggag atttttcatg aattaaccct 60
cactaaaggg cgg 73

<210> SEQ ID NO 89
<211> LENGTH: 74
<212> TYPE: DNA
<213> ORGANISM: Artificial Sequence
<220> FEATURE:
<223> OTHER INFORMATION: Synthetic Construct

<400> SEQUENCE: 89
cgggaagcga ggcgcttccc atcacgttat tatttttcaa cctgctgaac taatacgact 60
cactataggg ctcg 74

<210> SEQ ID NO 90
<211> LENGTH: 73
<212> TYPE: DNA
<213> ORGANISM: Artificial Sequence
<220> FEATURE:
<223> OTHER INFORMATION: Synthetic Construct

<400> SEQUENCE: 90
ttttgatatt gaagtgctgg aaatcgatcc ggcactggag gcgtaacatg aattaaccct 60
cactaaaggg cgg 73

<210> SEQ ID NO 91
<211> LENGTH: 74
<212> TYPE: DNA
<213> ORGANISM: Artificial Sequence
<220> FEATURE:
<223> OTHER INFORMATION: Synthetic Construct

<400> SEQUENCE: 91
attttcgcat aacttaggct gctaatgact taatcgactt cacgaatatc taatacgact 60
cactataggg ctcg 74

<210> SEQ ID NO 92
<211> LENGTH: 40
<212> TYPE: DNA
<213> ORGANISM: Artificial Sequence
<220> FEATURE:
<223> OTHER INFORMATION: Synthetic Construct

<400> SEQUENCE: 92
cggcgcagta acagacgggt aacgcgggag atttttcatg 40

<210> SEQ ID NO 93
<211> LENGTH: 38
<212> TYPE: DNA
<213> ORGANISM: Artificial Sequence
<220> FEATURE:
<223> OTHER INFORMATION: Synthetic Construct

<400> SEQUENCE: 93
cgcttcccat cacgttatta tttttcaacc tgctgaac 38

<210> SEQ ID NO 94
<211> LENGTH: 40
<212> TYPE: DNA
<213> ORGANISM: Artificial Sequence
<220> FEATURE:
<223> OTHER INFORMATION: Synthetic Construct

<400> SEQUENCE: 94
gaagtgctgg aaatcgatcc ggcactggag gcgtaacatg 40

<210> SEQ ID NO 95
<211> LENGTH: 38
<212> TYPE: DNA
<213> ORGANISM: Artificial Sequence
<220> FEATURE:
<223> OTHER INFORMATION: Synthetic Construct

<400> SEQUENCE: 95
cttaggctgc taatgactta atcgacttca cgaatatc 38

<210> SEQ ID NO 96
<211> LENGTH: 144
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 31
<223> OTHER INFORMATION: n = A,T,C or G

<400> SEQUENCE: 96
gaggaattcg cgagccgtca cgcccttgac natgccacat cctgagcaaa taattcaacc 60
actaaacaaa tcaaccgcgt ttcccggagg taaccggatc caaggagata taccatgcat 120
aaccaggctc caattcaacg taga 144

<210> SEQ ID NO 97
<211> LENGTH: 38
<212> TYPE: DNA
<213> ORGANISM: Artificial Sequence
<220> FEATURE:
<223> OTHER INFORMATION: Synthetic Construct

<400> SEQUENCE: 97
atatcctgca gttatagcat tctatgaatt tgcctgtc 38

<210> SEQ ID NO 98
<211> LENGTH: 17
<212> TYPE: DNA
<213> ORGANISM: Artificial Sequence
<220> FEATURE:
<223> OTHER INFORMATION: Synthetic Construct

<400> SEQUENCE: 98
gtaaaacgac ggccagt 17

<210> SEQ ID NO 99
<211> LENGTH: 17
<212> TYPE: DNA
<213> ORGANISM: Artificial Sequence
<220> FEATURE:
<223> OTHER INFORMATION: Synthetic Construct

<400> SEQUENCE: 99
caggaaacag ctatgac 17

<210> SEQ ID NO 100
<211> LENGTH: 21
<212> TYPE: DNA
<213> ORGANISM: Artificial Sequence
<220> FEATURE:
<223> OTHER INFORMATION: Synthetic Construct

<400> SEQUENCE: 100
caggagccag aacgcaactg c 21

<210> SEQ ID NO 101
<211> LENGTH: 21
<212> TYPE: DNA
<213> ORGANISM: Artificial Sequence
<220> FEATURE:
<223> OTHER INFORMATION: Synthetic Construct

<400> SEQUENCE: 101
cactttcgcc tgatgttcac c 21

<210> SEQ ID NO 102
<211> LENGTH: 22
<212> TYPE: DNA
<213> ORGANISM: Artificial Sequence
<220> FEATURE:
<223> OTHER INFORMATION: Synthetic Construct

<400> SEQUENCE: 102
cattcagtct cttgcagggg tc 22

<210> SEQ ID NO 103
<211> LENGTH: 21
<212> TYPE: DNA
<213> ORGANISM: Artificial Sequence
<220> FEATURE:
<223> OTHER INFORMATION: Synthetic Construct

<400> SEQUENCE: 103
gcatagtgcc gctcatctgc c 21

<210> SEQ ID NO 104
<211> LENGTH: 35
<212> TYPE: DNA
<213> ORGANISM: Artificial Sequence
<220> FEATURE:
<223> OTHER INFORMATION: Synthetic Construct

<400> SEQUENCE: 104
gaaactgaaa cccatatgga agctcgtcgt tctgc 35

<210> SEQ ID NO 105
<211> LENGTH: 44
<212> TYPE: DNA
<213> ORGANISM: Artificial Sequence
<220> FEATURE:
<223> OTHER INFORMATION: Synthetic Construct

<400> SEQUENCE: 105
cccgcgctta ctcgaggcgt tcaaacggca gaatcggttc agtg 44

<210> SEQ ID NO 106
<211> LENGTH: 30
<212> TYPE: DNA
<213> ORGANISM: Artificial Sequence
<220> FEATURE:
<223> OTHER INFORMATION: Synthetic Construct

<400> SEQUENCE: 106
gatcggatcc attcgccctt aggaggtaaa 30

<210> SEQ ID NO 107
<211> LENGTH: 40
<212> TYPE: DNA
<213> ORGANISM: Artificial Sequence
<220> FEATURE:
<223> OTHER INFORMATION: Synthetic Construct

<400> SEQUENCE: 107
gatcgcggcc gccagctgca ggacgcgttg ttatagcatt 40

<210> SEQ ID NO 108
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 108
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500
gatccttttt ttctgcgcgt aatctgctgc ttgcaaacaa aaaaaccacc gctaccagcg 1560
gtggtttgtt tgccggatca agagctacca actctttttc cgaaggtaac tggcttcagc 1620
agagcgcaga taccaaatac tgtccttcta gtgtagccgt agttaggcca ccacttcaag 1680
aactctgtag caccgcctac atacctcgct ctgctaatcc tgttaccagt ggctgctgcc 1740
agtggcgata agtcgtgtct taccgggttg gactcaagac gatagttacc ggataaggcg 1800
cagcggtcgg gctgaacggg gggttcgtgc acacagccca gcttggagcg aacgacctac 1860
accgaactga gatacctaca gcgtgagcta tgagaaagcg ccacgcttcc cgaagggaga 1920
aaggcggaca ggtatccggt aagcggcagg gtcggaacag gagagcgcac gagggagctt 1980
ccagggggaa acgcctggta tctttatagt cctgtcgggt ttcgccacct ctgacttgag 2040
cgtcgatttt tgtgatgctc gtcagggggg cggagcctat ggaaaaacgc cagcaacgcg 2100
gcctttttac ggttcctggc cttttgctgg ccttttgctc acatgttctt tcctgcgtta 2160
tcccctgatt ctgtggataa ccgtattacc gcctttgagt gagctgatac cgctcgccgc 2220
agccgaacga ccgagcgcag cgagtcagtg agcgaggaag cggaagagcg cctgatgcgg 2280
tattttctcc ttacgcatct gtgcggtatt tcacaccgca tatatggtgc actctcagta 2340
caatctgctc tgatgccgca tagttaagcc agtatacact ccgctatcgc tacgtgactg 2400
ggtcatggct gcgccccgac acccgccaac acccgctgac gcgccctgac gggcttgtct 2460
gctcccggca tccgcttaca gacaagctgt gaccgtctcc gggagctgca tgtgtcagag 2520
gttttcaccg tcatcaccga aacgcgcgag gcagctgcgg taaagctcat cagcgtggtc 2580
gtgaagcgat tcacagatgt ctgcctgttc atccgcgtcc agctcgttga gtttctccag 2640
aagcgttaat gtctggcttc tgataaagcg ggccatgtta agggcggttt tttcctgttt 2700
ggtcactgat gcctccgtgt aagggggatt tctgttcatg gggtaatga taccgatgaa 2760
acgagagagg atgctcacga tacgggttac tgatgatgaa catgcccggt tactggaacg 2820
ttgtgagggt aaacaactgg cggtatggat gcggcgggac cagagaaaaa tcactcaggg 2880
tcaatgccag cgcttcgtta atacagatgt aggtgttcca cagggtagcc agcagcatcc 2940
tgcgatgcag atccggaaca taatggtgca gggcgctgac ttccgcgttt ccagacttta 3000
cgaaacacgg aaaccgaaga ccattcatgt tgttgctcag gtcgcagacg ttttgcagca 3060
gcagtcgctt cacgttcgct cgcgtatcgg tgattcattc tgctaaccag taaggcaacc 3120
ccgccagcct agccgggtcc tcaacgacag gagcacgatc atgcgcaccc gtggggccgc 3180
catgccggcg ataatggcct gcttctcgcc gaaacgtttg gtggcgggac cagtgacgaa 3240
ggcttgagcg agggcgtgca agattccgaa taccgcaagc gacaggccga tcatcgtcgc 3300
gctccagcga aagcggtcct cgccgaaaat gacccagagc gctgccggca cctgtcctac 3360
gagttgcatg ataaagaaga cagtcataag tgcggcgacg atagtcatgc cccgcgccca 3420
ccggaaggag ctgactgggt tgaaggctct caagggcatc ggtcgagatc ccggtgccta 3480
atgagtgagc taacttacat taattgcgtt gcgctcactg cccgctttcc agtcgggaaa 3540
cctgtcgtgc cagctgcatt aatgaatcgg ccaacgcgcg gggagaggcg gtttgcgtat 3600
tgggcgccag ggtggttttt cttttcacca gtgagacggg caacagctga ttgcccttca 3660
ccgcctggcc ctgagagagt tgcagcaagc ggtccacgct ggtttgcccc agcaggcgaa 3720
aatcctgttt gatggtggtt aacggcggga tataacatga gctgtcttcg gtatcgtcgt 3780
atcccactac cgagatatcc gcaccaacgc gcagcccgga ctcggtaatg gcgcgcattg 3840
cgcccagcgc catctgatcg ttggcaacca gcatcgcagt gggaacgatg ccctcattca 3900
gcatttgcat ggtttgttga aaaccggaca tggcactcca gtcgccttcc cgttccgcta 3960
tcggctgaat ttgattgcga gtgagatatt tatgccagcc agccagacgc agacgcgccg 4020
agacagaact taatgggccc gctaacagcg cgatttgctg gtgacccaat gcgaccagat 4080
gctccacgcc cagtcgcgta ccgtcttcat gggagaaaat aatactgttg atgggtgtct 4140
ggtcagagac atcaagaaat aacgccggaa cattagtgca ggcagcttcc acagcaatgg 4200
catcctggtc atccagcgga tagttaatga tcagcccact gacgcgttgc gcgagaagat 4260
tgtgcaccgc cgctttacag gcttcgacgc cgcttcgttc taccatcgac accaccacgc 4320
tggcacccag ttgatcggcg cgagatttaa tcgccgcgac aatttgcgac ggcgcgtgca 4380
gggccagact ggaggtggca acgccaatca gcaacgactg tttgcccgcc agttgttgtg 4440
ccacgcggtt gggaatgtaa ttcagctccg ccatcgccgc ttccactttt tcccgcgttt 4500
tcgcagaaac gtggctggcc tggttcacca cgcgggaaac ggtctgataa gagacaccgg 4560
catactctgc gacatcgtat aacgttactg gtttcacatt caccaccctg aattgactct 4620
cttccgggcg ctatcatgcc ataccgcgaa aggttttgcg ccattcgatg gtgtccggga 4680
tctcgacgct ctcccttatg cgactcctgc attaggaagc agcccagtag taggttgagg 4740
ccgttgagca ccgccgccgc aaggaatggt gcatgcaagg agatggcgcc caacagtccc 4800
ccggccacgg ggcctgccac catacccacg ccgaaacaag cgctcatgag cccgaagtgg 4860
cgagcccgat cttccccatc ggtgatgtcg gcgatatagg cgccagcaac cgcacctgtg 4920
gcgccggtga tgccggccac gatgcgtccg gcgtagagga tcgagatctc gatcccgcga 4980
aattaatacg actcactata ggggaattgt gagcggataa caattcccct ctagaaataa 5040
ttttgtttaa ctttaagaag gagatataca tatggaagct cgtcgttctg cgaactacga 5100
acctaacagc tgggactatg attacctgct gtcctccgac acggacgagt ccatcgaagt 5160
atacaaagac aaagcgaaaa agctggaagc cgaagttcgt cgcgagatta ataacgaaaa 5220
agcagaattt ctgaccctgc tggaactgat tgacaacgtc cagcgcctgg gcctgggtta 5280
ccgtttcgag tctgatatcc gtggtgcgct ggatcgcttc gtttcctccg gcggcttcga 5340
tgcggtaacc aagacttccc tgcacggtac ggcactgtct ttccgtctgc tgcgtcaaca 5400
cggttttgag gtttctcagg aagcgttcag cggcttcaaa gaccaaaacg gcaacttcct 5460
ggagaacctg aaggaagata tcaaagctat cctgagcctg tacgaggcca gcttcctggc 5520
tctggaaggc gaaaacatcc tggacgaggc gaaggttttc gcaatctctc atctgaaaga 5580
actgtctgaa gaaaagatcg gtaaagagct ggcagaacag gtgaaccatg cactggaact 5640
gccactgcat cgccgtactc agcgtctgga agcagtatgg tctatcgagg cctaccgtaa 5700
aaaggaggac gcgaatcagg ttctgctgga gctggcaatt ctggattaca acatgatcca 5760
gtctgtatac cagcgtgatc tgcgtgaaac gtcccgttgg tggcgtcgtg tgggtctggc 5820
gaccaaactg cactttgctc gtgaccgcct gattgagagc ttctactggg ccgtgggtgt 5880
agcattcgaa ccgcaatact ccgactgccg taactccgtc gcaaaaatgt tttctttcgt 5940
aaccattatc gacgatatct acgatgtata cggcaccctg gacgaactgg agctgtttac 6000
tgatgcagtt gagcgttggg acgtaaacgc catcaacgac ctgccggatt acatgaaact 6060
gtgctttctg gctctgtata acactattaa cgaaatcgcc tacgacaacc tgaaagataa 6120
aggtgagaac atcctgccgt atctgaccaa agcctgggct gacctgtgca acgctttcct 6180
gcaagaagcc aagtggctgt acaacaaatc tactccgacc tttgacgact acttcggcaa 6240
cgcatggaaa tcctcttctg gcccgctgca actggtgttc gcttacttcg ctgtcgtgca 6300
gaacattaaa aaggaagaga tcgaaaacct gcaaaaatac catgacacca tctctcgtcc 6360
ttcccatatc ttccgtctgt gcaatgacct ggctagcgcg tctgcggaaa ttgcgcgtgg 6420
tgaaaccgca aatagcgttt cttgttacat gcgcactaaa ggtatctccg aagaactggc 6480
taccgaaagc gtgatgaatc tgatcgatga aacctggaaa aagatgaaca aggaaaaact 6540
gggtggtagc ctgttcgcga aaccgttcgt ggaaaccgcg atcaacctgg cacgtcaatc 6600
tcactgcact tatcataacg gcgacgcgca tacctctccg gatgagctga cccgcaaacg 6660
cgttctgtct gtaatcactg aaccgattct gccgtttgaa cgctaaggat ccgaattcga 6720
gctccgtcga caagcttgcg gccgcactcg agcaccacca ccaccaccac tgagatccgg 6780
ctgctaacaa agcccgaaag gaagctgagt tggctgctgc caccgctgag caataactag 6840
cataacccct tggggcctct aaacgggtct tgaggggttt tttgctgaaa ggaggaacta 6900
tatccggat 6909

<210> SEQ ID NO 109
<211> LENGTH: 9685
<212> TYPE: DNA
<213> ORGANISM: Artificial Sequence
<220> FEATURE:
<223> OTHER INFORMATION: Synthetic Construct

<400> SEQUENCE: 109
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500
gatccttttt ttctgcgcgt aatctgctgc ttgcaaacaa aaaaaccacc gctaccagcg 1560
gtggtttgtt tgccggatca agagctacca actctttttc cgaaggtaac tggcttcagc 1620
agagcgcaga taccaaatac tgtccttcta gtgtagccgt agttaggcca ccacttcaag 1680
aactctgtag caccgcctac atacctcgct ctgctaatcc tgttaccagt ggctgctgcc 1740
agtggcgata agtcgtgtct taccgggttg gactcaagac gatagttacc ggataaggcg 1800
cagcggtcgg gctgaacggg gggttcgtgc acacagccca gcttggagcg aacgacctac 1860
accgaactga gatacctaca gcgtgagcta tgagaaagcg ccacgcttcc cgaagggaga 1920
aaggcggaca ggtatccggt aagcggcagg gtcggaacag gagagcgcac gagggagctt 1980
ccagggggaa acgcctggta tctttatagt cctgtcgggt ttcgccacct ctgacttgag 2040
cgtcgatttt tgtgatgctc gtcagggggg cggagcctat ggaaaaacgc cagcaacgcg 2100
gcctttttac ggttcctggc cttttgctgg ccttttgctc acatgttctt tcctgcgtta 2160
tcccctgatt ctgtggataa ccgtattacc gcctttgagt gagctgatac cgctcgccgc 2220
agccgaacga ccgagcgcag cgagtcagtg agcgaggaag cggaagagcg cctgatgcgg 2280
tattttctcc ttacgcatct gtgcggtatt tcacaccgca tatatggtgc actctcagta 2340
caatctgctc tgatgccgca tagttaagcc agtatacact ccgctatcgc tacgtgactg 2400
ggtcatggct gcgccccgac acccgccaac acccgctgac gcgccctgac gggcttgtct 2460
gctcccggca tccgcttaca gacaagctgt gaccgtctcc gggagctgca tgtgtcagag 2520
gttttcaccg tcatcaccga aacgcgcgag gcagctgcgg taaagctcat cagcgtggtc 2580
gtgaagcgat tcacagatgt ctgcctgttc atccgcgtcc agctcgttga gtttctccag 2640
aagcgttaat gtctggcttc tgataaagcg ggccatgtta agggcggttt tttcctgttt 2700
ggtcactgat gcctccgtgt aagggggatt tctgttcatg ggggtaatga taccgatgaa 2760
acgagagagg atgctcacga tacgggttac tgatgatgaa catgcccggt tactggaacg 2820
ttgtgagggt aaacaactgg cggtatggat gcggcgggac cagagaaaaa tcactcaggg 2880
tcaatgccag cgcttcgtta atacagatgt aggtgttcca cagggtagcc agcagcatcc 2940
tgcgatgcag atccggaaca taatggtgca gggcgctgac ttccgcgttt ccagacttta 3000
cgaaacacgg aaaccgaaga ccattcatgt tgttgctcag gtcgcagacg ttttgcagca 3060
gcagtcgctt cacgttcgct cgcgtatcgg tgattcattc tgctaaccag taaggcaacc 3120
ccgccagcct agccgggtcc tcaacgacag gagcacgatc atgcgcaccc gtggggccgc 3180
catgccggcg ataatggcct gcttctcgcc gaaacgtttg gtggcgggac cagtgacgaa 3240
ggcttgagcg agggcgtgca agattccgaa taccgcaagc gacaggccga tcatcgtcgc 3300

```
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
```

```
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt ttctttcgt    5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaaatac catgacacca tctctcgtcc   6360
ttcccatatc ttccgtctgt gcaatgacct ggctagcgcg tctgcggaaa ttgcgcgtgg   6420
tgaaaccgca aatagcgttt cttgttacat gcgcactaaa ggtatctccg aagaactggc   6480
taccgaaagc gtgatgaatc tgatcgatga aacctggaaa aagatgaaca aggaaaaact   6540
gggtggtagc ctgttcgcga aaccgttcgt ggaaaccgcg atcaacctgg cacgtcaatc   6600
tcactgcact tatcataacg gcgacgcgca tacctctccg gatgagctga cccgcaaacg   6660
cgttctgtct gtaatcactg aaccgattct gccgtttgaa cgctaaggat ccattcgccc   6720
ttaggaggta aaaaaacatg agttttgata ttgccaaata cccgaccctg gcactggtcg   6780
actccaccca ggagttacga ctgttgccga aagagagttt accgaaactc tgcgacgaac   6840
tgcgccgcta tttactcgac agcgtgagcc gttccagcgg gcacttcgcc tccgggctgg   6900
gcacggtcga actgaccgtg gcgctgcact atgtctacaa caccccgttt gaccaattga   6960
tttgggatgt ggggcatcag gcttatccgc ataaaatttt gaccggacgc cgcgacaaaa   7020
tcggcaccat ccgtcagaaa ggcggtctgc acccgttccc gtggcgcggc gaaagcgaat   7080
atgacgtatt aagcgtcggg cattcatcaa cctccatcag tgccggaatt ggtattgcgg   7140
ttgctgccga aaaagaaggc aaaaatcgcc gcaccgtctg tgtcattggc gatggcgcga   7200
ttaccgcagg catggcgttt gaagcgatga atcacgcggg cgatatccgt cctgatatgc   7260
tggtgattct caacgacaat gaaatgtcga tttccgaaaa tgtcggcgcg ctcaacaacc   7320
atctggcaca gctgctttcc ggtaagcttt actcttcact gcgcgaaggc gggaaaaaag   7380
ttttctctgg cgtgccgcca attaaagagc tgctcaaacg caccgaagaa catattaaag   7440
gcatggtagt gcctggcacg ttgtttgaag agctgggctt taactacatc ggcccggtgg   7500
acggtcacga tgtgctgggg cttatcacca cgctaaagaa catgcgcgac ctgaaaggcc   7560
cgcagttcct gcatatcatg accaaaaaag gtcgtggtta tgaaccggca gaaaaagacc   7620
cgatcacttt ccacgccgtg cctaaatttg atccctccag cggttgtttg ccgaaaagta   7680
gcggcggttt gccgagctat tcaaaaatct ttggcgactg gttgtgcgaa acggcagcga   7740
aagacaacaa gctgatggcg attactccgg cgatgcgtga aggttccggc atggtcgagt   7800
tttcacgtaa attcccggat cgctacttcg acgtggcaat tgccgagcaa cacgcggtga   7860
cctttgctgc gggtctggcg attggtgggt acaaacccat tgtcgcgatt tactccactt   7920
tcctgcaacg cgcctatgat caggtgctgc atgacgtggc gattcaaaag cttccggtcc   7980
tgttcgccat cgaccgcgcg ggcattgttg gtgctgacgg tcaaacccat cagggtgctt   8040
ttgatctctc ttacctgcgc tgcataccgg aaatggtcat tatgaccccg agcgatgaaa   8100
```

acgaatgtcg ccagatgctc tataccggct atcactataa cgatggcccg tcagcggtgc 8160
gctacccgcg tggcaacgcg gtcggcgtgg aactgacgcc gctggaaaaa ctaccaattg 8220
gcaaaggcat tgtgaagcgt cgtggcgaga aactggcgat ccttaacttt ggtacgctga 8280
tgccagaagc ggcgaaagtc gccgaatcgc tgaacgccac gctggtcgat atgcgttttg 8340
tgaaaccgct tgatgaagcg ttaattctgg aaatggccgc cagccatgaa gcgctggtca 8400
ccgtagaaga aaacgccatt atgggcggcg caggcagcgg cgtgaacgaa gtgctgatgg 8460
cccatcgtaa accagtaccc gtgctgaaca ttggcctgcc ggacttcttt attccgcaag 8520
gaactcagga agaaatgcgc gccgaactcg gcctcgatgc cgctggtatg gaagccaaaa 8580
tcaaggcctg gctggcataa ctgcatcgcc cttaggaggt aaaaaaaaat gactgccgac 8640
aacaatagta tgccccatgg tgcagtatct agttacgcca aattagtgca aaaccaaaca 8700
cctgaagaca ttttggaaga gtttcctgaa attattccat tacaacaaag acctaatacc 8760
cgatctagtg agacgtcaaa tgacgaaagc ggagaaacat gtttttctgg tcatgatgag 8820
gagcaaatta agttaatgaa tgaaaattgt attgttttgg attgggacga taatgctatt 8880
ggtgccggta ccaagaaagt ttgtcattta atggaaaata ttgaaaaggg tttactacat 8940
cgtgcattct ccgtctttat tttcaatgaa caaggtgaat tacttttaca acaaagagcc 9000
actgaaaaaa taactttccc tgatctttgg actaacacat gctgctctca tccactatgt 9060
attgatgacg aattaggttt gaagggtaag ctagacgata agattaaggg cgctattact 9120
gcggcggtga gaaaactaga tcatgaatta ggtattccag aagatgaaac taagacaagg 9180
ggtaagtttc actttttaaa cagaatccat tacatggcac caagcaatga accatggggt 9240
gaacatgaaa ttgattacat cctattttat aagatcaacg ctaaagaaaa cttgactgtc 9300
aacccaaacg tcaatgaagt tagagacttc aaatgggttt caccaaatga tttgaaaact 9360
atgtttgctg acccaagtta caagtttacg ccttggttta agattatttg cgagaattac 9420
ttattcaact ggtgggagca attagatgac ctttctgaag tggaaaatga caggcaaatt 9480
catagaatgc tataacaacg cgtcctgcag ctggcggccg cactcgagca ccaccaccac 9540
caccactgag atccggctgc taacaaagcc cgaaaggaag ctgagttggc tgctgccacc 9600
gctgagcaat aactagcata accccttggg gcctctaaac gggtcttgag gggttttttg 9660
ctgaaaggag gaactatatc cggat 9685

<210> SEQ ID NO 110
<211> LENGTH: 9685
<212> TYPE: DNA
<213> ORGANISM: Artificial Sequence
<220> FEATURE:
<223> OTHER INFORMATION: Synthetic Construct

<400> SEQUENCE: 110
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480

```
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
```

-continued

```
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
```

ccgtttcgag tctgatatcc gtggtgcgct ggatcgcttc gtttcctccg gcggcttcga 5340
tgcggtaacc aagacttccc tgcacggtac ggcactgtct ttccgtctgc tgcgtcaaca 5400
cggttttgag gtttctcagg aagcgttcag cggcttcaaa gaccaaaacg gcaacttcct 5460
ggagaacctg aaggaagata tcaaagctat cctgagcctg tacgaggcca gcttcctggc 5520
tctggaaggc gaaaacatcc tggacgaggc gaaggttttc gcaatctctc atctgaaaga 5580
actgtctgaa gaaaagatcg gtaaagagct ggcagaacag gtgaaccatg cactggaact 5640
gccactgcat cgccgtactc agcgtctgga agcagtatgg tctatcgagg cctaccgtaa 5700
aaaggaggac gcgaatcagg ttctgctgga gctggcaatt ctggattaca acatgatcca 5760
gtctgtatac cagcgtgatc tgcgtgaaac gtcccgttgg tggcgtcgtg tgggtctggc 5820
gaccaaactg cactttgctc gtgaccgcct gattgagagc ttctactggg ccgtgggtgt 5880
agcattcgaa ccgcaatact ccgactgccg taactccgtc gcaaaaatgt tttctttcgt 5940
aaccattatc gacgatatct acgatgtata cggcaccctg gacgaactgg agctgtttac 6000
tgatgcagtt gagcgttggg acgtaaacgc catcaacgac ctgccggatt acatgaaact 6060
gtgctttctg gctctgtata acactattaa cgaaatcgcc tacgacaacc tgaaagataa 6120
aggtgagaac atcctgccgt atctgaccaa agcctgggct gacctgtgca acgctttcct 6180
gcaagaagcc aagtggctgt acaacaaatc tactccgacc tttgacgact acttcggcaa 6240
cgcatggaaa tcctcttctg gcccgctgca actggtgttc gcttacttcg ctgtcgtgca 6300
gaacattaaa aaggaagaga tcgaaaacct gcaaaaatac catgacacca tctctcgtcc 6360
ttcccatatc ttccgtctgt gcaatgacct ggctagcgcg tctgcggaaa ttgcgcgtgg 6420
tgaaaccgca aatagcgttt cttgttacat gcgcactaaa ggtatctccg aagaactggc 6480
taccgaaagc gtgatgaatc tgatcgatga aacctggaaa aagatgaaca aggaaaaact 6540
gggtggtagc ctgttcgcga aaccgttcgt ggaaaccgcg atcaacctgg cacgtcaatc 6600
tcactgcact tatcataacg gcgacgcgca tacctctccg gatgagctga cccgcaaacg 6660
cgttctgtct gtaatcactg aaccgattct gccgtttgaa cgctaaggat ccattcgccc 6720
ttaggaggta aaaaaacatg agttttgata ttgccaaata cccgaccctg gcactggtcg 6780
actccaccca ggagttacga ctgttgccga aagagagttt accgaaactc tgcgacgaac 6840
tgcgccgcta tttactcgac agcgtgagcc gttccagcgg gcacttcgcc tccgggctgg 6900
gcacggtcga actgaccgtg gcgctgcact atgtctacaa caccccgttt gaccaattga 6960
tttgggatgt ggggcatcag gcttatccgc ataaaatttt gaccggacgc cgcgacaaaa 7020
tcggcaccat ccgtcagaaa ggcggtctgc acccgttccc gtggcgcggc gaaagcgaat 7080
atgacgtatt aagcgtcggg cattcatcaa cctccatcag tgccggaatt ggtattgcgg 7140
ttgctgccga aaaagaaggc aaaaatcgcc gcaccgtctg tgtcattggc gatggcgcga 7200
ttaccgcagg catggcgttt gaagcgatga atcacgcggg cgatatccgt cctgatatgc 7260
tggtgattct caacgacaat gaaatgtcga tttccgaaaa tgtcggcgcg ctcaacaacc 7320
atctggcaca gctgctttcc ggtaagcttt actcttcact gcgcgaaggc gggaaaaaag 7380
ttttctctgg cgtgccgcca attaaagagc tgctcaaacg caccgaagaa catattaaag 7440
gcatggtagt gcctggcacg ttgtttgaag agctgggctt taactacatc ggcccggtgg 7500
acggtcacga tgtgctgggg cttatcacca cgctaaagaa catgcgcgac ctgaaaggcc 7560
cgcagttcct gcatatcatg accaaaaaag gtcgtggtta tgaaccggca gaaaaagacc 7620
cgatcacttt ccacgccgtg cctaaatttg atccctccag cggttgtttg ccgaaaagta 7680
gcggcggttt gccgagctat tcaaaaatct ttggcgactg gttgtgcgaa acggcagcga 7740
aagacaacaa gctgatggcg attactccgg cgatgcgtga aggttccggc atggtcgagt 7800
tttcacgtaa attcccggat cgctacttcg acgtggcaat tgccgagcaa cacgcggtga 7860
cctttgctgc gggtctggcg attggtgggt acaaacccat tgtcgcgatt tactccactt 7920
tcctgcaacg cgcctatgat caggtgctgc atgacgtggc gattcaaaag cttccggtcc 7980
tgttcgccat cgaccgcgcg ggcattgttg gtgctgacgg tcaaacccat cagggtgctt 8040
ttgatctctc ttacctgcgc tgcataccgg aaatggtcat tatgaccccg agcgatgaaa 8100
acgaatgtcg ccagatgctc tataccggct atcactataa cgatggcccg tcagcggtgc 8160
gctacccgcg tggcaacgcg gtcggcgtgg aactgacgcc gctggaaaaa ctaccaattg 8220
gcaaaggcat tgtgaagcgt cgtggcgaga aactggcgat ccttaacttt ggtacgctga 8280
tgccagaagc ggcgaaagtc gccgaatcgc tgaacgccac gctggtcgat atgcgttttg 8340
tgaaaccgct tgatgaagcg ttaattctgg aaatggccgc cagccatgaa gcgctggtca 8400
ccgtagaaga aaacgccatt atgggcggcg caggcagcgg cgtgaacgaa gtgctgatgg 8460
cccatcgtaa accagtaccc gtgctgaaca ttggcctgcc ggacttcttt attccgcaag 8520
gaactcagga agaaatgcgc gccgaactcg gcctcgatgc cgctggtatg gaagccaaaa 8580
tcaaggcctg gctggcataa ctgcatcgcc cttaggaggt aaaaaaaaat gactgccgac 8640
aacaatagta tgccccatgg tgcagtatct agttacgcca aattagtgca aaaccaaaca 8700
cctgaagaca ttttggaaga gtttcctgaa attattccat tacaacaaag acctaatacc 8760
cgatctagtg agacgtcaaa tgacgaaagc ggagaaacat gtttttctgg tcatgatgag 8820
gagcaaatta agttaatgaa tgaaaattgt attgttttgg attgggacga taatgctatt 8880
ggtgccggta ccaagaaagt ttgtcattta atggaaaata ttgaaaaggg tttactacat 8940
cgtgcattct ccgtctttat tttcaatgaa caaggtgaat tacttttaca acaaagagcc 9000
actgaaaaaa taactttccc tgatctttgg actaacacat gctgctctca tccactatgt 9060
attgatgacg aattaggttt gaagggtaag ctagacgata agattaaggg cgctattact 9120
gcggcggtga gaaaactaga tcatgaatta ggtattccag aagatgaaac taagacaagg 9180
ggtaagtttc actttttaaa cagaatccat tacatggcac caagcaatga accatggggt 9240
gaacatgaaa ttgattacat cctattttat aagatcaacg ctaaagaaaa cttgactgtc 9300
aacccaaacg tcaatgaagt tagagacttc aaatgggttt caccaaatga tttgaaaact 9360
atgtttgctg acccaagtta caagtttacg ccttggttta agattatttg cgagaattac 9420
ttattcaact ggtgggagca attagatgac ctttctgaag tggaaaatga caggcaaatt 9480
catagaatgc tataacaacg cgtcctgcag ctggcggccg cactcgagca ccaccaccac 9540
caccactgag atccggctgc taacaaagcc cgaaaggaag ctgagttggc tgctgccacc 9600
gctgagcaat aactagcata accccttggg gcctctaaac gggtcttgag gggttttttg 9660
ctgaaaggag gaactatatc cggat 9685

<210> SEQ ID NO 111
<211> LENGTH: 32
<212> TYPE: DNA
<213> ORGANISM: Artificial Sequence
<220> FEATURE:
<223> OTHER INFORMATION: Synthetic Construct

<400> SEQUENCE: 111
cagcagcagg gatccgacgc gttgttatag ca 32

<210> SEQ ID NO 112
<211> LENGTH: 32
<212> TYPE: DNA
<213> ORGANISM: Artificial Sequence
<220> FEATURE:
<223> OTHER INFORMATION: Synthetic Construct

<400> SEQUENCE: 112
cagcagcagc atatgactgc cgacaacaat ag 32

<210> SEQ ID NO 113
<211> LENGTH: 25
<212> TYPE: DNA
<213> ORGANISM: Artificial Sequence
<220> FEATURE:
<223> OTHER INFORMATION: Synthetic Construct

<400> SEQUENCE: 113
gaaacctaca tccaatcttt tgccc 25

<210> SEQ ID NO 114
<211> LENGTH: 25
<212> TYPE: DNA
<213> ORGANISM: Artificial Sequence
<220> FEATURE:
<223> OTHER INFORMATION: Synthetic Construct

<400> SEQUENCE: 114
gctatgcttc attagatcct tatcg 25

<210> SEQ ID NO 115
<211> LENGTH: 24
<212> TYPE: DNA
<213> ORGANISM: Artificial Sequence
<220> FEATURE:
<223> OTHER INFORMATION: Synthetic Construct

<400> SEQUENCE: 115
ttgccaatca tatgattgaa aatc 24

<210> SEQ ID NO 116
<211> LENGTH: 23
<212> TYPE: DNA
<213> ORGANISM: Artificial Sequence
<220> FEATURE:
<223> OTHER INFORMATION: Synthetic Construct

<400> SEQUENCE: 116
gaaatagccc cattagaagt atc 23

<210> SEQ ID NO 117
<211> LENGTH: 26
<212> TYPE: DNA
<213> ORGANISM: Artificial Sequence
<220> FEATURE:
<223> OTHER INFORMATION: Synthetic Construct

<400> SEQUENCE: 117
atgacaattg ggattgataa aattag 26

<210> SEQ ID NO 118
<211> LENGTH: 20
<212> TYPE: DNA
<213> ORGANISM: Artificial Sequence
<220> FEATURE:
<223> OTHER INFORMATION: Synthetic Construct

<400> SEQUENCE: 118
cttaaatcat ttaaaatagc 20

<210> SEQ ID NO 119
<211> LENGTH: 26
<212> TYPE: DNA
<213> ORGANISM: Artificial Sequence
<220> FEATURE:
<223> OTHER INFORMATION: Synthetic Construct

<400> SEQUENCE: 119
atgaaaacag tagttattat tgatgc 26

<210> SEQ ID NO 120
<211> LENGTH: 33
<212> TYPE: DNA
<213> ORGANISM: Artificial Sequence
<220> FEATURE:
<223> OTHER INFORMATION: Synthetic Construct

<400> SEQUENCE: 120
cgatctagaa aggcccagtc tttcgactga gcc 33

<210> SEQ ID NO 121
<211> LENGTH: 34
<212> TYPE: DNA
<213> ORGANISM: Artificial Sequence
<220> FEATURE:
<223> OTHER INFORMATION: Synthetic Construct

<400> SEQUENCE: 121
atgctcgagc tgttgacaat taatcatccg gctc 34

<210> SEQ ID NO 122
<211> LENGTH: 452
<212> TYPE: DNA
<213> ORGANISM: Artificial Sequence
<220> FEATURE:
<223> OTHER INFORMATION: Synthetic Construct

<400> SEQUENCE: 122
aaagaccgac caagcgacgt ctgagagctc cctggcgaat tcggtaccaa taaaagagct 60
ttattttcat gatctgtgtg ttggtttttg tgtgcggcgc ggaagttcct attctctaga 120
aagtatagga acttcctcga gccctatagt gagtcgtatt agcccttgac aatgccacat 180
cctgagcaaa taattcaacc acttttattc actaacaaat agctggtgga atatatgaag 240
caactcacca ttctgggctc gaccggctcg attggttgca gcacgctgga cgtggtgcgc 300
cataatcccg aacacttccg cgtagttgcg ctggtggcag gcaaaaatgt cactcgcatg 360
gtagaacagt gcctggaatt ctctccccgc tatgccgtaa tggacgatga agcgagtgcg 420
aaacttctta aaacgatgct acagcaacag gg 452

<210> SEQ ID NO 123
<211> LENGTH: 337
<212> TYPE: DNA
<213> ORGANISM: Artificial Sequence
<220> FEATURE:
<223> OTHER INFORMATION: Synthetic Construct

<400> SEQUENCE: 123
aaagaccgac caagcgacgt ctgagagctc cctggcgaat tcggtaccaa taaaagagct 60
ttattttcat gatctgtgtg ttggtttttg tgtgcggcgc ggaagttcct attctctaga 120
aagtatagga acttcctcga gccctatagt gagtcgtatt aagataacca tctgcggtga 180
taaattatct ctggcggtgt tgacataaat accactggcg gtgatactga gcacatcagc 240
aggacgcact gcaaaggagg taaaaaaaca tgagttttga tattgccaaa tacccgaccc 300
tggcactggt cgactccacc caggagttac gactgtt 337

<210> SEQ ID NO 124
<211> LENGTH: 22
<212> TYPE: DNA
<213> ORGANISM: Artificial Sequence
<220> FEATURE:
<223> OTHER INFORMATION: Synthetic Construct

<400> SEQUENCE: 124
ccctgttgct gtagcatcgt tt 22

<210> SEQ ID NO 125
<211> LENGTH: 200
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 133
<223> OTHER INFORMATION: n = A,T,C or G

<400> SEQUENCE: 125
aacagtcgta actcctgggt ggagtcgacc agtgccaggg tcgggtattt ggcaatatca 60
aaactcatgt ttttttacct cctttgcagt gcgtcctgct gatgtgctca gtatcaccgc 120
cagtggtatt tangtcaaca ccgccagaga taatttatca ccgcagatgg ttatcttaat 180
acgactcact atagggctcg 200

<210> SEQ ID NO 126
<211> LENGTH: 103
<212> TYPE: DNA
<213> ORGANISM: Artificial Sequence
<220> FEATURE:
<223> OTHER INFORMATION: Synthetic Construct

<400> SEQUENCE: 126
acaaaaacgc cgctcagtag atccttgcgg atcggctggc ggcgttttgc tttttattct 60
gtctcaactc tggatgtttc aattaaccct cactaaaggg cgg 103

<210> SEQ ID NO 127
<211> LENGTH: 177
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 144
<223> OTHER INFORMATION: n = A,T,C or G

<400> SEQUENCE: 127
tgttcgggat tatggcgcac cacgtccagc gtgctgcaac caatcgagcc ggtcgagccc 60
agaatggtga gttgcttcat atattccacc agctatttgt tagtgaataa aagtggttga 120
attatttgct caggatgtgg catngtcaag ggctaatacg actcactata gggctcg 177

<210> SEQ ID NO 128
<211> LENGTH: 103

<212> TYPE: DNA
<213> ORGANISM: Artificial Sequence
<220> FEATURE:
<223> OTHER INFORMATION: Synthetic Construct

<400> SEQUENCE: 128
tcgatacctc ggcactggaa gcgctagcgg actacatcat ccagcgtaat aaataaacaa 60
taagtattaa taggcccctg aattaaccct cactaaaggg cgg 103

<210> SEQ ID NO 129
<211> LENGTH: 1702
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1636
<223> OTHER INFORMATION: n = A,T,C or G

<400> SEQUENCE: 129
actaaagggc ggccgcgaag ttcctattct ctagaaagta taggaacttc attctaccgg 60
gtaggggagg cgcttttccc aaggcagtct ggagcatgcg ctttagcagc cccgctgggc 120
acttggcgct acacaagtgg cctctggcct cgcacacatt ccacatccac cggtaggcgc 180
caaccggctc cgttctttgg tggccccttc gcgccacctt ccactcctcc cctagtcagg 240
aagttccccc ccgccccgca gctcgcgtcg tgcaggacgt gacaaatgga agtagcacgt 300
ctcactagtc tcgtgcagat ggacagcacc gctgagcaat ggaagcgggt aggcctttgg 360
ggcagcggcc aatagcagct ttgctccttc gctttctggg ctcagaggct gggaaggggt 420
gggtccgggg gcgggctcag gggcgggctc aggggcgggg cgggcgcccg aaggtcctcc 480
ggaggcccgg cattctgcac gcttcaaaag cgcacgtctg ccgcgctgtt ctcctcttcc 540
tcatctccgg gcctttcgac ctgcagcagc acgtgttgac aattaatcat cggcatagta 600
tatcggcata gtataatacg acaaggtgag gaactaaacc atgggatcgg ccattgaaca 660
agatggattg cacgcaggtt ctccggccgc ttgggtggag aggctattcg gctatgactg 720
ggcacaacag acgatcggct gctctgatgc cgccgtgttc cggctgtcag cgcaggggcg 780
cccggttctt tttgtcaaga ccgacctgtc cggtgccctg aatgaactgc aggacgaggc 840
agcgcggcta tcgtggctgg ccacgacggg cgttccttgc gcagctgtgc tcgacgttgt 900
cactgaagcg ggaagggact ggctgctatt gggcgaagtg ccggggcagg atctcctgtc 960
atctcacctt gctcctgccg agaaagtatc catcatggct gatgcaatgc ggcggctgca 1020
tacgcttgat ccggctacct gcccattcga ccaccaagcg aaacatcgca tcgagcgagc 1080
acgtactcgg atggaagccg gtcttgtcga tcaggatgat ctggacgaag agcatcaggg 1140
gctcgcgcca gccgaactgt tcgccaggct caaggcgcgc atgcccgacg gcgaggatct 1200
cgtcgtgacc catggcgatg cctgcttgcc gaatatcatg gtggaaaatg gccgcttttc 1260
tggattcatc gactgtggcc ggctgggtgt ggcggaccgc tatcaggaca tagcgttggc 1320
tacccgtgat attgctgaag agcttggcgg cgaatgggct gaccgcttcc tcgtgcttta 1380
cggtatcgcc gctcccgatt cgcagcgcat cgccttctat cgccttcttg acgagttctt 1440
ctgagcggga ctctggggtt cgaataaaga ccgaccaagc gacgtctgag agctccctgg 1500
cgaattcggt accaataaaa gagctttatt ttcatgatct gtgtgttggt ttttgtgtgc 1560
ggcgcggaag ttcctattct ctagaaagta taggaacttc ctcgagccct atagtgagtc 1620
gtattagccc ttgacnatgc cacatcctga gcaaataatt caaccacttt tattcactaa 1680

-continued

```
caaatagctg gtggaatata tg                                          1702

<210> SEQ ID NO 130
<211> LENGTH: 1724
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1657
<223> OTHER INFORMATION: n = A,T,C or G

<400> SEQUENCE: 130

cgcgaagttc ctattctcta gaaagtatag gaacttcatt ctaccgggta ggggaggcgc     60
ttttcccaag gcagtctgga gcatgcgctt tagcagcccc gctgggcact tggcgctaca    120
caagtggcct ctggcctcgc acacattcca catccaccgg taggcgccaa ccggctccgt    180
tctttggtgg ccccttcgcg ccaccttcca ctcctcccct agtcaggaag ttcccccccg    240
ccccgcagct cgcgtcgtgc aggacgtgac aaatggaagt agcacgtctc actagtctcg    300
tgcagatgga cagcaccgct gagcaatgga agcgggtagg cctttggggc agcggccaat    360
agcagctttg ctccttcgct ttctgggctc agaggctggg aaggggtggg tccgggggcg    420
ggctcagggg cgggctcagg ggcggggcgg gcgcccgaag gtcctccgga ggcccggcat    480
tctgcacgct tcaaaagcgc acgtctgccg cgctgttctc ctcttcctca tctccgggcc    540
tttcgacctg cagcagcacg tgttgacaat taatcatcgg catagtatat cggcatagta    600
taatacgaca aggtgaggaa ctaaaccatg ggatcggcca ttgaacaaga tggattgcac    660
gcaggttctc cggccgcttg ggtggagagg ctattcggct atgactgggc acaacagacg    720
atcggctgct ctgatgccgc cgtgttccgg ctgtcagcgc aggggcgccc ggttcttttt    780
gtcaagaccg acctgtccgg tgccctgaat gaactgcagg acgaggcagc gcggctatcg    840
tggctggcca cgacgggcgt tccttgcgca gctgtgctcg acgttgtcac tgaagcggga    900
agggactggc tgctattggg cgaagtgccg gggcaggatc tcctgtcatc tcaccttgct    960
cctgccgaga aagtatccat catggctgat gcaatgcggc ggctgcatac gcttgatccg   1020
gctacctgcc cattcgacca ccaagcgaaa catcgcatcg agcgagcacg tactcggatg   1080
gaagccggtc ttgtcgatca ggatgatctg gacgaagagc atcaggggct cgcgccagcc   1140
gaactgttcg ccaggctcaa ggcgcgcatg cccgacggcg aggatctcgt cgtgacccat   1200
ggcgatgcct gcttgccgaa tatcatggtg gaaaatggcc gcttttctgg attcatcgac   1260
tgtggccggc tgggtgtggc ggaccgctat caggacatag cgttggctac ccgtgatatt   1320
gctgaagagc ttggcggcga atgggctgac cgcttcctcg tgctttacgg tatcgccgct   1380
cccgattcgc agcgcatcgc cttctatcgc cttcttgacg agttcttctg agcgggactc   1440
tggggttcga ataaagaccg accaagcgac gtctgagagc tccctggcga attcggtacc   1500
aataaaagag ctttattttc atgatctgtg tgttggtttt tgtgtgcggc gcggaagttc   1560
ctattctcta gaaagtatag gaacttcctc gagccctata gtgagtcgta ttaagataac   1620
catctgcggt gataaattat ctctggcggt gttgacntaa ataccactgg cggtgatact   1680
gagcacatca gcaggacgca ctgcaaagga ggtaaaaaaa catg                    1724

<210> SEQ ID NO 131
<211> LENGTH: 18
<212> TYPE: DNA
<213> ORGANISM: Artificial Sequence
```

<220> FEATURE:
<223> OTHER INFORMATION: Synthetic Construct

<400> SEQUENCE: 131
ggcgatagaa ggcgatgc 18

<210> SEQ ID NO 132
<211> LENGTH: 20
<212> TYPE: DNA
<213> ORGANISM: Artificial Sequence
<220> FEATURE:
<223> OTHER INFORMATION: Synthetic Construct

<400> SEQUENCE: 132
gagcgcccaa tacgcaaacc 20

<210> SEQ ID NO 133
<211> LENGTH: 21
<212> TYPE: DNA
<213> ORGANISM: Artificial Sequence
<220> FEATURE:
<223> OTHER INFORMATION: Synthetic Construct

<400> SEQUENCE: 133
cacgacaggt ttcccgactg g 21

<210> SEQ ID NO 134
<211> LENGTH: 21
<212> TYPE: DNA
<213> ORGANISM: Artificial Sequence
<220> FEATURE:
<223> OTHER INFORMATION: Synthetic Construct

<400> SEQUENCE: 134
ggactcaaga cgatagttac c 21

<210> SEQ ID NO 135
<211> LENGTH: 22
<212> TYPE: DNA
<213> ORGANISM: Artificial Sequence
<220> FEATURE:
<223> OTHER INFORMATION: Synthetic Construct

<400> SEQUENCE: 135
gtgatattgc tgaagagctt gg 22

<210> SEQ ID NO 136
<211> LENGTH: 20
<212> TYPE: DNA
<213> ORGANISM: Artificial Sequence
<220> FEATURE:
<223> OTHER INFORMATION: Synthetic Construct

<400> SEQUENCE: 136
gaactccaag acgaggcagc 20

<210> SEQ ID NO 137
<211> LENGTH: 20
<212> TYPE: DNA
<213> ORGANISM: Artificial Sequence
<220> FEATURE:
<223> OTHER INFORMATION: Synthetic Construct

<400> SEQUENCE: 137
cgtcgtttta caacgtcgtg 20

<210> SEQ ID NO 138
<211> LENGTH: 112
<212> TYPE: DNA
<213> ORGANISM: Artificial Sequence
<220> FEATURE:
<223> OTHER INFORMATION: Synthetic Construct

<400> SEQUENCE: 138
ggatccgtaa tctgtttcct gtgtgaaatt gttatccgct cacaattcca cacattatac 60
gagccgatga ttaattgtca acagaattcc tttccagtcg ggaaacctgt cg 112

<210> SEQ ID NO 139
<211> LENGTH: 79
<212> TYPE: DNA
<213> ORGANISM: Artificial Sequence
<220> FEATURE:
<223> OTHER INFORMATION: Synthetic Construct

<400> SEQUENCE: 139
taactttaag gaggtataca tatggagctc acgcgtgcgg ccgcctcgag ctgcagtaca 60
aataaaaaag gcacgtcag 79

<210> SEQ ID NO 140
<211> LENGTH: 94
<212> TYPE: DNA
<213> ORGANISM: Artificial Sequence
<220> FEATURE:
<223> OTHER INFORMATION: Synthetic Construct

<400> SEQUENCE: 140
ggttaatcat ttcactcttc aattatctat aatgatgagt gatcagaatt acatgtgaga 60
aattaattaa ccctcactaa agggcggccg cgaa 94

<210> SEQ ID NO 141
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 64
<223> OTHER INFORMATION: n = A,T,C or G

<400> SEQUENCE: 141
atattccacc agctatttgt tagtgaataa aagtggttga attatttgct caggatgtgg 60
catngtcaag ggctaatacg actcactata gggctcgagg 100

<210> SEQ ID NO 142
<211> LENGTH: 100
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 10
<223> OTHER INFORMATION: n = A,T,C or G

<400> SEQUENCE: 142
gcccttgacn atgccacatc ctgagcaaat aattcaacca cttttattca ctaacaaata 60
gctggtggaa tatatgactg ccgacaacaa tagtatgccc 100

<210> SEQ ID NO 143
<211> LENGTH: 82

<212> TYPE: DNA
<213> ORGANISM: Artificial Sequence
<220> FEATURE:
<223> OTHER INFORMATION: Synthetic Construct

<400> SEQUENCE: 143
gatgcgtcca gtaaaataag cattacgtta tgctcataac cccggcaaat gtcggggttt 60
tttatagcat tctatgaatt tg 82

<210> SEQ ID NO 144
<211> LENGTH: 21
<212> TYPE: DNA
<213> ORGANISM: Artificial Sequence
<220> FEATURE:
<223> OTHER INFORMATION: Synthetic Construct

<400> SEQUENCE: 144
actgaaacgt tttcatcgct c 21

<210> SEQ ID NO 145
<211> LENGTH: 35
<212> TYPE: DNA
<213> ORGANISM: Artificial Sequence
<220> FEATURE:
<223> OTHER INFORMATION: Synthetic Construct

<400> SEQUENCE: 145
gatgcgtcca gtaaaataag cattacgtta tgctc 35

<210> SEQ ID NO 146
<211> LENGTH: 21
<212> TYPE: DNA
<213> ORGANISM: Artificial Sequence
<220> FEATURE:
<223> OTHER INFORMATION: Synthetic Construct

<400> SEQUENCE: 146
gtcaggctgg aatactcttc g 21

<210> SEQ ID NO 147
<211> LENGTH: 20
<212> TYPE: DNA
<213> ORGANISM: Artificial Sequence
<220> FEATURE:
<223> OTHER INFORMATION: Synthetic Construct

<400> SEQUENCE: 147
gacgctttcg ccaagtcagg 20

<210> SEQ ID NO 148
<211> LENGTH: 30
<212> TYPE: DNA
<213> ORGANISM: Artificial Sequence
<220> FEATURE:
<223> OTHER INFORMATION: Synthetic Construct

<400> SEQUENCE: 148
gaggaataaa ccatggaagc tcgtcgttct 30

<210> SEQ ID NO 149
<211> LENGTH: 30
<212> TYPE: DNA
<213> ORGANISM: Artificial Sequence
<220> FEATURE:
<223> OTHER INFORMATION: Synthetic Construct

<400> SEQUENCE: 149
agaacgacga gcttccatgg tttattcctc 30

<210> SEQ ID NO 150
<211> LENGTH: 23
<212> TYPE: DNA
<213> ORGANISM: Artificial Sequence
<220> FEATURE:
<223> OTHER INFORMATION: Synthetic Construct

<400> SEQUENCE: 150
gacagcttat catcgactgc acg 23

<210> SEQ ID NO 151
<211> LENGTH: 22
<212> TYPE: DNA
<213> ORGANISM: Artificial Sequence
<220> FEATURE:
<223> OTHER INFORMATION: Synthetic Construct

<400> SEQUENCE: 151
gcactgtctt tccgtctgct gc 22

<210> SEQ ID NO 152
<211> LENGTH: 20
<212> TYPE: DNA
<213> ORGANISM: Artificial Sequence
<220> FEATURE:
<223> OTHER INFORMATION: Synthetic Construct

<400> SEQUENCE: 152
ctcgtacagg ctcaggatag 20

<210> SEQ ID NO 153
<211> LENGTH: 20
<212> TYPE: DNA
<213> ORGANISM: Artificial Sequence
<220> FEATURE:
<223> OTHER INFORMATION: Synthetic Construct

<400> SEQUENCE: 153
ttacgtccca acgctcaact 20

<210> SEQ ID NO 154
<211> LENGTH: 20
<212> TYPE: DNA
<213> ORGANISM: Artificial Sequence
<220> FEATURE:
<223> OTHER INFORMATION: Synthetic Construct

<400> SEQUENCE: 154
cttcggcaac gcatggaaat 20

<210> SEQ ID NO 155
<211> LENGTH: 23
<212> TYPE: DNA
<213> ORGANISM: Artificial Sequence
<220> FEATURE:
<223> OTHER INFORMATION: Synthetic Construct

<400> SEQUENCE: 155
ccaggcaaat tctgttttat cag 23

<210> SEQ ID NO 156
<211> LENGTH: 544
<212> TYPE: PRT
<213> ORGANISM: Artificial Sequence
<220> FEATURE:
<223> OTHER INFORMATION: Synthetic Construct

<400> SEQUENCE: 156

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400
```

```
Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540
```

<210> SEQ ID NO 157
<211> LENGTH: 6020
<212> TYPE: DNA
<213> ORGANISM: Artificial Sequence
<220> FEATURE:
<223> OTHER INFORMATION: Synthetic Construct

<400> SEQUENCE: 157

```
gtttgacagc ttatcatcga ctgcacggtg caccaatgct tctggcgtca ggcagccatc     60

ggaagctgtg gtatggctgt gcaggtcgta aatcactgca taattcgtgt cgctcaaggc    120

gcactcccgt tctggataat gttttttgcg ccgacatcat aacggttctg gcaaatattc    180

tgaaatgagc tgttgacaat taatcatccg gctcgtataa tgtgtggaat tgtgagcgga    240

taacaatttc acacaggaaa cagcgccgct gagaaaaagc gaagcggcac tgctctttaa    300

caatttatca gacaatctgt gtgggcactc gaccggaatt atcgattaac tttattatta    360

aaaattaaag aggtatatat taatgtatcg attaaataag gaggaataaa ccatggaagc    420

tcgtcgttct gcgaactacg aacctaacag ctgggactat gattacctgc tgtcctccga    480

cacggacgag tccatcgaag tatacaaaga caaagcgaaa aagctggaag ccgaagttcg    540

tcgcgagatt aataacgaaa aagcagaatt tctgaccctg ctggaactga ttgacaacgt    600

ccagcgcctg ggcctgggtt accgtttcga gtctgatatc cgtggtgcgc tggatcgctt    660

cgtttcctcc ggcggcttcg atgcggtaac caagacttcc ctgcacggta cggcactgtc    720

tttccgtctg ctgcgtcaac acggttttga ggtttctcag gaagcgttca gcggcttcaa    780

agaccaaaac ggcaacttcc tggagaacct gaaggaagat atcaaagcta tcctgagcct    840

gtacgaggcc agcttcctgg ctctggaagg cgaaaacatc ctggacgagg cgaaggtttt    900

cgcaatctct catctgaaag aactgtctga agaaaagatc ggtaaagagc tggcagaaca    960

ggtgaaccat gcactggaac tgccactgca tcgccgtact cagcgtctgg aagcagtatg   1020

gtctatcgag gcctaccgta aaaaggagga cgcgaatcag gttctgctgg agctggcaat   1080

tctggattac aacatgatcc agtctgtata ccagcgtgat ctgcgtgaaa cgtcccgttg   1140

gtggcgtcgt gtgggtctgg cgaccaaact gcactttgct cgtgaccgcc tgattgagag   1200

cttctactgg gccgtgggtg tagcattcga accgcaatac tccgactgcc gtaactccgt   1260

cgcaaaaatg ttttctttcg taaccattat cgacgatatc tacgatgtat acggcaccct   1320
```

ggacgaactg gagctgttta ctgatgcagt tgagcgttgg gacgtaaacg ccatcaacga 1380
cctgccggat tacatgaaac tgtgctttct ggctctgtat aacactatta acgaaatcgc 1440
ctacgacaac ctgaaagata aaggtgagaa catcctgccg tatctgacca aagcctgggc 1500
tgacctgtgc aacgctttcc tgcaagaagc caagtggctg tacaacaaat ctactccgac 1560
ctttgacgac tacttcggca acgcatggaa atcctcttct ggcccgctgc aactggtgtt 1620
cgcttacttc gctgtcgtgc agaacattaa aaaggaagag atcgaaaacc tgcaaaaata 1680
ccatgacacc atctctcgtc cttcccatat cttccgtctg tgcaatgacc tggctagcgc 1740
gtctgcggaa attgcgcgtg gtgaaaccgc aaatagcgtt tcttgttaca tgcgcactaa 1800
aggtatctcc gaagaactgg ctaccgaaag cgtgatgaat ctgatcgatg aaacctggaa 1860
aaagatgaac aaggaaaaac tgggtggtag cctgttcgcg aaaccgttcg tggaaaccgc 1920
gatcaacctg gcacgtcaat ctcactgcac ttatcataac ggcgacgcgc atacctctcc 1980
ggatgagctg acccgcaaac gcgttctgtc tgtaatcact gaaccgattc tgccgtttga 2040
acgctaactg cagctggtac catatgggaa ttcgaagctt tctagaacaa aaactcatct 2100
cagaagagga tctgaatagc gccgtcgacc atcatcatca tcatcattga gtttaaacgg 2160
tctccagctt ggctgttttg gcggatgaga gaagattttc agcctgatac agattaaatc 2220
agaacgcaga agcggtctga taaaacagaa tttgcctggc ggcagtagcg cggtggtccc 2280
acctgacccc atgccgaact cagaagtgaa acgccgtagc gccgatggta gtgtggggtc 2340
tccccatgcg agagtaggga actgccaggc atcaaataaa acgaaaggct cagtcgaaag 2400
actgggcctt tcgttttatc tgttgtttgt cggtgaacgc tctcctgagt aggacaaatc 2460
cgccgggagc ggatttgaac gttgcgaagc aacggcccgg agggtggcgg gcaggacgcc 2520 cgcccataaac tgccaggcat caaattaagc agaaggccat cctgacggat ggcctttttg 2580
cgtttctaca aactcttttt gtttattttt ctaaatacat tcaaatatgt atccgctcat 2640
gagacaataa ccctgataaa tgcttcaata atattgaaaa aggaagagta tgagtattca 2700
acatttccgt gtcgccctta ttcccttttt tgcggcattt tgccttcctg tttttgctca 2760
cccagaaacg ctggtgaaag taaaagatgc tgaagatcag ttgggtgcac gagtgggtta 2820
catcgaactg gatctcaaca gcggtaagat ccttgagagt tttcgccccg aagaacgttt 2880
tccaatgatg agcactttta aagttctgct atgtggcgcg gtattatccc gtgttgacgc 2940
cgggcaagag caactcggtc gccgcataca ctattctcag aatgacttgg ttgagtactc 3000
accagtcaca gaaaagcatc ttacggatgg catgacagta agagaattat gcagtgctgc 3060
cataaccatg agtgataaca ctgcggccaa cttacttctg acaacgatcg gaggaccgaa 3120
ggagctaacc gcttttttgc acaacatggg ggatcatgta actcgccttg atcgttggga 3180
accggagctg aatgaagcca taccaaacga cgagcgtgac accacgatgc ctgtagcaat 3240
ggcaacaacg ttgcgcaaac tattaactgg cgaactactt actctagctt cccggcaaca 3300
attaatagac tggatggagg cggataaagt tgcaggacca cttctgcgct cggcccttcc 3360
ggctggctgg tttattgctg ataaatctgg agccggtgag cgtgggtctc gcggtatcat 3420
tgcagcactg gggccagatg gtaagccctc ccgtatcgta gttatctaca cgacggggag 3480
tcaggcaact atggatgaac gaaatagaca gatcgctgag ataggtgcct cactgattaa 3540
gcattggtaa ctgtcagacc aagtttactc atatatactt tagattgatt taaaacttca 3600
tttttaattt aaaaggatct aggtgaagat cctttttgat aatctcatga ccaaaatccc 3660
ttaacgtgag ttttcgttcc actgagcgtc agaccccgta gaaaagatca aaggatcttc 3720

```
ttgagatcct ttttttctgc gcgtaatctg ctgcttgcaa acaaaaaaac caccgctacc   3780
agcggtggtt tgtttgccgg atcaagagct accaactctt tttccgaagg taactggctt   3840
cagcagagcg cagataccaa atactgtcct tctagtgtag ccgtagttag gccaccactt   3900
caagaactct gtagcaccgc ctacatacct cgctctgcta atcctgttac cagtggctgc   3960
tgccagtggc gataagtcgt gtcttaccgg gttggactca agacgatagt taccggataa   4020
ggcgcagcgg tcgggctgaa cggggggttc gtgcacacag cccagcttgg agcgaacgac   4080
ctacaccgaa ctgagatacc tacagcgtga gctatgagaa agcgccacgc ttcccgaagg   4140
gagaaaggcg gacaggtatc cggtaagcgg cagggtcgga acaggagagc gcacgaggga   4200
gcttccaggg ggaaacgcct ggtatcttta tagtcctgtc gggtttcgcc acctctgact   4260
tgagcgtcga tttttgtgat gctcgtcagg ggggcggagc ctatggaaaa acgccagcaa   4320
cgcggccttt ttacggttcc tggccttttg ctggcctttt gctcacatgt tctttcctgc   4380
gttatcccct gattctgtgg ataaccgtat taccgccttt gagtgagctg ataccgctcg   4440
ccgcagccga acgaccgagc gcagcgagtc agtgagcgag gaagcggaag agcgcctgat   4500
gcggtatttt ctccttacgc atctgtgcgg tatttcacac cgcatatggt gcactctcag   4560
tacaatctgc tctgatgccg catagttaag ccagtataca ctccgctatc gctacgtgac   4620
tgggtcatgg ctgcgccccg acacccgcca acacccgctg acgcgccctg acgggcttgt   4680
ctgctcccgg catccgctta cagacaagct gtgaccgtct ccgggagctg catgtgtcag   4740
aggttttcac cgtcatcacc gaaacgcgcg aggcagcaga tcaattcgcg cgcgaaggcg   4800
aagcggcatg catttacgtt gacaccatcg aatggtgcaa aacctttcgc ggtatggcat   4860
gatagcgccc ggaagagagt caattcaggg tggtgaatgt gaaaccagta acgttatacg   4920
atgtcgcaga gtatgccggt gtctcttatc agaccgtttc ccgcgtggtg aaccaggcca   4980
gccacgtttc tgcgaaaacg cgggaaaaag tggaagcggc gatggcggag ctgaattaca   5040
ttcccaaccg cgtggcacaa caactggcgg gcaaacagtc gttgctgatt ggcgttgcca   5100
cctccagtct ggccctgcac gcgccgtcgc aaattgtcgc ggcgattaaa tctcgcgccg   5160
atcaactggg tgccagcgtg gtggtgtcga tggtagaacg aagcggcgtc gaagcctgta   5220
aagcggcggt gcacaatctt ctcgcgcaac gcgtcagtgg gctgatcatt aactatccgc   5280
tggatgacca ggatgccatt gctgtggaag ctgcctgcac taatgttccg gcgttatttc   5340
ttgatgtctc tgaccagaca cccatcaaca gtattatttt ctcccatgaa gacggtacgc   5400
gactgggcgt ggagcatctg gtcgcattgg gtcaccagca aatcgcgctg ttagcgggcc   5460
cattaagttc tgtctcggcg cgtctgcgtc tggctggctg gcataaatat ctcactcgca   5520
atcaaattca gccgatagcg gaacgggaag gcgactggag tgccatgtcc ggttttcaac   5580
aaaccatgca aatgctgaat gagggcatcg ttcccactgc gatgctggtt gccaacgatc   5640
agatggcgct gggcgcaatg cgcgccatta ccgagtccgg gctgcgcgtt ggtgcggata   5700
tctcggtagt gggatacgac gataccgaag acagctcatg ttatatcccg ccgtcaacca   5760
ccatcaaaca ggattttcgc ctgctggggc aaaccagcgt ggaccgcttg ctgcaactct   5820
ctcagggcca ggcggtgaag ggcaatcagc tgttgcccgt ctcactggtg aaaagaaaaa   5880
ccaccctggc gcccaatacg caaaccgcct ctccccgcgc gttggccgat tcattaatgc   5940
agctggcacg acaggtttcc cgactggaaa gcgggcagtg agcgcaacgc aattaatgtg   6000
agttagcgcg aattgatctg                                               6020
```

<210> SEQ ID NO 158
<211> LENGTH: 21
<212> TYPE: DNA
<213> ORGANISM: Artificial Sequence
<220> FEATURE:
<223> OTHER INFORMATION: Synthetic Construct

<400> SEQUENCE: 158
tgattccgca agactgcctg t 21

<210> SEQ ID NO 159
<211> LENGTH: 21
<212> TYPE: DNA
<213> ORGANISM: Artificial Sequence
<220> FEATURE:
<223> OTHER INFORMATION: Synthetic Construct

<400> SEQUENCE: 159
ttcggtatta ccggtgtcgc t 21

<210> SEQ ID NO 160
<211> LENGTH: 67
<212> TYPE: DNA
<213> ORGANISM: Artificial Sequence
<220> FEATURE:
<223> OTHER INFORMATION: Synthetic Construct

<400> SEQUENCE: 160
ctatgattgc ctttatccgt gggcaatttt ccacccccat aattaaccct cactaaaggg 60
cggccgc 67

<210> SEQ ID NO 161
<211> LENGTH: 152
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 105
<223> OTHER INFORMATION: n = A,T,C or G

<400> SEQUENCE: 161
aagatgccag tgatagccat gagtgaaata acctcttgaa ggttacctcc gggaaacgcg 60
gttgatttgt ttagtggttg aattatttgc tcaggatgtg gcatngtcaa gggcgtgacg 120
gctcgctaat acgactcact atagggctcg ag 152

<210> SEQ ID NO 162
<211> LENGTH: 38
<212> TYPE: DNA
<213> ORGANISM: Artificial Sequence
<220> FEATURE:
<223> OTHER INFORMATION: Synthetic Construct

<400> SEQUENCE: 162
agataaccat ctgcggtgat aaattatctc tggcggtg 38

<210> SEQ ID NO 163
<211> LENGTH: 21
<212> TYPE: DNA
<213> ORGANISM: Artificial Sequence
<220> FEATURE:
<223> OTHER INFORMATION: Synthetic Construct

<400> SEQUENCE: 163
ggtttagttc ctcaccttgt c 21

<210> SEQ ID NO 164
<211> LENGTH: 31
<212> TYPE: DNA
<213> ORGANISM: Artificial Sequence
<220> FEATURE:
<223> OTHER INFORMATION: Synthetic Construct

<400> SEQUENCE: 164
cgaggtcgac gcgagccgtc acgcccttga c 31

<210> SEQ ID NO 165
<211> LENGTH: 44
<212> TYPE: DNA
<213> ORGANISM: Artificial Sequence
<220> FEATURE:
<223> OTHER INFORMATION: Synthetic Construct

<400> SEQUENCE: 165
gctctcgcga gagcccgcgg tcaggcattg agaatttcgt cgag 44

<210> SEQ ID NO 166
<211> LENGTH: 52
<212> TYPE: DNA
<213> ORGANISM: Artificial Sequence
<220> FEATURE:
<223> OTHER INFORMATION: Synthetic Construct

<400> SEQUENCE: 166
tccaccgcgg gctcgaagga gatataccat gcataaccag gctccaattc aa 52

<210> SEQ ID NO 167
<211> LENGTH: 34
<212> TYPE: DNA
<213> ORGANISM: Artificial Sequence
<220> FEATURE:
<223> OTHER INFORMATION: Synthetic Construct

<400> SEQUENCE: 167
gctctcgcga ttatttttca acctgctgaa cgtc 34

<210> SEQ ID NO 168
<211> LENGTH: 20
<212> TYPE: DNA
<213> ORGANISM: Artificial Sequence
<220> FEATURE:
<223> OTHER INFORMATION: Synthetic Construct

<400> SEQUENCE: 168
gttgtaaaac gacggccagt 20

<210> SEQ ID NO 169
<211> LENGTH: 50
<212> TYPE: DNA
<213> ORGANISM: Artificial Sequence
<220> FEATURE:
<223> OTHER INFORMATION: Synthetic Construct

<400> SEQUENCE: 169
tacgggatcc atttgaggag taagccatgc ataaccaggc tccaattcaa 50

<210> SEQ ID NO 170
<211> LENGTH: 37
<212> TYPE: DNA
<213> ORGANISM: Artificial Sequence
<220> FEATURE:
<223> OTHER INFORMATION: Synthetic Construct

<400> SEQUENCE: 170
gctggagctc cacttatttt tcaacctgct gaacgtc 37

<210> SEQ ID NO 171
<211> LENGTH: 22
<212> TYPE: DNA
<213> ORGANISM: Artificial Sequence
<220> FEATURE:
<223> OTHER INFORMATION: Synthetic Construct

<400> SEQUENCE: 171
gatgatcaac atgacgcatg gc 22

<210> SEQ ID NO 172
<211> LENGTH: 20
<212> TYPE: DNA
<213> ORGANISM: Artificial Sequence
<220> FEATURE:
<223> OTHER INFORMATION: Synthetic Construct

<400> SEQUENCE: 172
cattccgatc cgtattggcg 20

<210> SEQ ID NO 173
<211> LENGTH: 21
<212> TYPE: DNA
<213> ORGANISM: Artificial Sequence
<220> FEATURE:
<223> OTHER INFORMATION: Synthetic Construct

<400> SEQUENCE: 173
tcacacagga aacagctatg a 21

<210> SEQ ID NO 174
<211> LENGTH: 33
<212> TYPE: DNA
<213> ORGANISM: Artificial Sequence
<220> FEATURE:
<223> OTHER INFORMATION: Synthetic Construct

<400> SEQUENCE: 174
cagtctatta atatgaagca aacagtttat atc 33

<210> SEQ ID NO 175
<211> LENGTH: 35
<212> TYPE: DNA
<213> ORGANISM: Artificial Sequence
<220> FEATURE:
<223> OTHER INFORMATION: Synthetic Construct

<400> SEQUENCE: 175
tagcagccgg atccttagtg tgcgttaacc accac 35

<210> SEQ ID NO 176
<211> LENGTH: 8911
<212> TYPE: DNA
<213> ORGANISM: Artificial Sequence
<220> FEATURE:
<223> OTHER INFORMATION: Synthetic Construct

<400> SEQUENCE: 176
accttcggga gcgcctgaag cccgttctgg acgccctggg gccgttgaat cgggatatgc 60
aggccaaggc cgccgcgatc atcaaggccg tgggcgaaaa gctgctgacg gaacagcggg 120
aagtccagcg ccagaaacag gcccagcgcc agcaggaacg cgggcgcgca catttccccg 180

```
aaaagtgcca cctggcggcg ttgtgacaat ttaccgaaca actccgcggc cgggaagccg    240
atctcggctt gaacgaattg ttaggtggcg gtacttgggt cgatatcaaa gtgcatcact    300
tcttcccgta tgcccaactt tgtatagaga gccactgcgg gatcgtcacc gtaatctgct    360
tgcacgtaga tcacataagc accaagcgcg ttggcctcat gcttgaggag attgatgagc    420
gcggtggcaa tgccctgcct ccggtgctcg ccggagactg cgagatcata gatatagatc    480
tcactacgcg gctgctcaaa cctgggcaga acgtaagccg cgagagcgcc aacaaccgct    540
tcttggtcga aggcagcaag cgcgatgaat gtcttactac ggagcaagtt cccgaggtaa    600
tcggagtccg gctgatgttg ggagtaggtg gctacgtctc cgaactcacg accgaaaaga    660
tcaagagcag cccgcatgga tttgacttgg tcagggccga gcctacatgt gcgaatgatg    720
cccatacttg agccacctaa ctttgtttta gggcgactgc cctgctgcgt aacatcgttg    780
ctgctgcgta acatcgttgc tgctccataa catcaaacat cgacccacgg cgtaacgcgc    840
ttgctgcttg gatgcccgag gcatagactg tacaaaaaaa cagtcataac aagccatgaa    900
aaccgccact gcgccgttac caccgctgcg ttcggtcaag gttctggacc agttgcgtga    960
gcgcatacgc tacttgcatt acagtttacg aaccgaacag gcttatgtca actgggttcg   1020
tgccttcatc cgtttccacg gtgtgcgtcc atgggcaaat attatacgca aggcgacaag   1080
gtgctgatgc cgctggcgat tcaggttcat catgccgttt gtgatggctt ccatgtcggc   1140
agaatgctta atgaattaca acagttttta tgcatgcgcc caatacgcaa accgcctctc   1200
cccgcgcgtt ggccgattca ttaatgcagc tggcacgaca ggtttcccga ctggaaagcg   1260
ggcagtgagc gcaacgcaat taatgtgagt tagctcactc attaggcacc ccaggcttta   1320
cactttatgc ttccggctcg tatgttgtgt ggaattgtga gcggataaca atttcacaca   1380
ggaaacagct atgaccatga ttacgccaag cgcgcaatta accctcacta aagggaacaa   1440
aagctgggta ccgggccccc cctcgagctg ttgacaatta atcatccggc tcgtataatg   1500
tgtggaattg tgagcggata acaatttcac acaggaaaca gcgccgctga gaaaaagcga   1560
agcggcactg ctctttaaca atttatcaga caatctgtgt gggcactcga ccggaattat   1620
cgattaactt tattattaaa aattaaagag gtatatatta atgtatcgat taaataagga   1680
ggaataaacc atggatccga gctcaggagg taaaaaaaca tgaaaacagt agttattatt   1740
gatgcattac gaacaccaat tggaaaatat aaaggcagct taagtcaagt aagtgccgta   1800
gacttaggaa cacatgttac aacacaactt ttaaaaagac attccactat ttctgaagaa   1860
attgatcaag taatctttgg aaatgtttta caagctggaa atggccaaaa tcccgcacga   1920
caaatagcaa taaacagcgg tttgtctcat gaaattcccg caatgacggt taatgaggtc   1980
tgcggatcag gaatgaaggc cgttattttg gcgaaacaat tgattcaatt aggagaagcg   2040
gaagttttaa ttgctggcgg gattgagaat atgtcccaag cacctaaatt acaacgtttt   2100
aattacgaaa cagaaagcta cgatgcgcct ttttctagta tgatgtatga tggattaacg   2160
gatgccttta gtggtcaggc aatgggctta actgctgaaa atgtggccga aaagtatcat   2220
gtaactagag aagagcaaga tcaattttct gtacattcac aattaaaagc agctcaagca   2280
caagcagaag ggatattcgc tgacgaaata gccccattag aagtatcagg aacgcttgtg   2340
gagaaagatg aagggattcg ccctaattcg agcgttgaga agctaggaac gcttaaaaca   2400
gtttttaaag aagacggtac tgtaacagca gggaatgcat caaccattaa tgatggggct   2460
tctgctttga ttattgcttc acaagaatat gccgaagcac acggtcttcc ttatttagct   2520
attattcgag acagtgtgga agtcggtatt gatccagcct atatgggaat ttcgccgatt   2580
```

aaagccattc aaaaactgtt agcgcgcaat caacttacta cggaagaaat tgatctgtat 2640
gaaatcaacg aagcatttgc agcaacttca atcgtggtcc aaagagaact ggctttacca 2700
gaggaaaagg tcaacattta tggtggcggt atttcattag gtcatgcgat tggtgccaca 2760
ggtgctcgtt tattaacgag tttaagttat caattaaatc aaaaagaaaa gaaatatgga 2820
gtggcttctt tatgtatcgg cggtggctta ggactcgcta tgctactaga gagacctcag 2880
caaaaaaaaa acagccgatt ttatcaaatg agtcctgagg aacgcctggc ttctcttctt 2940
aatgaaggcc agatttctgc tgatacaaaa aaagaatttg aaaatacggc tttatcttcg 3000
cagattgcca atcatatgat tgaaaatcaa atcagtgaaa cagaagtgcc gatgggcgtt 3060
ggcttacatt taacagtgga cgaaactgat tatttggtac caatggcgac agaagagccc 3120
tcagttattg cggctttgag taatggtgca aaaatagcac aaggatttaa aacagtgaat 3180
caacaacgct taatgcgtgg acaaatcgtt ttttacgatg ttgcagatcc cgagtcattg 3240
attgataaac tacaagtaag agaagcggaa gtttttcaac aagcagagtt aagttatcca 3300
tctatcgtta aacggggcgg cggcttaaga gatttgcaat atcgtacttt tgatgaatca 3360
tttgtatctg tcgacttttt agtagatgtt aaggatgcaa tgggggcaaa tatcgttaac 3420
gctatgttgg aaggtgtggc cgagttgttc cgtgaatggt ttgcggagca aaagatttta 3480
ttcagtattt taagtaatta tgccacggag tcggttgtta cgatgaaaac ggctattcca 3540
gtttcacgtt taagtaaggg gagcaatggc cgggaaattg ctgaaaaaat tgttttagct 3600
tcacgctatg cttcattaga tccttatcgg gcagtcacgc ataacaaagg aatcatgaat 3660
ggcattgaag ctgtagtttt agctacagga aatgatacac gcgctgttag cgcttcttgt 3720
catgcttttg cggtgaagga aggtcgctac caaggcttga ctagttggac gctggatggc 3780
gaacaactaa ttggtgaaat ttcagttccg cttgctttag ccacggttgg cggtgccaca 3840
aaagtcttac ctaaatctca agcagctgct gatttgttag cagtgacgga tgcaaaagaa 3900
ctaagtcgag tagtagcggc tgttggtttg gcacaaaatt tagcggcgtt acgggcctta 3960
gtctctgaag gaattcaaaa aggacacatg gctctacaag cacgttcttt agcgatgacg 4020
gtcggagcta ctggtaaaga agttgaggca gtcgctcaac aattaaaacg tcaaaaaacg 4080
atgaaccaag accgagccat ggctatttta aatgatttaa gaaaacaata aaggaggtaa 4140
aaaaacatga caattgggat tgataaaatt agtttttttg tgccccctta ttatattgat 4200
atgacggcac tggctgaagc cagaaatgta gaccctggaa aatttcatat tggtattggg 4260
caagaccaaa tggcggtgaa cccaatcagc caagatattg tgacatttgc agccaatgcc 4320
gcagaagcga tcttgaccaa agaagataaa gaggccattg atatggtgat tgtcgggact 4380
gagtccagta tcgatgagtc aaaagcggcc gcagttgtct tacatcgttt aatggggatt 4440
caaccttcg ctcgctcttt cgaaatcaag gaagcttgtt acggagcaac agcaggctta 4500
cagttagcta agaatcacgt agccttacat ccagataaaa aagtcttggt cgtagcggca 4560
gatattgcaa aatatggctt aaattctggc ggtgagccta cacaaggagc tggggcggtt 4620
gcaatgttag ttgctagtga accgcgcatt ttggctttaa aagaggataa tgtgatgctg 4680
acgcaagata tctatgactt ttggcgtcca acaggccacc cgtatcctat ggtcgatggt 4740
cctttgtcaa acgaaaccta catccaatct tttgcccaag tctgggatga acataaaaaa 4800
cgaaccggtc ttgattttgc agattatgat gctttagcgt tccatattcc ttacacaaaa 4860
atgggcaaaa aagccttatt agcaaaaatc tccgaccaaa ctgaagcaga acaggaacga 4920
attttagccc gttatgaaga aagtatcgtc tatagtcgtc gcgtaggaaa cttgtatacg 4980
ggttcacttt atctgggact catttccctt ttagaaaatg caacgacttt aaccgcaggc 5040
aatcaaattg gtttattcag ttatggttct ggtgctgtcg ctgaattttt cactggtgaa 5100
ttagtagctg gttatcaaaa tcatttacaa aaagaaactc atttagcact gctggataat 5160
cggacagaac tttctatcgc tgaatatgaa gccatgtttg cagaaacttt agacacagac 5220
attgatcaaa cgttagaaga tgaattaaaa tatagtattt ctgctattaa taataccgtt 5280
cgttcttatc gaaactaaag atctgcagct ggtaccatat gggaattcga agcttgggcc 5340
cgaacaaaaa ctcatctcag aagaggatct gaatagcgcc gtcgaccatc atcatcatca 5400
tcattgagtt taaacggtct ccagcttggc tgttttggcg gatgagagaa gattttcagc 5460
ctgatacaga ttaaatcaga acgcagaagc ggtctgataa aacagaattt gcctggcggc 5520
agtagcgcgg tggtcccacc tgaccccatg ccgaactcag aagtgaaacg ccgtagcgcc 5580
gatggtagtg tggggtctcc ccatgcgaga gtagggaact gccaggcatc aaataaaacg 5640
aaaggctcag tcgaaagact gggcctttct agagcggccg ccaccgcggt ggagctccaa 5700
ttcgccctat agtgagtcgt attacgcgcg ctcactggcc gtcgttttac aacgtcgtga 5760
ctgggaaaac cctggcgtta cccaacttaa tcgccttgca gcacatcccc ctttcgccag 5820
ctggcgtaat agcgaagagg cccgcaccga tcgcccttcc caacagttgc gcagcctgaa 5880
tggcgaatgg aaattgtaag cgttaatatt ttgttaaaat tcgcgttaaa tttttgttaa 5940
atcagctcat tttttaacca ataggccgac tgcgatgagt ggcagggcgg ggcgtaattt 6000
ttttaaggca gttattggtg cccttaaacg cctggtgcta cgcctgaata agtgataata 6060
agcggatgaa tggcagaaat tcgaaagcaa attcgacccg gtcgtcggtt cagggcaggg 6120
tcgttaaata gccgcttatg tctattgctg gtttaccggt ttattgacta ccggaagcag 6180
tgtgaccgtg tgcttctcaa atgcctgagg ccagtttgct caggctctcc ccgtggaggt 6240
aataattgac gatatgatca tttattctgc ctcccagagc ctgataaaaa cggtgaatcc 6300
gttagcgagg tgccgccggc ttccattcag gtcgaggtgg cccggctcca tgcaccgcga 6360
cgcaacgcgg ggaggcagac aaggtatagg gcggcgaggc ggctacagcc gatagtctgg 6420
aacagcgcac ttacgggttg ctgcgcaacc caagtgctac cggcgcggca gcgtgacccg 6480
tgtcggcggc tccaacggct cgccatcgtc cagaaaacac ggctcatcgg gcatcggcag 6540
gcgctgctgc ccgcgccgtt cccattcctc cgtttcggtc aaggctggca ggtctggttc 6600
catgcccgga atgccgggct ggctgggcgg ctcctcgccg gggccggtcg gtagttgctg 6660
ctcgcccgga tacagggtcg ggatgcggcg caggtcgcca tgccccaaca gcgattcgtc 6720
ctggtcgtcg tgatcaacca ccacggcggc actgaacacc gacaggcgca actggtcgcg 6780
gggctggccc cacgccacgc ggtcattgac cacgtaggcc gacacggtgc cggggccgtt 6840
gagcttcacg acggagatcc agcgctcggc caccaagtcc ttgactgcgt attggaccgt 6900
ccgcaaagaa cgtccgatga gcttggaaag tgtcttctgg ctgaccacca cggcgttctg 6960
gtggcccatc tgcgccacga ggtgatgcag cagcattgcc gccgtgggtt tcctcgcaat 7020
aagcccggcc cacgcctcat gcgctttgcg ttccgtttgc acccagtgac cgggcttgtt 7080
cttggcttga atgccgattt ctctggactg cgtggccatg cttatctcca tgcggtaggg 7140
tgccgcacgg ttgcggcacc atgcgcaatc agctgcaact tttcggcagc gcgacaacaa 7200
ttatgcgttg cgtaaaagtg gcagtcaatt acagattttc tttaacctac gcaatgagct 7260
attgcggggg gtgccgcaat gagctgttgc gtaccccccct tttttaagtt gttgattttt 7320
aagtctttcg catttcgccc tatatctagt tctttggtgc ccaaagaagg gcacccctgc 7380
ggggttcccc cacgccttcg gcgcggctcc ccctccggca aaaagtggcc cctccggggc 7440
ttgttgatcg actgcgcggc cttcggcctt gcccaaggtg gcgctgcccc cttggaaccc 7500
ccgcactcgc cgccgtgagg ctcgggggc aggcgggcgg gcttcgcctt cgactgcccc 7560
cactcgcata ggcttgggtc gttccaggcg cgtcaaggcc aagccgctgc gcggtcgctg 7620
cgcgagcctt gacccgcctt ccacttggtg tccaaccggc aagcgaagcg cgcaggccgc 7680
aggccggagg cttttcccca gagaaaatta aaaaaattga tggggcaagg ccgcaggccg 7740
cgcagttgga gccggtgggt atgtggtcga aggctgggta gccggtgggc aatccctgtg 7800
gtcaagctcg tgggcaggcg cagcctgtcc atcagcttgt ccagcagggt tgtccacggg 7860
ccgagcgaag cgagccagcc ggtggccgct cgcggccatc gtccacatat ccacgggctg 7920
gcaagggagc gcagcgaccg cgcagggcga agcccggaga gcaagcccgt agggcgccgc 7980
agccgccgta ggcggtcacg actttgcgaa gcaaagtcta gtgagtatac tcaagcattg 8040
agtggcccgc cggaggcacc gccttgcgct gcccccgtcg agccggttgg acaccaaaag 8100
ggaggggcag gcatggcggc atacgcgatc atgcgatgca agaagctggc gaaaatgggc 8160
aacgtggcgg ccagtctcaa gcacgcctac cgcgagcgcg agacgcccaa cgctgacgcc 8220
agcaggacgc cagagaacga gcactgggcg gccagcagca ccgatgaagc gatgggccga 8280
ctgcgcgagt tgctgccaga gaagcggcgc aaggacgctg tgttggcggt cgagtacgtc 8340
atgacggcca gcccggaatg gtggaagtcg gccagccaag aacagcaggc ggcgttcttc 8400
gagaaggcgc acaagtggct ggcggacaag tacggggcgg atcgcatcgt gacggccagc 8460
atccaccgtg acgaaaccag cccgcacatg accgcgttcg tggtgccgct gacgcaggac 8520
ggcaggctgt cggccaagga gttcatcggc aacaaagcgc agatgacccg cgaccagacc 8580
acgtttgcgg ccgctgtggc cgatctaggg ctgcaacggg gcatcgaggg cagcaaggca 8640
cgtcacacgc gcattcaggc gttctacgag gccctggagc ggccaccagt gggccacgtc 8700
accatcagcc cgcaagcggt cgagccacgc gcctatgcac cgcagggatt ggccgaaaag 8760
ctgggaatct caaagcgcgt tgagacgccg gaagccgtgg ccgaccggct gacaaaagcg 8820
gttcggcagg ggtatgagcc tgccctacag gccgccgcag gagcgcgtga gatgcgcaag 8880
aaggccgatc aagcccaaga gacggcccga g 8911

<210> SEQ ID NO 177
<211> LENGTH: 113
<212> TYPE: DNA
<213> ORGANISM: Artificial Sequence
<220> FEATURE:
<223> OTHER INFORMATION: Synthetic Construct

<400> SEQUENCE: 177
tggcaaatat tctgaaatga gctgttgaca attaatcatc gaactagtta actagtacgc 60
aagttcacgt aaaaagggta tcgacatggt atcctgttct gcgccgggta aga 113

<210> SEQ ID NO 178
<211> LENGTH: 73
<212> TYPE: DNA
<213> ORGANISM: Artificial Sequence
<220> FEATURE:
<223> OTHER INFORMATION: Synthetic Construct

<400> SEQUENCE: 178
caagaaaaaa ggcacgtcat ctgacgtgcc ttttttattt gtattaatct actttcagac 60
cttgctcggt cgg 73

<210> SEQ ID NO 179
<211> LENGTH: 21
<212> TYPE: DNA
<213> ORGANISM: Artificial Sequence
<220> FEATURE:
<223> OTHER INFORMATION: Synthetic Construct

<400> SEQUENCE: 179
gatacgtatg tttctacctt c 21

<210> SEQ ID NO 180
<211> LENGTH: 21
<212> TYPE: DNA
<213> ORGANISM: Artificial Sequence
<220> FEATURE:
<223> OTHER INFORMATION: Synthetic Construct

<400> SEQUENCE: 180
gaaggtagaa acatacgtat c 21

<210> SEQ ID NO 181
<211> LENGTH: 24
<212> TYPE: DNA
<213> ORGANISM: Artificial Sequence
<220> FEATURE:
<223> OTHER INFORMATION: Synthetic Construct

<400> SEQUENCE: 181
gatagtaacg gctgcgctgc tacc 24

<210> SEQ ID NO 182
<211> LENGTH: 48
<212> TYPE: DNA
<213> ORGANISM: Artificial Sequence
<220> FEATURE:
<223> OTHER INFORMATION: Synthetic Construct

<400> SEQUENCE: 182
gggcccgttt aaactttaac tagactttaa tctactttca gaccttgc 48

<210> SEQ ID NO 183
<211> LENGTH: 9945
<212> TYPE: DNA
<213> ORGANISM: Artificial Sequence
<220> FEATURE:
<223> OTHER INFORMATION: Synthetic Construct

<400> SEQUENCE: 183
accttcggga gcgcctgaag cccgttctgg acgccctggg gccgttgaat cgggatatgc 60
aggccaaggc cgccgcgatc atcaaggccg tgggcgaaaa gctgctgacg gaacagcggg 120
aagtccagcg ccagaaacag gcccagcgcc agcaggaacg cgggcgcgca catttccccg 180
aaaagtgcca cctggcggcg ttgtgacaat ttaccgaaca actccgcggc cgggaagccg 240
atctcggctt gaacgaattg ttaggtggcg gtacttgggt cgatatcaaa gtgcatcact 300
tcttcccgta tgcccaactt tgtatagaga gccactgcgg gatcgtcacc gtaatctgct 360
tgcacgtaga tcacataagc accaagcgcg ttggcctcat gcttgaggag attgatgagc 420
gcggtggcaa tgccctgcct ccggtgctcg ccggagactg cgagatcata gatatagatc 480
tcactacgcg gctgctcaaa cctgggcaga acgtaagccg cgagagcgcc aacaaccgct 540
tcttggtcga aggcagcaag cgcgatgaat gtcttactac ggagcaagtt cccgaggtaa 600
tcggagtccg gctgatgttg ggagtaggtg gctacgtctc cgaactcacg accgaaaaga 660

-continued tcaagagcag cccgcatgga tttgacttgg tcagggccga gcctacatgt gcgaatgatg 720
cccatacttg agccacctaa ctttgtttta gggcgactgc cctgctgcgt aacatcgttg 780
ctgctgcgta acatcgttgc tgctccataa catcaaacat cgacccacgg cgtaacgcgc 840
ttgctgcttg gatgcccgag gcatagactg tacaaaaaaa cagtcataac aagccatgaa 900
aaccgccact gcgccgttac caccgctgcg ttcggtcaag gttctggacc agttgcgtga 960
gcgcatacgc tacttgcatt acagtttacg aaccgaacag gcttatgtca actgggttcg 1020
tgccttcatc cgtttccacg gtgtgcgtcc atgggcaaat attatacgca aggcgacaag 1080
gtgctgatgc cgctggcgat tcaggttcat catgccgttt gtgatggctt ccatgtcggc 1140
agaatgctta atgaattaca acagttttta tgcatgcgcc caatacgcaa accgcctctc 1200
cccgcgcgtt ggccgattca ttaatgcagc tggcacgaca ggtttcccga ctggaaagcg 1260
ggcagtgagc gcaacgcaat taatgtgagt tagctcactc attaggcacc ccaggcttta 1320
cactttatgc ttccggctcg tatgttgtgt ggaattgtga gcggataaca atttcacaca 1380
ggaaacagct atgaccatga ttacgccaag cgcgcaatta accctcacta aagggaacaa 1440
aagctgggta ccgggccccc cctcgagctg ttgacaatta atcatccggc tcgtataatg 1500
tgtggaattg tgagcggata acaatttcac acaggaaaca gcgccgctga gaaaaagcga 1560
agcggcactg ctctttaaca atttatcaga caatctgtgt gggcactcga ccggaattat 1620
cgattaactt tattattaaa aattaaagag gtatatatta atgtatcgat taaataagga 1680
ggaataaacc atggatccga gctcaggagg taaaaaaaca tgaaaacagt agttattatt 1740
gatgcattac gaacaccaat tggaaaatat aaaggcagct taagtcaagt aagtgccgta 1800
gacttaggaa cacatgttac aacacaactt ttaaaaagac attccactat ttctgaagaa 1860
attgatcaag taatctttgg aaatgtttta caagctggaa atggccaaaa tcccgcacga 1920
caaatagcaa taaacagcgg tttgtctcat gaaattcccg caatgacggt taatgaggtc 1980
tgcggatcag gaatgaaggc cgttattttg gcgaaacaat tgattcaatt aggagaagcg 2040
gaagttttaa ttgctggcgg gattgagaat atgtcccaag cacctaaatt acaacgtttt 2100
aattacgaaa cagaaagcta cgatgcgcct tttctagta tgatgtatga tggattaacg 2160
gatgccttta gtggtcaggc aatgggctta actgctgaaa atgtggccga aaagtatcat 2220
gtaactagag aagagcaaga tcaattttct gtacattcac aattaaaagc agctcaagca 2280
caagcagaag ggatattcgc tgacgaaata gccccattag aagtatcagg aacgcttgtg 2340
gagaaagatg aagggattcg ccctaattcg agcgttgaga agctaggaac gcttaaaaca 2400
gtttttaaag aagacggtac tgtaacagca gggaatgcat caaccattaa tgatggggct 2460
tctgctttga ttattgcttc acaagaatat gccgaagcac acggtcttcc ttatttagct 2520
attattcgag acagtgtgga agtcggtatt gatccagcct atatgggaat ttcgccgatt 2580
aaagccattc aaaaactgtt agcgcgcaat caacttacta cggaagaaat tgatctgtat 2640
gaaatcaacg aagcatttgc agcaacttca atcgtggtcc aaagagaact ggctttacca 2700
gaggaaaagg tcaacattta tggtggcggt atttcattag gtcatgcgat tggtgccaca 2760
ggtgctcgtt tattaacgag tttaagttat caattaaatc aaaaagaaaa gaaatatgga 2820
gtggcttctt tatgtatcgg cggtggctta ggactcgcta tgctactaga gagacctcag 2880
caaaaaaaaa acagccgatt ttatcaaatg agtcctgagg aacgcctggc ttctcttctt 2940
aatgaaggcc agatttctgc tgatacaaaa aaagaatttg aaaatacggc tttatcttcg 3000
cagattgcca atcatatgat tgaaaatcaa atcagtgaaa cagaagtgcc gatgggcgtt 3060
ggcttacatt taacagtgga cgaaactgat tatttggtac caatggcgac agaagagccc 3120
tcagttattg cggctttgag taatggtgca aaaatagcac aaggatttaa aacagtgaat 3180
caacaacgct taatgcgtgg acaaatcgtt ttttacgatg ttgcagatcc cgagtcattg 3240
attgataaac tacaagtaag agaagcggaa gtttttcaac aagcagagtt aagttatcca 3300
tctatcgtta aacggggcgg cggcttaaga gatttgcaat atcgtacttt tgatgaatca 3360
tttgtatctg tcgacttttt agtagatgtt aaggatgcaa tgggggcaaa tatcgttaac 3420
gctatgttgg aaggtgtggc cgagttgttc cgtgaatggt ttgcggagca aaagatttta 3480
ttcagtattt taagtaatta tgccacggag tcggttgtta cgatgaaaac ggctattcca 3540
gtttcacgtt taagtaaggg gagcaatggc cgggaaattg ctgaaaaaat tgttttagct 3600
tcacgctatg cttcattaga tccttatcgg gcagtcacgc ataacaaagg aatcatgaat 3660
ggcattgaag ctgtagtttt agctacagga aatgatacac gcgctgttag cgcttcttgt 3720
catgcttttg cggtgaagga aggtcgctac caaggcttga ctagttggac gctggatggc 3780
gaacaactaa ttggtgaaat ttcagttccg cttgctttag ccacggttgg cggtgccaca 3840
aaagtcttac ctaaatctca agcagctgct gatttgttag cagtgacgga tgcaaaagaa 3900
ctaagtcgag tagtagcggc tgttggtttg gcacaaaatt tagcggcgtt acgggcctta 3960
gtctctgaag gaattcaaaa aggacacatg gctctacaag cacgttcttt agcgatgacg 4020
gtcggagcta ctggtaaaga agttgaggca gtcgctcaac aattaaaacg tcaaaaaacg 4080
atgaaccaag accgagccat ggctatttta aatgatttaa gaaaacaata aaggaggtaa 4140
aaaaacatga caattgggat tgataaaatt agtttttttg tgcccccttta ttatattgat 4200
atgacggcac tggctgaagc cagaaatgta gaccctggaa aatttcatat tggtattggg 4260
caagaccaaa tggcggtgaa cccaatcagc caagatattg tgacatttgc agccaatgcc 4320
gcagaagcga tcttgaccaa agaagataaa gaggccattg atatggtgat tgtcgggact 4380
gagtccagta tcgatgagtc aaaagcggcc gcagttgtct tacatcgttt aatggggatt 4440
caaccctttcg ctcgctcttt cgaaatcaag gaagcttgtt acggagcaac agcaggctta 4500
cagttagcta agaatcacgt agccttacat ccagataaaa aagtcttggt cgtagcggca 4560
gatattgcaa aatatggctt aaattctggc ggtgagccta cacaaggagc tggggcggtt 4620
gcaatgttag ttgctagtga accgcgcatt ttggctttaa aagaggataa tgtgatgctg 4680
acgcaagata tctatgactt ttggcgtcca acaggccacc cgtatcctat ggtcgatggt 4740
cctttgtcaa acgaaaccta catccaatct tttgcccaag tctgggatga acataaaaaa 4800
cgaaccggtc ttgattttgc agattatgat gctttagcgt tccatattcc ttacacaaaa 4860
atgggcaaaa aagccttatt agcaaaaatc tccgaccaaa ctgaagcaga acaggaacga 4920
attttagccc gttatgaaga aagtatcgtc tatagtcgtc gcgtaggaaa cttgtatacg 4980
ggttcacttt atctgggact catttccctt ttagaaaatg caacgacttt aaccgcaggc 5040
aatcaaattg gtttattcag ttatggttct ggtgctgtcg ctgaattttt cactggtgaa 5100
ttagtagctg gttatcaaaa tcatttacaa aaagaaactc atttagcact gctggataat 5160
cggacagaac tttctatcgc tgaatatgaa gccatgtttg cagaaacttt agacacagac 5220
attgatcaaa cgttagaaga tgaattaaaa tatagtattt ctgctattaa taataccgtt 5280
cgttcttatc gaaactaaag atctgcagct ggtaccatat gggaattcga agcttgggcc 5340
cgaacaaaaa ctcatctcag aagaggatct gaatagcgcc gtcgaccatc atcatcatca 5400
tcattgagtt taaacggtct ccagcttggc tgttttggcg gatgagagaa gattttcagc 5460

-continued

```
ctgatacaga ttaaatcaga acgcagaagc ggtctgataa aacagaattt gcctggcggc   5520
agtagcgcgg tggtcccacc tgaccccatg ccgaactcag aagtgaaacg ccgtagcgcc   5580
gatggtagtg tggggtctcc ccatgcgaga gtagggaact gccaggcatc aaataaaacg   5640
aaaggctcag tcgaaagact gggcctttct agagcggccg ccaccgcggt ggagctccaa   5700
ttcgccctat agtgagtcgt attacgcgcg ctcactggcc gtcgttttac aacgtcgtga   5760
ctgggaaaac cctggcgtta cccaacttaa tcgccttgca gcacatcccc ctttcgccag   5820
ctggcgtaat agcgaagagg cccgcaccga tcgcccttcc caacagttgc gcagcctgaa   5880
tggcgaatgg aaattgtaag cgttaatatt ttgttaaaat tcgcgttaaa tttttgttaa   5940
atcagctcat tttttaacca ataggccgac tgcgatgagt ggcagggcgg ggcgtaattt   6000
ttttaaggca gttattggtg cccttaaacg cctggtgcta cgcctgaata agtgataata   6060
agcggatgaa tggcagaaat tcgaaagcaa attcgacccg gtcgtcggtt cagggcaggg   6120
tcgttaaata gccgcttatg tctattgctg gtttaccggt ttattgacta ccggaagcag   6180
tgtgaccgtg tgcttctcaa atgcctgagg ccagtttgct caggctctcc ccgtggaggt   6240
aataattgac gatatgatca tttattctgc ctcccagagc ctgataaaaa cggtgaatcc   6300
gttagcgagg tgccgccggc ttccattcag gtcgaggtgg cccggctcca tgcaccgcga   6360
cgcaacgcgg ggaggcagac aaggtatagg gcggcgaggc ggctacagcc gatagtctgg   6420
aacagcgcac ttacgggttg ctgcgcaacc caagtgctac cggcgcggca gcgtgacccg   6480
tgtcggcggc tccaacggct cgccatcgtc cagaaaacac ggctcatcgg gcatcggcag   6540
gcgctgctgc ccgcgccgtt cccattcctc cgtttcggtc aaggctggca ggtctggttc   6600
catgcccgga atgccgggct ggctgggcgg ctcctcgccg gggccggtcg gtagttgctg   6660
ctcgcccgga tacagggtcg ggatgcggcg caggtcgcca tgccccaaca gcgattcgtc   6720
ctggtcgtcg tgatcaacca ccacggcggc actgaacacc gacaggcgca actggtcgcg   6780
gggctggccc cacgccacgc ggtcattgac cacgtaggcc gacacggtgc cggggccgtt   6840
gagcttcacg acggagatcc agcgctcggc caccaagtcc ttgactgcgt attggaccgt   6900
ccgcaaagaa cgtccgatga gcttggaaag tgtcttctgg ctgaccacca cggcgttctg   6960
gtggcccatc tgcgccacga ggtgatgcag cagcattgcc gccgtgggtt tcctcgcaat   7020
aagcccggcc cacgcctcat gcgctttgcg ttccgtttgc acccagtgac cgggcttgtt   7080
cttggcttga atgccgattt ctctggactg cgtggccatg cttatctcca tgcggtaggg   7140
tgccgcacgg ttgcggcacc atgcgcaatc agctgcaact tttcggcagc gcgacaacaa   7200
ttatgcgttg cgtaaaagtg gcagtcaatt acagattttc tttaacctac gcaatgagct   7260
attgcggggg gtgccgcaat gagctgttgc gtaccccccct tttttaagtt gttgattttt   7320
aagtctttcg catttcgccc tatatctagt tctttggtgc ccaaagaagg gcacccctgc   7380
ggggttcccc cacgccttcg gcgcggctcc ccctccggca aaaagtggcc cctccggggc   7440
ttgttgatcg actgcgcggc cttcggcctt gcccaaggtg gcgctgcccc cttggaaccc   7500
ccgcactcgc cgccgtgagg ctcggggggc aggcgggcgg gcttcgcctt cgactgcccc   7560
cactcgcata ggcttgggtc gttccaggcg cgtcaaggcc aagccgctgc gcggtcgctg   7620
cgcgagcctt gacccgcctt ccacttggtg tccaaccggc aagcgaagcg cgcaggccgc   7680
aggccggagg cttttcccca gagaaaatta aaaaaattga tggggcaagg ccgcaggccg   7740
cgcagttgga gccggtgggt atgtggtcga aggctgggta gccggtgggc aatccctgtg   7800
gtcaagctcg tgggcaggcg cagcctgtcc atcagcttgt ccagcagggt tgtccacggg   7860
```

ccgagcgaag cgagccagcc ggtggccgct cgcggccatc gtccacatat ccacgggctg 7920
gcaagggagc gcagcgaccg cgcagggcga agcccggaga gcaagcccgt agggctggca 7980
aatattctga aatgagctgt tgacaattaa tcatcgaact agttaactag tacgcaagtt 8040
cacgtaaaaa gggtatcgac atggtatcct gttctgcgcc gggtaagatt tacctgttcg 8100
gtgaacacgc cgtagtttat ggcgaaactg caattgcgtg tgcggtggaa ctgcgtaccc 8160
gtgttcgcgc ggaactcaat gactctatca ctattcagag ccagatcggc cgcaccggtc 8220
tggatttcga aaagcaccct tatgtgtctg cggtaattga gaaaatgcgc aaatctattc 8280
ctattaacgg tgttttcttg accgtcgatt ccgacatccc ggtgggctcc ggtctgggta 8340
gcagcgcagc cgttactatc gcgtctattg gtgcgctgaa cgagctgttc ggctttggcc 8400
tcagcctgca agaaatcgct aaactgggcc acgaaatcga aattaaagta cagggtgccg 8460
cgtccccaac cgatacgtat gtttctacct tcggcggcgt ggttaccatc ccggaacgtc 8520
gcaaactgaa aactccggac tgcggcattg tgattggcga taccggcgtt ttctcctcca 8580
ccaaagagtt agtagctaac gtacgtcagc tgcgcgaaag ctacccggat ttgatcgaac 8640
cgctgatgac ctctattggc aaaatctctc gtatcggcga acaactggtt ctgtctggcg 8700
actacgcatc catcggccgc ctgatgaacg tcaaccaggg tctcctggac gccctgggcg 8760
ttaacatctt agaactgagc cagctgatct attccgctcg tgcggcaggt gcgtttggcg 8820
ctaaaatcac gggcgctggc ggcggtggct gtatggttgc gctgaccgct ccggaaaaat 8880
gcaaccaagt ggcagaagcg gtagcaggcg ctggcggtaa agtgactatc actaaaccga 8940
ccgagcaagg tctgaaagta gattaataca aataaaaaag gcacgtcaga tgacgtgcct 9000
tttttcttgg ccgcagccgc cgtaggcggt cacgactttg cgaagcaaag tctagtgagt 9060
atactcaagc attgagtggc ccgccggagg caccgccttg cgctgccccc gtcgagccgg 9120
ttggacacca aaagggaggg gcaggcatgg cggcatacgc gatcatgcga tgcaagaagc 9180
tggcgaaaat gggcaacgtg gcggccagtc tcaagcacgc ctaccgcgag cgcgagacgc 9240
ccaacgctga cgccagcagg acgccagaga acgagcactg ggcggccagc agcaccgatg 9300
aagcgatggg ccgactgcgc gagttgctgc cagagaagcg gcgcaaggac gctgtgttgg 9360
cggtcgagta cgtcatgacg gccagcccgg aatggtggaa gtcggccagc caagaacagc 9420
aggcggcgtt cttcgagaag gcgcacaagt ggctggcgga caagtacggg gcggatcgca 9480
tcgtgacggc cagcatccac cgtgacgaaa ccagcccgca catgaccgcg ttcgtggtgc 9540
cgctgacgca ggacggcagg ctgtcggcca aggagttcat cggcaacaaa gcgcagatga 9600
cccgcgacca gaccacgttt gcggccgctg tggccgatct agggctgcaa cggggcatcg 9660
agggcagcaa ggcacgtcac acgcgcattc aggcgttcta cgaggccctg gagcggccac 9720
cagtgggcca cgtcaccatc agcccgcaag cggtcgagcc acgcgcctat gcaccgcagg 9780
gattggccga aaagctggga atctcaaagc gcgttgagac gccggaagcc gtggccgacc 9840
ggctgacaaa agcggttcgg caggggtatg agcctgccct acaggccgcc gcaggagcgc 9900
gtgagatgcg caagaaggcc gatcaagccc aagagacggc ccgag 9945

<210> SEQ ID NO 184
<211> LENGTH: 35
<212> TYPE: DNA
<213> ORGANISM: Artificial Sequence
<220> FEATURE:
<223> OTHER INFORMATION: Synthetic Construct

<400> SEQUENCE: 184
ttttgcggcc gcaattaacc ctcactaaag ggcgg 35

<210> SEQ ID NO 185
<211> LENGTH: 103
<212> TYPE: DNA
<213> ORGANISM: Artificial Sequence
<220> FEATURE:
<223> OTHER INFORMATION: Synthetic Construct

<400> SEQUENCE: 185
gatcgatatc cctgcaggaa attgttatcc gctcacaatt ccacacatta tacgagccgg 60
atgattaatt gtcaacagct aatacgactc actatagggc tcg 103

<210> SEQ ID NO 186
<211> LENGTH: 8983
<212> TYPE: DNA
<213> ORGANISM: Artificial Sequence
<220> FEATURE:
<223> OTHER INFORMATION: Synthetic Construct

<400> SEQUENCE: 186
caagaaaaat gccccgctta cgcagggcat ccatttatta ctcaaccgta accgattttg 60
ccaggttacg cggctggtca acgtcggtgc ctttgatcag cgcgacatgg taagccagca 120
gctgcagcgg aacggtgtag aagatcggtg caatcacctc ttccacatgc ggcatctcga 180
tgatgtgcat gttatcgcta cttacaaaac ccgcatcctg atcggcgaag acatacaact 240
gaccgccacg cgcgcgaact tcttcaatgt tggatttcag tttttccagc aattcgttgt 300
tcggtgcaac aacaataacc ggcatatcgg catcaattag cgccagcgga ccgtgtttca 360
gttcgccagc agcgtaggct tcagcgtgaa tgtaagagat ctctttcaac ttcaatgcgc 420
cttccagcgc gattgggtac tgatcgccac ggcccaggaa cagcgcgtga tgtttgtcag 480
agaaatcttc tgccagcgct tcaatgcgtt tgtcctgaga cagcatctgc tcaatacggc 540
tcggcagcgc ctgcagacca tgcacgatgt catgttcaat ggaggcatcc agacctttca 600
ggcgagacag cttcgccacc agcatcaaca gcacagttaa ctgagtggtg aatgctttag 660
tggatgccac gccgatttct gtacccgcgt tggtcattag cgccagatcg gattcgcgca 720
ccagagaaga acccggaacg ttacagattg ccagtgaacc aaggtaaccc agctctttcg 780
acagacgcag gccagccagg gtatccgcgg tttcgccaga ctgtgacacg atcgcccttc 840
ccaacagttg cgcagcctat acgtacggca gtttaaggtt tacacctata aaagagagag 900
ccgttatcgt ctgtttgtgg atgtacagag tgatattatt gacacgccgg ggcgacggat 960
ggtgatcccc ctggccagtg cacgtctgct gtcagataaa gtctcccgtg aactttaccc 1020
ggtggtgcat atcggggatg aaagctggcg catgatgacc accgatatgg ccagtgtgcc 1080
ggtctccgtt atcggggaag aagtggctga tctcagccac cgcgaaaatg acatcaaaaa 1140
cgccattaac ctgatgttct ggggaatata aatgtcaggc atgagattat caaaaaggat 1200
cttcacctag atccttttca cgtagaaagc cagtccgcag aaacggtgct gaccccggat 1260
gaatgtcagc tactgggcta tctggacaag ggaaaacgca agcgcaaaga gaaagcaggt 1320
agcttgcagt gggcttacat ggcgatagct agactgggcg gttttatgga cagcaagcga 1380
accggaattg ccagctgggg cgccctctgg taaggttggg aagccctgca aagtaaactg 1440
gatggctttc tcgccgccaa ggatctgatg gcgcagggga tcaagctctg atcaagagac 1500
aggatgagga tcgtttcgca tgattgaaca agatggattg cacgcaggtt ctccggccgc 1560
ttgggtggag aggctattcg gctatgactg ggcacaacag acaatcggct gctctgatgc 1620
cgccgtgttc cggctgtcag cgcaggggcg cccggttctt tttgtcaaga ccgacctgtc 1680
cggtgccctg aatgaactgc aagacgaggc agcgcggcta tcgtggctgg ccacgacggg 1740
cgttccttgc gcagctgtgc tcgacgttgt cactgaagcg ggaagggact ggctgctatt 1800
gggcgaagtg ccggggcagg atctcctgtc atctcacctt gctcctgccg agaaagtatc 1860
catcatggct gatgcaatgc ggcggctgca tacgcttgat ccggctacct gcccattcga 1920
ccaccaagcg aaacatcgca tcgagcgagc acgtactcgg atggaagccg gtcttgtcga 1980
tcaggatgat ctggacgaag agcatcaggg gctcgcgcca gccgaactgt tcgccaggct 2040
caaggcgagc atgcccgacg gcgaggatct cgtcgtgacc catggcgatg cctgcttgcc 2100
gaatatcatg gtggaaaatg gccgcttttc tggattcatc gactgtggcc ggctgggtgt 2160
ggcggaccgc tatcaggaca tagcgttggc tacccgtgat attgctgaag agcttggcgg 2220
cgaatgggct gaccgcttcc tcgtgcttta cggtatcgcc gctcccgatt cgcagcgcat 2280
cgccttctat cgccttcttg acgagttctt ctgaattatt aacgcttaca atttcctgat 2340
gcggtatttt ctccttacgc atctgtgcgg tatttcacac cgcatacagg tggcactttt 2400
cggggaaatg tgcgcggaac ccctatttgt ttatttttct aaatacattc aaatatgtat 2460
ccgctcatga gacaataacc ctgataaatg cttcaataat agcacgtgag gagggccacc 2520
atggccaagt tgaccagtgc cgttccggtg ctcaccgcgc gcgacgtcgc cggagcggtc 2580
gagttctgga ccgaccggct cgggttctcc cctagtaacg gccgccagtg tgctggaatt 2640
caggcagttc aacctgttga tagtacgtac taagctctca tgtttcacgt actaagctct 2700
catgtttaac gtactaagct ctcatgttta acgaactaaa ccctcatggc taacgtacta 2760
agctctcatg gctaacgtac taagctctca tgtttcacgt actaagctct catgtttgaa 2820
caataaaatt aatataaatc agcaacttaa atagcctcta aggttttaag ttttataaga 2880
aaaaaaagaa tatataaggc ttttaaagct tttaaggttt aacggttgtg gacaacaagc 2940
cagggatgta acgcactgag aagcccttag agcctctcaa agcaattttc agtgacacag 3000
gaacacttaa cggctgacag cctgaattct gcagatatct gtttttccac tcttcgttca 3060
ctttcgccag gtagctggtg aagacgaagg aagtcccgga gccatctgcg cggcgtacta 3120
cagcaatgtt ttgtgaaggc agtttcagac ccggattcag tttggcgatg gcttcatcat 3180
cccacttctt gattttgccc aggtagatgt cgccgagggt tttaccatcc agcaccagtt 3240
cgccagactt cagccctgga atgttaaccg ccagcaccac gccgccaatc acggtcggga 3300
actggaacag accttcctga gccagttttt cgtcagacag cggcgcgtca gaggcaccaa 3360
aatcaacggt attagcgata atctgtttta cgccaccgga agaaccgata ccctggtagt 3420
taactttatt accggtttct ttctggtaag tgtcagccca tttggcatac accggcgcag 3480
ggaaggttgc acctgcacct gtcaggcttg cttctgcaaa cacagagaaa gcactcatcg 3540
ataaggtcgc ggcgacaaca gttgcgacgg tggtacgcat aactttcata atgtctcctg 3600
ggaggattca taaagcattg tttgttggct acgagaagca aaataggaca aacaggtgac 3660
agttatatgt aaggaatatg acagttttat gacagagaga taaagtcttc agtctgattt 3720
aaataagcgt tgatattcag tcaattacaa acattaataa cgaagagatg acagaaaaat 3780
tttcattctg tgacagagaa aaagtagccg aagatgacgg tttgtcacat ggagttggca 3840
ggatgtttga ttaaaagcgg ccgcgaagtt cctattctct agaaagtata ggaacttcat 3900
tctaccgggt aggggaggcg cttttcccaa ggcagtctgg agcatgcgct ttagcagccc 3960
cgctgggcac ttggcgctac acaagtggcc tctggcctcg cacacattcc acatccaccg 4020

-continued

```
gtaggcgcca accggctccg ttctttggtg gccccttcgc gccaccttcc actcctcccc   4080
tagtcaggaa gttccccccc gccccgcagc tcgcgtcgtg caggacgtga caaatggaag   4140
tagcacgtct cactagtctc gtgcagatgg acagcaccgc tgagcaatgg aagcgggtag   4200
gcctttgggg cagcggccaa tagcagcttt gctccttcgc tttctgggct cagaggctgg   4260
gaaggggtgg gtccgggggc gggctcaggg gcgggctcag gggcggggcg ggcgcccgaa   4320
ggtcctccgg aggcccggca ttctgcacgc ttcaaaagcg cacgtctgcc gcgctgttct   4380
cctcttcctc atctccgggc ctttcgacct gcagcagcac gtgttgacaa ttaatcatcg   4440
gcatagtata tcggcatagt ataatacgac aaggtgagga actaaaccat ggagaaaaaa   4500
atcactggat ataccaccgt tgatatatcc caatggcatc gtaaagaaca ttttgaggca   4560
tttcagtcag ttgctcaatg tacctataac cagaccgttc agctggatat tacggccttt   4620
ttaaagaccg taaagaaaaa taagcacaag ttttatccgg cctttattca cattcttgcc   4680
cgcctgatga atgctcatcc ggaattccgt atggcaatga aagacggtga gctggtgata   4740
tgggatagtg ttcacccttg ttacaccgtt ttccatgagc aaactgaaac gttttcatcg   4800
ctctggagtg aataccacga cgatttccgg cagtttctac acatatattc gcaagatgtg   4860
gcgtgttacg gtgaaaacct ggcctatttc cctaaagggt ttattgagaa tatgtttttc   4920
gtctcagcca atccctgggt gagtttcacc agttttgatt taaacgtggc caatatggac   4980
aacttcttcg cccccgtttt caccatgggc aaatattata cgcaaggcga caaggtgctg   5040
atgccgctgg cgattcaggt tcatcatgcc gtttgtgatg gcttccatgt cggcagaatg   5100
cttaatgaat tacaacagta ctgcgatgag tggcagggcg gggcgtaagc gggactctgg   5160
ggttcgaata aagaccgacc aagcgacgtc tgagagctcc ctggcgaatt cggtaccaat   5220
aaaagagctt tattttcatg atctgtgtgt tggtttttgt gtgcggcgcg gaagttccta   5280
ttctctagaa agtataggaa cttcctcgag ccctatagtg agtcgtatta gctgttgaca   5340
attaatcatc cggctcgtat aatgtgtgga attgtgagcg gataacaatt tcctgcaggg   5400
atcctgcacc cttaaggagg aaaaaaacat gtcagagttg agagccttca gtgccccagg   5460
gaaagcgtta ctagctggtg gatatttagt tttagataca aaatatgaag catttgtagt   5520
cggattatcg gcaagaatgc atgctgtagc ccatccttac ggttcattgc aagggtctga   5580
taagtttgaa gtgcgtgtga aaagtaaaca atttaaagat ggggagtggc tgtaccatat   5640
aagtcctaaa agtggcttca ttcctgtttc gataggcgga tctaagaacc ctttcattga   5700
aaaagttatc gctaacgtat ttagctactt taaacctaac atggacgact actgcaatag   5760
aaacttgttc gttattgata ttttctctga tgatgcctac cattctcagg aggatagcgt   5820
taccgaacat cgtggcaaca gaagattgag ttttcattcg cacagaattg aagaagttcc   5880
caaaacaggg ctgggctcct cggcaggttt agtcacagtt ttaactacag ctttggcctc   5940
ctttttgta tcggacctgg aaaataatgt agacaaatat agagaagtta ttcataattt   6000
agcacaagtt gctcattgtc aagctcaggg taaaattgga agcgggtttg atgtagcggc   6060
ggcagcatat ggatctatca gatatagaag attcccaccc gcattaatct ctaatttgcc   6120
agatattgga agtgctactt acggcagtaa actggcgcat ttggttgatg aagaagactg   6180
gaatattacg attaaaagta accatttacc ttcgggatta actttatgga tgggcgatat   6240
taagaatggt tcagaaacag taaaactggt ccagaaggta aaaaattggt atgattcgca   6300
tatgccagaa agcttgaaaa tatatacaga actcgatcat gcaaattcta gatttatgga   6360
tggactatct aaactagatc gcttacacga gactcatgac gattacagcg atcagatatt   6420
```

```
tgagtctctt gagaggaatg actgtacctg tcaaaagtat cctgaaatca cagaagttag   6480
agatgcagtt gccacaatta gacgttcctt tagaaaaata actaaagaat ctggtgccga   6540
tatcgaacct cccgtacaaa ctagcttatt ggatgattgc cagaccttaa aaggagttct   6600
tacttgctta atacctggtg ctggtggtta tgacgccatt gcagtgatta ctaagcaaga   6660
tgttgatctt agggctcaaa ccgctaatga caaaagattt tctaaggttc aatggctgga   6720
tgtaactcag gctgactggg gtgttaggaa agaaaaagat ccggaaactt atcttgataa   6780
ataacttaag gtagctgcat gcagaattcg cccttaagga ggaaaaaaaa atgaccgttt   6840
acacagcatc cgttaccgca cccgtcaaca tcgcaaccct taagtattgg gggaaaaggg   6900
acacgaagtt gaatctgccc accaattcgt ccatatcagt gactttatcg caagatgacc   6960
tcagaacgtt gacctctgcg gctactgcac ctgagtttga acgcgacact ttgtggttaa   7020
atggagaacc acacagcatc gacaatgaaa gaactcaaaa ttgtctgcgc gacctacgcc   7080
aattaagaaa ggaaatggaa tcgaaggacg cctcattgcc cacattatct caatggaaac   7140
tccacattgt ctccgaaaat aactttccta cagcagctgg tttagcttcc tccgctgctg   7200
gctttgctgc attggtctct gcaattgcta agttatacca attaccacag tcaacttcag   7260
aaatatctag aatagcaaga aaggggtctg gttcagcttg tagatcgttg tttggcggat   7320
acgtggcctg ggaaatggga aaagctgaag atggtcatga ttccatggca gtacaaatcg   7380
cagacagctc tgactggcct cagatgaaag cttgtgtcct agttgtcagc gatattaaaa   7440
aggatgtgag ttccactcag ggtatgcaat tgaccgtggc aacctccgaa ctatttaaag   7500
aaagaattga acatgtcgta ccaaagagat ttgaagtcat gcgtaaagcc attgttgaaa   7560
aagatttcgc cacctttgca aaggaaacaa tgatggattc caactctttc catgccacat   7620
gtttggactc tttccctcca atattctaca tgaatgacac ttccaagcgt atcatcagtt   7680
ggtgccacac cattaatcag ttttacggag aaacaatcgt tgcatacacg tttgatgcag   7740
gtccaaatgc tgtgttgtac tacttagctg aaaatgagtc gaaactcttt gcatttatct   7800
ataaattgtt tggctctgtt cctggatggg acaagaaatt tactactgag cagcttgagg   7860
ctttcaacca tcaatttgaa tcatctaact ttactgcacg tgaattggat cttgagttgc   7920
aaaaggatgt tgccagagtg attttaactc aagtcggttc aggcccacaa gaaacaaacg   7980
aatctttgat tgacgcaaag actggtctac caaaggaata agatcaattc gctgcatcgc   8040
ccttaggagg taaaaaaaaa tgactgccga caacaatagt atgccccatg gtgcagtatc   8100
tagttacgcc aaattagtgc aaaaccaaac acctgaagac attttggaag agtttcctga   8160
aattattcca ttacaacaaa gacctaatac ccgatctagt gagacgtcaa atgacgaaag   8220
cggagaaaca tgtttttctg gtcatgatga ggagcaaatt aagttaatga atgaaaattg   8280
tattgttttg gattgggacg ataatgctat tggtgccggt accaagaaag tttgtcattt   8340
aatggaaaat attgaaaagg gtttactaca tcgtgcattc tccgtcttta ttttcaatga   8400
acaaggtgaa ttacttttac aacaaagagc cactgaaaaa ataactttcc ctgatctttg   8460
gactaacaca tgctgctctc atccactatg tattgatgac gaattaggtt tgaagggtaa   8520
gctagacgat aagattaagg gcgctattac tgcggcggtg agaaaactag atcatgaatt   8580
aggtattcca gaagatgaaa ctaagacaag ggtaagttt cactttttaa acagaatcca   8640
ttacatggca ccaagcaatg aaccatgggg tgaacatgaa attgattaca tcctatttta   8700
taagatcaac gctaaagaaa acttgactgt caacccaaac gtcaatgaag ttagagactt   8760
caaatgggtt tcaccaaatg atttgaaaac tatgtttgct gacccaagtt acaagtttac   8820
```

gccttggttt aagattattt gcgagaatta cttattcaac tggtgggagc aattagatga 8880
cctttctgaa gtggaaaatg acaggcaaat tcatagaatg ctataacaac gcgtctacaa 8940
ataaaaaagg cacgtcagat gacgtgcctt ttttcttggg gcc 8983

<210> SEQ ID NO 187
<211> LENGTH: 40
<212> TYPE: DNA
<213> ORGANISM: Artificial Sequence
<220> FEATURE:
<223> OTHER INFORMATION: Synthetic Construct

<400> SEQUENCE: 187
aatcgtaggc cggataaggc gtttacgccg catccggcaa 40

<210> SEQ ID NO 188
<211> LENGTH: 107
<212> TYPE: DNA
<213> ORGANISM: Artificial Sequence
<220> FEATURE:
<223> OTHER INFORMATION: Synthetic Construct

<400> SEQUENCE: 188
agattgctgc gaaatcgtag gccggataag gcgtttacgc cgcatccggc aaaaatcctt 60
aaatataaga gcaaacctgc aattaaccct cactaaaggg cggccgc 107

<210> SEQ ID NO 189
<211> LENGTH: 182
<212> TYPE: DNA
<213> ORGANISM: Artificial Sequence
<220> FEATURE:
<223> OTHER INFORMATION: Synthetic Construct

<400> SEQUENCE: 189
agcgtgaagt gcaccaggac ggcgctattg ctctgtacag attcagacat gtttttacct 60
cctttgcagt gcgtcctgct gatgtgctca gtatcaccgc cagtggtatt tatgtcaaca 120
ccgccagaga taatttatca ccgcagatgg ttatcttaat acgactcact atagggctcg 180
ag 182

<210> SEQ ID NO 190
<211> LENGTH: 21
<212> TYPE: DNA
<213> ORGANISM: Artificial Sequence
<220> FEATURE:
<223> OTHER INFORMATION: Synthetic Construct

<400> SEQUENCE: 190
acgcatctta tccggcctac a 21

<210> SEQ ID NO 191
<211> LENGTH: 21
<212> TYPE: DNA
<213> ORGANISM: Artificial Sequence
<220> FEATURE:
<223> OTHER INFORMATION: Synthetic Construct

<400> SEQUENCE: 191
accgttgttg cgggtagact c 21

<210> SEQ ID NO 192
<211> LENGTH: 6578
<212> TYPE: DNA
<213> ORGANISM: Artificial Sequence
<220> FEATURE:
<223> OTHER INFORMATION: Synthetic Construct

<400> SEQUENCE: 192

```
ttcttgaaga cgaaagggcc tcgtgatacg cctattttta taggttaatg tcatgataat     60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtat gagtattcaa catttccgtg tcgcccttat    240
tccctttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttatcat atatacttta gattgattta aaacttcatt tttaatttaa aaggatctag   1140
gtgaagatcc tttttgataa tctcatgacc aaaatccctt aacgtgagtt ttcgttccac   1200
tgagcgtcag accccgtaga aaagatcaaa ggatcttctt gagatccttt ttttctgcgc   1260
gtaatctgct gcttgcaaac aaaaaaacca ccgctaccag cggtggtttg tttgccggat   1320
caagagctac caactctttt tccgaaggta actggcttca gcagagcgca gataccaaat   1380
actgtccttc tagtgtagcc gtagttaggc caccacttca agaactctgt agcaccgcct   1440
acatacctcg ctctgctaat cctgttacca gtggctgctg ccagtggcga taagtcgtgt   1500
cttaccgggt tggactcaag acgatagtta ccggataagg cgcagcggtc gggctgaacg   1560
gggggttcgt gcacacagcc cagcttggag cgaacgacct acaccgaact gagataccta   1620
cagcgtgagc tatgagaaag cgccacgctt cccgaaggga gaaaggcgga caggtatccg   1680
gtaagcggca gggtcggaac aggagagcgc acgagggagc ttccaggggg aaacgcctgg   1740
tatctttata gtcctgtcgg gtttcgccac ctctgacttg agcgtcgatt tttgtgatgc   1800
tcgtcagggg ggcggagcct atggaaaaac gccagcaacg cggccttttt acggttcctg   1860
gccttttgct ggccttttgc tcacatgttc tttcctgcgt tatcccctga ttctgtggat   1920
aaccgtatta ccgcctttga gtgagctgat accgctcgcc gcagccgaac gaccgagcgc   1980
agcgagtcag tgagcgagga agcggaagag cgcctgatgc ggtattttct ccttacgcat   2040
ctgtgcggta tttcacaccg catatatggt gcactctcag tacaatctgc tctgatgccg   2100
catagttaag ccagtataca ctccgctatc gctacgtgac tgggtcatgg ctgcgccccg   2160
acacccgcca acacccgctg acgcgccctg acgggcttgt ctgctcccgg catccgctta   2220
cagacaagct gtgaccgtct ccgggagctg catgtgtcag aggttttcac cgtcatcacc   2280
```

gaaacgcgcg aggcagctgc ggtaaagctc atcagcgtgg tcgtgaagcg attcacagat 2340
gtctgcctgt tcatccgcgt ccagctcgtt gagtttctcc agaagcgtta atgtctggct 2400
tctgataaag cgggccatgt taagggcggt tttttcctgt ttggtcactg atgcctccgt 2460
gtaaggggga tttctgttca tgggggtaat gataccgatg aaacgagaga ggatgctcac 2520
gatacgggtt actgatgatg aacatgcccg gttactggaa cgttgtgagg gtaaacaact 2580
ggcggtatgg atgcggcggg accagagaaa aatcactcag ggtcaatgcc agcgcttcgt 2640
taatacagat gtaggtgttc cacagggtag ccagcagcat cctgcgatgc agatccggaa 2700
cataatggtg cagggcgctg acttccgcgt ttccagactt tacgaaacac ggaaaccgaa 2760
gaccattcat gttgttgctc aggtcgcaga cgttttgcag cagcagtcgc ttcacgttcg 2820
ctcgcgtatc ggtgattcat tctgctaacc agtaaggcaa ccccgccagc ctagccgggt 2880
cctcaacgac aggagcacga tcatgcgcac ccgtggccag gacccaacgc tgcccgagat 2940
gcgccgcgtg cggctgctgg agatggcgga cgcgatggat atgttctgcc aagggttggt 3000
ttgcgcattc acagttctcc gcaagaattg attggctcca attcttggag tggtgaatcc 3060
gttagcgagg tgccgccggc ttccattcag gtcgaggtgg cccggctcca tgcaccgcga 3120
cgcaacgcgg ggaggcagac aaggtatagg gcggcgccta caatccatgc caacccgttc 3180
catgtgctcg ccgaggcggc ataaatcgcc gtgacgatca gcggtccagt gatcgaagtt 3240
aggctggtaa gagccgcgag cgatccttga agctgtccct gatggtcgtc atctacctgc 3300
ctggacagca tggcctgcaa cgcgggcatc ccgatgccgc cggaagcgag aagaatcata 3360
atggggaagg ccatccagcc tcgcgtcgcg aacgccagca agacgtagcc cagcgcgtcg 3420
gccgccatgc cggcgataat ggcctgcttc tcgccgaaac gtttggtggc gggaccagtg 3480
acgaaggctt gagcgagggc gtgcaagatt ccgaataccg caagcgacag gccgatcatc 3540
gtcgcgctcc agcgaaagcg gtcctcgccg aaaatgaccc agagcgctgc cggcacctgt 3600
cctacgagtt gcatgataaa gaagacagtc ataagtgcgg cgacgatagt catgccccgc 3660
gcccaccgga aggagctgac tgggttgaag gctctcaagg gcatcggtcg agatcccggt 3720
gcctaatgag tgagctaact tacattaatt gcgttgcgct cactgcccgc tttccagtcg 3780
ggaaacctgt cgtgccagct gcattaatga atcggccaac gcgcggggag aggcggtttg 3840
cgtattgggc gccagggtgg tttttctttt caccagtgag acgggcaaca gctgattgcc 3900
cttcaccgcc tggccctgag agagttgcag caagcggtcc acgctggttt gccccagcag 3960
gcgaaaatcc tgtttgatgg tggttaacgg cgggatataa catgagctgt cttcggtatc 4020
gtcgtatccc actaccgaga tatccgcacc aacgcgcagc ccggactcgg taatggcgcg 4080
cattgcgccc agcgccatct gatcgttggc aaccagcatc gcagtgggaa cgatgccctc 4140
attcagcatt tgcatggttt gttgaaaacc ggacatggca ctccagtcgc cttcccgttc 4200
cgctatcggc tgaatttgat tgcgagtgag atatttatgc cagccagcca gacgcagacg 4260
cgccgagaca gaacttaatg ggcccgctaa cagcgcgatt tgctggtgac ccaatgcgac 4320
cagatgctcc acgcccagtc gcgtaccgtc ttcatgggag aaaataatac tgttgatggg 4380
tgtctggtca gagacatcaa gaaataacgc cggaacatta gtgcaggcag cttccacagc 4440
aatggcatcc tggtcatcca gcggatagtt aatgatcagc ccactgacgc gttgcgcgag 4500
aagattgtgc accgccgctt tacaggcttc gacgccgctt cgttctacca tcgacaccac 4560
cacgctggca cccagttgat cggcgcgaga tttaatcgcc gcgacaattt gcgacggcgc 4620
gtgcagggcc agactggagg tggcaacgcc aatcagcaac gactgtttgc ccgccagttg 4680
ttgtgccacg cggttgggaa tgtaattcag ctccgccatc gccgcttcca ctttttcccg 4740
cgttttcgca gaaacgtggc tggcctggtt caccacgcgg gaaacggtct gataagagac 4800
accggcatac tctgcgacat cgtataacgt tactggtttc acattcacca ccctgaattg 4860
actctcttcc gggcgctatc atgccatacc gcgaaaggtt ttgcgccatt cgatggtgtc 4920
cgggatctcg acgctctccc ttatgcgact cctgcattag gaagcagccc agtagtaggt 4980
tgaggccgtt gagcaccgcc gccgcaagga atggtgcatg caaggagatg gcgcccaaca 5040
gtcccccggc cacggggcct gccaccatac ccacgccgaa acaagcgctc atgagcccga 5100
agtggcgagc ccgatcttcc ccatcggtga tgtcggcgat ataggcgcca gcaaccgcac 5160
ctgtggcgcc ggtgatgccg gccacgatgc gtccggcgta gaggatcgag atctcgatcc 5220
cgcgaaatta atacgactca ctatagggga attgtgagcg gataacaatt cccctctaga 5280
aataattttg tttaacttta agaaggagat ataccatggg ccatcatcat catcatcatc 5340
atcatcatca cagcagcggc catatcgaag gtcgtcatat gactgccgac aacaatagta 5400
tgccccatgg tgcagtatct agttacgcca aattagtgca aaaccaaaca cctgaagaca 5460
ttttggaaga gtttcctgaa attattccat tacaacaaag acctaatacc cgatctagtg 5520
agacgtcaaa tgacgaaagc ggagaaacat gtttttctgg tcatgatgag gagcaaatta 5580
agttaatgaa tgaaaattgt attgttttgg attgggacga taatgctatt ggtgccggta 5640
ccaagaaagt ttgtcattta atggaaaata ttgaaaaggg tttactacat cgtgcattct 5700
ccgtctttat tttcaatgaa caaggtgaat tacttttaca acaaagagcc actgaaaaaa 5760
taactttccc tgatctttgg actaacacat gctgctctca tccactatgt attgatgacg 5820
aattaggttt gaagggtaag ctagacgata agattaaggg cgctattact gcggcggtga 5880
gaaaactaga tcatgaatta ggtattccag aagatgaaac taagacaagg ggtaagtttc 5940
actttttaaa cagaatccat tacatggcac caagcaatga accatggggt gaacatgaaa 6000
ttgattacat cctattttat aagatcaacg ctaaagaaaa cttgactgtc aacccaaacg 6060
tcaatgaagt tagagacttc aaatgggttt caccaaatga tttgaaaact atgtttgctg 6120
acccaagtta caagtttacg ccttggttta agattatttg cgagaattac ttattcaact 6180
ggtgggagca attagatgac ctttctgaag tggaaaatga caggcaaatt catagaatgc 6240
tataacaacg cgtcggatcc ggctgctaac aaagcccgaa aggaagctga gttggctgct 6300
gccaccgctg agcaataact agcataaccc cttggggcct ctaaacgggt cttgaggggt 6360
tttttgctga aaggaggaac tatatccgga tatcccgcaa gaggcccggc agtaccggca 6420
taaccaagcc tatgcctaca gcatccaggg tgacggtgcc gaggatgacg atgagcgcat 6480
tgttagattt catacacggt gcctgactgc gttagcaatt taactgtgat aaactaccgc 6540
attaaagctt atcgatgata agctgtcaaa catgagaa 6578

<210> SEQ ID NO 193
<211> LENGTH: 323
<212> TYPE: DNA
<213> ORGANISM: Artificial Sequence
<220> FEATURE:
<223> OTHER INFORMATION: Synthetic Construct

<400> SEQUENCE: 193
agattgctgc gaaatcgtag gccggataag gcgtttacgc cgcatccggc aaaaatcctt 60
aaatataaga gcaaacctgc aattaaccct cactaaaggg cggccgcgaa gttcctattc 120
tctagaaagt ataggaactt cctcgagccc tatagtgagt cgtattaaga taaccatctg 180
cggtgataaa ttatctctgg cggtgttgac ataaatacca ctggcggtga tactgagcac 240
atcagcagga cgcactgcaa aggaggtaaa aacatgtctg aatctgtaca gagcaatagc 300
gccgtcctgg tgcacttcac gct 323

<210> SEQ ID NO 194
<211> LENGTH: 512
<212> TYPE: PRT
<213> ORGANISM: Artificial Sequence
<220> FEATURE:
<223> OTHER INFORMATION: Synthetic Construct

<400> SEQUENCE: 194

Met Ser Phe Asp Ile Ala Lys Tyr Pro Thr Leu Ala Leu Val Asp Ser
1 5 10 15

Thr Gln Glu Leu Arg Leu Leu Pro Lys Glu Ser Leu Pro Lys Leu Cys
20 25 30

Asp Glu Leu Arg Arg Tyr Leu Leu Asp Ser Val Ser Arg Ser Ser Gly
35 40 45

His Phe Ala Ser Gly Leu Gly Thr Val Glu Leu Thr Val Ala Leu His
50 55 60

Tyr Val Tyr Asn Thr Pro Phe Asp Gln Leu Ile Trp Asp Val Gly His
65 70 75 80

Gln Ala Tyr Pro His Lys Ile Leu Thr Gly Arg Arg Asp Lys Ile Gly
85 90 95

Thr Ile Arg Gln Lys Gly Gly Leu His Pro Phe Pro Trp Arg Gly Glu
100 105 110

Ser Glu Tyr Asp Val Leu Ser Val Gly His Ser Ser Thr Ser Ile Ser
115 120 125

Ala Gly Ile Gly Ile Ala Val Ala Ala Glu Lys Glu Gly Lys Asn Arg
130 135 140

Arg Thr Val Cys Val Ile Gly Asp Gly Ala Ile Thr Ala Gly Met Ala
145 150 155 160

Phe Glu Ala Met Asn His Ala Gly Asp Ile Arg Pro Asp Met Leu Val
165 170 175

Val Leu Asn Asp Asn Glu Met Ser Ile Ser Glu Asn Val Gly Ala Leu
180 185 190

Asn Asn His Leu Ala Gln Leu Leu Ser Gly Lys Leu Tyr Ser Ser Leu
195 200 205

Arg Glu Gly Gly Lys Lys Val Phe Ser Gly Val Pro Pro Ile Lys Glu
210 215 220

Leu Leu Lys Arg Thr Glu Glu His Ile Lys Gly Met Val Val Pro Gly
225 230 235 240

Thr Leu Phe Glu Glu Leu Gly Phe Asn Tyr Ile Gly Pro Val Asp Gly
245 250 255

His Asp Val Leu Gly Leu Ile Thr Thr Leu Lys Asn Met Arg Asp Leu
260 265 270

Lys Gly Pro Gln Phe Leu His Ile Met Thr Lys Lys Gly Arg Gly Tyr
275 280 285

Glu Pro Ala Glu Lys Asp Pro Ile Thr Phe His Ala Val Pro Lys Phe
290 295 300

Asp Pro Ser Ser Gly Cys Leu Pro Lys Ser Ser Gly Gly Leu Pro Ser
305 310 315 320

Tyr Ser Lys Ile Phe Gly Asp Trp Leu Cys Glu Thr Ala Ala Lys Asp
325 330 335

Asn Lys Leu Met Ala Ile Thr Pro Ala Met Arg Glu Gly Ser Gly Met
340 345 350

Val Glu Phe Ser Arg Lys Phe Pro Asp Arg Tyr Phe Asp Val Ala Ile
355 360 365

Ala Glu Gln His Ala Val Thr Phe Ala Ala Gly Leu Ala Ile Gly Gly
370 375 380

Tyr Lys Pro Ile Val Ala Ile Tyr Ser Thr Phe Leu Gln Arg Ala Tyr
385 390 395 400

Asp Gln Val Leu His Asp Val Ala Ile Gln Lys Leu Pro Val Leu Phe
405 410 415

Ala Ile Asp Arg Ala Gly Ile Val Gly Ala Asp Gly Gln Thr His Gln
420 425 430

Gly Ala Phe Asp Leu Ser Tyr Leu Arg Cys Ile Pro Glu Met Val Ile
435 440 445

Met Thr Pro Ser Asp Glu Asn Glu Cys Arg Gln Met Leu Tyr Thr Gly
450 455 460

Tyr His Tyr Asn Asp Gly Pro Ser Ala Val Arg Tyr Pro Arg Gly Asn
465 470 475 480

Ala Val Gly Val Glu Leu Thr Pro Leu Glu Lys Leu Pro Ile Gly Lys
485 490 495

Gly Ile Val Lys Arg Arg Gly Glu Lys Leu Ala Ile Leu Asn Phe Gly
500 505 510

<210> SEQ ID NO 195
<211> LENGTH: 471
<212> TYPE: PRT
<213> ORGANISM: Artificial Sequence
<220> FEATURE:
<223> OTHER INFORMATION: Synthetic Construct

<400> SEQUENCE: 195

Met Ser Glu Leu Leu Ser Arg Ile Gly Ser Pro Ser Asp Val Arg Ala
1 5 10 15

Leu Pro Glu Glu Ala Leu Pro Leu Leu Cys Gln Glu Leu Arg Glu Asp
20 25 30

Ile Ile Ser Ile Cys Gly Arg Val Gly Gly His Leu Gly Ala Ser Leu
35 40 45

Gly Ala Val Glu Leu Ile Val Ala Leu His Arg Val Phe His Ser Pro
50 55 60

Gln Asp Ala Leu Leu Phe Asp Val Gly His Gln Thr Tyr Ala His Lys
65 70 75 80

Leu Leu Thr Gly Arg Arg Asp Arg Met His Thr Leu Arg His Ala Gly
85 90 95

Gly Ile Ala Pro Phe Leu Asp Pro Arg Glu Ser Pro His Asp Ala Leu
100 105 110

Leu Ala Gly His Ser Cys Thr Ala Val Ser Ala Ala Leu Gly Val Leu
115 120 125

Glu Gly Arg Arg Gln Gln Gly His Arg Gly His Val Val Ala Val Leu
130 135 140

Gly Asp Gly Gly Leu Thr Gly Gly Leu Thr Phe Glu Gly Leu Asn Asn
145 150 155 160

Ala Gly Gly Ser Ser Leu Pro Leu Val Val Val Leu Asn Asp Asn Gln
165 170 175

Met Ser Ile Ser Ala Asn Val Gly Ala Ile Pro Ala Leu Leu Arg Thr
180 185 190

Arg Glu Ala Arg Asp Phe Phe Glu Gly Leu Gly Phe Thr Tyr Leu Gly

```
        195                 200                 205

Pro Val Asp Gly His Asp Leu Pro Ala Leu Ile Arg Ala Leu Arg Glu
    210                 215                 220

Ala Arg Ala Ser Ser Arg Pro Val Val Val His Ala Leu Thr Leu Lys
225                 230                 235                 240

Gly Lys Gly Phe Pro Pro Ala Glu Ala Asp Thr Gln Thr Arg Gly His
                245                 250                 255

Ala Met Gly Pro Tyr Glu Trp Arg Asp Gly Lys Leu Val Arg Ser Arg
            260                 265                 270

Gly Gly Gln Arg Thr Phe Ser Glu Ala Phe Ala Ala Val Leu Glu Asp
        275                 280                 285

Ala Met Ala Arg Asp Pro Arg Val Val Ala Val Thr Pro Ala Met Leu
    290                 295                 300

Glu Gly Ser Ala Leu Asn Ala Leu Lys Ala Arg Phe Pro Asp Arg Val
305                 310                 315                 320

His Asp Val Gly Ile Ala Glu Gln His Ala Val Thr Phe Ser Ala Gly
                325                 330                 335

Leu Ala Ser Ala Gly Ala Arg Pro Val Cys Cys Ile Tyr Ser Thr Phe
            340                 345                 350

Leu Gln Arg Ala Tyr Asp Gln Ile Ile His Asp Val Cys Leu Pro Gly
        355                 360                 365

Leu Pro Val Val Phe Ala Val Asp Arg Ala Gly Leu Val Gly Ala Asp
    370                 375                 380

Gly Ala Thr His Gln Gly Thr Tyr Asp Val Ala Ser Leu Arg Pro Leu
385                 390                 395                 400

Pro Asp Leu His Leu Trp Ser Pro Met Val Gly Glu Asp Leu Ala Pro
                405                 410                 415

Met Leu Asp Thr Ala Leu Ala Ala Pro His Ala Ser Val Ile Arg Phe
            420                 425                 430

Pro Arg Gly Thr Leu Pro Pro Leu Pro Glu Gly Leu Gly Ala Gly Glu
        435                 440                 445

Ala Pro Leu Arg Gly Ala Arg Trp Leu Leu Arg Ala Glu Gln Pro Arg
    450                 455                 460

Leu Thr Leu Val Thr Leu Gly
465                 470


<210> SEQ ID NO 196
<211> LENGTH: 479
<212> TYPE: PRT
<213> ORGANISM: Artificial Sequence
<220> FEATURE:
<223> OTHER INFORMATION: Synthetic Construct

<400> SEQUENCE: 196

Met Ala Lys Asn Ile Leu Asn His Ile Asp Ser Pro Glu Asp Leu Arg
 1               5                  10                  15

Lys Leu Asn Lys Lys Glu Leu Asp Leu Leu Ser Ile Glu Leu Arg Lys
            20                  25                  30

Phe Ile Ile Asp Ile Val Ala Thr Lys Glu Gly His Leu Gly Ala Ser
        35                  40                  45

Leu Gly Val Ile Glu Leu Thr Ile Ala Leu His Tyr Ile Phe Asn Thr
    50                  55                  60

Pro Glu Asp Leu Leu Val Trp Asp Val Gly His Gln Ala Tyr Gly His
65                  70                  75                  80

Lys Ile Leu Thr Gly Arg Arg Asp Ile Phe Glu Thr Asn Arg Gln Leu
                85                  90                  95
```

```
Asn Gly Leu Ser Gly Phe Pro Lys Arg Asp Glu Ser Glu Phe Asp Thr
            100                 105                 110

Phe Gly Val Gly His Ser Ser Thr Ser Ile Ser Ala Ala Leu Gly Met
        115                 120                 125

Ala Ile Ala Ser Asn Leu Lys Gly Glu Thr Glu Lys Gln His Ile Ala
    130                 135                 140

Val Ile Gly Asp Ala Ser Ile Ala Ser Gly Met Ala Phe Glu Gly Leu
145                 150                 155                 160

Asn His Ala Gly Val Thr Asn Ala Asn Leu Leu Val Ile Leu Asn Asp
                165                 170                 175

Asn Ala Ile Gly Ile Asp Pro Ser Val Gly Ala Leu Lys Glu Tyr Leu
            180                 185                 190

Thr Lys Ala Arg Val Gly Tyr Lys Pro Ala Ser Asp Asn Ile Ile Glu
        195                 200                 205

Ala Leu Asn Phe Lys Tyr Phe Gly Pro Val Asp Gly His Asp Leu Glu
    210                 215                 220

Gly Leu Leu Lys Thr Leu Lys Glu Met Lys Gln Ile Lys Gly Pro Lys
225                 230                 235                 240

Phe Leu His Val Ile Thr Lys Lys Gly Lys Gly Leu Lys Lys Ala Glu
                245                 250                 255

Glu Asp Gln Val Lys Tyr His Ala Pro Gly Lys Phe Glu Pro Asn Thr
            260                 265                 270

Gly Glu Leu Leu Lys Tyr Asp Thr Asp Gly Leu Pro Leu Lys Tyr Gln
        275                 280                 285

Asp Val Phe Gly Leu Thr Leu Val Glu Leu Ala Glu Lys Asn Glu Lys
    290                 295                 300

Ile Ile Gly Ile Thr Pro Ala Met Pro Thr Gly Ser Ser Leu Lys Tyr
305                 310                 315                 320

Met Met Lys Ala Phe Pro Glu Arg Ala Phe Asp Val Gly Ile Ala Glu
                325                 330                 335

Gln His Ala Val Thr Leu Ser Ala Gly Met Ala Thr Gln Gly Phe Thr
            340                 345                 350

Val Phe Cys Ala Ile Tyr Ser Thr Phe Leu Gln Arg Ala Tyr Asp Gln
        355                 360                 365

Leu Ile His Asp Val Ala Ile Gln Asn Leu Pro Val Val Phe Cys Leu
    370                 375                 380

Asp Arg Ala Gly Leu Val Gly Glu Asp Gly Ala Thr His His Gly Val
385                 390                 395                 400

Phe Asp Ile Ala Tyr Ala Arg Pro Ile Pro Asn Leu Met Ile Ala Ala
                405                 410                 415

Pro Arg Asn Glu Val Glu Leu Arg Asn Leu Leu Tyr Thr Ala Gln Leu
            420                 425                 430

Gly Leu Asp Ala Pro Met Ile Ile Arg Tyr Pro Arg Gly Arg Gly Val
        435                 440                 445

Leu Lys Glu Trp Lys Leu Pro Tyr Glu Lys Ala Glu Ile Gly Lys Ala
    450                 455                 460

Glu Cys Leu Lys Glu Gly Ser Glu Ile Ala Ile Leu Ser Leu Gly
465                 470                 475
```

<210> SEQ ID NO 197
<211> LENGTH: 482
<212> TYPE: PRT
<213> ORGANISM: Artificial Sequence
<220> FEATURE:
<223> OTHER INFORMATION: Synthetic Construct

<400> SEQUENCE: 197

```
Met Lys Ser Asp Leu Leu Ser Asn Ile Tyr Asn Pro Ala Asp Leu Arg
 1               5                  10                  15

Leu Leu Lys Glu Glu Gln Leu Thr Gln Val Ala Gln Glu Leu Arg Gln
            20                  25                  30

Phe Ile Ile Asp Val Val Ser Val Lys Glu Gly His Leu Gly Ala Ser
        35                  40                  45

Leu Gly Val Ile Glu Leu Thr Ile Ala Leu His Tyr Val Phe Asn Thr
    50                  55                  60

Pro Asp Asp Leu Leu Val Trp Asp Val Gly His Gln Ala Tyr Gly His
65                  70                  75                  80

Lys Ile Leu Thr Glu Arg Arg Glu Ile Phe His Thr Asn Arg Gln Ile
                85                  90                  95

Asp Gly Ile Ser Gly Phe Pro Lys Arg Thr Glu Ser Val Tyr Asp Thr
            100                 105                 110

Phe Gly Val Gly His Ser Ser Thr Ser Ile Ala Ala Leu Gly Met Ala
        115                 120                 125

Ile Ala Ser Lys Leu Lys Gly Asp Leu Asp Lys Gln His Ile Ala Val
    130                 135                 140

Ile Gly Asp Ala Ser Ile Ala Ser Gly Met Ala Phe Glu Gly Leu Asn
145                 150                 155                 160

His Ala Gly Val Thr Asp Ala Asn Ile Leu Val Ile Leu Asn Asp Asn
                165                 170                 175

Ala Ile Gly Ile Asp Pro Ser Val Gly Ala Leu Lys Lys Tyr Leu Thr
            180                 185                 190

Ala Val Lys Asn Gly Lys Asn Pro Lys Gln Asn Asn Ile Ile Lys Ser
        195                 200                 205

Leu Asn Phe Asp Tyr Ser Gly Pro Ile Asp Gly His Asp Phe Pro Thr
    210                 215                 220

Leu Ile Lys Glu Leu Lys Arg Leu Lys Lys Ile Lys Gly Pro Lys Phe
225                 230                 235                 240

Leu His Ile Val Thr Thr Lys Gly Lys Gly Leu Gln Gln Ala Glu Glu
                245                 250                 255

Asn Gln Val Lys Tyr His Ala Pro Gly Lys Phe Asp Ala Ser Thr Gly
            260                 265                 270

Glu Ile His Leu Lys Ser Glu Glu Asn Leu Pro Pro Lys Tyr Gln Asp
        275                 280                 285

Val Phe Gly Leu Thr Val Leu Asp Leu Ala Arg Lys Asn Glu Lys Ile
    290                 295                 300

Ile Gly Ile Thr Pro Ala Met Pro Ser Gly Ser Ser Leu Lys Phe Met
305                 310                 315                 320

Met Asp Glu Leu Pro Asp Arg Ala Phe Asp Val Gly Ile Ala Glu Gln
                325                 330                 335

His Ala Val Thr Leu Ala Ala Gly Met Thr Thr Gln Gly Met Met Val
            340                 345                 350

Tyr Cys Thr Ile Tyr Ser Thr Phe Leu Gln Arg Ala Tyr Asp Gln Leu
        355                 360                 365

Ile His Asp Val Ala Leu Gln Asn Leu Pro Val Ile Phe Cys Leu Asp
    370                 375                 380

Arg Ala Gly Leu Val Gly Glu Asp Gly Ala Thr His His Gly Val Phe
385                 390                 395                 400

Asp Ile Ala Tyr Leu Arg Ser Ile Pro Asn Met Ile Ile Tyr Ala Pro
                405                 410                 415
```

```
Ile Asn Glu Ile Ala Leu Gln Asn Ile Leu Tyr Thr Ala Gln Leu Gly
            420                 425                 430

Leu Asn Asn Pro Ile Ala Ile Arg Tyr Pro Arg Gly Arg Gly Val Ile
        435                 440                 445

Lys Asn Trp Glu Val Glu Asn Phe Gly Gln Tyr Glu Lys Ile Lys Ile
    450                 455                 460

Gly Glu Gly Asn Cys Leu Lys Asn Gly Thr Lys Thr Ala Val Leu Ser
465                 470                 475                 480

Thr Gly


<210> SEQ ID NO 198
<211> LENGTH: 528
<212> TYPE: PRT
<213> ORGANISM: Artificial Sequence
<220> FEATURE:
<223> OTHER INFORMATION: Synthetic Construct

<400> SEQUENCE: 198

Met Ala Asp Leu Val Ser Ala Pro Ala Met Ile Ser Gln Ala Tyr Pro
 1               5                  10                  15

Leu Leu Ser Ser Ile His Ser Pro Ala Asp Leu Lys Lys Leu Ser Leu
            20                  25                  30

His Glu Leu Glu Leu Val Ala Ala Glu Cys Arg Lys Lys Val Ile Glu
        35                  40                  45

Leu Val Ser Gln Asn Gly Gly His Phe Gly Ser Ser Leu Gly Val Val
    50                  55                  60

Glu Leu Thr Val Ala Leu His Tyr Val Tyr Gln Ser Pro Thr Asp Arg
65                  70                  75                  80

Ile Ile Trp Asp Val Gly His Gln Ala Tyr Val His Lys Ile Leu Thr
                85                  90                  95

Gly Arg Leu Ala Gln Met Glu Thr Asn Arg Arg Tyr His Gly Leu Ala
            100                 105                 110

Gly Phe Pro Lys Arg Ser Glu Ser Pro His Asp Ala Phe Gly Thr Gly
        115                 120                 125

His Ala Ser Thr Ser Ile Ser Ala Ala Ala Gly Leu Ala Ala Ala Arg
    130                 135                 140

Asp Leu Ala Gly Arg Lys Glu Lys Val Val Ala Ile Ile Gly Asp Gly
145                 150                 155                 160

Ser Leu Thr Gly Gly Met Ala Phe Glu Ala Met Asn His Leu Gly Asp
                165                 170                 175

Thr Lys Ser Asp Val Leu Val Ile Leu Asn Asp Asn Gln Met Ala Ile
            180                 185                 190

Ser Pro Ser Thr Gly Gly Leu Lys Asn Tyr Leu Val Asn Leu Thr Leu
        195                 200                 205

Asn Lys Thr Tyr Asn Arg Leu Arg Lys Phe Val Trp Asp Ser Leu Ser
    210                 215                 220

Leu Leu His Asn Glu Ile Gly Glu Thr Ala Lys Thr Ala Val His Arg
225                 230                 235                 240

Ile Glu Asp Gly Ile Lys Ala Ala Phe Thr Pro Gly Ala Tyr Phe Glu
                245                 250                 255

Ala Leu Gly Phe Arg Tyr Phe Gly Pro Ile Asp Gly His Asn Met Glu
            260                 265                 270

Gln Leu Ile Lys Ala Leu Arg Glu Met Arg Gln Leu His His Pro Lys
        275                 280                 285

Leu Leu His Val Ile Thr Thr Lys Gly Lys Gly Phe Lys Pro Ala Glu
```

```
    290                 295                 300

Glu Asn Gln Pro Lys Trp His Ala Ser Val Gly Gly Phe Asp Ile Glu
305                 310                 315                 320

Thr Gly Lys Asn Val Lys Ala Pro Gly Lys Pro Ala Lys Pro Lys Tyr
                325                 330                 335

Gln Glu Val Phe Gly Glu Ala Leu Val Glu Leu Ala Leu Lys Asp Pro
            340                 345                 350

Thr Ile Thr Ala Ile Thr Ala Ala Met Pro Ser Gly Thr Ser Leu Asp
        355                 360                 365

Leu Phe Gln Gln Ala Ile Pro Ser Arg Cys Phe Asp Val Gly Ile Ala
    370                 375                 380

Glu Gln His Ala Val Thr Phe Ala Ala Gly Leu Ala Cys Gly Gly Phe
385                 390                 395                 400

Lys Pro Val Phe Ala Val Tyr Ser Thr Phe Leu Gln Arg Ala Tyr Asp
                405                 410                 415

Gln Leu Ile His Asp Val Ala Leu Gln Asn Leu His Val Val Phe Ala
            420                 425                 430

Ile Asp Arg Ala Gly Leu Val Gly Glu Asp Gly Pro Thr His His Gly
        435                 440                 445

Ala Phe Asp Leu Ser Tyr Leu Asn Val Val Pro Asn Leu Thr Ile Met
    450                 455                 460

Ala Pro Gly Asp Glu Gln Glu Leu Arg Asn Met Leu Tyr Thr Ala Leu
465                 470                 475                 480

Tyr Asp Ile Lys Gly Pro Val Ala Ile Arg Tyr Pro Arg Gly Ser Gly
                485                 490                 495

Ser Gly Ala Thr Leu His Lys Glu Phe Thr Pro Val Pro Val Gly Arg
            500                 505                 510

Gly Arg Ile Leu Arg Asp Gly Lys Ser Val Ala Leu Leu Gly Ile Gly
        515                 520                 525


<210> SEQ ID NO 199
<211> LENGTH: 514
<212> TYPE: PRT
<213> ORGANISM: Artificial Sequence
<220> FEATURE:
<223> OTHER INFORMATION: Synthetic Construct

<400> SEQUENCE: 199

Met His Ile Ser Glu Leu Thr His Pro Asn Glu Leu Lys Gly Leu Ser
 1               5                  10                  15

Ile Arg Glu Leu Glu Glu Val Ser Arg Gln Ile Arg Glu Lys His Leu
            20                  25                  30

Gln Thr Val Ala Thr Ser Gly Gly His Leu Gly Pro Gly Leu Gly Val
        35                  40                  45

Val Glu Leu Thr Val Ala Leu Tyr Ser Thr Leu Asp Leu Asp Lys Asp
    50                  55                  60

Arg Val Ile Trp Asp Val Gly His Gln Ala Tyr Pro His Lys Met Leu
65                  70                  75                  80

Thr Gly Arg Tyr His Asp Phe His Thr Leu Arg Gln Lys Asp Gly Val
                85                  90                  95

Ala Gly Tyr Leu Lys Arg Ser Glu Ser Arg Phe Asp His Phe Gly Ala
            100                 105                 110

Gly His Ala Ser Thr Ser Ile Ser Ala Gly Leu Gly Met Ala Leu Ala
        115                 120                 125

Arg Asp Ala Lys Gly Glu Asp Phe Lys Val Val Ser Ile Ile Gly Asp
    130                 135                 140
```

Gly Ala Leu Thr Gly Gly Met Ala Leu Glu Ala Ile Asn His Ala Gly
145 150 155 160

His Leu Pro His Thr Arg Leu Met Val Ile Leu Asn Asp Asn Glu Met
165 170 175

Ser Ile Ser Pro Asn Val Gly Ala Ile Ser Arg Tyr Leu Asn Lys Val
180 185 190

Arg Leu Ser Ser Pro Met Gln Phe Leu Thr Asp Asn Leu Glu Glu Gln
195 200 205

Ile Lys His Leu Pro Phe Val Gly Asp Ser Leu Thr Pro Glu Met Glu
210 215 220

Arg Val Lys Glu Gly Met Lys Arg Leu Val Val Pro Lys Val Gly Ala
225 230 235 240

Val Ile Glu Glu Leu Gly Phe Lys Tyr Phe Gly Pro Ile Asp Gly His
245 250 255

Ser Leu Gln Glu Leu Ile Asp Thr Phe Lys Gln Ala Glu Lys Val Pro
260 265 270

Gly Pro Val Phe Val His Val Ser Thr Thr Lys Gly Lys Gly Tyr Asp
275 280 285

Leu Ala Glu Lys Asp Gln Val Gly Tyr His Ala Gln Ser Pro Phe Asn
290 295 300

Leu Ser Thr Gly Lys Ala Tyr Pro Ser Ser Lys Pro Lys Pro Pro Ser
305 310 315 320

Tyr Ser Lys Val Phe Ala His Thr Leu Thr Thr Leu Ala Lys Glu Asn
325 330 335

Pro Asn Ile Val Gly Ile Thr Ala Ala Met Ala Thr Gly Thr Gly Leu
340 345 350

Asp Lys Leu Gln Ala Lys Leu Pro Lys Gln Tyr Val Asp Val Gly Ile
355 360 365

Ala Glu Gln His Ala Val Thr Leu Ala Ala Gly Met Ala Cys Glu Gly
370 375 380

Ile Arg Pro Val Val Ala Ile Tyr Ser Thr Phe Leu Gln Arg Gly Tyr
385 390 395 400

Asp Gln Ile Ile His Asp Val Cys Ile Gln Lys Leu Pro Val Phe Phe
405 410 415

Cys Leu Asp Arg Ala Gly Ile Val Gly Ala Asp Gly Pro Thr His Gln
420 425 430

Gly Met Tyr Asp Ile Ala Tyr Leu Arg Cys Ile Pro Asn Leu Val Leu
435 440 445

Met Ala Pro Lys Asp Glu Ala Glu Leu Gln Gln Met Leu Val Thr Gly
450 455 460

Val Asn Tyr Thr Gly Gly Ala Ile Ala Met Arg Tyr Pro Arg Gly Asn
465 470 475 480

Gly Ile Gly Val Pro Leu Met Glu Glu Gly Trp Glu Pro Leu Glu Ile
485 490 495

Gly Lys Ala Glu Ile Leu Arg Ser Gly Asp Asp Val Leu Leu Leu Gly
500 505 510

Tyr Gly

<210> SEQ ID NO 200
<211> LENGTH: 516
<212> TYPE: PRT
<213> ORGANISM: Artificial Sequence
<220> FEATURE:
<223> OTHER INFORMATION: Synthetic Construct

<400> SEQUENCE: 200

```
Met Asn Leu Ser Asp Leu Ser His Pro Asn Gln Leu Arg Asp Leu Ser
 1               5                  10                  15

Val Ser Gln Leu Gly Arg Leu Ala Gln Gln Ile Arg Asp Lys His Leu
            20                  25                  30

Gln Thr Val Ala Ala Thr Gly Gly His Leu Gly Pro Gly Leu Gly Val
        35                  40                  45

Val Glu Leu Thr Leu Ala Leu Tyr Lys Thr Leu Asp Leu Asp Arg Asp
    50                  55                  60

Arg Val Val Trp Asp Val Gly His Gln Ala Tyr Pro His Lys Met Leu
65                  70                  75                  80

Thr Gly Arg Tyr Ala Asn Phe His Thr Leu Arg Gln Lys Asp Gly Leu
                85                  90                  95

Ala Gly Tyr Leu Lys Arg Ala Glu Ser Pro Phe Asp Cys Trp Gly Ala
            100                 105                 110

Gly His Ala Ser Thr Ser Ile Ser Ala Ala Leu Gly Met Ala Leu Ala
        115                 120                 125

Arg Asp Phe Gln Gly Leu Asn Arg Lys Val Val Ala Ile Ile Gly Asp
    130                 135                 140

Gly Ala Leu Thr Gly Gly Met Ala Leu Glu Ala Leu Asn His Ala Gly
145                 150                 155                 160

His Leu Ser Lys Thr Asn Leu Met Val Ile Leu Asn Asp Asn Glu Met
                165                 170                 175

Ser Ile Ser Glu Asn Val Gly Gly Leu Ser Leu Tyr Leu Asn Arg Leu
            180                 185                 190

Arg Thr Asp Pro Ala Leu Arg Gln Ile Arg Ser Asn Leu Glu Thr Gln
        195                 200                 205

Leu Arg Asn Ile Pro Leu Val Gly Pro Thr Phe Ser Pro Glu Phe Glu
    210                 215                 220

Arg Phe Lys Asp Thr Val Lys Tyr Met Thr Met Thr Arg Ser Lys Ala
225                 230                 235                 240

Gly Val Ile Phe Glu Glu Leu Gly Phe Thr Tyr Leu Gly Pro Ile Asp
                245                 250                 255

Gly His Asn Leu Gly Asp Leu Ile Glu Thr Phe Glu Phe Ala His Ser
            260                 265                 270

Leu Pro Gly Pro Val Phe Leu His Ala Ile Thr Val Lys Gly Lys Gly
        275                 280                 285

Tyr Glu Val Ala Glu Gln Asn Gln Ile Lys Tyr His Ala Gln Ser Ala
    290                 295                 300

Phe Asp Leu Ala Thr Gly Lys Ala Lys Pro Ala Ser Lys Pro Thr Pro
305                 310                 315                 320

Pro Ala Tyr Thr Ser Val Phe Ala Gln Thr Leu Val Lys Leu Ala Glu
                325                 330                 335

Gln Asn Glu Lys Ile Val Gly Ile Thr Ala Ala Met Pro Thr Gly Thr
            340                 345                 350

Gly Leu Asp Lys Phe Lys Glu Arg Phe Ala Asp Arg Tyr Phe Asp Val
        355                 360                 365

Gly Ile Ala Glu Gln His Ala Val Thr Met Ala Ala Gly Leu Ala Ala
    370                 375                 380

Asp Gly Met Arg Pro Val Ala Ala Ile Tyr Ser Thr Phe Leu Gln Arg
385                 390                 395                 400

Ala Phe Asp Gly Ile Ile His Asp Val Ala Ile Gln Asp Leu Pro Val
                405                 410                 415
```

Phe Phe Cys Leu Asp Arg Ala Gly Val Val Gly Glu Asp Gly Pro Thr
420 425 430

His His Gly Val Phe Asp Leu Ala Tyr Leu Arg Gln Ile Pro Gly Leu
435 440 445

Val Val Met Ala Pro Lys Asp Glu Ala Glu Leu Gln Arg Met Met Val
450 455 460

Thr Gly Ile Gln Tyr Thr Lys Gly Pro Ile Ala Val Arg Tyr Pro Arg
465 470 475 480

Gly Ser Gly Ser Gly Ala Pro Leu Met Ala Glu Gly Trp Asp Pro Val
485 490 495

Pro Ile Gly Lys Ala Glu Val Leu Arg Ser Gly Asp Asp Leu Leu Ile
500 505 510

Val Ala Ile Gly
515

<210> SEQ ID NO 201
<211> LENGTH: 510
<212> TYPE: PRT
<213> ORGANISM: Artificial Sequence
<220> FEATURE:
<223> OTHER INFORMATION: Synthetic Construct

<400> SEQUENCE: 201

Met Lys Met Lys Asn Ile Leu Asp Lys Tyr Gln Asp Phe Asp Ser Ile
1 5 10 15

Lys Ser Met Ser Ile Asn Glu Leu Asn Gln Phe Ser Tyr Glu Ile Arg
20 25 30

Glu Phe Leu Ile Asp Asn Val Ser Lys Thr Gly Gly His Leu Ala Ser
35 40 45

Asn Leu Gly Val Val Glu Leu Thr Leu Ser Ile Phe Asn Val Phe Asp
50 55 60

Leu Asn Lys Asp Lys Val Ile Trp Asp Val Gly His Gln Ala Tyr Val
65 70 75 80

His Lys Ile Leu Thr Gly Arg Lys Asp Lys Phe Asn Thr Leu Arg Gln
85 90 95

Tyr Gly Gly Leu Ser Gly Phe Pro Lys Ile Cys Glu Ser Pro Tyr Asp
100 105 110

Val Phe Glu Thr Gly His Ser Ser Thr Ser Ile Ser Ala Ala Leu Gly
115 120 125

Met Ala Arg Ala Arg Asp Ile Lys Gly Glu Asn Asn Lys Val Ile Ala
130 135 140

Val Ile Gly Asp Gly Ala Leu Thr Gly Gly Met Ala Leu Glu Ala Leu
145 150 155 160

Asn Asp Leu Gly Phe Asn Lys Thr Asp Leu Ile Ile Ile Leu Asn Asp
165 170 175

Asn Gln Met Ser Ile Ala Glu Asn Val Gly Gly Met Ser Ser Tyr Leu
180 185 190

Ser Lys Val Arg Leu Asp Pro Thr Tyr Asn Lys Leu Lys Lys Glu Val
195 200 205

Asn Asn Thr Leu Asn Lys Ile Pro Asn Val Gly Lys Gly Met Ala Arg
210 215 220

Ser Leu Glu Lys Val Lys Asn Gly Ile Lys Gln Met Ile Val Pro Gly
225 230 235 240

Met Leu Phe Glu Asn Leu Gly Ile Lys Tyr Leu Gly Pro Ile Asp Gly
245 250 255

His Asp Ile Lys Glu Leu Ser Lys Val Met Lys Met Ala Lys Asn Ile

```
            260                 265                 270

Asn Gly Pro Val Leu Ile His Thr Ile Thr Lys Lys Gly Lys Gly Tyr
        275                 280                 285

Ala Tyr Ala Glu Lys Lys Pro Asp Lys Phe His Gly Ile Gly Pro Phe
    290                 295                 300

Asp Cys Asp Ser Gly Glu Val Asn Ser Lys Thr Cys Leu Thr Tyr Ser
305                 310                 315                 320

Lys Val Phe Gly Glu Glu Leu Thr Lys Ile Ala Lys Glu Asp Lys Lys
                325                 330                 335

Val Val Ala Ile Thr Ala Ala Met Lys Asp Gly Thr Gly Leu Arg Lys
            340                 345                 350

Phe Gly Glu Thr Phe Pro Lys Arg Phe Phe Asp Val Gly Ile Ala Glu
        355                 360                 365

Gln His Ala Val Thr Leu Ala Ala Gly Ile Ala Thr Glu Gly Leu Lys
    370                 375                 380

Pro Val Phe Ala Val Tyr Ser Thr Phe Leu Gln Arg Ala Tyr Asp Gly
385                 390                 395                 400

Ile Leu His Asp Ile Cys Ile Gln Asn Leu Pro Val Val Leu Gly Ile
                405                 410                 415

Asp Arg Ala Gly Ile Val Gly Ser Asp Gly Glu Thr His Gln Gly Ile
            420                 425                 430

Phe Asp Leu Ser Tyr Leu Ser Ser Leu Pro Asn Met Thr Ile Ile Ala
        435                 440                 445

Pro Lys Cys Leu Glu Glu Met Gly Ile Met Leu Arg Trp Ala Leu Asn
    450                 455                 460

Gln Asn Ser Pro Val Ala Ile Arg Tyr Pro Arg Gly Gly Asp Ile Lys
465                 470                 475                 480

Ser Leu Glu Met Thr Pro Ile Lys Asn Met Lys Lys Gly Lys Trp Glu
                485                 490                 495

Val Ile Cys Glu Glu Gly Asp Ile Ala Ile Ile Ala Thr Gly
            500                 505                 510


<210> SEQ ID NO 202
<211> LENGTH: 509
<212> TYPE: PRT
<213> ORGANISM: Artificial Sequence
<220> FEATURE:
<223> OTHER INFORMATION: Synthetic Construct

<400> SEQUENCE: 202

Met Leu Gln Gln Ile Arg Gly Pro Ala Asp Leu Gln His Leu Ser Gln
 1               5                  10                  15

Ala Gln Leu Arg Glu Leu Ala Ala Glu Ile Arg Glu Phe Leu Ile His
            20                  25                  30

Lys Val Ala Ala Thr Gly Gly His Leu Gly Pro Asn Leu Gly Val Val
        35                  40                  45

Glu Leu Thr Leu Ala Leu His Arg Val Phe Asp Ser Pro His Asp Pro
    50                  55                  60

Ile Ile Phe Asp Thr Gly His Gln Ala Tyr Val His Lys Met Leu Thr
65                  70                  75                  80

Gly Arg Ser Gln Asp Phe Ala Thr Leu Arg Lys Lys Gly Gly Leu Ser
                85                  90                  95

Gly Tyr Pro Ser Arg Ala Glu Ser Glu His Asp Trp Val Glu Ser Ser
            100                 105                 110

His Ala Ser Ala Ala Leu Ser Tyr Ala Asp Gly Leu Ala Lys Ala Phe
        115                 120                 125
```

```
Glu Leu Thr Gly His Arg Asn Arg His Val Val Ala Val Val Gly Asp
    130                 135                 140

Gly Ala Leu Thr Gly Gly Met Cys Trp Glu Ala Leu Asn Asn Ile Ala
145                 150                 155                 160

Ala Ser Arg Arg Pro Val Ile Ile Val Val Asn Asp Asn Gly Arg Ser
                165                 170                 175

Tyr Ala Pro Thr Ile Gly Gly Val Ala Asp His Leu Ala Thr Leu Arg
            180                 185                 190

Leu Gln Pro Ala Tyr Glu Gln Ala Leu Glu Thr Gly Arg Asp Leu Val
        195                 200                 205

Arg Ala Val Pro Leu Val Gly Gly Leu Trp Phe Arg Phe Leu His Ser
    210                 215                 220

Val Lys Ala Gly Ile Lys Asp Ser Leu Ser Pro Gln Leu Leu Phe Thr
225                 230                 235                 240

Asp Leu Gly Leu Lys Tyr Val Gly Pro Val Asp Gly His Asp Glu Arg
                245                 250                 255

Ala Val Glu Val Ala Leu Arg Ser Ala Arg Arg Phe Gly Ala Pro Val
            260                 265                 270

Ile Val His Val Val Thr Arg Lys Gly Met Gly Tyr Pro Pro Ala Glu
        275                 280                 285

Ala Asp Gln Ala Glu Gln Met His Ser Thr Val Pro Ile Asp Pro Ala
    290                 295                 300

Thr Gly Gln Ala Thr Lys Val Ala Gly Pro Gly Trp Thr Ala Thr Phe
305                 310                 315                 320

Ser Asp Ala Leu Ile Gly Tyr Ala Gln Lys Arg Arg Asp Ile Val Ala
                325                 330                 335

Ile Thr Ala Ala Met Pro Gly Pro Thr Gly Leu Thr Ala Phe Gly Gln
            340                 345                 350

Arg Phe Pro Asp Arg Leu Phe Asp Val Gly Ile Ala Glu Gln His Ala
        355                 360                 365

Met Thr Ser Ala Ala Gly Leu Ala Met Gly Gly Leu His Pro Val Val
    370                 375                 380

Ala Ile Tyr Ser Thr Phe Leu Asn Arg Ala Phe Asp Gln Ile Met Met
385                 390                 395                 400

Asp Val Ala Leu His Lys Leu Pro Val Thr Met Val Leu Asp Arg Ala
                405                 410                 415

Gly Ile Thr Gly Ser Asp Gly Ala Ser His Asn Gly Met Trp Asp Leu
            420                 425                 430

Ser Met Leu Gly Ile Val Pro Gly Ile Arg Val Ala Ala Pro Arg Asp
        435                 440                 445

Ala Thr Arg Leu Arg Glu Glu Leu Gly Glu Ala Leu Asp Val Asp Asp
    450                 455                 460

Gly Pro Thr Ala Leu Arg Phe Pro Lys Gly Asp Val Gly Glu Asp Ile
465                 470                 475                 480

Ser Ala Leu Glu Arg Arg Gly Gly Val Asp Val Leu Ala Ala Pro Ala
                485                 490                 495

Asp Gly Leu Asn His Asp Val Leu Leu Val Ala Ile Gly
            500                 505
```

<210> SEQ ID NO 203
<211> LENGTH: 475
<212> TYPE: PRT
<213> ORGANISM: Artificial Sequence
<220> FEATURE:
<223> OTHER INFORMATION: Synthetic Construct

<400> SEQUENCE: 203

Met Asn Lys His Pro Glu Phe Leu Leu Asn Lys Ile Lys Ser Pro Lys
1 5 10 15

Asp Leu Lys Lys Leu Asp Leu Lys Glu Leu Glu Gln Leu Ala Ser Glu
20 25 30

Ile Arg Thr Leu Ile Leu Glu Lys Asp Ala Ala Lys Gly Gly His Leu
35 40 45

Gly Pro Asp Leu Gly Ile Val Glu Ala Thr Ile Ala Tyr His Tyr Val
50 55 60

Phe Asp Ala Pro Lys Asp Lys Ile Val Trp Asp Val Ser His Gln Thr
65 70 75 80

Tyr Pro His Lys Met Leu Thr Gly Arg Ala Tyr Gly Trp Leu Asp Pro
85 90 95

Asp Lys Tyr Glu Asp Val Thr Pro Tyr Ser Asn Pro Glu Glu Ser Pro
100 105 110

Tyr Asp Tyr Phe Ala Val Gly His Thr Ser Thr Ser Ile Ala Leu Ala
115 120 125

Thr Gly Met Ala Arg Ala Arg Asp Met Leu Gly Glu His Glu Asn Ile
130 135 140

Thr Ala Leu Ile Gly Asp Gly Ser Leu Thr Gly Gly Leu Ala Phe Glu
145 150 155 160

Gly Phe Asn Asn Ala Ala Asp Glu Lys His Asn Leu Ile Ile Val Val
165 170 175

Asn Asp Asn Gln Met Ser Ile Asp Asp Asn Val Gly Gly Val Val Thr
180 185 190

Ala Leu Lys Lys Leu Arg Glu Ser Asn Gly Gln Thr Ala Asp Asn Pro
195 200 205

Phe Thr Ala Met Gly Leu Asp Tyr Lys Tyr Val Asp Gln Gly Asn Asp
210 215 220

Leu Lys Ala Met Ile Asp Ala Phe Lys Ser Ile Lys Asp Ile Asp His
225 230 235 240

Pro Ile Val Leu His Ile Asn Thr Leu Lys Gly Lys Gly Tyr Glu Pro
245 250 255

Ala Ile Glu Asn Glu Ala Ser His His Trp Val Leu Pro Phe Asp Leu
260 265 270

Lys Thr Asp Lys Thr Thr Val Pro Ala Pro Lys Thr Pro Asn Pro Thr
275 280 285

Thr Val Val Leu Asp Phe Leu Lys Lys His Ile Glu Asn Gln Glu Asn
290 295 300

Ile Leu Ala Ile Asn Ala Ala Ile Pro Gly Val Phe Gly Leu Gly Glu
305 310 315 320

Ile Lys Asn Lys Tyr Pro Lys Asn Tyr Lys Asp Val Gly Ile Ala Glu
325 330 335

Gln Glu Ser Val Ala Phe Ala Ala Gly Ala Val Lys Glu Gly Ile Thr
340 345 350

Pro Val Leu Phe Glu Asn Ser Thr Phe Leu Gln Arg Ala Tyr Asp Gln
355 360 365

Leu Ser His Asp Val Ala Ala Asn Asp Leu Pro Val Val Met Val Val
370 375 380

Ala Gly Gly Gly Ile Thr Gly Thr Ser Lys Thr His Leu Gly Ile Phe
385 390 395 400

Asp Asn Ala Met Val Ala Asn Trp Pro Asn Trp Glu Tyr Leu Ala Pro
405 410 415

Thr Thr Leu Asn Glu Leu Lys Ser Met Leu Glu Trp Ala Val Lys Gln
420 425 430

Arg Lys His Pro Ile Ala Ile Lys Ser Pro Val Asn Pro Ile Pro Glu
435 440 445

Gly Glu Pro Val Asp Glu Asp Tyr Ser Thr Ile Lys Tyr Asp Val Lys
450 455 460

Pro Gly Ser Lys Val Ala Ile Ile Gly Leu Gly
465 470 475

<210> SEQ ID NO 204
<211> LENGTH: 431
<212> TYPE: PRT
<213> ORGANISM: Artificial Sequence
<220> FEATURE:
<223> OTHER INFORMATION: Synthetic Construct

<400> SEQUENCE: 204

Met Asn Lys His Pro Glu Phe Leu Leu Asn Lys Ile Glu Asn Pro Lys
1 5 10 15

Asp Leu Lys Lys Leu Asp Leu Lys Glu Leu Glu Gln Leu Ala Ser Glu
20 25 30

Ile Arg Thr Leu Ile Leu Glu Lys Asp Ala Ala Glu Gly Gly His Leu
35 40 45

Gly Pro Asp Leu Gly Ile Val Glu Ala Thr Ile Ala Tyr His Tyr Val
50 55 60

Phe Asp Ala Pro Lys Asp Lys Ile Ile Trp Asp Val Ser His Gln Thr
65 70 75 80

Tyr Pro His Lys Met Leu Thr Gly Arg Ala Tyr Ala Trp Leu Asp Pro
85 90 95

Asp Lys Tyr Glu Asp Val Thr Pro Tyr Ser Asn Pro Asp Glu Ser Pro
100 105 110

Tyr Asp Tyr Tyr Ala Val Gly His Thr Ser Thr Ser Val Ala Leu Ala
115 120 125

Thr Gly Met Ala Arg Ala Arg Asp Met Met Gly Asn His Glu Asn Ile
130 135 140

Thr Ala Leu Ile Gly Asp Gly Ser Leu Thr Gly Gly Leu Ala Phe Glu
145 150 155 160

Gly Phe Asn Asn Ala Ala Asp Glu Lys His Asn Leu Ile Ile Val Val
165 170 175

Asn Asp Asn Gln Met Ser Ile Asp Asp Asn Val Gly Gly Val Val Thr
180 185 190

Ala Leu Lys Lys Leu Arg Glu Ser Asn Gly Gln Ala Glu Asp Asn Pro
195 200 205

Phe Thr Ala Met Gly Leu Asp Tyr Lys Tyr Val Gly Gln Gly Asn Asp
210 215 220

Ile Lys Ser Met Ile Asp Ala Phe Lys Ala Val Lys Asp Ile Asp His
225 230 235 240

Pro Ile Val Leu His Ile Asn Thr Leu Lys Gly Lys Gly Tyr Glu Pro
245 250 255

Ala Ile Glu Asn Glu Ala Ser His His Trp Val Leu Pro Phe Asp Leu
260 265 270

Lys Thr Asp Lys Pro Thr Val Pro Ala Pro Lys Thr Pro Asn Ala Ser
275 280 285

Thr Val Ile Leu Asp Phe Leu Lys Lys His Ile Glu Asn Gln Glu Asn
290 295 300

Ile Leu Val Ile Asn Ala Ala Ile Pro Gly Val Phe Gly Leu Gly Glu
305 310 315 320

Ile Lys Asn Asn Tyr Pro Lys Asn Tyr Lys Asp Val Gly Ile Ala Glu
325 330 335

Gln Glu Ser Val Ala Phe Ala Ala Gly Ala Val Lys Glu Gly Ile Thr
340 345 350

Pro Ile Leu Phe Glu Asn Ser Thr Phe Leu Gln Arg Ala Tyr Asp Gln
355 360 365

Leu Ser His Asp Val Ala Ala Asn Asp Leu Pro Val Val Met Ile Val
370 375 380

Ala Gly Gly Gly Ile Thr Ala Ala Ser Lys Thr His Leu Gly Ile Phe
385 390 395 400

Asp Asn Thr Met Val Ala Asn Trp Pro Asn Trp Glu Tyr Leu Ala Pro
405 410 415

Thr Thr Leu Asn Glu Leu Lys Ser Met Leu Glu Trp Ala Val Lys
420 425 430

<210> SEQ ID NO 205
<211> LENGTH: 343
<212> TYPE: PRT
<213> ORGANISM: Artificial Sequence
<220> FEATURE:
<223> OTHER INFORMATION: Synthetic Construct

<400> SEQUENCE: 205

Met Ser Val Leu Glu Lys Ile Asp Ser Pro Ala Asp Leu Lys Lys Val
1 5 10 15

Ser Asn Gln Glu Leu Glu Glu Leu Ala Ser Glu Ile Arg Thr Ala Val
20 25 30

Leu His Lys Val Ser Asn Ile Gly Gly His Val Gly Pro Asn Leu Gly
35 40 45

Val Thr Glu Leu Thr Ile Ala Leu His Lys Val Phe Asn Ser Pro Ile
50 55 60

Asp Lys Phe Ile Trp Asp Val Ser His Gln Thr Tyr Pro His Lys Ile
65 70 75 80

Leu Thr Gly Arg Lys Asn Gly Phe Thr Asp Gly His Phe His Asp Ile
85 90 95

Thr Pro Tyr Thr Ser Gln Arg Glu Ser Glu His Asp Phe Phe Thr Val
100 105 110

Gly His Thr Ser Thr Ser Ile Ala Asn Ala Leu Gly Tyr Ala Lys Ala
115 120 125

Arg Asp Leu Thr Asn Asp Lys Gly Asn Ile Val Ala Val Ile Gly Asp
130 135 140

Gly Ser Leu Ser Gly Gly Leu Ala Met Glu Ala Leu Asn Asn Ala Gly
145 150 155 160

Asp Phe Lys Gly Asn Leu Ile Ile Leu Val Asn Asp Asn Gln Met Ser
165 170 175

Ile Ala Glu Asn His Gly Gly Leu Tyr Arg Asn Leu Ala Glu Leu Arg
180 185 190

Ala Thr Asn Gly Gln Ala Glu Asn Asn Phe Phe Lys Thr Phe Gly Leu
195 200 205

Asp Tyr Lys Tyr Leu Glu Asn Gly Asn Asp Ile Glu Ser Leu Ile His
210 215 220

Leu Phe Glu Glu Val Lys Asp Ile Asp His Pro Ile Val Leu His Ile
225 230 235 240

His Thr Glu Lys Gly Arg Gly Tyr Gln Pro Ala Leu Glu Asn Lys Glu

-continued

```
                245                 250                 255

Ala Phe His Trp His Met Pro Phe Asp Leu Glu Thr Gly Gln Ser Lys
            260                 265                 270

Val Ile Asp Ser Gly Lys Ser Tyr Ser Ser Val Met Leu Asp Tyr Met
        275                 280                 285

Asp Lys Lys Val Ser Glu Gly Leu Pro Leu Val Ala Ile Asn Ala Ala
    290                 295                 300

Ile Pro Gly Ile Phe Gly Leu Lys Gln Phe Ala Ala Lys Tyr Pro Asp
305                 310                 315                 320

Arg Tyr Ile Asp Ala Gly Ile Ala Glu Gln Phe Thr Ile Thr Phe Gly
                325                 330                 335

Gly Ala Met Ala Ala Ala Gly
            340
```

ISOPRENE PRODUCTION USING THE DXP AND MVA PATHWAY

CROSS-REFERENCE TO RELATED APPLICATIONS

This application claims priority to U.S. Provisional Patent Application No. 61/187,941, filed Jun. 17, 2009; U.S. Provisional Patent Application No. 61/187,930, filed Jun. 17, 2009; U.S. Provisional Patent Application No. 61/314,985, filed Mar. 17, 2010; U.S. Provisional Patent Application No. 61/314,979, filed Mar. 17, 2010; the disclosure of all of these applications are hereby incorporated herein by reference in its entirety.

FIELD OF THE INVENTION

The present invention relates generally to compositions and methods for improving the production of isoprene from cultured cells using the DXP pathway and MVA pathway.

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway (FIG. 19A). However, the yield of isoprene from naturally-occurring organisms is commercially unattractive. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Currently, the tire and rubber industry is based on the use of natural and synthetic rubber. Natural rubber is obtained from the milky juice of rubber trees or plants found in the rainforests of Africa. Synthetic rubber is based primarily on butadiene polymers. For these polymers, butadiene is obtained as a co-product from ethylene and propylene manufacture.

While isoprene can be obtained by fractionating petroleum, the purification of this material is expensive and time-consuming. Petroleum cracking of the C5 stream of hydrocarbons produces only about 15% isoprene. Thus, more economical methods for producing isoprene are needed. In particular, methods that produce isoprene at rates, titers, and purity that are sufficient to meet the demands of a robust commercial process are desirable. Also desired are systems for producing isoprene from inexpensive starting materials.

BRIEF SUMMARY OF THE INVENTION

The invention provides, inter alia, compositions and methods for the production of isoprene in increased amounts using various DXP pathway genes and polypeptides and various MVA pathway genes and polypeptides, iron-sulfur cluster-interacting redox genes and polypeptides, isoprene synthase, and optionally, various genes and polypeptides associated with the DXP pathway, various genes and polypeptides associated with the MVA pathway, and IDI genes and polypeptides. In one aspect, the invention features cells or cells in culture which have been engineered for producing isoprene in increased amounts by using a combination of various DXP pathway genes and polypeptides, various MVA pathway genes and polypeptides, iron-sulfur cluster-interacting redox genes and polypeptides, isoprene synthase genes and polypeptides, and optionally, DXP pathway associated genes and polypeptides, MVA pathway associated genes and polypeptides, and IDI genes and polypeptides.

In some embodiments, the cells or cells in culture comprise (i) a heterologous nucleic acid encoding an iron-sulfur cluster-interacting redox polypeptide, a DXP pathway polypeptide, a MVA pathway polypeptide, and an isoprene synthase polypeptide and/or (ii) a duplicate copy of an endogenous nucleic acid encoding an iron-sulfur cluster-interacting redox polypeptide, a DXP pathway polypeptide, a MVA pathway polypeptide, and an isoprene synthase polypeptide. In some embodiments, the cells or cells in culture comprise (i) one or more copies of heterologous or endogenous nucleic acid encoding an iron-sulfur cluster-interacting redox polypeptide, (ii) one or more copies of heterologous or endogenous nucleic acid encoding a DXP pathway polypeptide and/or a MVA pathway polypeptide, and (iii) one or more copies of heterologous or endogenous nucleic acid encoding an isoprene synthase polypeptide. In some embodiments, the iron-sulfur cluster-interacting redox polypeptide, the DXP pathway polypeptide, a MVA pathway polypeptide, and isoprene synthase polypeptide are operably linked to a promoter.

In some embodiments, the DXP pathway polypeptide is selected from the group consisting of DXS (1-deoxy-D-xylulose-5-phosphate synthase), DXR (1-deoxy-D-xylulose-5-phosphate reductoisomerase), MCT (4-diphosphocytidyl-2C-methyl-D-erythritol synthase), CMK (4-diphosphocytidyl-2-C-methyl-D-erythritol kinase), MCS (2C-methyl-D-erythritol 2,4-cyclodiphosphate synthase), HDS (1-hydroxy-2-methyl-2-(E)-butenyl 4-diphosphate synthase), and HDR (1-hydroxy-2-methyl-2-(E)-butenyl 4-diphosphate reductase). In some embodiments, the DXP pathway polypeptide is DXS, HDS, or HDR. In some embodiments, the cells further comprise a heterologous nucleic acid or a duplicate copy of an endogenous nucleic acid encoding an IDI (isopentenyl-diphosphate delta-isomerase) polypeptide.

In some embodiments, the MVA pathway polypeptide is selected from the group consisting acetyl-CoA acetyltransferase (AA-CoA thiolase), 3-hydroxy-3-methylglutaryl-CoA synthase (HMG-CoA synthase), 3-hydroxy-3-methylglutaryl-CoA reductase (HMG-CoA reductase), mevalonate kinase (MVK), phosphomevalonate kinase (PMK), diphosphomevalonte decarboxylase (MVD), phosphomevalonate decarboxylase (PMDC) and isopentenyl phosphate kinase (IPK). In some embodiments, the cells further comprise a heterologous nucleic acid or a duplicate copy of an endogenous nucleic acid encoding an IDI (isopentenyl-diphosphate delta-isomerase) polypeptide.

In one embodiment, both the DXP and MVA pathways can be present in any ratio to produce isoprene from each pathway in any proportion in cells or cells in culture. In another embodiment, about 10% to 50% of the isoprene is produced utilizing the DXP pathway and the remainder is produced utilizing the MVA pathway. In another embodiment, at least about 50% of the isoprene is produced utilizing the DXP pathway and the remainder is produced utilizing the MVA pathway.

In some embodiments, the invention provides cells or cells in culture that produce greater than about 400 nmole of isoprene/gram of cells for the wet weight of the cells/hour (nmole/$g_{wcm}$/hr) of isoprene. In some embodiments, the cells or cells in culture convert more than about 0.002% of the carbon in a cell culture medium into isoprene.

In some embodiments, the invention provides cells or cells in culture where the level of HMBPP and DMAPP are maintained below 1 mM for the duration of the fermentation run. In other embodiments, the invention provides cells in culture where the level of HMBPP and DMAPP are maintained below 1 mM during the exponential phase of the fermentation. In other embodiments, the invention provides cells or cells in culture in which late DXP pathway enzymes, particularly IspG and IspH are maintained at levels consistent with minimizing phosphorylation level of Dxr.

In some embodiments of any of the aspects of the invention, the iron-sulfur cluster-interacting redox polypeptide comprises flavodoxin (e.g., flavodoxin I), flavodoxin reductase, ferredoxin (e.g., ferredoxin I), ferredoxin-NADP+ oxidoreductase, and genes or polypeptides encoding thereof (e.g., fpr and fldA).

In some embodiments, the cells or cells in culture comprise (i) a heterologous nucleic acid encoding a ferredoxin polypeptide, a ferredoxin-NADP+ oxidoreductase polypeptide, a DXP pathway polypeptide, and an isoprene synthase polypeptide and/or (ii) a duplicate copy of an endogenous nucleic acid encoding a ferredoxin polypeptide, a ferredoxin-NADP+ oxidoreductase polypeptide, a DXP pathway polypeptide, and an isoprene synthase polypeptide. In some embodiments, the cells or cells in culture comprise IspG and fldA. In another embodiment, the cells or cells in culture comprise IspG, fldA, and IspH. In some embodiments, the ferredoxin polypeptide, the ferredoxin-NADP+ oxidoreductase, the DXP pathway polypeptide, and isoprene synthase polypeptide are operably linked to a promoter. In some embodiments, the cells further comprise a heterologous nucleic acid or a duplicate copy of an endogenous nucleic acid encoding an IDI polypeptide.

In some embodiments, the cells in culture comprise (i) a heterologous nucleic acid encoding a flavodoxin polypeptide, a DXP pathway polypeptide, a MVA pathway polypeptide, and an isoprene synthase polypeptide and/or (ii) a duplicate copy of an endogenous nucleic acid encoding a flavodoxin polypeptide, a DXP pathway polypeptide, a MVA pathway polypeptide, and an isoprene synthase polypeptide. In some embodiments, the flavodoxin polypeptide, the DXP pathway polypeptide, MVA pathway polypeptide, and isoprene synthase polypeptide are operably linked to a promoter. In some embodiments, the cells further comprise a heterologous nucleic acid or a duplicate copy of an endogenous nucleic acid encoding an IDI polypeptide.

In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In other aspects, the invention provides for methods of producing isoprene, the method comprising (a) culturing cells comprising (i) a heterologous nucleic acid encoding a heterologous nucleic acid encoding an iron-sulfur cluster-interacting redox polypeptide, a DXP pathway polypeptide, a MVA pathway polypeptide, and an isoprene synthase polypeptide or (ii) a duplicate copy of an endogenous nucleic acid encoding an iron-sulfur cluster-interacting redox polypeptide, a DXP pathway polypeptide, a MVA pathway polypeptide, and an isoprene synthase polypeptide under suitable culture conditions for the production of isoprene, and (b) producing isoprene. In one embodiment, the cells further comprise a heterologous nucleic acid or a duplicate copy of an endogenous nucleic acid encoding an IDI (isopentenyl-diphosphate delta-isomerase) polypeptide. In other embodiments, the cells in culture produce greater than about 400 nmole/$g_{wcm}$/hr of isoprene. In other embodiments, more than about 0.02 molar percent of the carbon that the cells consume from a cell culture medium is converted into isoprene.

In one aspect, the invention features methods of producing isoprene, such as methods of using any of the cells described herein to produce isoprene. In some embodiments, the method involves culturing cells comprising (i) a heterologous nucleic acid encoding a heterologous nucleic acid encoding an iron-sulfur cluster-interacting redox polypeptide, a DXP pathway polypeptide, and an isoprene synthase polypeptide, and/or (ii) a duplicate copy of an endogenous nucleic acid encoding an iron-sulfur cluster-interacting redox polypeptide, a DXP pathway polypeptide, and an isoprene synthase polypeptide. In some embodiments, the cells are cultured under suitable culture conditions for the production of isoprene, and isoprene is produced. In some embodiments, the iron-sulfur cluster-interacting redox polypeptide, isoprene synthase polypeptide, and DXP pathway polypeptide are operably linked to a promoter. In some embodiments, the DXP pathway polypeptide is selected from the group consisting of DXS (1-deoxy-D-xylulose-5-phosphate synthase), DXR (1-deoxy-D-xylulose-5-phosphate reductoisomerase), MCT (4-diphosphocytidyl-2C-methyl-D-erythritol synthase), CMK (4-diphosphocytidyl-2-C-methyl-D-erythritol kinase), MCS (2C-methyl-D-erythritol 2,4-cyclodiphosphate synthase), HDS (1-hydroxy-2-methyl-2-(E)-butenyl 4-diphosphate synthase), and HDR (1-hydroxy-2-methyl-2-(E)-butenyl 4-diphosphate reductase). In some embodiments, the DXP pathway polypeptide is DXS, HDS, or HDR. In some embodiments, the cells further comprise a heterologous nucleic acid or a duplicate copy of an endogenous nucleic acid encoding an IDI (isopentenyl-diphosphate delta-isomerase) polypeptide. In some embodiments, the method involves culturing cells under conditions sufficient to produce greater than about 400 nmole/$g_{wcm}$/hr of isoprene. In some embodiments, the method involves culturing cells under conditions sufficient to convert more than about 0.002% (mol/mol) of the carbon in a cell culture medium into isoprene.

In various embodiments, the amount of isoprene produced (such as the total amount of isoprene produced or the amount of isoprene produced per liter of broth per hour per $OD_{600}$) during stationary phase is greater than or about 2 or more times the amount of isoprene produced during the growth phase for the same length of time. In some embodiments, the gas phase comprises greater than or about 9.5% (volume) oxygen, and the concentration of isoprene in the gas phase is less than the lower flammability limit or greater than the upper flammability limit. In particular embodiments, (i) the concentration of isoprene in the gas phase is less than the lower flammability limit or greater than the upper flammability limit, and (ii) the cells produce greater than about 400 nmole/$g_{wcm}$/hr of isoprene.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time.

In one aspect, the invention features compositions and systems that comprise isoprene. In some embodiments, the composition comprises greater than or about 2, 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene (w/w) of the volatile organic fraction of the composition is isoprene.

In some embodiments, the composition comprises greater than or about 99.90, 99.92, 99.94, 99.96, 99.98, or 100% isoprene by weight compared to the total weight of all C5 hydrocarbons in the composition. In some embodiments, the composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such as 1,3-cyclopentadiene, cis-1,3-pentadiene, trans-1,3-pentadiene, 1,4-pentadiene, 1-pentyne, 2-pentyne, 3-methyl-1-butyne, pent-4-ene-1-yne, trans-pent-3-ene-1-yne, or cis-pent-3-ene-1-yne) by weight compared to the total weight of all C5 hydrocarbons in the composition. In some embodiments, the composition has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, or cis-pent-3-ene-1-yne by weight compared to the total weight of all C5 hydrocarbons in the composition. In particular embodiments, the composition has greater than about 2 mg of isoprene and has greater than or about 99.90, 99.92, 99.94, 99.96, 99.98, or 100% isoprene by weight compared to the total weight of all C5 hydrocarbons in the composition.

In some embodiments, the composition has less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In particular embodiments, the composition also has greater than about 2 mg of isoprene.

In some embodiments, the composition comprises (i) a gas phase that comprises isoprene and (ii) cells in culture that produce greater than about 400 nmole/$g_{wcm}$/hr of isoprene. In some embodiments, the composition comprises a closed system, and the gas phase comprises greater than or about 5, 10, 20, 30, 40, 50, 60, 70, 80, 90, 100 ug/L of isoprene when normalized to 1 mL of $OD_{600}$ cultured for 1 hour. In some embodiments, the composition comprises an open system, and the gas phase comprises greater than or about 5, 10, 20, 30, 40, 50, 60, 70, 80, 90, 100 ug/L of isoprene when sparged at a rate of 1 vvm. In some embodiments, the volatile organic fraction of the gas phase comprises greater than or about 99.90, 99.92, 99.94, 99.96, 99.98, or 100% isoprene by weight compared to the total weight of all C5 hydrocarbons in the volatile organic fraction. In some embodiments, the volatile organic fraction of the gas phase comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such as 1,3-cyclopentadiene, cis-1,3-pentadiene, trans-1,3-pentadiene, 1,4-pentadiene, 1-pentyne, 2-pentyne, 3-methyl-1-butyne, pent-4-ene-1-yne, trans-pent-3-ene-1-yne, or cis-pent-3-ene-1-yne) by weight compared to the total weight of all C5 hydrocarbons in the volatile organic fraction. In some embodiments, the volatile organic fraction of the gas phase has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, cis-1,3-pentadiene, trans-1,3-pentadiene, 1,4-pentadiene, 1-pentyne, 2-pentyne, 3-methyl-1-butyne, pent-4-ene-1-yne, trans-pent-3-ene-1-yne, or cis-pent-3-ene-1-yne by weight compared to the total weight of all C5 hydrocarbons in the volatile organic fraction. In particular embodiments, the volatile organic fraction of the gas phase has greater than about 2 mg of isoprene and has greater than or about 99.90, 99.92, 99.94, 99.96, 99.98, or 100% isoprene by weight compared to the total weight of all C5 hydrocarbons in the volatile organic fraction.

In some embodiments, the volatile organic fraction of the gas phase has less than or about 50, 40, 30, 20, 10, 5, 1, 0.5, 0.1, 0.05, 0.01, or 0.005 ug/L of a compound that inhibits the polymerization of isoprene for any compound in the volatile organic fraction of the gas phase that inhibits the polymerization of isoprene. In particular embodiments, the volatile organic fraction of the gas phase also has greater than about 2 mg of isoprene.

In some embodiments of any of the compositions of the invention, at least a portion of the isoprene is in a gas phase. In some embodiments, at least a portion of the isoprene is in a liquid phase (such as a condensate). In some embodiments, at least a portion of the isoprene is in a solid phase. In some embodiments, at least a portion of the isoprene is adsorbed to a solid support, such as a support that includes silica and/or activated carbon. In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments, the composition includes between about 4 to about 15% by weight of isoprene, such as between about 4 to about 8%, about 8 to about 12%, or about 12 to about 15% by weight of isoprene.

In some embodiments, the invention also features systems that include any of the cells and/or compositions described herein. In some embodiments, the system includes a reactor that chamber comprises cells in culture that produce greater than about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments, the system is not a closed system. In some embodiments, at least a portion of the isoprene is removed from the system. In some embodiments, the system includes a gas phase comprising isoprene. In various embodiments, the gas phase comprises any of the compositions described herein.

In one aspect, the invention provides a tire comprising polyisoprene. In some embodiments, the polyisoprene is produced by (i) polymerizing isoprene in any of the compositions described herein or (ii) polymerizing isoprene recovered from any of the compositions described herein. In some embodiments, the polyisoprene comprises cis-1,4-polyisoprene.

In some embodiments of any of the compositions, systems, and methods of the invention, a nonflammable concentration of isoprene in the gas phase is produced. In some embodiments, the gas phase comprises less than about 9.5% (volume) oxygen. In some embodiments, the gas phase comprises greater than or about 9.5% (volume) oxygen, and the concentration of isoprene in the gas phase is less than the lower flammability limit or greater than the upper flammability limit. In some embodiments, the portion of the gas phase other than isoprene comprises between about 0% to about 100% (volume) oxygen, such as between about 10% to about 100% (volume) oxygen. In some embodiments, the portion of the gas phase other than isoprene comprises between about 0% to about 99% (volume) nitrogen. In some embodiments, the portion of the gas phase other than isoprene comprises between about 1% to about 50% (volume) $CO_2$.

In some embodiments of any of the aspects of the invention, the cells further comprise a heterologous nucleic acid or a duplicate copy of an endogenous nucleic acid encoding a DXP pathway associated polypeptide.

In some embodiments of any of the aspects of the invention, the cells in culture produce isoprene at greater than or about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments of any of the aspects of the invention, the cells in culture convert greater than or about 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6%, or more of the carbon in the cell culture medium into isoprene. In some embodiments of any of the aspects of the invention, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments of any of the aspects of the invention, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). Other exemplary rates of isoprene production and total amounts of isoprene production are disclosed herein.

In some embodiments of any of the aspects of the invention, isoprene production can be further increased by using a mutant DXP pathway polypeptide and nucleic acid derived from thereof. In some embodiments, the mutant DXP pathway polypeptide is a HDR polypeptide with the iron-sulfur cluster regulator (iscR) removed. In some embodiments, the mutant DXP pathway polypeptide is a mutant HDR polypeptide that produces solely DMAPP or a majority of DMAPP relative to IPP.

In some embodiments of any of the aspects of the invention, isoprene production can be further increased by increasing the carbon flux through the DXP pathway and/or MVA pathway. In some embodiments, the carbon flux can be increased by avoiding any feedback inhibition of DXS activity by metabolites downstream the DXP pathway or/and intermediates of other pathways that use a DXP pathway polypeptide as a substrate. In some embodiments, the other pathway that uses DXP pathway polypeptide as a substrate (e.g., DXP) is the thiamine (Vitamin B1) or pyridoxal (Vitamin B6) pathway. In some embodiments, the carbon flux can be increased by expressing a DXP pathway polypeptide from a different organism that is not subject to inhibition by downstream products of the DXP pathway. In some embodiments, the carbon flux can be increased by deregulating glucose uptake. In other embodiments, the carbon flux can be increased by maximizing the balance between the precursors required for the DXP pathway and/or MVA pathway. In some embodiments, the balance of the DXP pathway precursors, pyruvate and glyceraldehydes-3-phosphate (G-3-P), can be achieved by redirecting the carbon flux with the effect of elevating or lowering pyruvate or G-3-P separately. In some embodiments, the carbon flux can be increased by using a CRP (cAMP Receptor Protein)-deleted mutant.

In some embodiments, the carbon flux can be increased by using a strain (containing one or more DXP pathway genes or one or more both DXP pathway and MVA pathway genes) containing a pyruvate dehydrogenase E1 subunit variant. In some embodiments, the pyruvate dehydrogenase (PDH) E1 subunit variant has an E636Q point mutation.

In some embodiments of any of the aspects of the invention, isoprene production can be further increased by utilizing the downstream genes or polypeptides of the DXP pathway by introducing a heterologous terpene synthase nucleic acid or a duplicate copy of an endogenous terpene synthase nucleic acid into the cells, which includes, but is not limited to ocimene synthase, farnesene synthase, and artemesinin synthase.

In some embodiments of any of the aspects of the invention, in some embodiments, the vector comprises a selective marker, such as an antibiotic resistance nucleic acid.

In some embodiments of any of the aspects of the invention, the heterologous isoprene synthase nucleic acid is operably linked to a T7 promoter, such as a T7 promoter contained in a medium or high copy plasmid. In some embodiments of any of the aspects of the invention, the heterologous isoprene synthase nucleic acid is operably linked to a Trc promoter, such as a Trc promoter contained in a medium or high copy plasmid. In some embodiments of any of the aspects of the invention, the heterologous isoprene synthase nucleic acid is operably linked to a Lac promoter, such as a Lac promoter contained in a low copy plasmid. In some embodiments of any of the aspects of the invention, the heterologous isoprene synthase nucleic acid is operably linked to an endogenous promoter, such as an endogenous alkaline serine protease promoter. In some embodiments, the heterologous isoprene synthase nucleic acid integrates into a chromosome of the cells without a selective marker.

In some embodiments, iron-sulfur cluster-interacting redox nucleic acid, any one or more of the nucleic acids in the DXP pathway, MVA pathway, and isoprene synthase nucleic acid are placed under the control of a promoter or factor that is more active in stationary phase than in the growth phase. In one embodiment, IDI nucleic acid is also included for IDI expression to produce a higher amount of isoprene than when IDI is not used. For example, one or more iron-sulfur cluster-interacting redox nucleic acid, DXP pathway nucleic acid, IDI nucleic acid, or isoprene synthase nucleic acid may be placed under control of a stationary phase sigma factor, such as RpoS. In some embodiments, one or more iron-sulfur cluster-interacting redox nucleic acid, DXP pathway nucleic acid, MVA pathway nucleic acid, IDI nucleic acid, or isoprene synthase nucleic acid are placed under control of a promoter inducible in stationary phase, such as a promoter inducible by a response regulator active in stationary phase.

In some embodiments of any of the aspects of the invention, cells expressing iron-sulfur cluster-interacting redox polypeptide, isoprene synthase polypeptide, and DXP pathway polypeptide are grown under non-inducing conditions. In some embodiments of any of the aspects of the invention, cells expressing iron-sulfur cluster-interacting redox polypeptide, DXP pathway polypeptide, IDI polypeptide, and isoprene synthase polypeptide are grown under non-inducing conditions. For example, the non-inducing condition is that IPTG-induced expression from the Trc promoter regulated gene constructs is not performed.

In some embodiments of any of the aspects of the invention, the cells express a second DXP pathway polypeptide, in addition to the first DXP pathway polypeptide, including DXS (1-deoxy-D-xylulose-5-phosphate synthase), DXR (1-deoxy-D-xylulose-5-phosphate reductoisomerase), MCT (4-diphosphocytidyl-2C-methyl-D-erythritol synthase), CMK (4-diphosphocytidyl-2-C-methyl-D-erythritol kinase), MCS (2C-methyl-D-erythritol 2,4-cyclodiphosphate synthase), HDS (1-hydroxy-2-methyl-2-(E)-butenyl 4-diphosphate synthase), and HDR (1-hydroxy-2-methyl-2-(E)-butenyl 4-diphosphate reductase). In some embodiments of any of the aspects of the invention, the cells express two or more DXP pathway polypeptides, in addition to the first DXP pathway polypeptide as described above. In some embodiments of any of the aspects of the invention, the cells express 2, 3, 4, 5, 6, or 7 DXP pathway polypeptides, in addition to the first DXP pathway polypeptide as described above.

In some embodiments of any of the aspects of the invention, the cells express a second MVA pathway polypeptide, in addition to the first MVA pathway polypeptide, including acetyl-CoA acetyltransferase (AA-CoA thiolase), 3-hydroxy-3-methylglutaryl-CoA synthase (HMG-CoA synthase), 3-hydroxy-3-methylglutaryl-CoA reductase (HMG-CoA reductase), mevalonate kinase (MVK), phosphomevalonate kinase (PMK), diphosphomevalonte decarboxylase (MVD), phosphomevalonate decarboxylase (PMDC) and isopentenyl phosphate kinase (IPK). In some embodiments of any of the aspects of the invention, the cells express two or more MVA pathway polypeptides, in addition to the first MVA pathway polypeptide as described above. In some embodiments of any of the aspects of the invention, the cells express 2, 3, 4, 5, 6, or 7 MVA pathway polypeptides, in addition to the first MVA pathway polypeptide as described above.

In some embodiments of any of the aspects of the invention, at least a portion of the cells maintain the heterologous iron-sulfur cluster-interacting redox nucleic acid, DXP pathway nucleic acid, and isoprene synthase nucleic acid for at least or about 5, 10, 20, 40, 50, 60, 65, or more cell divisions in a continuous culture (such as a continuous culture without dilution). In some embodiments of any of the aspects of the invention, at least a portion of the cells maintain the heterologous iron-sulfur cluster-interacting redox nucleic acid, IDI nucleic acid, DXP pathway nucleic acid, and isoprene synthase nucleic acid for at least or about 5, 10, 20, 40, 50, 60, 65, or more cell divisions in a continuous culture (such as a continuous culture without dilution). In some embodiments of any of the aspects of the invention, at least a portion of the cells maintain the heterologous isoprene synthase nucleic acid, DXS nucleic acid, IDI nucleic acid, and iron-sulfur cluster-interacting redox nucleic acid for at least or about 5, 10, 20, 40, 50, 60, 65, or more cell divisions in a continuous culture (such as a continuous culture without dilution). In some embodiments of any of the aspects of the invention, the nucleic acid comprising the iron-sulfur cluster-interacting redox nucleic acid, isoprene synthase nucleic acid, DXP pathway nucleic acid, and/or IDI nucleic acid also comprises a selective marker, such as an antibiotic resistance nucleic acid.

In some embodiments of any of the aspects of the invention, the isoprene synthase polypeptide is a polypeptide from a plant such as *Pueraria* (e.g., *Pueraria montana* or *Pueraria lobata*) or *Populus* (e.g., *Populus tremuloides, Populus alba, Populus nigra, Populus trichocarpa*, or the hybrid, *Populus alba*×*Populus tremula*).

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans, Streptomyces coelicolor*, or *Streptomyces griseus* cells) or cyanobacterial cells (e.g., *Thermosynechococcus* cells such as *Thermosynechococcus elongates* cells). In some embodiments of any of the aspects of the invention, the cells are gram-negative bacterial cells (e.g., *Escherichia* cells such as *Escherichia coli* cells or *Pantoea* cells such as *Pantoea citrea* cells) or cyanobacterial cells (e.g., *Thermosynechococcus* cells such as *Thermosynechococcus elongates* cells). In some embodiments of any of the aspects of the invention, the cells are fungal, cells such as filamentous fungal cells (e.g., *Trichoderma* cells such as *Trichoderma reesei* cells or *Aspergillus* cells such as *Aspergillus oryzae* and *Aspergillus niger*), or yeast cells (e.g., *Yarrowia* cells such as *Yarrowia lipolytica* cells).

In some embodiments of any of the aspects of the invention, the microbial polypeptide carbon source includes one or more polypeptides from yeast or bacteria. In some embodiments of any of the aspects of the invention, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

In one aspect, the invention features a product produced by any of the compositions or methods of the invention.

BRIEF DESCRIPTION OF THE DRAWINGS

FIG. 1 is the nucleotide sequence of a kudzu isoprene synthase gene codon-optimized for expression in *E. coli* (SEQ ID NO:1). The atg start codon is in italics, the stop codon is in bold and the added PstI site is underlined.

FIGS. 3A-3C is the nucleotide sequence of pTrcKudzu (SEQ ID NO:2). The RBS is underlined, the kudzu isoprene synthase start codon is in bold capitol letters and the stop codon is in bold, capitol, italics letters. The vector backbone is pTrcHis2B.

FIGS. 5A-5C is the nucleotide sequence of pETNHisKudzu (SEQ ID NO:5).

FIGS. 7A-7C is the nucleotide sequence of pCL-lac-Kudzu (SEQ ID NO:7).

FIG. 9A is a graph showing OD over time of fermentation of *E. coli* BL21/pTrcKudzu in a 14 liter fed batch fermentation.

FIG. 9B is a graph showing isoprene production over time of fermentation of *E. coli* BL21/pTrcKudzu in a 14 liter fed batch fermentation.

FIGS. 12A-12C is the nucleotide sequence of pBS Kudzu #2 (SEQ ID NO:56).

FIG. 13 is the nucleotide sequence of kudzu isoprene synthase codon-optimized for expression in *Yarrowia* (SEQ ID NO:8).

FIGS. 15A-15C is the nucleotide sequence of vector pSPZ1(MAP29Spb) (SEQ ID NO:11).

FIG. 16 is the nucleotide sequence of the synthetic kudzu (*Pueraria montana*) isoprene gene codon-optimized for expression in *Yarrowia* (SEQ ID NO:12).

FIG. 17 is the nucleotide sequence of the synthetic hybrid poplar (*Populus alba×Populus tremula*) isoprene synthase gene (SEQ ID NO:13). The ATG start codon is in bold and the stop codon is underlined.

FIGS. 18A1-18A2 shows a schematic outlining construction of vectors pYLA 1, pYL1 and pYL2 (SEQ ID NOS: 44, 45, 46, 47, 48 and 50).

FIG. 20 shows graphs representing results of the GC-MS analysis of isoprene production by recombinant *Y. lipolytica* strains without (left) or with (right) a kudzu isoprene synthase gene. The arrows indicate the elution time of the authentic isoprene standard.

FIGS. 22A-22D is the nucleotide sequence of pTrcKudzu yIDI DXS Kan (SEQ ID NO:20).

FIGS. 25A-25B is a nucleotide sequence of p9796-poplar (SEQ ID NO:21).

FIGS. 27A-27C is a nucleotide sequence of pTrcPoplar (SEQ ID NO:22).

FIGS. 29A-29C is a nucleotide sequence of pTrcKudzu yIDI Kan (SEQ ID NO:23).

FIGS. 31A-31C is a nucleotide sequence of pTrcKudzuDXS Kan (SEQ ID NO:24).

FIGS. 33A-33C is a nucleotide sequence of pCL PtrcKudzu (SEQ ID NO:25).

FIGS. 35A-35C is a nucleotide sequence of pCL PtrcKudzu A3 (SEQ ID NO:26).

FIGS. 37A-37C is a nucleotide sequence of pCL PtrcKudzu yIDI (SEQ ID NO:27).

FIGS. 39A-39D is a nucleotide sequence of pCL PtrcKudzu DXS (SEQ ID NO:28).

FIGS. 46F and 46G are the nucleotide sequence of pBAD33 (SEQ ID NO:51).

FIGS. 46I and 46J are the nucleotide sequence of pTrcHgS-pBAD33 (SEQ ID NO:52).

FIGS. 46L and 46M are the nucleotide sequence of pTrcHgSfldA-pBAD33 (SEQ ID NO:53).

FIGS. 55A-55C are the nucleotide sequence of T7-MEARR alba/pBBR1MCS-5 (SEQ ID NO:73).

FIGS. 56A-56B are the nucleotide sequence of Ptac-gcpE-petF-petH/pK184 (SEQ ID NO:74).

FIGS. 57A-57C are the nucleotide sequence of T7-(−3_alba/pBBR1MCS-5 (SEQ ID NO:75).

FIGS. 58A-58C are the nucleotide sequence of T7-MTE alba/pBBR1MCS-5 (SEQ ID NO:76).

FIGS. 59A-59B are the nucleotide sequence of Ptab-gcpE-LytB-petF-petH/pK184 (SEQ ID NO:77).

FIG. 63 is a cartoon representation of the DXP operon pET24a.

FIGS. 64A-64C are the nucleotide sequence of T7-MEARR alba/pBBR1MCS-5 (SEQ ID NO:78).

FIGS. 65A-65D are the nucleotide sequence of DXP operon pETt24a (SEQ ID NO:79).

FIGS. 71A-71B are the nucleotide sequence of pDu-39 (SEQ ID NO:108).

FIGS. 72A-72C are the nucleotide sequence of MCM596 (SEQ ID NO:109).

FIGS. 73A-C are the nucleotide sequence of pMCM596 (SEQ ID NO:110).

FIG. 74 shows comparison of DXS sequences in microorganisms synthesizing isoprenoids via the DXP pathway (*E. coli, Chlorobium tepidum* TLS, *Synechocystis* sp. PCC6803, *Gloeobacter violaceus* PCC 7421, *Clostridium botulinum* B1 str. Okra, *Mycobacterium tuberculosis* CDC1551) and via the MVA pathway (*Myxococcus xanthus* DK 1622, *Gramella forsetii* KT0803, *Flavobacterium johnsoniae* UW 101, *Lactobacillus johnsonii* NCC 533, *Lactobacillus gasseri* ATCC 33323, and *Lactococcus lactis* subsp. *lactis* I11403). Note the difference in amino acid sequence at positions 200-260 in the two groups of microorganisms.

FIGS. 75A and 75B are the nucleotide sequence of pDU-9 (SEQ ID NO: 192).

FIGS. 79A, 79B, 79C, 79D, and 79E) shows the results of 15-L scale fermentation comparison of strains CMP272, REMG39, and REM H8_12 for growth, isoprene production, and product yield on carbon. Panel (A) isoprene titer (g/L broth); Panel (B) specific productivity of isoprene generating cultures; Panel (C) cell growth depicted by optical density (550 nm); Panel (D) cell growth shown by respiration (carbon evolution rate, CER); Panel (E) overall percent yield of product from carbon (weight in grams of isoprene/weight in grams of carbon fed*100). The fermentation conditions are described in Example 24 Section F (CMP272), G (REMG39), and Example 29 Section E (REM H8_12).

FIGS. 81A and 81B) depicts one strategy for inserting GI1.X fldA into the BL21 (DE3) chromosome. Panel (A) The endogenous 150 bp BL21 (DE3) fldA locus is shown. The regions of homology within the GI1.X fldA PCR fragment to the desired 5' and 3' integration sites on the chromosome are depicted as gray block arrows.

The half-arrowhead lines show where the PCR primers used to verify the construct anneal to the chromosome. The ribosome binding site (RBS), start codon of the encoded fldA mRNA, and the endogenous DNA upstream of the fldA to be replaced by the GI1.X proter series is shown. Panel (B) The 313 bp BL21 (DE3) GI1.X fldA region generated via Gene Bridges methods (GI1.6 fldA of strain REM I6_4) is shown. The inserted GI1.X promoter sequence(s) is illustrated as a black block arrow; the placement of the FTR scar sequences generated from use of the Gene Bridges insertion method is indicated.

Figure 82:
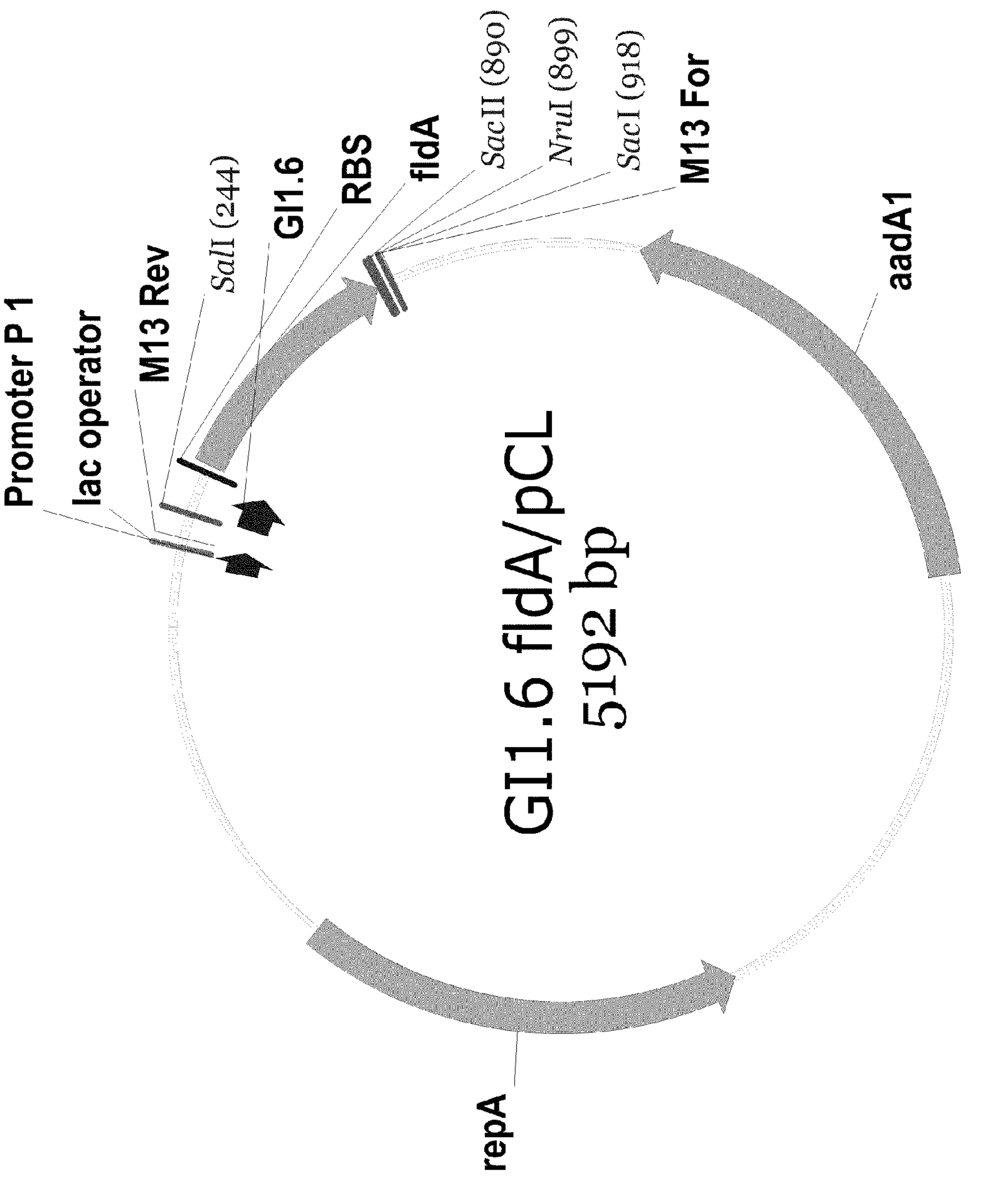

FIG. 82 depicts a plasmid map of GI1.6fldA/pCL. repA—plasmid replication protein; aad—aminoglycoside adenyltransferase; M13 for and M13 rev—binding sites for the respective primers; RBS—ribosome binding site; fldA—*E. coli* fldA gene.

Figure 83:
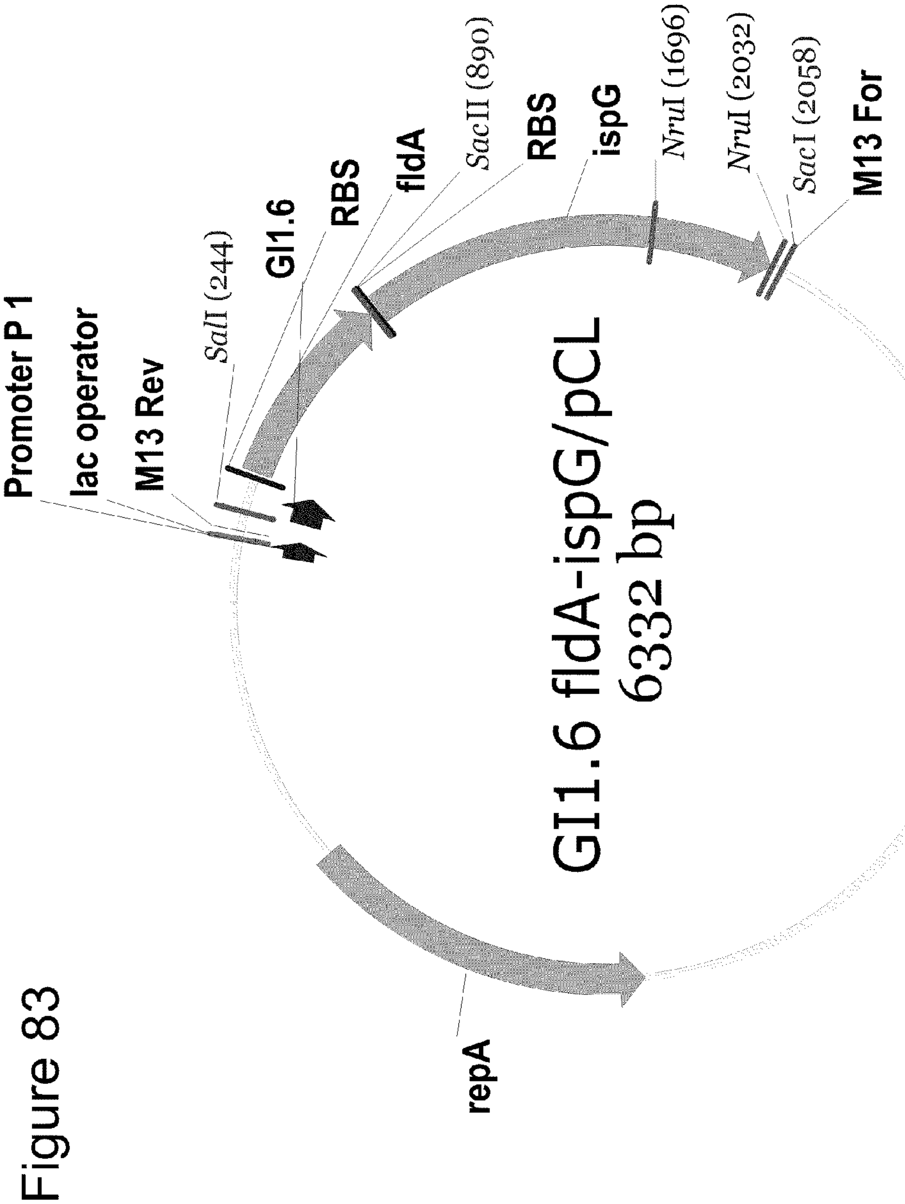

FIG. 83 depicts a plasmid map of GI1.6fldA-IspG/pCL. Same plasmid base as in FIG. 82: FldA—*E. coli* fldA gene; IspG—*E. coli* ispG gene.

Figure 84:
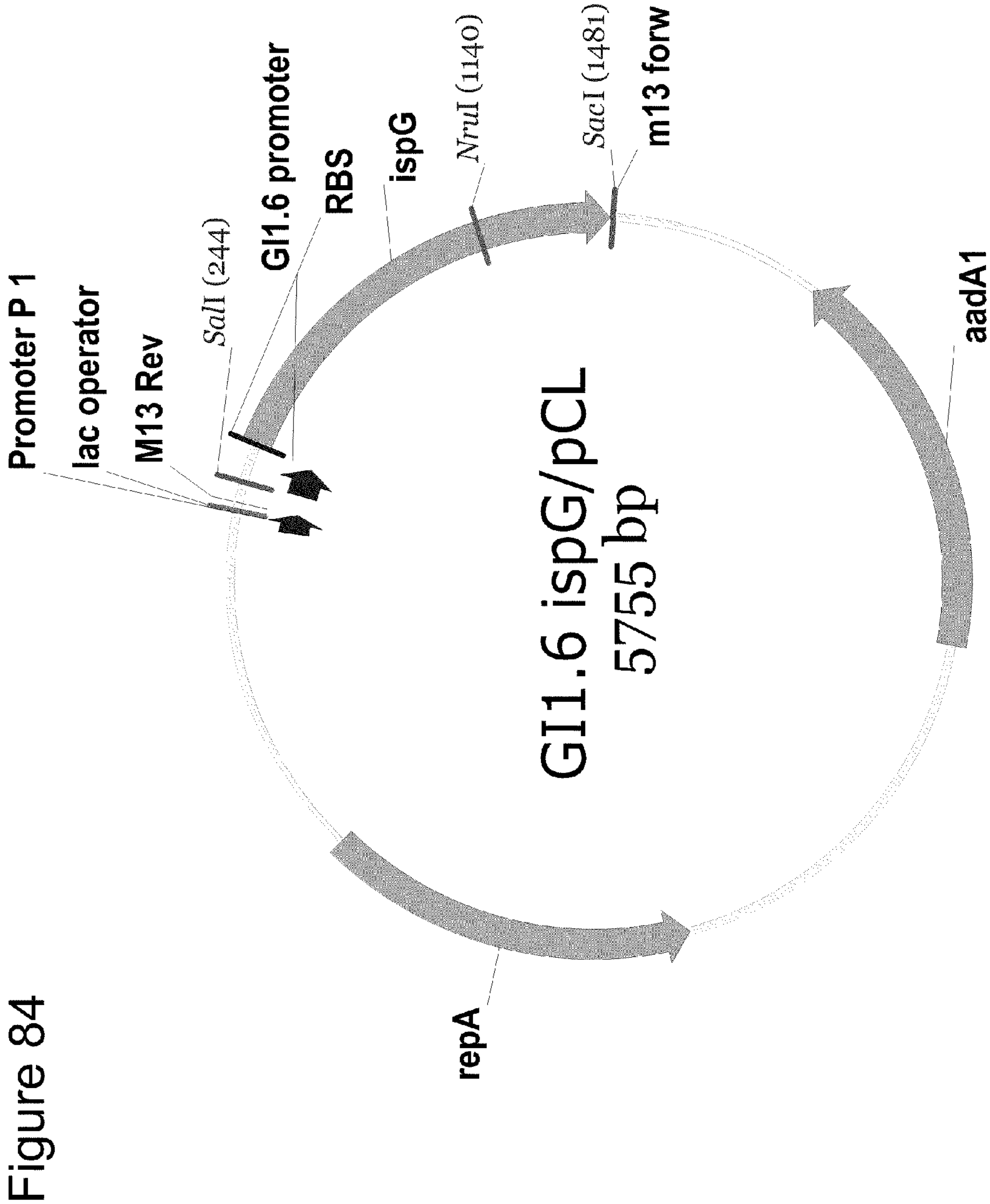

FIG. 84 depicts a plasmid map of GI1.6IspG/pCL. Same plasmid base as FIGS. 82 and 83: IspG—*E. coli* ispG gene.

Figure 85A:
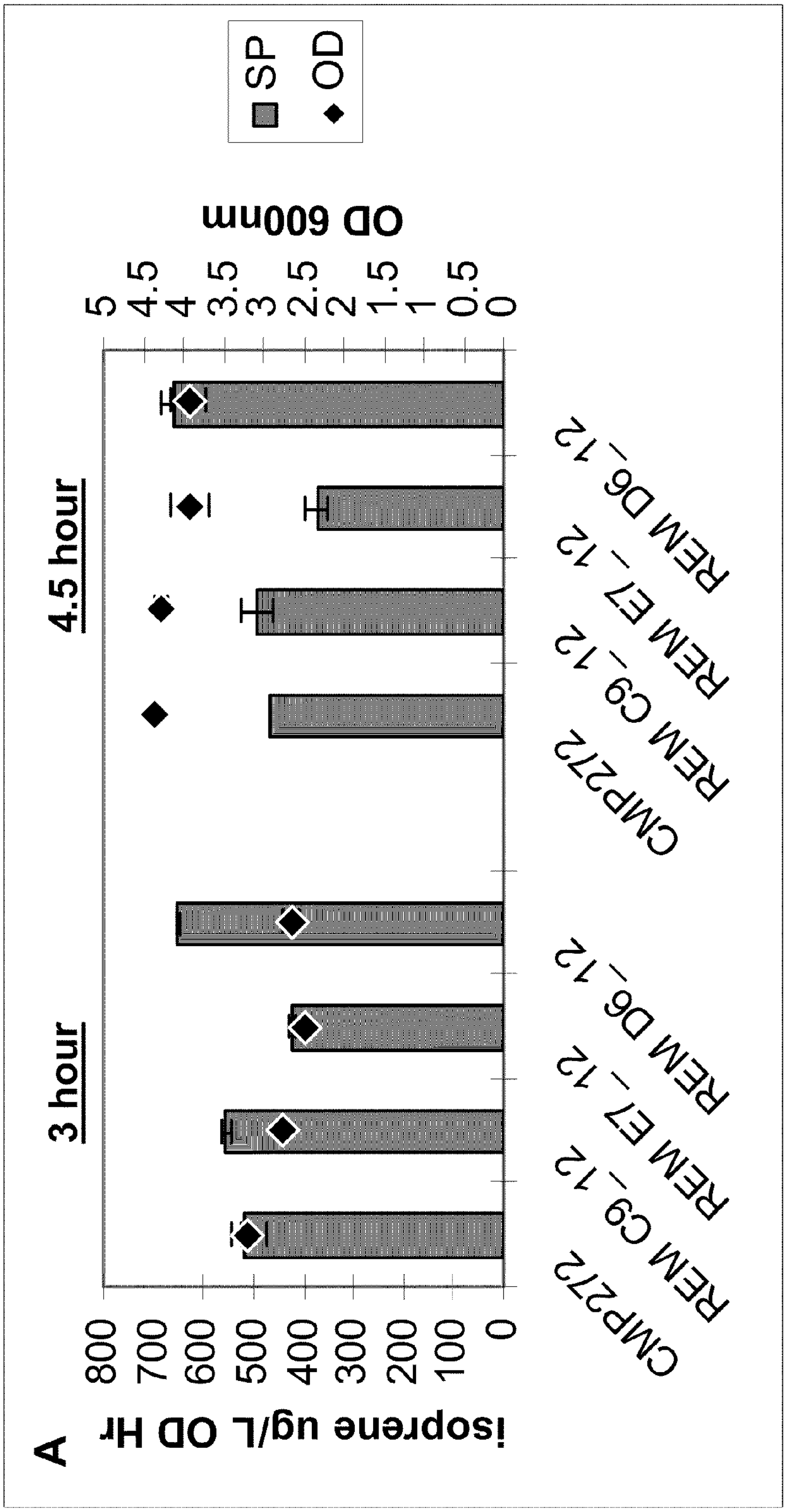
Figure 85B:
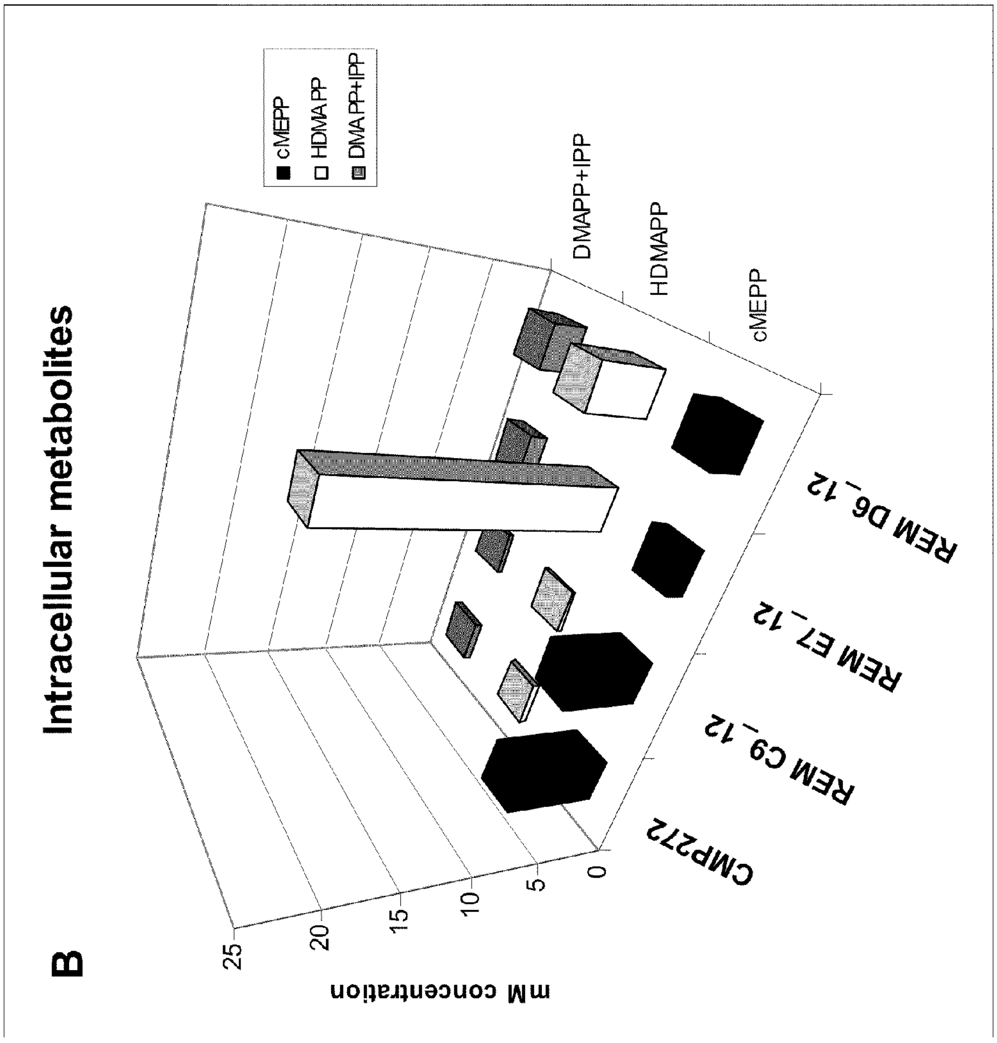

FIG. 85 (includes two panels, FIGS. 85A and 85B) depicts small scale comparison of strains, REMC9_12, REME7_12, and REMD6_12. Panel (A) Specific productivity (SP) of isoprene production relative to growth. The y1 axis, specific productivity of isoprene production (ug/L/OD/hr); y2 axis, cell density ($OD_{600}$). Specific productivity (solid bars) and $OD_{600}$ (diamonds). Measurements were taken at 3 and 4.5 h post-induction (600 uM IPTG) from at least 2 biological replicates. Panel (B) Intracellular metabolite concentrations. cMEPP: 2-C-methyl-D-erythritol 2,4-cyclodiphosphate; HDMAPP—hydroxydimethylallyl diphosphate; DMAPP—dimethylallyl diphosphate; IPP—isopentenyl diphosphate. Y-axis: metabolite concentration in mM. Measurements shown were taken at 3.75 h post-induction (600 uM IPTG); separate experimental samples from (A); replicates produced similar results.

Figure 86A:
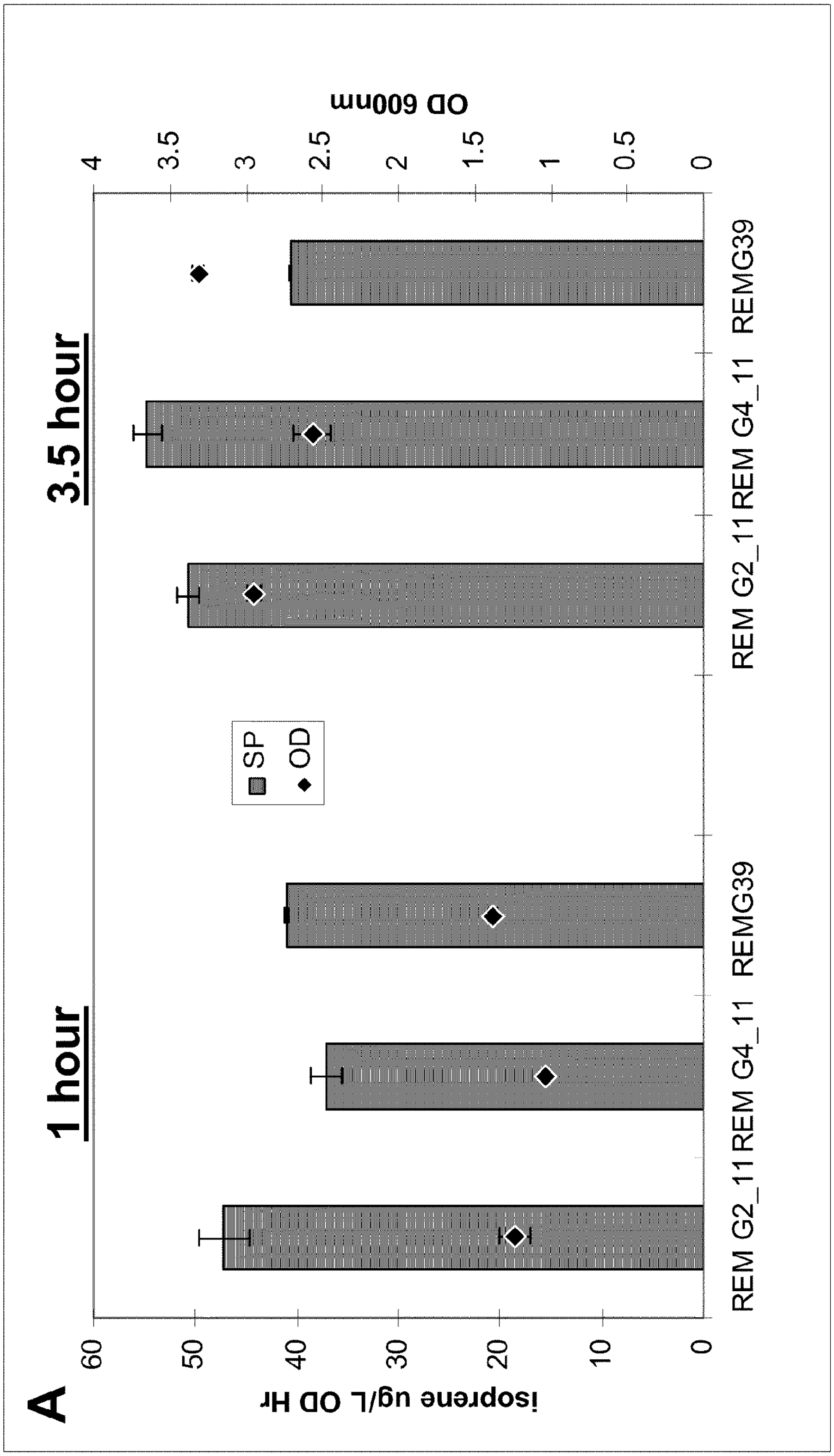
Figure 86B:
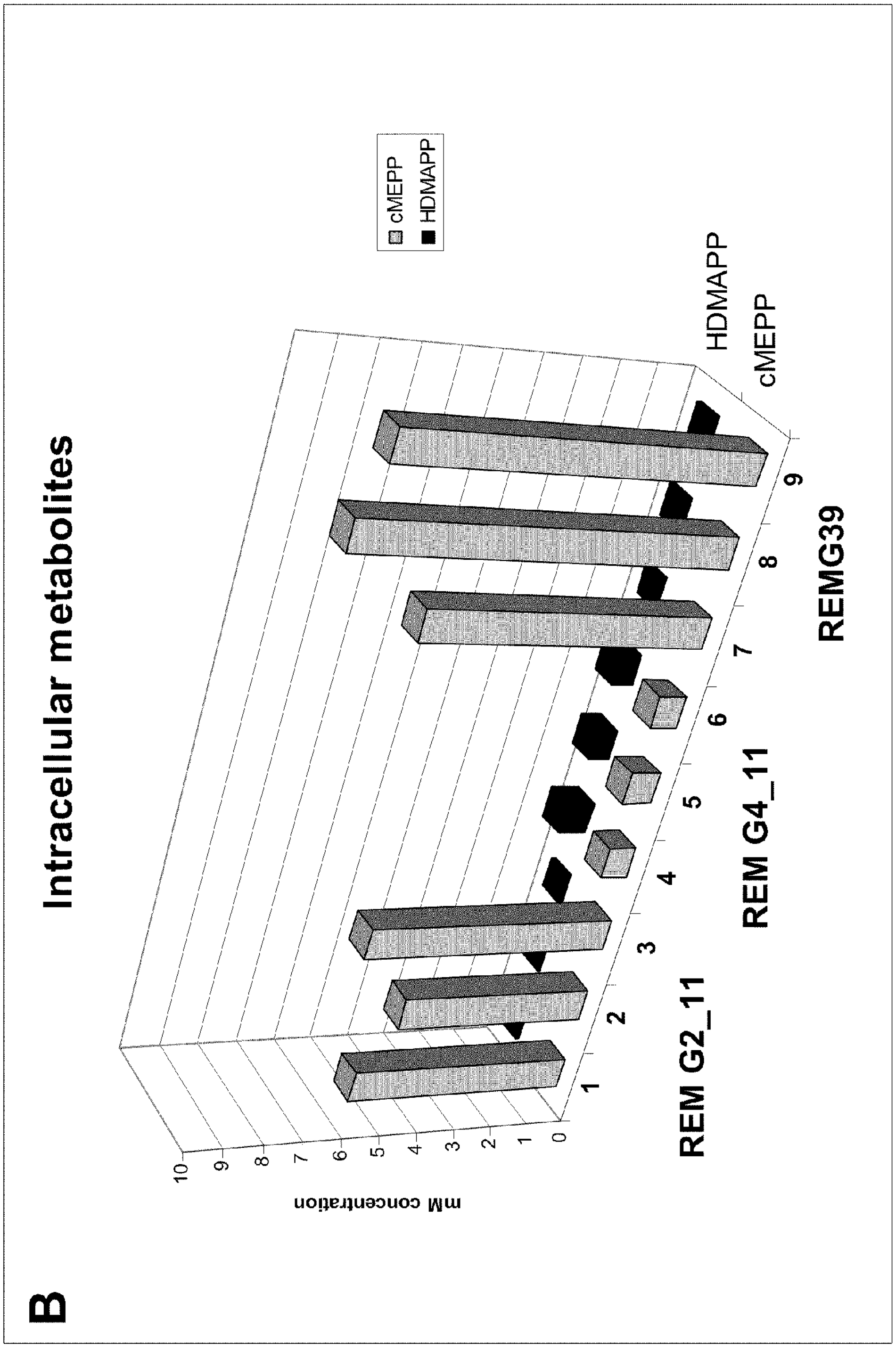

FIG. 86 (includes two panels: FIGS. 86A and 86B) shows the results of small scale comparisons of strains REMG2_11, REMG4_11 and REMG39. Panel (A) Specific productivity of isoprene production relative to growth of. The y1 axis, specific productivity of isoprene production (ug/L/OD/hr); y2 axis, cell density ($OD_{600}$). Specific productivity (solid bars) and OD600 (diamonds). Measurements are shown at 1 and 3.5 h post-induction (400 uM IPTG) from at least 2 biological replicates. Panel (B) Intracellular metabolite concentrations of strains. The y-axis is metabolite concentration in mM. cMEPP: 2-C-methyl-D-erythritol 2,4-cyclodiphosphate; HDMAPP-hydroxydimethylallyl diphosphate. Measurements are shown for the 3.5 h post-induction (400 uM IPTG) samples from (A); replicates produced similar results (rows 1-3: REM G2_11; rows 4-6: REM G4_11; rows 7-9: REMG39).

Figure 87:
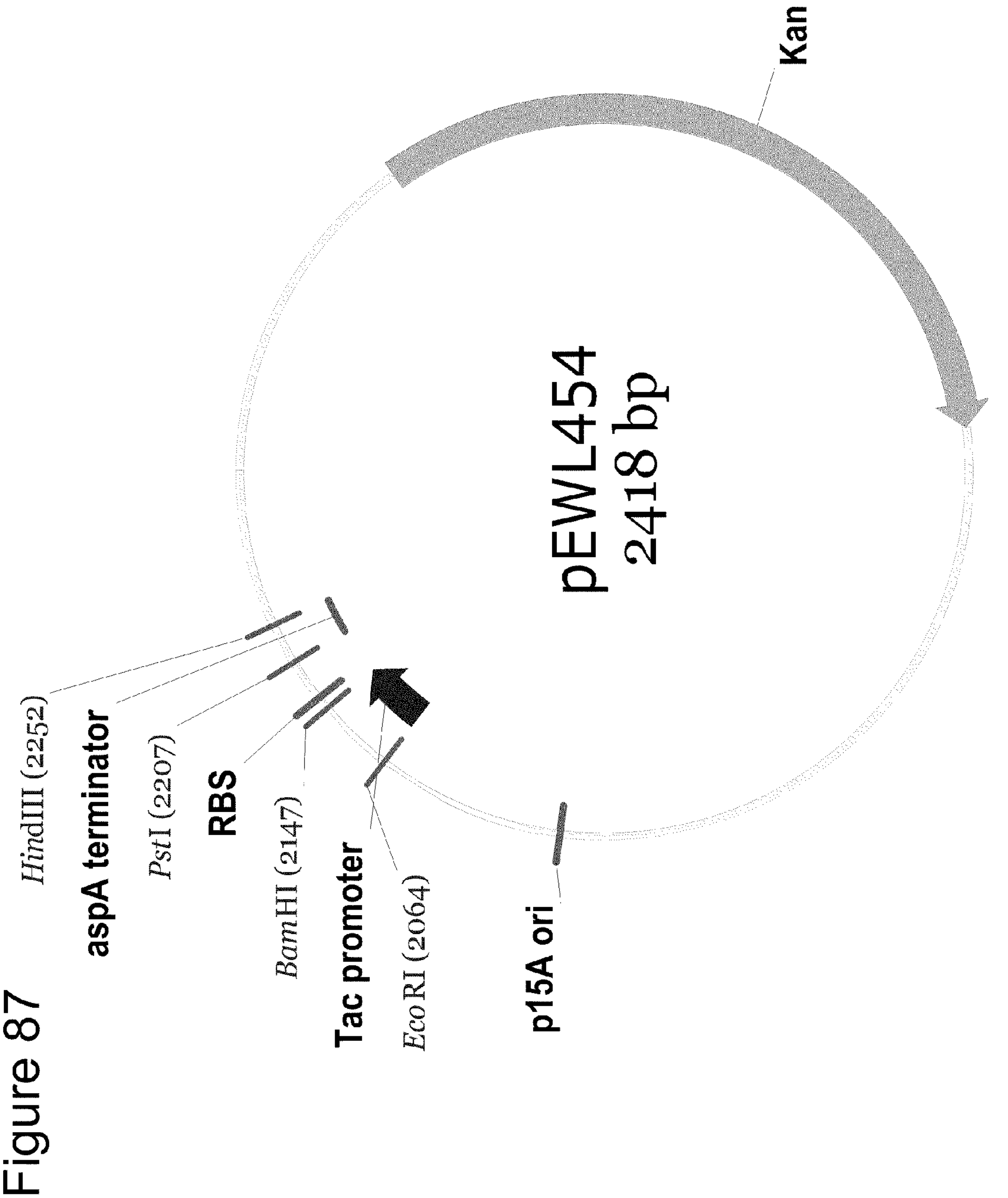

FIG. 87 depicts a plasmid map of pEWL454. The plasmid base is pK184. p15A ori—plasmid origin of replication; RBS—ribosome binding site; kan—kanamycin antibiotic resistance marker.

Figure 88:
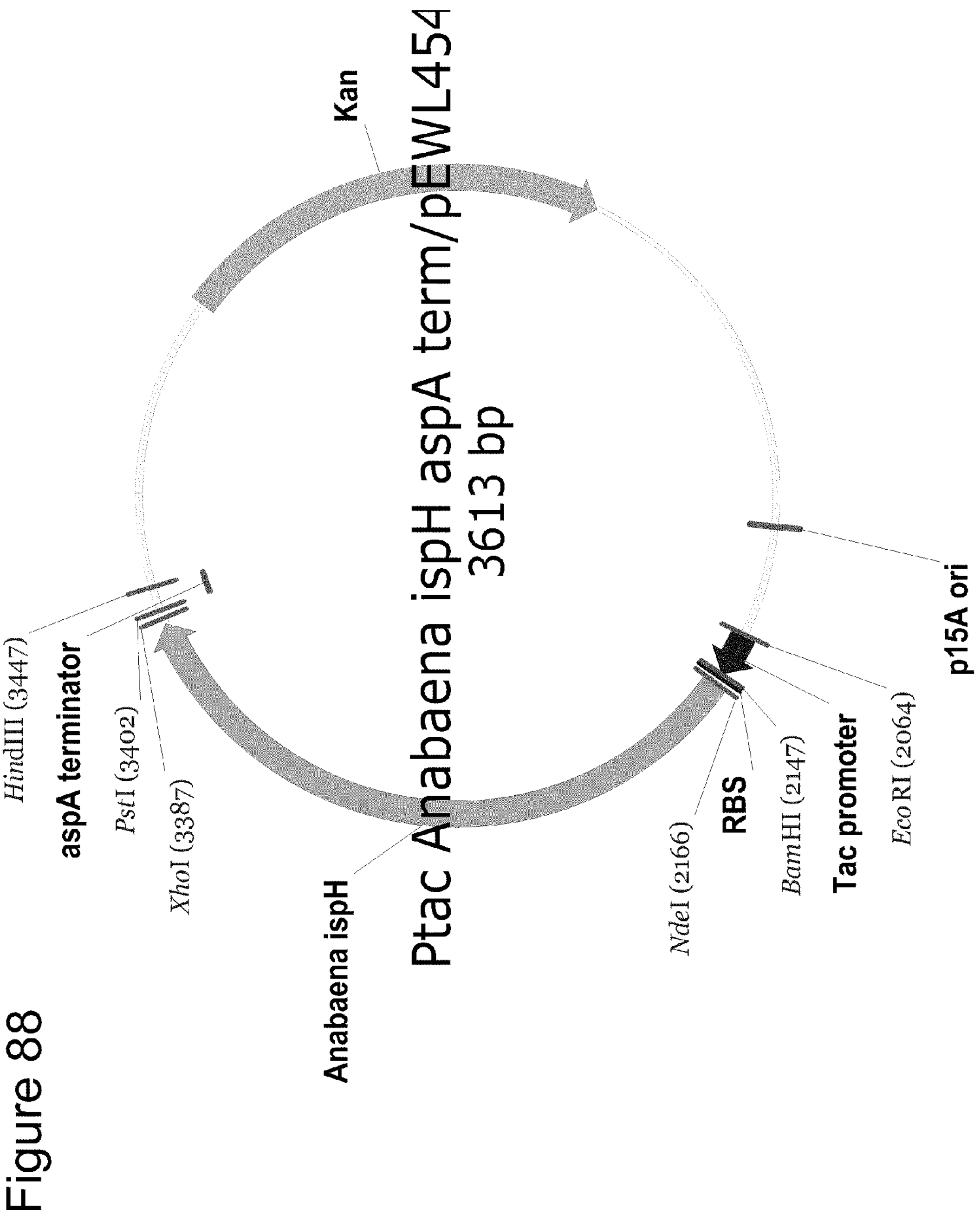

FIG. 88 depicts a plasmid map of PtacAnabaenaAspA terminator/pEWL454. This is the same plasmid base as in FIG. 87. Anabaena IspH—gene encoding the IspH enzyme from Anabaena.

Figure 89:
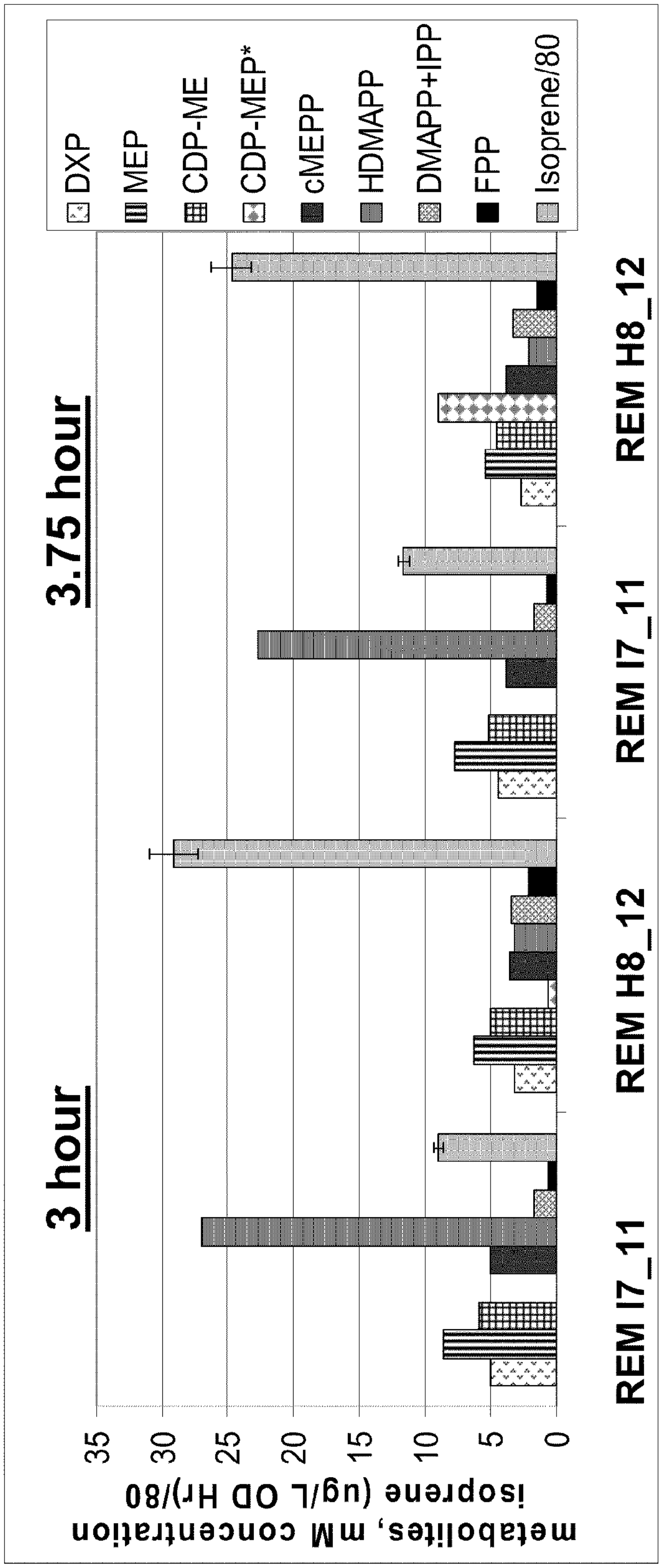

FIG. 89 depicts the specific productivity of isoprene production and intracellular metabolites of strains REMI7_11, and REMH8_12. The two strains were compared at 3 and 3.75 h following induction (500 uM IPTG). Isoprene measurements are shown from at least 2 biological replicates; replicates are not shown for the metabolite data, but produced similar results.

Figure 90A:
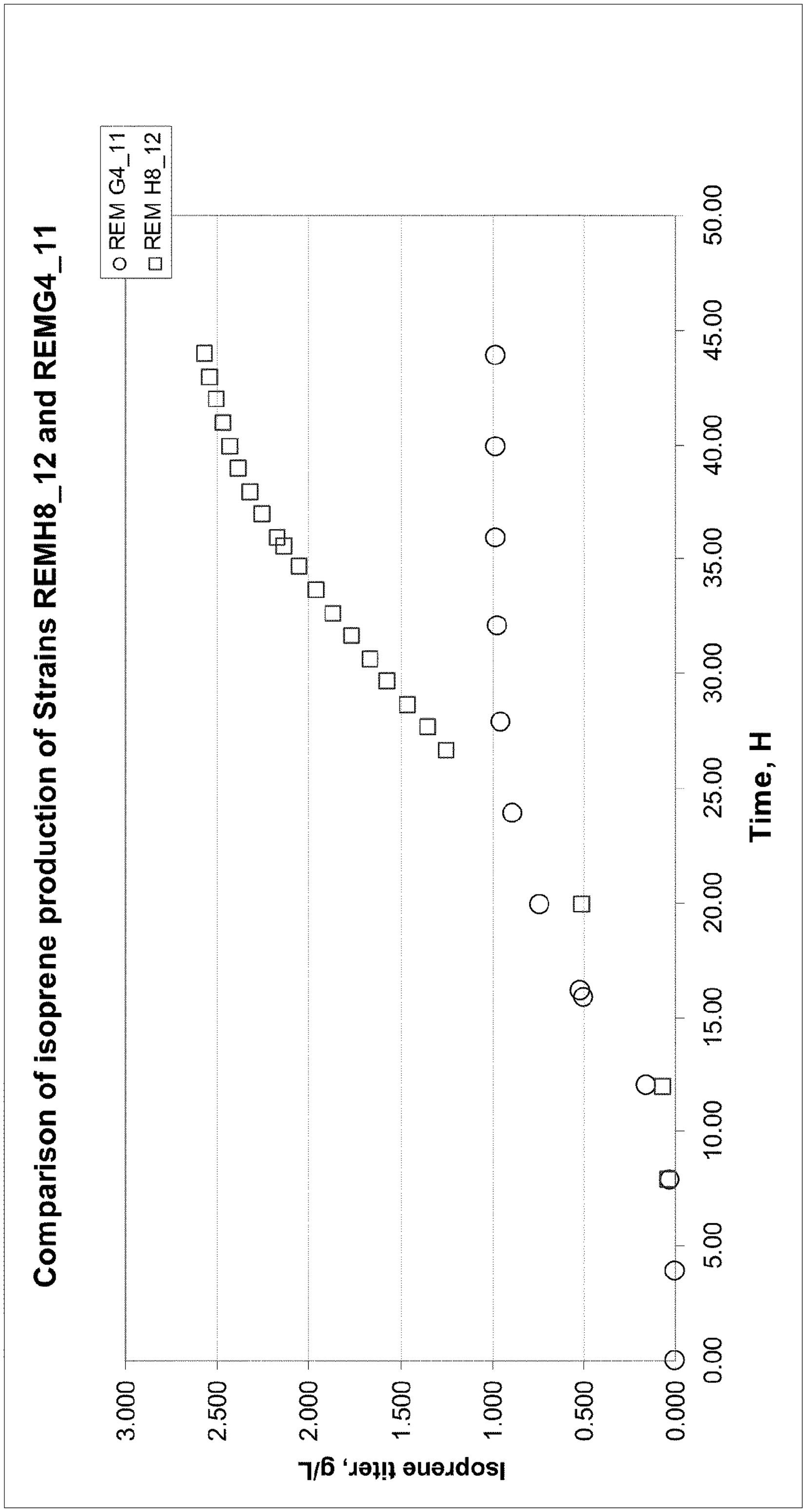
Figure 90B:
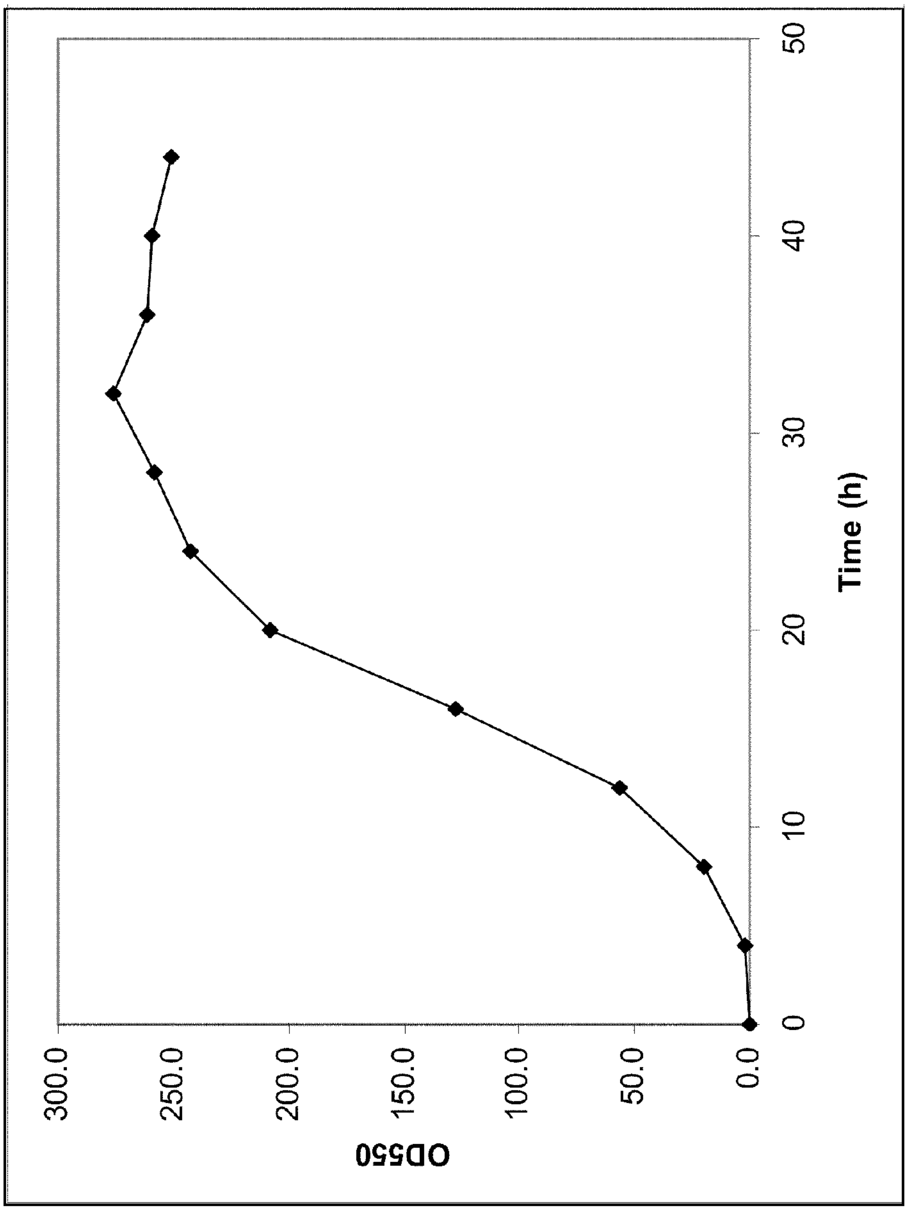
Figure 90C:
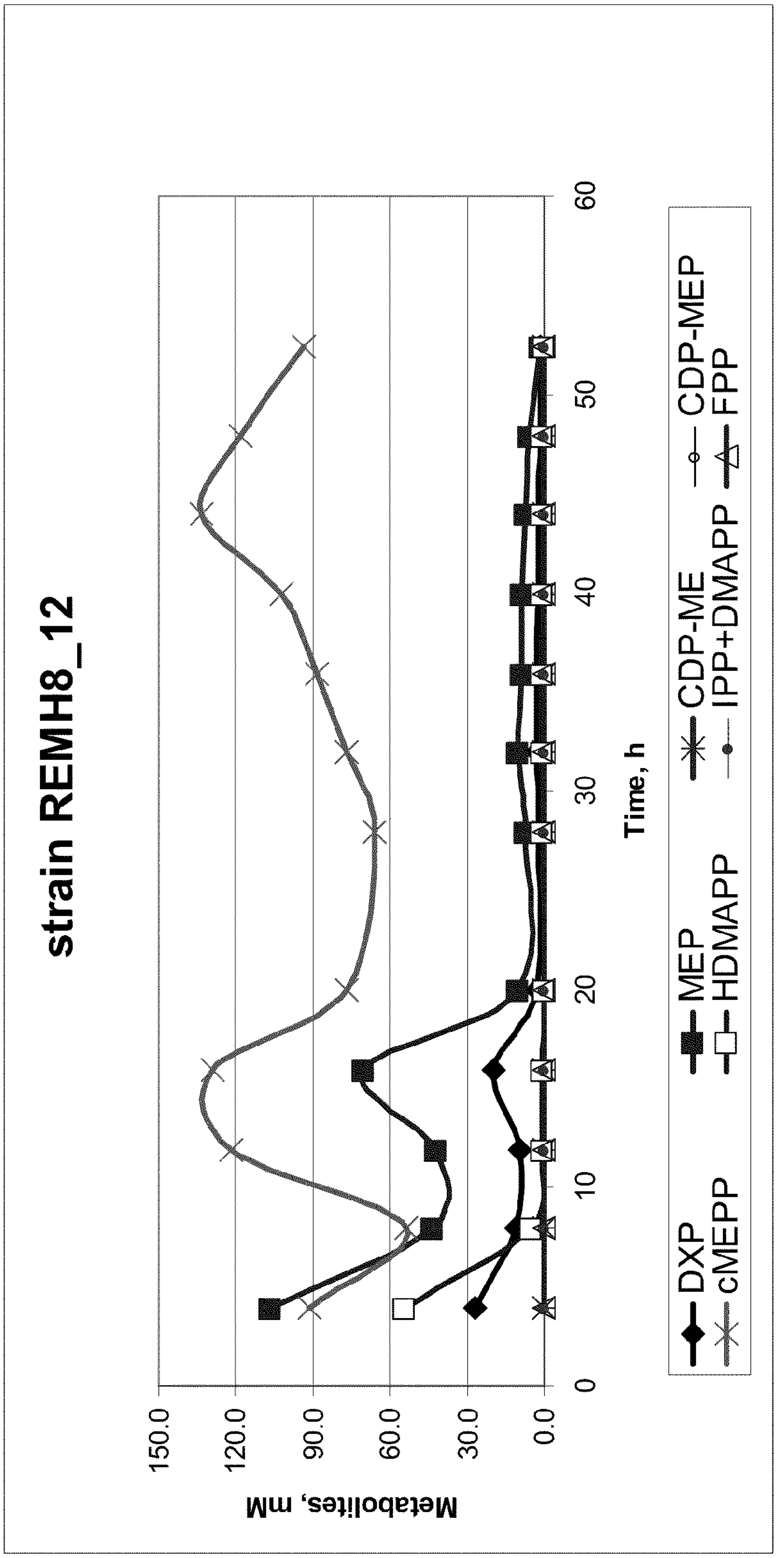

FIG. 90 (includes three panels: FIG. 90A, 90B and 90C) depicts the results from a 15-L scale fermentation of strain REM H8_12 and REM G4_11 (A). Panel (A) isoprene titer (g/L broth) for REMH 8_12 (open squares) and REM G4_11 (open circles); Panel (B) cell growth depicted by optical density (550 nm); Panel (C) DXP metabolites. A legend describing the metabolite profiles is shown at the bottom of (C); see FIG. 80 for metabolite descriptions.

Figure 91:
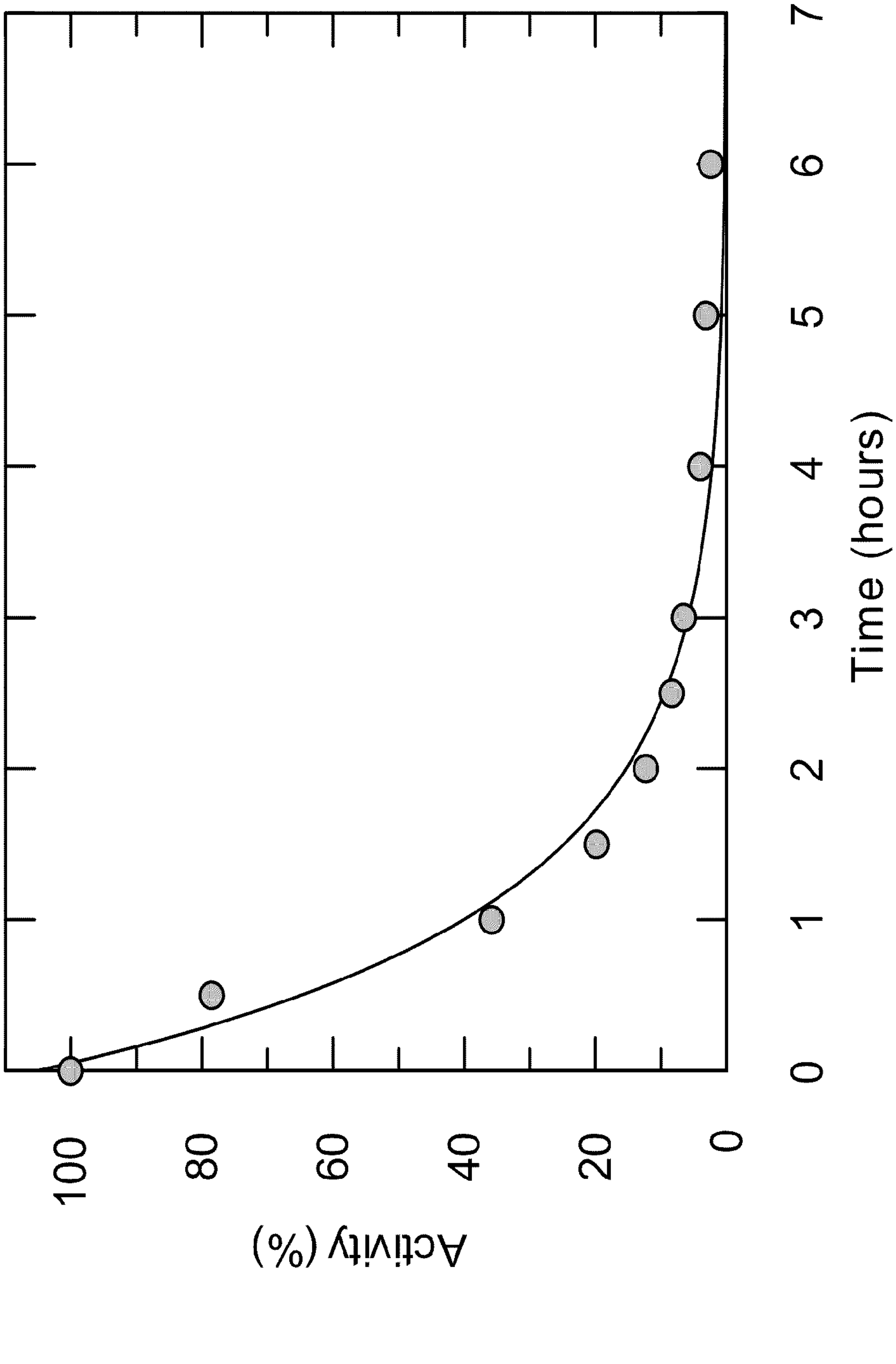

FIG. 91 depicts results from a preparative scale inactivation of Dxr by DMAPP.

Figure 92A:
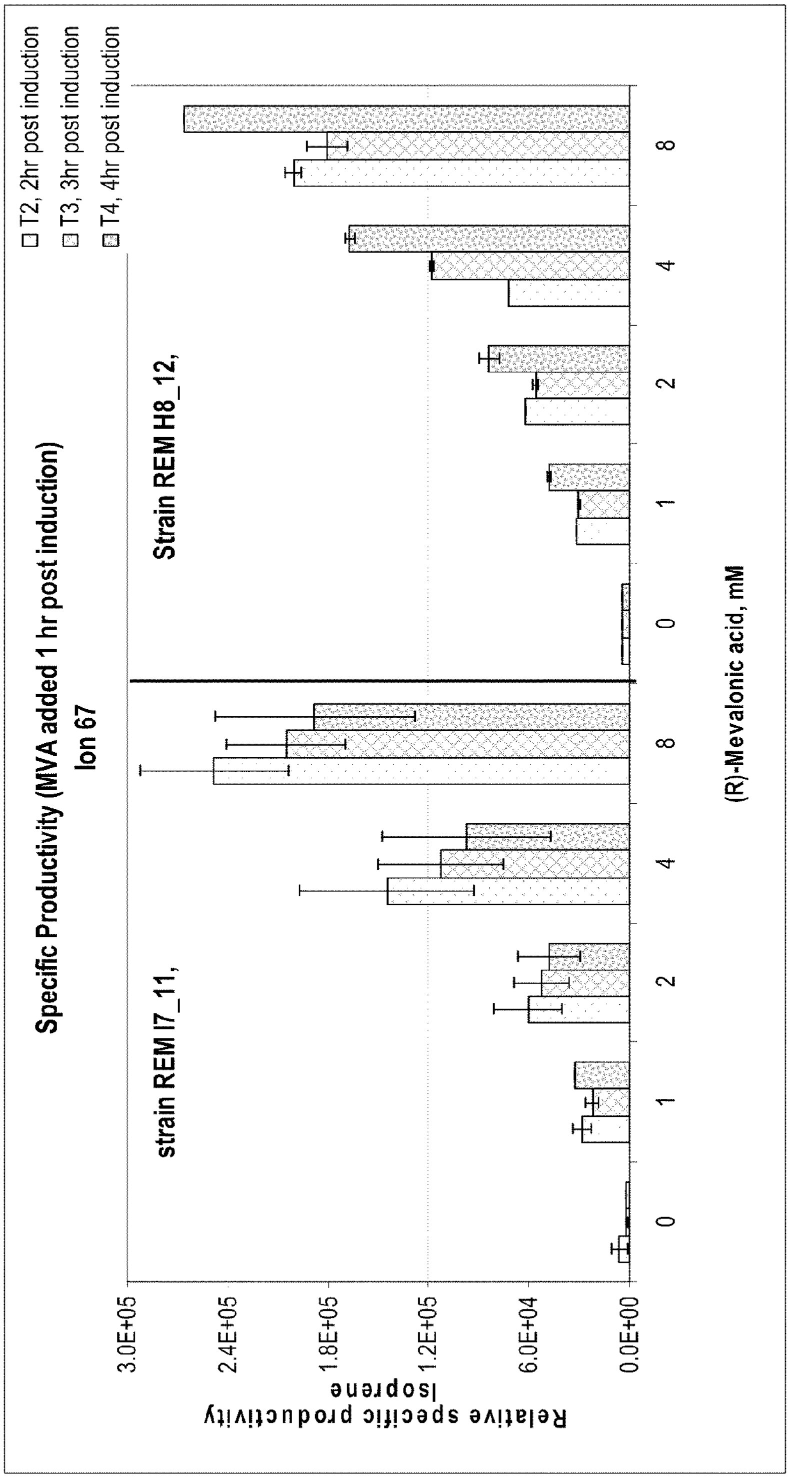
Figure 92B:
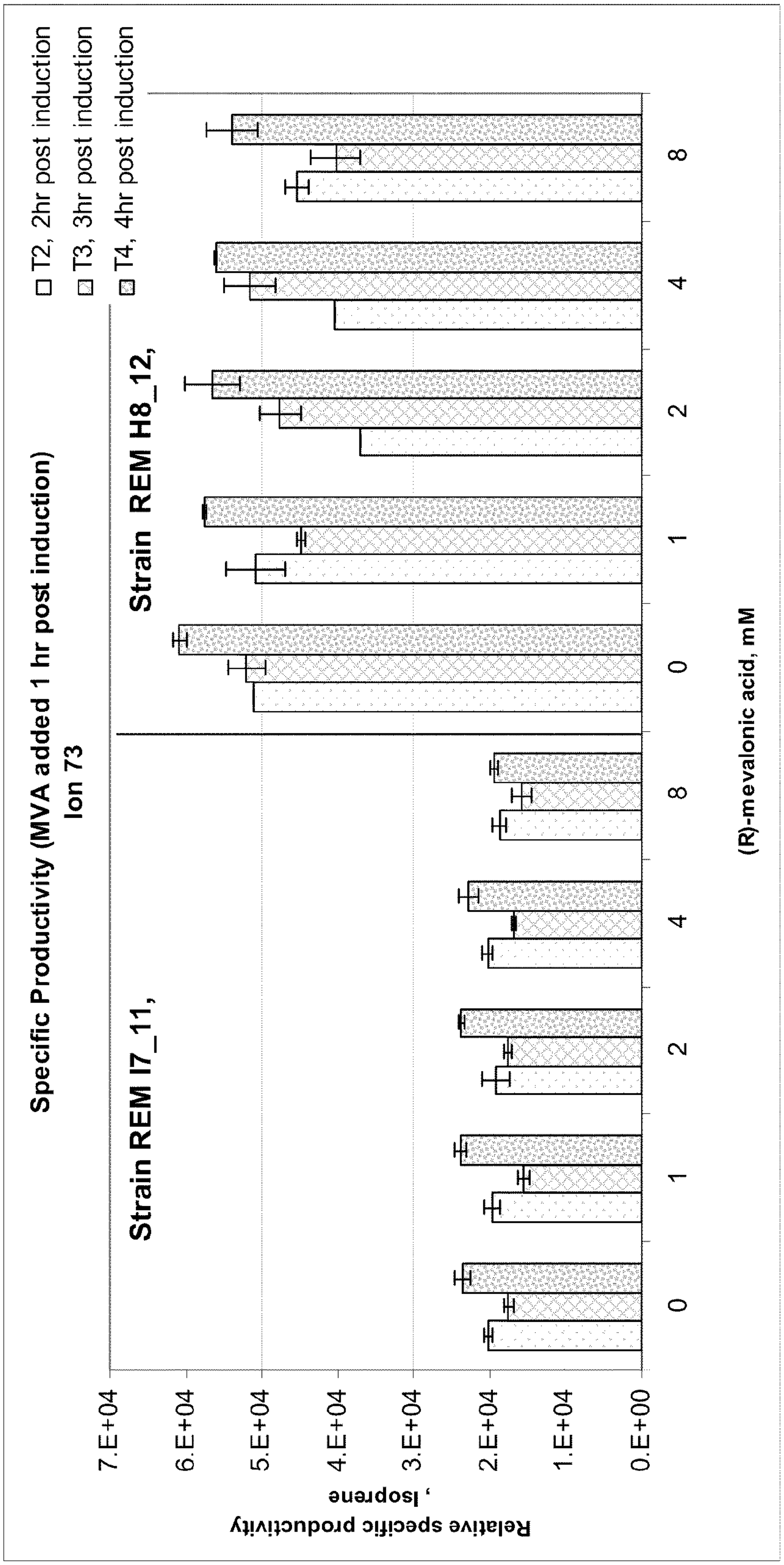

FIG. 92 (includes two panels: 92A and 92B) depicts isoprene production by strains REM H8_12 and REM I7_11 harboring an engineered DXP pathway and a lower MVA pathways. The top panel shows isoprene production specifically due to MVA fed at indicated concentrations to cultures grown on [U—$^{13}$C]-glucose. The lower panel shows isoprene production specifically arising from [U—$^{13}$C]-glucose]. Isoprene measurements were taken at indicated times after induction of the cultures with IPTG. Isoprene evolved was monitored by GC-MS with detection at m/z=67 as well as m/z=73. While m/z=67 reports on isoprene from MVA (all $^{12}$C), m/z=73 reports on isoprene derived from [U—$^{13}$C]-glucose.

Figure 93:
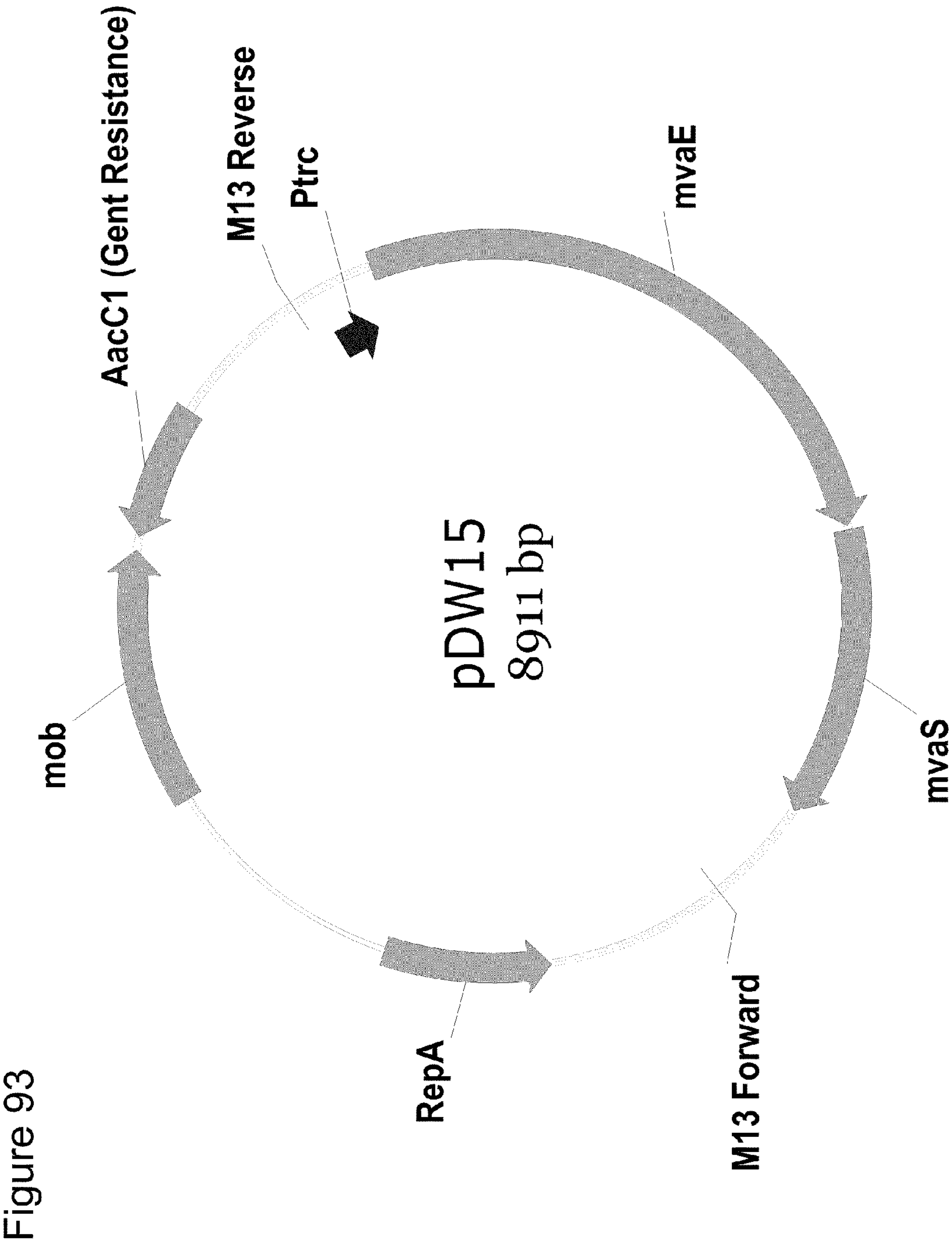

FIG. 93 depicts a plasmid map of pDW15. mob—plasmid mobilization region; AacC1 (Gent Resistance)—aminoglycoside acetyltransferase, gentamicin resistance gene; M13 Reverse and M13 Forward—binding sites for the respective primers; Ptrc, Trc promoter; mvaE and mvaS—*E. faecalis* genes encoding the Acetoacetyl-Coenzyme A Thiolase/3-Hydroxy-3-Methylglutaryl-Coenzyme A Reductase and 3-Hydroxy-3-Methylglutaryl-Coenzyme A Synthase, respectively; RepA—plasmid replication protein.

Figure 94:
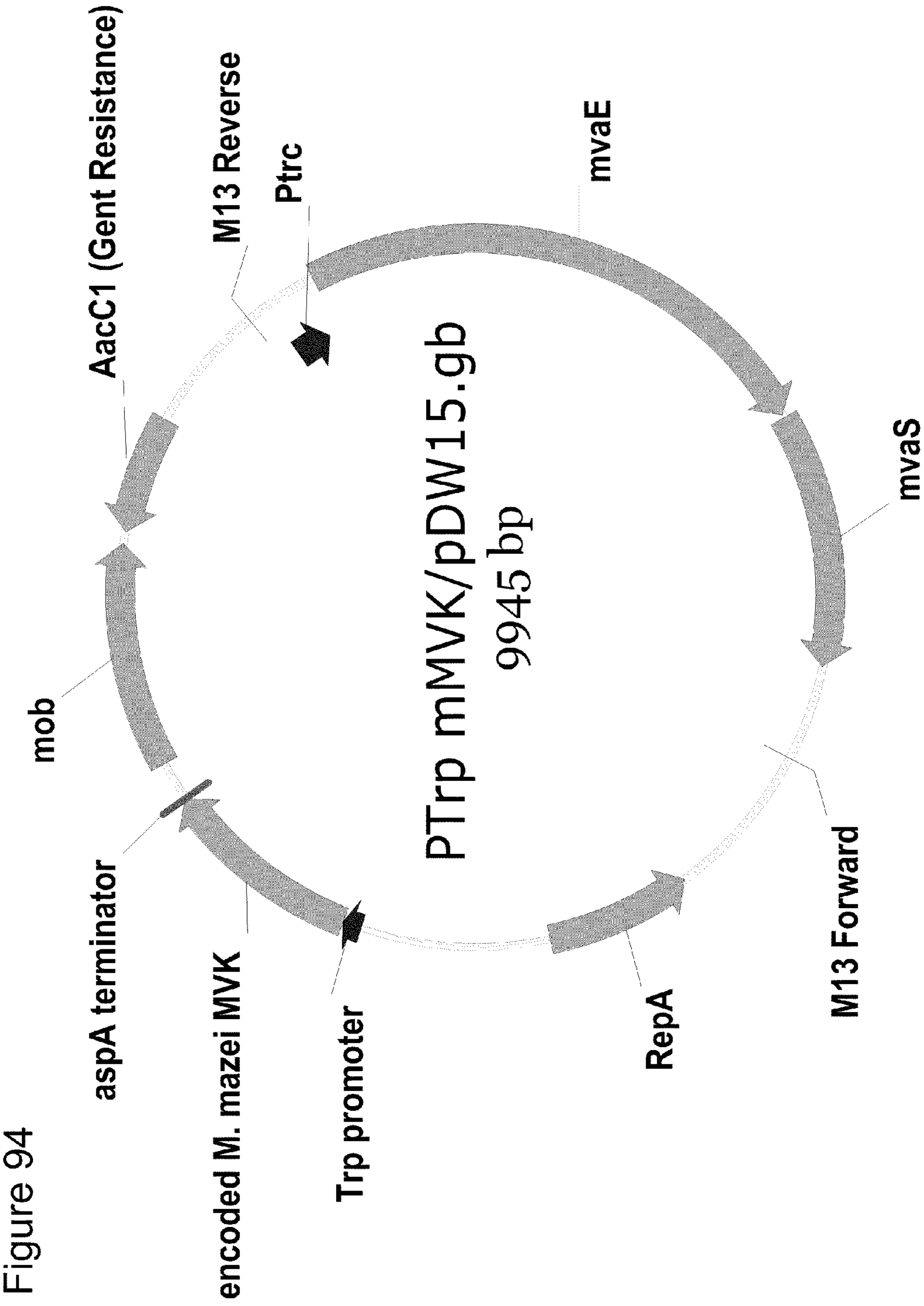

FIG. 94 depicts a plasmid map of PTrp mMVK/pDW15. Same plasmid base as in 1). Trp promoter; encoded *M. mazei* MVK—*M. mazei* gene encoding Mevalonate Kinase; aspA terminator.

Figure 95:
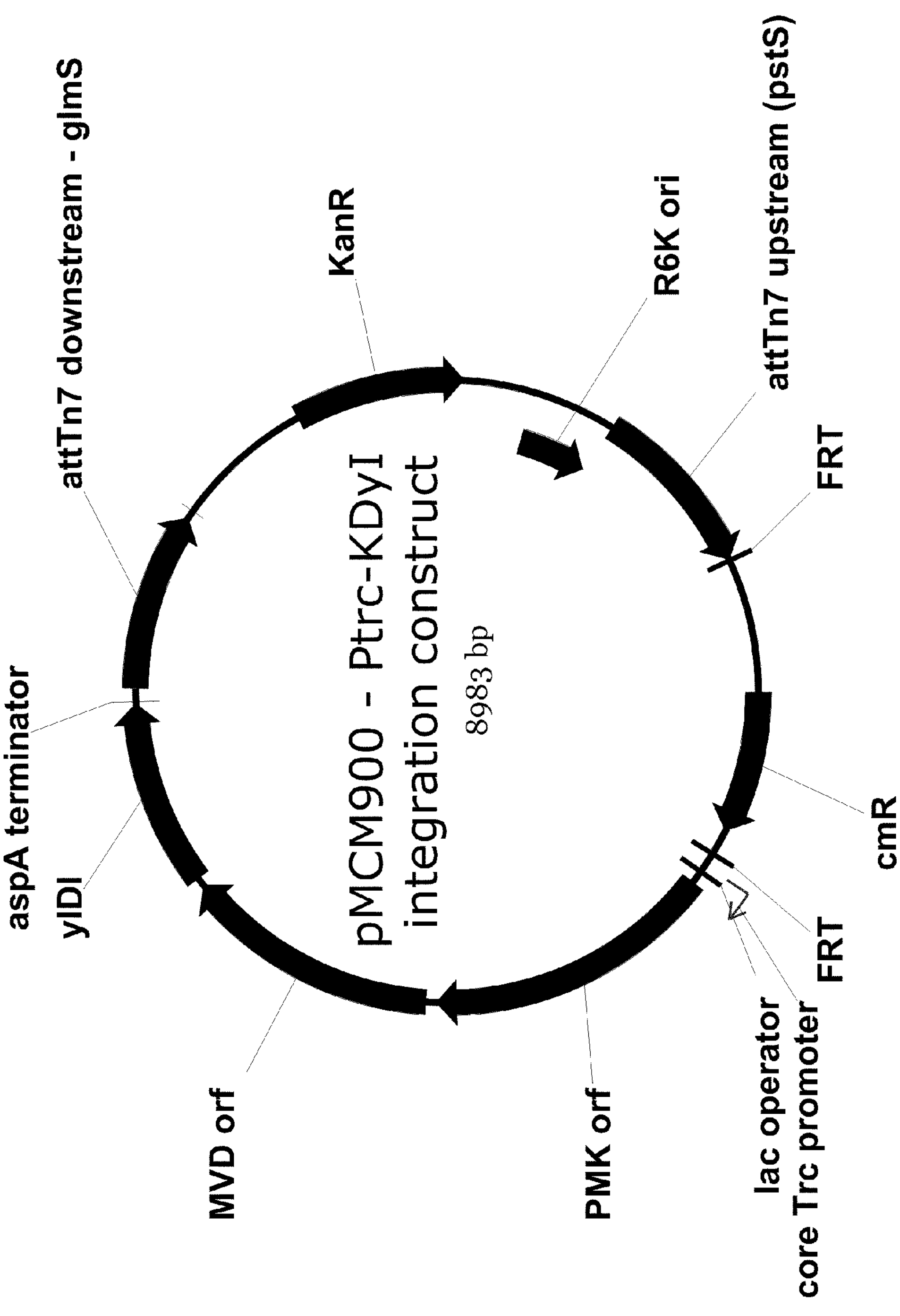

FIG. 95 depicts a plasmid map of pMCM900. FRT—Flip recombinase target site; core Trc promoter—RNA polymerase binding site; lac operator—Lad binding site; PMK orf—yeast phosphomevalonate kinase coding sequence; MVD orf—yeast diphosphomevalonate decarboxylase coding sequence; yIDI—yeast isopentenyl diphosphate isomerase coding sequence; aspA terminator—aspA transcriptional terminator; attTn7 downstream—glmS—downstream recombination targeting sequence; KanR—kanamycin resistance gene; R6K ori—plasmid origin of replication; attTn7 upstream (pstS)—upstream recombination targetting sequence.

Figure 96:
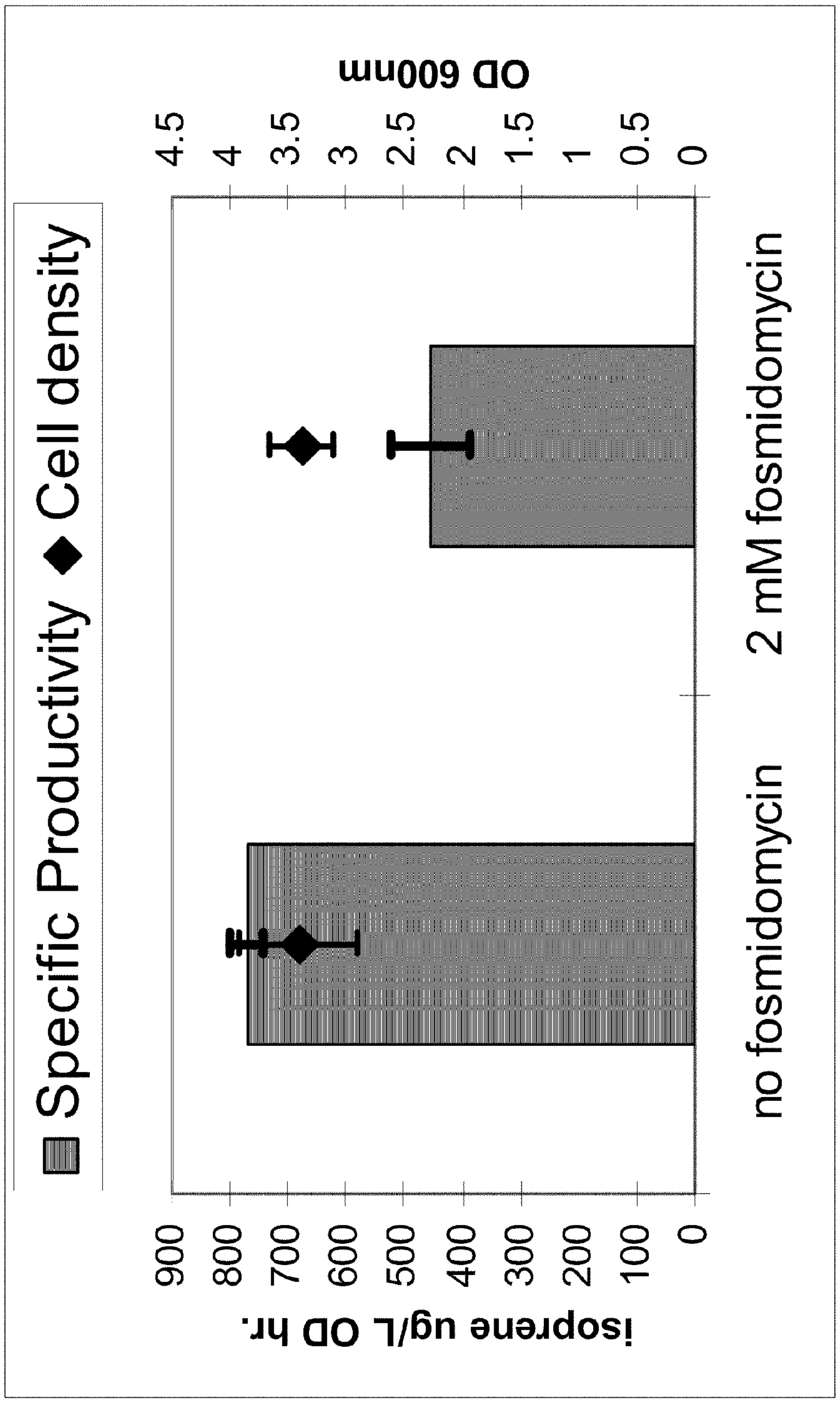

FIG. 96 depicts the results for experiments for determining the specific productivity relative to culture density in the presence and absence of fosmidomycin for strain REM A2_17 grown on unlabeled glucose. The y1 axis, specific productivity of isoprene production (ug/L OD hr); y2 axis, cell density ($OD_{600nm}$). Specific productivity (solid bars) and Cell density (diamonds). Measurements were taken approx. 45 minutes post-introduction of either 0 mM or 2 mM fosmidomycin; both occurring approx. 3 hours after induction with 400 uM IPTG. The data presented is the average of 3 biological; error bars are shown for specific productivity and cell density values. The data suggests a contribution of roughly 59% and 41% for isoprene generated via the MVA pathway and DXP pathway, respectively; MVA flux was determined by the fraction of isoprene produced during exposure to fosmidomycin relative to the amount of isoprene produced in the absence of the inhibitor.

Figure 97:
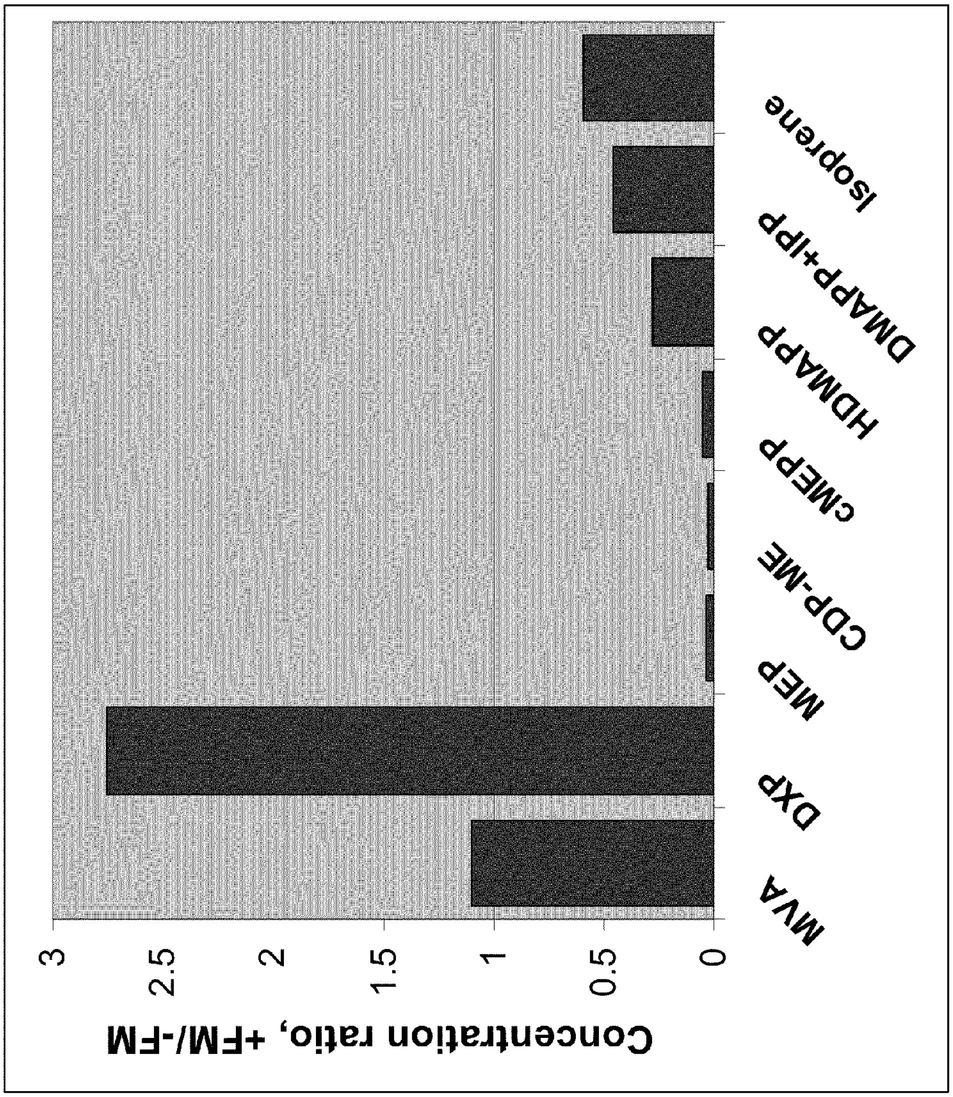

FIG. 97 depicts the results for experiments for determining the effect of fosmidomycin on accumulation of the DXP and MVA pathway metabolites and isoprene emission rate in REM A2_17 strain. The metabolite concentrations in pelleted cells (same cells depicted in FIG. 96) and isoprene emission rates were measured in the cultures at the end of a 45 min. incubation in the presence and in the absence of 2 mM fosmidomycin ("+FM" and "−FM", respectively). The results are expressed as an average ratio of the obtained concentrations and rates measured in three different cultures.

Figure 98:
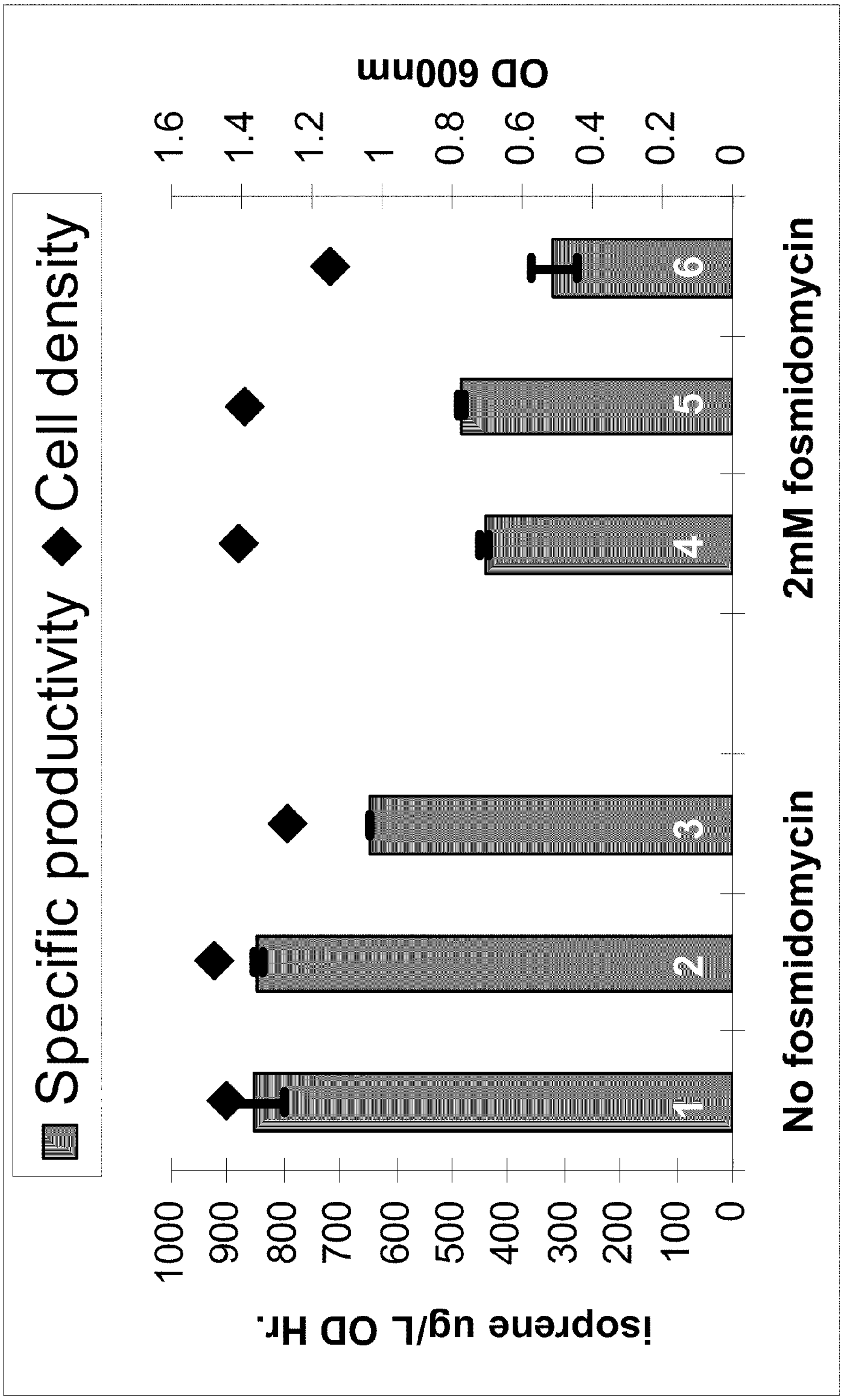

FIG. 98 depicts the results for experiments for determining the specific productivity relative to culture density in the presence and absence of fosmidomycin for strain REM A2_17 grown on unlabeled and 1-$^{13}$C labeled glucose. The y1 axis, specific productivity of isoprene production (ug/L OD hr); y2 axis, cell density ($OD_{600nm}$). Specific productivity (solid bars) and Cell density (diamonds). In lane 1: unlabeled culture without tryptophan and without fosmidomycin; lane 2: 1-$^{13}$C glucose culture without tryptophan and without fosmidomycin; lane 3: 1-$^{13}$C glucose culture with 50 uM tryptophan and without fosmidomycin; lane 4: unlabeled culture without tryptophan and with 2 mM fosmidomycin; lane 5: 1-$^{13}$C glucose culture with 50 uM tryptophan and with 2 mM fosmidomycin; lane 6: 1-$^{13}$C glucose culture with 50 uM tryptophan and with 2 mM fosmidomycin. Measurements were taken approx. 45 minutes post-introduction of either 0 mM or 2 mM fosmidomycin; both occurring approx. 3 hours after induction with 400 uM IPTG. The data presented is the average of 2 technical replicates; error bars are shown for specific productivity values. The data suggests a contribution of roughly 52% and 48% for isoprene generated via the MVA pathway and DXP pathway, respectively for the unlabeled culture. Similarly, the data shows a 57% MVA-flux to 43% DXP-flux and 49% MVA-flux to 51% DXP-flux contribution to the isoprene generated by the 1-$^{13}$Cglucose culture without and with 50 uM tryptophan, respectively. The repressed expression of the MVK enzyme mediated by the presence of tryptophan in the growth media for cultures represented by lanes 3 and 6 was reflected in the data as a 24% to 34% decrease in overall-flux compared to the cultures grown without the addition of tryptophan to the growth media. MVA flux was determined by the fraction of isoprene produced during exposure to fosmidomycin relative to the amount of isoprene produced in the absence of the inhibitor for each particular culture type.

Figure 99:
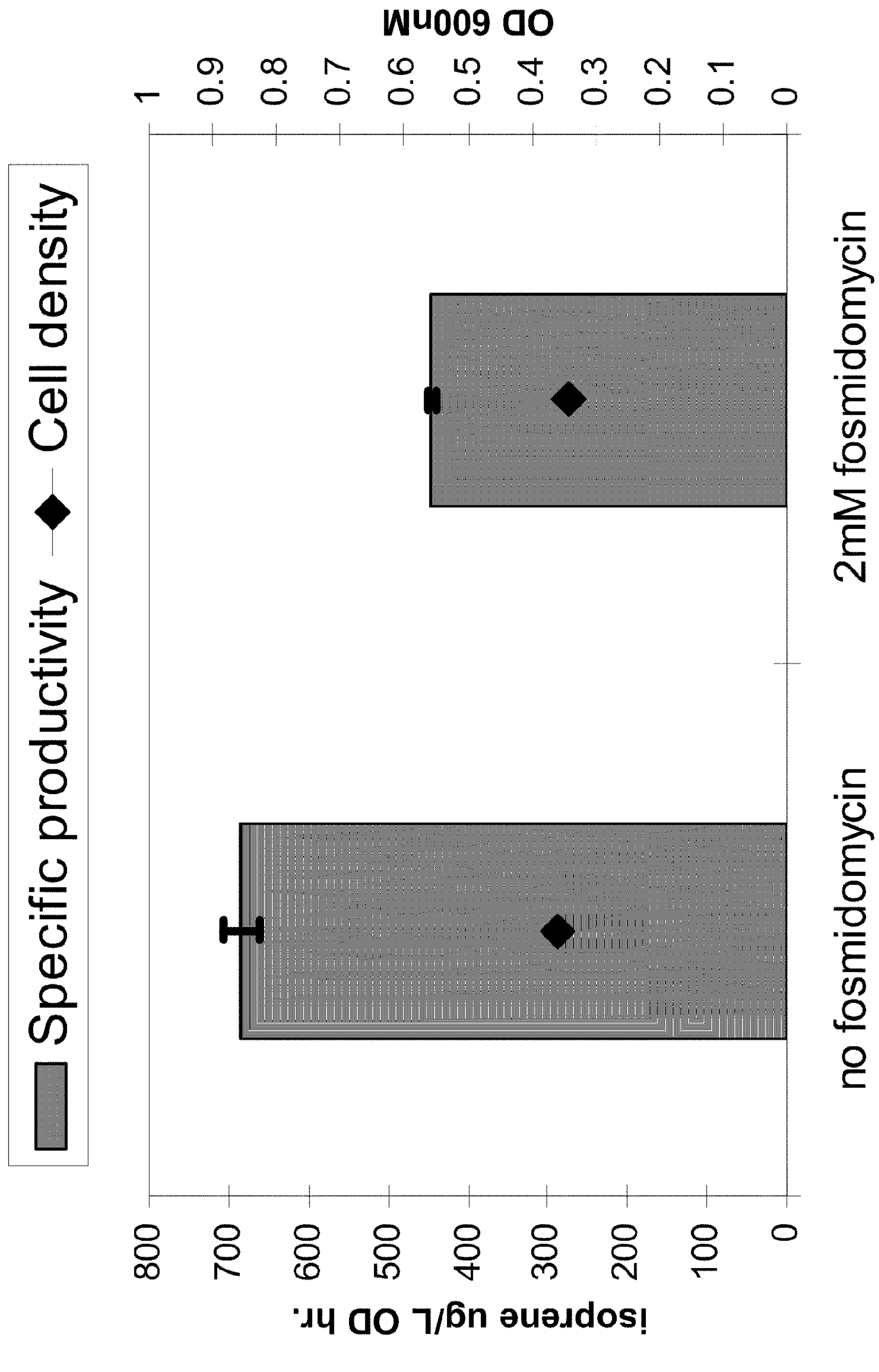

FIG. 99 depicts the results for experiments for determining the specific productivity relative to culture density in the presence and absence of fosmidomycin for strain REM A2_17 grown on 3-$^{13}$C glucose. The y1 axis, specific productivity of isoprene production (ug/L OD hr); y2 axis, cell density ($OD_{600nm}$). Specific productivity (solid bars) and Cell density (diamonds). Measurements were taken approx. 1 hour post-introduction of either 0 mM or 2 mM fosmidomycin; both occurring approx. 3 hours after induction with 400 uM IPTG. The data presented is the average of 2 technical replicates; error bars are shown for specific productivity values. The data suggests a contribution of roughly 58% and 42% for isoprene generated via the MVA pathway and DXP pathway, respectively; MVA flux was determined by the fraction of isoprene produced during exposure to fosmidomycin relative to the amount of isoprene produced in the absence of the inhibitor.

Figure 100:
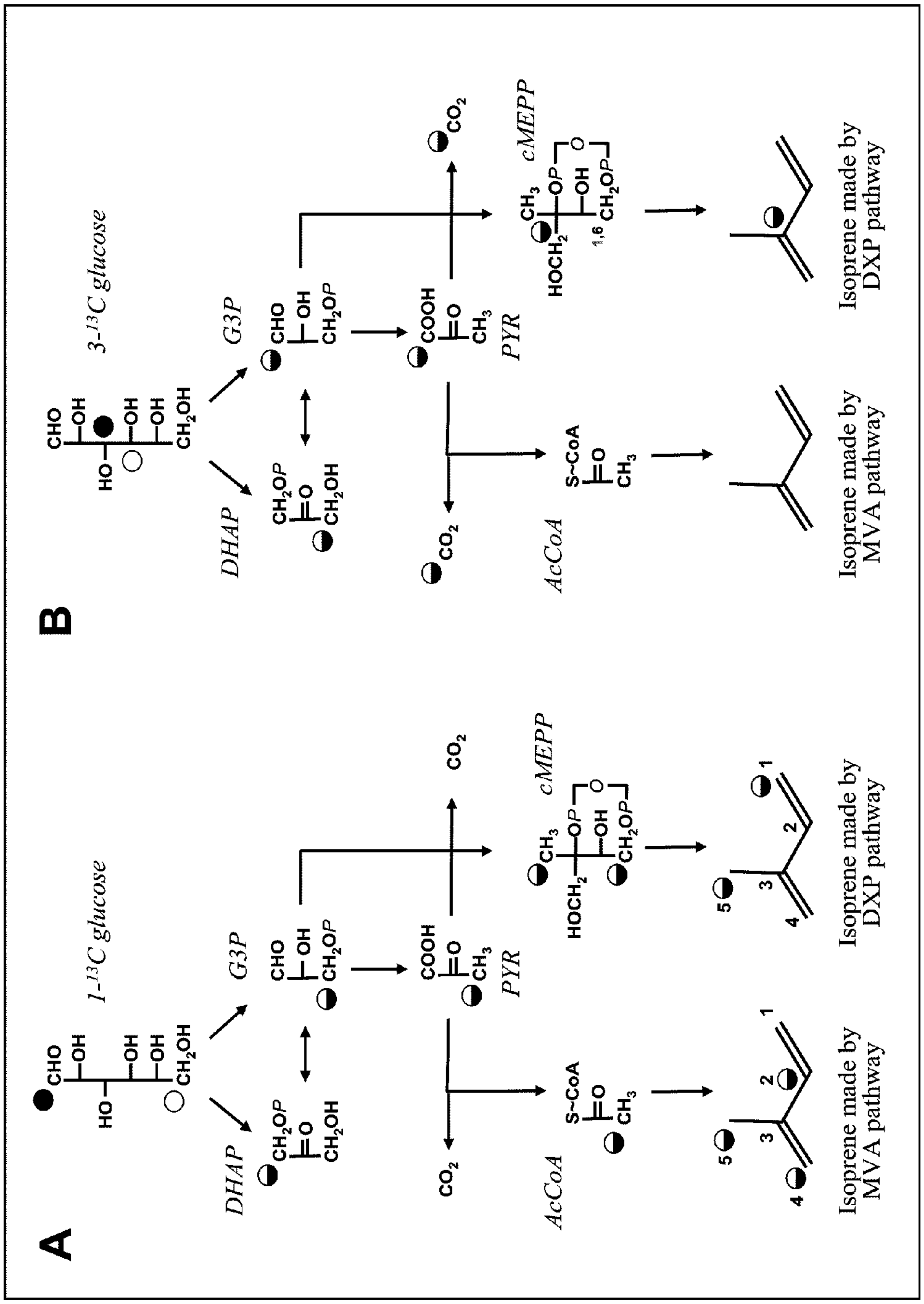

FIG. 100 (panels A and B) depicts the DXP and MVA pathway-specific labeling pattern of isoprene resulting from: A) 1-$^{13}$C glucose and B) 3-$^{13}$C glucose catabolism via glycolysis. Black circles indicate 100% abundance of $^{13}$C atoms at specified positions. Half-black circles indicate $^{13}$C abundance of 50% with the rest 50% being $^{12}$C atoms coming from the positions in glucose shown by open circles.

FIG. 101 (panels A and B) depicts the calculated distributions of isoprene and cMEPP cumomers in REM A2_17 strain grown on: A) 1-$^{13}$C glucose or B) 3-$^{13}$C glucose in the presence or in the absence of fosmidomycin (+FM and −FM, respectively).

Figure 102:
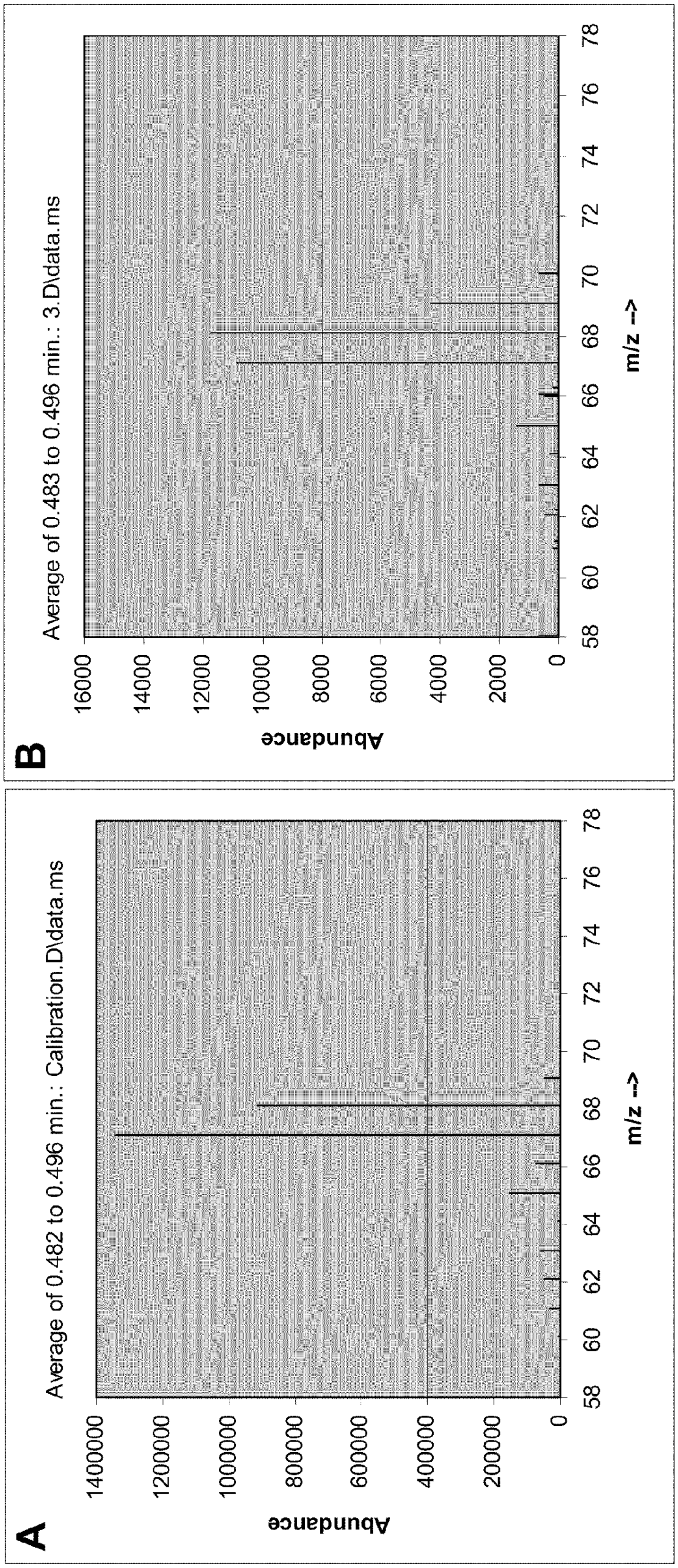

FIG. 102 (panels A and B) depicts the GC-MS spectra of: A) unlabeled (synthetic) isoprene standard having natural abundance of $^{13}$C and B) isoprene produced by the REM A2_17 strain grown on 3-$^{13}$C glucose. Note that intensities of m/z 68, 69 and 70 peaks relative to the m/z 67 peak are higher in the REM A2_17 strain compared to the isoprene standard because of $^{13}$C enrichment.

Figure 103:
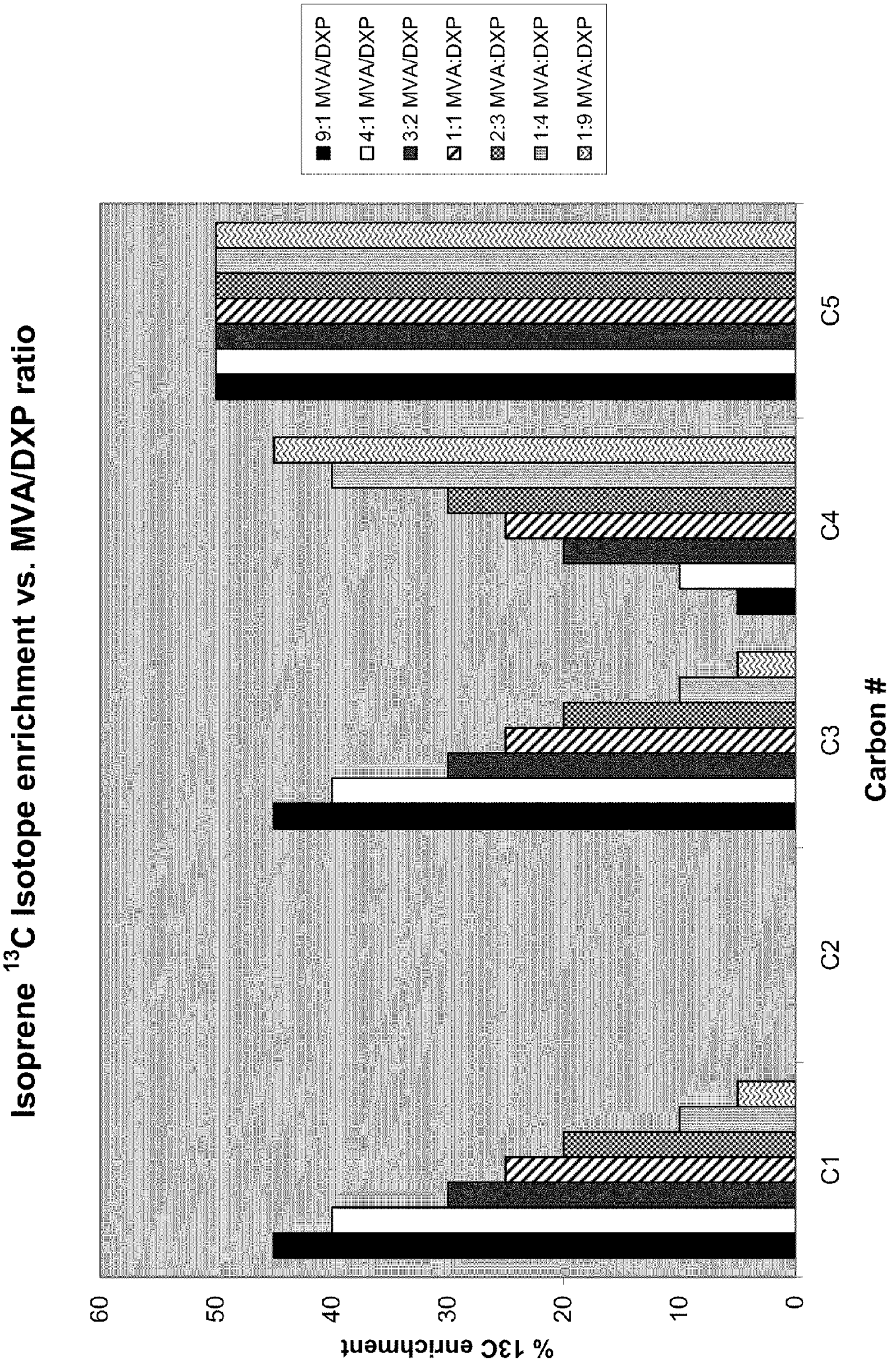

FIG. 103 depicts results of isoprene $^{13}$C isotope enrichment as a function of MVA/DXP pathway ratio.

Figure 104:
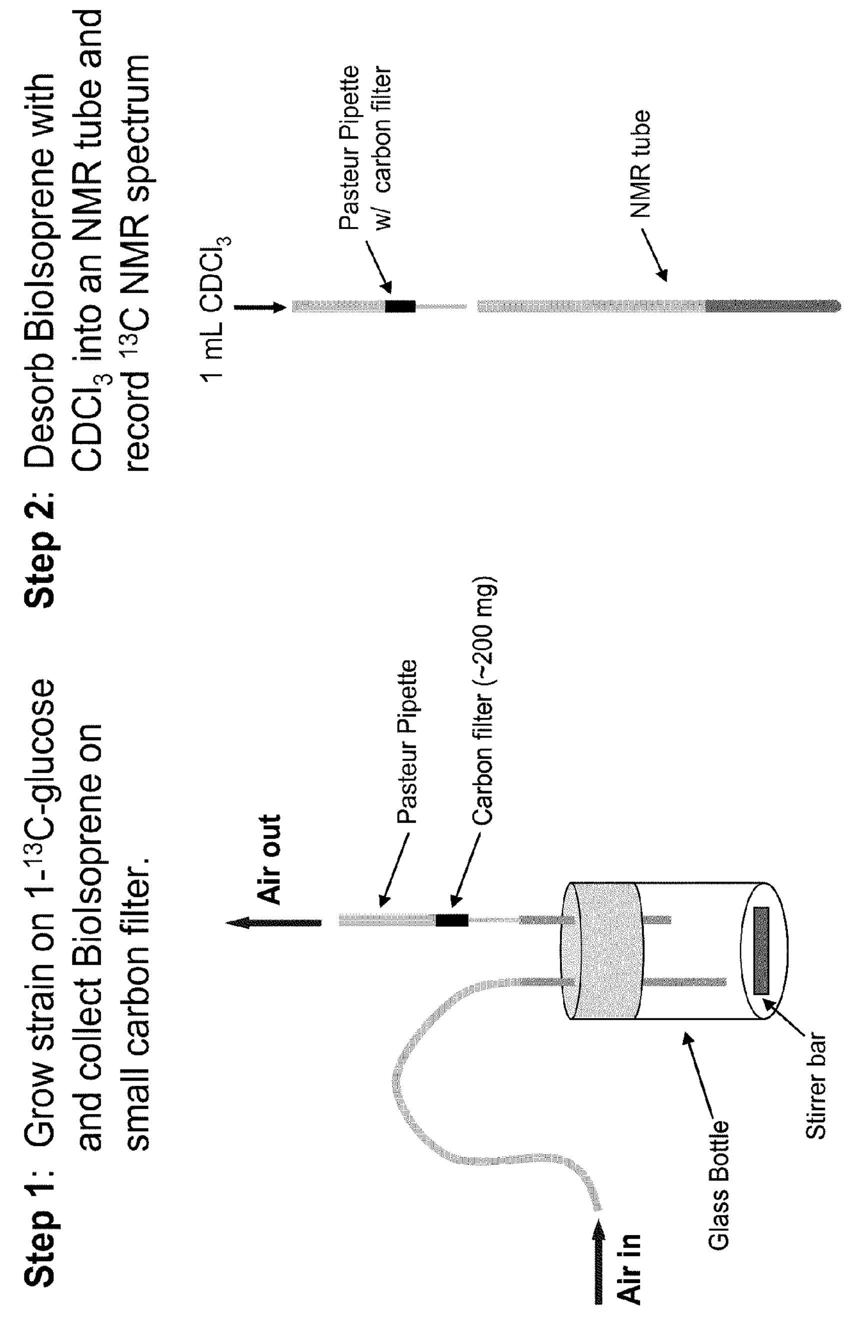

FIG. 104 depicts an exemplary apparatus for generation, collection and analysis of Bioisoprene™ product.

Figure 105:
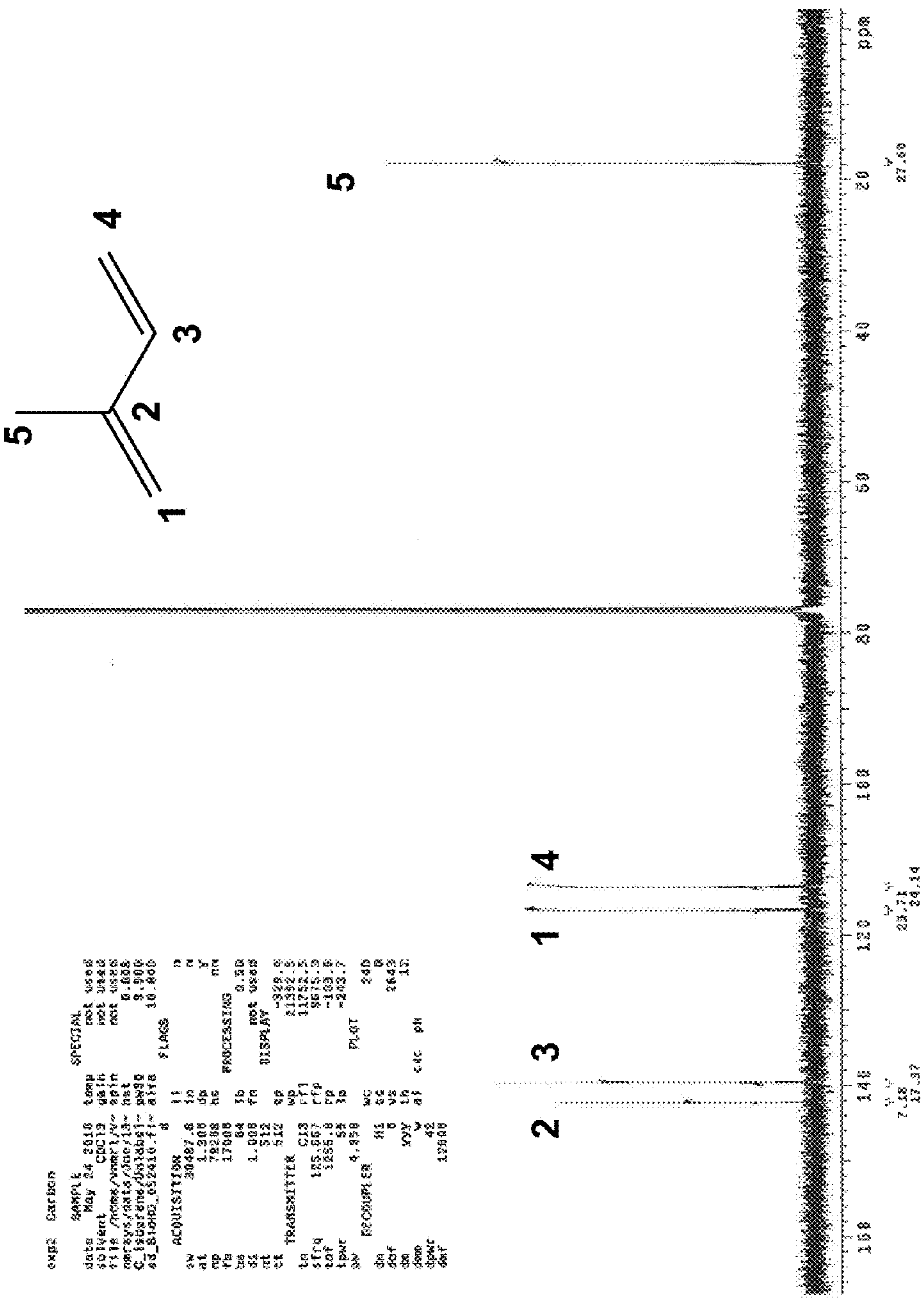

FIG. 105 depicts results showing the $^{13}$C NMR spectrum of natural $^{13}$C-abundance isoprene.

Figure 106:
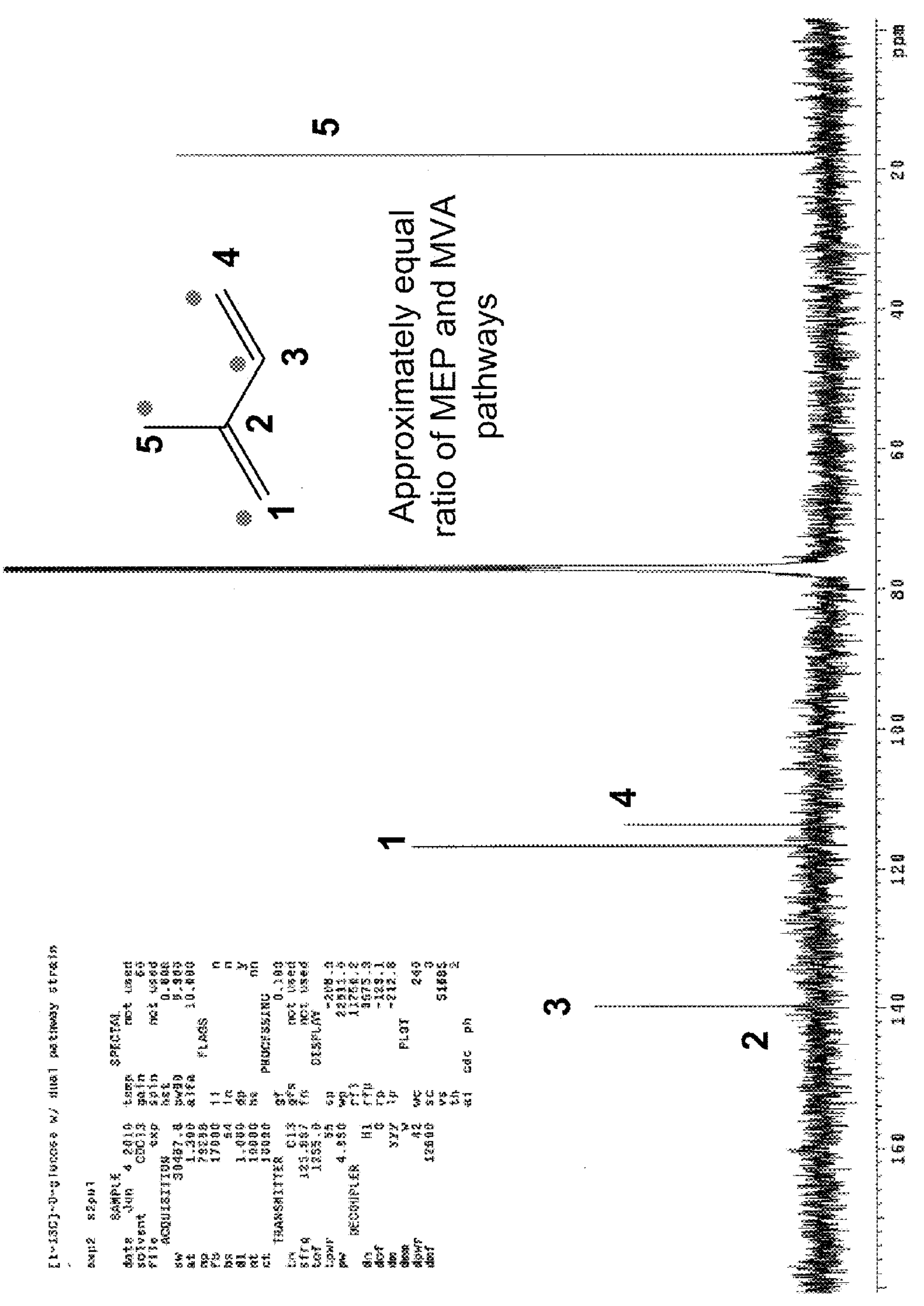

FIG. 106 depicts results showing the $^{13}$C NMR spectrum of isoprene derived from a MVA/DXP dual pathway strain. Both C-4 and C-1/C-3 are $^{13}$C-enriched relative to C-2, with a signal intensity equal or less than the noise level demonstrates the contribution of the both the MVA and DXP pathways to isoprene synthesis in this strain.

FIG. 107 depicts a diagram for a portion of the PL.6 fkpB locus. The nucleotide sequence of the region depicted in the figure is indicated by the 323 bases listed below the diagram. The 5' and 3' regions of homology used to integrate the PL.6 promoter upstream of fkpB are shown in gray. The sequence highlighted in black bold text represents the exogenous sequence left in the region after loopout of the Gene Bridges chloramphenicol resistance cassette, referred to in the figure as the Gene Bridges scar, with the remaining FRT (Flipase recognition target) site underlined. The PL.6 promoter sequence is shown in regular black text. The −35, −10, and RBS (ribosome binding site) positions are indicated in the figure.

Figure 108:
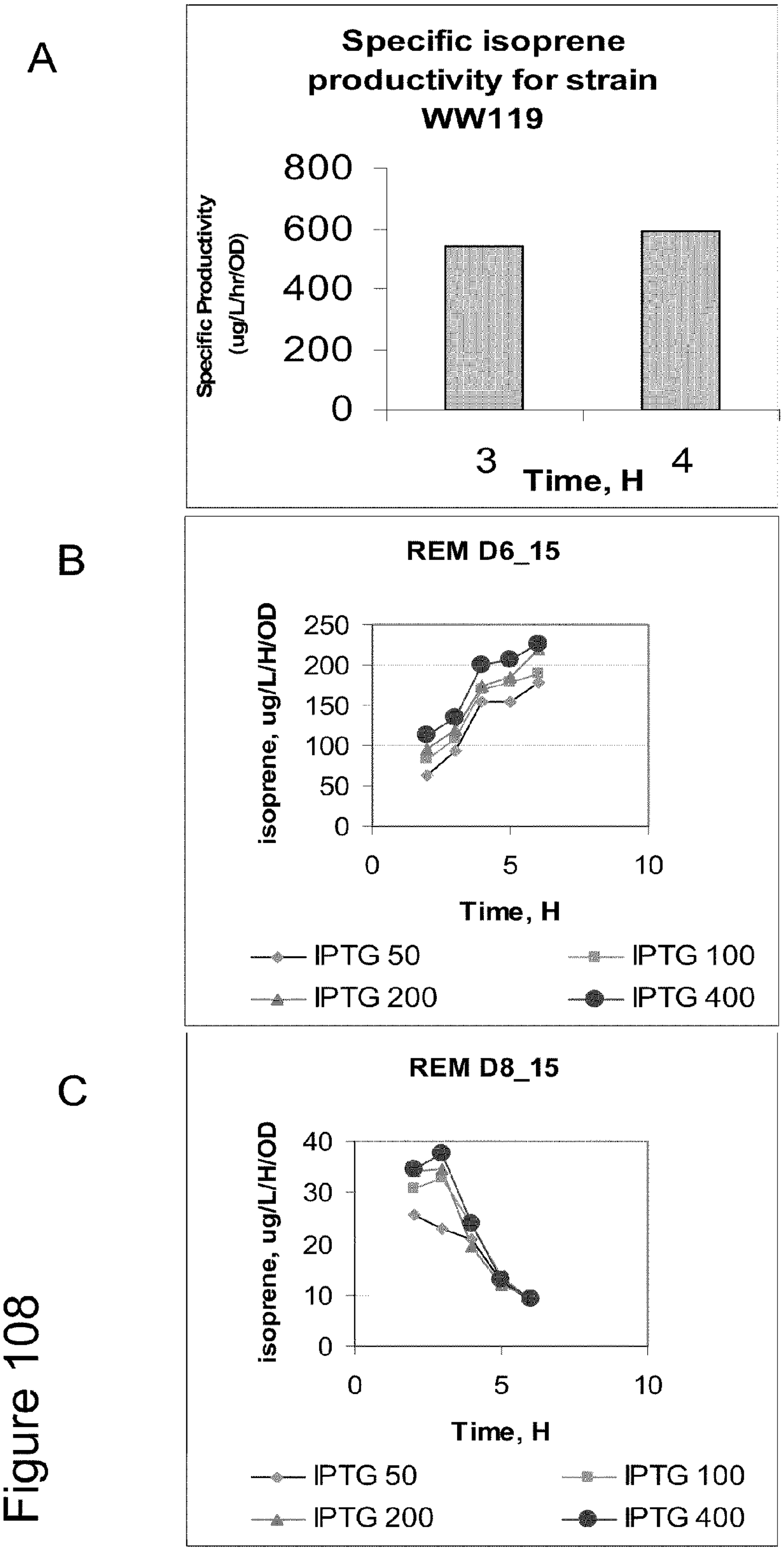

FIG. 108 (panels A, B, C, D) depicts a comparison of the isoprene productivity of 4 strains. Panel A, typical isoprene productivity of strain WW119 (parent to strains in panel B and C) at two time points at 200 uM IPTG. This experiment was performed as is described in the text for strains in panels B and C, except that isoprene monitoring was limited to 2 and 4 hours. $OD_{600}$ was monitored throughout culture period for all strains at hourly intervals. Panel B shows isoprene specific productivity for strains REM 6_15 (PL.6 fkpB-ispH ΔiscR) at several IPTG concentrations. Panel C shows isoprene specific productivity for strain REM D8_15 (PL.6 fkpB-ispH) at several IPTG concentrations. The data is consistent with that ΔiscR rescues isoprene productivity lost upon introduction of PL.6fkpB-ispH. Panel D shows isoprene specific productivity for strain REM D7_15 at several IPTG concentrations.

Figure 109:
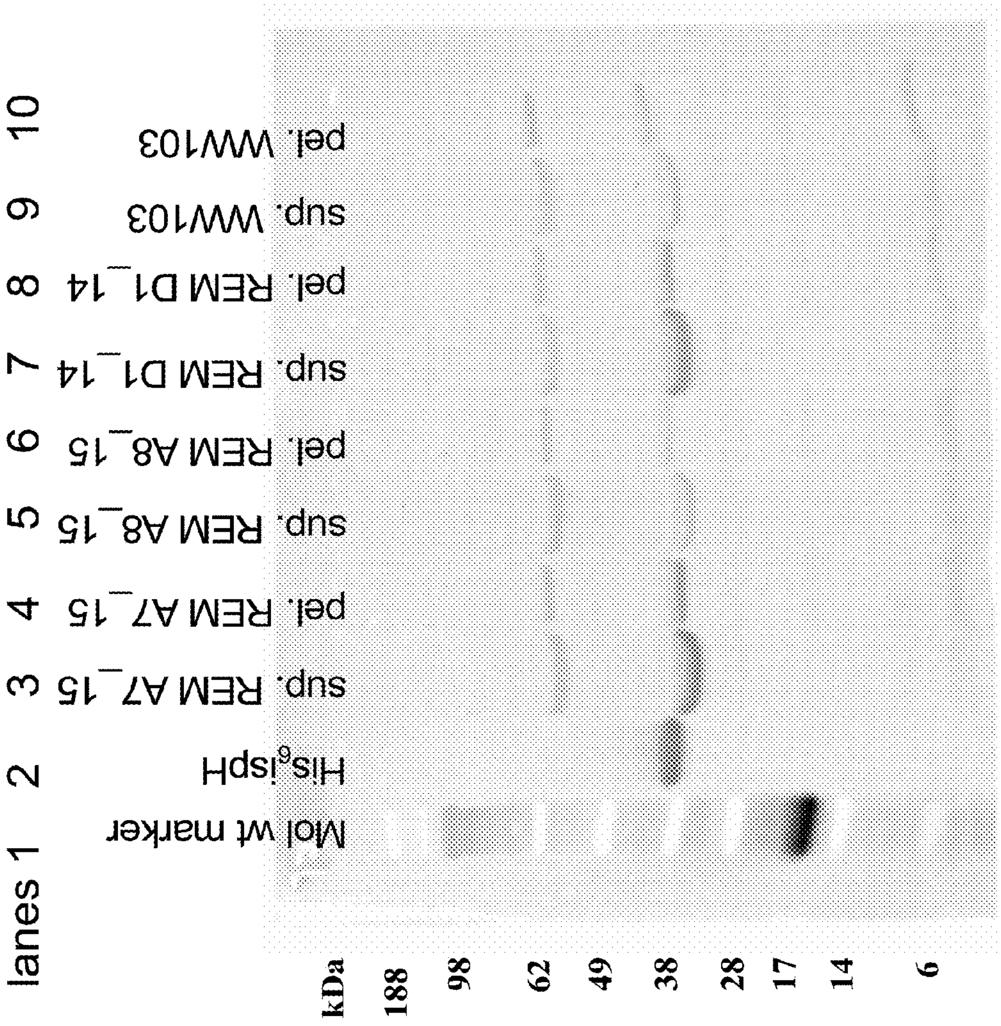

FIG. 109 shows an image of *E. coli* ispH western blot. Lane description is as follows: Lane 1, SeeBlue® Plus2 Pre-Stained Standard, Invitrogen, Lane 2, *E. coli* ispH purified standard (0.4 μg), Lane 3, REM A7_15 soluble fraction, Lane 4, REM A7_15 insoluble fraction, Lane 5, REM A8_15 soluble fraction, Lane 6, REM A8_15 insoluble fraction, Lane 6, REM D1_14 soluble fraction, Lane 7, REM D1_14 insoluble fraction, Lane 8, WW103 soluble fraction and, Lane 10, WW103 insoluble fraction. Development method: 1° Ab Anti-Rabbit *E. coli* ispH at 1:10,000 dilution, 2° Ab Alexa Fluor® 488 goat anti-rabbit IgG (H+L), Invitrogen, 1:1,000 dilution; see text for additional details. Gel was a Novagen 4 to 12% BT gel. Loading was normalized to equal $OD_{600}$. Pel, pellet; sup, supernatant.

FIG. 107 depicts a diagram for a portion of the PL.6 fkpB locus. The nucleotide sequence of the region depicted in the figure is indicated by the 323 bases listed below the diagram. The 5' and 3' regions of homology used to integrate the PL.6 promoter upstream of fkpB are shown in gray. The sequence highlighted in black bold text represents the exogenous sequence left in the region after loopout of the Gene Bridges chloramphenicol resistance cassette, referred to in the figure as the Gene Bridges scar, with the remaining FRT (Flipase recognition target) site underlined. The PL.6 promoter sequence is shown in regular black text. The −35, −10, and RBS (ribosome binding site) positions are indicated in the figure (SEQ ID NO: 193).

DETAILED DESCRIPTION OF THE INVENTION

The invention provides, inter alia, compositions and methods for the production of isoprene in increased amounts using various DXP pathway genes and polypeptides, various MVA pathway genes and polypeptides, iron-sulfur cluster-interacting redox genes and polypeptides, isoprene synthase genes and polypeptides, and optionally, IDI genes and polypeptides and various genes and polypeptides associated with the DXP pathway and/or MVA pathway.

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention. The headings provided herein are not limitations of the various aspects or embodiments of the invention which can be had by reference to the specification as a whole.

As used herein, the term "isoprene" or "2-methyl-1,3-butadiene" (CAS#78-79-5) refers to the direct and final volatile C5 hydrocarbon product from the elimination of pyrophosphate from 3,3-dimethylallyl pyrophosphate (DMAPP), and does not involve the linking or polymerization of one or more isopentenyl diphosphate (IPP) molecules to one or more DMAPP molecules. The term "isoprene" is not generally intended to be limited to its method of production.

As used herein, the phrase, "various genes and polypeptides associated with the DXP pathway," or "DXP pathway associated nucleic acid(s) or polypeptide(s)" refers to any nucleic acid or polypeptide that interacts with DXP pathway polypeptides or nucleic acids, including, but not limited to, a terpene synthase (e.g., ocimene synthase, farnesene synthase, and artemesinin synthase), either directly or indirectly.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments.

The present invention is based in part on the surprising discovery that an increased amount of an iron-sulfur cluster-interacting redox polypeptide increases the activity demonstrated by the DXP pathway polypeptides (such as HDS (GcpE or IspG) or HDR polypeptide (IspH or LytB). While not intending to be bound to a particular theory, it is believed that the increased expression of one or more endogenous or heterologous iron-sulfur interacting redox nucleic acids or polypeptides improve the rate of formation and the amount of DXP pathway polypeptides containing an iron sulfur cluster (such as HDS or HDR), and/or stabilize DXP pathway polypeptides containing an iron sulfur cluster (such as HDS or HDR). This in turn increases the carbon flux to isoprene synthesis in cells by increasing the synthesis of HMBPP and/or DMAPP and decreasing the cMEPP and HMBPP pools in the DXP pathway. For example, overexpression of an iron-sulfur cluster-interacting redox polypeptide (flavodoxin I) in cells overexpressing a DXP pathway polypeptide (DXS), isoprene synthase polypeptide, and IDI polypeptide resulted in increased production of isoprene by about 1- to 2-fold in comparison to cells overexpressing DXP pathway polypeptide, isoprene synthase polypeptide, and IDI polypeptide only. See Example 8. Overexpression of one or more iron-sulfur cluster-interacting redox polypeptide (ferredoxin and ferredoxin-NADP+ oxidoreductase), one or more DXP pathway polypeptide, isoprene synthase polypeptide, and IDI polypeptide resulted in increased production of isoprene. See Example 9.

Accordingly, in one aspect of the invention, cells in culture comprise (i) a heterologous nucleic acid encoding an iron-sulfur cluster-interacting redox polypeptide, a heterologous nucleic acid encoding DXP pathway polypeptide, and an heterologous nucleic acid encoding isoprene synthase and/or (ii) a duplicate copies of endogenous nucleic acids encoding an iron-sulfur cluster-interacting redox polypeptide, a DXP pathway polypeptide, and an isoprene synthase polypeptide. In some embodiments, the cells in culture comprise (i) one or more copies of heterologous or endogenous nucleic acid encoding an iron-sulfur cluster-interacting redox polypeptide, (ii) one or more copies of heterologous or endogenous nucleic acid encoding a DXP pathway polypeptide, and (iii) one or more copies of heterologous or endogenous nucleic acid encoding an isoprene synthase polypeptide.

In another aspect of the invention, provided are methods of producing isoprene. In one embodiments, the method comprises (a) culturing cells comprising (i) a heterologous nucleic acid encoding a heterologous nucleic acid encoding an iron-sulfur cluster-interacting redox polypeptide, a DXP pathway polypeptide, and an isoprene synthase polypeptide and/or (ii) a duplicate copy of an endogenous nucleic acid encoding an iron-sulfur cluster-interacting redox polypeptide, a DXP pathway polypeptide, and an isoprene synthase polypeptide under suitable culture conditions for the production of isoprene, and (b) producing isoprene.

As used herein, iron-sulfur cluster-interacting redox polypeptide is a polypeptide that is capable of transferring electrons to a polypeptide containing an iron-sulfur cluster. An iron-sulfur cluster-interacting redox polypeptide includes, but is not limited to, flavodoxin (e.g., flavodoxin I), flavodoxin reductase, ferredoxin (e.g., ferredoxin I), ferredoxin-NADP+ oxidoreductase, and genes or polypeptides encoding thereof (e.g., fpr or fldA). For example, DXP pathway polypeptide HDS (GcpE) is a metallo-enzyme possessing a $[4Fe-4S]^{2+}$ center and catalyzes the reduction of cMEPP into HMBPP via two successive one-electron transfers mediated by the reduction of $[4Fe-4S]^{2+}$ center in the presence of flavodoxin/flavodoxin reductase (see, Wolff et al., FEBS Letters, 541:115-120 (2003)), which is hereby incorporated by reference in its entirety). Similarly, DXP pathway polypeptide HDR (LytB) is also a Fe/S protein catalyzing the reduction of HMBPP into IPP or DMAPP via two successive one-electron transfers in the presence of flavodoxin/flavodoxin reductase/NADPH system. See, for example, Seemann, M. et al. *Agnew. Chem. Int. Ed.,* 41: 4337-4339 (2002); Wolff, M. et al., *FEBS Letters,* 541: 115-120 (2003), which are each hereby incorporated by reference in their entirety, particularly with respect to the description of GcpE, LytB, and flavodoxin/flavodoxin reductase/NADPH system).

As used herein, flavodoxin is a protein that is capable of transferring electrons and contains the prosthetic group flavin mononucleotide. In *Escherichia coli* (*E. coli*), flavodoxin is encoded by the fldA gene and reduced by the FAD-containing protein NADPH:ferredoxin oxidoreductase, and plays an essential role in the DXP pathway for isoprenoid biosynthesis (see, example, Kia-Joo, P. et al. *FEBS Letters,* 579: 3802-3806, 2005, which is hereby incorporated by reference in its entirety).

As used herein, ferredoxin is a protein that is capable of transferring electron and contains iron and labile sulfur in equal amounts and plays an essential role in the DXP pathway for isoprenoid biosynthesis. For example, HDS from plants and cyanobacteria have been shown to be ferredoxin, rather than flavodoxin-dependent, enzymes (Seemann et al., *FEBS Lett.,* 580(6):1547-52 (2006), which is hereby incorporated by reference in its entirety).

As used herein, Fpr encodes flavodoxin/ferredoxin NADPH-oxidoreductase and provides the necessary electron derived from NADPH via FldA for HDS and HDR to perform their catalytic functions (reviewed in report by L. A. Furgerson, *The Mevalonate-Independent Pathway to Isoprenoid Compounds: Discovery, Elucidation, and Reaction Mechanisms*, published Feb. 13, 2006, which is hereby incorporated by reference in its entirety).

Figure 19:
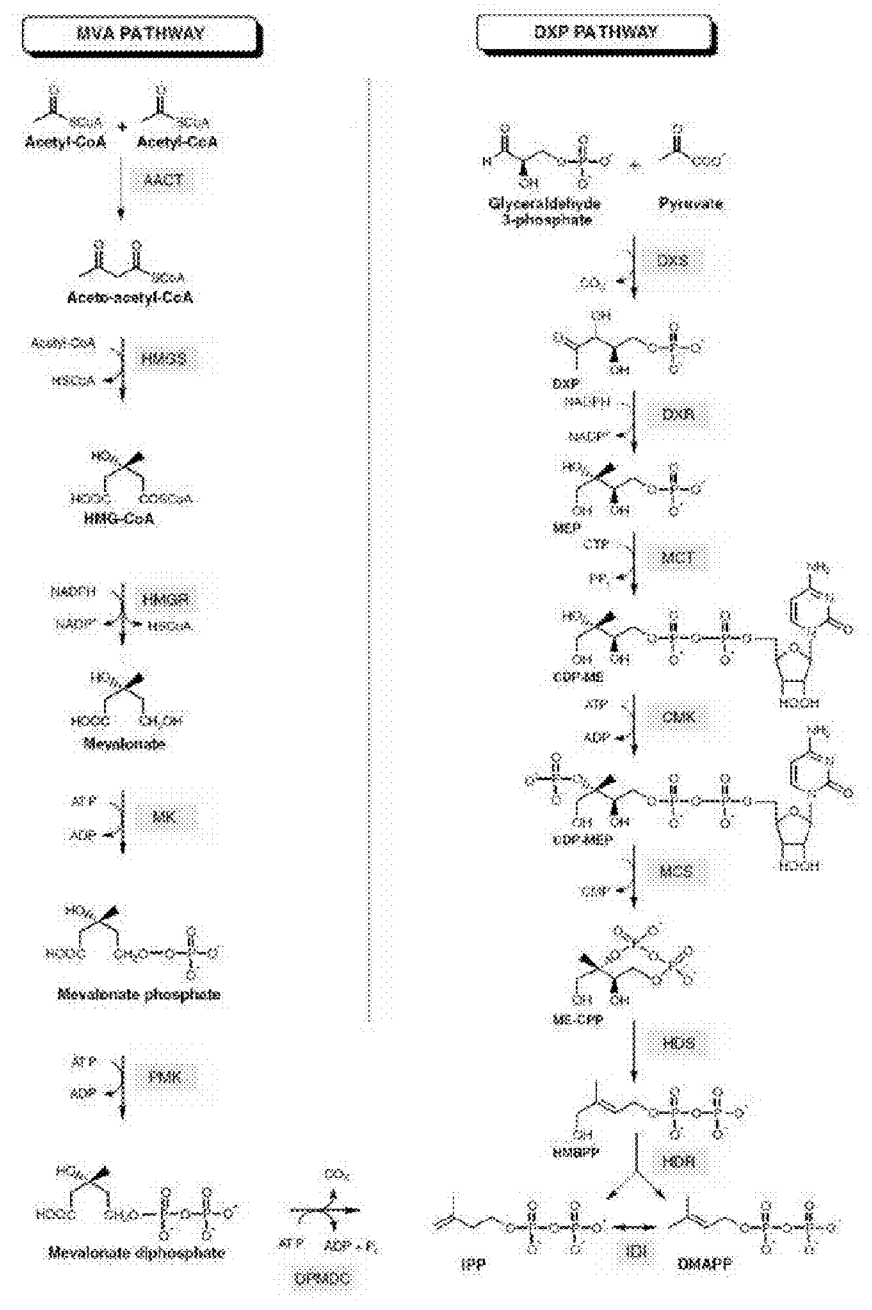
FIG. 19 shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet. 19:9-14, 1991. PMK; Phosphomevalonate kinase, ERGS, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-deoxy-D-xylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, GcpE, EC 1.17.4.3. Assay: J. Org. Chem., 70:9168-9174, 2005; HDR; 1-Hydroxy-2-methyl-2-(E)-butenyl 4-diphosphate reductase, IspH, LytB, EC 1.17.1.2. Assay: JACS, 126: 12847-12855, 2004.

As used herein, the encoded DXS, DXR, MCT, CMK, MCS, HDS, and HDR polypeptides are part of the DXP pathway for the biosynthesis of isoprene (FIG. 19A).

DXS polypeptides convert pyruvate and D-glyceraldehyde-3-phosphate into 1-deoxy-D-xylulose-5-phosphate (DXP). While not intending to be bound by any particular theory, it is believed that increasing the amount of DXS polypeptide increases the flow of carbon through the DXP pathway, leading to greater isoprene production.

DXR polypeptides convert 1-deoxy-D-xylulose 5-phosphate (DXP) into 2-C-methyl-D-erythritol 4-phosphate (MEP). While not intending to be bound by any particular theory, it is believed that increasing the amount of DXS polypeptide increases the flow of carbon through the DXP pathway, leading to greater isoprene production.

MCT polypeptides convert 2-C-methyl-D-erythritol 4-phosphate (MEP) into 4-(cytidine 5'-diphospho)-2-C-methyl-D-erythritol (CDP-Me). While not intending to be bound by any particular theory, it is believed that increasing the amount of MCT polypeptide increases the flow of carbon through the DXP pathway, leading to greater isoprene production.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). While not intending to be bound by any particular theory, it is believed that increasing the amount of CMK polypeptide increases the flow of carbon through the DXP pathway, leading to greater isoprene production.

MCS polypeptides convert 2-phospho-4-(cytidine 5'-diphospho)-2-C-methyl-D-erythritol (CDP-MEP) into 2-C-methyl-D-erythritol 2,4-cyclodiphoshphate (ME-CPP or cMEPP). While not intending to be bound by any particular theory, it is believed that increasing the amount of MCS polypeptide increases the flow of carbon through the DXP pathway, leading to greater isoprene production.

HDS polypeptides convert 2-C-methyl-D-erythritol 2,4-cyclodiphoshphate (ME-CPP or cMEPP) into (E)-4-hydroxy-3-methylbut-2-en-1-yl-diphosphate (HMBPP or HDMAPP). While not intending to be bound by any particular theory, it is believed that increasing the amount of HDS polypeptide increases the flow of carbon through the DXP pathway, leading to greater isoprene production.

HDR polypeptides convert (E)-4-hydroxy-3-methylbut-2-en-1-yl-diphosphate (HMBPP) into isopentenyl diphosphate (IPP) and dimethylallyl diphosphate (DMAPP). While not intending to be bound by any particular theory, it is believed that increasing the amount of HDR polypeptide increases the flow of carbon through the DXP pathway, leading to greater isoprene production.

Isoprene synthase polypeptides convert dimethylallyl diphosphate (DMAPP) into isoprene.

Heterologous iron-sulfur cluster-interacting redox polypeptide, DXP pathway polypeptide, and isoprene synthase polypeptide can be expressed in a variety of host cells, such as *Escherichia coli* (*E. coli*), *Panteoa citrea, Bacillus subtilis, Yarrowia lipolytica*, and *Trichoderma reesei*. All of these cells produced more isoprene than the naturally occurring DXP pathway alone.

As discussed further below, isoprene production by cells can be enhanced by increasing the amount of expression of an iron-sulfur cluster-interacting redox polypeptide, a DXP pathway polypeptide, and an isoprene synthase polypeptide. The DXP pathway polypeptides include DXS, DXR, MCT, CMK, MCS, HDS, and HDR. For example, one or more DXP pathway nucleic acids can be introduced into the cells, which includes DXS, DXR, MCT, CMK, MCS, HDS, and HDR. The DXS, DXR, MCT, CMK, MCS, HDS, or HDR nucleic acid may be a heterologous nucleic acid or a duplicate copy of an endogenous nucleic acid. Similarly, the iron-sulfur cluster-interacting redox nucleic acid may be a heterologous nucleic acid or duplicate copy of an endogenous nucleic acid. Similarly, the isoprene synthase nucleic acid may be a heterologous nucleic acid or a duplicate copy of an endogenous nucleic acid. In some embodiments, the amount of one or more iron-sulfur cluster-interacting redox polypeptide, one or more of DXS, DXR, MCT, CMK, MCS, HDS, or HDR polypeptide, and isoprene synthase polypeptide are increased by replacing one or more endogenous iron-sulfur cluster-interacting redox promoters or regulatory regions, one or more of the endogenous DXS, DXR, MCT, CMK, MCS, HDS, or HDR promoters or regulatory regions, and isoprene synthase promoter or regulatory region with other promoters and/or regulatory regions that result in greater transcription of iron-sulfur cluster-interacting redox nucleic acids, one or more of DXS, DXR, MCT, CMK, MCS, HDS, or HDR nucleic acids, and isoprene synthase nucleic acid.

In some embodiments, the presence of heterologous or extra endogenous iron-sulfur cluster-interacting redox nucleic acid, DXP pathway nucleic acid, and isoprene synthase nucleic acid cause cells to grow more reproducibly and/or remain viable for longer compared to the corresponding cell with only one or two of these heterologous or extra endogenous nucleic acids. While not intending to be bound to a particular theory, it is believed that the overexpressing an iron sulfur cluster-interacting redox polypeptide can increase the rate of formation or the amount of one or more DXP pathway polypeptides (e.g., GcpE and/or LytB) or stabilizes one or more DXP pathway polypeptides (e.g., GcpE and/or LytB), so that one or more DXP pathway polypeptides are active for a longer period of time, which in turn cause cells containing heterologous or extra endogenous iron-sulfur cluster-interacting redox nucleic acid, DXP pathway nucleic acid, and isoprene synthase nucleic acid to grow more reproducibly and/or remain viable for longer compared to the corresponding cell with only one or two of these heterologous or extra endogenous nucleic acids. For example, cells containing heterologous iron-sulfur cluster-interacting redox nucleic acid, DXP pathway nucleic acid, and isoprene synthase nucleic acid grow better than cells with only a DXP pathway nucleic acid, with only a heterologous iron-sulfur cluster-interacting redox nucleic acid, with a heterologous iron-sulfur cluster-interacting redox nucleic acid and DXP pathway nucleic acid, iron-sulfur cluster-interacting redox nucleic acid and isoprene synthase nucleic acid, or DXP pathway nucleic acid and isoprene synthase nucleic acid. Also, large amounts of iron-sulfur cluster-interacting redox polypeptide, DXP pathway polypeptide, and isoprene synthase polypeptide can be expressed in the cells without causing an excessive amount of toxicity to the cells.

In some embodiments of any of the aspects of the invention, the cells express a second DXP pathway polypeptide, in addition to the first DXP pathway polypeptide, including DXS (1-deoxy-D-xylulose-5-phosphate synthase), DXR (1-deoxy-D-xylulose-5-phosphate reductoisomerase), MCT (4-diphosphocytidyl-2C-methyl-D-erythritol synthase), CMK (4-diphosphocytidyl-2-C-methyl-D-erythritol kinase), MCS (2C-methyl-D-erythritol 2,4-cyclodiphosphate synthase), HDS (1-hydroxy-2-methyl-2-(E)-butenyl 4-diphosphate synthase), and HDR (1-hydroxy-2-methyl-2-(E)-butenyl 4-diphosphate reductase). In some embodiments of any of the aspects of the invention, the cells express two or more DXP pathway polypeptides, in addition to the first DXP pathway polypeptide as described above. In some embodiments of any of the aspects of the invention, the cells express 2, 3, 4, 5, 6, or 7 DXP pathway polypeptides, in addition to the first DXP pathway polypeptide as described above.

Additionally, isoprene production by cells that contain a heterologous iron-sulfur cluster-interacting redox nucleic acid, DXP pathway nucleic acid (e.g., DXS, DXR, MCT, CMK, MCS, HDS, or HDR), and isoprene synthase nucleic acid can be enhanced by increasing the amount of an IDI polypeptide expressed by the cells.

In some embodiments, isoprene production by cells that contain a heterologous iron-sulfur cluster-interacting redox nucleic acid, DXS nucleic acid, and isoprene synthase nucleic acid can be enhanced by increasing the amount of an IDI polypeptide expressed by the cells. In other embodiments, isoprene production by cells that contain a heterologous iron-sulfur cluster-interacting redox nucleic acid, HDS (IspG or GcpE), and isoprene synthase nucleic acids can be enhanced by increasing the amount of an IDI polypeptide expressed by the cells. In some embodiments, the cells comprise IspG and fldA. In another embodiment, the cells comprise IspG, fldA, and IspH.

In some embodiments, isoprene production by cells that contain a heterologous flavodoxin nucleic acid, DXS nucleic acid, and isoprene synthase nucleic acid can be enhanced by increasing the amount of an IDI polypeptide expressed by the cells. In other embodiments, isoprene production by cells that contain a heterologous flavodoxin nucleic acid, HDS (IspG or GcpE) nucleic acid, and isoprene synthase nucleic acid can be enhanced by increasing the amount of an IDI polypeptide expressed by the cells.

In some embodiments, isoprene production by cells that contain a heterologous ferredoxin nucleic acid, ferredoxin-NADP+ oxidoreductase nucleic acid, DXS nucleic acid, and isoprene synthase nucleic acid can be enhanced by increasing the amount of an IDI polypeptide expressed by the cells. In other embodiments, isoprene production by cells that contain a heterologous ferredoxin nucleic acid, ferredoxin-NADP+ oxidoreductase nucleic acid, HDS (IspG or GcpE) nucleic acid, and isoprene synthase nucleic acid can be enhanced by increasing the amount of an IDI polypeptide expressed by the cells.

In some embodiments, isoprene production by cells that contain a heterologous iron-sulfur cluster-interacting redox nucleic acid, HDR (IspH or LytB) nucleic acid, and isoprene synthase nucleic acid can be enhanced by increasing the amount of an IDI (isopentenyl-diphosphate delta-isomerase) polypeptide expressed by the cells. In some embodiments, the cells comprise IspG and fldA. In another embodiment, the cells comprise IspG, fldA, and IspH.

In some embodiments, isoprene production by cells that contain a heterologous flavodoxin, HDR (IspH or LytB), and isoprene synthase nucleic acids can be enhanced by increasing the amount of an IDI (isopentenyl-diphosphate delta-isomerase) polypeptide expressed by the cells.

In some embodiments, isoprene production by cells that contain a heterologous ferredoxin nucleic acid, ferredoxin-NADP+ oxidoreductase nucleic acid, HDR (IspH or LytB) nucleic acid, and isoprene synthase nucleic acids can be enhanced by increasing the amount of an IDI (isopentenyl-diphosphate delta-isomerase) polypeptide expressed by the cells.

In some embodiments, isoprene production by cells that contain a heterologous ferredoxin nucleic acid, ferredoxin-NADP+ oxidoreductase nucleic acid, HDS and HDR nucleic acids, and isoprene synthase nucleic acid can be enhanced by increasing the amount of an IDI (isopentenyl-diphosphate delta-isomerase) polypeptide expressed by the cells.

IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount (and conversion rate) of IPP that is converted into DMAPP, which in turn is converted into isoprene.

The IDI nucleic acid may be a heterologous nucleic acid or a duplicate copy of an endogenous nucleic acid. In some embodiments, the amount of iron-sulfur cluster-interacting redox polypeptide, one or more of DXP pathway polypeptide (e.g., DXS, DXR, MCT, CMK, MCS, HDS, or HDR), isoprene synthase polypeptide, and IDI polypeptide are increased by replacing endogenous iron-sulfur cluster-interacting redox promoter or regulatory region, one or more of the endogenous DXP pathway promoter or regulatory region, and IDI promoters or regulatory region with other promoters and/or regulatory regions that result in greater transcription of iron-sulfur cluster-interacting redox nucleic acid, DXP pathway nucleic acid, isoprene synthase nucleic acid, and IDI nucleic acid.

Heterologous IDI polypeptides can also be expressed in a variety of host cells in the presence of isoprene synthase, such as *Escherichia coli* (*E. coli*), *Panteoa citrea, Bacillus subtilis, Yarrowia lipolytica*, and *Trichoderma reesei*. All of these cells produced more isoprene than when IDI is not used.

Additionally, isoprene production by cells that contain a heterologous iron-sulfur cluster-interacting redox nucleic acid, DXP pathway nucleic acid (e.g., DXS, DXR, MCT, CMK, MCS, HDS, or HDR), isoprene synthase nucleic acid, and optionally IDI nucleic acid, can be enhanced by increasing the amount of a DXP pathway associated polypeptide expressed by the cells In some embodiments of any of the aspects of the invention, isoprene production can be further increased by using a mutant DXP pathway polypeptide or nucleic acid derived from thereof. In some embodiments, the mutant DXP pathway polypeptide is a HDR polypeptide with the iron-sulfur cluster regulator (iscR) removed. In some embodiments, the mutant DXP pathway polypeptide is a mutant HDR polypeptide that produces solely DMAPP or a majority of DMAPP relative to IPP. For example, the use of the LytBG120D in a DXP pathway-mediated isoprene production strain allows the unique generation of an isoprenoid product that is derived almost entirely from DMAPP. See Example 18.

As used herein, iscR is encoded by an ORF located immediately upstream of genes coding for the *E. coli* Fe—S cluster assembly proteins. In the DXP pathway, the implementation of a gene cassette directing the overexpression of the isc operon involved in the assembly of iron-sulfur clusters into an *E. coli* strain engineered for HDR protein anaerobically purified from this strain by a factor of at least 200. (Gräwert et al., *J Am Chem Soc.* 126(40):12847-55 (2004); Schwartz et al., *PNAS,* 98(26):14751-3 (2001); Akhtar and Jones, *Appl. Microbiol. Biotechnol.* 78(5):853-62 (2008), which are each hereby incorporated by reference in their entireties).

In some embodiments of any of the aspects of the invention, isoprene production can be further increased by increasing the carbon flux through the DXP pathway. In some embodiments, the carbon flux can be increased by avoiding any feedback inhibition of DXS activity by metabolites downstream the DXP pathway or/and intermediates of other pathways that use a DXP pathway polypeptide as a substrate (e.g., DXR). In some embodiments, the feedback inhibition by some DXP pathway polypeptides (e.g., DXR) can be alleviated by rebalancing pathyway enzymes and maintaining levels of HMBPP and DMAPP at concentrations below 1 to 2 mM DMAPP and 1 to 2 mM HMBPP. In some embodiments, the level of HMBPP and DMAPP are maintained below 1 mM for the duration of the fermentation run. In other embodiments, the level of HMBPP and DMAPP are maintained below 1 mM during the exponential phase of the fermentation. In other embodiments, late DXP pathway enzymes, particularly IspG and IspH, are maintained at levels consistent with minimizing phosphorylation level of Dxr.

In some embodiments, the other pathway that uses DXP pathway polypeptide as a substrate (e.g., DXP) is the thiamine (Vitamin B1) or pyridoxal (Vitamin B6) pathway. In some embodiments, the carbon flux can be increased by expressing a DXP pathway polypeptide from a different organism that is not subject to inhibition by downstream products of the DXP pathway. In some embodiments, the carbon flux can be increased by deregulating glucose uptake. In other embodiments, the carbon flux can be increased by maximizing the balance between the precursors required for the DXP pathway. In some embodiments, the balance of the DXP pathway precursors, pyruvate and glyceraldehydes-3-phosphate (G-3-P) can be achieved by redirecting the carbon flux with the effect of elevating or lowering pyruvate or G-3-P separately. In some embodiments, the carbon flux can be increased by using a strain (containing one or more DXP pathway genes or one or more both DXP pathway and MVA pathway genes) containing a pyruvate dehydrogenase E1 subunit variant. In some embodiments, the pyruvate dehydrogenase (PDH) E1 subunit variant has an E636Q point mutation. In some embodiments, the carbon flux can be increased by using a CRP-deleted mutant. As used herein, CRP (cAMP Receptor Protein) is a positive regulator protein activated by cyclic AMP. It is required for RNA polymerase to initiate transcription of certain (catabolite-sensitive) operons of *E. coli.*

In some embodiments of any of the aspects of the invention, isoprene production can be further increased by utilizing the downstream genes or polypeptides of the DXP pathway by introducing a heterologous terpene synthase nucleic acid or a duplicate copy of an endogenous terpene synthase nucleic acid into the cells, which includes, but is not limited to ocimene synthase, farnesene synthase, and artemesinin synthase.

In some embodiments, a renewable carbon source is used for the production of isoprene. In some embodiments, the concentrations of isoprene and any oxidants are within the nonflammable ranges to reduce or eliminate the risk that a fire may occur during production or recovery of isoprene. See for example, U.S. Appl. No. 61/133,947, which is hereby incorporated by reference in its entirety, particularly with respect to flammability modeling and testing of isoprene in Example 13 and WO2010/003007. The compositions and methods of the present invention are desirable because they allow high isoprene yield per cell, high carbon yield, high isoprene purity, high productivity, low energy usage, low production cost and investment, and minimal side reactions. This efficient, large scale, biosynthetic process for isoprene production provides an isoprene source for synthetic isoprene-based rubber and provides a desirable, low-cost alternative to using natural rubber.

In some embodiments, at least a portion of the cells maintain the heterologous iron-sulfur cluster-interacting redox nucleic acid, DXP pathway nucleic acid, DXP pathway associated nucleic acid, and isoprene synthase nucleic acid for at least about 5, 10, 20, 50, 75, 100, 200, 300, or more cell divisions in a continuous culture (such as a continuous culture without dilution). In some embodiments, at least a portion of the cells maintain the heterologous iron-sulfur cluster-interacting redox nucleic acid, DXP pathway nucleic acid, DXP pathway associated nucleic acid, isoprene synthase nucleic acid, and IDI nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous iron-sulfur cluster-interacting redox nucleic acid, DXP pathway nucleic acid, isoprene synthase nucleic acid, and/or IDI nucleic acid and DXP pathway associated nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

The amount of isoprene produced can be further increased by adding yeast extract to the cell culture medium. For example, the amount of isoprene produced that are linearly proportional to the amount of yeast extract in the cell medium for the concentrations are tested. Increasing the amount of yeast extract in the presence of glucose can result in more isoprene being produced than increasing the amount of glucose in the presence of yeast extract. Also, increasing the amount of yeast extract can allow the cells to produce a high level of isoprene for a longer length of time and improved the health of the cells.

Isoprene production can also be demonstrated using three types of hydrolyzed biomass (bagasse, corn stover, and soft wood pulp) as the carbon source. If desired, any other biomass carbon source can be used in the compositions and methods of the invention. Biomass carbon sources are desirable because they are cheaper than many conventional cell mediums, thereby facilitating the economical production of isoprene.

In some embodiments, an oil is included in the cell medium. See, for example, U.S. 61/134,094, which is hereby incorporated by reference in its entirety, particularly with respect to oils included in the cell medium In some embodiments, more than one oil (such as 2, 3, 4, 5, or more oils) is included in the cell medium. While not intending to be bound to any particular theory, it is believed that (i) the oil may increase the amount of carbon in the cells that is available for conversion to isoprene, (ii) the oil may increase the amount of glyceraldehyde 3-phosphate and/or pyruvate in the cells, thereby increasing the carbon flow through the DXP pathway, and/or (ii) the oil may provide extra nutrients to the cells, which is desirable since a lot of the carbon in the cells is converted to isoprene rather than other products. In some embodiments, cells that are cultured in a cell medium containing oil naturally use the DXP pathway to produce isoprene or are genetically modified to contain nucleic acids for the entire DXP pathway. In some embodiments, the oil is partially or completely hydrolyzed before being added to the cell culture medium to facilitate the use of the oil by the host cells.

Exemplary Polypeptides and Nucleic Acids

Various iron-sulfur cluster-interacting redox polypeptides and nucleic acids, DXP pathway polypeptides and nucleic acids, DXP pathway associated polypeptides and nucleic acids, isoprene synthase polypeptides and nucleic acids, and IDI polypeptides and nucleic acids can be used in the compositions and methods of the invention.

As used herein, "polypeptides" includes polypeptides, proteins, peptides, fragments of polypeptides, and fusion polypeptides. In some embodiments, the fusion polypeptide includes part or all of a first polypeptide (e.g., an iron-sulfur cluster-interacting redox polypeptide, DXP pathway polypeptide, DXP pathway associated polypeptide, isoprene synthase polypeptide, and IDI polypeptide, or catalytically active fragment thereof) and may optionally include part or all of a second polypeptide (e.g., a peptide that facilitates purification or detection of the fusion polypeptide, such as a His-tag). In some embodiments, the fusion polypeptide has an activity of two or more DXP pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments, the polypeptide includes a segment of or the entire amino acid sequence of any naturally-occurring iron-sulfur cluster-interacting redox polypeptide, DXP pathway polypeptide, DXP pathway associated polypeptide, isoprene synthase polypeptide, or IDI polypeptide. In some embodiments, the polypeptide has one or more mutations compared to the sequence of a wild-type (i.e., a sequence occurring in nature) iron-sulfur cluster-interacting redox polypeptide, DXP pathway polypeptide, DXP pathway associated polypeptide, isoprene synthase polypeptide, or IDI polypeptide.

In some embodiments, the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments, the polypeptide is a heterologous polypeptide. By "heterologous polypeptide" is meant a polypeptide whose amino acid sequence is not identical to that of another polypeptide naturally expressed in the same host cell. In particular, a heterologous polypeptide is not identical to a wild-type nucleic acid that is found in the same host cell in nature.

As used herein, a "nucleic acid" refers to two or more deoxyribonucleotides and/or ribonucleotides in either single or double-stranded form. In some embodiments, the nucleic acid is a recombinant nucleic acid. By "recombinant nucleic acid" means a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is hereby incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In various embodiments, a nucleic acid is a recombinant nucleic acid. In some embodiments, an iron-sulfur cluster-interacting redox nucleic acid, DXP pathway nucleic acid, DXP pathway associated nucleic acid, isoprene synthase nucleic acid, or IDI nucleic acid is operably linked to another nucleic acid encoding all or a portion of another polypeptide such that the recombinant nucleic acid encodes a fusion polypeptide that includes an iron-sulfur cluster-interacting redox polypeptide, DXP pathway polypeptide, DXP pathway associated polypeptide, isoprene synthase polypeptide, and/or IDI and all or part of another polypeptide (e.g., a peptide that facilitates purification or detection of the fusion polypeptide, such as a His-tag). In some embodiments, part or all of a recombinant nucleic acid is chemically synthesized. It is to be understood that mutations, including single nucleotide mutations, can occur within a nucleic acid as defined herein.

In some embodiments, the nucleic acid is a heterologous nucleic acid. By "heterologous nucleic acid" is meant a nucleic acid whose nucleic acid sequence is not identical to that of another nucleic acid naturally found in the same host cell.

In particular embodiments, the nucleic acid includes a segment of or the entire nucleic acid sequence of any naturally-occurring iron-sulfur cluster-interacting redox nucleic acid, DXP pathway nucleic acid, DXP pathway associated nucleic acid, isoprene synthase nucleic, or IDI nucleic acid. In some embodiments, the nucleic acid includes at least or about 50, 100, 150, 200, 300, 400, 500, 600, 700, 800, or more contiguous nucleotides from a naturally-occurring iron-sulfur cluster-interacting redox nucleic acid, DXP pathway nucleic acid, DXP pathway associated nucleic acid, isoprene synthase nucleic, or IDI nucleic acid. In some embodiments, the nucleic acid has one or more mutations compared to the sequence of a wild-type (i.e., a sequence occurring in nature) iron-sulfur cluster-interacting redox nucleic acid, DXP pathway nucleic acid, DXP pathway associated nucleic acid, isoprene synthase nucleic acid, or IDI nucleic acid. In some embodiments, the nucleic acid has one or more mutations (e.g., a silent mutation) that increase the transcription or translation of iron-sulfur cluster-interacting redox nucleic acid, DXP pathway nucleic acid, DXP pathway associated nucleic acid, isoprene synthase nucleic acid, or IDI nucleic acid. In some embodiments, the nucleic acid is a degenerate variant of any nucleic acid encoding an iron-sulfur cluster-interacting redox polypeptide, DXP pathway polypeptide, DXP pathway associated polypeptide, isoprene synthase polypeptide, or IDI polypeptide.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

The accession numbers of exemplary isoprene synthase and DXP pathway polypeptides and nucleic acids are listed in Appendix 1 (the accession numbers of Appendix 1 and their corresponding sequences are herein incorporated by reference in their entireties, particularly with respect to the amino acid and nucleic acid sequences of isoprene synthase and/or DXP pathway polypeptides and nucleic acids). The Kegg database also contains the amino acid and nucleic acid sequences of numerous exemplary isoprene synthase and/or DXP pathway polypeptides and nucleic acids (see, for example, the world-wide web at "genome.jp/kegg/pathway/map/map00100.html" and the sequences therein, which are each hereby incorporated by reference in their entireties, particularly with respect to the amino acid and nucleic acid sequences of isoprene synthase and/or DXP pathway polypeptides and nucleic acids). In some embodiments, one or more of the isoprene synthase and/or DXP pathway polypeptides and/or nucleic acids have a sequence identical to a sequence publicly available on Dec. 12, 2007 or Sep. 14, 2008 such as any of the sequences that correspond to any of the accession numbers in Appendix 1 or any of the sequences present in the Kegg database. Additional exemplary isoprene synthase and/or DXP pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. In an exemplary assay, cell extracts are prepared by growing a strain (e.g., the *E. coli*/pTrcKudzu strain described herein) in the shake flask method as described in Example 1. After induction is complete, approximately 10 mL of cells are pelleted by centrifugation at 7000×g for 10 minutes and resuspended in 5 ml of PEB without glycerol. The cells are lysed using a French Pressure cell using standard procedures. Alternatively the cells are treated with lysozyme (Ready-Lyse lysozyme solution; EpiCentre) after a freeze/thaw at −80 C.

Isoprene synthase polypeptide activity in the cell extract can be measured, for example, as described in Silver et al., J. Biol. Chem. 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 μL of 1M $MgCl_2$, 1 mM (250 μg/ml) DMAPP, 65 μL of Plant Extract Buffer (PEB) (50 mM Tris-HCl, pH 8.0, 20 mM $MgCl_2$, 5% glycerol, and 2 mM DTT) is added to 25 μL of cell extract in a 20 ml Headspace vial with a metal screw cap and teflon coated silicon septum (Agilent Technologies) and cultured at 37° C. for 15 minutes with shaking. The reaction is quenched by adding 200 μL of 250 mM EDTA and quantified by GC/MS as described in Example 1, part II.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, such as the Faboideae subfamily. In some embodiments, the isoprene synthase polypeptide or nucleic acid is a polypeptide or nucleic acid from *Pueraria montana* (kudzu) (Sharkey et al., Plant Physiology 137: 700-712, 2005), *Pueraria lobata*, poplar (such as *Populus alba, Populus nigra, Populus trichocarpa*, or *Populus alba×tremula* (CAC35696) Miller et al., Planta 213: 483-487, 2001) aspen (such as *Populus tremuloides*) Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by Genbank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is a naturally-occurring polypeptide or nucleic acid from poplar. In some embodiments, the isoprene synthase nucleic acid or polypeptide is not a naturally-occurring polypeptide or nucleic acid from poplar.

Exemplary DXP Pathway Polypeptides and Nucleic Acids

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, IDI polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-d-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2,4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). Standard methods can be used to determine whether a polypeptide has HDR polypeptides activity by measuring the ability of the polypeptide to convert HMBPP in vitro, in a cell extract, or in vivo.

IDI polypeptides convert isopentenyl diphosphate into dimethylallyl diphosphate. Standard methods can be used to determine whether a polypeptide has IDI polypeptides activity by measuring the ability of the polypeptide to convert isopentenyl diphosphate in vitro, in a cell extract, or in vivo.

Exemplary MVA Pathway Polypeptides and Nucleic Acids

In some aspects of the invention, the cells described in any of the compositions or methods described herein comprise a nucleic acid encoding an MVA pathway polypeptide. In some embodiments, the MVA pathway polypeptide is an endogenous polypeptide. In some embodiments, the cells comprise one or more additional copies of an endogenous nucleic acid encoding an MVA pathway polypeptide. In some embodiments, the endogenous nucleic acid encoding an MVA pathway polypeptide operably linked to a constitutive promoter. In some embodiments, the endogenous nucleic acid encoding an MVA pathway polypeptide operably linked to a constitutive promoter. In some embodiments, the endogenous nucleic acid encoding an MVA pathway polypeptide is operably linked to a strong promoter. In a particular embodiment, the cells are engineered to over-express the endogenous MVA pathway polypeptide relative to wild-type cells.

In some embodiments, the MVA pathway polypeptide is a heterologous polypeptide. In some embodiments, the cells comprise more than one copy of a heterologous nucleic acid encoding an MVA pathway polypeptide. In some embodiments, the heterologous nucleic acid encoding an MVA pathway polypeptide is operably linked to a constitutive promoter. In some embodiments, the heterologous nucleic acid encoding an MVA pathway polypeptide is operably linked to a strong promoter.

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein. In addition, variants of MVA pathway polypeptide that confer the result of better isoprene production can also be used as well.

Types of MVA pathway polypeptides and/or DXP pathway polypeptides which can be used and methods of making microorganisms (e.g., facultative anaerobes such as *E. coli*) encoding MVA pathway polypeptides and/or DXP pathway polypeptides are also described in International Patent Application Publication No. WO2009/076676; U.S. patent application Ser. Nos. 12/496,573, 12/560,390, 12/560,317, 12/560,370, 12/560,305, and 12/560,366; and U.S. Provisional Patent Application Nos. 61/187,930, 61/187,934, and 61/187,959.

One of skill in the art can readily select and/or use suitable promoters to optimize the expression of isoprene synthase or and one or more MVA pathway polypeptides and/or one or more DXP pathway polypeptides. Similarly, one of skill in the art can readily select and/or use suitable vectors (or transfer vehicle) to optimize the expression of isoprene synthase or and one or more MVA pathway polypeptides and/or one or more DXP pathway polypeptides. In some embodiments, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some embodiments, an isoprene synthase or MVA pathway nucleic acid integrates into a chromosome of the cells without a selective marker.

Exemplary Iron-Sulfur Cluster-Interacting Redox Polypeptides and Nucleic Acids

As noted above, the iron-sulfur cluster-interacting redox polypeptide plays an essential role in the DXP pathway for isoprenoid biosynthesis. Exemplary iron-sulfur cluster-interacting redox polypeptides include polypeptides, fragments of polypeptides, peptides, and fusions polypeptides that have at least one activity of a iron-sulfur cluster-interacting redox polypeptide. Standard methods can be used to determine whether a polypeptide has iron-sulfur cluster-interacting redox polypeptide activity by using a hydrogenase-linked assay measuring the rate of metronidazole[1-(2-hydroxyethyl)-2-methyl-5-nitroimidazole] reduction (Chen and Blanchard, Analytical Biochem, 93:216-222 (1979)), which is hereby incorporated by reference in its entirety, especially with respect to the hydrogenase-linked assay for ferredoxin and flavodoxin).

Exemplary iron-sulfur cluster-interacting redox polypeptide nucleic acids include nucleic acids that encode a polypeptide, fragment of a polypeptide, peptide, or fusion polypeptide that has at least one activity of an iron-sulfur cluster-interacting redox polypeptide. Exemplary iron-sulfur cluster-interacting redox polypeptides and nucleic acids include naturally-occurring polypeptides and nucleic acids from any of the source organisms described herein as well as mutant polypeptides and nucleic acids derived from any of the source organisms described herein.

Exemplary Methods for Isolating Nucleic Acids

Iron-sulfur cluster-interacting redox nucleic acid, DXP pathway nucleic acid, DXP pathway associated nucleic acid, isoprene synthase nucleic, or IDI nucleic acid can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is hereby incorporated by reference in its entirety, particularly with respect to PCR methods) to obtain amounts of DNA suitable for transformation using appropriate vectors.

Alternatively, iron-sulfur cluster-interacting redox nucleic acid, DXP pathway nucleic acid, DXP pathway associated nucleic acid, isoprene synthase nucleic, and/or IDI nucleic acid (such as any isoprene synthase nucleic acid, iron-sulfur cluster-interacting redox nucleic acid, DXP pathway nucleic acid, and/or IDI nucleic acid with a known nucleic acid sequence) can be chemically synthesized using standard methods.

Additional iron-sulfur cluster-interacting redox nucleic acid, DXP pathway nucleic acid, DXP pathway associated nucleic acid, isoprene synthase nucleic, and/or IDI nucleic acid which may be suitable for use in the compositions and methods described herein can be identified using standard methods. For example, cosmid libraries of the chromosomal DNA of organisms known to produce isoprene naturally can be constructed in organisms such as *E. coli*, and then screened for isoprene production. In particular, cosmid libraries may be created where large segments of genomic DNA (35-45 kb) are packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the heterologous DNA. In addition to the cos sequence, these vectors also contain an origin of replication such as ColEI and drug resistance markers such as a nucleic acid resistant to ampicillin or neomycin. Methods of using cosmid vectors for the transformation of suitable bacterial hosts are well described in Sambrook et al., Molecular Cloning: A Laboratory Manual, 2$^{nd}$ ed., Cold Spring Harbor, 1989, which is hereby incorporated by reference in its entirety, particularly with respect to transformation methods.

Typically to clone cosmids, heterologous DNA is isolated using the appropriate restriction endonucleases and ligated adjacent to the cos region of the cosmid vector using the appropriate ligases. Cosmid vectors containing the linearized heterologous DNA are then reacted with a DNA packaging vehicle such as bacteriophage. During the packaging process, the cos sites are cleaved and the heterologous DNA is packaged into the head portion of the bacterial viral particle. These particles are then used to transfect suitable host cells such as *E. coli*. Once injected into the cell, the heterologous DNA circularizes under the influence of the cos sticky ends. In this manner, large segments of heterologous DNA can be introduced and expressed in host cells.

Additional methods for obtaining iron-sulfur cluster-interacting redox nucleic acid, DXP pathway nucleic acid, DXP pathway associated nucleic acid, isoprene synthase nucleic acid, and/or IDI nucleic acid include screening a metagenomic library by assay (such as the headspace assay (see for example, in U.S. application Ser. No. 12/335,071 and PCT/US2008/086809, which are hereby incorporated by reference in their entireties, particularly with respect to headspace assay for isoprene production in Example 1 and 7) or by PCR using primers directed against nucleotides encoding for a length of conserved amino acids (for example, at least 3 conserved amino acids). Conserved amino acids can be identified by aligning amino acid sequences of known iron-sulfur cluster-interacting redox polypeptide, DXP pathway polypeptide, DXP pathway associated polypeptide, isoprene synthase polypeptide, and/or IDI polypeptide. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (see, for example, Julsing et al., *Applied. Microbiol. Biotechnol.* 75: 1377-84, 2007; Withers et al., *Appl Environ Microbiol.* 73(19):6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXP pathway polypeptides and nucleic acids based on the similarity of their primary and/or predicted polypeptide secondary structure with that of known DXP pathway polypeptides and nucleic acids. Standard databases such as the swissprot-trembl database (world-wide web at "expasy.org", Swiss Institute of Bioinformatics Swiss-Prot group CMU—1 rue Michel Servet CH-1211 Geneva 4, Switzerland) can also be used to identify isoprene synthase, flavodoxin I, DXP pathway, and/or IDI polypeptides and nucleic acids. The secondary and/or tertiary structure of an iron-sulfur cluster-interacting redox polypeptide, DXP pathway polypeptide, DXP pathway associated polypeptide, isoprene synthase polypeptide, and/or IDI polypeptide can be predicted using the default settings of standard structure prediction programs, such as PredictProtein (630 West, 168 Street, BB217, New York, N.Y. 10032, USA). Alternatively, the actual secondary and/or tertiary structure of an iron-sulfur cluster-interacting redox polypeptide, DXP pathway polypeptide, DXP pathway associated polypeptide, isoprene synthase polypeptide, and/or IDI polypeptide can be determined using standard methods. Additional iron-sulfur cluster-interacting redox nucleic acid, DXP pathway nucleic acid, DXP pathway associated nucleic acid, isoprene synthase nucleic acid, and/or IDI nucleic acid can also be identified by hybridization to probes generated from known iron-sulfur cluster-interacting redox nucleic acid, DXP pathway nucleic acid, DXP pathway associated nucleic acid, isoprene synthase nucleic acid, and/or IDI nucleic acid.

Exemplary Promoters and Vectors

Any of the iron-sulfur cluster-interacting redox nucleic acid, DXP pathway nucleic acid, DXP pathway associated nucleic acid, isoprene synthase nucleic acid, or IDI nucleic acid described herein can be included in one or more vectors. Accordingly, the invention also features vectors with one more nucleic acids encoding any of the iron-sulfur cluster-interacting redox polypeptide, DXP pathway polypeptide, DXP pathway associated polypeptide, isoprene synthase polypeptide, and/or IDI polypeptide that are described herein. As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. Exemplary nutritional selective markers include those markers known in the art as amdS, argB, and pyr4. Markers useful in vector systems for transformation of *Trichoderma* are known in the art (see, e.g., Finkelstein, Chapter 6 in Biotechnology of Filamentous Fungi, Finkelstein et al., Eds. Butterworth-Heinemann, Boston, Mass., Chap. 6., 1992; and Kinghorn et al., Applied Molecular Genetics of Filamentous Fungi, Blackie Academic and Professional, Chapman and Hall, London, 1992, which are each hereby incorporated by reference in their entireties, particularly with respect to selective markers). In some embodiments, the selective marker is the amdS nucleic acid, which encodes the enzyme acetamidase, allowing transformed cells to grow on acetamide as a nitrogen source. The use of an *A. nidulans* amdS nucleic acid as a selective marker is described in Kelley et al., *EMBO J.* 4:475-479, 1985 and Penttila et al., *Gene* 61:155-164, 1987 (which are each hereby incorporated by reference in their entireties, particularly with respect to selective markers). In some embodiments, an isoprene synthase, flavodoxin I, DXP pathway, or IDI nucleic acid integrates into a chromosome of the cells without a selective marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Sambrook et al., Molecular Cloning: A Laboratory Manual, $2^{nd}$ ed., Cold Spring Harbor, 1989, which is hereby incorporated by reference in its entirety, particularly with respect to the use of vectors).

Promoters are well known in the art. Any promoter that functions in the host cell can be used for expression of an iron-sulfur cluster-interacting redox nucleic acid, DXP pathway nucleic acid, DXP pathway associated nucleic acid, isoprene synthase nucleic acid, or IDI nucleic acid in the host cell. Initiation control regions or promoters, which are useful to drive expression of iron-sulfur cluster-interacting redox nucleic acid, DXP pathway nucleic acid, DXP pathway associated nucleic acid, isoprene synthase nucleic acid, and/or IDI nucleic acid in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to, CYC1, HIS3, GAL1, GAL10, ADH1, PGK, PHO5, GAPDH, ADCI, TRP1, URA3, LEU2, ENO, and TPI (useful for expression in *Saccharomyces*); AOX1 (useful for expression in *Pichia*); and lac, trp, $\lambda P_L$, $\lambda P_R$, T7, tac, and trc (useful for expression in *E. coli*).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132,527).

In various embodiments, an iron-sulfur cluster-interacting redox nucleic acid, DXP pathway nucleic acid, DXP pathway associated nucleic acid, isoprene synthase nucleic acid, or IDI nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous iron-sulfur cluster-interacting redox nucleic acid, DXP pathway nucleic acid, DXP pathway associated nucleic acid, isoprene synthase nucleic acid, or IDI nucleic acid is operably linked to a T7 promoter. In some embodiments, the heterologous or extra endogenous iron-sulfur cluster-interacting redox nucleic acid, DXP pathway nucleic acid, DXP pathway associated nucleic acid, isoprene synthase nucleic acid, or IDI nucleic acid operably linked to a T7 promoter is contained in a medium or high copy plasmid. In some embodiments, the heterologous or extra endogenous iron-sulfur cluster-interacting redox nucleic acid, DXP pathway nucleic acid, DXP pathway associated nucleic acid, isoprene synthase nucleic acid, or IDI nucleic acid is operably linked to a Trc promoter. In some embodiments, the heterologous or extra endogenous is iron-sulfur cluster-interacting redox nucleic acid, DXP pathway nucleic acid, DXP pathway associated nucleic acid, isoprene synthase nucleic acid, or IDI nucleic acid operably linked to a Trc promoter is contained in a medium or high copy plasmid. In some embodiments, the heterologous or extra endogenous iron-sulfur cluster-interacting redox nucleic acid, DXP pathway nucleic acid, DXP pathway associated nucleic acid, isoprene synthase nucleic acid, or IDI nucleic acid is operably linked to a Lac promoter. In some embodiments, the heterologous or extra endogenous iron-sulfur cluster-interacting redox nucleic acid, DXP pathway nucleic acid, DXP pathway associated nucleic acid, isoprene synthase nucleic acid, or IDI nucleic acid operably linked to a Lac promoter is contained in a low copy plasmid. In some embodiments, the heterologous or extra endogenous iron-sulfur cluster-interacting redox nucleic acid, DXP pathway nucleic acid, DXP pathway associated nucleic acid, isoprene synthase nucleic acid, or IDI nucleic acid is operably linked to an endogenous promoter, such as an endogenous *Escherichia, Panteoa, Bacillus, Yarrowia, Streptomyces, Trichoderma* or *Thermosynechococcus* promoter or an endogenous alkaline serine protease iron-sulfur cluster-interacting redox promoter, DXP pathway promoter, DXP pathway associated promoter, isoprene synthase promoter, or IDI promoter. In some embodiments, the heterologous or extra endogenous isoprene synthase nucleic acid, iron-sulfur cluster-interacting redox nucleic acid, DXP pathway nucleic acid, DXP pathway associated nucleic acid, and/or IDI nucleic acid operably linked to an endogenous promoter is contained in a high copy plasmid. In some embodiments, the vector is a replicating plasmid that does not integrate into a chromosome in the cells. In some embodiments, part or all of the vector integrates into a chromosome in the cells.

In some embodiments, the vector is any vector which when introduced into a fungal host cell is integrated into the host cell genome and is replicated. Reference is made to the Fungal Genetics Stock Center Catalogue of Strains (FGSC, the world-wide web at "fgsc.net" and the references cited therein, which are each hereby incorporated by reference in their entireties, particularly with respect to vectors) for a list of vectors. Additional examples of suitable expression and/or integration vectors are provided in Sambrook et al., Molecular Cloning: A Laboratory Manual, $2^{nd}$ ed., Cold Spring Harbor, 1989, Current Protocols in Molecular Biology (F. M. Ausubel et al. (eds) 1987, Supplement 30, section 7.7.18); van den Hondel et al. in Bennett and Lasure (Eds.) More Gene Manipulations in Fungi, Academic Press pp. 396-428, 1991; and U.S. Pat. No. 5,874,276, which are each hereby incorporated by reference in their entireties, particularly with respect to vectors. Particularly useful vectors include pFB6, pBR322, PUC18, pUC100, and pENTR/D.

In some embodiments, iron-sulfur cluster-interacting redox nucleic acid, DXP pathway nucleic acid, DXP pathway associated nucleic acid, isoprene synthase nucleic acid, or IDI nucleic acid is operably linked to a suitable promoter that shows transcriptional activity in a fungal host cell. The promoter may be derived from one or more nucleic acids encoding a polypeptide that is either endogenous or heterologous to the host cell. In some embodiments, the promoter is useful in a *Trichoderma* host. Suitable non-limiting examples of promoters include cbh1, cbh2, egl1, egl2, pepA, hfb1, hfb2, xyn1, and amy. In some embodiments, the promoter is one that is native to the host cell. For example, in some embodiments when *T. reesei* is the host, the promoter is a native *T. reesei* promoter. In some embodiments, the promoter is *T. reesei* cbh1, which is an inducible promoter and has been deposited in GenBank under Accession No. D86235, which is hereby incorporated by reference in its entirety, particularly with respect to promoters. In some embodiments, the promoter is one that is heterologous to the fungal host cell. Other examples of useful promoters include promoters from the genes of *A. awamori* and *A. niger* glucoamylase (glaA) (Nunberg et al., *Mol. Cell. Biol.* 4:2306-2315, 1984 and Boel et al., *EMBO J.* 3:1581-1585, 1984, which are each hereby incorporated by reference in their entireties, particularly with respect to promoters); *Aspergillus niger* alpha amylases, *Aspergillus oryzae* TAKA amylase, *T. reesei* xln1, and the *T. reesei cellobiohydrolase* 1 (EP 137280, which is hereby incorporated by reference in its entirety, particularly with respect to promoters).

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell. A particularly suitable terminator sequence is cbh1 derived from a *Trichoderma* strain (such as *T. reesei*). Other useful fungal terminators include the terminator from an *A. niger* or *A. awamori* glucoamylase nucleic acid (Nunberg et al., *Mol. Cell. Biol.* 4:2306-2315, 1984 and Boel et al., *EMBO J.* 3:1581-1585, 1984; which are each hereby incorporated by reference in their entireties, particularly with respect to fungal terminators). Optionally, a termination site may be included. For effective expression of the polypeptides, DNA encoding the polypeptide are linked operably through initiation codons to selected expression control regions such that expression results in the formation of the appropriate messenger RNA.

In some embodiments, the promoter, coding, region, and terminator all originate from the iron-sulfur cluster-interacting redox nucleic acid, DXP pathway nucleic acid, DXP pathway associated nucleic acid, isoprene synthase nucleic acid, or IDI nucleic acid to be expressed. In some embodiments, the coding region for iron-sulfur cluster-interacting redox nucleic acid, DXP pathway nucleic acid, DXP pathway associated nucleic acid, isoprene synthase nucleic acid, or IDI nucleic acid is inserted into a general-purpose expression vector such that it is under the transcriptional control of the expression construct promoter and terminator sequences. In some embodiments, genes or part thereof are inserted downstream of the strong cbh1 promoter.

An iron-sulfur cluster-interacting redox nucleic acid, DXP pathway nucleic acid, DXP pathway associated nucleic acid, isoprene synthase nucleic acid, or IDI nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an iron-sulfur cluster-interacting redox nucleic acid, DXP pathway nucleic acid, DXP pathway associated nucleic acid, isoprene synthase nucleic acid, or IDI nucleic acid), a promoter, a terminator, and other sequences and to insert them into a suitable vector are well known in the art. For example, restriction enzymes can be used to cleave the iron-sulfur cluster-interacting redox nucleic acid, DXP pathway nucleic acid, DXP pathway associated nucleic acid, isoprene synthase nucleic acid, or IDI nucleic acid and the vector. Then, the compatible ends of the cleaved iron-sulfur cluster-interacting redox nucleic acid, DXP pathway nucleic acid, DXP pathway associated nucleic acid, isoprene synthase nucleic acid, or IDI nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, $2^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express iron-sulfur cluster-interacting redox nucleic acid, DXP pathway nucleic acid, DXP pathway associated nucleic acid, isoprene synthase nucleic acid, or IDI nucleic acid at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, $2^{nd}$ ed., Cold Spring Harbor, 1989, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990 and Ausubel et al., Eds. Current Protocols in Molecular Biology, 1994, which are each hereby incorporated by reference in their entireties, particularly with respect to molecular biology and cloning techniques.

Exemplary Source Organisms

Iron-sulfur cluster-interacting redox nucleic acid, DXP pathway nucleic acid, DXP pathway associated nucleic acid, isoprene synthase nucleic acid, or IDI nucleic acid (and their encoded polypeptides) can be obtained from any organism that naturally contains iron-sulfur cluster-interacting redox nucleic acid, DXP pathway nucleic acid, DXP pathway associated nucleic acid, isoprene synthase nucleic acid, and/or IDI nucleic acid. As noted above, isoprene is formed naturally by a variety of organisms, such as bacteria, yeast, plants, and animals. Organisms contain the MVA pathway, DXP pathway, or both the MVA and DXP pathways for producing isoprene (FIG. 19A). Thus, DXS, DXR, MCT, CMK, MCS, HDS, or HDR nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways.

In some embodiments, the nucleic acid sequence of the iron-sulfur cluster-interacting redox nucleic acid, DXP pathway nucleic acid, DXP pathway associated nucleic acid, isoprene synthase nucleic acid, or IDI nucleic acid is identical to the sequence of a nucleic acid that is produced by any of the following organisms in nature. In some embodiments, the amino acid sequence of iron-sulfur cluster-interacting redox polypeptide, DXP pathway polypeptide, DXP pathway associated polypeptide, isoprene synthase polypeptide, or IDI polypeptide is identical to the sequence of a polypeptide that is produced by any of the following organisms in nature. In some embodiments, the iron-sulfur cluster-interacting redox nucleic acid, DXP pathway nucleic acid, DXP pathway associated nucleic acid, isoprene synthase nucleic acid, or IDI nucleic acid or its encoded polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some embodiments, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens, H. lanuginose*, or *H. grisea*); *Chrysosporium* sp. (e.g., *C. lucknowense*), *Gliocladium* sp., *Aspergillus* sp. (e.g., *A. oryzae, A. niger, A sojae, A. japonicus, A. nidulans*, or *A. awamori*) (Ward et al., Appl. Microbiol. Biotechnol. 39: 7380743, 1993 and Goedegebuur et al., Genet. 41: 89-98, 2002), *Fusarium* sp., (e.g., *F. roseum, F. graminum F. cerealis, F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., *Sci.* 228: 21-26, 1985). The term "*Trichoderma*" or "*Trichoderma* sp." or "*Trichoderma* spp." refer to any fungal genus previously or currently classified as *Trichoderma.*

In some embodiments, the fungus is *A. nidulans, A. awamori, A. oryzae, A. aculeatus, A. niger, A. japonicus, T. reesei, T. viride, F. oxysporum*, or *F. solani*. *Aspergillus* strains are disclosed in Ward et al., Appl. Microbiol. Biotechnol. 39:738-743, 1993 and Goedegebuur et al., Curr Gene 41:89-98, 2002, which are each hereby incorporated by reference in their entireties, particularly with respect to fungi. In particular embodiments, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some embodiments, the host strain is a derivative of RL-P37. RL-P37 is disclosed in Sheir-Neiss et al., Appl. Microbiol. Biotechnology 20:46-53, 1984, which is hereby incorporated by reference in its entirety, particularly with respect to strains of *T. reesei.*

In some embodiments, the source organism is a yeast, such as *Saccharomyces* sp., *Schizosaccharomyces* sp., *Pichia* sp., or *Candida* sp.

In some embodiments, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Thermosynechococcus* such as *T. elongatus*, strains of *Sinorhizobium* such as *S. meliloti*, strains of *Helicobacter* such as *H. pylori*, strains of *Agrobacterium* such as *A. tumefaciens*, strains of *Deinococcus* such as *D. radiodurans*, strains of *Listeria* such as *L. monocytogenes*, strains of *Lactobacillus* such as L. spp, or strains of *Escherichia* such as *E. coli.*

As used herein, "the genus *Bacillus*" includes all species within the genus "*Bacillus*," as known to those of skill in the art, including but not limited to *B. subtilis, B. lichenifonnis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

In some embodiments, the source organism is a gram-positive bacterium. Non-limiting examples include strains of *Streptomyces* (e.g., *S. lividans, S. coelicolor*, or *S. griseus*), *Bacillus, Listeria* (e.g., *L. monocytogenes*) or *Lactobacillus* (e.g., L. spp). In some embodiments, the source organism is a gram-negative bacterium, such as *E. coli, Pseudomonas* sp, or *H. pylori.*

In some embodiments, the source organism is a plant, such as a plant from the family Fabaceae, such as the Faboideae subfamily. In some embodiments, the source organism is kudzu, poplar (such as *Populus alba×tremula* CAC35696), aspen (such as *Populus tremuloides*), *Quercus robur, Arabidopsis* (such as *A. thaliana*), or *Zea* (such as *Z. mays*).

In some embodiments, the source organism is an algae, such as a green algae, red algae, glaucophytes, chlorarachniophytes, euglenids, chromista, or dinoflagellates.

In some embodiments, the source organism is a cyanobacterium, such as cyanobacteria classified into any of the following groups based on morphology: *Chroococcales, Pleurocapsales, Oscillatoriales, Nostocales*, or *Stigonematales*. In some embodiments, the cyanobacterium is *Thermosynechococcus elongates*.

Exemplary Host Cells

A variety of host cells can be used to express iron-sulfur cluster-interacting redox polypeptide, DXP pathway polypeptide, DXP pathway associated polypeptide, MVA pathway polypeptide, MVA pathway associated polypeptide, isoprene synthase polypeptide, or IDI polypeptide and to produce isoprene in the methods of the claimed invention. Exemplary host cells include cells from any of the organisms listed in the prior section under the heading "Exemplary Source Organisms." The host cell may be a cell that naturally produces isoprene or a cell that does not naturally produce isoprene. In some embodiments, the host cell naturally produces isoprene using the DXP pathway and an isoprene synthase, and one or more DXP pathway polypeptide and iron-sulfur cluster-interacting redox polypeptides are added to enhance production of isoprene using this pathway. In some embodiments, the host cell naturally produces isoprene using the DXP pathway and isoprene synthase, and one or more DXP pathway nucleic acids, one or more iron-sulfur cluster-interacting redox nucleic acids, and IDI are added to enhance production of isoprene using this pathway.

Exemplary Transformation Methods iron-sulfur cluster-interacting redox nucleic acid, DXP pathway nucleic acid, DXP pathway associated nucleic acid, isoprene synthase nucleic acid, or IDI nucleic acid or its vectors containing them can be inserted into a host cell (e.g., a plant cell, a fungal cell, a yeast cell, or a bacterial cell described herein) using standard techniques for expression of the encoded iron-sulfur cluster-interacting redox polypeptide, DXP pathway polypeptide, DXP pathway associated polypeptide, isoprene synthase polypeptide, and/or IDI polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., *Curr. Genet.* 16:53-56, 1989, which are each hereby incorporated by reference in their entireties, particularly with respect to transformation methods). The expression of heterologous polypeptide in *Trichoderma* is described in U.S. Pat. No. 6,022,725; U.S. Pat. No. 6,268,328; U.S. Pat. No. 7,262,041; WO 2005/001036; Harkki et al.; *Enzyme Microb. Technol.* 13:227-233, 1991; Harkki et al., *Bio Technol.* 7:596-603, 1989; EP 244,234; EP 215,594; and Nevalainen et al., "*The Molecular Biology of Trichoderma and its Application to the Expression of Both Homologous and Heterologous Genes*," in Molecular Industrial Mycology, Eds. Leong and Berka, Marcel Dekker Inc., NY pp. 129-148, 1992, which are each hereby incorporated by reference in their entireties, particularly with respect to transformation and expression methods). Reference is also made to Cao et al., (Sci. 9:991-1001, 2000; EP 238023; and Yelton et al., *Proceedings. Natl. Acad. Sci. USA* 81:1470-1474, 1984 (which are each hereby incorporated by reference in their entireties, particularly with respect to transformation methods) for transformation of *Aspergillus* strains. The introduced nucleic acids may be integrated into chromosomal DNA or maintained as extrachromosomal replicating sequences.

Any method known in the art may be used to select transformants. In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on a solid non-selective medium (e.g., a medium that lacks acetamide), harvesting spores from this culture medium, and determining the percentage of these spores which subsequently germinate and grow on selective medium containing acetamide.

In some embodiments, fungal cells are transformed by a process involving protoplast formation and transformation of the protoplasts followed by regeneration of the cell wall in a known manner. In one specific embodiment, the preparation of *Trichoderma* sp. for transformation involves the preparation of protoplasts from fungal mycelia (see, Campbell et al., *Curr. Genet.* 16:53-56, 1989, which is hereby incorporated by reference in its entirety, particularly with respect to transformation methods). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M. It is desirable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. In addition to the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). While not intending to be bound to any particular theory, it is believed that the polyethylene glycol acts to fuse the cell membranes, thus permitting the contents of the medium to be delivered into the cytoplasm of the *Trichoderma* sp. strain and the plasmid DNA to be transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL (such as $2\times10^6$/mL) are used in the transformation. A volume of 100 μL of these protoplasts or cells in an appropriate solution (e.g., 1.2 M sorbitol and 50 mM $CaCl_2$) are mixed with the desired DNA. Generally, a high concentration of PEG is added to the uptake solution. From 0.1 to 1 volume of 25% PEG 4000 can be added to the protoplast suspension. In some embodiments, about 0.25 volumes are added to the protoplast suspension. Additives such as dimethyl sulfoxide, heparin, spermidine, potassium chloride, and the like may also be added to the uptake solution and aid in transformation. Similar procedures are available for other fungal host cells (see, e.g., U.S. Pat. Nos. 6,022,725 and 6,268,328, which are each hereby incorporated by reference in their entireties, particularly with respect to transformation methods).

Generally, the mixture is then cultured at approximately 0° C. for a period of between 10 to 30 minutes. Additional PEG is then added to the mixture to further enhance the uptake of the desired nucleic acid sequence. The 25% PEG 4000 is generally added in volumes of 5 to 15 times the volume of the transformation mixture; however, greater and lesser volumes may be suitable. The 25% PEG 4000 is desirably about 10 times the volume of the transformation mixture. After the PEG is added, the transformation mixture is then cultured either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

The transformation of bacterial cells may be performed according to conventional methods, e.g., as described in Sambrook et al., Molecular Cloning: A Laboratory Manual, Cold Spring Harbor, 1982, which is hereby incorporated by reference in its entirety, particularly with respect to transformation methods.

Exemplary Cell Culture Media

The invention also includes a cell or a population of cells in culture that produce isoprene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharids), invert sugar (e.g., enzymatically treated sucrose syrup), glycerol, glycerine (e.g., a glycerine byproduct of a biodiesel or soap-making process), dihydroxyacetone, one-carbon source, oil (e.g., a plant or vegetable oil such as corn, palm, or soybean oil), animal fat, animal oil, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

In some embodiments, the cells are cultured under limited glucose conditions. By "limited glucose conditions" is meant that the amount of glucose that is added is less than or about 105% (such as about 100%) of the amount of glucose that is consumed by the cells. In particular embodiments, the amount of glucose that is added to the culture medium is approximately the same as the amount of glucose that is consumed by the cells during a specific period of time. In some embodiments, the rate of cell growth is controlled by limiting the amount of added glucose such that the cells grow at the rate that can be supported by the amount of glucose in the cell medium. In some embodiments, glucose does not accumulate during the time the cells are cultured. In various embodiments, the cells are cultured under limited glucose conditions for greater than or about 1, 2, 3, 5, 10, 15, 20, 25, 30, 35, 40, 50, 60, or 70 hours. In various embodiments, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions may allow more favorable regulation of the cells.

In some embodiments, the cells are cultured in the presence of an excess of glucose. In particular embodiments, the amount of glucose that is added is greater than about 105% (such as about or greater than 110, 120, 150, 175, 200, 250, 300, 400, or 500%) or more of the amount of glucose that is consumed by the cells during a specific period of time. In some embodiments, glucose accumulates during the time the cells are cultured.

Exemplary lipids are any substance containing one or more fatty acids that are C4 and above fatty acids that are saturated, unsaturated, or branched.

Exemplary oils are lipids that are liquid at room temperature. In some embodiments, the lipid contains one or more C4 or above fatty acids (e.g., contains one or more saturated, unsaturated, or branched fatty acid with four or more carbons). In some embodiments, the oil is obtained from soy, corn, canola, jatropha, palm, peanut, sunflower, coconut, mustard, rapeseed, cottonseed, palm kernel, olive, safflower, sesame, linseed, oleagineous microbial cells, Chinese tallow, or any combination of two or more of the foregoing.

Exemplary fatty acids include compounds of the formula RCOOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{1-2}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, oil, fat, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, oil, fat, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, oil, fat, fatty acid, monoglyceride, diglyceride, or triglyceride that is added before and/or during the culturing of the host cells. In some embodiments, the carbon source includes both (i) a lipid, oil, fat, fatty acid, monoglyceride, diglyceride, or triglyceride and (ii) a carbohydrate, such as glucose. In some embodiments, the ratio of the lipid, oil, fat, fatty acid, monoglyceride, diglyceride, or triglyceride to the carbohydrate is about 1:1 on a carbon basis (i.e., one carbon in the lipid, oil, fat, fatty acid, monoglyceride, diglyceride, or triglyceride per carbohydrate carbon). In particular embodiments, the amount of the lipid, oil, fat, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., Bioresource *Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry to dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.,* 53 (2) 541-543, 1989, which is hereby incorporated by reference in its entirety, particularly with respect to carbon sources) and in bacteria (Hunter et. al., *Biochemistry,* 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd*., [Int. Symp.], $7^{th}$ ed., 415-32. Editors: Murrell et al., Publisher: Intercept, Andover, UK, 1993, which is hereby incorporated by reference in its entirety, particularly with respect to carbon sources). Similarly, various species of *Candida* metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988 and Ilmen et al., *Appl. Environ. Microbiol.* 63:1298-1306, 1997, which are each hereby incorporated by reference in their entireties, particularly with respect to cell medias). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase nucleic acid, iron-sulfur cluster-interacting redox nucleic acid, DXP pathway nucleic acid, DXP pathway associated nucleic acid, or IDI nucleic acid is under the control of an inducible promoter, the inducing agent (e.g., a sugar, metal salt or antimicrobial), is desirably added to the medium at a concentration effective to induce expression of an isoprene synthase polypeptide, iron-sulfur cluster-interacting redox polypeptide, DXP pathway polypeptide, DXP pathway associated polypeptide, or IDI polypeptide. In some embodiments, cell medium has an antibiotic (such as kanamycin) that corresponds to the antibiotic resistance nucleic acid (such as a kanamycin resistance nucleic acid) on a vector that has one or more isoprene synthase nucleic acid, iron-sulfur cluster-interacting redox nucleic acid, DXP pathway nucleic acid, DXP pathway associated nucleic acid, or IDI nucleic acid.

Exemplary Cell Culture Conditions

Materials and methods suitable for the maintenance and growth of bacterial cultures are well known in the art. Exemplary techniques may be found in *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass., which are each hereby incorporated by reference in their entireties, particularly with respect to cell culture techniques. In some embodiments, the cells are cultured in a culture medium under conditions permitting the expression of one or more isoprene synthase polypeptide, iron-sulfur cluster-interacting redox polypeptide, DXP pathway polypeptide, DXP pathway associated polypeptide, or IDI polypeptide encoded by a nucleic acid inserted into the host cells.

Standard cell culture conditions can be used to culture the cells (see, for example, WO 2004/033646 and references cited therein, which are each hereby incorporated by reference in their entireties, particularly with respect to cell culture and fermentation conditions). Cells are grown and maintained at an appropriate temperature, gas mixture, and pH (such as at about 20 to about 37° C., at about 6% to about 84% $CO_2$, and at a pH between about 5 to about 9). In some embodiments, cells are grown at 35° C. in an appropriate cell medium. In some embodiments, e.g., cultures are cultured at approximately 28° C. in appropriate medium in shake cultures or fermentors until desired amount of isoprene production is achieved. In some embodiments, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells. Exemplary culture conditions for a given filamentous fungus are known in the art and may be found in the scientific literature and/or from the source of the fungi such as the American Type Culture Collection and Fungal Genetics Stock Center.

In various embodiments, the cells are grown using any known mode of fermentation, such as batch, fed-batch, or continuous processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, “batch” fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprene production. In some embodiments, cells in stationary phase produce isoprene.

In some embodiments, a variation on the standard batch system is used, such as the Fed-Batch system. Fed-Batch fermentation processes comprise a typical batch system with the exception that the carbon source is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., glucose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, cells are immobilized on a substrate as whole cell catalysts and subjected to fermentation conditions for isoprene production.

In some embodiments, bottles of liquid culture are placed in shakers in order to introduce oxygen to the liquid and maintain the uniformity of the culture. In some embodiments, an incubator is used to control the temperature, humidity, shake speed, and/or other conditions in which a culture is grown. The simplest incubators are insulated boxes with an adjustable heater, typically going up to ~65° C. More elaborate incubators can also include the ability to lower the temperature (via refrigeration), or the ability to control humidity or $CO_2$ levels. Most incubators include a timer; some can also be programmed to cycle through different temperatures, humidity levels, etc. Incubators can vary in size from tabletop to units the size of small rooms.

If desired, a portion or all of the cell medium can be changed to replenish nutrients and/or avoid the build up of potentially harmful metabolic byproducts and dead cells. In the case of suspension cultures, cells can be separated from the media by centrifuging or filtering the suspension culture and then resuspending the cells in fresh media. In the case of adherent cultures, the media can be removed directly by aspiration and replaced. In some embodiments, the cell medium allows at least a portion of the cells to divide for at least or about 5, 10, 20, 40, 50, 60, 65, or more cell divisions in a continuous culture (such as a continuous culture without dilution).

In some embodiments, a constitutive or leaky promoter (such as a Trc promoter) is used and a compound (such as IPTG) is not added to induce expression of the isoprene synthase nucleic acid, iron-sulfur cluster-interacting redox nucleic acid, DXP pathway nucleic acid, DXP pathway associated nucleic acid, or IDI nucleic acid, operably linked to the promoter. In some embodiments, a compound (such as IPTG) is added to induce expression of the isoprene synthase nucleic acid, iron-sulfur cluster-interacting redox nucleic acid, DXP pathway nucleic acid, DXP pathway associated nucleic acid, or IDI nucleic acid operably linked to the promoter.

Exemplary Methods for Decoupling Isoprene Production from Cell Growth.

The invention provides, inter alia, compositions and methods for increasing the production of isoprene from cultured cells. When feedstock is used, it is desirable for the carbon from the feedstock to be converted to isoprene rather than to the growth and maintenance of the cells. In some embodiments, the cells are grown to a low to medium $OD_{600}$, then production of isoprene is started or increased. This strategy permits a large portion of the carbon to be converted to isoprene.

In some embodiments, cells reach an optical density such that they no longer divide or divide extremely slowly, but continue to make isoprene for several hours (such as about 2, 4, 6, 8, 10, 15, 20, 25, 30, or more hours). In some cases, the optical density at 550 nm decreases over time (such as a decrease in the optical density after the cells are no longer in an exponential growth phase due to cell lysis), and the cells continue to produce a substantial amount of isoprene. In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr) during this time period. In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium) during this time period. In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene during this time period. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells are in stationary phase. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells divide slowly or not at all such that the optical density at 550 nm of the cells increases by less than or about 50% (such as by less than or about 40, 30, 20, 10, 5, or 0%). In some embodiments, isoprene is only produced in the growth phase.

In some embodiments, one or more isoprene synthase nucleic acid, iron-sulfur cluster-interacting redox nucleic acid, DXP pathway nucleic acid, DXP pathway associated nucleic acid, and/or IDI nucleic acid are placed under the control of a promoter or factor that is more active in stationary phase than in the growth phase. For example, one or more isoprene synthase nucleic acid, iron-sulfur cluster-interacting redox nucleic acid, DXP pathway nucleic acid, DXP pathway associated nucleic acid, and/or IDI nucleic acid may be placed under control of a stationary phase sigma factor, such as RpoS. In some embodiments, one or more isoprene synthase nucleic acid, iron-sulfur cluster-interacting redox nucleic acid, DXP pathway nucleic acid, DXP pathway associated nucleic acid, and/or IDI nucleic acid are placed under control of a promoter inducible in stationary phase, such as a promoter inducible by a response regulator active in stationary phase.

Production of Isoprene within Safe Operating Ranges

The invention provides, inter alia, compositions and methods for increasing the production of isoprene from cultured cells. The production of isoprene within safe operating levels according to its flammability characteristics simplifies the design and construction of commercial facilities, vastly improves the ability to operate safely, and limits the potential for fires to occur. In particular, the optimal ranges for the production of isoprene are within the safe zone, i.e., the nonflammable range of isoprene concentrations. In one such aspect, the invention features a method for the production of isoprene within the nonflammable range of isoprene concentrations (outside the flammability envelope of isoprene).

Thus, computer modeling and experimental testing were used to determine the flammability limits of isoprene (such as isoprene in the presence of $O_2$, $N_2$, $CO_2$, or any combination of two or more of the foregoing gases) in order to ensure process safety. The flammability envelope is characterized by the lower flammability limit (LFL), the upper flammability limit (UFL), the limiting oxygen concentration (LOC), and the limiting temperature. For a system to be flammable, a minimum amount of fuel (such as isoprene) must be in the presence of a minimum amount of oxidant, typically oxygen. The LFL is the minimum amount of isoprene that must be present to sustain burning, while the UFL is the maximum amount of isoprene that can be present. Above this limit, the mixture is fuel rich and the fraction of oxygen is too low to have a flammable mixture. The LOC indicates the minimum fraction of oxygen that must also be present to have a flammable mixture. The limiting temperature is based on the flash point of isoprene and is that lowest temperature at which combustion of isoprene can propagate. These limits are specific to the concentration of isoprene, type and concentration of oxidant, inerts present in the system, temperature, and pressure of the system. Compositions that fall within the limits of the flammability envelope propagate combustion and require additional safety precautions in both the design and operation of process equipment.

The following conditions were tested using computer simulation and mathematical analysis and experimental testing. If desired, other conditions (such as other temperature, pressure, and permanent gas compositions) may be tested using the methods described herein to determine the LFL, UFL, and LOC concentrations.

(1) Computer Simulation and Mathematical Analysis

Test Suite 1:

isoprene: 0 wt %-14 wt %

$O_2$: 6 wt %-21 wt %

$N_2$: 79 wt %-94 wt %

Test Suite 2:

isoprene: 0 wt %-14 wt %

$O_2$: 6 wt %-21 wt %

$N_2$: 79 wt %-94 wt %

Saturated with $H_2O$

Test Suite 3:

isoprene: 0 wt %-14 wt %

$O_2$: 6 wt %-21 wt %

$N_2$: 79 wt %-94 wt %

$CO_2$: 5 wt %-30 wt %

(2) Experimental Testing for Final Determination of Flammability Limits

Test Suite 1:

isoprene: 0 wt %-14 wt %

$O_2$: 6 wt %-21 wt %

$N_2$: 79 wt %-94 wt %

Test Suite 2:

isoprene: 0 wt %-14 wt %

$O_2$: 6 wt %-21 wt %

$N_2$: 79 wt %-94 wt %

Saturated with $H_2O$

Simulation software was used to give an estimate of the flammability characteristics of the system for several different testing conditions. $CO_2$ showed no significant affect on the system's flammability limits. Test suites 1 and 2 were confirmed by experimental testing. The modeling results were in-line with the experimental test results. Only slight variations were found with the addition of water.

The LOC was determined to be 9.5 vol % for an isoprene, $O_2$, $N_2$, and $CO_2$ mixture at 40° C. and 1 atmosphere. The addition of up to 30% $CO_2$ did not significantly affect the flammability characteristics of an isoprene, $O_2$, and $N_2$ mixture. Only slight variations in flammability characteristics were shown between a dry and water saturated isoprene, $O_2$, and $N_2$ system. The limiting temperature is about −54° C. Temperatures below about −54° C. are too low to propagate combustion of isoprene.

In some embodiments, the LFL of isoprene ranges from about 1.5 vol. % to about 2.0 vol %, and the UFL of isoprene ranges from about 2.0 vol. % to about 12.0 vol. %, depending on the amount of oxygen in the system. In some embodiments, the LOC is about 9.5 vol % oxygen. In some embodiments, the LFL of isoprene is between about 1.5 vol. % to about 2.0 vol %, the UFL of isoprene is between about 2.0 vol. % to about 12.0 vol. %, and the LOC is about 9.5 vol % oxygen when the temperature is between about 25° C. to about 55° C. (such as about 40° C.) and the pressure is between about 1 atmosphere and 3 atmospheres.

In some embodiments, isoprene is produced in the presence of less than about 9.5 vol % oxygen (that is, below the LOC required to have a flammable mixture of isoprene). In some embodiments in which isoprene is produced in the presence of greater than or about 9.5 vol % oxygen, the isoprene concentration is below the LFL (such as below about 1.5 vol. %). For example, the amount of isoprene can be kept below the LFL by diluting the isoprene composition with an inert gas (e.g., by continuously or periodically adding an inert gas such as nitrogen to keep the isoprene composition below the LFL). In some embodiments in which isoprene is produced in the presence of greater than or about 9.5 vol % oxygen, the isoprene concentration is above the UFL (such as above about 12 vol. %). For example, the amount of isoprene can be kept above the UFL by using a system (such as any of the cell culture systems described herein) that produces isoprene at a concentration above the UFL. If desired, a relatively low level of oxygen can be used so that the UFL is also relatively low. In this case, a lower isoprene concentration is needed to remain above the UFL.

In some embodiments in which isoprene is produced in the presence of greater than or about 9.5 vol % oxygen, the isoprene concentration is within the flammability envelope (such as between the LFL and the UFL). In some embodiments when the isoprene concentration may fall within the flammability envelope, one or more steps are performed to reduce the probability of a fire or explosion. For example, one or more sources of ignition (such as any materials that may generate a spark) can be avoided. In some embodiments, one or more steps are performed to reduce the amount of time that the concentration of isoprene remains within the flammability envelope. In some embodiments, a sensor is used to detect when the concentration of isoprene is close to or within the flammability envelope. If desired, the concentration of isoprene can be measured at one or more time points during the culturing of cells, and the cell culture conditions and/or the amount of inert gas can be adjusted using standard methods if the concentration of isoprene is close to or within the flammability envelope. In particular embodiments, the cell culture conditions (such as fermentation conditions) are adjusted to either decrease the concentration of isoprene below the LFL or increase the concentration of isoprene above the UFL. In some embodiments, the amount of isoprene is kept below the LFL by diluting the isoprene composition with an inert gas (such as by continuously or periodically adding an inert gas to keep the isoprene composition below the LFL).

In some embodiments, the amount of flammable volatiles other than isoprene (such as one or more sugars) is at least about 2, 5, 10, 50, 75, or 100-fold less than the amount of isoprene produced. In some embodiments, the portion of the gas phase other than isoprene gas comprises between about 0% to about 100% (volume) oxygen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 100% (volume) oxygen. In some embodiments, the portion of the gas phase other than isoprene gas comprises between about 0% to about 99% (volume) nitrogen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 99% (volume) nitrogen.

In some embodiments, the portion of the gas phase other than isoprene gas comprises between about 1% to about 50% (volume) $CO_2$, such as between about 1% to about 10%, about 10% to about 20%, about 20% to about 30%, about 30% to about 40%, or about 40% to about 50% (volume) $CO_2$.

In some embodiments, an isoprene composition also contains ethanol. For example, ethanol may be used for extractive distillation of isoprene, resulting in compositions (such as intermediate product streams) that include both ethanol and isoprene. Desirably, the amount of ethanol is outside the flammability envelope for ethanol. The LOC of ethanol is about 8.7 vol %, and the LFL for ethanol is about 3.3 vol % at standard conditions, such as about 1 atmosphere and about 60° F. (NFPA 69 *Standard on Explosion Prevention Systems,* 2008 edition, which is hereby incorporated by reference in its entirety, particularly with respect to LOC, LFL, and UFL values). In some embodiments, compositions that include isoprene and ethanol are produced in the presence of less than the LOC required to have a flammable mixture of ethanol (such as less than about 8.7% vol %). In some embodiments in which compositions that include isoprene and ethanol are produced in the presence of greater than or about the LOC required to have a flammable mixture of ethanol, the ethanol concentration is below the LFL (such as less than about 3.3 vol. %).

In various embodiments, the amount of oxidant (such as oxygen) is below the LOC of any fuel in the system (such as isoprene or ethanol). In various embodiments, the amount of oxidant (such as oxygen) is less than about 60, 40, 30, 20, 10, or 5% of the LOC of isoprene or ethanol. In various embodiments, the amount of oxidant (such as oxygen) is less than the LOC of isoprene or ethanol by at least 2, 4, 5, or more absolute percentage points (vol %). In particular embodiments, the amount of oxygen is at least 2 absolute percentage points (vol %) less than the LOC of isoprene or ethanol (such as an oxygen concentration of less than 7.5 vol % when the LOC of isoprene is 9.5 vol %). In various embodiments, the amount of fuel (such as isoprene or ethanol) is less than or about 25, 20, 15, 10, or 5% of the LFL for that fuel.

Exemplary Production of Isoprene

The invention provides, inter alia, compositions and methods for increasing the production of isoprene from cultured cells using various DXP pathway enzymes in combination with iron-sulfur cluster-interacting redox genes or polypeptides and isoprene synthase genes or polypeptides, optionally with IDI and DXP pathway associated genes and polypeptides. In some embodiments, the cells are cultured in a culture medium under conditions permitting the production of isoprene by the cells. By "peak absolute productivity" is meant the maximum absolute amount of isoprene in the off-gas during the culturing of cells for a particular period of time (e.g., the culturing of cells during a particular fermentation run). By "peak absolute productivity time point" is meant the time point during a fermentation run when the absolute amount of isoprene in the off-gas is at a maximum during the culturing of cells for a particular period of time (e.g., the culturing of cells during a particular fermentation run). In some embodiments, the isoprene amount is measured at the peak absolute productivity time point. In some embodiments, the peak absolute productivity for the cells is about any of the isoprene amounts disclosed herein.

By "peak specific productivity" is meant the maximum amount of isoprene produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprene produced per cell is at a maximum. The specific productivity is determined by dividing the total productivity by the amount of cells, as determined by optical density at 600 nm ($OD_{600}$). In some embodiments, the isoprene amount is measured at the peak specific productivity time point. In some embodiments, the peak specific productivity for the cells is about any of the isoprene amounts per cell disclosed herein.

By "cumulative total productivity" is meant the cumulative, total amount of isoprene produced during the culturing of cells for a particular period of time (e.g., the culturing of cells during a particular fermentation run). In some embodiments, the cumulative, total amount of isoprene is measured. In some embodiments, the cumulative total productivity for the cells is about any of the isoprene amounts disclosed herein.

By "relative detector response" refers to the ratio between the detector response (such as the GC/MS area) for one compound (such as isoprene) to the detector response (such as the GC/MS area) of one or more compounds (such as all C5 hydrocarbons). The detector response may be measured as described herein, such as the GC/MS analysis performed with an Agilent 6890 GC/MS system fitted with an Agilent HP-5MS GC/MS column (30 m×250 μm; 0.25 μm film thickness). If desired, the relative detector response can be converted to a weight percentage using the response factors for each of the compounds. This response factor is a measure of how much signal is generated for a given amount of a particular compound (that is, how sensitive the detector is to a particular compound). This response factor can be used as a correction factor to convert the relative detector response to a weight percentage when the detector has different sensitivities to the compounds being compared. Alternatively, the weight percentage can be approximated by assuming that the response factors are the same for the compounds being compared. Thus, the weight percentage can be assumed to be approximately the same as the relative detector response.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some embodiments, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h. The amount of isoprene in ng/$g_{wcm}$/h can be calculated by multiplying the value for isoprene production in the units of nmole/$g_{wcm}$/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some embodiments, the cells in culture produce at least about 2 g/$L_{broth}$, at least about 2.1 g/$L_{broth}$, at least about 2.2 g/$L_{broth}$, at least about 2.3 g/$L_{broth}$, at least about 2.4 g/$L_{broth}$, at least about 2.5 g/$L_{broth}$, at least about 2.6 g/$L_{broth}$, at least about 2.7 g/$L_{broth}$, at least about 2.8 g/$L_{broth}$, at least about 2.9 g/$L_{broth}$, at least about 3.0 g/$L_{broth}$, at least about 3.2 g/$L_{broth}$, at least about 3.5 g/$L_{broth}$, at least about 3.7 g/$L_{broth}$, or at least about 4.0 g/$L_{broth}$.

The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace (as described, for example, in Example I, part II). If the $OD_{600}$ value is not 1.0, then the measurement can be normalized to an $OD_{600}$ value of 1.0 by dividing by the $OD_{600}$ value. The value of mg isoprene/L headspace can be converted to mg/$L_{broth}$/hr/$OD_{600}$ of culture broth by multiplying by a factor of 38. The value in units of mg/$L_{broth}$/hr/$OD_{600}$ can be multiplied by the number of hours and the $OD_{600}$ value to obtain the cumulative titer in units of mg of isoprene/L of broth.

The instantaneous isoprene production rate in mg/$L_{broth}$/hr in a fermentor can be measured by taking a sample of the fermentor off-gas, analyzing it for the amount of isoprene (in units such as mg of isoprene per $L_{gas}$) as described, for example, in Example I, part II and multiplying this value by the rate at which off-gas is passed though each liter of broth (e.g., at 1 vvm (volume of air/volume of broth/minute) this is 60 $L_{gas}$ per hour). Thus, an off-gas level of 1 mg/$L_{gas}$ corresponds to an instantaneous production rate of 60 mg/$L_{broth}$/hr at air flow of 1 vvm. If desired, the value in the units mg/$L_{broth}$/hr can be divided by the $OD_{600}$ value to obtain the specific rate in units of mg/$L_{broth}$/hr/OD. The average value of mg isoprene/$L_{gas}$ can be converted to the total product productivity (grams of isoprene per liter of fermentation broth, mg/$L_{broth}$) by multiplying this average off-gas isoprene concentration by the total amount of off-gas sparged per liter of fermentation broth during the fermentation. Thus, an average off-gas isoprene concentration of 0.5 mg/$L_{broth}$/hr over 10 hours at 1 vvm corresponds to a total product concentration of 300 mg isoprene/$L_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

% Carbon Yield=(moles carbon in isoprene produced)/(moles carbon in carbon source)*100 — Equation 1

For this calculation, yeast extract can be assumed to contain 50% w/w carbon. As an example, for the 500 liter described in Example 7, part VIII, the percent conversion of carbon into isoprene can be calculated as shown in Equation 2.

% Carbon Yield=(39.1 g isoprene*1/68.1 mol/g*5 C/mol)/[(181221 g glucose*1/180 mol/g*6 C/mol)+(17780 g yeast extract*0.5*1/12 mol/g)]*100=0.042% — Equation 2

For the two 500 liter fermentations described herein (Example 7, parts VII and VIII), the percent conversion of carbon into isoprene was between 0.04-0.06%. A 0.11-0.16% carbon yield has been achieved using 14 liter systems as described herein.

One skilled in the art can readily convert the rates of isoprene production or amount of isoprene produced into any other units. Exemplary equations are listed below for interconverting between units.

Units for Rate of Isoprene Production (Total and Specific)

1 g isoprene/$L_{broth}$/hr=14.7 mmol isoprene/$L_{broth}$/hr (total volumetric rate) — Equation 3

1 nmol isoprene/$g_{wcm}$/hr=1 nmol isoprene/$L_{broth}$/hr/$OD_{600}$(This conversion assumes that one liter of broth with an $OD_{600}$ value of 1 has a wet cell weight of 1 gram.) — Equation 4

1 nmol isoprene/$g_{wcm}$/hr=68.1 ng isoprene/$g_{wcm}$/hr (given the molecular weight of isoprene) — Equation 5

1 nmol isoprene/$L_{gas}O_2$/hr=90 nmol isoprene/$L_{broth}$/hr (at an $O_2$ flow rate of 90 L/hr per L of culture broth) — Equation 6

1 ug isoprene/$L_{gas}$ isoprene in off-gas=60 ug isoprene/$L_{broth}$/hr at a flow rate of 60 $L_{gas}$ per $L_{broth}$ (1 vvm) — Equation 7

Units for Titer (Total and Specific)

1 nmol isoprene/mg cell protein=150 nmol isoprene/$L_{broth}$/$OD_{600}$ (This conversion assumes that one liter of broth with an $OD_{600}$ value of 1 has a total cell protein of approximately 150 mg) (specific productivity) — Equation 8

1 g isoprene/$L_{broth}$=14.7 mmol isoprene/$L_{broth}$ (total titer) — Equation 9

If desired, Equation 10 can be used to convert any of the units that include the wet weight of the cells into the corresponding units that include the dry weight of the cells.

Dry weight of cells=(wet weight of cells)/3.3 — Equation 10

If desired, Equation 11 can be used to convert between units of ppm and ug/L. In particular, "ppm" means parts per million defined in terms of ug/g (w/w). Concentrations of gases can also be expressed on a volumetric basis using "ppmv" (parts per million by volume), defined in terms of uL/L (vol/vol). Conversion of ug/L to ppm (e.g., ug of analyte per g of gas) can be performed by determining the mass per L of off-gas (i.e., the density of the gas). For example, a liter of air at standard temperature and pressure (STP; 101.3 kPa (1 bar) and 273.15K) has a density of approximately 1.29 g/L. Thus, a concentration of 1 ppm (ug/g) equals 1.29 ug/L at STP (equation 11). The conversion of ppm (ug/g) to ug/L is a function of both pressure, temperature, and overall composition of the off-gas.

1 ppm (ug/g) equals 1.29 ug/L at standard temperature and pressure (STP; 101.3 kPa (1 bar) and 273.15K). — Equation 11

Conversion of ug/L to ppmv (e.g., uL of analyte per L of gas) can be performed using the Universal Gas Law (equation 12). For example, an off-gas concentration of 1000 ug/$L_{gas}$ corresponds to 14.7 umol/$L_{gas}$. The universal gas constant is 0.082057 L.atm $K^{-1}$ $mol^{-1}$, so using equation 12, the volume occupied by 14.7 umol of HG at STP is equal to 0.329 mL. Therefore, the concentration of 1000 ug/L HG is equal to 329 ppmv or 0.0329% (v/v) at STP.

PV=nRT, where "P" is pressure, "V" is volume, "n" is moles of gas, "R" is the Universal gas constant, and "T" is temperature in Kelvin. — Equation 12

The amount of impurities in isoprene compositions are typically measured herein on a weight per volume (w/v) basis in units such as ug/L. If desired, measurements in units of ug/L can be converted to units of $mg/m^3$ using equation 13.

1 ug/L=1 $mg/m^3$ — Equation 13

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXP pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

In some embodiments, the isoprene composition comprises greater than or about 99.90, 99.92, 99.94, 99.96, 99.98, or 100% isoprene by weight compared to the total weight of all C5 hydrocarbons in the composition. In some embodiments, the composition has a relative detector response of greater than or about 99.90, 99.91, 99.92, 99.93, 99.94, 99.95, 99.96, 99.97, 99.98, 99.99, or 100% for isoprene compared to the detector response for all C5 hydrocarbons in the composition. In some embodiments, the isoprene composition comprises between about 99.90 to about 99.92, about 99.92 to about 99.94, about 99.94 to about 99.96, about 99.96 to about 99.98, about 99.98 to 100% isoprene by weight compared to the total weight of all C5 hydrocarbons in the composition.

In some embodiments, the isoprene composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, or cis-pent-3-ene-1-yne) by weight compared to the total weight of all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for C5 hydrocarbons other than isoprene compared to the detector response for all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, or cis-pent-3-ene-1-yne compared to the detector response for all C5 hydrocarbons in the composition. In some embodiments, the isoprene composition comprises between about 0.02 to about 0.04%, about 0.04 to about 0.06%, about 0.06 to 0.08%, about 0.08 to 0.10%, or about 0.10 to about 0.12% C5 hydrocarbons other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, or cis-pent-3-ene-1-yne) by weight compared to the total weight of all C5 hydrocarbons in the composition.

In some embodiments, the isoprene composition comprises less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a compound that inhibits the polymerization of isoprene for any compound in the composition that inhibits the polymerization of isoprene. In some embodiments, the isoprene composition comprises less than or about 50, 40, 30, 20, 10, 5, 1, 0.5, 0.1, 0.05, 0.01, or 0.005 ug/L of a hydrocarbon other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, or cis-pent-3-ene-1-yne). In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a hydrocarbon other than isoprene. In some embodiments, the isoprene composition comprises less than or about 50, 40, 30, 20, 10, 5, 1, 0.5, 0.1, 0.05, 0.01, or 0.005 ug/L of a protein or fatty acid (such as a protein or fatty acid that is naturally associated with natural rubber).

In some embodiments, the isoprene composition comprises less than or about 10, 5, 1, 0.8, 0.5, 0.1, 0.05, 0.01, or 0.005 ppm of alpha acetylenes, piperylenes, acetonitrile, or 1,3-cyclopentadiene. In some embodiments, the isoprene composition comprises less than or about 5, 1, 0.5, 0.1, 0.05, 0.01, or 0.005 ppm of sulfur or allenes. In some embodiments, the isoprene composition comprises less than or about 30, 20, 15, 10, 5, 1, 0.5, 0.1, 0.05, 0.01, or 0.005 ppm of all acetylenes (such as pentyne-1, butyne-2, 2 MB1-3yne, and 1-pentyne-4-yne). In some embodiments, the isoprene composition comprises less than or about 2000, 1000, 500, 200, 100, 50, 40, 30, 20, 10, 5, 1, 0.5, 0.1, 0.05, 0.01, or 0.005 ppm of isoprene dimers, such as cyclic isoprene dimmers (e.g., cyclic C10 compounds derived from the dimerization of two isoprene units).

In some embodiments, the composition comprises greater than about 2 mg of isoprene, such as greater than or about 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene. In some embodiments, the amount of isoprene in the composition is between about 2 to about 5,000 mg, such as between about 2 to about 100 mg, about 100 to about 500 mg, about 500 to about 1,000 mg, about 1,000 to about 2,000 mg, or about 2,000 to about 5,000 mg. In some embodiments, the amount of isoprene in the composition is between about 20 to about 5,000 mg, about 100 to about 5,000 mg, about 200 to about 2,000 mg, about 200 to about 1,000 mg, about 300 to about 1,000 mg, or about 400 to about 1,000 mg. In some embodiments, greater than or about 20, 25, 30, 40, 50, 60, 70, 80, 90, or 95% by weight of the volatile organic fraction of the composition is isoprene.

In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments in which the composition includes ethanol, the composition also includes between about 4 to about 15% by weight of isoprene, such as between about 4 to about 8%, about 8 to about 12%, or about 12 to about 15% by weight of isoprene.

Exemplary Isoprene Purification Methods

In some embodiments, any of the methods described herein further include recovering the isoprene. For example, the isoprene produced using the compositions and methods of the invention can be recovered using standard techniques, such as gas stripping, membrane enhanced separation, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In one embodiment, the isoprene is recovered by absorption stripping (see, e.g., U.S. Appl. 61/288,142). In particular, embodiments, extractive distillation with an alcohol (such as ethanol, methanol, propanol, or a combination thereof) is used to recover the isoprene. In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation (such as condensation due to exposure to a condensation coil or do to an increase in pressure). In some embodiments, membrane enrichment of a dilute isoprene vapor stream above the dew point of the vapor resulting in the condensation of liquid isoprene. In some embodiments, the isoprene is compressed and condensed.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent. In one embodiment, the isoprene is recovered by using absorption stripping as described in U.S. Provisional Appl. No. 61/288,142.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some embodiments, at least a portion of the gas phase remaining after one or more recovery steps for the removal of isoprene is recycled by introducing the gas phase into a cell culture system (such as a fermentor) for the production of isoprene.

In some embodiments, any of the methods described herein further include polymerizing the isoprene. For example, standard methods can be used to polymerize the purified isoprene to form cis-polyisoprene or other down stream products using standard methods. Accordingly, the invention also features a tire comprising polyisoprene, such as cis-1,4-polyisoprene and/or trans-1,4-polyisoprene made from any of the isoprene compositions disclosed herein.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Production of Isoprene in *E. Coli* Expressing Recombinant Kudzu Isoprene Synthase I. Construction of Vectors for Expression of the Kudzu Isoprene Synthase in *E. Coli*

Figure 2:
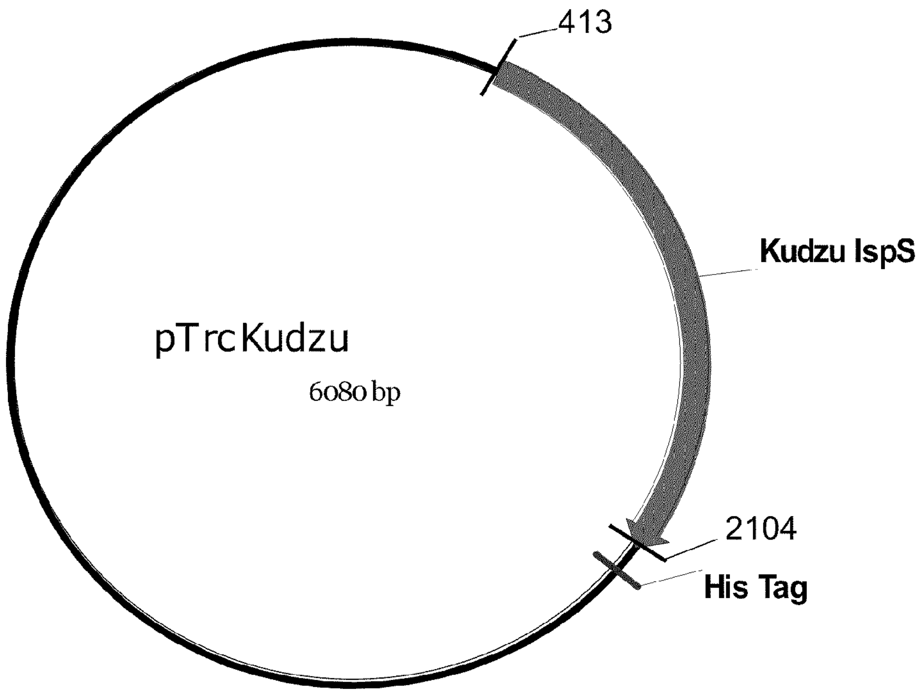
FIG. 2 is a map of pTrcKudzu.

The protein sequence for the kudzu (*Pueraria montana*) isoprene synthase gene (IspS) was obtained from GenBank (AAQ84170). A kudzu isoprene synthase gene, optimized for *E. coli* codon usage, was purchased from DNA2.0 (SEQ ID NO:1). The isoprene synthase gene was removed from the supplied plasmid by restriction endonuclease digestion with BspLU11I/PstI, gel-purified, and ligated into pTrcHis2B (Invitrogen) that had been digested with NcoI/PstI. The construct was designed such that the stop codon in the isoprene synthase gene 5' to the PstI site. As a result, when the construct was expressed the His-Tag is not attached to the isoprene synthase protein. The resulting plasmid, pTrcKudzu, was verified by sequencing (FIGS. 2 and 3).

Figure 4:
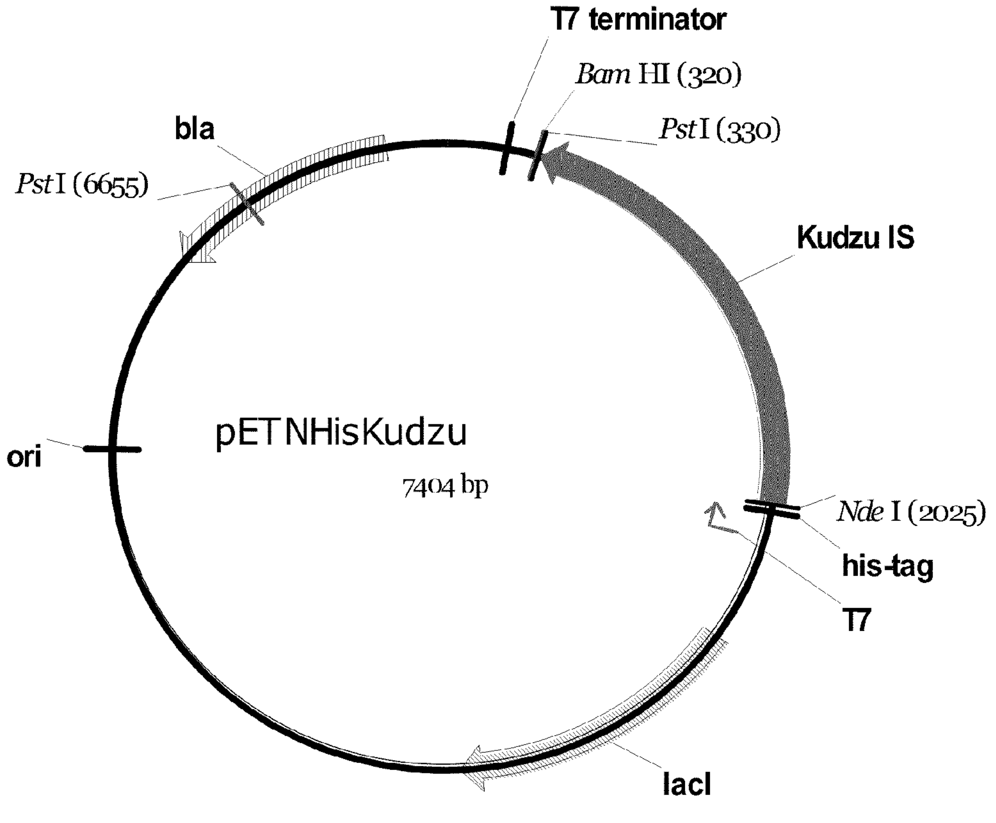
FIG. 4 is a map of pETNHisKudzu.

The isoprene synthase gene was also cloned into pET16b (Novagen). In this case, the isoprene synthase gene was inserted into pET16b such that the recombinant isoprene synthase protein contained the N-terminal His tag. The isoprene synthase gene was amplified from pTrcKudzu by PCR using the primer set pET-His-Kudzu-2F: 5'-CGTGAGATCATATGTGTGCGACCTCTTCTCAATTTAC (SEQ ID NO:3) and pET-His-Kudzu-R: 5'-CGGTCGACGGATCCCTGCAGTTAGACATACATCAGCTG (SEQ ID NO:4). These primers added an NdeI site at the 5'-end and a BamH1 site at the 3' end of the gene respectively. The plasmid pTrcKudzu, described above, was used as template DNA, Herculase polymerase (Stratagene) was used according to manufacture's directions, and primers were added at a concentration of 10 pMols. The PCR was carried out in a total volume of 25 μl. The PCR product was digested with NdeI/BamH1 and cloned into pET16b digested with the same enzymes. The ligation mix was transformed into *E. coli* Top10 (Invitrogen) and the correct clone selected by sequencing. The resulting plasmid, in which the kudzu isoprene synthase gene was expressed from the T7 promoter, was designated pET-NHisKudzu (FIGS. 4 and 5).

Figure 6:
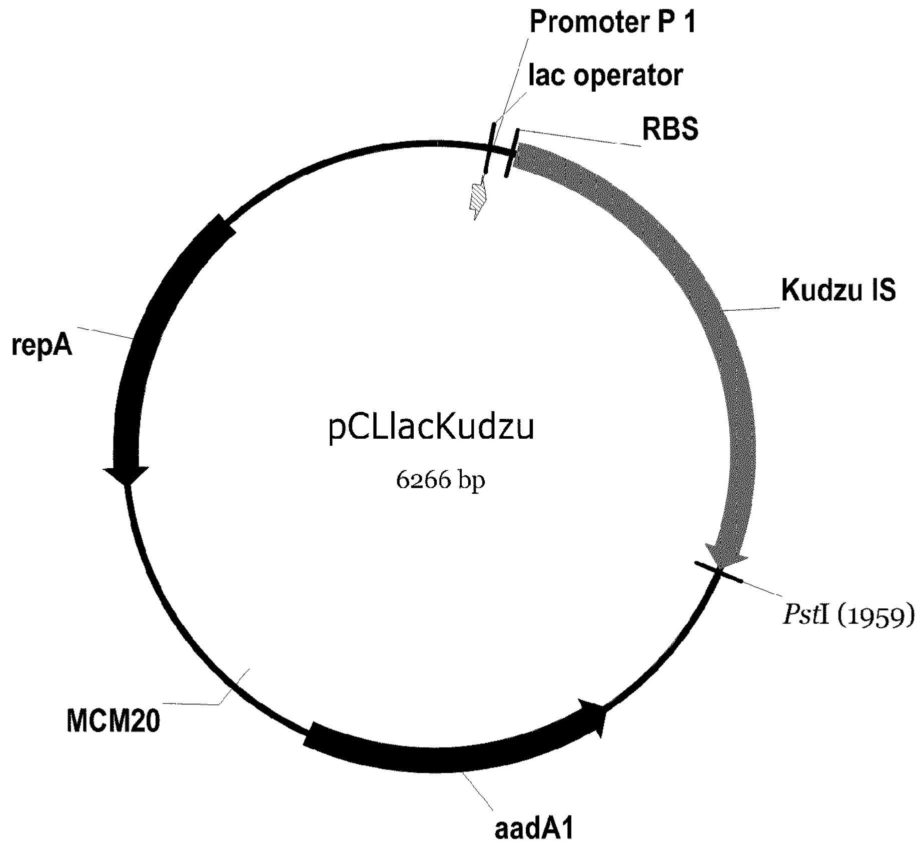
FIG. 6 is a map of pCL-lac-Kudzu.
Figure 8A:
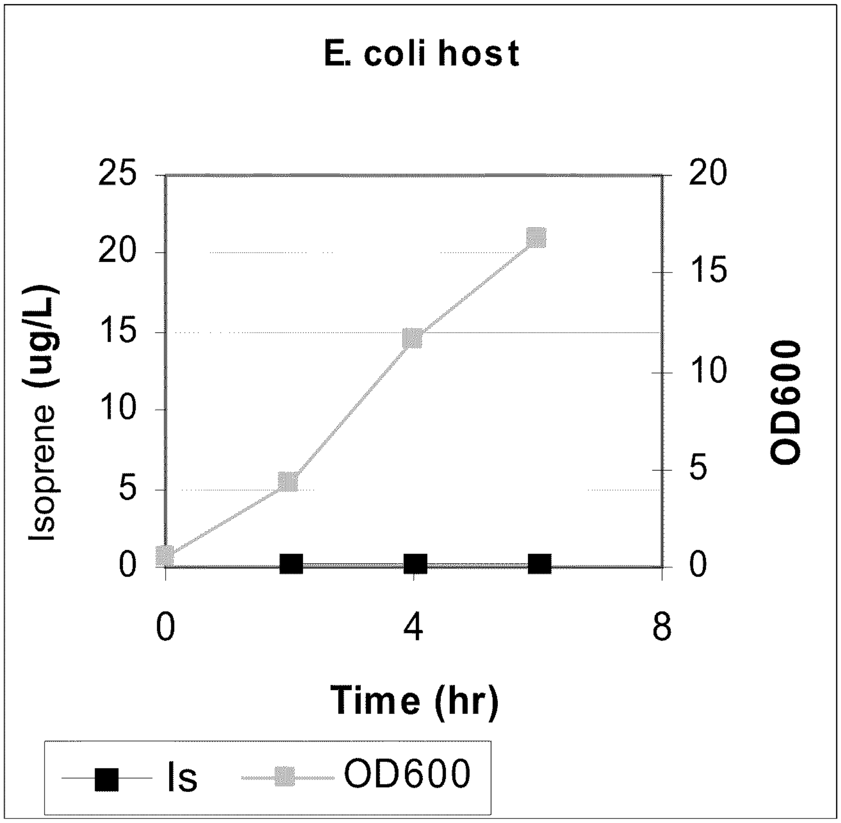
FIG. 8A is a graph showing the production of isoprene in *E. coli* BL21 cells with no vector.
Figure 8B:
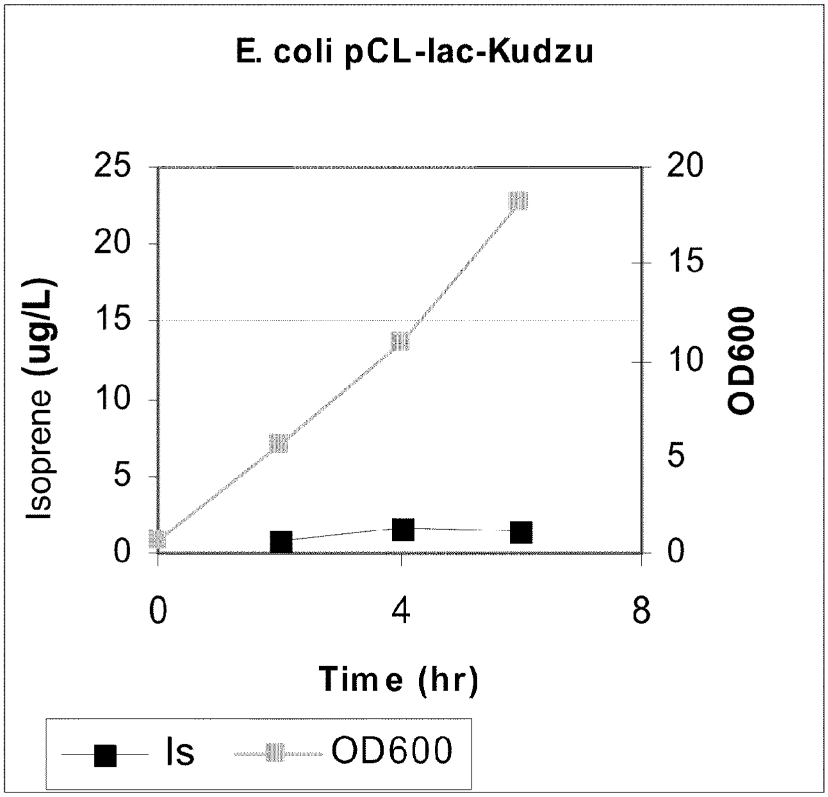
FIG. 8B is a graph showing the production of isoprene in *E. coli* BL21 cells with pCL-lac-Kudzu
Figure 8C:
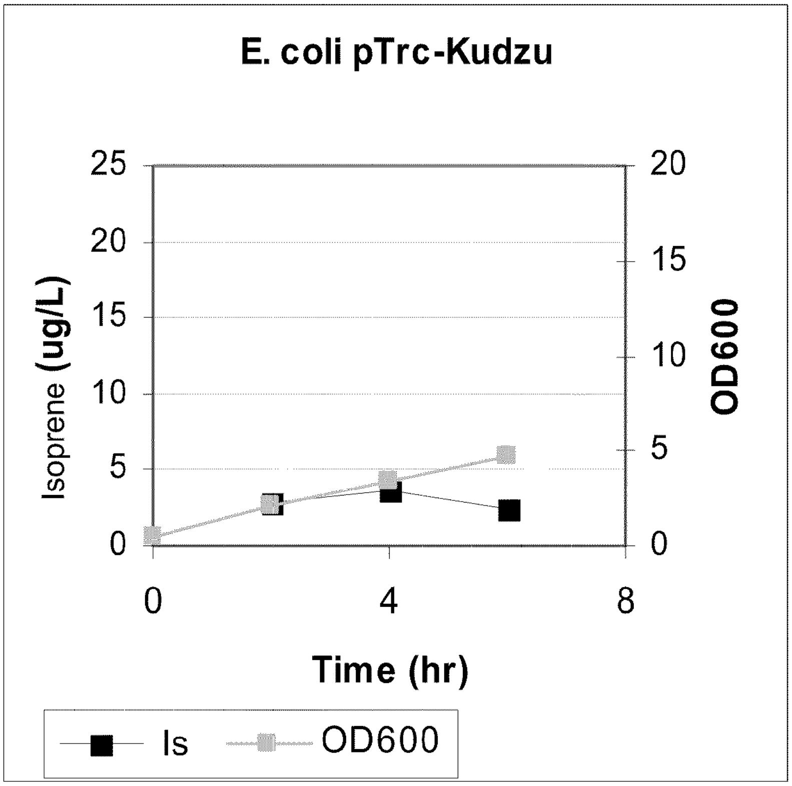
FIG. 8C is a graph showing the production of isoprene in *E. coli* BL21 cells with pTrcKudzu.
Figure 8D:
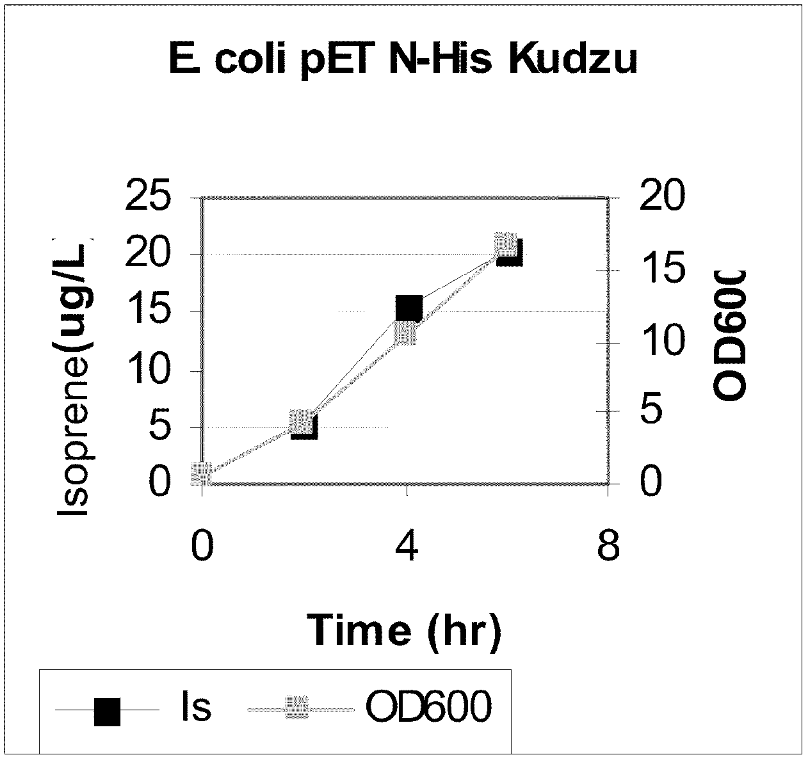
FIG. 8D is a graph showing the production of isoprene in *E. coli* BL21 cells with pETN-HisKudzu.

The kudzu isoprene synthase gene was also cloned into the low copy number plasmid pCL1920. Primers were used to amplify the kudzu isoprene synthase gene from pTrcKudzu described above. The forward primer added a HindIII site and an *E. coli* consensus RBS to the 5' end. The PstI cloning site was already present in pTrcKudzu just 3' of the stop codon so the reverse primer was constructed such that the final PCR product includes the PstI site. The sequences of the primers were: HindIII-rbs-Kudzu F: 5'-CATATGAAAGCTTGTATCGATTAAATAAGGAGGAATAAACC (SEQ ID NO:6) and BamH1-Kudzu R:

5'-CGGTCGACGGATCCCTGCAGTTAGACATACATCAGCTG (SEQ ID NO:4). The PCR product was amplified using Herculase polymerase with primers at a concentration of 10 pmol and with 1 ng of template DNA (pTrcKudzu). The amplification protocol included 30 cycles of (95° C. for 1 minute, 60° C. for 1 minute, 72° C. for 2 minutes). The product was digested with HindIII and PstI and ligated into pCL1920 which had also been digested with HindIII and PstI. The ligation mix was transformed into *E. coli* Top10. Several transformants were checked by sequencing. The resulting plasmid was designated pCL-lac-Kudzu (FIGS. 6 and 7).

II. Determination of Isoprene Production

For the shake flask cultures, one ml of a culture was transferred from shake flasks to 20 ml CTC headspace vials (Agilent vial cat#5188 2753; cap cat#5188 2759). The cap was screwed on tightly and the vials incubated at the equivalent temperature with shaking at 250 rpm. After 30 minutes the vials were removed from the incubator and analyzed as described below (see Table 1 for some experimental values from this assay).

In cases where isoprene production in fermentors was determined, samples were taken from the off-gas of the fermentor and analyzed directly as described below (see Table 2 for some experimental values from this assay).

The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 μm film thickness) was used for separation of analytes. The sampler was set up to inject 500 μL of headspace gas. The GC/MS method utilized helium as the carrier gas at a flow of 1 ml/min. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 μg/L to 2000 μg/L. The limit of detection was estimated to be 50 to 100 ng/L using this method.

III. Production of Isoprene in Shake Flasks Containing *E. Coli* Cells Expressing Recombinant Isoprene Synthase The vectors described above were introduced to *E. coli* strain BL21 (Novagen) to produce strains BL21/ptrcKudzu, BL21/pCL-lac-Kudzu and BL21/pETHisKudzu. The strains were spread for isolation onto LA (Luria agar)+carbenicillin (50 μg/ml) and incubated overnight at 37° C. Single colonies were inoculated into 250 ml baffled shake flasks containing 20 ml Luria Bertani broth (LB) and carbenicillin (100 μg/ml). Cultures were grown overnight at 20° C. with shaking at 200 rpm. The $OD_{600}$ of the overnight cultures were measured and the cultures were diluted into a 250 ml baffled shake flask containing 30 ml MagicMedia (Invitrogen)+carbenicillin (100 μg/ml) to an $OD_{600}$ ~0.05. The culture was incubated at 30° C. with shaking at 200 rpm. When the $OD_{600}$ ~0.5-0.8, 400 μM IPTG was added and the cells were incubated for a further 6 hours at 30° C. with shaking at 200 rpm. At 0, 2, 4 and 6 hours after induction with IPTG, 1 ml aliquots of the cultures were collected, the $OD_{600}$ was determined and the amount of isoprene produced was measured as described above. Results are shown in FIG. 8.

IV. Production of Isoprene from BL21/ptrcKudzu in 14 Liter Fermentation

Large scale production of isoprene from *E. coli* containing the recombinant kudzu isoprene synthase gene was determined from a fed-batch culture. The recipe for the fermentation media (TM2) per liter of fermentation medium was as follows: $K_2HPO_4$ 13.6 g, $KH_2PO_4$ 13.6 g, MgSO4*7$H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components were added together and dissolved in di$H_2O$. The pH was adjusted to 6.8 with potassium hydroxide (KOH) and q.s. to volume. The final product was filter sterilized with 0.22μ filter (only, do not autoclave). The recipe for 1000× Modified Trace Metal Solution was as follows: Citric Acids*$H_2O$ 40 g, $MnSO_4$*$H_2O$ 30 g, NaCl 10 g, $FeSO_4$*7$H_2O$ 1 g, $CoCl_2$*6$H_2O$ 1 g, $ZnSO_4$*7$H_2O$ 1 g, $CuSO_4$*5$H_2O$ 100 mg, $H_3BSO_3$ 100 mg, $NaMoO_4$*2$H_2O$ 100 mg. Each component was dissolved one at a time in di$H_2O$, pH to 3.0 with HCl/NaOH, then q.s. to volume and filter sterilized with a 0.22μ filter.

This experiment was carried out in 14 L bioreactor to monitor isoprene formation from glucose at the desired fermentation, pH 6.7 and temperature 34° C. An inoculum of *E. coli* strain BL21/ptrcKudzu taken from a frozen vial was prepared in soytone-yeast extract-glucose medium. After the inoculum grew to $OD_{550}$=0.6, two 600 ml flasks were centrifuged and the contents resuspended in 70 ml supernatant to transfer the cell pellet (70 ml of OD 3.1 material) to the bioreactor. At various times after inoculation, samples were removed and the amount of isoprene produced was determined as described above. Results are shown in FIG. 9.

Example 2

Figure 26:
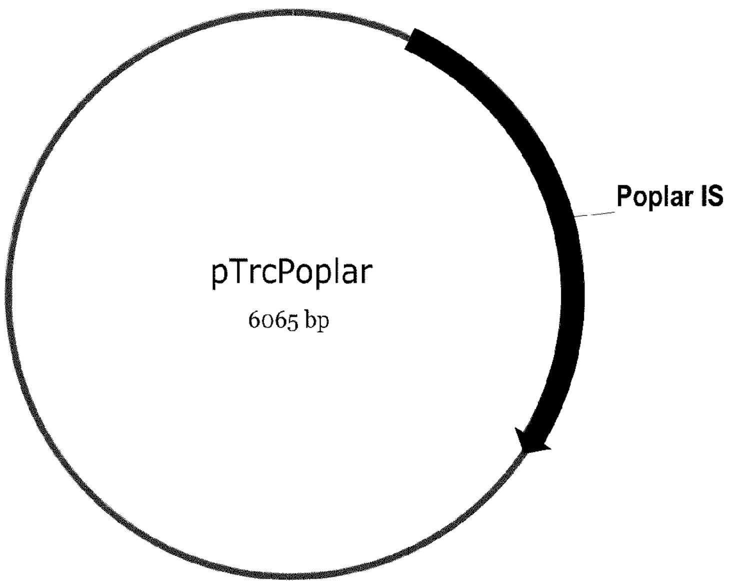
FIG. 26 is a map of pTrcPoplar.

Production of Isoprene in *E. Coli* Expressing Recombinant Poplar Isoprene Synthase The protein sequence for the poplar (*Populus alba*×*Populus tremula*) isoprene synthase (Schnitzler, J-P, et al. (2005) *Planta* 222:777-786) was obtained from GenBank (CAC35696). A gene, codon optimized for *E. coli*, was purchased from DNA2.0 (p9796-poplar, FIGS. 30 and 31). The isoprene synthase gene was removed from the supplied plasmid by restriction endonuclease digestion with BspLU11I/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid pTrcPoplar (FIGS. 26 and 27), was verified by sequencing.

Example 3

Figure 10A:
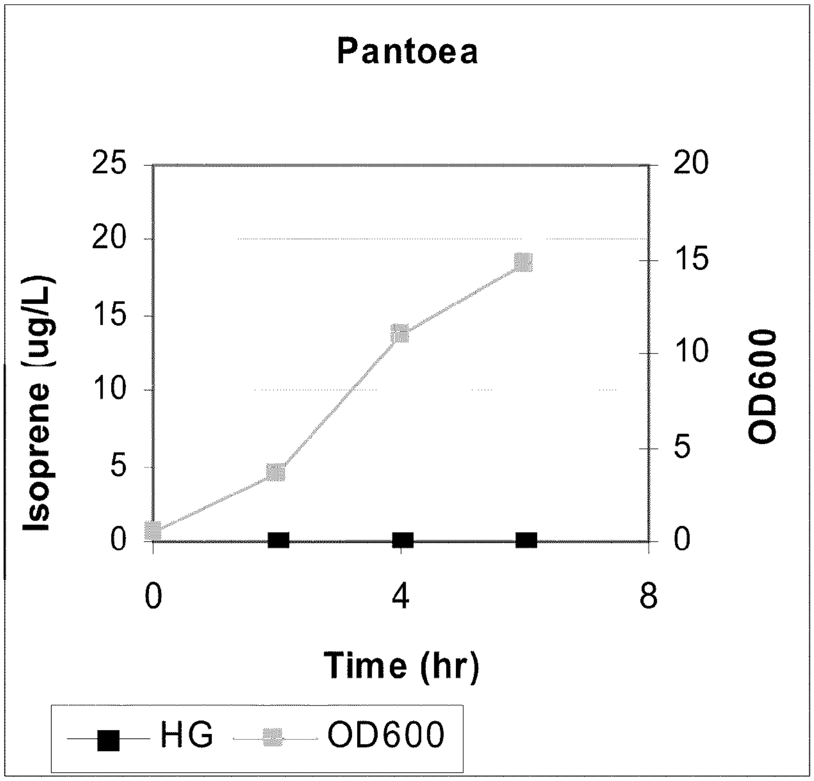
FIG. 10A is a graph showing the production of isoprene in *Panteoa citrea*. Control cells without recombinant kudzu isoprene synthase. Grey diamonds represent isoprene synthesis, black squares represent $OD_{600}$.

Production of Isoprene in *Panteoa Citrea* Expressing Recombinant Kudzu Isoprene Synthase The pTrcKudzu and pCL-lac Kudzu plasmids described in Example 1 were electroporated into *P. citrea* (U.S. Pat. No. 7,241,587). Transformants were selected on LA containing carbenicillin (200 μg/ml) or spectinomycin (50 μg/ml) respectively. Production of isoprene from shake flasks and determination of the amount of isoprene produced was performed as described in Example 1 for *E. coli* strains expressing recombinant kudzu isoprene synthase. Results are shown in FIG. 10.

Example 4

Production of Isoprene in *Bacillus subtilis* Expressing Recombinant Kudzu Isoprene Synthase I. Construction of a *B. Subtilis* Replicating Plasmid for the Expression of Kudzu Isoprene Synthase The kudzu isoprene synthase gene was expressed in *Bacillus subtilis* aprEnprE Pxyl-comK strain (BG3594comK) using a replicating plasmid (pBS19 with a chloramphenicol resistance cassette) under control of the aprE promoter. The isoprene synthase gene, the aprE promoter and the transcription terminator were amplified separately and fused using PCR. The construct was then cloned into pBS19 and transformed into *B. subtilis.* a) Amplification of the aprE Promoter

The aprE promoter was amplified from chromosomal DNA from *Bacillus subtilis* using the following primers:

```
CF 797 (+) Start aprE promoter MfeI
                                    (SEQ ID NO: 29)
5'-GACATCAATTGCTCCATTTTCTTCTGCTATC

CF 07-43 (-) Fuse aprE promoter to Kudzu ispS
                                    (SEQ ID NO: 30)
5'-ATTGAGAAGAGGTCGCACACACTCTTTACCCTCTCCTTTTA
```

b) Amplification of the Isoprene Synthase Gene

The kudzu isoprene synthase gene was amplified from plasmid pTrcKudzu (SEQ ID NO:2). The gene had been codon optimized for *E. coli* and synthesized by DNA 2.0. The following primers were used:

```
CF 07-42 (+) Fuse the aprE promoter to kudzu
isoprene synthase gene (GTG start codon)
                                    (SEQ ID NO: 31)
5'-TAAAAGGAGAGGGTAAAGAGTGTGTGCGACCTCTTCTCAAT

CF 07-45 (-) Fuse the 3' end of kudzu isoprene
synthase gene to the terminator
                                    (SEQ ID NO: 32)
5'-CCAAGGCCGGTTTTTTTTAGACATACATCAGCTGGTTAATC
```

c) Amplification of the Transcription Terminator

The terminator from the alkaline serine protease of *Bacillus amyliquefaciens* was amplified from a previously sequenced plasmid pJHPms382 using the following primers:

```
CF 07-44 (+) Fuse the 3' end of kudzu isoprene
synthase to the terminator
                                    (SEQ ID NO: 33)
5'-GATTAACCAGCTGATGTATGTCTAAAAAAAACCGGCCTTGG

CF 07-46 (-) End of B. amyliquefaciens terminator
(BamHI)
                                    (SEQ ID NO: 34)
5'-GACATGACGGATCCGATTACGAATGCCGTCTC
```

The kudzu fragment was fused to the terminator fragment using PCR with the following primers:

```
CF 07-42 (+) Fuse the aprE promoter to kudzu
isoprene synthase gene (GTG start codon)
                                    (SEQ ID NO: 32)
5'-TAAAAGGAGAGGGTAAAGAGTGTGTGCGACCTCTTCTCAAT

CF 07-46 (-) End of B. amyliquefaciens terminator
(BamHI)
                                    (SEQ ID NO: 34)
5'-GACATGACGGATCCGATTACGAATGCCGTCTC
```

The kudzu-terminator fragment was fused to the promoter fragment using PCR with the following primers:

```
CF 797 (+) Start aprE promoter MfeI
                                    (SEQ ID NO: 29)
5'-GACATCAATTGCTCCATTTTCTTCTGCTATC

CF 07-46 (-) End of B. amyliquefaciens terminator
(BamHI)
                                    (SEQ ID NO: 34)
5'-GACATGACGGATCCGATTACGAATGCCGTCTC
```

The fusion PCR fragment was purified using a Qiagen kit and digested with the restriction enzymes MfeI and BamHI. This digested DNA fragment was gel purified using a Qiagen kit and ligated to a vector known as pBS19, which had been digested with EcoRI and BamHI and gel purified.

The ligation mix was transformed into *E. coli* Top 10 cells and colonies were selected on LA+50 carbenicillin plates. A total of six colonies were chosen and grown overnight in LB+50 carbenicillin and then plasmids were isolated using a Qiagen kit. The plasmids were digested with EcoRI and BamHI to check for inserts and three of the correct plasmids were sent in for sequencing with the following primers:

```
CF 149 (+) EcoRI start of aprE promoter
                                    (SEQ ID NO: 36)
5'-GACATGAATTCCTCCATTTTCTTCTGC

CF 847 (+) Sequence in pXX 049 (end of aprE
promoter)
                                    (SEQ ID NO: 37)
5'-AGGAGAGGGTAAAGAGTGAG

CF 07-45 (-) Fuse the 3' end of kudzu isoprene
synthase to the terminator
                                    (SEQ ID NO: 32)
5'-CCAAGGCCGGTTTTTTTTAGACATACATCAGCTGGTTAATC

CF 07-48 (+) Sequencing primer for kudzu isoprene
synthase
                                    (SEQ ID NO: 38)
5'-CTTTTCCATCACCCACCTGAAG

CF 07-49 (+) Sequencing in kudzu isoprene synthase
                                    (SEQ ID NO: 39)
5'-GGCGAAATGGTCCAACAACAAAATTATC
```

Figure 44:
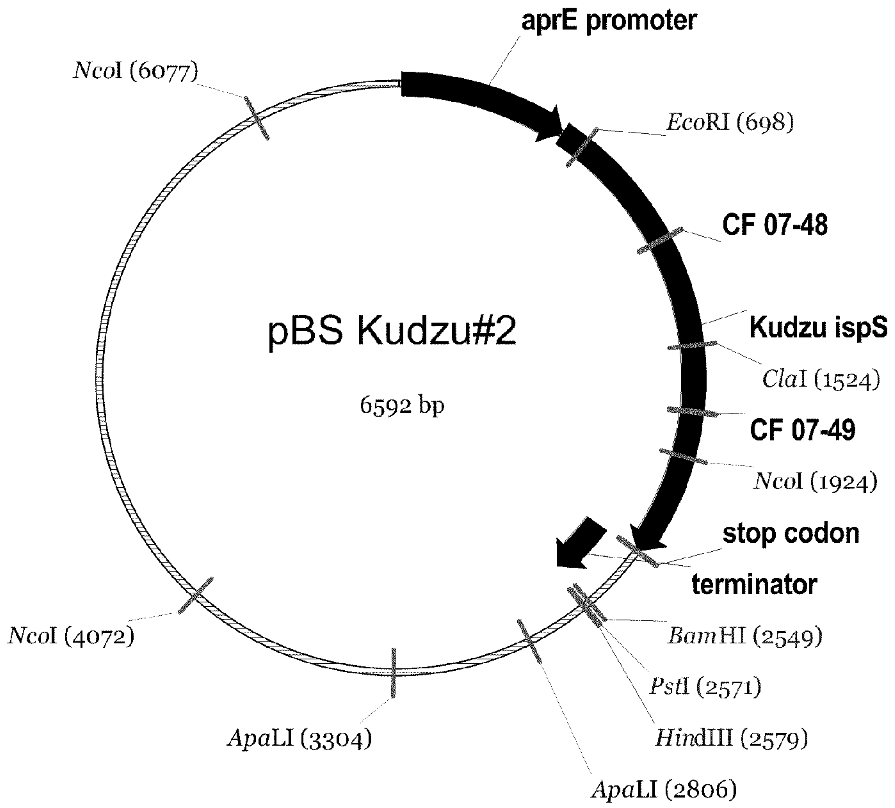
FIG. 44 is a map of pBS Kudzu #2.

The plasmid designated pBS Kudzu #2 (FIGS. 44 and 12) was correct by sequencing and was transformed into BG 3594 comK, a *Bacillus subtilis* host strain. Selection was done on LA+5 chloramphenicol plates. A transformant was chosen and struck to single colonies on LA+5 chloramphenicol, then grown in LB+5 chloramphenicol until it reached an $OD_{600}$ of 1.5. It was stored frozen in a vial at −80° C. in the presence of glycerol. The resulting strain was designated CF 443.

Figure 11:
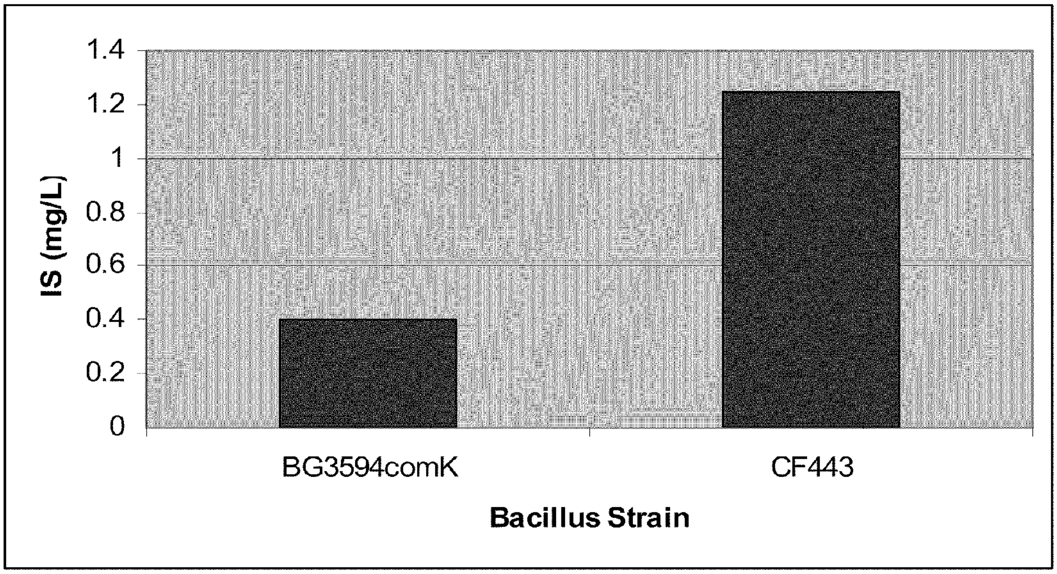
FIG. 11 is a graph showing the production of isoprene in *Bacillus subtilis* expressing recombinant isoprene synthase. BG3594comK is a *B. subtilis* strain without plasmid (native isoprene production). CF443-BG3594comK is a *B. subtilis* strain with pBSKudzu (recombinant isoprene production). IS on the y-axis indicates isoprene.

II. Production of Isoprene in Shake Flasks Containing *B. Subtilis* Cells Expressing Recombinant Isoprene Synthase Overnight cultures were inoculated with a single colony of CF 443 from a LA+Chloramphenicol (Cm, 25 μg/ml). Cultures were grown in LB+Cm at 37° C. with shaking at 200 rpm. These overnight cultures (1 ml) were used to inoculate 250 ml baffled shake flasks containing 25 ml Grants II media and chloramphenicol at a final concentration of 25 μg/ml. Grants II Media recipe was 10 g soytone, 3 ml 1M $K_2HPO_4$, 75 g glucose, 3.6 g urea, 100 ml 10×MOPS, q.s. to 1 L with $H_2O$, pH 7.2; 10×MOPS recipe was 83.72 g MOPS, 7.17 g tricine, 12 g KOH pellets, 10 ml 0.276M $K_2SO_4$ solution, 10 ml 0.528M $MgCl_2$ solution, 29.22 g NaCl, 100 ml 100× micronutrients, q.s. to 1 L with $H_2O$; and 100× micronutrients recipe was 1.47 g $CaCl_2*2H_2O$, 0.4 g $FeSO_4*7H_2O$, 0.1 g $MnSO_4*H_2O$, 0.1 g $ZnSO_4*H_2O$, 0.05 g $CuCl_2*2H_2O$, 0.1 g $CoCl_2*6H_2O$, 0.1 g $Na_2MoO_4*2H_2O$, q.s. to 1 L with $H_2O$, Shake flasks were incubated at 37° C. and samples were taken at 18, 24, and 44 hours. At 18 hours the headspaces of CF443 and the control strain were sampled. This represented 18 hours of accumulation of isoprene. The amount of isoprene was determined by gas chromatography as described in Example 1. Production of isoprene was enhanced significantly by expressing recombinant isoprene synthase (FIG. 11).

III. Production of Isoprene by CF443 in 14 L Fermentation

Figure 45A:
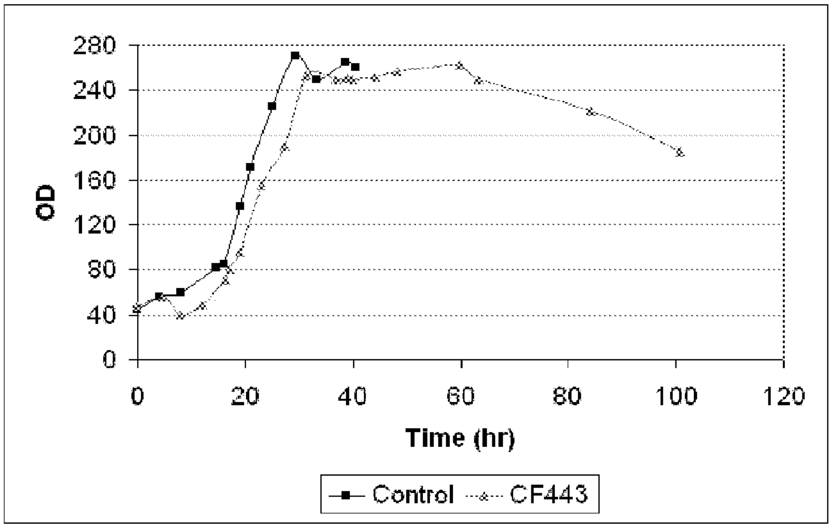
FIG. 45A is a graph showing growth during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).
Figure 45B:
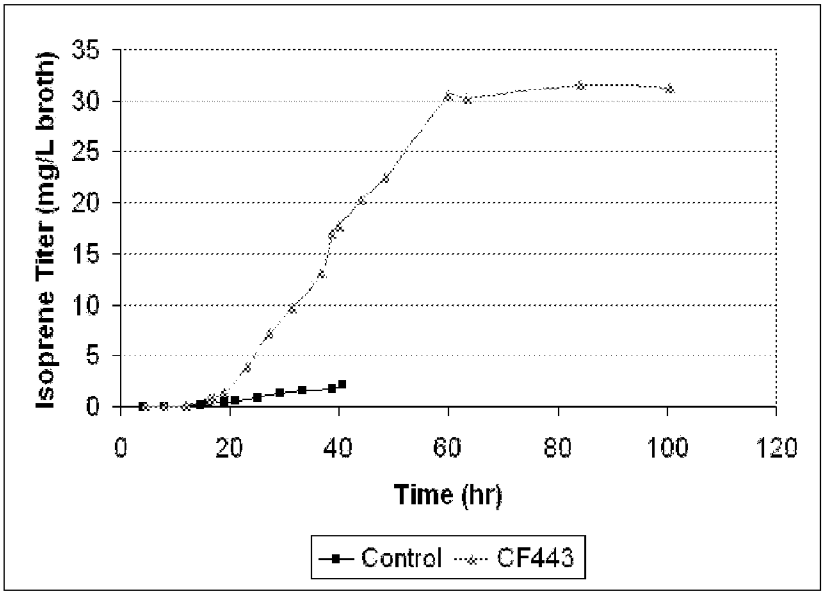
FIG. 45B is a graph showing isoprene production during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).
Figure 46A:
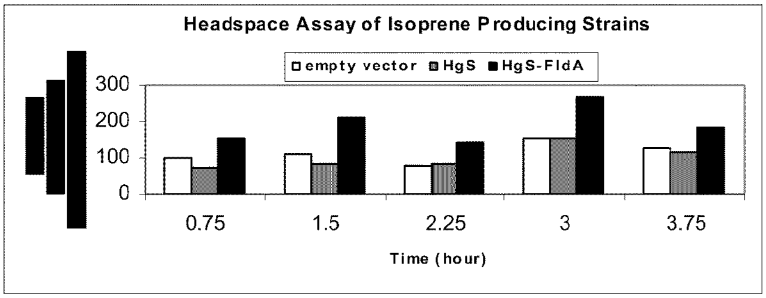
FIGS. 46A-46D depict the growth rate and specific productivity of isoprene generation for the empty vector (control), HgS, and HgS-FldA strains.
Figure 46B:
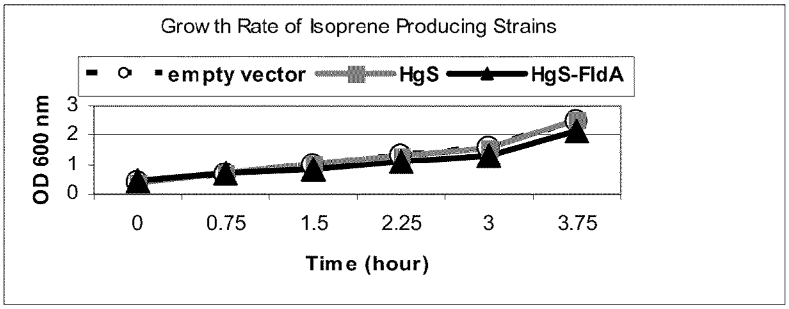
Figure 46C:
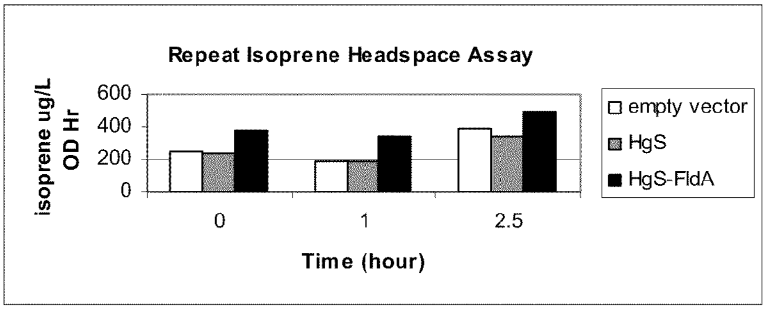
Figure 46D:
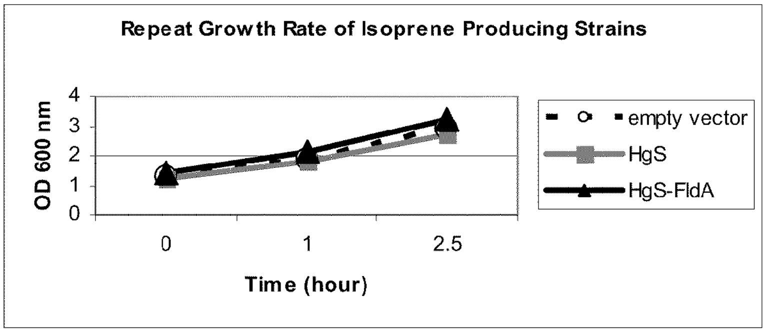
Figure 46E:
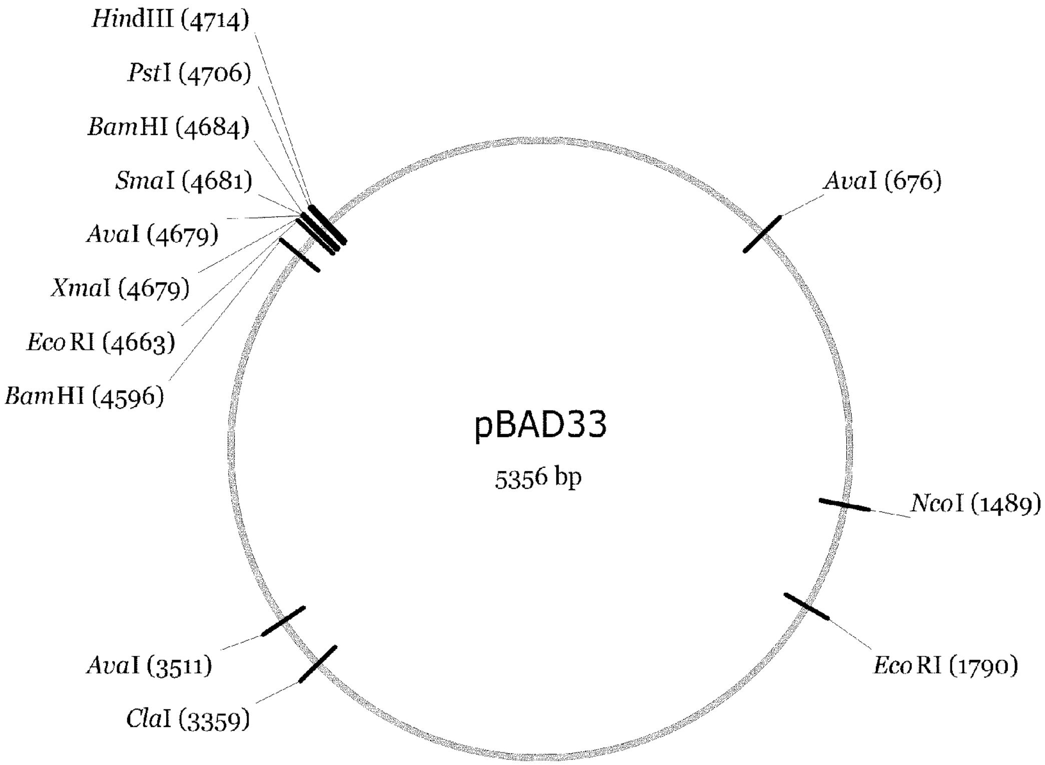
FIG. 46E is a map of pBAD33.
Figure 46H:
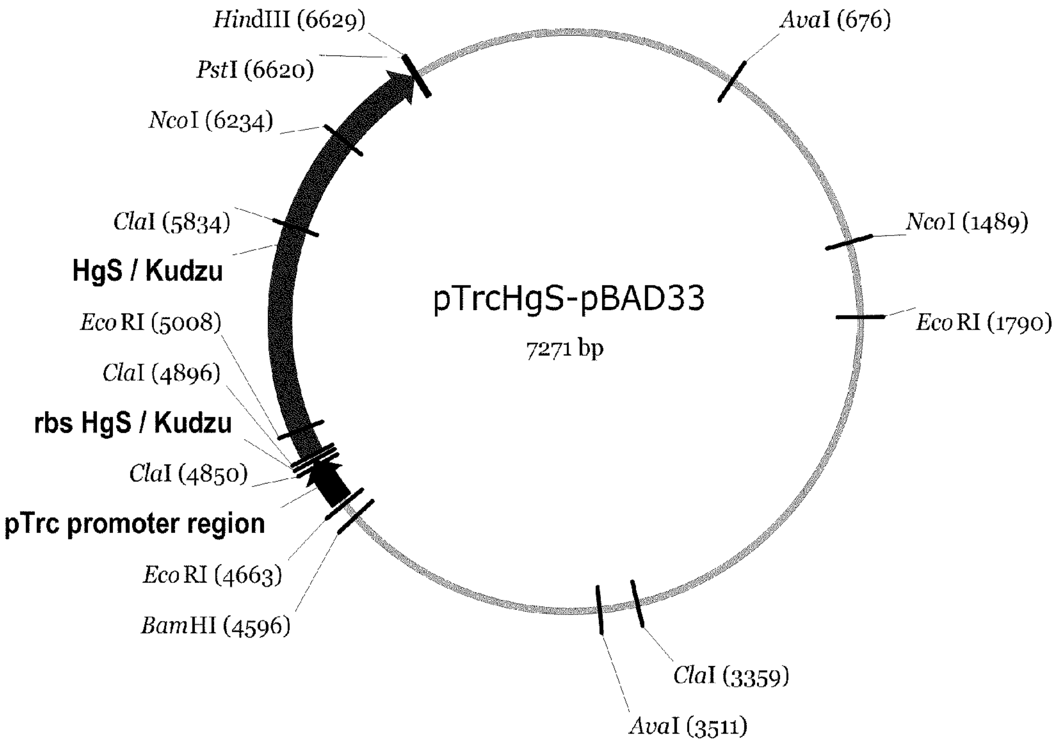
FIG. 46H is a map of pTrcHgS-pBAD33.
Figure 46K:
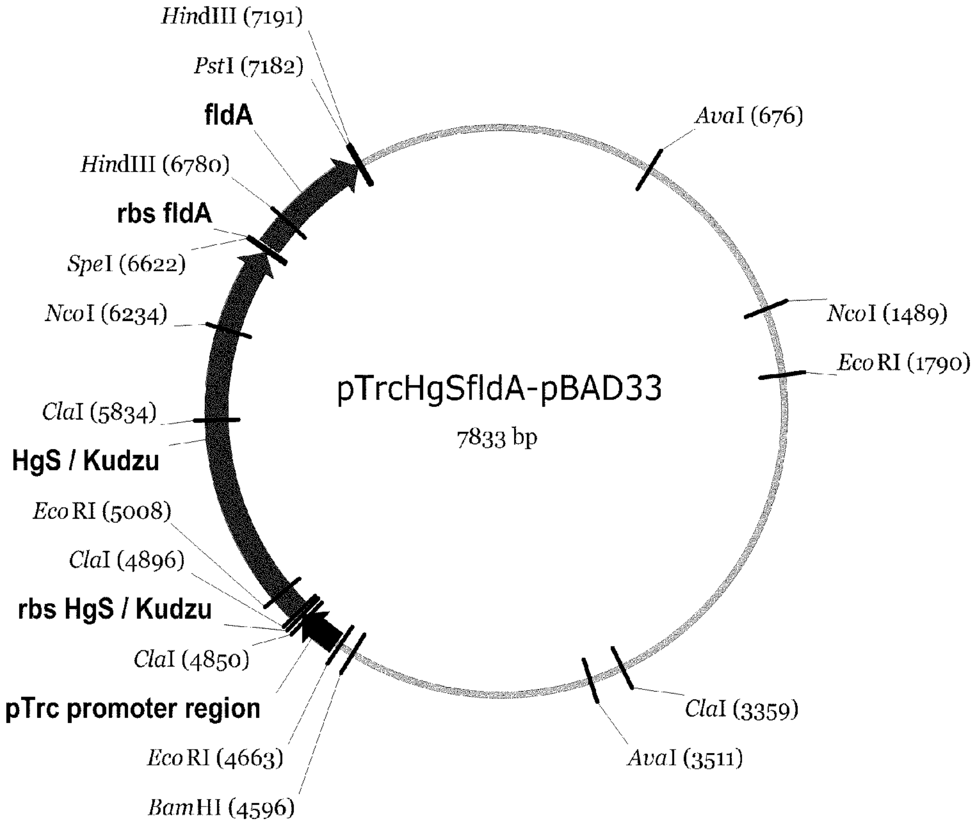
FIG. 46K is a map of pTrcHgSfldA-pBAD33.

Large scale production of isoprene from *B. subtilis* containing the recombinant kudzu isoprene synthase gene on a replication plasmid was determined from a fed-batch culture. *Bacillus* strain CF 443, expressing a kudzu isoprene synthase gene, or control stain which does not express a kudzu isoprene synthase gene were cultivated by conventional fed-batch fermentation in a nutrient medium containing soy meal (Cargill), sodium and potassium phosphate, magnesium sulfate and a solution of citric acid, ferric chloride and manganese chloride. Prior to fermentation the media is macerated for 90 minutes using a mixture of enzymes including cellulases, hemicellulases and pectinases (see, WO95/04134). 14-L batch fermentations are fed with 60% wt/wt glucose (Cargill DE99 dextrose, ADM Versadex greens or Danisco invert sugar) and 99% wt/wt oil (Western Family soy oil, where the 99% wt/wt is the concentration of oil before it was added to the cell culture medium). Feed was started when glucose in the batch was non-detectable. The feed rate was ramped over several hours and was adjusted to add oil on an equal carbon basis. The pH was controlled at 6.8-7.4 using 28% w/v ammonium hydroxide. In case of foaming, antifoam agent was added to the media. The fermentation temperature was controlled at 37° C. and the fermentation culture was agitated at 750 rpm. Various other parameters such as pH, D0%, airflow, and pressure were monitored throughout the entire process. The DO % is maintained above 20. Samples were taken over the time course of 36 hours and analyzed for cell growth ($OD_{550}$) and isoprene production. Results of these experiments are presented in FIGS. 45A and 45B.

IV. Integration of the Kudzu Isoprene Synthase (ispS) in *B. Subtilis.*

The kudzu isoprene synthase gene was cloned in an integrating plasmid (pJH101-cmpR) under the control of the aprE promoter. Under the conditions tested, no isoprene was detected.

Example 5

Production of Isoprene in *Trichoderma*

I. Construction of Vectors for Expression of the Kudzu Isoprene Synthase in *Trichoderma Reesei*

The *Yarrowia lipolytica* codon-optimized kudzu IS gene was synthesized by DNA 2.0 (SEQ ID NO:8) (FIG. 13). This plasmid served as the template for the following PCR amplification reaction: 1 μl plasmid template (20 ng/ul), 1 μl Primer EL-945 (10 uM) 5'-GCTTATGGATCCTCTAGACTATTACACGTACATCAATTGG (SEQ ID NO:9), 1 μl Primer EL-965 (10 uM) 5'-CACCATGTGTGCAACCTCCTCCCAGTTTAC (SEQ ID NO:10), 1 μl dNTP (10 mM), 5 μl 10× PfuUltra II Fusion HS DNA Polymerase Buffer, 1 μl PfuUltra II Fusion HS DNA Polymerase, 40 μl water in a total reaction volume of 50 μl. The forward primer contained an additional 4 nucleotides at the 5'-end that did not correspond to the *Y. lipolytica* codon-optimized kudzu isoprene synthase gene, but was required for cloning into the pENTR/D-TOPO vector. The reverse primer contained an additional 21 nucleotides at the 5'-end that did not correspond to the *Y. lipolytica* codon-optimized kudzu isoprene synthase gene, but were inserted for cloning into other vector backbones. Using the MJ Research PTC-200 Thermocycler, the PCR reaction was performed as follows: 95° C. for 2 minutes (first cycle only), 95° C. for 30 seconds, 55° C. for 30 seconds, 72° C. for 30 seconds (repeat for 27 cycles), 72° C. for 1 minute after the last cycle. The PCR product was analyzed on a 1.2% E-gel to confirm successful amplification of the *Y. lipolytica* codon-optimized kudzu isoprene synthase gene.

The PCR product was then cloned using the TOPO pENTR/D-TOPO Cloning Kit following manufacturer's protocol: 1 μl PCR reaction, 1 μl Salt solution, 1 μl TOPO pENTR/D-TOPO vector and 3 μl water in a total reaction volume of 6 μl. The reaction was incubated at room temperature for 5 minutes. One microliter of TOPO reaction was transformed into TOP10 chemically competent *E. coli* cells. The transformants were selected on LA+50 μg/ml kanamycin plates. Several colonies were picked and each was inoculated into a 5 ml tube containing LB+50 μg/ml kanamycin and the cultures grown overnight at 37° C. with shaking at 200 rpm. Plasmids were isolated from the overnight culture tubes using QIAprep Spin Miniprep Kit, following manufacturer's protocol. Several plasmids were sequenced to verify that the DNA sequence was correct.

A single pENTR/D-TOPO plasmid, encoding a *Y. lipolytica* codon-optimized kudzu isoprene synthase gene, was used for Gateway Cloning into a custom-made pTrex3g vector. Construction of pTrex3g is described in WO 2005/001036 A2. The reaction was performed following manufacturer's protocol for the Gateway LR Clonase II Enzyme Mix Kit (Invitrogen): 1 μl *Y. lipolytica* codon-optimized kudzu isoprene synthase gene pENTR/D-TOPO donor vector, 1 μl pTrex3g destination vector, 6 μl TE buffer, pH 8.0 in a total reaction volume of 8 μl. The reaction was incubated at room temperature for 1 hour and then 1 μl proteinase K solution was added and the incubation continued at 37° C. for 10 minutes. Then 1 μl of reaction was transformed into TOP10 chemically competent *E. coli* cells. The transformants were selected on LA+50 μg/ml carbenicillin plates. Several colonies were picked and each was inoculated into a 5 ml tube containing LB+50 μlg/ml carbenicillin and the cultures were grown overnight at 37° C. with shaking at 200 rpm. Plasmids were isolated from the overnight culture tubes using QIAprep Spin Miniprep Kit (Qiagen, Inc.), following manufacturer's protocol. Several plasmids were sequenced to verify that the DNA sequence was correct.

Figure 14:
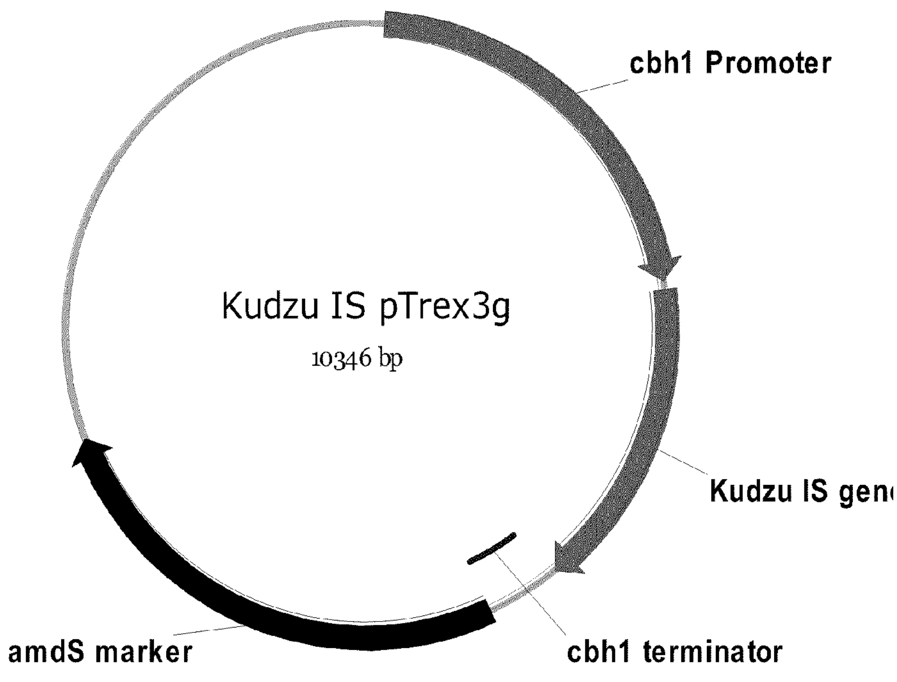
FIG. 14 is a map of pTrex3g comprising a kudzu isoprene synthase gene codon-optimized for expression in *Yarrowia.*

Biolistic transformation of *Y. lipolytica* codon-optimized kudzu isoprene synthase pTrex3g plasmid (FIG. 14) into a quad delete *Trichoderma reesei* strain was performed using the Biolistic PDS-1000/HE Particle Delivery System (see WO 2005/001036 A2). Isolation of stable transformants and shake flask evaluation was performed using protocol listed in Example 11 of patent publication WO 2005/001036 A2.

II. Production of Isoprene in Recombinant Strains of *T. Reesei*

One ml of 15 and 36 hour old cultures of isoprene synthase transformants described above were transferred to head space vials. The vials were sealed and incubated for 5 hours at 30° C. Head space gas was measured and isoprene was identified by the method described in Example 1. Two of the transformants showed traces of isoprene. The amount of isoprene could be increased by a 14 hour incubation. The two positive samples showed isoprene at levels of about 0.5 μg/L for the 14 hour incubation. The untransformed control showed no detectable levels of isoprene. This experiment shows that *T. reesei* is capable of producing isoprene from endogenous precursor when supplied with an exogenous isoprene synthase.

Example 6

Production of Isoprene in *Yarrowia*

I. Construction of Vectors for Expression of the Kudzu Isoprene Synthase in *Yarrowia lipolytica.*

The starting point for the construction of vectors for the expression of the kudzu isoprene synthase gene in *Yarrowia lipolytica* was the vector pSPZ1 (MAP29Spb). The complete sequence of this vector (SEQ ID No:11) is shown in FIG. 15.

The following fragments were amplified by PCR using chromosomal DNA of a *Y. lipolytica* strain GICC 120285 as the template: a promotorless form of the URA3 gene, a fragment of 18S ribosomal RNA gene, a transcription terminator of the *Y. lipolytica* XPR2 gene and two DNA fragments containing the promoters of XPR2 and ICL1 genes. The following PCR primers were used:

```
ICL1 3
5'-GGTGAATTCAGTCTACTGGGGATTCCCAAATCTATATATACTGCAGGTGAC (SEQ ID NO: 40)

ICL1 5
5'-GCAGGTGGGAAACTATGCACTCC                             (SEQ ID NO: 41)

XPR 3
5'-CCTGAATTCTGTTGGATTGGAGGATTGGATAGTGGG                (SEQ ID NO: 42)

XPR 5
5'-GGTGTCGACGTACGGTCGAGCTTATTGACC                      (SEQ ID NO: 43)

XPRT3
5'-GGTGGGCCCGCATTTTGCCACCTACAAGCCAG                    (SEQ ID NO: 44)

XPRT 5
5'-GGTGAATTCTAGAGGATCCCAACGCTGTTGCCTACAACGG            (SEQ ID NO: 45)

Y18S3
5'-GGTGCGGCCGCTGTCTGGACCTGGTGAGTTTCCCCG                (SEQ ID NO: 46)

Y18S 5
5'-GGTGGGCCCATTAAATCAGTTATCGTTTATTTGATAG               (SEQ ID NO: 47)

YURA3
5'-GGTGACCAGCAAGTCCATGGGTGGTTTGATCATGG                 (SEQ ID NO: 48)

YURA 50
5'-GGTGCGGCCGCCTTTGGAGTACGACTCCAACTATG                 (SEQ ID NO: 49)

YURA 51
5'-GCGGCCGCAGACTAAATTTATTTCAGTCTCC                     (SEQ ID NO: 50)
```

For PCR amplification the PfuUltraII polymerase (Stratagene), supplier-provided buffer and dNTPs, 2.5 μM primers and the indicated template DNA were used as per the manufacturer's instructions. The amplification was done using the following cycle: 95° C. for 1 min; 34× (95° C. for 30 sec; 55° C. for 30 sec; 72° C. for 3 min) and 10 min at 72° C. followed by a 4° C. incubation.

Figure 18B:
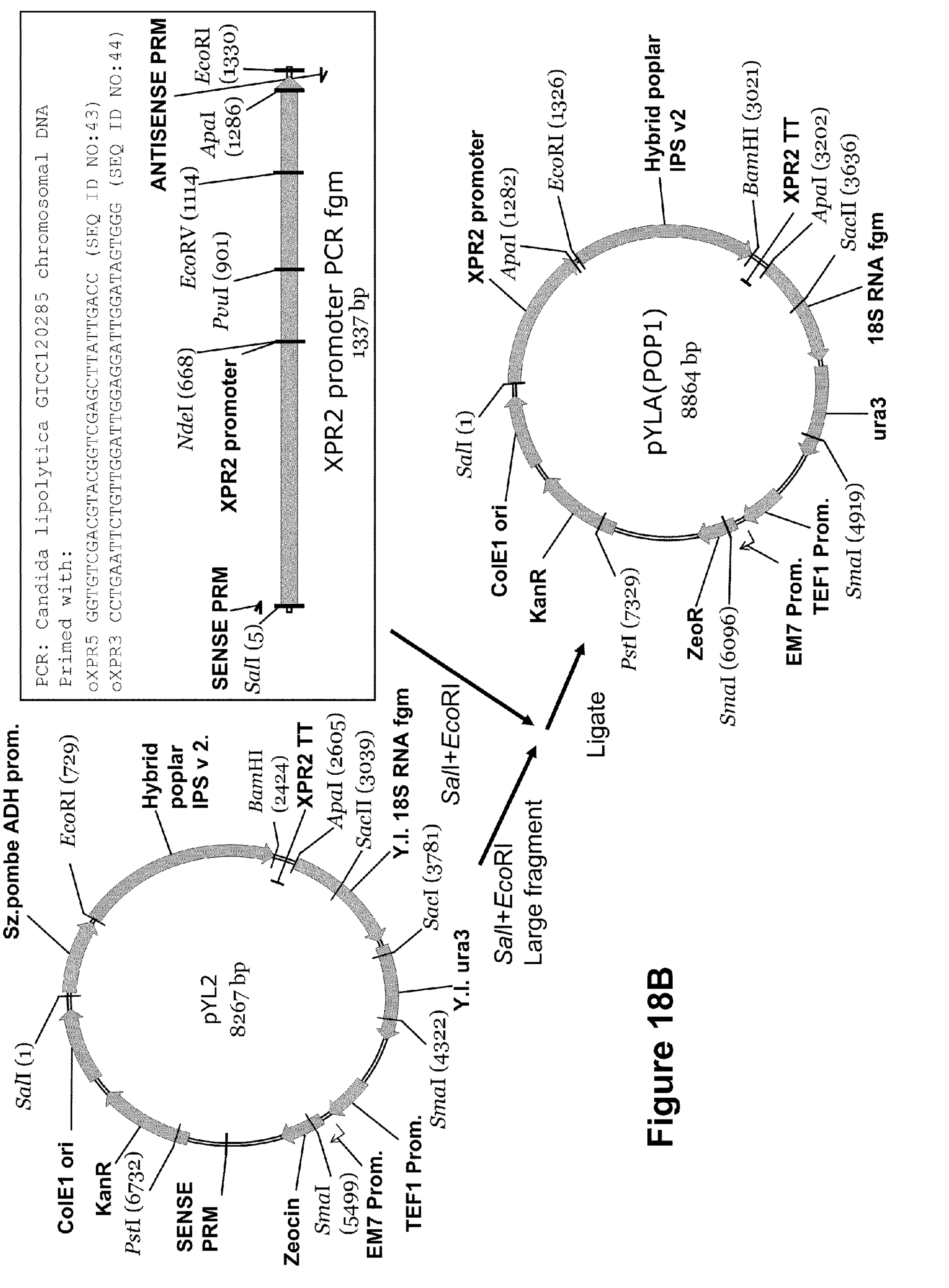
FIG. 18B shows a schematic outlining construction of the vector pYLA(POP1) (SEQ ID NOS: 43 and 44).
Figure 18C:
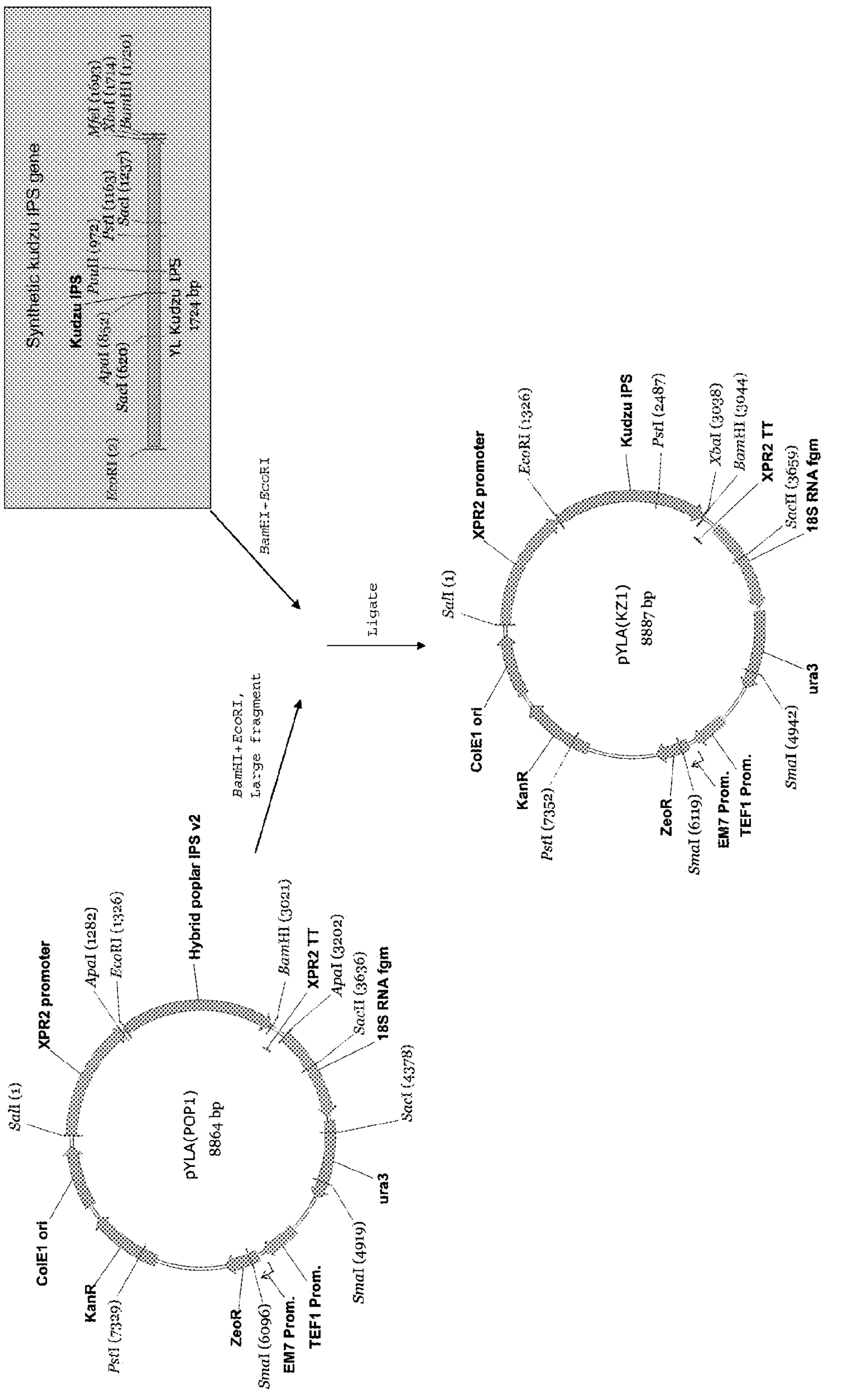
FIG. 18C shows a schematic outlining construction of the vector pYLA(KZ1)
Figure 18D:
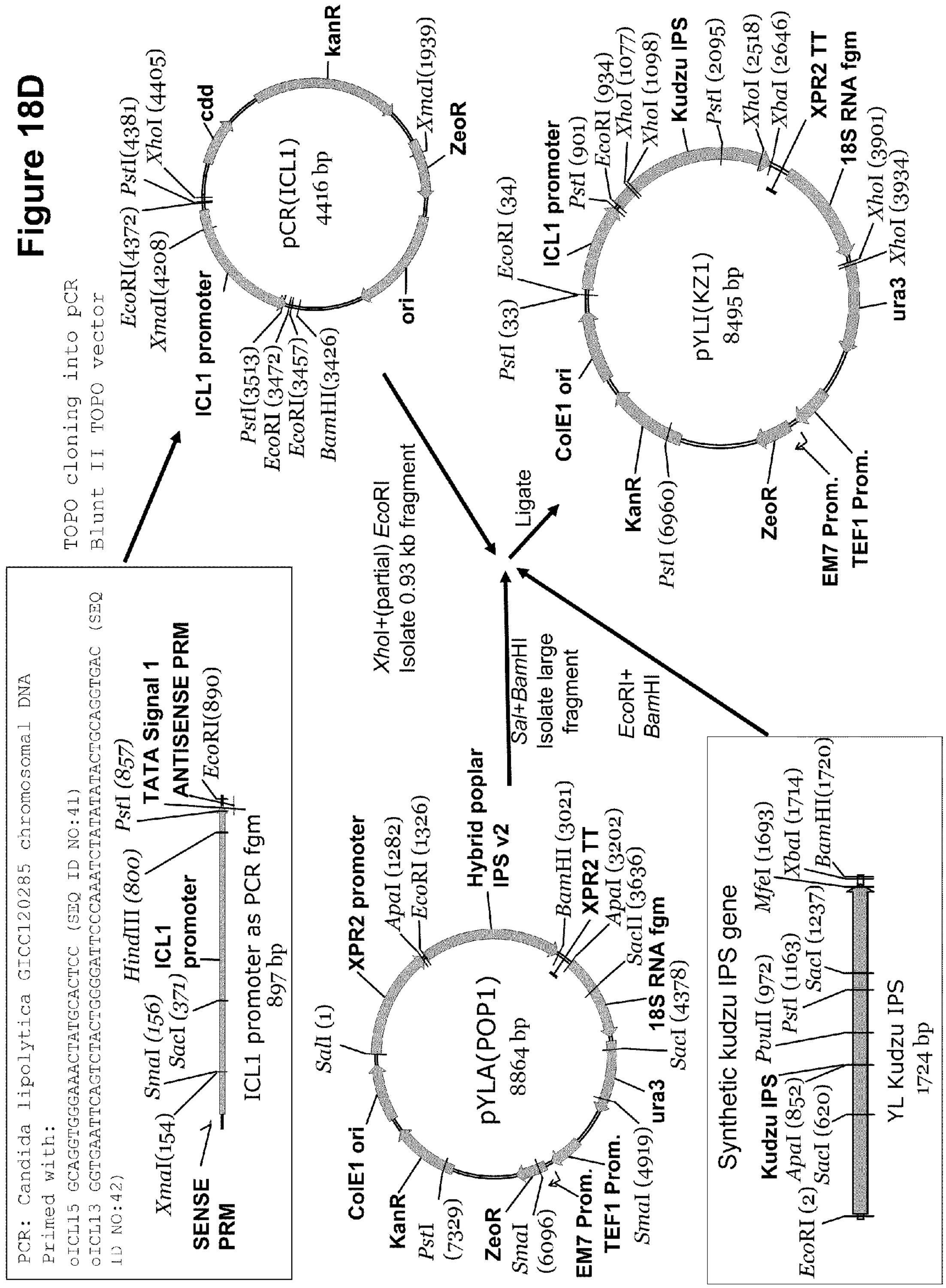
FIG. 18D shows a schematic outlining construction of the vector pYLI(KZ1) (SEQ ID NOS: 41, 42).
Figure 18E:
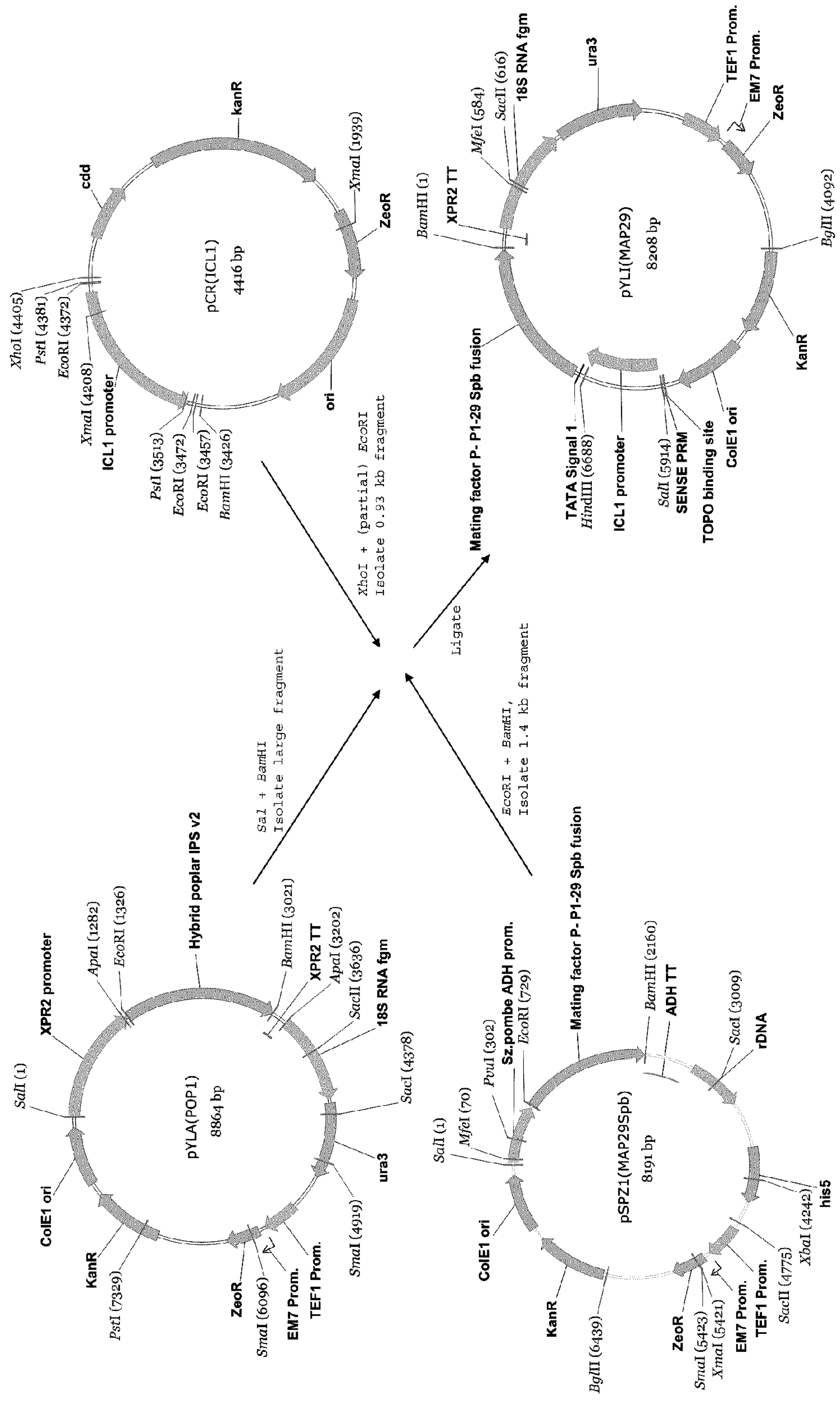
FIG. 18E shows a schematic outlining construction of the vector pYLI(MAP29)
Figure 18F:
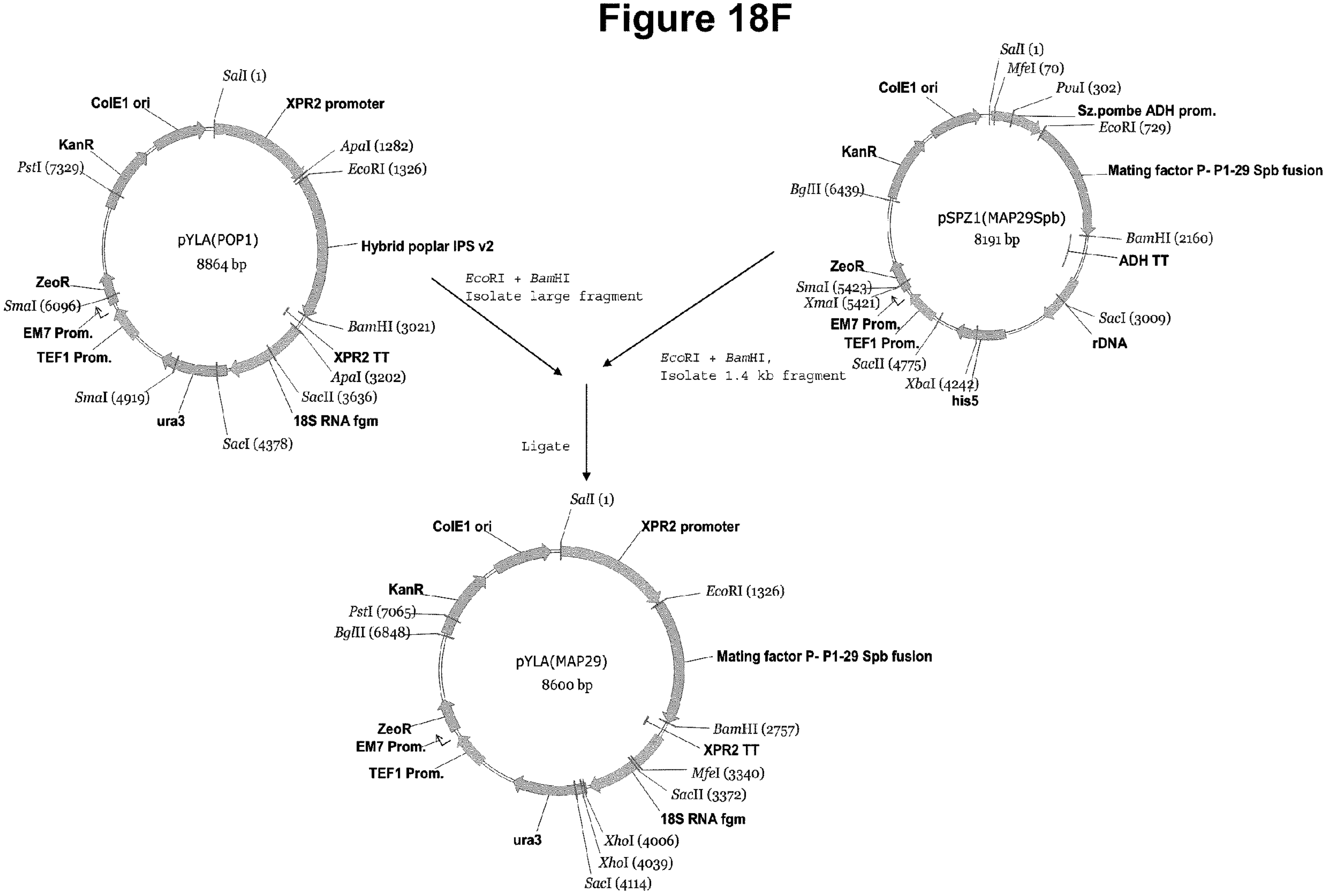
FIG. 18F shows a schematic outlining construction of the vector pYLA(MAP29)

Synthetic DNA molecules encoding the kudzu isoprene synthase gene, codon-optimized for expression in *Yarrowia*, was obtained from DNA 2.0 (FIG. 16; SEQ ID NO:12). Full detail of the construction scheme of the plasmids pYLA (KZ1) and pYLI(KZ1) carrying the synthetic kudzu isoprene synthase gene under control of XPR2 and ICL1 promoters respectively is presented in FIG. 18. Control plasmids in which a mating factor gene (MAP29) is inserted in place of an isoprene synthase gene were also constructed (FIGS. 18E and 18F).

A similar cloning procedure can be used to express a poplar (*Populus alba*×*Populus tremula*) isoprene synthase gene. The sequence of the poplar isoprene is described in Miller B. et al. (2001) *Planta* 213, 483-487 and shown in FIG. 17 (SEQ ID NO:13). A construction scheme for the generation the plasmids pYLA(POP1) and pYLI(POP1) carrying synthetic poplar isoprene synthase gene under control of XPR2 and ICL1 promoters respectively is presented in FIGS. 18A and B.

II. Production of Isoprene by Recombinant Strains of *Y. Lipolytica.*

Vectors pYLA(KZ1), pYLI(KZ1), pYLA(MAP29) and pYLI(MAP29) were digested with SacII and used to transform the strain *Y. lipolytica* CLIB 122 by a standard lithium acetate/polyethylene glycol procedure to uridine prototrophy. Briefly, the yeast cells grown in YEPD (1% yeast extract, 2% peptone, 2% glucose) overnight, were collected by centrifugation (4000 rpm, 10 min), washed once with sterile water and suspended in 0.1 M lithium acetate, pH 6.0. Two hundred μl aliquots of the cell suspension were mixed with linearized plasmid DNA solution (10-20 μg), incubated for 10 minutes at room temperature and mixed with 1 ml of 50% PEG 4000 in the same buffer. The suspensions were further incubated for 1 hour at room temperature followed by a 2 minutes heat shock at 42° C. Cells were then plated on SC his leu plates (0.67% yeast nitrogen base, 2% glucose, 100 mg/L each of leucine and histidine). Transformants appeared after 3-4 days of incubation at 30° C.

Three isolates from the pYLA(KZ1) transformation, three isolates from the pYLI(KZ1) transformation, two isolates from the pYLA(MAP29) transformation and two isolates from the pYLI(MAP29) transformation were grown for 24 hours in YEP7 medium (1% yeast extract, 2% peptone, pH 7.0) at 30° C. with shaking. Cells from 10 ml of culture were collected by centrifugation, resuspended in 3 ml of fresh YEP7 and placed into 15 ml screw cap vials. The vials were incubated overnight at room temperature with gentle (60 rpm) shaking. Isoprene content in the headspace of these vials was analyzed by gas chromatography using mass-spectrometric detector as described in Example 1. All transformants obtained with pYLA(KZ1) and pYLI(KZ1) produced readily detectable amounts of isoprene (0.5 μg/L to 1 μg/L, FIG. 20). No isoprene was detected in the headspace of the control strains carrying phytase gene instead of an isoprene synthase gene.

Example 7

Production of Isoprene in *E. Coli* Expressing Kudzu Isoprene Synthase and idi, or dxs, or idi and dxs I. Construction of Vectors Encoding Kudzu Isoprene Synthase and idi, or dxs, or idi and dxs for the Production of Isoprene in *E. coli* i) Construction of pTrcKudzuKan

Figure 28:
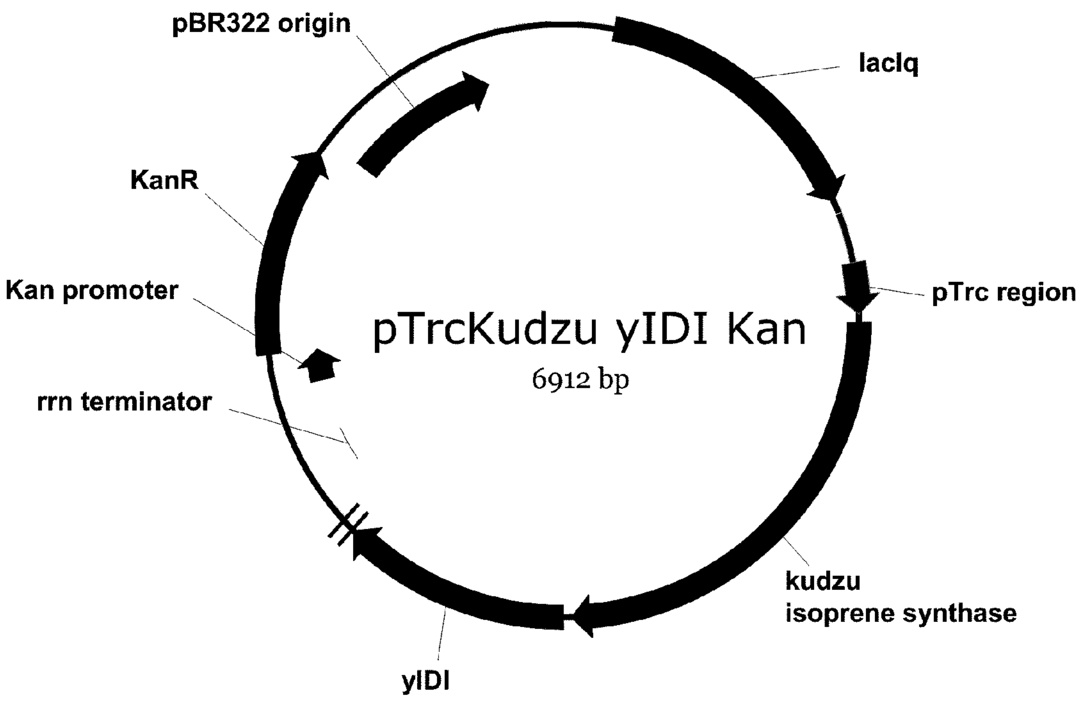
FIG. 28 is a map of pTrcKudzu yIDI Kan.

The bla gene of pTrcKudzu (described in Example 1) was replaced with the gene conferring kanamycin resistance. To remove the bla gene, pTrcKudzu was digested with BspHI, treated with Shrimp Alkaline Phosphatase (SAP), heat killed at 65° C., then end-filled with Klenow fragment and dNTPs. The 5 kbp large fragment was purified from an agarose gel and ligated to the kan$^r$ gene which had been PCR amplified from pCR-Blunt-II-TOPO using primers MCM22 5'-GATCAAGCTTAACCGGAATTGCCAGCTG (SEQ ID NO:14) and MCM23 5'-GATCCGATCGTCAGAAGAACTCGTCAAGAAGGC (SEQ ID NO:15), digested with HindIII and PvuI, and end-filled. A transformant carrying a plasmid conferring kanamycin resistance (pTrcKudzuKan) was selected on LA containing kanamycin 50 μg/ml.

ii) Construction of pTrcKudzu yIDI Kan pTrcKudzuKan was digested with PstI, treated with SAP, heat killed and gel purified. It was ligated to a PCR product encoding idi from *S. cerevisiae* with a synthetic RBS. The primers for PCR were NsiI-YIDI 1 F 5'-CATCAATGCATCGCCCTTAGGAGGTAAAAAAAAATGAC (SEQ ID NO:16) and PstI-YIDI 1 R 5'-CCTTCTGCAGGACGCGTTGTTATAGC (SEQ ID NO:17); and the template was *S. cerevisiae* genomic DNA. The PCR product was digested with NsiI and PstI and gel purified prior to ligation. The ligation mixture was transformed into chemically competent TOP10 cells and selected on LA containing 50 μg/ml kanamycin. Several transformants were isolated and sequenced and the resulting plasmid was called pTrcKudzu-yIDI(kan) (FIGS. 28 and 29).

iii) Construction of pTrcKudzu DXS Kan

Figure 21:
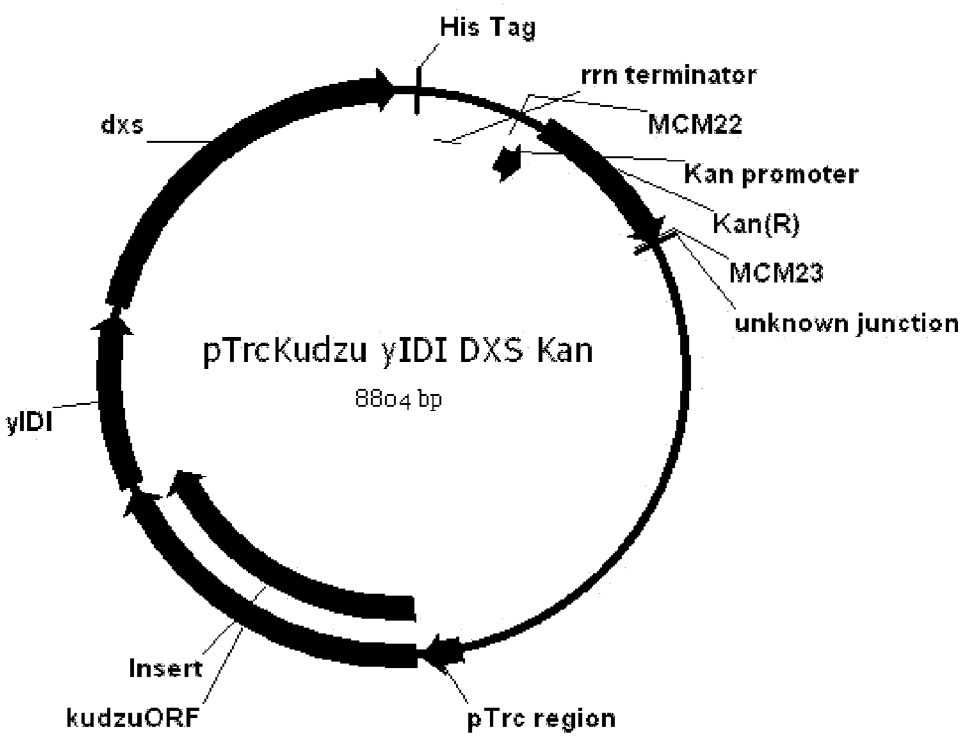
FIG. 21 is a map of pTrcKudzu yIDI DXS Kan.
Figure 30:
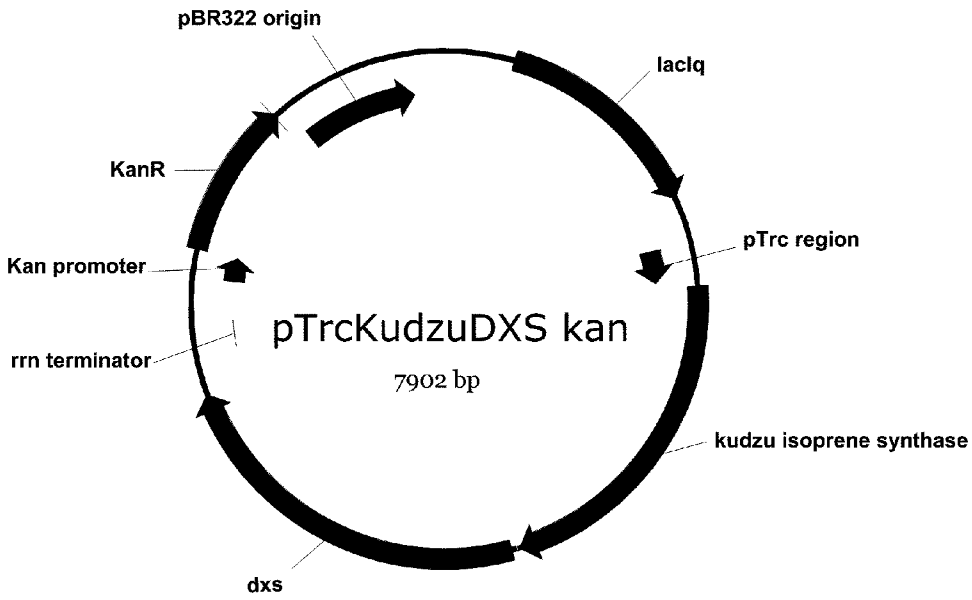
FIG. 30 is a map of pTrcKudzuDXS Kan.
Figure 32:
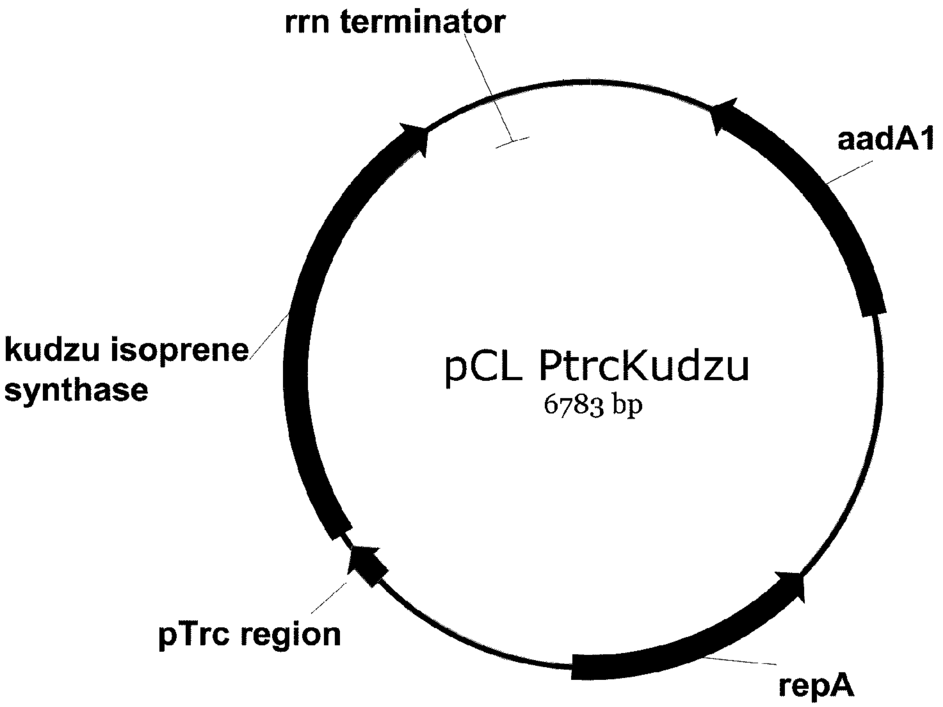
FIG. 32 is a map of pCL PtrcKudzu.
Figure 34:
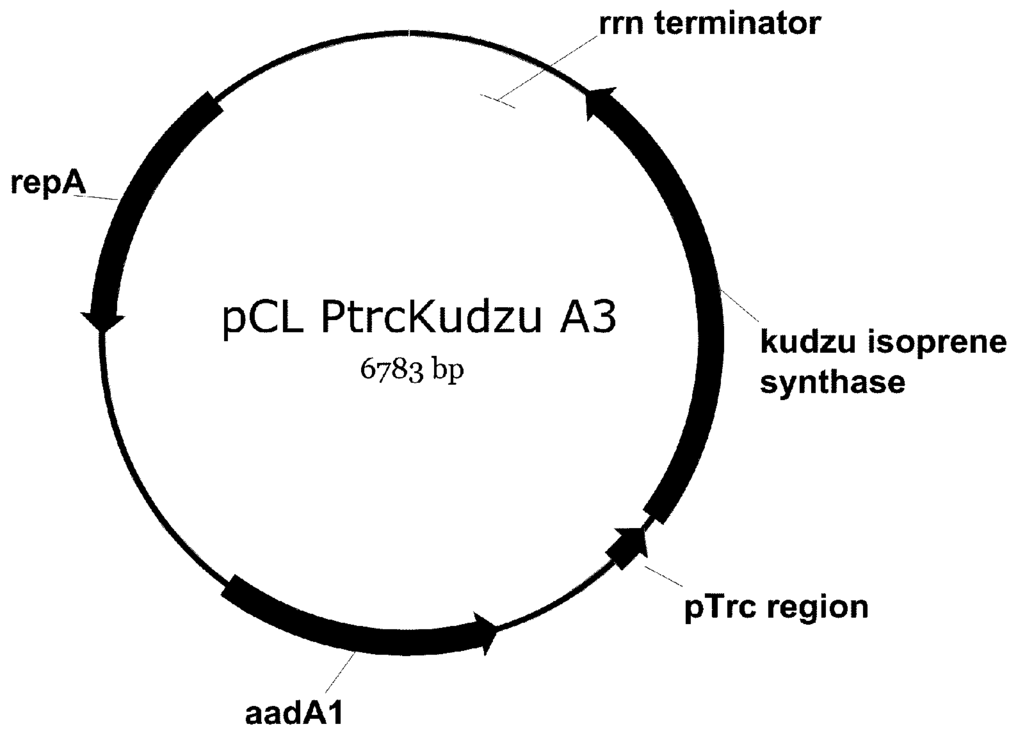
FIG. 34 is a map of pCL PtrcKudzu A3.

Plasmid pTrcKudzuKan was digested with PstI, treated with SAP, heat killed and gel purified. It was ligated to a PCR product encoding dxs from *E. coli* with a synthetic RBS. The primers for PCR were MCM13 5'-GATCATGCATTCGCCCTTAGGAGGTAAAAAAACATGAGTTTTGATATTGCCA AATACCCG (SEQ ID NO:18) and MCM14 5'-CATGCTGCAGTTATGCCAGCCAGGCCTTGAT (SEQ ID NO:19); and the template was *E. coli* genomic DNA. The PCR product was digested with NsiI and PstI and gel purified prior to ligation. The resulting transformation reaction was transformed into TOP10 cells and selected on LA with kanamycin 50 μg/ml. Several transformants were isolated and sequenced and the resulting plasmid was called pTrcKudzu-DXS(kan) (FIGS. 30 and 31).

iv) Construction of pTrcKudzu-yIDI-dxs (kan)

pTrcKudzu-yIDI(kan) was digested with PstI, treated with SAP, heat killed and gel purified. It was ligated to a PCR product encoding *E. coli* dxs with a synthetic RBS (primers MCM13 5'-GATCATGCATTCGCCCTTAGGAGGTAAAAAAACATGAGTTTTGATATTGCCA AATACCCG (SEQ ID NO:18) and MCM14 5'-CATGCTGCAGTTATGCCAGCCAGGCCTTGAT (SEQ ID NO:19); template TOP10 cells) which had been digested with NsiI and PstI and gel purified. The final plasmid was called pTrcKudzu-yIDI-dxs (kan) (FIGS. 21 and 22).

v) Construction of pCL PtrcKudzu

A fragment of DNA containing the promoter, structural gene and terminator from Example 1 above was digested from pTrcKudzu using SspI and gel purified. It was ligated to pCL1920 which had been digested with PvuII, treated with SAP and heat killed. The resulting ligation mixture was transformed into TOP10 cells and selected in LA containing spectinomycin 50 μg/ml. Several clones were isolated and sequenced and two were selected. pCL PtrcKudzu and pCL PtrcKudzu (A3) have the insert in opposite orientations (FIGS. 32-35).

vi) Construction of pCL PtrcKudzu yIDI

Figure 36:
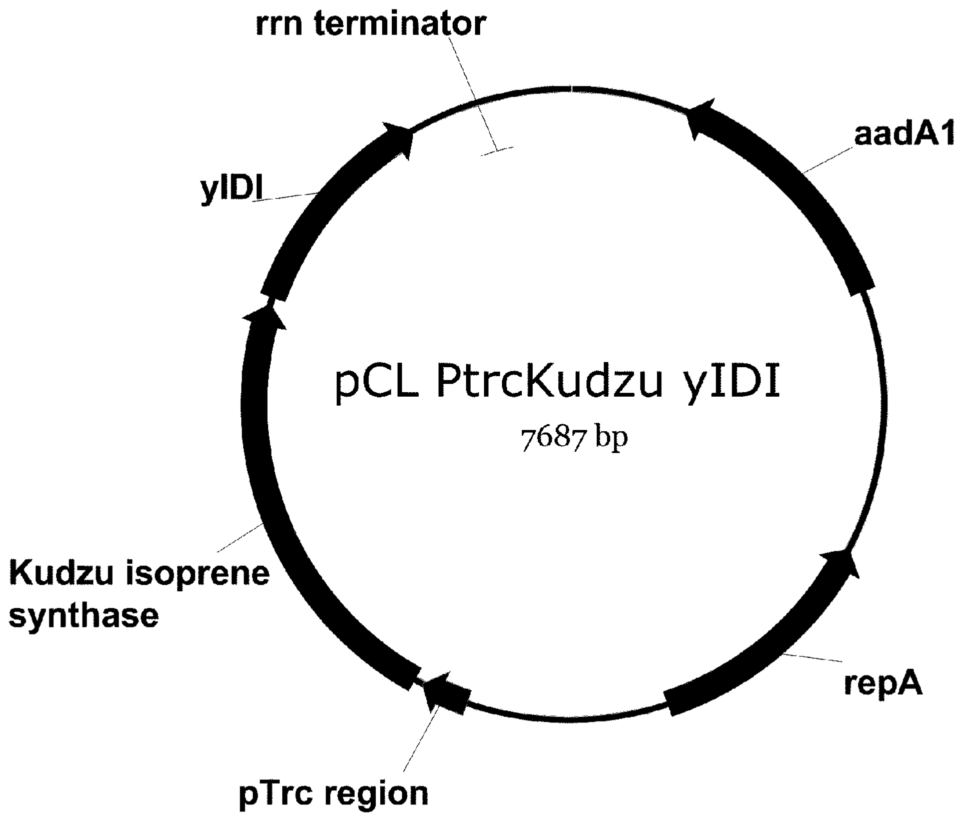
FIG. 36 is a map of pCL PtrcKudzu yIDI.

The NsiI-PstI digested, gel purified, IDI PCR amplicon from (ii) above was ligated into pCL PtrcKudzu which had been digested with PstI, treated with SAP, and heat killed. The ligation mixture was transformed into TOP10 cells and selected in LA containing spectinomycin 50 μg/ml. Several clones were isolated and sequenced and the resulting plasmid is called pCL PtrcKudzu yIDI (FIGS. 36 and 37).

vii) Construction of pCL PtrcKudzu DXS

Figure 38:
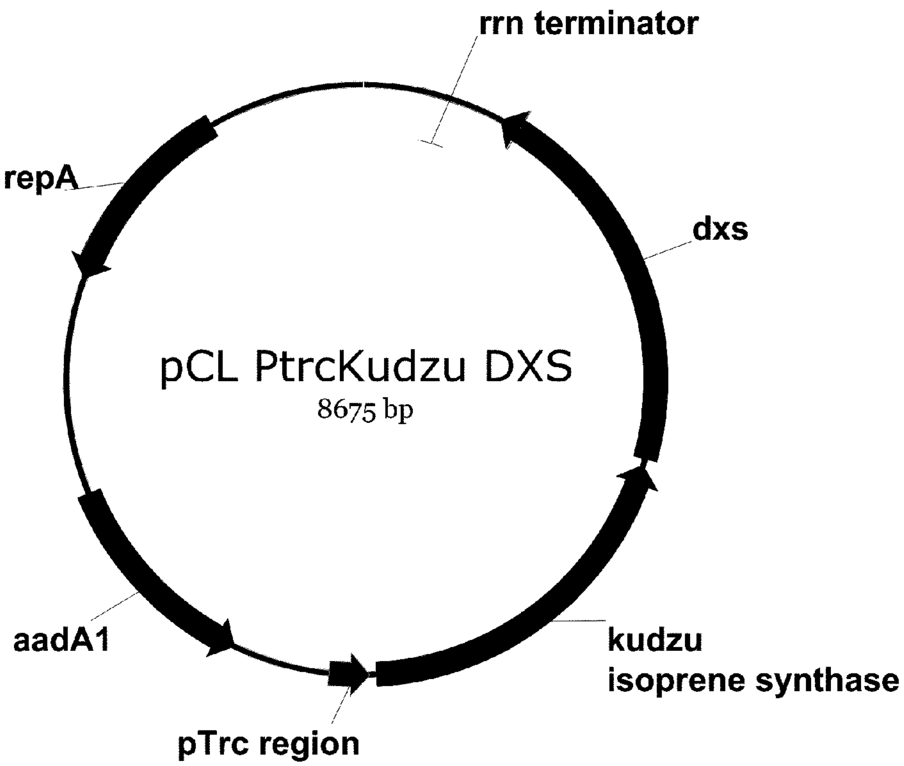
FIG. 38 is a map of pCL PtrcKudzu DXS.
Figure 40A:
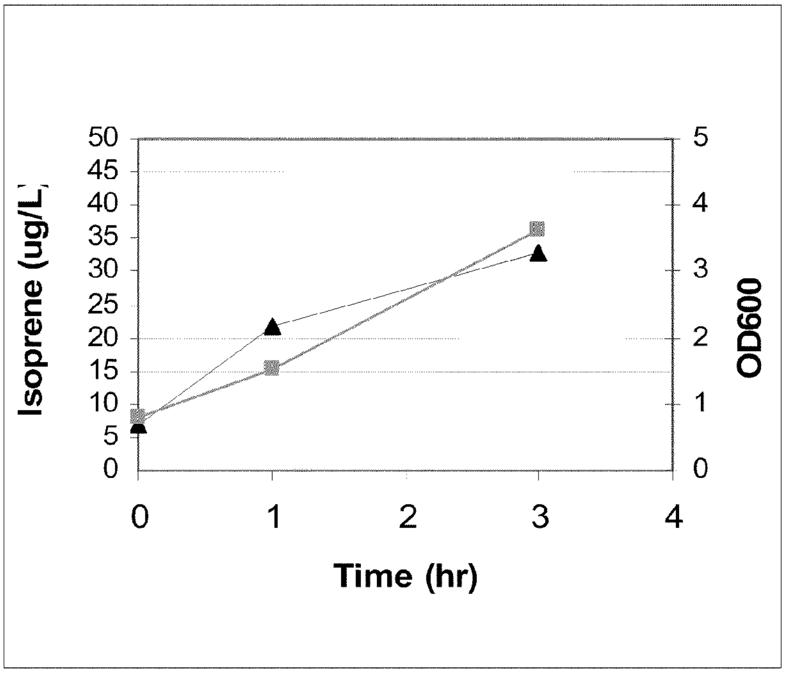
FIG. 40 shows graphs representing isoprene production from biomass feedstocks. Panel A shows isoprene production from corn stover, Panel B shows isoprene production from bagasse, Panel C shows isoprene production from softwood pulp, Panel D shows isoprene production from glucose, and Panel E shows isoprene production from cells with no additional feedstock. Grey squares represent $OD_{600}$ measurements of the cultures at the indicated times post-inoculation and black triangles represent isoprene production at the indicated times post-inoculation.
Figure 40B:
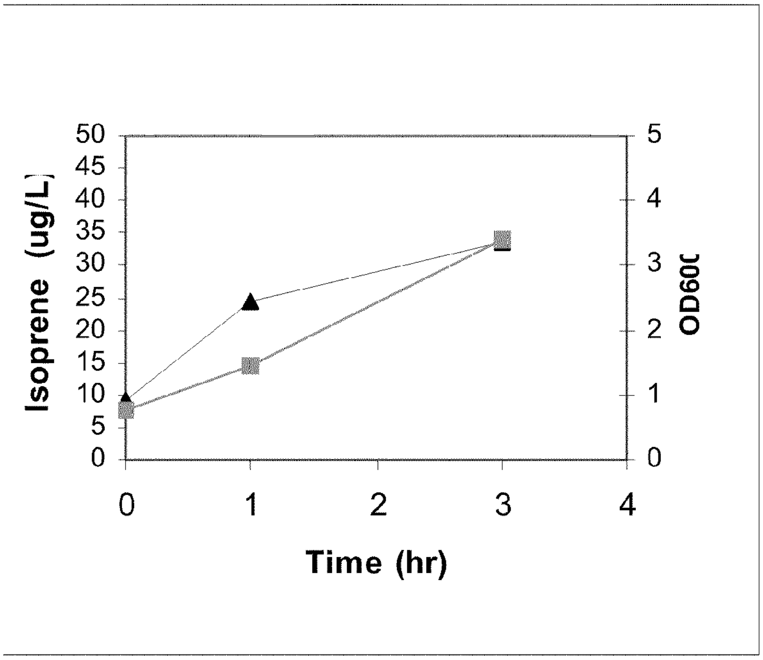
Figure 40C:
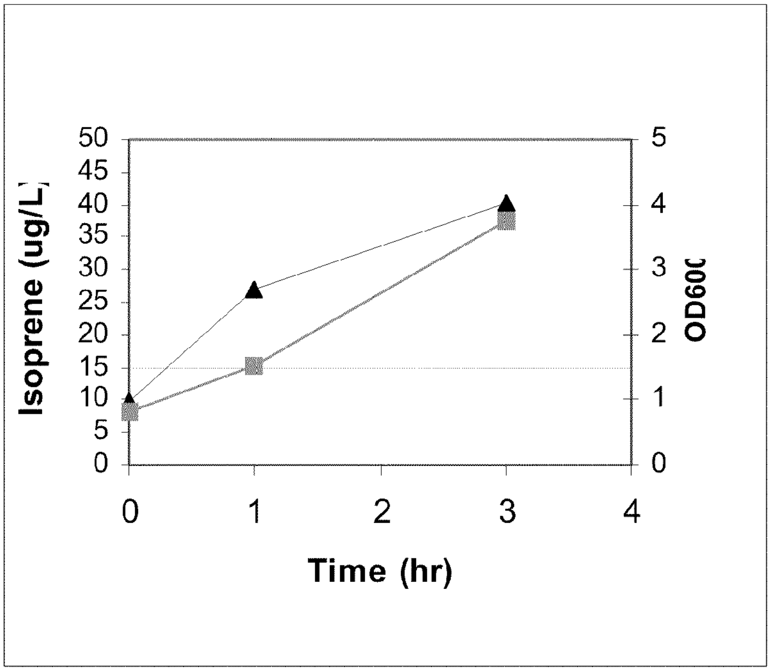
Figure 40D:
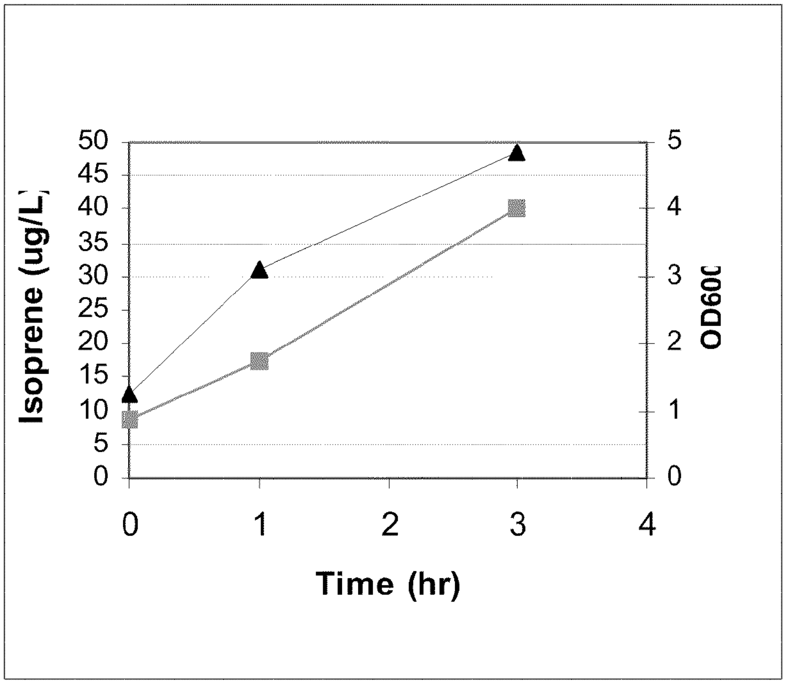
Figure 40E:
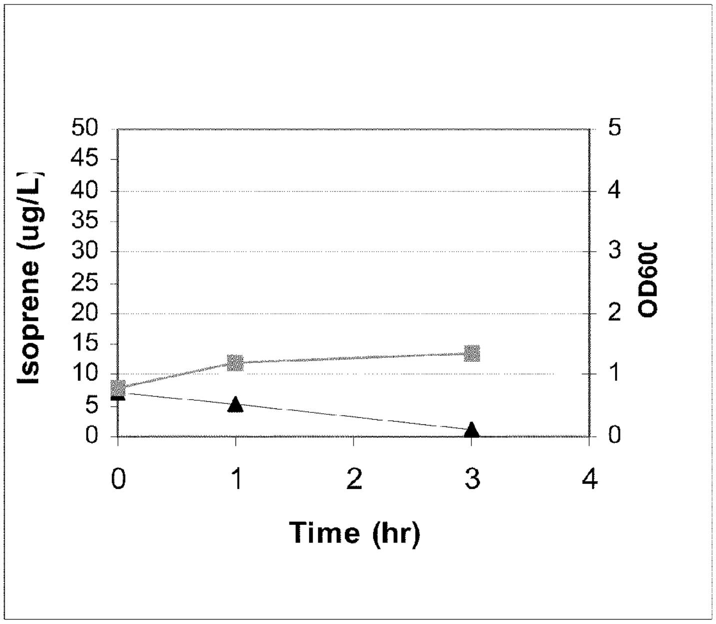
Figure 41A:
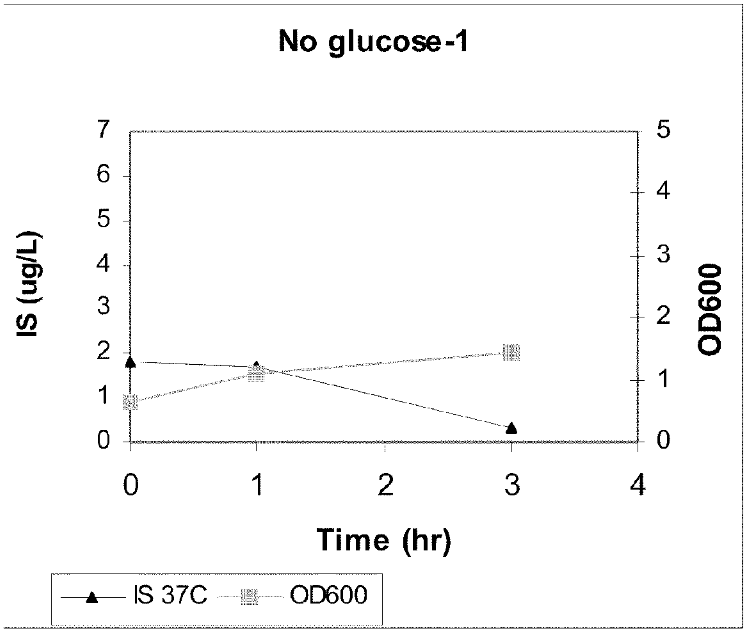
FIG. 41A shows a graph representing isoprene production by BL21 (λDE3) pTrcKudzu yIDI DXS (kan) in a culture with no glucose added. Squares represent $OD_{600}$, and triangles represent isoprene produced (μg/ml).
Figure 41B:
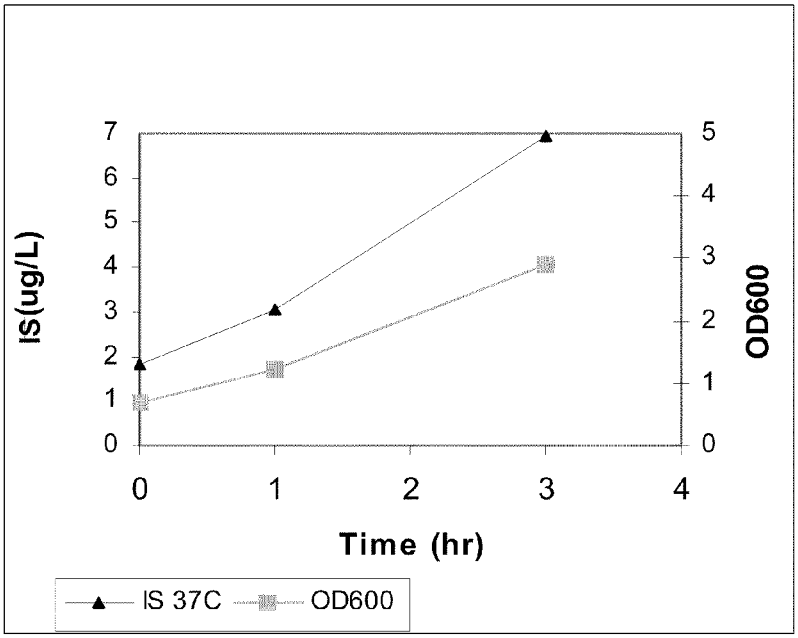
FIG. 41B shows a graph representing isoprene production from 1% glucose feedstock invert sugar by BL21 (λDE3) pTrcKudzu yIDI DXS (kan). Squares represent $OD_{600}$, and triangles represent isoprene produced (μg/ml).
Figure 41C:
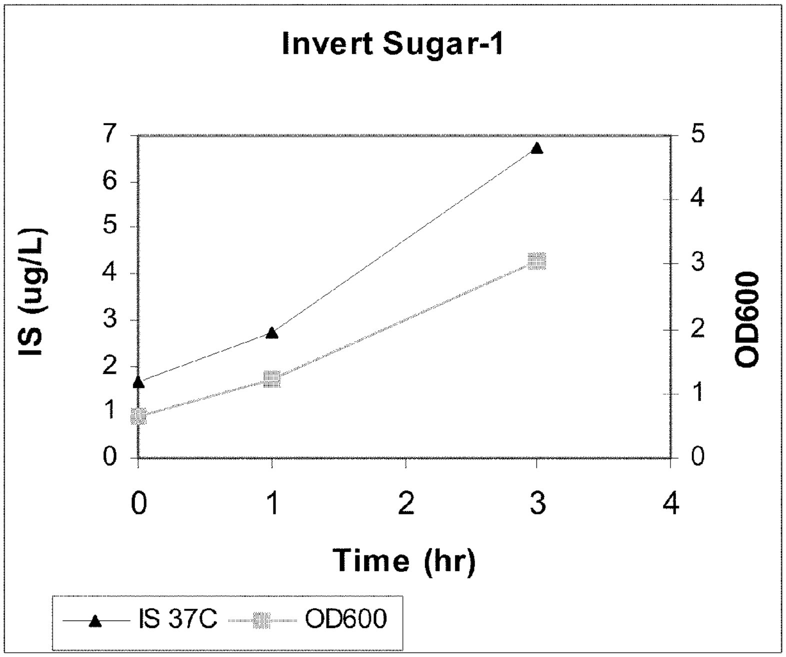
FIG. 41C shows a graph representing isoprene production from 1% invert sugar feedstock by BL21 (λDE3) pTrcKudzu yIDI DXS (kan). Squares represent $OD_{600}$, and triangles represent isoprene produced (μg/ml).
Figure 41D:
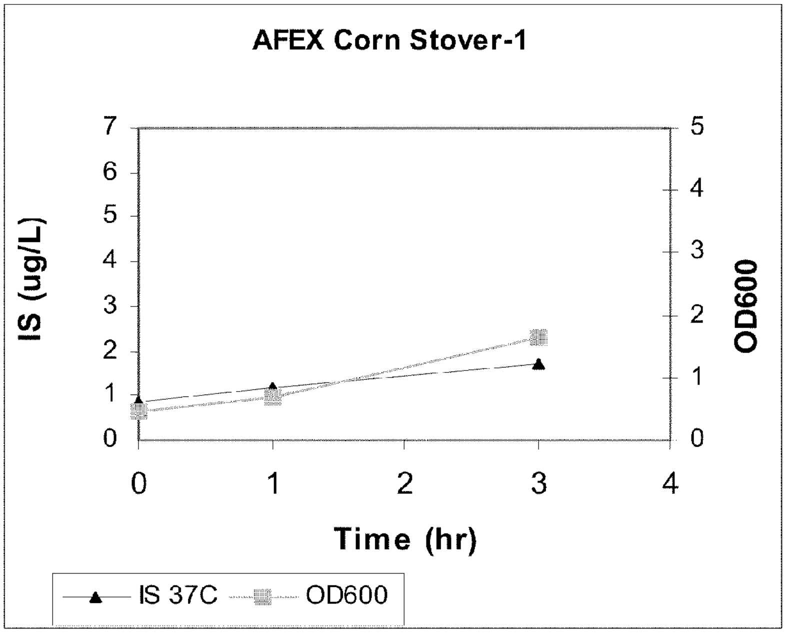
FIG. 41D shows a graph representing isoprene production from 1% AFEX corn stover feedstock by BL21 (λDE3) pTrcKudzu yIDI DXS (kan). Squares represent $OD_{600}$, and triangles represent isoprene produced (μg/ml).

The NsiI-PstI digested, gel purified, DXS PCR amplicon from (iii) above was ligated into pCL PtrcKudzu (A3) which had been digested with PstI, treated with SAP, and heat killed. The ligation mixture was transformed into TOP10 cells and selected in LA containing spectinomycin 50 μg/ml. Several clones were isolated and sequenced and the resulting plasmid is called pCL PtrcKudzu DXS (FIGS. 38 and 39).

II. Measurement of Isoprene in Headspace from Cultures Expressing Kudzu Isoprene Synthase, idi, and/or dxs at Different Copy Numbers.

Cultures of *E. coli* BL21 (λDE3) previously transformed with plasmids pTrcKudzu(kan) (A), pTrcKudzu-yIDI kan (B), pTrcKudzu-DXS kan (C), pTrcKudzu-yIDI-DXS kan (D) were grown in LB kanamycin 50 μg/mL. Cultures of pCL PtrcKudzu (E), pCL PtrcKudzu, pCL PtrcKudzu-yIDI (F) and pCL PtrcKudzu-DXS (G) were grown in LB spectinomycin 50 μg/mL. Cultures were induced with 400 μM IPTG at time 0 ($OD_{600}$ approximately 0.5) and samples taken for isoprene headspace measurement (see Example 1). Results are shown in FIG. 23A-23G.

Figure 23A:
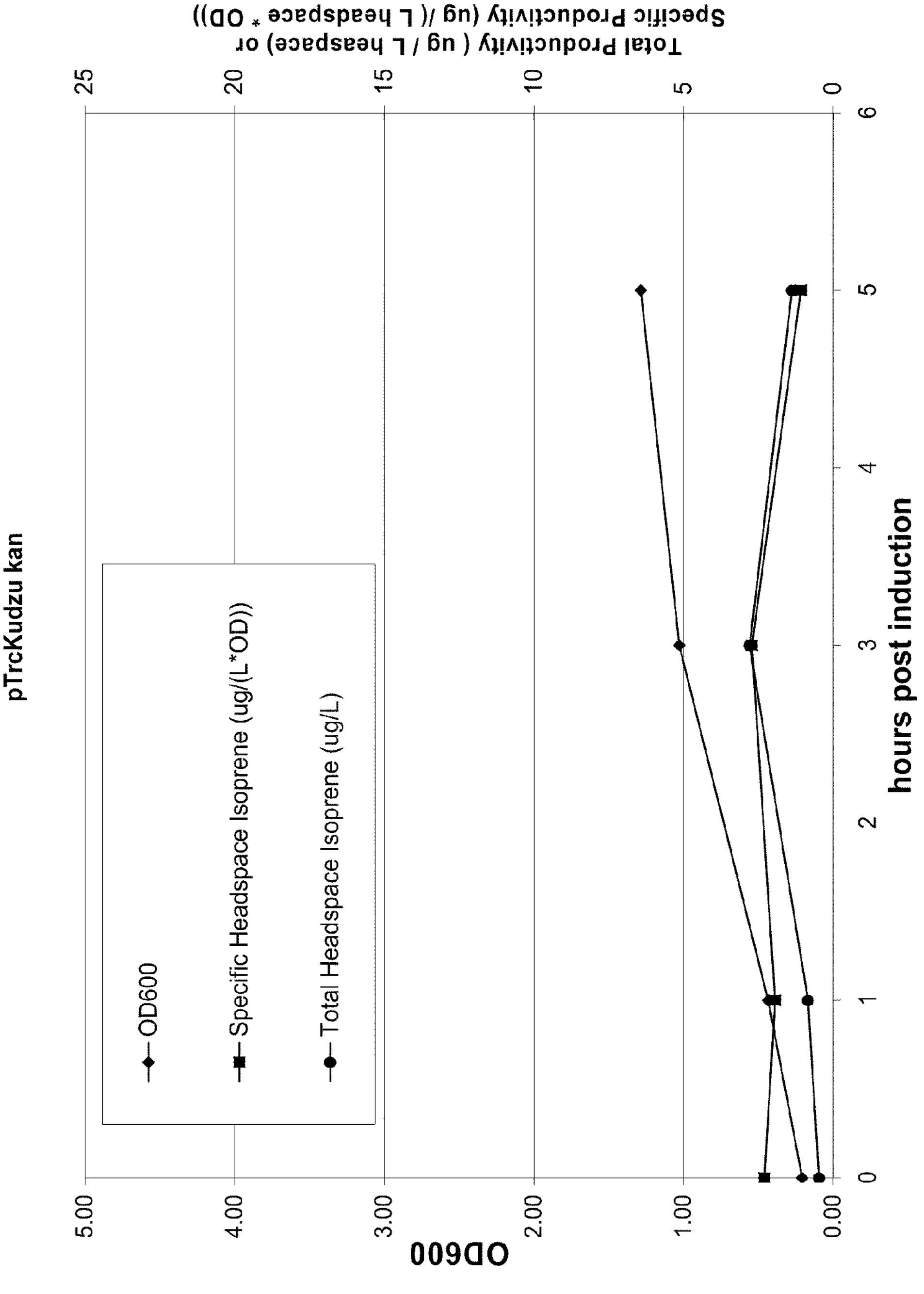
FIG. 23A is a graph showing production of isoprene from glucose in BL21/pTrcKudzukan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23B:
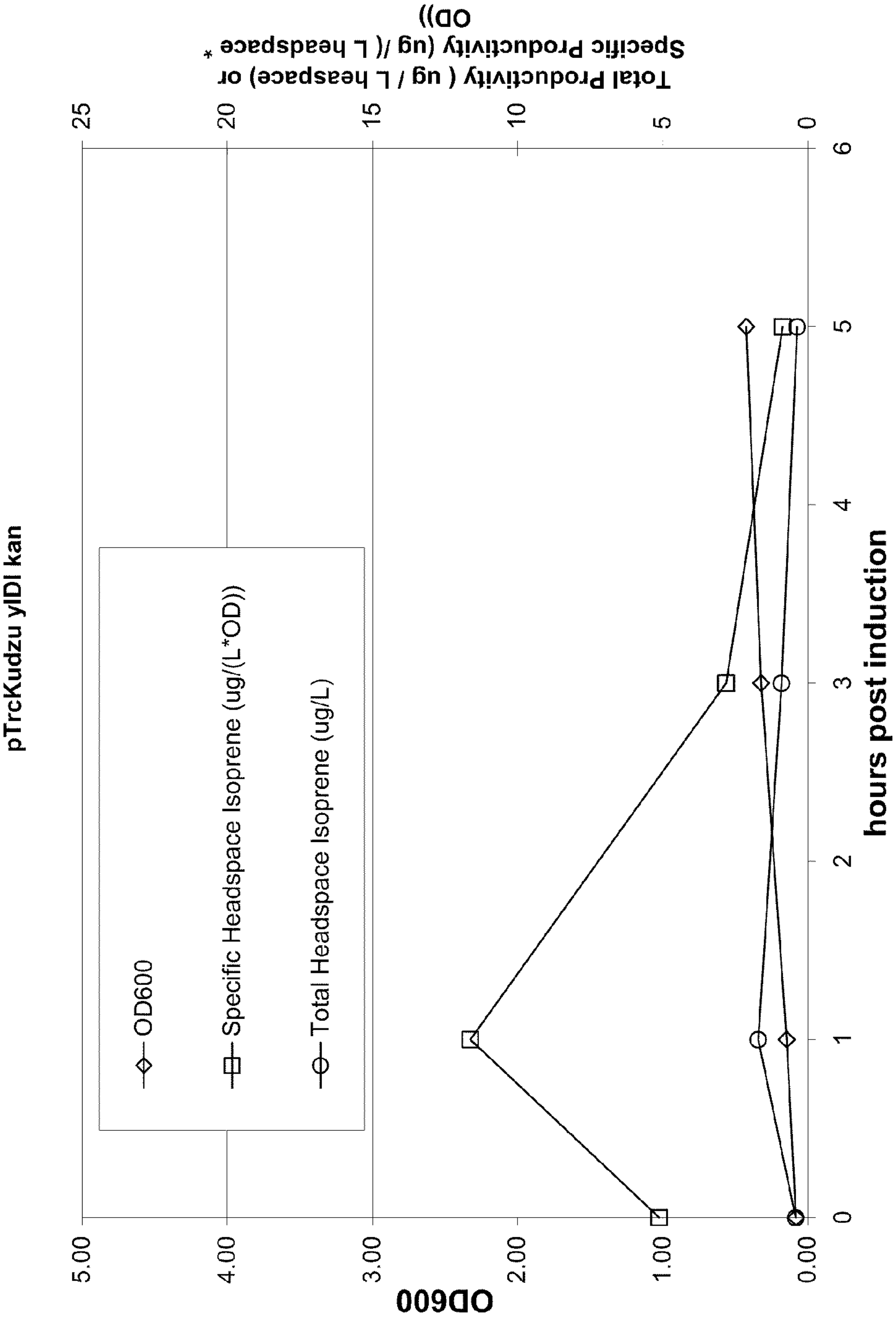
FIG. 23B is a graph showing production of isoprene from glucose in BL21/pTrcKudzu yIDI kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23C:
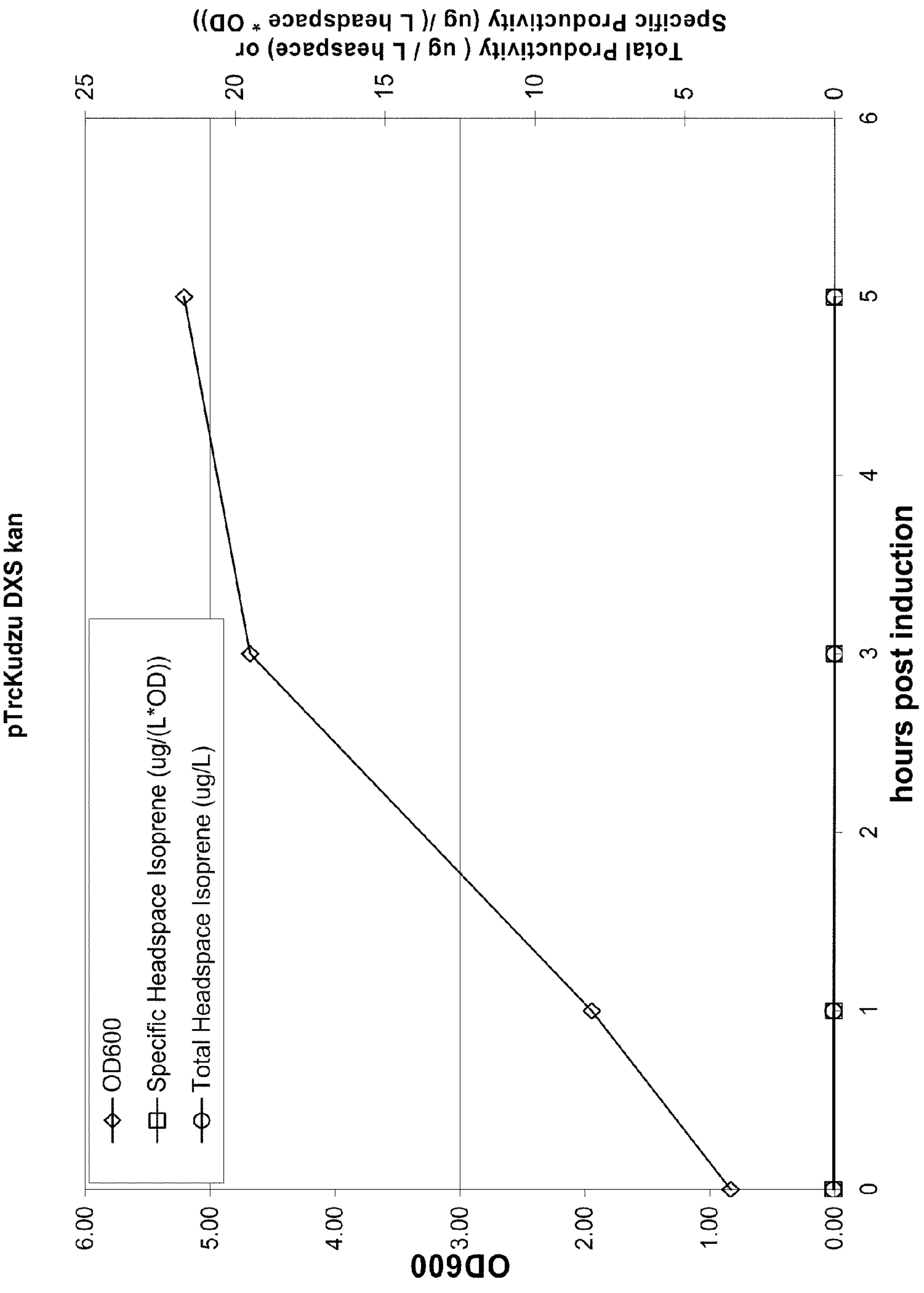
FIG. 23C is a graph showing production of isoprene from glucose in BL21/pTrcKudzu DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (m/L) and squares represent specific productivity of isoprene (μg/L/OD).
Figure 23D:
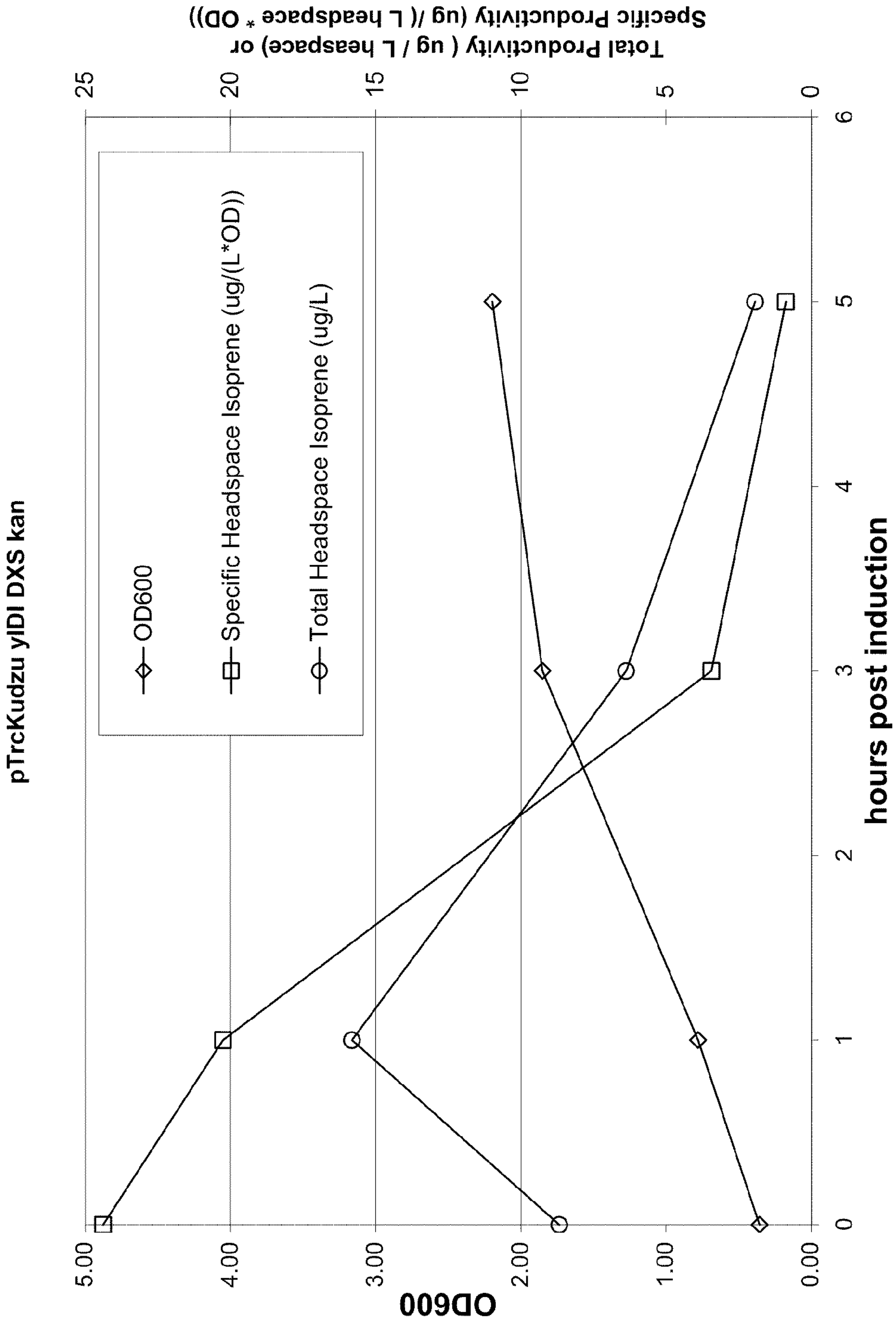
FIG. 23D is a graph showing production of isoprene from glucose in BL21/pTrcKudzu yIDI DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23E:
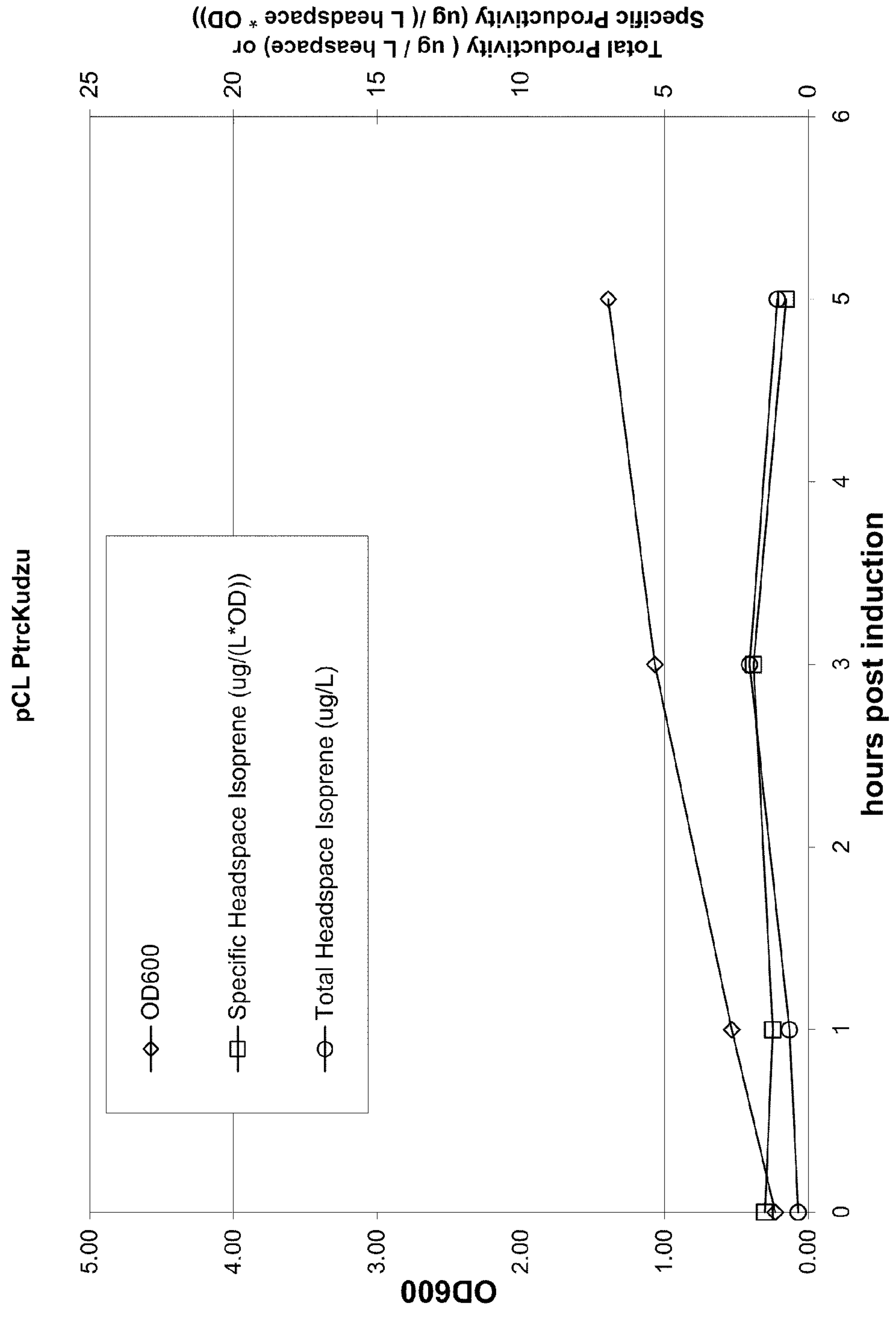
FIG. 23E is a graph showing production of isoprene from glucose in BL21/pCL PtrcKudzu. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (m/L) and squares represent specific productivity of isoprene (μg/L/OD).
Figure 23F:
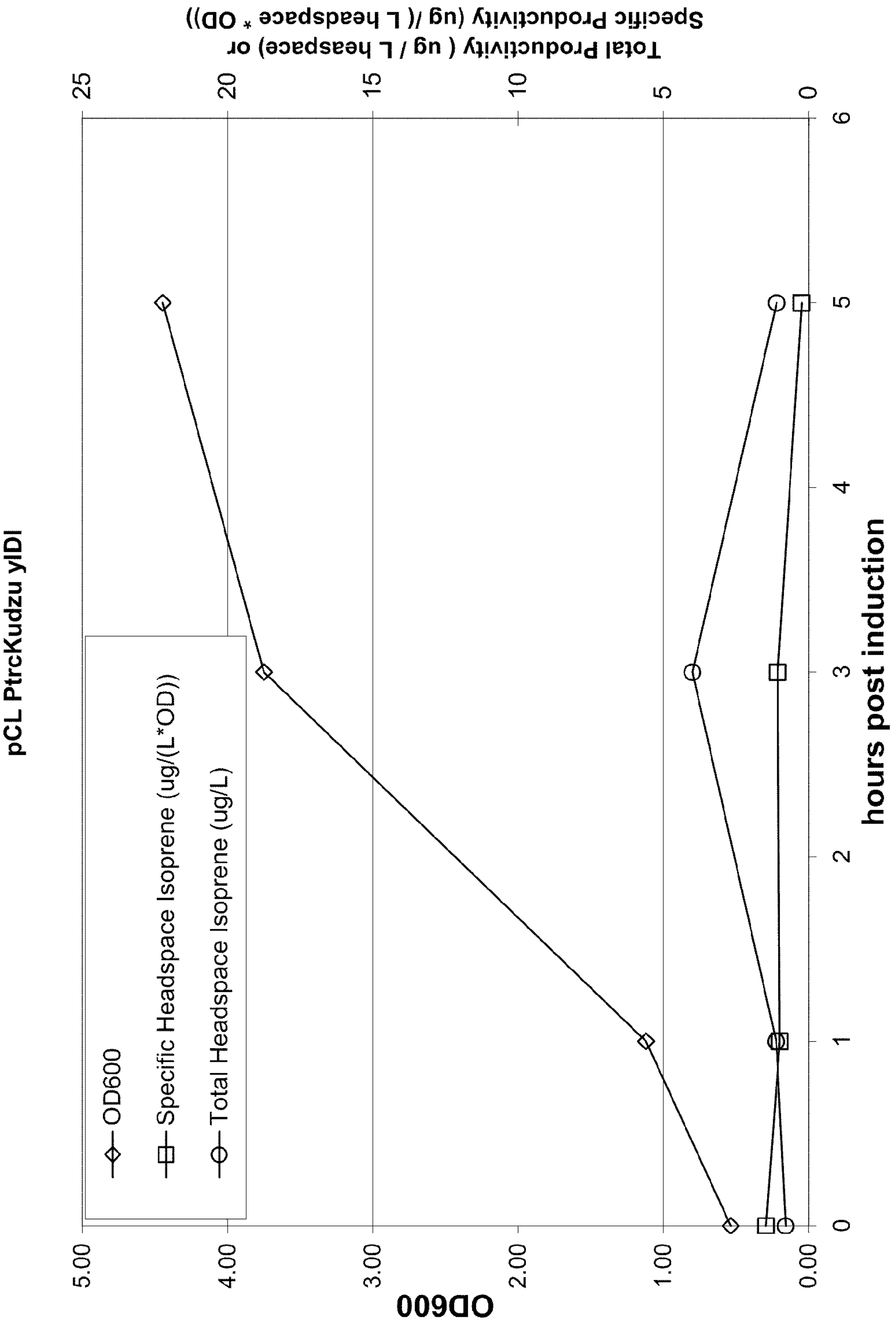
FIG. 23F is a graph showing production of isoprene from glucose in BL21/pCL PtrcKudzu yIDI. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (m/L) and squares represent specific productivity of isoprene (μg/L/OD).
Figure 23G:
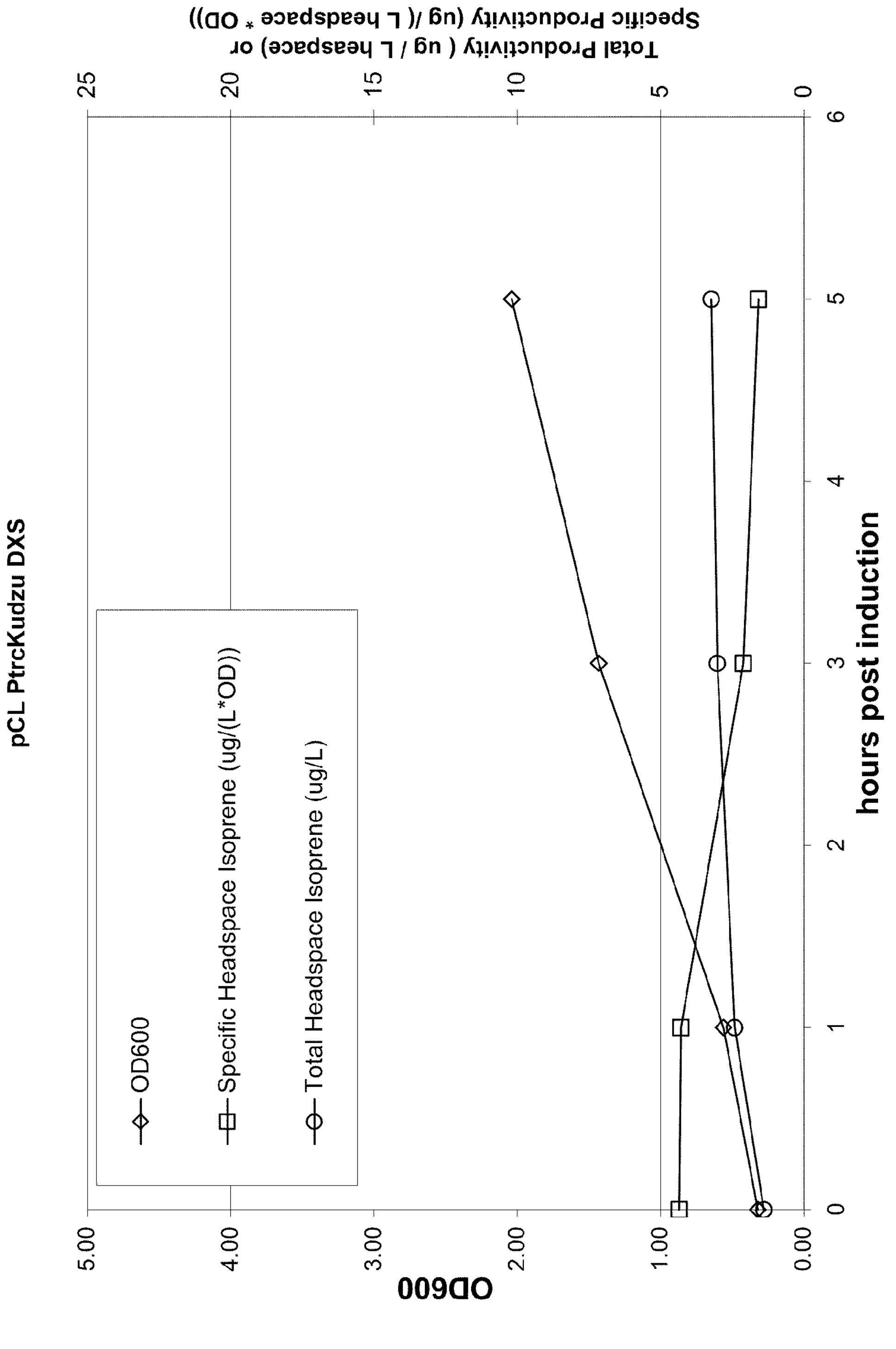
FIG. 23G is a graph showing production of isoprene from glucose in BL21/pCL PtrcKudzu DXS. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (m/L) and squares represent specific productivity of isoprene (μg/L/OD).
Figure 23H:
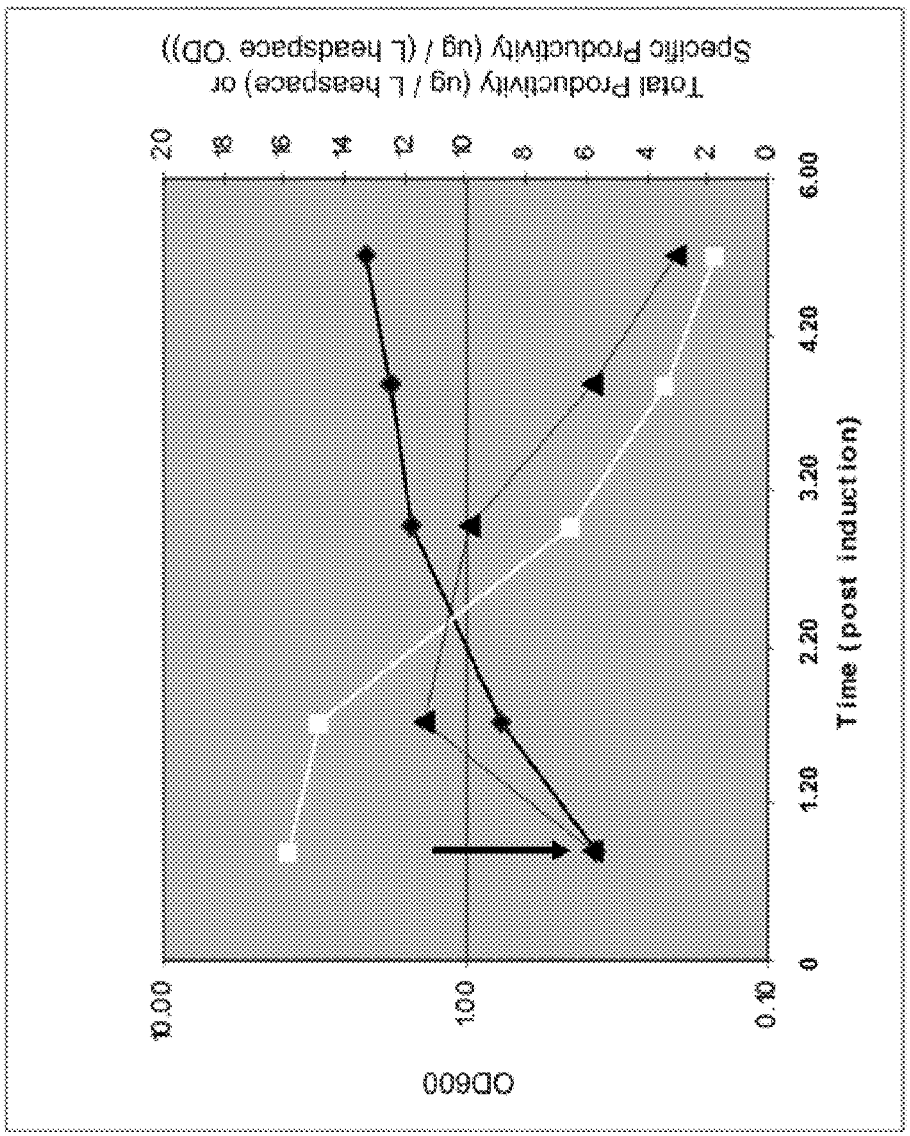
FIG. 23H is a graph showing production of isoprene from glucose in BL21/pTrcKudzuIDIDXSkan. The arrow indicates the time of induction with IPTG (400 μmol). The x-axis is time after induction; the y-axis is $OD_{600}$ and the y2-axis is total productivity of isoprene (μg/L headspace or specific productivity (μg/L headspace/OD). Black diamonds represent $OD_{600}$, black triangles represent isoprene productivity (μg/L) and white squares represent specific productivity of isoprene (m/L/OD).
Figure 24:
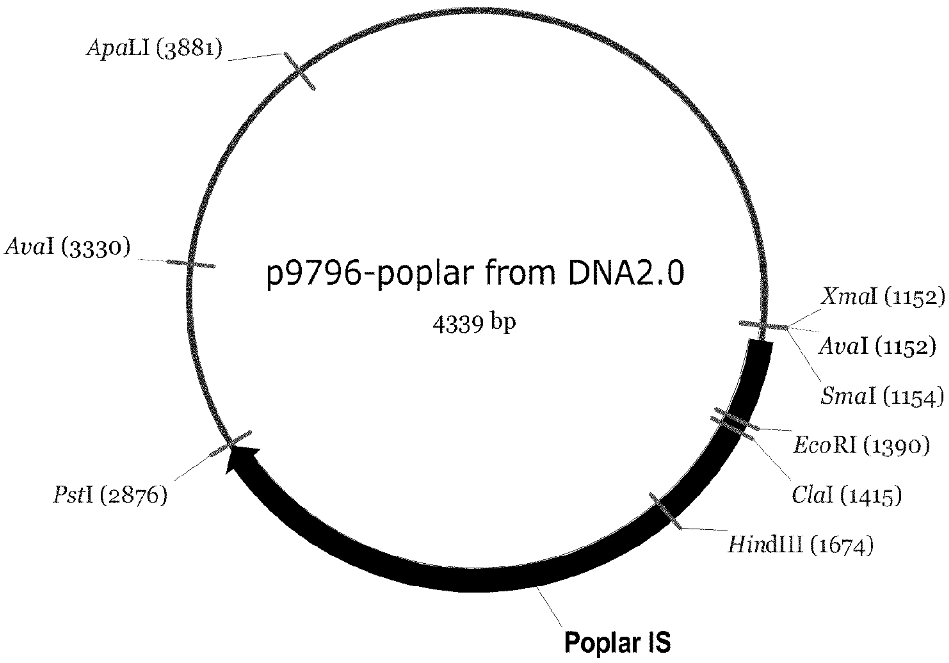
FIG. 24 is a map of p9796-poplar.

Plasmid pTrcKudzu-yIDI-dxs (kan) was introduced into *E. coli* strain BL21 by transformation. The resulting strain BL21/pTrc Kudzu IDI DXS was grown overnight in LB containing kanamycin (50 μg/ml) at 20° C. and used to inoculate shake flasks of TM3 (13.6 g $K_2PO_4$, 13.6 g $KH_2PO_4$, 2.0 g $MgSO_4$*$7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) containing 1% glucose. Flasks were incubated at 30° C. until an $OD_{600}$ of 0.8 was reached, and then induced with 400 μM IPTG. Samples were taken at various times after induction and the amount of isoprene in the head space was measured as described in Example 1. Results are shown in FIG. 23H.

III. Production of Isoprene from Biomass in *E. Coli*/pTrcKudzu yIDI DXS

The strain BL21 pTrcKudzuIDIDXS was tested for the ability to generate isoprene from three types of biomass; bagasse, corn stover and soft wood pulp with glucose as a control. Hydrolysates of the biomass were prepared by enzymatic hydrolysis (Brown, L. and Torget, R., 1996, NREL standard assay method Lap-009 "Enzymatic Saccharification of Lignocellulosic Biomass") and used at a dilution based upon glucose equivalents. In this example, glucose equivalents were equal to 1% glucose. A single colony from a plate freshly transformed cells of BL21 (DE3) pTrcKudzu yIDI DXS (kan) was used to inoculate 5 ml of LB plus kanamycin (50 μg/ml). The culture was incubated overnight at 25° C. with shaking. The following day the overnight culture was diluted to an $OD_{600}$ of 0.05 in 25 ml of TM3+0.2% YE+1% feedstock. The feedstock was corn stover, bagasse, or softwood pulp. Glucose was used as a positive control and no glucose was used as a negative control. Cultures were incubated at 30° C. with shaking at 180 rpm. The culture was monitored for $OD_{600}$ and when it reached an $OD_{600}$ of ~0.8, cultures were analyzed at 1 and 3 hours for isoprene production as described in Example 1. Cultures are not induced. All cultures containing added feedstock produce isoprene equivalent to those of the glucose positive control. Experiments were done in duplicate and are shown in FIG. 40.

IV. Production of Isoprene from Invert Sugar in *E. coli*/pTrcKudzuIDIDXS

A single colony from a plate freshly transformed cells of BL21 (λDE3)pTrcKudzu yIDI DXS (kan) was used to inoculate 5 mL of LB+kanamycin (50 μg/ml). The culture was incubated overnight at 25° C. with shaking. The following day the overnight culture was diluted to an $OD_{600}$ of 0.05 in 25 ml of TM3+0.2% YE+1% feedstock. Feedstock was glucose, inverted glucose or corn stover. The invert sugar feedstock (Danisco Invert Sugar) was prepared by enzymatically treating sucrose syrup. AFEX corn stover was prepared as described below (Part V). The cells were grown at 30° C. and the first sample was measured when the cultures reached an $OD_{600}$ ~0.8-1.0 (0 hour). The cultures were analyzed for growth as measured by $OD_{600}$ and for isoprene production as in Example 1 at 0, 1 and 3 hours. Results are shown in FIG. 41.

V. Preparation of Hydrolysate from AFEX Pretreated Corn Stover

AFEX pretreated corn stover was obtained from Michigan Biotechnology Institute. The pretreatment conditions were 60% moisture, 1:1 ammonia loading, and 90° C. for 30 minutes, then air dried. The moisture content in the AFEX pretreated corn stover was 21.27%. The contents of glucan and xylan in the AFEX pretreated corn stover were 31.7% and 19.1% (dry basis), respectively. The saccharification process was as follows; 20 g of AFEX pretreated corn stover was added into a 500 ml flask with 5 ml of 1 M sodium citrate buffer pH 4.8, 2.25 ml of Accellerase 1000, 0.1 ml of Grindamyl H121 (Danisco xylanase product from *Aspergillus niger* for bread-making industry), and 72.65 ml of DI water. The flask was put in an orbital shaker and incubated at 50° C. for 96 hours. One sample was taken from the shaker and analyzed using HPLC. The hydrolysate contained 38.5 g/l of glucose, 21.8 g/l of xylose, and 10.3 g/l of oligomers of glucose and/or xylose.

Figure 42A:
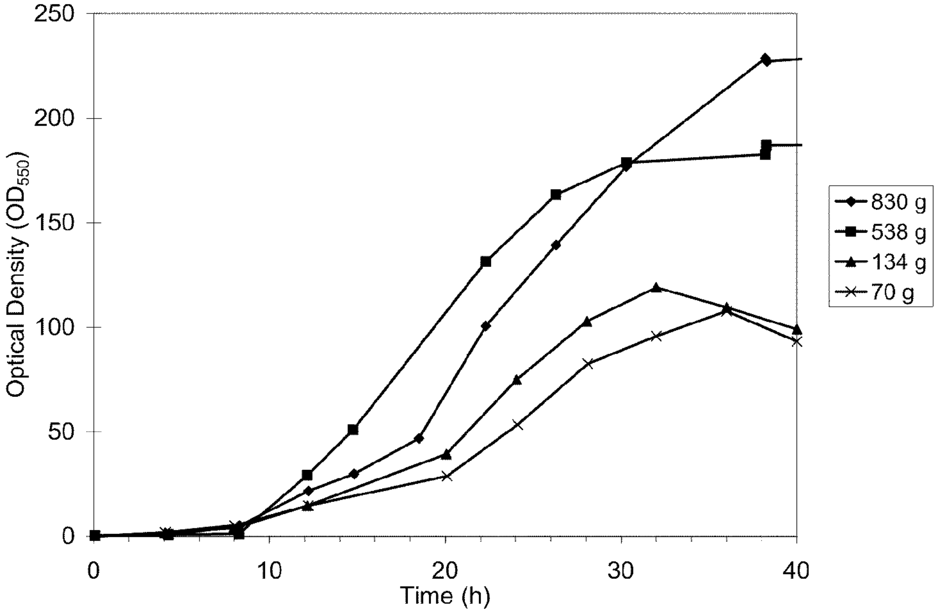
FIG. 42 shows graphs demonstrating the effect of yeast extract of isoprene production. Panel A shows the time course of optical density within fermentors fed with varying amounts of yeast extract. Panel B shows the time course of isoprene titer within fermentors fed with varying amounts of yeast extract. The titer is defined as the amount of isoprene produced per liter of fermentation broth. Panel C shows the effect of yeast extract on isoprene production in *E. coli* grown in fed-batch culture.
Figure 42B:
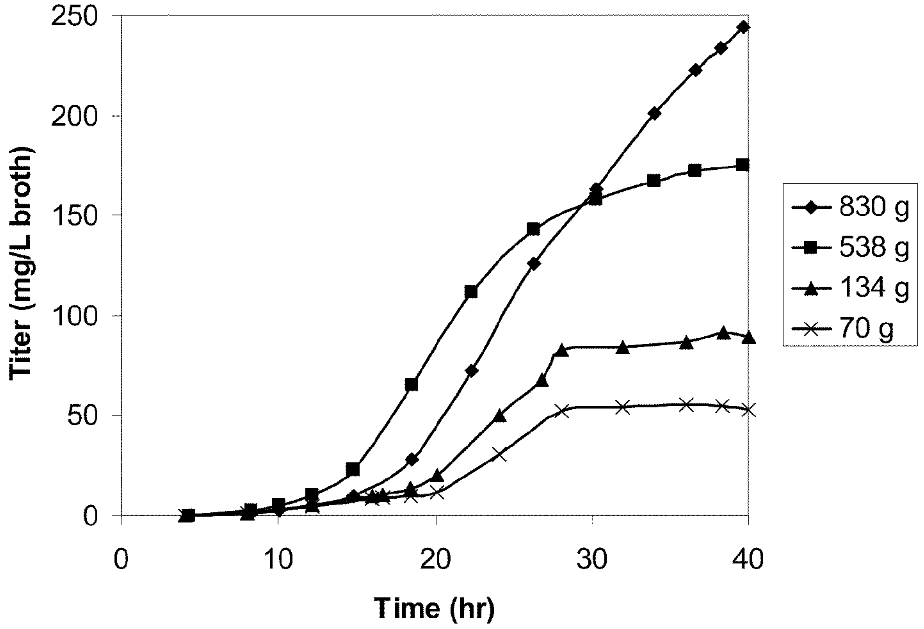
Figure 42C:
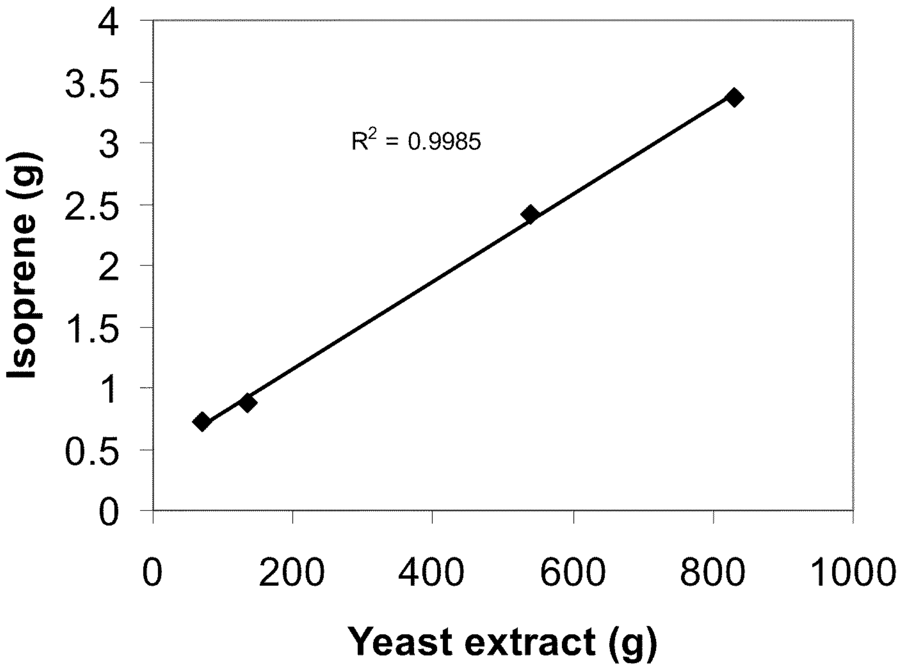

VI. The Effect of Yeast Extract on Isoprene Production in *E. Coli* Grown in Fed-Batch Culture Fermentation was performed at the 14-L scale as previously described with *E. coli* cells containing the pTrcKudzu yIDI DXS plasmid described above. Yeast extract (Bio Springer, Montreal, Quebec, Canada) was fed at an exponential rate. The total amount of yeast extract delivered to the fermentor was varied between 70-830 g during the 40 hour fermentation. Optical density of the fermentation broth was measured at a wavelength of 550 nm. The final optical density within the fermentors was proportional to the amount of yeast extract added (FIG. 42A). The isoprene level in the off-gas from the fermentor was determined as previously described. The isoprene titer increased over the course of the fermentation (FIG. 42B). The amount of isoprene produced was linearly proportional to the amount of fed yeast extract (FIG. 42C).

VII. Production of Isoprene in 500 L Fermentation of pTrcKudzu dxs yIDI

A 500 liter fermentation of *E. coli* cells with a kudzu isoprene synthase, *S. cerevisiae* IDI, and *E. coli* DXS nucleic acids (*E. coli* BL21 (λDE3) pTrc Kudzu dxs yidi) was used to produce isoprene. The levels of isoprene varied from 50 to 300 μg/L over a time period of 15 hours. On the basis of the average isoprene concentrations, the average flow through the device and the extent of isoprene breakthrough, the amount of isoprene collected was calculated to be approximately 17 g.

VIII. Production of Isoprene in 500 L Fermentation of *E. coli* Grown in Fed-Batch Culture Medium Recipe (Per Liter Fermentation Medium):

$K_2HPO_4$ 7.5 g, $MgSO_4$*7$H_2O$ 2 g, citric acid monohydrate 2 g, ferric ammonium citrate 0.3 g, yeast extract 0.5 g, 1000× Modified Trace Metal Solution 1 ml. All of the components were added together and dissolved in di$H_2O$. This solution was autoclaved. The pH was adjusted to 7.0 with ammonium gas ($NH_3$) and q.s. to volume. Glucose 10 g, thiamine*HCl 0.1 g, and antibiotic were added after sterilization and pH adjustment.

1000× Modified Trace Metal Solution:

Citric Acids*$H_2O$ 40 g, $MnSO_4$*$H_2O$ 30 g, NaCl 10 g, $FeSO_4$*7$H_2O$ 1 g, $CoCl_2$*6$H_2O$ 1 g, $ZnSO_4$*7$H_2O$ 1 g, $CuSO_4$*5$H_2O$ 100 mg, $H_3BSO_3$ 100 mg, $NaMoO_4$*2$H_2O$ 100 mg. Each component is dissolved one at a time in DI $H_2O$, pH to 3.0 with HCl/NaOH, then q.s. to volume and filter sterilized with 0.22 micron filter.

Fermentation was performed in a 500-L bioreactor with *E. coli* cells containing the pTrcKudzu yIDI DXS plasmid. This experiment was carried out to monitor isoprene formation from glucose and yeast extract at the desired fermentation pH 7.0 and temperature 30° C. An inoculum of *E. coli* strain taken from a frozen vial was prepared in soytone-yeast extract-glucose medium. After the inoculum grew to OD 0.15, measured at 550 nm, 20 ml was used to inoculate a bioreactor containing 2.5-L soytone-yeast extract-glucose medium. The 2.5-L bioreactor was grown at 30° C. to OD 1.0 and 2.0-L was transferred to the 500-L bioreactor.

Figure 43A:
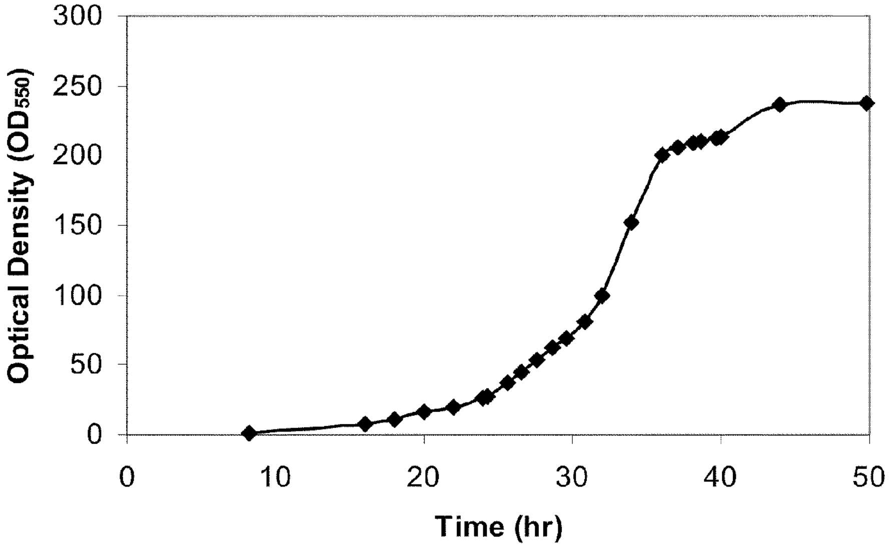
FIG. 43 shows graphs demonstrating isoprene production from a 500 L bioreactor with *E. coli* cells containing the pTrcKudzu+yIDI+DXS plasmid. Panel A shows the time course of optical density within the 500-L bioreactor fed with glucose and yeast extract. Panel B shows the time course of isoprene titer within the 500-L bioreactor fed with glucose and yeast extract. The titer is defined as the amount of isoprene produced per liter of fermentation broth. Panel C shows the time course of total isoprene produced from the 500-L bioreactor fed with glucose and yeast extract.
Figure 43B:
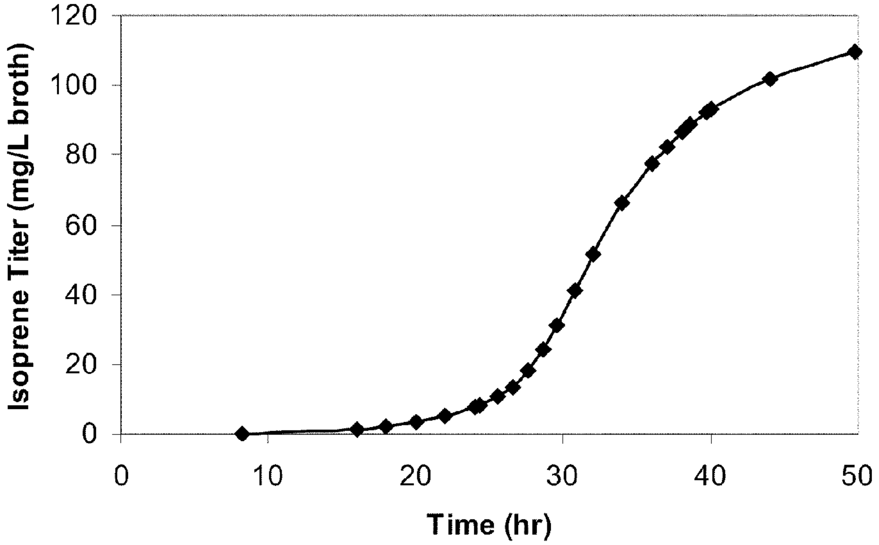
Figure 43C:
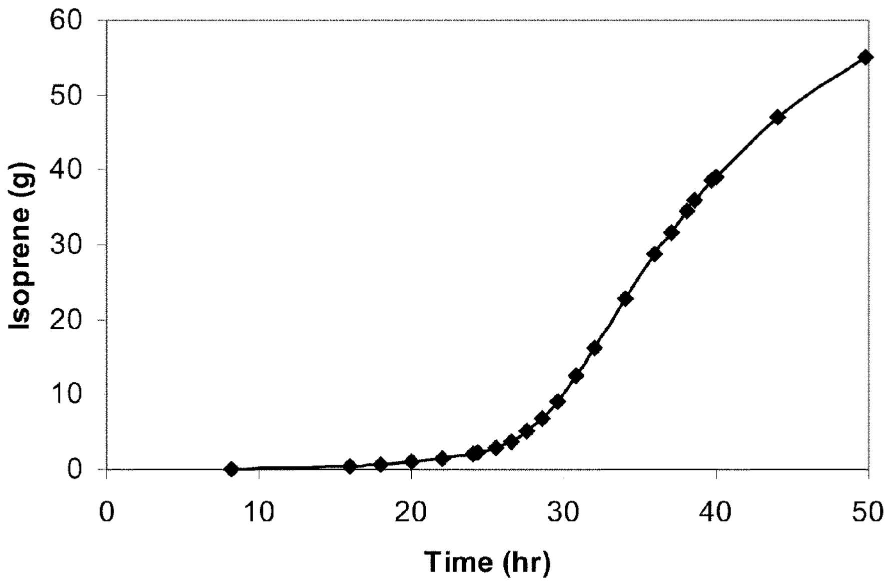

Yeast extract (Bio Springer, Montreal, Quebec, Canada) and glucose were fed at exponential rates. The total amount of glucose and yeast extract delivered to the bioreactor during the 50 hour fermentation was 181.2 kg and 17.6 kg, respectively. The optical density within the bioreactor over time is shown in FIG. 43A. The isoprene level in the off-gas from the bioreactor was determined as previously described. The isoprene titer increased over the course of the fermentation (FIG. 43B). The total amount of isoprene produced during the 50 hour fermentation was 55.1 g and the time course of production is shown in FIG. 43C.

Example 8

Overexpression of Flavodoxin I (fldA) Increase Isoprene Production in a Strain Expressing Over-Expressing *E. Coli* dxs, *Saccharomyces* idi, and Kudzu Isoprene Synthase BL21 (DE3) strain harboring pTrcKudzuDXSyIDI produced more isoprene under non-inducing conditions compared to IPTG induction conditions, and was observed to accumulate HMBPP ((E)-4-hydroxy-3-methyl-but-2-enyl pyrophosphate), the substrate of HDS (GcpE or IspG). Using the BL21 (DE3) strain harboring pTrcKudzuDXSyIDI as the parental host strain, the introduction of an additional plasmid-born copy of the Kudzu isoprene synthase gene alone and in combination with the fldA gene encoding flavodoxin I were assessed for the effects on isoprene production by the strains under non-inducing conditions relative to the empty vector control strain.

These experiments investigated whether an additional copy of the isoprene synthase improves isoprene production under non-inducing conditions in the BL21 (DE3) strain harboring the pTrcKudzuDXSyIDI construct. Under the non-inducing conditions, isoprene synthase may be limiting and an additional copy of the Kudzu enzyme may be able to improve the specific productivity of isoprene generation by the strain. The experiments also investigated whether other factor(s) contributed to the modest level of isoprene produced by the strain and whether a plasmid-born copy of fldA could increase isoprene production by the BL21 (DE3) strain that harbors the pTrcKudzuDXSyIDI construct under non-inducing conditions. The flavodoxin I encoded by fldA was intended to be expressed ectopically from the pTrcHgSfldA/pBAD33 construct at a level surpassing that generated from the endogenous fldA locus. An increased amount of flavodoxin I may increase the activity demonstrated by the DXP pathway enzymes GcpE (HDS or IspG) and LytB (HDR or IspH) in vivo, as was previously seen in vitro (Seemann, M. et al. *Agnew. Chem. Int. Ed.*, 41: 4337-4339, 2002; Wolff, M. et al. *FEBS Letters*, 541: 115-120, 2003), and possibly improve carbon flux to isoprene synthesis in the strain of interest over that of the comparable pTrcKudzuDXSyIDI-containing BL21 (DE3) control strain.

Bacterial transformation and molecular biology techniques were performed using standard protocols (Sambrook et al), which is hereby incorporated by reference in its entirety, particularly with respect to bacterial transformation. The *E. coli* strains BL21 (DE3) and TOP10 were obtained from Invitrogen. TOP10 cells were used during the preparation of the pTrcHgS/pBAD33 and pTrcHgSfldA/pBAD33 constructs described below. Vector constructs were moved via chemical transformation into the BL21 (DE3) strain for the subsequent assessment of isoprene production.

Constructs

```
Forward primer
Name:    5' fldA NsiI SpeI rbs

Sequence: GG ATGCAT ACTAGT TTCA AGAGG TATTTCACTC ATG   (SEQ ID NO: 54)

Features:    NsiI    SpeI        rbs            start

                   A                    G
          Region homologous to MG1655 fldA locus

Primers were purchased from Integrated DNA Technologies (Coralville,
Iowa). PCR reactions were performed with Herculase II Fusion
(Stratagene) according to manufacturer's specifications.

Reverse primer
Name:    3' fldA PstI stop

Sequence: ATC CTGCAG TCA GGCATTGAGAATTTCGTC           (SEQ ID NO: 55)

Features:    PstI    stop

                T                   C
          Region homologous to MG1655 fldA locus
```

Primers were purchased from Integrated DNA Technologies (Coralville, Iowa). PCR reactions were performed with Herculase II Fusion (Stratagene) according to manufacturer's specifications.

*E. coli* 12 MG1655 (world wide web at genome.wisc.edu/resources/strains.htm) was the source of genomic template used to amplify the fldA locus; cells were added directly to the PCR reaction using a sterile toothpick.

The fldA PCR product was cleaned utilizing the MinElute PCR Purification Kit (Qiagen). pBAD33 is described, for example, in Luz-Maria, G. et al., *J. Bacteriology*, 77: 4121-4130, 1995, which is hereby incorporated by reference in its entirety, particularly with respect to pBAD33. pTrcKudzu, and pTrcKudzuDXSyIDI kan, were described, for example, in U.S. application Ser. No. 12/335,071 and PCT/US2008/086809, which are hereby incorporated by reference in their entireties, particularly with respect to Examples 1 and 7.

pTrcHgS/pBAD33 was constructed here by cloning the SspI-PstI (1934 bp) fragment containing the Trc promoter region, rbs, and the coding sequence of the Kudzu isoprene synthase derived from pTrcKudzu into the SmaI-PstI sites of pBAD33.

pTrcHgSfldA/pBAD33 was constructed here. The NsiI-PstI (1471 bp) digested PCR amplified fldA fragment encompassing 22 by upstream of the fldA start, including the endogenous rbs, through the stop codon of the fldA gene was cloned into the PstI site located just downstream of the isoprene synthase open reading frame in pTrcHgS/pBAD33.

Constructs were verified by sequencing that was performed by Sequetech (Mountain View, Calif.).

Culture Conditions

Bacteria were grown at 25° C. and 30° C. on LB 1.5% agar plates and in TM3 liquid media (see description of TM3, for example, U.S. application Ser. No. 12/335,071 and PCT/US2008/086809, which are hereby incorporated by reference in their entireties, particularly with respect to TM3 liquid media) supplemented to a final concentration with 0.1% yeast extract and 1.0% glucose. When appropriate, kanamycin (Kan) and/or chloramphenicol (Cmp) were added to the growth media at 50 μg/ml and 10 μg/ml, respectively; pTrc-based constructs encode $Kan^R$ and pBAD33-based constructs encode $Cmp^R$. Bacterial growth was monitored by optical density measured at 600 nm.

Assessment of Isoprene Production

Headspace assay for isoprene production was described in Example 1. The specific productivity of each strain was reported as μg/L-OD-hour; note ratio of 1900 μl headspace: 100 μl broth in assay vials. Graphs depicting the growth rate and specific productivity of each strain were generated using Microsoft Office Excel 2003 software.

Construction of BL21 (DE3) Strains and Assessment of the Isoprene Production

The following BL21 (DE3) strains were constructed and assessed for the production of isoprene relative to one another: BL21 (DE3) harboring the pTrcKudzuDXSyIDI vector and either 1) empty pBAD33 vector (also referred to as "empty vector"); 2) pTrcHgS/pBAD33 construct (also referred to as "HgS"), or 3) pTrcHgSfldA/pBAD33 construct (as referred to as "HgS-FldA").

All three BL21 (DE3) test strains harbor $Kan^R$ and $Cmp^R$ and were grown under appropriate selection for both plasmid constructs. The empty vector strain represented the parental control strain; the HgS strain represented the parental strain harboring an addition plasmid-born copy of the Kudzu isoprene synthase gene; the HgS-FldA strain represented the parental strain harboring the addition plasmid-born copies of flavodoxin I and isoprene synthase genes.

The bacteria strains were grown overnight shaking (250 rpm) at 25° C. in 10 ml of supplemented TM3 media containing antibiotics; here and for the following experiments 50 μg/ml of kanamycin and 10 μg/ml of chloramphenicol were present in the growth media. The cultures were then diluted into fresh supplemented TM3 media containing antibiotics to an optical density at 600 nm of approximately 0.05 and allowed to grow shaking (250 rpm) at 30° C. in 12.5-25 ml of supplemented TM3 media containing antibiotics in 250 ml Erlenmeyer flasks. Strains were typically assessed for isoprene production once the optical density at 600 nm of the culture reached 0.4. In the most densely sampled experiments, once isoprene measurements commenced the isoprene production for each culture was monitored in 45 min. intervals. The results from two independent experiments depicting growth rate and specific productivity of isoprene generation for the empty vector (control), HgS, and HgS-FldA strains are shown in the FIGS. 46A-46D. The strains were grown under non-inducing conditions; meaning that IPTG-induced expression from the Trc promoter regulated gene constructs was not performed. All plasmid-born genes of interest in the experiments described here were governed by the IPTG-inducible Trc promoter. The Trc promoter is well known in the art to be active in the absence of the IPTG inducer.

Under the non-inducing conditions tested, the results obtained from the isoprene headspace assays performed on the empty vector, HgS, and HgS-FldA strains indicate that an additional copy of fldA present on the pTrcHgSfldA/pBAD33 construct substantially increases isoprene production in the HgS-FldA strain over that produced by both the HgS and empty vector control strains. The HgS-FldA strain was observed to exhibit increased specific productivity of isoprene generation ranging from 1.5- to 1.9-fold and 1.3- to 1.8-fold higher than the control strain over a 3.75-hour and 2.5-hour time course, respectively, during two independent experiments. The observed effect on isoprene production appears to be specific to the presence of the fldA-containing construct, as the HgS strain produces comparable levels of isoprene under the non-inducing conditions to that produced by the empty vector control strain.

Example 9

Expression of Alternative ispG (gcpE or HDS) and ispH (lytB or HDR) and Their Corresponding Reducing Shuttle System, from *Thermosynechococcus elongatus* BP-1 in an Isoprene-Producing *E. coli* to Improve Isoprene Production In this example, we demonstrated that the ferredoxin/ferredoxin-NADP oxidoreductase/NADPH reducing system together with the GcpE and LytB enzymes from *T. elongates* improve isoprene production in *E. coli* BL21 (DE3).

*T. elongatus*, like *E. coli*, synthesizes isoprenoids via the DXP pathway, but does not harbor any genes coding for a flavodoxin protein. It was previously shown that the plant GcpE enzyme is a ferredoxin-dependent enzyme, and that flavodoxin could not support the enzymatic conversion of cMEPP (ME-CPP) into HDMAPP(HMBPP) by this enzyme (see Seemann et al., *FEBS Lett.,* 580(6):1547-52 (2006), which is hereby incorporated by reference in its entirety). It was also demonstrated in vitro that GcpE of *T. elongatus* together with PetF (ferredoxin), Pet H (ferredoxin-NADP$^+$ oxidoreductase), and NADPH could convert cMEPP into HDMAPP (Okada and Hase, *J Biol Chem,* 280(21):20627-9 (2005)), which is hereby incorporated by reference in its entirety). With the lack of other small electron carrier proteins besides ferredoxin in the genome, it is likely that LytB of *T. elongatus* also utilizes the same reducing shuttle system as GcpE.

Demonstration of increased isoprene production and elevated cMEPP levels in REM23-26 by overexpression of GcpE, PetF, and PetH from *T. elongatus* BP-1

We have previously demonstrated that increased expression of dxs increases flux through the DXP pathway in *E. coli*. Isoprene-producing strains (REM19-22) harboring increased and varied levels of dxs expression were constructed by integrating the GI 1.X-promoter series immediately upstream of the dxs locus within the *E. coli* BL21 (DE3) genome. Subsequently, the test set of strains, REM23-26 were created by transformation with plasmids expressing the *T. elongatus* GcpE and its corresponding reducing shuttle system encoded by petF and petH. The parental and test strains were evaluated for growth, isoprene production, and the presence of DXP pathway metabolites. The results are presented in FIGS. 47-49.

Construction of MCM16 MCM640, MCM639, MCM641, and the parental strains to REM19-22

The GI 1.X-promoter insertions and subsequent loopout of the antibiotic resistance markers described in this example were carried out using the Red/ET system from Gene Bridges GmbH according to the manufacturer's instructions. The strain BL21 (DE3) (Invitrogen) was used.

```
Primer Sequences
MCM319:
                                        (SEQ ID NO: 57)
5'-ctctctttcggcaacagtcgtaactcctgggtggagtcgaccagtgc

cagggtcgggtatttggcaatatcaaaactcatatattccaccagctatt

tgttagtgaataaaagtggttgaattatttgctcaggatgtggcatNgtc

aagggctaatacgactcactatagggctc.

degenerate N base: A base yields GI 1.6-, T base
yields GI 1.5-, G base yields GI1.2-, and C base
yields GI 1.0-promoter.

MCM320:
                                        (SEQ ID NO: 58)
5'-tcgatacctcggcactggaagcgctagcggactacatcatccagcgt

aataaataaacaataagtattaataggcccctgaattaaccctcactaaa

gggcgg.

MCM327:
                                        (SEQ ID NO: 59)
5'- TTGTAGACATAGTGCAGCGCCA.

GB-DW:
                                        (SEQ ID NO: 60)
5'-aaagaccgaccaagcgacgtctga.
```

Strategy for Creating the MCM638-641 Strains

Figure 50:
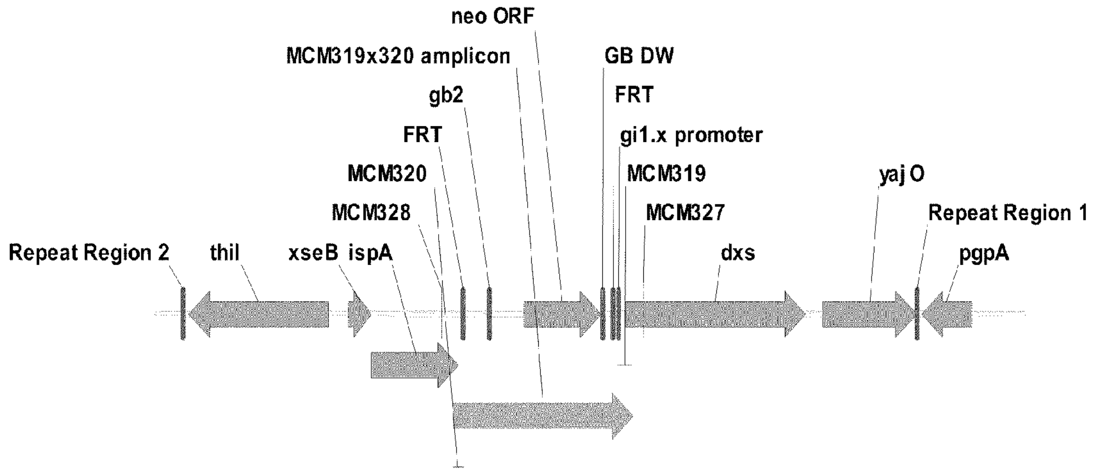
FIG. 50 depicts a cartoon representation of the strategy used to insert the GI 1.X-promoter series in front of dxs using the RED/ET system. REM29 (blue) and REMH86 (yellow) were assayed for growth rate (strains grew comparably) and isoprene production every 30 minutes across a 3 hour shake flask fermentation. At time 0 both cultures were induced with 400 uM IPTG. Over the course of the fermentation beginning at the first time point after induction, the test strain produced approximately 16% higher isoprene levels than the parental strain.

The strategy for inserting the GI1.X-promoter series in front of dxs is shown in FIG. 50. The antibiotic resistance cassette GB-NeoR was amplified by PCR using primer sets MCM319/MCM320. The primers contain 50 bases of homology to the region immediately 5' to the dxs coding region to allow recombination at the specific locus upon electroporation of the PCR product in the presence of the pRed-ET plasmid.

Amplification of the Deletion Cassettes

To amplify the GB-NeoR cassette for inserting the GI 1.X-promoters immediately upstream of the dxs locus the following PCR reactions were set up:

1 ul (100 ng GB-NeoR)
10 ul HerculaseII Buffer
0.5 ul dNTP's (100 mM)
1.25 ul primer (10 uM) MCM319
1.25 ul primer (10 uM) MCM320
35 ul diH2O
+1 ul of HerculaseII fusion from Stratagene Cycle Parameter 95° C.×2 minutes, [95° C.×20 seconds, 55° C.×20 seconds, 72° C.×50 seconds]×30 cycles; 72° C.×3 minutes, 4° C. until cool (BioRadPCR machine).

The resulting PCR fragments were separated on a 1.2% E-gel (Invitrogen) for verification of successful amplification, and purified using the QIAquick PCR Purification kits according to manufacturer's instructions. The resulting stock was GB-NeoR-GI 1.X-dxs fragment.

Integration of GB-NeoR—GI 1.X-dxs PCR product into BL21 (DE3)/pRed-ET Strain

The pRed-ET vector (Gene Bridges kit) was transformed into BL21 (DE3) by electroporation resulting in strain MCM327 (BL21 (DE3)/pRed-ET). Approximately 500 ng of the GB-NeoR-GI 1.x-dxs PCR fragment was electroporated into MCM327. The transformants were recovered in L Broth for 1 hour with shaking at 200 rpm at 37° C. and then plated on L agar containing kanamycin (10 ug/ml). Kanamycin resistant colonies were analyzed by PCR for the presence of the GB-NeoR cassette and the GI 1.X-promoters using primers GB-DW/MCM327. The PCR fragments from a number of transformants (MCM617-625) were sequenced using the MCM327 and GB-DW primers (Quintara; Berkeley, Calif.) and the various GI 1.X-dxs strains of interest identified. The correct strains were designated MCM617 (FRT-neo-FRT-GI1.0-dxs), MCM618 (FRT-neo-FRT-GI1.5-dxs), MCM623 (FRT-neo-FRT-GI1.2-dxs), and MCM625 (FRT-neo-FRT-GI1.6-dxs). The kanamycin resistance cassette was looped out of the strains using pCP20 from the RED/ET kit according to the manufacturer's instructions. Transformants were verified by loss of resistance to kanamycin (10 ug/ml) and PCR demonstrating loopout of the GB-NeoR cassette. The resulting strains were designated MCM638 (BL21 (DE3) GI1.0-dxs), MCM639 (BL21 (DE3) GI1.5-dxs), MCM640 (BL21 (DE3) GI 1.2-dxs) and MCM641 (BL21 (DE3) GI1.6-dxs).

Figure 51:
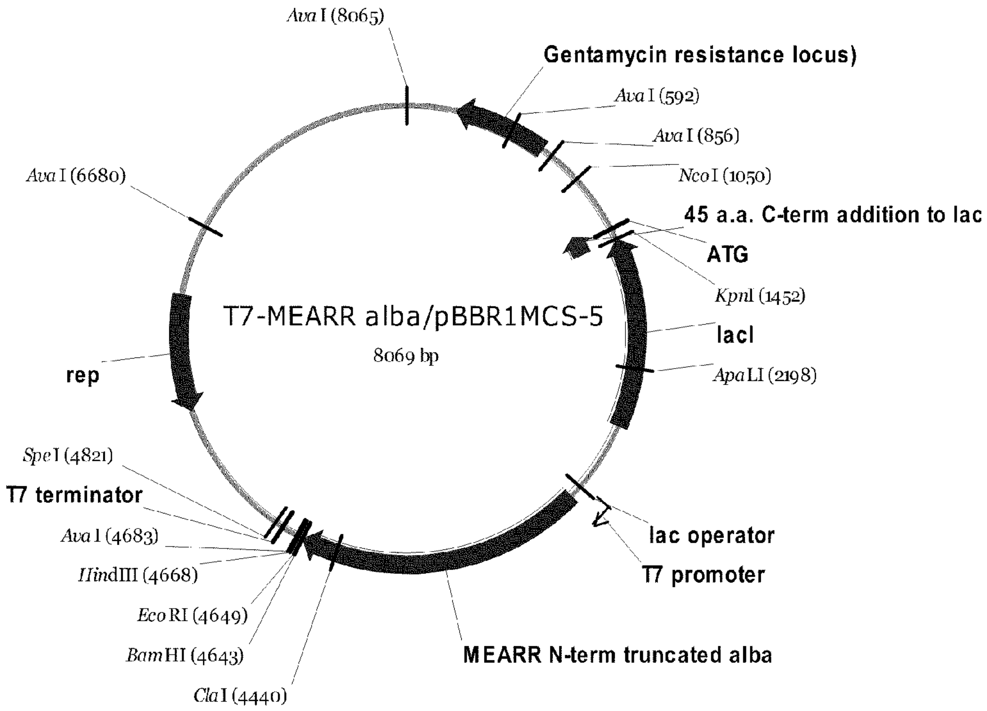
FIG. 51 is a map of T7-MEARR alba/pBBR1MCS-5.

Construction of the Parental Strains REM19-22 from MCM638, MCM640, MCM639, and MCM641, Respectively The construction of the T7-MEARR alba/pBBR1MCS-5 described in this example was carried out using standard molecular biology techniques (Sambrook et al., 1989, which is hereby incorporated by reference in its entirety). The pBBR1MCS-5 plasmid has been previously described (Kovach et al., *Biotechniques,* 16(5):800-2 (1994), which is hereby incorporated by reference in its entirety, particularly with respect to cloning of the pBBR1MCS). A picture illustrating the resulting plasmid construct is shown in FIG. 51. The MCM638-641 strains were used for the transformations described here.

```
Primer Sequences
5' KpnI to IacI MEARR T7 frag:
                                        (SEQ ID NO: 61)
5'-GCTGGGTACCCTGCCCGCTTTCCAGTCGGGAAACCT

3' SpeI to T7 terminator MEARR T7 frag:
                                        (SEQ ID NO: 62)
5'-TAGAACTAGTCAAAAAACCCCTCAAGACCCGTTTAG
```

-continued

```
M13 Forward (-20):
                                        (SEQ ID NO: 63)
5'-GTAAAACGACGGCCAGT

EL-1000:
                                        (SEQ ID NO: 64)
5'-GCACTGTCTTTCCGTCTGCTGC

A-rev:
                                        (SEQ ID NO: 65)
5'-CTCGTACAGGCTCAGGATAG

A-rev2:
                                        (SEQ ID NO: 66)
5'-TTACGTCCCAACGCTCAACT
```

Strategy for Creating the REM19-22 Strains

Electroporation of T7-MEARR alba/pBBR1MCS-5 into strains MCM638-641. The vector construct harboring the T7 polymerase governed MEARR alba allele, MD09-173 (BL21 (DE3)pLysS, pET24a-P.alba (MEA) Untagged (pDu39)), was used as the PCR template.

Amplification of the T7-MEARR Alba Fragment

To amplify the T7-MEARR alba fragment for cloning into the pBBR1MCS-5 plasmid the following PCR reaction was performed:

1 ul (approx. 120 ng MDO9-173)
10 ul HerculaseII Buffer
0.5 ul dNTP's (100 mM)
1.25 ul primer (10 uM) 5' KpnI to lacI MEARR T7 frag
1.25 ul primer (10 uM) 3' SpeI to T7 terminator MEARR T7 frag
35 ul diH2O
+1 ul of HerculaseII fusion from Stratagene.

Cycle Parameter:
95° C.×2 minutes, [95° C.×30 seconds, 63° C.×30 seconds, 72° C.×3 minutes]×29 cycles;
72° C.×5 minutes,
4° C. until cool (Biometra T3000 Combi Thermocycler).

The resulting PCR fragment was separated on a 1.2% E-gel (Invitrogen) for verification of successful amplification, and purified using the QIAquick PCR Purification kits (Qiagen) according to manufacturer's instructions. The resulting stock was T7-MEARR alba fragment.

Cloning of the T7-MEARR Alba Fragment into pBBR1MCS-5

Approximately 600 ng of the T7-MEARR alba fragment and 200 ng of the pBBR1MCS-5 plasmid were digested with KpnI and SpeI (Roche) according to the manufacturer's specifications. The digests were subsequently combined and cleaned using the Qiagen QiaQuick Gel Extraction Kit. Approximately a fourth to a third of the cleaned cut DNA was ligated using T4 DNA Ligase (New England Biolabs) according to the manufacturer's suggested protocol. Chemically competent TOP10 cells (Invitrogen) was transformed with the ligation reaction using a standard heat-shock protocol (See, e.g., Sambrook et al., 1989, which is hereby incorporated by reference in its entirety), recovered in L broth for 1 hour at 37° C. and then plated on L agar containing gentamycin (10 ug/ml) and 5-bromo-4-chloro-3-indolyl-beta-D-galactopyranoside (X-GAL at 40 ug/ml; Sigma). White, gentamycin resistant colonies were selected, grown overnight in L broth containing gentamycin (10 ug/ml), and harvested for plasmid preparation the following day. Plasmid constructs were isolated using Qiagen Qiaprep Spin Miniprep Kit and first analyzed by restriction enzyme digestion and electrophoresis (as described above) for the putative presence of the T7-MEARR alba fragment. Plasmid preparations of interest were sequenced (Sequetech; Mountain View, Calif.) using primers M13 Forward (−20), EL-1000, A-rev, and A-rev2, and the correct T7-MEARR alba/pBBR1MCS-5 clone identified.

Transformation of T7-MEARR alba/pBBR1MCS-5 into MCM638-641

To build the isoprene-producing strains REM19-22 the T7-MEARR alba/pBBR1MCS-5 plasmid was transformed by electroporation into MCM638-641. Transformants were recovered in L broth and plated on L agar containing gentamycin (10 ug/ml). The resulting strains were designated as such: REM19 (MCM638/T7-MEARR alba/pBBR1MCS-5), REM20 (MCM640/T7-MEARR alba/pBBR1MCS-5), REM21 (MCM639/T7-MEARR alba/pBBR1MCS-5), and REM22 (MCM641/T7-MEARR alba/pBBR1MCS-5).

Construction of the Test Strains REM23-26

Figure 52:
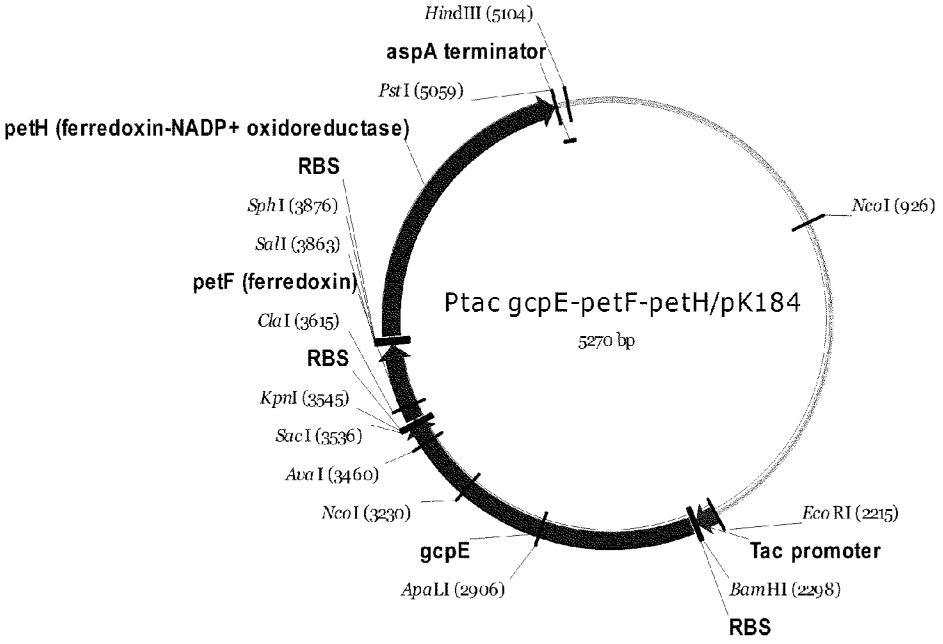
FIG. 52 is a map of the Ptac-gcpE-petF-petH/pK184 construct that was used to generate strains REM23-26.

REM23-26 were constructed by transformation of the Ptac-gcpE-petF-petH/pK184 construct into MCM638, MCM640, MCM639, and MCM641. The plasmid Ptac-gcpE-petF-petH/pK184 described in this example was synthesized by Gene Oracle, Inc. (Mountain View, Calif.) with codon optimization of gcpE, petF, and petH for expression in *E. coli*. The Ptac promoter and aspA terminator sequences have been previously described (Genbank accession # E02927 and CP001164, respectively). The pK184 cloning vector has been described, for example, by Jobling and Holmes, *Nucleic Acids Res.* 18(17):5315-6 (1990), which is hereby incorporated by reference in its entirety, particularly with respect to the pK184 cloning vector. A picture illustrating the resulting plasmid construct is shown in FIG. 52. The REM19-22 strains were used for the transformations described herein.

Strategy for Creating the REM23-26 Strains

Electroporation of Ptac-gcpE-petF-petH/pK184 into strains REM19-22. A plasmid preparation of Ptac-gcpE-petF-petH/pK184 was provided by Gene Oracle, Inc.

Transformation of Ptac-gcpE-petF-petH/pK184 into REM19-22

To build the isoprene-producing test strains, REM23-26, the Ptac-gcpE-petF-petH/pK184 plasmid was transformed by electroporation into REM19-22. Transformants were recovered in L broth and plated on L agar containing kanamycin (10 ug/ml) and gentamycin (10 ug/ml). The resulting strains were designated as such: REM23 (REM19/Ptac-gcpE-petF-petH/pK184), REM24 (REM20/Ptac-gcpE-petF-petH/pK184), REM25 (REM21/Ptac-gcpE-petF-petH/pK184), and REM26 (REM22/Ptac-gcpE-petF-petH/pK184).

Figure 47:
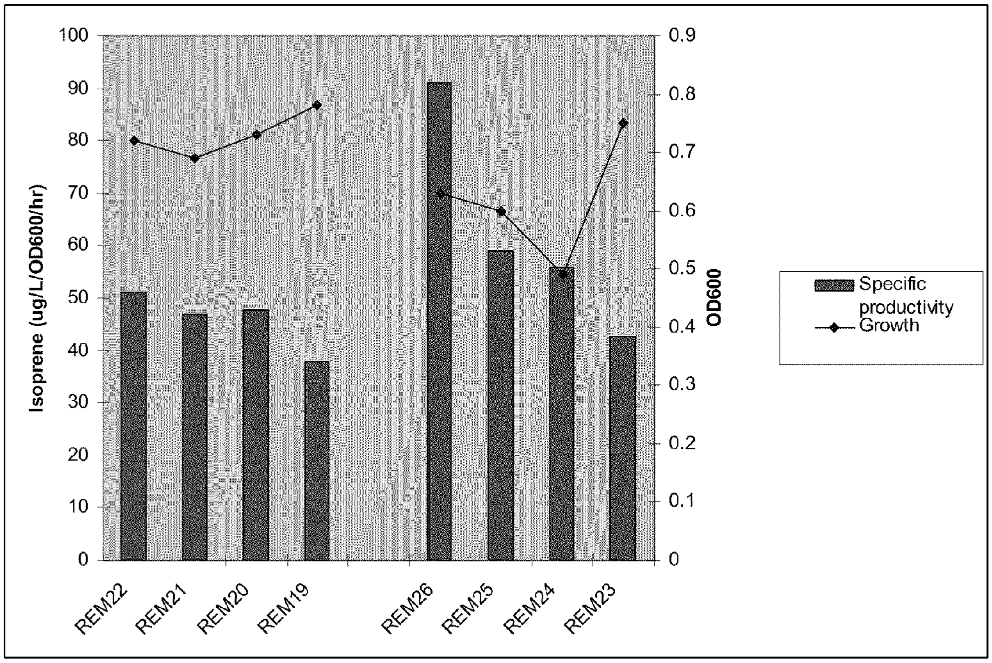
FIG. 47 shows the growth and isoprene production of strains REM19-22 compared to REM23-26. The expression of isoprene synthase in both sets of strains and the expression of the *T. elongatus* genes in the test set of strains was induced with 200 uM IPTG at time 0 when the cultures were at an $OD_{\lambda 600nm}$ of approximately 0.2-0.25. The data shown in the figure is that obtained 4 hours after the addition of IPTG to the cultures. Cells were grown shaking in the TM3 at 30° C. Comparison of the parental to test set strains indicates that isoprene production increases 10%, 20%, 30%, and 80% over the parental strains for the GI1.0-dxs, GI1.2-dxs, GI1.5-dxs, and GI-1.6-dxs test strains, respectively.
Figure 48:
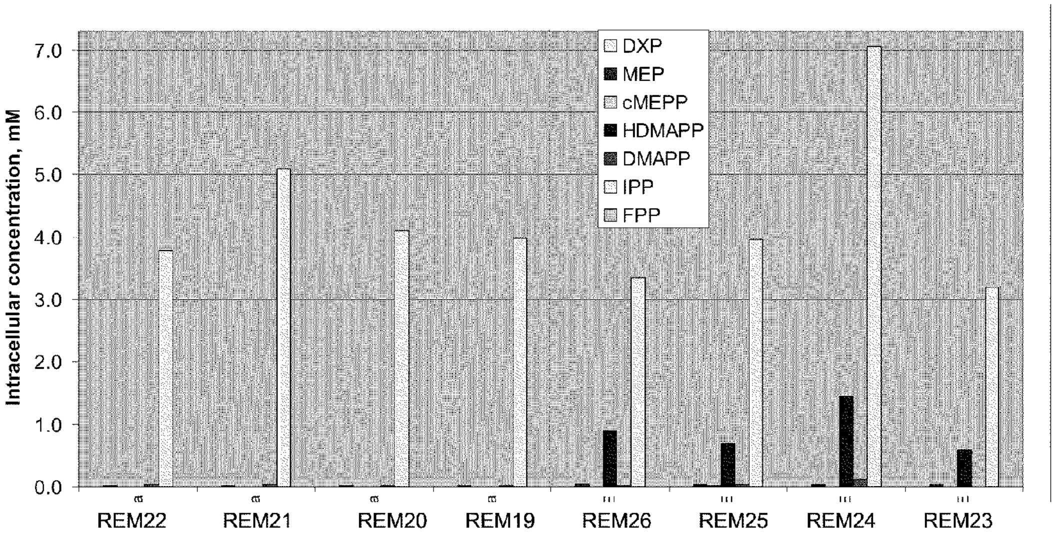
FIG. 48 shows the increased levels of the GcpE product, HDMAPP, accumulate in strains REM23-2. The concentrations of DXP metabolites and larger isoprenoid molecules were determined for REM19-26 (strain indicated on the x-axis) at a 5 hour IPTG-induction period. The DXP metabolites and isoprenoids measured are indicated in the figure legend; DXP, 1-deoxy-D-xylulose 5-phosphate; MEP, 2-C-methyl-D-erythritol 4-phosphate; cMEPP, 2-C-methyl-D-erythritol-2,4-cyclodiphosphate; HDMAPP, (E)-4-hydroxy-3-methylbut-2-enyl diphosphate; DMAPP, dimethylallyl diphosphate; IPP, isopentenyl diphosphate; FPP, farnesyl pyrophosphate.

Analysis of REM19-26 for Growth, Isoprene Production, and DXP Metabolite Generation The parental strains REM19-22 were compared against the test strains REM23-26 in a shake flask isoprene headspace assay as well as in a DXP metabolite determination study. The benefits of expressing the *T. elongatus* GcpE enzyme on DXP metabolite generation and isoprene production from the *E. coli* host is illustrated in FIGS. 47 and 48.

Growth

Strains REM19-26 were grown at 30° C. in TM3 liquid media (13.6 g $K_2PO_4$, 13.6 g $KH_2PO_4$, 2.0 g $MgSO_4*7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) supplemented to a final concentration with 0.1% yeast extract and 1.0% glucose and including kanamycin (10 ug/ml) and gentamycin (10 ug/ml). Growth was monitored periodically by recording each of the culture's optical density measured at 600 nm using an Eppendorf Biophotometer spectrometer (Eppendorf).

Isoprene Production

Isoprene production was analyzed using a headspace assay. For the shake flask cultures, one ml of a culture was transferred from shake flasks to 20 ml CTC headspace vials (Agilent vial cat#5188 2753; cap cat#5188 2759). The cap was screwed on tightly and the vials incubated at the equivalent temperature with shaking at 250 rpm. After 30 minutes the vials were removed from the incubator and analyzed. The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 μm film thickness) was used for separation of analytes. The sampler was set up to inject 500 μL of headspace gas. The GC/MS method utilized helium as the carrier gas at a flow of 1 ml/minutes The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 μg/L to 200 μg/L. The limit of detection was estimated to be 50 to 100 ng/L using this method. The specific productivity of each strain is reported as ug/L OD Hr. Note, ratio of 1900 ul headspace: 100 ul broth in assay vials for 30 min. incubation results in the following conversion of isoprene ug/L of culture to specific productivity: (isoprene/L determined by GC-MS) X (38)/(OD 600 nm of the culture).

DXP Metabolite Accumulation

The DXP metabolites of the isoprene-producing parental and test strains, REM19-22 and REM23-26, respectively, described above and depicted in FIG. 48 were isolated and quantified as follows:

Metabolite Quantification

Cell metabolism was rapidly inactivated by withdrawing 3.5 mL of the culture into a tube filled with 3.5 mL of dry ice-cold methanol. Cell debris was pelleted by centrifugation and the supernatant was loaded onto Strata-X-AW anion exchange column (Phenomenex) containing 30 mg of sorbent. The pellet was re-extracted twice, first with 3 mL of 50% MetOH containing 1 mM $NH_4HCO_3$ buffer (pH=7.0) and then with 3 mL of 75% MetOH/1 mM $NH_4HCO_3$ buffer (pH=7.0). After each extraction, cell debris was pelleted by centrifugation and the supernatants were consecutively loaded onto the same anion exchange column. During the extraction and centrifugation steps the samples were kept at below +4° C. Prior to metabolite elution, the anion exchange columns were washed with water and methanol (1 mL of each) and the analytes were eluted by adding 0.35 mL of concentrated $NH_4OH$/methanol (1:14, v/v) and then 0.35 mL of concentrated $NH_4OH$/water/methanol (1:2:12, v/v/v) mixtures. The eluant was neutralized with 30 μL of glacial acetic acid and cleared by centrifugation in a microcentrifuge.

Metabolite Quantification

Metabolites were analyzed using a Thermo Scientific TSQ Quantum Access mass spectrometer (Thermo Electron Corporation, San Jose, Calif.). All system control, data acquisition, and mass spectral data evaluation were performed using XCalibur and LCQuan software (Thermo Electron Corp). For the LC-ESI-MS/MS method, a chiral Nucleodex β-OH 5 μM HPLC column (100×2 mm, Macherey-Nagel, Germany) equipped with a CC 8/4 Nucleodex beta-OH guard cartridge was eluted with a mobile phase gradient shown in Table 1 (flow rate of 0.4 mL/min). The sample injection volume was 10 μL.

TABLE 1

HPLC gradient used to elute metabolites.

| Time, min | Mobile phase, % A (water) | B (100 mM ammonium bicarbonate, pH = 8.0) | C (acetonitrile) |
|---|---|---|---|
| 0.0 | 0.0 | 20.0 | 80.0 |
| 0.5 | 15.0 | 5.0 | 80.0 |
| 4.5 | 37.5 | 12.5 | 50.0 |
| 6.5 | 37.5 | 12.5 | 50.0 |
| 7.0 | 49.5 | 0.5 | 50.0 |
| 12.0 | 34.9 | 0.1 | 65.0 |
| 12.5 | 0.0 | 20.0 | 80.0 |
| 13.0 | 0.0 | 20.0 | 80.0 |

Mass detection was carried out using electrospray ionization in the negative mode. The following m/z values for precursor ions were selected to detect the metabolites of interest in SRM mode: 245.0 for IPP and DMAPP, 381.1 for FPP, 213.0 for DXP, 215.0 for MEP, 260.0 for HDMAPP, and 277.0 for cMEPP. Concentrations of metabolites were determined based on the integrated intensities of peaks generated by $PO_3^-$ product ion (m/z=79.0). Calibration curves obtained by injection of corresponding standards purchased from Echelon Biosciences Inc. Intracellular concentrations of metabolites were calculated based on the assumption that in 1 mL of the culture at OD=200 the integrated volume of all cells is 50 μL.

Demonstration of Increased Isoprene Production in REM31 and REM29 by Overexpression of GcpE, LytB PetF and PetH of *T. elongatus* BP-1

Figure 49:
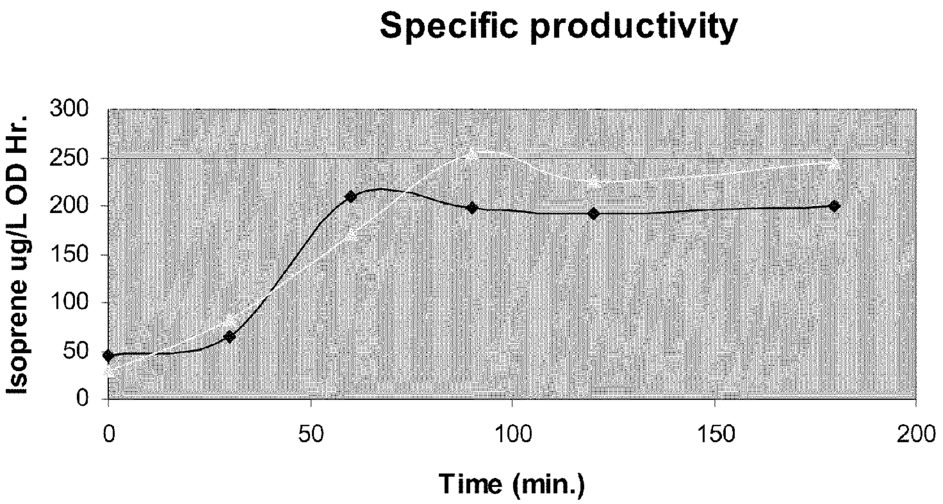
FIG. 49 shows specific productivity of isoprene production in strain REM29 compared to REMH86.

We have demonstrated that increased expression of dxs permits increased flux through the DXP pathway within *E. coli*, while the additional overexpression of an idi gene increases the production of downstream isoprenoids significantly. To demonstrate the benefits of expressing the non-flavodoxin-dependent GcpE and LytB enzymes on carbon flux through the endogenous *E. coli* DXP pathway to isoprene synthesis, *E. coli* BL21 (DE3) isoprene-producing strains with constitutive expression of dxs and the yeast IDI enzyme were constructed. The BL21 (DE3) GI1.6-dxs strain MCM641 is described above. The construction of the vector construct harboring the yeast IDI enzyme, pDU9-pET-16b rev-yIDI, is described herein. The T7-(−3) alba/pBBR1MCS-5 and T7-MTE alba/pBBR1MCS-5 *P. alba* isoprene synthase-containing constructs are described below. A set of parental isoprene-producing, IDI-overexpressing strains derived from MCM641 were created (REM H76 and REMH86) to compare to the newly generated test set of strains (REM31 and REM29) which harbor the *T. elongatus* GcpE, LytB, and their corresponding reducing shuttle system (described below). The parental and test strains were evaluated for growth, isoprene production, and the presence of DXP pathway metabolites. The results are depicted in FIG. 49.

Construction of pDU-9

The IPP isomerase from *Saccharomyces cerevisiae* (yIDI) was cloned into the vector pET16b (Invitrogen). The primer set Hg-yIDI-R2/Hg-yIDI-F2 was used for PCR with the template DNA pTrcKudzu yIDI Kan. The PCR cycle conditions:

PCR Reaction 1 ul of template (pMVK1-Fernando's template)

5 ul of 10× PfuII Ultra buffer 1 ul of dNTP 1 ul of primer (50 uM) Hg-MVK-F2-NdeI 1 ul of primer (50 uM) Hg-yIDI-R2

40 ul of DiH2O

+1 ul of Pfu UltraII Fusion DNA Polymerase from Stratagene

Cycle Parameter:

(95° C. 2 min., 95° C. 20 sec., 55° C. 20 sec., 72° C. 21 sec., 29X, 72 C 3 min., 4° C. until cool, use Eppendorf Mastercycler Gradient Machine)

The PCR product was purified using the QiaQuick PCR purification kit according to the manufacturer's suggestion. An aliquot of 5 uL purified of the PCR product was ligated to Invitrogen pET-16b Vector that was previously digested with NdeI-SAP (Shrimp Alkaline Phosphatase) treated using T4 ligase enzyme (NEB). The ligation was carried out overnight at 16° C.

5 uL of overnight ligation mixture was introduced into Invitrogen TOP10 cells and transformants were selected on L agar containing Carbenicillin (50 ug/ml) incubated at 37° C. Plasmids from transformants were isolated using QiaQuick spin miniprep kit. The insert is sequenced with T7 promoter and T7 terminator (Use Quintara Bio Sequencing Service). The resulting plasmid r is called pDu-9.

Once the sequence is verified, 1 ul of plasmid pDu-9 was transformed into BL21 (DE3) pLysS hst strain according to manufacturer's protocol. Transformants are selected on L agar containing Carbenicillin (50 ug/ml) plate and incubated at 37° C.

```
Primer sequences
Hg-yIDI-R2
                                        (SEQ ID NO: 111)
5' . . . cagcagcagGGATCCgacgcgttgttatagca

Hg-yIDI-F2
                                        (SEQ ID NO: 112)
5' . . . cagcagcagCATATGactgccgacaacaatag
```

Construction of REMD76 (MCM641/pDU9-pET-16b rev-yIDI), REMH76 and REMH86 (REMD76/T7-(−3) alba/pBBR1MCS-5 and REMD76/T7-MTE alba/pBBR1MCS-5, Respectively)

Strategy for Creating the REMD76 pDU9-pET-16b rev-yIDI was electroporated into MCM641.

Transformation of pDU9-pET-16b rev-yIDI into MCM641

To build the BL21 (DE3) GI1.6-dxs yIDI-overexpressing strain REMD76, the pDU9-pET-16b rev-yIDI plasmid expressing a yeast IDI (yIDI) allele was transformed by electroporation into MCM641. Transformants were recovered in L broth and plated on L agar containing carbinicillin (50 ug/ml). A carbinicillin resistant colony was selected and designated REMD76.

Figure 53A:
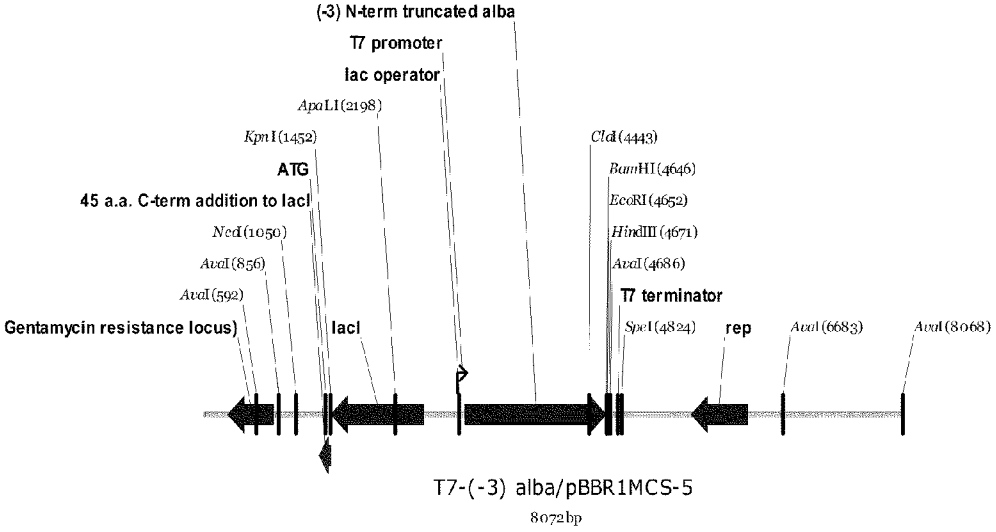
FIGS. 53A-53B shows a cartoon representation of the T7-(−3) alba/pBBR1MCS-5 (top) and T7-MTE alba/pBBR1MCS-5 (bottom) constructs that were used to generate strains REMH76 and REMH86.
Figure 53B:
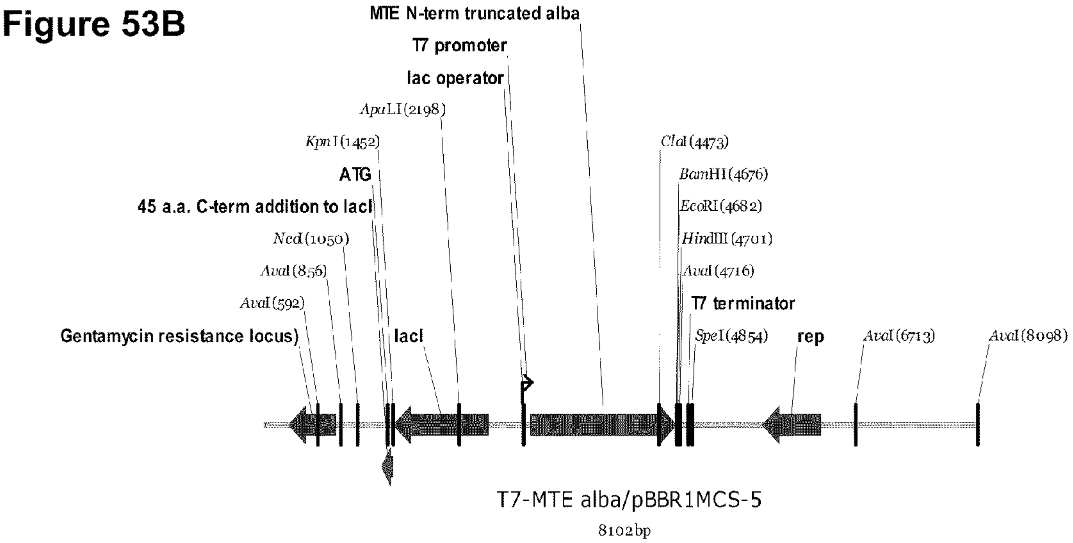

Generation of the Parental Strains REMH76 and REMH86 (REMD76/T7-(−3) alba/pBBR1MCS-5 and REMD76/T7-MTE alba/pBBR1MCS-5, Respectively The construction of the T7-(−3) alba/pBBR1MCS-5 and T7-MTE alba/pBBR1MCS-5 constructs described in this example were carried out using standard molecular biology techniques (ee, e.g., Sambrook et al., 1989). The pBBR1MCS-5 plasmid has been previously described (see, Kovach et al., Biotechniques, 16(5):800-2 (1994), which is hereby incorporated by reference in its entirety, particularly with respect to the pBBR1MCS-5 plasmid). The pictures illustrating the resulting plasmid constructs are shown in FIG. 53. The REMD76 strain was used for the transformations described herein.

Strategy for Creating the REMH76 and REMH86 Strains

Electroporation of T7-(−3) alba/pBBR1MCS-5 and T7-MTE alba/pBBR1MCS-5 into strain REMD76. The vector constructs harboring the T7 polymerase governed (−3) and MTE alba alleles, pDU47-3-pET24a-P.alba (−3) and pDU42 pET24a-P.alba-MTE untagged, were used as the PCR templates.

Electroporation of T7-(−3) alba/pBBR1MCS-5 and T7-MTE alba/pBBR1MCS-5 into strain REMD76. The vector constructs harboring the T7 polymerase governed (−3) and MTE alba alleles, pDU47-3-pET24a-P.alba (−3) and pDU42 pET24a-P.alba-MTE untagged, were used as the PCR templates.

```
Primer Sequences
5' KpnI to IacI MEARR T7 frag:
                                  (SEQ ID NO: 61)
5'-GCTGGGTACCCTGCCCGCTTTCCAGTCGGGAAACCT

3' SpeI to T7 terminator MEARR T7 frag:
                                  (SEQ ID NO: 62)
5'-TAGAACTAGTCAAAAAACCCCTCAAGACCCGTTTAG

M13 Forward (-20):
                                  (SEQ ID NO: 63)
5'-GTAAAACGACGGCCAGT

EL-1000:
                                  (SEQ ID NO: 64)
5'-GCACTGTCTTTCCGTCTGCTGC

A-rev:
                                  (SEQ ID NO: 65)
5'-CTCGTACAGGCTCAGGATAG

A-rev2:
                                  (SEQ ID NO: 66)
5'-TTACGTCCCAACGCTCAACT
```

Amplification of the T7-(−3) and T7-MTE Alba Fragments

To amplify the T7-(−3) and T7-MTE alba fragments for cloning into the pBBR1MCS-5 plasmid the following PCR reactions were performed: 1 ul (approx. 100 ng pDU47-3-pET24a-P.alba (−3) or pDU42 pET24a-P.alba-MTE untagged)

10ul HerculaseII Buffer 0.5ul dNTP's (100 mM)

1.25 ul primer (10 uM) 5' KpnI to lacI MEARR T7 frag 1.25 ul primer (10 uM) 3' SpeI to T7 terminator MEARR T7 frag 35 ul diH2O +1 ul of HerculaseII fusion from Stratagene Cycle Parameter:

95° C.×2 minutes, [95° C.×30 seconds, 63° C.×30 seconds, 72° C.×3 minutes.]×29 cycles; 72° C.×5 minutes, 4° C. until cool (Biometra T3000 Combi Thermocycler)

The resulting PCR fragments were separated on a 1.2% E-gel (Invitrogen) for verification of successful amplification, and purified using the QIAquick PCR Purification kits according to manufacturer's instructions. The resulting stocks were T7-(−3) alba fragment and T7-MTE alba fragment.

Cloning of the T7-(−3) alba and T7-MTE alba Fragments into pBBR1MCS-5

Approximately 600 ng of the T7-(−3) alba fragment or T7-MTE alba fragment and 200 ng of the pBBR1MCS-5 plasmid were digested with KpnI and SpeI from Roche according to the manufacturer's specifications. The digests were subsequently combined and cleaned using the Qiagen QiaQuick Gel Extraction Kit. Approximately a fourth to a third of the cleaned cut DNA was ligated using T4 DNA Ligase from New England Biolabs according to the manufacturer's suggested protocol.

Chemically competent TOP10 cells (Invitrogen) were transformed with the ligation reaction using a standard heat-shock protocol (Sambrook et al., 1989, which is hereby incorporated by reference in its entirety), recovered in L broth for 1 hour at 37° C. and then plated on L agar containing gentamycin (10 ug/ml) and 5-bromo-4-chloro-3-indolyl-beta-D-galactopyranoside (X-GAL at 40 ug/ml; Sigma). White gentamycin resistant colonies were selected, grown overnight in L broth containing gentamycin (10 ug/ml), and harvested for plasmid preparation the following day. Plasmid constructs were isolated using Qiagen Qiaprep Spin Miniprep Kit and first analyzed by restriction digest and electrophoresis (as described above) for the putative presence of the T7-(−3) alba fragment or T7-MTE alba fragment. Plasmid preparations of interest identified were sequenced (Sequetech; Mountain View, Calif.) using primers M13 Forward (−20), EL-1000, A-rev, and A-rev2, and the correct T7-(−3) alba/pBBR1MCS-5 and T7-MTE alba/pBBR1MCS-5 clones identified.

Construction of the Test Strains REM31 and REM29

Figure 54:
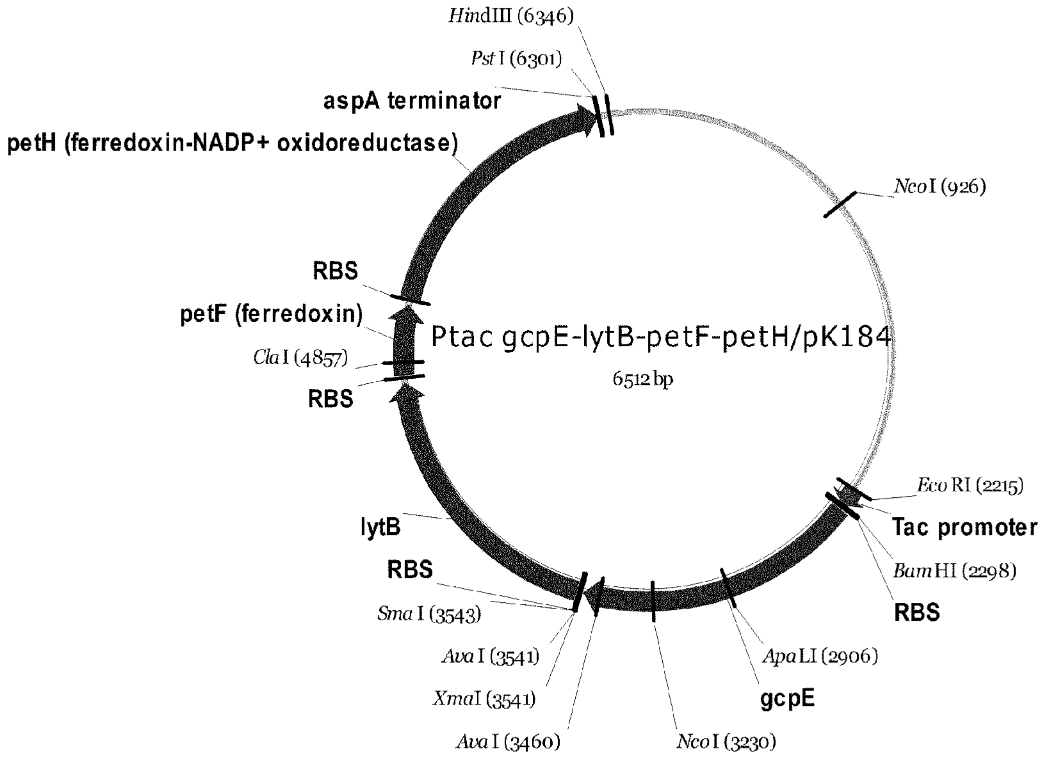
FIG. 54 is a map of the Ptac-gcpE-1ytB-petF-petH/pK184 construct that was used to generate strains REM31 and REM29.

To create strains REM31 and 29 the plasmid Ptac-gcpE-lytB-petF-petH/pK184 was transformed into REMH76 and REMH86. The synthesis and codon optimization for *E. coli* of the Ptac-gcpE-lytB-petF-petH/pK184 described in this example was performed by Gene Oracle, Inc. (Mopuntain View, Calif.). The Ptac promoter and aspA terminator sequences have been previously described (Genbank accession # E02927 and CP001164, respectively) and were also constructed synthetically. The pK184 cloning vector has been described previously (see, Jobling and Holmes, Nucleic Acids Res. 18(17):5315-6 (1990), which is hereby incorporated by reference in its entirety, particularly with respect to the pK184 cloning vector). A picture illustrating the resulting plasmid construct is shown in FIG. 54. The REMH76 and REMH86 strains were used for the transformations described herein.

Strategy for Creating the REM31 and REM29 Strains

Electroporation of Ptac-gcpE-lytB-petF-petH/pK184 into strains REMH76 and REMH86 strains: A plasmid preparation of Ptac-gcpE-lytB-petF-petH/pK184 was provided by Gene Oracle, Inc.

Transformation of Ptac-gcpE-lytB-petF-petH/pK184 into REMH76 and REMH86

To build the isoprene-producing test strains (REM31 and REM29) which harbor the *T. elognatus* GcpE and LytB enzymes to assess against the parental strains (REMH76 and REMH86) for benefits in DXP pathway flux and isoprene production, the Ptac-gcpE-lytB-petF-petH/pK184 plasmid was transformed by electroporation into REMH76 and REMH86. Transformants were recovered in L broth and plated on L agar containing carbinicillin (50 ug/ml), kanamycin (10 ug/ml), and gentamycin (10 ug/ml). The resulting strains are designated as such: REM31 (REMH76/Ptac-gcpE-lytB-petF-petH/pK184) and REM29 (REMH86/Ptac-gcpE-lytB-petF-petH/pK184).

Comparing REMH76 and REMH86 to REM31 and REM29 for Growth and Isoprene Production The parental strains REMH76 and REMH86 were compared against the test strains REM31 and REM29, respectively, in a shake flask isoprene headspace assay as well as in a DXP metabolite determination study. The benefit of expressing the *T. elongatus* GcpE and LytB enzymes on isoprene production from the *E. coli* host is illustrated in FIG. 48.

Growth

Parental strains REMH76 and REMH86 and test strains REM31 and REM29 were grown at 30° C. in TM3 liquid media (13.6 g $K_2PO_4$, 13.6 g $KH_2PO_4$, 2.0 g $MgSO_4$*$7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) supplemented to a final concentration with 0.1% yeast extract and 1.0% glucose and including carbinicillin, (50 ug/ml) kanamycin (10 ug/ml) and gentamycin (10 ug/ml). Growth was monitored periodically by recording each of the culture's optical density measured at 600 nm using an Eppendorf Biophotometer spectrometer (Eppendorf).

Isoprene Production

Isoprene production was analyzed using a headspace assay. For the shake flask cultures, one ml of a culture was transferred from shake flasks to 20 ml CTC headspace vials (Agilent vial cat#5188 2753; cap cat#5188 2759). The cap was screwed on tightly and the vials incubated at the equivalent temperature with shaking at 250 rpm. After 30 minutes the vials were removed from the incubator and analyzed. The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 μm film thickness) was used for separation of analytes. The sampler was set up to inject 500 μL of headspace gas. The GC/MS method utilized helium as the carrier gas at a flow of 1 ml/minutes The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 μg/L to 200 μg/L. The limit of detection was estimated to be 50 to 100 ng/L using this method.

The specific productivity of each strain was reported as ug/L OD Hr. Ratio of 1900 ul headspace: 100 ul broth in assay vials for 30 min. incubation resulted in the following conversion of isopreneug/L of culture to specific productivity: (isoprene/L determined by GC-MS)×(38)/(OD 600 nm of the culture).

DXP Metabolite Accumulation

The DXP metabolites of the isoprene-producing parental (REMH76 and REMH86) and test strains (REM31 and REM29) described above were isolated and quantified as described below. The resulting data is discussed in the legend to FIG. 48.

Metabolite Extraction

Cell metabolism was rapidly inactivated by withdrawing 3.5 mL of the culture into a tube filled with 3.5 mL of dry ice-cold methanol. Cell debris was pelleted by centrifugation and the supernatant was loaded onto Strata-X-AW anion exchange column (Phenomenex) containing 30 mg of sorbent. The pellet was re-extracted twice, first with 3 mL of 50% MetOH containing 1 mM $NH_4HCO_3$ buffer (pH=7.0) and then with 3 mL of 75% MetOH/1 mM $NH_4HCO_3$ buffer (pH=7.0). After each extraction, cell debris was pelleted by centrifugation and the supernatants were consecutively loaded onto the same anion exchange column. During the extraction and centrifugation steps the samples were kept at below +4° C. Prior to metabolite elution, the anion exchange columns were washed with water and methanol (1 mL of each) and the analytes were eluted by adding 0.35 mL of concentrated $NH_4OH$/methanol (1:14, v/v) and then 0.35 mL of concentrated $NH_4OH$/water/methanol (1:2:12, v/v/v) mixtures. The eluant was neutralized with 30 μL of glacial acetic acid and cleared by centrifugation in a microcentrifuge.

Metabolite Quantification

Metabolites were analyzed using a Thermo Scientific TSQ Quantum Access mass spectrometer (Thermo Electron Corporation, San Jose, Calif.). All system control, data acquisition, and mass spectral data evaluation were performed using XCalibur and LCQuan software (Thermo Electron Corp). For the LC-ESI-MS/MS method, a chiral Nucleodex β-OH 5 μM HPLC column (100×2 mm, Macherey-Nagel, Germany) equipped with a CC 8/4 Nucleodex beta-OH guard cartridge was eluted with a mobile phase gradient shown in Table 1 (flow rate of 0.4 mL/min). The sample injection volume was 10 μL.

Mass detection was carried out using electrospray ionization in the negative mode. The following m/z values for precursor ions were selected to detect the metabolites of interest in SRM mode: 245.0 for IPP and DMAPP, 381.1 for FPP, 213.0 for DXP, 215.0 for MEP, 260.0 for HDMAPP, and 277.0 for cMEPP. Concentrations of metabolites were determined based on the integrated intensities of peaks generated by $PO_3^-$ product ion (m/z=79.0). Calibration curves obtained by injection of corresponding standards purchased from Echelon Biosciences Inc. Intracellular concentrations of metabolites were calculated based on the assumption that in 1 mL of the culture at OD=200 the integrated volume of all cells is 50 μL.

Example 10

Deletion of iscR in *E. coli* BL21 (DE3) Genotype to Improve Isoprene Production Previous studies suggest that repair of damaged Fe—S centers and the turnover or regeneration of active 4Fe-4S centers within GcpE is partially contributable to the perceived bottleneck in DXP-mediated isoprenoid biosynthesis at the catalytic step carried out by GcpE. Increased levels of the related enzyme LytB have been obtained from *E. coli* engineered to overexpress the isc operon (Gräwert et al., *J Am Chem. Soc.* 126(40):12847-55 (2004), which is hereby incorporated by reference in its entirety). The enzymes encoded by the *E. coli* isc operon have been shown to play a role in Fe—S cluster biogenesis and maintenance (Tokumoto and Takahashi, *J. Biochem.,* 130: 63-71 (2001); Djaman et al., *J. of Biol. Chem.,* 279(43):44590-44599 (2004), which are each hereby incorporated by reference in their entireties). An alternative approach to overexpressing the isc operon in *E. coli* to generate increased levels of active 4Fe-4S cluster containing enzymes such as GcpE and LytB is to remove the IscR transcriptional repressor that inhibits expression of the isc operon (Schwartz et al., *PNAS,* 98(26):14751-3 (2001), which is hereby incorporated by reference in its entirety). Such an approach was recently proved successful for a group expressing Clostridial hydrogenase in *E. coli* BL21 (DE3) (Akhtar and Jones, *Appl. Microbiol. Biotechnol.* 78(5):853-62 (2008), which is hereby incorporated by reference in its entirety).

In this example, we demonstrated that the removal of iscR from the *E. coli* BL21 (DE3) genome significantly improves isoprene production over that produced from the corresponding wild-type strain.

Deletion of iscR from BL21 (DE3)/pRed/ET

The gene deletions and subsequent loopout of the antibiotic resistance markers described in this example were carried out using the Red/ET system from Gene Bridges GmbH according to the manufacturer's instructions. The strain BL21 (DE3) (Invitrogen) was used.

```
Primer sequences used
top iscR deletion:
                                        (SEQ ID NO: 80)
5'-GGGCGAGTTTGAGGTGAAGTAAGACATGAGACTGACATCTGAACCCT

CACTAAAGGGCGGCCGC

bottom iscR deletion:
                                        (SEQ ID NO: 81)
5'-TTCTTTTTATTAAGCGCGTAACTTAACGTCGATCGCGTCTTGAAGTT

CCTATACTTTCTAGAGAATAGGAACTTCTTACGCCCCGCCCTGCCACTCA

TCGCA

5' screen up of up iscR:
                                        (SEQ ID NO: 82)
5'-AGCCAGGAGTTGAATATCCTG

3' down of down iscR:
                                        (SEQ ID NO: 83)
5'-TGATGGACACGAGGATGGTGT
```

Strategy for Creating the Deletion Strains

Figure 61:
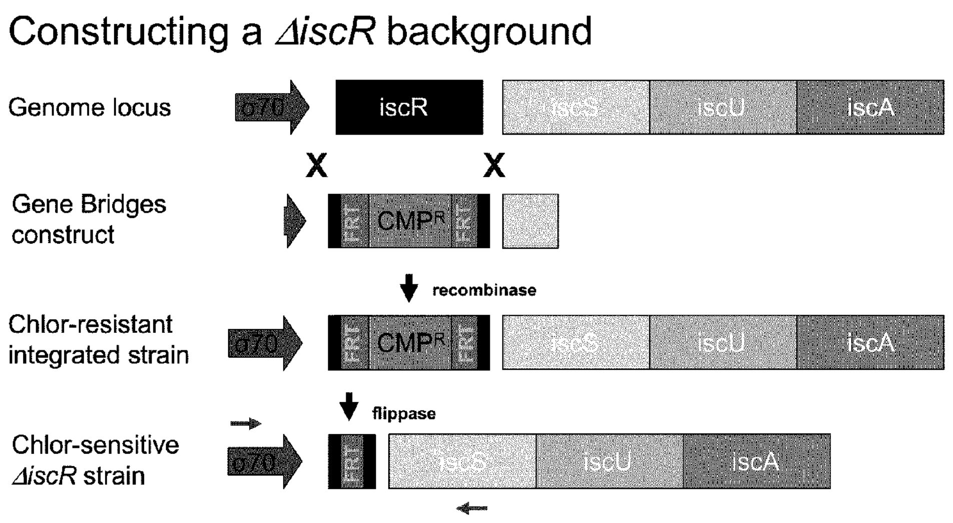
FIG. 61 is a cartoon representation of the strategy used to delete the iscR locus using the RED/ET system.
Figure 62:
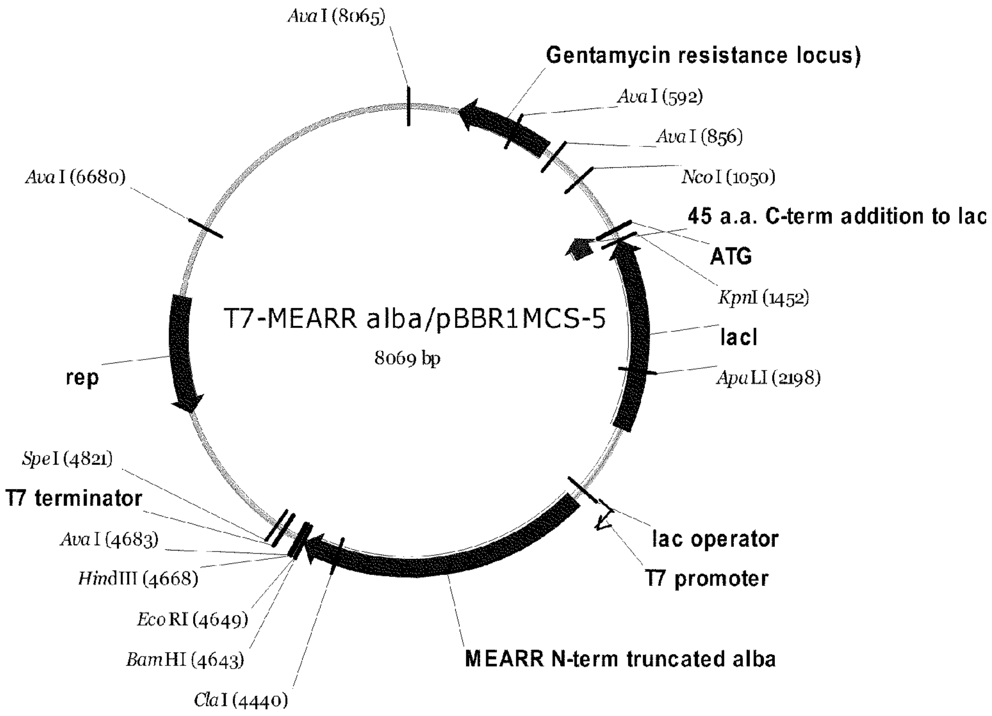
FIG. 62 is a cartoon representation of the T7-MEARR alba/pBBR1MCS-5.

The strategy for the deletion of iscR is shown in FIG. 61. The antibiotic resistance cassette GB-CmR was amplified by PCR using primer sets top iscR deletion/bottom iscR deletion for deletion of the iscR locus. The primers contain 50 bases of homology to the region flanking the iscR gene to allow recombination at the specific locus upon electroporation of the PCR product in the presence of the pRed-ET plasmid.

Amplification of the Deletion Cassettes

To amplify the GB-CmR cassette for deletion of iscR the following PCR reactions were set up:

1 ul (100 ng GB-CmR)
10 ul HerculaseII Buffer
0.5 ul dNTP's (100 mM)
1.25 ul primer (10 uM) top iscR deletion
1.25 ul primer (10 uM) bottom iscR deletion
35 ul diH2O
+1 ul of HerculaseII fusion from Stratagene Cycle Parameter:

95° C.×2 min., [95° C.×30 sec., 63° C.×30 sec., 72° C.×3 min]×29 cycles; 72° C.×5 min, 4° C. until cool (Biometra T3000 Combi Thermocycler).

The resulting PCR fragment was separated on a 1.2% E-gel (Invitrogen) to verify successful amplification, and purified using QIAquick PCR Purification kit according to manufacturer's instructions. The resulting stock was designated GB-CmR-iscR fragment.

Integration of GB-CmR—iscR product into the BL21 (DE3) genome

The pRed-ET vector (Gene Bridges) was transformed into electrocompetent BL21 (DE3) (Invitrogen) by electroporation resulting in strain BL21 (DE3)/pRed-ET. Approximately 500 ng of GB-CmR—iscR PCR fragment was electroporated into BL21 (DE3)/pRed-ET. The transformants were recovered in L Broth for 1 hour at 37° C. and then plated on L agar containing chloramphenical (10 ug/ml). Chloramphenicol resistant colonies were analyzed by PCR for the replacement of the iscR by the GB-CmR—iscR fragment using primers 5' screen up of up iscR/3' screen down of down iscR. The correct strain was designated REM14::CMP. The chloramphenicol resistance cassette was looped out of the strain using pCP20 from the RED/ET kit according to the manufacturer's instructions. Transformants were verified by loss of resistance to chloramphenicol (10 ug/ml) and PCR demonstrating loopout of the GB-CmR cassette. The resulting strain was designated REM14.

Creation of Strains REM65-1 and REM4, the Parental Strains to REM12 and REM13

The wild-type BL21 (DE3) (Invitrogen) and ΔiscR strain REM14 were transformed with the T7-MEARR alba/pBBR1MCS-5 construct to create the isoprene-producing strains REM65-1 and REM4 strains, respectively. A picture of the isoprene synthase containing vector, T7-MEARR alba/pBBR1MCS-5, is shown in FIG. 61. The construction of T7-MEARR alba/pBBR1MCS-5 is described in the Example: Expression of alternative ispG (gcpE) and ispH (lytB) and their corresponding reducing shuttle system, from *Thermosynechococcus elongatus* BP-1 in an isoprene-producing *E. coli* to improve isoprene production.

Transformation of T7-MEARR alba/pBBR1MCS-5 into BL21 (DE3) and REM14

To build the isoprene-producing strains REM65-1 and REM4 strains, the T7-MEARR alba/pBBR1MCS-5 plasmid was transformed by electroporation into BL21 (DE3) (Invitrogen) and REM14. Transformants were recovered in L broth and plated on L agar containing gentamycin (10 ug/ml). The resulting strains are designated as such: REM65-1 (BL21 (DE3)/T7-MEARR alba/pBBR1MCS-5 and REM4 (REM14/T7-MEARR alba/pBBR1MCS-5).

Construction of the test strains REM12 and REM13

Figure 63:
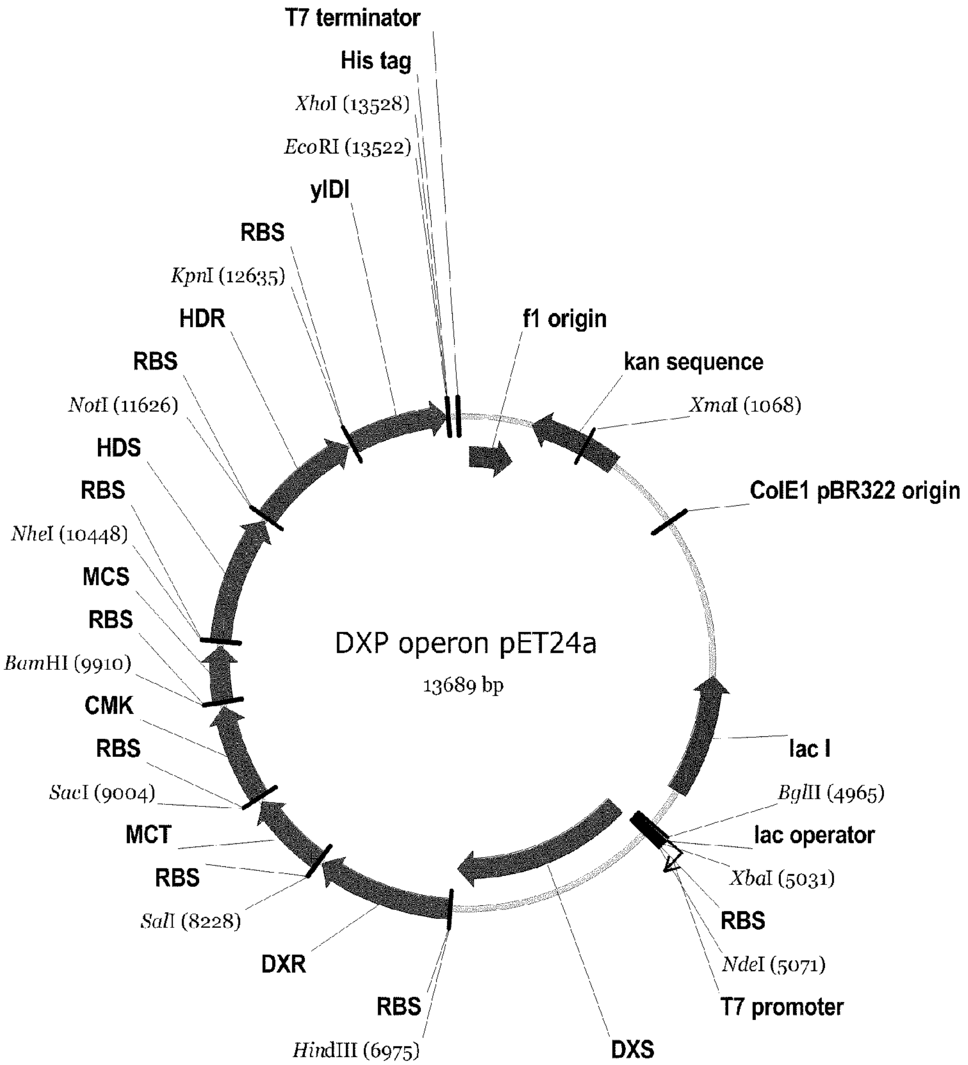

The entire DXP pathway from *E. coli* was synthesized by DNA2.0 (Menlo Park, Calif.) and cloned into pET24a (see FIG. 63).

To build the higher flux DXP pathway isoprene-producing REM12 and REM13 strains, the DXP operon pET24a plasmid was transformed by electroporation into REM65-1 and REM4. A picture of the DXP pathway enzyme containing vector, DXP operon pET24a plasmid, is shown in FIG. 63.

Transformation of DXP Operon pET24a into REM65-1 and REM4

To build the test strains REM12 and REM13 strains, the DXP operon pET24a plasmid was transformed by electroporation into REM65-1 and REM4. Transformants were recovered in L broth and plated on L agar containing gentamycin (10 ug/ml) and kanamycin (10 ug/ml). The resulting strains are designated as such: REM12 (REM65-1/DXP operon pET24a) and REM13 (REM4//DXP operon pET24a).

Analysis of REM12 and REM13 for Growth and Isoprene Production

Figure 60A:
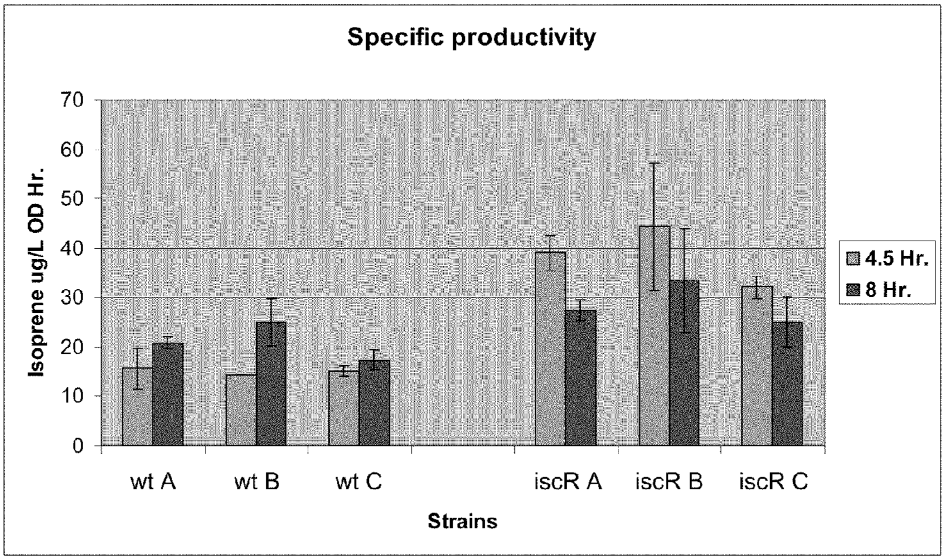
FIG. 60 shows that ΔiscR BL21 (DE3) supports increased isoprene production. Panel 60A shows the specific productivity of REM12 compared to the otherwise isogenic ΔiscR strain REM13. Isoprene levels were determined 4.5 hours and 8 hours after induction of the IPTG-inducible isoprene synthase and DXP enzymes harbored by the strains. Data from three groups (A-C) of three biological replicates for each strain are shown. Error bars depict the standard deviation occurring between the biological replicates of each group. From this data it was determined that isoprene levels generated from the ΔiscR strain were an average of 40% and 73% higher than that produced by the wild-type strain at the 4.5 hour and 8 hour time point, respectively. Panel 60B shows the growth rate of REM12 and REM13 isoprene-producing strains. The growth rate of the same strains depicted in panel A was monitored over the course of the eight hour experiment by periodically measuring the optical density of the cultures at 600 nm. Time 0 corresponds to the time that 50 uM IPTG was added to the cultures. Cells were grown shaking in TM3 at 30° C. The higher isoprene-producing strain ΔiscR (REM13) grows at a reduced rate relative to the lower isoprene-producing wild-type (REM12) strain.
Figure 60B:
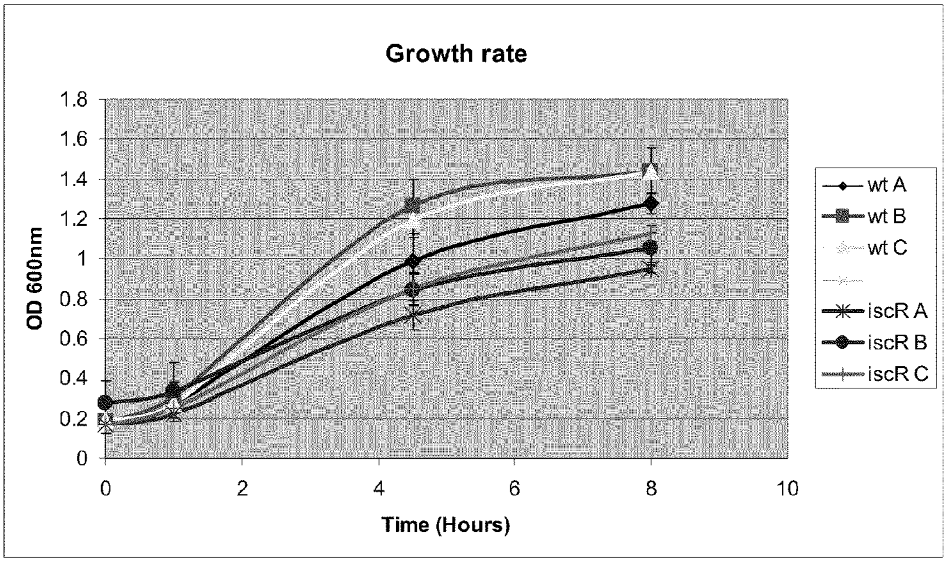

The wild-type strain REM12 and otherwise isogenic ΔiscR strain REM13 were compared in a shake flask isoprene headspace assay. The benefits on isoprene production and effect on growth rate the loss of iscR causes in the *E. coli* host are illustrated in FIG. 60.

Growth

Strains REM12 and REM13 were grown at 30° C. in TM3 liquid media (13.6 g $K_2PO_4$, 13.6 g $KH_2PO_4$, 2.0 g $MgSO_4{*}7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) supplemented to a final concentration with 0.1% yeast extract and 1.0% glucose and including kanamycin (10 ug/ml) and gentamycin (10 ug/ml). Growth was monitored periodically by recording each of the culture's optical density measured at 600 nm using an Eppendorf Biophotometer spectrometer (Eppendorf). 50 uM isopropyl β-D-1-thiogalactopyranoside (IPTG) was added to the cultures to induce expression of the isoprene synthase and DXP enzymes harbored by the strains at time zero, as indicated in the legend to FIG. 60.

Isoprene Production

Isoprene production was analyzed using a headspace assay. For the shake flask cultures, one ml of a culture was transferred from shake flasks to 20 ml CTC headspace vials (Agilent vial cat#5188 2753; cap cat#5188 2759). The cap was screwed on tightly and the vials incubated at the equivalent temperature with shaking at 250 rpm. After 30 minutes the vials were removed from the incubator and analyzed. The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 μm film thickness) was used for separation of analytes. The sampler was set up to inject 500 μL of headspace gas. The GC/MS method utilized helium as the carrier gas at a flow of 1 ml/minutes The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 μg/L to 200 μg/L. The limit of detection was estimated to be 50 to 100 ng/L using this method. The specific productivity of each strain is reported as ug/L OD Hr. Note, ratio of 1900 ul headspace: 100 ul broth in assay vials for 30 min. incubation results in the following conversion of isopreneug/L of culture to specific productivity: (isoprene/L determined by GC-MS)×(38)/(OD 600 nm of the culture).

Example 11

Evaluation of Alternative ispG (gcpE) and ispH (lytB) Alleles from Different Organisms by Complementation of ΔispG and/or ΔispH Strains of BL21 (DE3)PL.2 mKKDy1::FRT We constructed an *E. coli* strain expressing the lower mevalonic acid pathway (mevalonate kinase, phosphomevalonate kinase, diphosphomevalonte decarboxylase and IPP isomerase from yeast) as a base strain for testing the functionality of DXP pathway enzymes from heterologous organisms. This strain produces IPP and DMAPP from the lower mevalonate pathway if it is grown in the presence of mevalonate. Deletions of enzymes of the DXP pathway can be rescued by growing the stain in the presence of mevalonate. Therefore, functionality of heterologous DXP pathway genes can be expressed in the *E. coli* containing the lower MVA pathway and looking for growth in the absence of mevalonate.

Construction of MD09-170 (BL21 (DE3)PL.2 mKKDyI::FRT

A P1 phage lysate was generated from MCM521 (BL21 neo-PL.2-mKKDyl) and transduced into BL21 (DE3) (according to Procedure 12-Genetic Transduction Using P1 vir protocol). The transductants were selected on L agar plates containing kanamycin (20 ug/ml), with incubation at 37° C. overnight. Four colonies were verified by PCR to be correct transductants. One of these colonies was selected and designated MD09-169 (BL21 (DE3)PL.2 mKKDyI::Kan). The kanamycin resistance marker was looped out of this strain using pCP20 from the Red/ET system from Gene Bridges GmbH according to the manufacturer's instructions. The correct loopout was confirmed by testing for sensitivity to kanamycin (20 ug/ml) and then loss of the kanamycin resistance cassette was verified by PCR. The correct strain was designated MD09-170 (BL21 (DE3)PL.2 mKKDyI::FRT).

Deletion of ispG and ispH from MD09-170

The gene deletions and subsequent loopout of the antibiotic resistance markers described in this example were carried out using the Red/ET system from Gene Bridges GmbH according to the manufacturer's instructions. The strain MD09-170 was used.

```
Primer sequences used
MQ09-18F
                                        (SEQ ID NO: 88)
5'-GAACAATCACCGGCGCAGTAACAGACGGGTAACGCGGGAGATTTTC
ATGaattaaccctcactaaagggcgg
MQ09-18R
                                        (SEQ ID NO: 89)
5'-CGGGAAGCGAGGCGCTTCCCATCACGTTATTATTTTTCAACCTGCTG
AACTAATACGACTCACTATAGGGCTCG
MQ09-19F
                                        (SEQ ID NO: 90)
5'-TTTTGATATTGAAGTGCTGGAAATCGATCCGGCACTGGAGGCGTAAC
ATGaattaaccctcactaaagggcgg
MQ09-19R
                                        (SEQ ID NO: 91)
5'-ATTTTCGCATAACTTAGGCTGCTAATGACTTAATCGACTTCACGAAT
ATCTAATACGACTCACTATAGGGCTCG
MQ09-20F
                                        (SEQ ID NO: 92)
5'-cggcgcagtaacagacgggtaacgcgggagattttcatg
MQ09-20R
                                        (SEQ ID NO: 93)
5'-cgcttcccatcacgttattatttttcaacctgctgaac
MQ09-21F
                                        (SEQ ID NO: 94)
5'-gaagtgctggaaatcgatccggcactggaggcgtaacatg
MQ09-21R
                                        (SEQ ID NO: 95)
5'-cttaggctgctaatgacttaatcgacttcacgaatatc
```

```
Primer Sequences
MCM 161: 5'-CACCATGGTATCCTGTTCTGCG                          (SEQ ID NO: 84)
MCM162:  5'-TTAATCTACTTTCAGACCTTGC                          (SEQ ID NO: 85)
MCM143:  5'-aggaggtggtctcaaATGACTGCCGACAACAATAGTA           (SEQ ID NO: 86)
MCM144:  5'-aggaggtggtctcagcgctctgcagTTATAGCATTCTATGAATTTGCCTG (SEQ ID NO: 87)
```

Strategy for Creating the Deletion Strains

Figure 66:
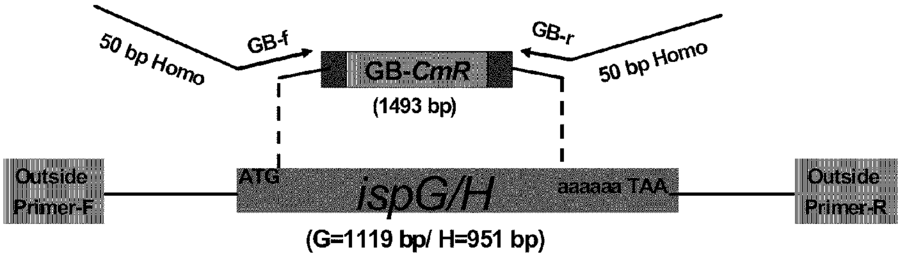
FIG. 66 is a cartoon representation of the strategy used to delete ispG and ispH using the RED/ET system.

The strategy for the deletion of ispG and ispH is shown in FIG. 66. The antibiotic resistance cassette GB-CmR was amplified by PCR using primer sets MQ09-18F/MQ09-18R or MQ09-19F/MQ09-19R for deletion of ispG or ispH respectively. The primers contain 50 bases of homology to the region flanking the ispG or ispH genes to allow recombination at the specific locus upon electroporation of the PCR product in the presence of the pRed-ET plasmid.

Amplification of the Deletion Cassettes

To amplify the GB-CmR cassette for deletion of ispG or ispH the following PCR reactions were set up:

2 ul (100 ng GB-CmR)
10 ul HerculaseII Buffer
0.5 ul dNTP's (100 mM)
1.25 ul primer (10 uM) MQ09-18F/19F
1.25 ul primer (10 uM) MQ09-18R/19R
2 ul DMSO
32 ul diH2O
+1 ul of HerculaseII fusion from Stratagene Cycle Parameter:

95° C.×2 min., [95° C.×20 sec., 55° C.×20 sec., 72° C.×50 sec]×29 cycles; 72° C.×3 min, 4° C. until cool (Eppendorf Mastercycler PCR machine)

The resulting PCR fragments were separated on a 1.2% E-gel (Invitrogen), and purified using the Qiagen QiaQuick Gel Extraction and QIAquick PCR Purification kits according to manufacturer's instructions. The resulting stocks were: GB-CmR—ispG fragment (1.593 kb)~180 ng/ul, and GB-CmR—ispH fragment (1.593 kb)—165 ng/ul.

Integration of GB-CmR—ispG or GB-CmR—ispH PCR Products into MD09-170/pRed-ET Strain The pRed-ET vector (Gene Bridges kit) was transformed into MD09-170 by electroporation resulting in strain MD09-170/pRed-ET. Approximately 300-500 ng of GB-CmR—ispG or GB-CmR—ispH PCR fragments were electroporated into MD09-170/pRed-ET. The transformants were recovered in L Broth containing 500 uM mevalonic acid (Sigma) for 1 hour at 37° C. and then plated on L agar containing chloramphenical (5 ug/ml) and mevalonic acid (MVA) (500 uM). Chloramphenicol resistant colonies were analyzed by PCR for the presence of the GB-CmR cassette and the absence of the ispG or ispH genes using primers MQ09-20F/MQ09-20R or MQ09-21F/MQ09-21R respectively. The correct strains were designated MD09-209(BL21 (DE3)PL.2 mKKDyI::FRT-ΔispG::Cm) and MD09-210 (BL21 (DE3)PL.2 mKKDyI::FRT-ΔispH::Cm). The chloramphenicol resistance cassette was looped out of both strains using pCP20 from the RED/ET kit according to the manufacturer's instructions. Transformants were verified by loss of resistance to chloramphenicol (5 ug/ml) and PCR demonstrating loopout of the GB-CmR cassette.

The resulting strains were designated MD09-219 (BL21 (DE3)PL.2 mKKDyI::FRT-ΔispG::FRT) and MD09-220 (BL21 (DE3)PL.2 mKKDyI::FRT-ΔispH::FRT).

Complementation of MD09-219 and MD09-220 with Alleles from *Thermosynechococcus Elongatus* BP-1

To test the functionality of the gcpE and lytB genes (annotated) from *T. elongates*, the following plasmids expressing these constructs or gcpE and lytB from *E. coli* were transformed by electroporation into MD09-219 and MD09-220:

1. *E. coli*: GI1.6-gcpE-lytB-yidi/pCR-Blunt II-TOPO (Kan) (positive control)
2. *T. elong*: Ptac-gcpE-petF-petH/pK184 (Kan)
3. *T. elong*: Ptac-gcpE-lytB-petF-petH/pK184 (Kan)

Transformants from 1. (*E. coli*) were recovered in L broth containing MVA (500 uM) and plated on L agar containing kanamycin (50 ug/ml). The resulting strain is designated MD09-219/GI1.6-gcpE-lytB-yidi/pCRII-TOPO (Kan).

Transformants from 2. (*T. elong*) or 3. (*T. elong*) were recovered in L broth containing MVA (500 uM) and IPTG (200 uM) and then plated on L agar containing on kanamycin (50 ug/ml) and IPTG (200 uM). The resulting strains were designated MD09-219/Ptac-gcpE-petF-petH/pK184 (Kan) and MD09-219/Ptac-gcpE-lytB-petF-petH/pK184 (Kan) respectively.

Several transformants were obtained on all of the plates suggesting that the *T. elongatus* gcpE and lytB were functional in *E. coli*. To confirm this, transformants were grown in L broth containing kanamycin (50 ug/ml) with and without IPTG (200 uM).

Construction of GI1.6-gcpE-lytB-yidi/pCR-Blunt II-TOPO

Figure 67:
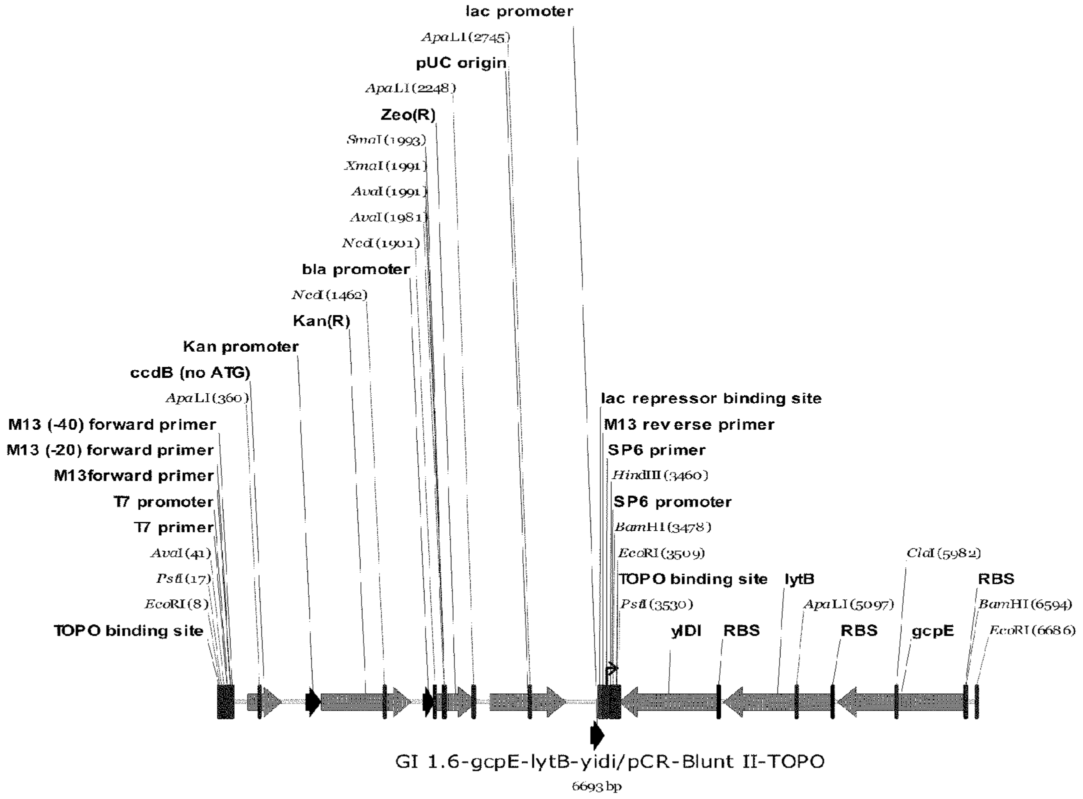
FIG. 67 is a cartoon representation of the GI 1.6-gcpE-1ytB-yidi/pCR-Blunt II-TOPO construct that was used to generate strain MD09-219/GI1.6-gcpE-1ytB-yidi/pCRII-TOPO (Kan).

The construction of the GI 1.6-gcpE-lytB-yidi/pCR-Blunt II-TOPO described in this example was carried out using standard molecular biology techniques (see, for example, Sambrook et al., Molecular Cloning: A Laboratory Manual, $2^{nd}$ ed., Cold Spring Harbor, 1989, which is hereby incorporated by reference in its entirety, particularly with respect to cloning techniques). A picture illustrating the resulting plasmid construct is shown in FIG. 67. The MD09-219 and MD09-220 strains were used for the transformations described herein.

```
Primer sequences
5' EcoRI-GI 1.X-BamHI gcpE DXP oper:
                                        (SEQ ID NO: 96)
5'-GAG GAA TTC GCG AGC CGT CAC GCC CTT GAC NAT GCC

ACA TCC TGA GCA AAT AAT TCA ACC ACT AAA CAA ATC

AAC CGC GTT TCC CGG AGG TAA CCG GAT CCA AGG AGA

TAT ACC ATG CAT AAC CAG GCT CCA ATT CAA CGT AGA

3' PstI idi DXP operon:
                                        (SEQ ID NO: 97)
5'-ATA TCC TGC AGT TAT AGC ATT CTA TGA ATT TGC

CTG TC

M13 Forward (-20):
                                (SEQ ID NOS: 63 and 69)
5'-GTAAAACGACGGCCAGT

M13 Reverse (-27):
                                        (SEQ ID NO: 99)
5'-CAGGAAACAGCTATGAC
```

degenerate N base: A base yields GI 1.6-, T base yields GI 1.5-, G base yields GI1.2-, and C base yields GI 1.0-promoter Strategy for constructing GI 1.6-gcpE-lytB-yidi/pCR-Blunt II-TOPO The vector construct harboring the T7 polymerase governed synthetic DXP operon, DXP operon pET24a, was used as the PCR template.

Amplification of the GI1.6-gcpE-lytB-yidi Fragment

To amplify the GI1.6-gcpE-lytB-yidi fragment (among the other GI 1.X—possibilities) for cloning into the pCR-Blunt II-TOPO vector the following PCR reaction was performed:

1 ul (approx. 100 ng DXP operon pET24a)
10 ul HerculaseII Buffer
0.5 ul dNTP's (100 mM)
1.25 ul primer (10 uM) 5' EcoRI-GI 1.X-BamHI gcpE DXP operon
1.25 ul primer (10 uM) 3' PstI idi DXP operon
35 ul diH2O
+1 ul of HerculaseII fusion from Stratagene Cycle Parameter:

95° C.×2 min., [95° C.×30 sec., 63° C.×30 sec., 72° C.×3.5 min.]×29 cycles; 72° C.×5 min, 4° C. until cool (Biometra T3000 Combi Thermocycler).

The resulting PCR fragment was separated on a 1.2% E-gel (Invitrogen) for verification of successful amplification, and purified using the QIAquick PCR Purification kits (Qiagen) according to manufacturer's instructions. The resulting stock was GI 1.X-gcpE-lytB-yidi fragments.

Cloning of the GI1.6-gcpE-lytB-yidi Fragment into pCR-Blunt II-TOPO

The GI 1.X-gcpE-lytB-yidi fragments were cloned into pCR-Blunt II-TOPO using Invitrogen's Zero Blunt® TOPO® PCR Cloning Kit using the suggested protocol. Chemically competent TOP10 cells (Invitrogen) were transformed with 2 ul of the ligation reaction using a standard heat-shock protocol, and recovered in L broth for 1 hour at 37° C. and then plated on L agar containing kanamycin (10 ug/ml). Resulting colonies were selected, grown overnight in L broth containing kanamycin (10 ug/ml), and harvested for plasmid preparation the following day. Plasmid constructs were isolated using Qiagen Qiaprep Spin Miniprep Kit. A number of plasmid preparations were sequenced (Quintara; Mountain View, Calif.) using primers M13 Forward (−20) and M13 Reverse (−27) and the correct GI1.6-gcpE-lytB-yidi/pCR-Blunt II-TOPO clone identified.

Example 12

Improving Isoprene Production in *E. Coli* by Deregulating Glucose Uptake

In *Escherichia coli*, glucose is transported using the phosphoenolpyruvate transport system (PTSglc), which consists of PtsHICRR and the transporter PtsG (see Tchieu et al., *J. Mol. Microbiol. Biotechnol.* 3(3):329-46 (2001), which is hereby incorporated by reference in its entirety). Glucose is phosphorylated as it is transported into the cell, with the phosphate originating from phosphoenol pyruvate. The resulting glucose-6-phosphate is metabolized via glycolysis regenerating the PEP. Glucose transport continues through exponential growth but is down-regulated as cells enter stationary phase. For commercial purposes it is desirable to maximize production time and yield of the desired molecule, which is difficult to achieve if the feedstock transporter is downregulated. To solve this problem, the PTSglc system is deleted by deleting ptsHIcrr, and in some embodiments, ptsG, and constitutively express galP and glk, encoding the galactose permease and glucokinase respectively. The galactose permease transports glucose without phosphorylation so it is necessary to express the glucokinase (see US Patent Application No. 20050079617, which is hereby incorporated by reference in its entirety).

The ptsHIcrr operon is deleted in BL21 using the Red/ET system from Gene Bridges. Electrocompetent BL21 (Invitrogen) are transformed with the pRed/ET plasmid and the resulting cells are made electrocompetent by washing 3-4× in ice cold $dH_2O$. The GB-cmR cassette is amplified using forward and reverse primers have at least 50 bases of homology to the regions immediately upstream of ptsH or immediately downstream of crr. The resulting PCR product is used to transform BL21/pRED and transformants are plated on MacConkey agar containing glucose (1%) and chloramphenical (5 ug/ml). Transformants that grown and are white in color will be the correct genotype. The ptsHIcrr knockout is transduced into the desired isoprene-producing hosts using P1 transduction.

The Ptrc-galP-cat and Ptrc-glk-cat cassettes are amplified by PCR from strains KLpts::gal-trc::Cm or KLgalPglk-trc-cat S (see U.S. Patent Application No. 20050079617, which is hereby incorporated by reference in its entirety) with at least 50 base pairs (bp) of homology on the 5' and 3' ends to allow homologous recombination into BL21 with either the DXP or the MVA or both pathways and isoprene synthase (example ispS from *P. alba* or a variant thereof) expressed and the ptsHIcrr and/or ptsG deleted. The desired strain is made competent and transformed with the pRed/ET plasmid, and after being made competent, the new strain is transformed with the galP-trc-cat cassette. Transformants are selected on MacConkey agar containing 1% glucose and chloramphenicol (5 ug/ml). Colonies which are slightly pink have the correct genotype. The CAT markers in these cassettes are flanked by loxP sites and can be looped out by standard methods (Palmeros et al., Gene 18; 247 (1-2):255-64 (2000)) which is hereby incorporated by reference in its entirety). The strain expressing galP from Ptrc is then transformed with the glk-trc-cat cassette and transformants are select on MacConkey agar containing 1% glucose and chloramphenicol (5 ug/ml). Colonies which are deep red in color are the correct colonies.

The resulting strains have the full MVA pathway, with or without the DXP pathway constitutively expressed, an isoprene synthase (example *P. alba* IspS or a variant thereof), a deletion of the ptsHIcrr and/or ptsG, and constitutive expression of the galactose permease and glucokinase. To demonstrate that isoprene production is enhanced and/or prolonged in these strains compared to the parent which transports glucose via the PTSglc system, the strains are tested in shake flask (TM3 containing 1% glucose, 0.1% yeast extract), microfermentor (TM3 containing 1% glucose, 0.1% yeast extract), and in 14-Liter fermentation. These strains are also tested using pretreated and saccharified biomass, for example corn fiber, corn stover, switch grass, forage sorghum, softwood pulp, hardwood pulp or other suitable biomass.

Isoprene production is enhanced and/or prolonged in the strains with ptsHIcrr and/or ptsG deletion and constitutive expression of the galactose permease and glucokinase compared to the compared to the parent strains without the deletion of ptsHIcrr and/or ptsG and constitutive expression of the galactose permease and glucokinase.

Example 13

Expression of Monoterpene and Sesquiterpene Synthases in Combination With the Expression of Isoprene Synthase Increases the Specific Productivity of Isoprene in *E. coli*

Isopentenyl pyrophosphate (IPP) and dimethyl allyl pyrophosphate (DMAPP) are biosynthesized by the DXP pathway (also called the non-mevalonate pathway and MEP pathway) in *E. coli*. IPP and DMAPP can be condensed to form geranyl pyrophosphate (GPP) and subsequently farnesyl pyrophosphate (FPP) by farnesene synthase (IspA). FPP can be converted to octaprenyl pyrophosphate (OPP) and undecaprenyl pyrophosphate (UPP) by extension of FPP with IPP. These products serve a variety of functions in *E. coli* including prenylation of tRNA (protein synthesis component) with DMAPP, formation of quinones (respiratory chain component) with OPP, and peptidoglycan formation (cell wall component) with UPP.

The products of the DXP pathway may be regulated by the production of IPP and DMAPP. Accordingly, the example shows that the introduction of a terpene synthase that utilizes downstream products of the DXP pathway in combination with isoprene synthase in *E. coli* results in increased flux through the DXP pathway and increased specific productivity of isoprene.

Methods

Strain Construction

The following strains are constructed.

Ocimene synthase, farnesene synthase and artemesinin synthase are cloned into pTrchis2A plasmids to give pTrcFPP, pTrcAS, or pTrcOS. Isoprene synthase (for example IspS from *P. alba* or variants thereof) is cloned into pBBR under control of the Ptrc promoter to give pBBRPtrcalba.

Strain set 1) BL21GI1.6yIDI/pBBRPtrcalba itself or combined with PtrcFPP or pTrcAS or pTrcOS.

Strain set 2) BL21GI1.6yIDIGI1.6DXS/pBBRPtrcalba itself or combined with PtrcFPP or pTrcAS or pTrcOS.

The strains in strain set 1) or 2) are grown in shake flask or in the microfermentor in TM3 containing 0.1% yeast extract and 1% glucose. The specific productivity of isoprene is measured over time.

The specific productivity of isoprene from strains in strain set 1) are compared. The specific productivity of isoprene in the strains containing FPP, OS, or AS is higher than in the strain without FPP, OS, or AS.

The specific productivity of isoprene from strains in strain set 2) are compared. The specific productivity of isoprene in the strains containing FPP, OS, or AS is higher than in the strain without FPP, OS, or AS.

Example 14

Deletion or Reduction of Carbon into Thiamine and Pyridoxine Paths for Relief of Inhibition 1-deoxy-D-xylulose-5-phosphate (DXP) is a substrate in three essential anabolic pathways in *E. coli*, namely isoprenoids, thiamine and pyridoxal synthesis. In order to avoid any feedback regulation from thiamine or pyridoxal pathways, which could then decrease the flux in the DXP pathway for isoprenoid production, we build strains mutated in the thiamine and/or pyridoxal pathways.

A: Construction of an *E. Coli* Strain Deleted in the Thiamine Synthesis Pathway Several enzymes are involved in the biosynthesis of thiamine from DXP. ThiG and ThiH combine to form a complex containing an iron-sulfur cluster (Leonardi et al. *FEBS Lett.* 539 (1-3):95-9 (2003), PMID: 12650933, which is hereby incorporated by reference in its entirety). Together, they are required for the synthesis of 4-methyl-5-(β-hydroxyethyl) thiazole phosphate, which is the rate-limiting step in thiamine synthesis (Leonardi et al. *J. Biol. Chem.* 279(17):17054-62 (2004), PMID: 14757766; Vander et al., J. Bacteriol. 175(4): 982-92 (1993), PMID: 8432721; which are hereby incorporated by reference in their entireties). Since it is in the rate-limiting step, and it is the first enzyme after 1-deoxy-D-xylulose-5-phosphate, thiG was chosen as the gene to be deleted.

A PCR product was obtained using primers GB400thiGF (caggagccagaacgcaactgc (SEQ ID NO:100) and GB400thiGR (CACTTTCGCCTGATGTTCACC (SEQ ID NO:101), and genomic DNA of strain JW5549 from the Keio collection (Baba et al., *Mol. Syst. Biol.* 2006.008 (2006), which is hereby incorporated by reference in its entirety). The PCR product contains a kanamycin cassette replacing most of the thiG gene and around 400 by flanking regions of both sides of the thiG gene.

A BL21 (DE3) thiG::Kan mutant is then obtained by Red/ET recombineering (Gene Bridges, Dresden, Germany) using the PCR product mentioned above. It is proven correct by amplification and sequencing. The strain is named CMP179.

B: Construction of an *E. Coli* Strain Deleted in the Pyridoxal Synthesis Pathway PdxJ catalyses the formation of pyridoxine-5-phosphate (precursor of pyridoxal-5-phosphate then pyridoxal) from 1-deoxy-D-xylulose-5-phosphate and 1-amino-propan-2-one-3-phosphate. The latter is produced by a sequence of reactions coming from erythrose-4-phsophate, the first one catalyzed by D-erythrose 4-phosphate dehydrogenase (epd). Thus both pdxJ and epd are good candidates for deleting the production of pyridoxal. However, epd has been reported not to be required for glycolysis or for synthesis of pyridoxal (Seta et al., *J. Bacteriol.* 179(16):5218-21 (1997), which is hereby incorporated by reference in its entirety). Thus, pdxJ is chosen as the target for mutation.

A PCR product is obtained using primers GB400pdxJF (CAT TCA GTC TCT TGC AGG GGT C (SEQ ID NO:102) and GB400pdxJR (gcatagtgccgctcatctgcc (SEQ ID NO:103)), and genomic DNA of strain JW2548 from the Keio collection (Baba et al. 2006). The PCR product contains a kanamycin cassette replacing most of the pdxJ gene and around 400 by flanking regions of both sides of the pdxJ gene.

A BL21 (DE3) pdxJ::Kan mutant is then obtained by Red/ET recombineering (Gene Bridges, Dresden, Germany) using the PCR product mentioned above. It is proven correct by amplification and sequencing. The strain is named CMP180.

C: Construction of an *E. Coli* Strain Deleted in the Thiamine and Pyridoxal Synthesis Pathways The kanamycin cassette is removed from CMP179 and/or CMP180 by Flp-mediated excision, using plasmid 706-Flp from Gene Bridges (Dresden, Germany). Then the PCR product described in section A is used to mutate BL21 (DE3) pdxJ through Red/ET recombineering.

D: Production of Isoprene Via the DXP Pathway, in a thiG and/or a pdxJ Mutant

The effect of the thiG, pdxJ or thiG pdxJ mutations on the production of isoprene through the DXP pathway is assessed in different constructs enhancing DXP pathway flux and expressing IspS (isoprene synthase) from *Populus alba*, such as MCM597 (BL21 (DE3)pLysS pET24 (MEA)alba-DXS-yIDI) or MCM719 (BL21 gi1.6-yIDI gi1.6-dxs, pTrc(MEA) alba)).

Strains are grown overnight at 30° C., 200 RPM, in HM1 medium (Table 2) plus appropriate antibiotics. The morning after, they are resuspended to an OD=0.2 in fresh HM1 medium+appropriate antibiotics. Flasks are incubated at 30° C., 200 RPM, and regularly sampled for OD and isoprene productivity.

TABLE 2

HM1 medium composition

| Compounds | Concentration (g/L) |
|---|---|
| K2HPO4 | 13.6 |
| KH2PO4 | 13.6 |
| MgSO4 * 7H2O | 2 |
| Citric Acid Monohydrate | 2 |
| Ferric Ammonium Citrate | 0.3 |
| (NH4)2SO4 | 3.2 |
| Trace metal solution | 1 ml |

Specific productivity (ug isoprene/OD·h) is increased when strains MCM597 or MCM719 contains thiG, pdxJ, or thiG pdxJ mutations.

Example 15

Figure 68:
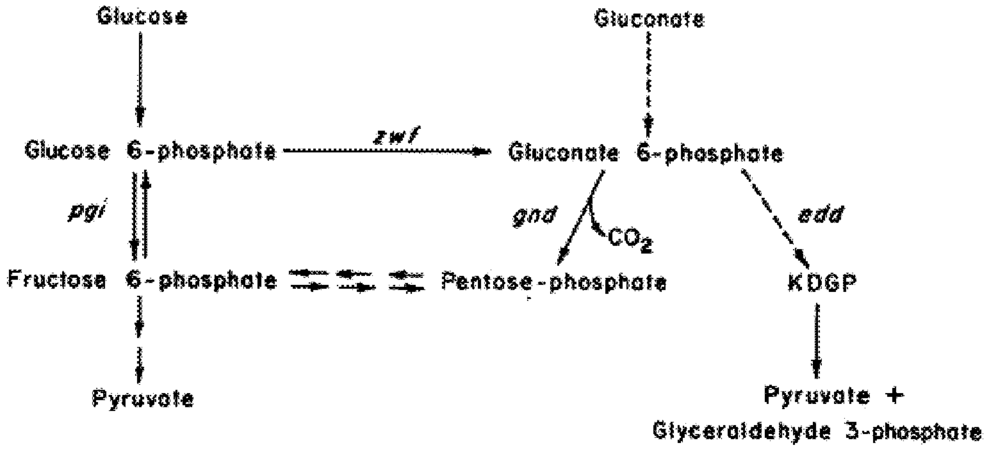
FIG. 68 depicts the Pentose Phosphate (PPP) and Entner-Doudoroff (ED) pathways (Fraenkel, J. Bact. 95:1267-1271 (1965), which is hereby incorporated by reference in its entirety).

Balancing Pyruvate and G-3-P (glyceraldehyde-3-phosphate) to Increase Isoprene Production Flux to the DXP pathway may be positively (more flux) effected to increase isoprene production by maximizing the balance between the two precursors required for the DXP pathway, pyruvate and G-3-P (glyceraldehyde-3-phosphate). Accordingly, adjusting the expression level of enzymes that determine flux into glycolysis, into the pentose phosphate pathway (PPP) and into the Entner-Doudoroff (ED) pathway (FIG. 68). In Sections B-D, flux of pyruvate and G-3-P are affected simultaneously. Optimal balance of the two precursors to the DXP pathway may also be achieved by redirecting flux with the effect of elevating or lowering pyruvate or G-3-P separately. Section E demonstrates this approach with the coexpression of the mevalonate pathway. In addition it is proposed that desired flux balance can be achieved by choice of feed stock, e.g., feeding a mixture of glucose+gluconic acid; Section A shows this approach. A combination of these approaches may prove to be additive in achieving precursor balance and maximize yield of isoprene; this is tested in Section F.

Section A

Cells that have been constructed by procedures known to practitioners of the art and as exemplified in this application to overexpress the DXP pathway or wild type cells are fed with various carbon sources, but more specifically cells are fed glucose plus gluconic acid or gluconic acid alone. The culture is sampled and analyzed for improved evolution of isoprene. This analysis is accomplished by monitoring the head space of the culture with a mass spectrometer either continuously or at specific time points during the cultivation of cells with different concentrations of the carbon sources.

Section B

Cells in Section A harboring the overexpressed DXP pathway or wild type cells are genetically engineered to overexpress glucose-6-phosphate dehydrogenase to redirect flux to PPP and ED. Effect and benefit of these mutations can be assessed by measuring isoprene specific productivity.

Section C

Cells in Section A harboring the overexpressed DXP pathway or wild type cells are genetically engineered to limit expression of glucose-6-phosphate isomerase to redirect flux to PPP and ED. Effect and benefit of these mutations can be assessed by measuring isoprene specific productivity.

Section D

Cells in Section A harboring the overexpressed DXP pathway or wild type cells are genetically engineered to limit expression of Gluconate-6-phosphate dehydrogenase (gnd) to limit flux to pentose phosphate and maximize flux to ED. Effect and benefit of these mutations can be assessed by measuring isoprene specific productivity.

Section E

In this section, the DXP precursor pyruvate is adjusted by the level of expression of the mevalonic acid pathway for which pyruvate is the sole precursor. Cells are constructed to overexpress the DXP pathway enzymes as well as the mevalonic acid pathway enzymes and expression of both pathways is adjusted, by choosing the appropriate promoter strengths, such that pyruvate flux is balanced with G-3-P flux and neither precursor accumulates in the cell. Similar, approaches in the presence of zwf, gnd, and pgi mutations, singly or in all possible combination, have potential for improved performance.

Section F

The strains created in Sections B-E, are combined for potential additivity. Combination of zwf and gnd in a overexpressed DXP pathway strain is tested for improved performance of the strain. Similarly, the combination of pgi and gnd is envisaged to provide similar results.

Example 16

Improved Carbon Flux Through the DXP Pathway in Strains Containing PDH E1 E636Q Subunit Variants This example describes methods for the construction of *E. coli* BL21 strains containing pyruvate dehydrogenase E1 subunit (PDH) variants that increase carbon flux through the DXP pathway. In particular, these strains contain a mutant aceE gene, encoding for a PDH variant with an E636Q point mutation which possesses a reduced activity (26% of wild-type PDH activity) for the conversion of pyruvate to acetyl-CoA. In addition, the PDH E636Q variant is thought to have a dxs-like activity that results in the production of 1-deoxyxylulose-5-phosphate (DXP) from the aldol condensation of pyruvate and glyceraldehyde-3-phosphate. The carboligase activity of the pyruvate dehydrogenase E1 E636Q mutant has been reported by Nemeria et al. (J. Biol. Chem., 280(22), 21473-21482 (2005), which is hereby incorporated by reference in its entirety). The net effect is increased carbon flux into the DXP pathway, and reduced carbon flux to acetyl-CoA relative to strains containing wild-type PDH E1 activity.

The construction of *E. coli* BL21 strains containing the PDH E1 E636Q mutant was as described by Sauret-Güeto et al. (FEBS Lett., 580, 736-740 (2006)), which is hereby incorporated by reference in its entirety. Briefly, the chromosomal copy of the dxs gene is disrupted by the insertion of a chloramphenicol acetyl transferase (CAT) containing cassette into the dxs locus of an *E. coli* BL21 strain that contains one or more plasmids encoding a heterologous mevalonic acid pathway (MVA). The resulting *E. coli* BL21 MVA+ (dxs::CAT) strain requires mevalonic acid for normal growth. When the strain is cultured in the absence of mevalonic acid, a suppressor mutation aceE gene arises at a low to moderate frequency that rescues the surviving clones from the otherwise lethal dxs-phenotype. Sequencing of the aceE gene and associated promoter region is performed in order to confirm the presence of the missense mutation that results in the PDH E636Q mutant.

The resulting *E. coli* BL21 dxs::CAT PDH E1 E636Q MVA+ strain is complemented with one or more functional copies of the dxs gene derived from *E. coli* or from a heterologous source as described herein. The resulting strains exhibits improved flux into the DXP pathway relative to strains that do not possess the PDH E1 E636Q variant.

Additionally, the resulting *E. coli* BL21 dxs::CAT PDH E1 E636Q MVA+ strain can be further complemented with one or more functional copies of a DXP pathway gene, a DXP pathway associated gene, an iron-sulfur cluster-interacting redox gene (e.g., fldA or fpr), and/or an IDI gene derived from *E. coli* or from a heterologous source as described herein.

The strains can also be transformed with one or more copies of genes encoding isoprene synthases, for example IspS from *P. alba* or variants thereof as described herein.

These strains produce isoprene by both the DXP and MVA pathways where a greater proportion of isoprene is derived from the DXP pathway relative to the MVA pathway, as compared to strains that do not possess the PDH E636Q variant. The ratio the DXP to MVA carbon flux is determined using isotope-labeling techniques known to those skilled in the art.

The strains can be optionally cured of the MVA pathway encoding plasmids (e.g., CHL18 or any other MVA pathway strains as described in U.S. Patent Application Nos. 61/097,186, 61/097,189, and 61/125,336, which are each hereby incorporated by reference in their entireties) if desired using techniques known to those skilled in the art.

Example 17

Mutation of CRP Increases Flux to the DXP Pathway and Increases the Production of Isoprene Catabolite repression, in which the transcription of sensitive operons is reduced by certain carbon sources, could be a major restriction to flux in the DXP pathway, thereby reducing the amount of isoprene which could be produced.

A CRP (cAMP Receptor Protein)-delete mutant is available from the Keio collection and could easily be assessed for the production of isoprene through the DXP pathway. Impact of its global transcriptional regulation has been studied (Perrenoud and Sauer, *J. Bact.* 187:3171-3179 (2005). which is hereby incorporated by reference in its entirety). Other types of CRP mutants could also be beneficial to the process. One such example is the CRP mutant described by Eppler and Boos (Eppler and Boos, *Mol. Microbiol.* 33:1221-1231 (1999), which is hereby incorporated by reference in its entirety). CRP* is a cAMP-independent CRP variant.

A: Construction of an Isoprene-Producing Crp* Mutant of *E. Coli*

CRP* mutation is introduced by P1 transduction (lysate prepared from *E. coli* strain ET25 (to be obtained from W. Boos)) in an isoprene-producing strain, such as MCM597 (BL21 (DE3)pLysS pET24(MEA)alba-DXS-yIDI) or MCM719 (BL21 gi1.6-yIDI gi1.6-dxs, pTrc(MEA)alba)) to form strains CMP220 and CMP221 respectively.

B: Production of Isoprene in a CRP* Mutant of *E. Coli*, Via the DXP Pathway

Strains CMP220 and CMP221, and strains MCM597 and MCM719, are grown overnight at 30 C, 200 RPM, in HM1 medium (Table 3) plus appropriate antibiotics+10 g/L glucose+1 g/L yeast extract. The morning after, they are resuspended to an OD=0.2 in fresh HM1 medium+appropriate antibiotics+5 g/L glucose+1 g/L yeast extract. Flasks are incubated at 30° C., 200 RPM, and regularly sampled for $OD_{600}$ and isoprene productivity.

TABLE 3

HM1 medium composition

| Compounds | Concentration (g/L) |
|---|---|
| K2HPO4 | 13.6 |
| KH2PO4 | 13.6 |
| MgSO4 * 7H2O | 2 |
| Citric Acid Monohydrate | 2 |
| Ferric Ammonium Citrate | 0.3 |
| (NH4)2SO4 | 3.2 |
| Trace metal solution | 1 ml |

Specific productivity (ug isoprene/OD·h) is increased in strains CMP220 and CMP221 in comparison to strains MCM597 or MCM719.

C: Production of Isoprene in a Crp* Mutant of *E. coli*, via the DXP Pathway, when the Strain is Grown on a Glucose/Xylose Mixture Pretreated biomass samples contain a mixture of glucose, xylose and acetate as the main components. Xylose consumption by *E. coli* is usually prevented in the presence of glucose. The CRP* mutation should be helpful to enhance glucose and xylose coconsumption (Cirino et al. biotech. Bioeng. 95:1167-1176 (2006), which is hereby incorporated by reference in its entirety).

Strains CMP220 and CMP221, and strains MCM597 and MCM719, are grown overnight at 30° C., 200 RPM, in HM1 medium (Table 3) plus appropriate antibiotics+10 g/L glucose+1 g/L yeast extract. The morning after, they are resuspended to an $OD_{600}$=0.2 in fresh HM1 medium+appropriate antibiotics+2.5 g/L xylose and 2.5 g/L glucose+1 g/L yeast extract. Flasks are incubated at 30° C., 200 RPM, and regularly sampled for $OD_{600}$, isoprene productivity and carbohydrate concentration. Carbohydrate concentration is determined by HPLC (Ion exclusion column Aminex HPX-87H, 300 mm×7.8 mm, 0.005 M H2504, 0.6 mL/min as the mobile phase).

While strains MCM597 and MCM719 show a diauxic growth curve, co-consumption of xylose and glucose is increased in strains CMP220 and CMP221. This allows the fermentation to be completed in a shorter time.

Example 18

Increased Isoprene Production in an *E. Coli* Strain with LytBG120D Mutation The primary issues of this concept involve the biochemical determination of the mutant DXP pathway enzyme LytBG120D and whether or not the anticipated function of the LytBG10D enzyme can help serve a relevant aspect of our target DXP pathway strain to be used for BioIsoprene production. In this example, the desired DXP pathway strain is to produce a majority (if not as close to all as possible) of isoprene via the dimethylallyl pyrophosphate (DMAPP) molecule derived directly from the LytBG120D catalysis of (E)-4-hydroxy-3-methylbutyl-2-enyl pyrophosphate (HMBPP); as opposed to DMAPP generated via the IDI enzyme, which isomerizes isopentenyl pyrophosphate (IPP) into DMAPP.

The wild-type LytB of *E. coli* and the LytB enzyme common to a number of other organisms, including plants and algae as well as other bacteria, have been reported to produce both DMAPP and IPP in ratios typically ranging from 1:4 to 1:6 (DMAPP:IPP). The work by Kia-Joo Puan et al. (*FEBS Letters,* 579:3802-3806 (2005), which is hereby incorporated by reference in its entirety) provides in vivo data that supports the hypothesis that the LytBG120D mutant enzyme can produce DMAPP, but can not generate sufficient levels of IPP to support the viability of an *E. coli* deficient for IDI. No in vitro data supporting the suggested activity for LytBG120D has been introduced to the field yet.

Currently, isoprenoid production systems derive the majority of their products from IPP. If the LytBG120D is determined to solely generate DMAPP or a majority of DMAPP relative to IPP, then the use of the lytBG120D allele in a DXP pathway-mediated isoprene production strain may allow the unique generation of an isoprenoid product that is derived almost entirely from DMAPP.

The lytBG12D is generated via PCR-based methods using *E. coli* MG1655 as a template and cloned into an expression vector (pET-15b). For comparison, the wild-type lytB is cloned into the same pET-15b expression vector backbone.

Each construct is moved into BL21 (DE3), or a comparable expression host, once the sequence of the construct has been verified. From the expression strains, LytB and LytBG120D is produced and subsequently purified using standard affinity purification procedures. The protein may need to be reconstituted under anaerobic conditions prior to activity assessment (protocols exist in the literature) for robust enzymatic function to be determined. LytB is a 4Fe-4S cluster containing enzyme and is known to be sensitive to oxygen. Alternatively, LytB and LytBG120D may be able to be assayed directly from cell lysates prior to purification if sufficient activity of each enzyme can be supported under those conditions and if an absence of significant Idi activity can be achieved. Expression of each enzyme is determined and quantified by gel electrophoresis and/or immuno-blot. Activity assays are described in the literature, but briefly may include incubation of each enzyme (purified or contained within a cell extract) in a previously described buffer including the substrate HMBPP and in the absence of Idi activity. After a defined time(s) the ratio of DMAPP to IPP is determined using HPLC methods. The resulting data are the first in vitro results for LytBG120D available to us.

If LytBG120D is found to solely produce DMAPP, or at least produce DMAPP in vast abundance to IPP, then the use of the lytBG120D allele is incorporated in the DXP pathway isoprene production strains. Initially, this is accomplished by overexpressing the lytBG120D gene relative to the wild-type allele under isoprene-production phases within a host background that supports carbon flux through the DXP pathway to isoprene synthase. As a control to assess, any benefits specific to generating increased DMAPP levels relative to IPP that are expected to accompany the overexpression of lytBG120D, a similar strain overexpressing the wild-type lytB gene is also constructed and assessed. The levels of DMAPP and IPP generated by these strains, as well as isoprene and other downstream isoprenoids, are determined by HPLC and/or GC-MS methods.

Our past findings indicate that increased IPP levels are not tolerated well by *E. coli*. Further more, we have seen that increased IPP levels accompanied by a significantly active Idi result in the synthesis of larger downstream isoprenoid products, which also cause a significant decrease in viability. Because LytB produces a majority of IPP to DMAPP, and because the endogenous IdI activity of *E. coli* is minimal, and because DMAPP is the substrate for isoprene synthase, our current DXP system relies on the use of an IdI derived from yeast. The use of LytBG120 in a DXP production strain removes the dependence our current system has on the yeast IdI (if LytBG120D is determined to produce mostly DMAPP). The use of LytBG120 is also expected to reduce the levels of downstream isoprenoid synthesis since IPP, the major subunit of larger isoprenoids, is not abundantly available.

Example 19

Host Change for Relief of Endogenous Regulation of DXP Pathway

The DXP pathway, required for isoprenoids production in most Prokaryotes, is a strongly regulated pathway. Indeed, it is essential but also needed in small amount, as it diverts carbon from the central metabolism intermediates glyceraldehyde-3-P and pyruvate. As such, it might be difficult to escape regulation when working with endogenous genes.

A solution to this problem may be to express the whole DXP pathway from one organism into another host organism, the latter organism being close or far on the phylogenetic tree. These host organisms include, but not limited to industrial organisms, such as *Escherichia coli, Pseudomonas fluorescens, Zymomonas mobilis, Bacillus* sp., *Saccharomyces cerevisiae, Clostridium* sp., *Corynebacterium glutamicum*, and *Saccharomyces cerevisiae*. The fact that all the genes involved in the pathway are cloned from one organism guarantees that the enzymes produced by those genes can work together to produce the end product DMAPP.

A: Construction of a DXP Pathway-Expressing Plasmid by Cloning *E. Coli* DXP Genes A Ptrc promoter, PCR-amplified from plasmid pTrcHis2A (Invitrogen, Carlsbad, Calif.) is cloned into pBBR1-MCS4 plasmid (Kovach et al, Gene, 166:175-176 (1995), which is hereby incorporated by reference in its entirety) multiple cloning site, leaving a PstI site downstream of the promoter. This plasmid is named pBBR4Ptrc. *E. coli* genes yajP (dxs), ispC (dxr), ispD, ispE, ispF, gcpE, lytB and idi are amplified from genomic DNA of *E. coli* MG1655 with primers containing an NsiI site and a RBS on the upstream primer, and a PstI site on the downstream primer. Genes are added one by one to the plasmid. Restriction digestion is used to check and select clones with the right orientation. Alternatively, a terminator is introduced after ispF and a new promoter (e.g. Ptrc) has been introduced in front of an operon constituted from gcpE, lytB and idi. The plasmid thus generated is named pBBR4PtrcDXPc and pBBR4PtrcDXPc2.

B: Construction of a Codon-Optimized DXP Pathway-Expressing Plasmid by Synthetic DNA Synthesis A synthetic operon similar to the one described above is designed and ordered, codon-optimized for *Pseudomonas fluorescens*, from GeneArt (Regensburg, Germany). It is subcloned in plasmid pBBR4Ptrc to generate plasmid pBBR4PtrcDXPa.

C: Expression of *E. coli* DXP Pathway in *Pseudomonas fluorescens*, and its Effect on Isoprene Production An ispS (isoprene synthase from *Populus*) gene codon optimized for *Pseudomonas* (see other *Pseudomonas* patent example) is cloned into plasmid pHRP309 (gentamycin resistant) (Parales and Harwood, Gene 133:23-30 (1993), which is hereby incorporated by reference in it entirety), and transformed by biparental mating into *Pseudomonas fluorescens* ATCC 13525. Plasmids pBBR4PtrcDXPc, PBBR4PtrcDXPc2 and pBBR4PtrcDXPa are transformed in *E. coli* S17-1 by electroporation and selection of transformants on LB+kanamycin 50 ug/ml. The plasmids are then transformed into *Pseudomonas fluorescens* with IspS-expressing pHRP309 by biparental mating and selection on M9 medium+16 mM sodium citrate+kanamycin 50 μg/ml+gentamycin 50 ug/ml, to form strain CMP222, CMP223 and CMP224 respectively.

When strains CMP222, CMP223 and CMP224 are grown in HM1 medium+10 g/L glucose, isoprene specific productivity is higher than for the *Pseudomonas fluorescens* strain devoid of the DXP pathway-expressing plasmids.

Example 20

Identification of Compounds Affecting Production of Isoprene Via the DXP Pathway Isoprene production and growth by a strain of *E. coli* that over-expresses DXP pathway enzymes and isoprene synthase was investigated using 96-well microtiter plates with a range of different carbon, nitrogen or phosphate sources. A number of compounds that affected production of isoprene to a significant degree either positively or negatively were surprisingly identified. Compounds positively or negatively affecting the specific productivity of isoprene may help identify metabolic pathways that affect isoprene production. Such pathways may be implicated directly in the production of isoprene or they may have regulatory roles. The identified compounds or metabolic pathways may be modified for example by genetic modification to optimize the production of isoprene. The identified carbon, nitrogen or phosphate sources may also be supplemented directly to the media for increased production of isoprene.

Experimental Procedure:

TM3 Media Recipe (Per Liter Fermentation Media):

$K_2HPO_4$ 13.6 g, $KH_2PO_4$ 13.6 g, citric acid monohydrate 2 g, ferric ammonium citrate 0.3 g, $(NH_4)_2SO_4$ 3.2 g, 1000× Trace Metal Solution 1 ml. All of the components were dissolved sequentially in $diH_2O$. The pH was adjusted to 6.8 with ammonium hydroxide (30%) and brought to volume. Media was filter sterilized with a 0.22 micron filter. Before use, $MgSO_4$*$7H_2O$ 2 g, yeast extract 0.2 g was added to the media. Carbon source was added to a final concentration of 0.5% if needed. Required antibiotics were added after sterilization and pH adjustment.

1000× Trace Metal Solution (Per Liter Fermentation Media):

Citric Acids*$H_2O$ 40 g, $MnSO_4$*H2O 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BSO_3$ 100 mg, $NaMoO_4$* $2H_2O$ 100 mg. Each component was dissolved one at a time in $diH_2O$, pH to 3.0 with HCl/NaOH, and then brought to volume and filter sterilized with 0.22 micron filter.

Strain:

MCM597

(i) Construction of MCM597 (BL21 (DE3) pLysS pet24 (MEA)albadxsyIDI

Construction of pDU-39

```
Primer sequences:
Alba TRC(MEA)-NdeI-F
                                        (SEQ ID NO: 104)
5'-gaaactgaaaccCATATGgaagctcgtcgttctgc

Alba FLTRC (-) TEV-R
                                        (SEQ ID NO: 105)
5'-cccgcgcttaCTCGAGgcgttcaaacggcagaatcggttcagtg
```

A truncated version of the *Populus* alba isoprene synthase was created by amplifying the gene using the primer set Alba TRC(MEA)-NdeI-F/Alba FLTRC(−) TER-R and the template pET24 alba HGS (described in Example 10, U.S. patent application Ser. No. 12/335,071, which is hereby incorporated in its entirety). The PCR reaction was set up as follows:

1 ul (pET24a-P. alba)
5 ul 10X PfuUltraII Fusion buffer
1 ul dNTP's (10 mM)
1 ul primer (50 uM) Set #1 forward
1 ul primer (50 uM) Set #1 reverse
41 ul diH2O
+1 ul of PfuUltra II Fusion DNA Polymerase from Stratagene Cycle Parameter:

95° C. 1 min. [95° C. 30 sec., 55° C. 20 sec., 72° C. 25 sec]×29 cycles, 72° C. 3 min, 4° C. until cool, (Eppendorf Mastercycler)

The PCR products were digested with NdeI-XhoI restriction endonucleases (Roche) and gel purified using the QIAquick Gel Extraction Kit (Qiagen) according to the manufacturer's instructions. An aliquot of 3 ul of the purified product was ligated using T4 ligase (New England BioLabs) to pET-24a vector (Invitrogen) that was previously digested with NdeI-XhoI, gel purified and treated with Shrimp Alkaline Phosphatase (SAP, Roche). The ligation was carried out overnight at 16° C.

An aliquot of 5 uL of the overnight ligation mixture was transformed into TOP10 cells (Invitrogen) and transformants were selected on L agar containing kanamycin (50 ug/ml) at 37° C. overnight.

Plasmids were isolated from a few of the transformants using the QiaQuick Spin Kit (Qiagen) according to the manufacturer's instructions. The insert was verified by digestion NdeI-XhoI restriction endonucleases and the clones were sequenced with the commercially available T7 promoter and T7 terminator (Quintara Bio Sequencing Service, Berkeley, Calif.).

Figure 69:
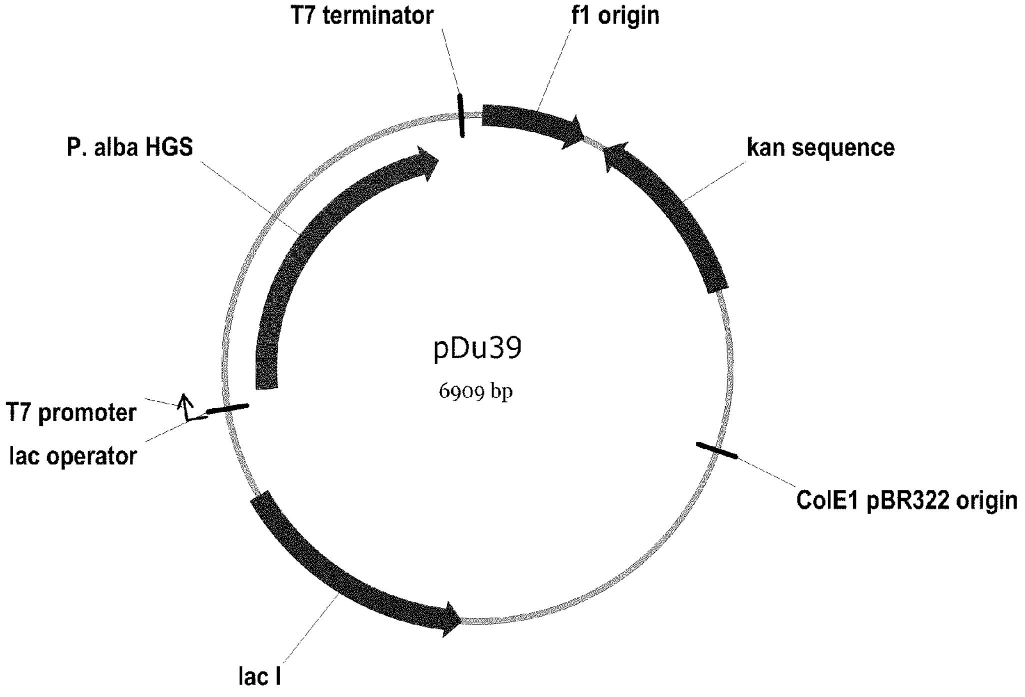
FIG. 69 is a map of pDu-39.
Figure 70:
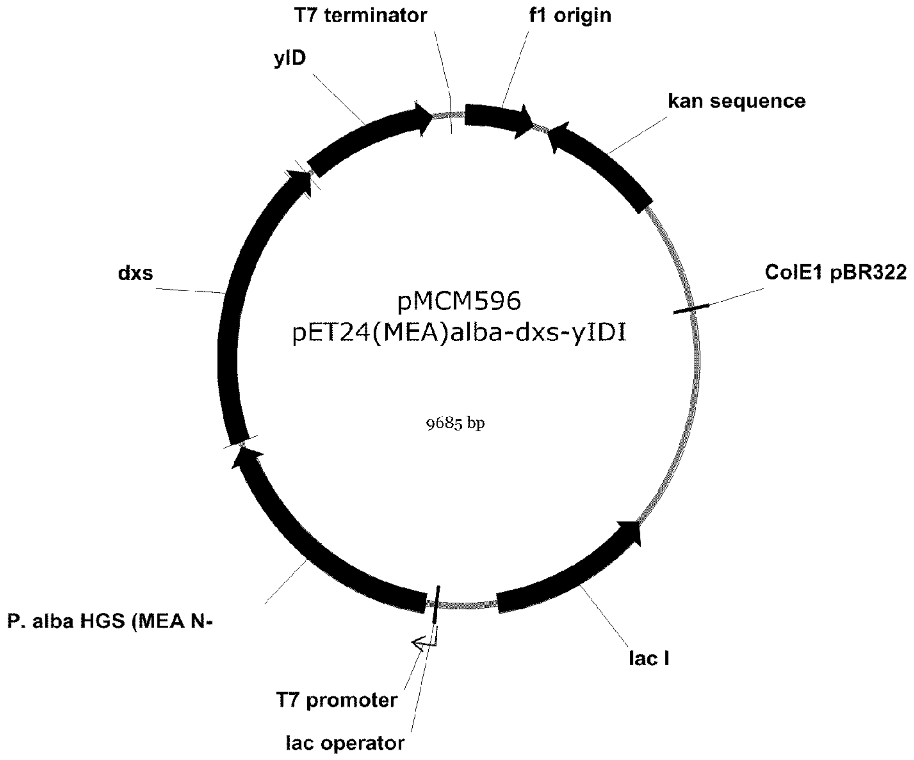
FIG. 70 is a map of pMCM596 pET24(MEA)alba-dxs-yIDI.
Figure 76:
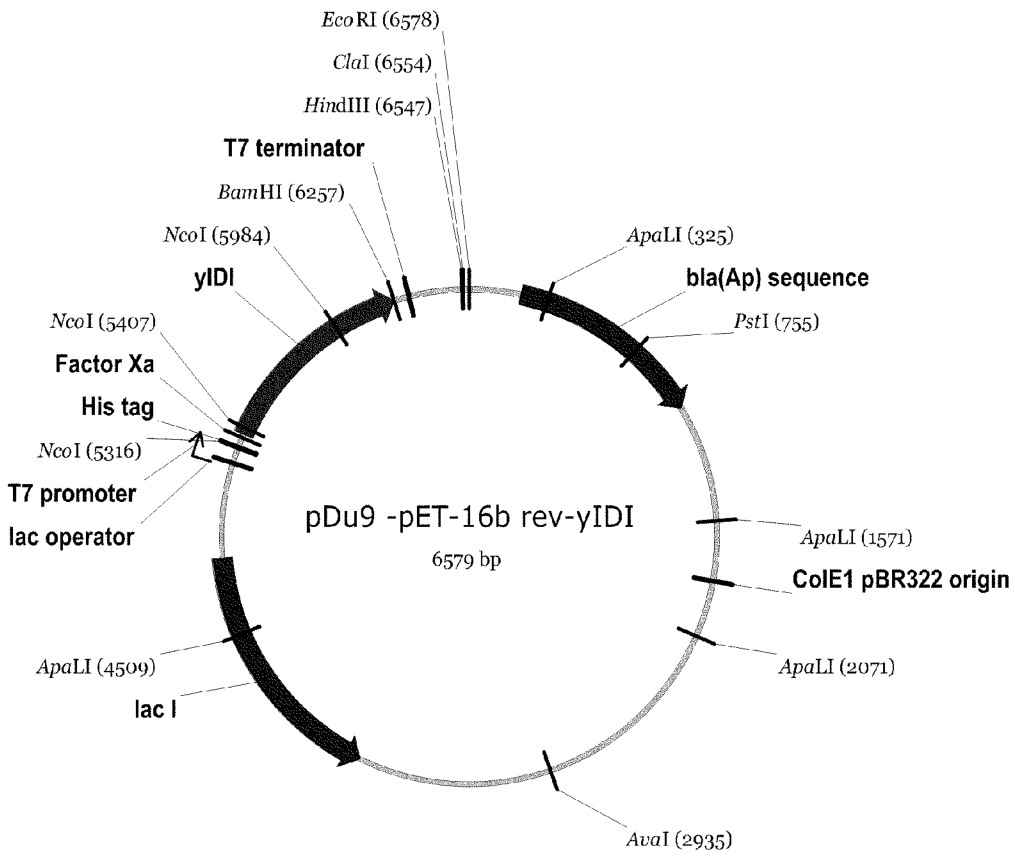
FIG. 76 is a map of pDu9-pET-16b rev-yIDI.

The correct plasmid was designated pDu-39 (FIG. 69)

Construction of MCM597

```
Primer Sequences
MCM270
                                        (SEQ ID NO: 106)
5'-GATCGGATCCATTCGCCCTTAGGAGGTAAA

MCM271
                                        (SEQ ID NO: 107)
5'-GATCGCGGCCGCCAGCTGCAGGACGCGTTGTTATAGCATT
```

The DXS-yIDI genes were amplified by PCR using primers MCM270/MCM271 and the template pMCM72 (described in Example 7 U.S. patent application Ser. No. 12/335,071, which is hereby incorporated by reference in its entirety). Two identical PCR reactions were set up according to the manufacturer's protocol for Herculase II Fusion (Stratagene). 35 uL water, 10 uL buffer, 1.25 uL each primer, 0.5 uL dNTPs, 1 uL polymerase. Reactions were cycled: 95C, 2:00; (95C 0:15, 55C 0:15, 72C 1:45)×30; 72C 3:00, 4C until cold.

The resulting PCR fragment was digested with BamHI and NotI (Roche), and then ligated using Roche Rapid Ligation Kit into pDu39 that had been digested with the same restriction endonucleases. The ligation reaction was set up in 10 uL containing 5 uL Buffer 1, 1 uL vector, 3 uL insert and 1 uL ligase and incubated for 1 hour at room temperature. An aliquot of 5 uL was transformed into *E. coli* Top10 chemically competent cells (Invitrogen). Transformants were selected on L agar containing kanamycin (50 ug/ml) at 37° C. overnight. Plasmids were purified from a few transformants and screened for the presence of insert using Herculase II Fusion (Stratagene). 17.5 uL water, 5 uL buffer, 0.625 uL each primer, 0.25 uL dNTPs, 0.5 uL polymerase. Reactions were cycled: 95C, 2:00; (95C 0:15, 52C 0:15, 72C 0:45)×30; 72C 3:00, 4C until cold. Clones with a PCR product near 1.5 kbp were sequenced (Quintara Biosciences, Berkeley Calif.). A correct plasmid was designated MCM596. The plasmid was then transformed into electrocompetent BL21 (DE3)pLysS cells (Invitrogen) and transformants were selected on L agar containing kanamycin (50 ug/ml) and chloramphenicol (35 ug/mL). One colony was selected and designated MCM597.

Experimental Protocol

An inoculum of the *E. coli* strain MCM597 over-expressing the DXP pathway enzymes dxs from *E. coli* and idi from *Saccharomyzes cereviciae* and the isoprene synthase ispS from *Populus alba* was taken from a frozen vial and streaked onto an LB broth agar plate (with antibiotics) and incubated at 30° C. overnight. A single colony was inoculated into TM3 media containing glucose as the only carbon source and grown overnight at 30° C. The overnight cultures were washed by centrifugation and resuspended into fresh TM3 media containing no glucose or yeast extract. The bacteria were then diluted into 20 mL of TM3 media to reach an optical density of 0.05 measured at 600 nm. For experiments testing the effect of different nitrogen sources using the Biolog PM3B microtiter plates (Biolog, USA), the bacteria were diluted into media containing 0.5% glucose and no yeast extract. For experiments testing the effect of different carbon sources using the Biolog PM1 and PM2A microtiter plates (Biolog, USA), the bacteria were diluted into media containing 0.2% yeast extract and either no or 0.5% glucose. A total of 120 μL of culture was dispensed into each well of the Biolog plates and the plate was incubated on an orbital shaker (250 rpm) at 30° C. The optical density was measured in the wells at 600 nm using a 384 well microtiter plate reader (Molecular Devices, Spectramax Plus 384) in the beginning of the experiment and every hour thereafter to follow growth of the bacteria. None of the compounds in the biolog plates were found to interfere with the optical density measurement at 600 nm. After four to six hours of growth, the optical density was measured again and two times 50 μL was transferred to two 96 well quartz glass blocks (Zinsser, Germany) and sealed with Biomek aluminum foil tape lids (Beckman Coulter, USA). The glass blocks were shaken at 450 rpm at 30° C. for 30 minutes and then heat treated for 12 minutes at 70° C. The produced isoprene was measured using a GC-MS (GC 7889A and MSD 5975C, Agilent Technologies, USA). To account for differences from glass block to glass block, the isoprene measurement was normalized to the block average. The specific isoprene productivity was calculated by dividing the isoprene production with the optical density for each well. Each Biolog experiment was performed in duplicate. Statistical analysis (students T-test) was used to identify compounds in the microtiter plates that affected specific isoprene productivity with statistical significance ($p<0.1$).

Results

Nitrogen Sources Affecting Isoprene Production:

When *E. coli* harboring the DXP pathway and isoprene synthase was grown on 0.5% glucose as the sole carbon source in media lacking yeast extract, a number of nitrogen containing compounds were found to either positively or negatively affect the production of isoprene through the DXP pathway. The PM3B plates from Biolog were used for these experiments. Statistical analysis was used to identify compounds that most significantly affect isoprene production (Table 4). The addition of nitrite, nitrate, ammonia and urea did not significantly change the specific isoprene production, suggesting the bacteria were not directly lacking nitrogen in the fermentation media. Compounds increasing the specific production of isoprene surprisingly include L-glutamic acid, L-aspartic acid, the purines inosine and guanosine, L-threonine, L-serine, L-tryptophan and L-asparagine. Compounds negatively affecting specific isoprene productivity particularly include adenine, and L-methionine, and L-tyrosine among others. Some of these compounds are involved in purine and thiamine biosynthesis, which are related to the DXP pathway, and may as such play important roles in the regulation of the DXP pathway.

Carbon Sources Affecting Isoprene Production During Growth on Glucose:

When *E. coli* harboring the DXP pathway and isoprene synthase was grown on 0.5% glucose in fermentation media containing 0.2% yeast extract, a range of carbon sources were found to affect the specific productivity of isoprene through the DXP pathway to a surprisingly high degree. The PM1 and PM2A carbon source plates from Biolog were used for these experiments. Statistical analysis was used to identify compounds that most significantly affect isoprene production (Table 5). Compounds most significantly increasing specific productivity of isoprene include, but are not limited to, phenylethylamine, propionic acid, D-galacturonic acid, inosine, L-galactonic acid-γ-lactone, D-psicose, glucuronamide, 2-aminoethanol, D-cellobiose, sucrose, mucic acid, L-malic acid, L-phenylalanine, 2,3-butanediol, L-ornithine, D-gluconic acid, D-glucosaminic acid, D-mannose. It is to be expected that the addition of these compounds to glucose fed fermentations would increase the specific productivity of isoprene. A range of other compounds were found to negatively affect specific productivity (Table 5). These effects may be caused by regulatory roles of the compounds or associated metabolic pathways, making these pathways interesting for genetic modification.

Identification of Carbon Sources Useful for the Production of Isoprene:

When *E. coli* harboring the DXP pathway and isoprene synthase was grown in media containing 0.2% yeast extract in micro titer plates containing a range of different carbon sources, it was possibly to identify carbon sources that lead to the production of isoprene with a surprisingly high specific productivity. The PM1 carbon source plate from Biolog was used for these experiments. A range of compounds that lead to a very high specific isoprene productivity is shown in Table 6. Compounds most significantly increasing specific productivity of isoprene include, but is not limited to, D-galacturonic acid, D-trehalose, N-acetyl-D-glucosamine, D-mannitol, D-fructose, D-glucose-6-phosphate, α-D-glucose. The final optical densities of the cultures grown on the different compounds are shown in Table 6. Some of these carbon sources may be used for the production of isoprene.

TABLE 4

| Compound | Isoprene production normalized to negative control | P-value (T-test) |
|---|---|---|
| L-Glutamic Acid | 2.13 | 0.003 |
| Gly-Gln | 1.80 | 0.008 |
| Gly-Glu | 1.48 | 0.008 |
| Ala-Gln | 1.46 | 0.045 |
| Ala-Glu | 1.45 | 0.030 |
| L-Aspartic Acid | 1.42 | 0.007 |
| δ-Amino-N-Valeric Acid | 1.40 | 0.012 |
| Inosine | 1.37 | 0.013 |
| Guanosine | 1.33 | 0.023 |
| Gly-Asn | 1.26 | 0.092 |
| L-Threonine | 1.22 | 0.022 |
| Ethanolamine | 1.22 | 0.055 |
| L-Serine | 1.21 | 0.059 |
| L-Tryptophan | 1.21 | 0.071 |
| Ala-Asp | 1.20 | 0.056 |
| L-Asparagine | 1.16 | 0.023 |
| Nitrate | 1.08 | 0.360 |
| Nitrite | 1.06 | 0.110 |
| Ammonia | 1.01 | 0.837 |
| Negative Control | 1.00 | 1.000 |
| Urea | 0.99 | 0.919 |
| D-Alanine | 0.84 | 0.046 |
| N-Phthaloyl-L-Glutamic Acid | 0.81 | 0.021 |

TABLE 4-continued

| | | |
|---|---|---|
| N-Acetyl-D-Mannosamine | 0.81 | 0.091 |
| Histamine | 0.80 | 0.036 |
| D-Valine | 0.80 | 0.061 |
| Tyramine | 0.76 | 0.037 |
| Ala-Thr | 0.72 | 0.013 |
| β-Phenylethylamine | 0.70 | 0.028 |
| L-Tyrosine | 0.69 | 0.012 |
| Gly-Met | 0.61 | 0.011 |
| D,L-α-Amino-N-Butyric Acid | 0.60 | 0.012 |
| Hydroxylamine | 0.60 | 0.010 |
| L-Methionine | 0.56 | 0.003 |
| Met-Ala | 0.55 | 0.007 |
| α-Amino-N-Valeric Acid | 0.52 | 0.004 |
| Adenine | 0.22 | 0.000 |

Nitrogen sources affecting specific production of isoprene through the DXP pathway in *E. coli*. Only compounds affecting the specific isoprene production with statistical significance ($p < 0.1$) are shown. Nitrate, nitrite, ammonia and urea have been included to illustrate that the addition of general nitrogen sources does not affect specific productivity of isoprene in the fermentation media (marked with grey).

TABLE 5

| Compound | Isoprene production normalized to negative control | P-value (T-test) |
|---|---|---|
| Phenylethylamine | 1.74 | 0.014 |
| Propionic Acid | 1.67 | 0.010 |
| D-Galacturonic Acid | 1.60 | 0.056 |
| Inosine | 1.60 | 0.015 |
| L-Galactonic Acid-γ-Lactone | 1.55 | 0.059 |
| D-Psicose | 1.53 | 0.055 |
| Glucuronamide | 1.50 | 0.093 |
| 2-Aminoethanol | 1.38 | 0.042 |
| D-Cellobiose | 1.38 | 0.044 |
| Sucrose | 1.37 | 0.080 |
| Mucic Acid | 1.35 | 0.095 |
| L-Malic Acid | 1.28 | 0.086 |
| L-Phenylalanine | 1.23 | 0.004 |
| 2,3-Butanediol | 1.22 | 0.044 |
| L-Ornithine | 1.21 | 0.010 |

TABLE 5-continued

| | | |
|---|---|---|
| D-Gluconic Acid | 1.17 | 0.035 |
| D-Threonine | 1.15 | 0.032 |
| D-Lactic Acid Methyl Ester | 1.15 | 0.011 |
| Chondroitin Sulfate C | 1.15 | 0.035 |
| L-Arginine | 1.15 | 0.099 |
| Salicin | 1.13 | 0.063 |
| M-Inositol | 1.13 | 0.033 |
| D-Glucosaminic Acid | 1.13 | 0.002 |
| D-Mannose | 1.11 | 0.036 |
| Negative Control | 1.00 | 1.000 |
| Turanose | 0.94 | 0.042 |
| β-D-Allose | 0.92 | 0.100 |
| L-Isoleucine | 0.90 | 0.040 |
| Sedoheptulosan | 0.89 | 0.049 |
| D-Tagatose | 0.87 | 0.090 |
| L-Arabitol | 0.85 | 0.090 |
| D,L-Malic Acid | 0.82 | 0.031 |
| L-Arabinose | 0.82 | 0.090 |
| a-Methyl-D-Glucoside | 0.82 | 0.068 |
| Stachyose | 0.82 | 0.033 |
| D-Glucose-6-Phosphate | 0.81 | 0.041 |
| D-Ribose | 0.74 | 0.007 |
| D-Galactose | 0.72 | 0.011 |
| Lacitol | 0.70 | 0.031 |
| β-Methyl-D-Galactoside | 0.70 | 0.011 |
| β-Methyl-D-Xyloside | 0.68 | 0.085 |
| α-Methyl-D-Galactoside | 0.62 | 0.062 |
| 2,3-Butanone | 0.51 | 0.013 |
| D-Melibiose | 0.49 | 0.001 |
| D-Raffinose | 0.45 | 0.001 |
| 4-Hydroxy Benzoic Acid | 0.41 | 0.005 |
| Sorbic Acid | 0.40 | 0.052 |
| Capric Acid | 0.35 | 0.008 |
| Dihydroxy Acetone | 0.22 | 0.002 |
| 2-Deoxy-D-Ribose | 0.20 | 0.002 |
| 2-Hydroxy Benzoic Acid | 0.18 | 0.000 |
| Caproic Acid | 0.18 | 0.001 |

Carbon sources affecting specific production of isoprene through the DXP pathway in *E. coli* during growth on glucose. All carbon sources are normalized to the negative control that was only fed glucose. Only compounds affecting the specific isoprene production with statistical significance ($p < 0.1$) are shown. Negative control is marked with grey.

TABLE 6

| Compound | Isoprene production normalized to α-D-Glucose | Growth OD600 |
|---|---|---|
| D-Galacturonic Acid | 1.36 | 0.217 |
| D-Trehalose | 1.31 | 0.243 |
| N-Acetyl-DGlucosamine | 1.17 | 0.283 |
| D-Mannitol | 1.16 | 0.270 |
| D-Fructose | 1.09 | 0.250 |
| D-Glucose-6-Phosphate | 1.09 | 0.299 |
| α-D-Glucose | 1.00 | 0.279 |
| D-Gluconic Acid | 1.00 | 0.276 |
| Methyl Pyruvate | 0.99 | 0.213 |
| Pyruvic Acid | 0.95 | 0.211 |
| Inosine | 0.93 | 0.191 |
| L-Serine | 0.92 | 0.213 |
| D-Serine | 0.90 | 0.221 |
| Adenosine | 0.88 | 0.187 |
| L-Glutamic Acid | 0.78 | 0.194 |
| α-D-Lactose | 0.75 | 0.198 |
| Thymidine | 0.66 | 0.202 |
| D-Fructose-6-Phosphate | 0.66 | 0.172 |
| Mucic Acid | 0.62 | 0.167 |
| 2-Deoxy Adenosine | 0.57 | 0.160 |
| Dulcitol | 0.53 | 0.182 |
| D-Glucose-1-Phosphate | 0.49 | 0.167 |
| m-Hydroxy Phenyl Acetic Acid | 0.48 | 0.170 |
| Propionic Acid | 0.35 | 0.131 |
| Sucrose | 0.31 | 0.147 |
| M-Tartaric Acid | 0.24 | 0.144 |
| Negative Control | 0.17 | 0.145 |

Carbon sources leading to a high specific production of isoprene in *E. coli* that over-expresses enzymes from the DXP pathway and isoprene synthase. The specific isoprene productivity was normalized to α-D-glucose. The final optical density (OD600) of the cultures is also shown in the table, indicating the growth of *E. coli* on the specific carbon sources. The negative control was not fed any carbon source and is marked with grey.

Example 21

Increased Expression of Fpr Improves Isoprene Production

In this example, we demonstrate an increase in activity of the GcpE and LytB enzymes of the DXP pathway by providing more of an essential auxiliary factor, Fpr, which has been shown to positively influence their in vitro and in vivo activities (Seemann, M. et al. Agnew. *Chem. Int. Ed.,* 41: 4337-4339 (2002); Wolff, M. et al. *FEBS Letters,* 541: 115-120 (2003), which are hereby incorporated by reference in their entireties). Fpr provides the necessary electrons derived from NADPH via FldA for GcpE and LytB to perform their catalytic functions (reviewed in report by L. A. Furgerson, *The mevalonate-independent Pathway to Isoprenoid Compounds: Discovery, Elucidation*, and Reaction Mechanisms, published Feb. 13, 2006, which is hereby incorporated by reference in its entirety).

The expression of fpr (encoding flavodoxin/ferredoxin NADPH-oxidoreductase) is increased in an engineered, isoprene producing strain of *E. coli*. Our previously tested higher DXP flux strains produce only modest isoprene levels, and are observed to accumulate significant levels of both cMEPP, 2-C-methyl-D-erythritol-2,4-cyclodiphosphate, and HMBPP, (E)-4-hydroxy-3-methylbut-2-enyl diphosphate. The cMEPP and HMBPP DXP intermediates are the substrates of GcpE and LytB, respectively. The increased amount of Fpr may increase the activity demonstrated by the DXP pathway enzymes GcpE and LytB resulting in improved carbon flux to isoprene synthesis in the strain of interest over that of the comparable BL21 (DE3) control strain producing only endogenous levels of Fpr. The improved flux is demonstrated by an increase in isoprene titer.

The flavodoxin/ferredoxin NADPH-oxidoreductase encoded by fpr is intended to be expressed at increased levels from the *E. coli* chromosome by incorporating a constitutive highly active GI1.6-promoter in front of the fpr open-reading frame, while replacing the endogenous promoter sequence. Alternatively, fpr can be expressed ectopically from a multi-copy vector construct. For either method, our goal is to express and accumulate Fpr at a level surpassing that generated from the endogenous fldA locus. Our preliminary qRT-PCR results suggest GI1.6-fpr generates more fpr-transcript than the endogenous locus, and will likely accumulate more Fpr than the control as a result of the increased level of fpr-message. This is confirmed by immuno-blot once we receive the antibodies to Fpr.

Using a BL21 (DE3) high DXP flux strain as the parental host strain, the introduction of the up-regulated fpr locus is assessed for the effects on isoprene production relative to the control strains. In addition, metabolite studies on the DXP intermediates provides insight into the beneficial affects of increased Fpr levels on GcpE and LytB activities.

Initially, the following BL21 (DE3) test strain is constructed and assessed for growth and the production of isoprene relative to the control: BL21 (DE3) GI1.6-dxs GI 1.6-fpr T7-MEARR alba/pBBR1MCS-5. This strain is compared to the parental control strain (BL21 (DE3) GI1.6-dxs T7-MEARR alba/pBBR1MCS-5) for growth, isoprene production, and DXP metabolite accumulation.

Growth

Strains are grown at 30° C. in TM3 liquid media (13.6 g $K_2PO_4$, 13.6 g $KH_2PO_4$, 2.0 g $MgSO_4*7H_2O$), 2.0 g citric acid monohydrate, 0.3 g ferric ammonium citrate, 3.2 g $(NH_4)_2\ SO_4$, 0.2 g yeast extract, 1.0 ml 1000× Modified Trace Metal Solution, adjusted to pH 6.8 and q.s. to $H_20$, and filter sterilized) supplemented to a final concentration with 0.1% yeast extract and 1.0% glucose and including the appropriate antibiotics. Growth is monitored periodically by recording each of the culture's optical density measured at 600 nm using an Eppendorf Biophotometer spectrometer (Eppendorf).

Isoprene Production

Isoprene production is analyzed using a headspace assay. For the shake flask cultures, one ml of a culture is transferred from shake flasks to 20 ml CTC headspace vials (Agilent vial cat#5188 2753; cap cat#5188 2759). The cap is screwed on tightly and the vials incubated at the equivalent temperature with shaking at 250 rpm. After 30 minutes the vials are removed from the incubator and analyzed. The analysis is performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 μm film thickness) is used for separation of analytes. The sampler is set up to inject 500 μL of headspace gas. The GC/MS method utilized helium as the carrier gas at a flow of 1 ml/minutes The injection port is held at 250° C. with a split ratio of 50:1. The oven temperature is held at 37° C. for the 2 minute duration of the analysis. The Agilent 5793N mass selective detector is run in single ion monitoring (SIM) mode on m/z 67. The detector was switched off from 1.4 to 1.7 minutes to allow the elution of permanent gases. Under these conditions isoprene (2-methyl-1,3-butadiene) is observed to elute at 1.78 minutes. A calibration table is used to quantify the absolute amount of isoprene and was found to be linear from 1 μg/L to 200 μg/L. The limit of detection is estimated to be 50 to 100 ng/L using this method. The specific productivity of each strain is reported as ug/L OD Hr. Ratio of 1900 ul headspace: 100 ul broth in assay vials for 30 min. incubation results in the following conversion of isopreneug/L of culture to specific productivity: (isoprene/L determined by GC-MS)×(38)/(OD 600 nm of the culture).

DXP Metabolite Accumulation

The DXP metabolites of the isoprene-producing parental and test strains will be isolated and quantified as follows:

Metabolite Extraction

Cell metabolism is rapidly inactivated by withdrawing 3.5 mL of the culture into a tube filled with 3.5 mL of dry ice-cold methanol. Cell debris is pelleted by centrifugation and the supernatant is loaded onto Strata-X-AW anion exchange column (Phenomenex) containing 30 mg of sorbent. The pellet is re-extracted twice, first with 3 mL of 50% MetOH containing 1 mM $NH_4HCO_3$ buffer (pH=7.0) and then with 3 mL of 75% MetOH/1 mM $NH_4HCO_3$ buffer (pH=7.0). After each extraction, cell debris is pelleted by centrifugation and the supernatants are consecutively loaded onto the same anion exchange column. During the extraction and centrifugation steps the samples are kept at below +4° C. Prior to metabolite elution, the anion exchange columns are washed with water and methanol (1 mL of each) and the analytes were eluted by adding 0.35 mL of concentrated $NH_4OH$/methanol (1:14, v/v) and then 0.35 mL of concentrated $NH_4OH$/water/methanol (1:2:12, v/v/v) mixtures. The eluant is neutralized with 30 μL of glacial acetic acid and cleared by centrifugation in a microcentrifuge.

Metabolite Quantification

Metabolites are analyzed using a Thermo Scientific TSQ Quantum Access mass spectrometer (Thermo Electron Corporation, San Jose, Calif.). All system control, data acquisition, and mass spectral data evaluation are performed using XCalibur and LCQuan software (Thermo Electron Corp). For the LC-ESI-MS/MS method, a chiral Nucleodex β-OH 5 μM HPLC column (100×2 mm, Macherey-Nagel, Germany) equipped with a CC ¾ Nucleodex beta-OH guard cartridge is eluted with a mobile phase gradient shown in Table 7 (flow rate of 0.4 mL/min). The sample injection volume was 10 μL.

TABLE 7

HPLC gradient used to elute metabolites.

| Time, min | Mobile phase, % A (water) | B (100 mM ammonium bicarbonate, pH = 8.0) | C (acetonitrile) |
|---|---|---|---|
| 0.0 | 0.0 | 20.0 | 80.0 |
| 0.5 | 15.0 | 5.0 | 80.0 |
| 4.5 | 37.5 | 12.5 | 50.0 |
| 6.5 | 37.5 | 12.5 | 50.0 |
| 7.0 | 49.5 | 0.5 | 50.0 |
| 12.0 | 34.9 | 0.1 | 65.0 |
| 12.5 | 0.0 | 20.0 | 80.0 |
| 13.0 | 0.0 | 20.0 | 80.0 |

Mass detection is carried out using electrospray ionization in the negative mode. The following m/z values for precursor ions are selected to detect the metabolites of interest in SRM mode: 245.0 for IPP and DMAPP, 381.1 for FPP, 213.0 for DXP, 215.0 for MEP, 260.0 for HDMAPP, and 277.0 for cMEPP. Concentrations of metabolites are determined based on the integrated intensities of peaks generated by $PO_3^-$ product ion (m/z=79.0). Calibration curves obtained by injection of corresponding standards purchased from Echelon Biosciences Inc. Intracellular concentrations of metabolites are calculated based on the assumption that in 1 mL of the culture at OD=200 the integrated volume of all cells is 50 μL

Example 22

Improved Carbon Flux into the DXP Pathway Using a Heterologous DXS

Living organisms synthesize isoprenoids via two distinct pathways: the mevalonate (MVA) pathway and 2-C-methyl-D-erythritol 4-phosphate (MEP) pathway. MEP pathway starts from 1-deoxy-D-xylulose 5-phosphate (DXP), which is synthesized by condensation of pyruvate and glyceraldehyde-3-phosphate. This reaction is catalyzed by 1-deoxy-D-xylulose-5-phosphate synthase (DXS). In some bacteria, including *E. coli*, DXP serves not only as a precursor of isoprenoids but is also used for biosynthesis of two important cofactors: thiamine (vitamin B1) and pyridoxol phosphate (vitamin B6).

The rate of isoprenoid synthesis in *E. coli* is regulated at the level of DXS. One of the mechanisms of this regulation may involve feedback inhibition of DXS activity by metabolites downstream the MEP pathway or/and intermediates of vitamin B1/B6 biosynthesis. Accordingly, the overall flux into the MEP pathway may be increased in *E. coli* by expressing an enzyme from a different organism that is not subject to inhibition by downstream products. Heterologous DXS may also be superior to the native *E. coli* DXS due lower $K_m$ or higher $K_{cat}$ values with respect to pyruvate or glyceraldehyde-3-phosphate. Earlier studies have shown that a single Y392F substitution in the DXS of *E. coli* results in two-fold increase in the activity of the enzyme in vitro, although catalytic properties of the modified enzyme have not been studied in detail.

The choice of the sources of DXS for heterologous expression in *E. coli* can be based on the following considerations (see Table 8). First, organisms which have genome coding for several dxs isogenes can be selected. These organisms include plants (different forms of DXS in plants are classified as DXS1 and DXS2), and bacteria (e.g. species of *Streptomyces*) having two or more dxs isogenes. Second, bacteria in which isoprenoids are synthesized via both the MEP (or DXP) pathway and the MVA pathway can be selected. Third, bacteria, which synthesize isoprenoids via the MVA pathway but contain a copy of the dxs gene in their genome specifically needed to make the vitamin cofactors. The DXS sequence this group of microorganisms is characterized by a significantly shorter loop corresponding to the amino acids 203-242 of *E. coli* DXS sequence (FIG. 74).

In one set of the experiment, DXS from a variety of organisms (examples are listed in Table 8) is introduced into *E. coli* cells over-expressing plant isoprene synthase and isopentenyl-diphosphate delta-isomerase (IDI). (IDI activity in *E. coli* is normally very low; therefore enhanced expression of this enzyme is necessary to provide efficient conversion of isopentenyl-diphosphate into dimethylallyl-diphosphate, the substrate of isoprene synthase.). The resulting strains are tested for isoprene production and accumulation of DXP pathway intermediates, including but not limited to DXP, MEP, 4-(cytidine 5'-diphospho)-2-C-methyl-D-erythritol, 2-phospho-4-(cytidine 5'-diphospho)-2-C-methyl-D-erythritol, 2-C-methyl-D-erythritol 2,4-cyclodiphosphate and 1-hydroxy-2-methyl-2-butenyl 4-diphosphate, and compared to the control strain containing native *E. coli* DXS expressed in the same context as in the tested mutants. Increased concentrations of DXP intermediates and/or elevated rate of isoprene evolution in mutants containing heterologous DXSs indicated that the enzyme from the particular organism has higher activity in *E. coli* and is not subject to feedback inhibition by accumulated products.

In another set of experiments, a set of mutants over-expressing either heterologous dxs genes or dxs from *E. coli* (the control) are introduced into the background *E. coli* strain containing plant isoprene synthase, IDI, and several enzymes of MVA pathway allowing that strain to synthesize excessive amounts of isoprenoids when grown in the media containing exogenous MVA. These strains are tested for the accumulation of the intermediates specific to the DXP pathway. As in the previous case, increased concentrations of DXP intermediates compared to the control showed that DXS from specific organisms have higher activity in *E. coli* than the native enzyme and is not subject to feedback inhibition by isopentenyl-diphosphate and/or downstream isoprenoid products. To verify that a particular mutant have an improved rate of the isoprene production specifically due to the modified DXS, isoprene production rate is measured in cells grown on $^{13}C$-uniformly labeled glucose in the presence of non-labeled MVA. In this case, $^{13}C$ composition of isoprene analyzed by mass spectrometry unequivocally indicated that this compound is synthesized via the DXP pathway from the labeled glucose, not from exogenous non-labeled MVA.

In a third set of experiments, experiments are performed to demonstrate that substitution of the tyrosine at position 392 of *E. coli* DXS for phenylalanine results in higher flux rate into the DXP pathway compared to the wild type enzyme. For this experiment the wild-type and the mutated DXS are over-expressed in an *E. coli* strain containing plant isoprene synthase and IDI. The two strains are compared for isoprene production rate and accumulation of DXP pathway intermediates. Increased concentrations of DXP intermediates and/or elevated rate of isoprene evolution in the strain bearing the superior properties of the engineered enzyme demonstrated the superior attributes of the mutant enzyme.

TABLE 8

Examples of organisms have kinetic properties of DXSs different from that of *E. coli*.

| Organism | Reason |
|---|---|
| *Myxococcus xanthus* DK 1622<br>*Gramella forsetii* KT0803<br>*Flavobacterium johnsoniae* UW101<br>*Lactobacillus johnsonii* NCC 533<br>*Lactobacillus gasseri* ATCC 33323,<br>*Lactococcus lactis* subsp. *lactis* Il1403 | DXS is needed to synthesize vitamin cofactor(s); isoprenoids are made via the MVA pathway |
| *Listeria monocytogenes* EGD-e<br>*Lactobacillus plantarum*<br>*Streptomyces griseolosporeus* MF730-N6 | Both MVA and DXP pathways are present in these organisms |
| *Streptomyces hygroscopicus* NRRL 3418<br>*Streptomyces spheroides* NCIMB 11891<br>*Streptomyces spheroides* NCIMB 11891<br>*Streptomyces griseolosporeus* MF730-N6<br>*Streptomyces coelicolor*<br>*Streptomyces griseolosporeus* MF730-N6<br>DXS type1 and DXS type 2 from higher plants | Organisms have multiple copies of DXS |

Example 23

The Identification of Combinations of Genes, Gene Expression or Mutations that Increase Flux Through the DXP Pathway Populations of cells with a high degree of genotypic diversity are generated to identify combinations of genes, gene expression or mutations that increase flux through the DXP pathway. Three different methods are used in this example. First, combinations of genes, either endogenous to *E. coli* or from heterologous organisms, are assembled using the Multisite Gateway (Invitrogen) procedure and introduced into the *E. coli* screening strain. Second, libraries of genomic DNA, either from *E. coli* or heterologous organisms, are generated and introduced in the *E. coli* screening strain. Third, transposons that can result in either gene disruption or activation due to an internal promoter that is directed towards the inverted repeat of the transposable element are introduced.

A. The Multisite Gateway (Invitrogen) Procedure for Generating Synthetic Operons Genes either endogenous to *E. coli* or from heterologous organisms are assembled into synthetic operons that are subsequently screened for increased flux through the DXP pathway and resulting isoprene production. The Multisite Gateway (Invitrogen) kit provides for a maximum of four discrete DNA "elements" that can be assembled together into one operon. Four genes are individually cloned into pENTR vectors, according to the manufacturer's protocol. For example, the last two genes in the DXP pathway, ispG and ispH are amplified by PCR with appropriate att recombination sites (according to manufacturer's protocol) and variable RBS (see Yarchuk et al., J. of Mol. Biol., 226(3):581-596 (1992), which is hereby incorporated by reference in its entirety) to generate plasmid pools with varying expression levels of each gene. The same procedure is applied to the electron carrier genes fldA and fpr, and the four resulting plasmid pools are recombined together onto Gateway destination vectors (pDEST-14 (Invitrogen), pET54-DEST or pCOLA-2-DEST (Novagen)) according to the manufacturer's protocol. The resulting plasmids harbor four gene operons with varying expression levels of each ORF. The pooled destination vectors are then introduced into *E. coli* strains by selecting for antibiotic resistance markers (kanamycin or ampicillin) and resulting pools are screened by GC-MS (described below).

B. Generation of Genomic Libraries

Genomic DNA either endogenous to *E. coli* or from heterologous organisms is cloned into the pSMART LCKan vector (Lucigen) according to the manufacturer's recommended protocol (see Lynch et al., Nat. Methods, 4(1):87-93 (2007), which is hereby incorporated by reference in its entirety). DNA from *E. coli* BL21 and K12 strains, *B. subtilis, Lb. plantarum, Lb. sakei, P. citrea, S. coelicolor, S. spheroides, L. monocytogenes, A. tumefaciens, S. meliloti*, and *C. jejuni* is used to generate libraries. The genomic DNA inserts of up to 20 kb in size are then introduced into *E. coli* strains for screening. Positive transformants are selected for by introduction of antibiotic resistance (kanamycin), pooled, and screened by GC-MS.

C. Transposon Mutagenesis and Gene Activation

A transposon that can both inactive genes by disruption of the ORF and also drive expression of proximal genes due to an endogenous promoter in the transposable element is introduced into *E. coli* for screening. The custom transposon is generated by inserting either a constitutive or inducible promoter into the MCS of the EZ-Tn5 transposon construction vectors (Epicentre). Examples of internal promoters include PT7, Ptrc, Ptac, Pbad, Plac, PL (phage lambda), the gi series, and Ptet. These promoters are cloned into the transposable element, and the resulting custom transposon is introduced into *E. coli*. Strains harboring transposon insertions are identified by antibiotic resistance, pooled, and subjected to screening by GC-MS.

*E. coli* Strains and Screening

Plasmid pools or transposons are introduced into different *E. coli* strains for screening. Positive transformants are identified by antibiotic resistance markers (typically Kan or Amp) located on the plasmid or within the transposable element. Strains include: A strain harboring a plasmid carrying dxs, dxr, idi, and IspS (isoprene synthase) under control of the T7 promoter; a strain harboring integrated and constitutively expressed dxs, dxr, and idi with ispS also integrated or expressed from a plasmid; a strain expressing the entire DXP operon under the control of the T7 Promoter; any strain harboring the current best conformation of DXP pathway genes for isoprene production, yet still displays clear accumulation of DXP pathway metabolites (e.g. HDMAPP). Individual transformants are pooled (in groups of 100 to 1000 individuals per pool) and screened via GC-MS in a 96-well glass block. The analysis is performed (for the 2 mL and 96-well plate methods) using an Agilent 6890 GC/MS system interfaced with a 5973 MS Leap CTC CombiPAL autosampler operating in headspace mode. An Agilent HP-5 (5% Phenyl Methyl Siloxane (15m×0.25 mm×0.25 uM)) column is used for separation of analytes. The sampler is set up to inject 100 μL of headspace gas. The GC/MS method utilizes helium as the carrier gas at a flow of 1 ml/min. The injection port is held at 250° C. with a split ratio of 50:1. The oven temperature is held at 37° C. for the 2 min duration of the analysis. The Agilent 5793N mass selective detector is run in single ion monitoring (SIM) mode on mass 67. The detector is switched off from 0.00 to 0.44 minutes to allow the elution of permanent gases and on 0.44 mins to 0.60 mins. Under these conditions isoprene (2-methyl-1,3-butadiene) is observed to elute at 0.49 minutes. A calibration table is used to quantify the absolute amount of isoprene and was found to be linear from 0 μg/L to 5600 mg/L (using calibration gas). Positive pools are then re-assayed to confirm any positive effect on isoprene production. The individual plasmids or constructs in strains or pools which display increased isoprene production are identified to determine the precise nature of positive influence on DXP pathway flux.

Genes of Organisms Examined

Genes including, but not limiting to, the following organisms are examined: *Arabidopsis thaliana, Zea mays, Campylobacter jejuni, Sinorhizobium meliloti, Helicobacter pylori Agrobacterium tumefaciens, Deinococcus radiodurans, Bacillus subtilis, Pantoea citrea, Listeria monocytogenes, Lactobacillus* spp., and *Streptomyces* spp.

Materials

Multisite Gateway kit (Invitrogen)

Lucigen (Clonesmart Cloning Kits)—library construction

EZ-Tn5 System (EpiCentre)—gene disruption/activation

Plasmids pET-PT7—driven full DXP pathway plasmid pET-PT7 driven dxs, dxr. idi, ispS pET—best conformation of DXP pathway genes for isoprene production pBBR-PT7 or Ptrc ispS pET-54-DEST, pCOLA-DEST vectors (Novagen)

pDEST14, pDEST15 (Invitrogen)

Example 24

Increased Isoprene Production in REMG39 by Overexpression of GcpE, LytB PetF and PetH of *T. elongatus* BP-1 within CMP272

This example provides further demonstration of increased isoprene production in REMG39 by overexpression of GcpE, LytB PetF and PetH of *T. elongatus* BP-1 within CMP272, a BL21 derived host.

As described and shown infra, increased expression of both dxs and yeast idi allow increased flux through the endogenous DXP pathway of *E. coli*. Previous work by the field (see, for example, Chao et al., *Biotechnol Prog.*, 18(2):394-400 (2002) and Zhang et al., *Protein Expression and Purification,* 29(1): 132-139 (May 2003)) has lead to the conclusion that T7-based expression systems are unstable and their behavior not entirely predictable when subjected to 14-L fermentation conditions. The CMP271 and subsequent CMP272 strain were constructed to: (1) replace our current T7-governed plasmid-based expression of yeast idi with expression originating from the chromosome; permitting the use of a non-T7 based expression strain for DXP-mediated isoprene production and/or (2) introduce the genomically encoded locus harboring the genes for the lower MVA pathway enzymes and yeast IDI to provide sufficient levels of yeast IDI for maximal flux to Isoprene Synthase.

The CMP271 strain was made into an isoprene generating strain by the addition of pDW33, harboring a *P. alba* isoprene synthase allele, via electroporation, and subsequently yielding strain CMP272.

Figure 77:
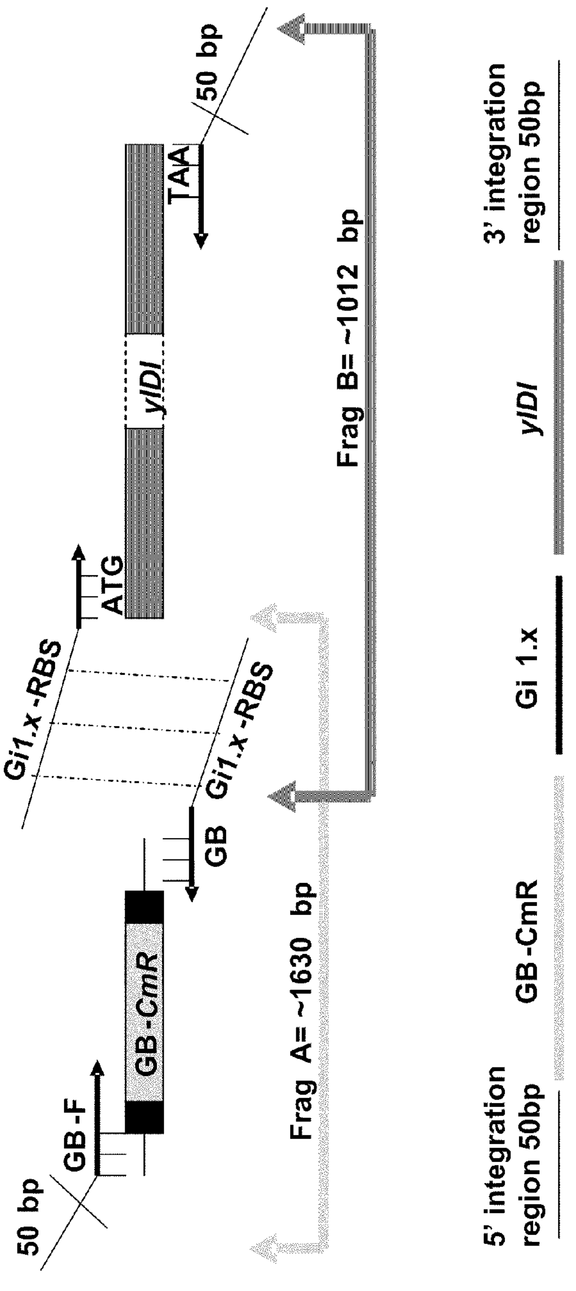
FIG. 77 depicts GB-CMP-GI1.X-yidi construct design. The final construct consists of Fragment A (Frag A) fused to Fragment B (Frag B) to create a GI1.X promoter library transcribing yIDI with the chloramphenicol antibiotic resistance marker upstream, and flanking 50 bp regions of homology to the desired integration site on the chromosome.

The CMP272 strain serves as the baseline host in which isoprene production has been successfully improved by the addition of the *T. elongatus* IspG (GcpE) and IspH (LytB) encoding genes along with their putative reducing shuttle system (PetF and PetH). The construct harboring the *T. elongatus* genes, Ptac-gcpE-lytB-petF-petH/pK184, has been described infra in the example utilizing *T. elongatus*. The parental CMP272 and test strain REMG39 were evaluate for growth, isoprene production, metabolite profile, and product yield on carbon under 14-L fermentation conditions described below. The results are depicted in FIG. 77.

A. Construction of Strains CMP271, CMP272, and REMG39

The GI 1.X-promoter insertions and subsequent loopout of the antibiotic resistance markers described in this example were carried out using the Red/ET system from Gene Bridges GmbH according to the manufacturer's instructions. The strain BL21 (Novagene) was used. P1 lysate preparations and transductions were performed as previously described (Thomason et al., 2007).

```
Primers
MQ09-10F-
                                        (SEQ ID NO: 140)
5'ggttaatcatttcactcttcaattatctataatgatgagtgatcagaa

ttacatgtgagaaattaattaaccctcactaaagggcggccgcgaa

MQ09-10R-
                                        (SEQ ID NO: 141)
5'atattccaccagctatttgttagtgaataaaagtggttgaattatttg

ctcaggatgtggcatNgtcaagggctaatacgactcactatagggctcga

gg

*for the case of GI1.6 N = T in the primer
sequence above.

MQ09-11F-
                                        (SEQ ID NO: 142)
5' gcccttgacNatgccacatcctgagcaaataattcaaccacttttat

tcactaacaaatagctggtggaatatatgactgccgacaacaatagtatg

ccc

*for the case of GI1.6 N = A in the primer
sequence above.

MQ09-11R-
                                        (SEQ ID NO: 143)
5' gatgcgtccagtaaaataagcattacgttatgctcataaccccggca

aatgtcggggatttatagcattctatgaatttg

top Gb's CMP
                                        (SEQ ID NO: 144)
5' ACTGAAACGTTTTCATCGCTC

MQ09-12R-
                                        (SEQ ID NO: 145)
5' gatgcgtccagtaaaataagcattacgttatgctc

galMR
                                        (SEQ ID NO: 146)
5' gtcaggctggaatactcttcg

galMF
                                        (SEQ ID NO: 147)
5' gacgctttcgccaagtcagg
```

The strategy for inserting the GI1.X-yidi series into the *E. coli* idi locus using the Gene Bridges GmbH methods is illustrated in FIG. 77. The antibiotic resistance cassette GB-CMP containing fragment (Frag A) was amplified by PCR using primer sets MQ09-10F/MQ09-10R. The GI1.X-yidi containing fragment (Frag B) was amplified by PCR using primer sets MQ09-11F/MQ09-11R. The GB-CMP-GI1.X-yidi fragment was ultimately generated using the primers MQ09-10F and MQ09-11R. The MQ09-10F and MQ09-11R primers each contain at least 50 bases of homology to the *E. coli* idi locus which allow recombination at the specific sites upon electroporation of the PCR product in the presence of the pRed-ET plasmid.

Amplification of the GB-CMP-GI1.X-yidi Fragment

PCR Reaction for GB-CmR (Frag A)

2 ul (100 ng GB-CmR)
10 ul HerculaseII Buffer
0.5 ul dNTP's (100 mM)
1.25 ul primer (10 uM) MQ09-10F
1.25 ul primer (10 uM) MQ09-10R
2 ul DMSO
32 ul diH2O
+1 ul of HerculaseII fusion from Stratagene PCR Reaction for GB-CmR (Frag B)

2 ul (100 ng GB-CmR)
10 ul HerculaseII Buffer
0.5 ul dNTP's (100 mM)
1.25 ul primer (10 uM) MQ09-11F
1.25 ul primer (10 uM) MQ09-11R
2 ul DMSO
32 ul diH2O
+1 ul of HerculaseII fusion from Stratagene PCR Reaction for GB-CmR (Frag A+B)

1 ul (Frag A)
1 ul (Frag B)
10 ul HerculaseII Buffer
0.5 ul dNTP's (100 mM)
1.25 ul primer (10 uM) MQ09-10F"
1.25 ul primer (10 uM) MQ09-11R
2 ul DMSO
32 ul diH2O
+1 ul of HerculaseII fusion from Stratagene Cycle Parameter:

Frag A (95° C. 2 min., 95° C. 20 sec., 55° C. 20 sec., 72° C. 1 min., 29×, 72° C. 3 min, 4° C. until cool, use Eppendorf Mastercycler)

Frag B (95° C. 2 min., 95° C. 20 sec., 55° C. 20 sec., 72° C. 35 sec., 29×, 72° C. 3 min, 4° C. until cool, use Eppendorf Mastercycler)

Frag A &B (95° C. 2 min., 95° C. 20 sec., 55° C. 20 sec., 72° C. 1.2 min., 29×, 72° C. 3 min, 4° C. until cool, use Eppendorf Mastercycler)

The resulting PCR fragments Frag A, B, and A+B were separated on a 1.2% E-gel (Invitrogen) for verification of successful amplification, and purified using the QIAquick PCR Purification kits according to manufacturer's instructions. The purified stocks of Frag A and Frag B were used in the Frag A+B PCR reaction described above. The resulting purified stock of Frag A+B is referred to as GB-CMP-GI1.X-yidi.

Amplification of the galM Locus of CMP263

One colony of CMP263 was stirred in 30 uL $H_2O$ and then heated to 95° C. for 5 min. The resulting solution was spun down to pellet debris and 2 uL of the supernatant was used as the template in the following PCR reaction:

2 ul colony in $H_2O$ (see above)
5 ul Herculase Buffer
1 ul dNTP's (100 mM)
1 ul galMF primer (10 uM)
1 ul galMR primer (10 uM)
39.5 ul $H_2O$
+0.5 ul of Herculase Enhanced DNA polymerase from Stratagene Cycle Parameter: 95° C.×2 min., [95° C.×30 sec., 52° C.×30 sec., 72° C.×60 sec]×30 cycles; 72° C.×7 min, 4° C. until cool (PCRExpress Thermocycler from ThermoHybaid).

The size of the resulting PCR fragment was determined on a 0.8% E-gel (Invitrogen), using DNA Molecular Weight X (Roche) as a ladder; a corresponding PCR product was not obtained from BL21 cells, as expected for the negative control.

Integration of GB-CMP GI 1.X-yidi PCR Product into BL21/pRed-ET Strain

The pRed-ET vector (Gene Bridges kit) was transformed into BL21 by electroporation using the BIO RAD Gene Pulser system and a transformation protocol suggested by the manufacturer (BIO RAD) resulting in strain MD08-114 (BL21/pRed-ET). Approximately 400 ug of the purified GB-CMP GI 1.X-yidi PCR fragment was electroporated into MD08-114. The transformants were recovered in L Broth and then plated on L agar containing chloramphenicol (5 ug/ml). Chloramphenicol resistant colonies were analyzed by PCR for the presence of the GB-CMP GI 1.X-yidi sequence at the desired locus using the top Gb's CMP and MQ09-12R primers. The PCR fragments from a number of transformants were sequenced using the MQ09-12R and top GB's CMP primers (Quintara; Albany, Calif.) and the various GI1.X-yidi strains of interest identified. One chloramphenicol resistant clone harboring the GI1.6-yidi locus (BL21 FRT-CmR-FRT GI1.6 (A)-yidi) was chosen and designated MD09-211.

B. Strategy for Creating the CMP271 Strain

The GI1.6-dxs::kan locus of strain MCM625, described in Example 9, was introduced into MD09-211 via P1-mediated transduction and the resulting kanamycin and chloramphenicol resistant strain named MD09-221. The antibiotic resistance markers of strain MD09-221 were looped out using pCP20 from the pRed-ET kit according to the manufacturer's instructions (GeneBridges). Transformants of interest were verified by the loss of resistance to chloramphenicol (5 ug/ml) and kanamycin (50 ug/ml); one chloramphenicol and kanamycin sensitive clone was chosen and designated MCM710. The FRT-Neo-FRT PL.2 mKKDyI locus (harboring an additional copy of the yeast idigene) of strain MCM521, described in U.S. Appl. No. 61/289,959, was moved into MCM710 by P1-mediated transduction. One kanamycin resistant clone was chosen and designated MCM783. MCM783 was transduced with a P1 lysate of *E. coli* K-12 MG1655, and selected on M9 medium (Na2HPO4 6 g/L, KH2PO4 3 g/L, NaCl 0.5 g/L, NH4Cl 0.5 g/L, 0.1 mM $CaCl_2$, 2 mM $MgSO_4$)+0.4% w/v galactose. One galactose ultizing clone was chosen and designated CMP263. The presence of the galM locus within the 17,257 by of MG1655 that is not endogenous to BL21, but was now harbored by CMP263, was verified by PCR using the primer set galMF/galMR; this PCR reaction is described above. The kanmycin resistance marker within strain CMP263 was looped out using Gene Bridges GmbH methods. One kanamycin sensitive clone was chosen and designated CMP271.

C. Strategy for Creating the CMP272 Strain

Figure 78:
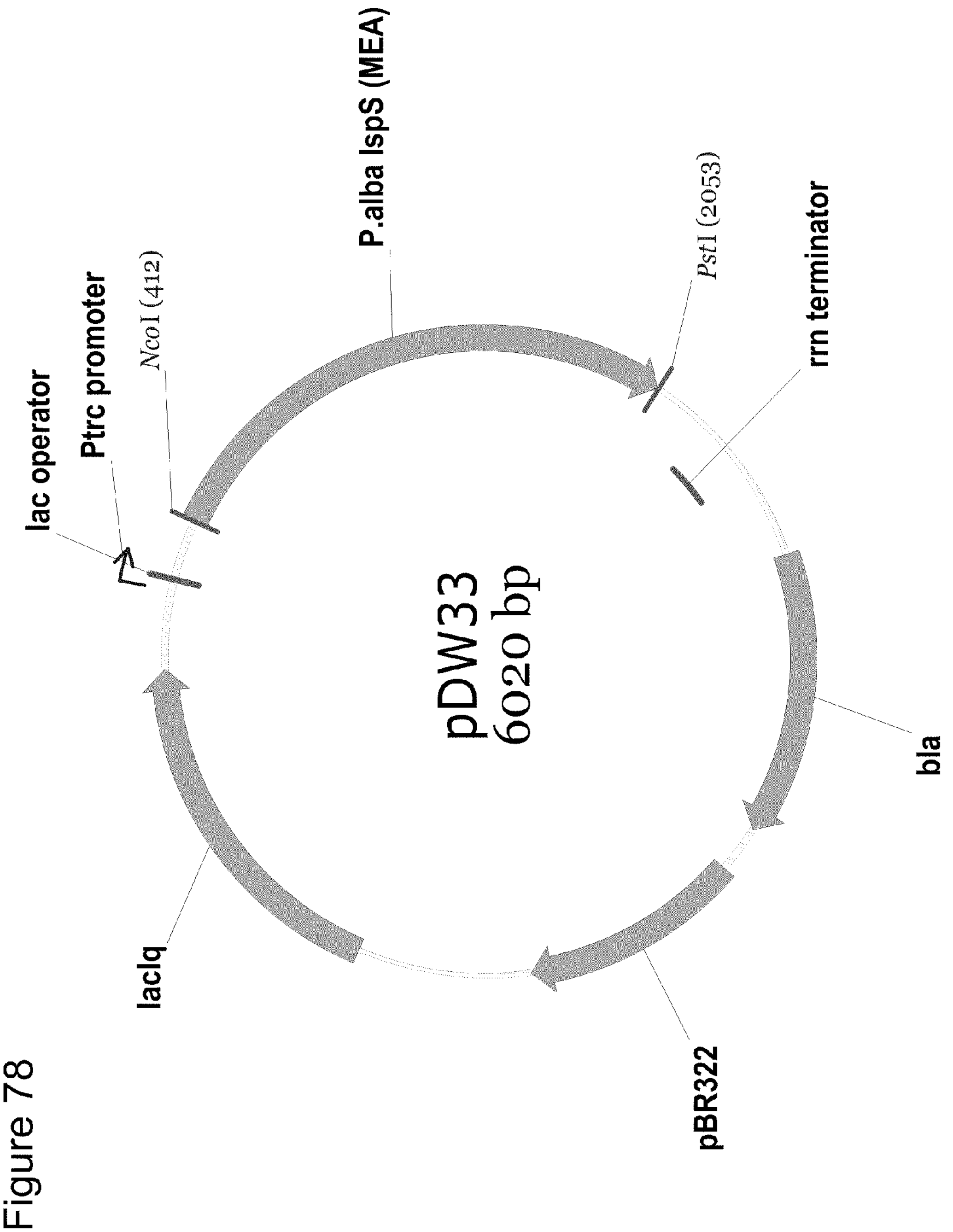
FIG. 78 depicts a plasmid map of pDW33. pBR322—plasmid origin of replication; lacIq-lac repressor; Ptrc—the trc promoter; lac operator—lac repressor binding site; *P. alba* IspS (MEA)—gene encoding the isoprene synthase; rrn terminator—transcription terminator; bla—beta lactamase gene.

Electroporation of pDW33 into strain CMP271 was done using the BIO RAD Gene Pulser system (0.1 cm cuvette cat.#165-2089) and a transformation protocol suggested by the manufacturer (BIO RAD). The vector construct harbors the PTrc-governed MEARR *P. alba* allele encoding a truncated form of Isoprene Synthase. The template for pDW33 construction, EWL230, has been described in US. Publ. No. 2009/0203102 and WO 2009/076676. A picture of the pDW33 vector map is presented in FIG. 78.

Construction of pDW33 pDW33 was constructed in order to generate an isoprene producing *Escherichia coli* strain harboring the truncated version of *P. alba* isoprene synthase (the MEA variant) under control of the Ptrc promoter.

Construction of Strain DW194:

The plasmid harboring truncated *P. alba* isoprene synthase (IspS) was constructed by Quikchange PCR mutagenesis (Stratagene—see Table below for primer sequences) upon the template EWL230 (aka pTrc-*P. alba*). PCR reaction and cycling parameters are described below. The PCR product was visualized by gel electrophoresis (E-gel, Invitrogen), and then treated with 1 µl DpnI restriction endonuclease (Roche) for three hours at 37° C. Ten µl of the PCR product was then de-salted using a microdialysis membrane (MilliPore) and transformed into electrocompetent *E. coli* strain MCM531 (previously described) using standard molecular biology techniques. Cells were recovered in one ml of LB medium for 1.5 hours at 30° C., plated onto LB solid agar plates containing 50 µg/ml carbenicillin and 5 mM mevalonic acid, and then incubated overnight at 37° C. The next day, positive colonies (of strain DW194, see below) were selected for growth and plasmid purification (Qiagen), and ultimately confirmed by DNA sequencing (Quintara) with the primers listed below. The final plasmid, pDW33, carries the open reading frame encoding the truncated version (MEA) of IspS.

```
Primers:
                                          (SEQ ID NO: 148)
QC EWL244 MEA F   gaggaataaaccatggaagctcgtcgttct

                                          (SEQ ID NO: 149)
QC EWL244 MEA R   agaacgacgagcttccatggtttattcctc

                                          (SEQ ID NO: 150)
EL-1006           gacagcttatcatcgactgcacg

                                          (SEQ ID NO: 151)
EL-1000           gcactgtctttccgtctgctgc

                                          (SEQ ID NO: 152)
A-rev             ctcgtacaggctcaggatag

                                          (SEQ ID NO: 153)
A-rev-2           ttacgtcccaacgctcaact

                                          (SEQ ID NO: 154)
QB1493            cttcggcaacgcatggaaat

                                          (SEQ ID NO: 155)
MCM66 (aka pTrc   ccaggcaaattctgttttatcag
Reverse)
```

| Strain | Background | Plasmid | Resistance | Genotype |
|---|---|---|---|---|
| DW194 | MCM531 | pDW33 | Carb | BL21 (Novagen) PL.2mKKDyI, + pTrc-*P. alba*(MEA) |

QuikChange PCR Reaction:
1 ul plasmid EWL230 (aka pTrc *P. alba*)
5 ul 10×PfuUltra HF buffer
1 ul dNTPs (100 mM)
1 ul (50 uM) QC EWL244 MEA F
1 ul (50 uM) QC EWL244 MEA R
2 ul DMSO
39 ul diH2O
1 ul PfuUltra HF Polymerase (Stratagene)
PCR Cycling Parameters:
1. 95° C. 1 min.
2. 95° C. 30 sec.
3. 55° C. 1 min.
4. 68° C. 6 min.
5. Go to step 2—18 cycles
6. 4° C.

```
Sequence of truncated P. alba IspS (MEA)
                                          (SEQ ID NO: 156)
mearrsanyepnswdydyllssdtdesievykdkakkleaevrreinnek

aefltllelidnvqrlglgyrfesdirgaldrfvssggfdavtktslhgt
```

-continued alsfrllrqhgfevsqeafsgfkdqngnflenlkedikailslyeasfla legenildeakvfaishlkelseekigkelaeqvnhalelplhrrtqrle avwsieayrkkedanqvllelaildynmiqsvyqrdlretsrwwrrvgla tklhfardrliesfywavgvafepqysdcrnsvakmfsfvtiiddiydvy gtldelelftdaverwdvnaindlpdymklcflalyntineiaydnlkdk genilpyltkawadlcnaflqeakwlynkstptfddyfgnawksssgplq lvfayfavvqnikkeeienlqkyhdtisrpshifrlcndlasasaeiarg etansyscymrtkgiseelatesvmnlidetwkkmnkeklggslfakpfv etainlarqshctyhngdahtspdeltrkrvlsvitepilpfer Sequence of pDW33:

(SEQ ID NO: 157)

gtttgacagcttatcatcgactgcacggtgcaccaatgcttctggcgtca ggcagccatcggaagctgtggtatggctgtgcaggtcgtaaatcactgca taattcgtgtcgctcaaggcgcactcccgttctggataatgttttttgcg ccgacatcataacggttctggcaaatattctgaaatgagctgttgacaat taatcatccggctcgtataatgtgtggaattgtgagcggataacaatttc acacaggaaacagcgccgctgagaaaaagcgaagcggcactgctctttaa caatttatcagacaatctgtgtgggcactcgaccggaattatcgattaac tttattattaaaaattaaagaggtatatattaatgtatcgattaaataag gaggaataaaccatggaagctcgtcgttctgcgaactacgaacctaacag ctgggactatgattacctgctgtcctccgacacggacgagtccatcgaag tatacaaagacaaagcgaaaaagctggaagccgaagttcgtcgcgagatt aataacgaaaaagcagaatttctgaccctgctggaactgattgacaacgt ccagcgcctgggcctgggttaccgtttcgagtctgatatccgtggtgcgc tggatcgcttcgtttcctccggcggcttcgatgcggtaaccaagacttcc ctgcacggtacggcactgtctttccgtctgctgcgtcaacacggttttga ggtttctcaggaagcgttcagcggcttcaaagaccaaaacggcaacttcc tggagaacctgaaggaagatatcaaagctatcctgagcctgtacgaggcc agcttcctggctctggaaggcgaaaacatcctggacgaggcgaaggtttt cgcaatctctcatctgaaagaactgtctgaagaaaagatcggtaaagagc tggcagaacaggtgaaccatgcactggaactgccactgcatcgccgtact cagcgtctggaagcagtatggtctatcgaggcctaccgtaaaaaggagga cgcgaatcaggttctgctggagctggcaattctggattacaacatgatcc agtctgtataccagcgtgatctgcgtgaaacgtcccgttggtggcgtcgt gtgggtctggcgaccaaactgcactttgctcgtgaccgcctgattgagag cttctactgggccgtgggtgtagcattcgaaccgcaatactccgactgcc gtaactccgtcgcaaaaatgttttctttcgtaaccattatcgacgatatc tacgatgtatacggcaccctggacgaactggagctgtttactgatgcagt tgagcgttgggacgtaaacgccatcaacgacctgccggattacatgaaac tgtgctttctggctctgtataacactattaacgaaatcgcctacgacaac ctgaaagataaaggtgagaacatcctgccgtatctgaccaaagcctgggc tgacctgtgcaacgctttcctgcaagaagccaagtggctgtacaacaaat -continued ctactccgacctttgacgactacttcggcaacgcatggaaatcctcttct ggcccgctgcaactggtgttcgcttacttcgctgtcgtgcagaacattaa aaaggaagagatcgaaaacctgcaaaaataccatgacaccatctctcgtc cttcccatatcttccgtctgtgcaatgacctggctagcgcgtctgcggaa attgcgcgtggtgaaaccgcaaatagcgtttcttgttacatgcgcactaa aggtatctccgaagaactggctaccgaaagcgtgatgaatctgatcgatg aaacctggaaaaagatgaacaaggaaaaactgggtggtagcctgttcgcg aaaccgttcgtggaaaccgcgatcaacctggcacgtcaatctcactgcac ttatcataacggcgacgcgcatacctctccggatgagctgacccgcaaac gcgttctgtctgtaatcactgaaccgattctgccgtttgaacgctaactg cagctggtaccatatgggaattcgaagctttctagaacaaaaactcatct cagaagaggatctgaatagcgccgtcgaccatcatcatcatcatcattga gtttaaacggtctccagcttggctgttttggcggatgagagaagattttc agcctgatacagattaaatcagaacgcagaagcggtctgataaaacagaa tttgcctggcggcagtagcgcggtggtcccacctgaccccatgccgaact cagaagtgaaacgccgtagcgccgatggtagtgtggggtctccccatgcg agagtagggaactgccaggcatcaaataaaacgaaaggctcagtcgaaag actgggcctttcgttttatctgttgtttgtcggtgaacgctctcctgagt aggacaaatccgccgggagcggatttgaacgttgcgaagcaacggcccgg agggtggcgggcaggacgcccgccataaactgccaggcatcaaattaagc agaaggccatcctgacggatggcctttttgcgtttctacaaactcttttt gtttatttttctaaatacattcaaatatgtatccgctcatgagacaataa ccctgataaatgcttcaataatattgaaaaaggaagagtatgagtattca acatttccgtgtcgcccttattcccttttttgcggcattttgccttcctg tttttgctcacccagaaacgctggtgaaagtaaaagatgctgaagatcag ttgggtgcacgagtgggttacatcgaactggatctcaacagcggtaagat ccttgagagttttcgccccgaagaacgttttccaatgatgagcactttta aagttctgctatgtggcgcggtattatcccgtgttgacgccgggcaagag caactcggtcgccgcatacactattctcagaatgacttggttgagtactc accagtcacagaaaagcatcttacggatggcatgacagtaagagaattat gcagtgctgccataaccatgagtgataacactgcggccaacttacttctg acaacgatcggaggaccgaaggagctaaccgcttttttgcacaacatggg ggatcatgtaactcgccttgatcgttgggaaccggagctgaatgaagcca taccaaacgacgagcgtgacaccacgatgcctgtagcaatggcaacaacg ttgcgcaaactattaactggcgaactacttactctagcttcccggcaaca attaatagactggatggaggcggataaagttgcaggaccacttctgcgct cggcccttccggctggctggtttattgctgataaatctggagccggtgag cgtgggtctcgcggtatcattgcagcactggggccagatggtaagccctc ccgtatcgtagttatctacacgacggggagtcaggcaactatggatgaac gaaatagacagatcgctgagataggtgcctcactgattaagcattggtaa -continued

```
ctgtcagaccaagtttactcatatatactttagattgatttaaaacttca
tttttaatttaaaaggatctaggtgaagatcctttttgataatctcatga
ccaaaatcccttaacgtgagttttcgttccactgagcgtcagaccccgta
gaaaagatcaaaggatcttcttgagatcctttttttctgcgcgtaatctg
ctgcttgcaaacaaaaaaaccaccgctaccagcggtggtttgtttgccgg
atcaagagctaccaactctttttccgaaggtaactggcttcagcagagcg
cagataccaaatactgtccttctagtgtagccgtagttaggccaccactt
caagaactctgtagcaccgcctacatacctcgctctgctaatcctgttac
cagtggctgctgccagtggcgataagtcgtgtcttaccgggttggactca
agacgatagttaccggataaggcgcagcggtcgggctgaacggggggttc
gtgcacacagcccagcttggagcgaacgacctacaccgaactgagatacc
tacagcgtgagctatgagaaagcgccacgcttcccgaagggagaaaggcg
gacaggtatccggtaagcggcagggtcggaacaggagagcgcacgaggga
gcttccagggggaaacgcctggtatctttatagtcctgtcgggtttcgcc
acctctgacttgagcgtcgatttttgtgatgctcgtcaggggggcggagc
ctatggaaaaacgccagcaacgcggcctttttacggttcctggccttttg
ctggccttttgctcacatgttctttcctgcgttatcccctgattctgtgg
ataaccgtattaccgcctttgagtgagctgataccgctcgccgcagccga
acgaccgagcgcagcgagtcagtgagcgaggaagcggaagagcgcctgat
gcggtattttctccttacgcatctgtgcggtatttcacaccgcatatggt
gcactctcagtacaatctgctctgatgccgcatagttaagccagtataca
ctccgctatcgctacgtgactgggtcatggctgcgccccgacacccgcca
acacccgctgacgcgccctgacgggcttgtctgctcccggcatccgctta
cagacaagctgtgaccgtctccgggagctgcatgtgtcagaggttttcac
cgtcatcaccgaaacgcgcgaggcagcagatcaattcgcgcgcgaaggcg
aagcggcatgcatttacgttgacaccatcgaatggtgcaaaacctttcgc
ggtatggcatgatagcgcccggaagagagtcaattcagggtggtgaatgt
gaaaccagtaacgttatacgatgtcgcagagtatgccggtgtctcttatc
agaccgtttcccgcgtggtgaaccaggccagccacgtttctgcgaaaacg
cgggaaaaagtggaagcggcgatggcggagctgaattacattcccaaccg
cgtggcacaacaactggcgggcaaacagtcgttgctgattggcgttgcca
cctccagtctggccctgcacgcgccgtcgcaaattgtcgcggcgattaaa
tctcgcgccgatcaactgggtgccagcgtggtggtgtcgatggtagaacg
aagcggcgtcgaagcctgtaaagcggcggtgcacaatcttctcgcgcaac
gcgtcagtgggctgatcattaactatccgctggatgaccaggatgccatt
gctgtggaagctgcctgcactaatgttccggcgttatttcttgatgtctc
tgaccagacacccatcaacagtattattttctcccatgaagacggtacgc
gactgggcgtggagcatctggtcgcattgggtcaccagcaaatcgcgctg
ttagcgggcccattaagttctgtctcggcgcgtctgcgtctggctggctg
gcataaatatctcactcgcaatcaaattcagccgatagcggaacgggaag
gcgactggagtgccatgtccggttttcaacaaaccatgcaaatgctgaat
```

-continued

```
gagggcatcgttcccactgcgatgctggttgccaacgatcagatggcgct
gggcgcaatgcgcgccattaccgagtccgggctgcgcgttggtgcggata
tctcggtagtgggatacgacgataccgaagacagctcatgttatatcccg
ccgtcaaccaccatcaaacaggattttcgcctgctggggcaaaccagcgt
ggaccgcttgctgcaactctctcagggccaggcggtgaagggcaatcagc
tgttgcccgtctcactggtgaaaagaaaaaccaccctggcgcccaatacg
caaaccgcctctccccgcgcgttggccgattcattaatgcagctggcacg
acaggtttcccgactggaaagcgggcagtgagcgcaacgcaattaatgtg
agttagcgcgaattgatctg
```

Transformation of pDW33 into CMP271

This step was done to build the isoprene-producing strain CMP272 the pDW33 plasmid was transformed by electroporation into CMP271. Transformants were recovered in L broth and plated on L agar containing carbenicillin (50 ug/ml). The resulting strain was designated as CMP272.

D. Strategy for Creating the REMG39 Strain

Electroporation of Ptac-gcpE-lytB-petF-petH/pK184 into strain CMP272 was performed using the BIO RAD Gene Pulser system (0.1 cm cuvette cat.#165-2089) and a transformation protocol suggested by the manufacturer (BIO RAD). A plasmid preparation of Ptac-gcpE-lytB-petF-petH/pK184 was provided by Gene Oracle, Inc. Ptac-gcpE-lytB-petF-petH/pK184 has been described infra (see, e.g., Example 11).

Transformation of Ptac-gcpE-lytB-petF-petH/pK184 into CMP272

To build the REMG39 test strain, Ptac-gcpE-lytB-petF-petH/pK184 was transformed by electroporation into CMP272. Transformants were recovered in L broth and plated on L agar containing carbenicillin (50 ug/ml) and kanamycin (50 ug/ml). The resulting strain was designated as REMG39.

Figure 79A:
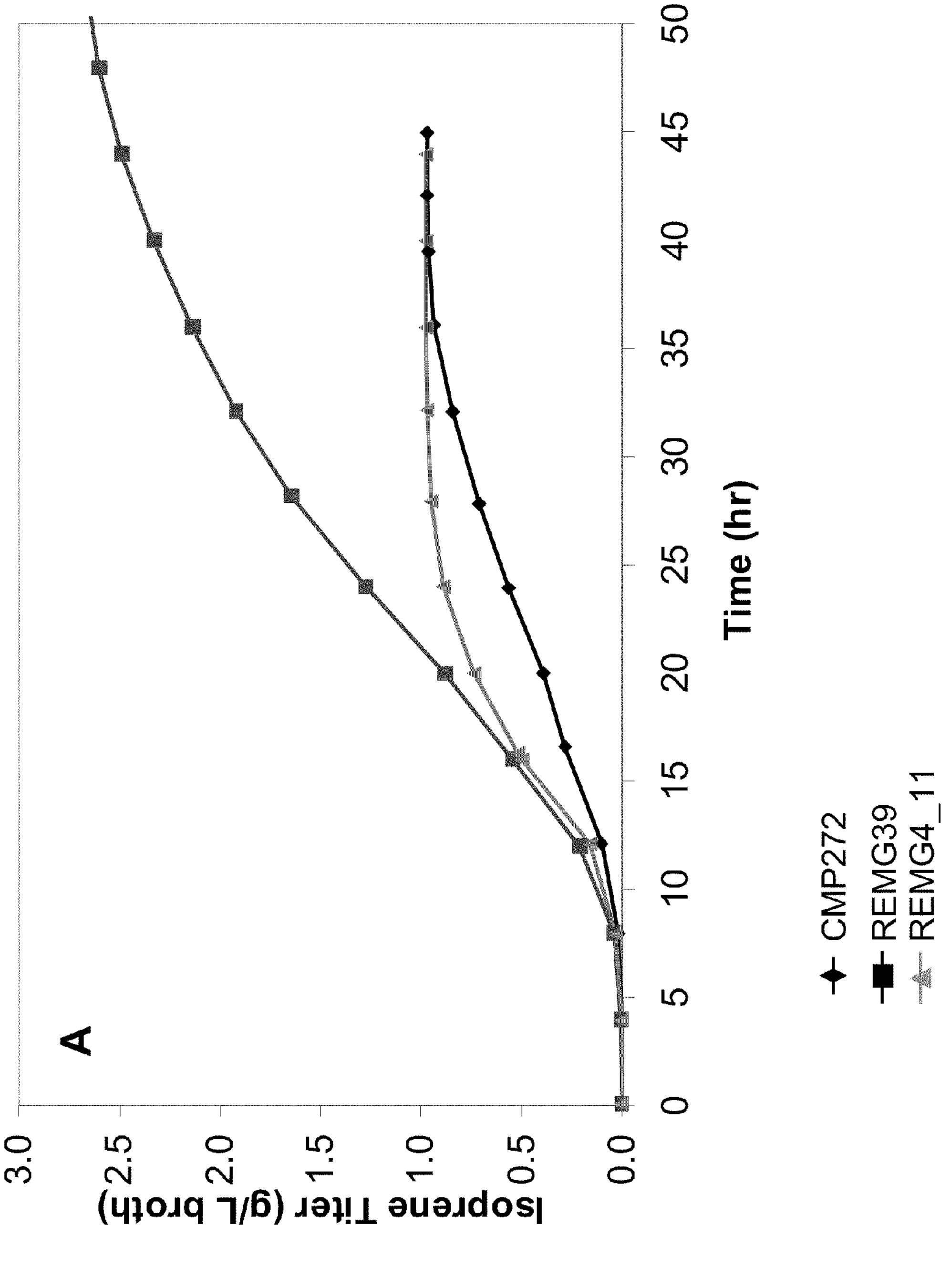
Figure 79B:
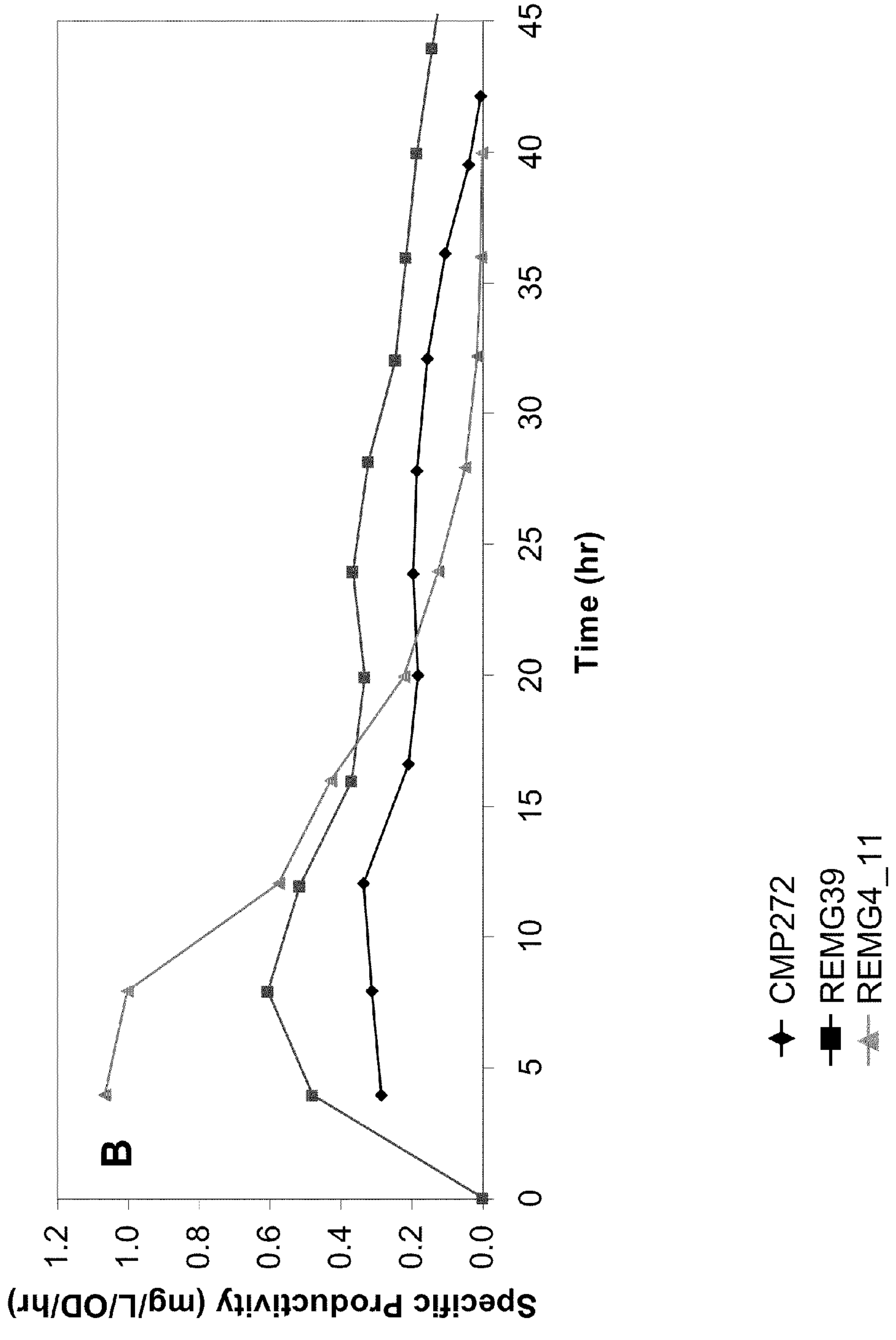
Figure 79C:
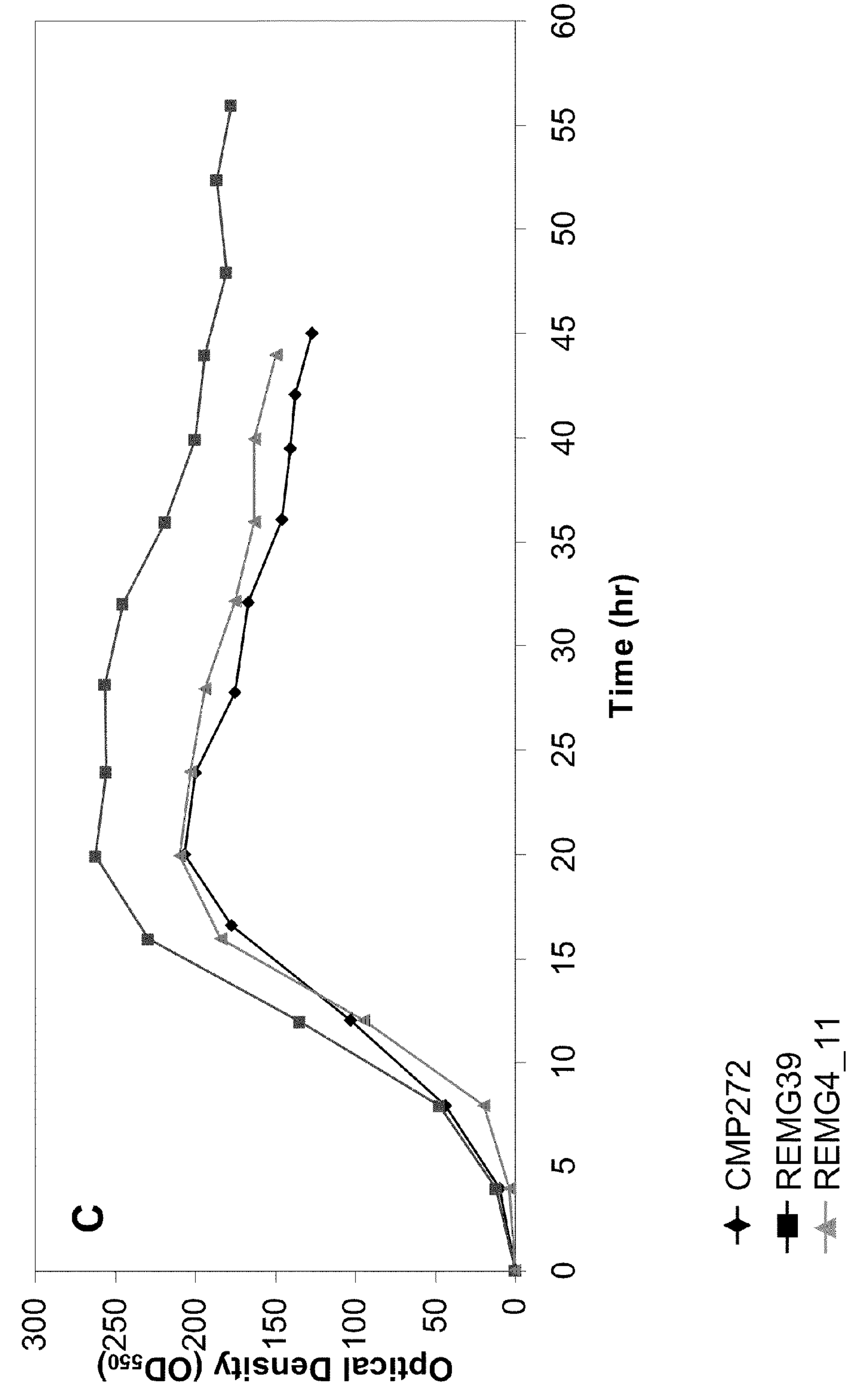
Figure 79:
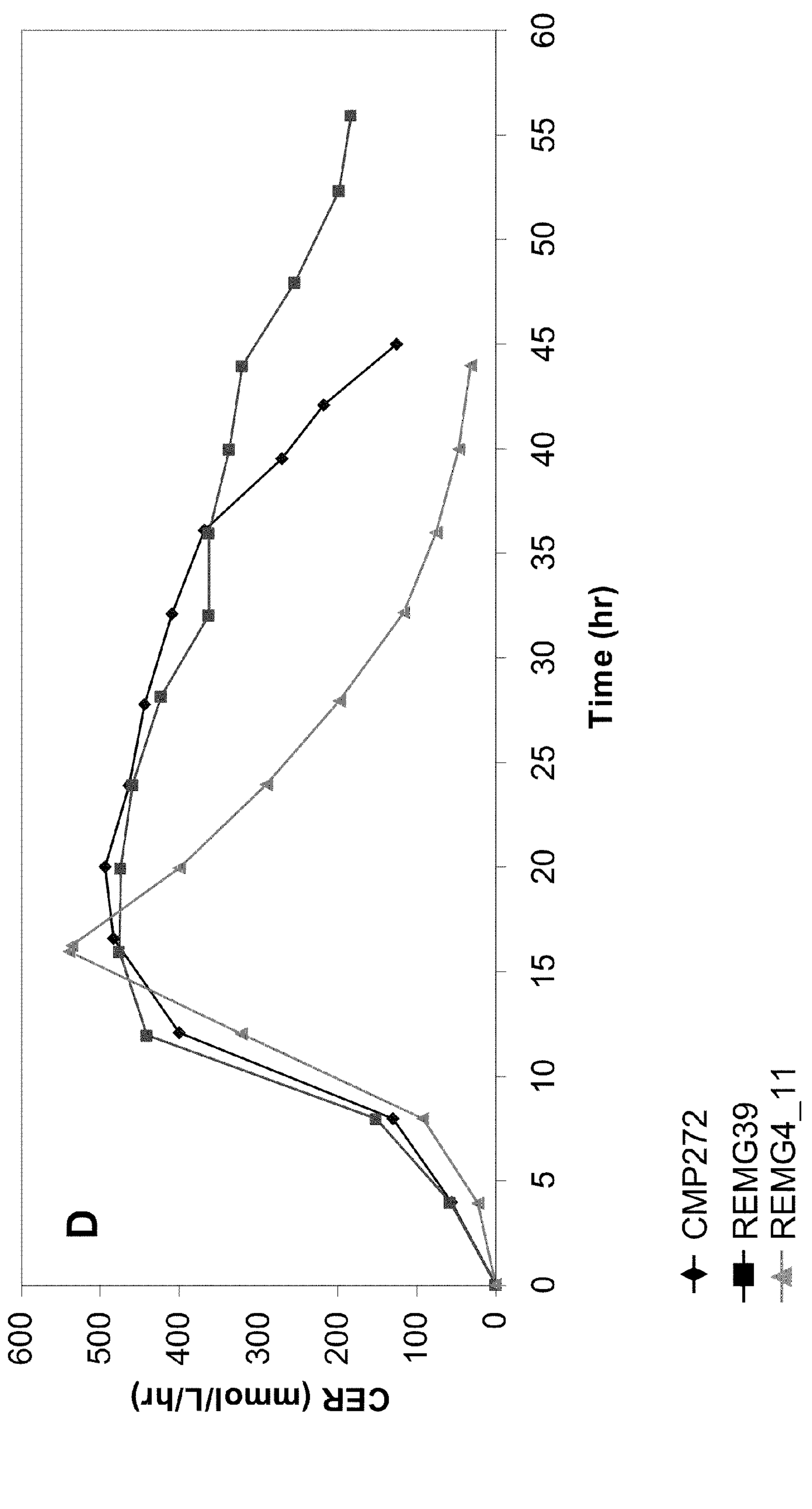
FIG. 79 (includes five panels.
Figure 79:
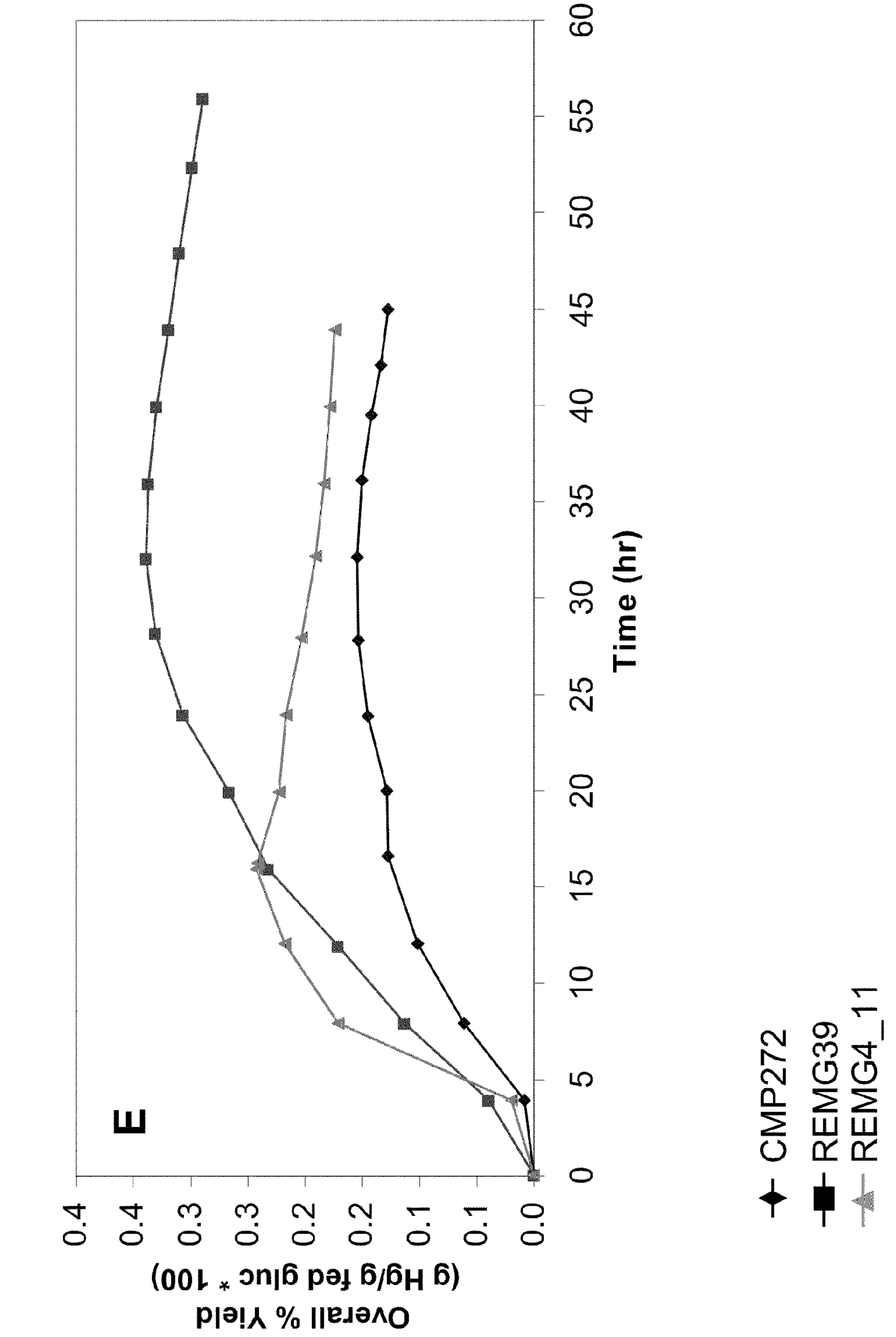
Figure 80A:
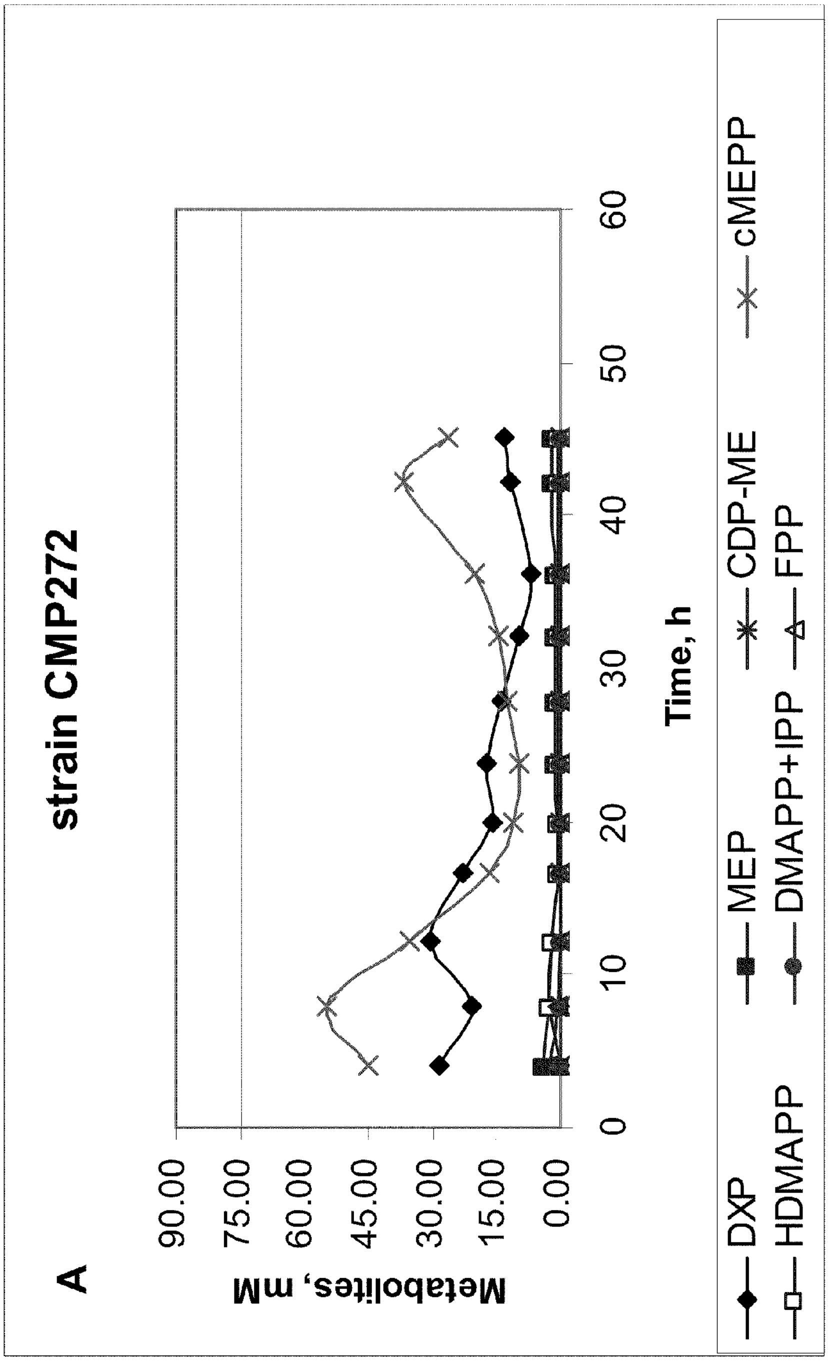
FIG. 80 (includes three panels, 80A, 80B, and 80C) shows the results of large scale fermentation comparison of strains CMP272, REMG39, and REM H8_12 for DXP metabolites. Panels (A-C) The same cells described in FIG. 79 are presented here. A legend describing the metabolite profiles is shown at the bottom of each panel. DXP, 1-Deoxy-D-xylulose 5-phosphate; MEP, 2-C-Methyl-D-erythritol 4-phosphate; CDP-ME, 4-(Cytidine 5'-diphospho)-2-C-methyl-D-erythritol; CDP-MEP, 2-Phospho-4-(cytidine 5'-diphospho)-2-C-methyl-D-erythritol; cMEPP, 2-C-methyl-D-erythritol-2,4-cyclodiphosphate; HDMAPP, 1-Hydroxy-2-methyl-2-buten-4-yl 4-diphosphate; DMAPP, Dimethylallyl diphosphate; IPP, Isopentenyl diphosphate; FPP, faresyl pyrophosphate.
Figure 80B:
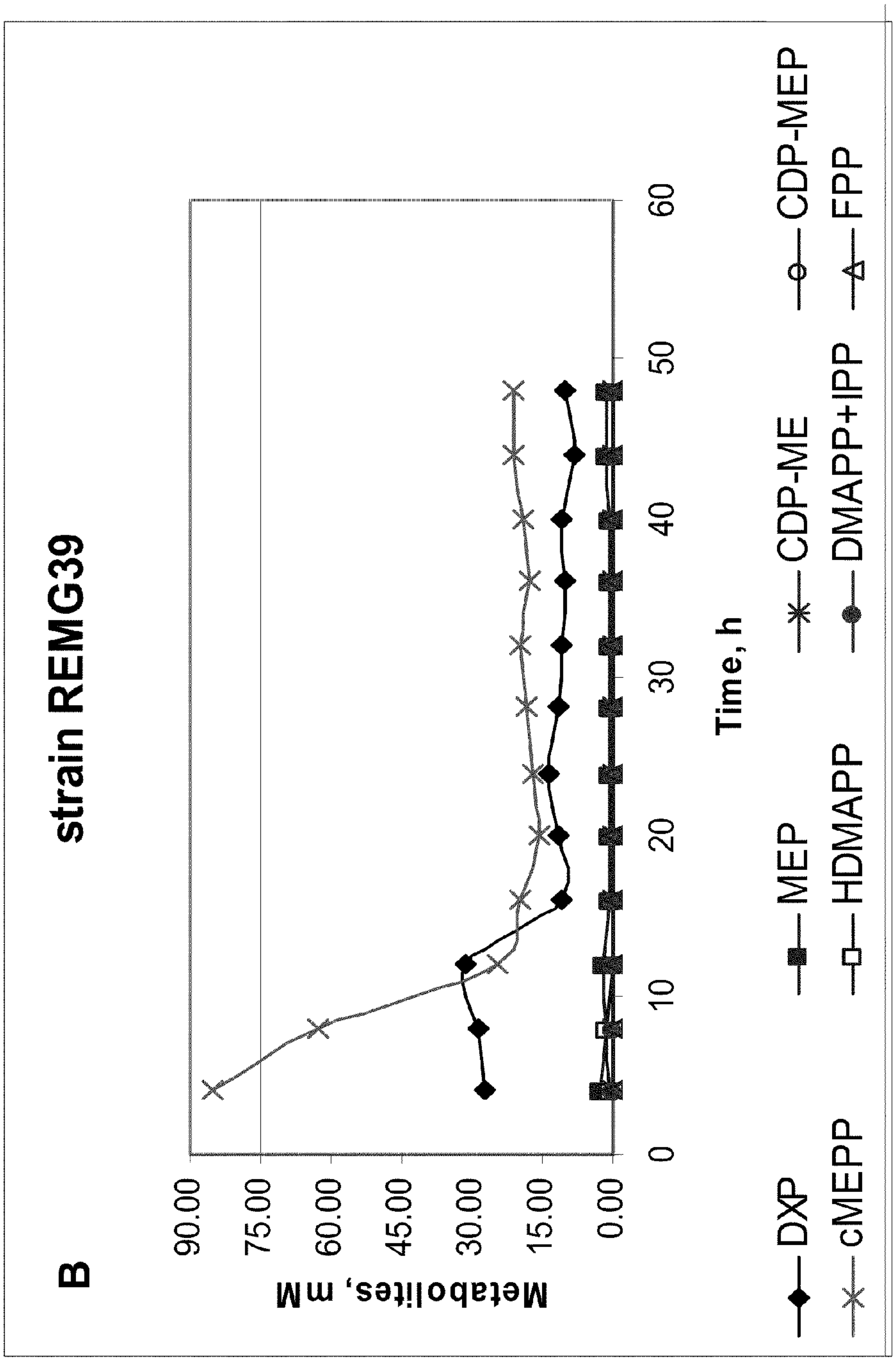

E. Comparing CMP272 to REMG39 for Growth, Isoprene Production, DXP Metabolite Profile, and Product Yield on Carbon During 14-L Fermentation The parental strain CMP272 was compared to the test strain REMG39 under 14-L fermentation conditions. The benefit of the *T. elongatus* IspG (GcpE) and IspH (LytB) activities on isoprene production and overall flux through the otherwise endogenous DXP pathway of *E. coli* is illustrated in FIG. 79 and FIG. 80A-B, respectively. Expression of the *T. elongatus* genes improved isoprene production approximately 2.7-fold over that of the parental strain CMP272. Despite the higher levels of cMEPP observed for the REM G39 strain during the initial 10 hour period, the REMG39 strain accumulated reduced levels of the cMEPP intermediate during the later portion of the fermentation compared to the parental strain, an observation that is correlated with increased specific productivity during post-exponential and maximal CER growth (see FIG. 3B-D).

F. Large Scale Fermentation of Strain CMP272

Isoprene production from *E. coli* expressing genes from the DXP pathway and isoprene synthase, grown in fed-batch culture at the 15-L scale.

Medium Recipe (per liter fermentation medium):

K2HPO4 7.5 g, MgSO4*7H2O 2 g, citric acid monohydrate 2 g, ferric ammonium citrate 0.3 g, yeast extract 5 g, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Mercury Vitamin Solution 8 mL, and antibiotics were added after sterilization and pH adjustment.

1000× Modified Trace Metal Solution (per liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Mercury Vitamin Solution (per Liter):

Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Feed Solution (per Kilogram):

Glucose 0.57 kg, Di H2O 0.38 kg, K2HPO4 7.5 g, and 100% Foamblast 10 g. All components were mixed together and autoclaved. Mercury Vitamin Solution 6.7 mL was added after the solution had cooled to 25° C.

Fermentation was performed in a 15-L bioreactor with *E. coli* BL21 cells overexpressing the first enzyme in the dxp pathway (GI1.6-dxs), the last enzyme in the DXP pathway (GI1.6y-IDI), the lower MVA pathway (PL.2-mKKDyl) and truncated isoprene synthase from *P. alba* (pDW33) and containing a restored 17,257 by chromosomal galM-containing region derived from MG1655 (strain name CMP272). This experiment was carried out to monitor isoprene formation from glucose at the desired fermentation pH 7.0 and temperature 34° C. A frozen vial of the *E. coli* strain was thawed and inoculated into tryptone-yeast extract medium for the bioreactor. After the inoculum grew to optical density 1.0, measured at 550 nm ($OD_{550}$), 500 mL was used to inoculate a 15-L bioreactor and bring the initial tank volume to 5 L.

The feed solution was fed at an exponential rate until a top feed rate of 4.8 g/min was reached. After this time, the glucose feed was fed to meet metabolic demands at rates less than or equal to 4.8 g/min. The total amount of glucose delivered to the bioreactor during the 45 hr fermentation was 5.6 kg. Induction was achieved by adding isopropyl-beta-D-1-thiogalactopyranoside (IPTG). A single shot of IPTG was added to the tank to bring the concentration to 200 uM when the cells were at an OD of 8.

The isoprene level in the off-gas from the bioreactors was determined using a Hiden mass spectrometer. The isoprene titer increased over the course of the fermentation to a maximum value of 0.97 g/L at 45 hr.

Equation for calculating Isoprene Titer: ∫(Instantaneous isoprene production rate, g/L/hr)dt from t=0 to 45 hrs[=]g/L broth Equation for calculating Specific Productivity levels: (mg isoprene$_t$−mg isoprene$_{t0}$)/[OD550$_t$*L broth$_t$−OD550$_{t0}$*L broth$_{t0}$)/(2.7 OD*L/g cell)]/(t−$t_0$) [=]mg isoprene/g cell/hr G. Large Scale Fermentation of Strain REMG39

Isoprene production from *E. coli* expressing genes from the DXP pathway and isoprene synthase, grown in fed-batch culture at the 15-L scale.

Medium Recipe (per liter fermentation medium):

K2HPO4 7.5 g, MgSO4*7H2O 2 g, citric acid monohydrate 2 g, ferric ammonium citrate 0.3 g, yeast extract 0.5 g, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Mercury Vitamin Solution 8 mL, and antibiotics were added after sterilization and pH adjustment.

1000× Modified Trace Metal Solution (per liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Mercury Vitamin Solution (per Liter):

Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Feed solution (per Kilogram):

Glucose 0.57 kg, Di H2O 0.38 kg, K2HPO4 7.5 g, and 100% Foamblast 10 g. All components were mixed together and autoclaved. Macro Salt Solution 3.4 mL, 1000× Modified Trace Metal Solution 0.8 ml, and Mercury Vitamin Solution 6.7 mL were added after the solution had cooled to 25° C.

Macro Salt Solution (per Liter):

MgSO4*7H2O 296 g, citric acid monohydrate 296 g, ferric ammonium citrate 49.6 g. All components were dissolved in water, q.s. to volume and filter sterilized with 0.22 micron filter.

Fermentation was performed in a 15-L bioreactor with *E. coli* BL21 cells overexpressing the first enzyme in the dxp pathway (GI1.6-dxs), the last enzyme in the DXP pathway (GI1.6-yIDI), the lower MVA pathway (PL.2-mKKDyl), various other genes from the DXP pathway of *T. elongatus* (Ptac-gcpE-lytB-petF-petH/pK184), and truncated isoprene synthase from *P. alba* (pDW33) and containing a restored 17,257 by chromosomal galM-containing region derived from MG1655 (strain name REMG39). This experiment was carried out to monitor isoprene formation from glucose at the desired fermentation pH 7.0 and temperature 34° C. A frozen vial of the *E. coli* strain was thawed and inoculated into tryptone-yeast extract medium for the bioreactor. After the inoculum grew to optical density 1.0, measured at 550 nm ($OD_{550}$), 500 mL was used to inoculate a 15-L bioreactor and bring the initial tank volume to 5 L.

The feed solution was fed at an exponential rate until a top feed rate of 4.8 g/min was reached. After this time, the glucose feed was fed to meet metabolic demands at rates less than or equal to 4.8 g/min. The total amount of glucose delivered to the bioreactor during the 56 hr fermentation was 7.0 kg. Induction was achieved by adding isopropyl-beta-D-1-thiogalactopyranoside (IPTG). A single shot of IPTG was added to the tank to bring the concentration to 300 uM when the cells were at an OD of 5. After a run time of 36 h, whole broth, including cell mass, was drawn off periodically to prevent overflow of the bioreactor.

The isoprene level in the off-gas from the bioreactors was determined using a Hiden mass spectrometer. The isoprene titer increased over the course of the fermentation to a maximum value of 2.7 g/L at 56 hr.

Equation for calculating Isoprene Titer: ∫(Instantaneous isoprene production rate, g/L/hr)dt from t=0 to 56 hrs[=]g/L broth Equation for calculating Specific Productivity levels:

(mg isoprene$_t$–mg isoprene$_{to}$)/[OD550$_t$*L broth$_t$–OD550$_{to}$*L broth$_{to}$)/(2.7 OD*L/g cell)]/(t–$t_0$) [=]mg isoprene/g cell/hr

Example 25

DXP Metabolite Determination

A. Metabolite Extraction: Processing 14-L Fermentor Samples.

Cell metabolism was rapidly inactivated by withdrawing several milliliters of the fermentor culture into a pre-weighed tube filled with 9.0 mL of dry ice-cold methanol. The resulting sample was weighed again to calculate the amount of withdrawn cell culture and then put to −80° C. for storage until further analysis. In order to extract metabolites, 500 μL of methanol-quenched fermentation sample was spun down by centrifugation for 4 min at 4500×g, at −9° C. The pellet was then re-extracted twice, first with 350 μL of 85% methanol buffered with 5 mM ammonium acetate in water (pH=7.0) and then with 350 μL of 50% methanol in the ammonium acetate buffer. After each extraction, cell debris was pelleted by centrifugation and all three supernatants were pooled together for further analysis.

Metabolite Quantitation

Extracted metabolites were analyzed by LC-ESI-MS/MS on a Quantum triple quadrupole mass spectrometer (Thermo Electron Corporation, San Jose, Calif.). The system control, data acquisition, and mass spectral data evaluation were performed using XCalibur and LCQuan software (Thermo Electron Corp). LC separation was done on a Synergi 45 μM Hydro-RP HPLC column (150×2 mm, Phenomenex, USA) at a flow rate of 0.4 mL/min and the column temperature of 40° C. The LC gradient was t=0 min, 12% B; t=5 min, 12% B; t=9 min, 23% B; t=20 min, 99% B; t=23 min, 99% B; t=24 min, 12% B; t=29 min, 12% B, where solvent A was 10 mM tributylamine/15 mM acetic acid in water and solvent B was LCMS-grade methanol. The sample injection volume was 10 μL.

Mass detection was carried out using electrospray ionization in the negative mode. The following m/z values for precursor ions were selected to detect the metabolites of interest in SRM mode: 213.0 for DXP, 215.0 for MEP, 245.0 for IPP and DMAPP, 260.0 for HDMAPP, and 277.0 for cMEPP, 381.1 for FPP, 520.1 for CDP-ME, 600.0 for CDP-MEP. Concentrations of metabolites were determined based on integrated intensities of peaks generated by $PO_3^-$ product ion (m/z=79.0) using calibration curves obtained by injection of corresponding standards (Echelon Biosciences Inc). The concentration of CDP-MEP was expressed in arbitrary units because of the unavailability of commercial standard. Intracellular concentrations of metabolites were calculated based on a standard assumption that in 1 mL of the culture at OD=200 the integrated volume of all cells is 50 μL.

Example 26

Result of Increased Activity of IspG

This example demonstrates that increased activity of IspG can be detrimental to isoprene production when it occurs in the absence of increased FldA expression.

Data obtained using 14-L REMG39 indicates that despite the increased production of isoprene in REMG39, the strain is still limited for IspG activity; this is suggested by the approx. 19 mM cMEPP level the REMG39 strain maintains across the majority of the fermentation (see FIG. 80B). One way to improve IspG activity is to increase its expression, as was observed for strain REM E7_12 (FIG. 85B). However, increasing IspG activity in the test strain REM E7_12 compared to the parental strain CMP272 proved to be detrimental to isoprene production (FIG. 9A). An alternative method to increase the IspG activity generated from the CMP272 strain background is to increase fldA expression (test strain REM C9_12; FIG. 85B). The largest benefit determined at small scale that increased both the increased IspG activity and endogenous IspH activity as well as improved isoprene production from the CMP272 background was to co-overexpress fldA and ispG (test strain REM D6_12; FIG. 85).

A. Construction of Test Strains REM C9_12, REM D6_12, and REM E7_12

The construction of GI1.6 fldA/pCL, GI1.6 fldA-ispG/pCL, and GI1.6 ispG/pCL were done using standard molecular biology techniques (Sambrook et al., 1989). The pCL1920 (pCL) cloning vector has been described in publications, see, e.g., Lerner, C. G. et al., *Nucleic Acids Research, Vol.* 18: 4631 (1990). FIG. 82-84 depict the resulting plasmid constructs. The CMP272 strain was used for the transformations described below.

Chromosomal DNA from strain REM I6_4 was used as a PCR template for the generation of the PCR fragment harboring GI1.6 fldA, which was used to create GI1.6 fldA/pCL. Generation of strain REM I6_4 is described below. The DNA ultimately derived from the DXP operon pET24a plasmid (see, e.g., Example 11) was used as the PCR template for both the generation of the PCR fragments harboring ispG and GI1.6 ispG, which were used to create GI1.6 fldA-ispG/pCL and GI1.6 ispG/pCL, respectively. The DXP operon pET24a plasmid and GI1.6 gcpE-lytB-yidi pCR Blunt II TOPO vector PCR templates utilized have been described previously (see, e.g., Example 11).

B. The generation of REM I6_4, the Precursor to GI1.6 fldA/pCL

The GI 1.X-promoter insertions and subsequent loopout of the antibiotic resistance markers described in this example were carried out using the Red/ET system from Gene Bridges GmbH according to the manufacturer's instructions. The strain BL21(DE3) (Invitrogen) was used. The BIO RAD Gene Pulser system (0.1 cm cuvette cat.#165-2089) and a transformation protocol suggested by the manufacturer (BIO RAD) was used for the electroporations described.

```
Primers
fldA confirm-F
                                        (SEQ ID NO: 158)
5' tgattccgcaagactgcctgt

fldA confirm-R
                                        (SEQ ID NO: 159)
5' ttcggtattaccggtgtcgct

fldA cmpGI1.X-F
                                        (SEQ ID NO: 160)
5' ctatgattgc ctttatccgt gggcaatttt ccaccccat

aattaaccctcactaaagggcggccgc

fldA cmpGI1.X-R
```

-continued (SEQ ID NO: 161)

5' aagatgccagtgatagccatgagtgaaataacctcttgaaggttacc tccgggaaacgcggttgatttgtttagtggttgaattatttgctcaggat gtggcatngtcaagggcgtgacggctcgctaatacgactcactatagggc tcgag

*for the case of GI1.6 fldA N = T in the primer sequence above.

top Gb's CMP (SEQ ID NO: 144)

5' actgaaacgttttcatcgctc bottom Pgb2

(SEQ ID NO: 163)

5' ggtttagttcctcaccttgtc

Figure 81:
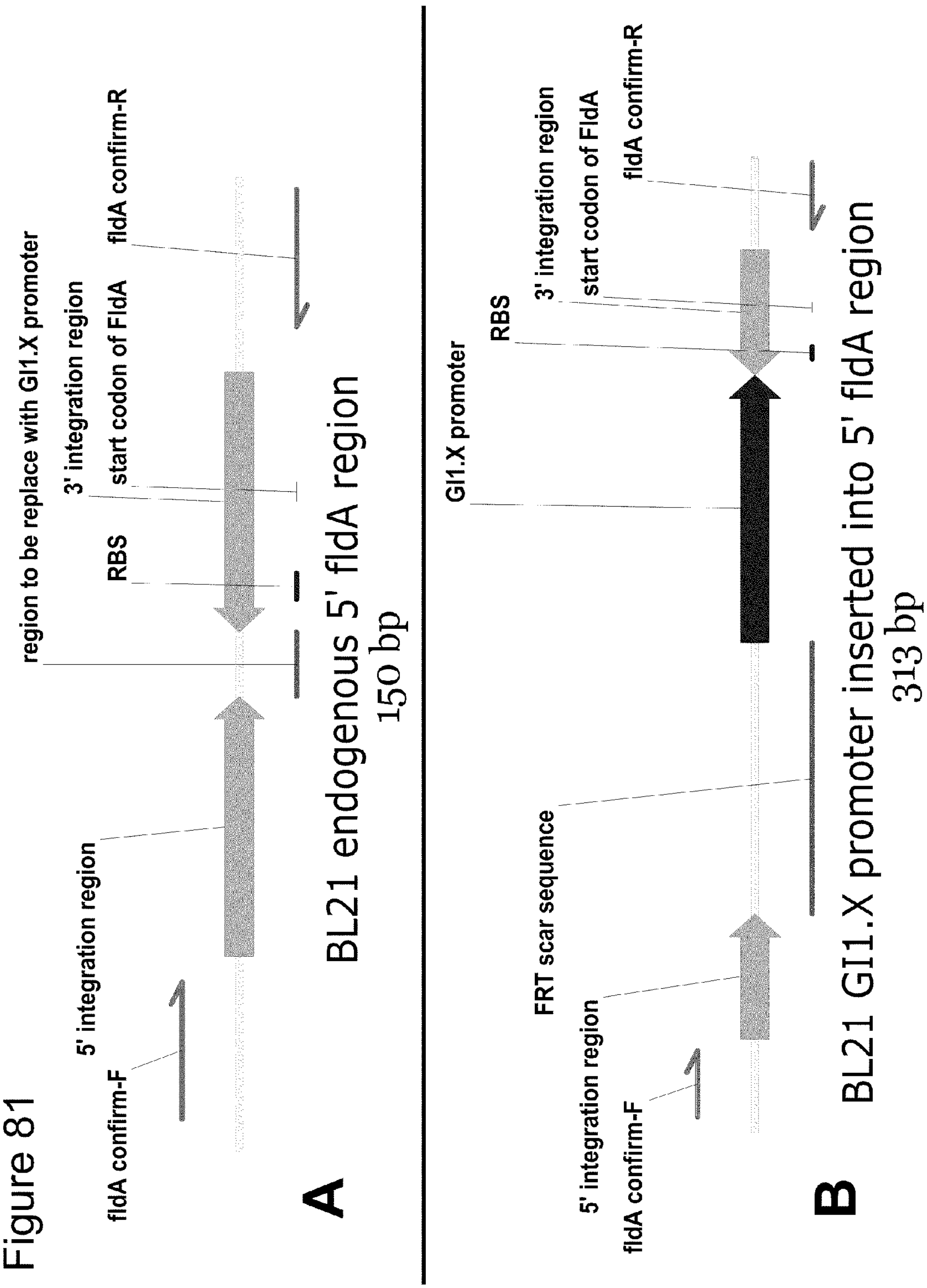
FIG. 81 (includes two panels.

The GI1.X promoters introduced upstream of the endogenous fldA coding region using the Gene Bridges GmbH methods are illustrated in FIG. 81. The antibiotic resistance cassette GB-CMP was amplified by PCR using primer sets fldA cmpGI1.X-F/fldA cmpGI1.X-R. The primers contain 40 bases of homology to the region immediately 5' to the fldA coding region to allow recombination at the specific locus upon electroporation of the PCR product in the presence of the pRed-ET plasmid. The FRT "scar" sequences remaining after Flipase-mediated excision of the antibiotic markers are also depicted in the figure.

Amplification of the GB-CmpR-fldA fragment

To amplify the GB-CmpR cassette for inserting the GI 1.X-promoters immediately upstream of the fldA locus the following PCR reaction was set up:

1 ul template (100 ng GB-CmpR)
10 ul HerculaseII Buffer
0.5 ul dNTP's (100 mM)
1.25 ul primer (10 uM) fldA cmpGI1.X-F
1.25 ul primer (10 uM) fldA cmpGI1.X-R
35 ul diH2O
+1 ul of HerculaseII fusion from Stratagene Cycle Parameter:

95° C.x2 min., (95° C.x30 sec., 63° C.x30 sec., 72° C.x2 min.)x29 cycles; 72° C.x5 min., 4° C. until cool (Biometra T3000 Combi Thermocycler)

The resulting PCR fragments were separated on a 0.8% E-gel (Invitrogen) for verification of successful amplification, and purified using the QIAquick PCR Purification kits (Qiagen) according to manufacturer's instructions. The resulting stock was GB-CmpR-GI 1.X-fldA fragment.

Integration of GB-CmpR-GI 1.X fldA PCR product into BL21 (DE3)/pRed-ET Strain

The pRed-ET vector (Gene Bridges kit) was transformed into BL21 (DE3) by electroporation resulting in strain DW30 (BL21 (DE3)/pRed-ET). The purified GB-CmpR-GI 1.X-fldA PCR fragment was electroporated into DW30. The transformants were recovered in L Broth and then plated on L agar containing chloramphenicol (10 ug/ml). Chloramphenicol resistant colonies were analyzed by PCR for the presence of the GB-CmpR cassette and the GI 1.X-promoters using primers fldA confirm-F, fldA confirm-R, top GB's CMP, and bottom Pgb2. The PCR fragments from a number of transformants were sequenced using the fldA confirm-R and top GB's CMP primers (Sequetech; Mountain View, Calif.) and the various GI 1.X fldA strains of interest identified. The chloramphenicol resistant strain, BL21 (DE3) CMP::GI1.6 fldA, was designated REM I6_4.

C. Strategy for Creating REM C9_12

Electroporation of GI1.6 fldA/pCL into CMP272 was performed using the BIO RAD Gene Pulser system (0.1 cm cuvette cat.#165-2089) and a transformation protocol suggested by the manufacturer (BIO RAD). Cells of the strain REM I6_4 encoding GI1.6 fldA were used as the PCR template for vector construction.

Primers Sequences

5' SalI GI1.X-

(SEQ ID NO: 164)

5' cgag gtcgac gcgagccgtcacgcccttgac

3' NruI/SacII fldA stop- (SEQ ID NO: 165)

5' gctc tcgcga gagc ccgcgg tcaggcattgagaatttcgtcgag

M13 (-20)

(SEQ ID NOS: 63, 69 and 98)

5' GTAAAACGACGGCCAGT

M13 reverse (SEQ ID NO: 99)

5' CAGGAAACAGCTATGAC

Amplification of the GI1.6 fldA Fragment

To amplify the GI1.6 fldA fragment for inserting the GI1.6 fldA fragment into pCL the following PCR reaction was set up:

1 ul template (approx. 1 ul volume of I6_4 cells)
10 ul HerculaseII Buffer
0.5 ul dNTP's (100 mM)
1.25 ul primer (10 uM) 5' SalI GI1.X
1.25 ul primer (10 uM) 3' NruI/SacII fldA stop
35 ul diH2O
+1 ul of HerculaseII fusion from Stratagene Cycle Parameter:

95° C.x2 min., [95° C.x30 sec., 60° C.x30 sec., 72° C.x3 min.]x29 cycles; 72° C.x5 min., 4° C. until cool (Biometra T3000 Combi Thermocycler)

The resulting PCR fragment was separated on a 1.2% E-gel (Invitrogen) for verification of successful amplification, and purified using the QIAquick PCR Purification kits according to manufacturer's instructions. The resulting stock was GI1.6-fldA fragment.

Cloning of the GI1.6 fldA Fragment into pCL

Approximately 600 ng of the GI1.6 fldA fragment was digested with SalI (Roche) according to the manufacturer's specifications and approx. 200 ng of the pCL plasmid was digested with SalI and SmaI (Roche) according to the manufacturer's specifications. The digests were subsequently combined and cleaned using the Qiagen QiaQuick Gel Extraction Kit. Approximately one half of the cleaned cut DNA was ligated using T4 DNA Ligase from New England Biolabs according to the manufacturer's suggested protocol. Chemically competent TOP10 cells (Invitrogen) were transformed with the ligation reaction using a standard heat-shock protocol (Sambrook et al., 1989), recovered in L broth for 1 hour at 37° C. and then plated on L agar containing spectinomycin (50 ug/ml) and 5-bromo-4-chloro-3-indolyl-beta-D-galactopyranoside (X-GAL at 40 ug/ml; Sigma). White, spectinomycin resistant colonies were selected, grown overnight in L broth containing spectinomycin (50 ug/ml), and harvested for subsequent plasmid preparation. Plasmid constructs were isolated using Qiagen Qiaprep Spin Miniprep Kit. Plasmid preparations of interest were sequenced (Sequetech; Mountain View, Calif.) using primers M13 (-20) and M13 Reverse, and the correct GI1.6 fldA/pCL clone identified, which has been designated as strain REM A1_11 (TOP10 w/GI1.6 fldA/pCL; 5' Sal I-3' SacII/NruI uncut (blunt 3') end PCR fragment into 5' SalI-3'Sma I of pCL). A picture of the GI1.6 fldA/pCL vector map is presented in FIG. 82.

Transformation of GI1.6 fldA/pCL into CMP271

To build the isoprene producing test strain REM C9_12, the GI1.6 fldA/pCL plasmid was transformed by electroporation into CMP272. Transformants were recovered in L broth and plated on L agar containing spectinomycin (50 ug/ml) and carbenicillin (50 ug/ml). The resulting strain was designated REM C9_12.

Strategy for Creating REM D6_12

Electroporation of GI1.6 fldA-ispG/pCL into CMP272 was performed using the BIO RAD Gene Pulser system (0.1 cm cuvette cat.#165-2089) and a transformation protocol suggested by the manufacturer (BIO RAD). The DXP operon pET24a plasmid was used as the PCR template for vector construction.

```
Primers Sequences
5' SacII Ec ispG w/rbs-
                                     (SEQ ID NO: 166)
5' tcca ccgcgg gctc gaa ggag atatacc atg cat aac

cag gct cca att caa

3' NruI Ec ispG stop-
                                     (SEQ ID NO: 167)
5' gctc tcgcga tta ttt ttc aac ctg ctg aac gtc

M13For-
                                     (SEQ ID NO: 168)
5' gttgtaaaacgacggccagt

5' BamHI Ec ispG w/rbs-
                                     (SEQ ID NO: 169)
5' tacg ggatcc atttga ggag taagcc atg cat aac cag

gct cca att caa

3' SacI Ec ispG w/stop-
                                     (SEQ ID NO: 170)
5' gctg gagctc cac tta ttt ttc aac ctg ctg aac gtc

pRA42-
                                     (SEQ ID NO: 171)
5' gatgatcaacatgacgcatggc

pRA43-
                                     (SEQ ID NO: 172)
5' cattccgatccgtattggcg
```

Amplification of the 5' SacII-ispG-3' NruI Fragment

To amplify the ispG fragment for inserting into GI1.6 fldA/pCL the following PCR reaction was set up:

1 ul template (approx. 1 ul volume of I6_4 cells)
10 ul HerculaseII Buffer
0.5 ul dNTP's (100 mM)
1.25 ul primer (10 uM) 5' SacII Ec ispG w/rbs
1.25 ul primer (10 uM) 3' NruI Ec ispG stop
35 ul diH2O
+1 ul of HerculaseII fusion from Stratagene Cycle Parameter:

95° C.×2 min., [95° C.×30 sec., 60° C.×30 sec., 72° C.×2 min.]×29 cycles; 72° C.×5 min., 4° C. until cool (Biometra T3000 Combi Thermocycler)

The resulting PCR fragment was separated on a 1.2% E-gel (Invitrogen) for verification of successful amplification, and purified using the QIAquick PCR Purification kits according to manufacturer's instructions. The resulting stock was 5' SacII-ispG-3' NruI fragment.

Cloning of the GI1.6 fldA Fragment into pCL

Approximately 600 ng of the 5' SacII-ispG-3' NruI fragment was digested with Sac II (New England BioLabs) according to the manufacturer's specifications and approx. 200 ng of the GI1.6 fldA/CL plasmid was digested with SacII and NruI (New England BioLabs) according to the manufacturer's specifications. The digests were subsequently combined and cleaned using the Qiagen QiaQuick Gel Extraction Kit. Approximately one half of the cleaned cut DNA was ligated using T4 DNA Ligase (New England Biolabs) according to the manufacturer's suggested protocol. Chemically competent TOP10 cells (Invitrogen) were transformed with the ligation reaction using a standard heat-shock protocol (Sambrook et al., 1989), recovered in L broth for 1 hour at 37° C. and then plated on L agar containing spectinomycin (50 ug/ml). Some spectinomycin resistant colonies were selected, grown overnight in L broth containing spectinomycin (50 ug/ml), and harvested for subsequent plasmid preparation. Plasmid constructs were isolated using Qiagen Qiaprep Spin Miniprep Kit. Plasmid preparations of interest were sequenced (Sequetech; Mountain View, Calif.) using primers 5' SacII Ec ispG, 3' NruI Ec ispG stop, M13 For, 5' BamHI Ec ispG w/rbs, 3' Sad Ec ispG w/stop, pRA42, and pRA43 and the correct GI1.6fldA-ispG/pCL clone identified, which has been designated as strain REM D9_11 (TOP10 w/GI1.6 fldA-ispG/pCL; 5' Sac II-3' NruI uncut (blunt 3' end) PCR fragment into 5' SacII-3'NruI of pCL). A picture of the GI1.6 fldA-ispG/pCL vector map is presented in FIG. 83.

Transformation of GI1.6 fldA-ispG/pCL into CMP271

To build the isoprene producing test strain REM D6_12, the GI1.6 fldA-ispG/pCL plasmid was transformed by electroporation into CMP272. Transformants were recovered in L broth and plated on L agar containing spectinomycin (50 ug/ml) and carbenicillin (50 ug/ml). The resulting strain was designated REM D6_12.

E. Strategy for creating REM E7_12

Electroporation of GI1.6 ispG/pCL into CMP272 was performed using the BIO RAD Gene Pulser system (0.1 cm cuvette cat.#165-2089) and a transformation protocol suggested by the manufacturer (BIO RAD). The GI1.6 gcpE-lytB-yidi pCR Blunt II TOPO vector was used as the PCR template for vector construction.

```
Primers Sequences
5' SalI GI1.X-
                                     (SEQ ID NO: 164)
5' cgag gtcgac gcgagccgtcacgcccttgac

3' SacI Ec ispG w/stop-
                                     (SEQ ID NO: 170)
5' gctg gagctc cac tta ttt ttc aac ctg ctg aac gtc

M13For
                                     (SEQ ID NO: 168)
5' gttgtaaaacgacggccagt

M13Rev
                                     (SEQ ID NO: 173)
5' tcacacaggaaacagctatga
```

Amplification of the GI1.6 ispG Fragment

To amplify the GI1.6 ispG fragment for inserting into pCL the following PCR reaction was set up:

1 ul template (approx. 1 ul volume of I6_4 cells)
10 ul HerculaseII Buffer
0.5 ul dNTP's (100 mM)
1.25 ul primer (10 uM) 5' SalI GI1.X
1.25 ul primer (10 uM) 3' Sad Ec ispG w/stop
35 ul diH2O
+1 ul of HerculaseII fusion from Stratagene Cycle Parameter:

95° C.×2 min., [95° C.×30 sec., 60° C.×30 sec., 72° C.×2 min.]×29 cycles; 72° C.×5 min., 4° C. until cool (Biometra T3000 Combi Thermocycler)

The resulting PCR fragment was separated on a 1.2% E-gel (Invitrogen) for verification of successful amplification, and purified using the QIAquick PCR Purification kits according to manufacturer's instructions. The resulting stock was GI1.6 ispG fragment.

Cloning of the GI1.6 ispG Fragment into pCL

Approximately 600 ng of the GI1.6 ispG fragment and 200 ng of the pCL vector were digested with SalI and Sad (Roche) according to the manufacturer's specifications. The digests were subsequently combined and cleaned using the Qiagen QiaQuick Gel Extraction Kit. Approximately one half of the cleaned cut DNA was ligated using T4 DNA Ligase (New England Biolabs) according to the manufacturer's suggested protocol. Chemically competent TOP10 cells (Invitrogen) were transformed with the ligation reaction using a standard heat-shock protocol (Sambrook et al., 1989), recovered in L broth for 1 hour at 37° C. and then plated on L agar containing spectinomycin (50 ug/ml) and 5-bromo-4-chloro-3-indolyl-beta-D-galactopyranoside (X-GAL at 40 ug/ml; Sigma). White spectinomycin resistant colonies were selected, grown overnight in L broth containing spectinomycin (50 ug/ml), and harvested for subsequent plasmid preparation. Plasmid constructs were isolated using Qiagen Qiaprep Spin Miniprep Kit. Plasmid preparations of interest were sequenced (Sequetech; Mountain View, Calif.) using primers 3' Sad Ec ispG w/stop, M13 For, and M13 Rev and the correct GI1.6 ispG/pCL clone identified, which has been designated as strain REM H5_11 (TOP10 w/GI1.6 ispG/pCL; 5' SalI-3' Sad PCR fragment into 5' SalI-3'SacI of pCL). A picture of the GI1.6 ispG/pCL vector map is presented in FIG. 84.

Transformation of GI1.6 ispG/pCL into CMP271

To build the isoprene producing test strain REM E7_12, the GI1.6 ispG/pCL plasmid was transformed by electroporation into CMP272. Transformants were recovered in L broth and plated on L agar containing spectinomycin (50 ug/ml) and carbenicillin (50 ug/ml). The resulting strain was designated REM E7_12.

F. Analysis of Test Strains REM C9_12, REM D6_12, and REM E7_12 and the Parental Strain CMP272 for Growth, Isoprene Production, and DXP Metabolite Accumulation.

The parental strain CMP272 was compared against the test strains (REM C9_12, REM D6_12, and REM E7_12) in a shake flask assay as well as in a DXP metabolite determination study FIG. 85A and FIG. 85B, respectively. The detriment, approximately 20% decrease in isoprene production, of expressing ispG alone within the CMP272 background (strain REM E7_12) is shown in FIG. 85A. The increased benefit on isoprene production in small scale of co-expressing fldA along with ispG in comparison to expressing either fldA or ispG alone from the CMP272 host is also depicted in FIG. 85A. A 1.4-fold improvement in isoprene production was observed for the REM D6_12 strain relative to the parental control strain CMP272. The benefit of increasing the level of fldA expression on endogenous levels of *E. coli* IspG and IspH activity in strain REM C9_12 as well as improving the activity of IspH within the ispG-overexpressing strain REM D6_12 is indicated by the metabolite profile described in FIG. 85B. More specifically, the additional FldA in strain REM C9_12 decreased the levels of both the IspG and IspH substrates, cMEPP and HDMAPP, respectively, relative to the parental strain CMP272 (cMEPP, 17% decrease; HDMAPP, 16% decrease); while the additional FldA within the co (fldA and ispG)-overexpression strain REM D6_12 compared to the REM E7_12 strain overexpressing ispG alone was seen to decrease HDMAPP roughly 4.3-fold.

Growth

Strains CMP272, REM C9_12, REM D6_12, and REM E7_12 were grown as 2-5 ml cultures at 30° C. in TM3 liquid media (13.6 g $K_2PO_4$, 13.6 g $KH_2PO_4$, 2.0 g $MgSO_4.7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) supplemented to a final concentration with 0.1% yeast extract and 1.0% glucose and including spectinomycin (50 ug/ml) and carbenicillin (50 ug/ml). Induction of LacI-regulated gene expression was achieved by adding isopropyl-beta-D-1-thiogalactopyranoside (IPTG) to a concentration of 600 uM. Growth was monitored periodically by recording each of the culture's optical density measured at 600 nm using an Eppendorf Biophotometer spectrometer (Eppendorf).

Isoprene Production

Isoprene production was anlayzed using a headspace assay. For the shake flask cultures, 200 ul of a culture was transferred from shake flasks to 2 ml CTC headspace vials (SUN-SRI2 mL HS vials, VWR#66020-950, and caps, VWR#66008-170). The cap was screwed on tightly and the vials incubated at the equivalent temperature with shaking at 250 rpm. After 30 minutes the vials were removed from the incubator and analyzed. The analysis was performed using an Agilent 6890 GC/MS system interfaced with a CTC Analytics (Switzerland) CombiPAL autosampler operating in headspace mode. An Agilent HP-5MS GC/MS column (15 m×0.25 mm; 0.25 μm film thickness) was used for separation of analytes. The sampler was set up to inject 100 μL of headspace gas. The GC/MS method utilized helium as the carrier gas at a flow of 1 ml/minutes The injection port was held at 250° C. with a split ratio of 50:1. The oven temperature was held at 37° C. for 0.6 minute, the duration of the analysis. The Agilent 5793N mass selective detector was run in single ion monitoring (SIM) mode on m/z 67. The detector was switched off from 0 to 0.42 minutes to allow the elution of permanent gases. Under these conditions isoprene (2-methyl-1,3-butadiene) was observed to elute at approx. 0.49 minutes. A calibration table was used to quantify the absolute amount of isoprene and was found to be linear from 1 μg/L to 5000 μg/L. The limit of detection was estimated to be 50 to 100 ng/L using this method. The specific productivity of each strain is reported as ug/L OD Hr. Note, ratio of 1900 ul headspace: 100 ul broth in assay vials for 30 min. incubation results in the following conversion of isoprene ug/L of culture to specific productivity: (isoprene/L determined by GC-MS)×(38)/(OD 600 nm of the culture).

DXP Metabolite Accumulation

The DXP metabolites of the isoprene-producing parental and test strains, CMP272 and REM C9_12, REM D6_12, and REM E7_12, respectively, that are described above and depicted in FIG. 85B were isolated and quantified as follows: Metabolite Extraction: Processing Samples from Small-Scale Experiments.

To measure accumulation of metabolites in small-scale experiments 0.4 to 1.5 mL of cell culture was centrifuged for 3 min at 7500×g, at −9° C. Immediately after centrifugation the supernatant was aspirated to a clean tube for analysis of excreted metabolites and 100 μL of dry ice-cold methanol was added to pelleted cells. The resulting samples were then stored at −80° C. until further processing.

To determine concentrations of excreted metabolites, 500 μL of methanol was added to 300 μL of the supernatant and the resulting mixture was centrifuged for 10 min at 20000×g at 4° C. to remove insoluble material before the LCMS analysis.

For metabolites extraction from the pellet (further referred as intracellular metabolites), 10 μL of water was added to methanol-containing samples, the pellet was resuspended in the resulting methanol/water mix and cell debris were spun down by 4-min centrifugation at 4500×g. The pellet was re-extracted two more times, first with 100 μL of 75% methanol buffered with 1 mM ammonium acetate in water (pH=8.0), then with 90 μL of 50% methanol in the ammonium acetate buffer. After each extraction, cell debris was pelleted by centrifugation and the supernatants from all three extractions were combined and analyzed by LCMS. During the extraction procedure, samples were kept on ice or in a refrigerated centrifuge whenever possible to minimize metabolites degradation.

Metabolite Quantitation

Extracted metabolites were analyzed by LC-ESI-MS/MS on a Quantum triple quadrupole mass spectrometer (Thermo Electron Corporation, San Jose, Calif.). The system control, data acquisition, and mass spectral data evaluation were performed using XCalibur and LCQuan software (Thermo Electron Corp). LC separation was done on a Synergi 45 μM Hydro-RP HPLC column (150×2 mm, Phenomenex, USA) at a flow rate of 0.4 mL/min and the column temperature of 40° C. The LC gradient was t=0 min, 12% B; t=5 min, 12% B; t=9 min, 23% B; t=20 min, 99% B; t=23 min, 99% B; t=24 min, 12% B; t=29 min, 12% B, where solvent A was 10 mM tributylamine/15 mM acetic acid in water and solvent B was LCMS-grade methanol. The sample injection volume was 10 μL.

Mass detection was carried out using electrospray ionization in the negative mode. The following m/z values for precursor ions were selected to detect the metabolites of interest in SRM mode: 213.0 for DXP, 215.0 for MEP, 245.0 for IPP and DMAPP, 260.0 for HDMAPP, and 277.0 for cMEPP, 381.1 for FPP, 520.1 for CDP-ME, 600.0 for CDP-MEP. Concentrations of metabolites were determined based on integrated intensities of peaks generated by $PO_3^-$ product ion (m/z=79.0) using calibration curves obtained by injection of corresponding standards (Echelon Biosciences Inc). The concentration of CDP-MEP was expressed in arbitrary units because of the unavailability of commercial standard. Intracellular concentrations of metabolites were calculated based on a standard assumption that in 1 mL of the culture at OD=200 the integrated volume of all cells is 50 μL.

Example 27

Effects of Increased Activity of IspG

This example demonstrates that increased activity of IspG can be detrimental to isoprene production as a result of insufficient IspH activity within strain REM G4_11.

Figure 80C:
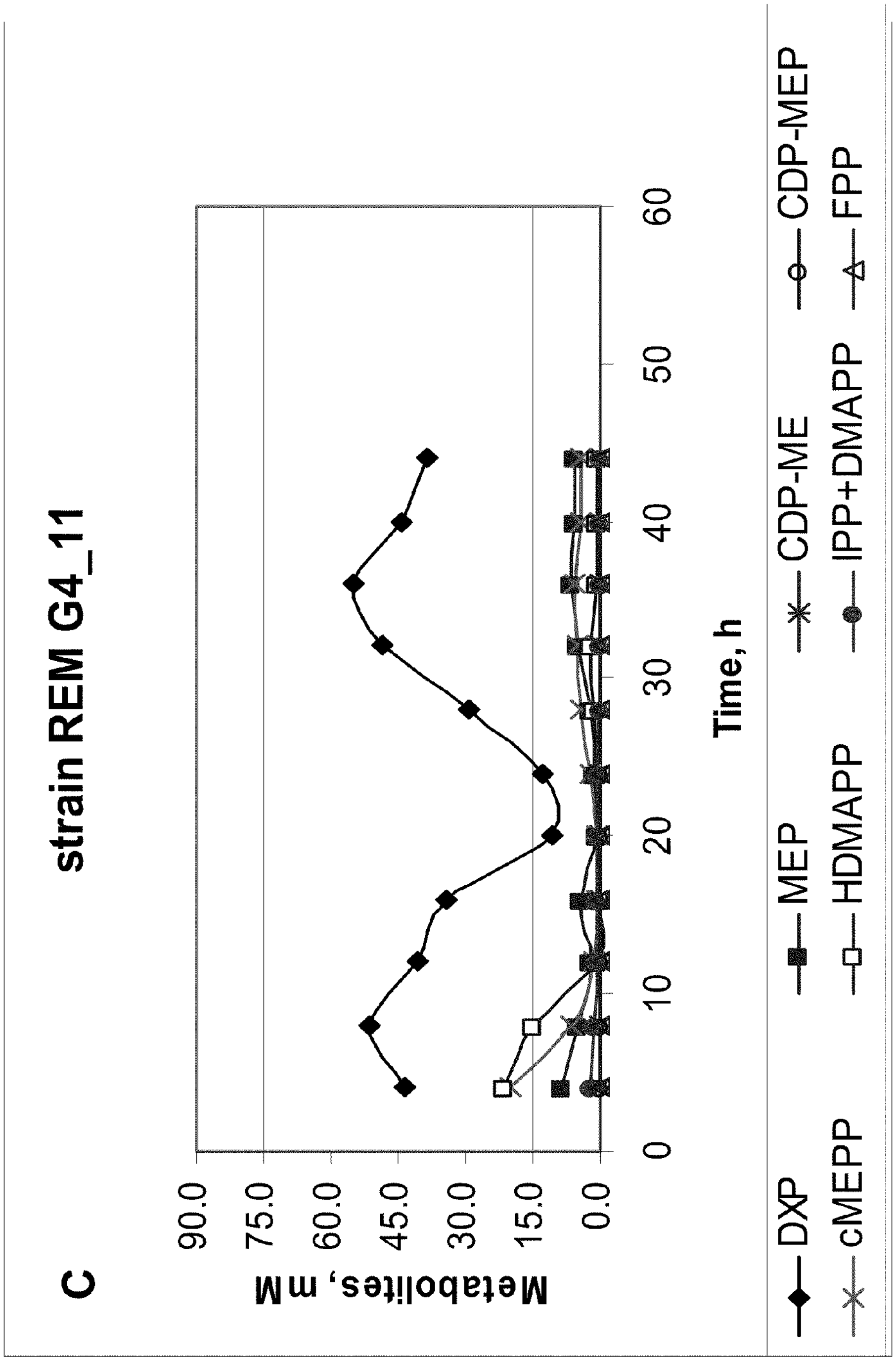

As described in the example above, increased expression of fldA alone or in combination with ispG within the CMP272 strain background improved isoprene production (FIG. 85). These learnings were applied to strain REMG39, as the overall goal was to improve IspG activity within this (benchmark) strain background. To reiterate, the REMG39 strain exhibited characteristics perceived to reflect a bottleneck at the point of IspG activity in flux through the DXP pathway toward isoprene production (see 14-L REMG39 example). In FIG. 86A, the benefit of increasing IspG activity within the REM G4_11 strain at small scale is made apparent (35% increase in isoprene production over the parental control;) however, as shown in FIGS. 79 and 80, this benefit did not translate to the large scale fermentation. Results of the large scale fermentation presented in FIG. 80 indicate that increased IspH activity is required by the REM G4_11 strain; this is suggested by the high (>15 mM) HDMAPP levels observed during exponential phase growth of REM G4_1 (FIG. 80C).

A. Construction of Test Strains REM G2_11 and REM G4_11

To further improve the IspG activity generated by the REMG39 strain background, the vector constructs GI1.6 fldA/pCL and GI1.6 fldA-ispG/pCL were introduced into the strain, subsequently generating the test strains REM G2_11 and REM G4_11, respectively.

B. Strategy for Creating REM G2_11 and REM G4_11

Electroporation of GI1.6 fldA/pCL and GI1.6 fldA-ispG/pCL into REMG39 was performed using the BIO RAD Gene Pulser system and a transformation protocol suggested by the manufacturer (BIO RAD). Plasmid preparations of GI1.6 fldA/pCL, generated from strain REM A1_11, and GI1.6 fldA-ispG/pCL, generated from strain REM D9_11, were used; these strains and constructs are described above.

Transformation of GI1.6 fldA/pCL and GI1.6 fldA-ispG/pCL into CMP271

To build the isoprene producing test strains REM G2_11 and REM G4_11, the GI1.6 fldA/pCL and GI1.6 fldA-ispG/pCL plasmids were transformed, separately, by electroporation into REMG39. Transformants were recovered in L broth and plated on L agar containing spectinomycin (50 ug/ml), kanamycin (50 ug/ml), and carbenicillin (50 ug/ml). The resulting strains were designated REM G2_11 and REM G4_11, respectively.

C. Analysis of Test Strains REM G2_11, REM G4_11, and the Parental Strain REMG39 for Growth, Isoprene Production, and DXP Metabolite Accumulation.

The parental strain REMG39 was compared against the test strains (REM G2_11, REM and REM G4_11) in a shake flask assay as well as in a DXP metabolite determination study. The increase in isoprene production provided by the presence of GI1.6 fldA/pCL and GI1.6 fldA-ispG/pCL within the REMG39 background is depicted in FIG. 86A. The test strain REM G4_11 produced approximately 1.35-fold more isoprene than the parental control strain REMG39 at the 3.5 hour time point, where REM G2_11 generated approximately 1.25-fold more isoprene than the parental control at the 3.5 hour time point. As seen in FIG. 86B, both of the test strains, REM G2_11 and REM G4_11, were found to accumulate less of the IspG substrate, cMEPP, than the parental strain REMG39 at the 3.5 hour time point (REMG2_11 had approx. 66% of the parental control cMEPP level; and REM G4_11 had approx. 9% of the parental control cMEPP level). The REM G4_11 strain did however accumulate a 5.4-fold higher level of HDMAPP, the substrate of IspH, than both the parental control and test strain REM G2_11 (FIG. 86B).

Growth

Strains REMG39, REM G2_11, and REM G4_11 were grown at 30° C. as 2-5 ml cultures in TM3 liquid media (13.6 g $K_2PO_4$, 13.6 g $KH_2PO_4$, 2.0 g $MgSO_4$*$7H_2O$), 2.0 g citric acid monohydrate, 0.3 g ferric ammonium citrate, 3.2 g $(NH_4)_2$ $SO_4$, 0.2 g yeast extract, 1.0 ml 1000× Modified Trace Metal Solution, adjusted to pH 6.8 and q.s. to $H_2O$, and filter sterilized) supplemented to a final concentration with 0.1% yeast extract and 1.0% glucose and including spectinomycin (50 ug/ml) and carbenicillin (50 ug/ml). Induction of LacI-regulated gene expression was achieved by adding isopropyl-beta-D-1-thiogalactopyranoside (IPTG) to a concentration of 400 uM. Growth was monitored periodically by recording each of the culture's optical density measured at 600 nm using an Eppendorf Biophotometer spectrometer (Eppendorf).

Isoprene Production

Isoprene production was anlayzed using a headspace assay. For the shake flask cultures, 200 ul of a culture was transferred from shake flasks to 2 ml CTC headspace vials (SUN-SRI 2 mL HS vials, VWR#66020-950, and caps, VWR#66008-170). The cap was screwed on tightly and the vials incubated at the equivalent temperature with shaking at 250 rpm. After 30 minutes the vials were removed from the incubator and analyzed. The analysis was performed using an Agilent 6890 GC/MS system interfaced with a CTC Analytics (Switzerland) CombiPAL autosampler operating in headspace mode. An Agilent HP-5MS GC/MS column (15 m×0.25 mm; 0.25 μm film thickness) was used for separation of analytes. The sampler was set up to inject 100 μL of headspace gas. The GC/MS method utilized helium as the carrier gas at a flow of 1 ml/minutes The injection port was held at 250° C. with a split ratio of 50:1. The oven temperature was held at 37° C. for 0.6 minute, the duration of the analysis. The Agilent 5793N mass selective detector was run in single ion monitoring (SIM) mode on m/z 67. The detector was switched off from 0 to 0.42 minutes to allow the elution of permanent gases. Under these conditions isoprene (2-methyl-1,3-butadiene) was observed to elute at approx. 0.49 minutes. A calibration table was used to quantify the absolute amount of isoprene and was found to be linear from 1 μg/L to 5000 μg/L. The limit of detection was estimated to be 50 to 100 ng/L using this method. The specific productivity of each strain is reported as ug/L OD Hr. Note, ratio of 1900 ul headspace: 100 ul broth in assay vials for 30 min. incubation results in the following conversion of isoprene ug/L of culture to specific productivity: (isoprene/L determined by GC-MS)×(38)/(OD 600 nm of the culture).

DXP Metabolite Accumulation

The DXP metabolites of the isoprene-producing parental and test strains, REMG39 and REM G2_11 and REM G4_11, respectively, that are described above and depicted in FIG. 10B were isolated and quantified as follows:

Metabolite Extraction: Processing Samples From Small-Scale Experiments.

To measure accumulation of metabolites in small-scale experiments 0.4 to 1.5 mL of cell culture was centrifuged for 3 min at 7500×g, at −9° C. Immediately after centrifugation the supernatant was aspirated to a clean tube for analysis of excreted metabolites and 100 μL of dry ice-cold methanol was added to pelleted cells. The resulting samples were then stored at −80° C. until further processing.

To determine concentrations of excreted metabolites, 500 μL of methanol was added to 300 μL of the supernatant and the resulting mixture was centrifuged for 10 min at 20000×g at 4° C. to remove insoluble material before the LCMS analysis.

For metabolites extraction from the pellet (further referred as intracellular metabolites), 10 μL of water was added to methanol-containing samples, the pellet was resuspended in the resulting methanol/water mix and cell debris were spun down by 4-min centrifugation at 4500×g. The pellet was re-extracted two more times, first with 100 μL of 75% methanol buffered with 1 mM ammonium acetate in water (pH=8.0), then with 90 μL of 50% methanol in the ammonium acetate buffer. After each extraction, cell debris was pelleted by centrifugation and the supernatants from all three extractions were combined and analyzed by LCMS. During the extraction procedure, samples were kept on ice or in a refrigerated centrifuge whenever possible to minimize metabolites degradation.

Metabolite Quantitation

Extracted metabolites were analyzed by LC-ESI-MS/MS on a Quantum triple quadrupole mass spectrometer (Thermo Electron Corporation, San Jose, Calif.). The system control, data acquisition, and mass spectral data evaluation were performed using XCalibur and LCQuan software (Thermo Electron Corp). LC separation was done on a Synergi 45 μM Hydro-RP HPLC column (150×2 mm, Phenomenex, USA) at a flow rate of 0.4 mL/min and the column temperature of 40° C. The LC gradient was t=0 min, 12% B; t=5 min, 12% B; t=9 min, 23% B; t=20 min, 99% B; t=23 min, 99% B; t=24 min, 12% B; t=29 min, 12% B, where solvent A was 10 mM tributylamine/15 mM acetic acid in water and solvent B was LCMS-grade methanol. The sample injection volume was 10 μL.

Mass detection was carried out using electrospray ionization in the negative mode. The following m/z values for precursor ions were selected to detect the metabolites of interest in SRM mode: 213.0 for DXP, 215.0 for MEP, 245.0 for IPP and DMAPP, 260.0 for HDMAPP, and 277.0 for cMEPP, 381.1 for FPP, 520.1 for CDP-ME, 600.0 for CDP-MEP. Concentrations of metabolites were determined based on integrated intensities of peaks generated by $PO_3^-$ product ion (m/z=79.0) using calibration curves obtained by injection of corresponding standards (Echelon Biosciences Inc). The concentration of CDP-MEP was expressed in arbitrary units because of the unavailability of commercial standard. Intracellular concentrations of metabolites were calculated based on a standard assumption that in 1 mL of the culture at OD=200 the integrated volume of all cells is 50 μL.

D. Analysis of Test Strain REM G4_11 for Growth, Isoprene Production, and DXP Metabolite Accumulation at Large Scale.

Figure 10B:
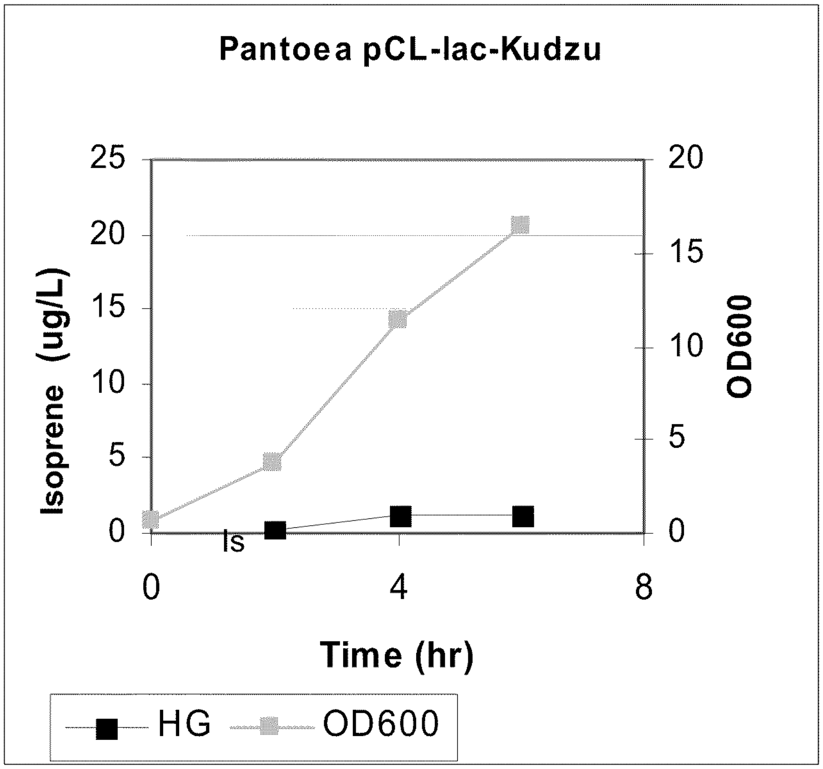
FIG. 10B is a graph showing the production of isoprene in *Panteoa citrea* expressing pCL-lac Kudzu. Grey diamonds represent isoprene synthesis, black squares represent $OD_{600}$.
Figure 10C:
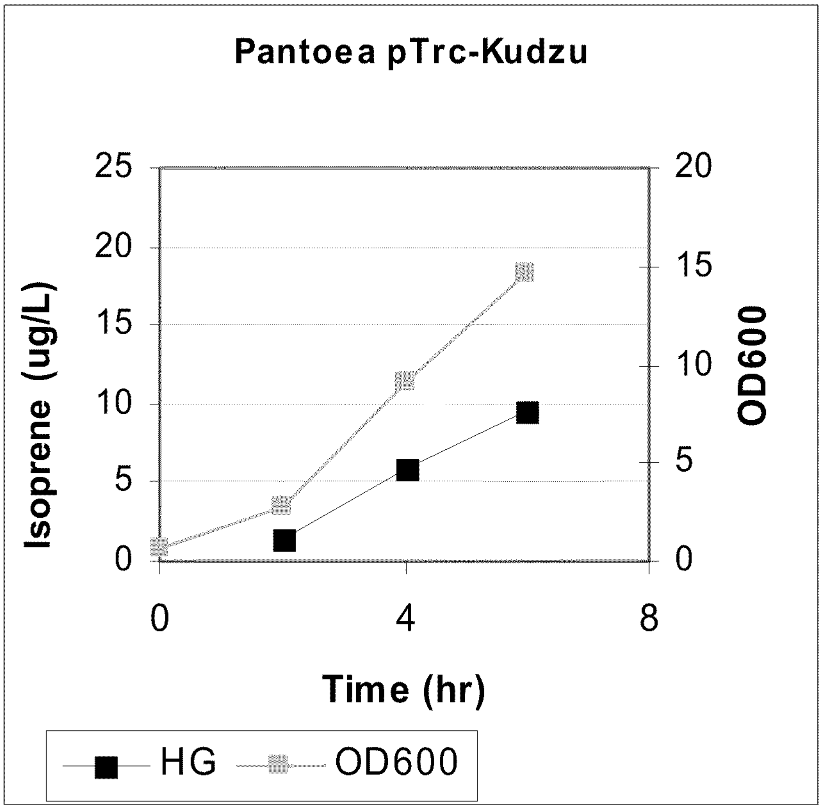
FIG. 10C is a graph showing the production of isoprene in *Panteoa citrea* expressing pTrcKudzu. Grey diamonds represent isoprene synthesis, black squares represent $OD_{600}$).

The increased HDMAPP present in the REM G4_11 cells was higher than the parental control strain; however, the averaged 0.63 mM HDMAPP intracellular concentration measured in the REM G4_11 cells was significantly less than the >10 mM intracellular HDMAPP level that has been correlated with poor cell growth and reduced isoprene production (see FIG. 10B). However, surprisingly strain REM G4_11 performed less well and produced roughly 3-fold less isoprene than the parental control at the 14-L fermentor scale (FIG. 3). The moderate accumulation of HDMAPP observed to occur in the REM G4_11 cells at small scale was found to be exaggerated under large scale fermentation conditions, reaching intracellular HDMAPP levels >20 mM (FIG. 4C). The decrease in cMEPP and corresponding increase in HDMAPP observed for the REM G4_11 strain relative to the parental control strain REMG39 strongly suggests that:

1) IspG activity has been improved within the REM G4_11 strain.
2) a bottleneck in DXP flux now occurs at the point of IspH activity in the REM G4_11 strain.

E. Large Scale Fermentation of Strain REM G4_11

The large scale fermentation of the parental strain REMG39 is described above. Isoprene production from *E. coli* expressing genes from the DXP pathway and isoprene synthase, grown in fed-batch culture at the 15-L scale.

Medium Recipe (per Liter Fermentation Medium):

K2HPO4 7.5 g, MgSO4*7H2O 2 g, citric acid monohydrate 2 g, ferric ammonium citrate 0.3 g, yeast extract 0.5 g, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s.

to volume. Glucose 10 g, Mercury Vitamin Solution 8 mL, and antibiotics were added after sterilization and pH adjustment.

1000× Modified Trace Metal Solution (per liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Mercury Vitamin Solution (per liter):

Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Feed Solution (per Kilogram):

Glucose 0.57 kg, Di H2O 0.38 kg, K2HPO4 7.5 g, and 100% Foamblast 10 g. All components were mixed together and autoclaved. Macro Salt Solution 3.4 mL, 1000× Modified Trace Metal Solution 0.8 ml, and Mercury Vitamin Solution 6.7 mL were added after the solution had cooled to 25° C.

Macro Salt Solution (per liter):

MgSO4*7H2O 296 g, citric acid monohydrate 296 g, ferric ammonium citrate 49.6 g. All components were dissolved in water, q.s. to volume and filter sterilized with 0.22 micron filter.

Fermentation was performed in a 15-L bioreactor with *E. coli* BL21 cells overexpressing the first enzyme in the dxp pathway (GI1.6-dxs), the last enzyme in the DXP pathway (GI1.6-yIDI), the lower MVA pathway (PL.2-mKKDyl), various other genes from the DXP pathway of *T. elongatus* (Ptac-gcpE-lytB-petF-petH/pK184), the *E. coli* ispG and fldA genes (GI1.6 fldA-ispG/pCL), and truncated isoprene synthase from *P. alba* (pDW33) and containing a restored 17,257 by chromosomal galM-containing region derived from MG1655 (strain name REM G4_11). This experiment was carried out to monitor isoprene formation from glucose at the desired fermentation pH 7.0 and temperature 34° C. A frozen vial of the *E. coli* strain was thawed and inoculated into tryptone-yeast extract medium for the bioreactor. After the inoculum grew to optical density 1.0, measured at 550 nm ($OD_{550}$), 500 mL was used to inoculate a 15-L bioreactor and bring the initial tank volume to 5 L.

The feed solution was fed at an exponential rate until a top feed rate of 4.9 g/min was reached. After this time the glucose feed was fed to meet metabolic demands a rates less than or equal to 4.9 g/min. The total amount of glucose delivered to the bioreactor during the 44 hr fermentation was 3.0 kg. Induction was achieved by adding isopropyl-beta-D-1-thiogalactopyranoside (IPTG). The initial IPTG concentration when the tank was first inoculated was 50 uM. Shots of 50 uM were added over the next five hours to bring the IPTG concentration to 350 uM when the cells were at an $OD_{550}$ of 10.

The isoprene level in the off-gas from the bioreactors was determined using a Hiden mass spectrometer. The isoprene titer increased over the course of the fermentation to a maximum value of 0.98 g/L at 44 hours.

Equation for calculating Isoprene Titer: ∫(Instantaneous isoprene production rate, g/L/hr)dt from t=0 to 44 hrs[=]g/L broth Equation for calculating Specific Productivity levels: (mg isoprene$_t$−mg isoprene$_{t0}$)/[(OD550$_t$*L broth$_t$−OD550$_{t0}$*L broth$_{t0}$)/(2.7 OD*L/g cell)]/(t−t$_0$) [=]mg isoprene/g cell/hr

Example 28

DXP Metabolite Determination

A. Metabolite Extraction: Processing 14-L Fermentor Samples.

Cell metabolism was rapidly inactivated by withdrawing several milliliters of the fermentor culture into a pre-weighted tube filled with 9.0 mL of dry ice-cold methanol. The resulting sample was weighted again to calculate the amount of withdrawn cell culture and then put to −80° C. for storage until further analysis. In order to extract metabolites, 500 μL of methanol-quenched fermentation sample was spun down by centrifugation for 4 min at 4500×g, at −9° C. The pellet was then re-extracted twice, first with 350 μL of 85% methanol buffered with 5 mM ammonium acetate in water (pH=7.0) and then with 350 μL of 50% methanol in the ammonium acetate buffer. After each extraction, cell debris was pelleted by centrifugation and all three supernatants were pooled together for further analysis.

B. Metabolite Quantitation

Extracted metabolites were analyzed by LC-ESI-MS/MS on a Quantum triple quadrupole mass spectrometer (Thermo Electron Corporation, San Jose, Calif.). The system control, data acquisition, and mass spectral data evaluation were performed using XCalibur and LCQuan software (Thermo Electron Corp). LC separation was done on a Synergi 45 μM Hydro-RP HPLC column (150×2 mm, Phenomenex, USA) at a flow rate of 0.4 mL/min and the column temperature of 40° C. The LC gradient was t=0 min, 12% B; t=5 min, 12% B; t=9 min, 23% B; t=20 min, 99% B; t=23 min, 99% B; t=24 min, 12% B; t=29 min, 12% B, where solvent A was 10 mM tributylamine/15 mM acetic acid in water and solvent B was LCMS-grade methanol. The sample injection volume was 10 μL.

Mass detection was carried out using electrospray ionization in the negative mode. The following m/z values for precursor ions were selected to detect the metabolites of interest in SRM mode: 213.0 for DXP, 215.0 for MEP, 245.0 for IPP and DMAPP, 260.0 for HDMAPP, and 277.0 for cMEPP, 381.1 for FPP, 520.1 for CDP-ME, 600.0 for CDP-MEP. Concentrations of metabolites were determined based on integrated intensities of peaks generated by $PO_3^-$ product ion (m/z=79.0) using calibration curves obtained by injection of corresponding standards (Echelon Biosciences Inc). The concentration of CDP-MEP was expressed in arbitrary units because of the unavailability of commercial standard. Intracellular concentrations of metabolites were calculated based on a standard assumption that in 1 mL of the culture at OD=200 the integrated volume of all cells is 50 μL.

Example 29

Increased Isoprene Production by Expression of the IspH Enzyme and Coincident Demonstration of Maintained Accumulation of Higher DXP Metabolite Levels This example demonstrates increased isoprene production by expression of the IspH enzyme from *Anabaena* sp. PCC7120 in strain REM H8_12 and coincident demonstration of maintained accumulation of higher DXP metabolite levels in the REM H8_12 strain exhibiting increased IspG activity.

Data in the above example(s) generated with test strain REM G4__11 indicates that increased IspG activity within an enhanced DXP fluxing strain needs to be balanced by sufficient IspH activity in order to avoid high levels of HDMAPP accumulation during 14-L fermentation. Intracellular levels of HDMAPP, the substrate for IspH, in excess of 10 mM have been correlated in both small scale and large scale experiments with poor cell growth, reduced flux through the DXP pathway, and subsequently reduced isoprene generation from isoprene production strains. Therefore, increased IspH activity within an enhanced DXP pathway strain (REM I7__11; described below) was achieved by over-expressing the ispH allele of *Anabaena* sp. PCC7120, generating test strain REM H8__12. Demonstrated in FIG. 89 is the small scale benefit increased IspH activity, provided by expression of the IpsH of *Anabaena* sp. PCC7120, has on isoprene production by test strain REM H8__12. At 14-L scale, the test strain REM H8__12 produced the highest (2.6 g/L) isoprene titer recorded for a strain exhibiting the enhanced IspG activity provided by GI1.6 fldA-ispG/pCL (FIG. 90A). Furthermore, unlike the REM G4__11 strain at the 14-L scale, strain REM H8__12 is able to maintain flux through the DXP pathway, as indicated by the maintained accumulation of the MEPP and cMEPP intermediates (compare FIG. 80C to FIG. 90C).

A. Construction of Test Strain REM H8__12, and the Parental Strain REM I7__11.

REM I7__11 and REM H8__12 are derivatives of WW119. This strain was constructed by electoporation of Strain WW103 with plasmid pDW33 (see Example 30 for construction of WW119). WW119 exhibits improved DXP-flux, but generates similar isoprene levels to that of the previous parental strain CMP272; this is potentially due to a bottleneck in flux at the point of IspG. WW119 harbors two improvements over the CMP272 strain. These beneficial modifications include increased dxs expression and increased dxr expression and are described infra. REM I7__11 was generated by introducing GI1.6 fldA-ispG/pCL into WW119 and REM H8__12 was made by moving Ptac Anabaena ispH aspA term/pEWL454 into REM I7__11; both plasmids were incorporated into their corresponding host strain via electroporation transformation methods.

```
Primers
5' AseI F-pgl pET-15b
                                    (SEQ ID NO: 174)
5' cagtct ATTAAT atgAAGCAAACAGTTTATATC

3' BamHI R-pgl pET-15b
                                    (SEQ ID NO: 175)
5' TAGCAGCC GGATCC TTAGTGTGCGTTAACCACCAC

EL-1098:
                                    (SEQ ID NO: 139)
5' TAACTTTAAGGAGGTATACATATGGAGCTCACGCGTGCGGCCGC

CTCGAGCTGCAGTACAAATAAAAAAGGCACGTCAG

EL-1099:
                                    (SEQ ID NO: 138)
5' GGATCCGTAATCTGTTTCCTGTGTGAAATTGTTATCCGCTCACAATT

CCACACATTATACGAGCCGATGATTAATTGTCAACAGAATTCCTTTC

CAGTCGGGAAACCTGTCG

EL-1100:
                                    (SEQ ID NO: 137)
5' CGTCGTTTTACAACGTCGTG
```

-continued

```
EL-1101:
                                    (SEQ ID NO: 136)
5' GAACTCCAAGACGAGGCAGC

EL-1102:
                                    (SEQ ID NO: 135)
5' GTGATATTGCTGAAGAGCTTGG

EL-1103:
                                    (SEQ ID NO: 134)
5' GGACTCAAGACGATAGTTACC

EL-1104:
                                    (SEQ ID NO: 133)
5' CACGACAGGTTTCCCGACTGG

EL-1150
                                    (SEQ ID NO: 132)
5' GAGCGCCCAATACGCAAACC

Neo.21
                                    (SEQ ID NO: 131)
5' GGCGATAGAAGGCGATGC
```

Amplification of the pgl Locus of REM I1__9

To verify/amplify the pgl locus of REM I1__9 the following PCR reaction was set up:

1 ul template (approx. 1 ul volume of I1__9 cells)
10 ul HerculaseII Buffer
0.5 ul dNTP's (100 mM)
1.25 ul primer (10 uM) 5' AseI F-pgl pET-15b
1.25 ul primer (10 uM) 3' BamHI R-pgl pET-15b
35 ul diH2O
+1 ul of HerculaseII fusion from Stratagene Cycle Parameter:

95° C.×2 min., [95° C.×30 sec., 55° C.×30 sec., 72° C.×2 min.]×29 cycles; 72° C.×5 min., 4° C. until cool (Biometra T3000 Combi Thermocycler)

The resulting PCR fragment was separated on a 1.2% E-gel (Invitrogen) for verification of successful amplification. A pgl+ verified clone was selected as REM I1__9

Amplification of the pEWL454 Fragment

To generate pEWL454 the following PCR reaction was set up:

1 ul template (approx. 1 ul volume of pK184 w/aspA term vector (Gene Oracle, Inc.))
5 ul 10X Pfu Ultra II Fusion DNA polymerase
2.5 ul dNTP's (10 mM)
1.0 primer (10 uM) EL-1098
1.0 primer (10 uM) EL-1099
39.5 ul diH2O
+1 ul of Pfu Ultra II Fusion DNA polymerase from Stratagene Cycle Parameter:

95° C.×2 min., [95° C.×30 sec., 60° C.×30 sec., 72° C.×52 sec.]×29 cycles; 72° C.×3 min., 4° C. until cool (MJ Research PTC-200 Peltier Thermal Cycler)

The resulting PCR fragment was separated on a 1.2% E-gel (Invitrogen) for verification of successful amplification.

Strain REM I19 Description

The strain REM I1__9 was used to clone the *Anabaena* sp. PCC7120 ispH allele, which had been codon optimized for expression in *E. coli* (provided by Gene Oracle, Inc.). Surprisingly Gene Oracle, Inc. was unable to provide an *E. coli* strain harboring the desired clone. Therefore, strain REM I1__9 was used as a host to obtain the Ptac Anabaena ispH aspA term/pEWL454 clone of interest using a survival based strategy.

Strain REM I1__9 is derived from MD09-220 (BL21 (DE3) PL.2 mKKDyI::FRT-ΔispH::FRT) and has been described previously. The FRT-neo-FRT-GI1.6-dxs locus of strain MCM625 was transduced into the genome of MD09-220 via standard P1 lystate/P1 transduction protocol (Thomason et al., 2007) and the resulting kanamycin resistant strain named REM C5__9. Using Gene Bridge's GmbH methods the antibiotic marker was looped out, generating strain REM H5__9. Subsequently, the pgl and galP region of MG1655 was transduced into strain REM H5__9 using standard P1 lystate/P1 transduction protocol (Thomason et al., 2007), and the cells selected for growth on M9 agar (Na2HPO4 6 g/L, KH2PO4 3 g/L, NaCl 0.5 g/L, NH4Cl 0.5 g/L, 0.1 mM $CaCl_2$, 2 mM MgSO4, 1.5% agar) containing 0.4% w/v galactose and 500 uM mevalonic acid. The presence of the pgl locus in the galactose-utilizing, mevalonic acid-dependent, kanamycin sensitive cells was verified by PCR (see above) and one clone selected as REM I1__9 (BL21 (DE3) PL.2 mKKDyI::FRT-ΔispH::FRT pgl$^+$ FRT::GI1.6-dxs).

Cloning of the *Anabaena* sp. PCC7120 ispH allele into pEWL454

Approximately 90 ng of a precut 5' BamHI—3' PstI purified DNA fragment harboring the *Anabaena* sp. PCC7120 ispH allele codon optimized for expression in *E. coli* (provided by Gene Oracle, Inc.) was ligated to precut 5' BamHI—3' PstI purified DNA vector backbone pEWL454 (provided by Gene Oracle, Inc.), harboring the tac promoter and aspA terminator sequences separated by a multiple cloning site (MCS) within a pK184 (Jobling and Holmes, 1990) derived plasmid, using T4 DNA Ligase (New England Biolabs) according to the manufacturer's suggested protocol. The aspA terminator sequences present in pEWL454 were synthesized by Gene Oracle, Inc. Using the PCR method outlined above, the lac promoter sequence present in pK184 was removed and the tac promoter and MCS harbored within pEWL454 was inserted using the oligos detailed above (Integrated DNA Technologies). The resulting PCR fragment was ligated using T4 DNA Ligase from New England Biolabs according to the manufacturer's suggested protocol. Chemically competent TOP10 cells (Invitrogen) were transformed with the ligation reaction using a standard heat-shock protocol (Sambrook et al., 1989), recovered in L broth for 1 hour at 37° C. and then plated on L agar containing kanamycin (50 ug/ml). A kanamycin resistant clone was selected, grown overnight in L broth containing kanamycin (50 ug/ml), and harvested for subsequent plasmid preparation. Plasmid constructs were isolated using Qiagen Qiaprep Spin Miniprep Kit. Plasmid preparations of interest were sequenced (Quintara; Albany, Calif.) using primers EL-1100, EL-1101, EL-1102, EL-1103, and EL-1104 and the correct pEWL454 clone identified, which has been designated as strain EWL454 (TOP10 w/pEWL454; pK184-derived cloning vector harboring Ptac-RBS-NdeI-SacI-MluI-NotI-XhoI-PstI-aspA terminator). A picture illustrating pEWL454 is shown in FIG. 87.

Water-washed REM I1__9 cells were transformed with the ligation reaction via electroporation using the BIO RAD Gene Pulser system (0.1 cm cuvette cat.#165-2089) and a transformation protocol suggested by the manufacturer (BIO RAD). The cells were recovered in L broth plus 500 uM mevalonic acid (available commercially, for example, Sigma-Aldrich) for 1 hour at 37° C. and then plated on L agar containing kanamycin (50 ug/ml). Kanamycin resistant colonies that grew in the absence of mevalonic acid were selected, grown overnight in L broth containing kanamycin (50 ug/ml), and harvested for subsequent plasmid preparation; the presence of the Anabaena ispH allele relieved the cell's dependence on mevalonic acid for growth. Plasmid constructs were isolated using Qiagen Qiaprep Spin Miniprep Kit. Plasmid preparations of interest were sequenced (Sequetech; Mountain View, Calif.) using primers EL-1105 and Neo. 21 and the correct Ptac Anabaena ispH aspA term/pEWL454 clone identified, which has been designated as strain REM F5__12 (REM I1__9 w/Ptac Anabaena ispH aspA term/pEWL454; 5' BamHI-3' PstI synthetic fragment into 5' BamHI-3' PstI of pEWL454). A picture of the resulting Ptac Anabaena ispH aspA term/pEWL454 construct is shown in FIG. 88.

B. Strategy for Creating REM I7__11 and REM H8__12

REM I7__11 was constructed by transformation of GI1.6 fldA-ispG/pCL into WW119. The transformation was performed by electroporation using a BIO RAD Gene Pulser system (0.1 cm cuvette cat.#165-2089) and a transformation protocol suggested by the manufacturer (BIO RAD). A plasmid preparation of GI1.6 fldA-ispG/pCL, generated from strain REM D9__11, was used; this strain and corresponding plasmid construct are described infra.

REM H8__12 was constructed by transformation of Ptac Anabaena ispH aspA term/pEWL454. The transformation was performed by electroporation using a BIO RAD Gene Pulser system (0.1 cm cuvette cat.#165-2089) and a transformation protocol suggested by the manufacturer (BIO RAD). A plasmid preparation of Ptac Anabaena ispH aspA term/pEWL454 was made from strain REM F5__12.

Transformation of GI1.6 fldA-ispG/pCL into WW119 and Ptac Anabaena ispH aspA term/pEWL454 into REM I7__11

To build the isoprene producing parental strain, REM I7__11, from which the test strain REM H8__12 is derived, the GI1.6 fldA-ispG/pCL plasmid was transformed by electroporation into WW119. Transformants were recovered in L broth and plated on L agar containing spectinomycin (50 ug/ml) and carbenicillin (50 ug/ml). The resulting strain was designated REM I7__11.

REM I7__11 was then transformed by electroporation with Ptac Anabaena ispH aspA term/pEWL454. Transformants were recovered in L broth and plated on L agar containing spectinomycin (50 ug/ml), kanamycin (50 ug/ml), and carbenicillin (50 ug/ml). The resulting strain was designated REM H8__12.

C. Analysis of Test Strain REM H8__12 and the Parental Strain REM I7__11 for Growth, Isoprene Production, and DXP Metabolite Accumulation at Small Scale.

The parental strain REM I7__11 was compared against the test strain REM H8__12 in a shake flask assay as well as in a DXP metabolite determination study. The increased benefit on isoprene production of the REM H8__12 strain harboring the Ptac Anabaena ispH aspA term/pEWL454 construct over the parental control strain REM I7__11 is depicted in FIG. 89. The increased IspH activity present in the REM H8__12 strain compared to the parent strain REM I7__11 is reflected by the averaged 10-fold decrease in HDMAPP across the 3 hour and 3.75 hour time points (FIG. 89). This elevated IspH activity provided by expression of the *Anabaena* sp. PCC7120 ispH allele permitted a 2.1 to 3.2-fold increase in isoprene production from the REM H8__12 test strain over the parental control (FIG. 89). The REM H8__12 test strain also grew moderately better (approx. 20% faster) than the parental strain REM I7__11.

Growth

Strains REM I7__11 and REM H8__12 were grown at 30° C. in 2-5 ml cultures of TM3 liquid media (13.6 g $K_2PO_4$, 13.6 g $KH_2PO_4$, 2.0 g $MgSO_4$*$7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) supplemented to a final concentration with 0.1% yeast extract and 1.0% glucose and including spectinomycin (50 ug/ml) and carbenicillin (50 ug/ml).). Induction of LacI-regulated gene expression was achieved by adding isopropyl-beta-D-1-thiogalactopyranoside (IPTG) to a concentration of 500 uM. Growth was monitored periodically by recording each of the culture's optical density measured at 600 nm using an Eppendorf Biophotometer spectrometer (Eppendorf).

Isoprene Production

Isoprene production was analyzed using a headspace assay. For the shake flask cultures, 200 ul of a culture was transferred from shake flasks to 2 ml CTC headspace vials (SUN-SRI 2 mL HS vials, VWR#66020-950, and caps, VWR#66008-170). The cap was screwed on tightly and the vials incubated at the equivalent temperature with shaking at 250 rpm. After 30 minutes the vials were removed from the incubator and analyzed. The analysis was performed using an Agilent 6890 GC/MS system interfaced with a CTC Analytics (Switzerland) CombiPAL autosampler operating in headspace mode. An Agilent HP-5MS GC/MS column (15 m×0.25 mm; 0.25 μm film thickness) was used for separation of analytes. The sampler was set up to inject 100 μL of headspace gas. The GC/MS method utilized helium as the carrier gas at a flow of 1 ml/minutes The injection port was held at 250° C. with a split ratio of 50:1. The oven temperature was held at 37° C. for 0.6 minute, the duration of the analysis. The Agilent 5793N mass selective detector was run in single ion monitoring (SIM) mode on m/z 67. The detector was switched off from 0 to 0.42 minutes to allow the elution of permanent gases. Under these conditions isoprene (2-methyl-1,3-butadiene) was observed to elute at approx. 0.49 minutes. A calibration table was used to quantify the absolute amount of isoprene and was found to be linear from 1 μg/L to 5000 μg/L. The limit of detection was estimated to be 50 to 100 ng/L using this method. The specific productivity of each strain is reported as ug/L OD Hr. Note, ratio of 1900 ul headspace: 100 ul broth in assay vials for 30 min. incubation results in the following conversion of isoprene ug/L of culture to specific productivity: (isoprene/L determined by GC-MS)×(38)/(OD 600 nm of the culture).

DXP Metabolite Accumulation

The DXP metabolites of the isoprene-producing parental strain REM I7_11 and test strain REM H8_12 that are described above and depicted in FIG. 89 were isolated and quantified as follows:

Metabolite Extraction: Processing Samples from Small-Scale Experiments.

To measure accumulation of metabolites in small-scale experiments 0.4 to 1.5 mL of cell culture was centrifuged for 3 min at 7500×g, at −9° C. Immediately after centrifugation the supernatant was aspirated to a clean tube for analysis of excreted metabolites and 100 μL of dry ice-cold methanol was added to pelleted cells. The resulting samples were then stored at −80° C. until further processing.

To determine concentrations of excreted metabolites, 500 μL of methanol was added to 300 μL of the supernatant and the resulting mixture was centrifuged for 10 min at 20000×g at 4° C. to remove insoluble material before the LCMS analysis.

For metabolites extraction from the pellet (further referred as intracellular metabolites), 10 μL of water was added to methanol-containing samples, the pellet was resuspended in the resulting methanol/water mix and cell debris were spun down by 4-min centrifugation at 4500×g. The pellet was re-extracted two more times, first with 100 μL of 75% methanol buffered with 1 mM ammonium acetate in water (pH=8.0), then with 90 μL of 50% methanol in the ammonium acetate buffer. After each extraction, cell debris was pelleted by centrifugation and the supernatants from all three extractions were combined and analyzed by LCMS. During the extraction procedure, samples were kept on ice or in a refrigerated centrifuge whenever possible to minimize metabolites degradation.

Metabolite Quantitation

Extracted metabolites were analyzed by LC-ESI-MS/MS on a Quantum triple quadrupole mass spectrometer (Thermo Electron Corporation, San Jose, Calif.). The system control, data acquisition, and mass spectral data evaluation were performed using XCalibur and LCQuan software (Thermo Electron Corp). LC separation was done on a Synergi 45 μM Hydro-RP HPLC column (150×2 mm, Phenomenex, USA) at a flow rate of 0.4 mL/min and the column temperature of 40° C. The LC gradient was t=0 min, 12% B; t=5 min, 12% B; t=9 min, 23% B; t=20 min, 99% B; t=23 min, 99% B; t=24 min, 12% B; t=29 min, 12% B, where solvent A was 10 mM tributylamine/15 mM acetic acid in water and solvent B was LCMS-grade methanol. The sample injection volume was 10 μL.

Mass detection was carried out using electrospray ionization in the negative mode. The following m/z values for precursor ions were selected to detect the metabolites of interest in SRM mode: 213.0 for DXP, 215.0 for MEP, 245.0 for IPP and DMAPP, 260.0 for HDMAPP, and 277.0 for cMEPP, 381.1 for FPP, 520.1 for CDP-ME, 600.0 for CDP-MEP. Concentrations of metabolites were determined based on integrated intensities of peaks generated by $PO_3^-$ product ion (m/z=79.0) using calibration curves obtained by injection of corresponding standards (Echelon Biosciences Inc). The concentration of CDP-MEP was expressed in arbitrary units because of the unavailability of commercial standard. Intracellular concentrations of metabolites were calculated based on a standard assumption that in 1 mL of the culture at OD=200 the integrated volume of all cells is 50 μL.

D. Analysis of Test Strain REM H8_12 for Growth, Isoprene Production, and DXP Metabolite Accumulation at 14-L Fermentation Scale.

REM_H8_12 produced 2.6 g/L isoprene in 14-L fermentation (FIG. 14A). In addition to increased isoprene, the REM H8_12 test strain maintained roughly 2-fold higher levels of the MEP metabolite (product of DXR) and greater than 15-fold higher levels of cMEPP (substrate for IspG) across the entire 14-L fermentation than previously observed for the GI1.6 fldA-ispG/pCL containing strain REM G4_11 (compare FIG. 80C to FIG. 90C).

E. Large Scale Fermentation of Strain REM H8_12

Isoprene production from *E. coli* expressing genes from the DXP pathway and isoprene synthase, grown in fed-batch culture at the 15-L scale.

1000× Modified Trace Metal Solution (per liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Mercury Vitamin Solution (per liter):

Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Feed Solution (per Kilogram):

Glucose 0.57 kg, Di H2O 0.38 kg, K2HPO4 7.5 g, and 100% Foamblast 10 g. All components were mixed together and autoclaved. Macro Salt Solution 3.4 mL, 1000× Modified Trace Metal Solution 0.8 ml, and Mercury Vitamin Solution 6.7 mL were added after the solution had cooled to 25° C.

Macro Salt Solution (per liter):

MgSO4*7H2O 296 g, citric acid monohydrate 296 g, ferric ammonium citrate 49.6 g. All components were dissolved in water, q.s. to volume and filter sterilized with 0.22 micron filter.

Fermentation was performed in a 15-L bioreactor with *E. coli* BL21 cells overexpressing the first enzyme in the dxp pathway (GI1.6-dxs), the last enzyme in the DXP pathway (GI1.6-yIDI), the lower MVA pathway (PL.2-mKKDyl), various other genes from the DXP pathway of *T. elongatus* (Ptac-gcpE-lytB-petF-petH/pK184), the *E. coli* ispG and fldA genes (GI1.6 fldA-ispG/pCL), and truncated isoprene synthase from *P. alba* (pDW33) and containing a restored 17,257 by chromosomal galM-containing region derived from MG1655 (strain name REM H8__12). This experiment was carried out to monitor isoprene formation from glucose at the desired fermentation pH 7.0 and temperature 34° C. A frozen vial of the *E. coli* strain was thawed and inoculated into tryptone-yeast extract medium for the bioreactor. After the inoculum grew to optical density 1.0, measured at 550 nm ($OD_{550}$), 500 mL was used to inoculate a 15-L bioreactor and bring the initial tank volume to 5 L.

The feed solution was fed at an exponential rate until a top feed rate of 5.8 g/min was reached. After this time, the glucose feed was fed to meet metabolic demands at rates less than or equal to 5.8 g/min. The total amount of glucose delivered to the bioreactor during the 44 hr fermentation was 4.4 kg. Induction was achieved by adding isopropyl-beta-D-1-thiogalactopyranoside (IPTG). A single shot of IPTG was added to the tank to bring the concentration to 300 uM when the cells were at an $OD_{550}$ of 7.

The isoprene level in the off-gas from the bioreactors was determined using a Hiden mass spectrometer. The isoprene titer increased over the course of the fermentation to a maximum value of 2.6 g/L at 44 hr.

Equation for calculating Isoprene Titer: ∫(Instantaneous isoprene production rate, g/L/hr)dt from t=0 to 84 hrs[=]g/L broth F. DXP Metabolite Determination Metabolite extraction: processing 14-L fermentor samples.

Cell metabolism was rapidly inactivated by withdrawing several milliliters of the fermentor culture into a pre-weighted tube filled with 9.0 mL of dry ice-cold methanol. The resulting sample was weighted again to calculate the amount of withdrawn cell culture and then put to −80° C. for storage until further analysis. In order to extract metabolites, 500 μL of methanol-quenched fermentation sample was spun down by centrifugation for 4 min at 4500×g, at −9° C. The pellet was then re-extracted twice, first with 350 μL of 85% methanol buffered with 5 mM ammonium acetate in water (pH=7.0) and then with 350 μL of 50% methanol in the ammonium acetate buffer. After each extraction, cell debris was pelleted by centrifugation and all three supernatants were pooled together for further analysis.

Metabolite Quantitation

Extracted metabolites were analyzed by LC-ESI-MS/MS on a Quantum triple quadrupole mass spectrometer (Thermo Electron Corporation, San Jose, Calif.). The system control, data acquisition, and mass spectral data evaluation were performed using XCalibur and LCQuan software (Thermo Electron Corp). LC separation was done on a Synergi 45 μM Hydro-RP HPLC column (150×2 mm, Phenomenex, USA) at a flow rate of 0.4 mL/min and the column temperature of 40° C. The LC gradient was t=0 min, 12% B; t=5 min, 12% B; t=9 min, 23% B; t=20 min, 99% B; t=23 min, 99% B; t=24 min, 12% B; t=29 min, 12% B, where solvent A was 10 mM tributylamine/15 mM acetic acid in water and solvent B was LCMS-grade methanol. The sample injection volume was 10 μL.

Mass detection was carried out using electrospray ionization in the negative mode. The following m/z values for precursor ions were selected to detect the metabolites of interest in SRM mode: 213.0 for DXP, 215.0 for MEP, 245.0 for IPP and DMAPP, 260.0 for HDMAPP, and 277.0 for cMEPP, 381.1 for FPP, 520.1 for CDP-ME, 600.0 for CDP-MEP. Concentrations of metabolites were determined based on integrated intensities of peaks generated by $PO_3^-$ product ion (m/z=79.0) using calibration curves obtained by injection of corresponding standards (Echelon Biosciences Inc). The concentration of CDP-MEP was expressed in arbitrary units because of the unavailability of commercial standard. Intracellular concentrations of metabolites were calculated based on a standard assumption that in 1 mL of the culture at OD=200 the integrated volume of all cells is 50 μL.

Example 30

Discovery of Apparent Biochemical Feedback Inhibition of Dxr and Alleviation of Negative Effects Thereof We made the surprising observation that in a DXP strain production of isoprene was shut off while cells were still in a vigorous growth phase. In addition these cells also accumulate1-deoxyxylulose-5-phosphate, the substrate for Dxr. Without being bound by theory, one possible hypothesis to explain this observation is that the pathway is subject to regulation either at the genetic level or at the biochemical level. Jawaid et. al., *PLoS One,* 4 (12):e8288 (2009) reported that a fraction of Dxr protein from *Francisella tularensis* was phosphorylated at ser177 when overexpressed in *E. coli*. This phosphorylation was presumed to inactivate the protein based on the observation that the mutations S177D and S177E led to inactive protein. We subsequently showed that purified Dxr from *E. coli* is inactivated when incubated with dimethylallyl diphosphate (DMAPP) or 1-hydroxy-2-methyl-2-(E)-butenyl 4-diphosphate (HMBPP). Further, an *E. coli* strain with a genetically modified deoxyxylulose phosphate (DXP) pathway was shown to accumulate DMAPP and/or HMBPP to levels higher than that observed in wild type. Without being bound by theory, based on the result of in vitro inactivation of Dxr and in vivo metabolite accumulation observed in the engineered DXP pathway strain, we postulate that the shut down of the pathway and the accumulation of 1-deoxyxylulose-5-phosphate is due to the in vivo inactivation of Dxr in the engineered strain. We discovered that shut down of the pathway in engineered strains is prevented by rebalancing pathway enzymes and maintaining levels of HDMAPP and DMAPP at concentrations below 1 to 2 mM DMAPP and 1 to 2 mM HDMAPP. These observations are exemplified in FIG. 90. FIG. 90A shows the isoprene production for strain REM H8__12, a strain with an improved DXP pathway as judged by sustained isoprene production and reaching a titer of 2.6 g/L, compared to REMG4__11 a less well balanced DXP pathway strain. Growth for REM H8__12 is shown in panel B of FIG. 90, while the growth of REMG4__11 is shown in FIG. 79C (grey triangles). Corresponding metabolite levels for REM H8__12 are shown in FIG. 90C. By 8 hours the HDMAPP levels are below 1 to 2 mM and isoprene production is maintained for a period of 30 hours or more (FIG. 90A open squares). In comparison FIG. 80C shows the metabolite levels for REM G4_11. The HDMAPP levels are significantly above 1 to 2 mM for a period of 10-12 hours and isoprene production is maintained only for about 10 to 15 hours, 15 to 20 hours short of expectation (FIG. 90A open circles). The final titer of this strain was 0.98 g/L.

A. Methods

Strains Description

REM I7_11—This strain arose from the modification of CMP271 detailed infra. CMP271 was transduced with P1 lysate MCM754, obtained as described below, harboring a modified PL.6 promoter (DNA seq.#1) replacing the native promoter in front of the dxs gene.

FRT-neo-FRT PL.x(trimmed) integrated at dxs.gb DNA seq.#1 sequence includes upstream FRT to and including ATG of dxs (SEQ ID NO: 130)

```
cgcgaagttcctattctctagaaagtataggaacttcattctaccgggta
ggggaggcgcttttcccaaggcagtctggagcatgcgctttagcagcccc
gctgggcacttggcgctacacaagtggcctctggcctcgcacacattcca
catccaccggtaggcgccaaccggctccgttctttggtggccccttcgcg
ccaccttccactcctcccctagtcaggaagttcccccccgccccgcagct
cgcgtcgtgcaggacgtgacaaatggaagtagcacgtctcactagtctcg
tgcagatggacagcaccgctgagcaatggaagcgggtaggcctttggggc
agcggccaatagcagctttgctccttcgctttctgggctcagaggctggg
aaggggtgggtccgggggcgggctcaggggcgggctcaggggcggggcgg
gcgcccgaaggtcctccggaggcccggcattctgcacgcttcaaaagcgc
acgtctgccgcgctgttctcctcttcctcatctccgggcctttcgacctg
cagcagcacgtgttgacaattaatcatcggcatagtatatcggcatagta
taatacgacaaggtgaggaactaaaccatgggatcggccattgaacaaga
tggattgcacgcaggttctccggccgcttgggtggagaggctattcggct
atgactgggcacaacagacgatcggctgctctgatgccgccgtgttccgg
ctgtcagcgcaggggcgcccggttctttttgtcaagaccgacctgtccgg
tgccctgaatgaactgcaggacgaggcagcgcggctatcgtggctggcca
cgacgggcgttccttgcgcagctgtgctcgacgttgtcactgaagcggga
agggactggctgctattgggcgaagtgccggggcaggatctcctgtcatc
tcaccttgctcctgccgagaaagtatccatcatggctgatgcaatgcggc
ggctgcatacgcttgatccggctacctgcccattcgaccaccaagcgaaa
catcgcatcgagcgagcacgtactcggatggaagccggtcttgtcgatca
ggatgatctggacgaagagcatcaggggctcgcgccagccgaactgttcg
ccaggctcaaggcgcgcatgcccgacggcgaggatctcgtcgtgacccat
ggcgatgcctgcttgccgaatatcatggtggaaaatggccgcttttctgg
attcatcgactgtggccggctgggtgtggcggaccgctatcaggacatag
cgttggctacccgtgatattgctgaagagcttggcggcgaatgggctgac
cgcttcctcgtgctttacggtatcgccgctcccgattcgcagcgcatcgc
cttctatcgccttcttgacgagttcttctgagcgggactctggggttcga
ataaagaccgaccaagcgacgtctgagagctccctggcgaattcggtacc
```

-continued

```
aataaaagagctttattttcatgatctgtgtgttggtttttgtgtgcggc
gcggaagttcctattctctagaaagtataggaacttcctcgagccctata
gtgagtcgtattaagataaccatctgcggtgataaattatctctggcggt
gttgacntaaataccactggcggtgatactgagcacatcagcaggacgca
ctgcaaaggaggtaaaaaaacatg
```

Looping out the associated antibiotic marker according to Gene Bridges instructions yielded strain WW102. This strain was additionally transduced with P1 lysate MCM755 harboring a promoter named gi1.6 (DNA seq.#2).

FRT-neo-FRT-gi1.x-dxr region BL21.gb DNA seq#2; sequence includes upstream FRT to and including ATG of dxr (SEQ ID NO: 129)

```
actaaagggcggccgcgaagttcctattctctagaaagtataggaacttc
attctaccgggtaggggaggcgcttttcccaaggcagtctggagcatgcg
ctttagcagccccgctgggcacttggcgctacacaagtggcctctggcct
cgcacacattccacatccaccggtaggcgccaaccggctccgttctttgg
tggccccttcgcgccaccttccactcctcccctagtcaggaagttccccc
ccgccccgcagctcgcgtcgtgcaggacgtgacaaatggaagtagcacgt
ctcactagtctcgtgcagatggacagcaccgctgagcaatggaagcgggt
aggcctttggggcagcggccaatagcagctttgctccttcgctttctggg
ctcagaggctgggaaggggtgggtccgggggcgggctcaggggcgggctc
aggggcggggcgggcgcccgaaggtcctccggaggcccggcattctgcac
gcttcaaaagcgcacgtctgccgcgctgttctcctcttcctcatctccgg
gcctttcgacctgcagcagcacgtgttgacaattaatcatcggcatagta
tatcggcatagtataatacgacaaggtgaggaactaaaccatgggatcgg
ccattgaacaagatggattgcacgcaggttctccggccgcttgggtggag
aggctattcggctatgactgggcacaacagacgatcggctgctctgatgc
cgccgtgttccggctgtcagcgcaggggcgcccggttctttttgtcaaga
ccgacctgtccggtgccctgaatgaactgcaggacgaggcagcgcggcta
tcgtggctggccacgacgggcgttccttgcgcagctgtgctcgacgttgt
cactgaagcgggaagggactggctgctattgggcgaagtgccggggcagg
atctcctgtcatctcaccttgctcctgccgagaaagtatccatcatggct
gatgcaatgcggcggctgcatacgcttgatccggctacctgcccattcga
ccaccaagcgaaacatcgcatcgagcgagcacgtactcggatggaagccg
gtcttgtcgatcaggatgatctggacgaagagcatcaggggctcgcgcca
gccgaactgttcgccaggctcaaggcgcgcatgcccgacggcgaggatct
cgtcgtgacccatggcgatgcctgcttgccgaatatcatggtggaaaatg
gccgcttttctggattcatcgactgtggccggctgggtgtggcggaccgc
tatcaggacatagcgttggctacccgtgatattgctgaagagcttggcgg
cgaatgggctgaccgcttcctcgtgctttacggtatcgccgctcccgatt
cgcagcgcatcgccttctatcgccttcttgacgagttcttctgagcggga
ctctggggttcgaataaagaccgaccaagcgacgtctgagagctccctgg
```

-continued

```
cgaattcggtaccaataaaagagctttattttcatgatctgtgtgttggt

ttttgtgtgcggcgcggaagttcctattctctagaaagtataggaacttc

ctcgagccctatagtgagtcgtattagcccttgacnatgccacatcctga

gcaaataattcaaccacttttattcactaacaaatagctggtggaatata

tg
```

This promoter was targeted to replace the native promoter of the dxr gene. Looping out the antibiotic marker according to Gene Bridges instructions yielded strain WW103. Strain WW103 was transformed by electroporation with plasmid pDW33 (Example 24 Part C) providing ispS, the isoprene synthase expression cassette and the resultant strain is designated WW119.

B. Detailed Strain Construction Protocols

Construction of Strain CMP271

Construction of Strain

Construction of P1 lysates MCM754 and MCM755 are detailed below:

```
Primers (provided by Integrated DNA Technologies;
Coralville, Iowa USA)
MCM320
                                        (SEQ ID NO: 128)
5'-tcgatacctcggcactggaagcgctagcggactacatcatccagcgt

aataaataaacaataagtattaataggcccctgaattaaccctcactaaa

gggcgg

MCM321
                                        (SEQ ID NO: 127)
5'-tgttcgggattatggcgcaccacgtccagcgtgctgcaaccaatcga

gccggtcgagcccagaatggtgagttgcttcatatattccaccagctatt

tgttagtgaataaaagtggttgaattatttgctcaggatgtggcatNgtc

aagggctaatacgactcactatagggctcg

MCM337
                                        (SEQ ID NO: 126)
5'-acaaaaacgccgctcagtagatccttgcggatcggctggcggcgttt

tgctttttattctgtctcaactctggatgtttcaattaaccctcactaaa

gggcgg

MCM347
                                        (SEQ ID NO: 125)
5'-aacagtcgtaactcctgggtggagtcgaccagtgccagggtcgggta

tttggcaatatcaaaactcatgtttttttacctcctttgcagtgcgtcct

gctgatgtgctcagtatcaccgccagtggtatttaNgtcaacaccgccag

agataatttatcaccgcagatggttatcttaatacgactcactatagggc

tcg

MCM327
                                         (SEQ ID NO: 59)
5'-ttgtagacatagtgcagcgcca

MCM330
                                        (SEQ ID NO: 124)
5' -ccctgttgctgtagcatcgttt

GB-DW
                                         (SEQ ID NO: 60)
5'-aaagaccgaccaagcgacgtctga
```

C. Creation of Amplicon for Promoter Integration

PL.6(trim)-dxs

PCR reactions were carried out in quadruplicate using the Herculase II Fusion Kit (Stratagene).

35 uL $ddH_2O$
10 uL 5× buffer
1.25 uL 10 uM primer MCM320, (gel purified)
1.25 uL 10 uM primer MCM347, (gel purified)
0.5 uL dNTPs
1 uL polymerase
1 uL FRT-PGK-gb2-neo-FRT template DNA, GeneBridges Cat. No. K006

Reactions were cycled as follows:

95 C×2 min followed by (95 C×15 sec; 55 C×15 sec; 72 C×1 min)×30 cycles 72 C×3 min 30 sec 4 C until cold.

gi1.6-dxr

Four PCR reactions were carried out in using the Herculase II Fusion Kit (Stratagene). Reactions varied by the presence or absence of 2 uL DMSO and an annealing temperature of 55 C or 60 C.

35 uL $ddH_2O$
10 uL 5× buffer
1.25 uL 10 uM primer MCM321, IDT (gel purified)
1.25 uL 10 uM primer MCM337, IDT (gel purified)
0.5 uL dNTPs
1 uL polymerase
1 uL FRT-PGK-gb2-neo-FRT template DNA, GeneBridges Cat. No. K006
+/−2 uL DMSO Reactions were cycled as follows:

95 C×2 min followed by (95 C×20 sec; 55 C or 60 C×20 sec; 72 C×1 min)×30 cycles 72 C'3 min; 4 C until For each amplicon, four reactions were pooled and purified using a QIAquick PCR Purification kit (Qiagen) PCR column, eluting in 30 uL EB.

D. Integration of Amplicon onto Chromosome

Strain MCM327 (BL21) carrying pRedET-carb (GeneBridges) was grown in L broth (LB) containing carbenicillin (50 ug/ml) at 30 C overnight and then diluted 1:100 into fresh LB+carb50 and cultured at 30 C for 2 hr. 130 uL of 10% arabinose was added and cells cultured at 37 C for approximately 2 hours. Cells were prepared for electroporation by washing 3× in one half culture volume iced $ddH_2O$ and resuspended in one tenth culture volume of the same. 100 uL of cell suspension was combined with 3 uL DNA amplicon in a 2 mm electroporation cuvette, electroporated at 25 uFD, 200 ohms, 2.5 kV, (Gene Pulser MXcell; BioRad) and immediately quenched with 500 uL LB. Cells were recovered shaking at 37 C for 1-3 hrs and then transformants selected overnight on L agar (LA) plates containing kanamycin (10 ug/ml) at 37 C.

Single colonies arising from transformations with each DNA amplicon were patched to LA+kan50 and grown overnight at 37 C. Clones were inoculated into 5 mL LB+kan10, grown to an $OD_{600}$~1 and then frozen by mixing 1 mL 50% glycerol and 0.5 mL culture, placing on dry ice until solid, and then storing at −80 C. These manipulations resulted in strain MCM754 [PL.6(trim) dxs] and strain MCM755 (gi1.6 dxr).

The integrated promoters were amplified for sequencing by colony PCR using the Herculase II Fusion kit (Stratagene).

35 uL $ddH_2O$
10 uL 5× buffer
1.25 uL 10 uM primers GB-DW
1.25 uL 10 uM primer MCM327 (dxs) or MCM330 (dxr)
0.5 uL dNTPs
1 uL polymerase Colony Scraping Reactions were cycled as follows:

95 C for 2 min; (95 C for 20 sec; 55 C for 20 sec; 72 C for 30 sec)×30 cycles; 72 C 3 min; 4 C until cold PCR products were sequenced (Quintara Biosciences) following treatment by ExoSAP.

```
P1 lysate MCM754, containing PL.6-dxs, was
sequenced with primers GB-DW and MCM327
                                    (SEQ ID NO: 123)
5'-Aaagaccgaccaagcgacgtctgagagctccctggcgaattcggtac

caataaaagagctttattttcatgatctgtgtgttggtttttgtgtgcgg

cgcggaagttcctattctctagaaagtataggaacttcctcgagccctat

agtgagtcgtattaagataaccatctgcggtgataaattatctctggcgg

tgttgacataaataccactggcggtgatactgagcacatcagcaggacgc

actgcaaaggaggtaaaaaaacatgagttttgatattgccaaatacccga

ccctggcactggtcgactccacccaggagttacgactgtt

P1 lysate MCM755, containing gi1.6-dxr, sequenced
with primers GB-DW and MCM330
                                    (SEQ ID NO: 122)
5'-aaagaccgaccaagcgacgtctgagagctccctggcgaattcggtac

caataaaagagctttattttcatgatctgtgtgttggtttttgtgtgcgg

cgcggaagttcctattctctagaaagtataggaacttcctcgagccctat

agtgagtcgtattagcccttgacaatgccacatcctgagcaaataattca

accacttttattcactaacaaatagctggtggaatatatgaagcaactca

ccattctgggctcgaccggctcgattggttgcagcacgctggacgtggtg

cgccataatcccgaacacttccgcgtagttgcgctggtggcaggcaaaaa

tgtcactcgcatggtagaacagtgcctggaattctctccccgctatgccg

taatggacgatgaagcgagtgcgaaacttcttaaaacgatgctacagcaa

caggg
```

E. Preparation of P1 Lysates from Strains MCM754 and MCM755.

100 uL of respective overnight cultures (LB+kan10) were diluted into 10 mL LB+0.2% glucose+5 mM $CaCl_2$, and grown with shaking at 250 rpm, 37 C. After 30 min., 100 uL of a generic P1 lysate from MG1655 was added and the culture returned to the shaker for ~3 hours. The lysed culture was transferred to a 15 mL tube, 200 uL chloroform added, and it was vortexed for 30 sec. The sample was centrifuged at 4500 g for 10 min and then the aqueous supernatant transferred to a fresh 15 mL tube. 200 uL chloroform was added and the lysate stored at 4 C.

F. Cloning and Purification of the Enzyme.

Dxr from *E. coli* was cloned and purified by methods well known to those of skill in the art. The gene was inserted into the pET15b vector as described by the vendor to include a N-terminal His tag sequence (Invitrogen, Carlsbad, Calif.). A BL21(λDE3) *E. coli* culture harboring the plasmid and expressing the protein was harvested, the cell pellet lysed in a French pressure cell and protein was purified using a Ni-NTA column following the protocol recommended by the manufacturer (GE Healthcare, Pittsburgh, Pa.).

G. Dxr Inactivation by Incubation with DMAPP and HDMAPP.

The purified protein, 5 uM, was incubated at several concentration of DMAPP or HMBPP (Echelon Bioscience, Salt Lake City, Utah) in buffer consisting of 100 mM Tris, 100 mM NaCl pH 8, 5 mM $MgCl_2$, 0.2 mM NADPH, 0.2 mM DXP, and 250 nM DXR. D at 37° C. for two hour in a total volume of 50 uL. Dxr activity was measured periodically according to standard assay, see, e.g., Koppisch et al, *Biochemistry,* 41:236-43 (2002) with a 20-fold dilution of the inactivation reaction mixture. Control incubations and assays of the enzyme were conducted under similar conditions in the absence of DMAPP or HMBPP in the inactivation reaction. Where appropriate additional control activity assays were conducted in the presence of a 20-fold diluted concentration of inactivators (DMAPP or HMBPP). A larger aliquot of enzyme (about 400 ug) was inactivated similarly with DMAPP for analysis by mass spectroscopy to verify the anticipated amino acid residue modification. As shown in FIG. 92 enzyme activity declined during the inactivation incubation and yielding an inactivation half-life of 0.72 hours.

Example 31

Co-Expression of DXP and MVA Pathways for the Production of Isoprene in *E. coli*

Comparison of the energetics and carbon utilization efficiency for the DXP pathway and the MVA pathway reveal that the DXP pathway is more efficient in carbon utilization but less efficient in redox balance than the MVA pathway. When glucose is the carbon source stoichiometric yield on carbon of the DXP pathway is about 85% (grams of isoprene produced per grams of glucose utilized). The energy balance of the DXP pathway is less efficient when compared to the MVA pathway. For DXP glucose to isoprene suffers a shortage of 3 moles of NAD(P)H per mole of isoprene formed and is minus 2 moles of ATP. For the similar comparison of glucose to isoprene via MVA this pathway produces an excess of 4 moles of NAD(P)H; ATP is balanced, however, the carbon utilization efficiency is only about 55%. Without being bound by theory, a more balanced and more efficient production host can be made by combining the two pathways in a single host to optimize redox chemistry and efficiency of carbon utilization.

In this example, we provide evidence consistent with that combination of the two pathways in a single host can be established in practice. Combination of the two pathways should lead to an improved process. A series of cultures comprising two strains, REM H8_12 and REM I7_11, described above, were set up in a 48-deep-well plate (cat# P-5mL-48-C-S Axygen Scientific, California, USA) with each well providing a 2 mL culture. The media, named TM3, is described below. The two strains were grown overnight at 30 degrees Celsius at 250 rpm in TM3 medium supplemented with 1% glucose and 0.1% yeast extract. In the morning, the two strains were inoculated into the 48-deep well block in replicate. The TM3 medium was supplemented with 1% [U-13C]-glucose and 0.1% yeast extract. The cultures were shaken at 30 degrees C. at 600 rpm (Shel-Lab Inc. Model SI6R Refrigerated Shaking Incubator; Oregon, USA). Culture OD was determined after two hours and then at timed intervals out to 4.25 hours. The cultures were induced at two hours of growth by the addition of 400 uM IPTG. After one hour of induction the cultures of each strain also received from 0 to 8 mM (R)-mevalonic acid [cat Sigma M4667]. At timed intervals a 100 uL aliquot of each culture was transferred to a 98-deep well glass block (cat#3600600 Zinsser; North America) which was immediately sealed with an impermeable adhesive aluminum film and incubated for 30 minutes with shaking at 450 rmp on an Eppendorf thermomixer (Eppendorf; North America.). The cultures were killed by heating at 70 degrees C. for 7 minutes on a second Eppendorf thermomixer. The glass block was transferred to an Agilent 6890 GC attached to an Agilent 5973 MS and outfitted with a LEAP CTC CombiPAL autosampler for head space analysis. The column was an Agilent HP-5 (5% Phenyl Methyl Siloxane (15m×0.25 mm×0.25 um)). A 100 uL gas volume was injected on the column. Other conditions were as follows. Oven Temperature: 37 C (held isothermal for 0.6 mins); Carrier Gas: Helium (flow—1 mL/min), split ratio of 50:1 at 250° C. on the injection port; Single Ion Monitoring mode (SIM) on mass 67 or 73; Detector off: 0.00 min-0.42 mins; Dectector on: 0.42 mins-0.60 mins; elution time for Isoprene (2-methyl-1,3 butadiene) was ~0.49 min for a total analysis time of 0.6 mins. Calibration of the instrument was performed by methods well known to those of skill in the art.

Isoprene head space measurements were normalized by culture $OD_{600}$ to yield a measure of specific isoprene production in units of ug/L/H/OD. All reactions were followed for 4 hours. FIGS. 92A and B show the results for this experiment. Isoprene is simultaneously produced from [U—$^{13}$C]-glucose (FIG. 92 panel B) as well as from mevalonic acid (FIG. 92 panel A). The data indicate that the isoprene produced from [U—$^{13}$C]-glucose by the two strains is independent of isoprene produced by mevalonate. Panel B of FIG. 92 further shows that the specific productivity of isoprene from [U-$^{13}$C]-glucose is the same for both strains at mevalonate concentrations ranging from 0 to 8 mM. These measurements were made at m/z of 73 indicative of [U—$^{13}$C]-glucose utilization. At the same time, the isoprene specific productivity increased with increasing mevalonic acid concentration over the same concentration range. This measurement was made at m/z of 67 indicative of mevalonate (all $^{12}$C) utilization. The overall conclusion of this experiment is that isoprene produced by the DXP pathway is not affected by isoprene produced from mevalonic acid by the lower MVA pathway.

TM3 (per Liter Fermentation Medium):

$K_2HPO_4$ 13.6 g, $KH_2PO_4$ 13.6 g, $MgSO_4$*7$H_2O$ 2 g, citric acid monohydrate 2 g, ferric ammonium citrate 0.3 g, yeast extract 1.0 g, 1000× Modified Trace Metal stock solution 1 ml. All of the components were added together and dissolved in Di H2O. The pH is adjusted to 6.8 with $NH_4OH$ and the solution is filter sterilized over a 0.22 micron membrane. Antibiotics were added post-sterile as needed. U—$^{13}$C-Glucose and [R]-mevalonic acid were added post sterile as indicated.

1000× Modified Trace Metal Stock Solution (per liter):

Citric Acids*H2O 40 g, $MnSO_4$*$H_2O$ 30 g, NaCl 10 g, $FeSO_4$*7$H_2O$ 1 g, $CoCl_2$*6$H_2O$ 1 g, $ZnSO_4$*7$H_2O$ 1 g, $CuSO_4$*5$H_2O$ 100 mg, $H_3BO_3$ 100 mg, $NaMoO_4$*2$H_2O$ 100 mg. Each component was dissolved one at a time in Di $H_2O$, pH was adjusted to 3.0 with HCl/NaOH, and then the solution was q.s. to volume and filter sterilized with a 0.22 micron filter.

Example 32

Demonstration of Isoprene Generated by Strain REM A2_17 via Dual Isoprenoid Biosynthetic Pathways Described here is the construction of an isoprene producing *E. coli* strain that harbors both an exogenous MVA isoprenoid biosynthetic pathway and an enhanced DXP biosynthetic pathway. Data presented here indicates that isoprene produced by strain REM A2_17 is derived from both types of isoprenoid biosynthetic pathways simultaneously. For this particular example, roughly 3:2 to 1:1 MVA-flux:DXP-flux contributions to isoprene production were observed; see FIG. 96-102.

Construction of Strain REM A2_17

The genomic insertions described in this example were carried out using the Red/ET system from Gene Bridges GmbH according to the manufacturer's instructions. The strain BL21 (Novagene) was used. P1 lysate preparations and transductions were performed as previously described (Thomason et al., 2007). The pBBR1MCS-5 vector has been described (Kovach et al., 1994) as have vector constructs MCM82, pMCM296, pDW34, pDW33, GI1.6 fldA-ispG/pCL, and Ptac Anabaena ispH aspA term/pEWL454 (see, e.g., Example 29 above and WO 2009/076676). MCM82 contains the pCL PtrcUpperPathway encoding encoding *E. faecelis* mvaE and mvaS). The Trc promoter, Trp promoter and aspA terminator sequences were obtained from the information provided by NCBI www.ncbi.nlm.nih.gov and EcoCyc www.ecocyc.org.

Construction of pDW15 (Ptrc-upper MVA pathway on pBBR1MCS-5)

To insert the upper MVA pathway onto the pBBR1MCS-5 vector, the entire expression cassette containing Ptrc, mvaE, mvaS, and the rrn terminator was amplified by PCR from MCM82 using the primers Upper5'XhoI and Upper3'XbaI. See below for PCR primer sequences (Table 9), reaction and cycling parameters. The approximately 4.2 kb PCR product was confirmed by gel electrophoresis (E-Gel, Invitrogen) and then purified using QiaQuick purification columns (Qiagen) according to the manufacturers recommended protocol. Purified PCR product and the pBBR1MCS-5 vector were then treated with XbaI and XhoI restriction endonucleases overnight at 37° C. See below for reaction conditions. The next day, reactions were heated to 65° C. to deactivate restriction enzymes prior to ligation. Ligation reactions (see below for conditions) were carried out at 4° C. overnight. Approximately 5 μl of the ligation reactions were transformed into chemically competent *E. coli* TOP10 cells (Invitrogen) according to the manufacturer's recommended protocol, recovered at 37° C. in LB for 1 hour, and then plated onto LB plates containing X-gal and Gentamicin at 10 μg/ml. Colonies displaying no β-galactosidase activity were selected for further analysis by PCR using primers M13 Reverse and MCM163 to confirm the presence of the insert. The plasmid from one of these colonies was purified (Qiagen) and completely sequenced (Quintara Biosciences, see Table 9 for primer sequences) to verify that it contained the complete upper MVA pathway expression cassette in the correct orientation. The sequence and map of pDW15 is listed below and in FIG. 93, respectively.

PCR Reaction and Cycling parameters:

1 μl MCM82 (approx. 30 ng)
10 μl 5× Herculase Buffer (Stratagene)
0.5 μl dNTPs (100 mM)
1 μl Upper5'XhoI (20 uM)
1 μl Upper3'XbaI (20 uM)
35.5 μl diH2O
1 μl Herculase DNA Polymerase (Stratagene)

1. 95° C. 4 min.
2. 95° C. 20 min, 52° C. 20sec., 72° C. 4 min., 5×
3. 95° C. 20 min, 55° C. 20sec., 72° C. 4 min., 25×
4. 72° C. 10 min,
5. 4° C. until cool DNA Digestion:

6 μl diH2O
2 μl 10× Buffer H (Roche)
10 μl DNA (pBBR1MCS-5 or PCR insert)

1 μl XhoI (Roche)
1 ul XbaI (Roche)
1. 37° C. overnight
2. 65° C. 20 min (heat kill)

Ligation:
2 μl diH2O
1 μl 10× ligase buffer (NEB)
1 μl T4 DNA ligase (NEB)
2 μl vector (pBBR1MCS-5)
4 μl insert (upper MVA expression cassette)
1. 4° C. overnight
2. microdialyze (Millipore) and transform into competent *E. coli* (Invitrogen)

TABLE 9

| PCR and Sequencing Primers | | |
|---|---|---|
| Upper5'XhoI | atgctcgagctgttgacaattaatcatccggctc | (SEQ ID NO: 121) |
| Upper3'XbaI | cgatctagaaaggcccagtctttcgactgagcc | (SEQ ID NO: 120) |
| MCM163 | | |
| CF07-58 | atgaaaacagtagttattattgatgc | (SEQ ID NO: 119) |
| CF07-59 | cttaaatcatttaaaatagc | (SEQ ID NO: 118) |
| CF07-82 | atgacaattgggattgataaaattag | (SEQ ID NO: 117) |
| CF07-86 | gaaatagccccattagaagtatc | (SEQ ID NO: 116) |
| CF07-87 | ttgccaatcatatgattgaaaatc | (SEQ ID NO: 115) |
| CF07-88 | gctatgcttcattagatccttatcg | (SEQ ID NO: 114) |
| CF07-89 | gaaacctacatccaatcttttgccc | (SEQ ID NO: 113) |

Sequence of pDW15
(SEQ ID NO: 176)

accttcgggagcgcctgaagcccgttctggacgccctggggccgttgaat cgggatatgcaggccaaggccgccgcgatcatcaaggccgtgggcgaaaa gctgctgacggaacagcgggaagtccagcgccagaaacaggcccagcgcc agcaggaacgcgggcgcgcacatttccccgaaaagtgccacctggcggcg ttgtgacaatttaccgaacaactccgcggccgggaagccgatctcggctt gaacgaattgttaggtggcggtacttgggtcgatatcaaagtgcatcact tcttcccgtatgcccaactttgtatagagagccactgcgggatcgtcacc gtaatctgcttgcacgtagatcacataagcaccaagcgcgttggcctcat gcttgaggagattgatgagcgcggtggcaatgccctgcctccggtgctcg ccggagactgcgagatcatagatatagatctcactacgcggctgctcaaa cctgggcagaacgtaagccgcgagagcgccaacaaccgcttcttggtcga aggcagcaagcgcgatgaatgtcttactacggagcaagttcccgaggtaa tcggagtccggctgatgttgggagtaggtggctacgtctccgaactcacg -continued accgaaaagatcaagagcagcccgcatggatttgacttggtcagggccga gcctacatgtgcgaatgatgcccatacttgagccacctaactttgtttta gggcgactgccctgctgcgtaacatcgttgctgctgcgtaacatcgttgc tgctccataacatcaaacatcgacccacggcgtaacgcgcttgctgcttg gatgcccgaggcatagactgtacaaaaaaacagtcataacaagccatgaa aaccgccactgcgccgttaccaccgctgcgttcggtcaaggttctggacc agttgcgtgagcgcatacgctacttgcattacagtttacgaaccgaacag gcttatgtcaactgggttcgtgccttcatccgtttccacggtgtgcgtcc atgggcaaatattatacgcaaggcgacaaggtgctgatgccgctggcgat tcaggttcatcatgccgtttgtgatggcttccatgtcggcagaatgctta atgaattacaacagtttttatgcatgcgcccaatacgcaaaccgcctctc cccgcgcgttggccgattcattaatgcagctggcacgacaggtttcccga ctggaaagcgggcagtgagcgcaacgcaattaatgtgagttagctcactc attaggcaccccaggctttacactttatgcttccggctcgtatgttgtgt ggaattgtgagcggataacaatttcacacaggaaacagctatgaccatga ttacgccaagcgcgcaattaaccctcactaaagggaacaaaagctgggta ccgggccccccctcgagctgttgacaattaatcatccggctcgtataatg tgtggaattgtgagcggataacaatttcacacaggaaacagcgccgctga gaaaaagcgaagcggcactgctctttaacaatttatcagacaatctgtgt gggcactcgaccggaattatcgattaactttattattaaaaattaaagag gtatatattaatgtatcgattaaataaggaggaataaaccatggatccga gctcaggaggtaaaaaaacatgaaaacagtagttattattgatgcattac gaacaccaattggaaaatataaaggcagcttaagtcaagtaagtgccgta gacttaggaacacatgttacaacacaacttttaaaaagacattccactat ttctgaagaaattgatcaagtaatctttggaaatgttttacaagctggaa atggccaaaatcccgcacgacaaatagcaataaacagcggtttgtctcat gaaattcccgcaatgacggttaatgaggtctgcggatcaggaatgaaggc cgttattttggcgaaacaattgattcaattaggagaagcggaagttttaa ttgctggcgggattgagaatatgtcccaagcacctaaattacaacgtttt aattacgaaacagaaagctacgatgcgcctttttctagtatgatgtatga tggattaacggatgcctttagtggtcaggcaatgggcttaactgctgaaa atgtggccgaaaagtatcatgtaactagagaagagcaagatcaattttct gtacattcacaattaaaagcagctcaagcacaagcagaagggatattcgc tgacgaaatagccccattagaagtatcaggaacgcttgtggagaaagatg aagggattcgccctaattcgagcgttgagaagctaggaacgcttaaaaca gtttttaaagaagacggtactgtaacagcagggaatgcatcaaccattaa tgatggggcttctgctttgattattgcttcacaagaatatgccgaagcac acggtcttccttatttagctattattcgagacagtgtggaagtcggtatt gatccagcctatatgggaatttcgccgattaaagccattcaaaaactgtt agcgcgcaatcaacttactacggaagaaattgatctgtatgaaatcaacg aagcatttgcagcaacttcaatcgtggtccaaagagaactggctttacca -continued gaggaaaaggtcaacatttatggtggcggtatttcattaggtcatgcgat
tggtgccacaggtgctcgtttattaacgagtttaagttatcaattaaatc
aaaaagaaaagaaatatggagtggcttctttatgtatcggcggtggctta
ggactcgctatgctactagagagacctcagcaaaaaaaaaacagccgatt
ttatcaaatgagtcctgaggaacgcctggcttctcttcttaatgaaggcc
agatttctgctgatacaaaaaaagaatttgaaaatacggctttatcttcg
cagattgccaatcatatgattgaaaatcaaatcagtgaaacagaagtgcc
gatgggcgttggcttacatttaacagtggacgaaactgattatttggtac
caatggcgacagaagagccctcagttattgcggctttgagtaatggtgca
aaaatagcacaaggatttaaaacagtgaatcaacaacgcttaatgcgtgg
acaaatcgtttttttacgatgttgcagatcccgagtcattgattgataaac
tacaagtaagagaagcggaagtttttcaacaagcagagttaagttatcca
tctatcgttaaacggggcggcggcttaagagatttgcaatatcgtacttt
tgatgaatcatttgtatctgtcgactttttagtagatgttaaggatgcaa
tgggggcaaatatcgttaacgctatgttggaaggtgtggccgagttgttc
cgtgaatggtttgcggagcaaaagattttattcagtattttaagtaatta
tgccacggagtcggttgttacgatgaaaacggctattccagtttcacgtt
taagtaaggggagcaatggccgggaaattgctgaaaaaattgttttagct
tcacgctatgcttcattagatccttatcgggcagtcacgcataacaaagg
aatcatgaatggcattgaagctgtagttttagctacaggaaatgatacac
gcgctgttagcgcttcttgtcatgcttttgcggtgaaggaaggtcgctac
caaggcttgactagttggacgctggatggcgaacaactaattggtgaaat
ttcagttccgcttgctttagccacggttggcggtgccacaaaagtcttac
ctaaatctcaagcagctgctgatttgttagcagtgacggatgcaaaagaa
ctaagtcgagtagtagcggctgttggtttggcacaaaatttagcggcgtt
acgggccttagtctctgaaggaattcaaaaaggacacatggctctacaag
cacgttctttagcgatgacggtcggagctactggtaaagaagttgaggca
gtcgctcaacaattaaaacgtcaaaaaacgatgaaccaagaccgagccat
ggctattttaaatgatttaagaaaacaataaaggaggtaaaaaaacatga
caattgggattgataaaattagtttttttgtgccccccttattatattgat
atgacggcactggctgaagccagaaatgtagaccctggaaaatttcatat
tggtattgggcaagaccaaatggcggtgaacccaatcagccaagatattg
tgacatttgcagccaatgccgcagaagcgatcttgaccaaagaagataaa
gaggccattgatatggtgattgtcgggactgagtccagtatcgatgagtc
aaaagcggccgcagttgtcttacatcgtttaatggggattcaacctttcg
ctcgctctttcgaaatcaaggaagcttgttacggagcaacagcaggctta
cagttagctaagaatcacgtagccttacatccagataaaaaagtcttggt
cgtagcggcagatattgcaaaatatggcttaaattctggcggtgagccta
cacaaggagctggggcggttgcaatgttagttgctagtgaaccgcgcatt
ttggctttaaaagaggataatgtgatgctgacgcaagatatctatgactt -continued ttggcgtccaacaggccacccgtatcctatggtcgatggtcctttgtcaa
acgaaacctacatccaatcttttgcccaagtctgggatgaacataaaaaa
cgaaccggtcttgattttgcagattatgatgctttagcgttccatattcc
ttacacaaaaatgggcaaaaaagccttattagcaaaaatctccgaccaaa
ctgaagcagaacaggaacgaattttagcccgttatgaagaaagtatcgtc
tatagtcgtcgcgtaggaaacttgtatacgggttcactttatctgggact
catttcccttttagaaaatgcaacgactttaaccgcaggcaatcaaattg
gtttattcagttatggttctggtgctgtcgctgaattttttcactggtgaa
ttagtagctggttatcaaaatcatttacaaaaagaaactcatttagcact
gctggataatcggacagaactttctatcgctgaatatgaagccatgtttg
cagaaactttagacacagacattgatcaaacgttagaagatgaattaaaa
tatagtatttctgctattaataataccgttcgttcttatcgaaactaaag
atctgcagctggtaccatatgggaattcgaagcttgggcccgaacaaaaa
ctcatctcagaagaggatctgaatagcgccgtcgaccatcatcatcatca
tcattgagtttaaacggtctccagcttggctgttttggcggatgagagaa
gattttcagcctgatacagattaaatcagaacgcagaagcggtctgataa
aacagaatttgcctggcggcagtagcgcggtggtcccacctgaccccatg
ccgaactcagaagtgaaacgccgtagcgccgatggtagtgtggggtctcc
ccatgcgagagtagggaactgccaggcatcaaataaaacgaaaggctcag
tcgaaagactgggcctttctagagcggccgccaccgcggtggagctccaa
ttcgccctatagtgagtcgtattacgcgcgctcactggccgtcgttttac
aacgtcgtgactgggaaaaccctggcgttacccaacttaatcgccttgca
gcacatccccctttcgccagctggcgtaatagcgaagaggcccgcaccga
tcgcccttcccaacagttgcgcagcctgaatggcgaatggaaattgtaag
cgttaatattttgttaaaattcgcgttaaatttttgttaaatcagctcat
tttttaaccaataggccgactgcgatgagtggcagggcggggcgtaattt
ttttaaggcagttattggtgcccttaaacgcctggtgctacgcctgaata
agtgataataagcggatgaatggcagaaattcgaaagcaaattcgacccg
gtcgtcggttcagggcagggtcgttaaatagccgcttatgtctattgctg
gtttaccggtttattgactaccggaagcagtgtgaccgtgtgcttctcaa
atgcctgaggccagtttgctcaggctctccccgtggaggtaataattgac
gatatgatcatttattctgcctcccagagcctgataaaaacggtgaatcc
gttagcgaggtgccgccggcttccattcaggtcgaggtggcccggctcca
tgcaccgcgacgcaacgcggggaggcagacaaggtatagggcggcgaggc
ggctacagccgatagtctggaacagcgcacttacgggttgctgcgcaacc
caagtgctaccggcgcggcagcgtgacccgtgtcggcggctccaacggct
cgccatcgtccagaaaacacggctcatcgggcatcggcaggcgctgctgc
ccgcgccgttcccattcctccgtttcggtcaaggctggcaggtctggttc
catgcccggaatgccgggctggctgggcggctcctcgccggggccggtcg
gtagttgctgctcgcccggatacagggtcgggatgcggcgcaggtcgcca
tgccccaacagcgattcgtcctggtcgtcgtgatcaaccaccacggcggc -continued

```
actgaacaccgacaggcgcaactggtcgcggggctggccccacgccacgc

ggtcattgaccacgtaggccgacacggtgccggggccgttgagcttcacg

acggagatccagcgctcggccaccaagtccttgactgcgtattggaccgt

ccgcaaagaacgtccgatgagcttggaaagtgtcttctggctgaccacca

cggcgttctggtggcccatctgcgccacgaggtgatgcagcagcattgcc

gccgtgggtttcctcgcaataagcccggcccacgcctcatgcgctttgcg

ttccgtttgcacccagtgaccgggcttgttcttggcttgaatgccgattt

ctctggactgcgtggccatgcttatctccatgcggtagggtgccgcacgg

ttgcggcaccatgcgcaatcagctgcaacttttcggcagcgcgacaacaa

ttatgcgttgcgtaaaagtggcagtcaattacagattttctttaacctac

gcaatgagctattgcgggggtgccgcaatgagctgttgcgtacccccct

tttttaagttgttgatttttaagtctttcgcatttcgccctatatctagt

tctttggtgcccaaagaagggcacccctgcggggttcccccacgccttcg

gcgcggctcccctccggcaaaaagtggcccctccggggcttgttgatcg

actgcgcggccttcggccttgcccaaggtggcgctgcccccttggaaccc

ccgcactcgccgccgtgaggctcgggggcaggcgggcgggcttcgcctt

cgactgcccccactcgcataggcttgggtcgttccaggcgcgtcaaggcc

aagccgctgcgcggtcgctgcgcgagccttgacccgccttccacttggtg

tccaaccggcaagcgaagcgcgcaggccgcaggccggaggcttttcccca

gagaaaattaaaaaaattgatggggcaaggccgcaggccgcgcagttgga

gccggtgggtatgtggtcgaaggctgggtagccggtgggcaatccctgtg

gtcaagctcgtgggcaggcgcagcctgtccatcagcttgtccagcagggt

tgtccacgggccgagcgaagcgagccagccggtggccgctcgcggccatc

gtccacatatccacgggctggcaagggagcgcagcgaccgcgcagggcga

agcccggagagcaagcccgtagggcgccgcagccgccgtaggcggtcacg

actttgcgaagcaaagtctagtgagtatactcaagcattgagtggcccgc

cggaggcaccgccttgcgctgcccccgtcgagccggttggacaccaaaag

ggaggggcaggcatggcggcatacgcgatcatgcgatgcaagaagctggc

gaaaatgggcaacgtggcggccagtctcaagcacgcctaccgcgagcgcg

agacgcccaacgctgacgccagcaggacgccagagaacgagcactgggcg

gccagcagcaccgatgaagcgatgggccgactgcgcgagttgctgccaga

gaagcggcgcaaggacgctgtgttggcggtcgagtacgtcatgacggcca

gcccggaatggtggaagtcggccagccaagaacagcaggcggcgttcttc

gagaaggcgcacaagtggctggcggacaagtacggggcggatcgcatcgt

gacggccagcatccaccgtgacgaaaccagcccgcacatgaccgcgttcg

tggtgccgctgacgcaggacggcaggctgtcggccaaggagttcatcggc

aacaaagcgcagatgacccgcgaccagaccacgtttgcggccgctgtggc

cgatctagggctgcaacggggcatcgagggcagcaaggcacgtcacacgc

gcattcaggcgttctacgaggccctggagcggccaccagtgggccacgtc

accatcagcccgcaagcggtcgagccacgcgcctatgcaccgcagggatt

ggccgaaaagctgggaatctcaaagcgcgttgagacgccggaagccgtgg

ccgaccggctgacaaaagcggttcggcaggggtatgagcctgccctacag

gccgccgcaggagcgcgtgagatgcgcaagaaggccgatcaagcccaaga

gacggcccgag
```

```
Construction of PTrp mMVK/pDW15
Primers
*primers were modified with 5' phosphorylation
*5' phos Ptrp 5' mMVK
                                        (SEQ ID NO: 177)
5'-TGGCAAATATTCTGAAATGAGCTGTTGACAATTAATCATCGAACTAG

TTAACTAGTACGCAAGTTCACGTAAAAAGGGTATCGACATGGTATCCTGT

TCTGCGCCGGGTAAGA

*3' phos aspA term 3' mMVK
                                        (SEQ ID NO: 178)
5'-CAAGAAAAAAGGCACGTCATCTGACGTGCCTT TTTTATTTGT

ATTAATCTACTTTCAGACCTTGCTCGGTCGG

5' mMVK seq prim
                                        (SEQ ID NO: 179)
5'-GATACGTATGTTTCTACCTTC

3' mMVK seq prim
                                        (SEQ ID NO: 180)
5'-GAAGGTAGAAACATACGTATC

EL1003
                                        (SEQ ID NO: 181)
5' -GATAGTAACGGCTGCGCTGCTACC

MCM 177
                                        (SEQ ID NO: 182)
5'-GGGCCCGTTTAAACTTTAACTAGACTTTAATCTACTTTCAGACCTTGC
```

Amplification of the PTrp mMVK Fragment
PCR Reaction for PTrp mMVK
0.5 ul vector template pDW34
10ul HerculaseII Buffer
0.5 ul dNTP's (100 mM)
1.25 ul primer (10 uM) 5' phos Ptrp 5' mMVK
1.25 ul primer (10 uM) 3' phos aspA term 3' mMVK
36 ul diH2O
+0.5 ul of HerculaseII fusion from Stratagene
Cycle Parameter:
95° C.×2 min., [95° C.×30sec., 60° C.×30sec., 72° C.×2 min.]×29 cycles; 72° C.×5 min., 4° C. until cool (Biometra T3000 Combi Thermocycler)

The resulting PCR fragment was separated on a 0.8% E-gel (Invitrogen) for verification of successful amplification, and purified using the QIAquick PCR Purification kits (Qiagen) according to manufacturer's instructions. The resulting purified stock is referred to as PTrp mMVK; note the primers used contained 5' phosphorylated ends.

Cloning of the PTrp mMVK Fragment into pDW15

Approximately 500 ng of the pDW15 plasmid was digested with SfoI (New England Biolabs) according to the manufacturer's specifications. The SfoI cut vector was then dephosphorylated using rAPpid Alkaline Phosphatase (Roche) according to the manufacturer's suggested protocol. The digested/dephosphorylated DNA was cleaned using the Qiagen QiaQuick Gel Extraction Kit prior to ligation. A portion of the PTrp mMVK fragment (5' ends phosphorylated) was ligated to the cleaned/SfoI cut/dephosphorylated pDW15 plasmid using T4 DNA Ligase from New England Biolabs according to the manufacturer's suggested protocol. Chemically competent TOP10 cells (Invitrogen) were transformed with the ligation reaction using a standard heat-shock protocol (Sambrook et al., 1989), recovered in L broth for 1 hour at 37° C. and then plated on L agar containing gentamicin (10 ug/ml). Gentamicin resistant colonies were selected, grown overnight in L broth containing gentamicin (10 ug/ml), and harvested for subsequent plasmid preparation. Plasmid constructs were isolated using Qiagen Qiaprep Spin Miniprep Kit. Plasmid preparations of interest were sequenced (Sequetech; Mountain View, Calif.) using primers 5' mMVK seq prim, 3' mMVK seq prim, EL1003, and MCM 177, and the correct PTrp mMVK/pDW15 clone identified; the resulting clone of interest has been designated as strain REM H9_14 (TOP10 w/PTrp mMVK/pDW15; SfoI site destroyed with PTrp mMVK inserted in the orientation as the Ptrc mvaE-mvaS operon present in the construct; see FIG. 94).

```
Sequence of PTrp mMVK/pDW15
                                          (SEQ ID NO: 183)
accttcgggagcgcctgaagcccgttctggacgccctggggccgttgaat

cgggatatgcaggccaaggccgccgcgatcatcaaggccgtgggcgaaaa

gctgctgacggaacagcgggaagtccagcgccagaaacaggcccagcgcc

agcaggaacgcgggcgcgcacatttccccgaaaagtgccacctggcggcg

ttgtgacaatttaccgaacaactccgcggccgggaagccgatctcggctt

gaacgaattgttaggtggcggtacttgggtcgatatcaaagtgcatcact

tcttcccgtatgcccaactttgtatagagagccactgcgggatcgtcacc

gtaatctgcttgcacgtagatcacataagcaccaagcgcgttggcctcat

gcttgaggagattgatgagcgcggtggcaatgccctgcctccggtgctcg

ccggagactgcgagatcatagatatagatctcactacgcggctgctcaaa

cctgggcagaacgtaagccgcgagagcgccaacaaccgcttcttggtcga

aggcagcaagcgcgatgaatgtcttactacggagcaagttcccgaggtaa

tcggagtccggctgatgttgggagtaggtggctacgtctccgaactcacg

accgaaaagatcaagagcagcccgcatggatttgacttggtcagggccga

gcctacatgtgcgaatgatgcccatacttgagccacctaactttgtttta

gggcgactgccctgctgcgtaacatcgttgctgctgcgtaacatcgttgc

tgctccataacatcaaacatcgacccacggcgtaacgcgcttgctgcttg

gatgcccgaggcatagactgtacaaaaaaacagtcataacaagccatgaa

aaccgccactgcgccgttaccaccgctgcgttcggtcaaggttctggacc

agttgcgtgagcgcatacgctacttgcattacagtttacgaaccgaacag

gcttatgtcaactgggttcgtgccttcatccgtttccacggtgtgcgtcc

atgggcaaatattatacgcaaggcgacaaggtgctgatgccgctggcgat

tcaggttcatcatgccgtttgtgatggcttccatgtcggcagaatgctta

atgaattacaacagtttttatgcatgcgcccaatacgcaaaccgcctctc

cccgcgcgttggccgattcattaatgcagctggcacgacaggtttcccga

ctggaaagcgggcagtgagcgcaacgcaattaatgtgagttagctcactc

attaggcaccccaggctttacactttatgcttccggctcgtatgttgtgt

ggaattgtgagcggataacaatttcacacaggaaacagctatgaccatga

ttacgccaagcgcgcaattaaccctcactaaagggaacaaaagctgggta

ccgggccccccctcgagctgttgacaattaatcatccggctcgtataatg
```

-continued

```
tgtggaattgtgagcggataacaatttcacacaggaaacagcgccgctga

gaaaaagcgaagcggcactgctctttaacaatttatcagacaatctgtgt

gggcactcgaccggaattatcgattaactttattattaaaaattaaagag

gtatatattaatgtatcgattaaataaggaggaataaaccatggatccga

gctcaggaggtaaaaaaacatgaaaacagtagttattattgatgcattac

gaacaccaattggaaaatataaaggcagcttaagtcaagtaagtgccgta

gacttaggaacacatgttacaacacaacttttaaaaagacattccactat

ttctgaagaaattgatcaagtaatctttggaaatgttttacaagctggaa

atggccaaaatcccgcacgacaaatagcaataaacagcggtttgtctcat

gaaattcccgcaatgacggttaatgaggtctgcggatcaggaatgaaggc

cgttattttggcgaaacaattgattcaattaggagaagcggaagttttaa

ttgctggcgggattgagaatatgtcccaagcacctaaattacaacgtttt

aattacgaaacagaaagctacgatgcgcctttttctagtatgatgtatga

tggattaacggatgcctttagtggtcaggcaatgggcttaactgctgaaa

atgtggccgaaaagtatcatgtaactagagaagagcaagatcaattttct

gtacattcacaattaaaagcagctcaagcacaagcagaagggatattcgc

tgacgaaatagccccattagaagtatcaggaacgcttgtggagaaagatg

aagggattcgccctaattcgagcgttgagaagctaggaacgcttaaaaca

gtttttaaagaagacggtactgtaacagcagggaatgcatcaaccattaa

tgatggggcttctgctttgattattgcttcacaagaatatgccgaagcac

acggtcttccttatttagctattattcgagacagtgtggaagtcggtatt

gatccagcctatatgggaatttcgccgattaaagccattcaaaaactgtt

agcgcgcaatcaacttactacggaagaaattgatctgtatgaaatcaacg

aagcatttgcagcaacttcaatcgtggtccaaagagaactggctttacca

gaggaaaaggtcaacatttatggtggcggtatttcattaggtcatgcgat

tggtgccacaggtgctcgtttattaacgagtttaagttatcaattaaatc

aaaaagaaaagaaatatggagtggcttctttatgtatcggcggtggctta

ggactcgctatgctactagagagacctcagcaaaaaaaaacagccgatt

ttatcaaatgagtcctgaggaacgcctggcttctcttcttaatgaaggcc

agatttctgctgatacaaaaaaagaatttgaaaatacggctttatcttcg

cagattgccaatcatatgattgaaaatcaaatcagtgaaacagaagtgcc

gatgggcgttggcttacatttaacagtggacgaaactgattatttggtac

caatggcgacagaagagccctcagttattgcggctttgagtaatggtgca

aaaatagcacaaggatttaaaacagtgaatcaacaacgcttaatgcgtgg

acaaatcgtttttttacgatgttgcagatcccgagtcattgattgataaac

tacaagtaagagaagcggaagtttttcaacaagcagagttaagttatcca

tctatcgttaaacggggcggcggcttaagagatttgcaatatcgtacttt

tgatgaatcatttgtatctgtcgacttttttagtagatgttaaggatgcaa

tgggggcaaatatcgttaacgctatgttggaaggtgtggccgagttgttc

cgtgaatggtttgcggagcaaaagattttattcagtattttaagtaatta

tgccacggagtcggttgttacgatgaaaacggctattccagtttcacgtt
```

-continued taagtaaggggagcaatggccgggaaattgctgaaaaaattgttttagct
tcacgctatgcttcattagatccttatcgggcagtcacgcataacaaagg
aatcatgaatggcattgaagctgtagttttagctacaggaaatgatacac
gcgctgttagcgcttcttgtcatgcttttgcggtgaaggaaggtcgctac
caaggcttgactagttggacgctggatggcgaacaactaattggtgaaat
ttcagttccgcttgctttagccacggttggcggtgccacaaaagtcttac
ctaaatctcaagcagctgctgatttgttagcagtgacggatgcaaaagaa
ctaagtcgagtagtagcggctgttggtttggcacaaaatttagcggcgtt
acgggccttagtctctgaaggaattcaaaaaggacacatggctctacaag
cacgttctttagcgatgacggtcggagctactggtaaagaagttgaggca
gtcgctcaacaattaaaacgtcaaaaaacgatgaaccaagaccgagccat
ggctatttaaatgatttaagaaaacaataaaggaggtaaaaaaacatga
caattgggattgataaaattagtttttttgtgccccttattatattgat
atgacggcactggctgaagccagaaatgtagaccctggaaaatttcatat
tggtattgggcaagaccaaatggcggtgaacccaatcagccaagatattg
tgacatttgcagccaatgccgcagaagcgatcttgaccaaagaagataaa
gaggccattgatatggtgattgtcgggactgagtccagtatcgatgagtc
aaaagcggccgcagttgtcttacatcgtttaatggggattcaacctttcg
ctcgctctttcgaaatcaaggaagcttgttacggagcaacagcaggctta
cagttagctaagaatcacgtagccttacatccagataaaaaagtcttggt
cgtagcggcagatattgcaaaatatggcttaaattctggcggtgagccta
cacaaggagctggggcggttgcaatgttagttgctagtgaaccgcgcatt
ttggctttaaaagaggataatgtgatgctgacgcaagatatctatgactt
ttggcgtccaacaggccacccgtatcctatggtcgatggtcctttgtcaa
acgaaacctacatccaatcttttgcccaagtctgggatgaacataaaaaa
cgaaccggtcttgattttgcagattatgatgctttagcgttccatattcc
ttacacaaaaatgggcaaaaaagccttattagcaaaaatctccgaccaaa
ctgaagcagaacaggaacgaattttagcccgttatgaagaaagtatcgtc
tatagtcgtcgcgtaggaaacttgtatacgggttcactttatctgggact
catttcccttttagaaaatgcaacgactttaaccgcaggcaatcaaattg
gtttattcagttatggttctggtgctgtcgctgaatttttcactggtgaa
ttagtagctggttatcaaaatcatttacaaaaagaaactcatttagcact
gctggataatcggacagaactttctatcgctgaatatgaagccatgtttg
cagaaactttagacacagacattgatcaaacgttagaagatgaattaaaa
tatagtatttctgctattaataataccgttcgttcttatcgaaactaaag
atctgcagctggtaccatatgggaattcgaagcttgggcccgaacaaaaa
ctcatctcagaagaggatctgaatagcgccgtcgaccatcatcatcatca
tcattgagtttaaacggtctccagcttggctgttttggcggatgagagaa
gattttcagcctgatacagattaaatcagaacgcagaagcggtctgataa
aacagaatttgcctggcggcagtagcgcggtggtcccacctgaccccatg -continued ccgaactcagaagtgaaacgccgtagcgccgatggtagtgtggggtctcc
ccatgcgagagtagggaactgccaggcatcaaataaaacgaaaggctcag
tcgaaagactgggcctttctagagcggccgccaccgcggtggagctccaa
ttcgccctatagtgagtcgtattacgcgcgctcactggccgtcgttttac
aacgtcgtgactgggaaaaccctggcgttacccaacttaatcgccttgca
gcacatccccctttcgccagctggcgtaatagcgaagaggcccgcaccga
tcgcccttcccaacagttgcgcagcctgaatggcgaatggaaattgtaag
cgttaatattttgttaaaattcgcgttaaatttttgttaaatcagctcat
tttttaaccaataggccgactgcgatgagtggcagggcggggcgtaattt
ttttaaggcagttattggtgcccttaaacgcctggtgctacgcctgaata
agtgataataagcggatgaatggcagaaattcgaaagcaaattcgacccg
gtcgtcggttcagggcagggtcgttaaatagccgcttatgtctattgctg
gtttaccggtttattgactaccggaagcagtgtgaccgtgtgcttctcaa
atgcctgaggccagtttgctcaggctctccccgtggaggtaataattgac
gatatgatcatttattctgcctcccagagcctgataaaaacggtgaatcc
gttagcgaggtgccgccggcttccattcaggtcgaggtggcccggctcca
tgcaccgcgacgcaacgcggggaggcagacaaggtatagggcggcgaggc
ggctacagccgatagtctggaacagcgcacttacgggttgctgcgcaacc
caagtgctaccggcgcggcagcgtgacccgtgtcggcggctccaacggct
cgccatcgtccagaaaacacggctcatcgggcatcggcaggcgctgctgc
ccgcgccgttcccattcctccgtttcggtcaaggctggcaggtctggttc
catgcccggaatgccgggctggctgggcggctcctcgccggggccggtcg
gtagttgctgctcgcccggatacagggtcgggatgcggcgcaggtcgcca
tgccccaacagcgattcgtcctggtcgtcgtgatcaaccaccacggcggc
actgaacaccgacaggcgcaactggtcgcggggctggccccacgccacgc
ggtcattgaccacgtaggccgacacggtgccggggccgttgagcttcacg
acggagatccagcgctcggccaccaagtccttgactgcgtattggaccgt
ccgcaaagaacgtccgatgagcttggaaagtgtcttctggctgaccacca
cggcgttctggtggcccatctgcgccacgaggtgatgcagcagcattgcc
gccgtgggtttcctcgcaataagcccggcccacgcctcatgcgctttgcg
ttccgtttgcacccagtgaccgggcttgttcttggcttgaatgccgattt
ctctggactgcgtggccatgcttatctccatgcggtagggtgccgcacgg
ttgcggcaccatgcgcaatcagctgcaacttttcggcagcgcgacaacaa
ttatgcgttgcgtaaaagtggcagtcaattacagatttctttaacctac
gcaatgagctattgcggggggtgccgcaatgagctgttgcgtaccccccct
tttttaagttgttgatttttaagtctttcgcatttcgccctatatctagt
tctttggtgcccaaagaagggcacccctgcggggttcccccacgccttcg
gcgcggctcccccctccggcaaaaagtggcccctccggggcttgttgatcg
actgcgcggccttcggccttgcccaaggtggcgctgccccctt ggaaccc
ccgcactcgccgccgtgaggctcgggggcaggcgggcgggcttcgcctt
cgactgcccccactcgcataggcttgggtcgttccaggcgcgtcaaggcc -continued aagccgctgcgcggtcgctgcgcgagccttgacccgccttccacttggtg tccaaccggcaagcgaagcgcgcaggccgcaggccggaggcttttcccca gagaaaattaaaaaaattgatggggcaaggccgcaggccgcgcagttgga gccggtgggtatgtggtcgaaggctgggtagccggtgggcaatccctgtg gtcaagctcgtgggcaggcgcagcctgtccatcagcttgtccagcagggt tgtccacgggccgagcgaagcgagccagccggtggccgctcgcggccatc gtccacatatccacgggctggcaagggagcgcagcgaccgcgcagggcga agcccggagagcaagcccgtagggctggcaaatattctgaaatgagctgt tgacaattaatcatcgaactagttaactagtacgcaagttcacgtaaaaa gggtatcgacatggtatcctgttctgcgccgggtaagatttacctgttcg gtgaacacgccgtagtttatggcgaaactgcaattgcgtgtgcggtggaa ctgcgtacccgtgttcgcgcggaactcaatgactctatcactattcagag ccagatcggccgcaccggtctggatttcgaaaagcaccccttatgtgtctg cggtaattgagaaaatgcgcaaatctattcctattaacggtgttttcttg accgtcgattccgacatcccggtgggctccggtctgggtagcagcgcagc cgttactatcgcgtctattggtgcgctgaacgagctgttcggctttggcc tcagcctgcaagaaatcgctaaactgggccacgaaatcgaaattaaagta cagggtgccgcgtccccaaccgatacgtatgtttctaccttcggcggcgt ggttaccatcccggaacgtcgcaaactgaaaactccggactgcggcattg tgattggcgataccggcgttttctcctccaccaaagagttagtagctaac gtacgtcagctgcgcgaaagctacccggatttgatcgaccgctgatgacc tactattggcaaaatctctcgtatcggcgaacaactggttctgtctggcg actacgcatccatcggccgcctgatgaacgtcaaccagggtctcctggac gccctgggcgttaacatcttagaactgagccagctgatctattccgctcg tgcggcaggtgcgtttggcgctaaaatcacgggcgctggcggcggtggct gtatggttgcgctgaccgctccggaaaaatgcaaccaagtggcagaagcg gtagcaggcgctggcggtaaagtgactatcactaaaccgaccgagcaagg tctgaaagtagattaatacaaataaaaaaggcacgtcagatgacgtgcct tttttcttggccgcagccgccgtaggcggtcacgactttgcgaagcaaag tctagtgagtatactcaagcattgagtggcccgccggaggcaccgccttg cgctgccccgtcgagccggttggacaccaaaagggaggggcaggcatgg cggcatacgcgatcatgcgatgcaagaagctggcgaaaatgggcaacgtg gcggccagtctcaagcacgcctaccgcgagcgcgagacgcccaacgctga cgccagcaggacgccagagaacgagcactgggcggccagcagcaccgatg aagcgatgggccgactgcgcgagttgctgccagagaagcggcgcaaggac gctgtgttggcggtcgagtacgtcatgacggccagcccggaatggtggaa gtcggccagccaagaacagcaggcggcgttcttcgagaaggcgcacaagt ggctggcggacaagtacggggcggatcgcatcgtgacggccagcatccac cgtgacgaaaccagcccgcacatgaccgcgttcgtggtgccgctgacgca ggacggcaggctgtcggccaaggagttcatcggcaacaaagcgcagatga -continued cccgcgaccagaccacgtttgcggccgctgtggccgatctagggctgcaa cggggcatcgagggcagcaaggcacgtcacacgcgcattcaggcgttcta cgaggccctggagcggccaccagtgggccacgtcaccatcagcccgcaag cggtcgagccacgcgcctatgcaccgcagggattggccgaaaagctggga atctcaaagcgcgttgagacgccggaagccgtggccgaccggctgacaaa agcggttcggcaggggtatgagcctgccctacaggccgccgcaggagcgc gtgagatgcgcaagaaggccgatcaagcccaagagacggcccgag Construction of Strain MCM928, BL21 t pgl FRT-cmp-FRT-Ptrc-PMK-MVD-yIDI Construction of Integration Construct pMCM900

The GI1.6 promoter and yeast MVK gene of pMCM296 were replaced with a chloramphenicol resistance cassette and Trc promoter. The cmR resistance cassette-Ptrc fragment was created by amplification from pMCM883 (GeneBridges cmR cassette) using primers MCM127 and MCM375. 2, 50 uL reactions were created according the manufacturer's protocol for Herculase II Fusion (Agilent #600679) containing 35 uL water, 10 uL buffer, 0.5 uL dNTPs, 1.25 uL each primer at 10 uM, 1 uL plasmid template, 1 L polymerase. Reactions were cycled as follows: 95° C., 2:00; 30× (95° C., 0:20; 55° C., 0:20; 72° C., 1:00); 72° C., 3:00; 4° C. until cold.

The ~1.6 kb amplicon and plasmid pMCM296 (described infra) were digested at 37° C. for 2 hour in 10 uL reactions containing 5 uL DNA, 1 uL EcoRV, 1 uL NotI (amplicon) or 1 L StuI (pMCM296), 1 uL Roche Buffer H, and 2 uL ddH2O. Reactions were heat-killed at 65° C. for 2 hr then digested DNA was purified on Qiagen PCR columns and eluted in 30 uL EB. The eluted DNAs were ligated 1 hr at room temperature in a 10 uL Roche Rapid Ligation kit reaction containing 1 uL pMCM296, 3 uL cut amplicon, 5 uL buffer 3, and 1 uL ligase. Ligated DNA was transformed into Invitrogen Pir1 chemically competent cells, recovered for 1 hr at 37° C., plated on LB/cmp 25 ug/mL, then grown overnight at 37° C. The resulting plasmids were purified and sequenced across the promoter region. Clone four was frozen as pMCM900; see FIG. 95.

Integration of cmR-Ptrc-KDyI into Host BL21 t pg1 to Create MCM928

Strain MCM865 is an aliquot of strain MD253 (BL21 t pgl pRedET-carb). MCM865 was grown in LB+carb50 at 30° C. overnight and then diluted 1:100 into fresh LB+carb50 and cultured at 30° C. for 2 hr. 130 uL 10% arabinose was added and cells cultured at 37° C. for approximately 2 hours. Cells were prepared for electroporation by washing 3× in one half culture volume iced ddH2O and resuspended in one tenth culture volume of the same. 100 uL of cell suspension was combined with 1 uL pMCM900 DNA in a 2 mm electroporation cuvette, electroporated at 25 uFD, 200 ohms, 2.5 kV, and immediately quenched with 500 uL LB. Cells were recovered shaking at 37° C. for 1-3 hrs and then transformants selected overnight on LB cmp5 plates at 37° C.

After restreaking on LB cmp5, transformants were tested for growth on LB cmp5, LB kan10 and LB carb50. A cmpR/carbS/kanS clone was frozen as MCM928.

Primers

MCM139

(SEQ ID NO: 184)

ttttgcggccgcaattaaccctcactaaagggcgg

MCM375

-continued (SEQ ID NO: 185)

gatcgatatccctgcaggaaattgttatccgctcacaattccacacatta tacgagccggatgattaattgtcaacagctaatacgactcactatagggc tcg Sequence of pMCM900

(SEQ ID NO: 186)

caagaaaaatgccccgcttacgcagggcatccatttattactcaaccgta accgattttgccaggttacgcggctggtcaacgtcggtgcctttgatcag cgcgacatggtaagccagcagctgcagcggaacggtgtagaagatcggtg caatcacctcttccacatgcggcatctcgatgatgtgcatgttatcgcta cttacaaaacccgcatcctgatcggcgaagacatacaactgaccgccacg cgcgcgaacttcttcaatgttggatttcagtttttccagcaattcgttgt tcggtgcaacaacaataaccggcatatcggcatcaattagcgccagcgga ccgtgtttcagttcgccagcagcgtaggcttcagcgtgaatgtaagagat ctctttcaacttcaatgcgccttccagcgcgattgggtactgatcgccac ggcccaggaacagcgcgtgatgtttgtcagagaaatcttctgccagcgct tcaatgcgtttgtcctgagacagcatctgctcaatacggctcggcagcgc ctgcagaccatgcacgatgtcatgttcaatggaggcatccagacctttca ggcgagacagcttcgccaccagcatcaacagcacagttaactgagtggtg aatgctttagtggatgccacgccgatttctgtacccgcgttggtcattag cgccagatcggattcgcgcaccagagaagaacccggaacgttacagattg ccagtgaaccaaggtaacccagctctttcgacagacgcaggccagccagg gtatccgcggtttcgccagactgtgacacgatcgcccttcccaacagttg cgcagcctatacgtacggcagtttaaggtttacacctataaaagagagag ccgttatcgtctgtttgtggatgtacagagtgatattattgacacgccgg ggcgacggatggtgatccccctggccagtgcacgtctgctgtcagataaa gtctcccgtgaactttacccggtggtgcatatcggggatgaaagctggcg catgatgaccaccgatatggccagtgtgccggtctccgttatcggggaag aagtggctgatctcagccaccgcgaaaatgacatcaaaaacgccattaac ctgatgttctggggaatataaatgtcaggcatgagattatcaaaaaggat cttcacctagatccttttcacgtagaaagccagtccgcagaaacggtgct gaccccggatgaatgtcagctactgggctatctggacaagggaaaacgca agcgcaaagagaaagcaggtagcttgcagtgggcttacatggcgatagct agactgggcggttttatggacagcaagcgaaccggaattgccagctgggg cgccctctggtaaggttgggaagccctgcaaagtaaactggatggctttc tcgccgccaaggatctgatggcgcaggggatcaagctctgatcaagagac aggatgaggatcgtttcgcatgattgaacaagatggattgcacgcaggtt ctccggccgcttgggtggagaggctattcggctatgactgggcacaacag acaatcggctgctctgatgccgccgtgttccggctgtcagcgcaggggcg cccggttctttttgtcaagaccgacctgtccggtgccctgaatgaactgc aagacgaggcagcgcggctatcgtggctggccacgacgggcgttccttgc -continued gcagctgtgctcgacgttgtcactgaagcgggaagggactggctgctatt gggcgaagtgccggggcaggatctcctgtcatctcaccttgctcctgccg agaaagtatccatcatggctgatgcaatgcggcggctgcatacgcttgat ccggctacctgcccattcgaccaccaagcgaaacatcgcatcgagcgagc acgtactcggatggaagccggtcttgtcgatcaggatgatctggacgaag agcatcaggggctcgcgccagccgaactgttcgccaggctcaaggcgagc atgcccgacggcgaggatctcgtcgtgacccatggcgatgcctgcttgcc gaatatcatggtggaaaatggccgcttttctggattcatcgactgtggcc ggctgggtgtggcggaccgctatcaggacatagcgttggctacccgtgat attgctgaagagcttggcggcgaatgggctgaccgcttcctcgtgcttta cggtatcgccgctcccgattcgcagcgcatcgccttctatcgccttcttg acgagttcttctgaattattaacgcttacaatttcctgatgcggtatttt ctccttacgcatctgtgcggtatttcacaccgcatacaggtggcactttt cggggaaatgtgcgcggaacccctatttgtttatttttctaaatacattc aaatatgtatccgctcatgagacaataaccctgataaatgcttcaataat agcacgtgaggagggccaccatggccaagttgaccagtgccgttccggtg ctcaccgcgcgcgacgtcgccggagcggtcgagttctggaccgaccggct cgggttctcccctagtaacggccgccagtgtgctggaattcaggcagttc aacctgttgatagtacgtactaagctctcatgtttcacgtactaagctct catgtttaacgtactaagctctcatgtttaacgaactaaaccctcatggc taacgtactaagctctcatggctaacgtactaagctctcatgtttcacgt actaagctctcatgtttgaacaataaaattaatataaatcagcaacttaa atagcctctaaggttttaagttttataagaaaaaaaagaatatataaggc ttttaaagcttttaaggtttaacggttgtggacaacaagccagggatgta acgcactgagaagcccttagagcctctcaaagcaattttcagtgacacag gaacacttaacggctgacagcctgaattctgcagatatctgtttttccac tcttcgttcactttcgccaggtagctggtgaagacgaaggaagtcccgga gccatctgcgcggcgtactacagcaatgttttgtgaaggcagtttcagac ccggattcagtttggcgatggcttcatcatcccacttcttgattttgccc aggtagatgtcgccgagggttttaccatccagcaccagttcgccagactt cagccctggaatgttaaccgccagcaccacgccgccaatcacggtcggga actggaacagaccttcctgagccagtttttcgtcagacagcggcgcgtca gaggcaccaaaatcaacggtattagcgataatctgttttacgccaccgga agaaccgataccctggtagttaactttattaccggtttctttctggtaag tgtcagcccatttggcatacaccggcgcagggaaggttgcacctgcacct gtcaggcttgcttctgcaaacacagagaaagcactcatcgataaggtcgc ggcgacaacagttgcgacggtggtacgcataactttcataatgtctcctg ggaggattcataaagcattgtttgttggctacgagaagcaaaataggaca aacaggtgacagttatatgtaaggaatatgacagttttatgacagagaga taaagtcttcagtctgatttaaataagcgttgatattcagtcaattacaa -continued acattaataacgaagagatgacagaaaaattttcattctgtgacagagaa aaagtagccgaagatgacggtttgtcacatggagttggcaggatgtttga ttaaaagcggccgcgaagttcctattctctagaaagtataggaacttcat tctaccgggtaggggaggcgcttttcccaaggcagtctggagcatgcgct ttagcagccccgctgggcacttggcgctacacaagtggcctctggcctcg cacacattccacatccaccggtaggcgccaaccggctccgttctttggtg gccccttcgcgccaccttccactcctcccctagtcaggaagttccccccc gccccgcagctcgcgtcgtgcaggacgtgacaaatggaagtagcacgtct cactagtctcgtgcagatggacagcaccgctgagcaatggaagcgggtag gcctttggggcagcggccaatagcagctttgctccttcgctttctgggct cagaggctgggaaggggtgggtccgggggcgggctcaggggcgggctcag gggcggggcgggcgcccgaaggtcctccggaggcccggcattctgcacgc ttcaaaagcgcacgtctgccgcgctgttctcctcttcctcatctccgggc ctttcgacctgcagcagcacgtgttgacaattaatcatcggcatagtata tcggcatagtataatacgacaaggtgaggaactaaaccatggagaaaaaa atcactggatataccaccgttgatatatcccaatggcatcgtaaagaaca ttttgaggcatttcagtcagttgctcaatgtacctataaccagaccgttc agctggatattacggcctttttaaagaccgtaaagaaaaataagcacaag ttttatccggcctttattcacattcttgcccgcctgatgaatgctcatcc ggaattccgtatggcaatgaaagacggtgagctggtgatatgggatagtg ttcacccttgttacaccgttttccatgagcaaactgaaacgttttcatcg ctctggagtgaataccacgacgatttccggcagtttctacacatatattc gcaagatgtggcgtgttacggtgaaaacctggcctatttccctaaagggt ttattgagaatatgtttttcgtctcagccaatccctgggtgagtttcacc agttttgatttaaacgtggccaatatggacaacttcttcgcccccgtttt caccatgggcaaatattatacgcaaggcgacaaggtgctgatgccgctgg cgattcaggttcatcatgccgtttgtgatggcttccatgtcggcagaatg cttaatgaattacaacagtactgcgatgagtggcagggcggggcgtaagc gggactctggggttcgaataaagaccgaccaagcgacgtctgagagctcc ctggcgaattcggtaccaataaaagagctttattttcatgatctgtgtgt tggtttttgtgtgcggcgcggaagttcctattctctagaaagtataggaa cttcctcgagccctatagtgagtcgtattagctgttgacaattaatcatc cggctcgtataatgtgtggaattgtgagcggataacaatttcctgcaggg atcctgcacccttaaggaggaaaaaaacatgtcagagttgagagccttca gtgccccagggaaagcgttactagctggtggatatttagttttagataca aaatatgaagcatttgtagtcggattatcggcaagaatgcatgctgtagc ccatccttacggttcattgcaagggtctgataagtttgaagtgcgtgtga aaagtaaacaatttaaagatggggagtggctgtaccatataagtcctaaa agtggcttcattcctgtttcgataggcggatctaagaaccctttcattga aaaagttatcgctaacgtatttagctactttaaacctaacatggacgact actgcaatagaaacttgttcgttattgatattttctctgatgatgcctac -continued cattctcaggaggatagcgttaccgaacatcgtggcaacagaagattgag ttttcattcgcacagaattgaagaagttcccaaaacagggctgggctcct cggcaggtttagtcacagttttaactacagctttggcctcctttttttgta tcggacctggaaaataatgtagacaaatatagagaagttattcataattt agcacaagttgctcattgtcaagctcagggtaaaattggaagcgggtttg atgtagcggcggcagcatatggatctatcagatatagaagattcccaccc gcattaatctctaatttgccagatattggaagtgctacttacggcagtaa actggcgcatttggttgatgaagaagactggaatattacgattaaaagta accatttaccttcgggattaactttatggatgggcgatattaagaatggt tcagaaacagtaaaactggtccagaaggtaaaaaattggtatgattcgca tatgccagaaagcttgaaaatatatacagaactcgatcatgcaaattcta gatttatggatggactatctaaactagatcgcttacacgagactcatgac gattacagcgatcagatatttgagtctcttgagaggaatgactgtacctg tcaaaagtatcctgaaatcacagaagttagagatgcagttgccacaatta gacgttcctttagaaaaataactaaagaatctggtgccgatatcgaacct cccgtacaaactagcttattggatgattgccagaccttaaaaggagttct tacttgcttaatacctggtgctggtggttatgacgccattgcagtgatta ctaagcaagatgttgatcttagggctcaaaccgctaatgacaaaagattt tctaaggttcaatggctggatgtaactcaggctgactggggtgttaggaa agaaaaagatccggaaacttatcttgataaataacttaaggtagctgcat gcagaattcgcccttaaggaggaaaaaaaaatgaccgtttacacagcatc cgttaccgcacccgtcaacatcgcaacccttaagtattggggaaaaggg acacgaagttgaatctgcccaccaattcgtccatatcagtgactttatcg caagatgacctcagaacgttgacctctgcggctactgcacctgagtttga acgcgacactttgtggttaaatggagaaccacacagcatcgacaatgaaa gaactcaaaattgtctgcgcgacctacgccaattaagaaaggaaatggaa tcgaaggacgcctcattgcccacattatctcaatggaaactccacattgt ctccgaaaataactttcctacagcagctggtttagcttcctccgctgctg gctttgctgcattggtctctgcaattgctaagttataccaattaccacag tcaacttcagaaatatctagaatagcaagaaaggggtctggttcagcttg tagatcgttgtttggcggatacgtggcctgggaaatgggaaaagctgaag atggtcatgattccatggcagtacaaatcgcagacagctctgactggcct cagatgaaagcttgtgtcctagttgtcagcgatattaaaaaggatgtgag ttccactcagggtatgcaattgaccgtggcaacctccgaactatttaaag aaagaattgaacatgtcgtaccaaagagatttgaagtcatgcgtaaagcc attgttgaaaaagatttcgccacctttgcaaaggaaacaatgatggattc caactctttccatgccacatgtttggactctttccctccaatattctaca tgaatgacacttccaagcgtatcatcagttggtgccacaccattaatcag ttttacggagaaacaatcgttgcatacacgtttgatgcaggtccaaatgc tgtgttgtactacttagctgaaaatgagtcgaaactctttgcatttatct -continued

```
ataaattgtttggctctgttcctggatgggacaagaaatttactactgag
cagcttgaggctttcaaccatcaatttgaatcatctaactttactgcacg
tgaattggatcttgagttgcaaaaggatgttgccagagtgattttaactc
aagtcggttcaggcccacaagaaacaaacgaatctttgattgacgcaaag
actggtctaccaaaggaataagatcaattcgctgcatcgcccttaggagg
taaaaaaaaatgactgccgacaacaatagtatgccccatggtgcagtatc
tagttacgccaaattagtgcaaaaccaaacacctgaagacattttggaag
agtttcctgaaattattccattacaacaaagacctaatacccgatctagt
gagacgtcaaatgacgaaagcggagaaacatgtttttctggtcatgatga
ggagcaaattaagttaatgaatgaaaattgtattgttttggattgggacg
ataatgctattggtgccggtaccaagaaagtttgtcatttaatggaaaat
attgaaaagggtttactacatcgtgcattctccgtctttattttcaatga
acaaggtgaattacttttacaacaaagagccactgaaaaaataactttcc
ctgatctttggactaacacatgctgctctcatccactatgtattgatgac
gaattaggtttgaagggtaagctagacgataagattaagggcgctattac
tgcggcggtgagaaaactagatcatgaattaggtattccagaagatgaaa
ctaagacaaggggtaagtttcacttttttaaacagaatccattacatggca
ccaagcaatgaaccatggggtgaacatgaaattgattacatcctatttta
taagatcaacgctaaagaaaacttgactgtcaacccaaacgtcaatgaag
ttagagacttcaaatgggtttcaccaaatgatttgaaaactatgtttgct
gacccaagttacaagtttacgccttggtttaagattatttgcgagaatta
cttattcaactggtgggagcaattagatgacctttctgaagtggaaaatg
acaggcaaattcatagaatgctataacaacgcgtctacaaataaaaaagg
cacgtcagatgacgtgccttttttcttggggcc
```

Construction of REM H4_15, the parent background of strain REM A2_17

The chloramphenicol marked PTrc PMK-MVD-yIDI locus of strain MCM928, described above, was introduced into strain WW103 (see, e.g., Examples 29 and 30) via P1-mediated transduction. The resulting chloramphenicol resistant strain was named REM H4_15 (BL21 pgl+ PL.6-dxs, GI1.6-dxr, GI1.6 yIDI, CMP::PTrc PMK-MVD-yIDI).

Strategy for creating REM A2_17

REM A2_17 was created by subsequent plasmid transformations of pDW33, PTrp mMVK/pDW15, Ptac Anabaena ispH aspA term/pEWL454, and lastly GI1.6 fldA-ispG/pCL initially into strain REM H4_15.

Water-washed REM H4_15 cells were transformed with pDW33 via electroporation using the BIO RAD Gene Pulser system (0.1 cm cuvette cat.#165-2089) and a transformation protocol suggested by the manufacturer (BIO RAD). The cells were recovered in L broth for 1 hour at 37° C. and then plated on L agar containing carbenicillin (50 ug/ml). One carbenicillin resistant colony was chosen, named REM A4_16, and subsequently transformed with PTrp mMVK/pDW15 via the method described; in this case L agar containing carbenicillin (50 ug/ml) and gentamicin (10 ug/ml) was used as a selection, resulting in the carbenicillin and gentamicin resistant strain REM I4_16. Similarly, REM I4_16 was transformed with Ptac Anabaena ispH aspA term/pEWL454 resulting in the carbenicillin (50 ug/ml), gentamicin (10 ug/ml) and kanamycin (50 ug/ml) resistant strain REM C5_16. Lastly, strain REM C5_16 was transformed with GI1.6 fldA-ispG/pCL resulting in the carbenicillin (50 ug/ml), gentamicin (10 ug/ml) kanamycin (50 ug/ml), and spectinomycin (50 ug/ml) resistant strain REM A2_17.

Example 33

Analysis of Strain REM A2_17 in the Presence and Absence of Fosmidomycin for Growth, Isoprene Production, and DXP and MVA Metabolite Accumulation Using Unlabeled, 1-$^{13}$C labeled, or 3-$^{13}$C Labeled Glucose as the Sole Carbon Source It was previously determined that the addition of 1 mM fosmidomycin to the growth media of an *E. coli* BL21 strain harboring the GI1.6-dxr locus common to the REM A2_17 strain could inhibit isoprene production to an undetectable level. Fosmidomycin inhibits the activity of the DXR enzyme that performs the committed step of the endogenous *E. coli* DXP pathway (Kuzuyama et al., 1998). Furthermore, the addition of 1 mM fosmidomycin to the growth media of a dxr null *E. coli* BL21 strain that harbors the same heterologous MVA isoprenoid biosynthetic pathway enzymes present in REM A2_17 was found to maintain the same level of isoprene production as that grown in the absence of fosmidomycin. This data indicates that the DXR inhibitor (fosmidomycin) does not adversely affect in vivo flux through the MVA isoprenoid biosynthetic pathway.

Specific Productivity of Isoprene Generated by REM A2_17 strain.

2 mM fosmidomycin in combination with 1-$^{13}$C (Isotec) or 3-$^{13}$C glucose (Omicron Biochemicals, Inc) was used in small scale headspace assays and corresponding DXP and MVA metabolite determination studies to demonstrate the simultaneous flux to isoprene via the dual MVA and DXP isoprenoid biosynthetic pathways expressed within REM A2_17. See below for the rationale of using 1-$^{13}$C glucose and 3-$^{13}$C glucose to generate uniquely labeled isoprene derived from the DXP pathway that can be differentiated from the isoprene generated via the MVA pathway. Shown in FIGS. 98 and 99 are the results of the headspace assays utilizing the 1-$^{13}$C and 3-$^{13}$C labeled glucose which indicate a 57-58% MVA-flux and 42-43% DXP-flux contribution to the isoprene generated by strain REM A2_17, as determined by isoprene specific productivity. These results are nearly identical to that observed in the unlabeled glucose experiment shown in FIG. 96 (58% MVA and 41% DXP). Interestingly, the results depicted in FIGS. 101 and 102 obtained from the GC/MS analysis on the various $^{12}$C and $^{13}$C isotope ratios present in the isoprene produced by REM A2_17 suggest a 58-62% MVA and 42-38% DXP-flux contribution to the isoprene generated, respectively. This data is in agreement with that determined by the isoprene specific productivity determination.

The dual flux of carbon to isoprene down the MVA and DXP isoprenoid biosynthetic pathways harbored by REM A2_17 was further support by use of tryptophan to repress expression of the MVK enzyme common to the MVA pathway (see FIG. 94 for an illustration of the PTrp-MVK containing vector). [The tryptophan promoter, PTrp, governs expression of MVK in REM A2_17; the Trp repressor inhibits activity of the Trp promoter when bound to tryptophan; please see information about the trp operon available through EcoCyc (www.ecocyc.org)]. The data in FIG. 98 indicates that the proportion of MVA-flux to isoprene is reduced by approximately 8% when REM A2_17 is grown in the presence of 50 uM tryptophan, resulting in a strain with nearly 1:1 MVA-flux:DXP-flux contribution to isoprene.

Accumulation of DXP and MVA Pathway Metabolites in the REM 8A2__17 Strain.

FIG. 97 compares accumulation of DXP and MVA pathway metabolites in the REM A2__17 strain grown in the presence and in the absence of fosmidomycin. Among the metabolites that were detected and quantified by LC-MS/MS were mevalonic acid (the MVA pathway intermediate), DXP, MEP, CDP-ME, cMEPP, HDMAPP (the DXP pathway intermediates), and IPP and DMAPP (intermediates of both DXP and MVA pathways). Growing cells in the presence of fosmidomycin, which inhibits DXP to MEP conversion, caused a significant increase in the DXP concentration and a drop in the concentration of MEP, CDP-ME and cMEPP, but did not change the concentration of MVA. The observed decrease in HDMAPP in fosmidomycin-treated samples was noticeably smaller that the decrease in other DXP pathway metabolites, such as MEP, CDP-ME and cMEPP, presumably due to a poor sensitivity of the LC-MS/MS method to HDMAPP and a large error associated with HDMAPP measurements. The cumulative amount of IPP and DMAPP decreased in the presence of fosmidomycin in average by 55% that correlates with a 41% decrease in the isoprene production rate. Taken altogether these data demonstrate that both DXP and MVA pathways are functional in the REM A2__17 strain and are consistent with the idea that the two pathways are contributing to the isoprene production in cells grown without fosmidomycin.

Rationale for use of Labeled Glucose to Measure Contribution of DXP and MVA Pathways to Isoprene Production To demonstrate that in the REM A2__17 strain isoprene is produced by the DXP and MVA pathways operating simultaneously, the above strain was grown on glucose containing $^{13}C$ isotope at specific positions. As illustrated in FIG. 100, when cells are grown on 1-$^{13}C$ glucose, it is expected that isoprene molecules synthesized by the MVA route will be more enriched in $^{13}C$ than the molecules synthesized by the DXP route, whereas when cells are grown on 3-$^{13}C$ glucose, the isoprene molecules synthesized by the MVA route should contain less $^{13}C$ than the isoprene molecules made by the DXP route because $^{13}C$-labeled carbon is released as $^{13}CO_2$ when pyruvate is converted to acetyl-CoA. When both pathways are operating simultaneously, $^{13}C$ labeling pattern of isoprene emitted by the cells should be represented by superposition of the labeling patterns of isoprene molecules produced by each of the two routes.

Isoprene Labeling Experiments

FIG. 101 shows calculated relative abundances of cMEPP and isoprene cumomers (cumulative isotopomers) produced by the REM A2__17 strain grown on: A) 1-$^{13}C$ or B) 3-$^{13}C$ glucose. The cumomer abundances of cMEPP and isoprene can be directly compared to each other because both compounds contain five carbon atoms in their molecules, whereas differences in the number of O, P, and H atoms can be neglected due to a very low natural abundance of isotopes other than $^{16}O$, $^{31}P$, and $^{1}H$. The measured distributions of cMEPP cumomer abundances should be equivalent to the cumomer distributions in isoprene made exclusively by the DXP pathway and were clearly different from the calculated distributions of isoprene cumomers for cells grown in the absence of fosmidomycin (compare the amplitudes of "Isoprene (−FM)" and cMEPP(−FM) bars in FIGS. 101A and 9B) indicating that the DXP and MVA pathways together contribute to the isoprene synthesized by the REM A2__17 strain.

The distribution of cumomers of isoprene produced exclusively via the MVA pathway by REM A2__17 cells grown on 1-$^{13}C$ or 3-$^{13}C$ glucose was estimated by measuring GC spectra of isoprene emitted in the presence of 2 mM fosmidomycin (FIGS. 101 and 102 and relative contribution of the DXP and MVA pathways to the total isoprene production was calculated by superimposing the "Isoprene (+FM)" and cMEPP cumomer spectra with the coefficients $\phi^{MVA}$ and $\phi^{DXP}$ to fit the "Isoprene (−FM)" spectra, as described in "Methods" section. Based on these calculations, the relative contribution of the DXP pathway to the total isoprene production was estimated to be 42% and 38% for the experiments with 1-$^{13}C$ and 3-$^{13}C$ glucose, respectively. These numbers are close to the DXP pathway contributions of 42% and 43%, respectively, estimated from the inhibition of total isoprene production rate by fosmidomycin.

Methods

Growth

Strains REM A2__17 was grown at 34° C. in TM3 liquid media (13.6 g $K_2PO_4$, 13.6 g $KH_2PO_4$, 2.0 g $MgSO_4*7H_2O$), 2.0 g citric acid monohydrate, 0.3 g ferric ammonium citrate, 3.2 g $(NH_4)_2SO_4$, 1.0 ml 1000× Modified Trace Metal Solution, adjusted to pH 6.8 and q.s. to $H_2O$, and filter sterilized) supplemented to a final concentration with either 1% unlabeled glucose and 0.1% yeast extract (FIGS. 96 and 97 experiment), or with 1% unlabeled glucose, no yeast extract, and no tryptophan; 1.0% 1-$^{13}C$ glucose (Isotec), no yeast extract, and with or without 50 uM tryptophan (FIGS. 98 and 101), or with 1.0% 3-$^{13}C$ glucose (Omicron Biochemicals, Inc.) and no yeast extract (FIGS. 99 and 10). All growth media also contained carbenicillin (50 ug/ml), gentamicin (10 ug/ml) kanamycin (50 ug/ml), and spectinomycin (50 ug/ml). The culture was induced with 400 uM IPTG and later DXP flux inhibited for half of the culture by the addition of 2 mM fosmidomycin (Invitrogen). Growth was monitored periodically by recording each of the culture's optical density measured at 600 nm using an Eppendorf Biophotometer spectrometer (Eppendorf).

GC Measurements of Isoprene

Isoprene production was analyzed using a headspace assay. For the headspace cultures, 100 uL to 200 ul of the cultures was transferred from the shake flasks to 2 ml CTC headspace vials (SUN-SRI 2 mL HS vials, VWR#66020-950, and caps, VWR#66008-170). The cap was screwed on tightly and the vials incubated at the equivalent temperature with shaking at 250 rpm. After approx. 30 min. to 1 hour the vials were removed from the incubator, heat killed at 70° C. for 7 min., and analyzed. The analysis was performed using an Agilent 6890 GC/MS system interfaced with a CTC Analytics (Switzerland) CombiPAL autosampler operating in headspace mode. An Agilent HP-5MS GC/MS column (15 m×0.25 mm; 0.25 μm film thickness) was used for separation of analytes. The sampler was set up to inject 100 μL of headspace gas. The GC/MS method utilized helium as the carrier gas at a flow of 1 ml/minute. The injection port was held at 250° C. with a split ratio of 50:1. The oven temperature was held at 37° C. for 0.6 minute, the duration of the analysis. The Agilent 5793N mass selective detector was run in single ion monitoring (SIM) mode on m/z 67 or in a full scan mode covering m/z from 25 to 80. The detector was switched off from 0 to 0.42 minutes to allow the elution of permanent gases. Under these conditions isoprene (2-methyl-1,3-butadiene) standard (SCOTTY® Analyzed Gases) was observed to elute at approx. 0.49 minutes. A calibration table was used to quantify the absolute amount of isoprene and was found to be linear from 1 μg/L to 5000 μg/L. The limit of detection was estimated to be 50 to 100 ng/L using this method. The specific productivity of each strain is reported as ug/L OD Hr. Note, ratio of 1800 μl headspace:200 μl broth in assay vials for 1 hour incubation results in the following conversion of isoprene ug/L of culture to specific productivity: (isoprene/L determined by GC-MS)×(9)/(OD 600 nm of the culture). To quantify the amount of isoprene produced from $^{13}C$-labeled glucose, the concentration obtained based on the calibration curve with the non-labeled standard was multiplied by the conversion factor K to compensate for isotopic effects. The conversion factors were calculated as $$K=(\Sigma(A_i)/A_{67})/(\Sigma(P_i)/P_{67}), \quad \text{(Eq. 1)}$$

where $A_i$ are the measured intensities of GC peaks produced by $^{13}C$-enriched isoprene and $P_i$ are the measured intensities of GC peaks produced by the isoprene standard (subscript indices i=60 . . . 72 indicate m/z values of corresponding peaks, which include peaks $A_{67}$ and $P_{67}$). For the experiments referred to in this document the conversion factors of 2.901 and 3.369 were applied to no fosmidomycin and to 2 mM fosmidomycin conditions, respectively, for cells grown on 1-$^{13}C$ glucose and the factors of 1.476 and 1.315 were applied to no fosmidomycin and to 2 mM fosmidomycin conditions, respectively, for cells grown on 3-$^{13}C$ glucose.

LC-MS/MS Analysis of Cellular Metabolites

For metabolite analysis 1.5 to 5 mL of cell culture was spun down by centrifugation and 100 or 150 uL of dry ice-cold methanol was added to pelleted cells after the centrifugation. The resulting samples were then stored at −80° C. until further processing. To extract cellular metabolites, 10 or 15 μL of water was added to methanol-containing samples, the pellet was resuspended in the resulting methanol/water mix and then cell debris were spun down for 4-min at 4500×g. The pellet was re-extracted two more times, first with 90 μL of 75% methanol buffered with 1 mM ammonium acetate in water (pH=8.0), then with 100 μL of 50% methanol in the ammonium acetate buffer. After each extraction, cell debris were spun down by centrifugation and the supernatants from all three extractions were combined. During the extraction procedure, samples were kept on ice or in a refrigerated centrifuge whenever possible to minimize metabolites degradation.

The extract was analyzed by LC-MS/MS on a TSQ Quantum triple quadrupole mass spectrometer (Thermo Electron Corporation, San Jose, Calif.) using electrospray ionization in the negative mode. The system control, data acquisition, and mass spectral data evaluation were performed using XCalibur and LCQuan software (Thermo Electron Corp). LC separation was done on a Synergi 45 μM Hydro-RP HPLC column (150×2 mm, Phenomenex, USA) at a flow rate of 0.4 mL/min and the column temperature of 40° C. The LC gradient was t=0 min, 12% B; t=5 min, 12% B; t=9 min, 23% B; t=20 min, 99% B; t=23 min, 99% B; t=24 min, 12% B; t=29 min, 12% B, where solvent A was 10 mM tributylamine/15 mM acetic acid in water and solvent B was LCMS-grade methanol. The sample injection volume was 10 to 25 μL.

Mass detection was carried out using electrospray ionization in the negative mode. The following MS/MS transitions were chosen to detect the metabolites of interest: 213→79 for DXP, 215→79 for MEP, 245→79 for IPP and DMAPP, 261→79 for HDMAPP, 277→79 for cMEPP, 520.1→79 for CDP-ME, 227→79 for MVP, 307→79 for MVPP, and 147→59 for MVA. Other mass spec settings were optimized to obtain the highest sensitivity using corresponding standards purchased from Echelon Biosciences Inc. or synthesized in house. To quantify the absolute concentrations of cellular metabolites a calibration table was constructed by injecting the known amounts of these standards. Note that the LC-MS/MS method that was used for metabolite analysis does not discriminate between structurally similar IPP and DMAPP, therefore their amount in samples was determined as a sum of concentrations of the two compounds.

Cumomer distribution analysis for cMEPP was done by calculating relative intensities of peaks arising from 277→79, 278→79, 279→79, 280→79, 281→79 and 282→79 MS/MS transitions corresponding to M0, M+1, M+2, M+3, M+4, and M+5 cumomers of this metabolite. In a separate experiment it has been verified that at t≈14.3 min (the retention time of cMEPP) extracts from *E. coli* cells grown on a regular glucose do not generate detectable peaks with MS/MS transitions 272→79, 273→79, 274→79, 275→79, 276→79. These control measurements exclude the possibility that compounds potentially co-eluting with cMEPP but having slightly lower molecular weight can contribute to the MS/MS peaks generated by cMEPP when cells are grown on $^{13}C$-enriched glucose.

Cumomer Analysis of $^{13}C$ Labeled Isoprene

To measure $^{13}C$ enrichment of isoprene emitted by cells grown on $^{13}C$-glucose, GC spectra were monitored from m/z 58 to m/z 68, i.e. over the range of mass to charge ratios that can originate from five-carbon isoprene derivatives. FIG. 102 shows typical GC spectra of synthetic isoprene containing the natural abundance of $^{13}C$ and of isoprene emitted by REM A2_17 strain grown on 3-$^{13}C$ glucose and therefore enriched in C.

The data shown in FIG. 102A were used to calculate the theoretical GC spectrum of isoprene containing no $^{13}C$ isotopes (all-$^{12}C_5$ isoprene) according to the following set of linear equations:

$$P_{60}=1.00000*k_{60}$$

$$P_{61}=0.05561*k_{60}+1.00000*k_{61}$$

$$P_{62}=0.01238*k_{60}+0.05561*k_{61}+1.00000*k_{62}$$

$$P_{63}=0.01238*k_{61}+0.05561*k_{62}+1.00000*k_{63}$$

$$P_{64}=0.01238*k_{62}+0.05561*k_{63}+1.00000*k_{64}$$

$$P_{65}=0.01238*k_{63}+0.05561*k_{64}+1.00000*k_{65}$$

$$P_{66}=0.01238*k_{64}+0.05561*k_{65}+1.00000*k_{66}$$

$$P_{67}=0.01238*k_{65}+0.05561*k_{66}+1.00000*k_{67}$$

$$P_{68}=0.01238*k_{66}+0.05561*k_{67}+1.00000*k_{68}$$

$$P_{69}=0.01238*k_{67}+0.05561*k_{68}+1.00000*k_{69}$$

$$P_{70}=0.01238*k_{68}+0.05561*k_{69}+1.00000*k_{70} \quad \text{(Eqs. 2)},$$

where $P_{60}$ . . . $P_{70}$ are the measured intensities of GC peaks produced by the isoprene standard (subscript indices indicate m/z values of corresponding peaks), $k_{60}$ . . . $k_{70}$ are the calculated intensities of GC peaks that would be generated by all-$^{12}C_5$ isoprene (subscript indices indicate m/z values of corresponding peaks), and the coefficients 1.00000, 0.05561, and 0.05561 are the estimated relative abundances of three $C_5$ cumomers containing zero, one or two $^{13}C$ isotopes per molecule assuming that this $C_5$ compound has natural abundance of $^{13}C$ isotope equal to 1.1%. (Note that in our calculations of all-$^{12}C_5$ isoprene spectrum it was assumed that the natural abundance of deuterium is too small to affect the final results). The positive values of $k_{60}$ . . . $k_{70}$ were obtained using lsqlin in solver (MATLAB 7.0, MathWorks). The calculated values of $k_{69}$ and $k_{70}$ were effectively zero indicating that GC spectrum of all-$^{12}C_5$ isoprene should not have any peaks with m/z=69 and higher.

Cumomer distribution analysis of labeled isoprene samples was done according to the following set of linear equations based on the values of $k_{62} \ldots k_{68}$ obtained as described above:

$$A_{67}=k_{67}*X_{M0}+k_{66}*X_{M+1}+k_{65}*X_{M+2}+k_{64}*X_{M+3}+k_{63}*X_{M+4}+k_{62}*X_{M+5}$$

$$A_{68}=k_{68}*X_{M0}+k_{67}*X_{M+1}+k_{66}*X_{M+2}+k_{65}*X_{M+3}+k_{64}*X_{M+4}+k_{63}*X_{M+5}$$

$$A_{69}=k_{68}*X_{M+1}+k_{67}*X_{M+2}+k_{66}*X_{M+3}+k_{65}*X_{M+4}+k_{64}*X_{M+5}$$

$$A_{70}=k_{68}*X_{M+2}+k_{67}*X_{M+3}+k_{66}*X_{M+4}+k_{65}*X_{M+5}$$

$$A_{70}=k_{68}*X_{M+3}+k_{67}*X_{M+4}+k_{66}*X_{M+5}$$

$$A_{71}=k_{68}*X_{M+4}+k_{67}*X_{M+5}$$

$$A_{72}=k_{68}*X_{M+5} \qquad \text{(Eqs. 3),}$$

where $A_{67}$-$A_{72}$ are the measured intensities of GC peaks produced by $^{13}C$-enriched isoprene (subscript indices indicate m/z values of corresponding peaks) and $X_{M0} \ldots X_{M+5}$ are the relative abundances of isoprene cumomers having from zero to five $^{13}C$ atoms ($X_{M0}$ corresponds to the isoprene molecules in which all carbons atoms are represented by the isotope $^{12}C$). The non-negative values of $X_{M0} \ldots X_{M+5}$ were obtained using the lsqlin solver (MATLAB 7.0, MathWorks).

Determination of Relative Contribution of DXP and MVA Pathways to the Isoprene Production The relative contribution of DXP and MVA pathways to the total isoprene production ($\phi^{DXP}$ and $\phi^{MVA}$, respectively) was estimated by solving in MATLAB (MathWorks) the following overdetermined system of linear equations:

$$X_{MO,Isp-FM}=\phi^{DXP}*X_{MO,cMEPP}+\phi^{MVA}*X_{MO,Isp+FM}$$

$$X_{M+1,\,Isp-FM}=\phi^{DXP}*X_{M+1,\,cMEPP}+\phi^{MVA}*X_{M+1,\,Isp+FM}$$

$$X_{M+2,\,Isp-FM}=\phi^{DXP}*X_{M+2,\,cMEPP}+\phi^{MVA}*X_{M+2,\,Isp+FM}$$

$$X_{M+3,\,Isp-FM}=\phi^{DXP}*X_{M+3,\,cMEPP}+\phi^{MVA}*X_{M+3,\,Isp+FM}$$

$$X_{M+4,\,Isp-FM}=\phi^{DXP}*X_{M+4,\,cMEPP}+\phi^{MVA}*X_{M+4,\,Isp+FM}$$

where $X_{M0,\,Isp-FM} \ldots X_{M+4,\,Isp-FM}$ and $X_{MO,Isp+FM} \ldots X_{M+4,\,Isp+FM}$ are the relative abundances of isoprene cumomers containing from zero to four $^{13}C$ atoms calculated according to Eqs. 3 (subscript indices "Isp+FM" and "Isp−FM" indicate that calculations were done for cells incubated with and without fosmidomycin, respectively), $X_{M0,\,cMEPP} \ldots X_{M+4,\,cMEPP}$ are the relative abundances of corresponding cMEPP cumomers measured by LC-MS/MS as described above.

Example 34

$^{13}C$ NMR Method for the Determination of Carbon Fluxes Through the MVA and MEP Pathways Leading to BioIsoprene™ Product In this Example, BioIsoprene™ refers to isoprene that is biologically produced, e.g., using the methods described herein. BioIsoprene™ was obtained from bioisoprene composition. The relative contributions of the two isoprenoid precursor pathways, the MVA and MEP (DXP) pathways, to isoprene production in a REM A2_17 dual pathway strain were determined by $^{13}C$ NMR spectroscopy and the resulting information used to calculate the MVA/MEP carbon ratio. Similar techniques have been used to determine the respective contributions of the MVA and MEP pathways to the biosynthesis of polyisoprenoids (Skorupinska-Tudek, K. et al. (2008) *J. Biol. Chem.,* 283 (30), pp. 21024-21035.) and isoprene (Wagner, W. P., Helmig, D. and Fall, R. (2000) *J. Nat. Prod.,* 63, pp. 37-40). The labeling patterns of isoprene derived from $^{13}C$ enriched glucose labels differ according to which pathway was utilized to channel carbon from the substrate to product. These patterns are shown in FIG. 100A for a [1-$^{13}C$]-D-glucose substrate and FIG. 100B for a [3-$^{13}C$]-D-glucose substrate.

As can be seen from FIG. 100A, carbon #3 (C-3) of isoprene is not enriched from either pathway from a [1-$^{13}C$]-D-glucose substrate, with the extent of $^{13}C$-enrichment equal to the natural abundance of 1.1% relative to $^{12}C$. In contrast, C-5 is labeled in both cases, thus the enrichment of C-5/C-3 allows the determination of the total extent of $^{13}C$-label incorporation. The maximum possible $^{13}C$ enrichment at C-5 of Biosoprene™ product derived from [1-$^{13}C$]-D-glucose is 50%, with less if oxidative pentose phosphate pathway is operating at a significant flux relative to glycolysis. The ratio of MVA/MEP pathways is determined by comparing the enrichment of C-1 relative to C-2 and C-4. This is shown in FIG. 103.

In the case where carbon flux though the MVA and MEP pathways is equal (1:1 MVA/MEP ratio), the extent of labeling at C-1 relative to C-2 and C-4 is also equivalent in the BioIsoprene™ product, with a maximum enrichment of 25%. At a MVA/MEP ratio of 9:1, C-1 is only enriched to the extent of 5%, whereas C-2 and C-4 are enriched to a level of 45%.

A method for the small-scale generation, collection and analysis of $^{13}C$-labeled BioIsoprene™ product was developed in order to determine the relative contributions of the MVA and MEP (DXP) pathways to isoprene production in strain REM A2_17. The strain was grown in HM-1 media with [1-$^{13}C$]-D-glucose (10 mg/mL) as the sole carbon source in a stirred bottle format and the resulting BioIsoprene™ product was adsorbed to a small carbon filter consisting of 200 mg activated carbon (Koby filters, MA) packed into a glass Pasteur pipette with cotton wool (Scheme xx-1). After overnight growth at 34° C., the carbon filter was removed and desorbed directly into a glass NMR tube with $CDCl_3$ (1 mL). A reference spectrum of unlabeled isoprene was obtained by diluting an isoprene standard (5 uL) (Sigma-Aldrich) into 0.75 mL of deuterochloroform (CDCl3) and acquiring a $^{13}C$ NMR spectrum.

Relative $^{13}C$-enrichment of isoprene at each carbon atom was determined by $^{13}C$ nuclear magnetic resonance spectroscopy ($^{13}C$-NMR) by determining the relative intensities of the signals corresponding to each carbon atom of isoprene and comparing these values to the relative intensities of the carbon signals from unlabeled (natural $^{13}C$ abundance) isoprene. $^{13}C$ NMR spectra were obtained on a Varian 500 MHz VNMRS system operating at 125.7 MHz. Acquisition parameters were sw=30487, at=1.3 sec, d1=1, nt=10000, dn=H1, dm=yyy, dmm=w, dpr=42, dmf=12600. $^{13}C$ signal intensity was determined by peak height and integrated peak area. The $^{13}C$-NMR spectrum of unlabeled isoprene (% $^{13}C$=1.1%) is shown in FIG. 105. The peak heights of carbons 1-4 are similar, with aliphatic C-5 showing a more intense signal.

The $^{13}C$ NMR spectrum of the BioIsoprene™ product derived from dual pathway strain REM A2_17 is shown in FIG. 106. The signals for C-1,3,4 and 5 are clearly evident, whereas the C-2 signal is equal or less than, or equal to the noise level. The relative peak heights of C-1, C-3 and C-4 indicate that the ratio of MVA/DXP pathway flux is more than 1:1 and less than 2:1. The enrichment of C-1, 3 and 4 relative to C-2 and C-5 indicate that both the MVA and DXP pathways are operating in strain REM A2_17 and contribute to overall carbon flux to isoprene.

Example 35 fkpB-ispH iscR

In this example, we show that when the promoter PL.6 replaced the native promoter of the operon fkpB-ispH in strain WW119 to create strain REM D8_15, isoprene production drops from ≈500 to 600 ug/L/H/OD seen in strain WW119 (see FIG. 108) to ≈50 ug/L/H/OD in strain REM D8_15 (see FIG. 108). Addition of ΔispR to WW119 showed a small decrease in isoprene specific productivity. The result observed for the introduction of PL.6 fkpB-ispH into WW119 was unanticipated. Our hypothesis was that more ispH would yield higher isoprene titer. We further show that when the iron sulfur cluster regulatory gene, iscR, is deleted from the latter strain, REM D8_15, to create strain REM D6_15 the ΔiscR mutation substantially restores isoprene production to strain REM D6_15. These observations suggest a beneficial interaction between ΔiscR and fkpB-ispH that can improve the process of isoprene production via the DXP pathway.

Construction of Strains for this Example.

Generation of the PL.6-fkpB Locus

Within the *E. coli* BL21 genome the ispH gene is located immediately downstream of the fkpB gene which encodes a FKBP-type peptidyl-prolyl cis-trans isomerase. Interestingly, the structure of the *E. coli* IspH enzyme shows that the protein has 2 proline residues that are isomerized (Gräwert, T. et al., 2009). The idea that FkpB could be involved in IspH function may also be reflected by the fact that the fkpB and ispH orfs are separated by just one nucleotide and together have been shown to be transcribed as the last 2 genes of the ribF-ileS-lspA-fkpB-ispH 5-gene operon (see www.ecocyc.org).

Further more, BLAST analysis of the 125 bases separating the stop codon of lspA and the start codon of fkpB revealed a highly conserved sequence that occurs many times throughout the *E. coli* genome. This commonly found sequence is:

(SEQ ID NO: 187)
AATCGTAGGCCGGATAAGGCGTTTACGCCGCATCCGGCAA

This sequence harbors characteristics of a transcriptional terminator, which includes the likely formation of a stem loop. The bases with potential of hybridizing together to form the stem loop are highlighted above in bold and underlined text (bold anneals to bold; underlined anneals to underlined). The location of this repeated sequence, in each instance observed, was always found just downstream of the 3' end of a single gene or downstream of the 3' ends of 2 genes transcribed toward one another. The repeated sequence was not found within the coding region of over 40 regions analyzed. Together, this information suggests that the sequence functions as a transcriptional terminator and hints at the possibility of fkpB and ispH being transcribed as an independent 2-gene operon.

Our in-house transcriptional analyses of BL21 14-L fermentations show the ispH transcript to be present at almost undetectable levels; a result inline with that previously reported in the field. Similarly, the level of IspH protein accumulates to low levels within these and small scale grown cells (for small scale result see FIG. 108). Increased expression of endogenous BL21 ispH and its effect on isoprene production was an aim of the work described here. The previously described PL.6-promoter is a strong constitutive promoter chosen to up-regulate the expression of ispH. Based on the speculation that FkpB and IspH as well as fkpB and ispH potentially share a functional and a transcriptional relationship, respectively (described above), the PL.6-promoter was inserted immediately upstream of the fkpB orf.

The PL.6-promoter insertion and subsequent loopout of the chloramphenicol resistance marker described in this example was carried out using the Red/ET system from Gene Bridges GmbH according to the manufacturer's instructions. The strain BL21 (Novagen) was used. P1 lysate preparations and transductions were performed as previously described (Thomason et al., 2007). The BIO RAD Gene Pulser system (0.1 cm cuvette cat.#165-2089) and a transformation protocol suggested by the manufacturer (BIO RAD) was used for the electroporations described.

```
Primers
5' CMP::80 bp up of fkpB
                                          (SEQ ID NO: 188)
5'-AGATTGCTGCGAAATCGTAGGCCGGATAAGGCGTTTACGC

CGCATCCGGCAAAAATCCTTAAATATAAGAGCAAACCTGCAA

TTAACCCTCACTAAAGGGCGGCCGC

3' CMP::PL.6-fkpB
                                          (SEQ ID NO: 189)
5'-AGCGTGAAGTGCACCAGGACGGCGCTATTGCTCTGTACAGATTCAGA

CATGTTTTTACCTCCTTTGCAGTGCGTCCTGCTGATGTGCTCAGTATCA

CCGCCAGTGGTATTTATGTCAACACCGCCAGAGATAATTTATCACCGCA

GATGGTTATCTTAATACGACTCACTATAGGGCTCGAG

5' confirm CMP::80 bp up of fkpB
                                          (SEQ ID NO: 190)
5'-ACGCATCTTA TCCGGCCTACA

3' confirm CMP::PL.6-fkpB
                                          (SEQ ID NO: 191)
5'-ACCGTTGTTGCGGGTAGACTC

5' primer to PL.6
                                          (SEQ ID NO: 162)
5'-AGATAACCATCTGCGGTGATAAATTATCTCTGGCGGTG

top Gb's CMP
                                          (SEQ ID NO: 144)
5'-ACTGAAACGTTTTCATCGCTC

bottom Pgb2
                                          (SEQ ID NO: 163)
5'-GGTTTAGTTCCTCACCTTGTC
```

The PL.6-promoter introduced upstream of the endogenous fkpB coding region using the Gene Bridges GmbH methods is illustrated in FIG. 107. The antibiotic resistance cassette GB-CMP was amplified by PCR using the primer set 5' CMP::80 bp up of fkpB and 3' CMP::PL.6-fkpB. The 5' CMP::80 bp up of fkpB primer contains 80 bases of homology to the region immediately 5' to the fkpB coding region and the 3' CMP::PL.6-fkpB primer contains 50 bases of homology to the 5' region of the fkpB orf (open reading frame) to allow recombination at the specific locus upon electroporation of the PCR product in the presence of the pRed-ET plasmid. The FRT (Flipase recognition target) "scar" sequence remaining after Flipase-mediated excision of the antibiotic marker is also depicted in the figure.

Amplification of the CMP::PL.6 fkpB Fragment

To amplify the GB-CmpR cassette for inserting the PL.6-promoter immediately upstream of the fkpB locus the following PCR reaction was set up:

1 ul template (100 ng GB-CmpR)
10 ul HerculaseII Buffer
0.5 ul dNTP's (100 mM)
1.25 ul primer (10 uM) 5' CMP::80 bp up of fkpB
1.25 ul primer (10 uM) 3' CMP::PL.6-fkpB
35 ul diH2O
+1 ul of HerculaseII fusion from Stratagene Cycle Parameter:

95° C.×2 min., [95° C.×30 sec., 60° C.×30 sec., 72° C.×3 min.]×29 cycles; 72° C.×5 min., 4° C. until cool (Biometra T3000 Combi Thermocycler)

The resulting PCR fragment was separated on a 0.8% E-gel (Invitrogen) for verification of successful amplification, and purified using the QIAquick PCR Purification kits (Qiagen) according to manufacturer's instructions. The resulting stock was CMP::PL.6 fkpB fragment.

Integration of CMP::PL.6 fkpB fragment PCR product into BL21/pRed-ET Strain

The pRed-ET vector (Gene Bridges kit) was transformed into BL21 (Novagen) by electroporation resulting in strain REM F7__13 (BL21/pRed-ET). The purified CMP::PL.6 fkpB PCR fragment was electroporated into REM F7__13. The transformants were recovered in L Broth and then plated on L agar containing chloramphenicol (10 ug/ml). Chloramphenicol resistant colonies were analyzed by PCR for the presence of the GB-CmpR cassette and the PL.6-promoter upstream of fkpB using primers 5' confirm CMP::80 bp up of fkpB and bottom Pgb2 as well as 3' confirm CMP::PL.6-fkpB and top Gb's CMP. The PCR fragments from a number of transformants were sequenced using the 3' confirm CMP::PL.6-fkpB and top GB's CMP primers (Sequetech; Mountain View, Calif.) and PL.6 fkpB strain of interest identified. The chloramphenicol resistant strain, BL21 CMP::PL.6fkpB, was designated REM A4__14.

Strategy for Creating REM D1__14

Verification of the Presence of PL.6 fkpB within REM D1__14

To verify the REM D1__14 strain harbored the PL.6 fkp locus the following PCR reaction was set up:

Approx. 0.5 ul cells from a colony
5 ul HerculaseII Buffer
0.25 ul dNTP's (100 mM)
0.625 ul primer (10 uM) 5' primer to PL.6
0.625 ul primer (10 uM) 3' confirm CMP::PL.6-fkpB
17.5 ul diH2O
+0.5 ul of HerculaseII fusion from Stratagene Cycle Parameter:

95° C.×2 min., [95° C.×30 sec., 60° C.×30 sec., 72° C.×2 min.]×29 cycles; 72° C.×5 min., 4° C. until cool (Biometra T3000 Combi Thermocycler)

The resulting PCR fragment was separated on a 2% E-gel (Invitrogen) for verification of successful amplification.

The chloramphenicol marked PL.6 fkpB locus of strain REM A4__14, described above, was introduced into strain WW103 via P1-mediated transduction. The resulting chloramphenicol resistant strain was named REM A9__14. After Flipase-mediated excision of the antibiotic cassette the resulting chloramphenicol sensitive strain was designated REM D1__14 (BL21 pgl$^+$PL.6-dxs, GI1.6-dxr, GI1.6 yIDI, PL.2 lower MVA pathway, CMP::PL.6 fkpB). The presence of the PL.6-promoter upstream of fkpB within REM D1__14 was verified by PCR using primers 5' primer to PL.6 and 3' confirm CMP::PL.6-fkpB, which are described above.

Strategy for Creating REM A8__15

The chloramphenicol marked ΔiscR locus of strain REM14::CMP, described previously, was introduced into strain WW103 via P1-mediated transduction. The resulting chloramphenicol resistant strain was named REM A5__15. After Flipase-mediated excision of the antibiotic cassette the resulting chloramphenicol sensitive strain was designated REM A8__15 (BL21 pgl$^+$PL.6-dxs, GI1.6-dxr, GI1.6 yIDI, PL.2 lower MVA pathway, ΔiscR).

Strategy for Creating REM A7__15

The chloramphenicol marked ΔiscR locus of strain REM14::CMP was introduced into strain REM D1__14 via P1-mediated transduction. The resulting chloramphenicol resistant strain was named REM A2__15. After Flipase-mediated excision of the antibiotic cassette the resulting chloramphenicol sensitive strain was designated REM A7__15 (BL21 pgl$^+$PL.6-dxs, GI1.6-dxr, GI1.6 yIDI, PL.2 lower MVA pathway, CMP::PL.6 fkpB, ΔiscR).

Verification of Increased Accumulation of IspH within REM D1__14 and REM A7__15

Western Blot Method

REM D1__14, REM A7__15, REM A8__15, and WW103 cells were grown in TM3 medium (1% glucose, 0.1% yeast extract) to limiting OD and cells were harvested by centrifugation and pellets stored at −80 deg until analyzed. For analysis culture pellets were resuspended in 0.05 M sodium phosphate, 0.3 M sodium chloride, 0.02 M imidazole, pH 8 with 0.2 mg/ml DNaseI to 100 OD/ml. Cells were broken by repeated pass through the French Press. 8 ml of each lysate was then clarified by ultracentrifugation at 50,000 rpm for 30 minutes. Soluble material was removed and the insoluble pellet was resuspended in 8 ml of 0.05 M sodium phosphate, 0.3 M sodium chloride, 0.02 M imidazole, pH 8 buffer. Analysis for *E. coli* ispH expression was performed using Nitrocellulose western blot, following transfer and development techniques recommended by Invitrogen as described in iBlot® and WesternBreeze® user manuals. The western blot was probed using primary polyclonal antibody produced against purified *E. coli* ispH in rabbit by ProSci Inc. The detection used a fluorescent secondary antibody from Invitrogen, Alexa Fluor® 488 goat anti-rabbit IgG (H+L). The raw data is shown in FIG. 109. Sample quantitation was performed using ImageQuant 5.2 software and the results are presented in FIG. 110.

Figure 110:
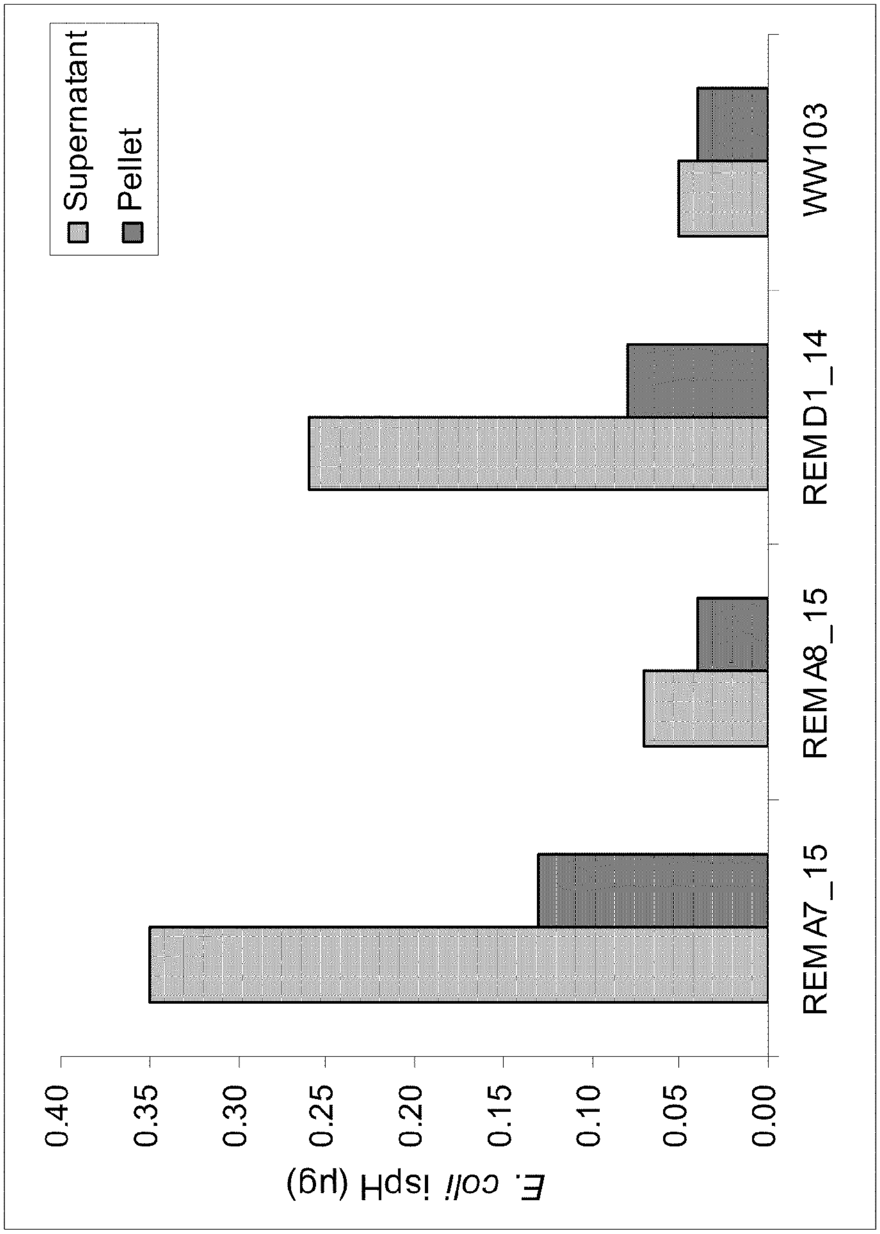

The increased expression of ispH driven by the PL.6-promoter located upstream of the fkpB-ispH 2 gene operon of strains REM D1__14 and REM A7__15 relative to strain REM A8__15 and WW103 was indirectly assessed by measuring the level of IspH accumulation via a Western blot method (see FIGS. 109 and 110). An approximately 5-fold increase in soluble IspH levels was determined for the PL.6αpB harboring strains REM D1__14 and REM A7__15 relative to the REM A8__15 and WW103 strains which harbor the endogenous wild type fkpB-ispH locus.

Strategy for Creating REM D8__15, REM D7__15, and REM D6__15

Strains WW119, REM D8__15, REM D7__15, and REM D6__15 were created by transforming pDW33 into WW103, REM D1__14, REM A8__15, and REM A7__15, respectively (strains described above).

Water-washed REM D1__14, REM A8__15, and REM A7__15 cells were transformed with pDW33 via electroporation using the BIO RAD Gene Pulser system (0.1 cm cuvette cat.#165-2089) and a transformation protocol suggested by the manufacturer (BIO RAD). The cells were recovered in L broth for 1 hour at 37° C. and then plated on L agar containing carbenicillin (50 ug/ml). One carbenicillin resistant colony was chosen for each strain. The resulting carbenicillin resistant strains were named as such:

REM D8_15 (BL21 pg1+PL.6-dxs, GI1.6-dxr, GI1.6 yIDI, PL.2 lower MVA pathway, PL.6 fkpB, and pDW33);

REM D7_15 (BL21 pg1+PL.6-dxs, GI1.6-dxr, GI1.6 yIDI, PL.2 lower MVA pathway, ΔiscR, and pDW33);

REM D6_15 15 (BL21 pg1+PL.6-dxs, GI1.6-dxr, GI1.6 yIDI, PL.2 lower MVA pathway, PL.6 fkpB, ΔiscR, and pDW33).

Method Section for Isoprene Production and Quantitation of ispH

Isoprene Measurements.

Cultures to measure isoprene production were set up in a 48-deep-well plate (cat# P-5mL-48-C-S Axygen Scientific, California, USA) with each well providing a 2 mL culture. The culture medium, named TM3, is described below. The strains to be compared were grown o/n at 30 degrees at 250 rpm in TM3 medium supplemented with 1% glucose and 0.1% yeast extract. In the morning the strains were inoculated at 1:100 in quadruplicate sets of wells in the 48-deep well block. The cultures were covered with a "Breath Easier"™ membrane (Electron Microscopy Sciences Cat#70536-10) and were continuously shaken at 600 rpm and 30 deg C. (Shel-Lab Inc. Model SI6R Refrigerated Shaking Incubator; Oregon, USA). Culture OD was determined after two hours and then at timed intervals out to 6 hours. Induction with IPTG was after two hours of growth by the addition of 50, 100, 200, and 400 uM IPTG to the quadruplicated sets of wells, one through four. At two hours post-induction and hourly thereafter out to six hours these cultures were samples for isoprene production assays as follow: A 100 uL aliquot of each culture was transferred to a 98-deep well glass block (cat#3600600 Zinsser; North America) which was immediately sealed with an impermeable adhesive aluminum film and incubated for 30 minutes with shaking at 450 rmp on an Eppendorf thermomixer (Eppendorf; North America.). The isoprene assay cultures were killed by heating at 70 deg C. for 7 min on a second Eppendorf thermomixer. The glass block was transferred to an Agilent 6890 GC attached to an Agilent 5973 MS and outfitted with a LEAP CTC CombiPAL autosampler for head space analysis. The column was an Agilent HP-5 (5% Phenyl Methyl Siloxane (15 m×0.25 mm×0.25 um)). A 100 uL gas volume was injected on the column. Other conditions were as follows. Oven Temperature: 37 C (held isothermal for 0.6 mins); Carrier Gas: Helium (flow—1 mL/min), split ratio of 50:1 at 250° C. on the injection port; Single Ion Monitoring mode (SIM) on mass 67; Detector off: 0.00 min-0.42 mins; Dectector on: 0.42 mins-0.60 mins; elution time for Isoprene (2-methyl-1,3 butadiene) was ~0.49 min for a total analysis time of 0.6 mins. Calibration of the instrument was performed by methods well known to those trained in the art.

Isoprene head space measurements were normalized by culture $OD_{600}$ to yield a measure of specific isoprene production in units of ug/L/H/OD. All reactions were followed for 4 to 8 hours. The surprising results from this experiment is that when the ΔiscR mutation is combined with the chromosomal mutation of PL.6 fkpB-ispH isoprene activity is restored. This result is consistent with that iscR in a background of overexpressed ispH takes on a regulatory role or at least interferes with flux through the DXP pathway. For high flux ispH needs to be overexpressed and under these condition ΔiscR expected to be beneficial for the process.

Verification of Increased isph Expression Level by Western Blot.

The substitution of the PL.6 promoter for the native promoter of the fkpB-ispH operon was expected to raise the level of ispH. This was confirmed in strain REM A7_15, REM D1_14 by comparison to control strains REM A8_15 and WW103 by western Blot with polyclonal antibody prepared against this enzyme as described; the promoter swap resulted in a 5-fold increase of soluble ispH. Cells were grown in TM3 medium (1% glucose, 0.1% yeast extract) to limiting OD and were harvested by centrifugation and the pellets were stored at −80 deg until the next day. For analysis pellets were resuspended in 0.05 M sodium phosphate, 0.3 M sodium chloride, 0.02 M imidazole, pH 8 with 0.2 mg/ml DNaseI to 100 OD/ml. Cells were broken by repeated passage through the French press. Eight ml of each lysate was clarified by ultracentrifugation at 100,000×g for 30 minutes. Supernatant was removed and the pellet was resuspended in 8 ml of buffer pH8, 0.05 M sodium phosphate, 0.3 M sodium chloride, 0.02 M imidazole. Western blot was performed as described in the users manuals iBlot® and WesternBreeze® (in Vitrogen). The primary polyclonal antibody was against purified *E. coli* IspH overexpressed in *E. coli* and raised in rabbit by ProSci Inc (Poway, Calif.). For detection a fluorescent secondary antibody from Invitrogen (Alexa Fluor® 488 goat anti-rabbit IgG H+L), was used. The raw data is shown in FIG. 109. Sample quantitation was performed using ImageQuant 5.2 software and the results are presented in FIG. 110.

TM3 (per Liter Fermentation Medium):

$K_2HPO_4$ 13.6 g, $KH_2PO_4$ 13.6 g, $MgSO_4*7H_2O$ 2 g, citric acid monohydrate 2 g, ferric ammonium citrate 0.3 g, yeast extract 1.0 g, 1000× Modified Trace Metal stock solution 1 ml. All of the components were added together and dissolved in Di H2O. The pH is adjusted to 6.8 with $NH_4OH$ and the solution is filter sterilized over a 0.22 micron membrane. Glucose was typically added at 1% and yeast extract was typically boosted to 0.1%. Antibiotics were added post-sterile as needed (TM3 medium was sometimes prepared w/o any $MgSO_4$ as this Mg++ led to precipitation over time. In this case $MgSO_4$ was added from a sterile 1M solution just prior to use).

1000× Modified Trace Metal Stock Solution (per Liter):

Citric Acids*H2O 40 g, $MnSO_4*H_2O$ 30 g, NaCl 10 g, $FeSO_4*7H_2O$ 1 g, $CoCl_2*$ $6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component was dissolved one at a time in Di $H_2O$, pH was adjusted to 3.0 with HCl/NaOH, and then the solution was q.s. to volume and filter sterilized with a 0.22 micron filter.

APPENDIX 1

Exemplary 1-deoxy-D-xylulose-5-phosphate synthase nucleic acids and polypeptides ATH: AT3G21500(DXPS1)
AT4G15560(CLA1) AT5G11380(DXPS3)
OSA: 4338768(Os05g0408900)
4340090(Os06g0142900)
4342614(Os07g0190000)
PPP: PHYPADRAFT_105028(DXS1)
PHYPADRAFT_137710
PHYPADRAFT_175220
PHYPADRAFT_73475
OLU: OSTLU_48774(DXS)
CRE: CHLREDRAFT_196568(DXS1)
CME: CMF089C
PFA: MAL13P1.186
PFD: PFDG_00954
PFH: PFHG_02940
PYO: PY04970
TAN: TA20470
TPV: TP01_0516
ECO: b0420(dxs)

APPENDIX 1-continued

ECJ: JW0410(dxs)
ECD: ECDH10B_0376(dxs)
ECE: Z0523(dxs)
ECS: ECs0474
ECC: c0531(dxs)
ECI: UTI89_C0443(dxs)
ECP: ECP_0479
ECV: APECO1_1590(dxs)
ECW: EcE24377A_0451(dxs)
ECX: EcHS_A0491(dxs)
ECM: EcSMS35_0456(dxs)
ECL: EcolC_3213
STY: STY0461(dxs)
STT: t2441(dxs)
SPT: SPA2301(dxs)
SPQ: SPAB_03161
SEC: SC0463(dxs)
SEH: SeHA_C0524(dxs)
SEE: SNSL254_A0469(dxs)
SEW: SeSA_A0482(dxs)
SES: SARI_02505
STM: STM0422(dxs)
YPE: YPO3177(dxs)
YPK: y1008(dxs)
YPM: YP_0754(dxs)
YPA: YPA_2671
YPN: YPN_0911
YPP: YPDSF_2812
YPG: YpAngola_A3074(dxs)
YPS: YPTB0939(dxs)
YPI: YpsIP31758_3112(dxs)
YPY: YPK_3253
YPB: YPTS_0980
YEN: YE3155(b0420)
SFL: SF0357(dxs)
SFX: S0365(dxs)
SFV: SFV_0385(dxs)
SSN: SSON_0397(dxs)
SBO: SBO_0314(dxs)
SBC: SbBS512_E0341(dxs)
SDY: SDY_0310(dxs)
ECA: ECA1131(dxs)
ETA: ETA_25270(dxs)
PLU: plu3887(dxs)
BUC: BU464(dxs)
BAS: BUsg448(dxs)
WBR: WGLp144(dxs)
SGL: SG0656
ENT: Ent638_0887
ESA: ESA_02882
KPN: KPN_00372(dxs)
CKO: CKO_02741
SPE: Spro_1078
BFL: Bfl238(dxs)
BPN: BPEN_244(dxs)
HIN: HI1439(dxs)
HIT: NTHI1691(dxs)
HIP: CGSHiEE_04795
HIQ: CGSHiGG_01080
HDU: HD0441(dxs)
HSO: HS_0905(dxs)
HSM: HSM_1383
PMU: PM0532(dxs)
MSU: MS1059(dxs)
APL: APL_0207(dxs)
APJ: APJL_0208(dxs)
APA: APP7_0210
ASU: Asuc_1372
XFA: XF2249
XFT: PD1293(dxs)
XFM: Xfasm12_1447
XFN: XfasM23_1378
XCC: XCC2434(dxs)
XCB: XC_1678
XCV: XCV2764(dxs)
XAC: XAC2565(dxs)
XOO: XOO2017(dxs)
XOM: XOO_1900(XOO1900)
SML: Smlt3355(dxs)
SMT: Smal_2779

APPENDIX 1-continued

VCH: VC0889
VCO: VC0395_A0412(dxs)
VVU: VV1_0315
VVY: VV0868
VPA: VP0686
VFI: VF0711
VHA: VIBHAR_01173
PPR: PBPRA0805
PAE: PA4044(dxs)
PAU: PA14_11550(dxs)
PAP: PSPA7_1057(dxs)
PPU: PP_0527(dxs)
PPF: Pput_0561
PPG: PputGB1_0572
PPW: PputW619_0579
PST: PSPTO_0698(dxs)
PSB: Psyr_0604
PSP: PSPPH_0599(dxs)
PFL: PFL_5510(dxs)
PFO: PflO1_5007
PEN: PSEEN0600(dxs)
PMY: Pmen_3844
PSA: PST_3706(dxs)
CJA: CJA_3336(dxs)
PAR: Psyc_0221(dxs)
PCR: Pcryo_0245
PRW: PsycPRwf_0411
ACI: ACIAD3247(dxs)
ACB: A1S_3106
ABM: ABSDF0389(dxs)
ABY: ABAYE0381
ABC: ACICU_03307
SON: SO_1525(dxs)
SDN: Sden_2571
SFR: Sfri_2790
SAZ: Sama_2436
SBL: Sbal_1357
SBM: Shew185_1343
SBN: Sbal195_1382
SLO: Shew_2771
SPC: Sputcn32_1275
SSE: Ssed_3329
SPL: Spea_2991
SHE: Shewmr4_2731
SHM: Shewmr7_2804
SHN: Shewana3_2901
SHW: Sputw3181_2831
SHL: Shal_3080
SWD: Swoo_3478
ILO: IL2138(dxs)
CPS: CPS_1088(dxs)
PHA: PSHAa2366(dxs)
PAT: Patl_1319
SDE: Sde_3381
MAQ: Maqu_2438
AMC: MADE_01425
PIN: Ping_2240
MCA: MCA0817(dxs)
FTU: FTT1018c(dxs)
FTF: FTF1018c(dxs)
FTW: FTW_0925(dxs)
FTL: FTL_1072
FTH: FTH_1047(dxs)
FTA: FTA_1131(dxs)
FTN: FTN_0896(dxs)
FTM: FTM_0932(dxs)
FPH: Fphi_1718
NOC: Noc_1743
AEH: Mlg_1381
HHA: Hhal_0983
HCH: HCH_05866(dxs)
CSA: Csal_0099
ABO: ABO_2166(dxs)
MMW: Mmwyl1_1145
AHA: AHA_3321(dxs)
ASA: ASA_0990(dxs)
BCI: BCI_0275(dxs)
RMA: Rmag_0386
VOK: COSY_0360(dxs)
NME: NMB1867(dxs)

APPENDIX 1-continued

NMA: NMA0589(dxs)
NMC: NMC0352(dxs)
NMN: NMCC_0354
NGO: NGO0036
NGK: NGK_0044
CVI: CV_2692(dxs)
RSO: RSc2221(dxs)
REU: Reut_A0882
REH: H16_A2732(dxs)
RME: Rmet_2615
BMA: BMAA0330(dxs)
BMV: BMASAVP1_1512(dxs)
BML: BMA10229_1706(dxs)
BMN: BMA10247_A0364(dxs)
BXE: Bxe_B2827
BVI: Bcep1808_4257
BUR: Bcep18194_B2211
BCN: Bcen_4486
BCH: Bcen2424_3879
BCM: Bcenmc03_3648
BAM: Bamb_3250
BAC: BamMC406_3776
BMU: Bmul_4820
BMJ: BMULJ_03696(dxs)
BPS: BPSS1762(dxs)
BPM: BURPS1710b_A0842(dxs)
BPL: BURPS1106A_A2392(dxs)
BPD: BURPS668_A2534(dxs)
BTE: BTH_II0614(dxs)
BPH: Bphy_3948
PNU: Pnuc_1704
PNE: Pnec_1422
BPE: BP2798(dxs)
BPA: BPP2464(dxs)
BBR: BB1912(dxs)
BPT: Bpet3060(dxs)
BAV: BAV2177(dxs)
RFR: Rfer_2875
POL: Bpro_1747
PNA: Pnap_1501
AAV: Aave_2015
AJS: Ajs_1038
VEI: Veis_3283
DAC: Daci_2242
MPT: Mpe_A2631
HAR: HEAR0279(dxs)
MMS: mma_0331
LCH: Lcho_3373
NEU: NE1161(dxs)
NET: Neut_1501
NMU: Nmul_A0236
EBA: ebA4439(dxs)
AZO: azo1198(dxs)
DAR: Daro_3061
TBD: Tbd_0879
MFA: Mfla_2133
HPY: HP0354
HPJ: jhp0328(dxs)
HPA: HPAG1_0349
HPS: HPSH_01830
HHE: HH0608(dxs)
HAC: Hac_0968(dxs)
WSU: WS1996
TDN: Suden_0475
CJE: Cj0321(dxs)
CJR: CJE0366(dxs)
CJJ: CJJ81176_0343(dxs)
CJU: C8J_0298(dxs)
CJD: JJD26997_1642(dxs)
CFF: CFF8240_0264(dxs)
CCV: CCV52592_1671(dxs)
CHA: CHAB381_1297(dxs)
CCO: CCC13826_1594(dxs)
ABU: Abu_2139(dxs)
NIS: NIS_0391(dxs)
SUN: SUN_2055(dxs)
GSU: GSU0686(dxs-1) GSU1764(dxs-2)
GME: Gmet_1934 Gmet_2822
GUR: Gura_1018 Gura_2175
GLO: Glov_2182 Glov_2235
PCA: Pcar_1667(dxs)
PPD: Ppro_1191 Ppro_2403
DVU: DVU1350(dxs)
DVL: Dvul_1718
DDE: Dde_2200
LIP: LI0408(dsx)
DPS: DP2700
DOL: Dole_1662
ADE: Adeh_1097
AFW: Anae109_1136
MXA: MXAN_4643(dxs)
SAT: SYN_02456
SFU: Sfum_1418
PUB: SAR11_0611(dxs)
MLO: mlr7474
MES: Meso_0735
PLA: Plav_0781
SME: SMc00972(dxs)
SMD: Smed_0492
ATU: Atu0745(dxs)
ATC: AGR_C_1351
RET: RHE_CH00913(dxs)
REC: RHECIAT_CH0001005(dxs)
RLE: RL0973(dxs)
BME: BMEI1498
BMF: BAB1_0462(dxs)
BMB: BruAb1_0458(dxs)
BMC: BAbS19_I04270
BMS: BR0436(dxs)
BMT: BSUIS_A0462(dxs)
BOV: BOV_0443(dxs)
BCS: BCAN_A0440(dxs)
OAN: Oant_0547
BJA: bll2651(dxs)
BRA: BRADO2161(dxs)
BBT: BBta_2479(dxs)
RPA: RPA0952(dxs)
RPB: RPB_4460
RPC: RPC_1149
RPD: RPD_4305
RPE: RPE_1067
RPT: Rpal_1022
NWI: Nwi_0633
NHA: Nham_0778
BHE: BH04350(dxs)
BQU: BQ03540(dxs)
BBK: BARBAKC583_0400(dxs)
BTR: Btr_0649
XAU: Xaut_4733
AZC: AZC_3111
MEX: Mext_1939 Mext_4309
MRD: Mrad2831_3459 Mrad2831_3992
MET: M446_6352 M446_6391
BID: Bind_1811
CCR: CC_2068
CAK: Caul_3314
SIL: SPO0247(dxs)
SIT: TMI1040_2920
RSP: RSP_0254(dxsA) RSP_1134(dxs)
RSH: Rsph17029_1897 Rsph17029_2795
RSQ: Rsph17025_2027 Rsph17025_2792
JAN: Jann_0088 Jann_0170
RDE: RD1_0101(dxs) RD1_0548(dxs)
PDE: Pden_0400
DSH: Dshi_3294 Dshi_3526
MMR: Mmar10_0849
HNE: HNE_1838(dxs)
ZMO: ZMO1234(dxs) ZMO1598(dxs)
NAR: Saro_0161
SAL: Sala_2354
SWI: Swit_1461
ELI: ELI_12520
GOX: GOX0252
GBE: GbCGDNIH1_0221
GbCGDNIH1_2404
ACR: Acry_1833
GDI: GDI1860(dxs)
RRU: Rru_A0054 Rru_A2619
MAG: amb2904
MGM: Mmc1_1048

APPENDIX 1-continued

SUS: Acid_1783
SWO: Swol_0582
CSC: Csac_1853
BSU: BSU24270(dxs)
BHA: BH2779
BAN: BA4400(dxs)
BAR: GBAA4400(dxs)
BAA: BA_4853
BAT: BAS4081
BCE: BC4176
BCA: BCE_4249(dxs)
BCZ: BCZK3930(dxs)
BCY: Bcer98_2870
BTK: BT9727_3919(dxs)
BTL: BALH_3785(dxs)
BWE: BcerKBAB4_4029
BLI: BL01523(dxs)
BLD: BLi02598(dxs)
BCL: ABC2462(dxs)
BAY: RBAM_022600
BPU: BPUM_2159
GKA: GK2392
GTN: GTNG_2322
LSP: Bsph_3509
ESI: Exig_0908
LMO: lmo1365(tktB)
LMF: LMOf2365_1382(dxs)
LIN: lin1402
LWE: lwe1380(tktB)
LLA: L108911(dxsA) L123365(dxsB)
LLC: LACR_1572 LACR_1843
LLM: llmg_0749(dxsB)
SAK: SAK_0263
LPL: lp_2610(dxs)
LJO: LJ0406
LAC: LBA0356
LSL: LSL_0209(dxs)
LGA: LGAS_0350
LRE: Lreu_0958
LRF: LAR_0902
LFE: LAF_1005
STH: STH1842
CAC: CAC2077 CA_P0106(dxs)
CPE: CPE1819
CPF: CPF_2073(dxs)
CPR: CPR_1787(dxs)
CTC: CTC01575
CNO: NT01CX_1983
CTH: Cthe_0828
CDF: CD1207(dxs)
CBO: CBO1881(dxs)
CBA: CLB_1818(dxs)
CBH: CLC_1825(dxs)
CBL: CLK_1271(dxs)
CBK: CLL_A1441 CLL_A2401(dxs)
CBB: CLD_2756(dxs)
CBF: CLI_1945(dxs)
CBE: Cbei_1706
CKL: CKL_1231(dxs)
CPY: Cphy_2511
AMT: Amet_2508
AOE: Clos_1607
CHY: CHY_1985(dxs)
DSY: DSY2348
DRM: Dred_1078
PTH: PTH_1196(dxs)
DAU: Daud_1027
HMO: HM1_0295(dxs)
TTE: TTE1298(dxs)
TEX: Teth514_1540
TPD: Teth39_1103
MTA: Moth_1511
MPE: MYPE730
MGA: MGA_1268(dxs)
MTU: Rv2682c(dxs1) Rv3379c(dxs2)
MTC: MT2756(dxs)
MRA: MRA_2710(dxs1) MRA_3419(dxs2)
MTF: TBFG_12697 TBFG_13415
MBO: Mb2701c(dxs1) Mb3413c(dxs2)
MBB: BCG_2695c(dxs1) BCG_3450c(dxs2)

APPENDIX 1-continued

MLE: ML1038(dxs)
MPA: MAP2803c(dxs)
MAV: MAV_3577(dxs)
MSM: MSMEG_2776(dxs)
MUL: MUL_3319(dxs1)
MVA: Mvan_2477
MGI: Mflv_3923
MAB: MAB_2990c
MMC: Mmcs_2208
MKM: Mkms_2254
MJL: Mjls_2197
MMI: MMAR_0276(dxs2)
MMAR_2032(dxs1)
CGL: NCgl1827(cgl1902)
CGB: cg2083(dxs)
CGT: cgR_1731
CEF: CE1796
CDI: DIP1397(dxs)
CJK: jk1078(dxs)
CUR: cu0909
NFA: nfa37410(dxs)
RHA: RHA1_ro06843
SCO: SCO6013(SC1C3.01)
SCO6768(SC6A5.17)
SMA: SAV1646(dxs1) SAV2244(dxs2)
SGR: SGR_1495(dxs)
TWH: TWT484
TWS: TW280(Dxs)
LXX: Lxx10450(dxs)
CMI: CMM_1660(dxsA)
AAU: AAur_1790(dxs)
RSA: RSal33209_2392
KRH: KRH_14140(dxs)
PAC: PPA1062
NCA: Noca_2859
TFU: Tfu_1917
FRA: Francci3_1326
FRE: Franean1_5184
FAL: FRAAL2088(dxs)
ACE: Acel_1393
KRA: Krad_1452 Krad_1578
SEN: SACE_1815(dxs)
STP: Strop_1489
SAQ: Sare_1454
BLO: BL1132(dxs)
BLJ: BLD_0889(dxs)
BAD: BAD_0513(dxs)
FNU: FN1208 FN1464
RBA: RB2143(dxs)
OTE: Oter_2780
MIN: Minf_1537(dxs)
AMU: Amuc_0315
CTR: CT331(dxs)
CTA: CTA_0359(dxs)
CTB: CTL0585
CTL: CTLon_0582(dxs)
CMU: TC0608(dxs)
CPN: CPn1060(tktB_2)
CPA: CP0790
CPJ: CPj1060(tktB_2)
CPT: CpB1102
CCA: CCA00304(dxs)
CAB: CAB301(dxs)
CFE: CF0699(dxs)
PCU: pc0619(dxs)
TPA: TP0824
TPP: TPASS_0824(dxs)
TDE: TDE1910(dxs)
LIL: LA3285(dxs)
LIC: LIC10863(dxs)
LBJ: LBJ_0917(dxs)
LBL: LBL_0932(dxs)
LBI: LEPBI_I2605(dxs)
LBF: LBF_2525(dxs)
SYN: sll1945(dxs)
SYW: SYNW1292(Dxs)
SYC: syc1087_c(dxs)
SYF: Synpcc7942_0430
SYD: Syncc9605_1430
SYE: Syncc9902_1069

APPENDIX 1-continued

SYG: sync_1410(dxs)
SYR: SynRCC307_1390(dxs)
SYX: SynWH7803_1223(dxs)
SYP: SYNPCC7002_A1172(dxs)
CYA: CYA_1701(dxs)
CYB: CYB_1983(dxs)
TEL: tll0623
MAR: MAE_62650
CYT: cce_1401(dxs)
GVI: gll0194
ANA: alr0599
NPU: Npun_F5466
AVA: Ava_4532
PMA: Pro0928(dxs)
PMM: PMM0907(Dxs)
PMT: PMT0685(dxs)
PMN: PMN2A_0300
PMI: PMT9312_0893
PMB: A9601_09541(dxs)
PMC: P9515_09901(dxs)
PMF: P9303_15371(dxs)
PMG: P9301_09521(dxs)
PMH: P9215_09851
PMJ: P9211_08521
PME: NATL1_09721(dxs)
TER: Tery_3042
AMR: AM1_5186(dxs)
BTH: BT_1403 BT_4099
BFR: BF0873 BF4306
BFS: BF0796(dxs) BF4114
BVU: BVU_1763 BVU_3090
PGI: PG2217(dxs)
PGN: PGN_2081
PDI: BDI_2664
CHU: CHU_3643(dxs)
GFO: GFO_3470(dxs)
FJO: Fjoh_1523
FPS: FP0279(dxs)
CTE: CT0337(dxs)
CPC: Cpar_1696
CPH: Cpha266_0671
CPB: Cphamn1_1826
PVI: Cvib_0498
PLT: Plut_0450
PPH: Ppha_2222
CTS: Ctha_0174
PAA: Paes_1686
DET: DET0745(dxs)
DEH: cbdb_A720(dxs)
DEB: DehaBAV1_0675
EMI: Emin_0268
DRA: DR_1475
DGE: Dgeo_0994
TTH: TTC1614
TTJ: TTHA0006
AAE: aq_881
HYA: HY04AAS1_1061
SUL: SYO3AOP1_0652
TMA: TM1770
TPT: Tpet_1058
TLE: Tlet_2013
TRQ: TRQ2_1054
TME: Tmel_0252
FNO: Fnod_1517
PMO: Pmob_1001

Exemplary 1-deoxy-D-xylulose-5-phosphate reductoisomerase nucleic acids and polypeptides ATH: AT5G62790(DXR)
OSA: 4326153(Os01g0106900)
PPP: PHYPADRAFT_127023
PHYPADRAFT_128953
OLU: OSTLU_31255(DXR)
CRE: CHLREDRAFT_196606(DXR1)
CME: CMG148C
PFA: PF14_0641
PFD: PFDG_00980
PYO: PY05578
TAN: TA14290
TPV: TP02_0073

APPENDIX 1-continued

ECO: b0173(dxr)
ECJ: JW0168(dxr)
ECD: ECDH10B_0153(dxr)
ECE: Z0184(yaeM)
ECS: ECs0175
ECI: UTI89_C0188(dxr)
ECP: ECP_0181
ECV: APECO1_1814(dxr)
ECW: EcE24377A_0177(dxr)
ECX: EcHS_A0175(dxr)
ECM: EcSMS35_0184(dxr)
ECL: EcolC_3487
STY: STY0243(dxr)
STT: t0221(dxr)
SPT: SPA0227(dxr)
SPQ: SPAB_00282
SEC: SC0220(dxr)
SEH: SeHA_C0258(dxr)
SEE: SNSL254_A0242(dxr)
SEW: SeSA_A0245(dxr)
SES: SARI_02782
STM: STM0220(dxr)
YPE: YPO1048(dxr)
YPK: y3131
YPM: YP_2802(dxr)
YPA: YPA_0524
YPN: YPN_2952
YPP: YPDSF_1664
YPG: YpAngola_A3431(dxr)
YPS: YPTB2999(dxr)
YPI: YpsIP31758_1017(dxr)
YPY: YPK_1070
YPB: YPTS_3119
YEN: YE3280(b0173)
SFL: SF0163(yaeM)
SFX: S0166(yaeM)
SFV: SFV_0156(yaeM)
SSN: SSON_0185(yaeM)
SBO: SBO_0161(yaeM)
SBC: SbBS512_E0166(dxr)
SDY: SDY_0189(yaeM)
ECA: ECA1035(dxr)
ETA: ETA_08940(dxr)
PLU: plu0676(dxr)
BUC: BU235(dxr)
BAS: BUsg229(dxr)
WBR: WGLp388(yaeM)
SGL: SG1939
ENT: Ent638_0711
ESA: ESA_03169
KPN: KPN_00186(ispC)
CKO: CKO_03194
SPE: Spro_3786
BFL: Bfl275(dxr)
BPN: BPEN_283(dxr)
HIN: HI0807
HIT: NTHI0971(dxr)
HIP: CGSHiEE_08025
HIQ: CGSHiGG_07530
HDU: HD1186(dxr)
HSO: HS_0985(dxr)
HSM: HSM_1463
PMU: PM1988(dxr)
MSU: MS1928(dxr)
APL: APL_0406(dxr)
APJ: APJL_0428(dxr)
APA: APP7_0430
ASU: Asuc_0657
XFA: XF1048
XFT: PD0328(dxr)
XFM: Xfasm12_0359
XFN: XfasM23_0324
XCC: XCC1367(dxr)
XCB: XC_2871
XCV: XCV1472(dxr)
XAC: XAC1415(dxr)
XOO: XOO1970(dxr)
XOM: XOO_1860(XOO1860)
SML: Smlt1500(dxr)
SMT: Smal_1259

APPENDIX 1-continued

VCH: VC2254
VCO: VC0395_A1845(dxr)
VVU: VV1_1866
VVY: VV2551
VPA: VP2312
VFI: VF1956
VHA: VIBHAR_03231
PPR: PBPRA2962
PAE: PA3650(dxr)
PAU: PA14_17130(dxr)
PAP: PSPA7_1489(dxr)
PPU: PP_1597(dxr)
PPF: Pput_4180
PPG: PputGB1_1152
PPW: PputW619_4076
PST: PSPTO_1540(dxr)
PSB: Psyr_1349
PSP: PSPPH_3834(dxr)
PFL: PFL_1182(dxr)
PFO: PflO1_1107
PEN: PSEEN4214(dxr)
PMY: Pmen_3047
PSA: PST_1543(dxr)
CJA: CJA_1118(dxr)
PAR: Psyc_1531(dxr)
PCR: Pcryo_1710
PRW: PsycPRwf_1798
ACI: ACIAD1376(dxr)
ACB: A1S_1971
ABM: ABSDF1684(dxr)
ABY: ABAYE1581
ABC: ACICU_02094
SON: SO_1635(dxr)
SDN: Sden_1560
SFR: Sfri_1276
SAZ: Sama_1145
SBL: Sbal_1456
SBM: Shew185_1451
SBN: Sbal195_1487
SLO: Shew_2629
SPC: Sputcn32_1354
SSE: Ssed_3155
SPL: Spea_2879
SHE: Shewmr4_2635
SHM: Shewmr7_2702
SHN: Shewana3_2809
SHW: Sputw3181_2749
SHL: Shal_2975
SWD: Swoo_3275
ILO: IL0839
CPS: CPS_1559(dxr)
PHA: PSHAa2030(dxr)
PAT: Patl_1255
SDE: Sde_2591
MAQ: Maqu_2542
AMC: MADE_01379
PIN: Ping_2970
MCA: MCA0573(dxr)
FTU: FTT1574c(dxr)
FTF: FTF1574c(dxr)
FTW: FTW_0352(dxr)
FTL: FTL_0534
FTH: FTH_0536(dxr)
FTA: FTA_0567(dxr)
FTN: FTN_1483(dxr)
FTM: FTM_0324(dxr)
FPH: Fphi_1195
NOC: Noc_0814
AEH: Mlg_1857
HHA: Hhal_1460
HCH: HCH_05246(dxr)
CSA: Csal_0569
ABO: ABO_1149(dxr)
MMW: Mmwyl1_1278
AHA: AHA_1179(dxr)
ASA: ASA_3154(dxr)
BCI: BCI_0531(dxr)
RMA: Rmag_0025
VOK: COSY_0025(dxr)
NME: NMB0184(dxr)

APPENDIX 1-continued

NMA: NMA0083(dxr)
NMC: NMC0175(dxr)
NMN: NMCC_1968
NGO: NGO1799
NGK: NGK_2475
CVI: CV_2202(dxr)
RSO: RSc1410(dxr)
REU: Reut_A1875
REH: H16_A2049(dxp)
RME: Rmet_1441
BMA: BMA1549(dxr)
BMV: BMASAVP1_A2050(dxr)
BML: BMA10229_A3261(dxr)
BMN: BMA10247_1322(dxr)
BXE: Bxe_A1688
BVI: Bcep1808_1919
BUR: Bcep18194_A5323
BCN: Bcen_6064
BCH: Bcen2424_2013
BCM: Bcenmc03_2033
BAM: Bamb_2046
BAC: BamMC406_1915
BMU: Bmul_1263
BMJ: BMULJ_01984(dxr)
BPS: BPSL2153(dxr)
BPM: BURPS1710b_2577(dxr)
BPL: BURPS1106A_2487(dxr)
BPD: BURPS668_2431(dxr)
BTE: BTH_I2033(dxr)
BPH: Bphy_1332
PNU: Pnuc_1445
PNE: Pnec_0513
BPE: BP1425(dxr)
BPA: BPP1533(dxr)
BBR: BB2611(dxr)
BPT: Bpet2529(dxr)
BAV: BAV1740(dxr)
RFR: Rfer_1994
POL: Bpro_2689
PNA: Pnap_1764
AAV: Aave_1829
AJS: Ajs_2579
VEI: Veis_1444
DAC: Daci_4942
MPT: Mpe_A1973
HAR: HEAR1341(dxr)
MMS: mma_2052
LCH: Lcho_2844
NEU: NE1712(dxr)
NET: Neut_2029
NMU: Nmul_A0663
EBA: ebA5994(dxr)
AZO: azo1903(dxr)
DAR: Daro_1748
TBD: Tbd_0791
MFA: Mfla_1524
HPY: HP0216
HPJ: jhp0202
HPA: HPAG1_0217
HPS: HPSH_01115
HHE: HH0524(dxr)
HAC: Hac_1502(dxr_fragment_2)
Hac_1503(dxr_fragment_1)
WSU: WS0812
TDN: Suden_0126
CJE: Cj1346c(dxr)
CJR: CJE1535(dxr)
CJJ: CJJ81176_1345(dxr)
CJU: C8J_1262(dxr)
CJD: JJD26997_0364(dxr)
CFF: CFF8240_0210(dxr)
CCV: CCV52592_0594(dxr)
CHA: CHAB381_0121(dxr)
CCO: CCC13826_0420(dxr)
ABU: Abu_0161(dxr)
NIS: NIS_1666(ispC)
SUN: SUN_0144
GSU: GSU1915(dxr)
GME: Gmet_1256
GUR: Gura_3727

APPENDIX 1-continued

GLO: Glov_2714
PCA: Pcar_1915(dxr)
PPD: Ppro_2050
DVU: DVU0866(dxr)
DVL: Dvul_2116
DDE: Dde_1123
LIP: LI0386(dxr)
DPS: DP1160
DOL: Dole_0480
ADE: Adeh_3583
AFW: Anae109_3704
SAT: SYN_00916
SFU: Sfum_1784
WOL: WD0992(dxr)
WBM: Wbm0179
WPI: WP0113(dxr)
AMA: AM743(dxr)
APH: APH_0440(dxr)
ERU: Erum4750(dxr)
ERW: ERWE_CDS_04970(dxr)
ERG: ERGA_CDS_04870(dxr)
ECN: Ecaj_0473
ECH: ECH_0557(dxr)
NSE: NSE_0443(dxr)
PUB: SAR11_0912(yaeM)
PLA: Plav_3190
SME: SMc03105(dxr)
SMD: Smed_2879
ATU: Atu2612(dxr)
ATC: AGR_C_4736
RET: RHE_CH03839(dxr)
REC: RHECIAT_CH0004120(dxr)
RLE: RL4372(dxr)
BJA: bll4855(dxr)
BRA: BRADO4134(dxr)
BBT: BBta_4511(dxr)
RPA: RPA2916(dxr)
RPB: RPB_2822
RPC: RPC_2442
RPD: RPD_2851
RPE: RPE_2559
RPT: Rpal_3262
NWI: Nwi_1853
NHA: Nham_1700
XAU: Xaut_4433
AZC: AZC_1699
MEX: Mext_2083
MRD: Mrad2831_3444
MET: M446_0636
BID: Bind_0297
CCR: CC_1917
CAK: Caul_2799
SIL: SPO1667(dxr)
SIT: TM1040_1410
RSP: RSP_2709(dxr)
RSH: Rsph17029_1366
RSQ: Rsph17025_2149
JAN: Jann_2455
RDE: RD1_2590(dxr)
PDE: Pden_3997
DSH: Dshi_1497
MMR: Mmar10_1386
HNE: HNE_1774(dxr)
ZMO: ZMO1150(dxr)
NAR: Saro_1375
SAL: Sala_1954
SWI: Swit_0466
ELI: ELI_03805
GOX: GOX1816
GBE: GbCGDNIH1_0938
ACR: Acry_2557
GDI: GDI2147(dxr)
RRU: Rru_A1592
MAG: amb2492
MGM: Mmc1_1846
ABA: Acid345_1419
SUS: Acid_7136
SWO: Swol_0889
CSC: Csac_2353
BSU: BSU16550(dxr)
BHA: BH2421
BAN: BA3409(dxr-1) BA3959(dxr-2)
BAR: GBAA3409(dxr-1) GBAA3959(dxr-2)
BAA: BA_4429
BAT: BAS3160 BAS3672
BCE: BC3341 BC3819
BCA: BCE_3862(dxr)
BCZ: BCZK3054(dxr) BCZK3580(dxr)
BCY: Bcer98_2128 Bcer98_2473
BTK: BT9727_3144(dxr) BT9727_3562(dxr)
BTL: BALH_3451
BWE: BcerKBAB4_3082 BcerKBAB4_3644
BLI: BL01237(dxr)
BLD: BLi01876(dxr)
BCL: ABC2236(dxr)
BAY: RBAM_016390
BPU: BPUM_1554
GKA: GK1255
GTN: GTNG_1109
LSP: Bsph_1590
ESI: Exig_1845
LMO: lmo1317
LMF: LMOf2365_1334(dxr)
LIN: lin1354
LWE: lwe1332(dxr)
STH: STH1499(dxr)
CAC: CAC1795
CPE: CPE1694
CPF: CPF_1948(dxr)
CPR: CPR_1666(dxr)
CTC: CTC01268
CNO: NT01CX_2143
CTH: Cthe_0999
CDF: CD2130(dxr)
CBO: CBO2426
CBA: CLB_2290(dxr)
CBH: CLC_2273(dxr)
CBL: CLK_1802(dxr)
CBK: CLL_A1265(dxr)
CBB: CLD_2214(dxr)
CBF: CLI_2482(dxr)
CBE: Cbei_1195
CKL: CKL_1423(dxr)
CPY: Cphy_2622
AMT: Amet_2682
AOE: Clos_1519
CHY: CHY_1778(dxr)
DSY: DSY2539
DRM: Dred_1970
PTH: PTH_1260(dxr)
DAU: Daud_0615
HMO: HM1_2264(dxr)
TTE: TTE1402(dxr)
TEX: Teth514_1654
TPD: Teth39_1218
MTA: Moth_1041
MPE: MYPE1470
MGA: MGA_0787(dxr)
MTU: Rv2870c(dxr)
MTC: MT2938(dxr)
MRA: MRA_2895(dxr)
MTF: TBFG_12886
MBO: Mb2895c(dxr)
MBB: BCG_2892c(dxr)
MLE: ML1583
MPA: MAP2940c
MAV: MAV_3727(dxr)
MSM: MSMEG_2578(dxr)
MUL: MUL_2085(dxr)
MVA: Mvan_2260
MGI: Mflv_4083
MAB: MAB_3171c
MMC: Mmcs_2042
MKM: Mkms_2088
MJL: Mjls_2025
MMI: MMAR_1836(dxr)
CGL: NCgl1940(cg12016)
CGB: cg2208(dxr)
CGT: cgR_1844
CEF: CE1905

APPENDIX 1-continued

CDI: DIP1500(dxr)
CJK: jk1167(ispC)
CUR: cu0831
NFA: nfa41200(dxr)
RHA: RHA1_ro06588(dxr)
SCO: SCO5694(dxr)
SMA: SAV2563(dxr)
SGR: SGR_1823
TWH: TWT089(dxr)
TWS: TW099(dxr)
LXX: Lxx12180(dxr)
CMI: CMM_2160(dxrA)
ART: Arth_1399
AAU: AAur_1543(dxr)
RSA: RSal33209_0635
KRH: KRH_16160(dxr)
PAC: PPA1510
NCA: Noca_3204
TFU: Tfu_0747
FRA: Francci3_3575
FRE: Franean1_1168
FAL: FRAAL5774(dxr)
ACE: Acel_1524
KRA: Krad_1427 Krad_4655
SEN: SACE_5994(dxr)
STP: Strop_1350
SAQ: Sare_1302
BLO: BL0097(ispC)
BLJ: BLD_0115(dxr)
BAD: BAD_1158(ispC)
RXY: Rxyl_1404
FNU: FN1324
RBA: RB5568(dxr)
OTE: Oter_4632
MIN: Minf_1972(dxr)
AMU: Amuc_1737
CTR: CT071(yaeM)
CTA: CTA_0076(dxr)
CTB: CTL0327
CTL: CTLon_0322(dxr)
CMU: TC0343(dxr)
CPN: CPn0345(yaeM)
CPA: CP0415
CPJ: CPj0344(yaeM)
CPT: CpB0352
CCA: CCA00441(dxr)
CAB: CAB427(dxr)
CFE: CF0566(yaeM)
PCU: pc0260(dxr)
TPA: TP0601
TPP: TPASS_0601(dxr)
TDE: TDE2342(dxr)
LIL: LA3292(dxr)
LIC: LIC10856(dxr)
LBJ: LBJ_0910(dxr)
LBL: LBL_0925(dxr)
LBI: LEPBI_I2611(dxr)
LBF: LBF_2531(dxr)
SYN: sll0019(dxr)
SYW: SYNW0698(dxr)
SYC: syc2498_d(dxr)
SYF: Synpcc7942_1513
SYD: Syncc9605_1970
SYE: Syncc9902_0689
SYG: sync_0920(dxr)
SYR: SynRCC307_1674(dxr)
SYX: SynWH7803_1622(dxr)
SYP: SYNPCC7002_A0818(dxr)
CYA: CYA_0193(dxr)
CYB: CYB_1233(dxr)
TEL: tlr1040
MAR: MAE_50310
CYT: cce_2124(dxr)
GVI: gll2252
ANA: alr4351
NPU: Npun_R5970
AVA: Ava_1300
PMA: Pro1236(dxr)
PMM: PMM1142(dxr)
PMT: PMT1161(dxr)

APPENDIX 1-continued

PMN: PMN2A_0751
PMI: PMT9312_1238
PMB: A9601_13171(dxr)
PMC: P9515_13061(dxr)
PMF: P9303_08651(dxr)
PMG: P9301_13311(dxr)
PMH: P9215_13461
PMJ: P9211_12161
PME: NATL1_15911(dxr)
TER: Tery_0416
AMR: AM1_0563(dxr)
BTH: BT_2002
BFR: BF3699
BFS: BF3492
BVU: BVU_1651
PGI: PG1364(dxr)
PGN: PGN_1151
PDI: BDI_0480
SRU: SRU_1849(dxr)
CHU: CHU_2996(dxr)
CTE: CT0125(dxr)
CPC: Cpar_0071
CCH: Cag_0008
CPH: Cpha266_2680
CPB: Cphamn1_0098
PVI: Cvib_0138
PLT: Plut_0077
PPH: Ppha_0080
CTS: Ctha_1044
PAA: Paes_0121
DET: DET0371(dxr)
DEH: cbdb_A314(dxr)
DEB: DehaBAV1_0353
EMI: Emin_0690
DRA: DR_1508
DGE: Dgeo_1044
TTH: TTC0504
TTJ: TTHA0856
AAE: aq_404
HYA: HY04AAS1_0095
SUL: SYO3AOP1_0479
TMA: TM0889
TPT: Tpet_0038
TLE: Tlet_0658
TRQ: TRQ2_0038
TME: Tmel_0037
FNO: Fnod_0950
PMO: Pmob_1939

Exemplary 4-diphosphocytidyl-2C-methyl-D-erythritol synthase nucleic acids and polypeptides ATH: AT2G02500(ISPD)
OSA: 4324893(Os01g0887100)
OLU: OSTLU_24843(CMS)
CRE: CHLREDRAFT_196604(CMS)
CME: CMH115C
TAN: TA02505
TPV: TP03_0057
ECO: b2747(ispD)
ECJ: JW2717(ispD)
ECD: ECDH10B_2915(ispD)
ECE: Z4055(ispD)
ECS: ECs3601(ispD)
ECC: c3314(ispD)
ECI: UTI89_C3118(ispD)
ECP: ECP_2729(ispD)
ECV: APECO1_3776(ispD)
ECW: EcE24377A_3048(ispD)
ECX: EcHS_A2885(ispD)
ECM: EcSMS35_2872(ispD)
ECL: EcolC_0965
STY: STY3055(ispD)
STT: t2831(ispD)
SPT: SPA2786(ispD)
SPQ: SPAB_03644
SEC: SC2862(ispD)
SEH: SeHA_C3120(ispD)
SEE: SNSL254_A3136(ispD)
SEW: SeSA_A3081(ispD)
SES: SARI_00026

APPENDIX 1-continued

STM: STM2930(ispD)
YPE: YPO3361(ispD)
YPK: y0828(ispD)
YPM: YP_0326(ispD)
YPA: YPA_2782(ispD)
YPN: YPN_0732(ispD)
YPP: YPDSF_2999(ispD)
YPG: YpAngola_A0964(ispD)
YPS: YPTB0770(ispD)
YPI: YpsIP31758_3299(ispD)
YPY: YPK_3431
YPB: YPTS_0804
YEN: YE0769(ispD)
SFL: SF2770(ispD)
SFX: S2963(ispD)
SFV: SFV_2751(ispD)
SSN: SSON_2895(ispD)
SBO: SBO_2773(ispD)
SBC: SbBS512_E3127(ispD)
SDY: SDY_2946(ispD)
ECA: ECA3535(ispD)
ETA: ETA_27010(ispD)
PLU: plu0713(ispD)
BUC: BU420(ygbP)
BAS: BUsg405(ygbP)
WBR: WGLp532(ygbP)
SGL: SG0526
ENT: Ent638_3218(ispD)
ESA: ESA_00544
KPN: KPN_03109(ispD)
CKO: CKO_04108
SPE: Spro_0826
BPN: BPEN_171(ispD)
HIN: HI0672(ispD)
HIT: NTHI0794(ispD)
HIP: CGSHiEE_08815(ispD)
HIQ: CGSHiGG_06635(ispD)
HDU: HD1329(ispD)
HSO: HS_1496(ispD)
HSM: HSM_0505
PMU: PM1608(ispD)
MSU: MS2275(ispD)
APL: APL_0802(ispD)
APJ: APJL_0807(ispD)
APA: APP7_0861
ASU: Asuc_2032
XFA: XF1293(ispD)
XFT: PD0545(ispD)
XFM: Xfasm12_0618
XFN: XfasM23_0570
XCC: XCC1702(ispD)
XCB: XC_2529(ispD)
XCV: XCV1754(ispD)
XAC: XAC1721(ispD)
XOO: XOO2961(ispD)
XOM: XOO_2812(ispD)
SML: Smlt1717(ispD)
SMT: Smal_1454
VCH: VC0528(ispD)
VCO: VC0395_A0056(ispD)
VVU: VV1_1582(ispD)
VVY: VV2816(ispD)
VPA: VP1320 VP2559(ispD)
VFI: VF2073(ispD)
VHA: VIBHAR_03523
PPR: PBPRA3077
PAE: PA3633(ispD)
PAU: PA14_17340(ispD)
PAP: PSPA7_1506(ispD)
PPU: PP_1614(ispD)
PPF: Pput_4163(ispD)
PPG: PputGB1_1168
PPW: PputW619_4061
PST: PSPTO_1556(ispD)
PSB: Psyr_1365(ispD)
PSP: PSPPH_3818(ispD)
PFL: PFL_1198(ispD)
PFO: PflO1_1123(ispD)
PEN: PSEEN4198(ispD)
PMY: Pmen_3031(ispD)

APPENDIX 1-continued

PSA: PST_1559(ispD)
CJA: CJA_2223(ispD)
PAR: Psyc_1634
PCR: Pcryo_1868
PRW: PsycPRwf_1662
ACI: ACIAD1999(ispD)
ACB: A1S_1895
ABM: ABSDF2025(ispD)
ABY: ABAYE1672
ABC: ACICU_02004
SON: SO_3438(ispD)
SDN: Sden_1198
SFR: Sfri_1054
SAZ: Sama_1038
SBL: Sbal_3125
SBM: Shew185_3134
SBN: Sbal195_3277
SLO: Shew_1207
SPC: Sputcn32_2755
SSE: Ssed_1292
SPL: Spea_1187
SHE: Shewmr4_1117
SHM: Shewmr7_1188
SHN: Shewana3_1118
SHW: Sputw3181_1257
SHL: Shal_1224
SWD: Swoo_3348
ILO: IL0752(ispD)
CPS: CPS_1072(ispD)
PHA: PSHAa0684(ispD)
PAT: Patl_3857
SDE: Sde_1247
MAQ: Maqu_0923
AMC: MADE_03721
PIN: Ping_0672
MCA: MCA2517(ispD)
FTU: FTT0711(ispD)
FTF: FTF0711(ispD)
FTW: FTW_1530(ispD)
FTL: FTL_1525
FTH: FTH_1475(ispD)
FTA: FTA_1609(ispD)
FTN: FTN_0623(ispD)
FTM: FTM_1371(ispD)
FPH: Fphi_0219
NOC: Noc_0854
AEH: Mlg_1837
HHA: Hhal_1435
HCH: HCH_01869(ispD)
CSA: Csal_2638
ABO: ABO_1166(ispD)
MMW: Mmwyl1_1301
AHA: AHA_0823(ispD)
ASA: ASA_3473(ispD)
BCI: BCI_0211(ispD)
RMA: Rmag_0755
VOK: COSY_0697(ispD)
NME: NMB1513
NMA: NMA1713
NMC: NMC1442
NMN: NMCC_1418
NGO: NGO0972
NGK: NGK_0824
CVI: CV_1258(ispD)
RSO: RSc1643(ispD)
REU: Reut_A1361(ispD)
REH: H16_A1456(ispD)
RME: Rmet_1954(ispD)
BMA: BMA1490(ispD)
BMV: BMASAVP1_A1987(ispD)
BML: BMA10229_A3319(ispD)
BMN: BMA10247_1259(ispD)
BXE: Bxe_A2312(ispD)
BVI: Bcep1808_1870(ispD)
BUR: Bcep18194_A5254(ispD)
BCN: Bcen_6136(ispD)
BCH: Bcen2424_1943(ispD)
BCM: Bcenmc03_1967
BAM: Bamb_1931(ispD)
BAC: BamMC406_1858

APPENDIX 1-continued

BMU: Bmul_1328
BMJ: BMULJ_01918(ispD)
BPS: BPSL2099(ispD)
BPM: BURPS1710b_2512(ispD)
BPL: BURPS1106A_2401(ispD)
BPD: BURPS668_2358(ispD)
BTE: BTH_I2089(ispD)
BPH: Bphy_0998
PNU: Pnuc_0930
PNE: Pnec_0911
BPE: BP0865(ispD)
BPA: BPP3366(ispD)
BBR: BB3817(ispD)
BPT: Bpet1695(ispD)
BAV: BAV1060(ispD)
RFR: Rfer_1332
POL: Bpro_2716
PNA: Pnap_2549
AAV: Aave_1581
AJS: Ajs_3156
VEI: Veis_4360
DAC: Daci_2849
MPT: Mpe_A1570
HAR: HEAR1912(ispD)
MMS: mma_1409
LCH: Lcho_2295
NEU: NE1412
NET: Neut_1525
NMU: Nmul_A2127
EBA: ebA6543(ispD)
AZO: azo1682
DAR: Daro_1973
TBD: Tbd_1003
MFA: Mfla_1116
HPY: HP1020(ispDF)
HPJ: jhp0404(ispDF)
HPA: HPAG1_0427(ispDF)
HHE: HH1582(ispDF)
HAC: Hac_1124(ispDF)
WSU: WS1940(ispDF)
TDN: Suden_1487(ispDF)
CJE: Cj1607(ispDF)
CJR: CJE1779(ispDF)
CJJ: CJJ81176_1594(ispDF)
CFF: CFF8240_0409(ispDF)
GSU: GSU3368(ispD)
GME: Gmet_0060
GUR: Gura_4163
GLO: Glov_0872
PCA: Pcar_0103(ispD)
PPD: Ppro_2969
DVU: DVU1454(ispD)
DVL: Dvul_1625
DDE: Dde_1726
LIP: LI0446
DPS: DP0257
DOL: Dole_2147
ADE: Adeh_1272
SAT: SYN_01401
SFU: Sfum_1637
WOL: WD1143
WBM: Wbm0409
AMA: AM1357(ispD)
APH: APH_1277(ispD)
ERU: Erum1030(ispD)
ERW: ERWE_CDS_01000(ispD)
ERG: ERGA_CDS_00960(ispD)
ECN: Ecaj_0103
ECH: ECH_0157(ispD)
NSE: NSE_0178
PUB: SAR11_0945(ispD)
MLO: mll0395(ispDF)
MES: Meso_1621(ispDF)
SME: SMc01040(ispDF)
ATU: Atu1443(ispF)
ATC: AGR_C_2659
RET: RHE_CH01945(ispDF)
RLE: RL2254(ispDF)
BME: BMEI0863(ispDF)
BMF: BAB1_1143(ispDF)

APPENDIX 1-continued

BMB: BruAb1_1126(ispDF)
BMS: BR1120(ispDF)
BJA: bll4485
BRA: BRADO3869(ispDF)
BBT: BBta_4067(ispDF)
RPA: RPA2590(ispD)
RPB: RPB_2885
RPC: RPC_2575
RPD: RPD_2587
RPE: RPE_2755
NWI: Nwi_1442
NHA: Nham_1834
BHE: BH05820
BQU: BQ04980(ispDF)
BBK: BARBAKC583_0540(ispDF)
BTR: Btr_0870
CCR: CC_1738(ispDF)
SIL: SPO2090(ispDF)
SIT: TM1040_1364
RSP: RSP_2835(ispD)
RSQ: Rsph17025_1485
RDE: RD1_2766(ispD)
PDE: Pden_3667
MMR: Mmar10_1439
HNE: HNE_2014(ispDF)
ZMO: ZMO1128(ispDF)
NAR: Saro_1925(ispDF)
SAL: Sala_1278
ELI: ELI_06290(ispDF)
GOX: GOX1669
GBE: GbCGDNIH1_1019
ACR: Acry_0551
RRU: Rru_A1674
MAG: amb2363
MGM: Mmc1_2672
ABA: Acid345_0188
SWO: Swol_2361
CSC: Csac_2198
BSU: BSU00900(ispD)
BHA: BH0107(ispD)
BAN: BA0084(ispD)
BAR: GBAA0084(ispD)
BAA: BA_0674
BAT: BAS0085(ispD)
BCE: BC0106(ispD)
BCA: BCE_0085(ispD)
BCZ: BCZK0081(ispD)
BCY: Bcer98_0080
BTK: BT9727_0082(ispD)
BTL: BALH_0085(ispD)
BWE: BcerKBAB4_0080
BLI: BL03265(ispD)
BLD: BLi00108(ispD)
BCL: ABC0125(ispD)
BAY: RBAM_001150(yacM)
BPU: BPUM_0075
GKA: GK0081(ispD)
GTN: GTNG_0081(ispD)
LSP: Bsph_4646
ESI: Exig_0071 Exig_0189
SAU: SA0241(ispD) SA0245(ispD)
SAV: SAV0251(ispD) SAV0255(ispD)
SAW: SAHV_0250 SAHV_0254
SAM: MW0227(ispD) MW0231(ispD)
SAR: SAR0246(ispD) SAR0252(ispD)
SAS: SAS0227(ispD) SAS0232(ispD)
SAC: SACOL0236(ispD) SACOL0240(ispD)
SAB: SAB0190 SAB0194(ispD)
SAA: SAUSA300_0245
SAUSA300_0249(ispD)
SAX: USA300HOU_0262(ispD2)
USA300HOU_0266
SAO: SAOUHSC_00220
SAOUHSC_00225(ispD)
SAJ: SaurJH9_0236 SaurJH9_0240(ispD)
SAH: SaurJH1_0242 SaurJH1_0246(ispD)
SAE: NWMN_0185 NWMN_0189(ispD)
SEP: SE0319
SER: SERP0196(ispD)
SSP: SSP0354(ispD)

APPENDIX 1-continued

LMO: lmo0235(ispD) lmo1086(ispD)
LMF: LMOf2365_0247(ispD)
LMOf2365_1100(ispD)
LIN: lin0267(ispD) lin1071(ispD)
LWE: lwe0199(ispD) lwe1061(ispD)
SPN: SP_1271(ispD)
SPR: spr1149(ispD)
SPD: SPD_1127(ispD)
SPV: SPH_1387
SPW: SPCG_1235(ispD)
SPX: SPG_1165
SAG: SAG1417
SAN: gbs1487
SAK: SAK_1452(ispD)
SSA: SSA_2214
SGO: SGO_2017
LPL: lp_1816
LCA: LSEI_1098
EFA: EF2172(ispD)
STH: STH3123
CAC: CAC3184
CPE: CPE2429(ispD)
CPF: CPF_2739(ispD)
CPR: CPR_2426(ispD)
CTC: CTC02626
CNO: NT01CX_1092(ispD)
CTH: Cthe_2941
CDF: CD0047(ispD)
CBO: CBO3504(ispD)
CBA: CLB_3564(ispD)
CBH: CLC_3453(ispD)
CBL: CLK_2951(ispD)
CBK: CLL_A0216(ispD)
CBB: CLD_0997(ispD)
CBF: CLI_3691(ispD)
CBE: Cbei_0129(ispD)
CKL: CKL_0200(ispD)
CPY: Cphy_0353
AMT: Amet_4506
AOE: Clos_0463
CHY: CHY_2342(ispD)
DSY: DSY0443 DSY3011
DRM: Dred_0187
PTH: PTH_0289(ispD)
DAU: Daud_0186
FMA: FMG_1230
TTE: TTE2322(ispD)
TEX: Teth514_0839
TPD: Teth39_0346
MTA: Moth_2487
MPE: MYPE2770
MTU: Rv3582c(ispD)
MTC: MT3688(ispD)
MRA: MRA_3621(ispD)
MTF: TBFG_13615(ispD)
MBO: Mb3613c(ispD)
MBB: BCG_3647c(ispD)
MLE: ML0321(ispD)
MPA: MAP0476(ispD)
MAV: MAV_0571(ispD)
MSM: MSMEG_6076(ispD)
MUL: MUL_4158(ispD)
MVA: Mvan_4129 Mvan_4130
MGI: Mflv_2528 Mflv_2529
MAB: MAB_0569
MMC: Mmcs_4739(ispD)
MKM: Mkms_4825(ispD)
MJL: Mjls_5125(ispD)
MMI: MMAR_5082(ispD)
CGL: NCgl2570(ispD)
CGB: cg2945(ispD)
CGT: cgR_2564(ispD)
CEF: CE2521(ispD)
CDI: DIP1973(ispD)
CJK: jk0308(ispD)
CUR: cu1675
NFA: nfa4360(ispD)
RHA: RHA1_ro04460(ispD)
SCO: SCO4233(ispD)
SMA: SAV3969(mecT)

APPENDIX 1-continued

SGR: SGR_4012
TWH: TWT348(ispDF)
TWS: TW422
LXX: Lxx18250(ispF)
AAU: AAur_0898(ispD)
RSA: RSal33209_0409
KRH: KRH_18710(ispD)
PAC: PPA0353
NCA: Noca_4038
FRA: Francci3_3932 Francci3_4254
FRE: Franean1_0363 Franean1_0798
FAL: FRAAL6243 FRAAL6524(ispD)
ACE: Acel_0080 Acel_1533
KRA: Krad_0899
SEN: SACE_0439(ispD)
STP: Strop_4261
SAQ: Sare_4691
BLO: BL0324(ispD)
BLJ: BLD_1082(ispD)
RXY: Rxyl_2176
FNU: FN1580
RBA: RB9133(ispD)
OTE: Oter_0455 Oter_2440
MIN: Minf_0787(ispD)
AMU: Amuc_0068
CTR: CT462(ispD)
CTA: CTA_0505(ispD)
CTB: CTL0722
CTL: CTLon_0718(ispD)
CMU: TC0747(ispD)
CPN: CPn0579(ispD)
CPA: CP0169(ispD)
CPJ: CPj0579(ispD)
CPT: CpB0603(ispD)
CCA: CCA00162(ispD)
CAB: CAB160(ispD)
CFE: CF0845(ispD)
PCU: pc0327(ispD)
TPA: TP0512
TDE: TDE2291(ispD)
LIL: LA1048(ygbP)
LIC: LIC12617(ispD)
LBJ: LBJ_0280(ispD)
LBL: LBL_2796(ispD)
LBI: LEPBI_I1435(ispD)
LBF: LBF_1381(ispD)
SYN: slr0951
SYW: SYNW1849(ispD)
SYC: syc0848_d(ispD)
SYF: Synpcc7942_0681(ispD)
SYD: Syncc9605_0620(ispD)
SYE: Syncc9902_1742(ispD)
SYG: sync_2140(ispD)
SYR: SynRCC307_0684(ispD)
SYX: SynWH7803_1858(ispD)
SYP: SYNPCC7002_A1905(ispD)
CYA: CYA_1505(ispD)
CYB: CYB_2706(ispD)
TEL: tlr0605
MAR: MAE_45830
CYT: cce_0963(ispD)
GVI: glr2791
ANA: all5167
NPU: Npun_F5020
AVA: Ava_2414(ispD)
PMA: Pro0453(ispD)
PMM: PMM0454(ispD)
PMT: PMT1330(ispD)
PMN: PMN2A_1786(ispD)
PMI: PMT9312_0454(ispD)
PMB: A9601_05101(ispD)
PMC: P9515_05171(ispD)
PMF: P9303_06551(ispD)
PMG: P9301_04791(ispD)
PMH: P9215_05341
PMJ: P9211_04551
PME: NATL1_05091(ispD)
TER: Tery_0609(ispD)
AMR: AM1_3984(ispD)
BTH: BT_2881 BT_3923(ispD)

APPENDIX 1-continued

BFR: BF3962(ispD)
BFS: BF3735(ispD)
BVU: BVU_0472(ispD) BVU_2951
PGI: PG1434(ispD)
PGN: PGN_0841
PDI: BDI_1351 BDI_2700(ispD) BDI_3625 BDI_3828
SRU: SRU_1652
CHU: CHU_3100(ispD)
CTE: CT1317(ispD)
CPC: Cpar_1335
CCH: Cag_0929
CPH: Cpha266_1642
CPB: Cphamn1_1025
PVI: Cvib_1049
PPH: Ppha_1615
CTS: Ctha_2474
PAA: Paes_1464
DET: DET0059(ispD)
DEH: cbdb_A74(ispD)
DEB: DehaBAV1_0053
DRA: DR_2604
DGE: Dgeo_0181
TTH: TTC1815
TTJ: TTHA0171
AAE: aq_1323
HYA: HY04AAS1_1287
SUL: SYO3AOP1_0708
TMA: TM1393
TPT: Tpet_1390
TLE: Tlet_0798
TRQ: TRQ2_1436
TME: Tmel_1925
FNO: Fnod_0183
PMO: Pmob_1218
HMA: rrnAC1932(ispD)
NMR: Nmar_1581

Exemplary 4-diphosphocytidyl-2-C-methyl-D-erythritol kinase nucleic acids and polypeptides ATH: AT2G26930(ATCDPMEK)
OSA: 4327968(Os01g0802100)
PPP: PHYPADRAFT_190580
OLU: OSTLU_4287(CMK)
CRE: CHLREDRAFT_137673(CMK1)
CME: CMS444C
PFA: PFE0150c
PFD: PFDG_01632
PFH: PFHG_02738
PYO: PY04665
ECO: b1208(ispE)
ECJ: JW1199(ispE)
ECD: ECDH10B_1261(ispE)
ECE: Z1979(ychB)
ECS: ECs1713
ECC: c1666(ispE)
ECI: UTI89_C1402(ychB)
ECP: ECP_1256
ECV: APECO1_324(ychB)
ECW: EcE24377A_1356(ispE)
ECX: EcHS_A1313(ispE)
ECM: EcSMS35_1934(ispE)
ECL: EcolC_2418
STY: STY1905(ipk)
STT: t1097(ipk)
SPT: SPA1094(ipk)
SPQ: SPAB_01449
SEC: SC1773(ipk)
SEH: SeHA_C1975(ispE)
SEE: SNSL254_A1911(ispE)
SEW: SeSA_A1917(ispE)
SES: SARI_01174
STM: STM1779(ipk)
YPE: YPO2014(ipk)
YPK: y2293
YPM: YP_1862(ipk)
YPA: YPA_1398
YPN: YPN_1496
YPP: YPDSF_1104
YPG: YpAngola_A2463(ispE)

APPENDIX 1-continued

YPS: YPTB2002(ipk)
YPI: YpsIP31758_2069(ispE)
YPY: YPK_2182
YPB: YPTS_2060
YEN: YE2434(ipk)
SFL: SF1211(ychB)
SFX: S1295(ychB)
SFV: SFV_1222(ychB)
SSN: SSON_1970(ychB)
SBO: SBO_1859(ychB)
SBC: SbBS512_E1372(ispE)
SDY: SDY_1257(ychB)
ECA: ECA2187(ispE)
ETA: ETA_18820(ispE)
PLU: plu2067(ispE)
BUC: BU170(ychB)
BAS: BUsg164(ipk)
WBR: WGLp348(ychB)
SGL: SG1879
ENT: Ent638_2340
ESA: ESA_01495
KPN: KPN_02237(ispE)
CKO: CKO_01272
SPE: Spro_1987
BFL: Bfl347(ipk)
BPN: BPEN_357(ispE)
HIN: HI1608
HIT: NTHI1434(ispE)
HIP: CGSHiEE_05690
HIQ: CGSHiGG_10080
HDU: HD1628(ispE)
HSO: HS_0997(ispE)
HSM: HSM_1475
PMU: PM0245
MSU: MS1535(ispE)
APL: APL_0776(ispE)
APJ: APJL_0779(ispE)
APA: APP7_0837
ASU: Asuc_1751
XFA: XF2645
XFT: PD2018(ispE)
XFM: Xfasm12_2208
XFN: XfasM23_2119
XCC: XCC0871(ipk)
XCB: XC_3359
XCV: XCV0979(ispE)
XAC: XAC0948(ipk)
XOO: XOO3604(ipk)
XOM: XOO_3406(XOO3406)
SML: Smlt0874(ipk)
SMT: Smal_0725
VCH: VC2182
VCO: VC0395_A1759
VVU: VV1_0256
VVY: VV0928
VPA: VP0740
VFI: VF0765
VHA: VIBHAR_01247
PPR: PBPRA2848
PAE: PA4669(ipk)
PAU: PA14_61750(ipk)
PAP: PSPA7_5318(ispE)
PPU: PP_0723(ipk)
PPF: Pput_0757(ipk)
PPG: PputGB1_0767
PPW: PputW619_4460
PST: PSPTO_1105(ispE)
PSB: Psyr_0945(ipk)
PSP: PSPPH_0993(ipk)
PFL: PFL_5163(ipk)
PFO: PflO1_4752(ipk)
PEN: PSEEN0858(ipk)
PMY: Pmen_1056(ipk)
PSA: PST_3186(ipk)
CJA: CJA_0646(ispE)
PAR: Psyc_0173(ispE)
PCR: Pcryo_0186
PRW: PsycPRwf_2104
ACI: ACIAD2903(ispE)
ACB: A1S_0834

ABC: ACICU_00788
SON: SO_3836(ispE)
SDN: Sden_0917
SFR: Sfri_0720
SAZ: Sama_2569
SBL: Sbal_0693
SBM: Shew185_3617
SBN: Sbal195_3740
SLO: Shew_2915
SPC: Sputcn32_0798
SSE: Ssed_3462
SPL: Spea_3129
SHE: Shewmr4_3172
SHM: Shewmr7_0794
SHN: Shewana3_0766
SHW: Sputw3181_3377
SHL: Shal_3214
SWD: Swoo_3688
ILO: IL0928(ispE)
CPS: CPS_3556(ispE)
PHA: PSHAa1055(ispE)
PAT: Patl_2566
SDE: Sde_3255
MAQ: Maqu_2364
AMC: MADE_02576
PIN: Ping_0912
MCA: MCA1055(ispE)
FTU: FTT0271(ispE)
FTF: FTF0271(ispE)
FTW: FTW_1830(ispE)
FTL: FTL_0151
FTH: FTH_0144(ispE)
FTA: FTA_0164(ispE)
FTN: FTN_0146(ispE)
FTM: FTM_1592(ispE)
FPH: Fphi_0678
NOC: Noc_0513
AEH: Mlg_0282
HHA: Hhal_0990
HCH: HCH_01727(ispE)
CSA: Csal_1525
ABO: ABO_0519(ispE)
MMW: Mmwyl1_3603
AHA: AHA_3152(ispE)
ASA: ASA_1172(ispE)
BCI: BCI_0292(ispE)
RMA: Rmag_0110
VOK: COSY_0115(ispE)
NME: NMB0874
NMA: NMA1092
NMC: NMC0815
NMN: NMCC_0833
NGO: NGO0440
NGK: NGK_0610
CVI: CV_4059(ispE)
RSO: RSc0396(ipk)
REU: Reut_A0343
REH: H16_A0374
RME: Rmet_0290
CTI: RALTA_A0318(ispE)
BMA: BMA3118(ispE)
BMV: BMASAVP1_A0086(ispE)
BML: BMA10229_A1504(ispE)
BMN: BMA10247_2932(ispE)
BXE: Bxe_A4132
BVI: Bcep1808_2906
BUR: Bcep18194_A6131
BCN: Bcen_2187
BCH: Bcen2424_2801
BCM: Bcenmc03_2812
BAM: Bamb_2861
BAC: BamMC406_2719
BMU: Bmul_0514
BMJ: BMULJ_02745(ispE)
BPS: BPSL0523
BPM: BURPS1710b_0755(ispE)
BPL: BURPS1106A_0587(ispE)
BPD: BURPS668_0571(ispE)
BTE: BTH_I0476(ispE)
BPH: Bphy_0316

PNU: Pnuc_1919
PNE: Pnec_1624
BPE: BP3126(ispE)
BPA: BPP0816(ispE)
BBR: BB0900(ispE)
BPT: Bpet4003(ispE)
BAV: BAV0536(ispE)
RFR: Rfer_1659
POL: Bpro_1294
PNA: Pnap_0900
AAV: Aave_3609
AJS: Ajs_0896
VEI: Veis_0952
DAC: Daci_5432
MPT: Mpe_A3230
HAR: HEAR2892(ispE)
MMS: mma_3127
LCH: Lcho_3497
NEU: NE1827(ipk)
NET: Neut_1139
NMU: Nmul_A0588
EBA: ebA1405(ispE)
AZO: azo0756(ispE)
DAR: Daro_3729
TBD: Tbd_0386
MFA: Mfla_0679
HPY: HP1443
HPJ: jhp1336
HPA: HPAG1_1369
HPS: HPSH_07385
HHE: HH0122
HAC: Hac_0175(ipk)
WSU: WS0881
TDN: Suden_0440
CJE: Cj1104
CJR: CJE1247(ispE)
CJJ: CJJ81176_1122(ispE)
CJU: C8J_1045
CJD: JJD26997_0618(ispE)
CFF: CFF8240_0713
CCV: CCV52592_0696(ispE)
CHA: CHAB381_1110
CCO: CCC13826_0061(ispE)
ABU: Abu_2083(ispE)
NIS: NIS_1475
SUN: SUN_0381
GSU: GSU0660(ispE)
GME: Gmet_2849
GUR: Gura_3683
GLO: Glov_2596
PCA: Pcar_2005(ispE)
PPD: Ppro_0738
DVU: DVU1576(ispE)
DVL: Dvul_1557
DDE: Dde_2125
LIP: LI0735(ychB)
DPS: DP2735
DOL: Dole_2816
ADE: Adeh_0123
AFW: Anae109_0127
SAT: SYN_03046
SFU: Sfum_3651
WOL: WD0360(ispE)
WBM: Wbm0173
WPI: WP0174(ispE)
AMA: AM493(ispE)
APH: APH_0574(ispE)
ERU: Erum3340(ispE)
ERW: ERWE_CDS_03410(ispE)
ERG: ERGA_CDS_03370(ispE)
ECN: Ecaj_0317
ECH: ECH_0757(ispE)
NSE: NSE_0720
PUB: SAR11_0105(ispE)
MLO: mll7422
MES: Meso_0706
PLA: Plav_0721
SME: SMc00862(ipk)
SMD: Smed_0456
ATU: Atu0632(ipk)

APPENDIX 1-continued

ATC: AGR_C_1122
RET: RHE_CH00873(ispE)
REC: RHECIAT_CH0000963(ispE)
RLE: RL0935
BME: BMEI1537
BMF: BAB1_0423(ispE)
BMB: BruAb1_0418(ispE)
BMC: BAbS19_I03890
BMS: BR0394(ispE)
BMT: BSUIS_A0420(ispE)
BOV: BOV_0403(ispE)
BCS: BCAN_A0398(ispE)
OAN: Oant_0512
BJA: blr2526(ipk)
BRA: BRADO2022(ispE)
BBT: BBta_2348(ispE)
RPA: RPA1039(ispE)
RPB: RPB_1086
RPC: RPC_4356
RPD: RPD_1213
RPE: RPE_4419
RPT: Rpal_1231
NWI: Nwi_2593
NHA: Nham_3216
BHE: BH04210(thrB1)
BQU: BQ03230(thrB)
BBK: BARBAKC583_0387(ispE)
BTR: Btr_0633
XAU: Xaut_1381
AZC: AZC_0910
MEX: Mext_3109
MRD: Mrad2831_5351
MET: M446_2748
BID: Bind_0858
CCR: CC_1336
CAK: Caul_2169
SIL: SPO0318(ispE)
SIT: TM1040_3743
RSP: RSP_1779(ispE)
RSH: Rsph17029_0426
RSQ: Rsph17025_2471
JAN: Jann_0486
RDE: RD1_3402(ispE)
PDE: Pden_0423
DSH: Dshi_3073
MMR: Mmar10_2186
HNE: HNE_0676(ispE)
ZMO: ZMO1182(ispE)
NAR: Saro_1782
SAL: Sala_1187
SWI: Swit_4106
ELI: ELI_06920
GOX: GOX1559
GBE: GbCGDNIH1_1848
ACR: Acry_2663
GDI: GDI0728
RRU: Rru_A0263
MAG: amb4435
MGM: Mmc1_0819
ABA: Acid345_4541
SUS: Acid_7097
SWO: Swol_0064
CSC: Csac_2225
BSU: BSU00460(ispE)
BHA: BH0061
BAN: BA0043(ispE)
BAR: GBAA0043(ispE)
BAA: BA_0633
BAT: BAS0044
BCE: BC0050
BCA: BCE_0043(ispE)
BCZ: BCZK0040(ispE)
BCY: Bcer98_0040
BTK: BT9727_0040(ispE)
BTL: BALH_0040(ispE)
BWE: BcerKBAB4_0040
BLI: BL00525(ispE)
BLD: BLi00059(ispE)
BCL: ABC0074(ispE)
BAY: RBAM_000550

APPENDIX 1-continued

BPU: BPUM_0030
OIH: OB0055
GKA: GK0039
GTN: GTNG_0039
LSP: Bsph_0065
ESI: Exig_0038
SAU: SA0453
SAV: SAV0495
SAW: SAHV_0492
SAM: MW0450
SAR: SAR0496
SAS: SAS0452
SAC: SACOL0538(ispE)
SAB: SAB0444
SAA: SAUSA300_0472(ispE)
SAO: SAOUHSC_00466
SAJ: SaurJH9_0516
SAH: SaurJH1_0529
SAE: NWMN_0458
SEP: SE2288
SER: SERP0133(ispE)
SHA: SH2516
SSP: SSP2261
LMO: lmo0190
LMF: LMOf2365_0201(ispE)
LIN: lin0229
LWE: lwe0159(ispE)
SPZ: M5005_Spy_0074 M5005_Spy_0075 M5005_Spy_0076
SPH: MGAS10270_Spy0077 MGAS10270_Spy0078
SPI: MGAS10750_Spy0082 MGAS10750_Spy0083
SPJ: MGAS2096_Spy0077 MGAS2096_Spy0078 MGAS2096_Spy0079
SPK: MGAS9429_Spy0074 MGAS9429_Spy0075 MGAS9429_Spy0076
SPA: M6_Spy0123 M6_Spy0124
SPB: M28_Spy0073 M28_Spy0074
SAG: SAG0153(ispE)
SAN: gbs0149
SAK: SAK_0216(ispE)
SMU: SMU.1996(ipk)
SEZ: Sez_0102(ispE)
LPL: lp_0460(ispE)
LSA: LSA1652(ispE)
LSL: LSL_0234(ispE)
LBR: LVIS_0460
LCA: LSEI_2591
LCB: LCABL_27570(ispE)
LRE: Lreu_0215
LRF: LAR_0206
LFE: LAF_0190
EFA: EF0051(ispE)
STH: STH3246
CAC: CAC2902
CPE: CPE2212(ipk)
CPF: CPF_2476(ipk)
CPR: CPR_2186(ipk)
CTC: CTC00283
CNO: NT01CX_0566(ipk)
CTH: Cthe_2403(ipk)
CDF: CD3566(ipk)
CBO: CBO0121(ipk)
CBA: CLB_0157(ispE)
CBH: CLC_0169(ispE)
CBL: CLK_3296(ispE)
CBK: CLL_A0471(ispE)
CBB: CLD_0665(ispE)
CBF: CLI_0176(ispE)
CBE: Cbei_0394(ipk)
CKL: CKL_3724(ispE)
CPY: Cphy_3793
AMT: Amet_4604
AOE: Clos_0285
CHY: CHY_0188(ispE)
DSY: DSY0148
DRM: Dred_0094
PTH: PTH_0096(ispE)
DAU: Daud_0058

APPENDIX 1-continued

HMO: HM1_0738(ispE)
FMA: FMG_0552
TTE: TTE2559(ispE)
TEX: Teth514_0599
TPD: Teth39_0176
MTA: Moth_0072
MPE: MYPE10380
MGA: MGA_0635
UUR: UU600
MTU: Rv1011(ispE)
MTC: MT1040
MRA: MRA_1020(ispE)
MTF: TBFG_11030
MBO: Mb1038(ispE)
MBB: BCG_1068(ispE)
MLE: ML0242
MPA: MAP0976
MAV: MAV_1149(ispE)
MSM: MSMEG_5436(ispE)
MUL: MUL_4649(ispE)
MVA: Mvan_4799
MGI: Mflv_1934
MAB: MAB_1139
MMC: Mmcs_4262
MKM: Mkms_4348
MJL: Mjls_4641
MMI: MMAR_4477(ispE)
CGL: NCgl0874(cgl0911)
CGB: cg1039
CGT: cgR_1012
CEF: CE0973
CDI: DIP0876
CJK: jk1510(ispE)
CUR: cu0564
NFA: nfa49010(cmeK)
RHA: RHA1_ro05684
SCO: SCO3148(SCE66.27c)
SMA: SAV3586(cmeK)
SGR: SGR_4357
TWH: TWT605(ispE)
TWS: TW159(ispE)
LXX: Lxx17480(ispE)
CMI: CMM_2367(ispE)
AAU: AAur_1338(ispE)
RSA: RSal33209_2993
KRH: KRH_17370(ispE)
PAC: PPA0527
NCA: Noca_3855
TFU: Tfu_0407
FRA: Francci3_3958
FRE: Franean1_0773
FAL: FRAAL6276(ispE)
ACE: Acel_0181
KRA: Krad_1046
SEN: SACE_0807(ispE)
STP: Strop_0783
SAQ: Sare_0727
BLO: BL0656(ispE)
BAD: BAD_1616(ispE)
RXY: Rxyl_0893
FNU: FN0021
RBA: RB10537(ispE)
OTE: Oter_2442
MIN: Minf_1286(ispE)
AMU: Amuc_1195
CTR: CT804(ychB)
CTA: CTA_0876(ispE)
CTB: CTL0173
CTL: CTLon_0174(ispE)
CMU: TC0187
CPJ: CPj0954 CPj0955
CPT: CpB0991 CpB0992
CCA: CCA00815(ispE)
CAB: CAB784
CFE: CF0199(ispE)
PCU: pc1589
TPA: TP0371
TPP: TPASS_0371
TDE: TDE1338(ispE)
LIL: LA3824(ychB)

APPENDIX 1-continued

LIC: LIC10426(ispE)
LBJ: LBJ_2584(ispE)
LBL: LBL_0528(ispE)
LBI: LEPBI_I0238(ispE)
LBF: LBF_0232(ispE)
SYN: sll0711(ipk)
SYW: SYNW1053(ispE)
SYC: syc1203_d(ispE)
SYF: Synpcc7942_0310
SYD: Syncc9605_1188
SYE: Syncc9902_1282
SYG: sync_1593(ispE)
SYR: SynRCC307_1314(ispE)
SYX: SynWH7803_1365(ispE)
SYP: SYNPCC7002_A2416(ispE)
CYA: CYA_0285(ispE)
CYB: CYB_1390(ispE)
TEL: tll0500
MAR: MAE_04520
CYT: cce_1317(ispE)
GVI: gll0102
ANA: alr3230
NPU: Npun_R4911
AVA: Ava_4887
PMA: Pro0764(ispE)
PMM: PMM0932(ispE)
PMT: PMT0620(ispE)
PMN: PMN2A_0279
PMI: PMT9312_0867
PMB: A9601_09281(ispE)
PMC: P9515_10151(ispE)
PMF: P9303_16181(ispE)
PMG: P9301_09261(ispE)
PMH: P9215_09581
PMJ: P9211_07121
PME: NATL1_09481(ispE)
TER: Tery_4700
AMR: AM1_1752(ispE)
BTH: BT_0624
BFR: BF2589
BFS: BF2610
BVU: BVU_3466
PGI: PG0935(ispE)
PGN: PGN_1012
PDI: BDI_0715
SRU: SRU_0689(ispE)
CHU: CHU_1210(ispE)
CTE: CT1495(ispE)
CPC: Cpar_1582
CCH: Cag_1333
CPH: Cpha266_1884
CPB: Cphamn1_0845
PVI: Cvib_1321
PLT: Plut_1496
PPH: Ppha_1063
CTS: Ctha_0721
PAA: Paes_1591
DET: DET0405(ispE)
DEH: cbdb_A356(ispE)
DEB: DehaBAV1_0384
EMI: Emin_0501
DRA: DR_2605
DGE: Dgeo_0180
TTH: TTC1816
TTJ: TTHA0170
AAE: aq_915
HYA: HY04AAS1_1414
SUL: SYO3AOP1_0238
TMA: TM1383
TPT: Tpet_1400
TLE: Tlet_1489
TRQ: TRQ2_1446
TME: Tmel_0318
FNO: Fnod_1663
PMO: Pmob_0160

Exemplary 2-C-methyl-D-erythritol 2,4-cyclodiphosphate synthase nucleic acids and polypeptides ATH: AT1G63970(ISPF)
OSA: 4330320(Os02g0680600)

APPENDIX 1-continued

PPP: PHYPADRAFT_150209
OLU: OSTLU_44114(MCS)
CRE: CHLREDRAFT_188593
CME: CMT435C
PFA: PFB0420w
PFH: PFHG_00813
PYO: PY00321
TAN: TA04155
TPV: TP03_0365
TET: TTHERM_01003920
ECO: b2746(ispF)
ECJ: JW2716(ispF)
ECD: ECDH10B_2914(ispF)
ECE: Z4054(ispF)
ECS: ECs3600(ispF)
ECC: c3313(ispF)
ECI: UTI89_C3117(ispF)
ECP: ECP_2728(ispF)
ECV: APECO1_3777(ispF)
ECW: EcE24377A_3047(ispF)
ECX: EcHS_A2884(ispF)
ECM: EcSMS35_2871(ispF)
ECL: EcolC_0966
STY: STY3054(ispF)
STT: t2830(ispF)
SPT: SPA2785(ispF)
SPQ: SPAB_03643
SEC: SC2861(ispF)
SEH: SeHA_C3119(ispF)
SEE: SNSL254_A3135(ispF)
SEW: SeSA_A3080(ispF)
SES: SARI_00027
STM: STM2929(ispF)
YPE: YPO3360(ispF)
YPK: y0829(ispF)
YPM: YP_0327(ispF)
YPA: YPA_2783(ispF)
YPN: YPN_0733(ispF)
YPP: YPDSF_3000(ispF)
YPG: YpAngola_A0963(ispF)
YPS: YPTB0771(ispF)
YPI: YpsIP31758_3298(ispF)
YPY: YPK_3430
YPB: YPTS_0805
YEN: YE0770(ispF)
SFL: SF2769(ispF)
SFX: S2962(ispF)
SFV: SFV_2752(ispF)
SSN: SSON_2894(ispF)
SBO: SBO_2774(ispF)
SBC: SbBS512_E3128(ispF)
SDY: SDY_2945(ispF)
ECA: ECA3534(ispF)
ETA: ETA_27000(ispF)
PLU: plu0714(ispF)
BUC: BU419(ygbB)
BAS: BUsg404(ygbB)
WBR: WGLp531(ygbB)
SGL: SG0527(ispF)
ENT: Ent638_3217(ispF)
ESA: ESA_00545
KPN: KPN_03108(ispF)
CKO: CKO_04107
SPE: Spro_0827
BPN: BPEN_172(ispF)
HIN: HI0671(ispF)
HIT: NTHI0793(ispF)
HIP: CGSHiEE_08820(ispF)
HIQ: CGSHiGG_06630(ispF)
HDU: HD1328(ispF)
HSO: HS_1498(ispF)
HSM: HSM_0503
PMU: PM1609
MSU: MS2274(ispF)
APL: APL_0803(ispF)
APJ: APJL_0808(ispF)
APA: APP7_0862
ASU: Asuc_2031
XFA: XF1294(ispF)
XFT: PD0546(ispF)

APPENDIX 1-continued

XFM: Xfasm12_0619
XFN: XfasM23_0571
XCC: XCC1703(ispF)
XCB: XC_2528(ispF)
XCV: XCV1755(ispF)
XAC: XAC1722(ispF)
XOO: XOO2960(ispF)
XOM: XOO_2811(ispF)
SML: Smlt1718(ispF)
SMT: Smal_1455
VCH: VC0529(ispF)
VCO: VC0395_A0057(ispF)
VVU: VV1_1583(ispF)
VVY: VV2814(ispF)
VPA: VP2558(ispF)
VFI: VF2072(ispF)
VHA: VIBHAR_03522
PPR: PBPRA3076(ispF)
PAE: PA3627(ispF)
PAU: PA14_17420(ispF)
PAP: PSPA7_1512(ispF)
PPU: PP_1618(ispF)
PPF: Pput_4159(ispF)
PPG: PputGB1_1172
PPW: PputW619_4057
PST: PSPTO_1560(ispF)
PSB: Psyr_1369(ispF)
PSP: PSPPH_3814(ispF)
PFL: PFL_1202(ispF)
PFO: PflO1_1127(ispF)
PEN: PSEEN4194(ispF)
PMY: Pmen_3026(ispF)
PSA: PST_1566(ispF)
CJA: CJA_2222(ispF)
PAR: Psyc_1243(ispF)
PCR: Pcryo_1149
PRW: PsycPRwf_0962
ACI: ACIAD1996(ispF)
ACB: A1S_1982
ABM: ABSDF1672(ispF)
ABY: ABAYE1569
ABC: ACICU_02105
SON: SO_3437(ispF)
SDN: Sden_1199
SFR: Sfri_1055
SAZ: Sama_1039
SBL: Sbal_3124
SBM: Shew185_3133
SBN: Sbal195_3276
SLO: Shew_1208
SPC: Sputcn32_2754
SSE: Ssed_1293
SPL: Spea_1188
SHE: Shewmr4_1118
SHM: Shewmr7_1189
SHN: Shewana3_1119
SHW: Sputw3181_1258
SHL: Shal_1225
SWD: Swoo_3347
ILO: IL0751(ispF)
CPS: CPS_1073(ispF)
PHA: PSHAa0685(ispF)
PAT: Patl_3858
SDE: Sde_1248
MAQ: Maqu_0924
AMC: MADE_03722
PIN: Ping_0673
MCA: MCA2518(ispF)
FTU: FTT1128(ispF)
FTF: FTF1128(ispF)
FTW: FTW_1161(ispF)
FTL: FTL_0833
FTH: FTH_0823(ispF)
FTA: FTA_0882(ispF)
FTN: FTN_1110(ispF)
FTM: FTM_1296(ispF)
FPH: Fphi_1496
NOC: Noc_0855
AEH: Mlg_1836
HHA: Hhal_1434

APPENDIX 1-continued

HCH: HCH_01870(ispF)
CSA: Csal_2637
ABO: ABO_1167(ispF)
MMW: Mmwyl1_1302
AHA: AHA_0824(ispF)
ASA: ASA_3472(ispF)
BCI: BCI_0210(ispF)
RMA: Rmag_0756(ispF)
VOK: COSY_0698(ispF)
NME: NMB1512(ispF)
NMA: NMA1712(ispF)
NMC: NMC1441(ispF)
NMN: NMCC_1417
NGO: NGO0971(ispF)
NGK: NGK_0825
CVI: CV_1259(ispF)
RSO: RSc1644(RS04019)
REU: Reut_A1362
REH: H16_A1457
RME: Rmet_1953
BMA: BMA1489(ispF)
BMV: BMASAVP1_A1986(ispF)
BML: BMA10229_A3320(ispF)
BMN: BMA10247_1258(ispF)
BXE: Bxe_A2311
BVI: Bcep1808_1869
BUR: Bcep18194_A5253
BCN: Bcen_6137
BCH: Bcen2424_1942
BCM: Bcenmc03_1966
BAM: Bamb_1930
BAC: BamMC406_1857
BMU: Bmul_1329
BMJ: BMULJ_01917(ispF)
BPS: BPSL2098(ispF)
BPM: BURPS1710b_2511(ispF)
BPL: BURPS1106A_2400(ispF)
BPD: BURPS668_2357(ispF)
BTE: BTH_I2090(ispF)
BPH: Bphy_0999
PNU: Pnuc_0931
PNE: Pnec_0910
BPE: BP0866(ispF)
BPA: BPP3365(ispF)
BBR: BB3816(ispF)
BPT: Bpet1696(ispF)
BAV: BAV1059(ispF)
RFR: Rfer_1332
POL: Bpro_2715
PNA: Pnap_2548
AAV: Aave_1582
AJS: Ajs_3155
VEI: Veis_4361
DAC: Daci_2850
MPT: Mpe_A1571
HAR: HEAR1911(ispF)
MMS: mma_1410
LCH: Lcho_2293
NEU: NE1402
NET: Neut_1300
NMU: Nmul_A2126
EBA: ebA6542(ispF)
AZO: azo1683(ispF)
DAR: Daro_1974(ispF)
TBD: Tbd_1004
MFA: Mfla_1117
HPY: HP1020(ispDF)
HPJ: jhp0404(ispDF)
HPA: HPAG1_0427(ispDF)
HPS: HPSH_02215(ispDF)
HHE: HH1582(ispDF)
HAC: Hac_1124(ispDF)
WSU: WS1940(ispDF)
TDN: Suden_1487(ispDF)
CJE: Cj1607(ispDF)
CJR: CJE1779(ispDF)
CJJ: CJJ81176_1594(ispDF)
CJU: C8J_1508
CJD: JJD26997_1961
CFF: CFF8240_0409(ispDF)

APPENDIX 1-continued

CCV: CCV52592_0202
CHA: CHAB381_0932
CCO: CCC13826_1467
ABU: Abu_0126(ispDF)
NIS: NIS_0595
SUN: SUN_0522
GSU: GSU3367(ispF)
GME: Gmet_0059
GUR: Gura_4164
GLO: Glov_3480
PCA: Pcar_0102(ispF)
PPD: Ppro_0012
DVU: DVU1454(ispD)
DVL: Dvul_1625
DDE: Dde_1726
LIP: LI0446
DPS: DP0257
DOL: Dole_1666
ADE: Adeh_1272
AFW: Anae109_2497
SAT: SYN_01400
SFU: Sfum_1636
WOL: WD1143
WBM: Wbm0409
WPI: WP0969
AMA: AM1356(ispF)
APH: APH_1276(ispF)
ERU: Erum1020(ispF)
ERW: ERWE_CDS_00990(ispF)
ERG: ERGA_CDS_00950(ispF)
ECN: Ecaj_0102
ECH: ECH_0156(ispF)
NSE: NSE_0134(ispF)
MLO: mll0395(ispDF)
MES: Meso_1621(ispDF)
PLA: Plav_3132
SME: SMc01040(ispDF)
SMD: Smed_1087(ispDF)
ATU: Atu1443(ispF)
ATC: AGR_C_2659
RET: RHE_CH01945(ispDF)
REC: RHECIAT_CH0002043(ispDF)
RLE: RL2254(ispDF)
BME: BMEI0863(ispDF)
BMF: BAB1_1143(ispDF)
BMB: BruAb1_1126(ispDF)
BMC: BAbS19_I10610
BMS: BR1120(ispDF)
BMT: BSUIS_A1169(ispF)
BOV: BOV_1078(ispDF)
BCS: BCAN_A1139(ispF)
OAN: Oant_2069
BJA: bll4485
BRA: BRADO3869(ispDF)
BBT: BBta_4067(ispDF)
RPA: RPA2590(ispD)
RPB: RPB_2885
RPC: RPC_2575
RPD: RPD_2587
RPE: RPE_2755
RPT: Rpal_2860
NWI: Nwi_1442
NHA: Nham_1834
BHE: BH05820
BQU: BQ04980(ispDF)
BBK: BARBAKC583_0540(ispDF)
BTR: Btr_0870
XAU: Xaut_4402
AZC: AZC_3089
MEX: Mext_2817
MRD: Mrad2831_2171
MET: M446_5927
BID: Bind_1516
CCR: CC_1738(ispDF)
CAK: Caul_2603
SIL: SPO2090(ispDF)
SIT: TM1040_1364
RSP: RSP_6071(ispF)
RSH: Rsph17029_1460
RSQ: Rsph17025_1484

APPENDIX 1-continued

RDE: RD1_2767(ispF)
PDE: Pden_3667
DSH: Dshi_1577
MMR: Mmar10_1439
ZMO: ZMO1128(ispDF)
NAR: Saro_1925(ispDF)
SAL: Sala_1278
SWI: Swit_0244(ispDF)
ELI: ELI_06290(ispDF)
GOX: GOX1669
GBE: GbCGDNIH1_1019
ACR: Acry_2031
GDI: GDI2269
RRU: Rru_A1674
MAG: amb2363
MGM: Mmc1_2673
ABA: Acid345_0187
SUS: Acid_1861
SWO: Swol_2360
CSC: Csac_1587
BSU: BSU00910(ispF)
BHA: BH0108(ispF)
BAN: BA0085(ispF)
BAR: GBAA0085(ispF)
BAA: BA_0675(ygbB)
BAT: BAS0086(ispF)
BCE: BC0107(ispF)
BCA: BCE_0086(ispF)
BCZ: BCZK0082(ispF)
BCY: Bcer98_0081
BTK: BT9727_0083(ispF)
BTL: BALH_0086(ispF)
BWE: BcerKBAB4_0081
BLI: BL03266(ispF)
BLD: BLi00109(ispF)
BCL: ABC0126(ispF)
BAY: RBAM_001160(yacN)
BPU: BPUM_0076
GKA: GK0082(ispF)
GTN: GTNG_0082(ispF)
LSP: Bsph_4645
ESI: Exig_0072
LMO: lmo0236(ispF)
LMF: LMOf2365_0248(ispF)
LIN: lin0268(ispF)
EFA: EF0042(ispF)
CAC: CAC0434
CPE: CPE2316(ispF)
CPF: CPF_2616(ispF)
CPR: CPR_2302(ispF)
CTC: CTC00232
CNO: NT01CX_0736(ispF)
CTH: Cthe_2946(ispF)
CDF: CD0048(ispF)
CBO: CBO0066(ispF)
CBA: CLB_0102(ispF)
CBH: CLC_0114(ispF)
CBL: CLK_3243(ispF)
CBK: CLL_A0353(ispF)
CBB: CLD_0719(ispF)
CBF: CLI_0123(ispF)
CBE: Cbei_0297
CKL: CKL_3774(ispF)
CPY: Cphy_3326
AMT: Amet_4505
AOE: Clos_0464
CHY: CHY_2341(ispF)
DSY: DSY0444
DRM: Dred_0188
PTH: PTH_0290(ispF)
HMO: HM1_1354(ispD)
FMA: FMG_1229
TTE: TTE2320(ispF)
TEX: Teth514_0841
TPD: Teth39_0348
MTA: Moth_2486
MPE: MYPE10270
MGA: MGA_0657
MTU: Rv3581c(ispF)
MTC: MT3687(ispF)

APPENDIX 1-continued

MRA: MRA_3620(ispF)
MTF: TBFG_13614(ispF)
MBO: Mb3612c(ispF)
MBB: BCG_3646c(ispF)
MLE: ML0322(ispF)
MPA: MAP0477(ispF)
MAV: MAV_0572(ispF)
MSM: MSMEG_6075(ispF)
MUL: MUL_4157(ispF)
MVA: Mvan_5339(ispF)
MGI: Mflv_1445(ispF)
MAB: MAB_0570
MMC: Mmcs_4738(ispF)
MKM: Mkms_4824(ispF)
MJL: Mjls_5124(ispF)
MMI: MMAR_5081(ispF)
CGL: NCgl2569(ispF)
CGB: cg2944(ispF)
CGT: cgR_2563(ispF)
CEF: CE2520(ispF)
CDI: DIP1972(ispF)
CJK: jk0309(ispF)
CUR: cu1674
NFA: nfa4370(ispF)
RHA: RHA1_ro04461(ispF)
SCO: SCO4234(ispF)
SMA: SAV3968(ispF)
SGR: SGR_4013
TWH: TWT348(ispDF)
TWS: TW422
LXX: Lxx18250(ispF)
CMI: CMM_2489(ispDF)
ART: Arth_0728
AAU: AAur_0899(ispF)
RSA: RSal33209_0410
KRH: KRH_18700(ispF)
PAC: PPA0354(ispF)
NCA: Noca_4024(ispF)
TFU: Tfu_2906(ispF)
FRA: Francci3_4253(ispF)
FRE: Franean1_0364
FAL: FRAAL6523(ispF)
ACE: Acel_0081
KRA: Krad_0900
SEN: SACE_0440(ispF)
STP: Strop_4260
SAQ: Sare_4690
BLO: BL0997(ispF)
BAD: BAD_0669(ispF)
RXY: Rxyl_2175
FNU: FN1788
RBA: RB3451(ispF)
OTE: Oter_2439
MIN: Minf_0771(ispF)
AMU: Amuc_1243
CTR: CT434(ispF)
CTA: CTA_0474(ispF)
CTB: CTL0693
CTL: CTLon_0689(ispF)
CMU: TC0718(ispF)
CPN: CPn0547(ispF)
CPA: CP0205(ispF)
CPJ: CPj0547(ispF)
CPT: CpB0568(ispF)
CCA: CCA00195(ispF)
CAB: CAB191(ispF)
CFE: CF0812(ispF)
PCU: pc0227(ispF)
TPA: TP0512
TPP: TPASS_0512
TDE: TDE2292(ispF)
LIL: LA3591(ygbB)
LIC: LIC10610(ispF)
LBJ: LBJ_0323(ispF)
LBL: LBL_2753(ispF)
LBI: LEPBI_I0322(ispF)
LBF: LBF_0313(ispF)
SYN: slr1542
SYW: SYNW1610
SYC: syc0380_d(ispF)

APPENDIX 1-continued

SYF: Synpcc7942_1170(ispF)
SYE: Syncc9902_1508
SYG: sync_0781(ispF)
SYR: SynRCC307_1730(ispF)
SYX: SynWH7803_1723(ispF)
SYP: SYNPCC7002_A1166(ispF)
CYA: CYA_0267(ispF)
CYB: CYB_0783(ispF)
TEL: tlr2035
MAR: MAE_31930
CYT: cce_0476(ispF)
GVI: glr3547
ANA: alr3883
NPU: Npun_F5826
AVA: Ava_1811(ispF)
PMA: Pro1354(trmD)
PMM: PMM1280
PMT: PMT0356
PMN: PMN2A_0847
PMI: PMT9312_1374
PMB: A9601_14791(trmD)
PMC: P9515_14411(trmD)
PMF: P9303_19461(trmD)
PMG: P9301_14651(trmD)
PMH: P9215_15051
PMJ: P9211_13261
PME: NATL1_17001(trmD)
TER: Tery_4716(ispF)
AMR: AM1_2915(ispF)
BTH: BT_3884
BFR: BF4006
BFS: BF3780(ispF)
BVU: BVU_1639
PGI: PG0028(ispF)
PGN: PGN_0024
PDI: BDI_2574
SRU: SRU_1651(ispF)
CHU: CHU_3180(ispF)
CTE: CT1601(ispF)
CPC: Cpar_1528
CCH: Cag_1782
CPH: Cpha266_0591
CPB: Cphamn1_0610
PVI: Cvib_1388
PLT: Plut_1598
PPH: Ppha_0719
CTS: Ctha_0565
PAA: Paes_0552
DET: DET0060(ispF)
DEH: cbdb_A75(ispF)
DEB: DehaBAV1_0054
EMI: Emin_1165
DRA: DR_0230
DGE: Dgeo_0073
TTH: TTC1438
TTJ: TTHA1790
AAE: aq_957
HYA: HY04AAS1_1161
SUL: SYO3AOP1_1107
TMA: TM0647
TPT: Tpet_0283
TLE: Tlet_0532
TRQ: TRQ2_0281
TME: Tmel_0239
FNO: Fnod_1503
PMO: Pmob_1172

Exemplary 1-hydroxy-2-methyl-2-(E)-butenyl 4-diphosphate synthase nucleic acids and polypeptides ATH: AT5G60600(GcpE)
OSA: 4329911(Os02g0603800)
PPP: PHYPADRAFT_130936(HDS3)
PHYPADRAFT_55802
OLU: OSTLU_12863(HDS)
CRE: CHLREDRAFT_55268(HDS1)
CME: CML284C
PFA: PF10_0221
PFH: PFHG_04116
PYO: PY01664
TAN: TA14455

APPENDIX 1-continued

TPV: TP02_0667
ECO: b2515(ispG)
ECJ: JW2499(ispG)
ECD: ECDH10B_2681(ispG)
ECE: Z3778(ispG)
ECS: ECs3377(ispG)
ECC: c3037(ispG)
ECI: UTI89_C2836(ispG)
ECP: ECP_2520
ECV: APECO1_4009(ispG)
ECW: EcE24377A_2799(ispG)
ECX: EcHS_A2666(ispG)
ECM: EcSMS35_2667(ispG)
ECL: EcolC_1162
STY: STY2768(ispG)
STT: t0333(ispG)
SPT: SPA0344(ispG)
SPQ: SPAB_00417
SEC: SC2520(ispG)
SEH: SeHA_C2781(ispG)
SEE: SNSL254_A2718(ispG)
SEW: SeSA_A2762(ispG)
SES: SARI_00355
STM: STM2523(ispG)
YPE: YPO2879(ispG)
YPK: y1353(ispG)
YPM: YP_2745(ispG)
YPA: YPA_2319(ispG)
YPN: YPN_1259
YPP: YPDSF_2224(ispG)
YPG: YpAngola_A0418(ispG)
YPS: YPTB2841(ispG)
YPI: YpsIP31758_1186(ispG)
YPY: YPK_1293
YPB: YPTS_2950
YEN: YE1073(ispG)
SFL: SF2561(ispG)
SFX: S2733(ispG)
SFV: SFV_2562(ispG)
SSN: SSON_2597(ispG)
SBO: SBO_2539(ispG)
SBC: SbBS512_E2890(ispG)
SDY: SDY_2711(ispG)
ECA: ECA3220(ispG)
ETA: ETA_10280(ispG)
PLU: plu1376(ispG)
BUC: BU287(gcpE)
BAS: BUsg276(gcpE)
WBR: WGLp573(gcpE)
SGL: SG1760(ispG)
ENT: Ent638_3009(ispG)
ESA: ESA_00745
KPN: KPN_02845(ispG)
CKO: CKO_00270
SPE: Spro_3609
BPN: BPEN_551(ispG)
HIN: HI0368(ispG)
HIT: NTHI0488(ispG)
HIP: CGSHiEE_01170
HIQ: CGSHiGG_04650(ispG)
HDU: HD1037(ispG)
HSO: HS_0404(ispG)
HSM: HSM_0729
PMU: PM2010(ispG)
MSU: MS1919(ispG)
APL: APL_1176(ispG)
APJ: APJL_1198(ispG)
APA: APP7_1235
ASU: Asuc_2027
XFA: XF2575(ispG)
XFT: PD1956(ispG)
XFM: Xfasm12_2147
XFN: XfasM23_2062
XCC: XCC1781(ispG)
XCB: XC_2455(ispG)
XCV: XCV1829(ispG)
XAC: XAC1799(ispG)
XOO: XOO2229(ispG)
XOM: XOO_2095(ispG)
SML: Smlt1786

SMT: Smal_1524
VCH: VC0759(ispG)
VCO: VC0395_A0288(ispG)
VVU: VV1_0427(ispG)
VVY: VV0766(ispG)
VPA: VP0608(ispG)
VFI: VF0629(ispG)
VHA: VIBHAR_01067
PPR: PBPRA0763(ispG)
PAE: PA3803(ispG)
PAU: PA14_14880(ispG)
PAP: PSPA7_1311(ispG)
PPU: PP_0853(ispG)
PPF: Pput_0883(ispG)
PPG: PputGB1_0896
PPW: PputW619_4325
PST: PSPTO_1434(ispG)
PSB: Psyr_1248(ispG)
PSP: PSPPH_1320(ispG)
PFL: PFL_4954(ispG)
PFO: PflO1_4601(ispG)
PEN: PSEEN1021(ispG)
PMY: Pmen_3500
PSA: PST_3031(ispG)
CJA: CJA_1481(ispG)
PAR: Psyc_0682(gcpE)
PCR: Pcryo_0652
PRW: PsycPRwf_1902
ACI: ACIAD0561(ispG)
ACB: A1S_0502
ABM: ABSDF3001(ispG)
ABY: ABAYE3263
ABC: ACICU_00511
SON: SO_3312(ispG)
SDN: Sden_1256(ispG)
SFR: Sfri_1116(ispG)
SAZ: Sama_2365(ispG)
SBL: Sbal_2990
SBM: Shew185_3005
SBN: Sbal195_3148
SLO: Shew_1290
SPC: Sputcn32_2652(ispG)
SSE: Ssed_1432
SPL: Spea_1305
SHE: Shewmr4_1228(ispG)
SHM: Shewmr7_1299(ispG)
SHN: Shewana3_1229(ispG)
SHW: Sputw3181_1355
SHL: Shal_1367
SWD: Swoo_1544
ILO: IL2034(ispG)
CPS: CPS_4252(ispG)
PHA: PSHAb0138(ispG)
PAT: Patl_3126
SDE: Sde_1434(ispG)
MAQ: Maqu_1127(ispG)
AMC: MADE_02981
PIN: Ping_1168
MCA: MCA2483(ispG)
FTU: FTT0607(ispG)
FTF: FTF0607(ispG)
FTW: FTW_1121(ispG)
FTL: FTL_0875(ispG)
FTH: FTH_0861(ispG)
FTA: FTA_0926(ispG)
FTN: FTN_1076(ispG)
FTM: FTM_0682(ispG)
FPH: Fphi_0034
NOC: Noc_1749
AEH: Mlg_1461(ispG)
HHA: Hhal_0132(ispG)
HCH: HCH_04456(ispG)
CSA: Csal_2854(ispG)
ABO: ABO_1860(ispG)
MMW: Mmwyl1_1356
AHA: AHA_1759(ispG)
ASA: ASA_2599(ispG)
BCI: BCI_0008(ispG)
RMA: Rmag_0384
VOK: COSY_0358(ispG)

NME: NMB1310(ispG)
NMA: NMA1524(ispG)
NMC: NMC1247(ispG)
NMN: NMCC_1223
NGO: NGO0594(ispG)
NGK: NGK_1324
CVI: CV_3538(ispG)
RSO: RSc1215(ispG)
REU: Reut_A2086(ispG)
REH: H16_A2364(ispG)
RME: Rmet_2106(ispG)
BMA: BMA1345(ispG)
BMV: BMASAVP1_A1835(ispG)
BML: BMA10229_A0062(ispG)
BMN: BMA10247_1107(ispG)
BXE: Bxe_A1594(ispG)
BVI: Bcep1808_1739
BUR: Bcep18194_A5113(ispG)
BCN: Bcen_6267(ispG)
BCH: Bcen2424_1812
BCM: Bcenmc03_1836
BAM: Bamb_1750(ispG)
BAC: BamMC406_1723
BMU: Bmul_1463
BMJ: BMULJ_01780(gcpE)
BPS: BPSL1513(ispG)
BPM: BURPS1710b_2355(ispG)
BPL: BURPS1106A_2228(ispG)
BPD: BURPS668_2190(ispG)
BTE: BTH_I2234(ispG)
BPH: Bphy_1420
PNU: Pnuc_1291(ispG)
PNE: Pnec_0664
BPE: BP2199(ispG)
BPA: BPP2855(ispG)
BBR: BB3176(ispG)
BPT: Bpet2019(ispG)
BAV: BAV2344(gcpE)
RFR: Rfer_2307
POL: Bpro_2608(ispG)
PNA: Pnap_1872(ispG)
AAV: Aave_1424(ispG)
AJS: Ajs_1170(ispG)
VEI: Veis_0080(ispG)
DAC: Daci_5019
MPT: Mpe_A1996(ispG)
HAR: HEAR1264(ispG)
MMS: mma_2127
LCH: Lcho_2868
NEU: NE0148 NE0149
NET: Neut_2168(ispG)
NMU: Nmul_A2377
EBA: ebA1261(ispG)
AZO: azo0927(ispG)
DAR: Daro_2985(ispG)
TBD: Tbd_0594(ispG)
MFA: Mfla_1620(ispG)
HPY: HP0625(ispG)
HPJ: jhp0569(ispG)
HPA: HPAG1_0608(ispG)
HPS: HPSH_03735(ispG)
HHE: HH0807(ispG)
HAC: Hac_0735(ispG)
WSU: WS1302(ispG)
TDN: Suden_0376(ispG)
CJE: Cj0686(ispG)
CJR: CJE0785(ispG)
CJJ: CJJ81176_0709(ispG)
CJU: C8J_0654(ispG)
CJD: JJD26997_1321(ispG)
CFF: CFF8240_0983(ispG)
CCV: CCV52592_0322(ispG)
CHA: CHAB381_0996(ispG)
CCO: CCC13826_0680(ispG)
ABU: Abu_0656(ispG)
NIS: NIS_0337(ispG)
SUN: SUN_2134(ispG)
GSU: GSU1459(ispG)
GME: Gmet_1353
GUR: Gura_2799

APPENDIX 1-continued

GLO: Glov_1907
PCA: Pcar_2368(ispG)
PPD: Ppro_1751
DVU: DVU1344(ispG)
DVL: Dvul_1724
DDE: Dde_2207
LIP: LI0024(gcpE)
DPS: DP1163
DOL: Dole_2059
ADE: Adeh_3949
AFW: Anae109_0476
SAT: SYN_00906
SFU: Sfum_2112
WOL: WD0116(ispG)
WBM: Wbm0782(ispG)
WPI: WP0196(ispG)
AMA: AM741(ispG)
APH: APH_0442(ispG)
ERU: Erum4730(ispG)
ERW: ERWE_CDS_04950(ispG)
ERG: ERGA_CDS_04850(ispG)
ECN: Ecaj_0471(ispG)
ECH: ECH_0559(ispG)
NSE: NSE_0799(ispG)
PUB: SAR11_0517(ispG)
MLO: mll3792(ispG)
MES: Meso_3337(ispG)
PLA: Plav_1746
SME: SMc03888(ispG)
SMD: Smed_3133(ispG)
ATU: Atu2723(gcpE)
ATC: AGR_C_4936
RET: RHE_CH04009(ispG)
REC: RHECIAT_CH0004297(gcpE)
RLE: RL4630(ispG)
BME: BMEI0269(ispG)
BMF: BAB1_1788(ispG)
BMB: BruAb1_1761(ispG)
BMC: BAbS19_I16710
BMS: BR1778(ispG)
BMT: BSUIS_B1254(ispG)
BOV: BOV_1713(ispG)
BCS: BCAN_A1816(ispG)
OAN: Oant_1123
BJA: blr0936(ispG)
BRA: BRADO0546(ispG)
BBT: BBta_7633(ispG)
RPA: RPA0519(ispG)
RPB: RPB_0522(ispG)
RPC: RPC_0491(ispG)
RPD: RPD_0317(ispG)
RPE: RPE_0183(ispG)
RPT: Rpal_0520
NWI: Nwi_0494(ispG)
NHA: Nham_0620(ispG)
BHE: BH15270(ispG)
BQU: BQ12180(ispG)
BBK: BARBAKC583_0119(ispG)
BTR: Btr_2457(gcpE)
XAU: Xaut_1889
AZC: AZC_4581
MEX: Mext_1597
MRD: Mrad2831_3931
MET: M446_5049
BID: Bind_0434
CCR: CC_0851
CAK: Caul_0957
SIL: SPO2594(ispG)
SIT: TM1040_0862(ispG)
RSP: RSP_2982(ispG)
RSH: Rsph17029_1628
RSQ: Rsph17025_1861
JAN: Jann_1935(ispG)
RDE: RD1_2825(ispG)
PDE: Pden_1820(ispG)
DSH: Dshi_1184
MMR: Mmar10_2256(ispG)
HNE: HNE_0621(ispG)
ZMO: ZMO0180(ispG)
NAR: Saro_0417

APPENDIX 1-continued

SAL: Sala_1848(ispG)
SWI: Swit_2126
ELI: ELI_10365(ispG)
GOX: GOX0034(ispG)
GBE: GbCGDNIH1_0604(ispG)
ACR: Acry_1012(ispG)
GDI: GDI1913(ispG)
RRU: Rru_A0747(ispG)
MAG: amb1616(ispG)
MGM: Mmc1_3591
ABA: Acid345_1423(ispG)
SUS: Acid_1193
SWO: Swol_0891
CSC: Csac_2351
BSU: BSU25070(ispG)
BHA: BH1401(ispG)
BAN: BA4502(ispG)
BAR: GBAA4502(ispG)
BAA: BA_4950
BAT: BAS4180(ispG)
BCE: BC4276(ispG)
BCA: BCE_4358(ispG)
BCZ: BCZK4028(ispG)
BCY: Bcer98_3006
BTK: BT9727_4018(ispG)
BTL: BALH_3871(ispG)
BWE: BcerKBAB4_4131
BLI: BL03725(ispG)
BLD: BLi02683(ispG)
BCL: ABC1708(ispG)
BAY: RBAM_023380
BPU: BPUM_2235
GKA: GK2466(ispG)
GTN: GTNG_2403(ispG)
LSP: Bsph_3646
ESI: Exig_0854
LMO: lmo1441(ispG)
LMF: LMOf2365_1460(ispG)
STH: STH1501
CAC: CAC1797(gcpE)
CPE: CPE1692(ispG)
CPF: CPF_1946(ispG)
CPR: CPR_1664(ispG)
CTC: CTC01270(gcpE)
CNO: NT01CX_2141(ispG)
CTH: Cthe_0997
CDF: CD2128(ispG)
CBO: CBO2424(ispG)
CBA: CLB_2288(gcpE)
CBH: CLC_2271(gcpE)
CBL: CLK_1800(gcpE)
CBK: CLL_A1267(ispG)
CBB: CLD_2216(gcpE)
CBF: CLI_2480(gcpE)
CBE: Cbei_1197(ispG)
CKL: CKL_1425(ispG)
CPY: Cphy_2620
AMT: Amet_2680
AOE: Clos_1521
CHY: CHY_1776(ispG)
DSY: DSY2537
DRM: Dred_1968
PTH: PTH_1262(gcpE)
DAU: Daud_0617
HMO: HM1_2266(ispG)
FMA: FMG_0730
TTE: TTE1400(ispG)
TEX: Teth514_1652
TPD: Teth39_1216
MTA: Moth_1043
MPE: MYPE9400
MGA: MGA_1156
MTU: Rv2868c(ispG)
MTC: MT2936(ispG)
MRA: MRA_2893(ispG)
MTF: TBFG_12884(ispG)
MBO: Mb2893c(ispG)
MBB: BCG_2890c(ispG)
MLE: ML1581(ispG)
MPA: MAP2938c(ispG)

APPENDIX 1-continued

MAV: MAV_3725(ispG)
MSM: MSMEG_2580(ispG)
MUL: MUL_2087(ispG)
MVA: Mvan_2262
MGI: Mflv_4081(ispG)
MAB: MAB_3169c
MMC: Mmcs_2044(ispG)
MKM: Mkms_2090(ispG)
MJL: Mjls_2027(ispG)
MMI: MMAR_0275(gcpE_2)
MMAR_1838(ispG)
CGL: NCgl1938(ispG)
CGB: cg2206(ispG)
CGT: cgR_1842(ispG)
CEF: CE1903(ispG)
CDI: DIP1498(ispG)
CJK: jk1165(ispG)
CUR: cu0833
NFA: nfa41180(ispG)
RHA: RHA1_ro06590(ispG)
SCO: SCO5696(ispG) SCO6767(ispG)
SMA: SAV1647(ispG) SAV2561(ispG)
SGR: SGR_1821(gcpE)
TWH: TWT186(ispG)
TWS: TW586(ispG)
LXX: Lxx12200(ispG)
CMI: CMM_2156(ispG)
ART: Arth_1404(ispG)
AAU: AAur_1546(ispG)
RSA: RSal33209_0641
KRH: KRH_16120(ispG)
PAC: PPA1506(ispG)
NCA: Noca_3202
TFU: Tfu_0749(ispG)
FRA: Francci3_3573(ispG)
FRE: Franean1_1170
FAL: FRAAL5772(ispG)
ACE: Acel_1522
KRA: Krad_1429
SEN: SACE_5992(ispG)
STP: Strop_1352(ispG)
SAQ: Sare_1304
BLO: BL0098(ispG)
BLJ: BLD_0116(gcpE)
BAD: BAD_1157(ispG)
RXY: Rxyl_1406
FNU: FN0478
RBA: RB2118(gcpE)
OTE: Oter_4634
MIN: Minf_1968(gcpE)
AMU: Amuc_1388
CTR: CT057(gcpE)
CTA: CTA_0061(gcpE)
CTB: CTL0313(gcpE)
CTL: CTLon_0308(gcpE)
CMU: TC0327(gcpE)
CPN: CPn0373(gcpE)
CPA: CP0383
CPJ: CPj0373(gcpE)
CPT: CpB0385(aarC)
CCA: CCA00423(gcpE)
CAB: CAB409
CFE: CF0584(gcpE)
PCU: pc0740(gcpE)
TPA: TP0446
TPP: TPASS_0446(gcpE)
TDE: TDE1265(ispG)
LIL: LA3160(gcpE)
LIC: LIC10955(gcpE)
LBJ: LBJ_0737(gcpE)
LBL: LBL_2341(gcpE)
LBI: LEPBI_I1285(ispG)
LBF: LBF_1231(gcpE)
SYN: slr2136(gcpE)
SYW: SYNW1174(ispG)
SYC: syc0817_d(ispG)
SYF: Synpcc7942_0713(ispG)
SYD: Syncc9605_1298(ispG)
SYE: Syncc9902_1179(ispG)
SYG: sync_1674(ispG)

APPENDIX 1-continued

SYR: SynRCC307_1462(ispG)
SYX: SynWH7803_1475(ispG)
SYP: SYNPCC7002_A0743(ispG)
CYA: CYA_2387(ispG)
CYB: CYB_0121(ispG)
TEL: tlr0996
MAR: MAE_28180
CYT: cce_2312(ispG)
GVI: gll3622
ANA: all2501
NPU: Npun_F5054
AVA: Ava_0433(ispG)
PMA: Pro1015(ispG)
PMM: PMM0676(ispG)
PMT: PMT0777(ispG)
PMN: PMN2A_0109(ispG)
PMI: PMT9312_0676(ispG)
PMB: A9601_07311(ispG)
PMC: P9515_07491(ispG)
PMF: P9303_14341(ispG)
PMG: P9301_07291(ispG)
PMH: P9215_07611(gcpE)
PMJ: P9211_07901(gcpE)
PME: NATL1_07341(ispG)
TER: Tery_4522(ispG)
AMR: AM1_0149(ispG)
BTH: BT_2517
BFR: BF4365
BFS: BF4164
BVU: BVU_1415
PGI: PG0952(ispG)
PGN: PGN_0998
PDI: BDI_3173
SRU: SRU_0682(ispG)
CHU: CHU_2192(ispG)
CTE: CT0147(gcpE)
CPC: Cpar_1891
CCH: Cag_0349
CPH: Cpha266_0225
CPB: Cphamn1_0311
PVI: Cvib_1613
PLT: Plut_1970
PPH: Ppha_2687
CTS: Ctha_1524
PAA: Paes_0280
DET: DET0369(ispG)
DEH: cbdb_A311(ispG)
DEB: DehaBAV1_0351
EMI: Emin_0687
DRA: DR_0386(ispG)
DGE: Dgeo_0704(ispG)
TTH: TTC1677(ispG)
TTJ: TTHA0305(ispG)
AAE: aq_1540(gcpE)
HYA: HY04AAS1_1229
SUL: SYO3AOP1_0412
TMA: TM0891
TPT: Tpet_0036
TLE: Tlet_0656
TRQ: TRQ2_0036
TME: Tmel_0263
FNO: Fnod_0952
PMO: Pmob_1941

Exemplary 1-hydroxy-2-methyl-2-(E)-butenyl 4-diphosphate reductase nucleic acids and polypeptides ATH: AT4G34350(CLB6)
OSA: 4334003(Os03g0731900)
PPP: PHYPADRAFT_194018
PHYPADRAFT_206243
OLU: OSTLU_32979(IDS)
CRE: CHLREDRAFT_59822(IDS1)
CME: CMJ152C
PFA: MAL1P1.35
PFD: PFDG_01560
PFH: PFHG_00328
PYO: PY01243
TAN: TA17670
TPV: TP03_0674
ECO: b0029(ispH)

APPENDIX 1-continued

ECJ: JW0027(ispH)
ECD: ECDH10B_0030(ispH)
ECE: Z0034(ispH)
ECS: ECs0032(ispH)
ECC: c0033(ispH)
ECI: UTI89_C0031(ispH)
ECP: ECP_0027
ECV: APECO1_1954(ispH)
ECW: EcE24377A_0029(ispH)
ECX: EcHS_A0031(ispH)
ECM: EcSMS35_0027(ispH)
ECL: EcolC_3626
STY: STY0058(ispH)
STT: t0051(ispH)
SPT: SPA0050(ispH)
SPQ: SPAB_00059
SEC: SC0043(ispH)
SEH: SeHA_C0053(ispH)
SEE: SNSL254_A0053(ispH)
SEW: SeSA_A0054(ispH)
SES: SARI_02945
STM: STM0049(ispH)
YPE: YPO0477(ispH)
YPK: y3697(ispH)
YPM: YP_3702(ispH)
YPA: YPA_4071(ispH)
YPN: YPN_0350
YPP: YPDSF_3154(ispH)
YPG: YpAngola_A0787(ispH)
YPS: YPTB0620(ispH)
YPI: YpsIP31758_3457(ispH)
YPY: YPK_3585
YPB: YPTS_0644
YEN: YE0619(ispH)
SFL: SF0026(ispH)
SFX: S0028(ispH)
SFV: SFV_0023(ispH)
SSN: SSON_0034(ispH)
SBO: SBO_0028(ispH)
SBC: SbBS512_E0033(ispH)
SDY: SDY_0051(ispH)
ECA: ECA3873(ispH)
ETA: ETA_07150(ispH)
PLU: plu0594(ispH)
BUC: BU147(lytB)
BAS: BUsg140(lytB)
WBR: WGLp292(lytB)
SGL: SG0417(ispH)
ENT: Ent638_0587(ispH)
ESA: ESA_03309
KPN: KPN_00024(ispH)
CKO: CKO_03363
SPE: Spro_0701
BPN: BPEN_124(ispH)
HIN: HI1007(ispH)
HIT: NTHI1182(ispH)
HIP: CGSHiEE_06935(ispH)
HIQ: CGSHiGG_08635(ispH)
HDU: HD0064(ispH)
HSO: HS_0184(ispH)
HSM: HSM_0050
PMU: PM1664(ispH)
MSU: MS1749(ispH)
APL: APL_1520(ispH)
APJ: APJL_1546(ispH)
APA: APP7_1580
ASU: Asuc_1874
XFA: XF2416(ispH)
XFT: PD1435(ispH)
XFM: Xfasm12_1576
XFN: XfasM23_1519
XCC: XCC1157(ispH)
XCB: XC_3085(ispH)
XCV: XCV1292(ispH)
XAC: XAC1256(ispH)
XOO: XOO1628(ispH)
XOM: XOO_1514(ispH)
SML: Smlt1342(ispH)
SMT: Smal_1127
VCH: VC0685(ispH)

APPENDIX 1-continued

VCO: VC0395_A0217(ispH)
VVU: VV1_0504(ispH)
VVY: VV0690(ispH)
VPA: VP0537(ispH)
VFI: VF0470(ispH)
VHA: VIBHAR_00983
PPR: PBPRA0594(ispH)
PAE: PA4557(ispH)
PAU: PA14_60330(ispH)
PAP: PSPA7_3192(ispH2)
PSPA7_5197(ispH1)
PPU: PP_0606(ispH)
PPF: Pput_0647(ispH)
PPG: PputGB1_0652
PPW: PputW619_4556
PST: PSPTO_0809(ispH)
PSB: Psyr_0713(ispH)
PSP: PSPPH_0724(ispH)
PFL: PFL_5318(ispH)
PFO: PflO1_4849(ispH)
PEN: PSEEN4689(ispH)
PMY: Pmen_0956
PSA: PST_0967(ispH)
CJA: CJA_3214(ispH)
PAR: Psyc_1722(lytB)
PCR: Pcryo_2002
PRW: PsycPRwf_0578
ACI: ACIAD3322(ispH)
ACB: A1S_3169
ABM: ABSDF0323(ispH)
ABY: ABAYE0313
ABC: ACICU_03371
SON: SO_3529(lytB)
SDN: Sden_2720
SFR: Sfri_2887
SAZ: Sama_0927
SBL: Sbal_1057
SBM: Shew185_1124
SBN: Sbal195_1159
SLO: Shew_1102
SPC: Sputcn32_1062
SSE: Ssed_1197
SPL: Spea_1086
SHE: Shewmr4_2954
SHM: Shewmr7_3036
SHN: Shewana3_3133
SHW: Sputw3181_3103
SHL: Shal_1134
SWD: Swoo_1294
ILO: IL1125(lytB)
CPS: CPS_1211(ispH)
PHA: PSHAa0921(ispH)
PAT: Patl_3175
SDE: Sde_2563
MAQ: Maqu_0865
AMC: MADE_03027
PIN: Ping_3268
MCA: MCA1815(ispH)
FTU: FTT0833(ispH)
FTF: FTF0833(ispH)
FTW: FTW_1353(ispH)
FTL: FTL_0327
FTH: FTH_0325
FTA: FTA_0348(ispH)
FTM: FTM_0425(lytB)
FPH: Fphi_0475
NOC: Noc_1744
AEH: Mlg_0854
HHA: Hhal_1834
HCH: HCH_05930(ispH)
CSA: Csal_0484
ABO: ABO_0462(lytB)
MMW: Mmwyl1_4227
AHA: AHA_0685(ispH)
ASA: ASA_0687(lytB)
BCI: BCI_0558(ispH)
RMA: Rmag_1023
VOK: COSY_0924(lytB)
NME: NMB1831(ispH)
NMA: NMA0624(ispH)

APPENDIX 1-continued

NMC: NMC0385(ispH)
NMN: NMCC_0391(lytB)
NGO: NGO0072(ispH)
NGK: NGK_0106
CVI: CV_3567(ispH)
RSO: RSc2442(ispH)
REU: Reut_A2730(ispH) Reut_B4898(ispH)
REH: H16_A3031(ispH) H16_B2169(ispH)
RME: Rmet_2868(ispH) Rmet_4169(ispH)
BMA: BMA2228(ispH) BMAA1962(ispH)
BMV: BMASAVP1_0980(ispH)
BMASAVP1_A2644(ispH)
BML: BMA10229_1267(ispH)
BMA10229_A1018(ispH)
BMN: BMA10247_2097(ispH)
BMA10247_A2242(ispH)
BXE: Bxe_A0820(ispH) Bxe_B0018(ispH)
BVI: Bcep1808_2577 Bcep1808_3716
BUR: Bcep18194_A5831(ispH)
Bcep18194_B0106(ispH)
BCN: Bcen_1888(ispH) Bcen_5308(ispH)
BCH: Bcen2424_2499 Bcen2424_5552
BCM: Bcenmc03_2524 Bcenmc03_4720
BAM: Bamb_2546(ispH) Bamb_4876(ispH)
BAC: BamMC406_2417 BamMC406_5423
BMU: Bmul_0795 Bmul_3253
BMJ: BMULJ_02464(lytB)
BMULJ_05272(lytB)
BPS: BPSL0919(ispH) BPSS2168(ispH)
BPM: BURPS1710b_1141(ispH)
BURPS1710b_A1285(ispH)
BPL: BURPS1106A_0986(ispH)
BURPS1106A_A2929(ispH)
BPD: BURPS668_0981(ispH)
BURPS668_A3054(ispH)
BTE: BTH_I0783(ispH-1) BTH_II2243(ispH-2)
BPH: Bphy_0587 Bphy_4130
PNU: Pnuc_1731
PNE: Pnec_1449
BPE: BP1237(ispH)
BPA: BPP1852(ispH)
BBR: BB3256(ispH)
BPT: Bpet3147(lytB)
BAV: BAV2403(ispH)
RFR: Rfer_3248
POL: Bpro_0951
PNA: Pnap_3337
AAV: Aave_3771
AJS: Ajs_3448
VEI: Veis_1652
DAC: Daci_1906
MPT: Mpe_A2693
HAR: HEAR2466(ispH)
MMS: mma_2549
LCH: Lcho_0693
NEU: NE0649(lytB)
NET: Neut_1903
NMU: Nmul_A0089
EBA: ebA4444(ispH)
AZO: azo1202(ispH)
DAR: Daro_3043
TBD: Tbd_1860
MFA: Mfla_2431
HPY: HP0400(ispH)
HPJ: jhp0981(ispH)
HPA: HPAG1_0992(ispH)
HPS: HPSH_05405(ispH)
HHE: HH0138(ispH)
HAC: Hac_0458(ispH)
WSU: WS1310(ispH)
TDN: Suden_0872(ispH)
CJE: Cj0894c(ispH)
CJR: CJE0973(ispH)
CJJ: CJJ81176_0903(ispH)
CJU: C8J_0831(lytB)
CJD: JJD26997_0919(ispH)
CFF: CFF8240_1251(ispH)
CCV: CCV52592_0515(ispH)
CHA: CHAB381_0483(ispH)
CCO: CCC13826_1566(ispH)

APPENDIX 1-continued

ABU: Abu_2050(ispH)
NIS: NIS_0662(ispH)
SUN: SUN_0548(ispH)
GSU: GSU2604(lytB)
GME: Gmet_0866
GUR: Gura_1466
GLO: Glov_2146
PCA: Pcar_1883(lytB)
PPD: Ppro_1349
DVU: DVU0055(ispH)
DVL: Dvul_2906
DDE: Dde_0390
LIP: LI0728(lytB)
DPS: DP2166
DOL: Dole_0383
ADE: Adeh_1519
AFW: Anae109_2302
SAT: SYN_02454
SFU: Sfum_1812
WOL: WD1274(ispH)
WBM: Wbm0046(ispH)
WPI: WP0811(lytB)
AMA: AM804(ispH)
APH: APH_0380(ispH)
ERU: Erum5180(ispH)
ERW: ERWE_CDS_05430(ispH)
ERG: ERGA_CDS_05330(ispH)
ECN: Ecaj_0526(ispH)
ECH: ECH_0502(ispH)
NSE: NSE_0438(ispH)
PUB: SAR11_0124(lytB)
MLO: mlr7502(ispH)
MES: Meso_0748(ispH)
PLA: Plav_0686
SME: SMc00016(ispH)
SMD: Smed_0527(ispH)
ATU: Atu0774(lytB)
ATC: AGR_C_1414(lytB)
RET: RHE_CH00961(ispH)
REC: RHECIAT_CH0001056(ispH)
RLE: RL1030(ispH)
BME: BMEI1459(ispH)
BMF: BAB1_0501(ispH)
BMB: BruAb1_0497(ispH)
BMC: BAbS19_I04640
BMS: BR0475(ispH)
BMT: BSUIS_A0502(ispH)
BOV: BOV_0480(ispH)
BCS: BCAN_A0482(ispH)
OAN: Oant_0589
BJA: bll3007(ispH) blr1314
BRA: BRADO2632(ispH)
BRADO6588(ispH1)
BBT: BBta_0948(ispH1) BBta_2972(ispH)
RPA: RPA3734(ispH) RPA4271(lytB2)
RPB: RPB_1340 RPB_1729(ispH)
RPC: RPC_1726(ispH) RPC_4078
RPD: RPD_3570(ispH) RPD_4030
RPE: RPE_1816(ispH) RPE_4130
RPT: Rpal_4255 Rpal_4751
NWI: Nwi_2266(ispH) Nwi_2689
NHA: Nham_2679(ispH) Nham_3745
BHE: BH04410(ispH)
BQU: BQ03600(ispH)
BBK: BARBAKC583_0406(ispH)
BTR: Btr_0655(lytB)
XAU: Xaut_2355
AZC: AZC_1468
MEX: Mext_2593
MRD: Mrad2831_4312
MET: M446_6025
BID: Bind_1904
CCR: CC_3361
CAK: Caul_4391
SIL: SPO3207(ispH)
SIT: TM1040_2569
RSP: RSP_1666(lytB)
RSH: Rsph17029_0299
RSQ: Rsph17025_2580
JAN: Jann_0507

APPENDIX 1-continued

RDE: RD1_1355(ispH)
PDE: Pden_3619
DSH: Dshi_0188
MMR: Mmar10_2215
HNE: HNE_2713(ispH)
ZMO: ZMO0875(ispH)
NAR: Saro_1087
SAL: Sala_1136
SWI: Swit_2692
ELI: ELI_01560
GOX: GOX0179
GBE: GbCGDNIH1_1875
ACR: Acry_1832
GDI: GDI3102(ispH)
RRU: Rru_A0059
MAG: amb0764
MGM: Mmc1_3428
ABA: Acid345_1739
SUS: Acid_1259
BSU: BSU25160(ispH)
BHA: BH1382(ispH)
BAN: BA4511(ispH)
BAR: GBAA4511(ispH)
BAA: BA_4959
BAT: BAS4190(ispH)
BCA: BCE_4368(ispH)
BCZ: BCZK4038(ispH)
BCY: Bcer98_3015
BTK: BT9727_4028(ispH)
BTL: BALH_3881(ispH)
BWE: BcerKBAB4_4140
BLI: BL03721(ispH)
BLD: BLi02695(ispH)
BCL: ABC1694(ispH)
BAY: RBAM_023470(yqfP)
BPU: BPUM_2249(yqfP)
GKA: GK2477(ispH)
GTN: GTNG_2414(ispH)
LSP: Bsph_3685
ESI: Exig_0836
LMO: lmo1451(ispH)
LMF: LMOf2365_1470(ispH)
STH: STH910(ispH)
CPE: CPE1085(lytB)
CPF: CPF_1341(ispH)
CPR: CPR_1152(ispH)
CTC: CTC01314
CNO: NTO1CX_2096
CTH: Cthe_0714
CDF: CD1818(ispH)
AMT: Amet_2625
AOE: Clos_1562
DRM: Dred_1154
TTE: TTE1352(lytB)
TEX: Teth514_1606
TPD: Teth39_1169
MPE: MYPE1330
MTU: Rv1110(ispH) Rv3382c(lytB1)
MTC: MT1141(ispH) MT3490(lytB-2)
MRA: MRA_1121(ispH) MRA_3422(lytB1)
MTF: TBFG_11132(ispH) TBFG_13416
MBO: Mb1140(ispH) Mb3414c(lytB1)
MBB: BCG_1170(ispH) BCG_3451c(lytB1)
MLE: ML1938(ispH)
MPA: MAP2684c(ispH)
MAV: MAV_1230(ispH)
MSM: MSMEG_5224(ispH)
MUL: MUL_0168(ispH)
MVA: Mvan_4631
MGI: Mflv_2079(ispH)
MAB: MAB_1257
MMC: Mmcs_4105(ispH)
MKM: Mkms_4181(ispH)
MJL: Mjls_4336(ispH)
MMI: MMAR_0277(lytB2)
MMAR_4355(ispH)
CGL: NCgl0982(ispH)
CGB: cg1164(ispH)
CGT: cgR_1109(ispH)
CEF: CE1079(ispH)

APPENDIX 1-continued

CDI: DIP0943(ispH)
CJK: jk1449(ispH)
CUR: cu0618
NFA: nfa47950(ispH)
RHA: RHA1_ro05870(ispH)
SCO: SCO5058(ispH)
SMA: SAV3210(ispH)
SGR: SGR_2472
TWH: TWT642(ispH)
TWS: TW664(ispH)
LXX: Lxx16760(ispH)
CMI: CMM_2228(ispH)
ART: Arth_2833(ispH)
RSA: RSal33209_1156
KRH: KRH_07120(ispH)
PAC: PPA0572(ispH)
NCA: Noca_1075
TFU: Tfu_0471(ispH)
FRA: Francci3_0824 Francci3_3881(ispH)
FRE: Franean1_0845 Franean1_5712
FAL: FRAAL1433(ispH) FRAAL6150(ispH)
ACE: Acel_1858
KRA: Krad_1123
SEN: SACE_0939(ispH) SACE_4326(ispH)
STP: Strop_0879(ispH)
SAQ: Sare_0824
BLO: BL1361(ispH)
BLJ: BLD_0227(lytB)
BAD: BAD_1081(ispH)
RXY: Rxyl_2212
RBA: RB9288(lytB)
OTE: Oter_3652
MIN: Minf_2119(lytB)
AMU: Amuc_1646
CTR: CT859(ispH)
CTA: CTA_0937(ispH)
CTB: CTL0234
CTL: CTLon_0234(ispH)
CMU: TC0249(ispH)
CPN: CPn1017(ispH)
CPA: CP0836(ispH)
CPJ: CPj1017(ispH)
CPT: CpB1055(ispH)
CCA: CCA00744(ispH)
CAB: CAB711(ispH)
CFE: CF0272(ispH)
PCU: pc1078(ispH)
TPA: TP0547
TPP: TPASS_0547(lytB)
TDE: TDE1096(ispH)
LIL: LA2420(lytB)
LIC: LIC11529(lytB)
LBJ: LBJ_1807(lytB)
LBL: LBL_1476(lytB)
LBI: LEPBI_I1588(ispH)
LBF: LBF_1537(lytB)
SYN: slr0348
SYW: SYNW0252(lytB)
SYC: syc1431_d(lytB)
SYF: Synpcc7942_0073
SYD: Syncc9605_0246
SYE: Syncc9902_0275
SYG: sync_0292(ispH)
SYR: SynRCC307_2319(lytB)
SYX: SynWH7803_0296(lytB)
SYP: SYNPCC7002_A0517(ispH)
CYA: CYA_1148(ispH)
CYB: CYB_2643(ispH)
TEL: tlr1041
MAR: MAE_16190
CYT: cce_1108
GVI: glr3299
ANA: all0985
NPU: Npun_R3286
AVA: Ava_2949
PMA: Pro0296(lytB)
PMM: PMM0264(lytB)
PMT: PMT1854(lytB)
PMN: PMN2A_1630
PMI: PMT9312_0266

APPENDIX 1-continued

PMB: A9601_02861(lytB)
PMC: P9515_02971(lytB)
PMF: P9303_24821(lytB)
PMG: P9301_02871(lytB)
PMH: P9215_02881(lytB)
PMJ: P9211_02911(lytB)
PME: NATL1_03421(lytB)
TER: Tery_4479
AMR: AM1_4950(ispH)
BTH: BT_2061(ispH)
BFR: BF3748(ispH)
BFS: BF3536(ispH)
BVU: BVU_1936
PGI: PG0604(ispH)
PGN: PGN_0647
PDI: BDI_3740(ispH)
SRU: SRU_1880(ispH)
CHU: CHU_0087(ispH)
CTE: CT0283(ispH)
CPC: Cpar_1751
CCH: Cag_0579(ispH)
CPH: Cpha266_0414(ispH)
CPB: Cphamn1_0456
PVI: Cvib_1518(ispH)
PLT: Plut_1736(ispH)
PPH: Ppha_0448
CTS: Ctha_0114
PAA: Paes_0419
DET: DET1344(ispH)
DEH: cbdb_A1294(ispH)
DEB: DehaBAV1_1155
EMI: Emin_0409
DRA: DR_2164
DGE: Dgeo_1010
TTH: TTC1983(lytB)
TTJ: TTHA0015
AAE: aq_1739(lytB)
HYA: HY04AAS1_1048
SUL: SYO3AOP1_1148
TMA: TM1444
TPT: Tpet_1350
TLE: Tlet_1650
TRQ: TRQ2_1336
PMO: Pmob_1619

Exemplary isopentenyl-diphosphate delta-isomerase nucleic acids and polypeptides HSA: 3422(IDI1) 91734(IDI2)
PTR: 450262(IDI2) 450263(IDI1)
MCC: 710052(LOC710052) 721730(LOC721730)
MMU: 319554(Idi1)
RNO: 89784(Idi1)
BTA: 514293(IDI1)
MDO: 100021550(LOC100021550) 100021613(LOC100021613) 100021638(LOC100021638)
OAA: 100080658(LOC100080658)
GGA: 420459(IDI1)
XLA: 494671(LOC494671)
XTR: 496783(idi2)
SPU: 586184(LOC586184)
NVE: NEMVE_v1g121175(NEMVEDRAFT_v1g121175)
DME: Dmel_CG5919(CG5919)
DPO: Dpse_GA19228
AGA: AgaP_AGAP001704
AAG: AaeL_AAEL006144
TCA: 660176(LOC660176)
CEL: K06H7.9(idi-1)
CBR: CBG22969
BMY: Bm1_16940
ATH: AT3G02780(IDI2/IPIAT1/IPP2) AT5G16440(IPP1)
OSA: 4338791(Os05g0413400) 4343523(Os07g0546000)
PPP: PHYPADRAFT_56143
OLU: OSTLU_13493
CRE: CHLREDRAFT_24471(IDI1)
CME: CMB062C APPENDIX 1-continued SCE: YPL117C(IDI1)
AGO: AGOS_ADL268C
KLA: KLLA0F00924g
DHA: DEHA0G20009g
PIC: PICST_68990(IDI1)
VPO: Kpol_479p9
CGR: CAGL0J06952g
YLI: YALI0F04015g
SPO: SPBC106.15(idi1)
NCR: NCU07719
PAN: PODANSg7228
MGR: MGG_07125
FGR: FG09722.1
ANI: AN0579.2
AFM: AFUA_6G11160
AOR: AO090023000500
ANG: An08g07570
CNE: CNA02550
CNB: CNBA2380
LBC: LACBIDRAFT_291469
UMA: UM04838.1
MGL: MGL_1929
ECU: ECU02_0230
MBR: MONBRDRAFT_34433
GLA: GL50803_6335
DDI: DDB_0191342(ipi)
TET: TTHERM_00237280 TTHERM_00438860
PTM: GSPATT00007643001 GSPATT00011951001
TBR: Tb09.211.0700
TCR: 408799.19 510431.10
LMA: LmjF35.5330
EHI: EHI_194410
TVA: TVAG_116230 TVAG_495540
ECO: b2889(idi)
ECJ: JW2857(idi)
ECD: ECDH10B_3063(idi)
ECE: Z4227
ECS: ECs3761
ECC: c3467
ECI: UTI89_C3274
ECP: ECP_2882
ECV: APECO1_3638
ECW: EcE24377A_3215(idi)
ECX: EcHS_A3048(idi)
ECM: EcSMS35_3022(idi)
ECL: EcolC_0820
STY: STY3195
STT: t2957
SPT: SPA2907(idi)
SPQ: SPAB_03786
SEC: SC2979(idi)
SEH: SeHA_C3270(idi)
SEE: SNSL254_A3273(idi)
SEW: SeSA_A3207(idi)
SES: SARI_04611
STM: STM3039(idi)
SFL: SF2875
SFX: S3074
SFV: SFV_2937
SSN: SSON_3042 SSON_3489(yhfK)
SBO: SBO_3103
SBC: SbBS512_E3308(idi)
SDY: SDY_3193
ECA: ECA2789
ETA: ETA_22390(idi)
PLU: plu3987
ENT: Ent638_3307
ESA: ESA_00346
KPN: KPN_03317(idi)
CKO: CKO_04250
SPE: Spro_2201
VPA: VPA0278
VFI: VF0403
VHA: VIBHAR_04924
PPR: PBPRA0469
PEN: PSEEN4850
PSA: PST_3876
CBU: CBU_0607(mvaD)

APPENDIX 1-continued

CBS: COXBURSA331__A0720(mvaD)
CBD: CBUD__0619(mvaD)
LPN: lpg2051
LPF: lpl2029
LPP: lpp2034
LPC: LPC__1537(fni)
TCX: Tcr__1718
HHA: Hhal__1623
DNO: DNO__0798
EBA: ebA5678 p2A143
DVU: DVU1679(idi)
DDE: Dde__1991
LIP: LI1134
BBA: Bd1626
AFW: Anae109__4082
MXA: MXAN__5021(fni)
SCL: sce1761(idi)
RPR: RP452
RTY: RT0439(idi)
RCO: RC0744
RFE: RF__0785(fni)
RBE: RBE__0731(fni)
RBO: A1I__04760
RAK: A1C__04195
RCM: A1E__02555
RRI: A1G__04195
RRJ: RrIowa__0882
RMS: RMA__0766(fni)
MLO: mlr6371
MES: Meso__4299
RET: RHE__PD00245(ypd00046)
REC: RHECIAT__PB0000285
XAU: Xaut__4134
SIL: SPO0131
SIT: TM1040__3442
RSP: RSP__0276
RSH: Rsph17029__1919
RSQ: Rsph17025__1019
JAN: Jann__0168
RDE: RD1__0147(idi)
DSH: Dshi__3527
SWO: Swol__1341
BSU: BSU22870(ypgA)
BAN: BA1520
BAR: GBAA1520
BAA: BA__2041
BAT: BAS1409
BCE: BC1499
BCA: BCE__1626
BCZ: BCZK1380(fni)
BCY: Bcer98__1222
BTK: BT9727__1381(fni)
BTL: BALH__1354
BWE: BcerKBAB4__1422
BLI: BL02217(fni)
BLD: BLi02426
BAY: RBAM__021020(fni)
BPU: BPUM__2020(fni)
OIH: OB0537
SAU: SA2136(fni)
SAV: SAV2346(fni)
SAW: SAHV__2330(fni)
SAM: MW2267(fni)
SAR: SAR2431(fni)
SAS: SAS2237
SAC: SACOL2341(fni)
SAB: SAB2225c(fni)
SAA: SAUSA300__2292(fni)
SAX: USA300HOU__2327
SAO: SAOUHSC__02623
SAJ: SaurJH9__2370
SAH: SaurJH1__2416
SAE: NWMN__2247(idi)
SEP: SE1925
SER: SERP1937(fni-2)
SHA: SH0712(fni)
SSP: SSP0556
LMO: lmo1383
LMF: LMOf2365__1402(fni)
LIN: lin1420

APPENDIX 1-continued

LWE: lwe1399(fni)
LLA: L11083(yebB)
LLC: LACR__0457
LLM: llmg__0428(fni)
SPY: SPy__0879
SPZ: M5005__Spy__0685
SPM: spyM18__0940
SPG: SpyM3__0598
SPS: SPs1255
SPH: MGAS10270__Spy0743
SPI: MGAS10750__Spy0777
SPJ: MGAS2096__Spy0756
SPK: MGAS9429__Spy0740
SPF: SpyM51123(fni)
SPA: M6__Spy0702
SPB: M28__Spy0665
SPN: SP__0384
SPR: spr0341(fni)
SPD: SPD__0349(fni)
SPV: SPH__0491(fni)
SPW: SPCG__0379(fni)
SPX: SPG__0349
SAG: SAG1323
SAN: gbs1393
SAK: SAK__1354(fni)
SMU: SMU.939
STC: str0562(idi)
STL: stu0562(idi)
STE: STER__0601
SSA: SSA__0336
SSU: SSU05__0292
SSV: SSU98__0288
SGO: SGO__0242
SEZ: Sez__1081
LPL: lp__1732(idi1)
LJO: LJ1208
LAC: LBA1171
LSA: LSA0905(idi)
LSL: LSL__0682
LDB: Ldb0996(fni)
LBU: LBUL__0903
LBR: LVIS__0861
LCA: LSEI__1493
LCB: LCABL__17150(fni)
LGA: LGAS__1036
LRE: Lreu__0912
LRF: LAR__0859
LHE: lhv__1278
LFE: LAF__1195
EFA: EF0901
OOE: OEOE__1103
LME: LEUM__1388
LCI: LCK__00620
STH: STH1674
DRM: Dred__0474
HMO: HM1__1981(fni)
FMA: FMG__1144
MTA: Moth__1328
ACL: ACL__0797(idi)
MTU: Rv1745c(idi)
MTC: MT1787(idi)
MRA: MRA__1756(idi)
MTF: TBFG__11763
MBO: Mb1774c(idi)
MBB: BCG__1784c(idi)
MPA: MAP3079c
MAV: MAV__3894(fni)
MSM: MSMEG__1057(fni)
MSMEG__2337(fni)
MUL: MUL__0380(idi2)
MVA: Mvan__1582 Mvan__2176
MGI: Mflv__1842 Mflv__4187
MAB: MAB__3242
MMC: Mmcs__1954
MKM: Mkms__2000
MJL: Mjls__1934
MMI: MMAR__3218(idi) MMAR__4812(idi2)
CGL: NCgl2223(cgl2305)
CGB: cg2531(idi)
CGT: cgR__2177

APPENDIX 1-continued

CEF: CE2207
CDI: DIP1730(idi)
NFA: nfa19790 nfa22100
RHA: RHA1_ro00239
SCO: SCO6750(SC5F2A.33c)
SMA: SAV1663(idi)
SGR: SGR_977
LXX: Lxx23810(idi)
CMI: CMM_2889(idiA)
AAU: AAur_0321(idi)
KRH: KRH_03040(idi)
PAC: PPA2115
FRA: Francci3_4188
FRE: Franean1_5570
FAL: FRAAL6504(idi)
KRA: Krad_3991
SEN: SACE_2627(idiB_2) SACE_5210(idi)
STP: Strop_4438
SAQ: Sare_4564 Sare_4928
RXY: Rxyl_0400
BBU: BB0684
BGA: BG0707
BTU: BT0684
SYN: sll1556
SYC: syc2161_c
SYF: Synpcc7942_1933
SYP: SYNPCC7002_A1132(fni)
CYA: CYA_2395(fni)
CYB: CYB_2691(fni)
TEL: tll1403
MAR: MAE_56570
CYT: cce_1202
ANA: all4591
NPU: Npun_R1243
AVA: Ava_2461 Ava_B0346
TER: Tery_1589
AMR: AM1_4374(fni)
SRU: SRU_1900(idi)
CHU: CHU_0674(idi)
GFO: GFO_2363(idi)
FJO: Fjoh_0269
FPS: FP1792(idi)
CTE: CT0257
CPC: Cpar_1777
CCH: Cag_1445
CPH: Cpha266_0385
CPB: Cphamn1_0417
PVI: Cvib_1545
PLT: Plut_1764
PPH: Ppha_0414
CTS: Ctha_0403
PAA: Paes_0384
RRS: RoseRS_2437
RCA: Rcas_2215
CAU: Caur_3877
HAU: Haur_4687
DRA: DR_1087
DGE: Dgeo_1381
TTH: TT_P0067
TTJ: TTHB110
MJA: MJ0862
MMP: MMP0043

APPENDIX 1-continued

MMQ: MmarC5_1637
MMX: MmarC6_0906
MMZ: MmarC7_1040
MAE: Maeo_1184
MVN: Mevan_1058
MAC: MA0604(idi)
MBA: Mbar_A1419
MMA: MM_1764
MBU: Mbur_2397
MTP: Mthe_0474
MHU: Mhun_2888
MLA: Mlab_0683 Mlab_1665
MEM: Memar_1814
MBN: Mboo_2211
MTH: MTH48
MST: Msp_0856(fni)
MSI: Msm_1441
MKA: MK0776(lldD)
AFU: AF2287
HAL: VNG1818G(idi) VNG6081G(crt_1) VNG6445G(crt_2) VNG7060 VNG7149
HSL: OE3560F(idiA) OE6213R(idiB2) OE7093R(idiB1)
HMA: rrnAC3484(idi)
HWA: HQ2772A(idiA) HQ2847A(idiB)
NPH: NP0360A(idiB_1) NP4826A(idiA) NP5124A(idiB_2)
TAC: Ta0102
TVO: TVN0179
PTO: PTO0496
PHO: PH1202
PAB: PAB1662
PFU: PF0856
TKO: TK1470
RCI: LRC397(fni)
APE: APE_1765.1(fni)
SMR: Smar_0822
IHO: Igni_0804
HBU: Hbut_0539
SSO: SSO0063
STO: ST2059
SAI: Saci_0091
MSE: Msed_2136
PAI: PAE0801
PIS: Pisl_1093
PCL: Pcal_0017
PAS: Pars_0051
CMA: Cmaq_0231 Cmaq_1145
TNE: Tneu_0048
TPE: Tpen_0272
NMR: Nmar_0313
KCR: Kcr_1016

| Exemplary isoprene synthase nucleic acids and polypeptides Genbank Accession Nos. |
|---|
| AY341431 |
| AY316691 |
| AY279379 |
| AJ457070 |
| AY182241 |

What is claimed is:

1. An isolated host cell capable of producing isoprene comprising (i) a heterologous nucleic acid encoding an iron-sulfur cluster-interacting redox polypeptide or a duplicate copy of an endogenous nucleic acid encoding an iron-sulfur cluster-interacting redox polypeptide, and (ii) a non-mevalonate (DXP) pathway polypeptide, a mevalonate (MVA) pathway polypeptide, and an isoprene synthase polypeptide, wherein the cells are capable of producing isoprene, and wherein at least 35% of the isoprene is generated from DXP pathway flux contribution.

2. The cells of claim 1, wherein the cells further comprise a heterologous nucleic acid or a duplicate copy of an endogenous nucleic acid encoding an IDI (isopentenyl-diphosphate delta-isomerase) polypeptide.

3. The cells of claim 1, wherein the cells produce greater than about 400 nmole/$g_{wcm}$/hr of isoprene.

4. The cells of claim 1, wherein more than about 0.02 molar percent of the carbon that the cells consume from a cell culture medium is converted into isoprene.

5. A method of producing isoprene, the method comprising (a) culturing isolated cells comprising (i) a heterologous nucleic acid encoding an iron-sulfur cluster-interacting redox polypeptide or a duplicate copy of an endogenous nucleic acid encoding an iron-sulfur cluster-interacting redox polypeptide, and (ii) a non-mevalonate (DXP) pathway polypeptide, a mevalonate (MVA) pathway polypeptide, and an isoprene synthase polypeptide under suitable culture conditions for the production of isoprene, and (b) producing isoprene, and wherein at least 35% of the isoprene is generated from DXP pathway flux contribution.

6. The method of claim 5, wherein the cells further comprise a heterologous nucleic acid or a duplicate copy of an endogenous nucleic acid encoding an IDI (isopentenyl-diphosphate delta-isomerase) polypeptide.

7. The method of claim 5, wherein the cells in culture produce greater than about 400 nmole/$g_{wcm}$/hr of isoprene.

8. The method of claim 5, wherein more than about 0.02 molar percent of the carbon that the cells consume from a cell culture medium is converted into isoprene.

9. The cells of claim 1, wherein at least 40% of the isoprene is generated from DXP pathway flux contribution.

10. The cells of claim 1, wherein at least 45% of the isoprene is generated from DXP pathway flux contribution.

11. The cells of claim 1, wherein at least 50% of the isoprene is generated from DXP pathway flux contribution.

12. The cells of claim 1, wherein the cells further comprise a deletion of the gene encoding the IscR transcriptional repressor from the cells' genome.

13. The method of claim 5, wherein at least 40% of the isoprene is generated from DXP pathway flux contribution.

14. The method of claim 5, wherein at least 45% of the isoprene is generated from DXP pathway flux contribution.

15. The method of claim 5, wherein at least 50% of the isoprene is generated from DXP pathway flux contribution.

16. The method of claim 5, wherein the cells further comprise a deletion of the gene encoding the IscR transcriptional repressor from the cells' genome.

* * * * *